(12) United States Patent
Crew et al.

(10) Patent No.: US 10,994,015 B2
(45) Date of Patent: May 4, 2021

(54) EGFR PROTEOLYSIS TARGETING CHIMERIC MOLECULES AND ASSOCIATED METHODS OF USE

(71) Applicants: Arvinas Operations, Inc., New Haven, CT (US); Yale University, New Haven, CT (US)

(72) Inventors: Andrew P. Crew, Chester, CT (US); Kurt Zimmermann, Durham, CT (US); Jing Wang, Milford, CT (US); Craig M. Crews, New Haven, CT (US); Saul Jaime-Figueroa, Morris Plains, NJ (US); George Burslem, Sandwich (GB)

(73) Assignees: ARVINAS OPERATIONS, INC., New Haven, CT (US); YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/852,854

(22) Filed: Dec. 22, 2017

(65) Prior Publication Data

US 2018/0193470 A1    Jul. 12, 2018

Related U.S. Application Data

(60) Provisional application No. 62/563,494, filed on Sep. 26, 2017, provisional application No. 62/438,901, filed on Dec. 23, 2016.

(51) Int. Cl.

| | | |
|---|---|---|
| *C07D 471/04* | (2006.01) | |
| *A61P 35/00* | (2006.01) | |
| *A61K 31/506* | (2006.01) | |
| *A61K 47/54* | (2017.01) | |
| *A61K 47/55* | (2017.01) | |
| *A61K 31/519* | (2006.01) | |
| *A61K 31/427* | (2006.01) | |
| *A61K 31/454* | (2006.01) | |
| *A61K 31/517* | (2006.01) | |
| *A61K 31/55* | (2006.01) | |
| *A61K 31/496* | (2006.01) | |
| *A61K 31/551* | (2006.01) | |
| *A61K 45/06* | (2006.01) | |
| *A61K 38/07* | (2006.01) | |
| *A61K 31/52* | (2006.01) | |

(52) U.S. Cl.
CPC .......... *A61K 47/545* (2017.08); *A61K 31/427* (2013.01); *A61K 31/454* (2013.01); *A61K 31/496* (2013.01); *A61K 31/506* (2013.01); *A61K 31/517* (2013.01); *A61K 31/519* (2013.01); *A61K 31/52* (2013.01); *A61K 31/55* (2013.01); *A61K 31/551* (2013.01); *A61K 38/07* (2013.01); *A61K 45/06* (2013.01); *A61K 47/55* (2017.08); *C07D 471/04* (2013.01)

(58) Field of Classification Search
CPC .. C07D 221/00; C07D 227/04; C07D 227/12; C07D 235/00; C07D 239/24; C07D 401/14; C07D 487/04; A61K 47/545; A61K 47/55; A61K 31/4545; A61K 31/454; A61K 31/506; A61K 31/513
See application file for complete search history.

(56) References Cited

U.S. PATENT DOCUMENTS

| | | | |
|---|---|---|---|
| 6,268,391 B1 | 7/2001 | Dickerson et al. | |
| 6,306,663 B1 | 10/2001 | Kenten et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |
| 7,208,157 B2 | 4/2007 | Sakamoto et al. | |
| 7,244,851 B2 | 7/2007 | Cohen et al. | |
| 7,345,081 B2 | 3/2008 | Cohen et al. | |
| 7,419,975 B2 | 9/2008 | Palermo et al. | |
| 7,517,906 B2 | 4/2009 | Condon et al. | |
| 7,915,293 B2 | 3/2011 | Ramesh | |
| 9,500,653 B2 | 11/2016 | Crews et al. | |

(Continued)

FOREIGN PATENT DOCUMENTS

| | | |
|---|---|---|
| CN | 1844118 A | 10/2006 |
| CN | 103374000 | 10/2013 |

(Continued)

OTHER PUBLICATIONS

Byrn, Stephen. Solid-State Chemistry of Drugs, 2nd Ed. (1999), Ch. 11 Hydrates and Solvates, 233-247.*
A.M. Rouhi, Chem. & Eng. News, (2003), 81(8), 32-35.*
Morissette, Sherry. Adv. Drug Delivery Rev. 2004, 56, 275-300.*
Banker, Gilbert. Modern Pharmaceutics 3rd ed. Marcel Dekker, Inc. New York, 1996.*
Ahn, et al., "HIF-lalpha peptide derivatives with modifications at the hydroxyproline residue as activators of HIF-lalpha", Bioorg Med Chem Lett. 19(15), 2009, 4403-4405.

(Continued)

*Primary Examiner* — Emily A Bernhardt
*Assistant Examiner* — Laura M Daniel
(74) *Attorney, Agent, or Firm* — Bryan D. Zerhusen, Esq.; Cantor Colburn LLP

(57) ABSTRACT

The present disclosure relates to bifunctional compounds, which find utility as modulators of receptor tyrosine kinase (RTK) proteins. In particular, the present disclosure is directed to bifunctional compounds, which contain on one end a ligand which binds to an E3 ubiquitin ligase and on the other end a moiety which binds a target protein, such that the target protein is placed in proximity to the ubiquitin ligase to effectuate ubiquitination, and therefore, degradation (and inhibition) of the target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

25 Claims, 242 Drawing Sheets

(56) References Cited

U.S. PATENT DOCUMENTS

| | | |
|---|---|---|
| 9,632,089 B2 | 4/2017 | Crews et al. |
| 2006/0128632 A1 | 6/2006 | Sharma et al. |
| 2007/0099844 A1 | 5/2007 | Prendergast et al. |
| 2007/0281907 A1 | 12/2007 | Watkins |
| 2008/0051432 A1 | 2/2008 | Zhang |
| 2008/0214501 A1 | 9/2008 | Pan et al. |
| 2008/0269140 A1 | 10/2008 | Wang et al. |
| 2010/0203012 A1 | 8/2010 | Laurent et al. |
| 2011/0195043 A1 | 8/2011 | Sun et al. |
| 2012/0270800 A1 | 10/2012 | Verdine et al. |
| 2014/0088143 A1 | 3/2014 | Jain |
| 2014/0235629 A1 | 8/2014 | Bartberger et al. |
| 2014/0243372 A1 | 8/2014 | Rew |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0141402 A1 | 5/2015 | Behenna et al. |
| 2015/0152083 A1 | 6/2015 | Lelais |
| 2015/0259288 A1 | 9/2015 | Nam et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |

FOREIGN PATENT DOCUMENTS

| | | |
|---|---|---|
| CN | 103688176 A | 3/2014 |
| CN | 104418860 | 3/2015 |
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1997/030034 | 8/1997 |
| WO | WO 1998/003502 | 1/1998 |
| WO | WO 2000/066119 | 11/2000 |
| WO | WO 2002/066512 | 8/2002 |
| WO | WO 2002/076986 | 10/2002 |
| WO | WO 2002/080926 | 10/2002 |
| WO | WO 2002/100845 | 12/2002 |
| WO | WO 2003/013541 | 2/2003 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/061299 | 5/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/081718 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2014/210354 | 12/2014 |
| WO | WO 2015/000868 | 1/2015 |
| WO | WO 2015/006524 | 1/2015 |
| WO | WO 2015/160845 | 10/2015 |
| WO | WO 2015/175632 | 11/2015 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/004383 | 1/2017 |
| WO | WO 2017/011590 | 1/2017 |
| WO | WO 2017/024318 A1 | 2/2017 |
| WO | WO 2017/024319 A1 | 2/2017 |
| WO | WO 2017/030814 | 2/2017 |
| WO | WO 2017/046036 | 3/2017 |
| WO | WO 2017/079267 | 5/2017 |
| WO | WO 2017/117474 | 7/2017 |
| WO | WO 2017/185036 | 10/2017 |
| WO | WO 2017/197051 | 11/2017 |
| WO | WO 2018/148440 | 8/2018 |

OTHER PUBLICATIONS

Anido, J., et al., "ZD1839, a Specific Epidermal Growth Factor Receptor (EGFR) Tyrosine Kinase Inhibitor, Induces the Formation of Inactive EGFR/HER2 and EGFR/HER3 Heterodimers and Prevents Heregulin Signaling in HER2-overexpressing Breast Cancer Cells", Clinical Cancer Research 9, 1274-1283 (2003).

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Asaoka, Y., et al., "Gastric cancer cell line Hs746T harbors a splice site mutation of c-Met causing juxtamembrane domain deletion", Biochem Biophys Res Commun 394, 1042-1046 (2010).

(56) References Cited

OTHER PUBLICATIONS

Bargagna-Mohan, et al., "Use of PROTACS as molecular probes of angiogenesis", Bioorg Med Chem Left. 15(11) 2005, 2724-2727.
Barker, A.J. et al., "Studies Leading to the Identification of ZD1839 (IressaTM ): An Orally Active, Selective Epidermal Growth Factor Receptor Tyrosine Kinase Inhibitor Targeted to the Treatment of Cancer", Bioorganic and Medicinal Chemistry Letters 2001, 11(14), 1911-1914.
Bolen, et al., "Leukocyte protein tyrosine kinases: potential targets for drug discovery", Annual review of Immunology. 15: 371-404 (1997).
Bondeson, et al., (2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and H1F1a", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.
Burslem, et al., (2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS Registry No. 1004933-70-3, which entered STN on Feb. 21, 2008.
CAS Registry No. 871986-52-6 entered STN Jan. 16, 2006.
Chan, B. K. et al., "Discovery of a Noncovalent, Mutant-Selective Epidermal Growth Factor Receptor Inhibitor" , Journal of Medicinal Chemistry, 2016, vol. 59, pp. 9080-9093, [Epub]Aug. 26, 2016.
Chene, P., et al., "Inhibiting the p. 53-MDM2 interaction: an important target for cancer therapy" Nat. Rev. Cancer (2003), 3, 102-109.
Cheng, H. et al . , "Discovery of 1-{(3R ,4R)-3-[ ( {5-Chloro-2-[ (1-methyl-1H-pyrazol-4-yl ) amino]-7H-pyrrolo [2,3-d] pyrimidin-4-yl loxy) met hyl ]-4-ethoxypyrrol id in-1-yl }prop-2-en-1.-one (PF-06459988) , a Potent, {VT Sparing, Irreversible Inhibitor of T790M-Containing EGFR Mutants", Journal of Medicinal Chemistry, 2016, vol. 59, pp. 2005-2024, [Epub]Jan. 12, 2016.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antagonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol 17*, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Dassonville, O., et al., "EGFR targeting therapies: Monoclonal antibodies versus tyrosine kinase inhibitors", Critical Reviews in Oncology/Hematology 62, 53-61 (2007).
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol 13*, 549-555, doi:S1367-5931(09)00107-0 [pii] 10.1016/j.cbpa.2009.08.003 (2009).
Engleman, J.A., et al., <em>MET</em> "Amplification Leads to Gefitinib Resistance in Lung Cancer by Activating ERBB3 Signaling", Science 316, 1039-1043 (2007).
Finlay, M. et al., "Discovery of a potent and selective EGFR inhibitor (AZD9291) of both sensitizing and T790M resistance mutations that spares the wild type form of the receptor", Journal of Medicinal Chemistry 2014, 57 (20), 8249-8267.
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 (2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Gangjee. A. et al . , "The contribution of a 2-amino group on receptor tyrosine kinase inhibition and antiangiogenic activity in 4-anilinosubstituted pyrrolo [2,3-d] pyrimidines", Bioorganic & Medicinal Chemistry Letters, 2010, vol. 20, No. 10, pp. 3177-3181.
Goldstein, et al. "Biological Efficacy of a Chimeric Antibody to the Epidermal Growth Factor Receptor in a Human Tumor", (1995), Clin Cancer Res. vol. 1, Nov. 1995, 1311-1318.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Graves, Lee M., et al, "The dynamic nature of the kinome", Biochemical Journal, Feb. 15; 450(1), 1-8 (2013).
Gschwind, A., et al., "The discovery of receptor tyrosine kinases: targets for cancer therapy", Nat Rev Cancer 4, 361-370 (2004).
Hanan, et al, "Discovery of selective and noncovalent diaminopyrimidine-based inhibitors of epidermal growth factor receptor containing the T790M resistance mutation", J. Med Chem. 57(23), 2014, 10176-10191.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in Hlf-1 alpha by pVHL", Nature 417, Jun. 27, 2002, 975-978.

(56) References Cited

OTHER PUBLICATIONS

Huang, et al., (2016) "Drugging the undruggables: exploring the ubiquitin system for drug development." Cell Res 26(4):484-498.
Hughes, et al., (2017) "Molecular recognition of ternary complexes: a new dimension in the structure-guided design of chemical degraders." Essays Biochem 61(5):505-516.
Iqbal, N., "Human Epidermal Growth Factor Receptor 2 (HER2) in Cancers: Overexpression and Therapeutic Implications", Molecular Biology International 2014 Article ID 852748 (2014).
Ishikawa, T. et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry 2011, 54 (23), 8030-8050.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Jia, Y. et al., "Overcoming EGFR (T790M) and EGFR (C797S) resistance with mutant-selective allosteric inhibitors", Nature, Jun. 2, 2016, vol. 534, pp. 129-132.
Jo, M., et al., "Cross-talk between Epidermal Growth Factor Receptor and c-Met Signal Pathways in Transformed Cells", J Biol Chem 275, 8806-8811 (2000).
Kim, K.S., "Discovery of tetrahydroisoquinoline-based bivalent heterodimeric IAP antagonists", Bioorg. Med. Chem. Lett. 24(21), 5022-5029 (2014).
Knickelbein, K., et al., Mutant KRAS as a critical determinant of the therapeutic response of colorectal cancer, Genes Dis. Mar. 2015; 2(1):4-12.
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Konecny, G.E., et al., "Activity of the Dual Kinase Inhibitor Lapatinib (GW572016) against HER-2-Overexpressing and Trastuzumab-Treated Breast Cancer Cells", Cancer Research 66, 1630-1639 (2006).
Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." Nat Rev Drug Discov 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistent (T790M) EGFR mutants for the treatment of EGFR mutant non-small-cell lung cancers", Journal of Medicinal Chemistry 2016, 59(14), 6671-6689.
Lemmon, M.A., et al., "Cell Signaling by Receptor Tyrosine Kinases", Cell 141, 1117-1134 (2010).
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.

Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Mahalingam, D., et al., "Targeting HSP90 for cancer therapy", Br J Cancer 100, 1523-1529 (2009).
Maniaci C, et al. (2017) "Homo-PROTACs: bivalent small-molecule dimerizers of the VHL E3 ubiquitin ligase to induce self-degradation." Nat Commun 8(1):830 1-13.
Mannhold, R., et al., "IAP antagonists: promising candidates for cancer therapy", Drug Discov. Today, 15 (5-6), 210-219 (2010).
Martinez-Iacaci, L., et al, "RAS transformation causes sustained activation of epidermal growth factor receptor and elevation of mitogen-activated protein kinase in human mammary epithelial cells", Int. J. Cancer (2000), 88(1), 44-52.
Martin-Kohler, A. et al ., "Furo [2,3-d] pyrimidines and Oxazolo [5,4-d] pyrimidines as Inhibitors of Receptor Tyrosine Kinases (RTK)", He I vet ica Chimica Act a , 2004, vol. 87, No. 4, pp. 956-975.
Medline Plus Trusted Health Information for You, www.nlm.nih.gov/medlineplus/cancer.html pp. 1-10, (2007).
Min, Jung-hyun, et al., "Structure of an HIV-1-alpha-pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." ACS Chem Biol 12(10):2570-2578.
Ottis, et al., (2017) "Proteolysis-Targeting Chimeras: Induced Protein Degradation as a Therapeutic Strategy." ACS Chem Biol 12(4):892-898.
Park, S. et al., "CGP74514A enhances TRAIL-induced apoptosis in breast cancer cells by reducing X-linked inhibitor of apoptosis protein", Anticancer Research, 2014, vol. 34, pp. 3557-3562.
Perez, HL,"Discovery of potent heterodimeric antagonists of inhibitor of apoptosis proteins (IAPs) with sustained antitumor activity", J. Med. Chem. 58(3), 1556-1562 (2015).
Perez-Torres, M., et al., "Epidermal Growth Factor Receptor (EGFR) Antibody Down-regulates Mutant Receptors and Inhibits Tumors Expressing EGFR Mutations", J Biol Chem 281, 40183-40192 (2006).
Pillay, V., et al., "The Plasticity of Oncogene Addiction: Implications for Targeted Therapies Directed to Receptor Tyrosine Kinases[1,2]", Neoplasia 11, 448-458 (2009).

(56) References Cited

OTHER PUBLICATIONS

Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." Curr Opin Chem Biol 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." Angew Chem Int Ed Engl 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157.
Richters, A., et al., "Identification and further development of potent TBK1 inhibitors", ACS Chemical Biology, vol. 10, No. 1, Jan. 16, 2015, pp. 289-298 (2015).
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Sausville, E.A., "Cyclin-dependent kinase modulators studied at the NCI: pre-clinical and clinical studies", Curr. Med. Chem. Anti-Canc Agents 3:47-56 (2003).
Scagliotti, G., et al., "Phase III Multinational, Randomized, Double-Blind, Placebo-Controlled Study of Tivantinib (ARQ 197) Plus Erlotinib Versus Erlotinib Alone in Previously Treated Patients With Locally Advanced or Metastatic Nonsquamous Non-Small-Cell Lung Cancer", Journal of Clinical Oncology 33, 2667-2674 (2015).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Sequist, L.V., et al., "Randomized Phase II Study of Erlotinib Plus Tivantinib Versus Erlotinib Plus Placebo in Previously Treated Non-Small-Cell Lung Cancer", Journal of Clinical Oncology 29, 3307-3315 (2011).
Sinha, S. and Corey, S.J., "Implications for Src kinases in hematopoiesis: signal transduction therapeutics", Journal of Hematotherapy and Stem Cell Research 8 (5): 465-480 (1999).
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Solca, F., et al., "Target Binding Properties and Cellular Activity of Afatinib (BIBW 2992), an Irreversible ErbB Family Blocker", J Pharmacol Exp Ther 343, 342-350 (2012).
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur Chromophores v. Complex cyanines".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Stuhlmiller, Timothy J., et al., "Inhibition of Lapatinib-Induced Kinome Reprogramming in ERBB2-Positive Breast Cancer by Targeting BET Family Bromodomains", Cell Reports 11, 390-404 (2015).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Takeuchi, et al., "Receptor Tyrosine Kinases and Targeted Cancer Therapeutics", Biol Pharm Bull 34, 1774-1780 (2011).
Thelemann, A., Petti, F., Griffin, G., Iwata, K., Hunt, T., Settinari, T., Fenyo, D., Gibson, N., and Haley, J.D. (2005). "Phosphotyrosine Signaling Networks in Epidermal Growth Factor Receptor Overexpressing Squamous Carcinoma Cells", Molecular & Cellular Proteomics 4.4, 356-376.
Toure, et al., (2016) "Small-Molecule PROTACS: New Approaches to Protein Degradation." Angew Chem Int Ed Engl 55(6):1966-1973.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vlahos, et al. "A specific inhibitor of phosphatidylinositol 3-kinase, 2-(4-morpholinyl)-8-phenyl-4H-1-benzopyran-4-one (LY294002)", J. Biol. Chem. 269:5241-5248 (1994).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Winter, et al., "Phthalimide Conjugation as a strategy for in vivo target protein degradation", Science, 2015 vol. 348 (6241), pp. 1376-1381 [Pub online: May 21, 2015].
Wood, K., et al., "Prognostic and Predictive Value in KRAS in Non-Small-Cell Lung Cancer: A Review", JAMA Oncol. Jun. 1, 2016;2(6):805-12.
Wurz, R. et al., "Oxopyrido[2,3-d]pyrimidines as covalent L858R/T790M mutant selective epidermal growth factor receptor (EGFR) inhibitors", ACS Medicinal Chemistry Letters 2015, 6, 987-992.
Xie, T., et al., "Pharmacological targeting of the pseudokinase Her3", Nat Chem Biol 10, 1006-1012 (2014).

(56) References Cited

OTHER PUBLICATIONS

Xu, A.M., et al., "Receptor Tyrosine Kinase Coactivation Networks in Cancer", Cancer Research 70, 3857-3860 (2010).

Xu, S. et al., "Design, synthesis and biological evaluation of new molecules inhibiting epidermal growth factor receptor threonine $^{790}$-methionine $^{790}$ mutant", Medicinal Chemistry Communications 2012, 3, 1155-1159.

Xu, T. et al., "C5-substituted pyrido[2,3-d]pyrimidin-7-ones as highly specific kinase inhibitors targeting the clinical resistance-related EGFR$^{T790M}$ mutant", Medicinal Chemistry Communications 2015, 6, 1693-1697.

Yasuda, H., et al., "Structural, Biochemical, and Clinical Characterization of Epidermal Growth Factor Receptor (EGFR) Exon 20 Insertion Mutations in Lung Cancer", Science Translational Medicine 5, 216ra177-216ra177 (2013).

Yewale, C., et al., "Epidermal growth factor receptor targeting in cancer: A review of trends and strategies", Biomaterials 34, 8690-8707 (2013).

Zengerle, et al., "Selective Small Molecule Induced Degradation of the BET Bromodomain Protein BRD4" ACS Chemical Biology, Jun. 2, 2015, vol. 10, pp. 1770-1777.

Zhang B. et al., "Small-molecule MDM2-p53 inhibitors: recent advances", Future Med. Chem. (2015) 7, 631-645.

Zhang, D. et al., "Targeted Degradation of Proteins by Small Molecules: A Novel Tool for Functional Proteomics," comb Chem. High Throughput Screen., 2004, vol. 7, No. 7, pp. 689-697.

Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).

\* cited by examiner

FIG. 2
Table of Exemplary RTK PROTAC compounds.

| Ex. # | Structure | Name | (M+H)+ | H1-NMR | Synthesis |
|---|---|---|---|---|---|
| 1 | 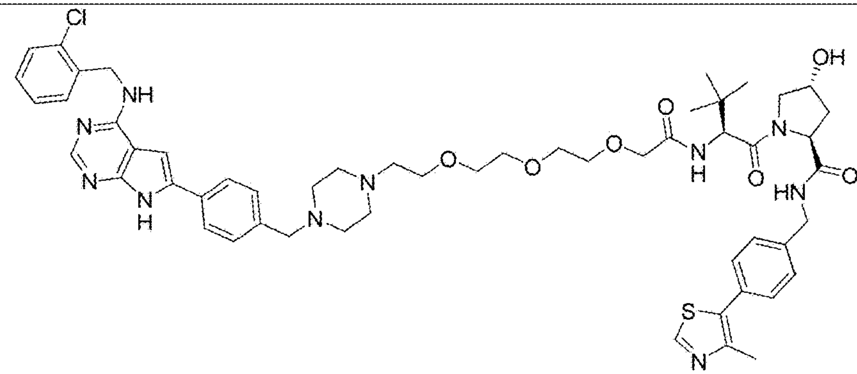 | (2S,4R)-1-((S)-2-(tert-butyl)-14-(4-(4-((2-chlorobenzyl)amino)-7H-pyrrolo[2,3-d]pyrimidin-6-yl)benzyl)piperazin-1-yl)-4-oxo-6,9,12-trioxa-3-azatetradecanoyl)-4-hydroxy-N-(4-(4-methylthiazol-5-yl)benzyl)pyrrolidine-2-carboxamide | 1035.4 1037.4 | (400 MHz, MeOD): δ 8.85 (s, 1H), 8.10 (s, 1H), 7.74 (d, J = 8.0 Hz, 2H), 7.37–7.44 (m, 8H), 7.23–7.25 (m, 2H), 6.92 (s, 1H), 4.69 (s, 1H), 4.48–4.59 (m, 5H), 4.30 (s, 1H), 4.00 (d, J = 5.60 Hz, 2H), 3.87 (d, J = 11.08 Hz, 1H), 3.80 (d, J = 3.80 Hz, 1H), 3.63–3.68 (m, 12H), 2.90 (s, 4H), 2.65 (s, 3H), 2.45 (s, 3H), 2.22 (m, 1H), 2.21 (m, 1H), 1.03 (s, 9H). | Synthesis of example 1 as described |
| 2 | 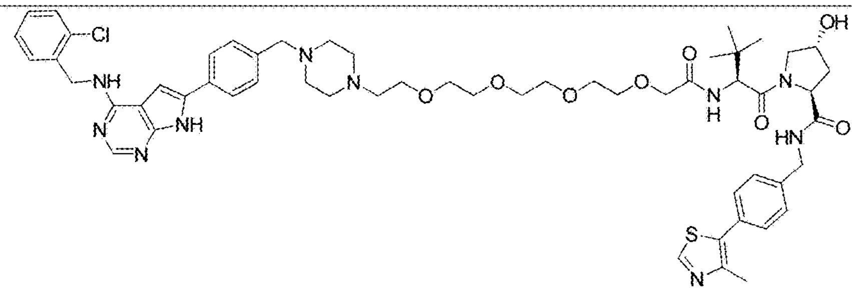 | (2S,4R)-1-((S)-2-(tert-butyl)-17-(4-(4-((2-chlorobenzyl)amino)-7H-pyrrolo[2,3-d]pyrimidin-6-yl)benzyl)piperazin-1-yl)-4-oxo-6,9,12,15-tetraoxa-3-azaheptadecanoyl)-4-hydroxy-N-(4-(4-methylthiazol-5-yl)benzyl)pyrrolidine-2-carboxamide | 1079.5 1081.5 | (400 MHz, MeOD): δ 8.87 (s, 1H), 8.26 (s, 1H), 7.79 (d, J = 8.0 Hz, 2H), 7.52 (d, J = 7.2 Hz, 1H), 7.37–7.80 (m, 9H), 4.67 (s, 1H), 4.53–4.56 (m, 1H), 4.50 (t, J = 4.4 Hz, 1H), 4.38 (s, 1H), 4.01 (d, J = 2.8 Hz, 2H), 3.81 (s, 6H), 3.62 (s, 12H), 3.31 (s, 3H), 2.91 (s, 3H), 2.45 (s, 3H), 2.21 (m, 1H), 2.10 (m, 2H), 1.28 (s, 6H), 1.02 (s, 9H). | following route described for example 1 |

FIG. 2 (continued)

| Ex. # | Structure | Name | (M+H)⁺ | H¹-NMR | Synthesis |
|---|---|---|---|---|---|
| 3 | 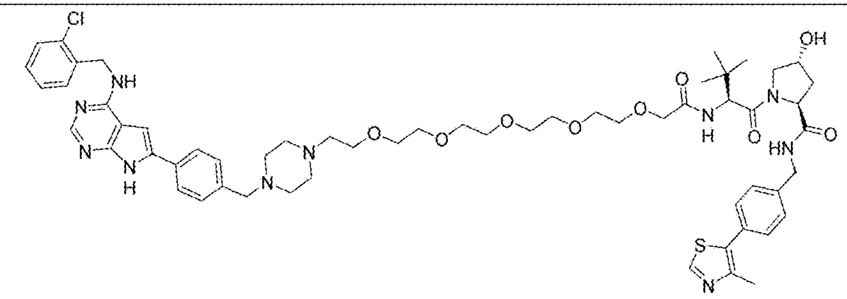 | (2S,4R)-1-((S)-2-(tert-butyl)-20-(4-(4-(4-((2-chlorobenzyl)amino)-7H-pyrrolo[2,3-d]pyrimidin-6-yl)benzyl)piperazin-1-yl)-4-oxo-6,9,12,15,18-pentaoxa-3-azaicosanoyl)-4-hydroxy-N-(4-(4-methylthiazol-5-yl)benzyl)pyrrolidine-2-carboxamide | 1123.5 1125.5 | (400 MHz, CDCl3): δ 8.85 (s, 1H), 8.11 (s, 1H), 7.76 (d, J = 8.0 Hz, 2H), 7.39 (m, 9H), 7.24 (m, 2H), 6.93 (s, 1H), 4.87 (s, 1H), 4.68 (s, 1H), 4.52 (m, 4H), 4.35 (q, 1H), 4.01 (d, J = 5.6 Hz, 2H), 3.72 (m, 21H), 2.62 (m, 6H), 2.45 (s, 3H), 2.18 (s, 2H), 1.01 (s, 9H). | following route described for example 1 |
| 4 | 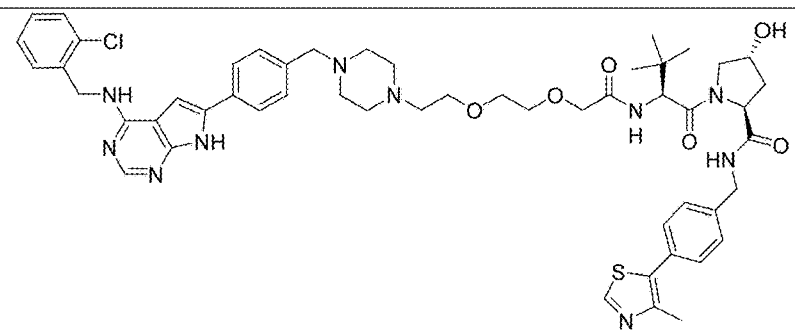 | (2S,4R)-1-((S)-2-(2-(2-(4-(4-(4-((2-chlorobenzyl)amino)-7H-pyrrolo[2,3-d]pyrimidin-6-yl)benzyl)piperazin-1-yl)ethoxy)ethoxy)acetamido)-3,3-dimethylbutanoyl)-4-hydroxy-N-(4-(4-methylthiazol-5-yl)benzyl)pyrrolidine-2-carboxamide | 991.4 993.4 | (400 MHz, CDCl3): δ 8.67 (s, 1H), 8.36 (s, 1H), 7.63 (d, J = 8.4 Hz, 2H). 7.49 (s, 2H), 7.33 (m. 3H), 7.23 (s, 4H), 7.22 (m, 2H), 6.60 (s, 1H), 5.58 (s, 1H), 4.98 (d, J = 6.0 Hz, 1H), 4.76 (t, J = 8.0 Hz, 1H), 4.57 (d, J = 6.4 Hz, 1H), 4.33 (q, 1H), 3.90-4.06 (m, 2H), 3.66 (m, 9H), 2.74 (s, 9H), 2.48 (s, 4H), 2.25 (s. 5H), 0.95 (s, 9H). | following route described for example 1 |

FIG. 2 (continued)

| Ex. # | Structure | Name | (M+H)+ | H¹-NMR | Synthesis |
|---|---|---|---|---|---|
| 5 | 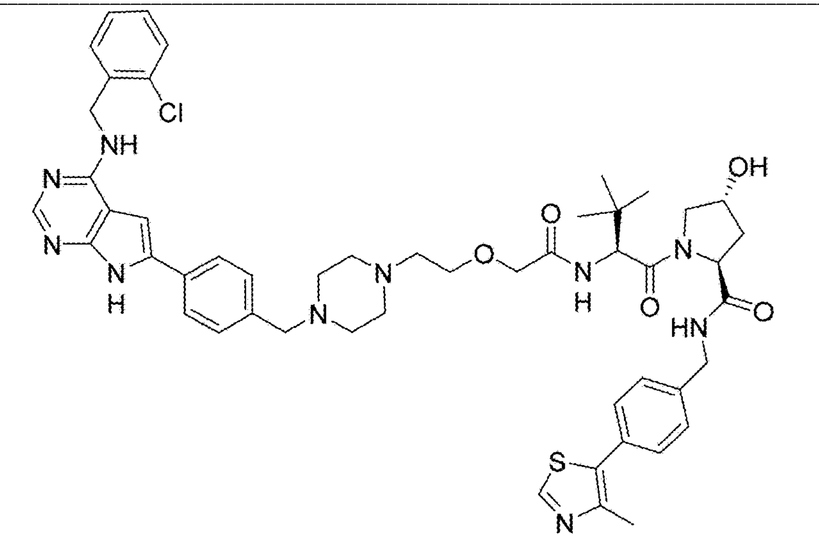 | (2S,4R)-1-((S)-2-(2-(2-(4-(4-(4-((2-chlorobenzyl)amino)-7H-pyrrolo[2,3-d]pyrimidin-6-yl)benzyl)piperazin-1-yl)ethoxy)acetamido)-3,3-dimethylbutanoyl)-4-hydroxy-N-(4-(4-methylthiazol-5-yl)benzyl)pyrrolidine-2-carboxamide | 947.4 949.4 | (400 MHz, CDCl3): δ 8.67 (s, 1H), 8.37 (s, 1H), 7.64 (d, J = 8.0 Hz, 2H), 7.49 (m, 1H), 7.31 (m, 9H), 6.59 (s, 1H), 5.65 (m, 1H), 4.98 (d, J = 8.0 Hz, 2H), 4.73 (m, 1H), 4.52 (m, 3H), 4.49 (m, 1H), 3.96 (m, 3H), 3.61 (m, 5H), 2.58 (m, 14H), 2.23 (m, 1H), 0.90 (s, 9H). | following route described for example 1 |
| 6 | 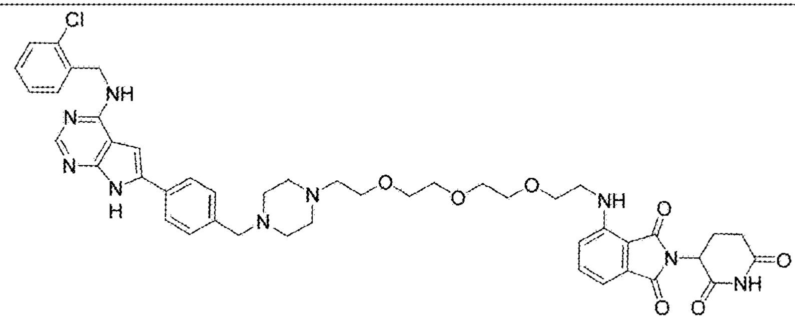 | 4-((2-(2-(2-(2-(4-(4-((2-chlorobenzyl)amino)-7H-pyrrolo[2,3-d]pyrimidin-6-yl)benzyl)piperazin-1-yl)ethoxy)ethoxy)ethoxy)ethyl)amino)-2-(2,6-dioxopiperidin-3-yl)isoindoline-1,3-dione | 864.3 866.3 | (400 MHz, CDCl3): δ 11.72 (s, 1H), 8.38 (s, 1H), 7.63–7.61 (m, 2H), 7.51–7.39 (m, 3H), 7.35–7.31 (m, 2H), 7.24–7.21 (m, 2H), 7.08–7.06 (m, 1H), 6.88–6.86 (m, 1H), 6.60 (s, 1H), 6.44 (s, 1H), 5.79 (s, 1H), 4.98–4.90 (m, 3H), 3.71–3.54 (m, 18H), 3.40–3.39 (m, 2H), 2.86–2.63 (m, 13H), 2.11–2.10 (m, 1H). | following route described for example 8 |

FIG. 2 (continued)

| Ex. # | Structure | Name | (M+H)⁺ | H¹-NMR | Synthesis |
|---|---|---|---|---|---|
| 7 | 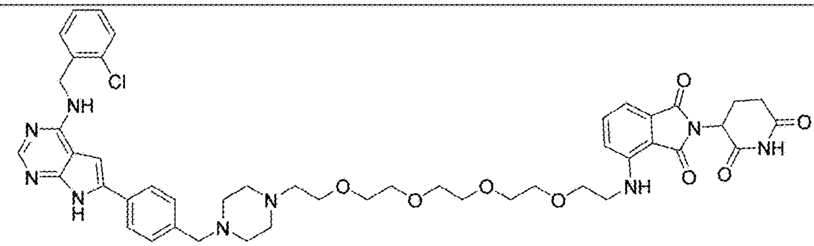 | 4-((14-(4-(4-(4-((2-chlorobenzyl)amino)-7H-pyrrolo[2,3-d]pyrimidin-6-yl)benzyl)piperazin-1-yl)-3,6,9,12-tetraoxatetradecyl)amino)-2-(2,6-dioxopiperidin-3-yl)isoindoline-1,3-dione | 908.3 910.3 | (400 MHz, MeOD): δ 8.10 (s, 1H), 7.74 (d, J = 8.0 Hz, 2H), 7.46–7.48 (m, 1H), 7.41–7.43 (m, 4H), 7.23–7.25 (m, 2H), 7.00 (t, J = 8.0 Hz, 1H), 6.90 (s, 1H), 5.02–5.04 (m, 1H), 5.00 (s, 2H), 4.54 (s, 4H), 3.60–3.68 (m, 18H), 3.41 (t, J = 5.2 Hz, 1H), 2.64–2.88 (m, 8H), 2.08–2.10 (m, 1H) | following route described for example 8 |
| 8 | 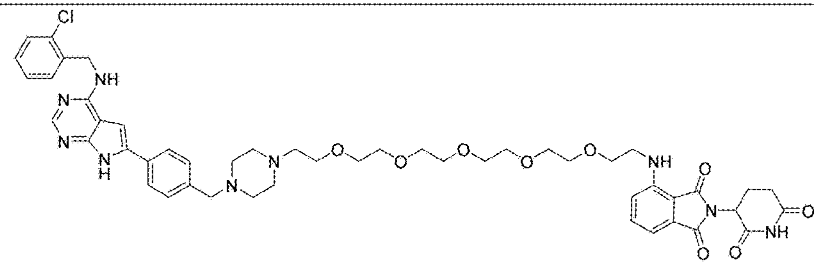 | 4-((17-(4-(4-(4-((2-chlorobenzyl)amino)-7H-pyrrolo[2,3-d]pyrimidin-6-yl)benzyl)piperazin-1-yl)-3,6,9,12,15-pentaoxaheptadecyl)amino)-2-(2,6-dioxopiperidin-3-yl)isoindoline-1,3-dione | 952.3 954.3 | (400 MHz, CD3OD): δ 8.26 (s, 1H), 7.77 (d, J = 7.6 Hz, 2H), 7.47–7.51 (m, 5H), 7.36–7.39 (m, 2H), 7.15 (s, 1H), 6.99–7.02 (m, 2H), 5.00–5.04 (m, 1H), 4.93 (s, 2H), 3.81 (s, 4H), 3.42–3.69 (m, 24H), 2.69–3.00 (m, 8H), 2.03–2.09 (m, 1H), 1.25–1.32 (m, 1H). | Synthesis of example 8 as described |
| 9 | 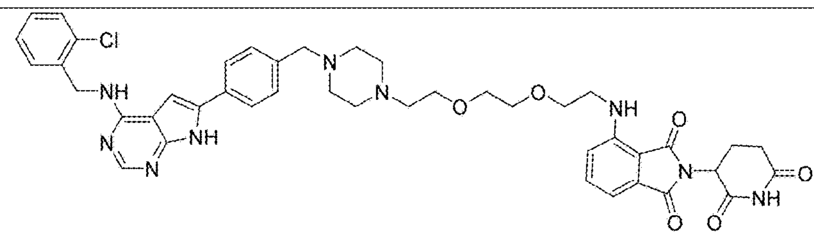 | 4-((2-(2-(2-(4-(4-(4-((2-chlorobenzyl)amino)-7H-pyrrolo[2,3-d]pyrimidin-6-yl)benzyl)piperazin-1-yl)ethoxy)ethoxy)ethyl)amino)-2-(2,6-dioxopiperidin-3-yl)isoindoline-1,3- | 820.3 822.3 | (400 MHz, MeOD): δ 8.11 (s, 1H), 7.73 (d, J = 8.4 Hz, 2H), 7.52–7.50 (m, 1H), 7.48–7.36 (m, 4H), 7.26–7.24 (m, 2H), 7.06–7.01 (m, 2H), 6.92 (s, 1H), 5.06–5.02 (m, 1H), 4.88 (s, 2H), 4.81–4.78 (m, 4H), 3.77–3.64 (m, 10H), 3.49–3.47 (m, 2H), 3.07 (s, 4H), | following route described for example 8 |

FIG. 2 (continued)

| Ex. # | Structure | Name | (M+H)+ | H1-NMR | Synthesis |
|---|---|---|---|---|---|
| 10 | 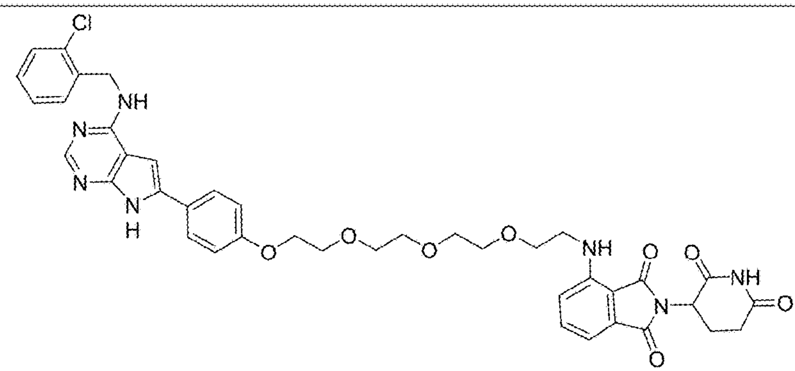 | y1)isoindoline-1,3-dione 4-((2-(2-(2-(2-(4-(4-((2-chlorobenzyl)amino)-7H-pyrrolo[2,3-d]pyrimidin-6-yl)phenoxy)ethoxy)ethoxy)ethoxy)ethyl)amino)-2-(2,6-dioxopiperidin-3-yl)isoindoline-1,3-dione | 782.2 784.2 | 2.81–2.65 (m, 5H), 2.15–2.08 (m, 1H) (400 MHz, CDCl3): δ 11.38 (br, 1H), 10.29 (s, 1H), 8.34 (s, 1H), 7.49–7.53 (m, 3H), 7.39–7.44 (m, 2H), 7.22–7.24 (m, 2H), 7.05 (d, J = 7.2 Hz, 1H), 6.95 (d, J = 8.4 Hz, 1H), 6.88 (d, J = 8.8 Hz, 2H), 6.47 (s, 1H), 6.39–6.42 (m, 3H), 4.95–4.98 (m, 3H), 4.12 (t, J = 5.2 Hz, 2H), 3.85 (t, J = 5.2 Hz, 2H), 3.67–3.73 (m, 10H), 3.42–3.46 (m, 2H), 2.65–2.91 (m, 3H), 2.09–2.15 (m, 2H) | Synthesis of example 10 as described |
| 11 | 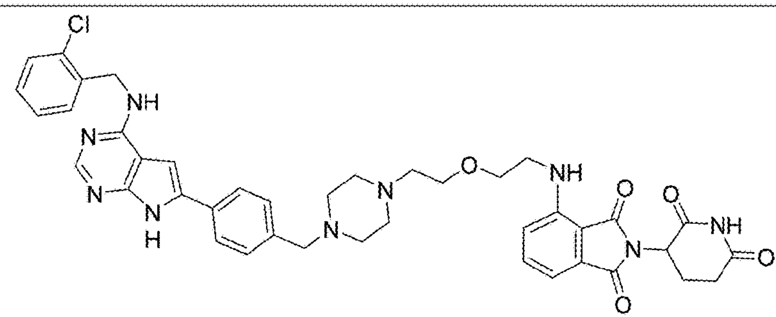 | 4-((2-(4-(4-(4-((2-chlorobenzyl)amino)-7H-pyrrolo[2,3-d]pyrimidin-6-yl)benzyl)piperazin-1-yl)ethoxy)ethyl)amino)-2-(2,6-dioxopiperidin-3-yl)isoindoline-1,3-dione | 776.2 778.2 | (400 MHz, CDCl3): δ 8.35 (s, 1H), 7.52-7.48 (m, 4H), 7.42-7.39 (m, 1H), 7.33-7.31 (m, 2H), 7.24-7.22 (m, 2H), 7.11 (d, J = 6.8 Hz, 2H), 6.97 (d, J = 8.8 Hz, 1H), 6.55 (s, 1H), 6.48 (s, 1H), 4.97 (s, 2H), 4.92-4.88 (m, 2H), 3.48 (s, 2H), 3.68 (s, 4H), 3.50-3.46 (m, 2H), 3.00- | following route described for example 8 |

FIG. 2 (continued)

| Ex. # | Structure | Name | (M+H)+ | H1-NMR | Synthesis |
|---|---|---|---|---|---|
| 12 | 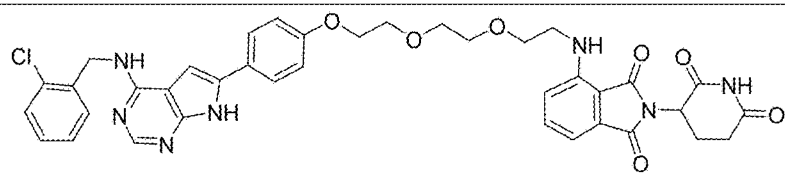 | 4-((2-(2-(2-(4-(4-((2-chlorobenzyl)amino)-7H-pyrrolo[2,3-d]pyrimidin-6-yl)phenoxy)ethoxy)ethoxy)ethyl)amino)-2-(2,6-dioxopiperidin-3-yl)isoindoline-1,3-dione | 738.2 740.2 | (400 MHz, MeOD): δ 8.08 (s, 1H), 7.63(d, J = 8.8Hz, 2H), 7.41—7.42 (m, 3H), 7.24-7.26 (m, 2H), 6.96—7.04 (m, 4H), 6.75 (s, 1H), 5.02—5.15 (m, 1H), 4.88 (s, 4H), 4.15 (t, J = 4.8Hz, 2H), 3.86 (t, J = 4.8Hz, 2H), 3.69—3.74 (m, 4H), 3.45 (t, J = 5.2Hz, 2H), 2.65—2.82 (m, 3H), 2.19—2.22 (m, 1H), 2.02—2.04 (m, 3H), 1.29—1.33 (m, 1H). 2.68 (m, 14H), 2.11(br, 2H). | following route described for example 10 |
| 13 | 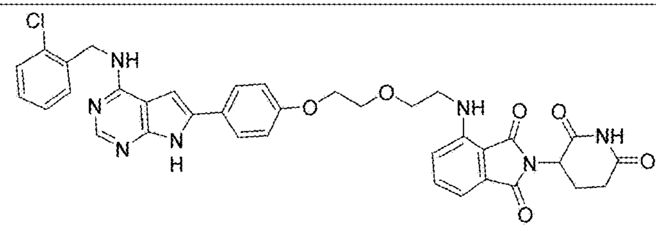 | 4-((2-(2-(4-(4-((2-chlorobenzyl)amino)-7H-pyrrolo[2,3-d]pyrimidin-6-yl)phenoxy)ethoxy)ethyl)amino)-2-(2,6-dioxopiperidin-3-yl)isoindoline-1,3-dione | 694.1 696.1 | (400 MHz, CDCl3): δ 11.55 (br, 1H), 10.50 (br, 1H), 8.37 (s, 1H), 7.35—7.60 (m, 5H), 7.21—7.26(m, 2H), 7.09 (d, J = 7.2 Hz, 1H), 6.95 (m, 3H), 6.54 (m, 1H), 6.45 (s, 1H), 5.85 (br, 1H), 4.96 (m, 3H), 4.20 (t, J = 4.4 Hz, 2H), 4.80 (m, 5H), 3.49 (m, 2H), 2.80 (m, 4H), 2.10 (m, 2H). | following route described for example 10 |

FIG. 2 (continued)

| Ex. # | Structure | Name | (M+H)+ | H1-NMR | Synthesis |
|---|---|---|---|---|---|
| 14 | 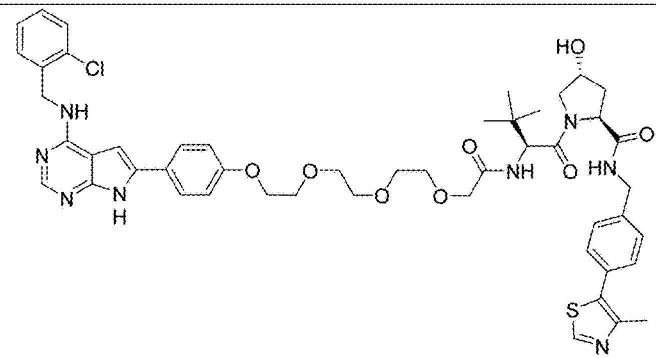 | (2S,4R)-1-((S)-2-(tert-butyl)-14-(4-(4-((2-chlorobenzyl)amino)-7H-pyrrolo[2,3-d]pyrimidin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide | 953.3 955.3 | (400 MHz, MeOD): δ 8.84 (s, 1H), 8.09 (s, 1H), 7.69 (d, J = 8.4 Hz, 2H), 7.37–7.44 (m, 6H), 7.24–7.26 (m, 2H), 7.00 (d, J = 8.8 Hz, 2H), 6.79 (s, 1H), 4.02–4.70 (m, 10H), 3.70–3.88 (m, 12H), 2.45 (s, 3H), 2.15–2.42 (m, 2H), 1.05 (s, 9H). | Synthesis of example 14 as described |
| 15 | 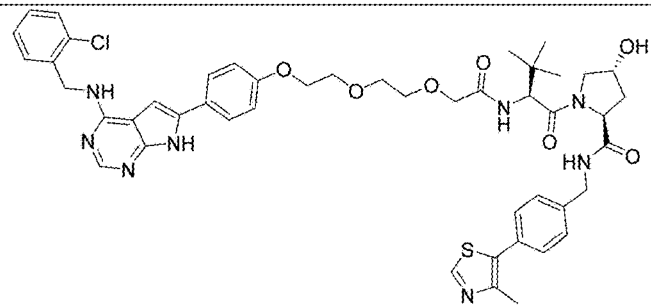 | (2S,4R)-1-((S)-2-(2-(2-(4-(4-(4-((2-chlorobenzyl)amino)-7H-pyrrolo[2,3-d]pyrimidin-6-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide | 909.3 911.3 | (400 MHz, MeOD): δ 8.82 (s, 1H), 8.09 (s, 1H), 7.66–7.68 (m, 3H), 7.35–7.44 (m, 5H), 7.24–7.26 (m, 2H), 6.99–7.01 (d, J = 8.0 Hz, 2H), 6.78 (s, 1H), 4.71–4.73 (d, J = 8.0 Hz, 1H), 4.50–4.60 (m, 6H), 4.35 (d, J = 8.0 Hz, 1H), 4.22 (t, J = 4.0 Hz, 2H), 4.06–4.07 (m, 2H), 3.76–3.93 (m, 9H), 2.43 (s, 3H), 2.23–2.27 (m, 1H), 2.08–2.17 (m, 1H), 1.05 (s, 9H). | following route described for example 14 |

FIG. 2 (continued)

| Ex. # | Structure | Name | (M+H)+ | H1-NMR | Synthesis |
|---|---|---|---|---|---|
| 16 | 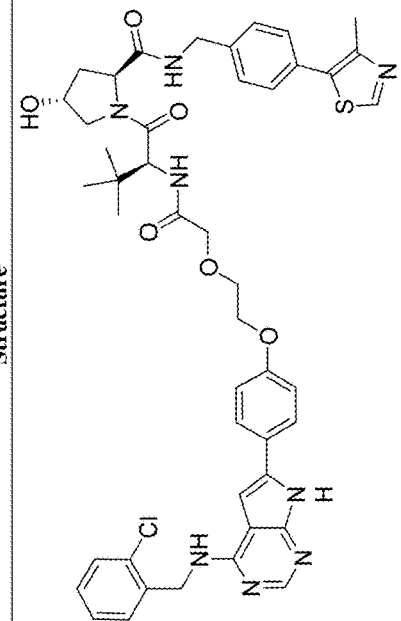 | (2S,4R)-1-((S)-2-(2-(2-(4-(4-((2-chlorobenzyl)amino)-7H-pyrrolo[2,3-d]pyrimidin-6-yl)phenoxy)ethoxy)acetamido)-3,3-dimethylbutanoyl)-4-hydroxy-N-(4-(4-methylthiazol-5-yl)benzyl)pyrrolidine-2-carboxamide | 865.2 867.2 | (400 MHz, DMSO-d6): δ 11.97 (s, 1H), 8.92 (s, 1H), 8.58–8.62 (m, 1H), 8.08 (s, 1H), 7.69–7.94 (m, 1H), 7.47 (d, J = 4.8 Hz, 2H), 7.36–7.46 (m, 8H), 7.26–7.29 (m, 2H), 7.07 (d, J = 4.8 Hz, 2H), 6.85 (s, 1H), 5.15 (d, J = 3.6 Hz, 1H), 4.78 (d, J = 9.6 Hz, 2H), 4.60 (d, J = 9.6 Hz, 1H), 3.86–4.45 (m, 11H), 2.40 (s, 3H), 1.87–2.15 (m, 2H), 0.95 (s, 9H). | following route described for example 14 |
| 17 | 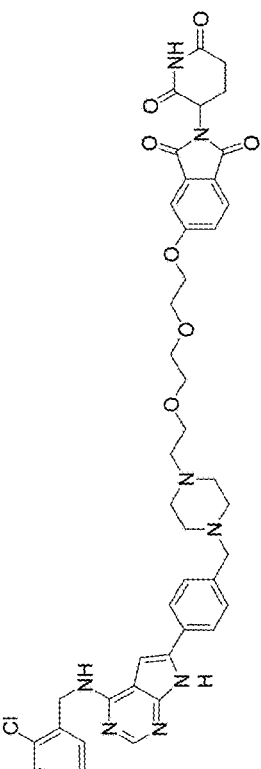 | 5-(2-(2-(2-(4-(4-(4-((2-chlorobenzyl)amino)-7H-pyrrolo[2,3-d]pyrimidin-6-yl)benzyl)piperazin-1-yl)ethoxy)ethoxy)ethoxy)-2-(2,6-dioxopiperidin-3-yl)isoindoline-1,3-dione | 821.3 823.3 | (400 MHz, DMSO-d6): δ 12.09 (s, 1H), 11.14 (s, 1H), 8.06-8.11 (m, 2H), 7.74-7.85 (m, 3H), 7.30-7.46 (m, 8H), 7.01 (s, 1H), 5.13 (d, J = 7.6 Hz, 1H), 4.79 (d, J = 4.4 Hz, 2H), 4.43 (s, 2H), 3.79 (s, 2H), 3.38-3.59 (m, 10H), 2.06-2.62 (m, 10H), 1.91 (s, 2H). | Synthesis of example 17 as described |

FIG. 2 (continued)

| Ex. # | Structure | Name | (M+H)⁺ | H¹-NMR | Synthesis |
|---|---|---|---|---|---|
| 18 | 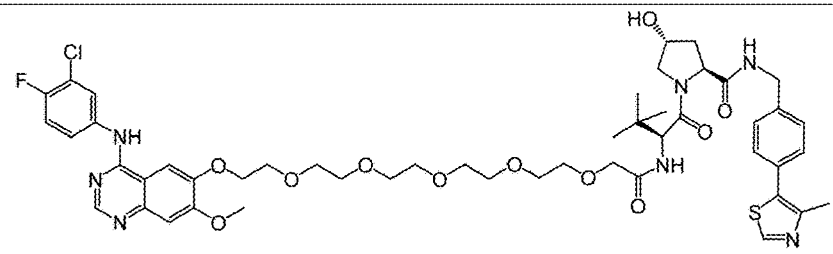 | (2S,4R)-1-((S)-2-(tert-butyl)-20-((3-chloro-4-fluorophenyl)amino)-7-methoxyquinazolin-6-yl)oxy)-4-oxo-6,9,12,15,18-pentaoxa-3-azaicosanoyl)-4-hydroxy-N-(4-(4-methylthiazol-5-yl)benzyl)pyrrolidine-2-carboxamide | 1010.5 1012.5 | (CD3OD, ppm): δ = 8.89(s, 1H), 8.46(s, 1H), 8.02-7.99(dd, J=4.0 Hz, 5.6Hz, 1H), 7.75 (s, 1H), 7.69-7.65 (m, 1H), 7.41-7.18(m, 6H), 4.87(s, 1H), 4.68-4.49 (m, 3H), 4.36-4.31(m, 3H), 4.10(m, 9H), 3.80-3.73 (m, 3H), 3.68-3.60(m, 13H), 3.30 (s, 3H), 2.47-2.21(m, 1H), 2.11-2.07(m, 1H), 1.56-1.54(m, 1H), 1.29 (s,1H), 1.02-1.00 (t, J=8.8Hz, 9H). | Synthesis described in detail |
| 19 | 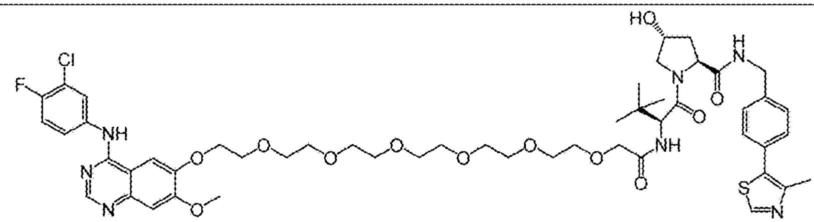 | (2S,4R)-1-((S)-2-(tert-butyl)-23-((3-chloro-4-fluorophenyl)amino)-7-methoxyquinazolin-6-yl)oxy)-4-oxo-6,9,12,15,18,21-hexaoxa-3-azatricosanoyl)-4-hydroxy-N-(4-(4-methylthiazol-5-yl)benzyl)pyrrolidine-2-carboxamide | 1054.5 1056.5 | (CD3OD, ppm): δ = 8.88(s, 1H), 8.712(s, 1H). 8.19-7.81(m, 2H), 7.76-7.61(m, 1H), 7.59-7.31 (m, 5H), 7.23-7.13 (s, 1H), 4.62-4.45(m, 4H), 4.42-4.36(m, 3H), 3.93-4.11 (m, 7H), 3.91-3.56 (m, 23H), 2.56-2.43 (s, 3H) 2.41-2.18 (m, 1H) 2.16-2.03 (m, 1H) 1.03-1.01 (m, 1H). | following routes described for examples 18 and 39 |

FIG. 2 (continued)

| Ex. # | Structure | Name | (M+H)+ | H¹-NMR | Synthesis |
|---|---|---|---|---|---|
| 20 | 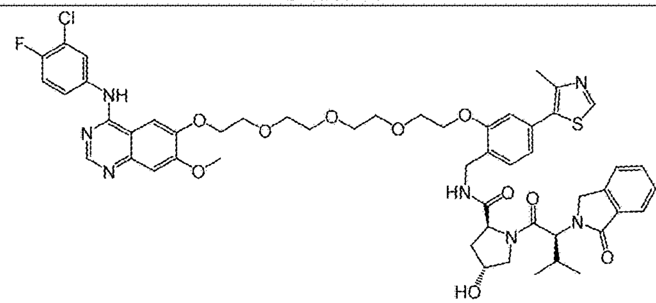 | (2S,4R)-N-(2-(2-(2-(2-(4-((3-chloro-4-fluorophenyl)amino)-7-methoxyquinazolin-6-yl)oxy)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1026.4 1028.4 | (400 MHz, CD3OD): δ 8.81(s, 1H), 8.60(s, 1H), 7.81-7.80(m, 2H), 7.79-7.78(d, J=4Hz, 1H), 7.67-7.39(m, 5H), 7.27-7.24(m, 2H), 7.09(s, 1H), 6.88-6.84(m, 2H), 4.79-4.72(m, 1H), 4.49-3.76(m, 18H), 3.62-3.58(m, 8H), 2.45(s, 3H), 2.34-2.34(m, 1H), 2.19-1.90(d, 2H), 0.94(d, 3H), 0.72(d, 3H) | following routes described for examples 18 and 256 |
| 21 | 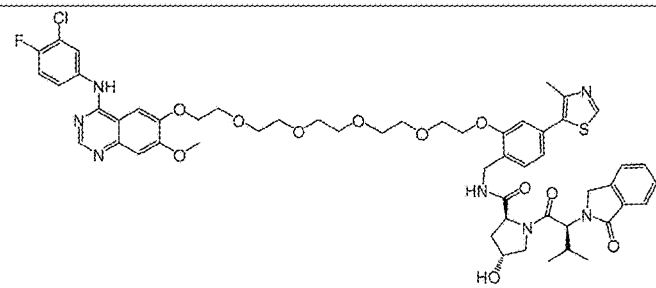 | (2S,4R)-N-(2-((14-((3-chloro-4-fluorophenyl)amino)-7-methoxyquinazolin-6-yl)oxy)-3,6,9,12-tetraoxatetradecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1070.5 1072.5 | (300 MHz, CD3OD): δ = 8.91 (s, 1H), 8.72 (s, 1H), 7.93-7.91(m, 2H), 7.90-7.89(m, 1H), 7.76-7.58(m, 4H), 7.39-7.35(m, 2H), 7.22 (s, 1H), 6.99-6.97(m, 2H), 4.88(m, 1H), 4.67-4.39 (m, 10H), 4.17-3.89 (m, 11H), 3.78-3.64 (m, 12H), 2.45 (s, 3H), 2.45-2.00 (m, 3H), 1.05-1.03 (m, 3H), 0.83-0.81(m, 3H). | following routes described for examples 18 and 256 |

FIG. 2 (continued)

| Ex. # | Structure | Name | (M+H)+ | H¹-NMR | Synthesis |
|---|---|---|---|---|---|
| 22 |  | (2S,4R)-N-(2-((17-((4-((3-chloro-4-fluorophenyl)amino)-7-methoxyquinazolin-6-yl)oxy)-3,6,9,12,15-pentaoxaheptadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1114.5 1116.5 | (400 MHz, CD3OD): δ = 8.91 (s, 1H), 8.73 (s, 1H), 7.95-7.94(m, 2H), 7.80-7.78(m, 1H), 7.63-7.59(m, 3H), 7.42-7.40(m, 1H), 7.39-7.27 (m, 2H), 7.23(s, 1H), 7.02-7.00(m, 2H), 4.90-4.87 (m, 1H), 4.84-4.19 (m, 10H), 4.00 (s, 3H), 3.97-3.88 (m, 6H), 3.78-3.58 (m, 17H), 2.49 (s, 3H), 2.40-2.39 (m, 1H), 2.26-2.20(m, 1H), 2.10-2.05(m, 1H), 1.04-1.04 (m. 3H), 0.84-0.84(m. 3H). | following routes described for examples 18 and 256 |
| 23 |  | (2S,4R)-N-(2-((15-((4-((3-chloro-4-fluorophenyl)amino)-7-methoxyquinazolin-6-yl)oxy)-3,6,10,13-tetraoxapentadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1084.5 1086.5 | (CD3OD, ppm): δ8.76 (1H, s), 8.37 (1H, s), 6.90-7.68 (12H, s), 3.39-4.78 (32H, m), 2.37 (3H,s), 1.90-2.35 (3H, m). 1.64-1.67 (2H, m), 0.93 (3H, d, J = 6.4Hz), 0.71 (3H, d, J = 6.8Hz). | following routes described for examples 18 and 256 |

FIG. 2 (continued)

| Ex. # | Structure | Name | (M+H)+ | H1-NMR | Synthesis |
|---|---|---|---|---|---|
| 24 | 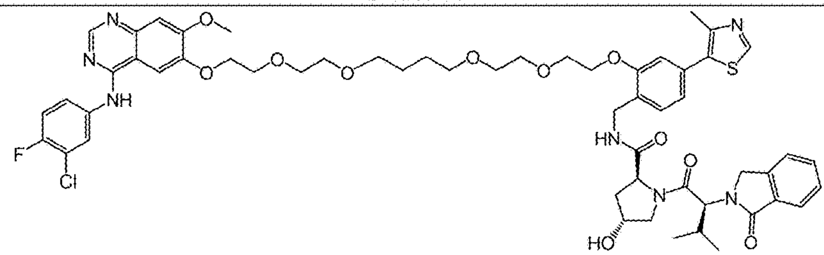 | (2S,4R)-N-(2-((16-(((4-((3-chloro-4-fluorophenyl)amino)-7-methoxyquinazolin-6-yl)oxy)-3,6,11,14-tetraoxahexadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1098.5 1100.5 | (CD3OD, ppm): δ 8.75 (1H, s), 8.34 (1H, s), 6.87-7.90 (12H, s), 3.30-4.85 (32H, m), 2.37 (3H, s), 1.90-2.35 (3H, m), 1.46 (4H, s), 0.93 (3H, d, J = 8.6Hz), 0.72 (3H, d, J = 8.6Hz). | following routes described for examples 18 and 256 |
| 25 | 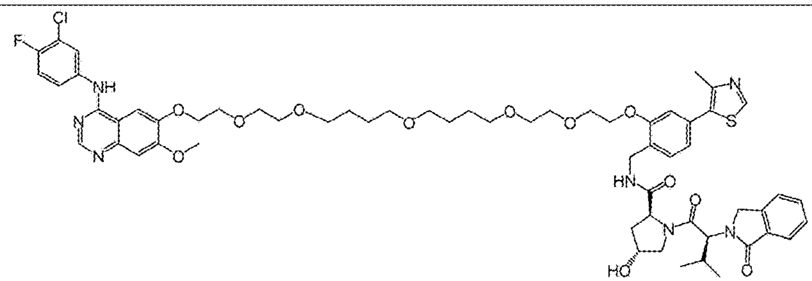 | (2S,4R)-N-(2-((21-(((4-((3-chloro-4-fluorophenyl)amino)-7-methoxyquinazolin-6-yl)oxy)-3,6,11,16,19-pentaoxahenicosyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1170.6 1172.6 | (CD3OD, ppm): δ 8.75 (1H, s), 8.33 (1H, s), 6.90-7.90 (12H, s), 3.21-4.77 (36H, m), 2.38 (3H, s), 1.90-2.37 (3H, m), 1.41-1.46 (8H, m), 0.93 (3H, d, J = 6.4Hz), 0.72 (3H, d, J = 6.4Hz). | following routes described for examples 18 and 256 |

FIG. 2 (continued)

| Ex. # | Structure | Name | (M+H)+ | H1-NMR | Synthesis |
|---|---|---|---|---|---|
| 26 | 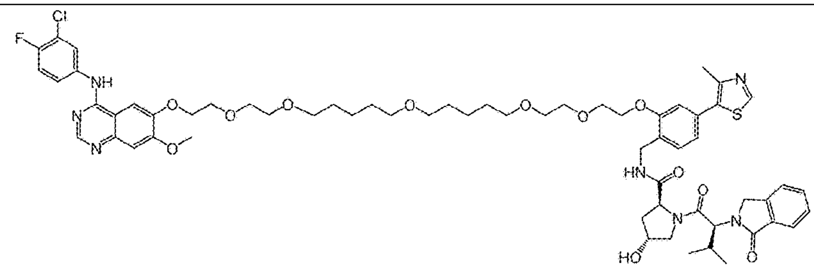 | (2S,4R)-N-(2-((23-((4-((3-chloro-4-fluorophenyl)amino)-7-methoxyquinazolin-6-yl)oxy)-3,6,12,18,21-pentaoxatricosyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1198.6 1200.6 | (CD3OD, ppm): δ8.75 (1H, s), 8.33 (1H, s), 6.90-7.90 (12H, m), 3.20-4.75 (36H, m), 2.38 (3H, s), 1.90-2.37 (3H, m), 1.31-1.50 (8H, m), 1.20-1.35 (4H, m), 0.93 (3H, d, J = 6.8Hz), 0.72 (3H, d, J = 6.8Hz). | following routes described for examples 18 and 256 |
| 27 | 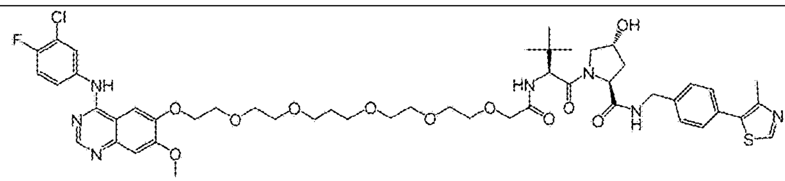 | (2S,4R)-1-((S)-2-(tert-butyl)-21-((4-((3-chloro-4-fluorophenyl)amino)-7-methoxyquinazolin-6-yl)oxy)-4-oxo-6,9,12,16,19-pentaoxa-3-azahenicosanoyl)-4-hydroxy-N-(4-(4-methylthiazol-5-yl)benzyl)pyrrolidine-2-carboxamide | 1024.4 1026.4 | (CD3OD, ppm): δ8.90 (s, 1H), 8.47 (s, 1H), 8.03 (b, 1H), 7.15-7.80 (m, 8H), 3.50-4.70 (m, 32H), 2.48 (s, 3H), 2.05-2.30 (m, 2H), 1.85-1.90 (m, 2H), 1.03 (s, 9H). | following routes described for examples 18 and 39 |

FIG. 2 (continued)

| Ex. # | Structure | Name | (M+H)+ | H¹-NMR | Synthesis |
|---|---|---|---|---|---|
| 28 | 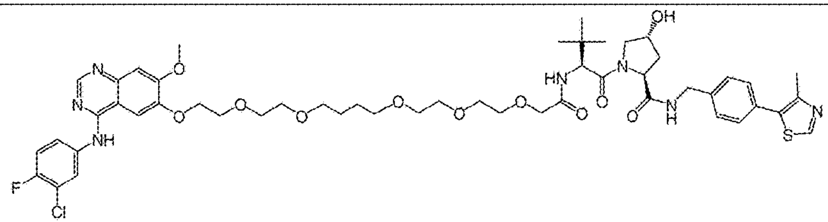 | (2S,4R)-1-((S)-2-(tert-butyl)-22-((4-((3-chloro-4-fluorophenyl)amino)-7-methoxyquinazolin-6-yl)oxy)-4-oxo-6,9,12,17,20-pentaoxa-3-azadocosanoyl)-4-hydroxy-N-(4-(4-methylthiazol-5-yl)benzyl)pyrrolidine-2-carboxamide | 1038.4 1040.4 | (CD3OD, ppm): δ8.41 (1H, s), 8.02 (1H, s), 8.00-8.01 (1H, m), 7.42-7.60 (2H, m), 7.07-7.38 (6H, m), 4.28-4.89 (7H, m), 3.32-4.03 (25H, m), 2.05-2.47 (5H, m), 1.57 (4H, b), 1.04 (9H, m). | following routes described for examples 18 and 39 |
| 29 | 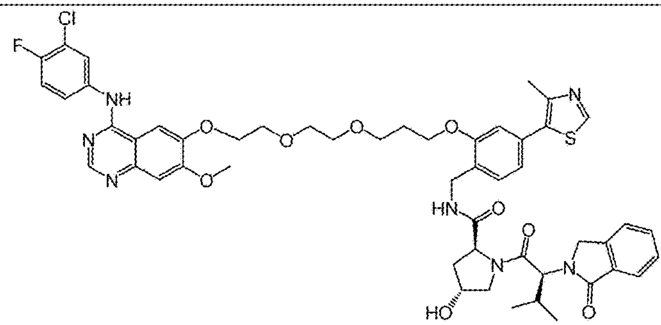 | (2S,4R)-N-(2-(3-(2-(2-((4-((3-chloro-4-fluorophenyl)amino)-7-methoxyquinazolin-6-yl)oxy)ethoxy)ethoxy)propoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 996.4 998.4 | (300 MHz, CD3OD, 25oC): 8.80 (s, 1H), 8.47 (s, 1H), 8.03 (dd, 1H), 7.80 (dd, 1H), 7.62-7.50 (m, 5H), 7.39 (d, 1H), 7.30 (t, 1H), 7.15 (s, 1H), 6.99-6.95 (m, 2H), 4.84-4.81 (m, 1H), 4.60-4.43 (m, 6H), 4.28-4.23 (m, 2H), 4.18 (t, 2H), 3.97-3.85 (m, 7H), 3.79-3.67 (m, 6H), 2.46-2.40 (m, 4H), 2.27-2.06 (m, 4H), 1.07 (d, 3H), 0.85 (d, 3H) | following routes described for examples 18 and 256 |

FIG. 2 (continued)

| Ex. # | Structure | Name | (M+H)+ | H¹-NMR | Synthesis |
|---|---|---|---|---|---|
| 30 | 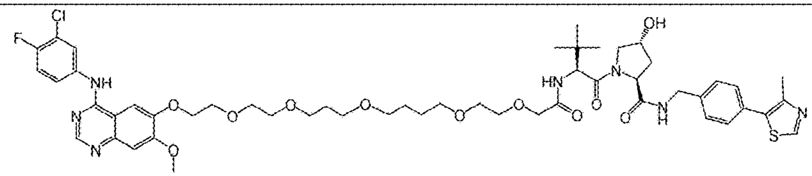 | (2S,4R)-1-((S)-2-(tert-butyl)-23-((4-((3-chloro-4-fluorophenyl)amino)-7-methoxyquinazolin-6-yl)oxy)-4-oxo-6,9,14,18,21-pentaoxa-3-azatricosanoyl)-4-hydroxy-N-(4-(4-methylthiazol-5-yl)benzyl)pyrrolidine-2-carboxamide | 1052.4 1054.4 | (CD3OD, ppm): δ8.90 (s, 1H), 8.46 (s, 1H), 8.03 (m, 1H), 7.15-7.80 (m, 8H). 3.30-4.80 (m, 32H), 2.47 (s, 3H), 2.05-2.30 (m, 2H), 1.30-1.75 (m, 6H), 1.03 (s, 9H). | following routes described for examples 18 and 39 |
| 31 | 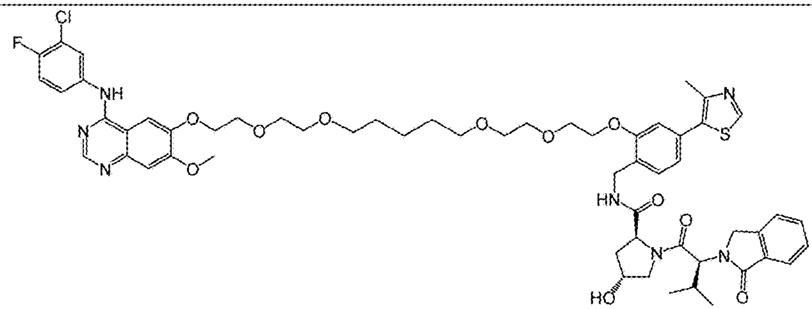 | (2S,4R)-N-(2-((17-((4-((3-chloro-4-fluorophenyl)amino)-7-methoxyquinazolin-6-yl)oxy)-3,6,12,15-tetraoxaheptadecyl)oxy)-4-(4-methylthiazol-5-yl)benzyl)-4-hydroxy-1-((S)-3-methyl-2-(3-methyl-2-(1-oxoisoindolin-2-yl)butanoyl)pyrrolidine-2-carboxamide | 1112.4 1114.4 | (CD3OD, ppm): δ8.75 (1H, s), 8.34 (1H, s), 6.87-7.90 (12H, m), 3.30-4.85 (32H, m), 2.37 (3H, s), 1.37-1.41 (4H, m), 1.20-1.30 (2H, m), 0.93 (3H, d, J = 6.4Hz), 0.72 (3H, d, J = 6.8Hz). | following routes described for examples 18 and 256 |

FIG. 2 (continued)

| Ex. # | Structure | Name | (M+H)+ | H¹-NMR | Synthesis |
|---|---|---|---|---|---|
| 32 | 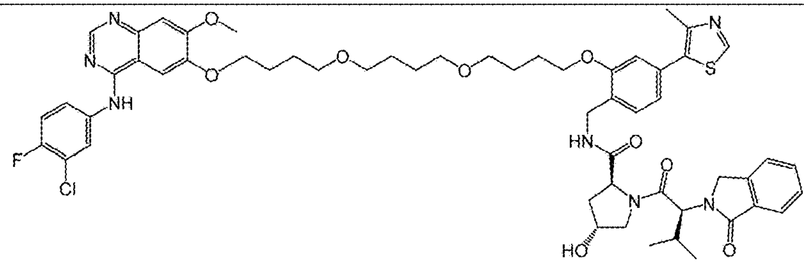 | (2S,4R)-N-(2-(4-(4-(4-((3-chloro-4-fluorophenyl)amino)-7-methoxyquinazolin-6-yl)oxy)butoxy)butox y)butoxy)-4-(4-methylthiazol-5-yl)benzyl)-4-hydroxy-1-((S)-3-methyl-2-(1-oxoisoindolin-2-yl)butanoyl)pyrrolid ine-2-carboxamide | 1066.4 1068.4 | (300 MHz, CDCl3, 25 oC): 8.88 (s, 1H), 8.50 (s, 1H), 7.77 (d, 1H), 7.78-7.86 (m, 2H), 7.51-7.03 (m, 4H), 7.03 (d, 2H), 7.00 (d, 1H), 6.98 (s, 1H), 4.72-4.41 (m, 5H), 4.23-4.33 (m, 2H), 3.88-4.08 (m, 7H), 3.44-3.68 (m, 8H), 2.52 (s, 3H), 2.49-1.72 (m, 11H), 1.62-1.74 (brs, 4H), 1.05 (d, 3H), 0.86 (d, 3H) | following routes described for examples 18 and 256 |
| 33 | 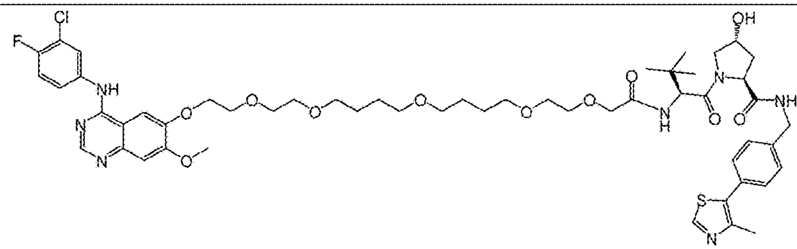 | (2S,4R)-1-((S)-2-(tert-butyl)-24-((4-((3-chloro-4-fluorophenyl)amino)-7-methoxyquinazolin-6-yl)oxy)-4-oxo-6,9,14,19,22-pentaoxa-3-azatetracosanoyl)-4-hydroxy-N-(4-(4-methylthiazol-5-yl)benzyl)pyrrolidin e-2-carboxamide | 1066.5 1068.5 | (CDCl3, ppm): 8.90 (s, 1H), 8.70 (s, 1H), 8.52 (s, 1H), 8.05 (m, 1H), 7.15-7.85 (m, 9H), 3.30-4.85 (m, 32H), 2.49 (s, 3H), 2.10-2.25 (m, 2H), 1.57 (s, 8H), 1.05 (s, 9H) | following routes described for examples 18 and 39 |

FIG. 2 (continued)

| Ex. # | Structure | Name | (M+H)⁺ | H¹-NMR | Synthesis |
|---|---|---|---|---|---|
| 34 | 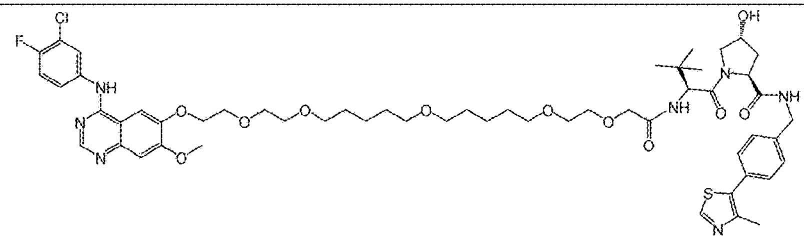 | (2S,4R)-1-((S)-2-(tert-butyl)-26-((4-((3-chloro-4-fluorophenyl)amino)-7-methoxyquinazolin-6-yl)oxy)-4-oxo-6,9,15,21,24-pentaoxa-3-azahexacosanoyl)-4-hydroxy-N-(4-(4-methylthiazol-5-yl)benzyl)pyrrolidine-2-carboxamide | 1094.5 1096.5 | (CD3OD, ppm): 8.90 (s, 1H), 8.70 (s, 1H), 8.51 (s, 1H), 8.05 (m, 1H), 7.19-7.79 (m, 9H), 3.30-4.85 (m, 32H), 2.49 (s, 3H), 2.10-2.25 (m, 2H), 1.34-1.59 (m, 12H), 1.05 (s, 9H). | following routes described for examples 18 and 39 |
| 35 | 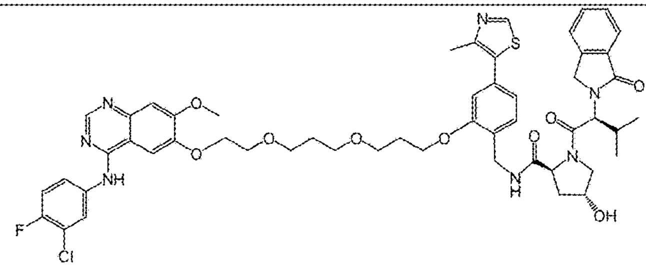 | (2S,4R)-N-(2-(3-(2-(4-((3-chloro-4-fluorophenyl)amino)-7-methoxyquinazolin-6-yl)oxy)ethoxy)propoxy)-4-methylthiazol-5-yl)benzyl)-4-hydroxy-1-((S)-3-methyl-2-(1-oxoisoindolin-2-yl)butanoyl)pyrrolidine-2-carboxamide | 1010.4 1012.4 | (400 MHz, CD3OD, 23oC):δ8.49 (s, 1H), 8.47 (s, 1H), 8.01 (s, 1H), 7.77-7.06 (m, 11H), 4.88-4.43 (m, 7H), 4.02-4.00 (m, 2H), 3.99-3.58 (m, 12H), 2.45-2.43 (m, 4H), 2.39-2.05 (m, 2H), 1.35-1.32 (m, 4H), 1.30-1.28 (m, 3H), 1.20-1.04 (m, 3H), 0.82-0.79 (m, 3H). | following routes described for examples 18 and 256 |

FIG. 2 (continued)

| Ex. # | Structure | Name | (M+H)⁺ | H¹-NMR | Synthesis |
|---|---|---|---|---|---|
| 36 | 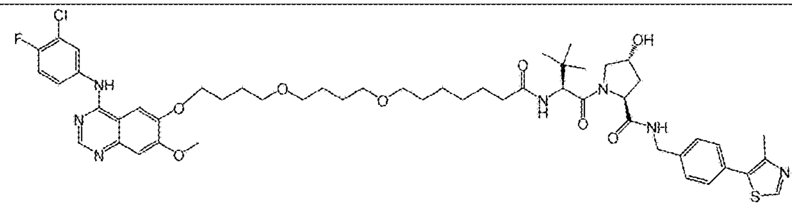 | (2S,4R)-1-((S)-2-(7-(4-(4-((3-chloro-4-fluorophenyl)amino)-7-methoxyquinazolin-6-yl)oxy)butoxy)butoxy)heptanamido)-3,3-dimethylbutanoyl)-4-hydroxy-N-(4-(4-methylthiazol-5-yl)benzyl)pyrrolidine-2-carboxamide | 1004.45 502.73 | (300 MHz, MeOD, 25°C): 8.88 (s, 1H), 8.49 (s, 1H), 7.80-7.99 (m, 1H), 7.98-7.76 (d, 1H), 7.70-7.62 (m, 1H), 7.48-7.41 (m, 4H), 7.32-7.21 (m, 3H), 4.65-4.64 (m, 1H), 4.63-4.56 (m, 2H), 4.56-4.53 (m, 2H), 4.40-4.32 (m, 1H), 4.27-4.23 (m, 2H), 4.04-4.03 (s, 3H), 3.95-3.86 (d, 1H), 3.84-3.78 (m, 1H), 3.59-3.54 (m, 2H), 3.51-3.45 (m, 2H), 3.44-3.39 (m, 3H), 2.48 (s, 3H), 2.29-2.23 (m, 3H), 2.13-2.05 (m, 1H), 2.02-1.98 (m, 2H), 1.85-1.82 (m, 2H), 1.64-1.52 (m, 8H), 1.39-1.29 (m, 4H), 1.05-1.01 (s, 9H). | following routes described for examples 18 and 39 |
| 37 | 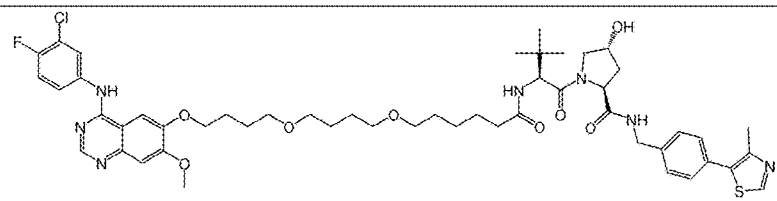 | (2S,4R)-1-((S)-2-(6-(4-(4-((3-chloro-4-fluorophenyl)amino)-7-methoxyquinazolin-6-yl)oxy)butoxy)butoxy)hexanamido)-3,3-dimethylbutanoyl)-4-hydroxy-N-(4-(4-methylthiazol-5- | 990.2 992.4 | (300 MHz, DMSO, 25°C): 9.53 (s, 1H), 8.98 (s, 1H), 8.55-8.49 (m, 2H), 8.13-8.10 (m, 1H), 7.85-7.79 (m, 3H), 7.47-7.36 (m, 5H), 7.21 (s, 1H), 5.11 (d, 1H), 4.55-4.15 (m, 7H), 3.94 (s, 3H), 3.69-3.59 (m, 2H), 3.47-3.23 (m, 8H), 3.44 (s, 3H), 2.29-2.21 (m, 2H), 2.12-2.01 (m, 2H), 1.91-1.83 (m, 2H), 1.75- | following routes described for examples 18 and 39 |

FIG. 2 (continued)

| Ex. # | Structure | Name | (M+H)+ | H1-NMR | Synthesis |
|---|---|---|---|---|---|
| | | yl)benzyl)pyrrolidine-2-carboxamide | | 1.67 (m, 2H), 1.52-1.43 (m, 8H), 1.28-1.24 (m, 2H). 0.93 (s, 9H) | |
| 38 | 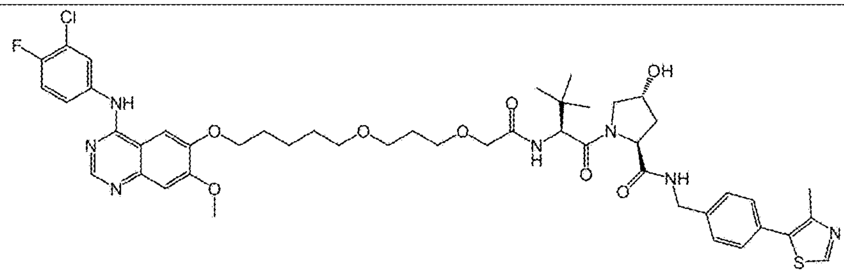 | (2S,4R)-1-((S)-2-(2-(3-((5-((4-((3-chloro-4-fluorophenyl)amino)-7-methoxyquinazolin-6-yl)oxy)pentyl)oxy)propoxy)acetamido)-3,3-dimethylbutanoyl)-4-hydroxy-N-(4-(4-methylthiazol-5-yl)benzyl)pyrrolidine-2-carboxamide | 934.4 936.4 | (400MHz, CD3OD): δ8.86 (s, 1H), 8.46 (s, 1H), 7.99 (m, 1H), 7.72 (s, 1H), 7.69 (m, 1H), 7.59 (m, 1H). 7.45 (m, 4H), 7.29 (m, 1H), 7.18 (s, 1H), 4.72 (m, 1H), 4.59 (m, 3H), 4.38 (m, 1H), 4.20 (m, 2H), 4.02 (m, 5H), 3.86 (m, 2H), 3.67 (m, 2H), 3.61 (m, 2H), 3.54 (m, 2H), 2.48 (s, 3H), 2.29 (m, 1H), 2.14 (m, 1H), 1.94 (m, 4H), 1.73 (m, 4H), 1.19-1.04 (m, 4H), 1.02 (s, 9H) | following routes described for examples 18 and 39 |
| 39 | 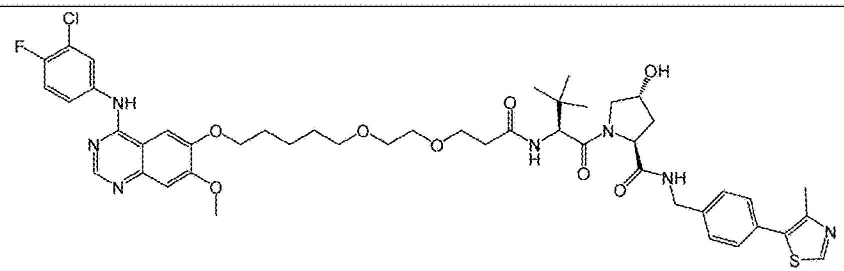 | (2S,4R)-1-((S)-2-(3-(2-((5-((4-((3-chloro-4-fluorophenyl)amino)-7-methoxyquinazolin-6-yl)oxy)pentyl)oxy)ethoxy)propanamido)-3,3-dimethylbutanoyl)-4-hydroxy-N-(4-(4-methylthiazol-5-yl)benzyl)pyrrolidine-2-carboxamide | 934.4 936.4 | (300 MHz, CD3OD, 25 oC): 8.89 (s, 1H), 8.45 (s, 1H), 7.95-8.05 (d, 1H), 7.65-7.74 (m, 2H), 7.36-7.49 (m, 3H), 7.17-7.31 (m, 2H), 4.68-4.34 (m, 5H), 4.15-4.23 (m, 2H), 4.02 (s, 3H), 3.91-3.72 (m, 4H), 3.62 (s, 4H), 3.52-3.54 (m, 2H), 2.58-2.45 (m, 4H), 2.25-1.52 (m, 8H), 1.05 (s, 9H). | Synthesis of example 38 as described |

FIG. 2 (continued)

| Ex. # | Structure | Name | (M+H)+ | H¹-NMR | Synthesis |
|---|---|---|---|---|---|
| 40 | 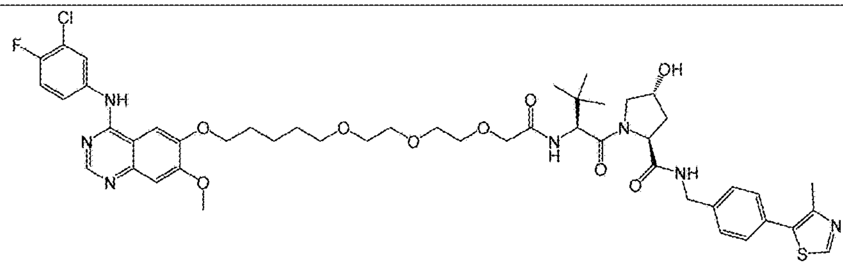 | (2S,4R)-1-((S)-2-(tert-butyl)-17-((4-((3-chloro-4-fluorophenyl)amino)-7-methoxyquinazolin-6-yl)oxy)-4-oxo-6,9,12-trioxa-3-azaheptadecanoyl)-4-hydroxy-N-(4-(4-methylthiazol-5-yl)benzyl)pyrrolidine-2-carboxamide | 964.4 966.4 | (400 MHz, DMSO, 25oC): 9.65 (s, 1H), 8.98 (s, 1H), 8.61 (t, 1H), 8.52 (s, 1H), 8.11 (dd, 1H), 7.82-7.75 (m, 2H), 7.48-7.36 (m, 6H), 7.21 (s, 1H), 5.16 (d, 1H), 4.57 (d, 1H), 4.45-4.21 (m, 4H), 4.14 (t, 2H), 3.96 (d, 5H), 3.65-3.49 (m, 10H), 3.39 (t, 2H), 2.44 (s, 3H), 2.08-1.82 (m, 4H), 1.58-1.46 (m, 4H), 0.93 (s, 9H). | following routes described for examples 18 and 39 |
| 41 | 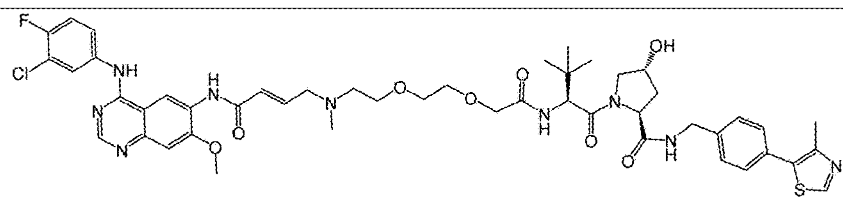 | (2S,4R)-1-((S,E)-2-(tert-butyl)-16-((4-((3-chloro-4-fluorophenyl)amino)-7-methoxyquinazolin-6-yl)amino)-12-methyl-4,16-dioxo-6,9-dioxa-3,12-diazahexadec-14-enoyl)-4-hydroxy-N-(4-(4-methylthiazol-5-yl)benzyl)pyrrolidine-2-carboxamide | 974.4 976.4 | (400 MHz, CD3OD): δ1.04, 1.06 (two singles, 9H), 2.06-2.11 (m, 1H), 2.25-2.30 (m, 1H), 2.44 (s, 3H), 2.83, 2.85 (two singles, 3H), 3.77-4.16 (m, 15H), 4.42-4.63 (m, 4H), 4.76-4.81 (m, 1H), 6.76 (d, J = 15.2 Hz, 1H), 7.04-7.08 (m, 1H), 7.24-7.28 (m, 2H), 7.36-7.40 (m, 4H), 7.67-7.68 (m, 1H), 7.99 (br, 1H), 8.37 (br, 1H), 8.49 (s, 1H), 8.85(s, 1H), 8.93 (s, 1H). | Synthesis of example 41 as described |

FIG. 2 (continued)

| Ex. # | Structure | Name | (M+H)+ | H¹-NMR | Synthesis |
|---|---|---|---|---|---|
| 42 | 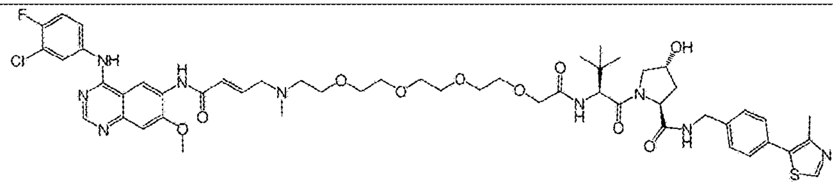 | (E)-N19-(4-((3-chloro-4-fluorophenyl)amino)-7-methoxyquinazolin-6-yl)-N1-((2S,4R)-4-hydroxy-2-((4-(4-methylthiazol-5-yl)benzyl)carbamoyl)pyrrolidin-1-yl)-3,3-dimethyl-1-oxobutan-2-yl)-15-methyl-3,6,9,12-tetraoxa-15-azanonadec-17-enediamide | 1062.4 1064.4 | (400 MHz, CD3OD): δ1.02, 1.05 (two singles, 9H), 2.07-2.12 (m, 1H), 2.22-2.27 (m, 1H), 2.46, 2.47 (two singles, 3H), 2.61, 2.66 (two singles, 3H), 2.97-3.01 (m, 2H), 3.65-3.90 (m, 18H), 4.01-4.09 (m, 5H), 4.32-4.70 (m, 5H), 6.65-6.71 (m, 1H), 7.01-7.08 (m, 1H), 7.23-7.29 (m, 2H), 7.39-7.45 (m, 4H), 7.67-7.71 (m, 1H), 8.02 (dd, J=6.8Hz, 2.8 Hz, 1H), 8.49, 8.50 (two singles, 1H), 8.88, 8.94 (two singles, 2H). | following route described for example 41 |
| 43 | 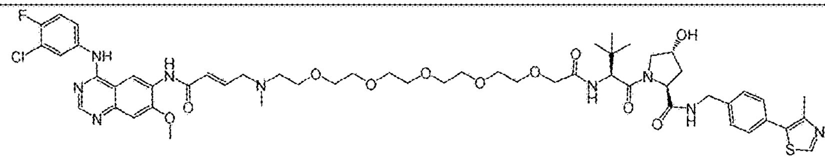 | (E)-N22-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-18-methyl-3,6,9,12,15-pentaoxa-18-azanonadec-20-enediamide | 1106.5 1108.5 | (400 MHz, CD3OD): δ 1.02, 1.05 (two singles, 9H), 2.06-2.12 (m, 1H), 2.22-2.27 (m, 1H), 2.47 (s, 3H), 2.81, 2.85 (two singles, 3H), 3.22-3.24 (m, 2H), 3.65-3.71 (m, 16H), 3.80-3.92 (m, 6H), 4.05-4.09 (m, 5H), 4.32-4.38 (m, 1H), 4.49-4.61 (m, 3H), 4.71 (d, J = 6.4 Hz, 1H), 6.76 (d, J = 15.2 Hz, 1H), 7.00-7.08 (m, 1H), 7.24-7.29 (m, 2H), 7.39-7.45 (m, 4H), 7.67-7.70 | following route described for example 41 |

FIG. 2 (continued)

| Ex. # | Structure | Name | (M+H)+ | H1-NMR | Synthesis |
|---|---|---|---|---|---|
| 44 | 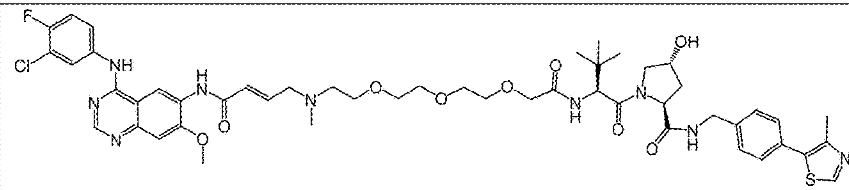 | (E)-N16-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-12-methyl-3,6,9-trioxa-12-azahexadec-14-enediamide | 1018.4 1020.4 | (400 MHz, CD3OD): δ 1.03, 1.05 (two singles, 9H), 2.06-2.12 (m, 1H), 2.23-2.28 (m, 1H), 2.44, 2.46 (two singles, 3H), 2.82, 2.88 (two singles, 3H), 3.26 (s, 2H), 3.72-4.08 (m, 19H), 4.41-4.73 (m, 5H), 6.75 (d, J = 14.8 Hz, 1H), 7.00-7.08 (m, 1H), 7.22-7.27 (m, 2H), 7.37-7.44 (m, 4H), 7.65-7.67 (m, 1H), 8.00 (d, J = 4.4 Hz, 1H), 8.49 (s, 2H), 8.89 (d, J = 15.6 Hz, 2H). (m, 1H), 8.01-8.03 (m, 1H), 8.50 (s, 1H), 8.88-8.95 (m, 2H). | following route described for example 41 |
| 45 | 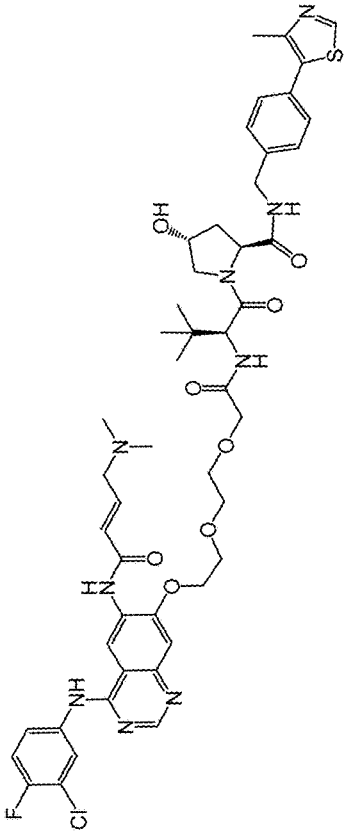 | (2S,4R)-1-((S)-2-(2-(2-(2-((4-((3-chloro-4-fluorophenyl)amino)-6-((E)-4-(dimethylamino)but-2-enamido)quinazolin-7-yl)oxy)ethoxy)ethoxy)acetamido)-3,3-dimethylbutanoyl)-4-hydroxy-N-(4-(4- | 974.4 976.4 | (400 MHz, CD3OD): δ 0.88, 0.92 (two singles, 9H), 1.98-2.16 (m, 3H), 2.30 (s, 3H), 2.51, 2.52 (two singles, 6H), 3.48 (d, J = 6.8 Hz, 2H), 3.67-3.77 (m, 6H), 3.91-3.98 (m, 4H), 4.13-4.17 (m, 1H), 4.30-4.32 (m, 1H), 4.39-4.43 (m, 3H), 4.52 (t, J = 4.4 Hz, 1H), 4.61-4.63 (m, 1H), 6.47-6.51 (m, 1H), 6.84-6.92 (m, 1H), 7.12- | following route described for examples 59 and 66 |

FIG. 2 (continued)

| Ex. # | Structure | Name | (M+H)+ | H¹-NMR | Synthesis |
|---|---|---|---|---|---|
| | | methylthiazol-5-yl)benzyl)pyrrolidine-2-carboxamide | | 7.29 (m, 7H), 7.53-7.60 (m, 2H), 7.88-7.90 (m, 1H), 8.33 (s, 1H), 8.71 (s, 1H), 8.77 (s, 1H). | |
| 46 | 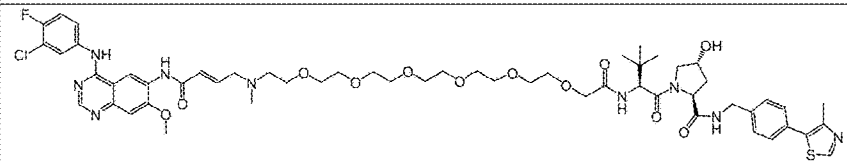 | (E)-N25-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-21-methyl-3,6,9,12,15,18-hexaoxa-21-azapentacos-23-enediamide | 1150.5 1152.5 | (400 MHz, CD3OD): δ 0.91, 0.93 (two singles, 9H), 1.94-2.01 (m, 1H), 2.10-2.15 (m, 1H), 2.35 (s, 3H), 2.62, 2.65 (two singles, 3H), 3.02-3.03 (m, 2H), 3.49-3.97 (m, 28H), 4.22-4.58 (m, 5H), 5.39-5.67 (m, 1H), 5.99-6.19 (m, 1H), 6.60-6.64 (m, 1H), 6.89-6.96 (m, 1H), 7.13-7.56 (m, 7H), 7.89-7.92 (m, 1H), 8.38 (s, 1H), 8.76 (s, 1H), 8.83 (s, 1H). | following route described for example 41 |
| 47 | 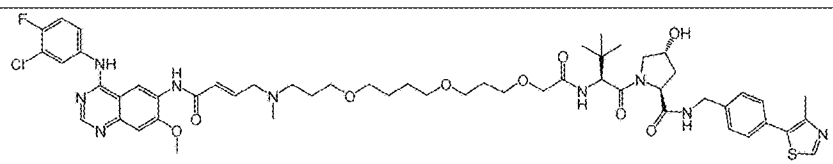 | (E)-N20-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl | 1074.5 1076.5 | (400 MHz, CD3OD): δ 1.02, 1.04 (two singles, 9H), 1.59-1.62 (m, 4H), 1.82-1.91 (m, 4H), 2.06-2.13 (m, 1H), 2.22-2.27 (m, 1H), 2.47-2.53 (m, 6H), 2.75-2.79 (m, 2H), 3.42-3.61 (m, 12H), 3.79-3.97 (m, 4H), 4.08 (s, 3H), 4.36 (d, J = 15.2 Hz, 1H), | following route described for example 41 |

FIG. 2 (continued)

| Ex. # | Structure | Name | (M+H)⁺ | H¹-NMR | Synthesis |
|---|---|---|---|---|---|
| | | )pyrrolidin-1-yl)-3,3-dimethyl-1-oxobutan-2-yl)-16-methyl-3,7,12-trioxa-16-azaicos-18-enediamide | | 4.52-4.61 (m, 3H), 4.70-4.72 (m, 1H), 6.63 (d, J = 15.2 Hz, 1H), 7.00-7.07 (m, 1H), 7.23-7.28 (m, 2H), 7.40-7.55 (m, 5H), 7.67-7.70 (m, 1H), 8.01-8.04 (m, 1H), 8.49 (s, 1H), 8.88 (s, 1H), 8.93 (s, 1H). | |
| 48 | 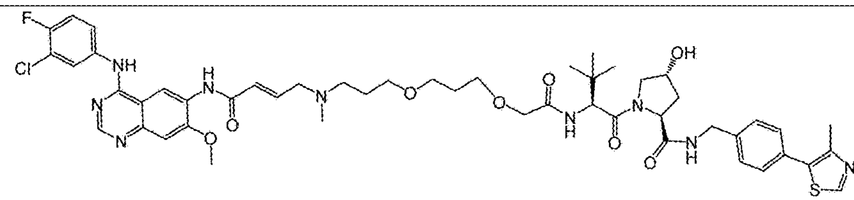 | (2S,4R)-1-((S,E)-2-(tert-butyl)-18-((4-((3-chloro-4-fluorophenyl)amino)-7-methoxyquinazolin-6-yl)amino)-14-methyl-4,18-dioxo-6,10-dioxa-3,14-diazaoctadec-16-enoyl)-4-hydroxy-N-(4-(4-methylthiazol-5-yl)benzyl)pyrrolidine-2-carboxamide | 1002.4 1004.4 | (400 MHz, CD3OD): δ0.91, 0.92(two singles, 9H), 1.76-1.82 (m, 4H), 1.94-2.00 (m, 1H), 2.09-2.16 (m, 1H), 2.34, 2.35 (two singles, 3H), 2.42, 2.48 (two singles, 3H), 2.69-2.79 (m, 2H), 3.41-3.54 (m, 8H), 3.66-3.91 (m, 4H), 3.96 (s, 3H), 4.23-4.60 (m, 5H), 6.51, 6.55 (two singles, 1H), 6.87-6.95 (m, 1H), 7.09-7.16 (m, 2H), 7.27-7.34 (m, 4H), 7.54-7.57 (m, 1H), 7.90 (dd, J = 6.8 Hz, 2.8 Hz, 1H), 8.35, 8.36 (two singles, 1H), 8.75, 8.76 (two singles, 1H), 8.80, 8.81 (two singles, 1H). | following route described for example 41 |

FIG. 2 (continued)

| Ex. # | Structure | Name | (M+H)+ | H¹-NMR | Synthesis |
|---|---|---|---|---|---|
| 49 | 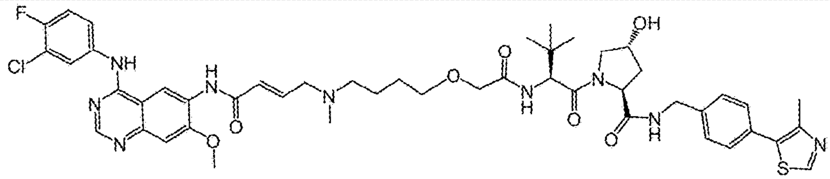 | (2S,4R)-1-((S)-2-(2-(4-(((E)-4-((4-((3-chloro-4-fluorophenyl)amino)-7-methoxyquinazolin-6-yl)amino)-4-oxobut-2-en-1-yl)(methyl)amino)butoxy)acetamido)-3,3-dimethylbutanoyl)-4-hydroxy-N-(4-(4-methylthiazol-5-yl)benzyl)pyrrolidine-2-carboxamide | 958.4 960.4 | (400 MHz, CD3OD): δ 1.04, 1.07 (two singles, 9H), 1.78-1.83 (m, 2H), 1.93-1.99 (m, 2H), 2.05-2.12 (m, 1H), 2.23-2.28 (m, 1H), 2.44-2.46 (two singles, 3H), 2.90, 2.91 (two singles, 3H), 3.21-3.27 (m, 2H), 3.61-3.69 (m, 2H), 3.81-4.15 (m, 9H), 4.37-4.70 (m, 5H), 6.78 (d, J = 15.2 Hz, 1H), 7.00-7.08 (m, 1H), 7.24-7.42 (m, 6H), 7.67-7.71 (m, 1H), 7.99-8.02 (m, 1H), 8.29 (br, 2H), 8.51 (s, 1H), 8.85-8.94 (m, 2H). | following route described for example 41 |
| 50 | 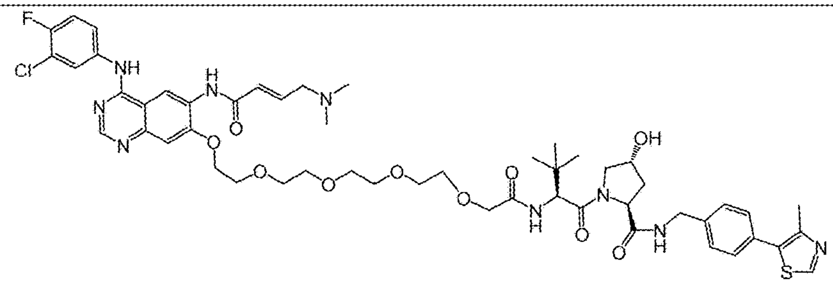 | (2S,4R)-1-((S)-2-(tert-butyl)-17-((4-((3-chloro-4-fluorophenyl)amino)-6-((E)-4-(dimethylamino)but-2-enamido)quinazolin-7-yl)oxy)-4-oxo-6,9,12,15-tetraoxa-3-azaheptadecanoyl)-4-hydroxy-N-(4-(4-methylthiazol-5-yl)benzyl)pyrrolidin | 1062.4 1064.4 | (400 MHz, CD3OD): δ 1.01, 1.03 (two singles, 9H), 2.06-2.12 (m, 1H), 2.22-2.27 (m, 1H), 2.46, 2.47 (two singles, 3H), 2.81, 2.82 (two singles, 6H), 3.62-3.71 (m, 10H), 3.76-3.90 (m, 6H), 4.00-4.03 (m, 4H), 4.33-4.41 (m, 3H), 4.47-4.51 (m, 2H), 4.58-4.62 (m, 1H), 4.68-4.70 (m, 1H), 6.71-6.75 (m, 1H), 6.97-7.04 (m, 1H), 7.23-7.28 (m, 2H), 7.37-7.43 (m, 4H), 7.66-7.70 (m, 1H), 8.01 | following route described for examples 59 and 66 |

FIG. 2 (continued)

| Ex. # | Structure | Name | (M+H)+ | H¹-NMR | Synthesis |
|---|---|---|---|---|---|
| | | e-2-carboxamide | | (dd, J = 6.8 Hz, 2.8 Hz, 1H), 8.49 (s. 1H), 8.86, 8.87 (two singles, 1H), 8.94 (s, 1H). | |
| 51 | 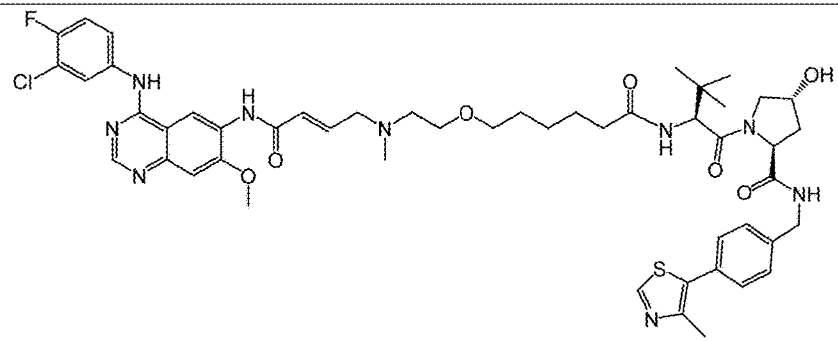 | (2S,4R)-1-((S)-2-(6-(2-(((E)-4-((3-chloro-4-fluorophenyl)amino)-7-methoxyquinazolin-6-yl)amino)-4-oxobut-2-en-1-yl)(methyl)amino)ethoxy)hexanamido)-3,3-dimethylbutanoyl)-4-hydroxy-N-(4-(4-methylthiazol-5-yl)benzyl)pyrrolidine-2-carboxamide | 986.4 988.4 | NMR (400 MHz, CD3OD): δ 8.90 (s. 1H), 8.87 (s, 1H), 8.47 (s, 1H), 8.02 (d, J = 6.8 Hz, 1H). 7.68 (s, 1H), 7.42 (m, 4H), 7.27 (m, 2H), 7.03 (m. 1H), 6.53 (d, J = 15.6 Hz. 1H), 4.64 (s, 1H), 4.55 (m. 3H), 4.34 (m, 1H), 4.07 (s, 3H), 3.90 (m, 1H), 3.80 (m, 1H), 3.60 (t, J = 5.2 Hz, 2H), 3.47 (t, J = 5.2 Hz, 2H), 3.33 (m, 2H), 2.68 (t, J = 5.2 Hz, 2H), 2.47 (s, 3H), 2.34 (s, 3H), 2.25 (m, 3H), 2.06 (m, 1H), 1.65 (m, 4H), 1.45 (m, 2H). 1.00 (s, 9H) | following route described for example 41 |
| 52 | 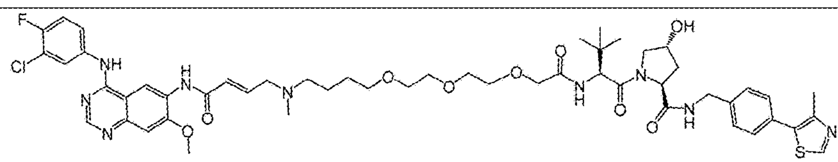 | (E)-N18-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl | 1046.4 1048.4 | (400 MHz, CD3OD): δ 1.05 (s, 9H), 1.68-1.89 (m, 4H), 2.05-2.12 (m, 1H), 2.22-2.27 (m, 1H), 2.45, 2.47 (two singles, 3H), 2.81, 2.84 (two singles, 3H), 3.09-3.16 (m, 2H), 3.54-3.92 (m, 14H), 4.09 (s, 5H), 4.35-4.71 (m, 5H), 6.77 (d, J = 15.2 Hz, 1H), | following route described for example 41 |

FIG. 2 (continued)

| Ex. # | Structure | Name | (M+H)+ | H¹-NMR | Synthesis |
|---|---|---|---|---|---|
| | | )pyrrolidin-1-yl)-3,3-dimethyl-1-oxobutan-2-yl)-14-methyl-3,6,9-trioxa-14-azaoctadec-16-enediamide | | 6.99-7.06 (m, 1H), 7.22-7.44 (m, 6H), 7.67-7.69 (m, 1H), 8.02 (d, J = 4.8 Hz, 1H), 8.50 (s, 1H), 8.86-8.94 (m, 2H) | |
| 53 | 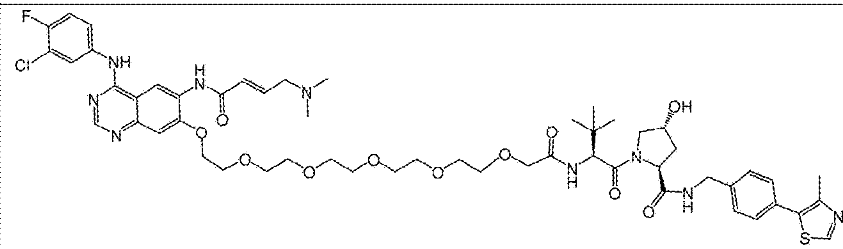 | (2S,4R)-1-((S)-2-(tert-butyl)-20-((3-chloro-4-fluorophenyl)amino)-6-((E)-4-(dimethylamino)but-2-enamido)quinazolin-7-yl)oxy)-4-oxo-6,9,12,15,18-pentaoxa-3-azaicosanoyl)-4-hydroxy-N-(4-(4-methylthiazol-5-yl)benzyl)pyrrolidine-2-carboxamide | 1106.5 1108.5 | (400 MHz, CD3OD): δ 0.89, 0.91 (two singles, 9H), 1.95-1.99 (m, 1H), 2.07-2.13 (m, 1H), 2.34, 2.35 (two singles, 3H), 2.59 (s, 6H), 3.47-3.78 (m, 20H), 3.90-3.92(m, 4H), 4.21-4.47 (m, 6H), 4.57 (s, 1H), 6.56-6.60 (m, 1H), 6.86-6.93 (m, 1H), 7.12-7.17 (m, 2H), 7.26-7.32 (m, 4H), 7.56-7.58 (m, 1H), 7.81 (dd, J = 6.4 Hz, 2.4 Hz, 1H), 8.38 (s. 1H), 8.75-8.83(two singles, 2H) | following route described for examples 59 and 66 |
| 54 | 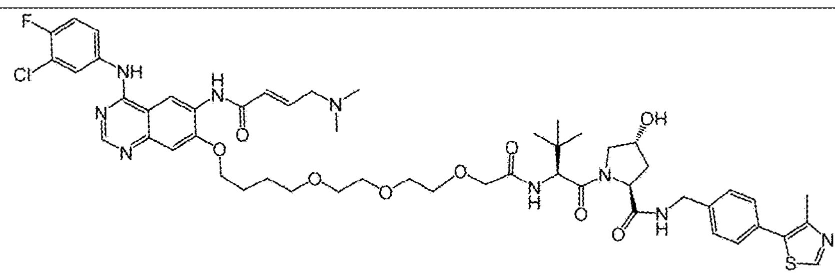 | (2S,4R)-1-((S)-2-(tert-butyl)-16-((3-chloro-4-fluorophenyl)amino)-6-((E)-4-(dimethylamino)but-2-enamido)quinazolin-7-yl)oxy)-4-oxo-6,9,12-trioxa-3- | 1046.4 1048.4 | (400 MHz, CD3OD):δ 1.02, 1.04 (two singles, 9H), 1.78-1.85 (m, 2H), 1.97-2.13 (m, 3H), 2.23-2.28 (m, 1H), 2.47 (s, 3H), 2.64 (s, 6H), 3.58-3.87 (m, 14H), 4.05 (d, J = 2.0 Hz, 2H), 4.28-4.37 (m, 3H), 4.50-4.68 (m, 4H), 6.69 (d, J = 15.6 Hz, 1H), 6.99-7.06 | following route described for examples 59 and 66 |

FIG. 2 (continued)

| Ex. # | Structure | Name | (M+H)+ | H¹-NMR | Synthesis |
|---|---|---|---|---|---|
| | | azahexadecanoyl)-4-hydroxy-N-(4-(4-methylthiazol-5-yl)benzyl)pyrrolidine-2-carboxamide | | (m, 1H), 7.24-7.30 (m, 2H), 7.38-7.45 (m, 4H), 7.67-7.71 (m, 1H), 8.04 (dd, J = 9.6 Hz, 1H), 8.50 (s, 1H), 8.87-8.90 (m, 2H) | |
| 55 | 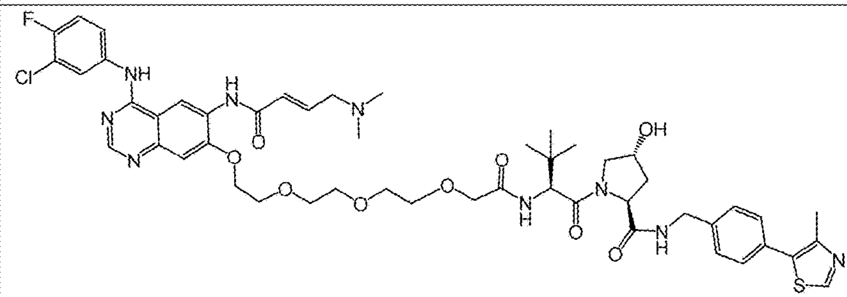 | (2S,4R)-1-((S)-2-(tert-butyl)-14-((4-((3-chloro-4-fluorophenyl)amino)-6-((E)-4-(dimethylamino)but-2-enamido)quinazolin-7-yl)oxy)-4-oxo-6,9,12-trioxa-3-azatetradecanoyl)-4-hydroxy-N-(4-(4-methylthiazol-5-yl)benzyl)pyrrolidine-2-carboxamide | 1018.4 1020.4 | (400 MHz, CD3OD): δ 0.88, 0.92 (two singles, 9H), 1.98-2.01 (m, 1H), 2.09-2.17 (m, 1H), 2.33, 2.35 (two singles, 3H), 2.45, 2.47 (two singles, 6H), 3.41-3.45 (m, 2H), 3.59-3.94 (m, 14H), 4.19-4.58 (m, 7H), 6.48-6.56 (m, 1H), 6.85-6.94 (m, 1H), 7.12-7.30 (m, 6H), 7.55-7.58 (m, 1H), 7.90-7.92 (m, 1H), 8.36, 8.40 (two singles, 1H), 8.73-8.81 (m, 2H). | following route described for examples 59 and 66 |
| 56 | 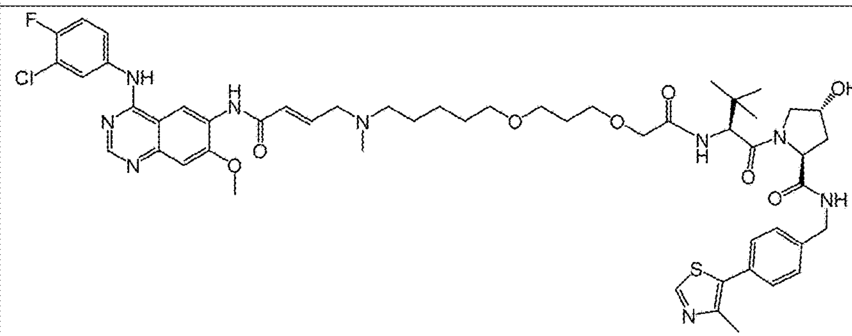 | (2S,4R)-1-((S,E)-2-(tert-butyl)-20-((4-((3-chloro-4-fluorophenyl)amino)-7-methoxyquinazolin-6-yl)amino)-16-methyl-4,20-dioxo-6,10-dioxa-3,16-diazaicos-18-enoyl)-4-hydroxy-N-(4-(4-methylthiazol-5- | 1030.4 1032.4 | (400 MHz, CD3OD): δ 8.95 (s, 1H), 8.88 (s, 1H), 8.50 (s, 1H), 8.03 (d, J = 4.0 Hz, 1H), 7.70 (m, 1H), 7.42 (m, 4H), 7.27 (m, 2H), 7.03 (m, 1H), 6.54 (d, J = 14.8 Hz, 1H), 4.70 (s, 1H), 4.55 (m, 3H), 4.34 (m, 1H), 4.09 (s, 3H), 3.96 (m, 2H), 3.80 (m, 1H), 3.78 (m, 1H), 3.63 (m, 2H), 3.57 (t, J = 5.2 Hz, | following route described for example 41 |

FIG. 2 (continued)

| Ex. # | Structure | Name | (M+H)+ | H1-NMR | Synthesis |
|---|---|---|---|---|---|
| 57 | 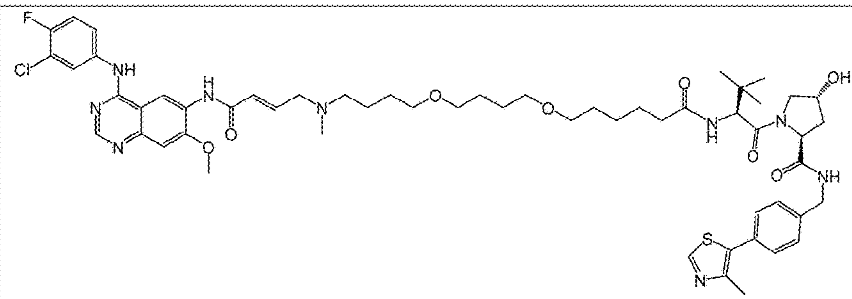 | (2S,4R)-1-((S,E)-2-(tert-butyl)-24-((4-(3-chloro-4-fluorophenyl)amino)-7-methoxyquinazolin-6-yl)amino)-20-methyl-4,24-dioxo-10,15-dioxa-3,20-diazatetracos-22-enoyl)-4-hydroxy-N-(4-(4-methylthiazol-5-yl)benzyl)pyrrolidine-2-carboxamide | 1086.5 1088.5 | 2H), 3.47 (t, J = 5.2 Hz, 2H), 3.30 (m, 2H), 2.47 (m, 5H), 2.31 (s, 3H), 2.24 (m, 1H), 2.07 (m, 1H), 1.90 (m, 2H), 1.58 (m, 4H), 1.38 (m, 2H), 1.02 (s, 9H); (400 MHz, CD3OD): δ 8.94 (s, 1H), 8.88 (s, 1H), 8.51 (s, 1H), 8.04 (d, J = 6.8 Hz, 1H), 7.74 (m, 1H), 7.42 (m, 4H), 7.27 (m, 2H), 7.04 (m, 1H), 6.54 (d, J = 15.6 Hz, 1H), 4.60 (s, 1H), 4.55 (m, 3H), 4.34 (m, 1H), 4.09 (s, 3H), 3.89 (m, 2H), 3.78 (m, 1H), 3.48 (m, 8H), 2.45 (m, 5H), 2.30 (s, 3H), 2.21 (m, 3H), 2.08 (m, 1H), 1.65 (m, 12H), 1.37 (m, 3H), 1.02 (s, 9H) | following route described for example 41 |
| 58 | 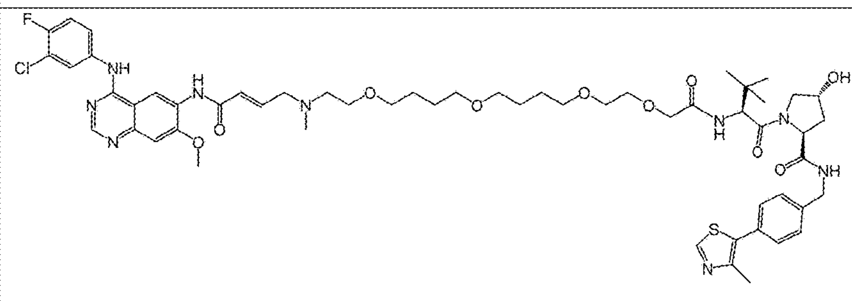 | (E)-N23-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl | 1118.5 1120.5 | (400 MHz, CD3OD): δ 8.95 (s, 1H), 8.88 (s, 1H), 8.51 (s, 1H), 8.04 (d, J = 6.8 Hz, 1H), 7.70 (m, 1H), 7.42 (m, 4H), 7.27 (m, 2H), 7.04 (m, 1H), 6.54 (d, J = 15.2 Hz, 1H), 4.69 (s, 1H), 4.55 (m, 3H), 4.34 (m, 1H), 4.10 (s, 3H), 4.08 (s, 2H), 3.88 (m, 1H), 3.78 | following route described for example 41 |

FIG. 2 (continued)

| Ex. # | Structure | Name | (M+H)+ | H1-NMR | Synthesis |
|---|---|---|---|---|---|
| | | )pyrrolidin-1-yl)-3,3-dimethyl-1-oxobutan-2-yl)-19-methyl-3,6,11,16-tetraoxa-19-azatricos-21-enediamide | | (m, 1H), 3.60 (m, 2H), 3.52 (m, 4H), 3.48 (m, 4H), 3.40 (m, 4H), 3.30 (m, 2H), 2.69 (m, 2H), 2.45 (s, 3H), 2.36 (s, 3H), 2.21 (m, 1H), 2.10 (m, 1H), 1.63 (m, 8H), 1.03 (s, 9H) | |
| 59 | [structure] | (2S,4R)-1-((S)-2-(6-(2-((4-((3-chloro-4-fluorophenyl)amino)-6-((E)-4-(dimethylamino)but-2-enamido)quinazolin-7-yl)oxy)ethoxy)hexanamido)-3,3-dimethylbutanoyl)-4-hydroxy-N-(4-(4-methylthiazol-5-yl)benzyl)pyrrolidine-2-carboxamide | 986.4 988.4 | (300 MHz, CD3OD) δ 8.92 (s, 1H), 8.83 (s, 1H), 8.45 (s, 1H), 8.01-7.99 (d, J = 8.4 Hz, 1H), 7.70-7.60 (m, 1H), 7.43-7.36 (m, 4H), 7.25-7.19 (m, 2H), 7.02-6.97 (m, 1H), 6.50-6.45(d, J = 15.3 Hz, 1H), 4.58 (s, 1H), 4.52-4.47 (m, 3H), 4.39-4.33 (m, 3H), 3.93-3.92 (m, 2H), 3.90-3.83 (m, 1H), 3.82-3.70(m, 1H), 3.60-3.56 (m, 2H), 3.20-3.18 (m, 2H), 2.42 (s, 3H), 2.29 (s, 6H), 2.29-2.12 (m, 3H), 2.10-2.00 (m, 1H), 1.65-1.60(m, 4H), 1.38-1.29 (m, 2H), 0.97 (s, 9H) | Synthesis of example 59 as described |

FIG. 2 (continued)

| Ex. # | Structure | Name | (M+H)⁺ | H¹-NMR | Synthesis |
|---|---|---|---|---|---|
| 60 | 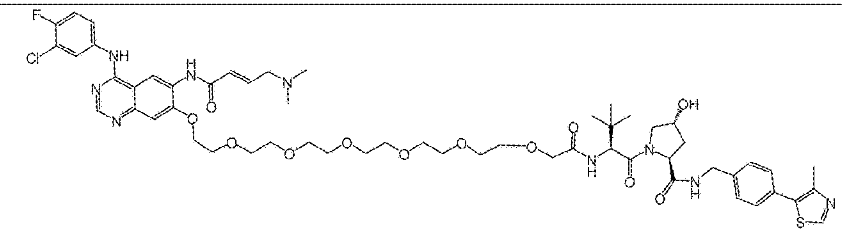 | (2S,4R)-1-((S)-2-(tert-butyl)-23-((4-((3-chloro-4-fluorophenyl)amino)-6-((E)-4-(dimethylamino)but-2-enamido)quinazolin-7-yl)oxy)-4-oxo-6,9,12,15,18,21-hexaoxa-3-azatricosanoyl)-4-hydroxy-N-(4-(4-methylthiazol-5-yl)benzyl)pyrrolidine-2-carboxamide | 1150.5 1152.5 | (400 MHz, CD3OD):δ0.90, 0.92 (two singles, 9H),1.94-2.00 (m, 1H),2.09-2.15 (m, 1H),2.35 (s, 3H),2.57, 2.76 (two singles, 6H),3.44-3.67 (m, 24H),3.90-3.93 (m, 4H),4.25-4.57 (m, 7H), 6.55-6.59 (m, 1H),6.87-6.94 (m, 1H),7.12-7.16 (m, 2H), 7.26-7.33 (m, 4H),7.55-7.58(m,1H), 7.89-7.91(m, 1H), 8.37(s, 1H), 8.75-8.82(m, 2H). | following route described for examples 59 and 66 |
| 61 | 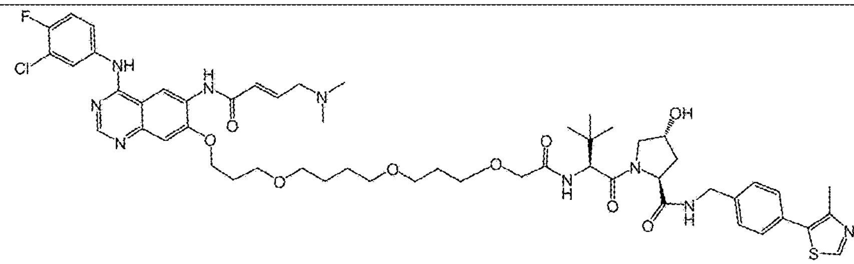 | (2S,4R)-1-((S)-2-(tert-butyl)-18-((4-((3-chloro-4-fluorophenyl)amino)-6-((E)-4-(dimethylamino)but-2-enamido)quinazolin-7-yl)oxy)-4-oxo-6,10,15-trioxa-3-azaoctadecanoyl)-4-hydroxy-N-(4-(4-methylthiazol-5-yl)benzyl)pyrrolidine-2-carboxamide | 1074.5 1076.5 | (400 MHz, CD3OD): δ 1.02, 1.03 (two singles, 9H), 1.61 (m, 4H), 1.83-1.86 (m, 2H), 2.18-2.21 (m, 4H), 2.47, 2.48 (two singles, 3H), 2.61 (s, 6H), 3.40-3.51 (m, 6H), 3.58-3.68 (m, 4H), 3.87-3.99 (m, 4H), 4.33-4.37 (m, 3H), 4.51-4.61 (m, 3H), 4.70 (m, 1H), 6.63-6.67 (m, 1H), 6.98-7.06 (m, 1H), 7.22-7.27 (m, 2H), 7.38-7.45 (m, 4H), 7.66-7.68 (m, 1H), 8.00-8.03 (m, 1H), 8.48 (s, 1H), 8.87 | following route described for examples 59 and 66 |

FIG. 2 (continued)

| Ex. # | Structure | Name | (M+H)+ | H1-NMR | Synthesis |
|---|---|---|---|---|---|
| 62 | 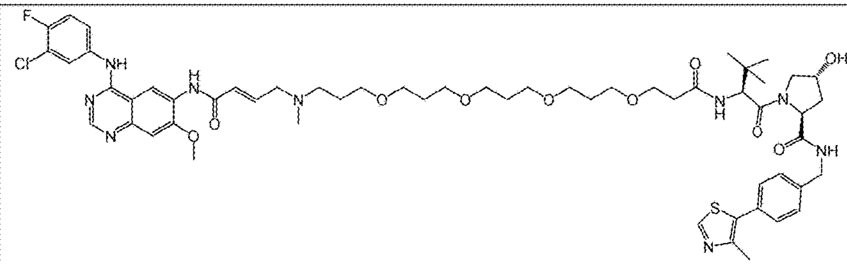 | (E)-N24-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-20-methyl-4,8,12,16-tetraoxa-20-azatetracos-22-enediamide | 1132.5 1134.5 | (400 MHz, CD3OD): δ 8.95 (s, 1H), 8.88 (s, 1H), 8.51 (s, 1H), 8.04 (d, J = 6.4 Hz, 1H), 7.70 (m, 1H), 7.42 (m, 4H), 7.27 (m, 2H), 7.04 (m, 1H), 6.54 (d, J = 14.8 Hz, 1H), 4.65 (s, 1H), 4.55 (m, 3H), 4.34 (m, 1H), 4.10 (s, 3H), 3.88 (m, 1H), 3.78 (m, 1H), 3.65 (m, 2H), 3.48 (m, 14H), 3.28 (m, 2H), 2.55 (m, 3H), 2.45 (s, 4H), 2.30 (s, 3H), 2.21 (m, 1H), 2.10 (m, 1H), 1.75 (m, 8H), 1.02 (s, 9H) | following route described for example 41 |
| 63 | 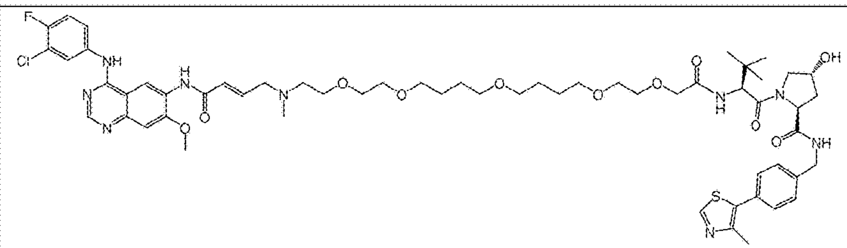 | (E)-N26-(4-((3-chloro-4-fluorophenyl)amino)-7-methoxyquinazolin-6-yl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-22-methyl- | 1162.5 1164.5 | (400 MHz, CD3OD): δ 8.95 (s, 1H), 8.88 (s, 1H), 8.51 (s, 1H), 8.04 (d, J = 6.4 Hz, 1H), 7.70 (m, 1H), 7.42 (m, 4H), 7.27 (m, 2H), 7.04 (m, 1H), 6.56 (d, J = 15.6 Hz, 1H), 4.70 (s, 1H), 4.60 (m, 3H), 4.34 (m, 1H), 4.10 (s, 3H), 4.05 (s, 2H), 3.88 (m, 1H), 3.80 (m, 1H), 3.65 (m, 10H), 3.45 (m, 4H), 3.33 (m, 6H), 2.71 (m, 2H), 2.47 (s, 3H), 2.35 (s, 3H), 2.21 (m, 2H) | following route described for example 41 |

FIG. 2 (continued)

| Ex. # | Structure | Name | (M+H)+ | H¹-NMR | Synthesis |
|---|---|---|---|---|---|
| | | 3,6,11,16,19-pentaoxa-22-azahexacos-24-enediamide | | 1H), 2.10 (m, 1H), 1.60 (m, 8H), 1.03 (s, 9H) | |
| 64 | 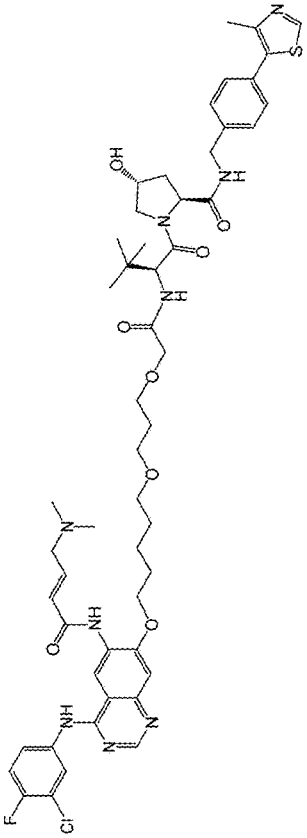 | (2S,4R)-1-((S)-2-(2-(3-((5-((4-((3-chloro-4-fluorophenyl)amino)-6-((E)-4-(dimethylamino)but-2-enamido)quinazolin-7-yl)oxy)pentyl)oxy)propoxy)acetamido)-3,3-dimethylbutanoyl)-4-hydroxy-N-(4-(4-methylthiazol-5-yl)benzyl)pyrrolidine-2-carboxamide | 1030.4 1032.4 | (300 MHz, CD3OD) δ 8.88-8.85 (d, J = 8.4 Hz, 2H), 8.49 (s, 1H), 8.04-8.02(d, J = 4.2Hz, 1H), 7.68 (m, 1H), 7.45-7.40 (m, 4H), 7.37-7.23 (m, 2H), 7.05-7.00 (m, 1H), 6.54-6.49 (d, J = 15.0 Hz, 1H), 4.69 (s, 1H), 4.58-4.54 (m, 3H), 4.49-4.37 (s, 1H), 4.32-4.24 (m, 2H), 3.97-3.96 (m, 2H), 3.85-3.80(m, 2H), 3.65-3.61 (m, 2H), 3.59-3.55 (m, 2H), 3.52-3.50 (m, 2H), 3.18-3.15 (m, 2H), 2.46 (s, 3H), 2.32 (s, 6H), 2.31-2.20 (m, 1H), 2.15-2.05(m, 1H), 1.98-1.89 (m, 4H), 1.66-1.60 (m, 4H), 1.02-1.00 (s, 9H) | following route described for examples 59 and 66 |

FIG. 2 (continued)

| Ex. # | Structure | Name | (M+H)+ | H1-NMR | Synthesis |
|---|---|---|---|---|---|
| 65 | 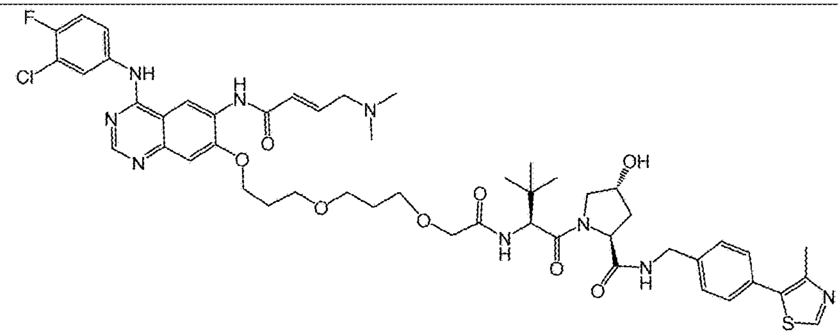 | (2S,4R)-1-((S)-2-(2-(3-((4-((3-chloro-4-fluorophenyl)amino)-6-((E)-4-(dimethylamino)but-2-enamido)quinazolin-7-yl)oxy)propoxy)propoxy)acetamido)-3,3-dimethylbutanoyl)-4-hydroxy-N-(4-(4-methylthiazol-5-yl)benzyl)pyrrolidine-2-carboxamide | 1002.4 1004.4 | (400 MHz, CD3OD):δ1.00, 1.04 (two singles, 9H),1.90-1.93 (m, 2H),2.07-2.14 (m, 1H),2.23-2.26 (m, 3H),2.46, 2.48 (two singles, 3H),2.97 (s, 6H),3.61-3.73 (m, 6H), 3.83-4.70 (m, 6H), 4.38-4.70 (m, 7H),6.81-6.87 (m, 1H),6.96-7.04 (m, 1H), 7.29-7.44 (m, 6H),7.65-7.69(m, 1H), 7.95-7.98(m, 1H), 8.65(m, 1H), 8.67(m, 1H), 9.11 (m, 1H). | following route described for examples 59 and 66 |
| 66 | 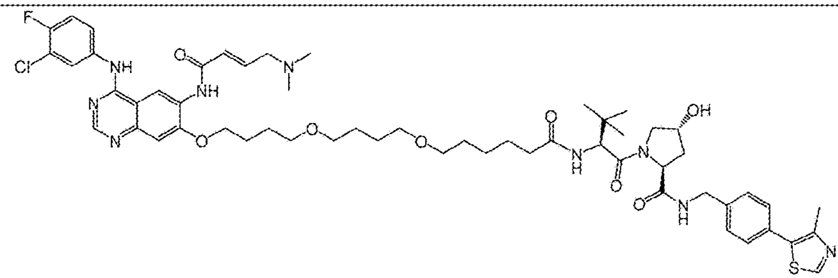 | (2S,4R)-1-((S)-2-(6-(4-(4-((3-chloro-4-fluorophenyl)amino)-6-((E)-4-(dimethylamino)but-2-enamido)quinazolin-7-yl)oxy)butoxy)butoxy)hexanamido)-3,3-dimethylbutanoyl)-4-hydroxy-N-(4-(4-methylthiazol-5-yl)methylthiazol- | 1086.5 1088.5 | (300 MHz, CD3OD): δ 8.88 (s, 1H), 8.49 (s, 1H), 8.04-8.02 (d, J = 6.9 Hz, 1H). 7.75-7.65 (m, 1H). 7.47-7.41 (m, 4H), 7.38-7.26 (m, 2H), 7.05-7.00 (m, 1H), 6.55-6.50 (d, J = 15.3 Hz, 1H), 4.63 (s, 1H), 4.56-4.49 (m, 3H), 4.37-4.30 (m, 3H), 3.92-3.78 (m, 2H), 3.57-3.53 (m, 2H). 3.47-3.46 (m, 2H), 3.46-3.40 (m, 4H), 3.24-3.21 (m, 2H), 2.47 (s, 3H), 2.32 (s, 6H), 2.30-2.23 (m, 3H), 2.30-2.23 (m, 3H), | Synthesis of example 66 as described |

FIG. 2 (continued)

| Ex. # | Structure | Name | (M+H)⁺ | H¹-NMR | Synthesis |
|---|---|---|---|---|---|
| 67 | 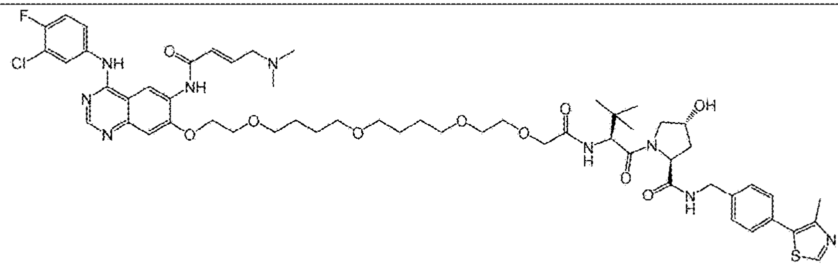 | (2S,4R)-1-((S)-2-(tert-butyl)-21-((4-((3-chloro-4-fluorophenyl)amino)-6-((E)-4-(dimethylamino)but-2-enamido)quinazolin-7-yl)oxy)-4-oxo-6,9,14,19-tetraoxa-3-azahenicosanoyl)-4-hydroxy-N-(4-(4-methylthiazol-5-yl)benzyl)pyrrolidine-2-carboxamide | 1118.5 1120.5 | (300 MHz, CD3OD): δ 8.94 (s, 1H), 8.56 (s, 1H), 8.48 (s, 1H), 8.04-8.02 (d, J = 6.9 Hz, 1H), 7.75-7.65 (m, 1H), 7.45-7.40 (m, 4H), 7.37-7.29 (m, 2H), 7.05-7.00 (m, 1H), 6.55-6.50 (d, J = 15.3 Hz, 1H), 4.63 (s, 1H), 4.57-4.50 (m, 3H), 4.39-4.30 (m, 3H), 4.01 (s, 2H), 4.00-3.90 (m, 2H), 3.85-3.67 (m, 2H), 3.66-3.58 (m, 6H), 3.48-3.42 (m, 4H), 3.23-3.21 (m, 2H), 2.47 (s, 3H), 2.32 (s, 6H), 2.23-2.21 (m, 1H), 2.15-2.00 (m, 1H), 1.68-1.57 (m, 8H), 1.01 (s, 9H) | following route described for examples 59 and 66 |
| 68 | 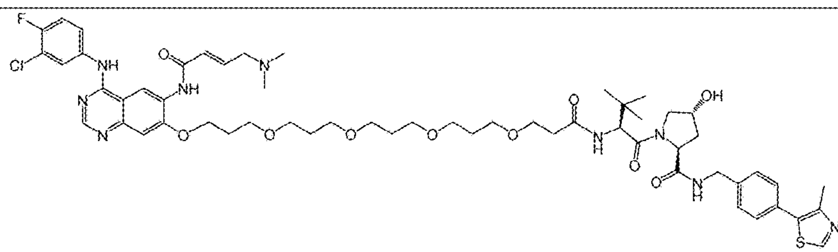 | (2S,4R)-1-((S)-2-(tert-butyl)-22-((4-((3-chloro-4-fluorophenyl)amino)-6-((E)-4-(dimethylamino)but-2-enamido)quinazolin-7-yl)oxy)-4-oxo- | 1132.5 1134.5 | (300 MHz, CD3OD): δ 8.89-8.86 (d, J =8.1 Hz, 1H), 8.49 (s, 1H), 8.04-8.03 (d, J =4.2 Hz, 1H), 7.76-7.65 (m, 1H), 7.45-7.41 (m, 4H), 7.38-7.23 (m, 2H), 7.08-6.95 (m, 1H), 6.55-6.50 (d, J = 15.3 Hz, 1H), 4.65 (s, 1H), | following route described for examples 59 and 66 |

FIG. 2 (continued)

| Ex. # | Structure | Name | (M+H)⁺ | H¹-NMR | Synthesis |
|---|---|---|---|---|---|
| | | 7,11,15,19-tetraoxa-3-azadocosanoyl)-4-hydroxy-N-(4-(4-methylthiazol-5-yl)benzyl)pyrrolidine-2-carboxamide | | 4.56-4.51 (m, 3H), 4.38-4.31 (m, 3H), 3.86-3.74 (m, 2H), 3.70-3.64 (m, 4H), 3.56-3.51 (m, 3H), 3.49-3.42 (m, 10H), 3.23-3.21 (m, 2H), 2.55-2.50 (m, 1H), 2.47 (s, 3H), 2.32 (s, 6H), 2.23-2.21 (m, 3H), 2.18-2.00 (m, 1H), 1.78-1.69 (m, 6H), 1.00 (s, 9H) | |
| 69 | 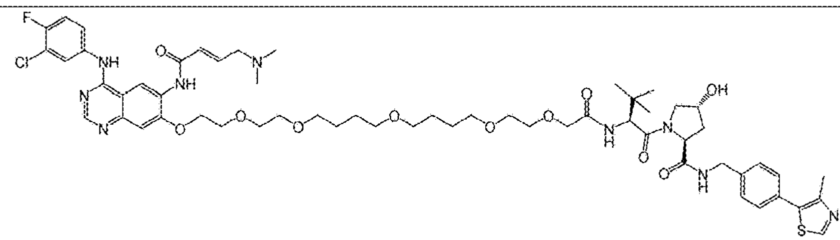 | (2S,4R)-1-((S)-2-(tert-butyl)-24-((4-((3-chloro-4-fluorophenyl)amino)-6-((E)-4-(dimethylamino)but-2-enamido)quinazolin-7-yl)oxy)-4-oxo-6,9,14,19,22-pentaoxa-3-azatetracosanoyl)-4-hydroxy-N-(4-(4-methylthiazol-5-yl)benzyl)pyrrolidine-2-carboxamide | 1162.5 1164.5 | (300 MHz, CD3OD): δ 8.97 (s, 1H), 8.86 (s, 1H), 8.50 (s, 1H), 8.04-8.03 (d, J = 4.2 Hz, 1H), 7.76-7.65 (m, 1H), 7.46-7.41 (m, 4H), 7.38-7.24 (m, 2H), 7.06-7.01 (m, 1H), 6.55-6.50 (d, J = 15.3 Hz, 1H), 4.65 (s, 1H), 4.56-4.51 (m, 3H), 4.36-4.31 (m, 3H), 4.03 (m, 4H), 3.85-3.74 (m, 4H), 3.70-3.57 (m, 7H), 3.56-3.51 (m, 4H), 3.33-3.32 (m, 2H), 3.24-3.22 (m, 2H), 2.47 (s, 3H), 2.32 (s, 6H), 2.23-2.11 (m, 1H), 2.11-2.00 (m, 1H), 1.56-1.53 (m, 9H), 1.01 (s, 9H) | following route described for examples 59 and 66 |

FIG. 2 (continued)

| Ex. # | Structure | Name | (M+H)+ | H1-NMR | Synthesis |
|---|---|---|---|---|---|
| 70 | 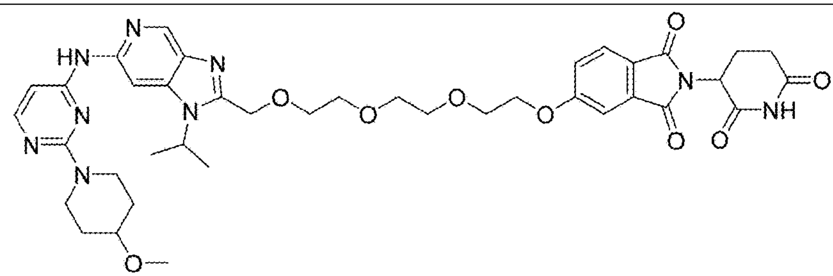 | 2-(2,6-dioxopiperidin-3-yl)-5-[2-(2-{[6-{[2-(4-methoxypiperidin-1-yl)pyrimidin-4-yl]amino}-1-(propan-2-yl)-1H-imidazo[4,5-c]pyridin-2-yl]methoxy}ethoxy)ethoxy]-2,3-dihydro-1H-isoindole-1,3-dione | 786.27 393.62 | (400 MHz, CDCl3): δ 12.59 (s, 1H), 8.65—8.71 (m, 3H), 8.12 (s, 1H), 7.72 (d, J = 8.0 Hz, 1H), 7.32 (s, 1H), 7.17 (d, J = 8.0 Hz, 1H), 6.60 (s, 1H), 5.30—5.31 (m, 1H), 4.94—4.96 (m, 2H), 4.24 (s, 2H), 3.87—4.03 (m, 2H), 3.72—3.85 (m, 4H), 3.60—3.82 (m, 10H), 3.39 (s, 3H), 2.71—2.92 (m, 3H), 2.09—2.11 (m, 1H), 1.86—2.00 (m, 2H), 1.75—1.86 (m, 2H), 1.66—1.68 (m, 6H). | Synthesis of example 70 as described |
| 71 | 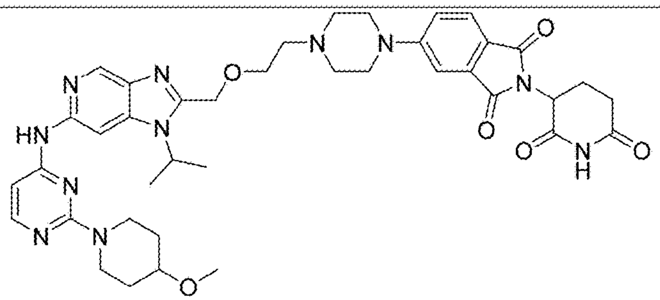 | 2-(2,6-dioxopiperidin-3-yl)-5-(4-{2-[(6-{[2-(4-methoxypiperidin-1-yl)pyrimidin-4-yl]amino}-1-(propan-2-yl)-1H-imidazo[4,5-c]pyridin-2-yl)methoxy]ethyl}piperazin-1-yl)-2,3-dihydro-1H-isoindole-1,3-dione | 766.29 383.64 | (400 MHz, DMSO): δ 11.06 (s, 1H), 9.77 (s. 1H), 8.64 (s, 1H), 8.45 (s, 1H), 7.97 (d, J = 6.4 Hz, 1H), 7.67 (d, J = 8.4 Hz, 1H), 7.33 (s, 1H), 7.22 (d, J = 8.4 Hz, 1H), 6.42 (d, J = 6.0 Hz, 1H), 5.05—5.09 (m, 1H), 4.90—4.93 (m, 1H), 4.79 (s, 2H), 4.21—4.24 (m, 1H), 3.65 (s, 2H), 3.30—3.50 (m, 11H), 2.82—2.92 (m, 1H), 2.51—2.55 (m, 7H), 2.00—2.09 (m, 1H), 1.85—1.95 (m, 2H), 1.60 (d, J = 6.8 Hz, 6H), 1.44—1.46 | Synthesis of example 71 as described |

FIG. 2 (continued)

| Ex. # | Structure | Name | (M+H)+ | H¹-NMR | Synthesis |
|---|---|---|---|---|---|
| 72 | 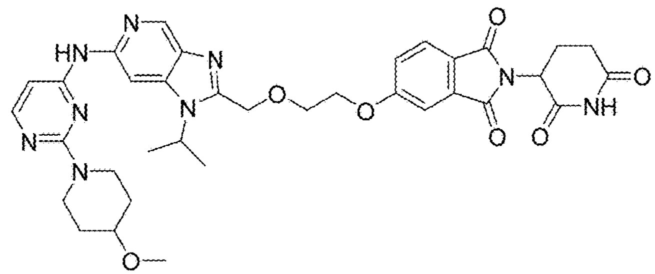 | 2-(2,6-dioxopiperidin-3-yl)-5-{2-{(6-{[2-(4-methoxypiperidin-1-yl)pyrimidin-4-yl]amino}-1-(propan-2-yl)-1H-imidazo[4,5-c]pyridin-2-yl)methoxy]ethoxy}-2,3-dihydro-1H-isoindole-1,3-dione | 698.29 349.65 | (400 MHz, CDCl3): δ 8.70 (m, 2H), 8.54 (s, 1H), 8.48 (s, 1H), 8.05 (d, J = 5.6 Hz, 1H), 7.76 (d, J = 8.4 Hz, 1H), 7.61 (s, 1H), 7.29 (s, 1H), 7.15 – 7.13 (m, 1H), 6.05 (d, J = 5.6 Hz, 1H), 4.96 – 4.89 (m, 4H), 4.39 – 4.35 (m, 2H), 4.25 – 4.24 (m, 2H), 3.94 – 3.93 (m, 2H), 3.51 – 3.41 (m, 6H), 2.88 – 2.78 (m, 3H), 2.17 – 2.15 (m, 1H), 1.99 – 1.97 (m, 2H), 1.67 – 1.60 (m, 8H). | following route described for example 70 |
| 73 | 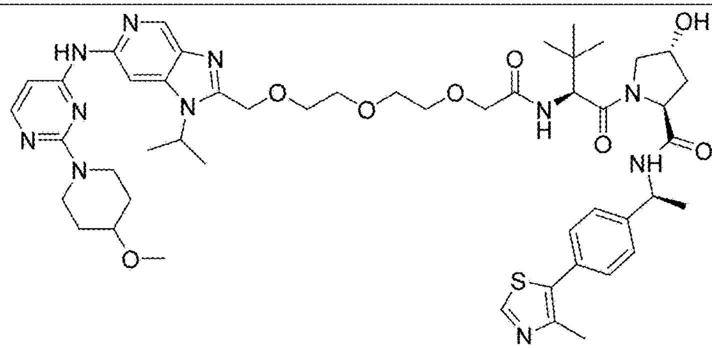 | (2S,4R)-4-hydroxy-1-[(2S)-2-[2-(2-{2-[(6-{[2-(4-methoxypiperidin-1-yl)pyrimidin-4-yl]amino}-1-(propan-2-yl)-1H-imidazo[4,5-c]pyridin-2-yl)methoxy]ethoxy}ethoxy)acetamido]-3,3-dimethylbutanoyl]-N-{(1S)-1-[4-(4-methyl-1,3-thiazol- | 970.39 485.69 | (400 MHz, MeOD): δ 8.85 (s, 1H), 8.61 (s, 1H), 8.46 (s, 1H), 7.92 – 7.94 (d, J = 8.0 Hz, 1H), 7.37 – 7.42 (m, 4H), 6.35 – 6.36 (d, J = 4.0 Hz, 1H), 4.92 – 5.06 (m, 2H), 4.85 – 4.90 (m, 2H), 4.67 (s, 1H), 4.51 – 4.57 (m, 1H), 4.42 (s, 1H), 4.20 – 4.30 (m, 2H), 4.01 (s, 2H), 3.80 – 3.82 (d, J = 4.0 Hz, 1H), 3.67 – 3.79 (m, 9H), 3.41 – 3.55 (m, 3H), 3.36 (s, 3H), 2.45 (s, | following route described for example 81 |

| Ex. # | Structure | Name | (M+H)+ | H¹-NMR | Synthesis |
|---|---|---|---|---|---|
| | | 5-yl)phenyl]ethyl]pyrrolidine-2-carboxamide | | 3H), 2.12—2.20 (m, 1H), 1.91—2.07 (m, 3H), 1.64—1.70 (m, 6H), 1.50—1.62 (m, 3H), 1.46—1.47 (d, J = 4.0 Hz,3H), 1.01 (s, 9H) | |
| 74 | 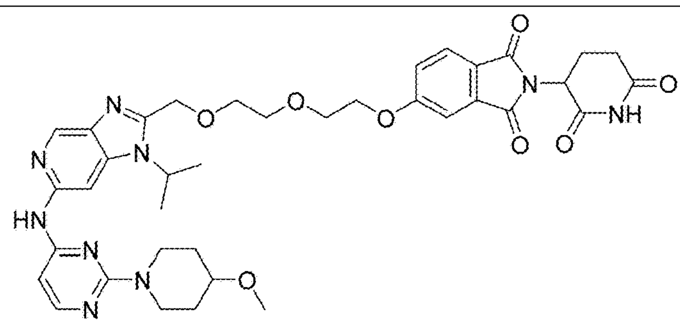 | 2-(2,6-dioxopiperidin-3-yl)-5-(2-{2-[(6-{[2-(4-methoxypiperidin-1-yl)pyrimidin-4-yl]amino}-1-(propan-2-yl)-1H-imidazo[4,5-c]pyridin-2-yl)methoxy]ethoxy)-2,3-dihydro-1H-isoindole-1,3-dione | 742.25 371.61 | (400 MHz, CDCl3): δ 8.69 (s, 1H),8.36—8.50 (m, 2H), 8.03 (d, J = 5.6 Hz, 1H), 7.74 (d, J = 8.4 Hz, 1H), 7.30 (s, 1H), 7.16 (d, J = 8.0 Hz, 1H), 6.15 (s, 1H), 4.93—4.95 (m, 2H), 4.83 (s, 2H), 4.31—4.33 (m, 2H), 4.14—4.16 (m, 2H), 3.83—3.85 (m,2H), 3.72 (s, 4H), 3.50—3.52 (m, 3H), 3.41 (s, 3H), 2.77—2.93 (m, 3H), 2.14—2.15 (m, 1H), 1.95—2.15 (m, 2H), 1.75—1.86 (m, 2H), 1.66—1.68 (m, 6H). | following route described for example 70 |

FIG. 2 (continued)

| Ex. # | Structure | Name | (M+H)+ | H1-NMR | Synthesis |
|---|---|---|---|---|---|
| 75 | 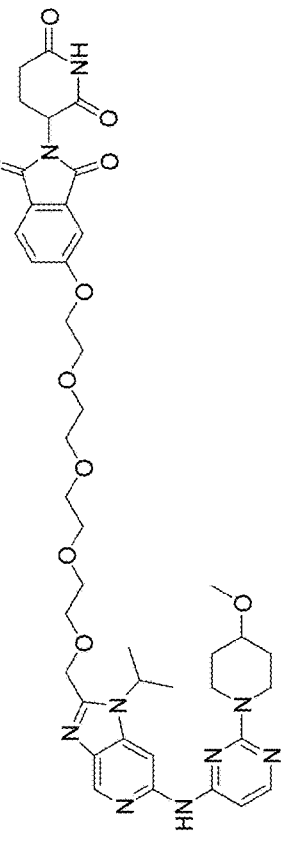 | 2-(2,6-dioxopiperidin-3-yl)-5-{[1-(6-{[2-(4-methoxypiperidin-1-yl)pyrimidin-4-yl]amino}-1-(propan-2-yl)-1H-imidazo[4,5-c]pyridin-2-yl)-2,5,8,11-tetraoxatridecan-13-yl]oxy}-2,3-dihydro-1H-isoindole-1,3-dione | 830.29 415.63 | (400 MHz, CDCl3): δ 8.47 (s, 1H), 8.35 (s, 1H), 7.83 (d, J = 6 Hz, 1H), 7.59 (d, J = 8.4 Hz, 1H), 7.18—7.17 (m, 1H), 7.11—7.10 (m, 1H), 6.17 (d, J = 5.6 Hz, 1H), 5.09—4.79 (m, 8H), 4.29—4.27 (m, 2H), 4.05—4.03 (m, 2H), 3.70—3.69 (m, 2H), 3.61—3.51 (m, 13H), 3.50—3.30 (m, 3H), 3.21 (s, 4H), 2.66—2.61 (m, 3H), 2.09—2.01 (m, 1H), 1.89—1.86 (m, 2H), 1.58—1.56 (m, 6H), 1.48—1.44 (m, 2H). | following route described for example 70 |
| 76 | 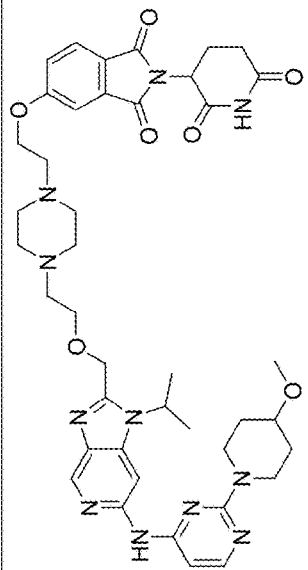 | 2-(2,6-dioxopiperidin-3-yl)-5-[2-(4-{[2-(6-{[2-(4-methoxypiperidin-1-yl)pyrimidin-4-yl]amino}-1-(propan-2-yl)-1H-imidazo[4,5-c]pyridin-2-yl)methoxy]ethyl}piperazin-1-yl)ethoxy]-2,3-dihydro-1H-isoindole-1,3-dione | 810.38 405.70 | (400 MHz, CDCl3): δ 8.73 (br, 1H), 8.71 (s. 1H), 8.47 (s, 1H), 8.04 (d, J = 5.6 Hz, 1H), 7.78 (d, J = 8.4 Hz, 1H), 7.66 (s, 1H), 7.35 (s, 1H), 7.20-7.18 (m, 1H), 6.06 (d, J = 5.6 Hz, 1H), 4.97-4.93 (m, 2H), 4.79 (s, 2H), 4.39-4.36 (m, 2H), 4.21-4.19 (m, 2H), 3.64-3.61 (m, 2H), 3.50-3.48 (m, 3H), 3.41 (s, 3H), 2.88-2.82 (m, 5H), 2.61-2.52 (m, 10H), 2.14-2.11 (m, 1H), 2.09-1.96 (m, 2H), | Synthesis of example 76 as described |

FIG. 2 (continued)

| Ex. # | Structure | Name | (M+H)+ | H1-NMR | Synthesis |
|---|---|---|---|---|---|
| 77 | 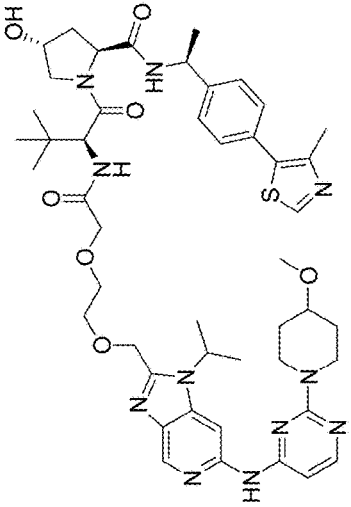 | (2S,4R)-4-hydroxy-1-[(2S)-2-(2-{2-[(6-{[2-(4-methoxypiperidin-1-yl)pyrimidin-4-yl]amino}-1-(propan-2-yl)-1H-imidazo[4,5-c]pyridin-2-yl)methoxy]ethoxy}acetamido)-3,3-dimethylbutanoyl]-N-[(1S)-1-{4-(4-methyl-1,3-thiazol-5-yl)phenyl]ethyl}pyrrolidine-2-carboxamide | 926.37 463.68 | (400 MHz, CDCl3): δ 8.88 (s, 1H), 8.64 (s, 1H), 8.53 (s, 1H), 7.97 (d, J = 6.0 Hz, 1H), 7.40-7.46 (m, 4H), 6.35 (d, J = 5.6 Hz, 1H), 5.11-5.16 (m, 1H), 4.95-5.02 (m, 3H), 4.93-4.94 (m, 1H), 4.71(s, 1H), 4.50-4.58 (m, 1H), 4.44 (s, 1H), 4.30-4.33 (m, 2H), 4.06 (s, 2H), 3.75-3.84 (m. 6H), 3.40-3.61 (m, 3H), 3.42 (s, 3H), 2.48 (s, 3H), 2.18-2.22 (m, 1H), 1.92-2.06 (m, 3H), 1.73 (d, J = 6.8 Hz, 6H), 1.53-1.62 (m, 2H), 1.49 (d, J = 7.2 Hz, 3H), 1.04 (s, 9H). | following route described for example 81 |
| 78 | 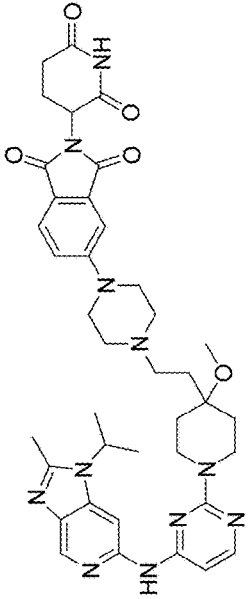 | 2-(2,6-dioxopiperidin-3-yl)-5-(4-{2-[4-methoxy-1-(4-{[2-methyl-1-(propan-2-yl)-1H-imidazo[4,5-c]pyridin-6-yl]amino}pyrimidin-2-yl)piperidin-4-yl]ethyl}piperazin-1-yl)-2,3-dihydro-1H-isoindole-1,3-dione | 750.37 375.69 | (400 MHz, DMSO-d6): δ: 11.08 (s, 1H), 9.69 (s, 1H), 8.50 (s, 1H), 8.40 (s, 1H), 7.95 (d, J = 5.6 Hz, 1H), 7.67 (d, J = 7.2 Hz, 1H), 7.33 (s, 1H), 7.25 (d, J = 7.2 Hz, 1H), 6.39 (d, J = 4.0 Hz, 1H), 5.04-5.09 (m, 1H), 4.71(t, J = 6.4 Hz, 1H), 4.34 (d, J = 12.4 Hz, 2H), 3.42 (s, 4H), 3.21-3.24 (m, 3H), 3.15 (s, 3H), 3.31 (s, 3H), 2.55 (s, 3H), | Synthesis of example 78 as described |

| Ex. # | Structure | Name | (M+H)⁺ | H¹-NMR | Synthesis |
|---|---|---|---|---|---|
| | | | | 2.37 (s, 3H), 1.98-2.02 (m, 2H), 1.71-1.78 (m, 4H), 1.51 (s, 6H). | |
| 79 | 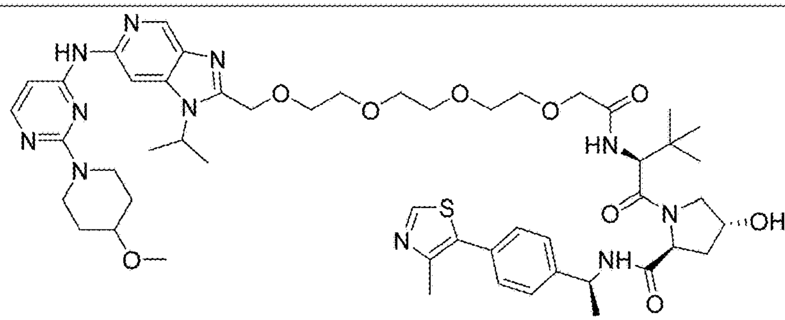 | (2S,4R)-4-hydroxy-1-[(2S)-2-[1-(6-{[2-(4-methoxypiperidin-1-yl)pyrimidin-1-yl]amino}-1-(propan-2-yl)-1H-imidazo[4,5-c]pyridin-2-yl)-2,5,8,11-tetraoxatridecan-13-amido]-3,3-dimethylbutanoyl]-N-[(1S)-1-{4-(4-methyl-1,3-thiazol-5-yl)phenyl]ethyl]pyrrolidine-2-carboxamide | 1014.42 1036.40 [M+Na]⁺ 507.70 | (400 MHz, CDCl3): δ 8.56 — 8.61 (m, 3H), 8.06 — 8.07 (m, 1H), 7.29 — 7.31 (m, 5H), 6.46 (s, 1H), 5.28 — 5.38 (m, 1H), 4.99 — 5.01 (m, 1H), 4.82 — 4.91 (m, 1H), 4.79 (s, 2H), 4.63 — 4.65 (m, 1H), 4.45 — 4.48 (m, 2H), 3.93 — 4.07 (m, 6H), 3.47 — 3.63 (m, 17H), 3.32 (s, 3H), 2.45 (s, 4H), 1.87 — 1.91 (m, 3H), 1.59 — 1.67 (m, 8H), 1.39 — 1.40 (m, 3H), 1.19 — 1.24 (m, 5H), 0.97 (s, 10H). | following route described for example 81 |

FIG. 2 (continued)

| Ex. # | Structure | Name | (M+H)+ | H1-NMR | Synthesis |
|---|---|---|---|---|---|
| 80 | 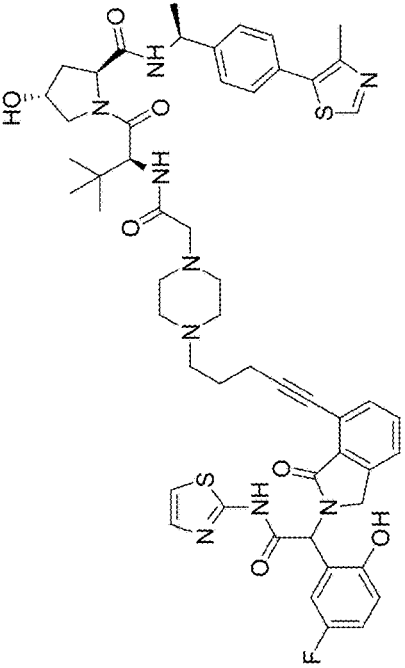 | (2S,4R)-1-[(2S)-2-[2-[4-(5-{2-[(5-fluoro-2-hydroxyphenyl)[(1,3-thiazol-2-yl)carbamoyl]methyl]-3-oxo-2,3-dihydro-1H-isoindol-4-yl)pent-4-yn-1-yl)piperazin-1-yl]acetamido]-3,3-dimethylbutanoyl]-4-hydroxy-N-[(1S)-1-[4-(4-methyl-1,3-thiazol-5-yl)phenyl]ethyl]pyrrolidine-2-carboxamide | 1018.39 509.70 | (400 MHz, DMSO-d6): δ 0.96 (s, 9H), 1.34-1.36 (m, 3H), 1.45-1.51 (m, 1H), 1.74-1.83 (m, 1H), 1.96-2.06 (m, 2H), 2.11-2.21 (m, 2H), 2.44-2.45 (m, 3H), 3.00-3.16 (m, 6H), 3.61-3.62 (m, 1H), 3.67-3.73 (m, 2H), 3.81-3.98 (m, 4H), 4.23-4.29 (m, 1H), 4.42-4.46 (m, 1H), 4.52-4.65 (m, 2H), 4.88-4.93 (m, 1H), 5.14 (s, 1H), 6.32 (s, 1H), 6.84-6.87 (m, 1H), 6.99-7.02 (m, 1H), 7.13 (s, 2H), 7.26 (s, 2H), 7.36-7.42 (m, 4H), 7.47-7.49 (m, 1H), 7.52-7.54 (m, 1H), 7.59-7.61 (m, 1H), 7.66-7.70 (m, 1H), 7.81-7.83 (m, 1H), 8.18 (s, 1H), 8.39-8.40 (m, 1H), 8.98 (s, 1H), 10.13 (s, 1H), 12.64 (s, 1H). | Synthesis of example 80 as described |

FIG. 2 (continued)

| Ex. # | Structure | Name | (M+H)⁺ | H¹-NMR | Synthesis |
|---|---|---|---|---|---|
| 81 | 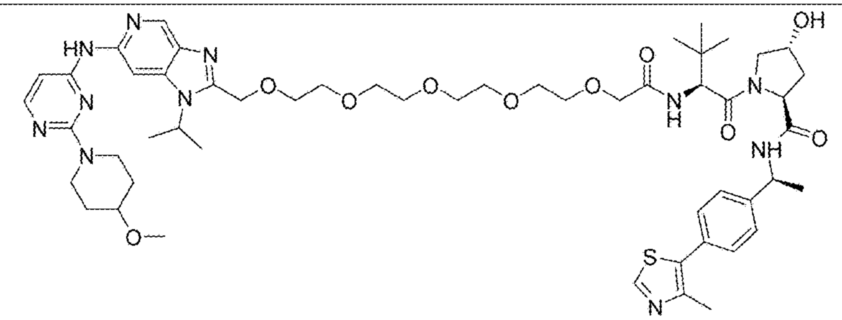 | (2S,4R)-4-hydroxy-1-[(2S)-2-[1-(6-{[2-(4-methoxypiperidin-1-yl)pyrimidin-4-yl]amino}-1-(propan-2-yl)-1H-imidazo[4,5-c]pyridin-2-yl)-2,5,8,11,14-pentaoxahexadecan-16-amido]-3,3-dimethylbutanoyl]-N-[(1S)-1-{4-(4-methyl-1,3-thiazol-5-yl)phenyl]ethyl}pyrrolidine-2-carboxamide | 1080.43 [M+Na]⁺ 1058.44 529.71 | (400 MHz, CD3OD): δ: 8.77(s, 1H), 8.60(s, 1H), 8.45 (s, 1H), 8.24(br.s, 1H), 7.77(d, J = 4.0 Hz, 1H), 7.52(d, J = 12.0 Hz, 1H), 7.28-7.33(m, 4H), 4.88-4.94(m, 3H), 4.76(d, J = 12.0 Hz, 1H), 4.56-4.59(m, 1H), 4.47(s, 1H), 3.91-4.00(m, 2H), 3.51-3.66(m, 20H), 3.31(s, 3H), 2.37(s, 3H), 2.09-2.16(m, 2H), 1.86-1.89(m, 3H), 1.60(s, 1H), 1.58(s, 1H), 1.39(d, J = 8.0 Hz, 3H), 0.93(s, 9H) | Synthesis of example 81 as described |
| 82 | 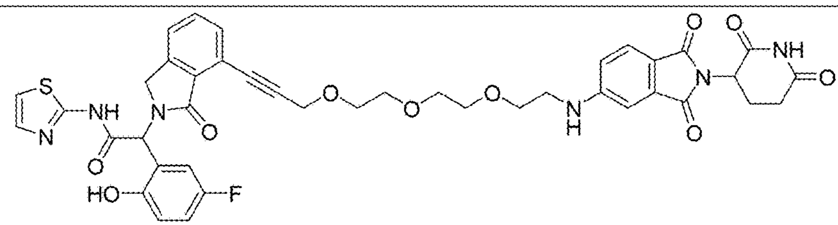 | 2-(7-{1-[2-(2,6-dioxopiperidin-3-yl)-1,3-dioxo-2,3-dihydro-1H-isoindol-5-yl]-4,7,10-trioxa-1-azatridec-12-yn-13-yl}-1-oxo-2,3-dihydro-1H-isoindol-2-yl)-2-(5-fluoro-2-hydroxyphenyl)-N-(1,3-thiazol-2- | 825.22 413.11 | (400 Hz, DMSO-d6): δ 1.41-1.47 (m, 1H) 1.92-2.00 (m, 4H), 2.33 (s, 1H), 2.58-2.68(m, 1H), 2.83-2.91(m, 1H), 3.55-3.58(m, 6H), 3.66-3.76 (m, 2H), 3.91 (d, J = 17.6 Hz, 1H), 4.43 (s, 2H), 4.56 (d, J = 18.0 Hz, 1H), 5.00-5.05 (m, 1H), 5.31-5.33 (m, 1H), 6.27 (s, 1H), 6.83-6.92(m, 2H), 6.99 (s, 1H), 7.10-7.41 (m, 4H), 7.47-7.58 (m, 4H), 9.97 (s, 1H), | Synthesis of example 82 as described |

| Ex. # | Structure | Name | (M+H)+ | H1-NMR | Synthesis |
|---|---|---|---|---|---|
| 83 | 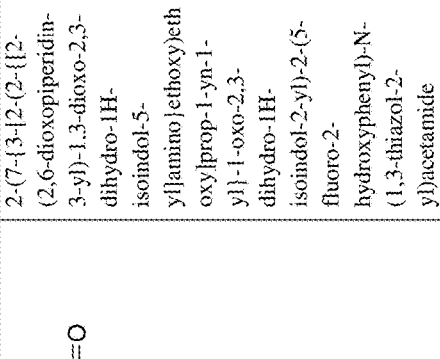 | 2-(7-{3-[2-(2-{[2-(2,6-dioxopiperidin-3-yl)-1,3-dioxo-2,3-dihydro-1H-isoindol-5-yl]amino}ethoxy)ethoxy]prop-1-yn-1-yl}-1-oxo-2,3-dihydro-1H-isoindol-2-yl)-2-(5-fluoro-2-hydroxyphenyl)-N-(1,3-thiazol-2-yl)acetamide | 781.12 391.05 | (400 Hz. CDCl3): δ 1.43-1.46 (m, 1H), 1.63-1.68 (m, 1H), 1.96-2.01 (m, 3H), 2.18-2.25 (m, 1H), 2.82-2.90(m, 1H), 3.59-3.64(m, 3H), 3.73-3.75 (m, 2H), 3.94 (d, J = 17.6 Hz, 2H), 4.45 (s, 2H), 4.56 (d, J = 17.6 Hz, 1H), 5.00-5.05 (m, 1H), 6.26(s, 1H), 6.84-6.92(m, 3H), 6.99-7.00 (m, 1H), 7.08-7.22 (m, 2H), 7.26-7.29 (m, 1H), 7.47-7.59 (m, 5H), 9.97 (s, 1H), 11.05 (s, 1H), 12.60 (s, 1H). | following route described for example 82 |
| 84 | 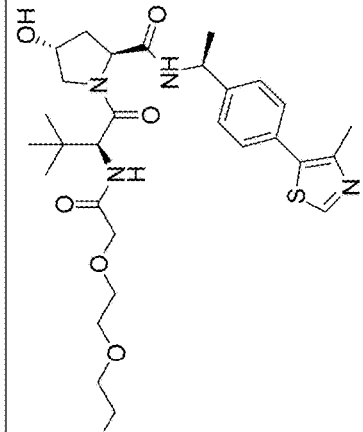 | (2S,4R)-1-[(2S)-2-[2-(2-{2-[(3-{2-[(5-fluoro-2-hydroxyphenyl)(1,3-thiazol-2-yl)carbamoyl]methyl]-3-oxo-2,3-dihydro-1H-isoindol-4-yl}prop-2-yn-1-yl)oxy]ethoxy}ethoxy)acetamido]-3,3-dimethylbutanoyl]-4-hydroxy-N-[(1S)- | 1010.26 505.62 | (400 MHz, DMSO-d6): δ 0.93 (s, 9H), 1.36-1.46 (m, 3H), 1.77-1.81 (m, 1H), 1.97-2.05 (m, 2H), 2.45 (s, 3H), 3.56-3.66 (m, 6H), 3.69-3.79 (m, 2H), 3.87-4.03 (m, 3H), 4.21-4.34 (m, 1H), 4.45 (s, 3H), 4.51-4.59 (m, 2H), 4.84-4.93 (m, 1H), 5.22-5.37(m, 3H), 6.28 (s, 1H), 6.85-6.92 (m, 2H), 7.09-7.12 (m, 1H), 7.26 (s, 1H),7.35-7.61 (m, 9H), 8.42-8.44 (m, 1H), | following route described for examples 80 and 82 |

| Ex. # | Structure | Name | (M+H)+ | H¹-NMR | Synthesis |
|---|---|---|---|---|---|
| | | 1-[4-(4-methyl-1,3-thiazol-5-yl)phenyl]ethyl]pyrrolidine-2-carboxamide | | 8.98 (s, 1H), 9.96 (s, 1H), 12.60 (s, 1H). | |
| 85 | 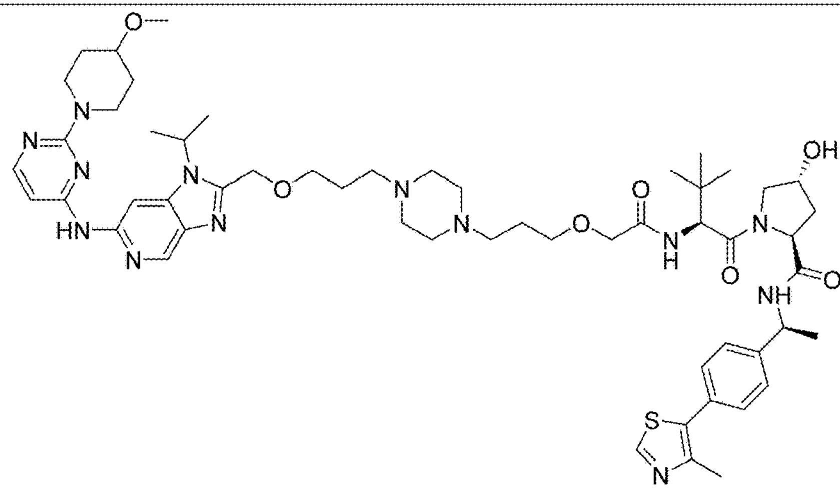 | (2S,4R)-4-hydroxy-1-[(2S)-2-{2-[3-(4-{3-[(6-{[2-(4-methoxypiperidin-1-yl)pyrimidin-4-yl]amino}-1-(propan-2-yl)-1H-imidazo[4,5-c]pyridin-2-yl)methoxy]propyl}piperazin-1-yl)propoxy]acetamido}-3,3-dimethylbutanoyl]-N-[(1S)-1-[4-(4-methyl-1,3-thiazol-5-yl)phenyl]ethyl]pyrrolidine-2-carboxamide | 1066.25 533.67 | (400 MHz, CDCl3): δ 8.67 (d, J = 4.4 Hz, 2H), 8.45 (s, 1H), 8.04 (d, J = 5.6 Hz, 1H), 7.46 (d, J = 7.6 Hz, 1H), 7.37-7.42 (m, 6H), 7.18 (d, J = 8.4 Hz, 1H), 6.04 (d, J = 5.2 Hz, 1H), 5.34-5.35 (m, 1H), 5.02-5.12 (m, 1H), 4.85- 4.95 (m, 1H), 4.75 (s, 3H), 4.51-4.53 (m, 2H), 4.36-4.39 (m, 2H), 4.12-4.15 (m, 1H), 3.93-3.95 (m, 2H). 3.46-3.56 (m, 8H), 3.42 (s, 3H), 2.53 (s, 3H), 2.41-2.45 (m, 12H), 2.20-2.22 (m, 1H), 1.65-1.67 (m, 5H), 1.64 (s, 9H), 1.47 (d, J = 4.8 Hz, 3H), 1.06 (s, 9H). | Synthesis of example 85 as described |

FIG. 2 (continued)

| Ex. # | Structure | Name | (M+H)+ | H1-NMR | Synthesis |
|---|---|---|---|---|---|
| 86 | 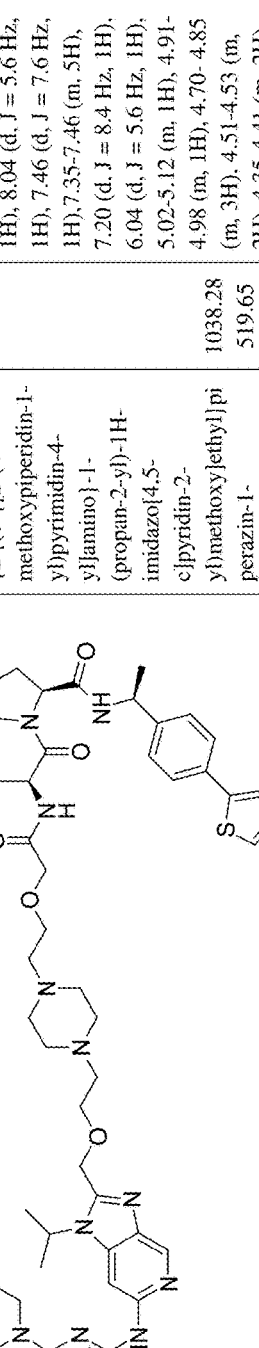 | (2S,4R)-4-hydroxy-1-[(2S)-2-{2-[2-(4-{2-[(6-{[2-(4-methoxypiperidin-1-yl)pyrimidin-4-yl]amino}-1-(propan-2-yl)-1H-imidazo[4,5-c]pyridin-2-yl)methoxy]ethyl}piperazin-1-yl)ethoxy]acetamido}-3,3-dimethylbutanoyl]-N-[(1S)-1-{4-(4-methyl-1,3-thiazol-5-yl)phenyl]ethyl}pyrrolidine-2-carboxamide | 1038.28 519.65 | (400 MHz, CDCl3): δ 8.67 (d, J = 2.4 Hz, 2H), 8.44 (s, 1H), 8.04 (d, J = 5.6 Hz, 1H), 7.46 (d, J = 7.6 Hz, 1H), 7.35-7.46 (m, 5H), 7.20 (d, J = 8.4 Hz, 1H), 6.04 (d, J = 5.6 Hz, 1H), 5.02-5.12 (m, 1H), 4.91-4.98 (m, 1H), 4.70- 4.85 (m, 3H), 4.51-4.53 (m, 2H), 4.35-4.41 (m, 2H), 4.12-4.16 (m, 1H), 3.96-3.99 (m, 2H), 3.62-3.64 (m, 5H), 3.46-3.55 (m, 3H), 3.41 (s, 3H), 2.52 (s, 3H), 2.41-2.60 (m ,12H), 1.91 -2.06 (m, 3H), 1.65 (s, 9H), 1.47 (d, J = 6.8 Hz, 3H), 1.06 (s, 9H). | following route described for example 85 |
| 87 | 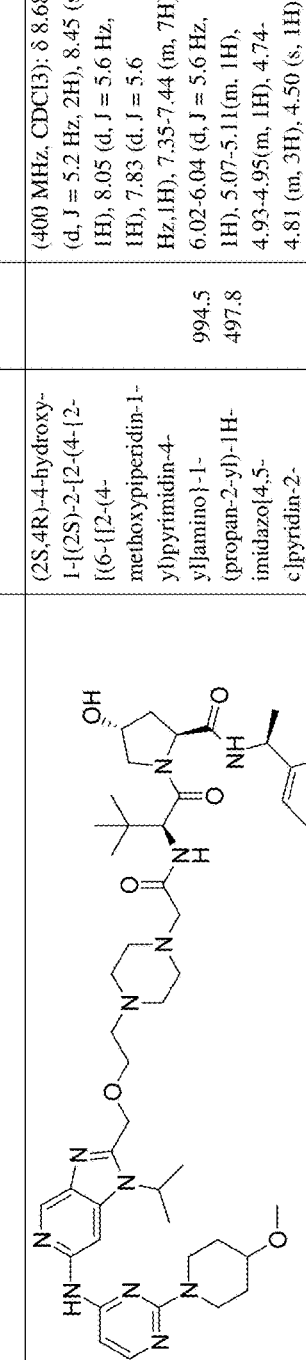 | (2S,4R)-4-hydroxy-1-[(2S)-2-{2-(4-{2-[(6-{[2-(4-methoxypiperidin-1-yl)pyrimidin-4-yl]amino}-1-(propan-2-yl)-1H-imidazo[4,5-c]pyridin-2-yl)methoxy]ethyl}piperazin-1-yl)acetamido]-3,3-dimethylbutanoyl]- | 994.5 497.8 | (400 MHz, CDCl3): δ 8.68 (d, J = 5.2 Hz, 2H), 8.45 (s, 1H), 8.05 (d, J = 5.6 Hz, 1H), 7.83 (d, J = 5.6 Hz,1H), 7.35-7.44 (m, 7H), 6.02-6.04 (d, J = 5.6 Hz, 1H), 5.07-5.11 (m, 1H), 4.93-4.95(m, 1H), 4.74-4.81 (m, 3H), 4.50 (s, 1H), 4.32-4.43 (m, 3H), 4.22 (d, J = 6.4 Hz, 1H), 3.52-3.65 (m, 3H), 3.43-3.51 (m, 3H), 3.42 (s, 3H), 3.01 (d, J = | following route described for example 85 |

FIG. 2 (continued)

| Ex. # | Structure | Name | (M+H)⁺ | H¹-NMR | Synthesis |
|---|---|---|---|---|---|
| 88 | 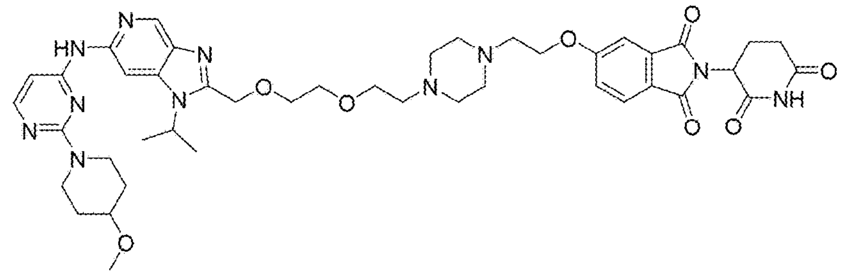 | N-[(1S)-1-[4-(4-methyl-1,3-thiazol-5-yl)phenyl]ethyl]pyrrolidine-2-carboxamide | | 6.4 Hz, 3H), 2.53-2.60 (m, 12H), 1.95-2.12 (m, 3H), 1.62-1.67 (m, 10H) , 1.47 (d, J = 6.8 Hz, 3H), 1.06 (s, 9H). | |
|  | | 2-(2,6-dioxopiperidin-3-yl)-5-{2-[4-(2-{2-[(6-{[2-(4-methoxypiperidin-1-yl)pyrimidin-4-yl]amino}-1-(propan-2-yl)-1H-imidazo[4,5-c]pyridin-2-yl)methoxy]ethoxy}ethyl)piperazin-1-yl]ethoxy}-2,3-dihydro-1H-isoindole-1,3-dione | 854.14 427.62 | (400 MHz, CDCl3): δ 9.46 (s, 1H), 8.72 (s, 1H), 8.50 (s, 1H), 8.03 (d, J = 5.6 Hz, 1H), 7.97 (s, 1H), 7.77 (d, J = 8.4 Hz, 1H), 7.35 (s, 1H), 7.19-7.17 (m, 1H), 6.07 (d, J = 5.6 Hz, 1H), 4.96-4.94 (m, 2H), 4.82 (s, 2H), 4.39-4.35 (m, 2H), 4.20-4.18 (m, 2H), 3.64-3.60 (m, 6H), 3.50-3.48 (m, 3H), 3.41 (s, 3H), 2.88-2.78 (m, 5H), 2.60-2.53 (m, 10H), 2.14-2.11 (m, 1H), 2.09-1.98 (m, 2H), 1.67-1.65 (m, 8H). | following route described for example 76 |
| 89 | 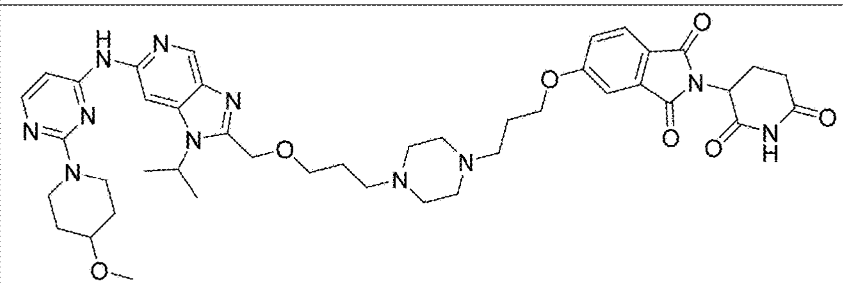 | 2-(2,6-dioxopiperidin-3-yl)-5-[3-(4-{3-[(6-{[2-(4-methoxypiperidin-1-yl)pyrimidin-4-yl]amino}-1-(propan-2-yl)-1H-imidazo[4,5-c]pyridin-2- | 838.38 419.68 | (400 MHz, CDCl3): δ 8.72 (s, 1H), 8.47 (s, 1H), 8.04 (d, J = 5.6 Hz, 1H), 7.77 (d, J = 8.4 Hz, 1H), 7.60 (s, 1H), 7.35 (d, J = 1.6 Hz, 1H), 7.19 (dd, J = 8.4, 2.0 Hz, 1H), 6.05 (d, J = 5.6 Hz ,1H), 4.91-4.93 (m. 2H), 4.76 (s, 2H), 4.36-4.40 (m, 2H), 4.14 (t, J = | following route described for example 76 |

| Ex. # | Structure | Name | (M+H)+ | H¹-NMR | Synthesis |
|---|---|---|---|---|---|
| 90 | 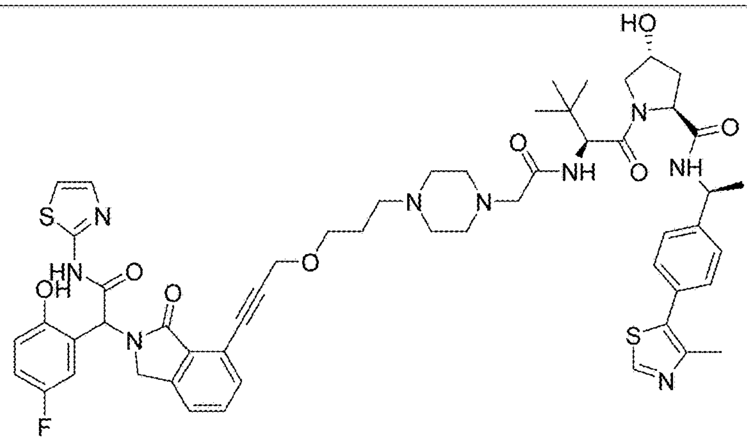 | (2S,4R)-1-[(2S)-2-[2-(4-{3-[(3-{2-[(5-fluoro-2-hydroxyphenyl)[(1,3-thiazol-2-yl)carbamoyl]methyl]-3-oxo-2,3-dihydro-1H-isoindol-4-yl}prop-2-yn-1-yl)oxy]propyl]piperazin-1-yl)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide | 1048.36 524.67 | (400 MHz, DMSO-d6): δ 0.93 (s, 9H), 1.37 (d, J = 6.8 Hz, 3H), 1.73-1.79 (m, 2H), 1.95-2.07 (m, 3H), 2.33-2.42 (m, 3H), 2.45 (s, 3H), 2.73-3.11 (m, 5H), 3.17 (d, J = 5.2 Hz, 1H), 3.54-3.70 (m, 4H), 3.94 (d, J = 17.6 Hz, 1H), 4.25-4.31 (m, 1H), 4.37-4.45 (m, 3H), 4.50 (d, J =9.6 Hz, 1H), 4.56 (d, J = 17.6 Hz, 1H), 4.85-4.91 (m, 1H), 5.13 (d, J =3.2 Hz, 1H), 6.26 (s, 1H), 6.86 (dd, J =2.8, 9.2 Hz, 1H), 6.90-6.94 (m, 1H), 7.09-7.14 (m, 1H), 7.27 (d, J = 3.2 Hz, 1H), 7.36 (d, J =8.4 Hz, 2H), 7.44 (d, J =8.0 Hz, 2H), 7.49 (d, J = 3.2 Hz, 1H), 7.52-7.59 (m, 3H), 7.68-7.75 (m, 1H), 8.42 (d, J =7.6 Hz, 1H), 8.98 (s, 1H), 9.99 (s, 1H). | following routes described for examples 80 and 82 |

FIG. 2 (continued)

| Ex. # | Structure | Name | (M+H)+ | H1-NMR | Synthesis |
|---|---|---|---|---|---|
| 91 | 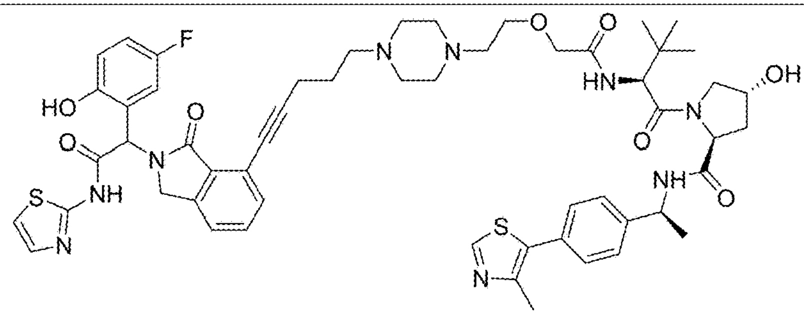 | (2S,4R)-1-[(2S)-2-(2-{2-[4-(5-{2-[(5-fluoro-2-hydroxyphenyl)[(1,3-thiazol-2-yl)carbamoyl]methyl]-3-oxo-2,3-dihydro-1H-isoindol-4-yl}pent-4-yn-1-yl)piperazin-1-yl]ethoxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide | 1062.4 531.7 | (400 MHz, DMSO-d6): δ 12.61 (s, 1H), 0.94 (s, 9H), 1.35-1.38 (m, 3H), 1.43-1.48 (m, 3H), 1.73-1.79 (m, 4H), 1.96-2.03 (m, 7H), 2.45 (s, 3H), 3.30 (s, 3H), 3.55-3.61 (m, 4H), 3.94-3.97 (m, 2H), 4.29 (br, 1H), 4.43-4.46 (m, 1H), 4.50-4.55(m, 2H), 4.87-4.92(m, 1H), 5.13 (s, 1H), 6.25 (s, 1H), 6.66 (br, 1H), 6.86 (d, J = 9.2 Hz, 1H), 6.91 (d, J = 8.8 Hz, 1H), 7.09-7.16 (m, 1H), 7.20 (br, 1H), 7.26 (d, J = 3.6 Hz, 1H), 7.36 (d, J = 8.4 Hz, 2H), 7.44 (t, J = 6.8 Hz, 3H), 7.48 (d, J = 3.6 Hz, 1H), 7.51 (d, J = 5.2 Hz, 1H), 7.54 (d, J = 7.2 Hz, 1H), 8.43 (d, J =4.8 Hz, 1H), 8.88 (s, 1H), 9.97 (br, 1H). | following routes described for examples 80 and 82 |

| Ex. # | Structure | Name | (M+H)+ | H1-NMR | Synthesis |
|---|---|---|---|---|---|
| 92 | 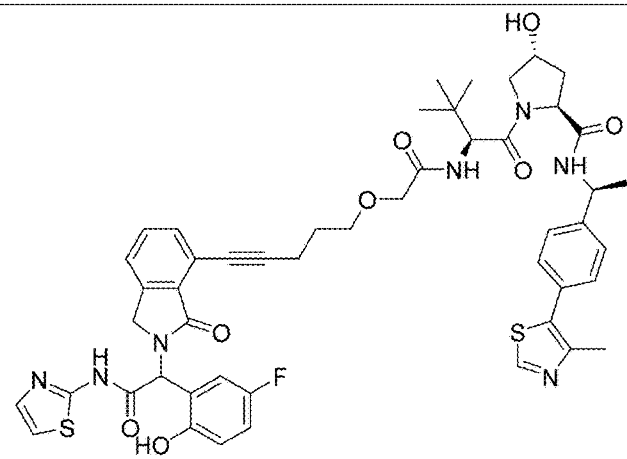 | (2S,4R)-1-[(2S)-2-{2-[(5-{2-[(5-fluoro-2-hydroxyphenyl)](1,3-thiazol-2-yl)carbamoyl]methyl}-3-oxo-2,3-dihydro-1H-isoindol-4-yl)pent-4-yn-1-yl]oxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide | 950.15 475.58 | (400 MHz, DMSOd-6): δ 0.92 (s, 9H), 1.36-1.48 (m, 3H), 1.73-1.78 (m, 1H), 1.86 (t, J =6.8 Hz, 2H), 2.06 (t, J =9.6 Hz, 1H), 2.46 (s, 3H), 2.56 (t, J =7.2 Hz, 2H), 3.30-3.31 (m, 1H), 3.55-3.62 (m, 2H), 3.65-3.72 (m, 2H), 3.90-3.97 (m, 3H), 4.28 (br, 1H), 4.46 (t, J =8.4 Hz, 1H), 4.53-4.57 (m, 2H), 4.49 (t, J =7.2 Hz, 1H) 5.13 (d, J =3.6 Hz, 1H), 6.28 (d, J =4.4 Hz, 1H), 6.84-6.93 (m, 2H), 7.09-7.14 (m, 1H), 7.26 (d, J =3.2 Hz, 1H), 7.37 (d, J =8.4 Hz, 2H), 7.43-7.57 (m, 6H), 8.46, 8.48 (d, J =7.6 Hz, 1H), 8.99 (s, 1H), 9.97 (s, 1H), 12.60 (s, 1H). | following routes described for examples 80 and 82 |

| Ex. # | Structure | Name | (M+H)⁺ | H¹-NMR | Synthesis |
|---|---|---|---|---|---|
| 93 | 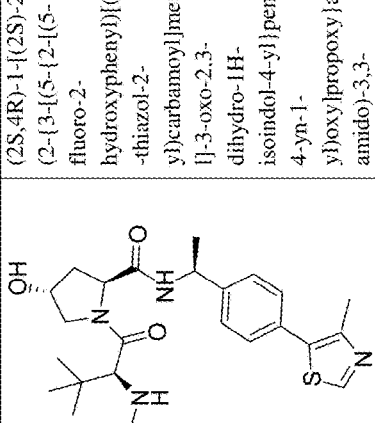 | (2S,4R)-1-{(2S)-2-(2-{3-[(5-{2-[(5-fluoro-2-hydroxyphenyl)](1,3-thiazol-2-yl)carbamoyl]methyl]-3-oxo-2,3-dihydro-1H-isoindol-4-yl]pent-4-yn-1-yl)oxy]propoxy)acetamido)-3,3-dimethylbutanoyl]-4-hydroxy-N-[(1S)-1-[4-(4-methyl-1,3-thiazol-5-yl)phenyl]ethyl]pyrrolidine-2-carboxamide | 1008.30 504.65 | (400 Hz, DMSO-d6): δ 0.93 (s, 9H), 1.36-1.47 (m, 3H), 1.73-1.86 (m, 5H), 2.03-2.12 (m, 1H), 2.45 (s, 3H), 3.43-3.56 (m, 9H), 3.85-3.95 (m, 3H), 4.28 (br, 1H), 4.23-4.56 (m, 3H), 4.88-4.92 (m, 1H), 5.14 (br, 1H), 6.26 (s, 1H), 6.84-6.92(m, 2H), 7.11-7.14 (m, 1H), 7.26-7.54 (m, 10H), 8.47-8.48 (m, 1H), 8.99 (s, 1H), 10.02 (br, 1H). | following routes described for examples 80 and 82 |
| 94 | 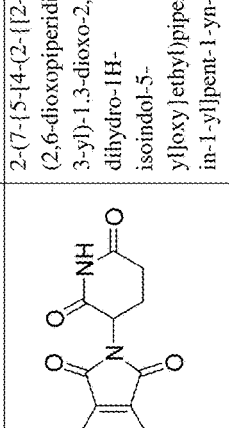 | 2-(7-{5-[4-(2-{[2-(2,6-dioxopiperidin-3-yl)-1,3-dioxo-2,3-dihydro-1H-isoindol-5-yl]oxy}ethyl)piperazin-1-yl]pent-1-yn-1-yl}-1-oxo-2,3-dihydro-1H-isoindol-2-yl)-2-(5-fluoro-2-hydroxyphenyl)-N-(1,3-thiazol-2- | 834.2 417.6 | (400 MHz, DMSO-d6): δ 1.41-1.49 (m, 2H), 1.91-2.09 (m, 6H), 2.10-2.33 (m, 2H), 2.33-2.39 (m, 2H), 2.560-2.66 (m, 2H), 2.68-2.80 (m, 1H), 2.88-3.07 (m, 3H), 3.43-3.65 (m, 3H), 3.95 (d, J = 17.2 Hz, 1H), 4.23-4.32 (m, 1H), 4.55 (d, J = 17.6 Hz, 1H), 4.09-5.15 (m, 1H), 6.25 (s, 1H), 6.62-6.70 (m, 1H), 6.84-6.98 (m, 2H), 7.10-7.15 (m, 1H), 7.22- | following routes described for examples 80 and 82 |

FIG. 2 (continued)

| Ex. # | Structure | Name | (M+H)⁺ | H¹-NMR | Synthesis |
|---|---|---|---|---|---|
| | | yl)acetamide | | 7.29 (m, 1H), 7.35-7.41 (m, 1H), 7.43-7.50 (m, 2H), 7.51-7.61 (m, 2H), 7.86 (d, J = 8.0 Hz, 1H), 9.37-9.50 (m, 1H), 10.02 (s, 1H), 11.11 (s, 1H). | |
| 95 | 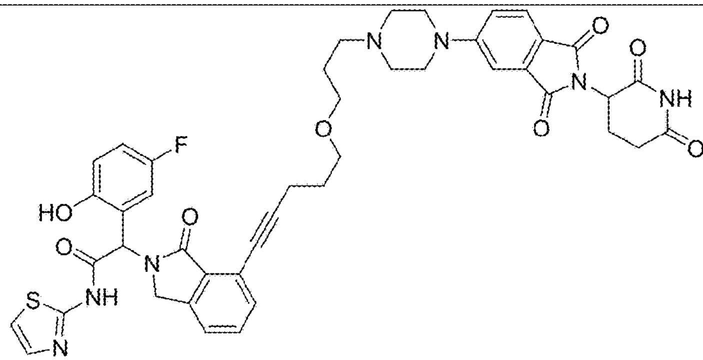 | 2-[7-[5-(3-{4-[2-(2,6-dioxopiperidin-3-yl)-1,3-dioxo-2,3-dihydro-1H-isoindol-5-yl]piperazin-1-yl}propoxy)pent-1-yn-1-yl]-1-oxo-2,3-dihydro-1H-isoindol-2-yl]-2-(5-fluoro-2-hydroxyphenyl)-N-(1,3-thiazol-2-yl)acetamide | 848.23 424.61 | (400 MHz, DMSO-d6): δ 1.22-1.23 (m, 1H), 1.60-1.81 (m, 4H), 1.98-2.05 (m, 1H), 2.30-2.46 (m, 4H), 2.52-2.56 (m, 4H), 2.56-2.68 (m, 2H), 2.83-2.93 (m, 1H), 3.26-3.32 (m, 2H), 3.34-3.40 (m, 2H), 3.44 (t, J = 6.0 Hz, 2H), 3.57 (t, J = 6.0 Hz, 2H), 3.90 (d, J = 17.6 Hz, 1H), 4.53 (d, J = 17.6 Hz, 1H), 5.05-5.11 (m, 1H), 5.76 (s, 1H), 6.26 (s, 1H), 6.83-6.93 (m, 2H), 7.20-7.30 (m, 2H), 7.43-7.55 (m, 3H), 9.99 (s, 1H), 11.12 (s, 1H), 12.62 (s, 1H). | following routes described for examples 80 and 82 |
| 96 | 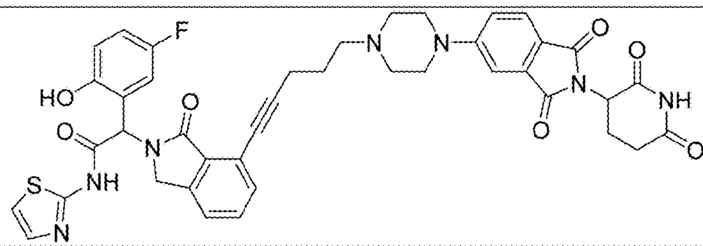 | 2-[7-(5-{4-[2-(2,6-dioxopiperidin-3-yl)-1,3-dioxo-2,3-dihydro-1H-isoindol-5-yl]piperazin-1-yl}pent-1-yn-1-yl)- | 790.2 395.6 | (400 MHz, DMSO-d6): δ 1.74-1.80 (m, 2H), 1.95-2.04 (m, 2H), 2.52-2.59 (m, 8H), 2.82-2.92 (m, 2H), 2.14-2.15 (m, 2H), 3.40 (s, 2H), 3.90 (d, J = 16.0 Hz, 1H), 4.50 (d, J = | following routes described for examples 80 and 82 |

FIG. 2 (continued)

| Ex. # | Structure | Name | (M+H)+ | H1-NMR | Synthesis |
|---|---|---|---|---|---|
| | | 1-oxo-2,3-dihydro-1H-isoindol-2-yl]-2-(5-fluoro-2-hydroxyphenyl)-N-(1,3-thiazol-2-yl)acetamide | | 20.0 Hz, 1H), 5.03-5.09 (m, 1H), 6.24 (s, 1H), 6.84-6.85 (m, 1H), 6.91-6.94 (m, 1H), 7.07-7.26 (m, 5H), 7.44-7.49 (m, 4H), 7.67-7.68 (m, 1H), 10.02 (s, 1H), 11.07 (s, 1H), 12.62 (s, 1H). | |
| 97 | 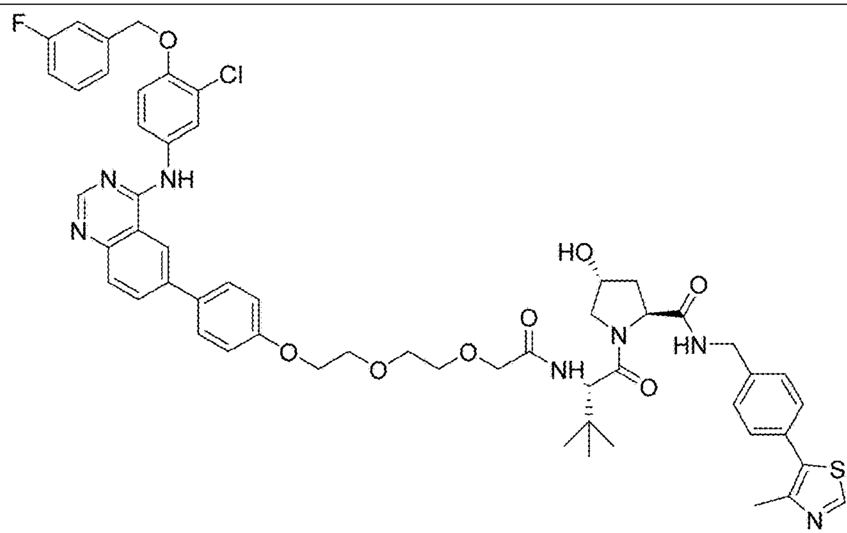 | (2S,4R)-1-((S)-2-(2-(2-(2-(4-(4-((3-chloro-4-((3-fluorobenzyl)oxy)phenyl)amino)quinazolin-6-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide | 1030.4 | (500 MHz, DMSO-d6) δ 9.87 (s, 1H), 8.95 (s, 1H), 8.72 (s, 1H), 8.57 (d, J = 2.6 Hz, 2H), 8.13 (dd, J = 8.7, 1.9 Hz, 1H), 8.02 (d, J = 2.4 Hz, 1H), 7.81 (dd, J = 8.6, 4.9 Hz, 3H), 7.76 (dd, J = 9.0, 2.6 Hz, 1H), 7.55 – 7.24 (m, 9H), 7.18 (t, J = 8.6 Hz, 1H), 7.10 (d, J = 8.7 Hz, 2H), 5.26 (s, 2H), 5.15 (d, J = 3.4 Hz, 1H), 4.58 (d, J = 9.6 Hz, 1H), 4.50 – 4.22 (m, 5H), 4.19 (t, J = 4.6 Hz, 2H), 4.00 (s, 2H), 3.89 – 3.77 (m, 2H), 3.75 – 3.54 (m, 6H), 2.41 (s, 3H), 2.11 – 2.01 (m, 1H), 1.95 – 1.87 (m, 1H), 0.95 (s, 9H). | Synthesis of example 97 as described |

FIG. 2 (continued)

| Ex. # | Structure | Name | (M+H)+ | H1-NMR | Synthesis |
|---|---|---|---|---|---|
| 98 |  | (2R,4S)-1-((S)-2-(2-(2-(2-(4-(4-((3-chloro-4-((3-fluorobenzyl)oxy)phenyl)amino)quinazolin-6-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide | 1030.38 | (500 MHz, CDCl3) δ 8.67 (s, 1H), 8.62 (s, 1H), 8.54 (s, 1H), 7.96 (dd, J = 8.7, 1.7 Hz, 1H), 7.91 (d, J = 8.6 Hz, 1H), 7.84 (dd, J = 8.8, 2.6 Hz, 1H), 7.71 (d, J = 2.5 Hz, 1H), 7.56 (t, J = 6.8 Hz, 3H), 7.34 (dd, J = 8.0, 6.2 Hz, 2H), 7.22 (t, J = 9.3 Hz, 2H), 7.14 (t, J = 8.3 Hz, 4H), 7.07 – 6.99 (m, 3H), 6.96 (d, J = 8.9 Hz, 1H), 5.14 (s, 2H), 4.88 (dd, J = 8.7, 5.0 Hz, 1H), 4.62 (p, J = 5.4 Hz, 1H), 4.36 (dt, J = 15.4, 7.3 Hz, 2H), 4.29 (d, J = 6.6 Hz, 1H), 4.17 – 4.06 (m, 5H), 3.91 – 3.81 (m, 3H), 3.73 – 3.58 (m, 4H), 3.47 – 3.36 (m, 2H), 2.41 (s, 3H), 2.38 (t, J = 5.3 Hz, 1H), 2.27 (ddd, J = 13.8, 8.7, 5.9 Hz, 1H), 1.12 (s, 9H). | Following routes described for examples 97 and 320 |

FIG. 2 (continued)

| Ex. # | Structure | Name | (M+H)⁺ | H¹-NMR | Synthesis |
|---|---|---|---|---|---|
| 99 | 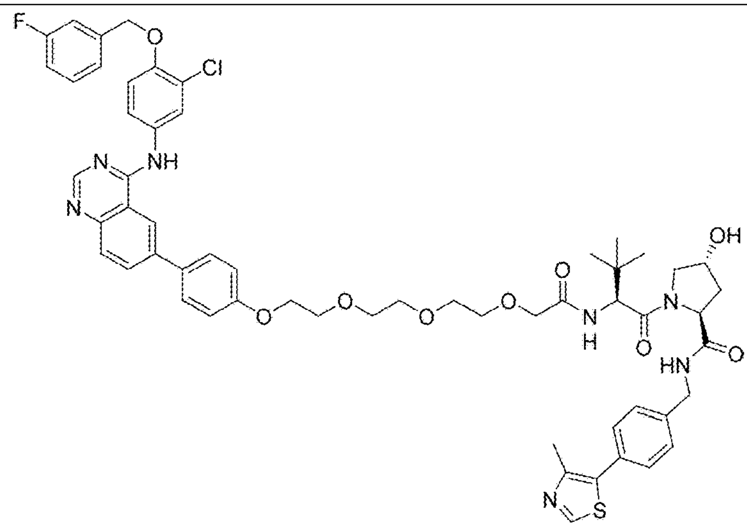 | (2S,4R)-1-((S)-2-(tert-butyl)-14-(4-(4-((3-chloro-4-((3-fluorobenzyl)oxy)phenyl)amino)quinazolin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide | 1074.42 | (400 MHz, DMSO-d6) δ 9.87 (s, 1H), 8.95 (s, 1H). 8.72 (s, 1H), 8.59 (t, J = 6.0 Hz, 1H), 8.55 (s, 1H). 8.13 (dd, J = 8.7, 1.9 Hz. 1H), 8.00 (d, J = 2.5 Hz, 1H), 7.89 – 7.76 (m, 3H), 7.73 (dd, J = 9.0, 2.6 Hz, 1H), 7.54 – 7.23 (m, 8H), 7.22 – 7.12 (m, 1H), 7.09 (d, J = 8.8 Hz, 2H), 5.24 (s, 2H), 5.15 (d, J = 3.5 Hz, 1H), 4.55 (d, J = 9.6 Hz, 1H), 4.48 – 4.18 (m, 5H), 4.18 – 4.06 (m, 2H), 3.95 (s, 2H), 3.80 – 3.69 (m, 2H), 3.69 – 3.51 (m, 8H), 2.41 (s, 3H), 2.08 – 2.00 (m, 1H), 1.93 – 1.82 (m, 1H), 0.92 (s, 9H). | Following routes described for examples 97 and 320 |

FIG. 2 (continued)

| Ex. # | Structure | Name | (M+H)+ | H1-NMR | Synthesis |
|---|---|---|---|---|---|
| 100 | 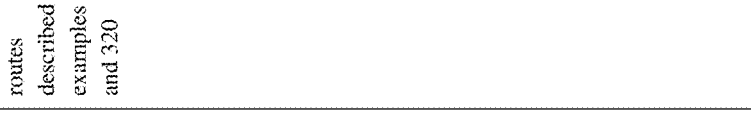 | (2S,4S)-1-((S)-2-(tert-butyl)-14-(4-(4-((3-fluorobenzyl)oxy)phenyl)amino)quinazolin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide | 1074.39 | (400 MHz, DMSO-d6) δ 9.95 (s, 1H), 9.04 (s, 1H), 8.84 – 8.77 (m, 1H), 8.73 (t, J = 6.0 Hz, 1H), 8.64 (s, 1H), 8.22 (dd, J = 8.8, 1.8 Hz, 1H), 8.10 (d, J = 2.6 Hz, 1H), 7.89 (dd, J = 8.8, 1.8 Hz, 3H), 7.83 (dd, J = 9.0, 2.6 Hz, 1H), 7.65 – 7.30 (m, 9H), 7.25 (td, J = 8.8, 8.3, 2.6 Hz, 1H), 7.18 (d, J = 8.8 Hz, 2H), 5.51 (d, J = 7.2 Hz, 1H), 5.33 (s, 2H), 4.59 (d, J = 9.2 Hz, 1H), 4.52 – 4.41 (m, 2H), 4.40 – 4.25 (m, 2H), 4.26 – 4.19 (m, 2H), 4.03 (s, 2H), 3.99 – 3.91 (m, 1H), 3.88 – 3.80 (m, 2H), 3.68 (ddt, J = 6.7, 5.2, 3.3 Hz, 8H), 3.59 – 3.44 (m, 1H), 2.50 (s, 3H), 2.44 – 2.35 (m, 1H), 1.81 (dt, J = 12.4, 6.1 Hz, 1H), 1.03 (s, 9H). | Following routes described for examples 97 and 320 |

FIG. 2 (continued)

| Example | Structure | Name | (M+H)+ | H¹-NMR | Synthesis |
|---|---|---|---|---|---|
| 101 | 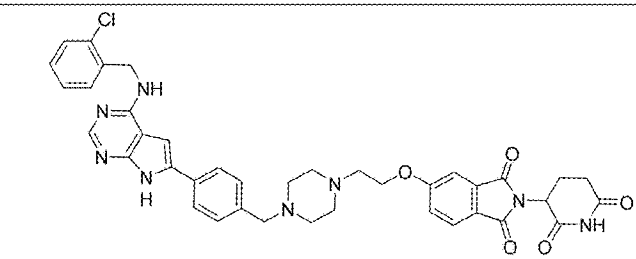 | 5-(2-(4-(4-(4-((2-chlorobenzyl)amino)-7H-pyrrolo[2,3-d]pyrimidin-6-yl)benzyl)piperazin-1-yl)ethoxy)-2-(2,6-dioxopiperidin-3-yl)isoindoline-1,3-dione | 732.77 366.94 | (400 MHz, DMSO-d6): δ 12.09 (s, 1H), 11.12 (s, 1H), 8.10 (s, 1H), 8.04 (s, 1H), 7.83 (d, J = 8.8 Hz, 1H), 7.74 (d, J = 7.6 Hz, 2H), 7.46 (d, J = 9.6 Hz, 2H), 7.28-7.35 (m, 6H), 7.01 (s, 1H), 5.14 (d, J = 5.6 Hz, 1H), 5.10 (d, J = 5.2 Hz, 2H), 4.78 (d, J = 5.2 Hz, 2H), 4.28 (s, 2H), 3.48 (s, 2H), 2.33-2.89 (m, 10H). | following route described for example 102 |
| 102 | 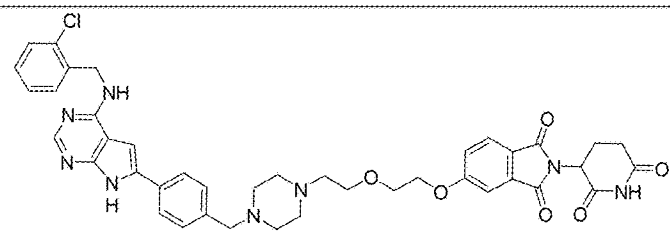 | 5-(2-(2-(4-(4-((2-chlorobenzyl)amino)-7H-pyrrolo[2,3-d]pyrimidin-6-yl)benzyl)piperazin-1-yl)ethoxy)ethoxy)-2-(2,6-dioxopiperidin-3-yl)isoindoline-1,3-dione | 777.50 389.27 | (400 MHz, DMSO-d6): δ 12.09 (s, 1H), 8.18 (s, 1H), 8.10 (s, 1H), 8.05 (s, 1H), 7.74 (d, J = 7.2 Hz, 3H), 7.46 (d, J = 3.6 Hz, 1H), 7.35 (d, J = 8.0 Hz, 3H), 7.28-7.30 (m, 2H), 7.15-7.18 (m, 2H), 7.00 (s, 1H), 5.13-5.18 (m, 1H), 4.78 (d, J = | Synthesis of example 102 as described |

| Example | Structure | Name | (M+H)+ | H1-NMR | Synthesis |
|---|---|---|---|---|---|
| | | | | 5.2 Hz, 2H), 3.86-3.89 (m, 2H), 3.75-3.79 (m, 2H), 2.72-3.04 (m, 3H), 2.35-2.48 (m, 9H), 2.08-2.13 (m, 1H). | |
| 103 | 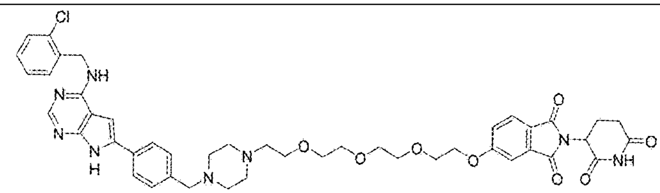 | 5-(2-(2-(2-(2-(4-(4-((2-chlorobenzyl)amino)-7H-pyrrolo[2,3-d]pyrimidin-6-yl)benzyl)piperazin-1-yl)ethoxy)ethoxy)ethoxy)ethoxy)-2-(2,6-dioxopiperidin-3-yl)isoindoline-1,3-dione | 864.86 432.78 | (400 MHz, DMSO-d6): δ 12.08 (s, 1H), 11.12 (s, 1H), 8.09 (s, 1H), 8.03 (s, 1H), 7.82 (d, J = 8.0 Hz, 1H), 7.73 (d, J = 8.0 Hz, 2H), 7.45 (s, 2H), 7.35 (s, 4H), 7.29-7.27 (m, 2H), 7.00 (s, 1H), 5.14-5.09 (m, 1H), 4.77 (s, 2H), 4.29 (s, 2H), 4.05-4.02 (m, 9H), 3.77 (s, 1H), 3.58-3.46 (m, 11H), 2.93-2.84 (m, 1H), 2.60-2.40 (m, 5H). | following route described for example 17 |

| Example | Structure | Name | (M+H)+ | H¹-NMR | Synthesis |
|---|---|---|---|---|---|
| 104 | 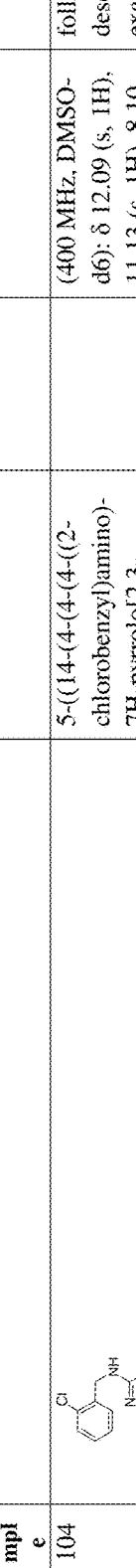 | 5-((14-(4-(4-(4-((2-chlorobenzyl)amino)-7H-pyrrolo[2,3-d]pyrimidin-6-yl)benzyl)piperazin-1-yl)-3,6,9,12-tetraoxatetradecyl)oxy)-2-(2,6-dioxopiperidin-3-yl)isoindoline-1,3-dione | 908.83 455.02 | (400 MHz, DMSO-d6): δ 12.09 (s, 1H), 11.13 (s, 1H), 8.10 (s, 1H), 8.05 (s, 1H), 7.83 (d, J = 8.0 Hz, 1H), 7.74 (d, J = 7.2 Hz, 2H), 7.45 (s, 2H), 7.36 (s, 4H), 7.29 (d, J = 3.2 Hz, 2H), 7.01 (s, 1H), 5.10-5.14 (m, 1H), 4.78 (d, J = 4.8 Hz, 2H), 4.30 (s, 2H), 3.77 (s, 2H), 3.49-3.58 (m, 17H), 2.86-2.89 (m, 1H), 2.39-2.57 (m, 8H), 2.04-2.05 (m, 1H). | following route described for example 17 |
| 105 | 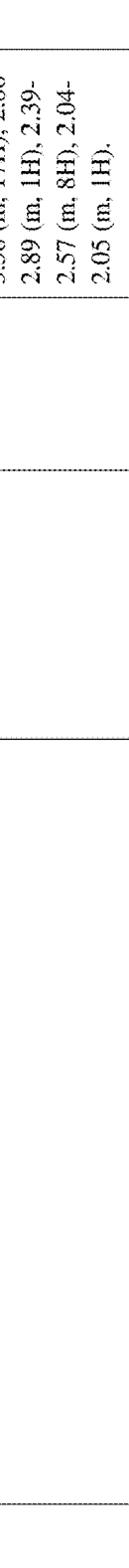 | 5-((17-(4-(4-(4-((2-chlorobenzyl)amino)-7H-pyrrolo[2,3-d]pyrimidin-6-yl)benzyl)piperazin-1-yl)-3,6,9,12,15-pentaoxaheptadecyl)oxy)-2-(2,6-dioxopiperidin-3-yl)isoindoline-1,3- | 952.48 974.43 [M+Na] 476.77 | (400 MHz, DMSO-d6): δ 12.08 (s, 1H), 11.12 (s, 1H), 8.10 (s, 1H), 8.04 (s, 1H), 7.83 (d, J = 8.4 Hz, 1H), 7.74 (d, J = 8.0 Hz, 2H), 7.46 (d, J = 9.6 Hz, 2H), 7.27-7.35 (m, 6H), 7.01 (s, 1H), 5.13 (d, J = | following route described for example 17 |

FIG. 2 (continued)

| Example | Structure | Name | (M+H)+ | H1-NMR | Synthesis |
|---|---|---|---|---|---|
| | | dione | | 5.2 Hz, 1H), 5.10 (d, J = 5.2 Hz, 2H), 4.78 (d, J = 5.2 Hz, 2H), 4.30 (s, 2H), 3.77 (s, 2H), 3.54-3.58 (m, 22H), 2.33-2.88 (m, 10H). | |
| 106 | 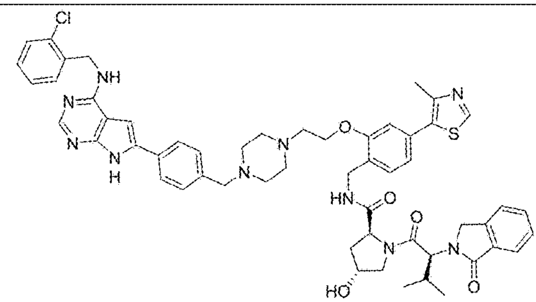 | (2S,4R)-N-(2-(2-(4-(4-(4-((2-chlorobenzyl)amino)-7H-pyrrolo[2,3-d]pyrimidin-6-yl)benzyl)piperazin-1-yl)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1007.38 504.20 | (400 MHz, CD3OD): δ 8.88(s, 1H), 8.09(s, 1H), 7.73-7.76 (m, 3H), 7.37-7.57 (m, 9H), 7.22-7.24 (m, 2H), 7.03-7.05 (m, 2H), 6.93 (s, 1H), 4.95 (s, 2H), 4.39-4.60 (m, 7H), 4.24 (s, 2H), 3.82-3.96 (m, 2H), 3.57 (s, 1H), 2.96 (s, 2H), 2.60-2.77 (m, 8H), 2.49 (s, 3H), 2.01-2.33 (m, 3H), 0.98 (d, J = 6.4 Hz, 3H), 0.78 (d, J = 6.4 Hz, 3H) | Synthesis of example 106 as descibed |

FIG. 2 (continued)

| Example | Structure | Name | (M+H)+ | H1-NMR | Synthesis |
|---|---|---|---|---|---|
| 107 | 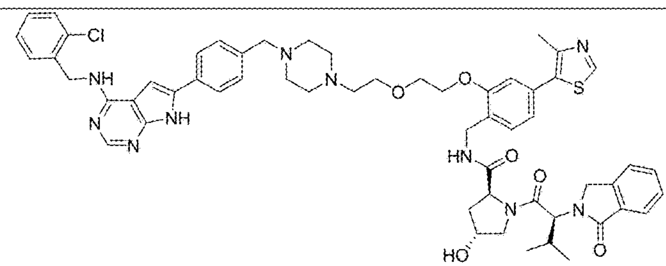 | (2S,4R)-N-(2-(2-(2-(4-(4-((2-chlorobenzyl)amino)-7H-pyrrolo[2,3-d]pyrimidin-6-yl)benzyl)piperazin-1-yl)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1051.39 526.20 | (400 MHz, MeOD): δ 8.86 (s, 1H), 8.10 (s, 1H), 7.72-7.76 (m, 3H), 7.37-7.57 (m, 9H), 7.23-7.25 (m, 2H), 7.01-7.05 (m, 2H), 6.92 (s, 1H), 4.43-4.57 (m, 6H), 4.24 (s, 2H), 3.72-3.85 (m, 4H), 3.70 (s, 2H), 3.52 (s, 2H), 2.61 (s, 3H), 2.43-2.55 (m, 6H), 2.01-2.33 (m, 3H), 1.03 (d, J = 6.4 Hz, 3H), 0.81 (d, J = 6.4 Hz, 3H). | following routes described for examples 106 and 108 |
| 108 | 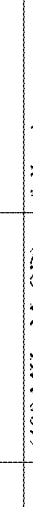 | (2S,4R)-N-(2-(2-(2-(4-(4-((2-chlorobenzyl)amino)-7H-pyrrolo[2,3-d]pyrimidin-6-yl)benzyl)piperazin-1-yl)ethoxy)ethoxy)-4-(4-methylthiazol-5-yl)benzyl)-4-hydroxy-1-((S)-3-methyl-2-(1- | 1094.50 547.76 | (400 MHz, CDCl3): δ 8.64 (s, 1H), 8.31 (s, 1H), 7.67 (d, J = 7.2 Hz, 3H), 7.46-7.47 (m, 1H), 7.30-7.41 (m, 8H), 7.20 (s, 2H), 6.94 (d, J = 5.6 Hz, 1H), 6.84 (s, 1H), 6.63 (s, 1H), 6.04 (s, 1H), 4.95 (d, J = 4.4 Hz, 2H), | Synthesis of example 108 as descibed |

FIG. 2 (continued)

| Example | Structure | Name | (M+H)+ | H1-NMR | Synthesis |
|---|---|---|---|---|---|
| | | oxoisoindolin-2-yl)butanoyl)pyrrolidine-2-carboxamide | | 4.14-4.79 (m, 10H), 3.46-3.85 (m, 13H), 2.48-2.65 (m, 16H), 1.99 (d, J = 6.0 Hz, 3H), 0.82 (d, J = 6.4 Hz, 3H) | |
| 109 | 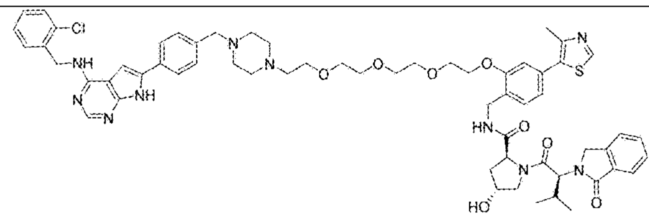 | (2S,4R)-N-(2-(2-(2-(2-(2-(4-(4-((2-chlorobenzyl)amino)-7H-pyrrolo[2,3-d]pyrimidin-6-yl)benzyl)piperazin-1-yl)benzyl)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1139.46 570.24 | (400 MHz, MeOD): δ 8.86 (s, 1H), 8.14 (s, 1H), 7.74-7.77 (m, 3H), 7.43-7.54 (m, 3H), 7.37-7.42 (m, 5H), 7.23-7.25 (m, 2H), 6.93-7.01 (m, 3H), 4.84-4.87 (m, 4H), 4.46-4.59 (m, 6H), 4.16 (d, J = 4 Hz, 2H), 3.70-4.02 (m, 4H), 3.57-3.66 (m, 13H), 2.48-2.83 (m, 13H), 2.02-2.28 (m, 2H), 1.05 (d, J = 6.4 Hz, 3H), 0.81 (d, J = 6.8 Hz, 3H) | following route described for example 108 |

FIG. 2 (continued)

| Example | Structure | Name | (M+H)+ | H¹-NMR | Synthesis |
|---|---|---|---|---|---|
| 110 | 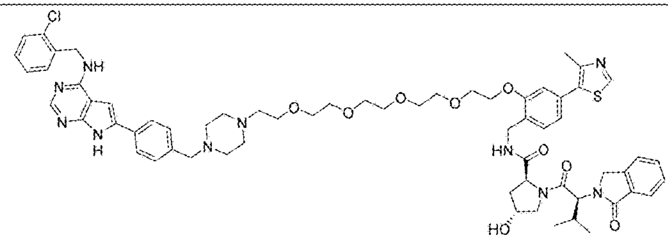 | (2S,4R)-N-(2-((14-(4-(4-(4-((2-chlorobenzyl)amino)-7H-pyrrolo[2,3-d]pyrimidin-6-yl)benzyl)piperazin-1-yl)-3,6,9,12-tetraoxatetradecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1183.49 1205.47 [M+Na] 592.25 | (400 MHz, MeOD): δ 8.85 (s, 1H), 8.08 (s, 1H), 7.53-7.75 (m, 6H), 7.38-7.40 (m, 5H), 7.22-7.24 (m, 2H), 6.92-7.02 (m, 3H), 4.57-4.60 (m, 3H), 4.43-4.47 (m, 5H), 4.15 (d, J = 3.6 Hz, 2H), 3.64-3.81 (m, 8H), 3.57-3.62 (m, 13H), 2.03-2.93 (m, 14H), 1.03 (d, J = 6.8 Hz, 3H), 0.80 (d, J = 6.4 Hz, 3H). | following route described for example 108 |
| 111 | 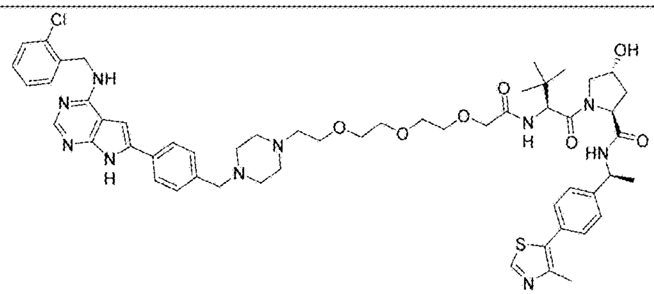 | (2S,4R)-1-((S)-2-(tert-butyl)-14-(4-(4-(4-((2-chlorobenzyl)amino)-7H-pyrrolo[2,3-d]pyrimidin-6-yl)benzyl)piperazin-1-yl)-4-oxo-6,9,12-trioxa-3-azatetradecanoyl)-4-hydroxy-N-((S)-1-(4-(4-methylthiazol-5-yl)phenyl)ethyl)pyrroli | | | |

FIG. 2 (continued)

| Example | Structure | Name | (M+H)+ | H1-NMR | Synthesis |
|---|---|---|---|---|---|
| | | dine-2-carboxamide | | | |
| 112 | 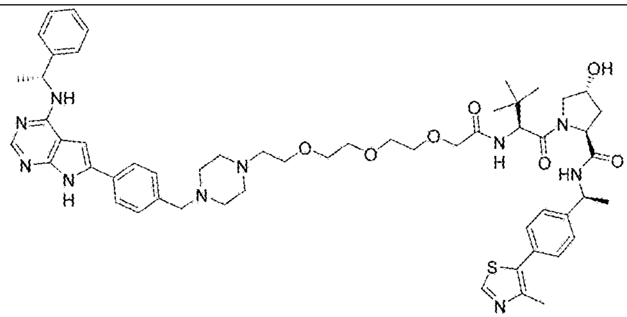 | (2S,4R)-1-((S)-2-(tert-butyl)-4-oxo-14-(4-(4-(4-(((R)-1-phenylethyl)amino)-7H-pyrrolo[2,3-d]pyrimidin-6-yl)benzyl)piperazin-1-yl)-6,9,12-trioxa-3-azatetradecanoyl)-4-hydroxy-N-((S)-1-(4-(4-methylthiazol-5-yl)phenyl)ethyl)pyrrolidine-2-carboxamide | | | |
| 113 | 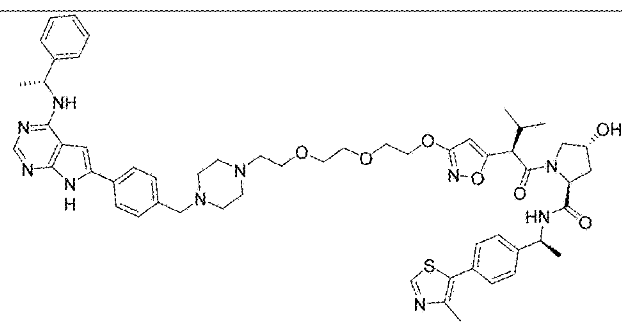 | (2S,4R)-4-hydroxy-1-((R)-3-methyl-2-(3-(2-(2-(2-(4-(4-(4-(((R)-1-phenylethyl)amino)-7H-pyrrolo[2,3-d]pyrimidin-6-yl)benzyl)piperazin-1-yl)ethoxy)ethoxy)isoxazol-5-yl)butanoyl)-N-((S)-1-(4-(4-methylthiazol-5-yl)phenyl)ethyl)pyrrolidine-2-carboxamide | | | |

FIG. 2 (continued)

| Example | Structure | Name | (M+H)+ | H¹-NMR | Synthesis |
|---|---|---|---|---|---|
| 114 | 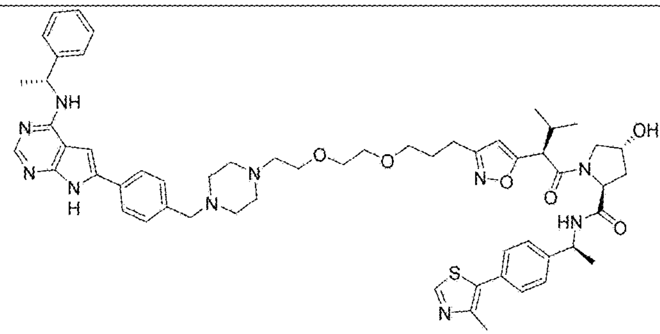 | (2S,4R)-4-hydroxy-1-((R)-3-methyl-2-(3-(3-(2-(2-(4-(4-(4-(((R)-1-phenylethyl)amino)-7H-pyrrolo[2,3-d]pyrimidin-6-yl)benzyl)piperazin-1-yl)ethoxy)ethoxy)prop yl)isoxazol-5-yl)butanoyl)-N-((S)-1-(4-(4-methylthiazol-5-yl)phenyl)ethyl)pyrroli dine-2-carboxamide | | | |
| 115 | 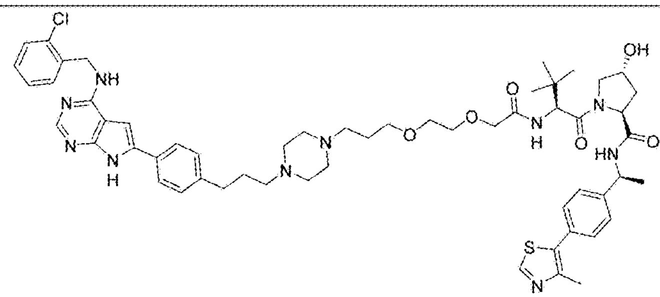 | (2S,4R)-1-((S)-2-(2-(2-(3-(4-(3-(4-(4-((2-chlorobenzyl)amino)-7H-pyrrolo[2,3-d]pyrimidin-6-yl)phenyl)propyl)piper azin-1-yl)propoxy)ethoxy)ace tamido)-3,3-dimethylbutanoyl)-4-hydroxy-N-((S)-1-(4-(4-methylthiazol-5-yl)phenyl)ethyl)pyrroli dine-2-carboxamide | | | |

FIG. 2 (continued)

| Example | Structure | Name | (M+H)+ | H1-NMR | Synthesis |
|---|---|---|---|---|---|
| 116 | 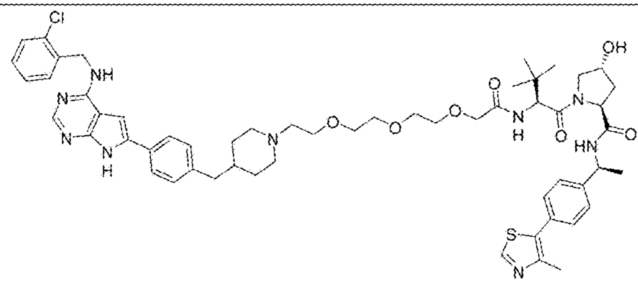 | (2S,4R)-1-((S)-2-(tert-butyl)-14-(4-(4-(4-((2-chlorobenzyl)amino)-7H-pyrrolo[2,3-d]pyrimidin-6-yl)benzyl)piperidin-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | | | |
| 117 | 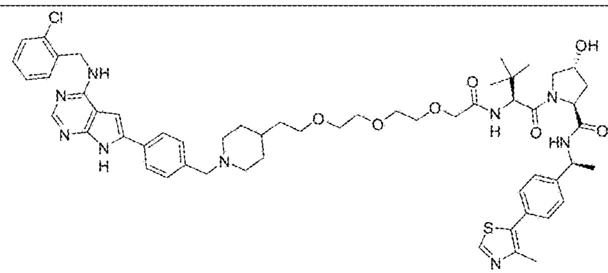 | (2S,4R)-1-((S)-2-(tert-butyl)-14-(1-(4-(4-((2-chlorobenzyl)amino)-7H-pyrrolo[2,3-d]pyrimidin-6-yl)benzyl)piperidin-4-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | | | |

FIG. 2 (continued)

| Example | Structure | Name | (M+H)⁺ | H¹-NMR | Synthesis |
|---|---|---|---|---|---|
| 118 | 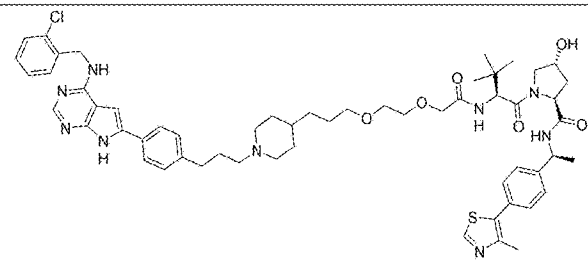 | (2S,4R)-1-((S)-2-(2-(2-(3-(1-(3-(4-(4-(2-chlorobenzyl)amino)-7H-pyrrolo[2,3-d]pyrimidin-6-yl)phenyl)propyl)piperidin-4-yl)propoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 119 | 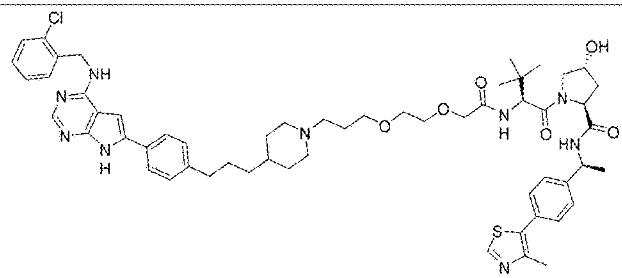 | (2S,4R)-1-((S)-2-(2-(2-(3-(4-(3-(4-(4-(2-chlorobenzyl)amino)-7H-pyrrolo[2,3-d]pyrimidin-6-yl)phenyl)propyl)piperidin-1-yl)propoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | | | |

FIG. 2 (continued)

| Example | Structure | Name | (M+H)+ | H¹-NMR | Synthesis |
|---|---|---|---|---|---|
| 120 | 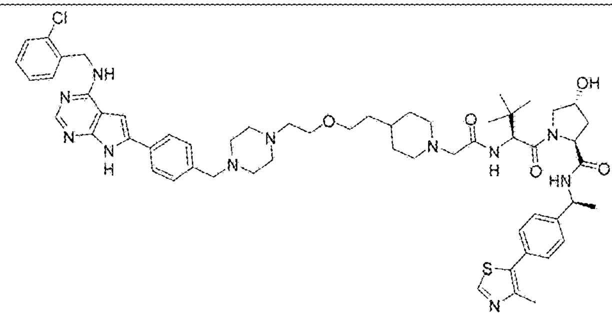 | (2S,4R)-1-((S)-2-(2-(4-(2-(2-(4-(4-((2-chlorobenzyl)amino)-7H-pyrrolo[2,3-d]pyrimidin-6-yl)benzyl)piperazin-1-yl)ethoxy)ethyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | | | |
| 121 | 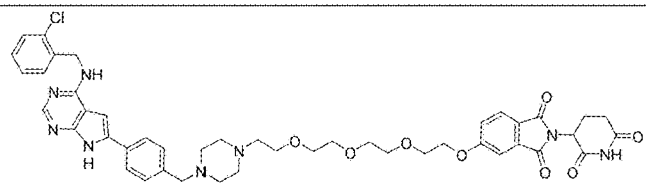 | 5-(2-(2-(2-(4-(4-((2-chlorobenzyl)amino)-7H-pyrrolo[2,3-d]pyrimidin-6-yl)benzyl)piperazin-1-yl)ethoxy)ethoxy)ethoxy)-2-(2,6-dioxopiperidin-3-yl)isoindoline-1,3-dione | 864.86 432.78 | (400 MHz, DMSO-d6): δ 12.08 (s, 1H), 11.12 (s, 1H), 8.09 (s, 1H), 8.03 (s, 1H), 7.82 (d, J = 8.0 Hz, 1H), 7.73 (d, J = 8.0 Hz, 2H), 7.45 (s, 2H), 7.35 (s, 4H), 7.29-7.27 (m, 2H), 7.00 (s, 1H), 5.14-5.09 (m, 1H), 4.77 (s, 2H), 4.29 (s, 2H), 4.05-4.02 (m, 9H), 3.77 (s, 1H), 3.58- | following route described for example 17 |

| Example | Structure | Name | (M+H)+ | H1-NMR | Synthesis |
|---|---|---|---|---|---|
| 122 | 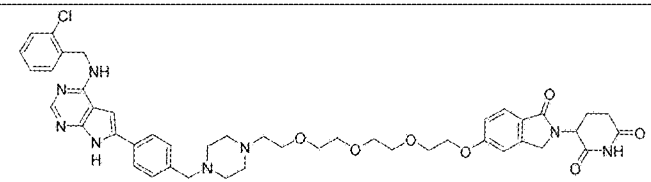 | 3-(5-(2-(2-(2-(2-(4-(4-(4-((2-chlorobenzyl)amino)-7H-pyrrolo[2,3-d]pyrimidin-6-yl)benzyl)piperazin-1-yl)ethoxy)ethoxy)ethoxy)ethoxy)-1-oxoisoindolin-2-yl)piperidine-2,6-dione | | 3.46 (m, 11H), 2.93-2.84 (m, 1H), 2.60-2.40 (m, 5H). | |
| 123 | 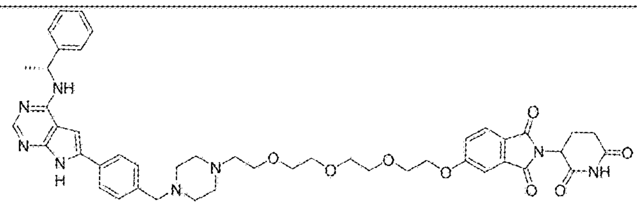 | 2-(2,6-dioxopiperidin-3-yl)-5-(2-(2-(2-(4-(4-(4-(((R)-1-phenylethyl)amino)-7H-pyrrolo[2,3-d]pyrimidin-6-yl)benzyl)piperazin-1-yl)ethoxy)ethoxy)ethoxy)ethoxy)isoindoline-1,3-dione | | | |

| Example | Structure | Name | (M+H)+ | H¹-NMR | Synthesis |
|---|---|---|---|---|---|
| 124 | 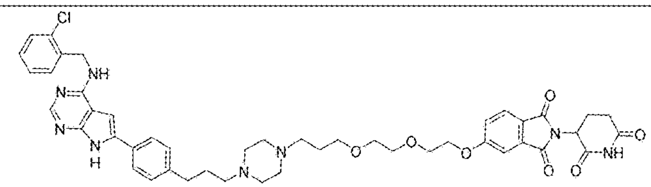 | 5-(2-(2-(3-(4-(3-(4-(4-((2-chlorobenzyl)amino)-7H-pyrrolo[2,3-d]pyrimidin-6-yl)phenyl)propyl)piperazin-1-yl)propoxy)ethoxy)ethoxy)-2-(2,6-dioxopiperidin-3-yl)isoindoline-1,3-dione | | | |
| 125 | 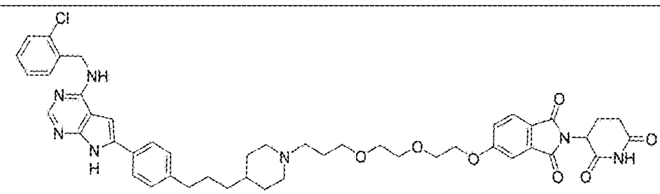 | 5-(2-(2-(3-(4-(3-(4-(4-((2-chlorobenzyl)amino)-7H-pyrrolo[2,3-d]pyrimidin-6-yl)phenyl)propyl)piperidin-1-yl)propoxy)ethoxy)ethoxy)-2-(2,6-dioxopiperidin-3-yl)isoindoline-1,3-dione | | | |

| Example | Structure | Name | (M+H)+ | H¹-NMR | Synthesis |
|---|---|---|---|---|---|
| 126 | 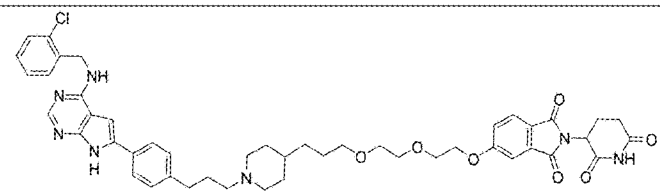 | 5-(2-(2-(3-(1-(3-(4-(4-((2-chlorobenzyl)amino)-7H-pyrrolo[2,3-d]pyrimidin-6-yl)phenyl)propyl)piperidin-4-yl)propoxy)ethoxy)eth oxy)-2-(2,6-dioxopiperidin-3-yl)isoindoline-1,3-dione | | | |
| 127 | 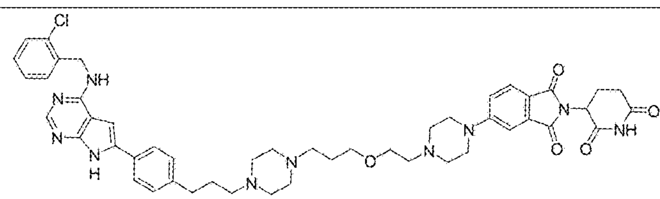 | 5-(4-(2-(3-(4-(3-(4-((2-chlorobenzyl)amino)-7H-pyrrolo[2,3-d]pyrimidin-6-yl)phenyl)propyl)piperazin-1-yl)propoxy)ethyl)piperazin-1-yl)-2-(2,6-dioxopiperidin-3-yl)isoindoline-1,3-dione | | | |

FIG. 2 (continued)

| Example | Structure | Name | (M+H)⁺ | H¹-NMR | Synthesis |
|---|---|---|---|---|---|
| 128 | 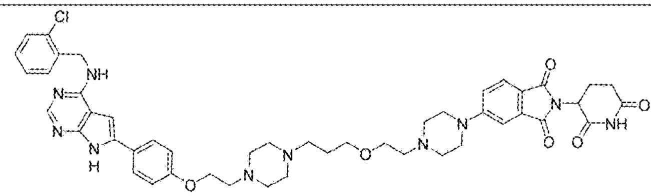 | 5-(4-(2-(3-(4-(2-(4-(4-((2-chlorobenzyl)amino)-7H-pyrrolo[2,3-d]pyrimidin-6-yl)phenoxy)ethyl)piperazin-1-yl)propoxy)ethyl)piperazin-1-yl)-2-(2,6-dioxopiperidin-3-yl)isoindoline-1,3-dione | | | |
| 129 | 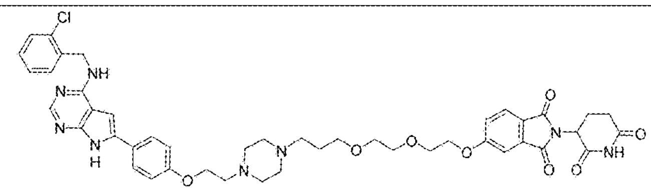 | 5-(2-(2-(3-(4-(2-(4-(4-((2-chlorobenzyl)amino)-7H-pyrrolo[2,3-d]pyrimidin-6-yl)phenoxy)ethyl)piperazin-1-yl)propoxy)ethoxy)-2-(2,6-dioxopiperidin-3-yl)isoindoline-1,3-dione | | | |

FIG. 2 (continued)

| Example | Structure | Name | (M+H)+ | H¹-NMR | Synthesis |
|---|---|---|---|---|---|
| 130 | 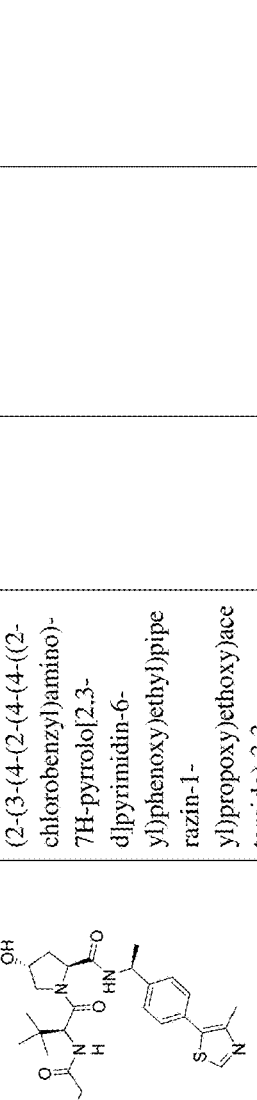 | (2S,4R)-1-((S)-2-(2-(2-(3-(4-(2-(4-(4-((2-chlorobenzyl)amino)-7H-pyrrolo[2,3-d]pyrimidin-6-yl)phenoxy)ethyl)piperazin-1-yl)propoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 131 | 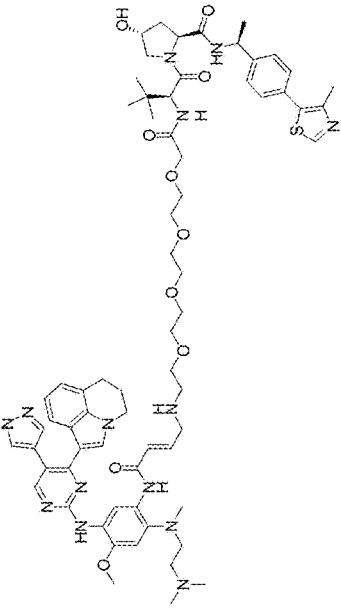 | (E)-N19-(5-((4-(5,6-dihydro-4H-pyrrolo[3,2,1-ij]quinolin-1-yl)-5-(1-methyl-1H-pyrazol-4-yl)pyrimidin-2-yl)amino)-2-(2-(dimethylamino)ethyl)(methyl)amino)-4-methoxyphenyl)-N1-((S)-1-((2S,4R)-4-hydroxy-2-(((S)-1-(4-(4-methylthiazol-5-yl)phenyl)ethyl)carba | | | |

FIG. 2 (continued)

| Example | Structure | Name | (M+H)+ | H¹-NMR | Synthesis |
|---|---|---|---|---|---|
| | | moyl)pyrrolidin-1-yl)-3,3-dimethyl-1-oxobutan-2-yl)-3,6,9,12-tetraoxa-15-azanonadec-17-enediamide | | | |
| 132 | 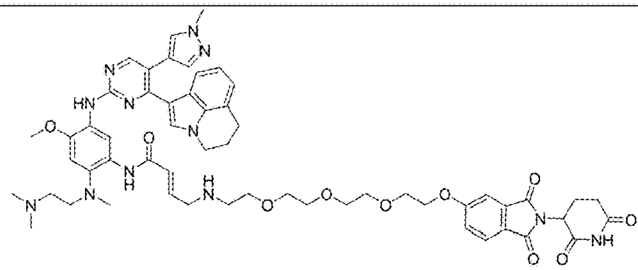 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)-1-((2-(2,6-dioxopiperidin-3-yl)-1,3-dioxoisoindolin-5-yl)oxy)-3,6,9-trioxa-12-azahexadec-14-en-16-amide | | | |

FIG. 2 (continued)

| Example | Structure | Name | (M+H)+ | H¹-NMR | Synthesis |
|---|---|---|---|---|---|
| 133 | 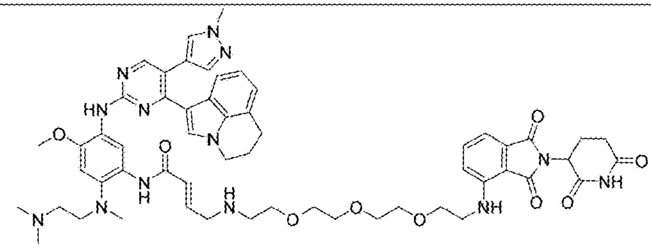 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)-1-((2-(2,6-dioxopiperidin-3-yl)-1,3-dioxoisoindolin-4-yl)amino)-3,6,9-trioxa-12-azahexadec-14-en-16-amide | | | |
| 134 | 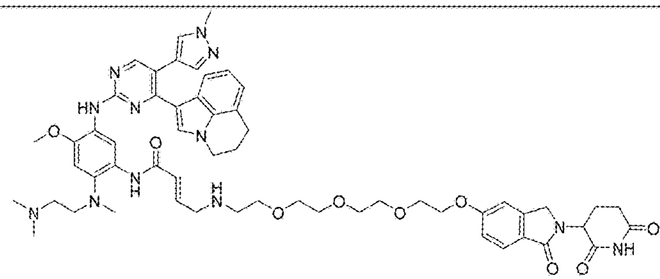 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)-1-((2-(2,6-dioxopiperidin-3-yl)-1-oxoisoindolin-5- | | | |

| Exa mpl e | Structure | Name | (M+H)+ | H1-NMR | Synthesis |
|---|---|---|---|---|---|
| | | yl)oxy)-3,6,9-trioxa-12-azahexadec-14-en-16-amide | | | |
| 135 | 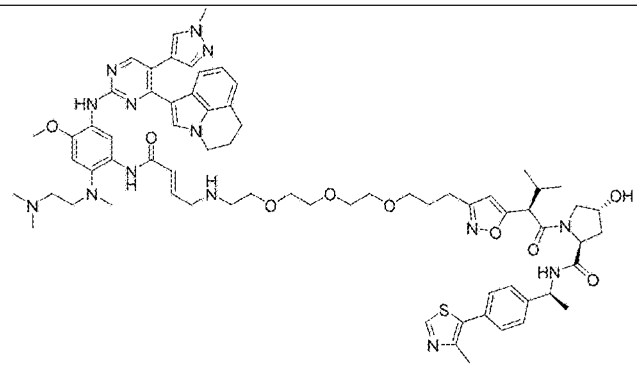 | (2S,4R)-1-((R)-2-(3-((E)-17-((5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)amino)-17-oxo-4,7,10-trioxa-13-azaheptadec-15-en-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | | | |

FIG. 2 (continued)

| Example | Structure | Name | (M+H)+ | H¹-NMR | Synthesis |
|---|---|---|---|---|---|
| 136 | 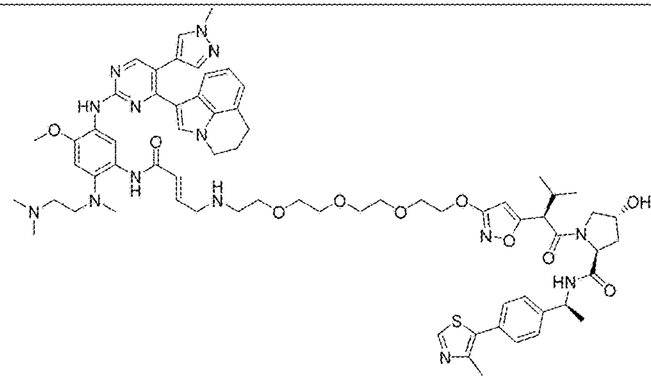 | (2S,4R)-1-((R)-2-(3-(((E)-16-((5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)amino)-16-oxo-3,6,9-trioxa-12-azahexadec-14-en-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | | | |
| 137 | 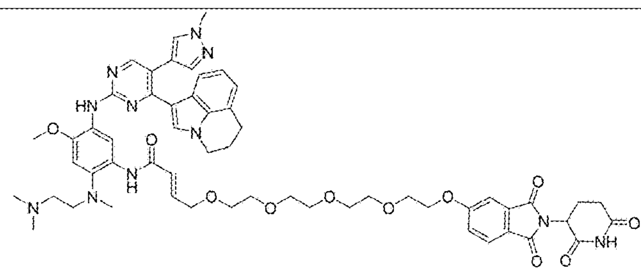 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4- | | | |

| Example | Structure | Name | (M+H)⁺ | H¹-NMR | Synthesis |
|---|---|---|---|---|---|
| | | methoxyphenyl)-1-((2-(2,6-dioxopiperidin-3-yl)-1,3-dioxoisoindolin-5-yl)oxy)-3,6,9,12-tetraoxahexadec-14-en-16-amide | | | |
| 138 | 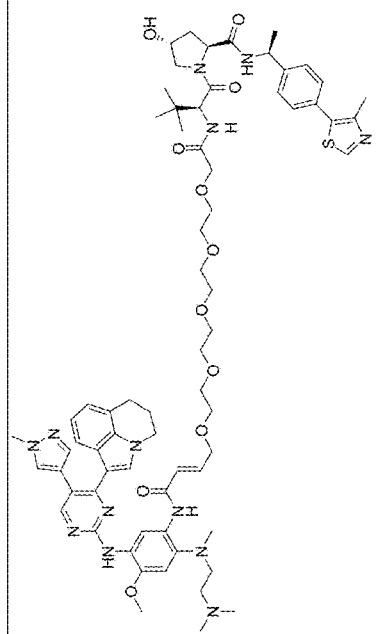 | (E)-N19-(5-(4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12,15-pentaoxanonadec-17-enediamide | | | |

FIG. 2 (continued)

| Example | Structure | Name | (M+H)+ | H1-NMR | Synthesis |
|---|---|---|---|---|---|
| 139 | 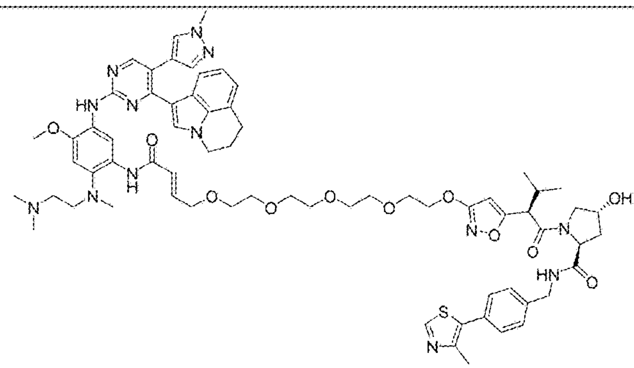 | (2S,4R)-1-((R)-2-(3-(((E)-16-((5-((4-(5,6-dihydro-4H-pyrrolo[3,2,1-ij]quinolin-1-yl)-5-(1-methyl-1H-pyrazol-4-yl)pyrimidin-2-yl)amino)-2-((2-(dimethylamino)ethyl)(methyl)amino)-4-methoxyphenyl)amino)-16-oxo-3,6,9,12-tetraoxahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H1-NMR | Synthesis |
|---|---|---|---|---|---|
| 140 | 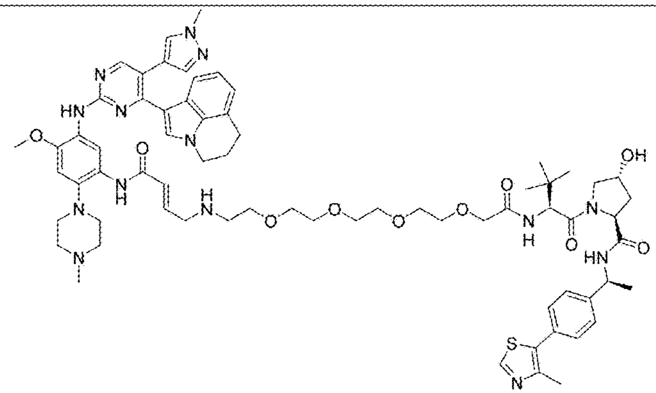 | (E)-N19-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |
| 141 | 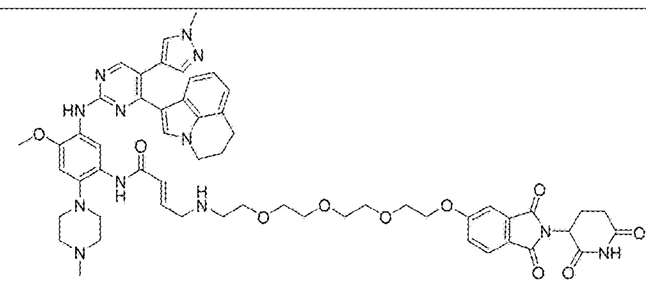 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)-1-((2- | | | |

FIG. 2 (continued)

| Example | Structure | Name | (M+H)+ | H¹-NMR | Synthesis |
|---|---|---|---|---|---|
| | | (2,6-dioxopiperidin-3-yl)-1,3-dioxoisoindolin-5-yl)oxy)-3,6,9-trioxa-12-azahexadec-14-en-16-amide | | | |
| 142 | 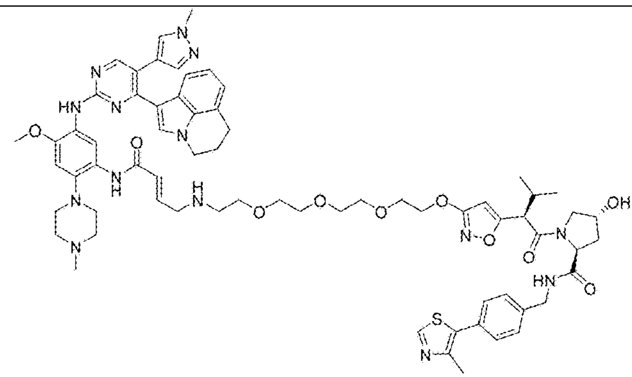 | (2S,4R)-1-((R)-2-(3-(((E)-16-((5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)amino)-16-oxo-3,6,9-trioxa-12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)⁺ | H¹-NMR | Synthesis |
|---|---|---|---|---|---|
| 143 | 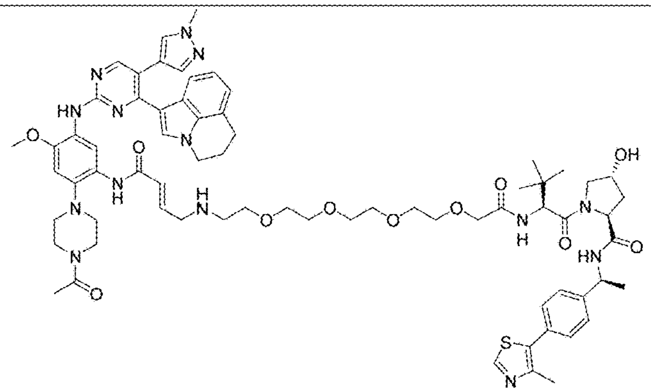 | (E)-N19-(2-(4-acetylpiperazin-1-yl)-5-((4-(5,6-dihydro-4H-pyrrolo[3,2,1-ij]quinolin-1-yl)-5-(1-methyl-1H-pyrazol-4-yl)pyrimidin-2-yl)amino)-4-methoxyphenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |
| 144 | 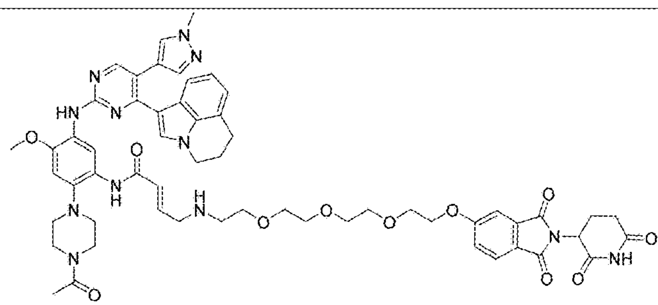 | (E)-N-(2-(4-acetylpiperazin-1-yl)-5-((4-(5,6-dihydro-4H-pyrrolo[3,2,1-ij]quinolin-1-yl)-5-(1-methyl-1H-pyrazol-4-yl)pyrimidin-2-yl)amino)-4-methoxyphenyl)-1-((2- | | | |

| Example | Structure | Name | (M+H)+ | H1-NMR | Synthesis |
|---|---|---|---|---|---|
| | | (2,6-dioxopiperidin-3-yl)-1,3-dioxoisoindolin-5-yl)oxy)-3,6,9-trioxa-12-azahexadec-14-en-16-amide | | | |
| 145 | 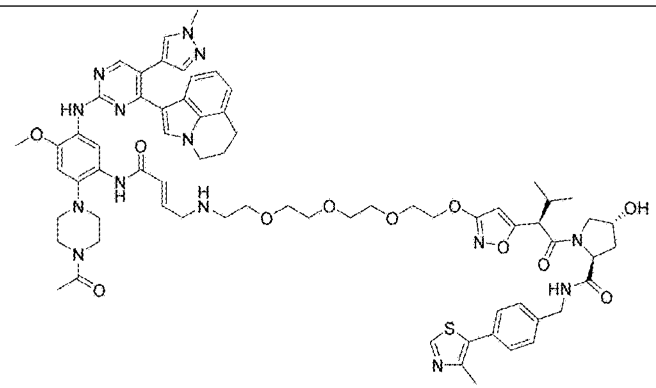 | (2S,4R)-1-((R)-2-(3-(((E)-16-((2-(4-acetylpiperazin-1-yl)-5-(4-(5,6-dihydro-4H-pyrrolo[3,2,1-ij]quinolin-1-yl)-5-(1-methyl-1H-pyrazol-4-yl)pyrimidin-2-yl)amino)-4-methoxyphenyl)amino)-16-oxo-3,6,9-trioxa-12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |

| Example | Structure | Name | (M+H)+ | H1-NMR | Synthesis |
|---|---|---|---|---|---|
| 146 | 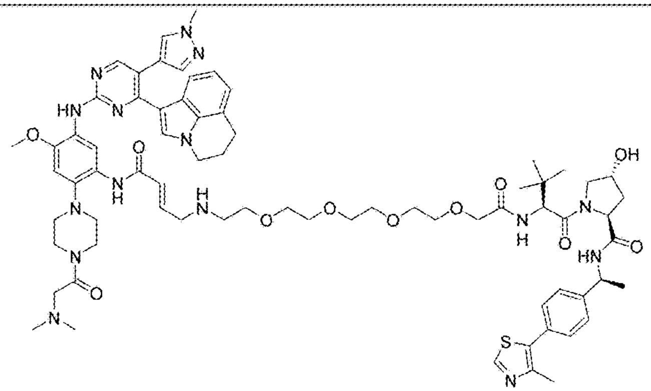 | (E)-N19-(5-((4-(5,6-dihydro-4H-pyrrolo[3,2,1-ij]quinolin-1-yl)-5-(1-methyl-1H-pyrazol-4-yl)pyrimidin-2-yl)amino)-2-(4-(dimethylglycyl)piperazin-1-yl)-4-methoxyphenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |

FIG. 2 (continued)

| Example | Structure | Name | (M+H)+ | H¹-NMR | Synthesis |
|---|---|---|---|---|---|
| 147 | 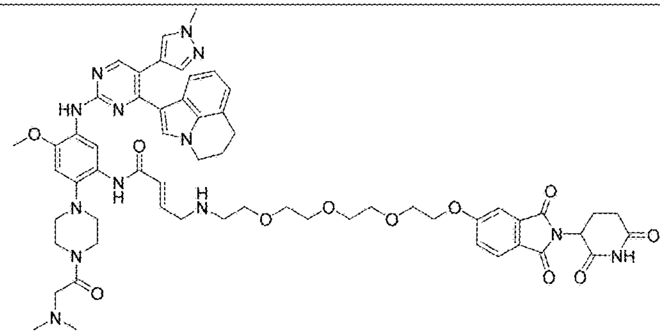 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-2-(4-(dimethylglycyl)piperazin-1-yl)-4-methoxyphenyl)-1-((2-(2,6-dioxopiperidin-3-yl)-1,3-dioxoisoindolin-5-yl)oxy)-3,6,9-trioxa-12-azahexadec-14-en-16-amide | | | |
| 148 | 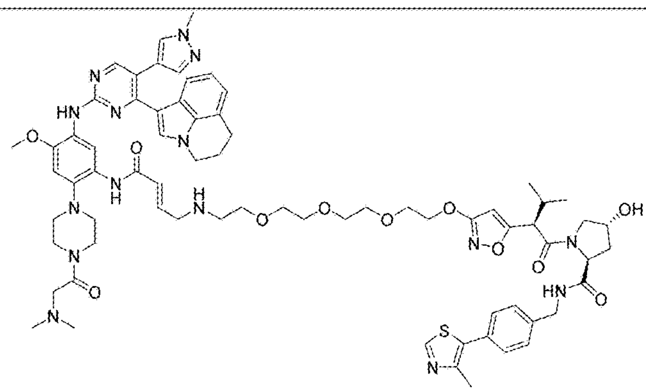 | (2S,4R)-1-((R)-2-(3-(((E)-16-((5-((4-(5,6-dihydro-4H-pyrrolo[3,2,1-ij]quinolin-1-yl)-5-(1-methyl-1H-pyrazol-4-yl)pyrimidin-2-yl)amino)-2-(4-(dimethylglycyl)piperazin-1-yl)-4-methoxyphenyl)amino)-16-oxo-3,6,9-trioxa- | | | |

FIG. 2 (continued)

| Example | Structure | Name | (M+H)+ | H¹-NMR | Synthesis |
|---|---|---|---|---|---|
| | | 12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |
| 149 | 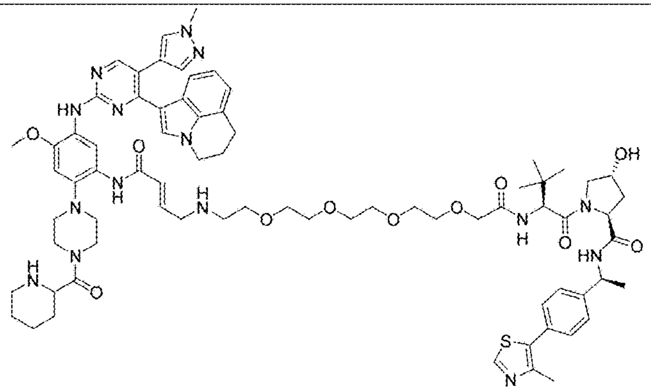 | (E)-N19-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-(piperidine-2-carbonyl)piperazin-1-yl)phenyl)-N1-((S)-1-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |

FIG. 2 (continued)

| Example | Structure | Name | (M+H)+ | H1-NMR | Synthesis |
|---|---|---|---|---|---|
| 150 | 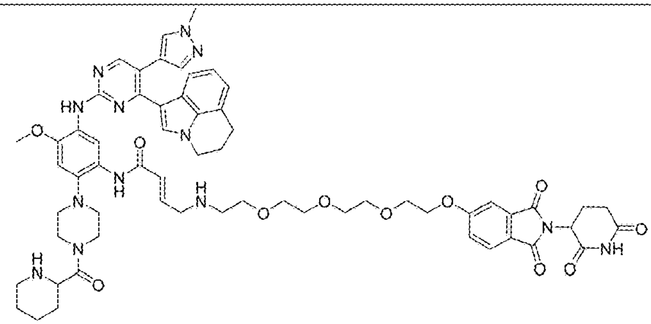 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-(piperidine-2-carbonyl)piperazin-1-yl)phenyl)-1-((2-(2,6-dioxopiperidin-3-yl)-1,3-dioxoisoindolin-5-yl)oxy)-3,6,9-trioxa-12-azahexadec-14-en-16-amide | | | |
| 151 | 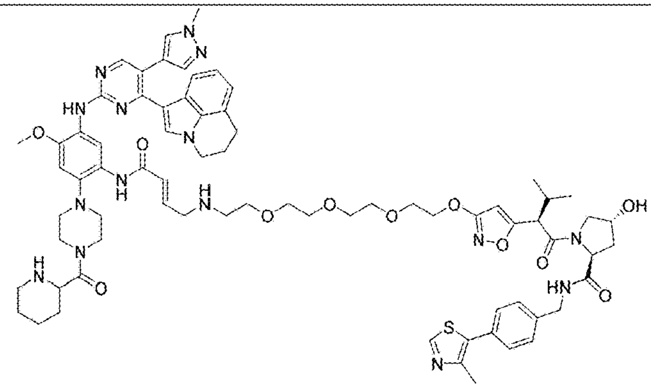 | (2S,4R)-1-((2R)-2-(3-(((E)-16-((5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-(piperidine-2-carbonyl)piperazin-1-yl)phenyl)amino)-16-oxo-3,6,9-trioxa-12-azahexadec-14-en-1- | | | |

FIG. 2 (continued)

| Example | Structure | Name | (M+H)⁺ | H¹-NMR | Synthesis |
|---|---|---|---|---|---|
| | | yl)oxy)isoxazol-5-yl)-3-methylbutanoyl)-4-hydroxy-N-(4-(4-methylthiazol-5-yl)benzyl)pyrrolidine-2-carboxamide | | | |
| 152 | 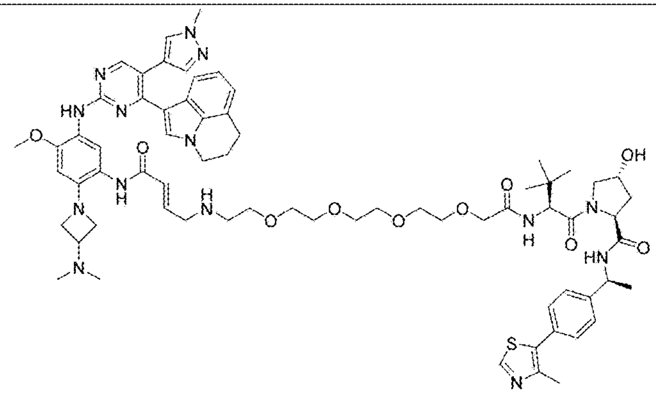 | (E)-N19-(5-(4-(5,6-dihydro-4H-pyrrolo[3,2,1-ij]quinolin-1-yl)-5-(1-methyl-1H-pyrazol-4-yl)pyrimidin-2-yl)amino)-2-(3-(dimethylamino)azetidin-1-yl)-4-methoxyphenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |

FIG. 2 (continued)

| Example | Structure | Name | (M+H)+ | H¹-NMR | Synthesis |
|---|---|---|---|---|---|
| 153 | 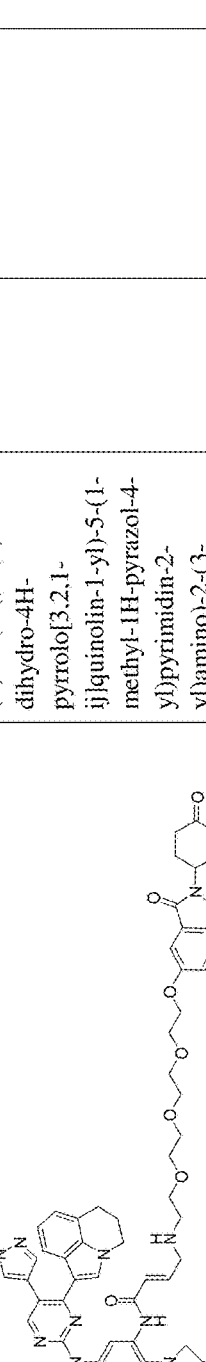 | (E)-N-(5-((4-(5,6-dihydro-4H-pyrrolo[3,2,1-ij]quinolin-1-yl)-5-(1-methyl-1H-pyrazol-4-yl)pyrimidin-2-yl)amino)-2-(3-(dimethylamino)azetidin-1-yl)-4-methoxyphenyl)-1-((2-(2,6-dioxopiperidin-3-yl)-1,3-dioxoisoindolin-5-yl)oxy)-3,6,9-trioxa-12-azahexadec-14-en-16-amide | | | |
| 154 | 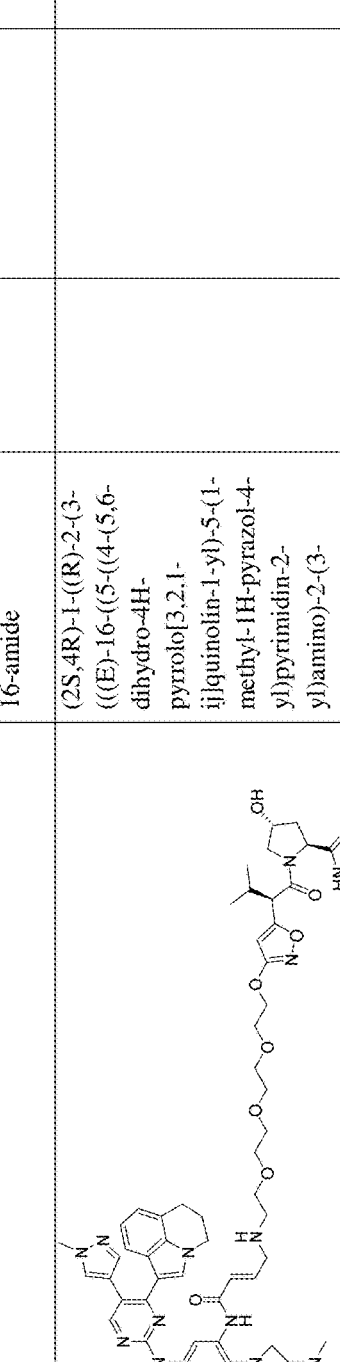 | (2S,4R)-1-((R)-2-(3-((((E)-16-((5-((4-(5,6-dihydro-4H-pyrrolo[3,2,1-ij]quinolin-1-yl)-5-(1-methyl-1H-pyrazol-4-yl)pyrimidin-2-yl)amino)-2-(3-(dimethylamino)azetidin-1-yl)-4-methoxyphenyl)amino)-16-oxo-3,6,9-trioxa- | | | |

FIG. 2 (continued)

| Example | Structure | Name | (M+H)+ | H¹-NMR | Synthesis |
|---|---|---|---|---|---|
| | | 12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |
| 155 | 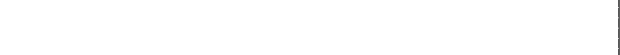 | (2S,4R)-1-((S)-2-(2-amino-4-((4-(5,6-dihydro-4H-pyrrolo[3,2,1-ij]quinolin-1-yl)-5-(1-methyl-1H-pyrazol-4-yl)pyrimidin-2-yl)amino)-5-methoxyphenyl)-22-(tert-butyl)-20-oxo-6,9,12,15,18-pentaoxa-2,21-diazatricosan-23-oyl)-4-hydroxy-N-((S)-1-(4-(4-methylthiazol-5-yl)phenyl)ethyl)pyrrolidine-2-carboxamide | | | |

FIG. 2 (continued)

| Example | Structure | Name | (M+H)+ | H¹-NMR | Synthesis |
|---|---|---|---|---|---|
| 156 | 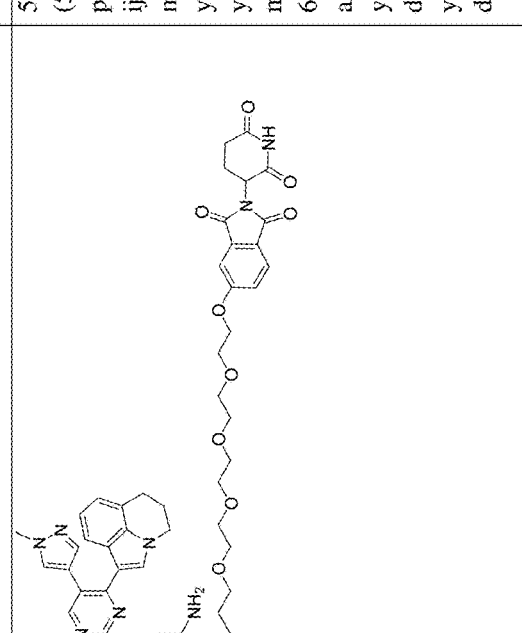 | 5-((2-(2-amino-4-((4-(5,6-dihydro-4H-pyrrolo[3,2,1-ij]quinolin-1-yl)-5-(1-methyl-1H-pyrazol-4-yl)pyrimidin-2-yl)amino)-5-methoxyphenyl)-6,9,12,15-tetraoxa-2-azaheptadecan-17-yl)oxy)-2-(2,6-dioxopiperidin-3-yl)isoindoline-1,3-dione | | | |
| 157 | 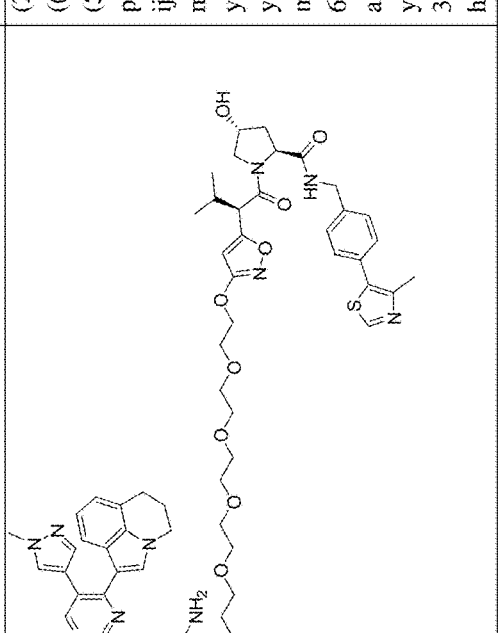 | (2S,4R)-1-((R)-2-(3-((2-(2-amino-4-((4-(5,6-dihydro-4H-pyrrolo[3,2,1-ij]quinolin-1-yl)-5-(1-methyl-1H-pyrazol-4-yl)pyrimidin-2-yl)amino)-5-methoxyphenyl)-6,9,12,15-tetraoxa-2-azaheptadecan-17-yl)oxy)isoxazol-5-yl)-3-methylbutanoyl)-4-hydroxy-N-(4-(4- | | | |

FIG. 2 (continued)

| Example | Structure | Name | (M+H)⁺ | H¹-NMR | Synthesis |
|---|---|---|---|---|---|
| 158 | 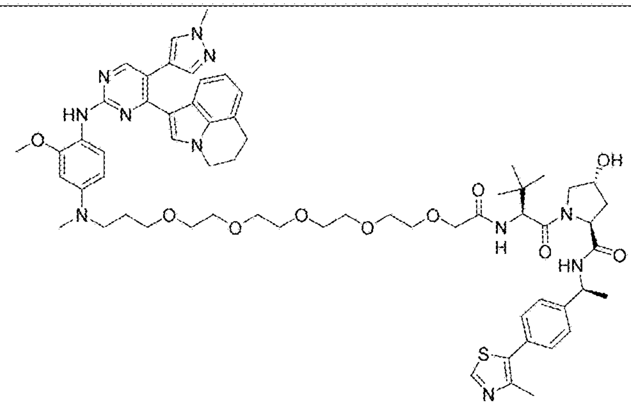 | (2S,4R)-1-((S)-22-(tert-butyl)-2-(4-((4-(5,6-dihydro-4H-pyrrolo[3,2,1-ij]quinolin-1-yl)-5-(1-methyl-1H-pyrazol-4-yl)pyrimidin-2-yl)amino)-3-methoxyphenyl)-20-oxo-6,9,12,15,18-pentaoxa-2,21-diazatricosan-23-oyl)-4-hydroxy-N-((S)-1-(4-(4-methylthiazol-5-yl)phenyl)ethyl)pyrrolidine-2-carboxamide | | | |
| 159 | 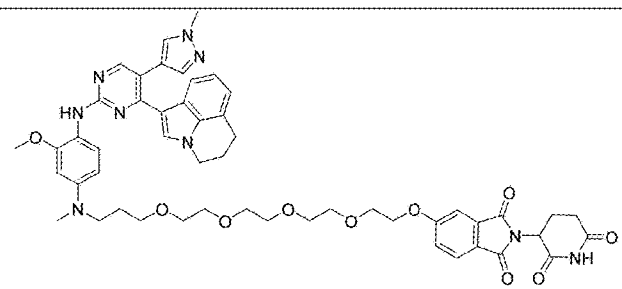 | 5-(2-(4-((4-(5,6-dihydro-4H-pyrrolo[3,2,1-ij]quinolin-1-yl)-5-(1-methyl-1H-pyrazol-4-yl)pyrimidin-2-yl)amino)-3-methoxyphenyl)-6,9,12,15-tetraoxa-2- | | | |

| Exa mpl e | Structure | Name | (M+H)+ | H1-NMR | Synthesis |
|---|---|---|---|---|---|
| | | azaheptadecan-17-yl)oxy)-2-(2,6-dioxopiperidin-3-yl)isoindoline-1,3-dione | | | |
| 160 | 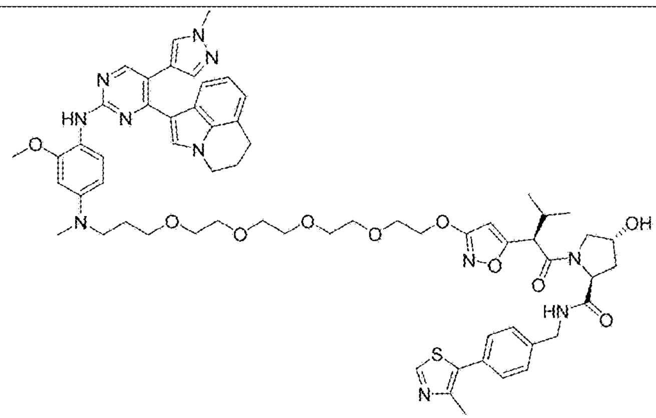 | (2S,4R)-1-((R)-2-(3-((2-(4-((5,6-dihydro-4H-pyrrolo[3,2,1-ij]quinolin-1-yl)-5-(1-methyl-1H-pyrazol-4-yl)pyrimidin-2-yl)amino)-3-methoxyphenyl)-6,9,12,15-tetraoxa-2-azaheptadecan-17-yl)oxy)isoxazol-5-yl)-3-methylbutanoyl)-4-hydroxy-N-(4-(4-methylthiazol-5-yl)benzyl)pyrrolidine-2-carboxamide | | | |

| Example | Structure | Name | (M+H)+ | H¹-NMR | Synthesis |
|---|---|---|---|---|---|
| 161 | 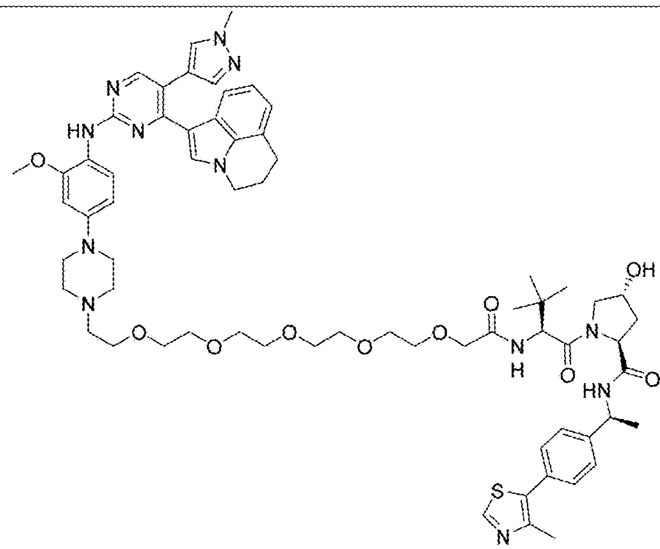 | (2S,4R)-1-((S)-2-(tert-butyl)-20-(4-(4-((4-(5,6-dihydro-4H-pyrrolo[3,2,1-ij]quinolin-1-yl)-5-(1-methyl-1H-pyrazol-4-yl)pyrimidin-2-yl)amino)-3-methoxyphenyl)piperazin-1-yl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | | | |

FIG. 2 (continued)

| Example | Structure | Name | (M+H)⁺ | H¹-NMR | Synthesis |
|---|---|---|---|---|---|
| 162 | 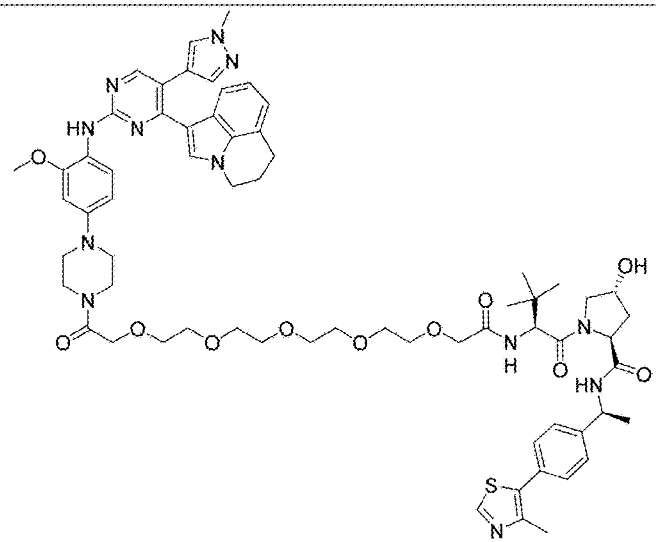 | (2S,4R)-1-((S)-2-(tert-butyl)-20-(4-(4-((5,6-dihydro-4H-pyrrolo[3,2,1-ij]quinolin-1-yl)-5-(1-methyl-1H-pyrazol-4-yl)pyrimidin-2-yl)amino)-3-methoxyphenyl)piperazin-1-yl)-4,20-dioxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | | | |
| 163 | 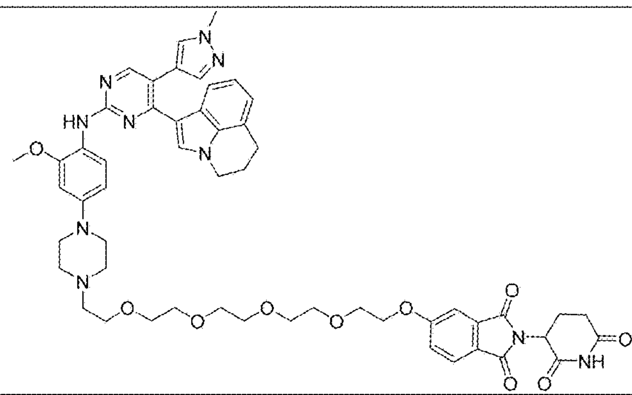 | 5-((14-(4-(4-((5,6-dihydro-4H-pyrrolo[3,2,1-ij]quinolin-1-yl)-5-(1-methyl-1H-pyrazol-4-yl)pyrimidin-2-yl)amino)-3-methoxyphenyl)piperazin-1-yl)-3,6,9,12-tetraoxatetradecyl)oxy)-2-(2,6- | | | |

FIG. 2 (continued)

| Example | Structure | Name | (M+H)⁺ | H¹-NMR | Synthesis |
|---|---|---|---|---|---|
| | | dioxopiperidin-3-yl)isoindoline-1,3-dione | | | |
| 164 | 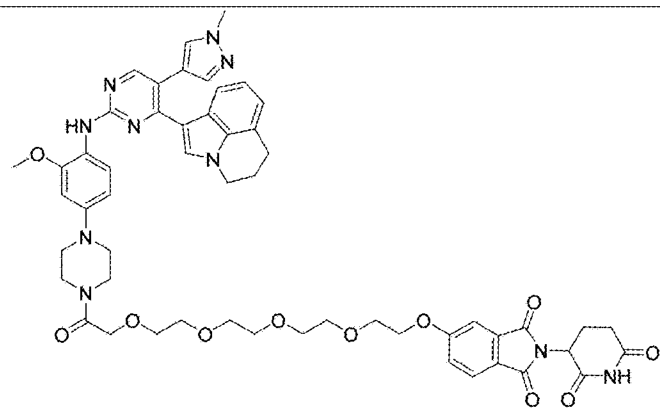 | 5-((14-(4-(4-((4-(5,6-dihydro-4H-pyrrolo[3,2,1-ij]quinolin-1-yl)-5-(1-methyl-1H-pyrazol-4-yl)pyrimidin-2-yl)amino)-3-methoxyphenyl)piperazin-1-yl)-14-oxo-3,6,9,12-tetraoxatetradecyl)oxy)-2-(2,6-dioxopiperidin-3-yl)isoindoline-1,3-dione | | | |

| Example | Structure | Name | (M+H)⁺ | H¹-NMR | Synthesis |
|---|---|---|---|---|---|
| 165 | 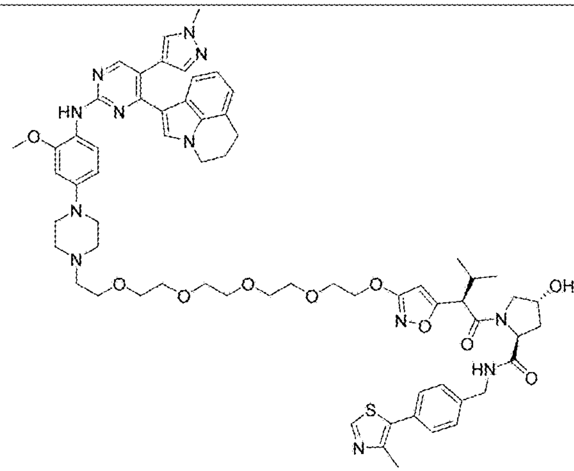 | (2S,4R)-1-((R)-2-(3-((14-(4-(4-(5,6-dihydro-4H-pyrrolo[3,2,1-ij]quinolin-1-yl)-5-(1-methyl-1H-pyrazol-4-yl)pyrimidin-2-yl)amino)-3-methoxyphenyl)piperazin-1-yl)-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H¹-NMR | Synthesis |
|---|---|---|---|---|---|
| 166 | 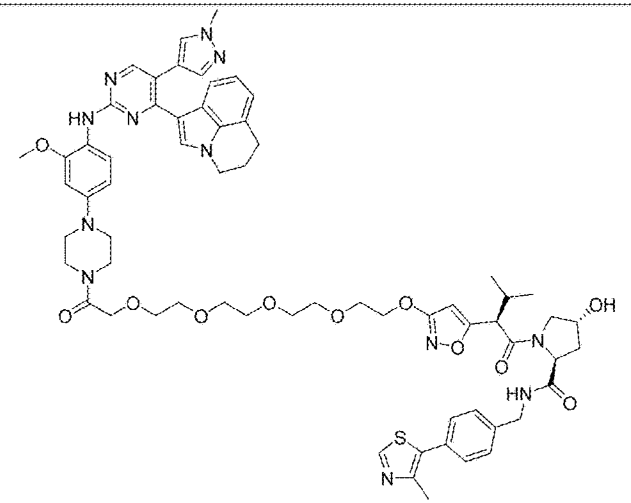 | (2S,4R)-1-((R)-2-(3-((14-(4-(4-(5,6-dihydro-4H-pyrrolo[3,2,1-ij]quinolin-1-yl)-5-(1-methyl-1H-pyrazol-4-yl)pyrimidin-2-yl)amino)-3-methoxyphenyl)piperazin-1-yl)-14-oxo-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |
| 167 | 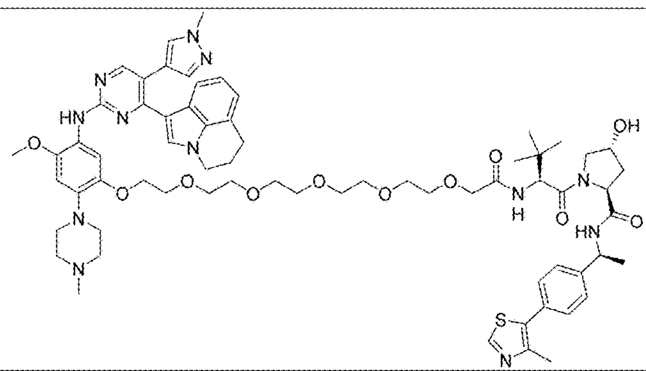 | (2S,4R)-1-((S)-2-(tert-butyl)-20-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenoxy)-4-oxo- | | | |

FIG. 2 (continued)

| Example | Structure | Name | (M+H)⁺ | H¹-NMR | Synthesis |
|---|---|---|---|---|---|
|  |  | 6,9,12,15,18-pentaoxa-3-azaicosanoyl)-4-hydroxy-N-((S)-1-(4-(4-methylthiazol-5-yl)phenyl)ethyl)pyrrolidine-2-carboxamide |  |  |  |
| 168 | 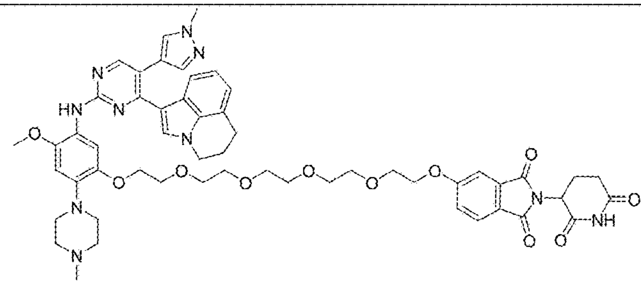 | 5-((14-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenoxy)-3,6,9,12-tetraoxatetradecyl)oxy)-2-(2,6-dioxopiperidin-3-yl)isoindoline-1,3-dione |  |  |  |

| Example | Structure | Name | (M+H)+ | H1-NMR | Synthesis |
|---|---|---|---|---|---|
| 169 | 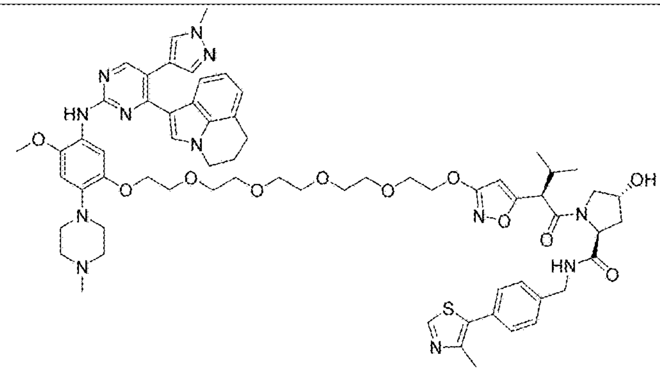 | (2S,4R)-1-((R)-2-(3-((14-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenoxy)-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H¹-NMR | Synthesis |
|---|---|---|---|---|---|
| 170 | 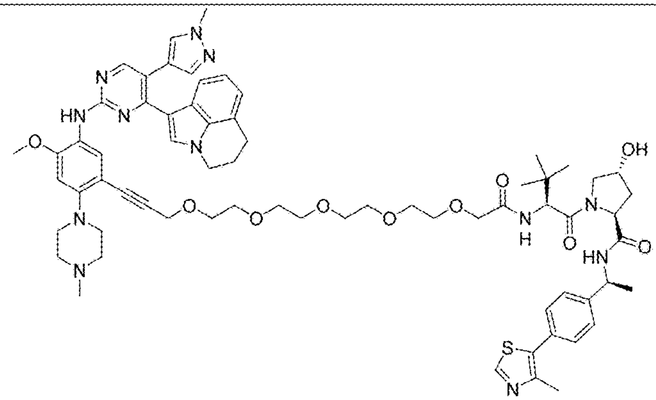 | (2S,4R)-1-((S)-2-(tert-butyl)-21-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)-4-oxo-6,9,12,15,18-pentaoxa-3-azahenicos-20-ynoyl)-4-hydroxy-N-((S)-1-(4-(4-methylthiazol-5-yl)phenyl)ethyl)pyrrolidine-2-carboxamide | | | |
| 171 | 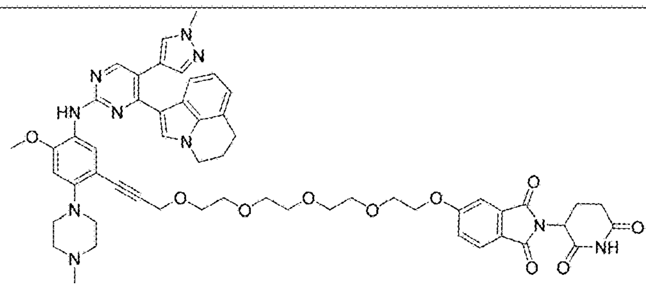 | 5-((15-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)-3,6,9,12-tetraoxapentadec-14-yn-1-yl)oxy)-2-(2,6- | | | |

FIG. 2 (continued)

| Example | Structure | Name | (M+H)⁺ | H¹-NMR | Synthesis |
|---|---|---|---|---|---|
| | | dioxopiperidin-3-yl)isoindoline-1,3-dione | | | |
| 172 | 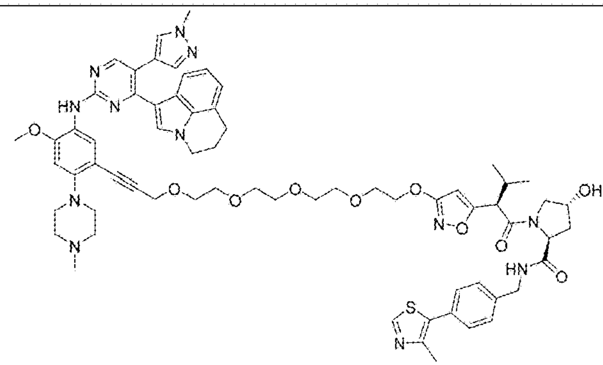 | (2S,4R)-1-((R)-2-(3-((15-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)-3,6,9,12-tetraoxapentadec-14-yn-1-yl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)⁺ | H¹-NMR | Synthesis |
|---|---|---|---|---|---|
| 173 | 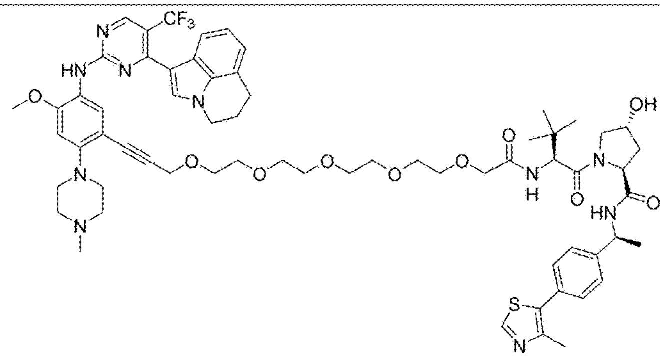 | (2S,4R)-1-((S)-2-(tert-butyl)-21-(5-((4-(5,6-dihydro-4H-pyrrolo[3,2,1-ij]quinolin-1-yl)-5-(trifluoromethyl)pyrimidin-2-yl)amino)-4-methoxy-2-(4-methylpiperazin-1-yl)phenyl)-4-oxo-6,9,12,15,18-pentaoxa-3-azahenicos-20-ynoyl)-4-hydroxy-N-((S)-1-(4-(4-methylthiazol-5-yl)phenyl)ethyl)pyrrolidine-2-carboxamide | | | |
| 174 | 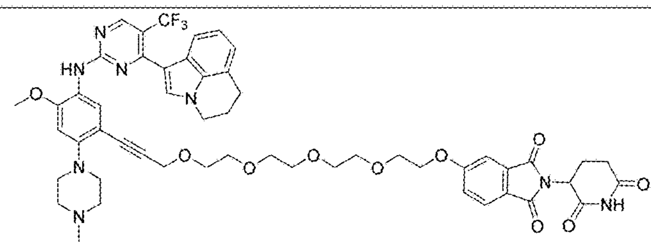 | 5-((15-(5-((4-(5,6-dihydro-4H-pyrrolo[3,2,1-ij]quinolin-1-yl)-5-(trifluoromethyl)pyrimidin-2-yl)amino)-4-methoxy-2-(4-methylpiperazin-1-yl)phenyl)-3,6,9,12-tetraoxapentadec-14-yn-1-yl)oxy)-2-(2,6- | | | |

FIG. 2 (continued)

| Example | Structure | Name | (M+H)+ | H1-NMR | Synthesis |
|---|---|---|---|---|---|
| | | dioxopiperidin-3-yl)isoindoline-1,3-dione | | | |
| 175 | 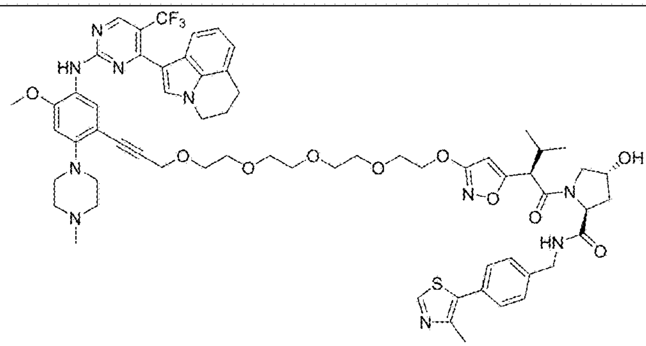 | (2S,4R)-1-((R)-2-(3-((15-(5-((4-(5,6-dihydro-4H-pyrrolo[3,2,1-ij]quinolin-1-yl)-5-(trifluoromethyl)pyrimidin-2-yl)amino)-4-methoxy-2-(4-methylpiperazin-1-yl)phenyl)-3,6,9,12-tetraoxapentadec-14-yn-1-yl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H¹-NMR | Synthesis |
|---|---|---|---|---|---|
| 176 | 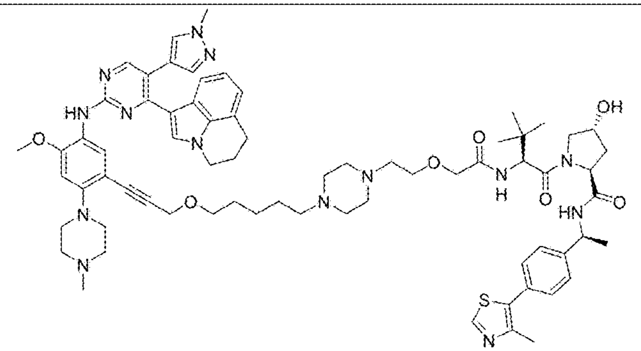 | (2S,4R)-1-((S)-2-(2-(2-(4-(5-((3-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)prop-2-yn-1-yl)oxy)pentyl)piperazin-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 177 | 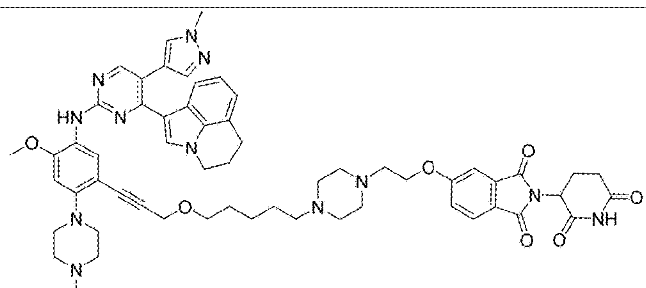 | 5-(2-(4-(5-((3-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin- | | | |

FIG. 2 (continued)

| Example | Structure | Name | (M+H)+ | H¹-NMR | Synthesis |
|---|---|---|---|---|---|
| | | 1-yl)phenyl)prop-2-yn-1-yl)oxy)pentyl)piperazin-1-yl)ethoxy)-2-(2,6-dioxopiperidin-3-yl)isoindoline-1,3-dione | | | |
| 178 | 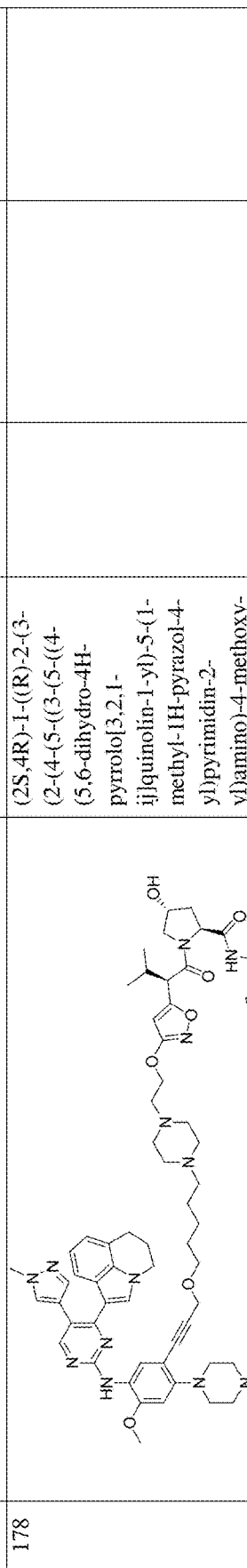 | (2S,4R)-1-((R)-2-(3-(2-(4-(5-((3-(5-((4-(5,6-dihydro-4H-pyrrolo[3,2,1-ij]quinolin-1-yl)-5-(1-methyl-1H-pyrazol-4-yl)pyrimidin-2-yl)amino)-4-methoxy-2-(4-methylpiperazin-1-yl)phenyl)prop-2-yn-1-yl)oxy)pentyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H¹-NMR | Synthesis |
|---|---|---|---|---|---|
| 179 | 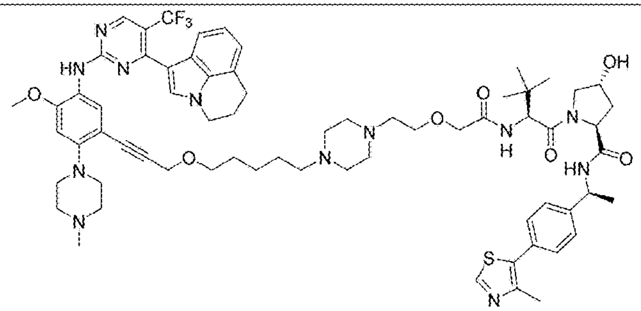 | (2S,4R)-1-((S)-2-(2-(2-(4-(5-((3-(5-((4-(5,6-dihydro-4H-pyrrolo[3,2,1-ij]quinolin-1-yl)-5-(trifluoromethyl)pyrimidin-2-yl)amino)-4-methoxy-2-(4-methylpiperazin-1-yl)phenyl)prop-2-yn-1-yl)oxy)pentyl)piperazin-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 180 | 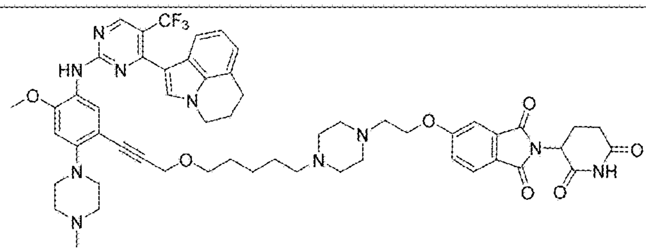 | 5-(2-(4-(5-((3-(5-((4-(5,6-dihydro-4H-pyrrolo[3,2,1-ij]quinolin-1-yl)-5-(trifluoromethyl)pyrimidin-2-yl)amino)-4-methoxy-2-(4-methylpiperazin-1- | | | |

FIG. 2 (continued)

| Example | Structure | Name | (M+H)+ | H1-NMR | Synthesis |
|---|---|---|---|---|---|
|  |  | yl)phenyl)prop-2-yn-1-yl)oxy)pentyl)piperazin-1-yl)ethoxy)-2-(2,6-dioxopiperidin-3-yl)isoindoline-1,3-dione |  |  |  |
| 181 | 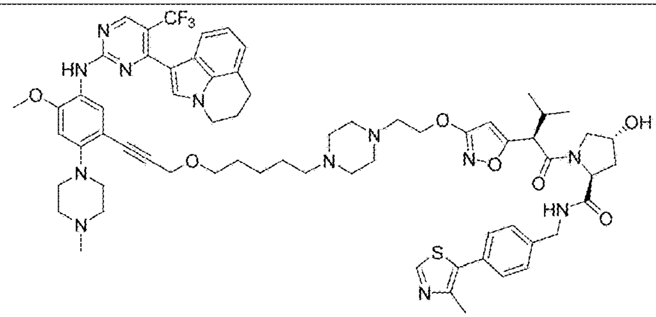 | (2S,4R)-1-((R)-2-(3-(2-(4-(5-((3-(5-((4-(5,6-dihydro-4H-pyrrolo[3,2,1-ij]quinolin-1-yl)-5-(trifluoromethyl)pyrimidin-2-yl)amino)-4-methoxy-2-(4-methylpiperazin-1-yl)phenyl)prop-2-yn-1-yl)oxy)pentyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide |  |  |  |

FIG. 2 (continued)

| Example | Structure | Name | (M+H)⁺ | H¹-NMR | Synthesis |
|---|---|---|---|---|---|
| 182 | 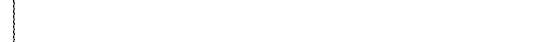 | (2S,4R)-1-((S)-20-(4-((4-(3-acrylamidophenoxy)-5-chloropyrimidin-2-yl)amino)-3-methoxyphenyl)piperazin-1-yl)-2-(tert-butyl)-4,20-dioxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | | | |
| 183 | 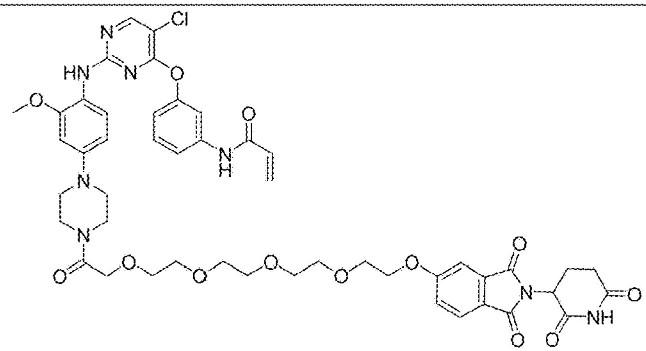 | N-(3-((5-chloro-2-((4-(4-((2-(2,6-dioxopiperidin-3-yl)-1,3-dioxoisoindolin-5-yl)oxy)-3,6,9,12-tetraoxatetradecanoyl)piperazin-1-yl)-2-methoxyphenyl)amino)pyrimidin-4-yl)oxy)phenyl)acrylamide | | | |

FIG. 2 (continued)

| Example | Structure | Name | (M+H)+ | H1-NMR | Synthesis |
|---|---|---|---|---|---|
| 184 | 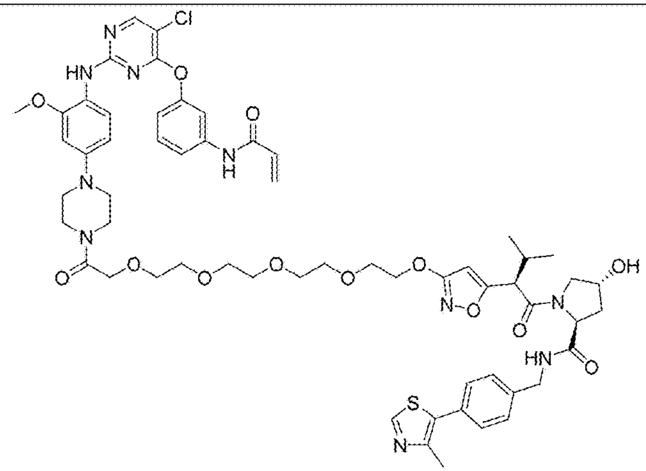 | (2S,4R)-1-((R)-2-(3-((14-(4-(4-(3-acrylamidophenoxy)-5-chloropyrimidin-2-yl)amino)-3-methoxyphenyl)piperazin-1-yl)-14-oxo-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |
| 185 | 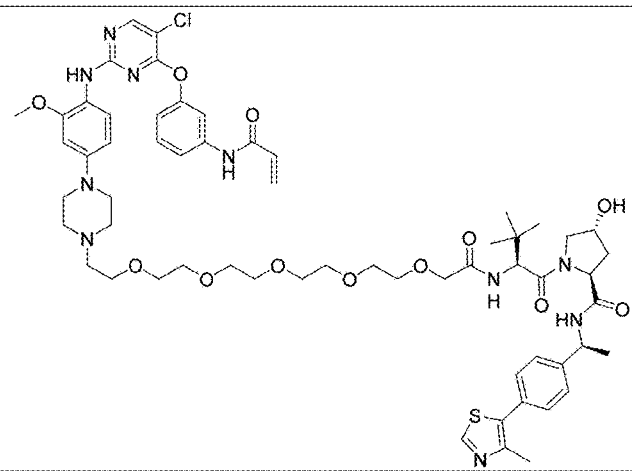 | (2S,4R)-1-((S)-20-(4-(4-(3-acrylamidophenoxy)-5-chloropyrimidin-2-yl)amino)-3-methoxyphenyl)piperazin-1-yl)-2-(tert-butyl)-4-oxo-6,9,12,15,18-pentaoxa-3-azaicosanoyl)-4-hydroxy-N-((S)-1-(4-(4-methylthiazol-5- | | | |

FIG. 2 (continued)

| Example | Structure | Name | (M+H)⁺ | H¹-NMR | Synthesis |
|---|---|---|---|---|---|
| | | yl)phenyl)ethyl)pyrrolidine-2-carboxamide | | | |
| 186 | 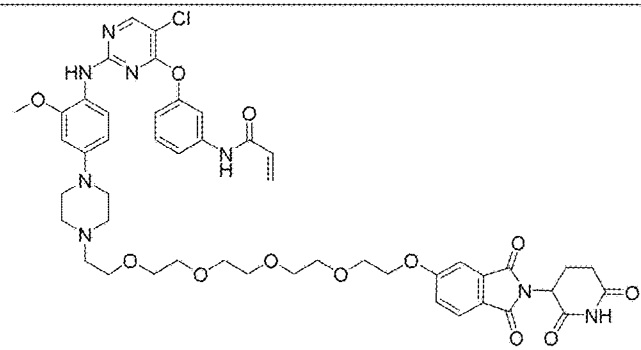 | N-(3-((5-chloro-2-((4-(4-(14-((2-(2,6-dioxopiperidin-3-yl)-1,3-dioxoisoindolin-5-yl)oxy)-3,6,9,12-tetraoxatetradecyl)piperazin-1-yl)-2-methoxyphenyl)amino)pyrimidin-4-yl)oxy)phenyl)acrylamide | | | |
| 187 | 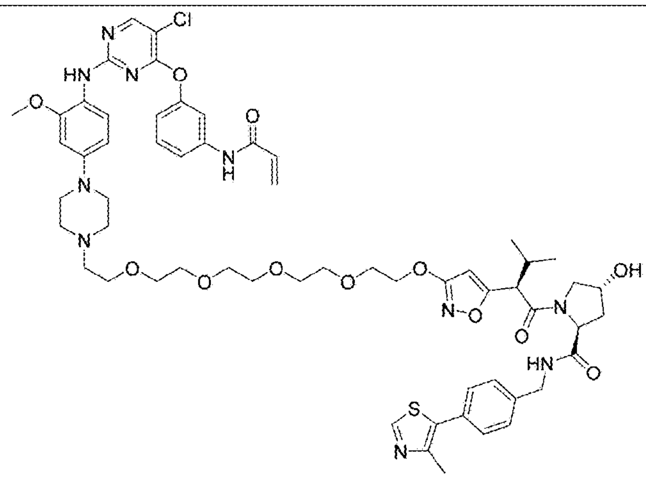 | (2S,4R)-1-((R)-2-(3-((14-(4-((4-(3-acrylamidophenoxy)-5-chloropyrimidin-2-yl)amino)-3-methoxyphenyl)piperazin-1-yl)-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H1-NMR | Synthesis |
|---|---|---|---|---|---|
| 188 |  | (E)-N19-(3-((5-chloro-2-((2-methoxy-4-(4-methylpiperazin-1-yl)phenyl)amino)pyrimidin-4-yl)oxy)phenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |
| 189 |  | (E)-N-(3-((5-chloro-2-((2-methoxy-4-(4-methylpiperazin-1-yl)phenyl)amino)pyrimidin-4-yl)oxy)phenyl)-1-((2-(2,6-dioxopiperidin-3-yl)-1,3-dioxoisoindolin-5-yl)oxy)-3,6,9-trioxa-12-azahexadec-14-en-16-amide | | | |

FIG. 2 (continued)

| Example | Structure | Name | (M+H)⁺ | H¹-NMR | Synthesis |
|---|---|---|---|---|---|
| 190 | 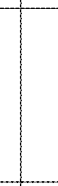 | (2S,4R)-1-((R)-2-(3-(((E)-16-((3-((5-chloro-2-((2-methoxy-4-(4-methylpiperazin-1-yl)phenyl)amino)pyrimidin-4-yl)oxy)phenyl)amino)-16-oxo-3,6,9-trioxa-12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |
| 191 | 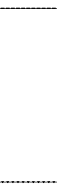 | (E)-N19-(3-(5-chloro-2-((2-methoxy-4-(4-methylpiperazin-1-yl)phenyl)amino)pyrimidin-4-yl)oxy)phenyl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1- | | | |

FIG. 2 (continued)

| Example | Structure | Name | (M+H)+ | H1-NMR | Synthesis |
|---|---|---|---|---|---|
| | | oxobutan-2-yl)-3,6,9,12-tetraoxanonadec-17-enediamide | | | |
| 192 | 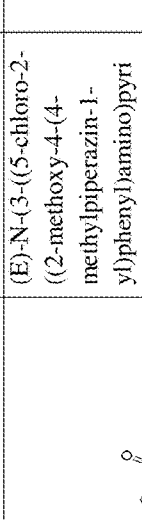 | (E)-N-(3-((5-chloro-2-((2-methoxy-4-(4-methylpiperazin-1-yl)phenyl)amino)pyrimidin-4-yl)oxy)phenyl)-7-(2-(2-(2-(2-(2,6-dioxopiperidin-3-yl)-1,3-dioxoisoindolin-5-yl)oxy)ethoxy)ethoxy)ethoxy)hept-2-enamide | | | |
| 193 | 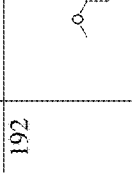 | (2S,4R)-1-((R)-2-(3-(2-(2-(2-(((E)-7-((3-((5-chloro-2-((2-methoxy-4-(4-methylpiperazin-1-yl)phenyl)amino)pyrimidin-4-yl)oxy)phenyl)amino)-7-oxohept-5-en-1-yl)oxy)ethoxy)ethoxy)ethoxy)isoxazol-5-yl)-3-methylbutanoyl)-4- | | | |

FIG. 2 (continued)

| Example | Structure | Name | (M+H)+ | H1-NMR | Synthesis |
|---|---|---|---|---|---|
|  |  | hydroxy-N-(4-(4-methylthiazol-5-yl)benzyl)pyrrolidine-2-carboxamide |  |  |  |
| 194 | 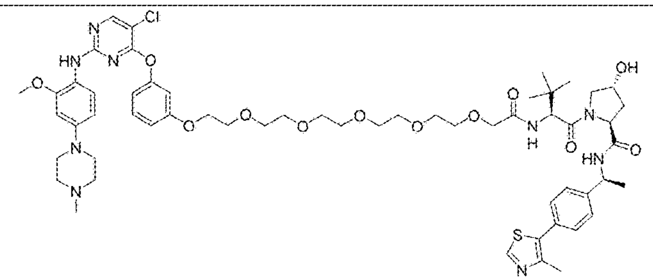 | (2S,4R)-1-((S)-2-(tert-butyl)-20-(3-((5-chloro-2-((2-methoxy-4-(4-methylpiperazin-1-yl)phenyl)amino)pyrimidin-4-yl)oxy)phenoxy)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide |  |  |  |
| 195 | 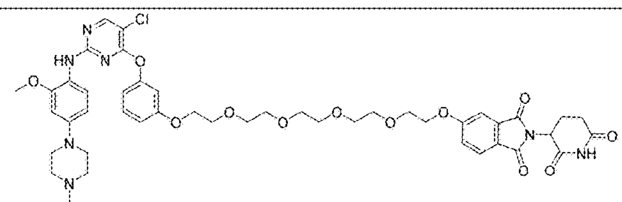 | 5-((14-(3-((5-chloro-2-((2-methoxy-4-(4-methylpiperazin-1-yl)phenyl)amino)pyrimidin-4-yl)oxy)phenoxy)-3,6,9,12-tetraoxatetradecyl)oxy)-2-(2,6- |  |  |  |

FIG. 2 (continued)

| Example | Structure | Name | (M+H)+ | H¹-NMR | Synthesis |
|---|---|---|---|---|---|
| | | dioxopiperidin-3-yl)isoindoline-1,3-dione | | | |
| 196 | 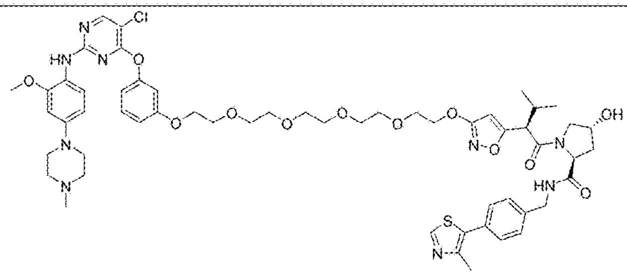 | (2S,4R)-1-((R)-2-(3-((14-(3-((5-chloro-2-((2-methoxy-4-(4-methylpiperazin-1-yl)phenyl)amino)pyrimidin-4-yl)oxy)phenoxy)-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |
| 197 | 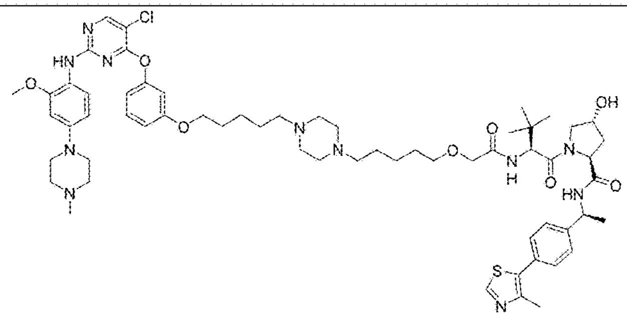 | (2S,4R)-1-((S)-2-(2-((5-(4-(5-(3-((5-chloro-2-((2-methoxy-4-(4-methylpiperazin-1-yl)phenyl)amino)pyrimidin-4-yl)oxy)phenoxy)pentyl)piperazin-1-yl)pentyl)oxy)acetami | | | |

| Exa mple | Structure | Name | (M+H)+ | H1-NMR | Synthesis |
|---|---|---|---|---|---|
| | | do)-3,3-dimethylbutanoyl)-4-hydroxy-N-((S)-1-(4-(4-methylthiazol-5-yl)phenyl)ethyl)pyrrolidine-2-carboxamide | | | |
| 198 | 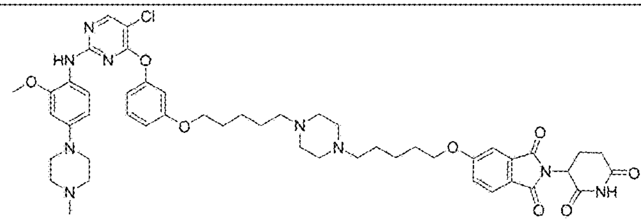 | 5-((5-(4-(5-(3-((5-chloro-2-((2-methoxy-4-(4-methylpiperazin-1-yl)phenyl)amino)pyrimidin-4-yl)oxy)phenoxy)pentyl)piperazin-1-yl)pentyl)oxy)-2-(2,6-dioxopiperidin-3-yl)isoindoline-1,3-dione | | | |
| 199 | 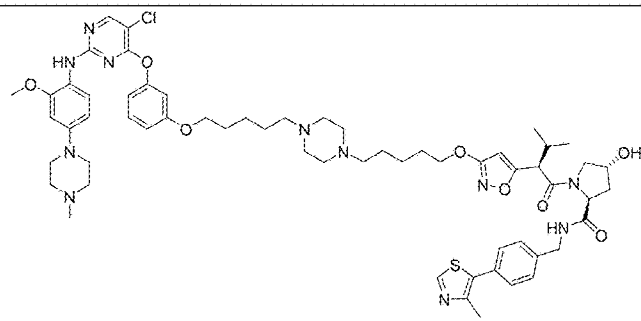 | (2S,4R)-1-((R)-2-(3-((5-(4-(5-(3-((5-chloro-2-((2-methoxy-4-(4-methylpiperazin-1-yl)phenyl)amino)pyrimidin-4-yl)oxy)phenoxy)pentyl)piperazin-1-yl)pentyl)oxy)isoxazol | | | |

| Example | Structure | Name | (M+H)+ | H¹-NMR | Synthesis |
|---|---|---|---|---|---|
| | | -5-yl)-3-methylbutanoyl)-4-hydroxy-N-(4-(4-methylthiazol-5-yl)benzyl)pyrrolidine-2-carboxamide | | | |
| 200 | 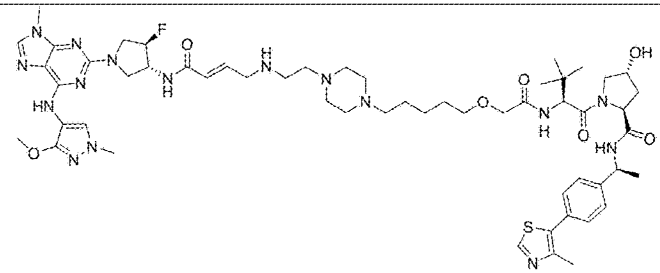 | (2S,4R)-1-((S)-2-(2-((5-(4-(2-(((3R,4R)-4-fluoro-1-(6-((3-methoxy-1-methyl-1H-pyrazol-4-yl)amino)-9-methyl-9H-purin-2-yl)pyrrolidin-3-yl)amino)-4-oxobut-2-en-1-yl)amino)ethyl)piperazin-1-yl)pentyl)oxy)acetamido)-3,3-dimethylbutanoyl)-4-hydroxy-N-((S)-1-(4-(4-methylthiazol-5-yl)phenyl)ethyl)pyrrolidine-2-carboxamide | | | |

FIG. 2 (continued)

| Example | Structure | Name | (M+H)⁺ | H¹-NMR | Synthesis |
|---|---|---|---|---|---|
| 201 | 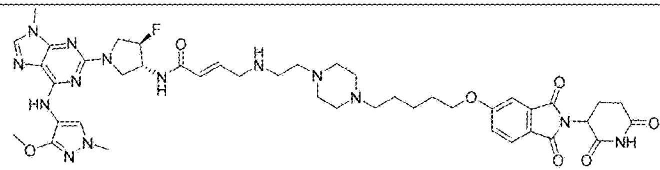 | (E)-4-((2-(4-(5-((2-(2,6-dioxopiperidin-3-yl)-1,3-dioxoisoindolin-5-yl)oxy)pentyl)piperazin-1-yl)ethyl)amino)-N-((3R,4R)-4-fluoro-1-(6-((3-methoxy-1-methyl-1H-pyrazol-4-yl)amino)-9-methyl-9H-purin-2-yl)pyrrolidin-3-yl)but-2-enamide | | | |
| 202 | 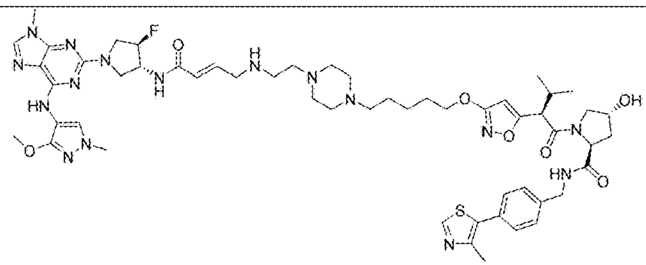 | (2S,4R)-1-((R)-2-(3-((5-(4-(2-(((E)-4-(((3R,4R)-4-fluoro-1-(6-((3-methoxy-1-methyl-1H-pyrazol-4-yl)amino)-9-methyl-9H-purin-2-yl)pyrrolidin-3-yl)amino)-4-oxobut-2-en-1-yl)amino)ethyl)piperazin-1-yl)pentyl)oxy)isoxazol-5-yl)-3-methylbutanoyl)-4- | | | |

FIG. 2 (continued)

| Example | Structure | Name | (M+H)+ | H1-NMR | Synthesis |
|---|---|---|---|---|---|
| 203 | 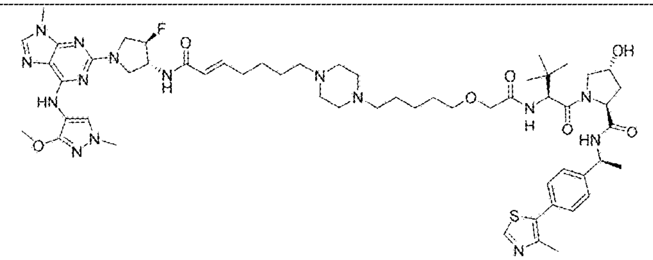 | hydroxy-N-(4-(4-methylthiazol-5-yl)benzyl)pyrrolidine-2-carboxamide (2S,4R)-1-((S)-2-(2-((5-(4-((E)-7-(((3R,4R)-4-fluoro-1-(6-((3-methoxy-1-methyl-1H-pyrazol-4-yl)amino)-9-methyl-9H-purin-2-yl)pyrrolidin-3-yl)amino)-7-oxohept-5-en-1-yl)piperazin-1-yl)pentyl)oxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 204 | 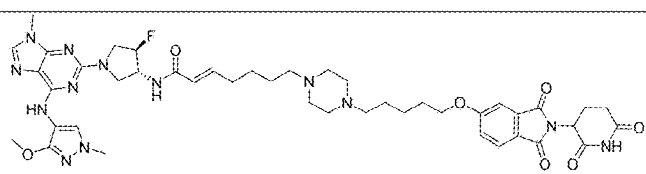 | (E)-7-(4-(5-((2-(2,6-dioxopiperidin-3-yl)-1,3-dioxoisoindolin-5-yl)oxy)pentyl)piperazin-1-yl)-N-((3R,4R)-4-fluoro-1-(6-((3-methoxy-1-methyl- | | | |

| Example | Structure | Name | (M+H)⁺ | H¹-NMR | Synthesis |
|---|---|---|---|---|---|
| | | 1H-pyrazol-4-yl)amino)-9-methyl-9H-purin-2-yl)pyrrolidin-3-yl)hept-2-enamide | | | |
| 205 | 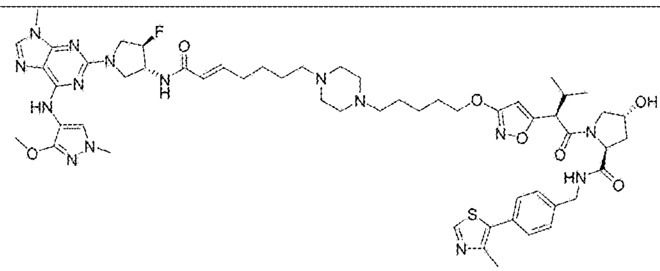 | (2S,4R)-1-((R)-2-(3-((5-(4-((E)-7-(((3R,4R)-4-fluoro-1-(6-((3-methoxy-1-methyl-1H-pyrazol-4-yl)amino)-9-methyl-9H-purin-2-yl)pyrrolidin-3-yl)amino)-7-oxohept-5-en-1-yl)piperazin-1-yl)pentyl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H1-NMR | Synthesis |
|---|---|---|---|---|---|
| 206 | 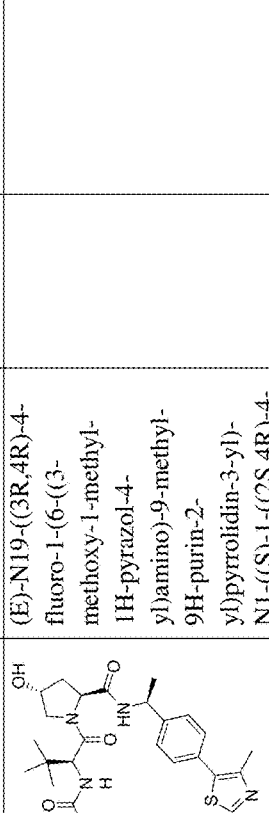 | (E)-N19-((3R,4R)-4-fluoro-1-(6-((3-methoxy-1-methyl-1H-pyrazol-4-yl)amino)-9-methyl-9H-purin-2-yl)pyrrolidin-3-yl)-N1-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-3,6,9,12-tetraoxa-15-azanonadec-17-enediamide | | | |
| 207 | 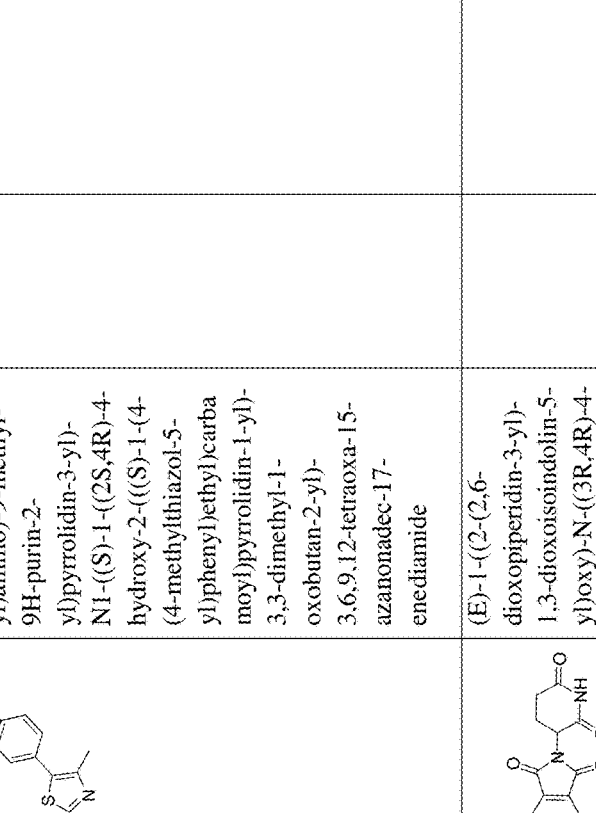 | (E)-1-(2-(2,6-dioxopiperidin-3-yl)-1,3-dioxoisoindolin-5-yl)oxy)-N-((3R,4R)-4-fluoro-1-(6-((3-methoxy-1-methyl-1H-pyrazol-4-yl)amino)-9-methyl-9H-purin-2-yl)pyrrolidin-3-yl)-3,6,9-trioxa-12- | | | |

| Example | Structure | Name | (M+H)+ | H1-NMR | Synthesis |
|---|---|---|---|---|---|
| 208 | 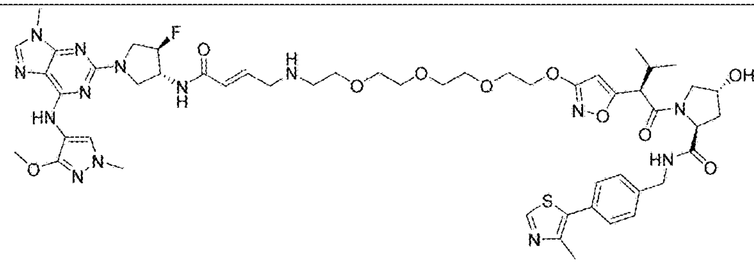 | azahexadec-14-en-16-amide (2S,4R)-1-((R)-2-(3-(((E)-16-(((3R,4R)-4-fluoro-1-(6-((3-methoxy-1-methyl-1H-pyrazol-4-yl)amino)-9-methyl-9H-purin-2-yl)pyrrolidin-3-yl)amino)-16-oxo-3,6,9-trioxa-12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H1-NMR | Synthesis |
|---|---|---|---|---|---|
| 209 | 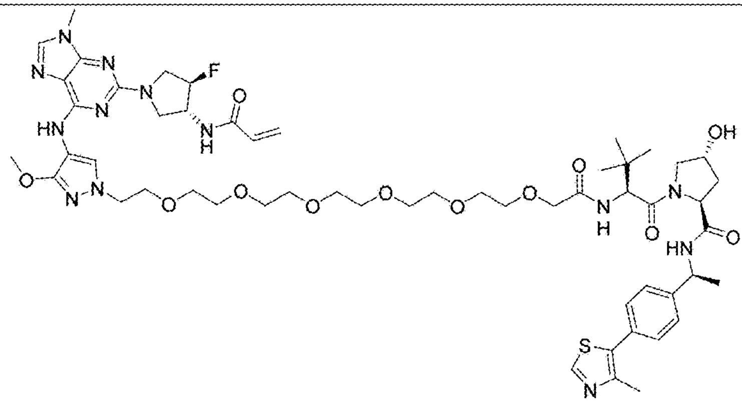 | (2S,4R)-1-((S)-23-(4-((2-((3R,4R)-3-acrylamido-4-fluoropyrrolidin-1-yl)-9-methyl-9H-purin-6-yl)amino)-3-methoxy-1H-pyrazol-1-yl)-2-(tert-butyl)-4-oxo-6,9,12,15,18,21-hexaoxa-3-azatricosanoyl)-4-hydroxy-N-((S)-1-(4-(4-methylthiazol-5-yl)phenyl)ethyl)pyrrolidine-2-carboxamide | | | |
| 210 | 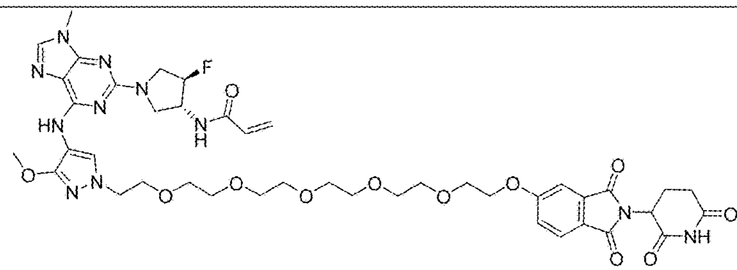 | N-((3R,4R)-1-(6-((1-(17-((2-(2,6-dioxopiperidin-3-yl)-1,3-dioxoisoindolin-5-yl)oxy)-3,6,9,12,15-pentaoxaheptadecyl)-3-methoxy-1H-pyrazol-4-yl)amino)-9-methyl-9H-purin-2-yl)-4-fluoropyrrolidin-3-yl)acrylamide | | | |

FIG. 2 (continued)

| Example | Structure | Name | (M+H)+ | H¹-NMR | Synthesis |
|---|---|---|---|---|---|
| 211 | 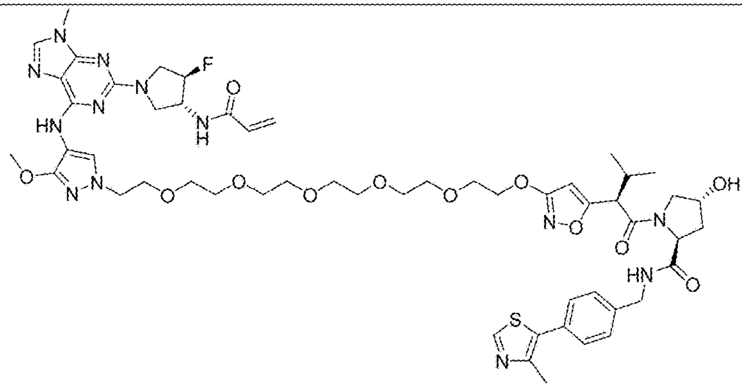 | (2S,4R)-1-((R)-2-(3-((17-(4-((2-((3R,4R)-3-acrylamido-4-fluoropyrrolidin-1-yl)-9-methyl-9H-purin-6-yl)amino)-3-methoxy-1H-pyrazol-1-yl)-3,6,9,12,15-pentaoxaheptadecyl)oxy)isoxazol-5-yl)-3-methylbutanoyl)-4-hydroxy-N-(4-(4-methylthiazol-5-yl)benzyl)pyrrolidine-2-carboxamide | | | |
| 212 | 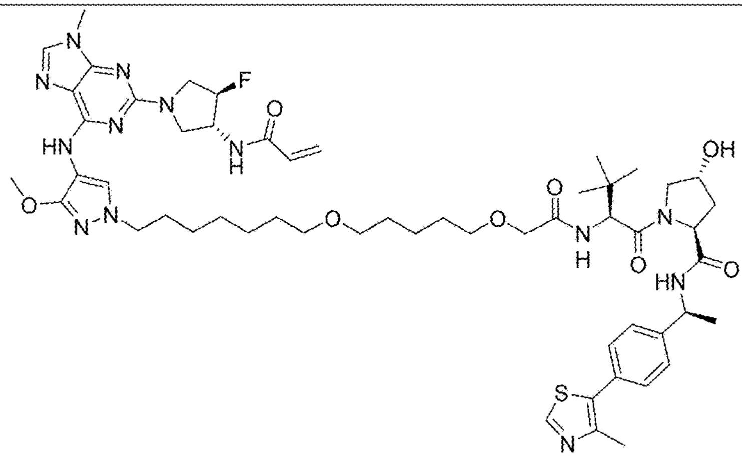 | (2S,4R)-1-((S)-2-(2-((5-(7-(4-((2-((3R,4R)-3-acrylamido-4-fluoropyrrolidin-1-yl)-9-methyl-9H-purin-6-yl)amino)-3-methoxy-1H-pyrazol-1-yl)heptyl)oxy)pentyl)oxy)acetamido)-3,3-dimethylbutanoyl)-4-hydroxy-N-((S)-1-(4-(4-methylthiazol-5- | | | |

FIG. 2 (continued)

| Example | Structure | Name | (M+H)⁺ | H¹-NMR | Synthesis |
|---|---|---|---|---|---|
| 213 | 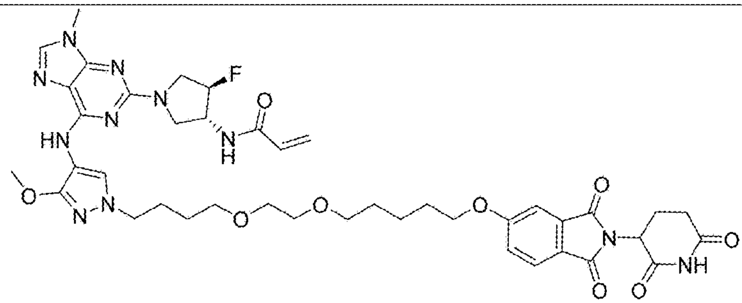 | yl)phenyl)ethyl)pyrrolidine-2-carboxamide N-((3R,4R)-1-(6-((1-(4-(2-((5-(2-(2,6-dioxopiperidin-3-yl)-1,3-dioxoisoindolin-5-yl)oxy)pentyl)oxy)ethoxy)butyl)-3-methoxy-1H-pyrazol-4-yl)amino)-9-methyl-9H-purin-2-yl)-4-fluoropyrrolidin-3-yl)acrylamide | | | |
| 214 | 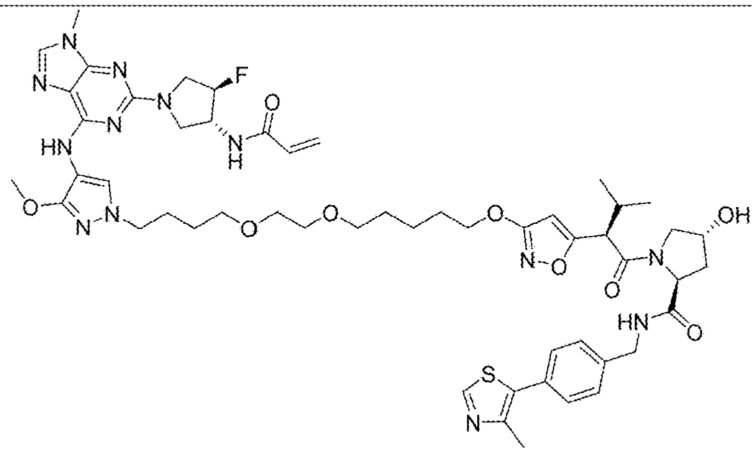 | (2S,4R)-1-((R)-2-(3-((5-(2-(4-(4-((3R,4R)-3-acrylamido-4-fluoropyrrolidin-1-yl)-9-methyl-9H-purin-6-yl)amino)-3-methoxy-1H-pyrazol-1-yl)butoxy)ethoxy)pentyl)oxy)isoxazol-5-yl)-3-methylbutanoyl)-4-hydroxy-N-(4-(4-methylthiazol-5-yl)benzyl)pyrrolidine- | | | |

| Exa mpl e | Structure | Name | (M+H)+ | H1-NMR | Synthesis |
|---|---|---|---|---|---|
| | | 2-carboxamide | | | |
| 215 | 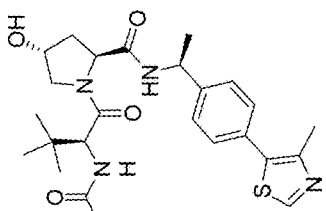 | (2S,4R)-1-((S)-2-(2-(4-(4-(5-(4-((2-((3R,4R)-3-acrylamido-4-fluoropyrrolidin-1-yl)-9-methyl-9H-purin-6-yl)amino)-3-methoxy-1H-pyrazol-1-yl)pentyl)piperazin-1-yl)butoxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 216 | 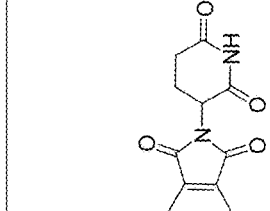 | N-((3R,4R)-1-(6-((1-(5-(4-(4-((2-(2,6-dioxopiperidin-3-yl)-1,3-dioxoisoindolin-5-yl)oxy)butyl)piperazin-1-yl)pentyl)-3-methoxy-1H-pyrazol-4-yl)amino)-9-methyl-9H-purin-2-yl)-4-fluoropyrrolidin-3- | | | |

FIG. 2 (continued)

| Example | Structure | Name | (M+H)+ | H1-NMR | Synthesis |
|---|---|---|---|---|---|
| | | yl)acrylamide | | | |
| 217 | 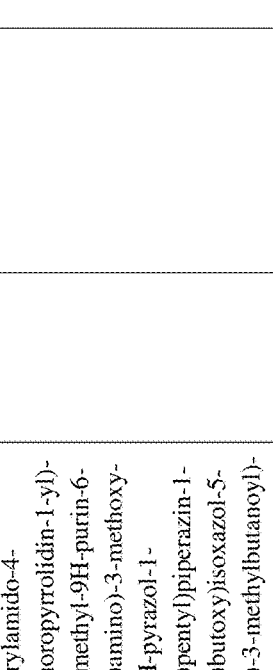 | (2S,4R)-1-((R)-2-(3-(4-(4-(5-(4-((2-((3R,4R)-3-acrylamido-4-fluoropyrrolidin-1-yl)-9-methyl-9H-purin-6-yl)amino)-3-methoxy-1H-pyrazol-1-yl)pentyl)piperazin-1-yl)butoxy)isoxazol-5-yl)-3-methylbutanoyl)-4-hydroxy-N-(4-(4-methylthiazol-5-yl)benzyl)pyrrolidine-2-carboxamide | | | |
| 218 | 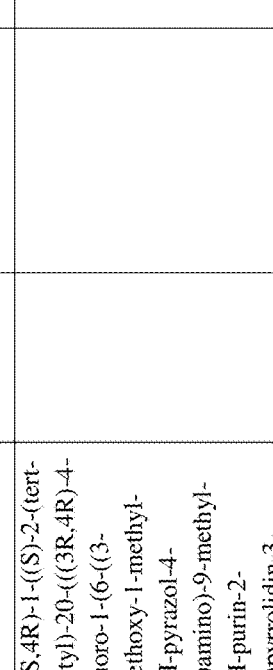 | (2S,4R)-1-((S)-2-(tert-butyl)-20-(((3R,4R)-4-fluoro-1-(6-((3-methoxy-1-methyl-1H-pyrazol-4-yl)amino)-9-methyl-9H-purin-2-yl)pyrrolidin-3-yl)amino)-4-oxo-6,9,12,15,18-pentaoxa-3-azaicosanoyl)-4- | | | |

| Example | Structure | Name | (M+H)⁺ | H¹-NMR | Synthesis |
|---|---|---|---|---|---|
| 219 | 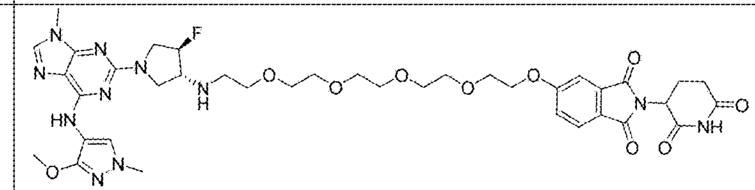 | 2-(2,6-dioxopiperidin-3-yl)-5-((14-(((3R,4R)-4-fluoro-1-(6-((3-methoxy-1-methyl-1H-pyrazol-4-yl)amino)-9-methyl-9H-purin-2-yl)pyrrolidin-3-yl)amino)-3,6,9,12-tetraoxatetradecyl)oxy)isoindoline-1,3-dione | | | |
| 220 | 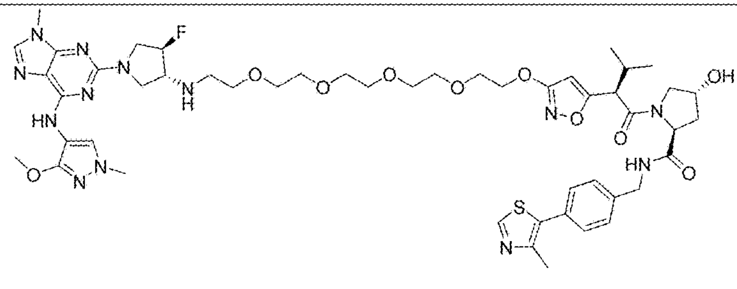 | (2S,4R)-1-((R)-2-(3-((14-(((3R,4R)-4-fluoro-1-(6-((3-methoxy-1-methyl-1H-pyrazol-4-yl)amino)-9-methyl-9H-purin-2-yl)pyrrolidin-3-yl)amino)-3,6,9,12-tetraoxatetradecyl)oxy)isoxazol-5-yl)-3-methylbutanoyl)-4-hydroxy-N-(4-(4- | | | |

FIG. 2 (continued)

| Example | Structure | Name | (M+H)+ | H¹-NMR | Synthesis |
|---|---|---|---|---|---|
| 221 | 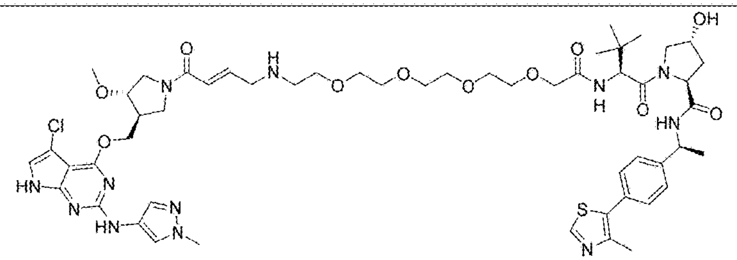 | methylthiazol-5-yl)benzyl)pyrrolidine-2-carboxamide (2S,4R)-1-((S,E)-2-(tert-butyl)-22-((3S,4S)-3-(((5-chloro-2-((1-methyl-1H-pyrazol-4-yl)amino)-7H-pyrrolo[2,3-d]pyrimidin-4-yl)oxy)methyl)-4-methoxypyrrolidin-1-yl)-4,22-dioxo-6,9,12,15-tetraoxa-3,18-diazadocos-20-enoyl)-4-hydroxy-N-((S)-1-(4-(4-methylthiazol-5-yl)phenyl)ethyl)pyrrolidine-2-carboxamide | | | |
| 222 | 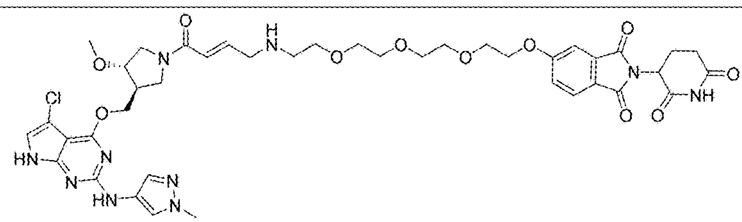 | 5-(((E)-16-((3S,4S)-3-(((5-chloro-2-((1-methyl-1H-pyrazol-4-yl)amino)-7H-pyrrolo[2,3-d]pyrimidin-4-yl)oxy)methyl)-4- | | | |

| Example | Structure | Name | (M+H)+ | H1-NMR | Synthesis |
|---|---|---|---|---|---|
| | | methoxypyrrolidin-1-yl)-16-oxo-3,6,9-trioxa-12-azahexadec-14-en-1-yl)oxy)-2-(2,6-dioxopiperidin-3-yl)isoindoline-1,3-dione | | | |
| 223 | 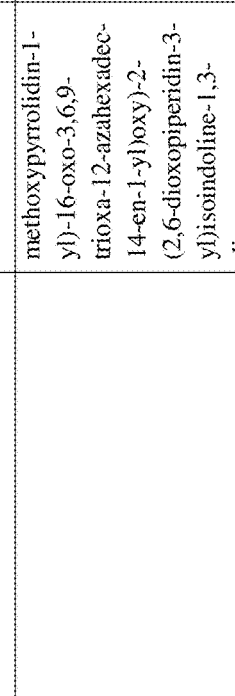 | (2S,4R)-1-((R)-2-(3-(((E)-16-((3S,4S)-3-(((5-chloro-2-((1-methyl-1H-pyrazol-4-yl)amino)-7H-pyrrolo[2,3-d]pyrimidin-4-yl)oxy)methyl)-4-methoxypyrrolidin-1-yl)-16-oxo-3,6,9-trioxa-12-azahexadec-14-en-1-yl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H¹-NMR | Synthesis |
|---|---|---|---|---|---|
| 224 | 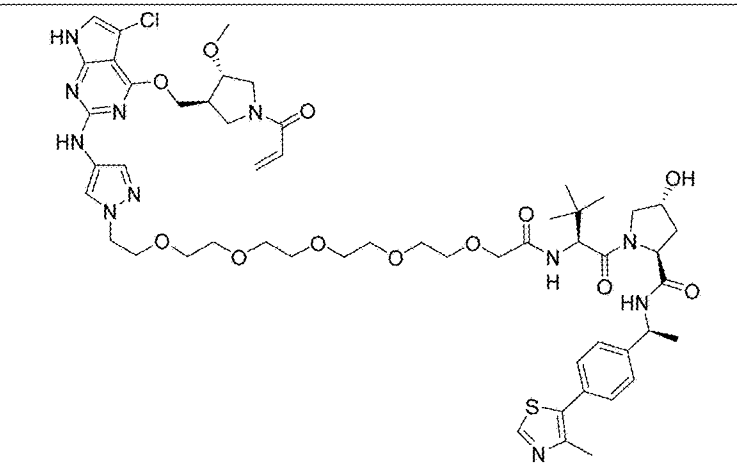 | (2S,4R)-1-((S)-20-(4-((4-(((3S,4S)-1-acryloyl-4-methoxypyrrolidin-3-yl)methoxy)-5-chloro-7H-pyrrolo[2,3-d]pyrimidin-2-yl)amino)-1H-pyrazol-1-yl)-2-(tert-butyl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | | | |
| 225 | 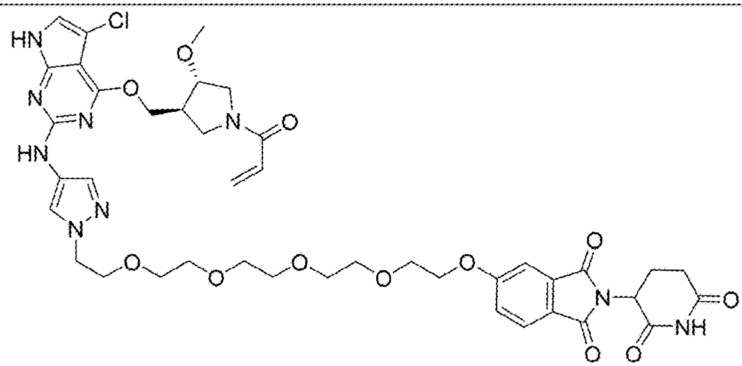 | 5-((14-(4-((((3S,4S)-1-acryloyl-4-methoxypyrrolidin-3-yl)methoxy)-5-chloro-7H-pyrrolo[2,3-d]pyrimidin-2-yl)amino)-1H-pyrazol-1-yl)-3,6,9,12-tetraoxatetradecyl)oxy)-2-(2,6-dioxopiperidin-3- | | | |

| Example | Structure | Name | (M+H)+ | H¹-NMR | Synthesis |
|---|---|---|---|---|---|
| | | y1)isoindoline-1,3-dione | | | |
| 226 | 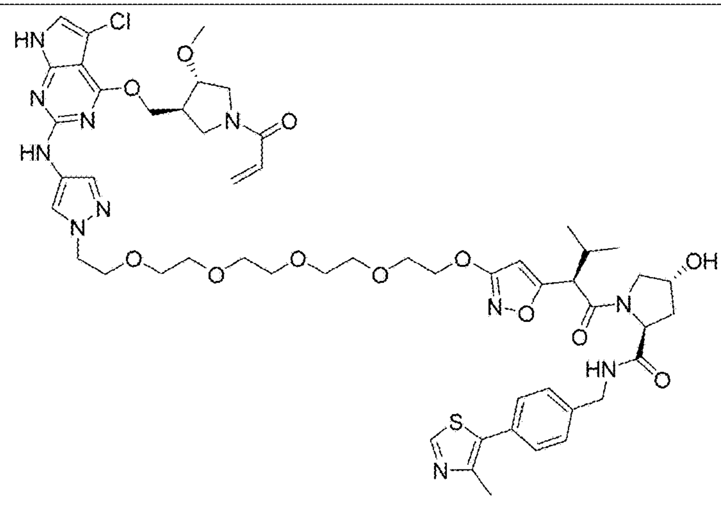 | (2S,4R)-1-((R)-2-(3-((14-(4-(4-(((3S,4S)-1-acryloyl-4-methoxypyrrolidin-3-yl)methoxy)-5-chloro-7H-pyrrolo[2,3-d]pyrimidin-2-yl)amino)-1H-pyrazol-1-yl)-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H¹-NMR | Synthesis |
|---|---|---|---|---|---|
| 227 | 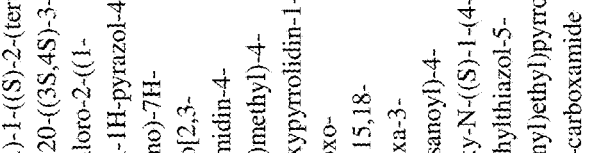 | (2S,4R)-1-((S)-2-(tert-butyl)-20-((3S,4S)-3-(((5-chloro-2-((1-methyl-1H-pyrazol-4-yl)amino)-7H-pyrrolo[2,3-d]pyrimidin-4-yl)oxy)methyl)-4-methoxypyrrolidin-1-yl)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide | | | |
| 228 | 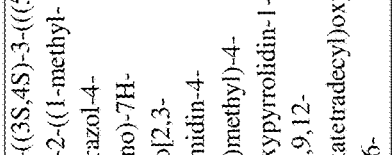 | 5-((14-((3S,4S)-3-(((5-chloro-2-((1-methyl-1H-pyrazol-4-yl)amino)-7H-pyrrolo[2,3-d]pyrimidin-4-yl)oxy)methyl)-4-methoxypyrrolidin-1-yl)-3,6,9,12-tetraoxatetradecyl)oxy)-2-(2,6- | | | |

FIG. 2 (continued)

| Example | Structure | Name | (M+H)+ | H¹-NMR | Synthesis |
|---|---|---|---|---|---|
| | | dioxopiperidin-3-yl)isoindoline-1,3-dione | | | |
| 229 | 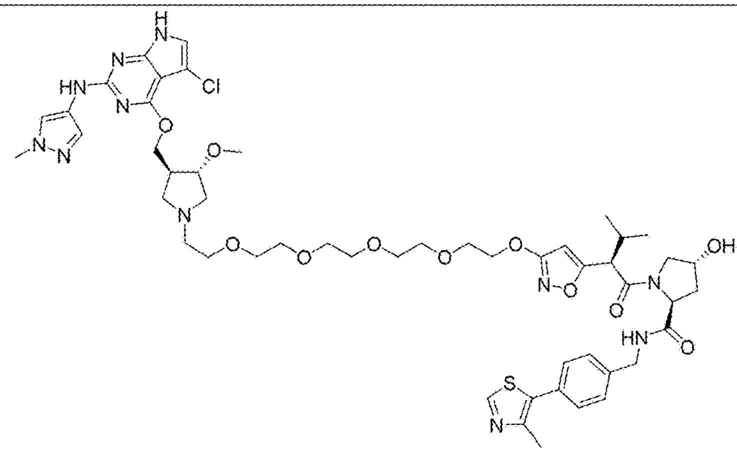 | (2S,4R)-1-((R)-2-(3-((14-((3S,4S)-3-(((5-chloro-2-(((1-methyl-1H-pyrazol-4-yl)amino)-7H-pyrrolo[2,3-d]pyrimidin-4-yl)oxy)methyl)-4-methoxypyrrolidin-1-yl)-3,6,9,12-tetraoxatetradecyl)oxy)isoxazol-5-yl)-3-methylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)+ | H1-NMR | Synthesis |
|---|---|---|---|---|---|
| 230 | 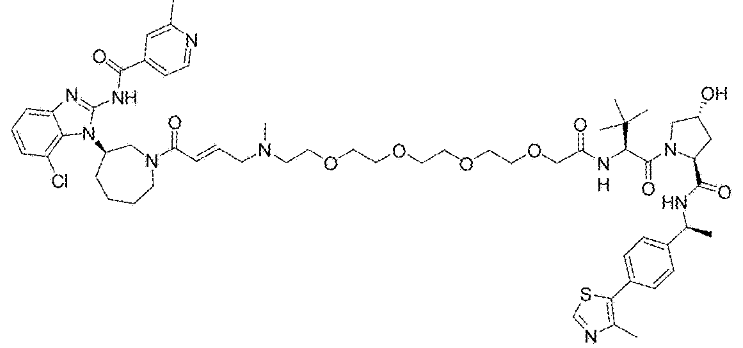 | N-(7-chloro-1-((R)-1-((S,E)-3-((2S,4R)-4-hydroxy-2-(((S)-1-(4-(4-methylthiazol-5-yl)phenyl)ethyl)carbamoyl)pyrrolidine-1-carbonyl)-2,2,19-trimethyl-5-oxo-7,10,13,16-tetraoxa-4,19-diazatricos-21-en-23-oyl)azepan-3-yl)-1H-benzo[d]imidazol-2-yl)-2-methylisonicotinamide | | | |
| 231 | 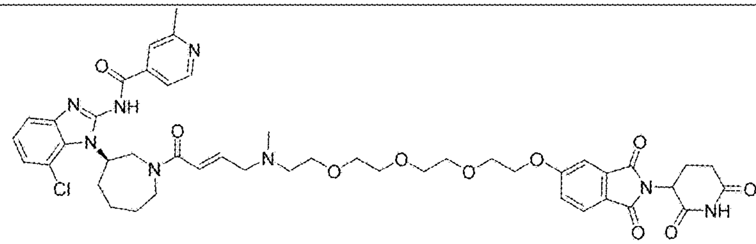 | N-(7-chloro-1-((3R)-1-((E)-1-(2-(2,6-dioxopiperidin-3-yl)-1,3-dioxoisoindolin-5-yl)oxy)-12-methyl-3,6,9-trioxa-12-azahexadec-14-en-16-oyl)azepan-3-yl)-1H-benzo[d]imidazol-2-yl)-2-methylisonicotinamide | | | |

FIG. 2 (continued)

| Example | Structure | Name | (M+H)+ | H1-NMR | Synthesis |
|---|---|---|---|---|---|
| 232 | 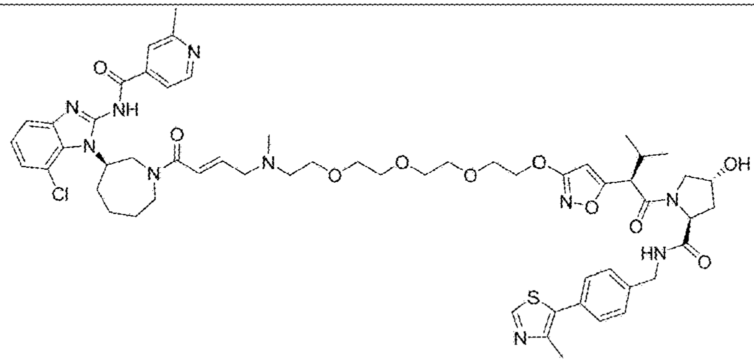 | N-(7-chloro-1-((R)-1-((E)-1-((5-((R)-1-((2S,4R)-4-hydroxy-2-((4-(4-methylthiazol-5-yl)benzyl)carbamoyl)pyrrolidin-1-yl)-3-methyl-1-oxobutan-2-yl)isoxazol-3-yl)oxy)-12-methyl-3,6,9-trioxa-12-azahexadec-14-en-16-oyl)azepan-3-yl)-1H-benzo[d]imidazol-2-yl)-2-methylisonicotinamide | | | |
| 233 | 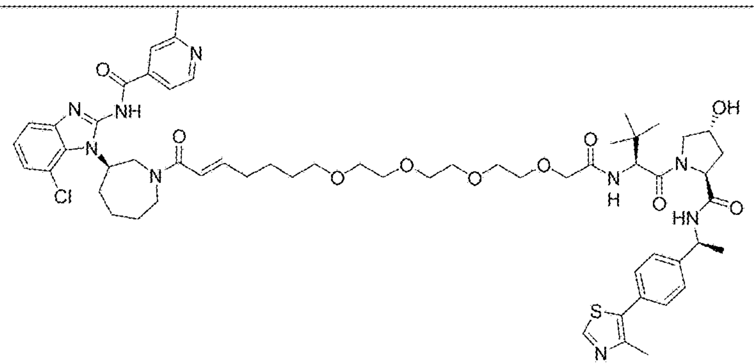 | N-(7-chloro-1-((R)-1-((S,E)-3-((2S,4R)-4-hydroxy-2-(((S)-1-(4-(4-methylthiazol-5-yl)phenyl)ethyl)carbamoyl)pyrrolidine-1-carbonyl)-2,2-dimethyl-5-oxo-7,10,13,16-tetraoxa-4-azatricos-21-en-23-oyl)azepan-3-yl)-1H-benzo[d]imidazol-2- | | | |

FIG. 2 (continued)

| Example | Structure | Name | (M+H)⁺ | H¹-NMR | Synthesis |
|---|---|---|---|---|---|
| | | yl)-2-methylisonicotinamide | | | |
| 234 | 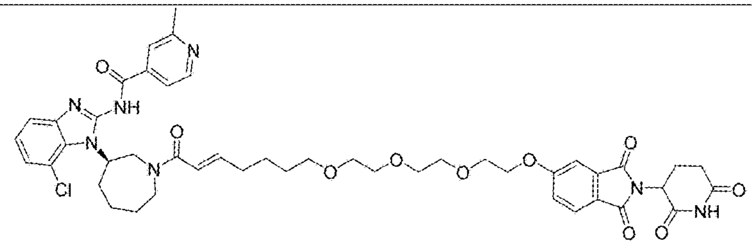 | N-(7-chloro-1-((3R)-1-((E)-7-(2-(2-(2-((2,6-dioxopiperidin-3-yl)-1,3-dioxoisoindolin-5-yl)oxy)ethoxy)ethoxy)hept-2-enoyl)azepan-3-yl)-1H-benzo[d]imidazol-2-yl)-2-methylisonicotinamide | | | |
| 235 | 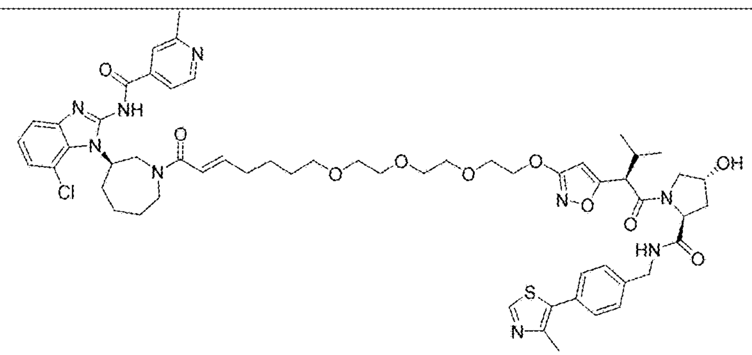 | N-(7-chloro-1-((R)-1-((E)-7-(2-(2-(2-((5-((R)-1-((2S,4R)-4-hydroxy-2-((4-(4-methylthiazol-5-yl)benzyl)carbamoyl)pyrrolidin-1-yl)-3-methyl-1-oxobutan-2-yl)isoxazol-3-yl)oxy)ethoxy)ethoxy)hept-2-enoyl)azepan-3-yl)-1H-benzo[d]imidazol-2-yl)-2- | | | |

FIG. 2 (continued)

| Example | Structure | Name | (M+H)⁺ | H¹-NMR | Synthesis |
|---|---|---|---|---|---|
| 236 | 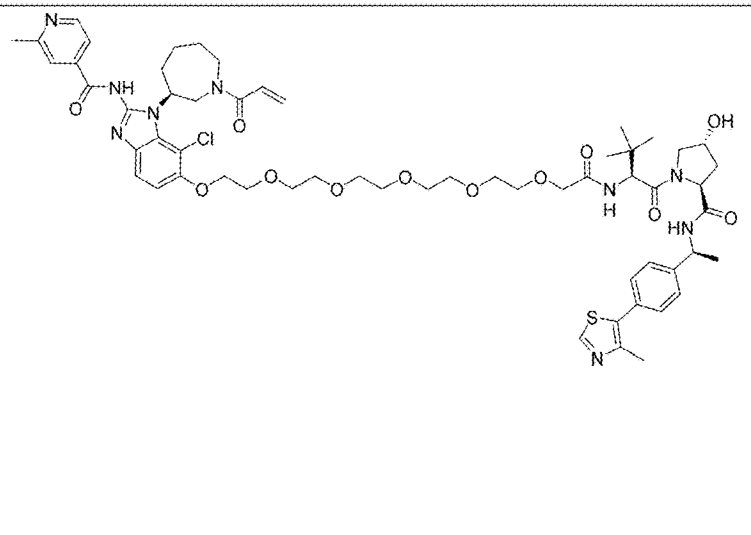 | N-(1-((S)-1-acryloylazepan-3-yl)-7-chloro-6-(((S)-19-((2S,4R)-4-hydroxy-2-(((S)-1-(4-(4-methylthiazol-5-yl)phenyl)ethyl)carbamoyl)pyrrolidine-1-carbonyl)-20,20-dimethyl-17-oxo-3,6,9,12,15-pentaoxa-18-azahenicosyl)oxy)-1H-benzo[d]imidazol-2-yl)-2-methylisonicotinamide | | | |
| 237 | 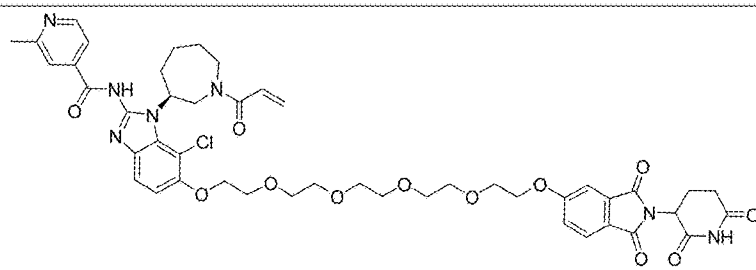 | N-(1-((S)-1-acryloylazepan-3-yl)-7-chloro-6-((14-((2-(2,6-dioxopiperidin-3-yl)-1,3-dioxoisoindolin-5-yl)oxy)-3,6,9,12-tetraoxatetradecyl)oxy)-1H-benzo[d]imidazol-2-yl)-2-methylisonicotinamide | | | |

FIG. 2 (continued)

| Example | Structure | Name | (M+H)⁺ | H¹-NMR | Synthesis |
|---|---|---|---|---|---|
| | | methylisonicotinamide | | | |
| 238 | 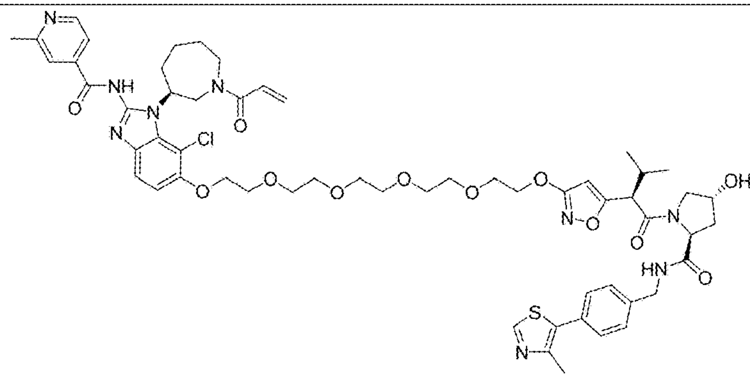 | N-(1-((S)-1-acryloylazepan-3-yl)-7-chloro-6-((14-((5-((R)-1-((2S,4R)-4-hydroxy-2-((4-(4-methylthiazol-5-yl)benzyl)carbamoyl)pyrrolidin-1-yl)-3-methyl-1-oxobutan-2-yl)isoxazol-3-yl)oxy)-3,6,9,12-tetraoxatetradecyl)oxy)-1H-benzo[d]imidazol-2-yl)-2-methylisonicotinamide | | | |

FIG. 2 (continued)

| Example | Structure | Name | (M+H)⁺ | H¹-NMR | Synthesis |
|---|---|---|---|---|---|
| 239 | 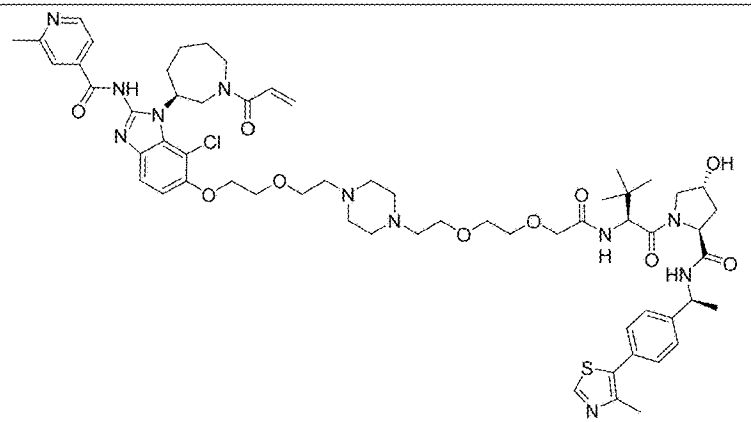 | N-(1-((S)-1-acryloylazepan-3-yl)-7-chloro-6-(2-(2-(4-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethoxy)piperazin-1-yl)ethoxy)ethoxy)-1H-benzo[d]imidazol-2-yl)-2-methylisonicotinamide | | | |
| 240 | 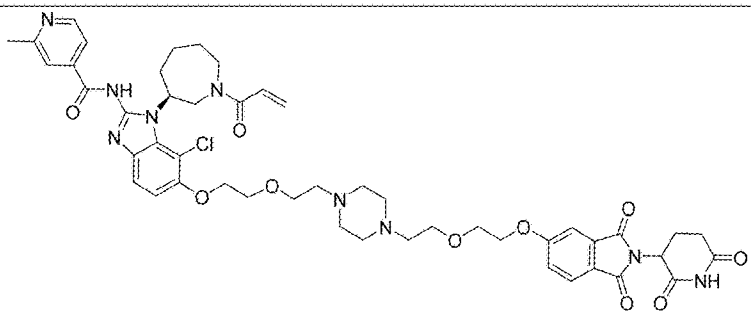 | N-(1-((S)-1-acryloylazepan-3-yl)-7-chloro-6-(2-(2-(4-(2-(2-((2-(2,6-dioxopiperidin-3-yl)-1,3-dioxoisoindolin-5-yl)oxy)ethoxy)ethyl)piperazin-1-yl)ethoxy)ethoxy)-1H-benzo[d]imidazol-2-yl)-2- | | | |

FIG. 2 (continued)

| Example | Structure | Name | (M+H)+ | H¹-NMR | Synthesis |
|---|---|---|---|---|---|
| 241 | 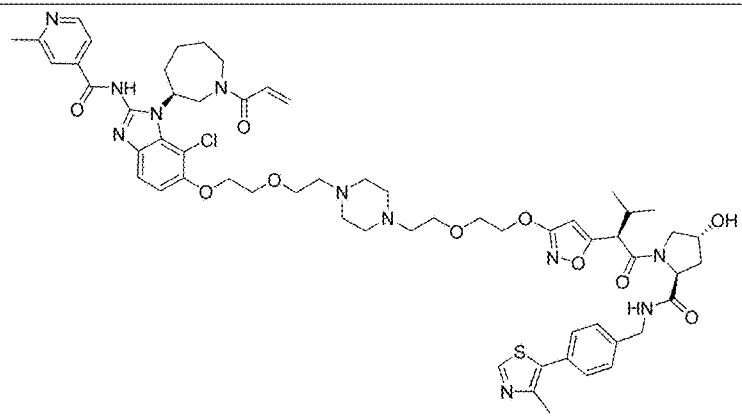 | N-(1-((S)-1-acryloylazepan-3-yl)-7-chloro-6-(2-(2-(4-(2-(2-((5-((R)-1-((2S,4R)-4-hydroxy-2-((4-(4-methylthiazol-5-yl)benzyl)carbamoyl)pyrrolidin-1-yl)-3-methyl-1-oxobutan-2-yl)isoxazol-3-yl)oxy)ethoxy)ethyl)piperazin-1-yl)ethoxy)ethoxy)-1H-benzo[d]imidazol-2-yl)-2-methylisonicotinamide | | | |

FIG. 2 (continued)

| Example | Structure | Name | (M+H)+ | H1-NMR | Synthesis |
|---|---|---|---|---|---|
| 242 | 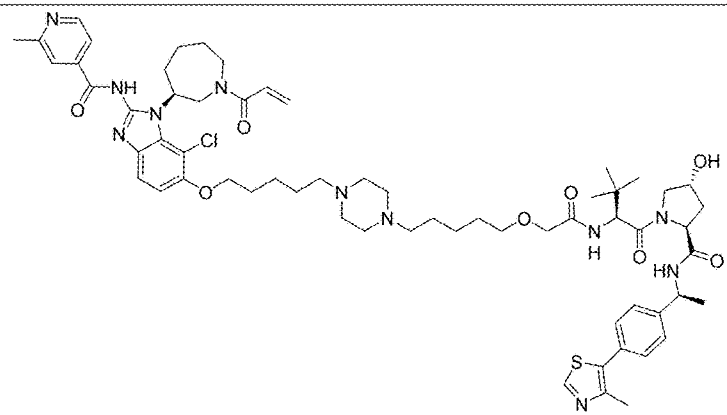 | N-(1-((S)-1-acryloylazepan-3-yl)-7-chloro-6-((5-(4-(5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentyl)piperazin-1-yl)pentyl)oxy)-1H-benzo[d]imidazol-2-yl)-2-methylisonicotinamide | | | |
| 243 | 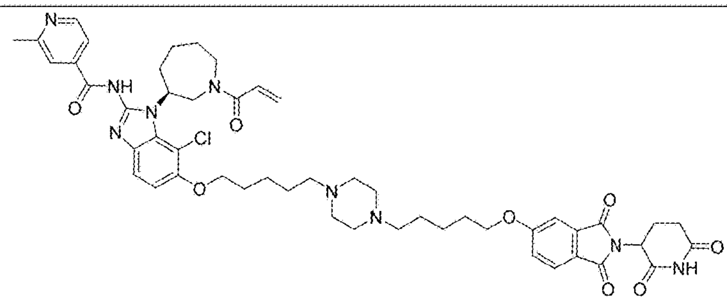 | N-(1-((S)-1-acryloylazepan-3-yl)-7-chloro-6-((5-(4-(5-((2-(2,6-dioxopiperidin-3-yl)-1,3-dioxoisoindolin-5-yl)oxy)pentyl)piperazin-1-yl)pentyl)oxy)-1H-benzo[d]imidazol-2-yl)-2-methylisonicotinamide | | | |

FIG. 2 (continued)

| Example | Structure | Name | (M+H)⁺ | H¹-NMR | Synthesis |
|---|---|---|---|---|---|
| 244 | 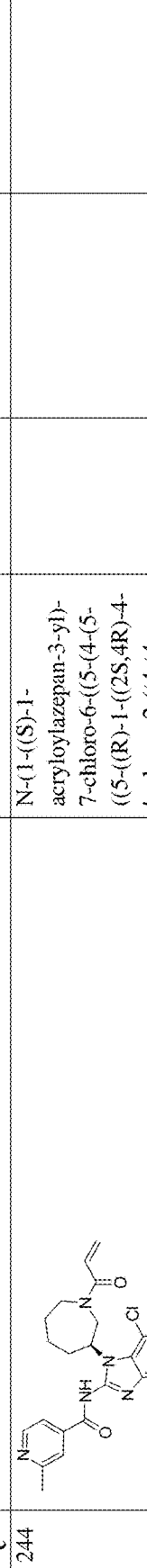 | N-(1-((S)-1-acryloylazepan-3-yl)-7-chloro-6-((5-(4-(5-((5-((R)-1-((2S,4R)-4-hydroxy-2-((4-(4-methylthiazol-5-yl)benzyl)carbamoyl)pyrrolidin-1-yl)-3-methyl-1-oxobutan-2-yl)isoxazol-3-yl)oxy)pentyl)piperazin-1-yl)pentyl)oxy)-1H-benzo[d]imidazol-2-yl)-2-methylisonicotinamide | | | |
| 245 | 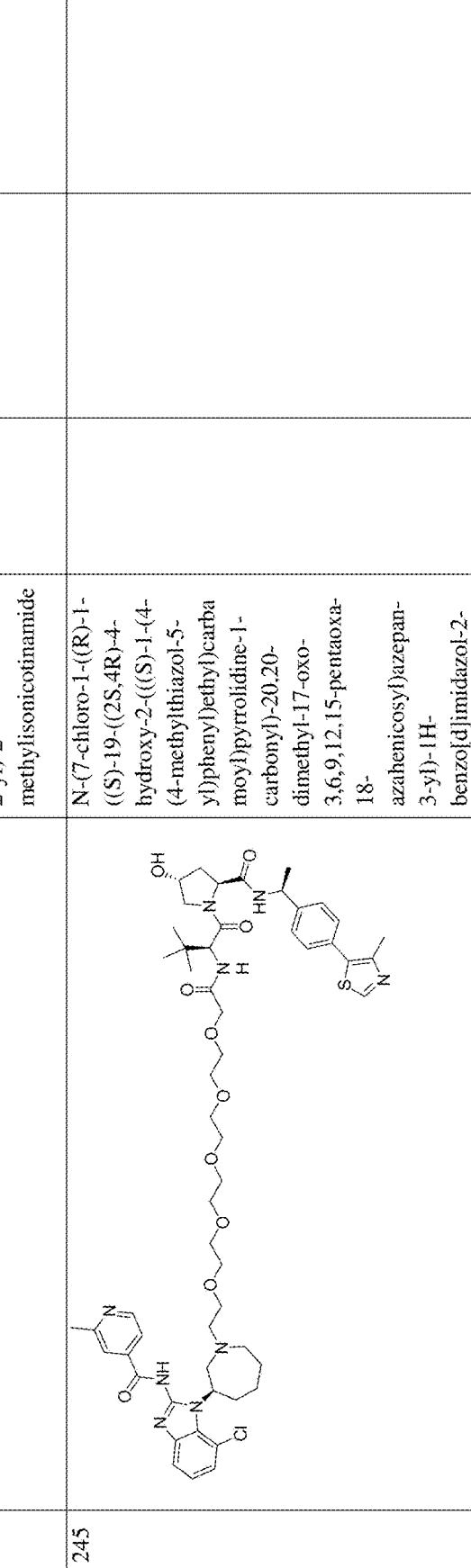 | N-(7-chloro-1-((R)-1-((S)-19-((2S,4R)-4-hydroxy-2-(((S)-1-(4-(4-methylthiazol-5-yl)phenyl)ethyl)carbamoyl)pyrrolidine-1-carbonyl)-20,20-dimethyl-17-oxo-3,6,9,12,15-pentaoxa-18-azahenicosyl)azepan-3-yl)-1H-benzo[d]imidazol-2- | | | |

FIG. 2 (continued)

| Example | Structure | Name | (M+H)+ | H1-NMR | Synthesis |
|---|---|---|---|---|---|
| 246 | 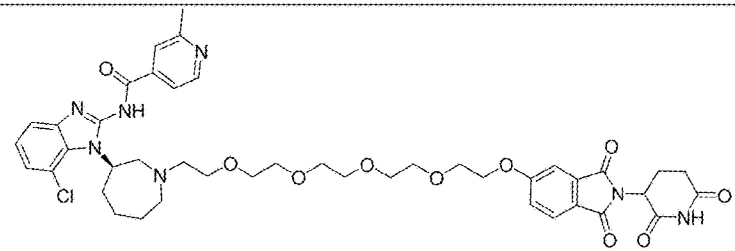 | yl)-2-methylisonicotinamide N-(7-chloro-1-((3R)-1-(14-((2-(2,6-dioxopiperidin-3-yl)-1,3-dioxoisoindolin-5-yl)oxy)-3,6,9,12-tetraoxatetradecyl)azepan-3-yl)-1H-benzo[d]imidazol-2-yl)-2-methylisonicotinamide | | | |
| 247 | 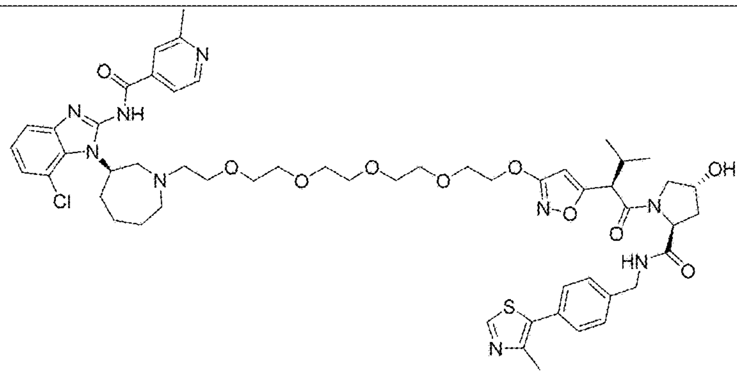 | N-(7-chloro-1-((R)-1-(14-((5-((R)-1-((2S,4R)-4-hydroxy-2-((4-(4-methylthiazol-5-yl)benzyl)carbamoyl)pyrrolidin-1-yl)-3-methyl-1-oxobutan-2-yl)isoxazol-3-yl)oxy)-3,6,9,12-tetraoxatetradecyl)azepan-3-yl)-1H-benzo[d]imidazol-2-yl)-2-methylisonicotinamide | | | |

FIG. 2 (continued)

| Example | Structure | Name | (M+H)+ | H1-NMR | Synthesis |
|---|---|---|---|---|---|
| 248 | 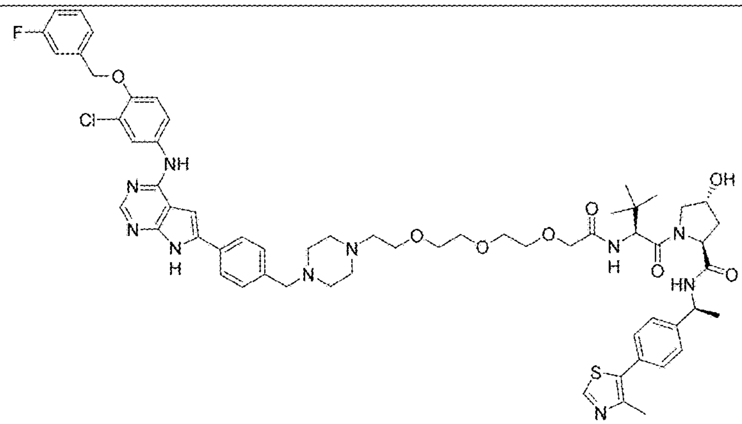 | (2S,4R)-1-((S)-2-(tert-butyl)-14-(4-(4-((3-chloro-4-((3-fluorobenzyl)oxy)phenyl)amino)-7H-pyrrolo[2,3-d]pyrimidin-6-yl)benzyl)piperazin-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | | | |
| 249 | 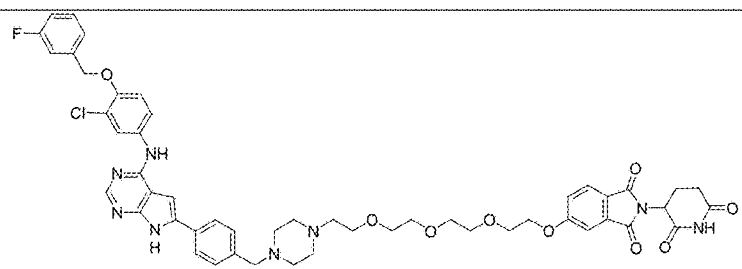 | 5-(2-(2-(2-(4-(4-((3-chloro-4-((3-fluorobenzyl)oxy)phenyl)amino)-7H-pyrrolo[2,3-d]pyrimidin-6-yl)benzyl)piperazin-1-yl)ethoxy)ethoxy)ethoxy)-2-(2,6-dioxopiperidin-3-yl)isoindoline-1,3-dione | | | |

FIG. 2 (continued)

| Example | Structure | Name | (M+H)+ | H¹-NMR | Synthesis |
|---|---|---|---|---|---|
| 250 | 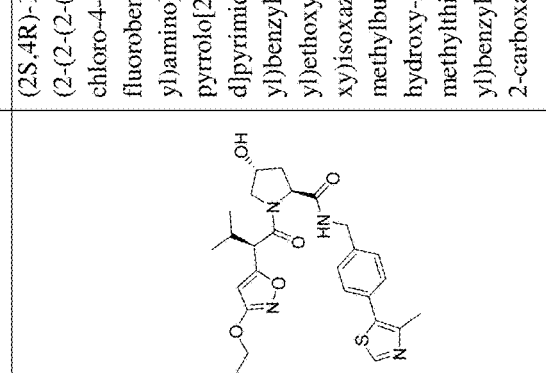 | (2S,4R)-1-((R)-2-(3-(2-(2-(2-(4-(4-((3-chloro-4-((3-fluorobenzyl)oxy)phenyl)amino)-7H-pyrrolo[2,3-d]pyrimidin-6-yl)benzyl)piperazin-1-yl)ethoxy)ethoxy)isoxazol-5-yl)-3-methylbutanoyl)-4-hydroxy-N-(4-(4-methylthiazol-5-yl)benzyl)pyrrolidine-2-carboxamide | | | |
| 251 | 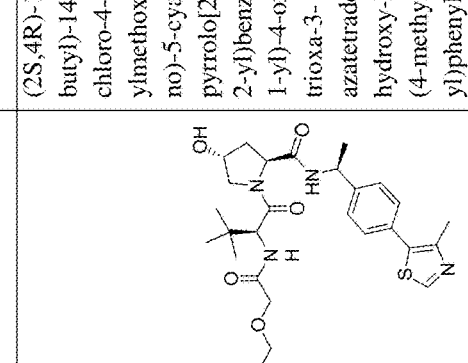 | (2S,4R)-1-((S)-2-(tert-butyl)-14-(4-(4-(4-((3-chloro-4-(pyridin-2-yl)methoxy)phenyl)amino)-5-cyano-1H-pyrrolo[2,3-b]pyridin-2-yl)benzyl)piperazin-1-yl)-4-oxo-6,9,12-trioxa-3-azatetradecanoyl)-4-hydroxy-N-((S)-1-(4-(4-methylthiazol-5-yl)phenyl)ethyl)pyrroli | | | |

FIG. 2 (continued)

| Example | Structure | Name | (M+H)⁺ | H¹-NMR | Synthesis |
|---|---|---|---|---|---|
| | | dine-2-carboxamide | | | |
| 252 | 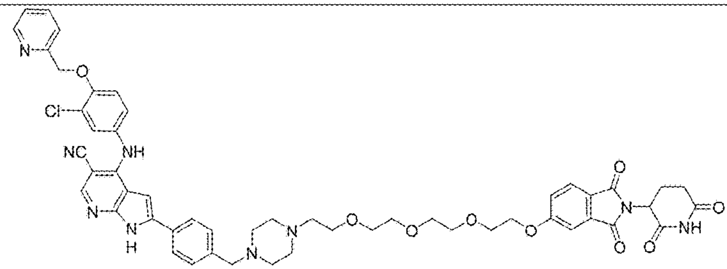 | 4-((3-chloro-4-(pyridin-2-ylmethoxy)phenyl)amino)-2-(4-((4-(2-(2-(2-(2-(2,6-dioxopiperidin-3-yl)-1,3-dioxoisoindolin-5-yl)oxy)ethoxy)ethoxy)ethoxy)ethyl)piperazin-1-yl)methyl)phenyl)-1H-pyrrolo[2,3-b]pyridine-5-carbonitrile | | | |
| 253 | 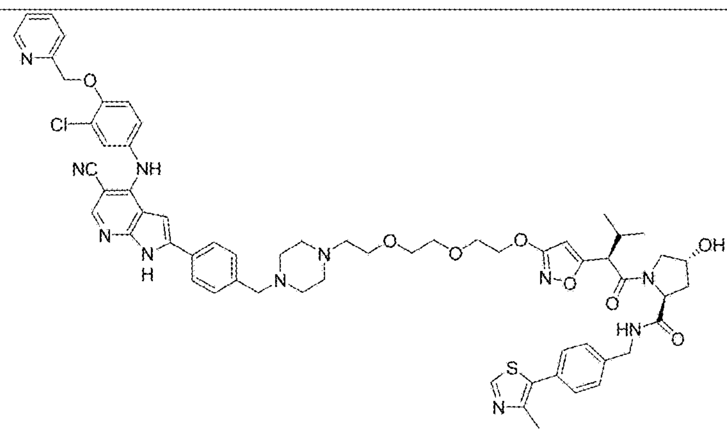 | (2S,4R)-1-((R)-2-(3-(2-(2-(2-(4-(4-(4-((3-chloro-4-(pyridin-2-ylmethoxy)phenyl)amino)-5-cyano-1H-pyrrolo[2,3-b]pyridin-2-yl)benzyl)piperazin-1-yl)ethoxy)ethoxy)ethoxy)isoxazol-5-yl)-3-methylbutanoyl)-4-hydroxy-N-(4-(4-methylthiazol-5-yl)benzyl)pyrrolidine- | | | |

| Exa mpl e | Structure | Name | (M+H)+ | H1-NMR | Synthesis |
|---|---|---|---|---|---|
| 254 | 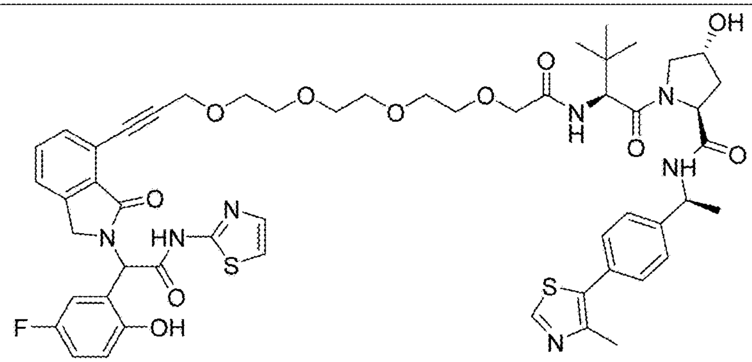 | (2S,4R)-1-((2S)-2-(tert-butyl)-18-(2-(1-(5-fluoro-2-hydroxyphenyl)-2-oxo-2-(thiazol-2-ylamino)ethyl)-3-oxoisoindolin-4-yl)-4-oxo-6,9,12,15-tetraoxa-3-azaoctadec-17-ynoyl)-4-hydroxy-N-((S)-1-(4-(4-methylthiazol-5-yl)phenyl)ethyl)pyrrolidine-2-carboxamide | 1054.33 527.67 | (400 MHz, DMSO-d6): δ 1.04 (s, 9H), 1.51 (d, J = 6.8 Hz, 2H), 1.97-2.06 (m, 3H), 2.19-2.27 (m, 2H), 2.48 (s, 3H), 2.91-2.98(m, 1H), 3.69-3.75 (m, 10H), 3.85-3.87 (m, 3H), 4.04-4.05 (m, 2H), 4.44-4.45 (m, 1H), 4.51-4.62 (m, 3H), 4.69-4.76 (m, 2H), 4.97-5.04 (m, 2H), 5.35-5.40 (m, 1H), 6.48 (s, 1H), 6.88-6.91 (m, 1H),6.97-7.04 (m, 2H), 7.15-7.16 (m, 1H), 7.40-7.59 (m, 8H), 8.88 (s, 1H). | following routes described for examples 80 and 82 |

| Example | Structure | Name | (M+H)+ | H¹-NMR | Synthesis |
|---|---|---|---|---|---|
| 255 | 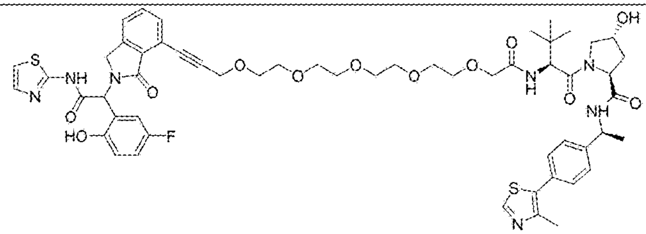 | (2S,4R)-1-((2S)-2-(tert-butyl)-21-(2-(1-(5-fluoro-2-hydroxyphenyl)-2-oxo-2-(thiazol-2-ylamino)ethyl)-3-oxoisoindolin-4-yl)-4-oxo-6,9,12,15,18-pentaoxa-3-azahenicos-20-ynoyl)-4-hydroxy-N-((S)-1-(4-(4-methylthiazol-5-yl)phenyl)ethyl)pyrrolidine-2-carboxamide | 1098.28 549.63 | (400 MHz, DMSO-d6): δ 0.93 (s, 9H),1.35-1.37 (m, 3H), 1.73-1.79 (m, 1H), 1.99-2.04 (m. 1H), 2.44 (s, 3H),3.51-3.59 (m, 17H), 3.70-3.72 (m, 2H), 3.95 (s, 2H ), 4.27 (s, 1H), 4.44 (s, 4.4Hz, 2H), 4.89 (t, 3H), 4.53 (t, J = J = 7.2 Hz, 1H). 5.13-5.14 (m, 1H), 6.27 (s, 1H), 6.84-6.92 (m, 2H), 7.08-7.13 (m, 1H), 7.26 (d, J = 3.6 Hz, 1H), 7.37 (t, J = 8.0 Hz, 3H), 7.43 (d, J = 8.4 Hz, 2H), 7.48 (d, J = 3.6 Hz, 1H), 7.53-7.59 (m, 3H), 8.45 (d, J = 8.0 Hz, 1H), 8.98 (s, 1H), 9.97-9.99 (m, 1H), 12.61-12.62 (m, 1H). | following routes described for examples 80 and 82 |

FIG. 2 (continued)

| Example | Structure | Name | (M+H)+ | H1-NMR | Synthesis |
|---|---|---|---|---|---|
| 256 | 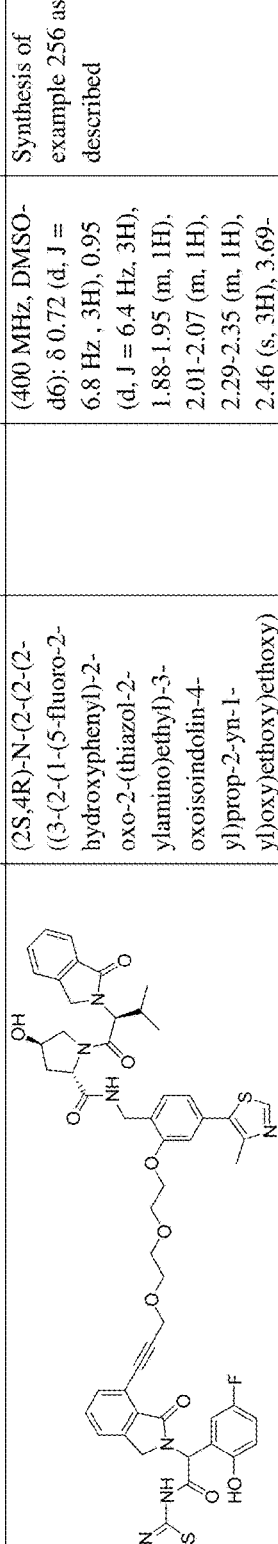<br>Diastereomere 1<br>Diastereoisomere of example 257 | (2S,4R)-N-(2-(2-(2-((3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1056.62<br>528.83 | (400 MHz, DMSO-d6): δ 0.72 (d, J = 6.8 Hz, 3H), 0.95 (d, J = 6.4 Hz, 3H), 1.88-1.95 (m, 1H), 2.01-2.07 (m, 1H), 2.29-2.35 (m, 1H), 2.46 (s, 3H), 3.69-3.71 (m, 3H), 3.75-3.77 (m, 3H), 3.80-3.82 (m, 2H), 3.95 (d, J = 18.4 Hz, 1H), 4.18 (t, J = 4.0 Hz, 2H), 4.25-4.33 (m, 3H), 4.38-4.47 (m, 4H), 4.52-4.59 (m, 2H), 4.70 (d, J = 10.8 Hz, 1H), 6.26 (s, 1H), 6.84-6.91 (m, 2H), 7.00 (d, J = 4.0 Hz, 1H), 7.04 (s, 1H), 7.07-7.12 (m, 1H), 7.23 (d, J = 3.2 Hz, 1H), 7.33 (d, J = 7.6 Hz, 1H), 7.46-7.53 (m, 3H), 7.55-7.57 (m, 2H), 7.60-7.62 (m, 2H), 7.70 (d, J = 7.6 Hz, 1H), | Synthesis of example 256 as described |

FIG. 2 (continued)

| Example | Structure | Name | (M+H)+ | H¹-NMR | Synthesis |
|---|---|---|---|---|---|
| | | | | 8.38 (t, J = 6.0 Hz, 1H), 8.98 (s, 1H). | |
| 257 | 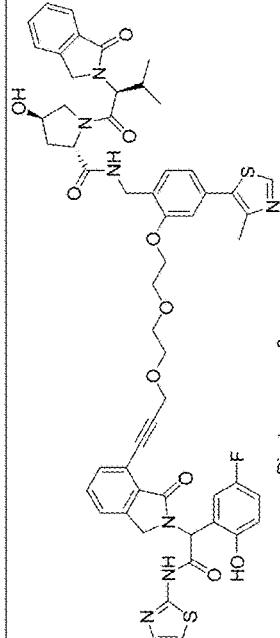Diastereomere 2 Diastereoisomere of example 256 | (2S,4R)-N-(2-(2-(2-((3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1056.62 528.83 | (400 MHz, DMSO-d6): δ 0.72 (d, J = 6.8 Hz, 3H), 0.98 (d, J = 6.8 Hz, 3H), 1.87-1.96 (m, 1H), 2.03-2.06 (m, 1H), 2.29-2.33 (m, 1H), 2.49 (s, 3H), 3.69-3.71 (m, 3H), 3.75-3.77 (m, 3H), 3.80-3.85 (m, 2H), 3.91-3.96 (m, 1H), 4.17-4.19 (m, 2H), 4.25-4.37 (m, 3H), 4.38-4.48 (m, 4H), 4.52-4.59 (m, 2H), 4.71 (d, J = 10.8 Hz, 1H), 5.09 (br, 1H), 6.27 (s, 1H), 6.84-6.87 (m, 1H), 6.88-6.92 (m, 1H), 6.99-7.03 (m, 2H), 7.08-7.13 (m, 1H), 7.24 (d, J = 3.6 Hz, 1H), 7.33 (d, J = 7.6 Hz, 1H), 7.46-7.53 (m, 3H), | Synthesis of example 257 as described |

FIG. 2 (continued)

| Example | Structure | Name | (M+H)+ | H¹-NMR | Synthesis |
|---|---|---|---|---|---|
| | | | | 7.54-7.57 (m, 2H), 7.60-7.62 (m, 2H), 7.70 (d, J = 7.6 Hz, 1H), 8.38 (t, J = 5.4 Hz, 1H), 8.98 (s, 1H), 9.98 (br, 1H), 10.60 (br, 1H). | |
| 258 | 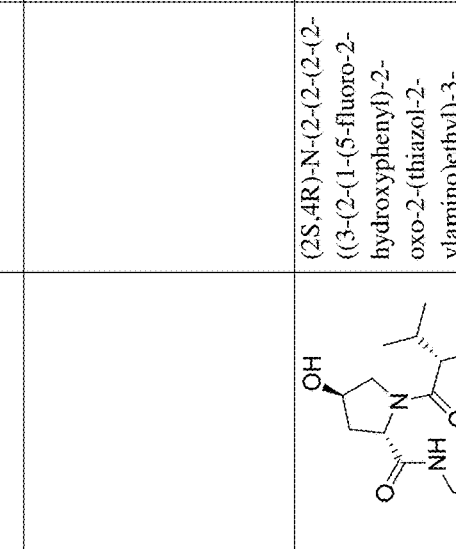 | (2S,4R)-N-(2-(2-(2-(2-((3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)ethoxy-4-(4-methylthiazol-5-yl)benzyl)-4-hydroxy-1-((S)-3-methyl-2-(1-oxoisoindolin-2-yl)butanoyl)pyrrolidine-2-carboxamide | 1100.66 550.85 | (400 MHz, DMSO-d6): δ 0.72 (d, J = 6.8 Hz, 3H), 0.02-0.93 (m, 1H), 0.96 (d, J = 6.8 Hz, 3H), 1.89-1.95 (m, 4H), 1.97-2.07 (m, 1H), 2.47 (s, 3H), 3.56-3.64 (m, 6H), 3.69-3.71 (m, 3H), 3.76-3.79 (m, 3H), 3.94 (d, J = 17.6 Hz, 1H), 4.16-4.34 (m, 5H), 4.38-4.48 (m, 4H), 4.53-4.59 (m, 2H), 4.70 (d, J = 11.2 Hz, 1H), 6.26 (s, 1H), 6.84-6.92 (m, 2H), 6.99-7.04 (m, 2H), 7.08-7.13 (m, 1H), 7.25 (d, J = 3.6 Hz, | following route described for example 256 |

FIG. 2 (continued)

| Example | Structure | Name | (M+H)+ | H¹-NMR | Synthesis |
|---|---|---|---|---|---|
| | | | | 1H), 7.31-7.34 (m, 1H), 7.47-7.62 (m, 7H), 7.70 (d, J = 7.6 Hz, 1H), 8.39 (t, J = 5.6 Hz, 1H), 8.98 (s, 1H). | |
| 259 | 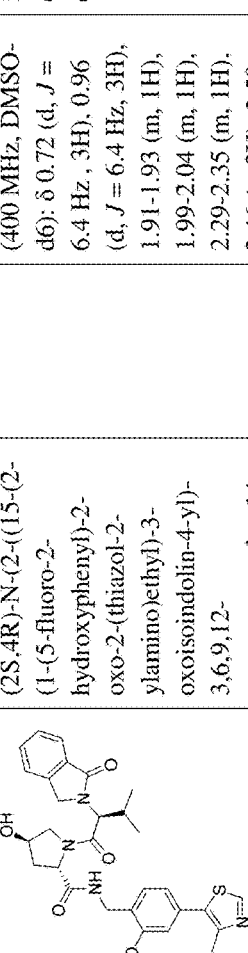 | (2S,4R)-N-(2-((15-(2-(1-(5-fluoro-2-hydroxyphenyl)-2-oxo-2-(thiazol-2-ylamino)ethyl)-3-oxoisoindolin-4-yl)-3,6,9,12-tetraoxapentadec-14-yn-1-yl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1144.68 572.87 | (400 MHz, DMSO-d6): δ 0.72 (d, J = 6.4 Hz, 3H), 0.96 (d, J = 6.4 Hz, 3H), 1.91-1.93 (m, 1H), 1.99-2.04 (m, 1H), 2.29-2.35 (m, 1H), 2.46 (s, 3H), 3.50-3.61 (m, 10H), 3.68-3.70 (m, 3H), 3.77-3.79 (m, 3H), 3.902 (d, J = 17.6 Hz, 1H), 4.16-4.18 (m, 2H), 4.24-4.29 (m, 2H), 4.31-4.33 (m, 1H), 4.38-4.40 (m, 1H), 4.43 (s, 2H), 4.48-4.57 (t, J = 19.2 Hz, 3H), 4.70 (d, J = 10.8 Hz, 1H), 5.09 (d, J = 4.0 Hz, 1H), 6.27 (s, 1H), 6.82- | following route described for example 256 |

FIG. 2 (continued)

| Example | Structure | Name | (M+H)+ | H¹-NMR | Synthesis |
|---|---|---|---|---|---|
| | | | | 6.91 (m, 2H), 7.00 (d, J = 7.6 Hz, 1H), 7.04 (s, 1H), 7.08-7.13 (m, 1H), 7.25 (d, J = 3.6 Hz, 1H), 7.33 (d, J = 8.0 Hz, 1H), 7.47-7.52 (m, 7H), 7.70 (d, J = 7.6 Hz, 1H), 8.367 (t, J = 6.0 Hz, 1H), 8.98 (s, 1H), 9.97 (s, 1H). | |
| 260 | 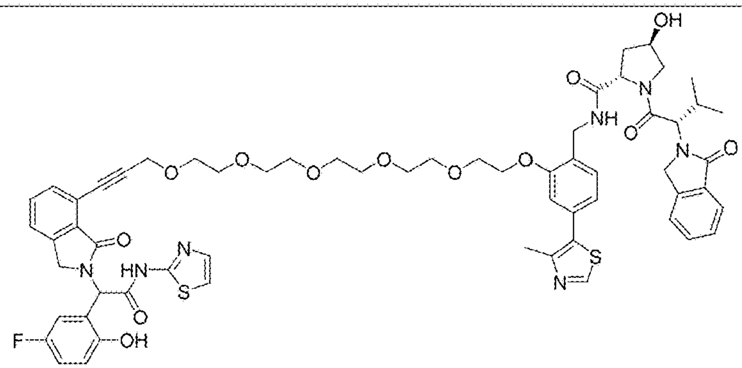 | (2S,4R)-N-(2-((18-(2-(1-(5-fluoro-2-hydroxyphenyl)-2-oxo-2-(thiazol-2-ylamino)ethyl)-3-oxoisoindolin-4-yl)-3,6,9,12,15-pentaoxaoctadec-17-yn-1-yl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide | 1188.72 594.89 | (400 MHz, DMSO-d6): δ 0.73 (d, J = 6.4 Hz, 3H), 0.96 (d, J = 6.4 Hz, 3H), 1.87-1.99 (m, 1H), 2.00-2.07 (m, 1H), 2.29-2.35 (m, 1H), 2.47 (s, 3H), 3.49-3.58 (m, 12H), 3.60-3.62 (m, 2H), 3.68-3.71 (m, 3H), 3.76-3.79 (m, 3H), 3.93 (d, J = 17.6 Hz, 1H), 4.17-4.29 (m, 4H), 4.32-4.34 (m, 1H), 4.38-4.43 (m, 3H), 4.53 (t, J = 19.6 Hz, | following route described for example 256 |

FIG. 2 (continued)

| Example | Structure | Name | (M+H)⁺ | H¹-NMR | Synthesis |
|---|---|---|---|---|---|
| | | | | 3H), 4.71 (d, J = 10.8 Hz, 1H), 5.10 (d, J = 4.0 Hz, 1H), 6.27 (s, 1H), 6.83-6.85 (m, 1H), 6.89-6.92 (m, 1H), 7.00 (d, J = 7.6 Hz, 1H), 7.04 (s, 1H), 7.08-7.14 (m, 1H), 7.25 (d, J = 3.2 Hz, 1H), 7.33 (d, J = 8.0 Hz, 1H), 7.48-7.52 (m, 3H), 7.53-7.58 (m, 2H), 7.59-7.62 (m, 2H), 7.71 (d, J = 7.6 Hz, 1H), 8.38 (t, J = 6.0 Hz, 1H), 8.98 (s, 1H), 9.98 (s, 1H), 12.61 (s, 1H). | |
| 261 | 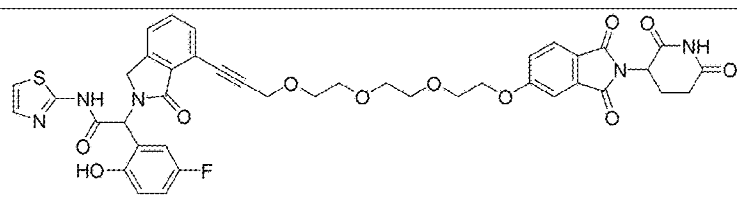 | 2-(7-(3-(2-(2-(2-(2-(2,6-dioxopiperidin-3-yl)-1,3-dioxoisoindolin-5-yl)oxy)ethoxy)ethoxy)ethoxy)prop-1-yn-1-yl)-1-oxoisoindolin-2-yl)-2-(5-fluoro-2-hydroxyphenyl)-N- | 826.09 413.54 | (400 MHz, DMSO-d6): δ 1.97-2.07 (m, 2H), 2.54-2.61 (m, 1H), 2.84-2.93 (m, J =7.2 H, 1H), 3.55-3.60 (m, 6H), 3.70-3.78 (m, 4H), 3.93 (d, J = 17.6 Hz, 1H), 4.29 (t, J =3.6 Hz, | following routes described for examples 80 and 82 |

FIG. 2 (continued)

| Example | Structure | Name | (M+H)+ | H¹-NMR | Synthesis |
|---|---|---|---|---|---|
| | | (thiazol-2-yl)acetamide | | 2H), 4.44 (s, 2H), 4.55 (d, J = 17.6 Hz, 1H), 5.10-5.14 (m, 1H), 6.27 (s, 1H), 6.84-6.87 (m, 1H), 6.89-6.92 (m, 1H), 7.08-7.13 (m, 1H), 7.26 (d, J = 3.2 Hz, 1H), 7.34-7.36 (m, 1H), 7.43 (d, J =2.0 Hz, 1H), 7.48 (d, J = 3.6 Hz, 1H), 7.51-7.58 (m, 3H), 7.80 (d, J = 8.0 Hz, 1H), 9.98 (s, 1H), 11.11 (s, 1H), 12.60 (s, 1H). | |
| 262 | 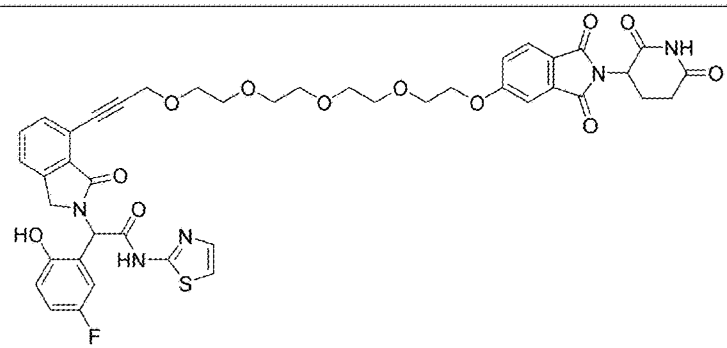 | 2-(7-(1-((2-(2,6-dioxopiperidin-3-yl)-1,3-dioxoisoindolin-5-yl)oxy)-3,6,9,12-tetraoxapentadec-14-yn-15-yl)-1-oxoisoindolin-2-yl)-2-(5-fluoro-2-hydroxyphenyl)-N-(thiazol-2-yl)acetamide | 870.11 435.55 | (400 MHz, DMSO-d6): δ 2.02-2.06 (m, 2H), 2.60-2.61 (m, 1H), 2.88-2.89 (m, 1H), 3.51-3.57 (m, 10H), 3.70-3.77 (m, 4H), 3.91 (d, J = 17.2 Hz, 1H), 4.29 (s, 2H), 4.44 (s, 2H), 4.53-4.58 (m, 1H), 5.10-5.12 (m, 1H), | following routes described for examples 80 and 82 |

| Example | Structure | Name | (M+H)⁺ | H¹-NMR | Synthesis |
|---|---|---|---|---|---|
| | | | | 6.27 (s, 1H), 6.86-6.90 (m, 1H), 7.11-7.13 (m, 1H), 7.26-7.27 (d, J = 1.2 Hz, 1H), 7.34-7.36 (m, 1H), 7.44-7.56 (m, 5H), 7.80-7.82 (m, 1H), 9.98 (s, 1H), 11.13 (s, 1H), 12.61 (s,1H). | |
| 263 | 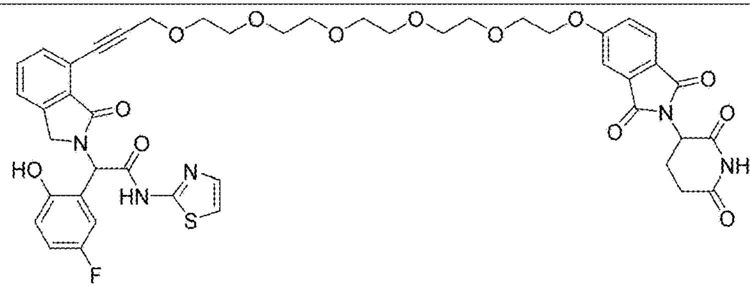 | 2-(7-(1-(2-(2,6-dioxopiperidin-3-yl)-1,3-dioxoisoindolin-5-yl)oxy)-3,6,9,12,15-pentaoxaoctadec-17-yn-18-yl)-1-oxoisoindolin-2-yl)-2-(5-fluoro-2-hydroxyphenyl)-N-(thiazol-2-yl)acetamide | 914.22 457.62 | (400 MHz, DMSO-d6): δ 2.02-2.06 (m, 1H), 2.53-2.60 (m, 2H), 2.84-2.92 (m, 1H), 3.33-3.38 (m, 1H), 3.48-3.61 (m, 13H), 3.69-3.77 (m, 4H), 3.94 (d, J = 17.6 Hz, 1H), 4.29 (t, J = 4.2 Hz, 2H), 4.43 (s, 2H), 4.56 (d, J = 17.6 Hz, 1H), 5.05 (dd, J = 12.8, 5.2 Hz, 1H), 6.26 (s, 1H), 6.84-6.92 (m, 2H), 7.08-7.13 (m, 1H), 7.25 (d, J = 3.6 Hz, 1H), 7.35 (dd, J | following routes described for examples 80 and 82 |

| Example | Structure | Name | (M+H)+ | H¹-NMR | Synthesis |
|---|---|---|---|---|---|
| | | | | = 8.4, 2.0 Hz, 1H), 7.43-7.59 (m, 5H), 7.82 (d, J = 8.4 Hz, 1H), 10.03 (br, 1H), 11.12 (s, 1H), 12.56 (br, 1H). | |
| 264 | 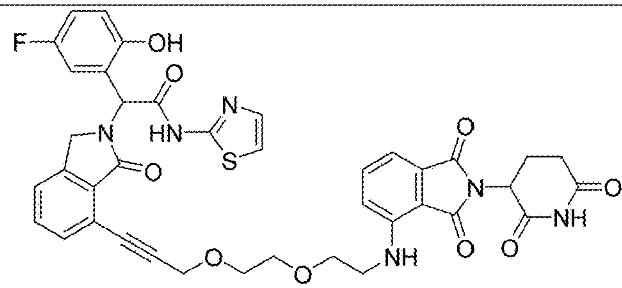 | 2-(7-(3-(2-(2-(2-(2-(2,6-dioxopiperidin-3-yl)-1,3-dioxoisoindolin-4-yl)amino)ethoxy)ethoxy)prop-1-yn-1-yl)-1-oxoisoindolin-2-yl)-2-(5-fluoro-2-hydroxyphenyl)-N-(thiazol-2-yl)acetamide | 781.17 391.09 | (400 MHz, DMSO-d6): δ 1.99-2.03 (m, 1H), 2.50-2.59 (m, 2H), 2.82-2.91 (m, 1H), 3.45-3.48 (m, 2H), 3.63-3.65 (m, 4H), 3.73-3.75 (m, 2H), 3.93 (d, J = 17.6 Hz, 1H), 4.44 (s, 2H), 4.55 (d, J = 17.6 Hz, 1H), 5.03-5.07 (m, 1H), 6.27 (s, 1H), 6.61 (t, J = 5.2 Hz, 1H), 6.85-6.87 (m, 1H), 6.89-6.93 (m, 1H), 7.00 (d, J = 7.2 Hz, 1H), 7.09-7.14 (m, 2H), 7.26 (d, J = 3.2 Hz, 1H), 7.48-7.57 (m, 5H), 9.99 (s, 1H), 11.10 (s, 1H), 12.61 | following routes described for examples 80 and 82 |

| Example | Structure | Name | (M+H)+ | H1-NMR | Synthesis |
|---|---|---|---|---|---|
| 265 | 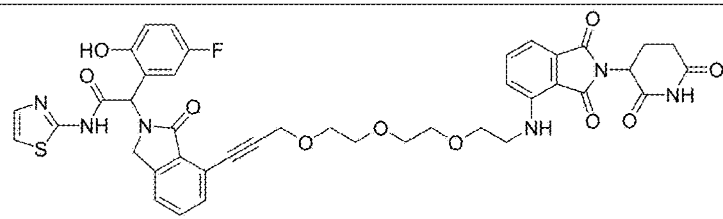 | 2-(7-(3-(2-(2-(2-((2-(2,6-dioxopiperidin-3-yl)-1,3-dioxoisoindolin-4-yl)amino)ethoxy)ethoxy)ethoxy)prop-1-yn-1-yl)-1-oxoisoindolin-2-yl)-2-(5-fluoro-2-hydroxyphenyl)-N-(thiazol-2-yl)acetamide | 825.20 413.10 | (400 MHz, DMSO-d6): δ 0.93 (s, 9H),1.35-1.37 (m, 3H), 1.73-1.79 (m, 1H), 1.99-2.04 (m, 1H), 2.44 (s, 3H),3.51-3.59 (m, 17H), 3.70-3.72 (m, 2H), 3.95 (s, 2H), 4.27 (s, 1H), 4.44 (s, 3H), 4.53 (t, J = 4.4Hz, 2H), 4.89 (t, J = 7.2 Hz, 1H), 5.13-5.14 (m, 1H), 6.27 (s, 1H), 6.84-6.92 (m, 2H), 7.08-7.13 (m, 1H), 7.26 (d, J = 3.6 Hz, 1H), 7.37 (t, J = 8.0 Hz, 3H), 7.43 (d, J = 8.4 Hz, 2H), 7.48 (d, J = 3.6 Hz, 1H), 7.53-7.59 (m, 3H), 8.45 (d, J = 8.0 Hz, 1H), 8.98 (s, 1H), 9.97-9.99 (m, 1H), 12.61-12.62 (m, 1H), (s, 1H). | following routes described for examples 80 and 82 |

FIG. 2 (continued)

| Example | Structure | Name | (M+H)+ | H1-NMR | Synthesis |
|---|---|---|---|---|---|
| 266 | 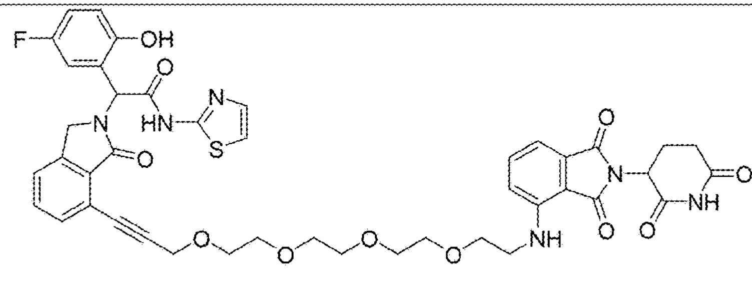 | 2-(7-(1-((2-(2,6-dioxopiperidin-3-yl)-1,3-dioxoisoindolin-4-yl)amino)-3,6,9,12-tetraoxapentadec-14-yn-15-yl)-1-oxoisoindolin-2-yl)-2-(5-fluoro-2-hydroxyphenyl)-N-(thiazol-2-yl)acetamide | 869.22 435.12 | (400 MHz, DMSO-d6): δ 1.99-2.02 (m, 2H), 3.44-3.56 (m, 16H), 3.68-3.69 (m, 2H), 4.02-4.07 (m, 2H), 4.43 (s, 2H), 1H), 4.63-4.67 (m, 1H), 5.03-5.07 (m, 1H), 6.20 (s, 1H), 6.57-6.60 (m, 1H), 6.84-6.89 (m, 2H), 7.01-7.14 (m, 4H), 7.42 (d, J = 2.8 Hz, 1H), 7.51-7.57 (m, 4H). | following routes described for examples 80 and 82 |
| 267 | 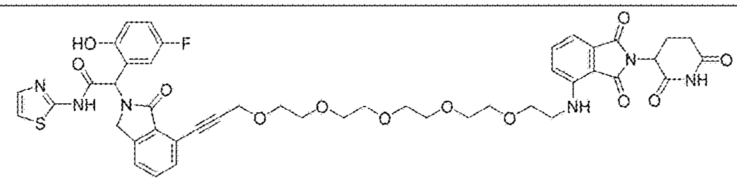 | 2-(7-(1-((2-(2,6-dioxopiperidin-3-yl)-1,3-dioxoisoindolin-4-yl)amino)-3,6,9,12,15-pentaoxaoctadec-17-yn-18-yl)-1-oxoisoindolin-2-yl)-2-(5-fluoro-2-hydroxyphenyl)-N-(thiazol-2-yl)acetamide | 913.24 457.13 | (400 MHz, DMSO-d6): δ 2.00-2.03 (m, 1H), 2.53-2.60 (m, 2H), 2.84-2.92 (m, 1H), 3.16 (d, J = 5.2 Hz, 1H), 3.48-3.61 (m, 17H), 3.69-3.71 (m, 2H), 3.93 (d, J = 18.0 Hz, 1H), 4.43 (s, 2H), 4.56 (d, J = 17.6 Hz, 1H), 5.05 (dd, J = 12.8, 5.2 Hz, 1H), 6.27 (s, 1H), 6.59 (t, J = 5.8 | following routes described for examples 80 and 82 |

FIG. 2 (continued)

| Example | Structure | Name | (M+H)+ | H¹-NMR | Synthesis |
|---|---|---|---|---|---|
| | | | | Hz, 1H), 6.84-6.92 (m, 2H), 7.02 (d, J = 6.8 Hz, 1H), 7.08-7.13 (m, 2H), 7.26 (d, J = 3.6 Hz, 1H), 7.48 (d, J = 3.6 Hz, 1H), 7.51-7.59 (m, 4H), 9.98 (br, 1H), 11.10 (s, 1H), 12.61 (br, 1H). | |
| 268 | 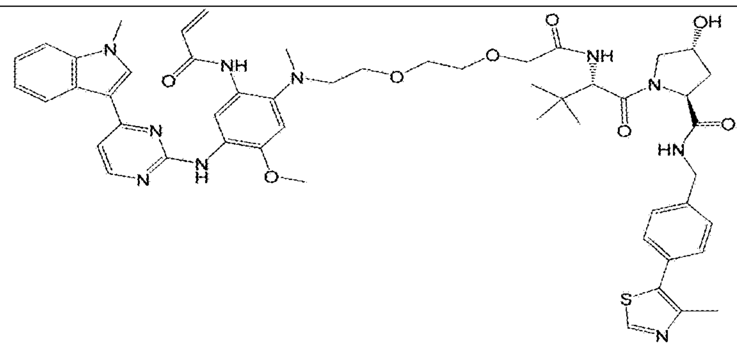 | (2S,4R)-1-((S)-2-(2-acrylamido-5-methoxy-4-((4-(1-methyl-1H-indol-3-yl)pyrimidin-2-yl)amino)phenyl)-12-(tert-butyl)-10-oxo-5,8-dioxa-2,11-diazatridecan-13-oyl)-4-hydroxy-N-(4-(4-methylthiazol-5-yl)benzyl)pyrrolidine-2-carboxamide | 987.51 | | following route outlined in scheme 14 |

FIG. 2 (continued)

| Example | Structure | Name | (M+H)+ | H1-NMR | Synthesis |
|---|---|---|---|---|---|
| 269 | 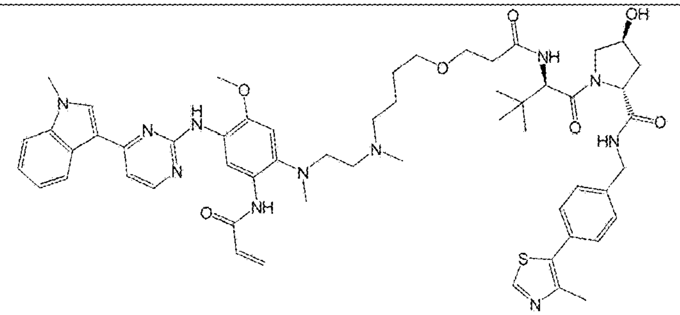 | (2S,4R)-1-((S)-2-(2-acrylamido-5-methoxy-4-((4-(1-methyl-1H-indol-3-yl)pyrimidin-2-yl)amino)phenyl)-15-(tert-butyl)-5-methyl-13-oxo-10-oxa-2,5,14-triazahexadecan-16-oyl)-4-hydroxy-N-(4-(4-methylthiazol-5-yl)benzyl)pyrrolidine-2-carboxamide | 1042.94 | | following route outlined in scheme 14 |
| 270 | 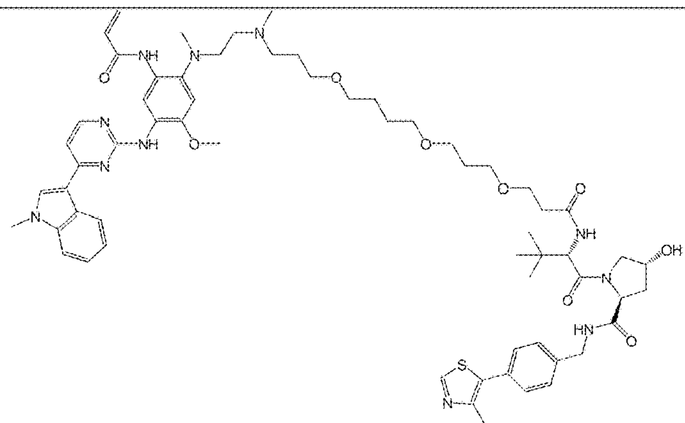 | (2S,4R)-1-((S)-2-(2-acrylamido-5-methoxy-4-((4-(1-methyl-1H-indol-3-yl)pyrimidin-2-yl)amino)phenyl)-23-(tert-butyl)-5-methyl-21-oxo-9,14,18-trioxa-2,5,22-triazatetracosan-24-oyl)-4-hydroxy-N-(4-(4-methylthiazol-5-yl)benzyl)pyrrolidine-2-carboxamide | 1159.09 | | following route outlined in scheme 14 |

| Example | Structure | Name | (M+H)+ | H1-NMR | Synthesis |
|---|---|---|---|---|---|
| 271 | 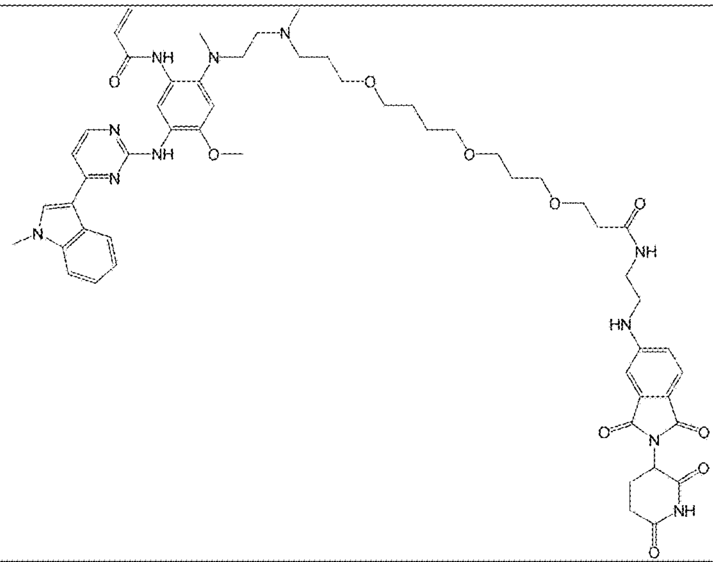 | 2-(2-acrylamido-5-methoxy-4-((4-(1-methyl-1H-indol-3-yl)pyrimidin-2-yl)amino)phenyl)-N-(2-((2-(2,6-dioxopiperidin-3-yl)-1,3-dioxoisoindolin-5-yl)amino)ethyl)-5-methyl-9,14,18-trioxa-2,5-diazahenicosan-21-amide | 1044.89 | | following route outlined in scheme 14 |

FIG. 2 (continued)

| Example | Structure | Name | (M+H)+ | H¹-NMR | Synthesis |
|---|---|---|---|---|---|
| 272 | 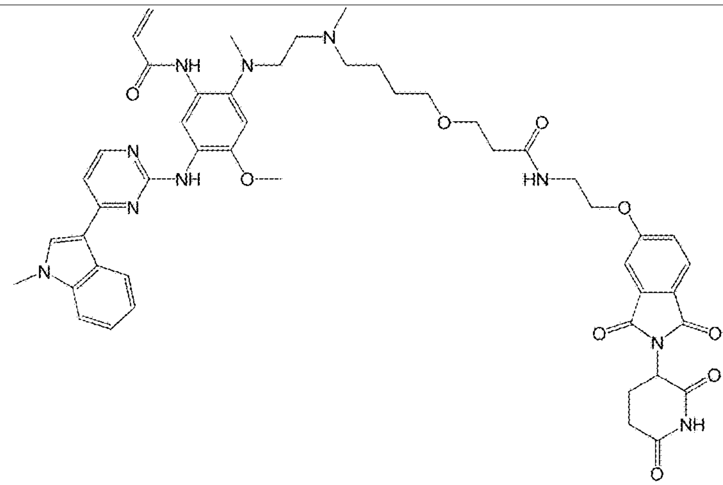 | N-(2-((2-((4-(3-((2-((2-(2,6-dioxopiperidin-3-yl)-1,3-dioxoisoindolin-5-yl)oxy)ethyl)amino)-3-oxopropoxy)butyl)(methyl)amino)ethyl)(methyl)amino)-4-methoxy-5-((4-(1-methyl-1H-indol-3-yl)pyrimidin-2-yl)amino)phenyl)acrylamide | | | |
| 273 | 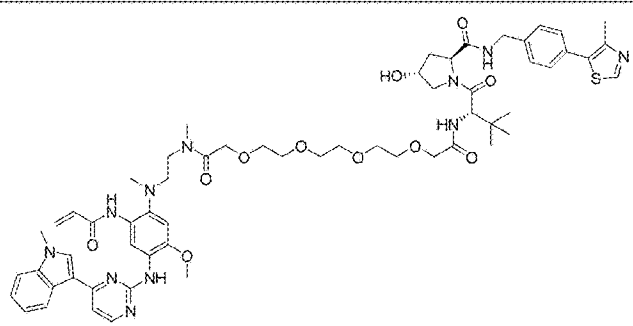 | N1-(2-((2-acrylamido-5-methoxy-4-((4-(1-methyl-1H-indol-3-yl)pyrimidin-2-yl)amino)phenyl)(methyl)amino)ethyl)-N14-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-3,6,9,12-tetraoxatetradecanediamide | 1147.61 | | following route outlined in scheme 14 |

FIG. 2 (continued)

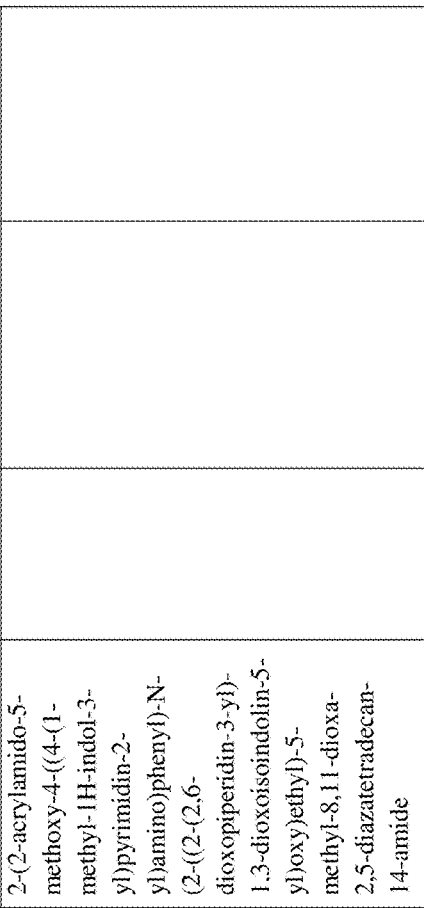

| Example | Structure | Name | (M+H)+ | H1-NMR | Synthesis |
|---|---|---|---|---|---|
| 274 | 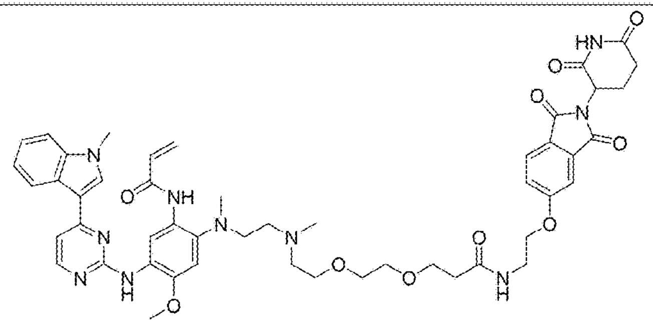 | 2-(2-acrylamido-5-methoxy-4-((4-(1-methyl-1H-indol-3-yl)pyrimidin-2-yl)amino)phenyl)-N-(2-((2-(2,6-dioxopiperidin-3-yl)-1,3-dioxoisoindolin-5-yl)oxy)ethyl)-5-methyl-8,11-dioxa-2,5-diazatetradecan-14-amide | | | |
| 275 | | (2S,4R)-1-((2S)-2-(tert-butyl)-24-(2-(1-(5-fluoro-2-hydroxyphenyl)-2-oxo-2-(thiazol-2-ylamino)ethyl)-3-oxoisoindolin-4-yl)-4-oxo-6,9,12,15,18,21-hexaoxa-3-azatetracos-23-ynoyl)-4-hydroxy-N-((S)-1-(4-(4-methylthiazol-5-yl)phenyl)ethyl)pyrrolidine-2-carboxamide | 1142.31 571.64 | (400 MHz, DMSO-d6): δ 0.93 (s, 9H), 1.37 (d, J = 6.8 Hz, 3H), 1.74-1.80 (m, 1H), 1.98-2.05 (m, 1H), 2.45 (s, 3H), 3.49-3.59 (m, 21H), 3.70-3.72 (m, 2H), 3.95 (s, 2H), 4.27-4.28 (m, 1H), 4.44 (t, J = 8.0 Hz, 3H), 4.52-4.58 (m, 2H), 4.88-4.92 (m, 1H), 4.56 (d, J = 7.6 Hz, 1H), 5.13 (d, J = 3.2 Hz, 1H), 6.27 (s, 1H), 6.84-6.92 (m, 2H), 7.08- | following routes described for examples 80 and 82 |

FIG. 2 (continued)

| Example | Structure | Name | (M+H)+ | H1-NMR | Synthesis |
|---|---|---|---|---|---|
| | | ((S)-1-(4-(4-methylthiazol-5-yl)phenyl)ethyl)pyrrolidine-2-carboxamide | | 7.13 (m, 1H), 7.26 (d, J = 3.6 Hz, 1H), 7.35-7.59 (m, 9H), 8.44 (d, J = 7.6 Hz, 1H), 8.98 (s, 1H), 9.97 (s, 1H), 12.60 (br, 1H). | |
| 276 | 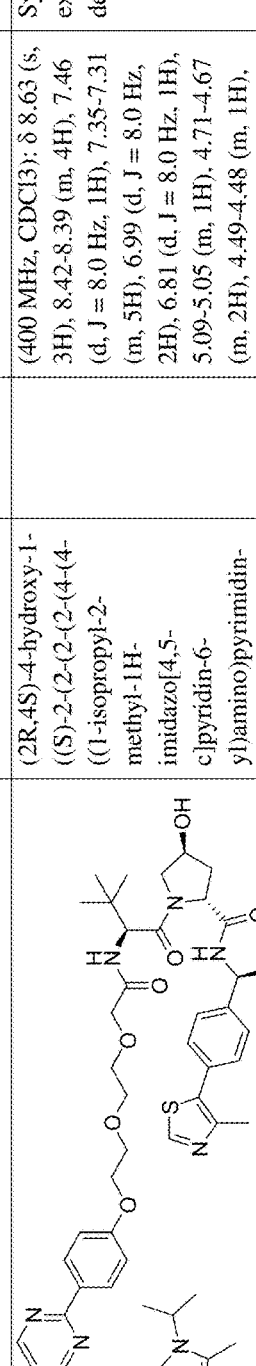 | (2R,4S)-4-hydroxy-1-((S)-2-(2-(2-(2-(2-(4-(4-((1-isopropyl-2-methyl-1H-imidazo[4,5-c]pyridin-6-yl)amino)pyrimidin-2-yl)phenoxy)ethoxy)ethoxy)acetamido)-3,3-dimethylbutanoyl)-N-((S)-1-(4-(4-methylthiazol-5-yl)phenyl)ethyl)pyrrolidine-2-carboxamide | 933.70 467.37 | (400 MHz, CDCl3): δ 8.63 (s, 3H), 8.42-8.39 (m, 4H), 7.46 (d, J = 8.0 Hz, 1H), 7.35-7.31 (m, 5H), 6.99 (d, J = 8.0 Hz, 2H), 6.81 (d, J = 8.0 Hz, 1H), 5.09-5.05 (m, 1H), 4.71-4.67 (m, 2H), 4.49-4.48 (m, 1H), 4.31-4.30 (m, 1H), 4.18 (s, 2H), 4.08-4.07 (m, 1H), 4.01 (s, 1H), 3.96 (s, 1H), 3.81-3.79 (m, 2H), 3.75-3.73 (m, 4H), 3.62 (dd, J = 5.6 Hz, 1H), 2.65 (s, 3H), 2.42-2.40 (m, 4H), 2.09-2.06 (t, J = 8.0 Hz, 1H), 1.73 (d, J = 8.0 Hz, 6H), 1.38 (d, J = 8.0 Hz, 3H), 1.08 (s, 9H). | Synthesis of example 276 as described |

FIG. 2 (continued)

| Example | Structure | Name | (M+H)⁺ | H¹-NMR | Synthesis |
|---|---|---|---|---|---|
| 277 | 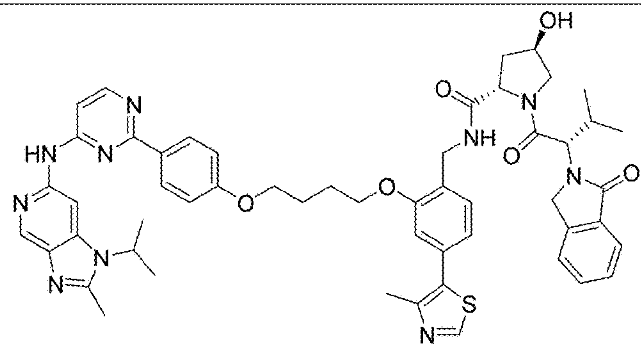 | (2S,4R)-4-hydroxy-N-(2-(4-(4-(4-((1-isopropyl-2-methyl-1H-imidazo[4,5-c]pyridin-6-yl)amino)pyrimidin-2-yl)phenoxy)butoxy)-4-(4-methylthiazol-5-yl)benzyl)-1-((S)-3-methyl-2-(1-oxoisoindolin-2-yl)butanoyl)pyrrolidine-2-carboxamide | 963.69  482.37 | (400 MHz, CDCl3): δ 8.68 (s, 1H), 8.62 (s, 2H), 8.52 (s, 1H), 8.41-8.38 (m, 3H), 7.75 (d, J = 5.6 Hz, 1H), 7.48-7.46 (m, 1H), 7.36-7.32 (m, 4H), 6.98-6.96 (m, 3H), 6.90 (s, 1H), 6.79 (d, J = 4.0 Hz, 1H), 4.77-4.72 (m, 1H), 4.69-4.64 (m, 3H), 4.52-4.46 (m, 3H), 4.34-4.25 (m, 2H), 4.15-4.12 (m, 4H), 3.68 (dd, J = 4.0 Hz, J = 12.0 Hz, 1H), 2.64 (s, 3H), 2.53-2.48 (m, 4H), 2.36-2.32 (m, 1H), 2.09-2.01 (m, 6H), 1.72 (d, J = 8.0 Hz, 6H), 0.91 (dd, J = 4.0 Hz, 6H). | following route described for example 276 and 256 |
| 278 | 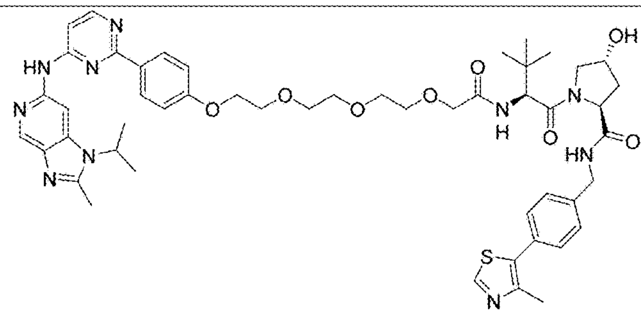 | (2S,4R)-1-((S)-2-(tert-butyl)-14-(4-(4-(((1-isopropyl-2-methyl-1H-imidazo[4,5-c]pyridin-6-yl)amino)pyrimidin-2-yl)phenoxy)-4-oxo-6,9,12-trioxa-3-azatetradecanoyl)-4-hydroxy-N-(4-(4-methylthiazol-5-yl)benzyl)pyrrolidine | 963.71  482.38 | (400 MHz, CDCl3): δ 8.73 (s, 1H), 8.66 (s, 1H), 8.59 (s, 1H), 8.43-8.38 (m, 3H), 8.33 (s, 1H), 7.36-7.28 (m, 6H), 7.00 (d, J = 8.4 Hz, 2H), 6.81 (d, J = 5.6 Hz, 1H), 4.72-4.70 (m, 2H), 4.53-4.49 (m, 4H), 4.35-4.30 (m, 2H), 4.22-4.20 (m, 2H), 4.06-3.99 (m, 3H), 3.89 (t, J = 4.8 Hz, 2H), 3.74 (d, J = 4.0 Hz, 2H), 3.72 (s, 6H), 3.69-3.68 (m, 1H), 2.65 (s, 3H), 2.56-2.50 (m, 4H), | following route described for example 276 |

FIG. 2 (continued)

| Example | Structure | Name | (M+H)+ | H¹-NMR | Synthesis |
|---|---|---|---|---|---|
| 279 | 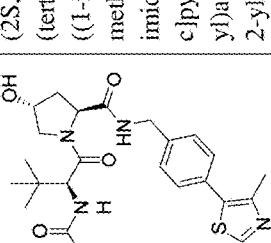 | (2S,4R)-1-((S)-2-(tert-butyl)-17-(4-(4-(((1-isopropyl-2-methyl-1H-imidazo[4,5-c]pyridin-6-yl)amino)pyrimidin-2-yl)phenoxy)-4-oxo-6,9,12,15-tetraoxa-3-azaheptadecanoyl)-4-hydroxy-N-(4-(4-methylthiazol-5-yl)benzyl)pyrrolidine-2-carboxamide | 1007.74 504.40 | (400 MHz, CDCl3): δ 8.66 (d, J = 8.8 Hz, 2H), 8.57 (s, 1H), 8.41-8.39 (m, 3H), 8.04 (s, 1H), 7.41 (s, 1H), 7.36-7.31 (m, 4H), 7.26-7.24 (m, 1H), 7.00 (d, J = 8.4 Hz, 2H), 6.79 (d, J = 5.2 Hz, 1H), 4.73-4.70 (m, 2H), 4.54-4.52 (m, 3H), 4.48-4.46 (m, 1H), 4.22-4.20 (m, 2H), 4.09-4.05 (m, 1H), 4.01-3.97 (m, 1H), 3.89-3.87 (m, 2H), 3.72-3.71 (m, 2H), 3.66-3.58 (m, 12H), 3.48 (s, 1H), 2.64 (s, 3H), 2.58-2.50 (m, 4H), 2.11-2.08 (m, 1H), 1.73 (d, J = 6.8 Hz, 6H), 0.94 (s, 9H). | following route described for example 276 |
| 280 | 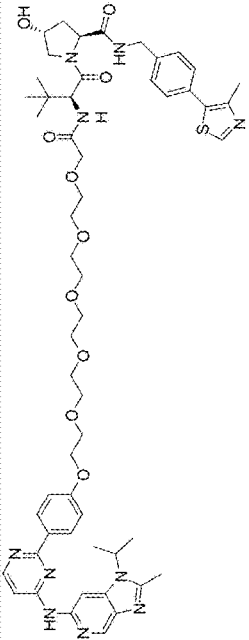 | (2S,4R)-1-((S)-2-(tert-butyl)-20-(4-(4-(((1-isopropyl-2-methyl-1H-imidazo[4,5-c]pyridin-6-yl)amino)pyrimidin-2-yl)phenoxy)-4-oxo-6,9,12,15,18-pentaoxa-3- | 1051.78 526.41 | (400 MHz, CDCl3): δ 8.66 (d, J = 6.8 Hz, 2H), 8.59 (s, 1H), 8.41-8.39 (m, 3H), 8.10 (s, 1H), 7.52-7.51 (m, 1H), 7.33 (d, J = 1.6 Hz, 4H), 7.26-7.25 (m, 1H), 7.00 (d, J = 8.8 Hz, 2H), 6.79 (d, J = 5.6 Hz, 1H), 4.74-4.70 (m, 2H), 4.54-4.49 (m, 3H), 4.35-4.30 (m, 1H), 4.22-4.20 (m, 2H), 4.09- | following route described for example 276 |

FIG. 2 (continued)

| Example | Structure | Name | (M+H)+ | H¹-NMR | Synthesis |
|---|---|---|---|---|---|
| | | azaicosanoyl)-4-hydroxy-N-(4-(4-methylthiazol-5-yl)benzyl)pyrrolidine-2-carboxamide | | 4.05 (m, 1H), 4.01-3.95 (m, 1H), 3.90-3.87 (m, 2H), 3.74-3.60 (m, 20H), 2.64 (s, 3H), 2.58-2.49 (m, 4H), 2.11-2.08 (m, 1H), 1.73 (d, J = 7.2 Hz, 6H), 0.95 (s, 9H). | |
| 281 | 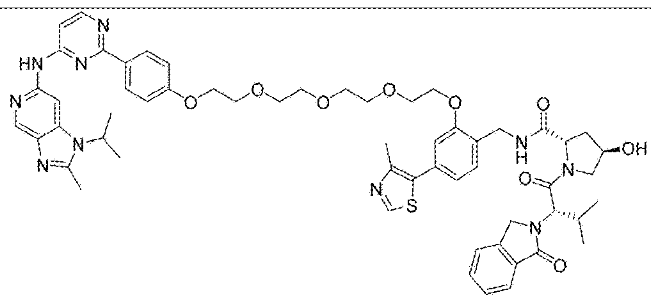 | (2S,4R)-4-hydroxy-N-(2-(2-(2-(2-(2-(4-(4-((1-isopropyl-2-methyl-1H-imidazo[4,5-c]pyridin-6-yl)amino)pyrimidin-2-yl)phenoxy)ethoxy)ethoxy)ethoxy)ethoxy)-4-(4-methylthiazol-5-yl)benzyl)-1-((S)-3-methyl-2-(1-oxoisoindolin-2-yl)butanoyl)pyrrolidine-2-carboxamide | 1067.76 534.40 | (400 MHz, CDCl3): δ 9.04 (s, 1H), 8.87 (s, 1H), 8.62-8.59 (d, J = 12.4 Hz, 2H), 8.27 (d, J = 8.0 Hz, 2H), 7.83 (d, J = 6.4 Hz, 1H), 7.52-7.50 (m, 1H), 7.43-7.31 (m, 4H), 7.26 (s, 1H), 7.00-6.95 (m, 3H), 6.88 (s, 1H), 4.78-4.74 (m, 3H), 4.58-4.50 (m, 3H), 4.43-4.39 (m, 3H), 4.18 (d, J = 3.6 Hz, 4H), 3.90 (s, 2H), 3.84 (s, 2H), 3.83-3.64 (m, 10H), 2.75 (s, 3H), 2.52 (s, 3H), 2.42-2.30 (m, 2H), 2.11-2.08 (m, 1H), 1.75 (d, J = 6.8 Hz, 6H), 0.97 (d, J = 6.4 Hz, 3H), 0.88 (d, J = 6.4 Hz, 3H). | following route described for example 276 and 256 |

FIG. 2 (continued)

| Example | Structure | Name | (M+H)⁺ | H¹-NMR | Synthesis |
|---|---|---|---|---|---|
| 282 | 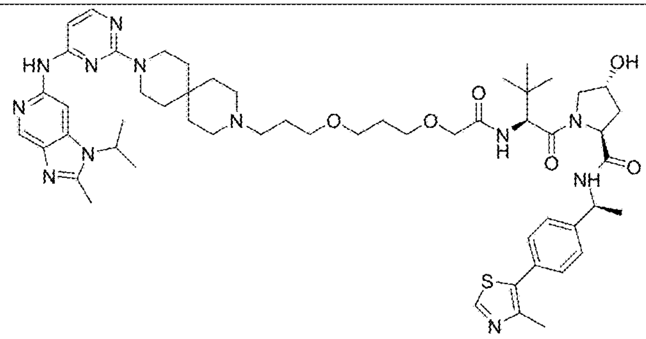 | (2S,4R)-4-hydroxy-1-((S)-2-(2-(3-(3-(9-(4-((1-isopropyl-2-methyl-1H-imidazo[4,5-c]pyridin-6-yl)amino)pyrimidin-2-yl)-3,9-diazaspiro[5.5]undecan-3-yl)propoxy)propoxy)acetamido)-3,3-dimethylbutanoyl)-N-((S)-1-(4-(4-methylthiazol-5-yl)phenyl)ethyl)pyrrolidine-2-carboxamide | 1021.84 511.44 | (400 MHz, CDCl3): δ 13.15 (bs, 1H), 11.30 (s, 1H), 8.88 (s, 1H), 8.65 (s, 1H), 8.54 (s, 1H), 7.99 (s, 1H), 7.44 (d, J = 7.2 Hz, 1H), 7.42 (s, 4H), 8.67 (d, J = 8.7 Hz, 1H), 6.69 (s, 1H), 5.08-5.10 (m, 1H), 4.71-4.77 (m, 2H), 4.60-4.62 (m, 1H), 4.51 (s, 1H), 3.91-4.02 (m, 6H), 3.53-3.64 (m, 9H), 3.10-3.13 (m, 2H), 2.85-2.88 (m, 2H), 2.88 (s, 3H), 2.55 (m, 3H), 2.33- 2.34 (m, 1H), 2.10- 2.12 (m, 1H), 1.86-2.00 (m, 11H), 1.69 (d, J = 6.8 Hz, 6H), 1.59-1.61 (m, 2H), 1.48 (d, J = 6.8 Hz, 3H),1.06 (s, 9H). | Synthesis of example 282 as described |
| 283 | 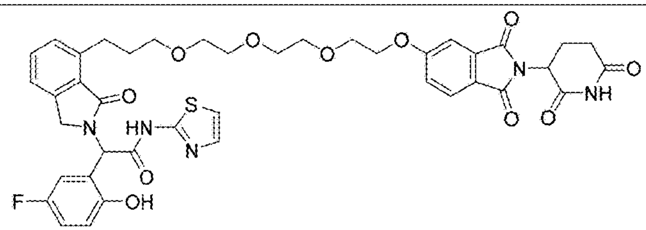 | 2-(7-(3-(2-(2-(2-((2-(2,6-dioxopiperidin-3-yl)-1,3-dioxoisoindolin-5-yl)oxy)ethoxy)ethoxy)propyl)-1-oxoisoindolin-2-yl)-2-(5-fluoro-2-hydroxyphenyl)-N-(thiazol-2-yl)acetamide | 830.47 415.76 | (400 MHz, DMSO-d6): δ 1.97-2.03 (m, 4H), 2.54-2.68 (m, 1H), 3.07 (t, J = 7.2 H. 1H), 3.38-3.41 (m, 4H), 3.47-3.48 (m, 2H), 3.52-3.56 (m, 4H), 3.58-3.60 (m, 2H), 3.78 (t, J = 4.0 Hz, 2H), 3.89-3.93 (m, 1H), 4.29 (t, J = 4.0 Hz. 2H), 4.52-4.56 (m, 1H), 5.09-5.14 (m, 1H), 5.36 (d, J = 4.8 Hz, 1H), 6.26 (s, 1H), 6.82-6.85 (m, 1H), 6.88-6.91 (m. | Synthesis of example 283 as described |

FIG. 2 (continued)

| Example | Structure | Name | (M+H)+ | H¹-NMR | Synthesis |
|---|---|---|---|---|---|
|  |  |  |  | 1H), 7.07-7.12 (m, 1H), 7.24-7.26 (m, 2H), 7.34-7.37 (m, 2H), .7.43-7.48 (m, 3H), 7.80 (d, J = 12.0 Hz, 1H), 8.32 (s, 1H), 11.14 (s, 1H). |  |
| 284 | 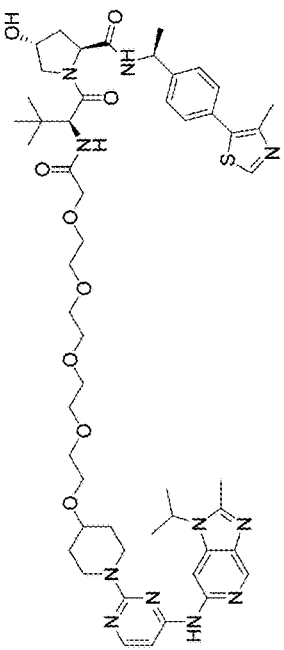 | (2S,4R)-1-((S)-2-(tert-butyl)-17-((1-(4-((1-isopropyl-2-methyl-1H-imidazo[4,5-c]pyridin-6-yl)amino)pyrimidin-2-yl)piperidin-4-yl)oxy)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide | 1028.80 514.92 | (400 MHz, CDCl3): δ 8.68 (s, 1H), 8.51 (s, 2H), 8.30 (s, 1H), 8.04 (d, J = 5.6 Hz, 1H), 7.55 (d, J = 7.6 Hz, 1H), 7.40-7.31 (m, 5H), 6.19 (d, J = 5.6 Hz, 1H), 5.10 (t, J = 7.2 Hz, 1H), 4.75-4.73 (m, 1H), 4.67-4.64 (m, 2H), 4.56-4.51 (m, 2H), 4.38-4.34 (m, 2H), 4.07-3.99 (m, 3H), 3.67-3.59 (m, 18H), 3.45 (t, J = 10.4 Hz, 2H), 2.64 (s, 3H), 2.52 (s, 4H), 2.09-2.04 (m, 1H), 2.00-1.95 (m, 2H), 1.67 (d, J = 6.8 Hz, 8H), 1.48 (d, J = 7.2 Hz, 3H), 1.06 (s, 9H). | following route described for example 282 |

FIG. 2 (continued)

| Example | Structure | Name | (M+H)⁺ | H¹-NMR | Synthesis |
|---|---|---|---|---|---|
| 285 | 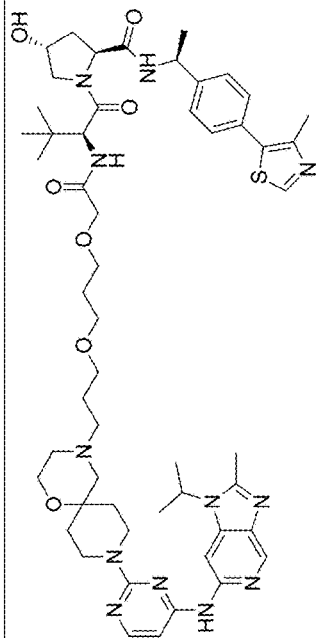 | (2S,4R)-4-hydroxy-1-((S)-2-(2-(3-(3-(9-(4-((1-isopropyl-2-methyl-1H-imidazo[4,5-c]pyridin-6-yl)amino)pyrimidin-2-yl)-1-oxa-4,9-diazaspiro[5.5]undecan-4-yl)propoxy)propoxy)acetamido)-3,3-dimethylbutanoyl)-N-((S)-1-(4-(4-methylthiazol-5-yl)phenyl)ethyl)pyrrolidine-2-carboxamide | 1023.82 512.43 | (400 MHz, CDCl3): δ 8.69 (s, 1H), 8.59 (s, 1H), 8.50 (s, 1H), 8.28 (bs, 1H), 8.05 (d, J = 5.6 Hz, 1H), 7.46 (d, J = 8.0 Hz, 1H), 7.41-7.35 (m, 4H), 7.23 (d, J = 4.8 Hz, 1H), 6.21 (d, J = 5.6 Hz, 1H), 5.10 (t, J = 7.2 Hz, 1H), 4.74-4.64 (m, 2H), 4.57 (d, J = 8.8 Hz, 1H), 4.51 (s, 1H), 4.43 (d, J = 12.8 Hz, 2H), 4.10 (d, J = 10.8 Hz, 3H), 4.00-3.97 (m, 3H), 3.92-3.86 (m, 3H), 3.62-3.59 (m, 3H), 3.52-3.45 (m, 6H), 2.64 (s, 5H), 2.52-2.49 (m, 5H), 2.11 (t, J = 10.8 Hz, 3H), 1.88-1.81 (m, 4H), 1.67 (d, J = 7.2 Hz, 6H), 1.63-1.57 (m, 2H), 1.48 (d, J = 6.8 Hz, 3H), 1.05 (s, 9H). | following route described for example 282 |
| 286 | 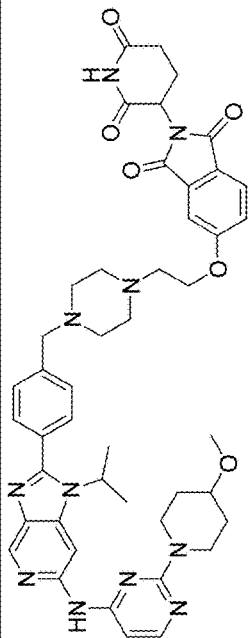 | 2-(2,6-dioxopiperidin-3-yl)-5-(2-(4-(4-(1-isopropyl-6-((2-(4-methoxypiperidin-1-yl)pyrimidin-4-yl)amino)-1H-imidazo[4,5-c]pyridin-2-yl)benzyl)piperazin- | 842.63 421.84 | (400 MHz, CD3OD): δ 8.65 (s, 1H), 8.57 (s, 1H), 7.95 (d, J = 6.0 Hz, 1H), 7.80 (d, J = 8.0 Hz, 1H), 7.65 (d, J = 8.0 Hz, 2H), 7.59 (d, J = 8.0 Hz, 2H), 7.58 (s, 1H), 7.43 (d, J = 2.0 Hz, 1H), 6.32 (d, J = 5.6 Hz, 1H), 5.31-5.34 (m, 2H), 5.05-5.15 (m, 1H), 4.29-4.32 (m, 4H), 3.67 (s, 2H), 3.34... | Synthesis of example 286 as described |

FIG. 2 (continued)

| Example | Structure | Name | (M+H)+ | H¹-NMR | Synthesis |
|---|---|---|---|---|---|
| 287 | 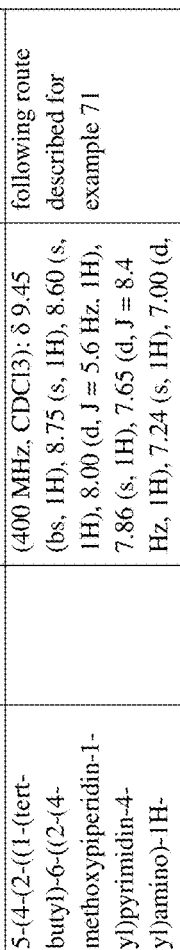 | 5-(4-(2-((1-(tert-butyl)-6-((2-(4-methoxypiperidin-1-yl)pyrimidin-4-yl)amino)-1H-imidazo[4,5-c]pyridin-2-yl)methoxy)ethyl)piperazin-1-yl)-2-(2,6-dioxopiperidin-3-yl)isoindoline-1,3-dione | 780.61 390.82 | 3.36 (m, 4H), 3.30 (m, 3H), 2.82–2.83 (m, 3H), 2.65–2.80 (m, 4H), 2.15–2.20 (m, 2H), 2.10–2.12 (m, 1H), 1.95–1.98 (m, 6H), 1.68 (d, J = 6.8 Hz, 6H). (400 MHz, CDCl3): δ 9.45 (bs, 1H), 8.75 (s, 1H), 8.60 (s, 1H), 8.00 (d, J = 5.6 Hz, 1H), 7.86 (s, 1H), 7.65 (d, J = 8.4 Hz, 1H), 7.24 (s, 1H), 7.00 (d, J = 8.0 Hz, 1H), 6.07 (d, J = 5.6 Hz, 1H), 4.94–4.97 (m, 3H), 4.33–4.37 (m, 2H), 3.63–3.66 (m, 2H), 3.45–3.47 (m, 2H), 3.40 (s, 3H), 3.32–3.36 (m, 4H), 2.74–2.91 (m, 3H), 2.60–2.62 (m, 6H), 2.10–2.12 (m, 1H), 1.94–1.96 (m, 3H), 1.90 (s, 9H), 1.60–1.62 (m, 2H). | following route described for example 71 |
| 288 | 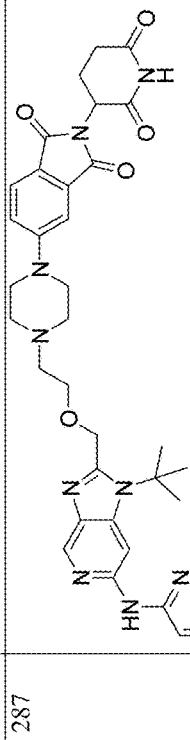 | 2-(2,6-dioxopiperidin-3-yl)-5-(4-(2-((6-((2-(4-methoxypiperidin-1-yl)pyrimidin-4-yl)amino)-1H-imidazo[4,5-c]pyridin-2- | 724.53 362.78 | (400 MHz, CD3OD): δ 8.57 (s, 1H), 8.29 (s, 1H), 7.89 (d, J = 6.0 Hz, 1H), 7.65 (d, J = 8.4 Hz, 1H), 7.34 (s, 1H), 7.19 (d, J = 9.2 Hz, 1H), 7.29 (d, J = 4.0 Hz, 1H), 5.32–5.33 (m, 1H), 5.06–5.09 (m, 1H), 4.17–4.21 (m, 2H), 3.82–3.83 | by-product from synthesis of example 287 |

FIG. 2 (continued)

| Example | Structure | Name | (M+H)+ | H1-NMR | Synthesis |
|---|---|---|---|---|---|
| | | y)methoxy)ethyl)piperazin-1-yl)isoindoline-1,3-dione | | (m, 2H), 3.30–3.34 (m, 6H), 3.31 (s, 3H), 2.73–2.81 (m, 7H), 2.16–2.21 (m, 1H), 1.90–1.92 (4H), 1.50–1.60 (m, 4H). | |
| 289 | 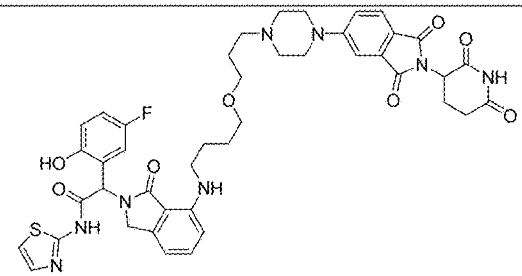 | 2-(7-((4-(3-(4-(2-(2,6-dioxopiperidin-3-yl)-1,3-dioxoisoindolin-5-yl)piperazin-1-yl)propoxy)butyl)amino)-1-oxoisoindolin-2-yl)-2-(5-fluoro-2-hydroxyphenyl)-N-(thiazol-2-yl)acetamide | 853.54 427.29 | (400 MHz, DMSO-d6): δ 1.55–1.71 (m, 6H), 1.99–2.05 (m, 1H), 2.33–2.37 (m, 2H), 2.42–2.47 (m, 4H), 2.53–2.59 (m, 1H), 2.84–2.93 (m, 1H), 3.16–3.24 (m, 3H), 3.31 (s, 1H), 3.36–3.44 (m, 7H), 3.83–3.87 (m, 1H), 4.44–4.49 (m, 1H), 5.05–5.10 (m, 1H), 6.19 (s, 1H), 6.54–6.63 (m, 3H), 6.81–6.84 (m, 1H), 6.88-6.91 (m, 1H), 7.07-7.12 (m, 1H), 7.21–7.32 (m, 4H), 7.47-7.48 (m, 1H), 7.65-7.68 (m, 1H), 9.95 (s, 1H), 11.09 (s, 1H), 12.59 (s, 1H). | following route described for example 307 |
| 290 | 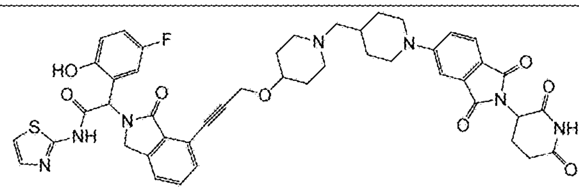 | 2-(7-(3-((1-((1-(2-(2,6-dioxopiperidin-3-yl)-1,3-dioxoisoindolin-5-yl)piperidin-4-yl)methyl)piperidin-4-yl)oxy)prop-1-yn-1-yl)-1- | 874.53 437.79 | (400 MHz, DMSO-d6): δ 1.14-1.20 (m, 2H), 1.53–1.60 (m, 2H), 1.97–2.03 (m, 7H), 2.54-2.60 (m, 2H), 2.92-2.98 (m, 3H), 3.31-3.32 (m, 4H), 3.63-3.80 (m, 2H), 3.93-4.05 (m, 3H), 4.46 (s, 2H), 4.55 (d, J = 17.6 Hz, 1H), 5.04-5.09 (m, | following routes described for examples 80 and 82 |

FIG. 2 (continued)

| Example | Structure | Name | (M+H)⁺ | H¹-NMR | Synthesis |
|---|---|---|---|---|---|
| | | oxoisoindolin-2-yl)-2-(5-fluoro-2-hydroxyphenyl)-N-(thiazol-2-yl)acetamide | | 1H), 6.27 (s, 1H), 6.87-6.93 (m, 2H), 7.09-7.14 (m, 1H), 7.33 (s, 1H), 7.48-7.67 (m, 5H), 10.00 (br, 1H), 11.08 (s, 1H), 12.60 (s, 1H). | |
| 291 | 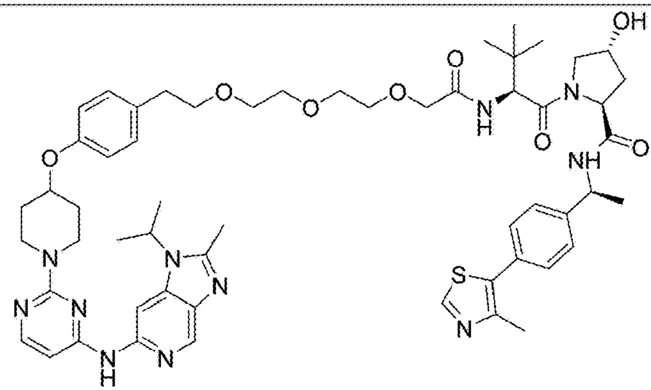 | (2S,4R)-1-((S)-2-(tert-butyl)-14-(4-((1-(4-(((1-isopropyl-2-methyl-1H-imidazo[4,5-c]pyridin-6-yl)amino)pyrimidin-2-yl)piperidin-4-yl)oxy)phenyl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 1060.81 530.93 | (400 MHz, CDCl3): δ 8.66 (s, 1H), 8.61 (s, 1H), 8.30 (s, 1H), 8.03 (d, J = 5.6 Hz, 1H), 7.32-7.41 (m, 7H), 7.14 (d, J = 8.4 Hz, 2H), 6.87 (d, J = 8.4 Hz, 2H), 6.09 (d, J = 5.6 Hz, 1H), 5.10 (t, J = 7.2 Hz, 1H), 4.73-4.76 (m, 1H), 4.62-4.66 (m, 1H), 4.50-4.52 (m, 3H), 4.22-4.28 (m, 2H), 4.12-4.15 (m, 1H), 3.95-4.10 (m, 2H), 3.63-3.75 (m, 13H), 2.84 (t, J = 7.2 Hz, 2H), 2.61 (s, 3H), 2.60-2.62 (m, 1H), 2.52 (m, 3H), 1.98-2.04 (m, 4H), 1.80-1.85 (m, 2H), 1.63 (d, J = 6.8 Hz, 6H), 1.53 (d, J = 6.4 Hz, 3H), 1.07 (s, 9H). | Synthesis of example 291 as described |

| Example | Structure | Name | (M+H)+ | H¹-NMR | Synthesis |
|---|---|---|---|---|---|
| 292 | 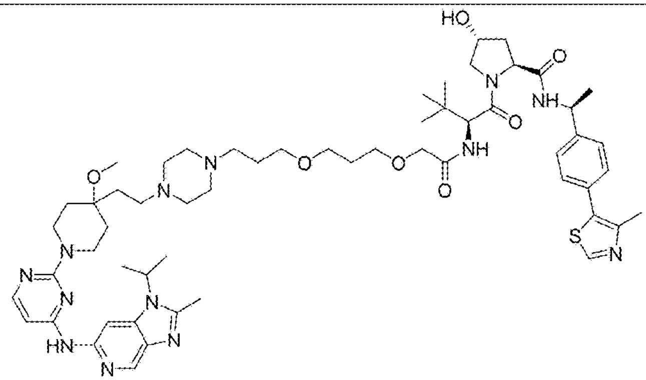 | (2S,4R)-4-hydroxy-1-((S)-2-(2-(3-(3-(4-(2-(1-(4-((1-isopropyl-2-methyl-1H-imidazo[4,5-c]pyridin-6-yl)amino)pyrimidin-2-yl)-4-methoxypiperidin-4-yl)ethyl)piperazin-1-yl)propoxy)propoxy)acetamido)-3,3-dimethylbutanoyl)-N-((S)-1-(4-(4-methylthiazol-5-yl)phenyl)ethyl)pyrrolidine-2-carboxamide | 1094.90 547.97 | (400 MHz, CDCl3): δ 8.59 (s, 1H), 8.53 (s, 1H), 8.31 (s, 1H), 7.94 (d, J = 5.6 Hz, 1H), 7.69 (s, 1H), 7.35–7.36 (m, 1H), 7.29–7.33 (m,4H), 7.15–7.17 (m, 1H), 5.98 (d, J = 5.2 Hz, 1H), 4.95–5.05 (m, 1H), 4.36–4.38 (m, 2H), 4.32–4.35 (m, 4H), 3.95–4.02 (m, 1H), 3.86 (d, J = 4.0 Hz, 2H), 3.51–3.54 (m, 3H), 3.42–3.43 (m, 4H), 3.25–3.27 (m, 2H), 3.16 (s, 3H), 2.54 (s, 3H), 2.43–2.46 (m, 9H), 2.35–2.38 (m, 6H), 1.98–2.02 (m, 2H), 1.76–1.78 (m, 5H), 1.67–1.69 (m, 3H), 1.65 (d, J = 6.8 Hz, 6H), 1.48–1.51 (m, 3H), 1.40 (d, J = 6.8 Hz, 3H), 0.98 (s, 9H). | following routes described for examples 78 and 282 |
| 293 | 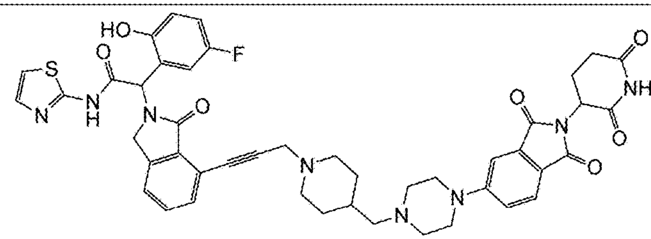 | 2-(7-(3-(4-((4-(2-(2,6-dioxopiperidin-3-yl)-1,3-dioxoisoindolin-5-yl)piperazin-1-yl)methyl)piperidin-1-yl)prop-1-yn-1-yl)-1-oxoisoindolin-2-yl)-2-(5-fluoro-2-hydroxyphenyl)-N- | 859.53 430.28 | (400 MHz, DMSO-d6): δ 1.34 (d, J = 4.4 Hz, 1H), 1.73–1.76 (m, 2H), 1.97–2.03 (m, 3H), 2.18–2.19 (m, 2H), 2.32–2.33 (m, 1H), 2.41–2.46 (m, 5H), 2.54–2.60 (m, 2H), 2.83–2.92 (m, 2H), 3.31–3.32 (m, 4H), 3.40–3.41 (m, 3H), 3.93 (d, J = 17.6 Hz, 1H), 4.55 (d, J = 17.6 Hz, 1H), 5.04-5.09 | following routes described for examples 80 and 82 |

| Example | Structure | Name | (M+H)+ | H1-NMR | Synthesis |
|---|---|---|---|---|---|
| | | (thiazol-2-yl)acetamide | | (m, 1H), 6.27 (s, 1H), 6.84-6.87 (m, 1H), 6.89-6.93 (m, 1H), 7.09-7.14 (m, 1H), 7.23-7.27 (m, 2H), 7.33 (s, 1H), 7.48 (d, J = 3.6 Hz, 1H), 7.51-7.59 (m, 3H),7.67-7.69 (m, 1H), 9.96 (s, 1H), 11.07 (s, 1H), 12.60 (s, 1H). | |
| 294 | 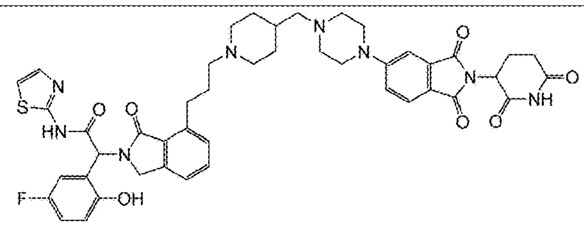 | 2-(7-(3-(4-((4-(2-(2,6-dioxopiperidin-3-yl)-1,3-dioxoisoindolin-5-yl)piperazin-1-yl)methyl)piperidin-1-yl)propyl)-1-oxoisoindolin-2-yl)-2-(5-fluoro-2-hydroxyphenyl)-N-(thiazol-2-yl)acetamide | 863.56 432.30 | (400 MHz, DMSO-d6): δ 1.43-1.47 (m, 1H), 1.74-1.87 (m, 4H), 1.97-2.02 (m, 4H), 2.16-2.18 (m, 2H), 2.32 (s, 1H), 2.50 (m, 5H), 2.56-2.67 (m, 2H), 2.82-2.93 (m, 2H), 3.03-3.17 (m, 4H), 3.31 (s, 1H), 3.43 (s, 3H), 3.92 (d, J = 17.6 Hz, 1H), 4.55 (d, J = 17.6 Hz, 1H), 5.04-5.09 (m, 1H), 6.27 (s, 1H), 6.84-6.87 (m, 1H), 6.92-6.95 (m, 1H), 7.09-7.14 (m, 1H), 7.25-7.27 (m, 2H), 7.32-7.34 (m, 2H), 7.42 (d, J = 7.6 Hz, 1H), 7.48 (d, J = 3.6Hz, 1H), 7.53 (t, J = 7.6 Hz, 1H), 7.68 (d, J = 8.4 Hz, 1H), 9.99 (s, 1H), 11.07 (s, 1H), 12.60 (s, 1H). | following routes described for examples 80 and 82 |

FIG. 2 (continued)

| Example | Structure | Name | (M+H)+ | H¹-NMR | Synthesis |
|---|---|---|---|---|---|
| 295 | 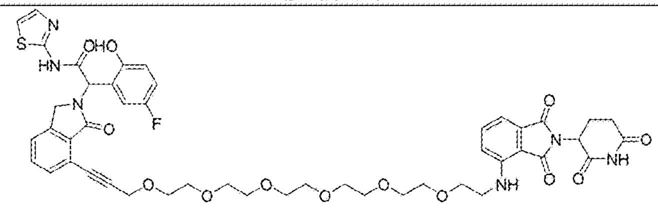 | 2-(7-(1-((2-(2,6-dioxopiperidin-3-yl)-1,3-dioxoisoindolin-4-yl)amino)-3,6,9,12,15,18-hexaoxahenicos-20-yn-21-yl)-1-oxoisoindolin-2-yl)-2-(5-fluoro-2-hydroxyphenyl)-N-(thiazol-2-yl)acetamide | 957.56 479.30 | (400 MHz, DMSO-d6): δ 2.00-2.04 (m, 2H), 2.56-2.67 (m, 2H), 2.84-2.93 (m, 2H), 3.47-3.61 (m, 22H), 3.69-3.73 (m, 2H), 3.95 (d, J = 18.0 Hz, 1H), 4.44 (s, 2H), 4.58 (d, J = 17.6 Hz, 1H), 5.03-5.07 (m, 1H), 6.26 (s, 1H), 6.58-6.61 (m, 1H), 6.85-6.92 (m, 2H), 7.03 (d, J = 7.2 Hz, 1H), 7.08-7.14 (m, 2H), 7.24 (s, 1H), 7.47 (d, J = 3.2 Hz, 1H), 7.53-7.59 (m, 4H), 11.11 (br. 1H). | following routes described for examples 80 and 82 |
| 296 | 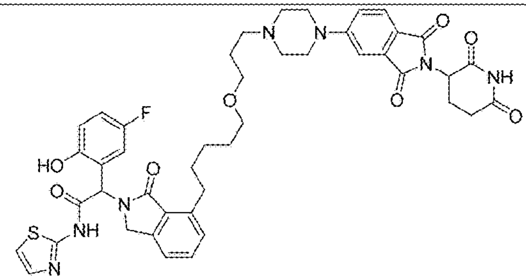 | 2-(7-(5-(3-(4-(2-(2,6-dioxopiperidin-3-yl)-1,3-dioxoisoindolin-5-yl)piperazin-1-yl)propoxy)pentyl)-1-oxoisoindolin-2-yl)-2-(5-fluoro-2-hydroxyphenyl)-N-(thiazol-2-yl)acetamide | 852.54 426.79 | (400 MHz, DMSO-d6): δ 1.33-1.37 (m, 3H), 1.51-1.61 (m, 5H), 1.99-2.03 (m, 2H), 2.33-2.36 (m, 1H), 2.55-2.67 (m, 3H), 2.84-2.93 (m, 1H), 3.06 (t, J = 7.6 Hz, 3H), 3.17 (d, J = 4.0 Hz, 2H), 3.35-3.39 (m, 7H), 3.89 (d, J = 17.6 Hz, 1H), 4.10-4.11 (m, 1H), 4.52 (d, J = 17.6 Hz, 1H), 5.06-5.10 (m, 1H), 6.26 (s, 1H), 6.82-6.85 (m, 1H), 6.91-6.94 (m, 1H), 7.08-7.13 (m, 1H), 7.25-7.36 (m, 5H), 7.45-7.49 (m, 2H), 7.70-7.71 (m, 1H), 9.99 (s, 1H), 11.09 (s, 1H), | following routes described for examples 80, 82 and 283 |

FIG. 2 (continued)

| Example | Structure | Name | (M+H)⁺ | H¹-NMR | Synthesis |
|---|---|---|---|---|---|
| 297 | 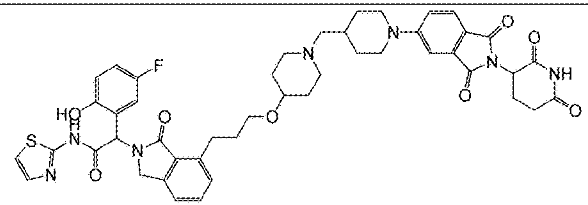 | 2-(7-(3-((1-((1-(2-(2,6-dioxopiperidin-3-yl)-1,3-dioxoisoindolin-5-yl)piperidin-4-yl)methyl)piperidin-4-yl)oxy)propyl)-1-oxoisoindolin-2-yl)-2-(5-fluoro-2-hydroxyphenyl)-N-(thiazol-2-yl)acetamide | 878.56 439.80 | (400 MHz, DMSO-d6): δ 1.83-2.12 (m, 11H), 2.31-2.35 (m, 1H), 2.54-2.68 (m, 3H), 2.84-2.99 (m, 6H), 3.17 (d, J = 5.6 Hz, 1H), 3.30 (s, 3H), 3.40-3.51 (m, 3H), 3.90 (d, J = 17.6 Hz, 1H), 4.03-4.10 (m, 2H), 4.52 (d, J = 17.6 Hz. 1H), 5.04-5.09 (m, 1H), 6.27 (s, 1H), 6.82-6.85 (m, 1H), 6.99-7.01 (m, 1H). 7.08-7.13 (m, 1H), 7.24-7.29 (m, 3H), 7.33-7.38 (m, 2H), 7.47-7.54 (m, 2H), 7.67 (d, J = 8.4 Hz, 1H), 9.97 (s, 1H), 11.08 (s, 1H), 12.61 (s, 1H) 12.58 (br, 1H). | following routes described for examples 80, 82 and 283 |
| 298 | 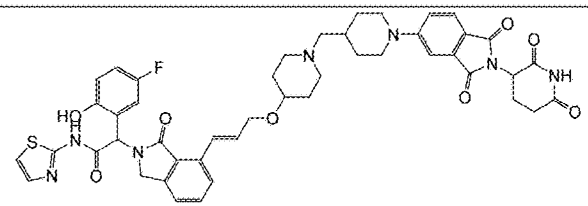 | (E)-2-(7-(3-((1-((1-(2-(2,6-dioxopiperidin-3-yl)-1,3-dioxoisoindolin-5-yl)piperidin-4-yl)methyl)piperidin-4-yl)oxy)prop-1-en-1-yl)-1-oxoisoindolin-2-yl)-2-(5-fluoro-2-hydroxyphenyl)-N-(thiazol-2- | 876.55 438.80 | (400 MHz, DMSO-d6): δ 1.83-2.12 (m, 9H), 2.32-2.33 (m, 1H), 2.54-2.67 (m, 3H), 2.83-3.00 (m, 6H), 3.30 (s, 3H), 3.40-3.51 (m, 2H), 3.93 (d, J = 17.6 Hz, 1H), 4.06-4.10 (m, 2H), 4.26-4.28 (m, 2H), 4.58 (d, J = 17.6 Hz, 1H), 5.04-5.09 (m, 1H), 6.27 (s, 1H), 6.82-6.85 (m, 1H), 6.91-6.94 (m, 1H), 7.10-7.14 (m, 1H), 7.25-7.27 (m, 2H), 7.33-7.35 (m, | by-product from synthesis of example 297 |

FIG. 2 (continued)

| Example | Structure | Name | (M+H)+ | H¹-NMR | Synthesis |
|---|---|---|---|---|---|
| 299 | 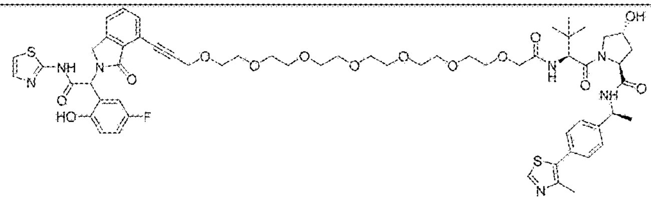 | (2S,4R)-1-((2S)-2-(tert-butyl)-27-(2-(1-(5-fluoro-2-hydroxyphenyl)-2-oxo-2-(thiazol-2-ylamino)ethyl)-3-oxoisoindolin-4-yl)-4-oxo-6,9,12,15,18,21,24-heptaoxa-3-azaheptacos-26-ynoyl)-4-hydroxy-N-((S)-1-(4-(4-methylthiazol-5-yl)phenyl)ethyl)pyrrolidine-2-carboxamide | 1186.75 593.90 | 1H), 7.43-7.50 (m, 3H), 7.59 (t, J = 7.6 Hz, 1H), 7.67 (d, J = 8.8Hz, 1H), 9.97 (s, 1H), 11.08 (s, 1H), 12.61 (s, 1H). (400 MHz, DMSO-d6): δ 0.94 (s, 9H), 1.35-1.38 (m, 3H), 1.74-1.80 (m, 1H), 1.92-2.05 (m, 1H), 2.45 (s, 3H), 3.49-3.61 (m, 23H), 3.71 (t, J = 5.2 Hz, 2H), 3.92-3.96 (m, 3H), 4.28 (s, 1H), 4.44 (t, J = 9.2 Hz, 3H), 4.53-4.59 (m, 2H), 4.90 (t, J = 7.2 Hz, 1H), 5.12 (d, J =3.6 Hz, 1H), 6.27 (s, 1H), 6.84-6.92 (m, 2H), 7.08-7.13 (m, 1H), 7.26 (d, J =3.2 Hz, 1H), 7.36-7.60 (m, 9H), 8.43 (d, J = 8.0 Hz, 1H), 8.98 (s, 1H), 9.97 (s, 1H), 12.60 (s, 1H). | following routes described for examples 80 and 82 |
| 300 | 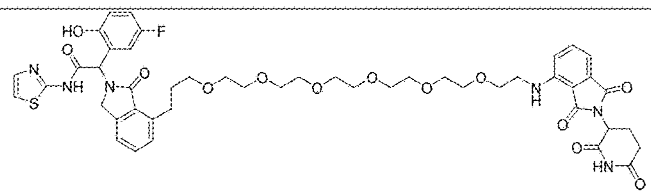 | 2-(7-(1-((2-(2,6-dioxopiperidin-3-yl)-1,3-dioxoisoindolin-4-yl)amino)-3,6,9,12,15,18-hexaoxahenicosan-21-yl)-1-oxoisoindolin-2-yl)-2-(5-fluoro-2- | 961.59 481.32 | (400 MHz, DMSO-d6): δ 1.80-1.83 (m, 2H), 1.99-2.04 (m,2H), 2.33 (s, 1H), 2.50-2.68 (m, 2H), 2.83-2.92 (m, 1H), 3.05-3.09 (m, 2H), 3.30-3.55 (m, 22H), 3.60 (t, J = 5.6 Hz, 2H), 3.90 (d, J = 17.6 Hz, 1H), 4.53 (d, J = 19.6 Hz, 1H), 5.04(d, J = 12.8 Hz, 1H). | following routes described for examples 80, 82 and 283 |

FIG. 2 (continued)

| Example | Structure | Name | (M+H)⁺ | H¹-NMR | Synthesis |
|---|---|---|---|---|---|
| | | hydroxyphenyl)-N-(thiazol-2-yl)acetamide | | 6.27 (s, 1H), 6.60 (t, J = 5.2 Hz, 1H), 6.83 (d, J = 9.2 Hz, 1H), 6.88-6.92 (m, 1H), 7.03(d, J = 7.2 Hz, 1H), 7.07-7.14 (m, 2H), 7.25-7.26 (m, 2H), 7.36(d, J = 7.2 Hz, 1H), 7.45-7.48 (m, 2H), 7.57 (t, J = 7.6 Hz, 1H), 9.94 (s, 1H), 11.09 (s, 1H), 12.59 (br, 1H). | |
| 301 | 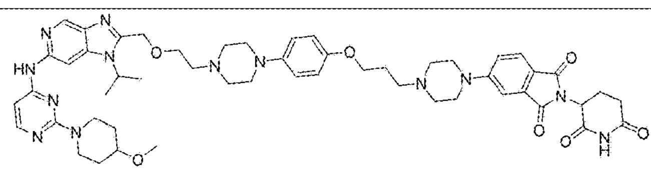 | 2-(2,6-dioxopiperidin-3-yl)-5-(4-(3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)propyl)piperazin-1-yl)isoindoline-1,3-dione | 984.77 492.91 | (400MHz, MeOD), δ 8.67(s, 1H), 8.50 (s, 1H), 7.96 (d, J=6.0 Hz, 1H), 7.73 (d, J=8.8 Hz, 1H), 7.43 (d, J=2.0 Hz, 1H), 7.30 (d, J=8.4, 2.4 Hz, 1H), 6.98 (d, J=9.2 Hz, 2H), 6.89 (d, J=8.8 Hz, 2H), 6.42-6.38 (m, 1H), 5.10-5.08 (m, 1H), 4.94 (s, 2H), 4.31-4.26 (m, 2H), 4.07-4.04 (m, 2H), 3.94-3.85 (m, 2H), 3.60-3.58 (m, 4H), 3.43-3.42 (m, 1H), 3.42 (s, 3H), 3.25-3.24 (m, 4H), 3.23-3.20 (m, 6H), 2.96-2.95 (m, 4H), 2.89-2.87 (m, 3H), 2.82-2.75 (m, 2H), 2.12-2.10 (m, 3H), 2.05-1.95 (m, 2H), 1.73 (d, J=6.8 Hz, 6H), 1.61-1.51 (m, 2H). | Synthesis of example 301 as described |

FIG. 2 (continued)

| Example | Structure | Name | (M+H)⁺ | H¹-NMR | Synthesis |
|---|---|---|---|---|---|
| 302 | 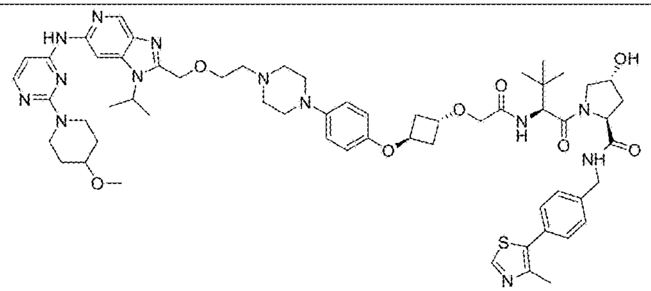 | (2S,4R)-4-hydroxy-1-((S)-2-(2-((1r,3s)-3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)cyclobutoxy)acetamido)-3,3-dimethylbutanoyl)-N-(4-(4-methylthiazol-5-yl)benzyl)pyrrolidine-2-carboxamide | 1142.87 571.96 | (400MHz, MeOD) δ: 8.84 (m, 1H), 8.64 (s, 1H), 8.47 (s, 1H), 8.37 (brs, 1H), 7.94 (d, J = 6.0 Hz, 1H), 7.38-7.48 (m, 4H), 6.88-6.94 (m, 2H), 6.70-6.76 (m, 2H), 6.36 (d, J = 6.0 Hz, 1H), 4.90-4.95 (m, 3H), 4.70-4.82 (m, 2H), 4.46-4.62 (m, 3H), 4.21-4.39 (m, 4H), 3.79-4.02 (m, 6H), 3.43-3.57 (m, 3H), 3.38 (s, 3H), 3.08-3.20 (m, 9H), 2.66 (s, 1H), 2.43-2.55 (m, 5H), 2.32-2.41 (m, 2H), 2.18-2.28 (m, 1H), 2.04-2.15 (m, 1H), 1.93-2.01 (m, 2H), 1.69 (d, J = 6.8 Hz, 6H), 1.51-1.62 (m, 2H), 1.04 (m, 9H). | Synthesis of example 302 as described |
| 303 | 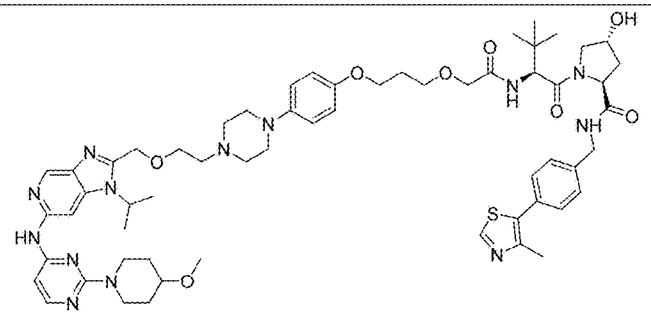 | (2S,4R)-4-hydroxy-1-((S)-2-(2-(3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)propoxy)acetamido)-3,3- | 1130.87 565.96 | (400MHz, MeOD) δ: 8.84 (s, 1H), 8.64 (s, 1H), 8.48 (s, 1H), 8.35 (brs, 1H), 7.94 (d, J = 6.0 Hz, 1H), 7.35-7.47 (m, 4H), 6.82-6.94 (m, 4H), 6.36 (d, J = 6.0 Hz, 1H), 4.89-4.94 (m, 3H), 4.67-4.75 (m, 2H), 4.47-4.60 (m, 3H), 4.22-4.37 (m, 3H), 3.97-4.11 (m, 4H), 3.84-3.93 (m, 3H), 3.69-3.83 (m, 3H), 3.43-3.57 (m, 3H), 3.39 (s, 3H), 3.06-3.18 (m, | following route described for example 302 |

FIG. 2 (continued)

| Example | Structure | Name | (M+H)⁺ | H¹-NMR | Synthesis |
|---|---|---|---|---|---|
| | | dimethylbutanoyl)-N-(4-(4-methylthiazol-5-yl)benzyl)pyrrolidine-2-carboxamide | | 9H), 2.44 (s, 3H), 2.18-2.28 (m, 1H), 2.02-2.13 (m, 3H), 1.92-2.00 (m, 2H), 1.70 (d, J = 7.2 Hz, 6H), 1.53-1.61 (m, 2H), 1.01 (s, 9H). | |
| 304 | (structure) | (2S,4R)-1-((S)-2-(2-((1r,3s)-3-(4-(4-(2-((6-((2-(1-(cyclopropylsulfonyl)-1H-pyrazol-4-yl)pyrimidin-4-yl)amino)-1-isopropyl-1H-imidazo[4,5-c]pyridin-2-yl)methoxy)ethyl)piperazin-1-yl)phenoxy)cyclobutoxy)acetamido)-3,3-dimethylbutanoyl)-4-hydroxy-N-(4-(4-methylthiazol-5-yl)benzyl)pyrrolidine-2-carboxamide | 1199.81 900.44 | (400MHz, MeOD). δ: 8.84 (s, 1H), 8.74 (s, 1H), 8.69 (d, J = 0.8 Hz, 1H), 8.52 (brs, 1H), 8.46 (s, 1H), 8.35 (d, J = 6.0 Hz, 1H), 7.55-7.61 (m, 1H), 7.38-7.47 (m, 4H), 7.15 (d, J = 6.0 Hz, 1H), 6.85-6.94 (m, 2H), 6.67-6.76 (m, 2H), 5.00-5.07 (m, 1H), 4.87-4.89 (m, 3H), 4.68-4.75 (m, 1H), 4.46-4.63 (m, 4H), 4.26-4.40 (m, 2H), 3.78-4.02 (m, 6H), 3.04-3.11 (m, 4H), 2.97-3.03 (m, 1H), 2.81-2.88 (m, 5H), 2.47-2.53 (m, 2H), 2.45 (s, 3H), 2.33-2.41 (m, 2H), 2.19-2.30 (m, 1H), 2.01-2.15 (m, 1H), 1.77 (d, J = 7.2 Hz, 6H), 1.35-1.43 (m, 2H), 1.19-1.28 (m, 2H), 1.04 (s, 9H). | following route described for example 302 |

FIG. 2 (continued)

| Example | Structure | Name | (M+H)+ | H¹-NMR | Synthesis |
|---|---|---|---|---|---|
| 305 | 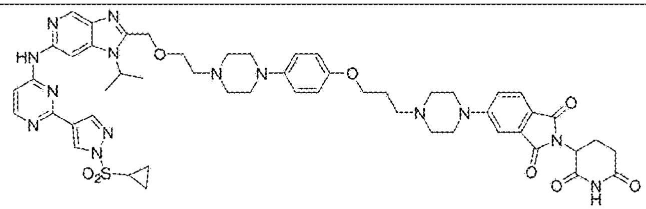 | 5-(4-(3-(4-(4-(2-((6-((2-(1-(cyclopropylsulfonyl)-1H-pyrazol-4-yl)pyrimidin-4-yl)amino)-1-isopropyl-1H-imidazo[4,5-c]pyridin-2-yl)methoxy)ethyl)piperazin-1-yl)phenoxy)propyl)-2-(2,6-dioxopiperidin-3-yl)isoindoline-1,3-dione | 1041.71 521.38 | (400MHz, MeOD), δ: 11.08 (s, 1H), 10.27 (s, 1H), 8.69 (s, 1H), 8.66 (s, 1H), 8.51 (brs, 1H), 8.47 (s, 1H), 8.40 (d, J = 6.0 Hz, 1H), 8.22 (s, 1H), 7.67 (d, J = 8.4 Hz, 1H), 7.33 (s, 1H), 7.20-7.28 (m, 2H), 6.75-6.87 (m, 4H), 4.95-5.11 (m, 2H), 4.78 (s, 2H), 3.92 (t, J = 6.0 Hz, 2H), 3.65 (t, J = 6.0 Hz, 2H), 3.14-3.29 (m, 6H), 2.82-2.97 (m, 6H), 2.54-2.63 (m, 6H), 2.42-2.48 (m, 4H), 1.97-2.06 (m, 1H), 1.82-1.89 (m, 2H), 1.66 (d, J = 7.2 Hz, 6H), 1.27-1.31 (m, 2H), 1.21-1.25 (m, 2H), 1.10 (d, J = 6.8 Hz, 2H). | following routes described for examples 301 and 302 |
| 306 | 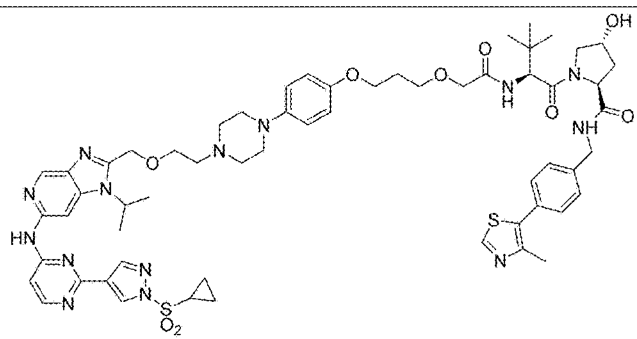 | (2S,4R)-1-((S)-2-(2-(3-(4-(4-(2-((6-((2-(1-(cyclopropylsulfonyl)-1H-pyrazol-4-yl)pyrimidin-4-yl)amino)-1-isopropyl-1H-imidazo[4,5-c]pyridin-2-yl)methoxy)ethyl)piperazin-1-yl)phenoxy)propoxy) | 1187.82 594.44 | (400MHz, MeOD), δ 8.84 (s, 1H), 8.74 (s, 1H), 8.69 (s, 1H), 8.52 (s, 1H), 8.47 (s, 1H), 8.40 (s, 1H), 8.35 (d, J=6.0 Hz, 1H), 7.44-7.43 (m, 2H), 7.37 (d, J=7.6 Hz, 2H), 7.18-7.12 (m, 1H), 6.90-6.83 (m, 4H), 5.01 (s, 1H), 4.88 (s, 2H), 4.72-4.71 (m, 1H), 4.60-4.57 (m, 2H), 4.53-4.51 (m, 2H), 4.37-4.33 (m, 1H), 4.06-3.99 (m, 4H), 3.85-3.80 (m, | following route described for example 302 |

FIG. 2 (continued)

| Example | Structure | Name | (M+H)+ | H¹-NMR | Synthesis |
|---|---|---|---|---|---|
| | | acetamido)-3,3-dimethylbutanoyl)-4-hydroxy-N-(4-(4-methylthiazol-5-yl)benzyl)pyrrolidine-2-carboxamide | | 4H), 3.73-3.72 (m, 2H), 3.10-3.05 (m, 4H), 3.04-2.97 (m, 1H), 2.93-2.84 (m, 5H), 2.47 (s, 3H), 2.24-2.19 (m, 1H), 2.08-2.05 (m, 3H), 1.77-1.76 (m, 6H), 1.41-1.39 (m, 2H), 1.25-1.23 (m, 2H), 1.01 (s, 9H). | |
| 307 | 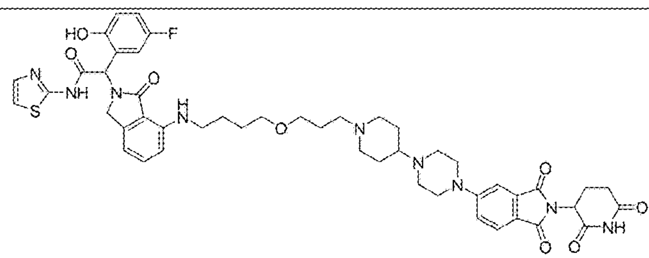 | 2-(7-((4-(3-(4-(4-(2-(2,6-dioxopiperidin-3-yl)-1,3-dioxoisoindolin-5-yl)piperazin-1-yl)piperidin-1-yl)propoxy)butyl)amino)-1-oxoisoindolin-2-yl)-2-(5-fluoro-2-hydroxyphenyl)-N-(thiazol-2-yl)acetamide | 936.62 468.83 | (400MHz, CDCl3, δ: 8.64 (s, 1H), 7.770 (d, J=8.8 Hz, 1H), 7.42 (d, J=3.6 Hz, 1H), 7.28-7.33 (m, 1H), 7.10-7.15 (m, 1H), 7.02-7.05 (m, 1H), 6.98 (d, J=3.6 Hz, 1H), 6.90-6.94 (m, 2H), 6.72 (s, 1H), 6.53-6.60 (m, 2H), 6.48 (d, J=8.4 Hz, 1H), 4.86-4.98 (m, 2H), 4.13 (d, J=17.2 Hz, 1H), 3.45-3.55 (m, 5H), 3.35-3.42 (m, 4H), 3.22-3.28 (m, 2H), 3.10-3.18 (m, 2H), 2.67-2.94 (m, 6H), 2.62-2.66 (m, 4H), 2.42-2.47 (m, 2H), 1.95-2.11 (m, 8H), 1.68-1.75 (m, 2H). | Synthesis of example 307 as described |

FIG. 2 (continued)

| Example | Structure | Name | (M+H)+ | H¹-NMR | Synthesis |
|---|---|---|---|---|---|
| 308 | 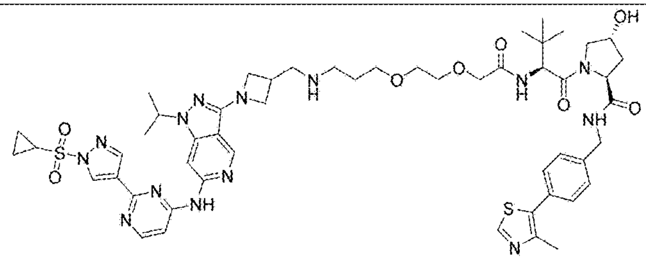 | (2S,4R)-1-((S)-13-(tert-butyl)-1-(1-(6-((2-(1-(cyclopropylsulfonyl)-1H-pyrazol-4-yl)pyrimidin-4-yl)amino)-1-isopropyl-1H-pyrazolo[4,3-c]pyridin-3-yl)azetidin-3-yl)-11-oxo-6,9-dioxa-2,12-diazatetradecan-14-oyl)-4-hydroxy-N-(4-(4-methylthiazol-5-yl)benzyl)pyrrolidine-2-carboxamide | 1081.75 541.40 | | following route described for example 302 |
| 309 | 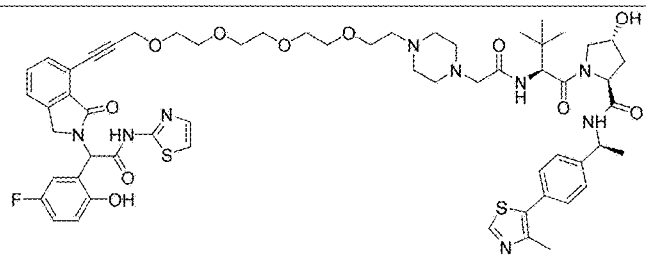 | (2S,4R)-1-((2S)-2-(2-(4-((15-(2-(1-(5-fluoro-2-hydroxyphenyl)-2-oxo-2-(thiazol-2-ylamino)ethyl)-3-oxoisoindolin-4-yl)-3,6,9,12-tetraoxapentadec-14-yn-1-yl)piperazin-1-yl)acetamido)-3,3-dimethylbutanoyl)-4-hydroxy-N-((S)-1-(4- | 1166.76 583.91 | | following routes described for examples 80 and 82 |

FIG. 2 (continued)

| Example | Structure | Name | (M+H)⁺ | H¹-NMR | Synthesis |
|---|---|---|---|---|---|
| 310 | 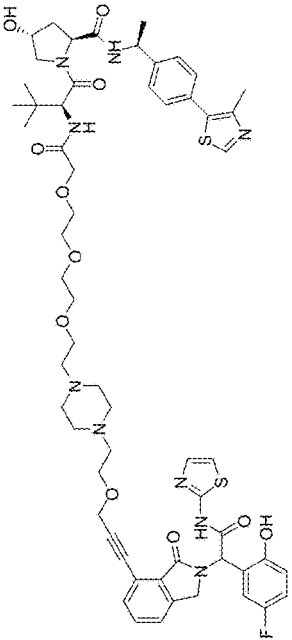 | (2S,4R)-1-((2S)-2-(tert-butyl)-14-(4-(2-((3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethyl)piperazin-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide | 1166.76 583.91 | | following routes described for examples 80 and 82 |
| 311 | 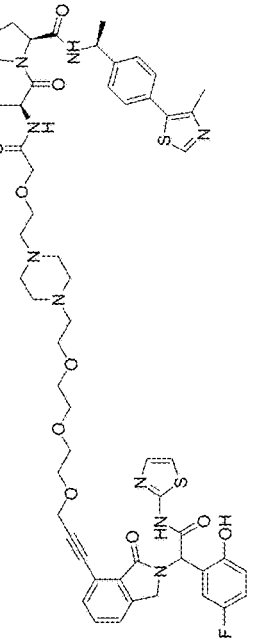 | (2S,4R)-1-((2S)-2-(2-(2-(4-(2-(2-(2-(3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)piperazin-1-yl)ethyl)piperazin-1- | 1166.76 583.91 | | following routes described for examples 80 and 82 |

FIG. 2 (continued)

| Example | Structure | Name | (M+H)⁺ | H¹-NMR | Synthesis |
|---|---|---|---|---|---|
| | | yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide | | | |
| 312 | 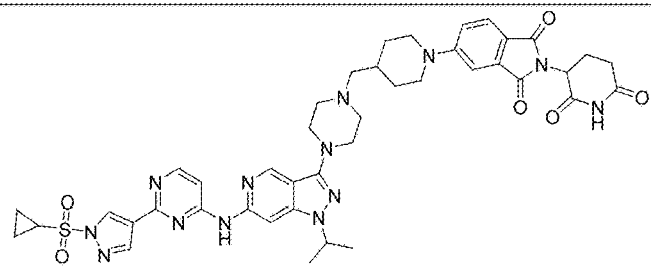 | 5-(4-((4-(6-((2-(1-(cyclopropylsulfonyl)-1H-pyrazol-4-yl)pyrimidin-4-yl)amino)-1-isopropyl-1H-pyrazolo[4,3-c]pyridin-3-yl)piperazin-1-yl)methyl)piperidin-1-yl)-2-(2,6-dioxopiperidin-3-yl)isoindoline-1,3-dione | 862.57 431.81 | | following routes described for examples 301 and 302 |

FIG. 2 (continued)

| Example | Structure | Name | (M+H)+ | H1-NMR | Synthesis |
|---|---|---|---|---|---|
| 313 | 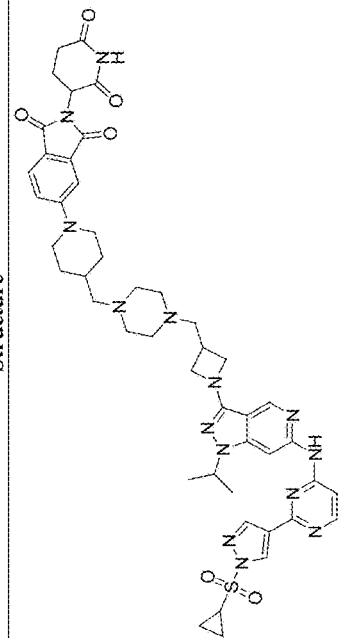 | 5-(4-((4-((1-(6-((2-(1-(cyclopropyl)sulfonyl)-1H-pyrazol-4-yl)pyrimidin-4-yl)amino)-1-isopropyl-1H-pyrazolo[4,3-c]pyridin-3-yl)azetidin-3-yl)methyl)piperazin-1-yl)methyl)piperidin-1-yl)-2-(2,6-dioxopiperidin-3-yl)isoindoline-1,3-dione | 931.64 466.34 | | following routes described for examples 301 and 302 |
| 314 | 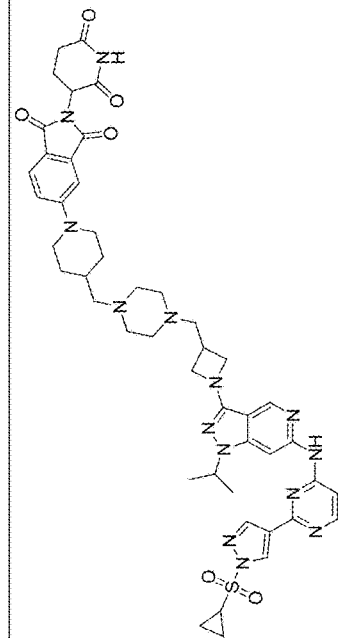 | (2S,4R)-1-((2S)-2-(2-(2-(2-(4-(2-(2-(3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethyl)piperazin-1-yl)ethoxy)ethoxy)acetamido)-3,3-dimethylbutanoyl)-4-hydroxy-N-((S)-1-(4- | 1166.76 1188.75 [M+Na] 583.91 | | following routes described for examples 80 and 82 |

| Example | Structure | Name | (M+H)⁺ | H¹-NMR | Synthesis |
|---|---|---|---|---|---|
| 315 | 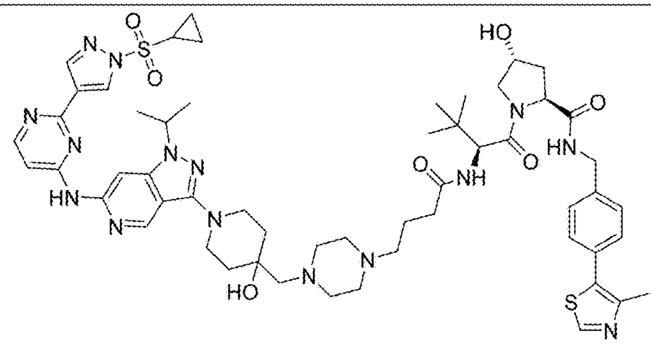 | (4-methylthiazol-5-yl)phenyl)ethyl)pyrrolidine-2-carboxamide (2S,4R)-1-((S)-2-(4-(4-((1-(6-((2-(1-(cyclopropylsulfonyl)-1H-pyrazol-4-yl)pyrimidin-4-yl)amino)-1-isopropyl-1H-pyrazolo[4,3-c]pyridin-3-yl)-4-hydroxypiperidin-4-yl)methyl)piperazin-1-yl)butanamido)-3,3-dimethylbutanoyl)-4-hydroxy-N-(4-(4-methylthiazol-5-yl)benzyl)pyrrolidine-2-carboxamide | | | |

FIG. 2 (continued)

| Example | Structure | Name | (M+H)⁺ | H¹-NMR | Synthesis |
|---|---|---|---|---|---|
| 316 | 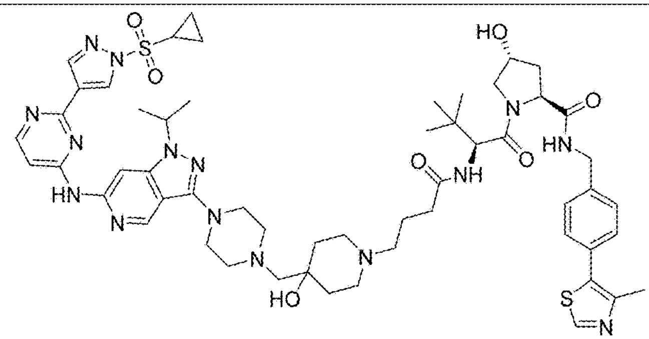 | (2S,4R)-1-((S)-2-(4-(4-(4-(6-((2-(1-(cyclopropylsulfonyl)-1H-pyrazol-4-yl)pyrimidin-4-yl)amino)-1-isopropyl-1H-pyrazolo[4,3-c]pyridin-3-yl)piperazin-1-yl)methyl)-4-hydroxypiperidin-1-yl)butanamido)-3,3-dimethylbutanoyl)-4-hydroxy-N-(4-(4-methylthiazol-5-yl)benzyl)pyrrolidine-2-carboxamide | | | |
| 317 | 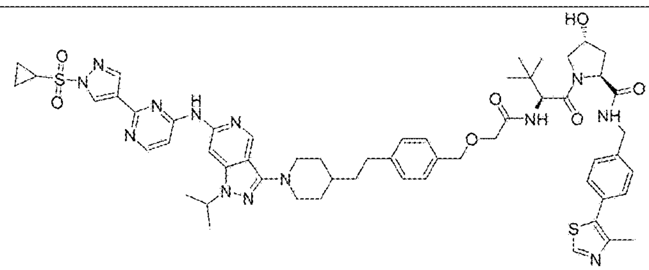 | (2S,4R)-1-((S)-2-(2-((4-(2-(1-(6-((2-(1-(cyclopropylsulfonyl)-1H-pyrazol-4-yl)pyrimidin-4-yl)amino)-1-isopropyl-1H-pyrazolo[4,3-c]pyridin-3-yl)piperidin-4-yl)ethyl)benzyl)oxy)acetamido)-3,3- | | | |

FIG. 2 (continued)

| Example | Structure | Name | (M+H)+ | H¹-NMR | Synthesis |
|---|---|---|---|---|---|
| | | dimethylbutanoyl)-4-hydroxy-N-(4-(4-methylthiazol-5-yl)benzyl)pyrrolidine-2-carboxamide | | | |
| 318 | 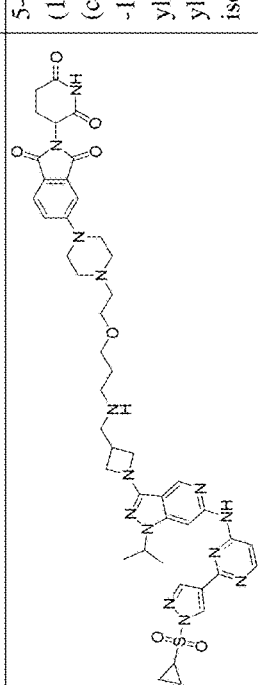 | 5-(4-(2-(3-(((1-(6-((2-(1-(cyclopropylsulfonyl)-1H-pyrazol-4-yl)pyrimidin-4-yl)amino)-1-isopropyl-1H-pyrazolo[4,3-c]pyridin-3-yl)azetidin-3-yl)methyl)amino)propoxy)ethyl)piperazin-1-yl)-2-(2,6-dioxopiperidin-3-yl)isoindoline-1,3-dione | | | |
| 319 | 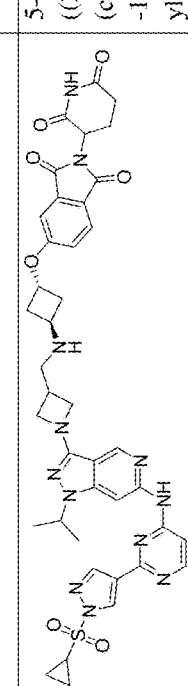 | 5-((1r,3r)-3-(((1-(6-((2-(1-(cyclopropylsulfonyl)-1H-pyrazol-4-yl)pyrimidin-4-yl)amino)-1-isopropyl-1H-pyrazolo[4,3- | 835.52 418.28 | | following routes described for examples 301 and 302 |

FIG. 2 (continued)

| Example | Structure | Name | (M+H)+ | H1-NMR | Synthesis |
|---|---|---|---|---|---|
| | | c]pyridin-3-yl)azetidin-3-yl)methyl)amino)cyclobutoxy)-2-(2,6-dioxopiperidin-3-yl)isoindoline-1,3-dione | | | |
| 320 | 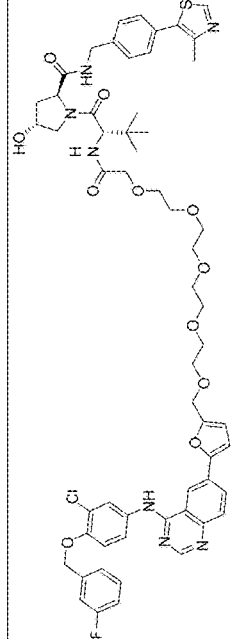 | (2S,4R)-1-((S)-18-(tert-butyl)-1-(5-(4-((3-chloro-4-((3-fluorobenzyl)oxy)phenyl)amino)quinazolin-6-yl)furan-2-yl)-16-oxo-2,5,8,11,14-pentaoxa-17-azamonadecan-19-oyl)-4-hydroxy-N-(4-(4-methylthiazol-5-yl)benzyl)pyrrolidine-2-carboxamide | 1122.42 | 1H NMR (400 MHz, DMSO-d6) δ 9.98 (s, 1H), 8.97 (s, 1H), 8.76 (s, 1H), 8.67 – 8.57 (m, 1H), 8.55 (s, 1H), 8.17 (d, J = 8.5 Hz, 1H), 8.00 (s, 1H), 7.80 (d, J = 8.7 Hz, 1H), 7.74 (d, J = 10.3 Hz, 1H), 7.64 – 7.24 (m, 9H), 7.19 (t, J = 8.2 Hz, 1H), 7.09 (d, J = 2.8 Hz, 1H), 6.65 (d, J = 2.7 Hz, 1H), 5.26 (s, 2H), 5.15 (d, 1H), 4.61 – 4.54 (m, 1H), 4.54 (s, 2H), 4.49 – 4.15 (m, 6H), 3.94 (s, 2H), 3.73 – 3.40 (m, 17H), 2.43 (s, 3H), 2.11 – 2.01 (m, 1H), 1.95 – 1.84 (m, 1H), 0.93 (s, 9H). | Synthesis of example 320 as described |

FIG. 2 (continued)

| Example | Structure | Name | (M+H)⁺ | H¹-NMR | Synthesis |
|---|---|---|---|---|---|
| 321 | 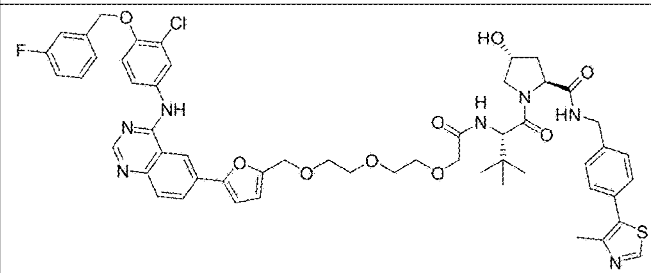 | (2S,4R)-1-((S)-12-(tert-butyl)-1-(5-(4-((3-chloro-4-((3-fluorobenzyl)oxy)phenyl)amino)quinazolin-6-yl)furan-2-yl)-10-oxo-2,5,8-trioxa-11-azatridecan-13-oyl)-4-hydroxy-N-(4-(4-methylthiazol-5-yl)benzyl)pyrrolidine-2-carboxamide | 1034.4 | 1H NMR (600 MHz, DMSO-d6) δ 8.96 (s, 1H), 8.87 (s, 1H), 8.82 (s, 1H), 8.63 – 8.54 (m, 1H), 8.37 – 8.29 (m, 1H), 7.96 – 7.87 (m, 1H), 7.85 (d, J = 8.8 Hz, 1H), 7.64 (d, J = 10.6 Hz, 3H), 7.55 – 7.25 (m, 9H), 7.20 (td, J = 8.7, 2.7 Hz, 1H), 7.14 (d, J = 3.3 Hz, 1H), 6.66 (d, J = 3.3 Hz, 2H), 5.30 (s, 2H), 4.55 (d, J = 14.5 Hz, 3H), 4.47 – 4.31 (m, 3H), 4.25 (dd, J = 15.7, 5.7 Hz, 1H), 3.96 (s, 2H), 3.70 – 3.55 (m, 16H), 2.42 (s, 3H), 2.09 – 2.01 (m, 1H), 1.92 – 1.86 (m, 1H), 0.92 (s, 9H). | following routes described for examples 97 and 320 |
| 322 | 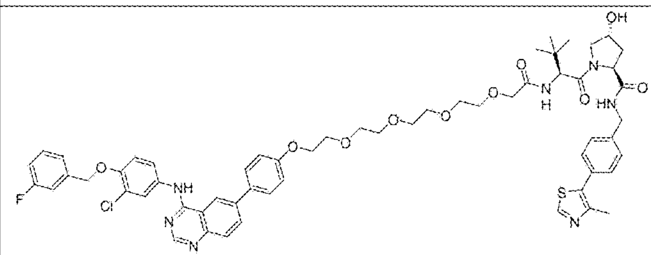 | (2S,4R)-1-((S)-2-(tert-butyl)-17-(4-(4-((3-chloro-4-((3-fluorobenzyl)oxy)phenyl)amino)quinazolin-6-yl)phenoxy)-4-oxo-6,9,12,15-tetraoxa-3-azaheptadecanoyl)-4-hydroxy-N-(4-(4-methylthiazol-5-yl)benzyl)pyrrolidine | 1118.52 | 1H NMR (400 MHz, DMSO-d6) δ 9.89 (s, 1H), 8.97 (s, 1H), 8.73 (s, 1H), 8.61 (t, J = 6.1 Hz, 1H), 8.57 (s, 1H), 8.20 – 8.10 (m, 1H), 8.03 (d, J = 2.5 Hz, 1H), 7.87 – 7.78 (m, 3H), 7.76 (dd, J = 9.0, 2.6 Hz, 1H), 7.54 – 7.25 (m, 8H), 7.18 (td, J = 10.4, 8.4, 2.7 Hz, 1H), 7.12 (d, J = 8.6 Hz, 2H), 5.26 (s, 2H), 5.16 (d, J = 3.5 Hz, 1H), 4.56 (d, J = 9.6 Hz, 1H), 4.51 – 4.19 (m, 5H), | following routes described for examples 97 and 320 |

FIG. 2 (continued)

| Example | Structure | Name | (M+H)⁺ | H¹-NMR | Synthesis |
|---|---|---|---|---|---|
| 323 | 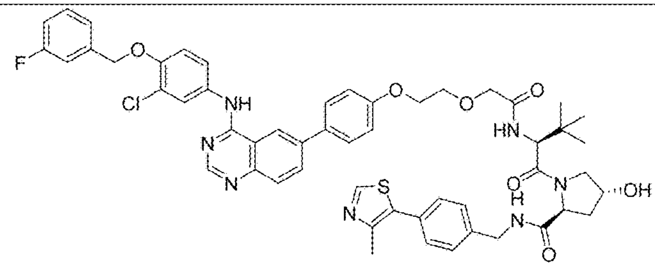 | (2S,4R)-1-((S)-2-(2-(2-(4-(4-((3-chloro-4-((3-fluorobenzyl)oxy)phenyl)amino)quinazolin-6-yl)phenoxy)ethoxy)acetamido)-3,3-dimethylbutanoyl)-4-hydroxy-N-(4-(4-methylthiazol-5-yl)benzyl)pyrrolidine-2-carboxamide | 986.35 | 1H NMR (500 MHz, DMSO-d6) δ 9.85 (s, 1H), 8.88 (s, 1H), 8.71 (d, J = 2.0 Hz, 1H), 8.62 – 8.49 (m, 2H), 8.08 (dd, J = 8.6, 1.9 Hz, 1H), 8.02 (d, J = 2.6 Hz, 1H), 7.84 – 7.70 (m, 3H), 7.57 – 7.23 (m, 9H), 7.24 – 7.13 (m, 3H), 5.26 (s, 2H), 5.15 (d, J = 3.6 Hz, 1H), 4.63 (d, J = 9.6 Hz, 1H), 4.51 – 4.33 (m, 3H), 4.32 – 4.19 (m, 3H), 4.08 (d, J = 1.5 Hz, 2H), 3.89 (t, J = 4.6 Hz, 3H), 3.74 – 3.60 (m, 2H), 2.38 (s, 3H), 2.12 – 2.02 (m, 1H), 1.96 – 1.88 (m, 1H), 0.98 (s, 9H). | following routes described for examples 97 and 320 |
| | | -2-carboxamide | | 4.16 (t, J = 5.6, 3.3 Hz, 2H), 3.96 (s, 2H), 3.76 (t, 2H), 3.71 – 3.43 (m, 12H), 2.43 (s, 3H), 2.11 – 2.00 (m, 1H), 1.94 – 1.85 (m, 1H), 0.94 (s, 9H). | |
| 324 | 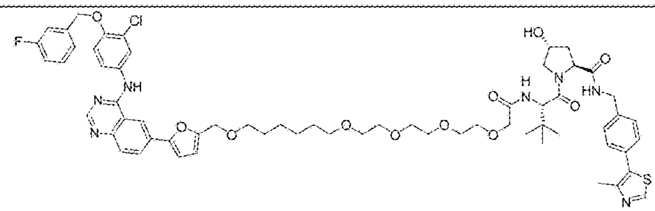 | (2S,4R)-1-((S)-22-(tert-butyl)-1-(5-(4-((3-chloro-4-((3-fluorobenzyl)oxy)phenyl)amino)quinazolin-6-yl)furan-2-yl)-20- | 1178.49 | 1H NMR (600 MHz, DMSO-d6) δ 9.97 (s, 1H), 8.97 (s, 0H), 8.75 (d, J = 1.6 Hz, 1H), 8.60 (t, J = 6.0 Hz, 1H), 8.55 (s, 1H), 8.17 (dd, J = 8.7, 1.7 Hz, 1H), 8.00 (d, J = 2.6 Hz, | following routes described for examples 97 and 320 |

FIG. 2 (continued)

| Example | Structure | Name | (M+H)⁺ | H¹-NMR | Synthesis |
|---|---|---|---|---|---|
| | | oxo-2,9,12,15,18-pentaoxa-21-azatricosan-23-oyl)-4-hydroxy-N-(4-(4-methylthiazol-5-yl)benzyl)pyrrolidine-2-carboxamide | | 1H), 7.80 (d, J = 8.7 Hz, 1H), 7.73 (dd, J = 8.9, 2.6 Hz, 1H), 7.54 – 7.25 (m, 9H), 7.18 (td, J = 8.5, 2.4 Hz, 1H), 7.08 (d, J = 3.3 Hz, 1H), 6.63 (d, J = 3.3 Hz, 1H), 5.26 (s, 2H), 5.15 (d, J = 3.5 Hz, 1H), 4.55 (d, J = 9.6 Hz, 1H), 4.49 (s, 2H), 4.47 – 4.31 (m, 5H), 4.23 (dd, J = 15.9, 5.6 Hz, 1H), 3.95 (s, 2H), 3.72 – 3.24 (m, 17H), 2.43 (s, 3H), 2.09 – 2.01 (m, 1H), 1.89 (ddd, J = 12.9, 8.8, 4.4 Hz, 1H), 1.56 – 1.47 (m, 2H), 1.48 – 1.38 (m, 2H), 1.33 – 1.20 (m, 4H), 0.93 (s, 9H). | |
| 325 | 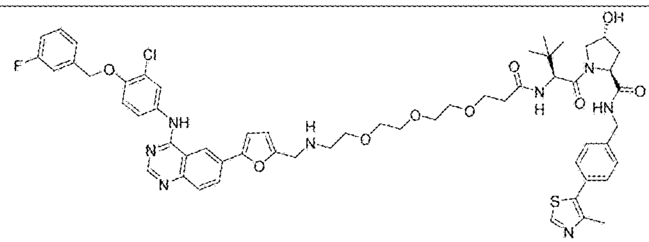 | (2S,4R)-1-((S)-16-(tert-butyl)-1-(5-(4-((3-chloro-4-((3-fluorobenzyl)oxy)phenyl)amino)quinazolin-6-yl)furan-2-yl)-14-oxo-5,8,11-trioxa-2,15-diazaheptadecan-17-oyl)-4-hydroxy-N-(4-(4-methylthiazol-5-yl)benzyl)pyrrolidine | 1091.45 | 1H NMR (400 MHz, DMSO-d6) δ 9.92 (s, 1H), 8.97 (s, 1H), 8.72 (d, J = 1.9 Hz, 1H), 8.63 – 8.53 (m, 1H), 8.54 (s, 1H), 8.15 (d, J = 9.4 Hz, 1H), 8.01 (d, J = 2.3 Hz, 1H), 7.92 (d, J = 9.3 Hz, 1H), 7.83 – 7.70 (m, 2H), 7.58 – 7.24 (m, 8H), 7.19 (ddd, J = 10.3, 5.9, 1.9 Hz, 1H), 7.04 (d, J = 3.1 Hz, 1H), 6.46 (d, J = 3.0 Hz, 1H), 5.27 (s, 2H), 5.13 (d, J = 3.5 Hz, 1H), 4.54 (d, J = 9.4 | following routes described for examples 97 and 320 |

FIG. 2 (continued)

| Example | Structure | Name | (M+H)+ | H¹-NMR | Synthesis |
|---|---|---|---|---|---|
| | | -2-carboxamide | | Hz, 1H), 4.47 – 4.29 (m, 3H), 4.21 (dd, J = 15.7, 5.2 Hz, 1H), 3.82 (s, 2H), 3.70 – 3.39 (m, 14H), 2.72 (t, J = 5.5 Hz, 2H), 2.57 – 2.47 (m, 1H), 2.38 – 2.29 (m, 1H), 2.08 – 1.99 (m, 1H), 1.93 – 1.85 (m, 1H), 0.92 (s, 9H). | |
| 326 | 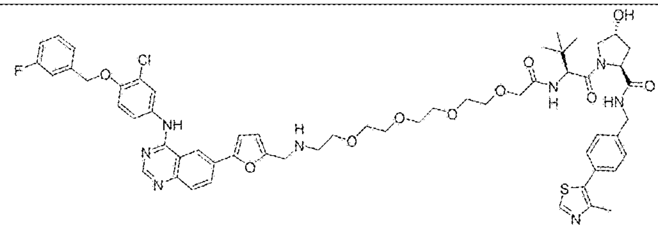 | (2S,4R)-1-((S)-18-(tert-butyl)-1-(5-(4-((3-chloro-4-((3-fluorobenzyl)oxy)phenyl)amino)quinazolin-6-yl)furan-2-yl)-16-oxo-5,8,11,14-tetraoxa-2,17-diazanonadecan-19-oyl)-4-hydroxy-N-(4-(4-methylthiazol-5-yl)benzyl)pyrrolidine-2-carboxamide | 1121.49 | 1H NMR (400 MHz, DMSO-d6) δ 9.92 (s, 1H), 8.97 (s, 1H), 8.72 (s, 1H), 8.60 (t, J = 5.7 Hz, 2H), 8.54 (s, 1H), 8.15 (d, J = 8.8 Hz, 1H), 8.00 (d, J = 2.1 Hz, 1H), 7.83 – 7.68 (m, 2H), 7.59 – 7.23 (m, 8H), 7.23 – 7.13 (m, 1H), 7.04 (d, J = 3.0 Hz, 1H), 6.46 (d, J = 2.7 Hz, 1H), 5.26 (s, 2H), 5.16 (d, J = 2.8 Hz, 1H), 4.55 (d, J = 9.5 Hz, 1H), 4.51 – 4.30 (m, 3H), 4.24 (dd, J = 15.8, 5.6 Hz, 1H), 3.94 (s, 2H), 3.83 (s, 2H), 3.72 – 3.40 (m, 14H), 2.73 (t, J = 5.2 Hz, 2H), 2.43 (s, 3H), 2.11 – 2.00 (m, 1H), 1.95 – 1.84 (m, 1H), 0.93 (s, 9H). | following routes described for examples 97 and 320 |

FIG. 2 (continued)

| Example | Structure | Name | (M+H)⁺ | H¹-NMR | Synthesis |
|---|---|---|---|---|---|
| 327 | 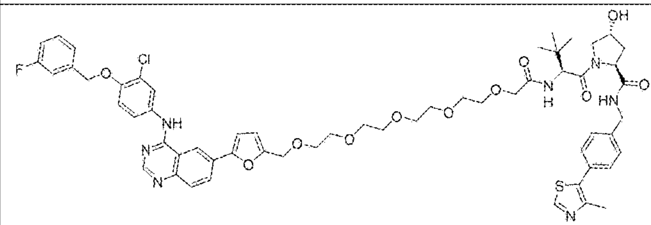 | (2S,4R)-1-((S)-18-(tert-butyl)-1-(5-(4-((3-fluorobenzyl)oxy)phenyl)amino)quinazolin-6-yl)furan-2-yl)-16-oxo-2,5,8,11,14-pentaoxa-17-azanonadecan-19-oyl)-4-hydroxy-N-(4-(4-methylthiazol-5-yl)benzyl)pyrrolidine-2-carboxamide | 1122.43 | 1H NMR (500 MHz, DMSO-d6) δ 10.00 (s, 1H), 8.97 (s, 1H), 8.82 – 8.75 (m, 2H), 8.69 (t, J = 6.1 Hz, 1H), 8.55 (s, 1H), 8.17 (dd, J = 8.8, 1.8 Hz, 1H), 8.01 (d, J = 2.6 Hz, 1H), 7.80 (d, J = 8.8 Hz, 1H), 7.74 (dd, J = 9.0, 2.6 Hz, 1H), 7.53 – 7.24 (m, 9H), 7.19 (td, J = 8.8, 8.4, 2.4 Hz, 1H), 7.10 (d, J = 3.3 Hz, 1H), 6.65 (d, J = 3.3 Hz, 1H), 5.46 (d, J = 7.2 Hz, 1H), 5.26 (s, 2H), 4.54 (s, 2H), 4.50 (d, J = 9.2 Hz, 1H), 4.45 – 4.15 (m, 5H), 3.93 (s, 2H), 3.92 – 3.83 (m, 1H), 3.64 – 3.38 (m, 16H), 2.43 (s, 3H), 2.38 – 2.28 (m, 1H), 1.77 – 1.68 (m, 1H), 0.94 (s, 9H). | following routes described for examples 97 and 320 |
| 328 | 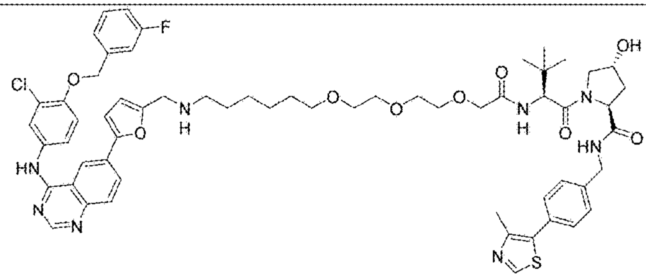 | (2S,4R)-1-((S)-19-(tert-butyl)-1-(5-(4-((3-fluorobenzyl)oxy)phenyl)amino)quinazolin-6-yl)furan-2-yl)-17-oxo-9,12,15-trioxa-2,18-diazaicosan-20-oyl)-4-hydroxy-N-(4-(4-methylthiazol-5- | 1133.49 | 1H NMR (400 MHz, DMSO-d6) δ 9.91 (s, 1H), 8.97 (s, 1H), 8.72 (d, J = 2.1 Hz, 1H), 8.61 (t, J = 6.0 Hz, 2H), 8.54 (s, 1H), 8.15 (dd, J = 8.7, 1.7 Hz, 1H), 8.01 (d, J = 2.5 Hz, 1H), 7.79 (d, J = 8.7 Hz, 1H), 7.74 (dd, J = 9.0, 2.6 Hz, 1H), 7.54 – 7.24 (m, 8H), 7.19 (td, J = 8.8, 2.7 Hz, 1H), 6.46 (d, | following routes described for examples 97 and 320 |

FIG. 2 (continued)

| Example | Structure | Name | (M+H)+ | H¹-NMR | Synthesis |
|---|---|---|---|---|---|
| | | yl)benzyl)pyrrolidine-2-carboxamide | | J = 3.1 Hz, 2H), 5.27 (s, 2H), 5.16 (d, J = 3.0 Hz, 1H), 4.56 (d, J = 9.6 Hz, 1H), 4.49 – 4.30 (m, 3H), 4.22 (dd, J = 15.8, 5.5 Hz, 1H), 3.95 (s, 2H), 3.81 (s, 2H), 3.71 – 3.25 (m, 12H), 2.56 (t, 2H), 2.43 (s, 3H), 2.08 – 2.01 (m, 1H), 1.94 – 1.84 (m, 1H), 1.55 – 1.34 (m, 4H), 1.32 – 1.15 (m, 4H), 0.93 (s, 9H). | |
| 329 | 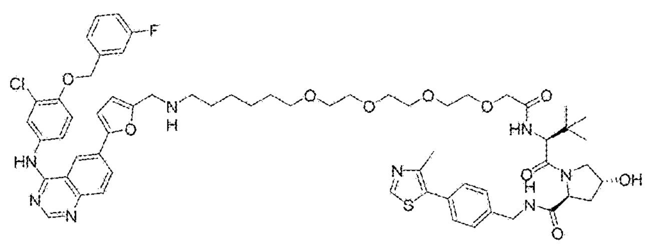 | (2S,4R)-1-((S)-2-(tert-butyl)-1-(5-(4-((3-chloro-4-((3-fluorobenzyl)oxy)phenyl)amino)quinazolin-6-yl)furan-2-yl)-20-oxo-9,12,15,18-tetraoxa-2,21-diazatricosan-23-oyl)-4-hydroxy-N-(4-(4-methylthiazol-5-yl)benzyl)pyrrolidine-2-carboxamide | 1177.47 | 1H NMR (400 MHz, DMSO-d6) δ 9.91 (s, 2H), 8.97 (s, 1H), 8.76 – 8.68 (m, 1H), 8.64 – 8.56 (m, 3H), 8.54 (s, 1H), 8.15 (d, J = 8.7 Hz, 3H), 8.01 (d, J = 2.5 Hz, 1H), 7.77 (dd, J = 20.0, 9.6 Hz, 5H), 7.59 – 7.25 (m, 8H), 7.19 (t, J = 8.8 Hz, 1H), 7.07 – 7.01 (m, 3H), 6.53 – 6.41 (m, 4H), 5.26 (s, 2H), 5.16 (d, J = 3.6 Hz, 1H), 4.56 (d, J = 9.5 Hz, 1H), 4.48 – 4.31 (m, 3H), 4.23 (dd, J = 15.9, 5.6 Hz, 1H), 3.95 (s, 2H), 3.82 (s, 2H), 3.72 – 3.41 (m, 16H), 2.66 – 2.53 (m, 2H), 2.43 (s, 3H), 2.05 (t, J = 10.2 Hz, 1H), 1.89 (tt, J = 8.8, 4.2 Hz, 1H), | following routes described for examples 97 and 320 |

FIG. 2 (continued)

| Example | Structure | Name | (M+H)⁺ | H¹-NMR | Synthesis |
|---|---|---|---|---|---|
| 330 | 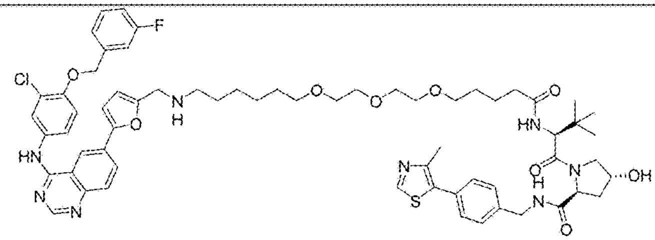 | (2S,4R)-1-((S)-2-(tert-butyl)-1-(5-(4-((3-chloro-4-((3-fluorobenzyl)oxy)phenyl)amino)quinazolin-6-yl)furan-2-yl)-20-oxo-9,12,15-trioxa-2,21-diazatricosan-23-oyl)-4-hydroxy-N-(4-(4-methylthiazol-5-yl)benzyl)pyrrolidine-2-carboxamide | 1175.53 | 1H NMR (400 MHz, DMSO-d6) δ 9.91 (s, 1H), 8.97 (s, 1H), 8.74 (s, 1H), 8.62 – 8.48 (m, 2H), 8.16 (d, J = 10.0 Hz, 1H), 8.01 (d, J = 2.3 Hz, 1H), 7.91 – 7.67 (m, 3H), 7.53 – 7.24 (m, 8H), 7.18 (td, J = 8.4, 7.9, 2.7 Hz, 1H), 7.05 (d, J = 3.2 Hz, 1H), 6.48 (d, J = 2.7 Hz, 1H), 5.27 (s, 2H), 5.12 (br s, 1H), 4.54 (d, J = 9.4 Hz, 1H), 4.48 – 4.15 (m, 5H), 3.84 (s, 2H), 3.64 (t, J = 7.9 Hz, 2H), 3.55 – 3.38 (m, 12H), 2.59 (t, J = 6.8 Hz, 2H), 2.43 (s, 3H), 2.32 – 1.82 (m, 6H), 1.62 – 1.37 (m, 6H), 1.35 – 1.19 (m, 6H), 0.92 (s, 9H). 1.43 (dt, J = 12.5, 7.3 Hz, 4H), 1.25 (d, J = 16.0 Hz, 4H), 0.93 (s, 9H). | following routes described for examples 97 and 320 |
| 331 | 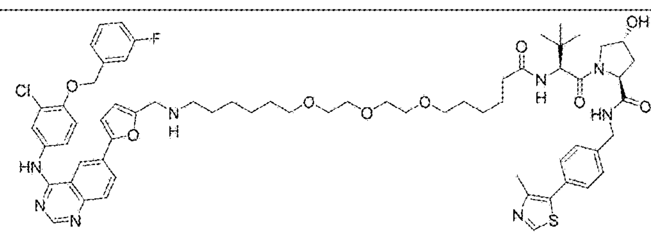 | (2S,4R)-1-((S)-23-(tert-butyl)-1-(5-(4-((3-chloro-4-((3-fluorobenzyl)oxy)phenyl)amino)quinazolin-6-yl)furan-2-yl)-21-oxo-9,12,15-trioxa- | 1189.51 | 1H NMR (400 MHz, DMSO-d6) δ 9.92 (s, 1H), 8.98 (s, 1H), 8.72 (s, 1H), 8.63 – 8.51 (m, 2H), 8.15 (d, J = 8.7 Hz, 1H), 8.01 (d, J = 2.5 Hz, 1H), 7.91 – 7.68 (m, 2H), 7.54 – 7.24 (m, 7H), 7.19 (t, J = 7.6 | following routes described for examples 97 and 320 |

FIG. 2 (continued)

| Example | Structure | Name | (M+H)+ | H¹-NMR | Synthesis |
|---|---|---|---|---|---|
| | | 2,22-diazatetracosan-24-oyl)-4-hydroxy-N-(4-(4-methylthiazol-5-yl)benzyl)pyrrolidine-2-carboxamide | | Hz, 1H), 7.04 (d, J = 3.1 Hz, 1H), 6.45 (d, J = 2.9 Hz, 1H), 5.27 (s, 2H), 5.13 (s, 1H), 4.57 – 4.15 (m, 6H), 3.80 (s, 2H), 3.64 (t, 1H), 3.51 – 3.34 (m, 12H), 2.56 (t, J = 6.9 Hz, 4H), 2.43 (s, 3H), 2.32 – 1.83 (m, 6H), 1.59 – 1.17 (m, 14H), 0.92 (s, 9H). | |
| 332 | 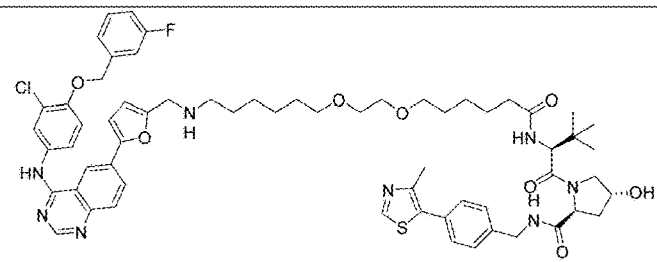 | (2S,4R)-1-((S)-20-(tert-butyl)-1-(5-(4-((3-chloro-4-((3-fluorobenzyl)oxy)phenyl)amino)quinazolin-6-yl)furan-2-yl)-18-oxo-9,12-dioxa-2,19-diazahenicosan-21-oyl)-4-hydroxy-N-(4-(4-methylthiazol-5-yl)benzyl)pyrrolidine-2-carboxamide | 1145.52 | 1H NMR (400 MHz, DMSO-d6) δ 9.91 (s, 1H), 8.98 (s, 1H), 8.72 (s, 1H), 8.62 – 8.47 (m, 2H), 8.15 (dd, J = 8.7, 1.7 Hz, 1H), 8.01 (d, J = 2.5 Hz, 1H), 7.88 – 7.69 (m, 3H), 7.55 – 7.24 (m, 7H), 7.18 (td, J = 8.7, 2.2 Hz, 1H), 7.04 (d, J = 3.2 Hz, 1H), 6.46 (d, J = 3.1 Hz, 1H), 5.27 (s, 2H), 5.12 (d, J = 2.9 Hz, 1H), 4.59 – 4.15 (m, 6H), 3.80 (s, 2H), 3.72 – 3.59 (m, 2H), 3.41 (s, 4H), 3.38 – 3.24 (m, 4H), 2.56 (t, J = 7.0 Hz, 2H), 2.44 (s, 3H), 2.32 – 1.83 (m, 6H), 1.56 – 1.36 (m, 8H), 1.36 – 1.16 (m, 6H), 0.92 (s, 9H). | following routes described for examples 97 and 320 |

FIG. 2 (continued)

| Example | Structure | Name | (M+H)⁺ | H¹-NMR | Synthesis |
|---|---|---|---|---|---|
| 333 | 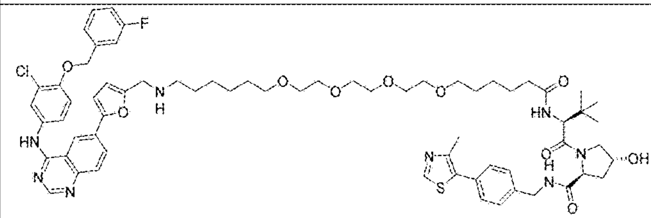 | (2S,4R)-1-((S)-26-(tert-butyl)-1-(5-(4-((3-fluorobenzyl)oxy)phenyl)amino)quinazolin-6-yl)furan-2-yl)-24-oxo-9,12,15,18-tetraoxa-2,25-diazaheptacosan-27-oyl)-4-hydroxy-N-(4-(4-methylthiazol-5-yl)benzyl)pyrrolidine-2-carboxamide | 1233.56 | 1H NMR (400 MHz, DMSO-d6) δ 9.91 (s, 1H), 8.97 (s, 1H), 8.72 (s, 1H), 8.60 – 8.51 (m, 1H), 8.15 (dd, J = 8.8, 1.7 Hz, 1H), 8.01 (d, J = 2.4 Hz, 1H), 7.90 – 7.68 (m, 3H), 7.53 – 7.25 (m, 7H), 7.18 (td, J = 8.5, 2.4 Hz, 1H), 7.04 (d, J = 3.2 Hz, 1H), 6.45 (d, J = 2.9 Hz, 1H), 5.27 (s, 2H), 5.16 – 5.08 (m, 1H), 4.60 – 4.15 (m, 6H), 3.80 (s, 2H), 3.71 – 3.59 (m, 2H), 3.54 – 3.32 (m, 16H), 2.56 (t, J = 7.1 Hz, 2H), 2.44 (s, 3H), 2.32 – 1.84 (m, 6H), 1.59 – 1.37 (m, 8H), 1.33 – 1.19 (m, 6H), 0.93 (s, 9H). | following routes described for examples 97 and 320 |
| 334 | 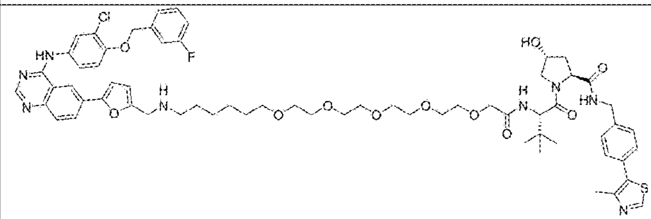 | (2S,4R)-1-((S)-25-(tert-butyl)-1-(5-(4-((3-fluorobenzyl)oxy)phenyl)amino)quinazolin-6-yl)furan-2-yl)-23-oxo-9,12,15,18,21-pentaoxa-2,24-diazahexacosan-26-oyl)-4-hydroxy-N-(4-(4-methylthiazol-5-yl)benzyl)pyrrolidine | 1221.52 | 1H NMR (400 MHz, DMSO-d6) δ 9.91 (s, 1H), 8.97 (s, 1H), 8.72 (s, 1H), 8.60 (t, J = 5.9 Hz, 1H), 8.54 (s, 1H), 8.19 – 8.11 (m, 1H), 8.01 (d, J = 2.4 Hz, 1H), 7.79 (d, J = 8.7 Hz, 1H), 7.74 (dd, J = 8.9, 2.4 Hz, 1H), 7.56 – 7.25 (m, 8H), 7.19 (t, J = 8.6 Hz, 1H), 7.04 (d, J = 3.2 Hz, 1H), 6.46 (d, J = 2.9 Hz, 1H), 5.27 (s, 2H), 5.16 (d, 1H), 4.56 (d, J = | following routes described for examples 97 and 320 |

FIG. 2 (continued)

| Example | Structure | Name | (M+H)⁺ | H¹-NMR | Synthesis |
|---|---|---|---|---|---|
| | | -2-carboxamide | | 9.5 Hz, 1H), 4.48 – 4.32 (m, 3H), 4.23 (dd, J = 15.8, 5.6 Hz, 1H), 3.95 (s, 2H), 3.80 (s, 2H), 3.70 – 3.23 (m, 20H), 2.56 (t, 2H), 2.43 (s, 3H), 2.11 – 2.00 (m, 1H), 1.93 – 1.85 (m, 1H), 1.52 – 1.35 (m, 4H), 1.34 – 1.15 (m, 4H), 0.93 (s, 9H). | |
| 335 | 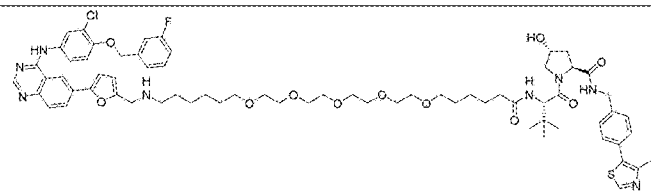 | (2S,4R)-1-((S)-29-(tert-butyl)-1-(5-(4-((3-chloro-4-((3-fluorobenzyl)oxy)phenyl)amino)quinazolin-6-yl)furan-2-yl)-27-oxo-9,12,15,18,21-pentaoxa-2,28-diazatriacontan-30-oyl)-4-hydroxy-N-(4-(4-methylthiazol-5-yl)benzyl)pyrrolidine-2-carboxamide | 1277.6 | 1H NMR (400 MHz, DMSO-d6) δ 9.92 (s, 1H), 8.98 (s, 1H), 8.75 (s, 1H), 8.63 – 8.49 (m, 2H), 8.16 (dd, J = 8.7, 1.7 Hz, 1H), 8.02 (d, J = 2.5 Hz, 1H), 7.87 – 7.71 (m, 3H), 7.55 – 7.24 (m, 8H), 7.18 (td, J = 8.7, 8.3, 2.3 Hz, 1H), 7.05 (d, J = 3.2 Hz, 1H), 6.49 (d, J = 2.9 Hz, 1H), 5.27 (s, 2H), 5.12 (s, 1H), 4.60 – 4.15 (m,7H), 3.85 (s, 2H), 3.72 – 3.59 (m, 2H), 3.53 – 3.32 (m, 20H), 2.60 (t, J = 7.0 Hz, 2H), 2.44 (s, 3H), 2.30 – 2.19 (m, 1H), 2.15 – 2.08 (m, 1H), 2.07 – 1.97 (m, 1H), 1.94 – 1.84 (m, 1H), 1.56 – 1.37 (m, 8H), 1.33 – 1.17 (m, 6H), 0.93 (s, 9H). | following routes described for examples 97 and 320 |

FIG. 2 (continued)

| Example | Structure | Name | (M+H)⁺ | H¹-NMR | Synthesis |
|---|---|---|---|---|---|
| 336 | 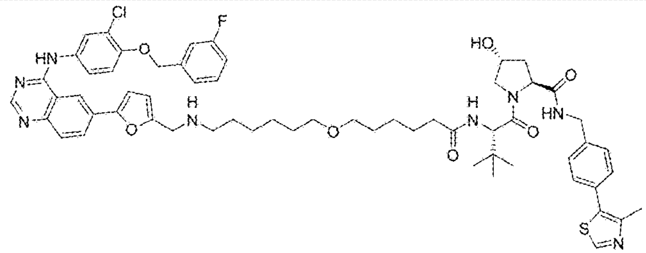 | (2S,4R)-1-((S)-2-(6-(((5-(4-((3-chloro-4-((3-fluorobenzyl)oxy)phenyl)amino)quinazolin-6-yl)furan-2-yl)methyl)amino)hexyl)oxy)hexanamido)-3,3-dimethylbutanoyl)-4-hydroxy-N-(4-(4-methylthiazol-5-yl)benzyl)pyrrolidine-2-carboxamide | 1101.5 | 1H NMR (400 MHz, DMSO-d6) δ 9.92 (s, 1H), 8.97 (s, 1H), 8.74 (s, 1H), 8.62 – 8.50 (m, 2H), 8.15 (dd, J = 8.8, 1.7 Hz, 1H), 8.01 (d, J = 2.4 Hz, 1H), 7.87 – 7.71 (m, 3H), 7.53 – 7.25 (m, 7H), 7.23 – 7.13 (m, 1H), 7.05 (d, J = 3.2 Hz, 1H), 6.48 (d, J = 3.0 Hz, 1H), 5.27 (s, 2H), 5.12 (s, 1H), 4.60 – 4.15 (m, 6H), 3.84 (s, 2H), 3.72 – 3.59 (m, 2H), 3.32 - 3.20 (m, 4H), 2.59 (t, J = 7.0 Hz, 2H), 2.44 (s, 3H), 2.29 – 2.20 (m, 1H), 2.14 – 1.98 (m, 2H), 1.94 – 1.85 (m, 1H), 1.58 – 1.37 (m, 8H), 1.35 – 1.16 (m, 6H), 0.92 (s, 9H). | following routes described for examples 97 and 320 |
| 337 | 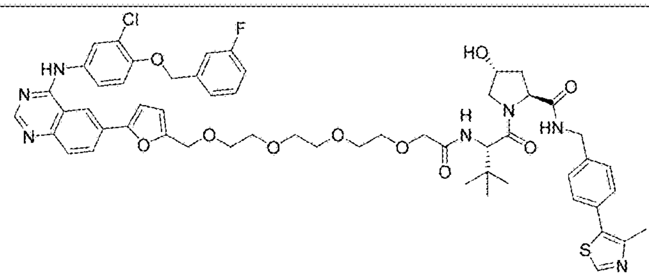 | (2S,4R)-1-((S)-15-(tert-butyl)-1-(5-(4-((3-chloro-4-((3-fluorobenzyl)oxy)phenyl)amino)quinazolin-6-yl)furan-2-yl)-13-oxo-2,5,8,11-tetraoxa-14-azahexadecan-16-oyl)-4-hydroxy-N-(4-(4-methylthiazol-5- | 1078.41 | 1H NMR (400 MHz, DMSO-d6) δ 9.97 (s, 1H), 8.96 (s, 1H), 8.76 (s, 1H), 8.61 – 8.52 (m, 2H), 8.16 (dd, J = 8.7, 1.8 Hz, 1H), 8.00 (d, J = 2.6 Hz, 1H), 7.80 (d, J = 8.7 Hz, 1H), 7.74 (dd, J = 9.0, 2.6 Hz, 1H), 7.56 – 7.25 (m, 9H), 7.18 (dd, 1H), 7.08 (d, J = 3.3 Hz, 1H), 6.64 (d, J = 3.3 Hz, 1H), 5.26 (s, 2H), 4.61 – | following routes described for examples 97 and 320 |

FIG. 2 (continued)

| Example | Structure | Name | (M+H)⁺ | H¹-NMR | Synthesis |
|---|---|---|---|---|---|
| 338 | 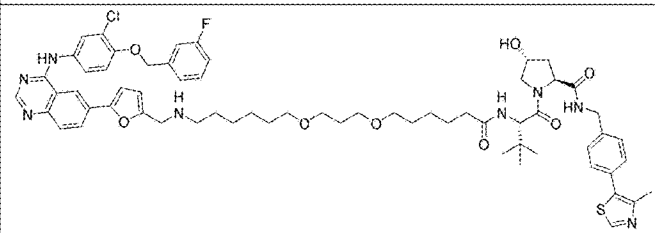 | yl)benzyl)pyrrolidine-2-carboxamide | | 4.49 (m, 3H), 4.48 – 4.17 (m, 5H), 3.94 (s, 2H), 3.70 – 3.48 (m, 14H), 2.43 (s, 3H), 2.14 – 1.80 (m, 2H), 0.92 (s, 9H). | following routes described for examples 97 and 320 |
| | | (2S,4R)-1-((S)-21-(tert-butyl)-1-(5-(4-((3-chloro-4-((3-fluorobenzyl)oxy)phenyl)amino)quinazolin-6-yl)furan-2-yl)-19-oxo-9,13-dioxa-2,20-diazadocosan-22-oyl)-4-hydroxy-N-(4-(4-methylthiazol-5-yl)benzyl)pyrrolidine-2-carboxamide | 1159.76 | 1H NMR (400 MHz, DMSO-d6) δ 9.91 (s, 1H), 8.98 (s, 1H), 8.75 (s, 1H), 8.62 – 8.49 (m, 2H), 8.16 (dd, 1H), 8.01 (d, J = 2.5 Hz, 1H), 7.87 – 7.72 (m, 3H), 7.55 – 7.24 (m, 7H), 7.22 – 7.14 (m, 1H), 7.05 (d, J = 3.2 Hz, 1H), 6.50 (d, 1H), 5.27 (s, 2H), 5.12 (s, 1H), 4.59 – 4.16 (m, 6H), 3.87 (s, 2H), 3.71 – 3.58 (m, 2H), 3.40 – 3.25 (m, 8H), 2.62 (t, 2H), 2.44 (s, 3H), 2.30 – 2.20 (m, 1H), 2.17 – 1.96 (m, 2H), 1.95 – 1.84 (m, 1H), 1.66 (p, J = 6.3 Hz, 2H), 1.58 – 1.38 (m, 6H), 1.35 – 1.17 (m, 8H), 0.93 (s, 9H). | |
| 339 | 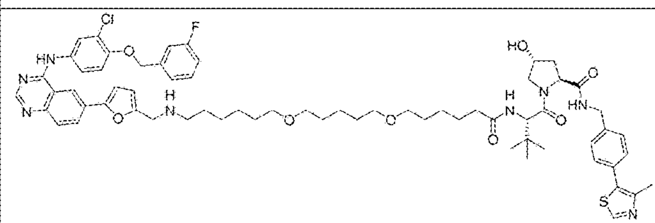 | (2S,4R)-1-((S)-23-(tert-butyl)-1-(5-(4-((3-chloro-4-((3-fluorobenzyl)oxy)phenyl)amino)quinazolin-6-yl)furan-2-yl)-21-oxo-9,15-dioxa-2,22- | 1187.6 | 1H NMR (400 MHz, DMSO-d6) δ 9.91 (s, 1H), 8.97 (s, 1H), 8.73 (s, 1H), 8.65 – 8.46 (m, 2H), 8.15 (d, J = 8.7 Hz, 1H), 8.01 (s, 1H), 7.86 – 7.70 (m, 3H), 7.56 – 7.24 (m, 8H), 7.18 (dt, J = 8.4, 4.7 Hz, 1H), | following routes described for examples 97 and 320 |

FIG. 2 (continued)

| Example | Structure | Name | (M+H)⁺ | H¹-NMR | Synthesis |
|---|---|---|---|---|---|
| | | diazatetracosan-24-oyl)-4-hydroxy-N-(4-(4-methylthiazol-5-yl)benzyl)pyrrolidine-2-carboxamide | | 7.04 (d, J = 3.3 Hz, 1H), 6.47 (d, J = 3.2 Hz, 1H), 5.27 (s, 2H), 5.12 (s, 1H), 4.57 – 4.17 (m, 6H), 3.82 (s, 2H), 3.71 – 3.59 (m, 2H), 3.32 – 3.22 (m, 8H), 2.58 (t, J = 7.0 Hz, 2H), 2.44 (s, 3H), 2.33 – 2.18 (m, 1H), 2.15 – 2.05 (m, 1H), 2.06 – 1.98 (m, 1H), 1.95 – 1.85 (m, 1H), 1.60 – 1.35 (m, 12H), 1.35 – 1.18 (m, 9H), 0.93 (s, 8H). | |
| 340 | 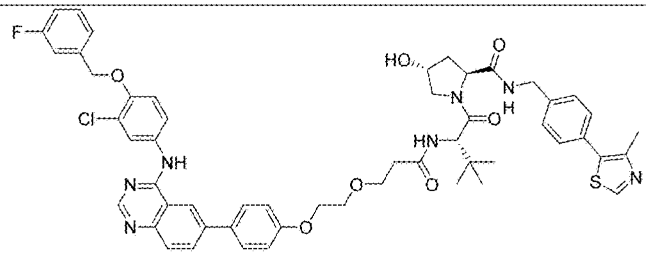 | (2S,4R)-1-((S)-2-(3-(2-(4-(4-((3-chloro-4-((3-fluorobenzyl)oxy)phenyl)amino)quinazolin-6-yl)phenoxy)ethoxy)propanamido)-3,3-dimethylbutanoyl)-4-hydroxy-N-(4-(4-methylthiazol-5-yl)benzyl)pyrrolidine-2-carboxamide | 1000.37 | 1H NMR (500 MHz, DMSO-d6) δ 9.88 (s, 1H), 8.96 (s, 1H), 8.73 (s, 1H), 8.56 (d, J = 7.2 Hz, 2H), 8.14 (dd, J = 8.7, 1.9 Hz, 1H), 8.03 (d, J = 2.5 Hz, 1H), 7.96 (d, J = 9.4 Hz, 1H), 7.82 (dd, J = 8.8, 2.1 Hz, 3H), 7.76 (dd, J = 8.9, 2.6 Hz, 1H), 7.56 – 7.23 (m, 8H), 7.22 – 7.14 (m, 1H), 7.11 (d, J = 8.8 Hz, 1H), 5.26 (s, 2H), 5.15 (d, J = 3.5 Hz, 1H), 4.58 (d, J = 9.4 Hz, 1H), 4.50 – 4.30 (m, 3H), 4.22 (dd, J = 15.8, 5.5 Hz, 1H), 4.16 (t, J = 4.7 Hz, 2H), 3.88 – 3.55 (m, 6H), 2.60 (dt, J = 14.0, 6.8 Hz, 1H), 2.43 (s, 3H), 2.48 – | following routes described for examples 97 and 320 |

FIG. 2 (continued)

| Example | Structure | Name | (M+H)+ | H1-NMR | Synthesis |
|---|---|---|---|---|---|
| 341 | 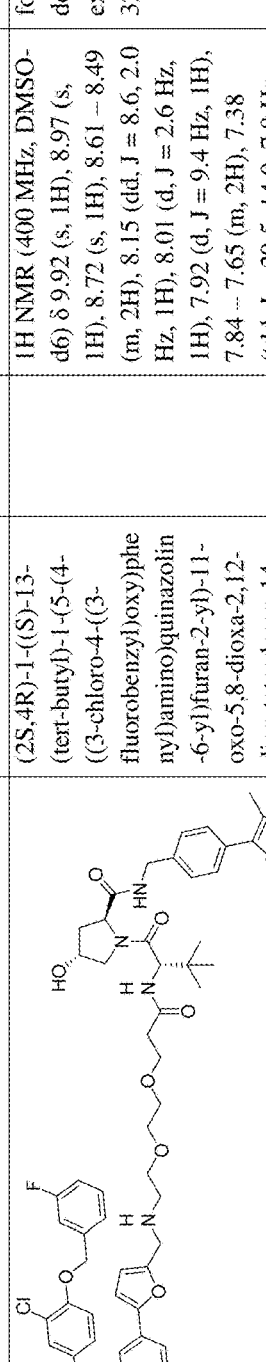 | (2S,4R)-1-((S)-13-(tert-butyl)-1-(5-(4-((3-chloro-4-((3-fluorobenzyl)oxy)phenyl)amino)quinazolin-6-yl)furan-2-yl)-11-oxo-5,8-dioxa-2,12-diazatetradecan-14-oyl)-4-hydroxy-N-(4-(4-methylthiazol-5-yl)benzyl)pyrrolidine-2-carboxamide | 1047.42 | 1H NMR (400 MHz, DMSO-d6) δ 9.92 (s, 1H), 8.97 (s, 1H), 8.72 (s, 1H), 8.61 – 8.49 (m, 2H), 8.15 (dd, J = 8.6, 2.0 Hz, 1H), 8.01 (d, J = 2.6 Hz, 1H), 7.92 (d, J = 9.4 Hz, 1H), 7.84 – 7.65 (m, 2H), 7.38 (tdd, J = 29.5, 14.0, 7.8 Hz, 8H), 7.19 (ddd, J = 10.2, 5.6, 2.1 Hz, 1H), 7.04 (d, J = 2.8 Hz, 1H), 6.47 (d, J = 2.6 Hz, 1H), 5.26 (s, 2H), 5.14 (s, 1H), 4.54 (d, J = 9.4 Hz, 1H), 4.49 – 4.09 (m, 5H), 3.84 (s, 2H), 3.72 – 3.40 (m, 10H), 2.73 (t, J = 5.8 Hz, 2H), 2.60 – 2.48 (m, 2H), 2.43 (s, 3H), 2.39 – 2.28 (m, 1H), 2.13 – 1.95 (m, 1H), 1.95 – 1.80 (m, 1H), 0.91 (s, 9H). | following routes described for examples 97 and 320 |

FIG. 2 (continued)

| Example | Structure | Name | (M+H)+ | H-NMR | Synthesis |
|---|---|---|---|---|---|
| 342 | 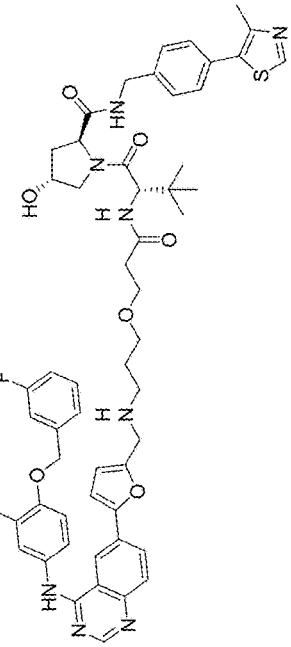 | (2S,4R)-1-((S)-2-(3-(3-(((5-(4-((3-chloro-4-((3-fluorobenzyl)oxy)phenyl)amino)quinazolin-6-yl)furan-2-yl)methyl)amino)propoxy)propanamido)-3,3-dimethylbutanoyl)-4-hydroxy-N-(4-(4-methylthiazol-5-yl)benzyl)pyrrolidine-2-carboxamide | 1017.39 | 1H NMR (600 MHz, Chloroform-d) δ 8.90 (s, 1H), 8.79 (s, 1H), 8.67 (s, 1H), 8.65 (s, 1H), 7.96 (d, J = 8.7 Hz, 1H), 7.85 (d, J = 8.7 Hz, 1H), 7.74 (d, J = 8.9 Hz, 1H), 7.70 (s, 1H), 7.43 – 7.15 (m, 7H), 7.02 (t, J = 8.4 Hz, 1H), 6.96 (d, J = 8.8 Hz, 2H), 6.53 (d, J = 2.6 Hz, 1H), 6.41 – 6.32 (m, 1H), 5.15 (s, 2H), 4.61 (t, J = 8.4 Hz, 1H), 4.55 – 4.40 (m, 2H), 4.32 – 4.19 (m, 1H), 3.99 – 3.87 (m, 2H), 3.72 (d, J = 14.1 Hz, 1H), 3.65 – 3.44 (m, 5H), 3.35 – 3.24 (m, 1H), 2.84 (dt, J = 12.1, 6.0 Hz, 1H), 2.73 (dt, J = 13.0, 5.9 Hz, 1H), 2.48 (s, 3H), 2.54 – 2.35 (m, 3H), 2.30 – 2.21 (m, 1H), 2.15 – 2.05 (m, 1H), 1.83 – 1.72 (m, 2H), 0.69 (s, 9H). | following routes described for examples 97 and 320 |

FIG. 2 (continued)

| Example | Structure | Name | (M+H)⁺ | H¹-NMR | Synthesis |
|---|---|---|---|---|---|
| 343 | 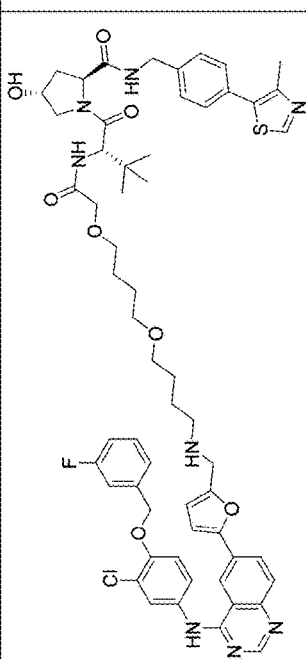 | (2S,4R)-1-((S)-16-(tert-butyl)-1-(5-(4-((3-chloro-4-((3-fluorobenzyl)oxy)phenyl)amino)quinazolin-6-yl)furan-2-yl)-14-oxo-7,12-dioxa-2,15-diazaheptadecan-17-oyl)-4-hydroxy-N-(4-(4-methylthiazol-5-yl)benzyl)pyrrolidine-2-carboxamide | 1089.45 | 1H NMR (400 MHz, DMSO-d6) δ 8.97 (s, 1H), 8.71 (s, 1H), 8.60 (t, J = 6.0 Hz, 1H), 8.54 (s, 1H), 8.15 (dd, J = 8.7, 1.8 Hz, 1H), 8.00 (d, J = 2.6 Hz, 1H), 7.83 – 7.68 (m, 2H), 7.55 – 7.23 (m, 8H), 7.18 (td, J = 8.8, 8.3, 2.9 Hz, 1H), 7.03 (d, J = 3.1 Hz, 1H), 6.44 (d, J = 3.0 Hz, 2H), 5.26 (s, 2H), 5.15 (d, J = 3.4 Hz, 1H), 4.65 – 4.17 (m, 6H), 3.90 (s, 2H), 3.78 (s, 2H), 3.70 – 3.54 (m, 2H), 3.45 (d, J = 6.4 Hz, 2H), 3.32 (s, 4H), 2.55 (t, J = 6.6 Hz, 2H), 2.43 (s, 3H), 2.10 – 2.00 (m, 1H), 1.95 – 1.84 (m, 1H), 1.63 – 1.38 (m, 8H), 0.93 (s, 9H). | following routes described for examples 97 and 320 |
| 344 | 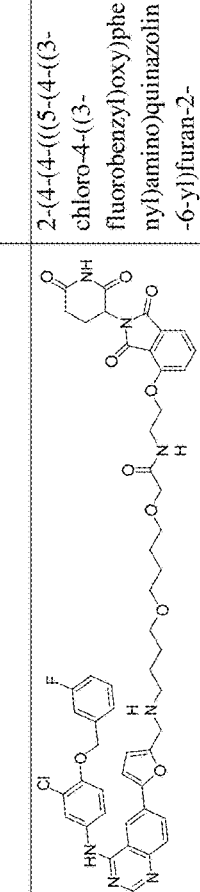 | 2-(4-(4-((5-(4-((3-chloro-4-((3-fluorobenzyl)oxy)phenyl)amino)quinazolin-6-yl)furan-2-yl)methyl)amino)butoxy)butoxy)-N-(2-((2,6-dioxopiperidin-3-yl)-1,3-dioxoisoindolin-4-yl)oxy)ethyl)acetamide | 976.35 | 1H NMR (500 MHz, DMSO-d6) δ 9.89 (s, 1H), 8.71 (s, 1H), 8.54 (s, 1H), 8.15 (dd, J = 8.7, 1.8 Hz, 1H), 8.00 (d, J = 2.6 Hz, 1H), 7.85 – 7.69 (m, 3H), 7.53 (d, J = 8.5 Hz, 1H), 7.51 – 7.39 (m, 2H), 7.40 – 7.25 (m, 3H), 7.24 – 7.13 (m, 1H), 7.03 (d, J = 3.3 Hz, 1H), 6.44 (d, J = 3.3 Hz, 1H), 5.26 (s, 2H), 5.07 (dd, J | following route described for examples 320 and 349 |

FIG. 2 (continued)

| Example | Structure | Name | (M+H)⁺ | H¹-NMR | Synthesis |
|---|---|---|---|---|---|
| 345 | 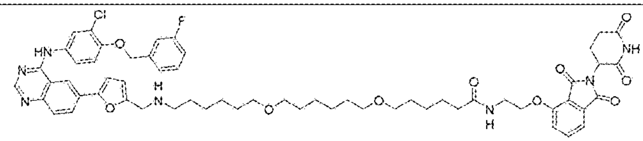 | 6-((6-((6-(((5-(4-((3-chloro-4-((3-fluorobenzyl)oxy)phenyl)amino)quinazolin-6-yl)furan-2-yl)methyl)amino)hexyl)oxy)hexyl)oxy)-N-(2-(2-(2,6-dioxopiperidin-3-yl)-1,3-dioxoisoindolin-4-yl)oxy)ethyl)hexanamide | 1088.48 | 1H NMR (400 MHz, DMSO-d6) δ 9.90 (s, 1H), 8.72 (s, 1H), 8.54 (s, 1H), 8.14 (d, J = 10.0 Hz, 1H), 7.88 – 7.66 (m, 3H), 7.59 – 7.39 (m, 3H), 7.37 – 7.24 (m, 3H), 7.18 (td, J = 8.7, 8.3, 2.8 Hz, 1H), 7.03 (d, J = 3.2 Hz, 1H), 6.45 (d, J = 3.2 Hz, 1H), 5.26 (s, 2H), 5.08 (dd, J = 12.8, 5.4 Hz, 1H), 4.23 (t, J = 5.8 Hz, 2H), 3.79 (s, 2H), 3.56 – 3.10 (m, 10H), 2.97 – 2.76 (m, 1H), 2.65 – 2.43 (m, 4H), 2.13 – 1.92 (m, 3H), 1.66 – 1.34 (m, 12H), 1.34 – 1.06 (m, 10H). | following route described for examples 320 and 349 |
| | | = 12.8, 5.5 Hz, 1H), 4.26 (t, J = 6.1 Hz, 2H), 3.83 (s, 2H), 3.78 (s, 2H), 3.52 (q, J = 6.1 Hz, 2H), 3.41 (t, J = 6.3 Hz, 2H), 3.36 – 3.21 (m, 6H), 2.88 (ddd, J = 16.9, 13.9, 5.4 Hz, 1H), 2.69 – 2.44 (m, 3H), 2.01 (dtd, J = 13.2, 5.5, 2.4 Hz, 1H), 1.65 – 1.35 (m, 8H). | | | |
| 346 | 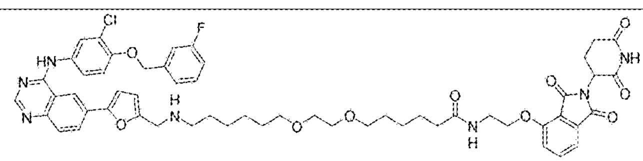 | 6-(2-((6-(((5-(4-((3-chloro-4-((3-fluorobenzyl)oxy)phenyl)amino)quinazolin | 1032.42 | 1H NMR (400 MHz, DMSO-d6) δ 11.09 (s, 1H), 9.90 (s, 1H), 8.71 (s, 1H), 8.54 (s, 1H), 8.15 (dd, J = 8.8, 1.6 Hz, | following route described for examples 320 and 349 |

FIG. 2 (continued)

| Example | Structure | Name | (M+H)+ | H¹-NMR | Synthesis |
|---|---|---|---|---|---|
| | | -6-yl)furan-2-yl)methyl)amino)hex yl)oxy)ethoxy)-N-(2-((2-(2,6-dioxopiperidin-3-yl)-1,3-dioxoisoindolin-4-yl)oxy)ethyl)hexanamide | | 2H), 8.01 (t, J = 4.0 Hz, 2H), 7.86 – 7.67 (m, 3H), 7.59 – 7.40 (m, 3H), 7.37 – 7.25 (m, 3H), 7.23 – 7.13 (m, 1H), 7.03 (d, J = 3.2 Hz, 1H), 6.45 (d, J = 3.2 Hz, 1H), 5.31 – 5.20 (m, 3H), 5.26 (s, 2H), 5.08 (dd, J = 12.8, 5.4 Hz, 1H), 4.22 (t, J = 5.8 Hz, 2H), 3.79 (s, 2H), 3.56 – 3.21 (m, 12H), 2.96 – 2.77 (m, 1H), 2.67 – 2.38 (m, 4H), 2.12 – 1.94 (m, 4H), 1.45 (tt, J = 14.5, 7.0 Hz, 8H), 1.36 – 1.08 (m, 6H). | |
| 347 | 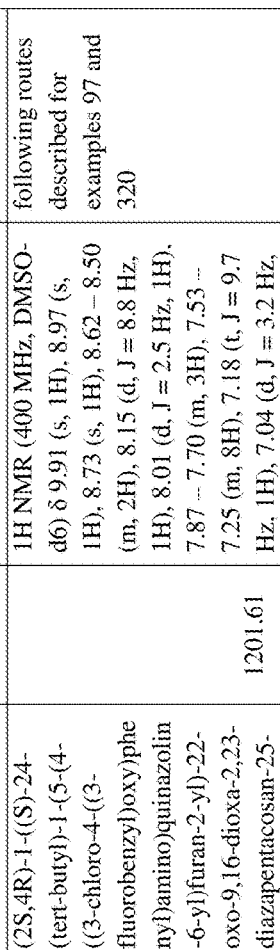 | (2S,4R)-1-((S)-24-(tert-butyl)-1-(5-(4-((3-chloro-4-((3-fluorobenzyl)oxy)phenyl)amino)quinazolin-6-yl)furan-2-yl)-22-oxo-9,16-dioxa-2,23-diazapentacosan-25-oyl)-4-hydroxy-N-(4-(4-methylthiazol-5-yl)benzyl)pyrrolidine-2-carboxamide | 1201.61 | 1H NMR (400 MHz, DMSO-d6) δ 9.91 (s, 1H), 8.97 (s, 1H), 8.73 (s, 1H), 8.62 – 8.50 (m, 2H), 8.15 (d, J = 8.8 Hz, 1H), 8.01 (d, J = 2.5 Hz, 1H), 7.87 – 7.70 (m, 3H), 7.53 – 7.25 (m, 8H), 7.18 (t, J = 9.7 Hz, 1H), 7.04 (d, J = 3.2 Hz, 1H), 6.46 (d, J = 3.1 Hz, 1H), 5.26 (s, 2H), 5.12 (s, 1H), 4.62 – 4.13 (m, 6H), 3.81 (s, 2H), 3.71 – 3.59 (m, 2H), 3.31 – 3.17 (m, 8H), 2.57 (t, J = 7.0 Hz, 2H), 2.44 (s, 3H), 2.25 (dt, J = 14.8, 7.6 Hz, | following routes described for examples 97 and 320 |

| Example | Structure | Name | (M+H)⁺ | H¹-NMR | Synthesis |
|---|---|---|---|---|---|
| 348 | 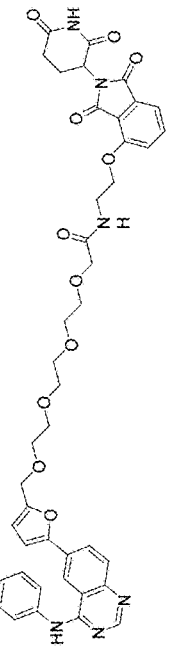 | 1-(5-(4-((3-chloro-4-((3-fluorobenzyl)oxy)phenyl)amino)quinazolin-6-yl)furan-2-yl)-N-(2-((2-(2,6-dioxopiperidin-3-yl)-1,3-dioxoisoindolin-4-yl)oxy)ethyl)-2,5,8,11-tetraoxatridecan-13-amide | 965.3 | 1H), 2.15 – 1.97 (m, 2H), 1.95 – 1.85 (m, 1H), 1.60 – 1.35 (m, 12H), 1.35 – 1.15 (m, 10H), 0.93 (s, 9H). 1H NMR (400 MHz, DMSO-d6) δ 11.44 (s, 1H), 11.09 (s, 1H), 9.04 (s, 1H), 8.86 (s, 1H), 8.36 (d, J = 8.5 Hz, 1H), 8.04 – 7.61 (m, 5H), 7.57 – 7.10 (m, 7H), 6.68 (d, J = 3.3 Hz, 1H), 5.31 (s, 2H), 5.07 (dd, J = 12.7, 5.3 Hz, 1H). 4.54 (s, 2H), 4.25 (t, J = 5.9 Hz, 2H), 3.88 (s, 2H), 3.69 – 3.36 (m, 14H), 2.87 (ddd, J = 17.7, 13.6, 5.2 Hz, 1H), 2.67 – 2.40 (m, 2H), 2.01 (ddd, J = 11.7, 6.6, 3.8 Hz, 1H). | following route described for examples 320 and 349 |
| 349 | 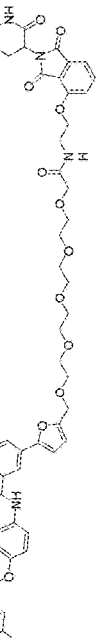 | 1-(5-(4-((3-chloro-4-((3-fluorobenzyl)oxy)phenyl)amino)quinazolin-6-yl)furan-2-yl)-N-(2-((2-(2,6-dioxopiperidin-3-yl)-1,3-dioxoisoindolin-4-yl)oxy)ethyl)-2,5,8,11,14-pentaoxahexadecan- | 1009.32 | 1H NMR (400 MHz, DMSO-d6) δ 10.27 (s, 1H), 9.14 (s, 1H), 7.93 (s, 1H), 7.72 (s, 1H), 7.34 (dd, J = 8.8, 1.7 Hz, 1H), 7.18 (d, J = 2.6 Hz. 1H), 7.08 – 6.87 (m, 4H), 6.76 – 6.56 (m, 3H), 6.56 – 6.42 (m, 3H), 6.36 (td, J = 8.8, 2.3 Hz, 1H), 6.26 (d, J = 3.3 Hz, 1H), 5.82 (d, J = 3.3 Hz, 1H), 4.44 (s, 2H), 4.25 (dd, J = 12.7, 5.4 | Synthesis of example 349 as described |

| Example | Structure | Name | (M+H)⁺ | H¹-NMR | Synthesis |
|---|---|---|---|---|---|
| | | 16-amide | | Hz, 1H), 3.71 (s, 2H), 3.43 (t, J = 6.0 Hz, 2H), 2.87 – 2.58 (m, 16H), 2.12 – 1.99 (m, 1H), 1.80 – 1.60 (m, 2H), 1.23 – 1.13 (m, 1H). | |
| 350 | 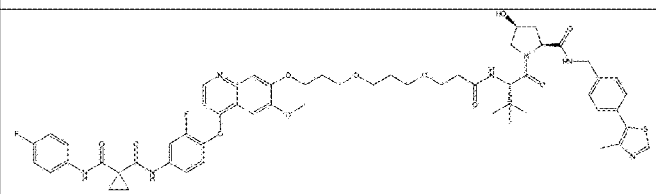 | N-(3-fluoro-4-(7-(3-(3-((S)-1-((2S,4S)-4-hydroxy-2-(4-(4-methylthiazol-5-yl)benzylcarbamoyl)pyrrolidin-1-yl)-3,3-dimethyl-1-oxobutan-2-ylamino)-3-oxopropoxy)propoxy)propoxy)-6-methoxyquinolin-4-yloxy)phenyl)-N-(4-fluorophenyl)cyclopropane-1,1-dicarboxamide | 1106.45 | 1H NMR (500 MHz, DMSO-d6) δ 10.38 (s, 1H), 10.00 (s, 1H), 8.97 (s, 1H), 8.56 (t, J = 6.1 Hz, 1H), 8.46 (d, J = 5.2 Hz, 1H), 7.96 – 7.85 (m, 2H), 7.69 – 7.59 (m, 2H), 7.51 (d, J = 8.8 Hz, 2H), 7.45 – 7.33 (m, 5H), 7.15 (t, J = 8.9 Hz, 2H), 6.41 (d, J = 5.1 Hz, 1H), 5.12 (d, J = 3.3 Hz, 1H), 4.55 (d, J = 9.4 Hz, 1H), 4.43 (ddd, J = 10.9, 6.7, 3.3 Hz, 2H), 4.27 – 4.16 (m, 3H), 3.94 (s, 3H), 3.76 – 3.33 (m, 10H), 2.58 – 2.51 (m, 1H), 2.43 (s, 3H), 2.35 – 2.25 (m, 1H), 2.03 (p, J = 5.7 Hz, 3H), 1.95 – 1.83 (m, 1H), 1.72 (p, J = 6.4 Hz, 2H), 1.48 (d, J = 3.9 Hz, 4H), 0.92 (s, 9H). 13C NMR (126 MHz, DMSO-d6) δ 171.89, 169.97, 169.51, 168.26, 167.88, 159.31, 159.22, 157.31, 154.21, 152.26, 151.90, 151.39, | Synthesis of example 350 as described |

FIG. 2 (continued)

| Example | Structure | Name | (M+H)+ | H1-NMR | Synthesis |
|---|---|---|---|---|---|
| | | | | 149.56, 148.75, 147.69, 146.29, 139.47, 138.01, 137.94, 135.70, 135.60, 135.17, 135.15, 131.13, 129.61, 128.81, 128.61, 127.40, 123.77, 122.46, 122.40, 116.90, 115.09, 114.92, 114.47, 109.53, 109.05, 108.87, 108.45, 101.94, 99.03, 68.85, 67.16, 67.09, 66.62, 66.54, 65.47, 58.69, 56.35, 56.24, 55.77, 41.64, 37.92, 35.69, 35.36, 31.87, 29.60, 28.89, 26.28, 15.91, 15.31. | |
| 351 | 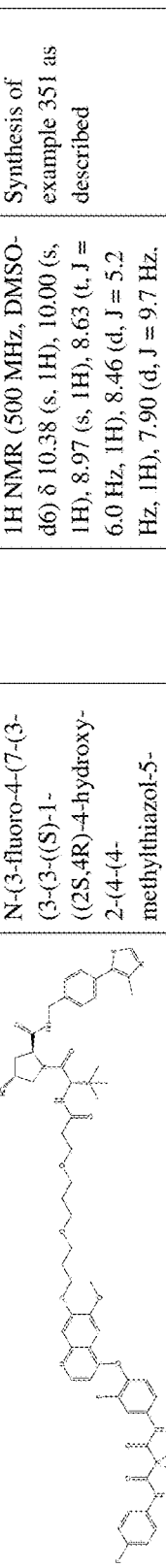 | N-(3-fluoro-4-(7-(3-(3-((S)-1-((2S,4R)-4-hydroxy-2-(4-(4-methylthiazol-5-yl)benzylcarbamoyl)pyrrolidin-1-yl)-3,3-dimethyl-1-oxobutan-2-ylamino)-3-oxopropoxy)propoxy)propoxy)-6-methoxyquinolin-4-yloxy)phenyl)-N-(4-fluorophenyl)cyclopropane-1,1- | 1106.50 | 1H NMR (500 MHz, DMSO-d6) δ 10.38 (s, 1H), 10.00 (s, 1H), 8.97 (s, 1H), 8.63 (t, J = 6.0 Hz, 1H), 8.46 (d, J = 5.2 Hz, 1H), 7.90 (d, J = 9.7 Hz, 2H), 7.71 – 7.57 (m, 2H), 7.51 (d, J = 8.7 Hz, 2H), 7.44 – 7.28 (m, 5H), 7.15 (t, J = 8.9 Hz, 2H), 6.41 (d, J = 5.1 Hz, 1H), 5.43 (d, J = 7.2 Hz, 1H), 4.56 – 4.38 (m, 2H), 4.36 (dd, J = 8.6, 6.1 Hz, 1H), 4.32 – 4.13 (m, 4H), 3.94 (s, 3H), 3.97 – 3.82 (m, 1H), 3.64 – 3.46 (m, 4H), 3.48 – | Synthesis of example 351 as described |

FIG. 2 (continued)

| Example | Structure | Name | (M+H)⁺ | H¹-NMR | Synthesis |
|---|---|---|---|---|---|
| | | dicarboxamide | | 3.35 (m, 4H), 2.57 – 2.45 (m, 2H), 2.43 (s, 3H), 2.36 – 2.26 (m, 2H), 2.03 (p, J = 6.3 Hz, 2H), 1.73 (dp, J = 13.0, 6.2 Hz, 3H), 1.55 – 1.38 (m, 4H), 0.93 (s, 9H). 13C NMR (126 MHz, DMSO-d6) δ 171.89, 169.97, 169.51, 168.26, 167.88, 159.31, 159.22, 157.31, 154.21, 152.26, 151.90, 151.39, 149.56, 148.75, 147.69, 146.29, 139.47, 138.01, 137.94, 135.70, 135.60, 135.17, 135.15, 131.13, 129.61, 128.81, 128.61, 127.40, 123.77, 122.46, 122.40, 116.90, 115.09, 114.92, 114.47, 109.53, 109.05, 108.87, 108.45, 101.94, 99.03, 68.85, 67.16, 67.09, 66.62, 66.54, 65.47, 58.69, 56.35, 56.24, 55.77, 41.64, 37.92, 35.69, 35.36, 31.87, 29.60, 28.89, 26.28, 15.91, 15.31. | |

FIG. 4G
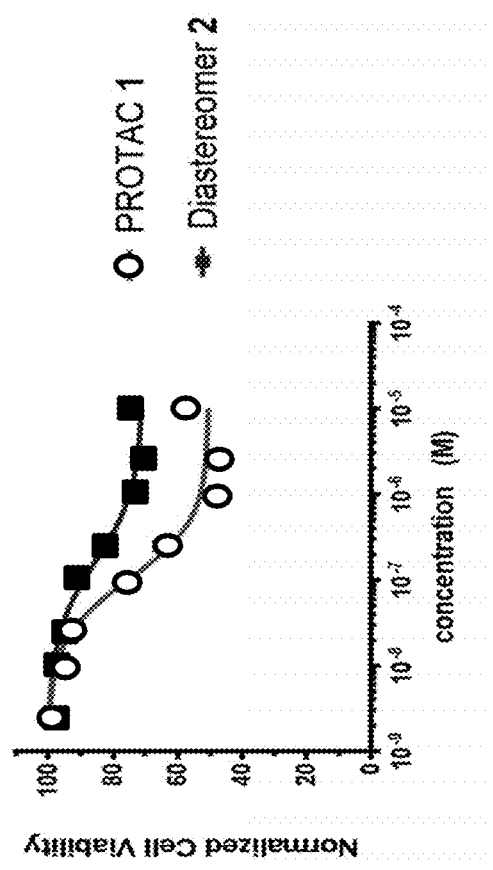
FIG. 5A
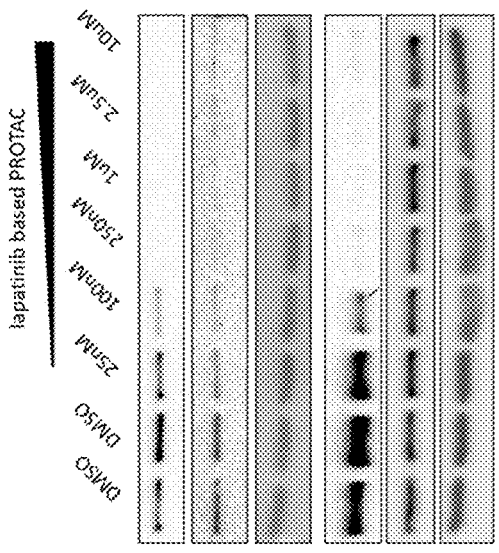
FIG. 5B

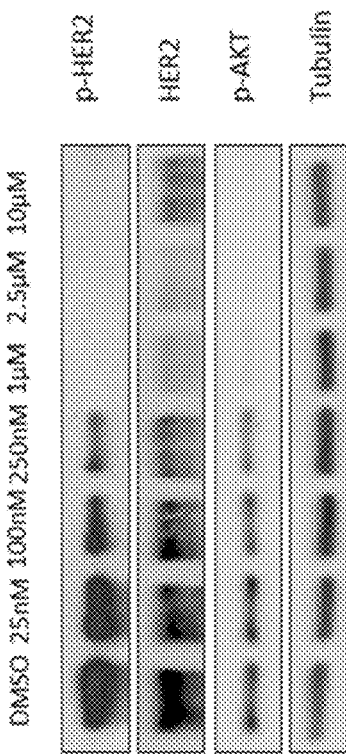
FIG. 6B
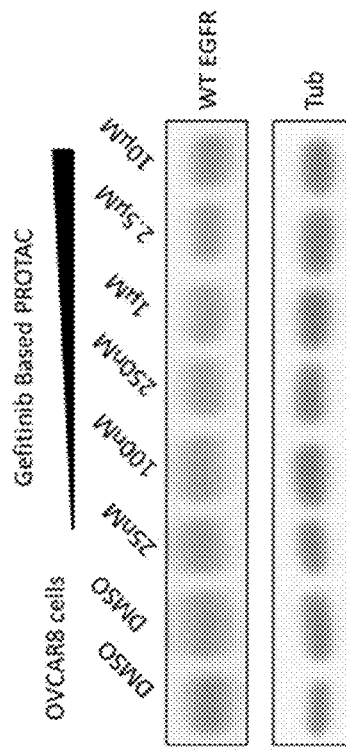
FIG. 6A
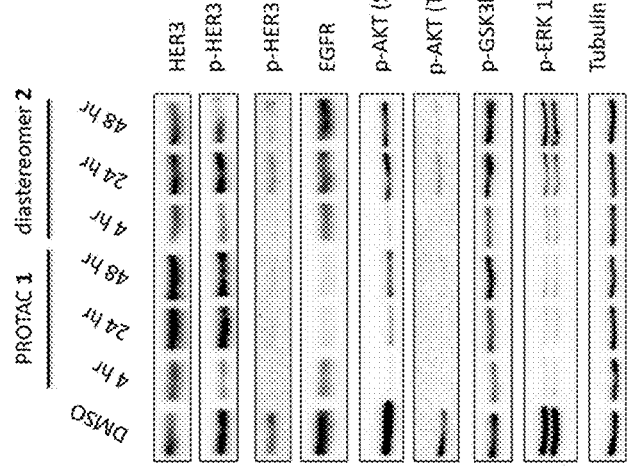
FIG. 5D
FIG. 5C

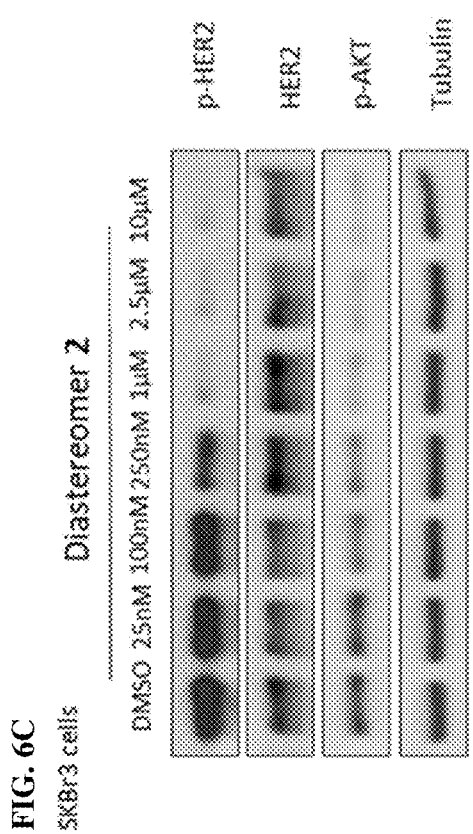
FIG. 6C
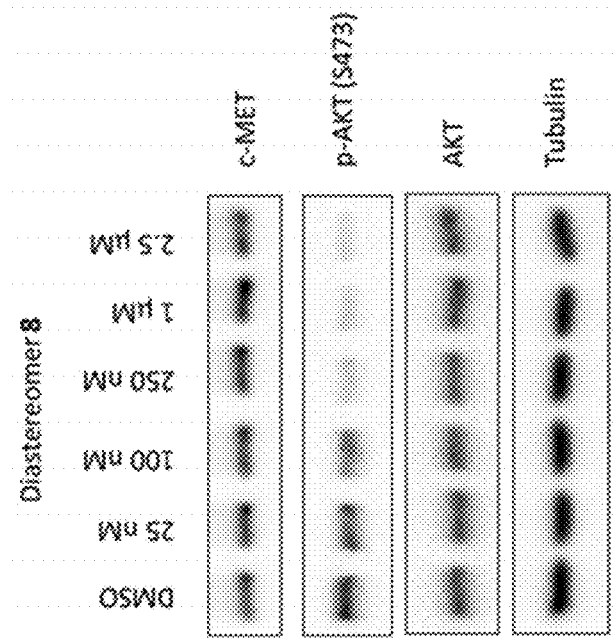
FIG. 7B
FIG. 7A

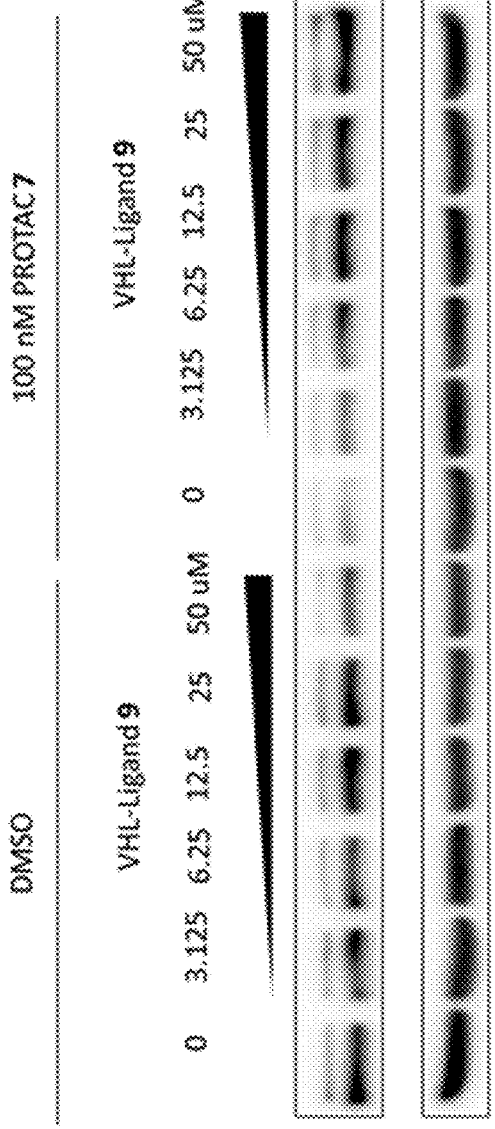
FIG. 7E
FIG. 7F
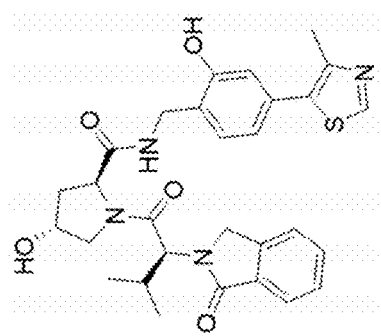
FIG. 8A
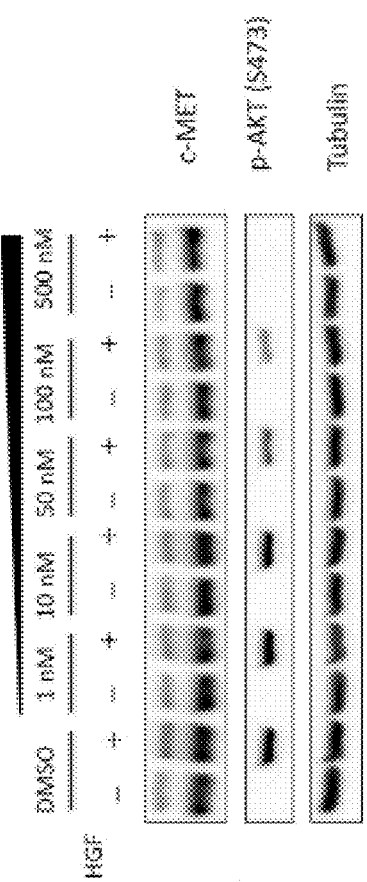
FIG. 8B
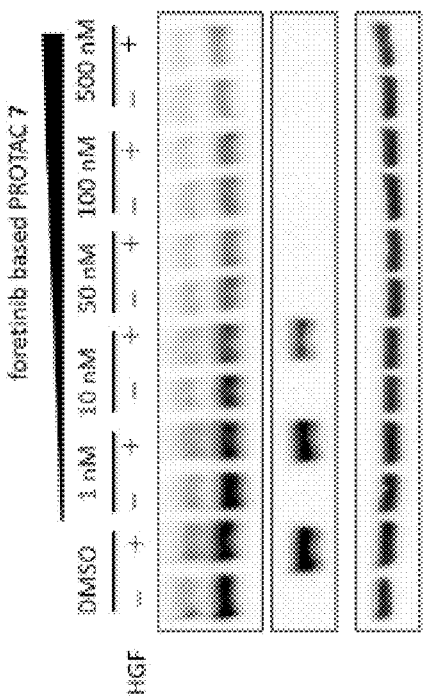

FIG. 10B
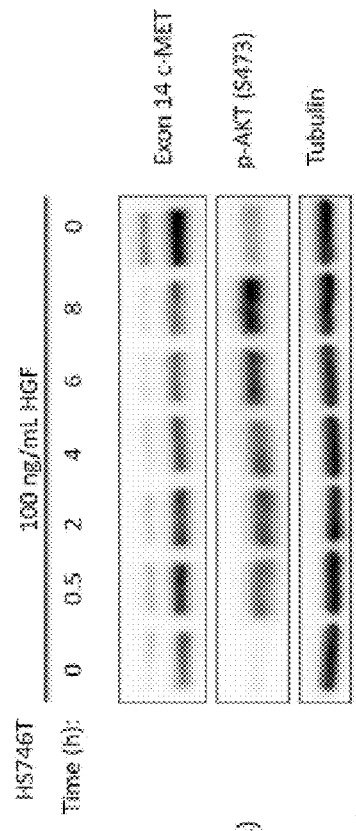
FIG. 10D
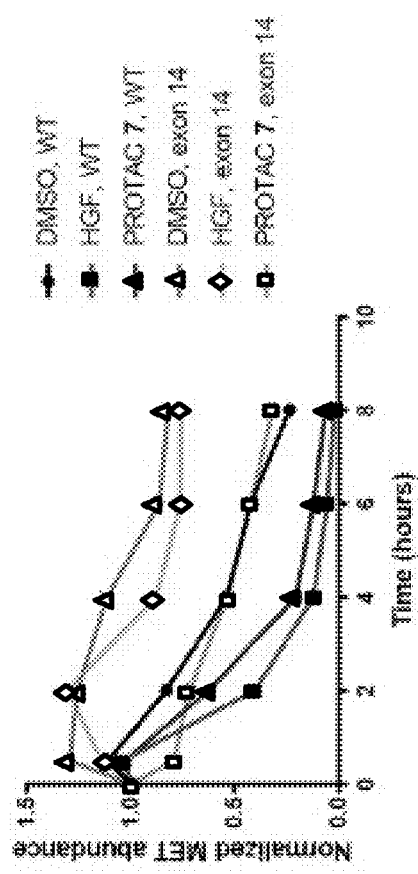
FIG. 10A
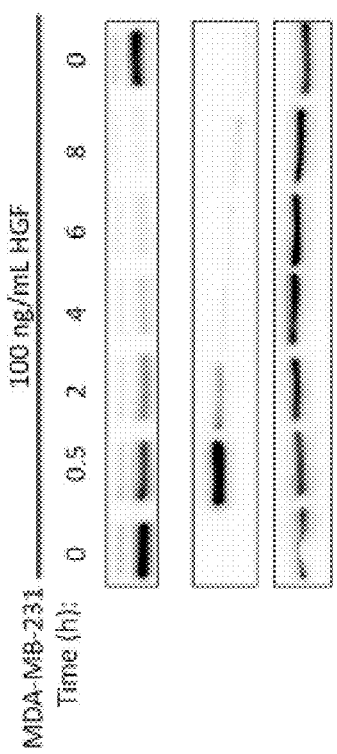
FIG. 10C

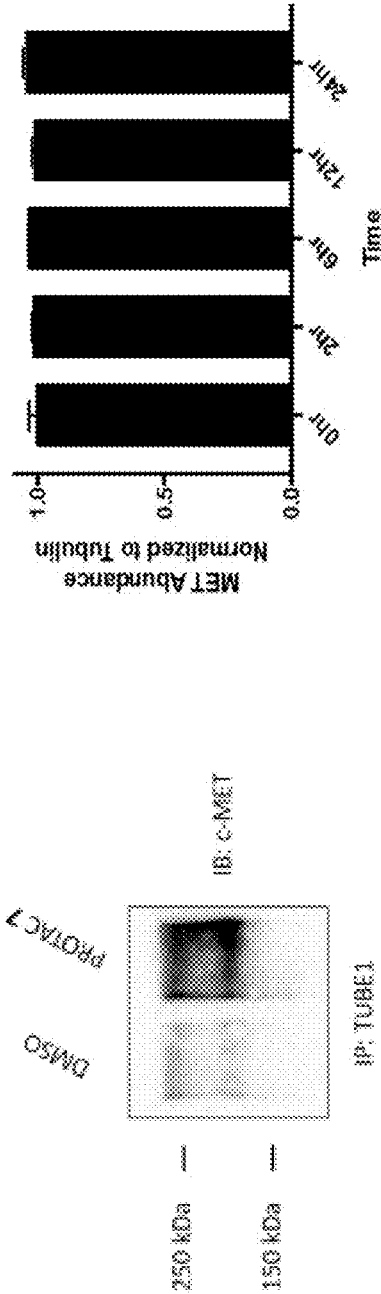
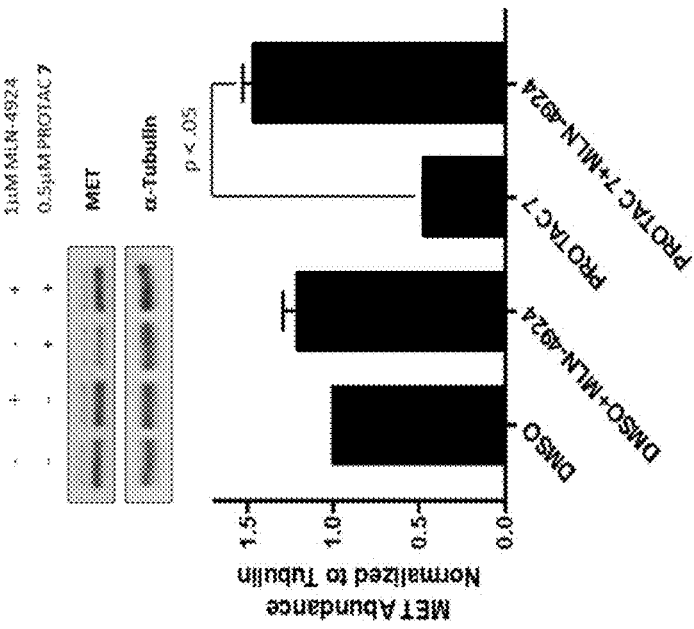
FIG. 10I
FIG. 11A
FIG. 11B
FIG. 11C

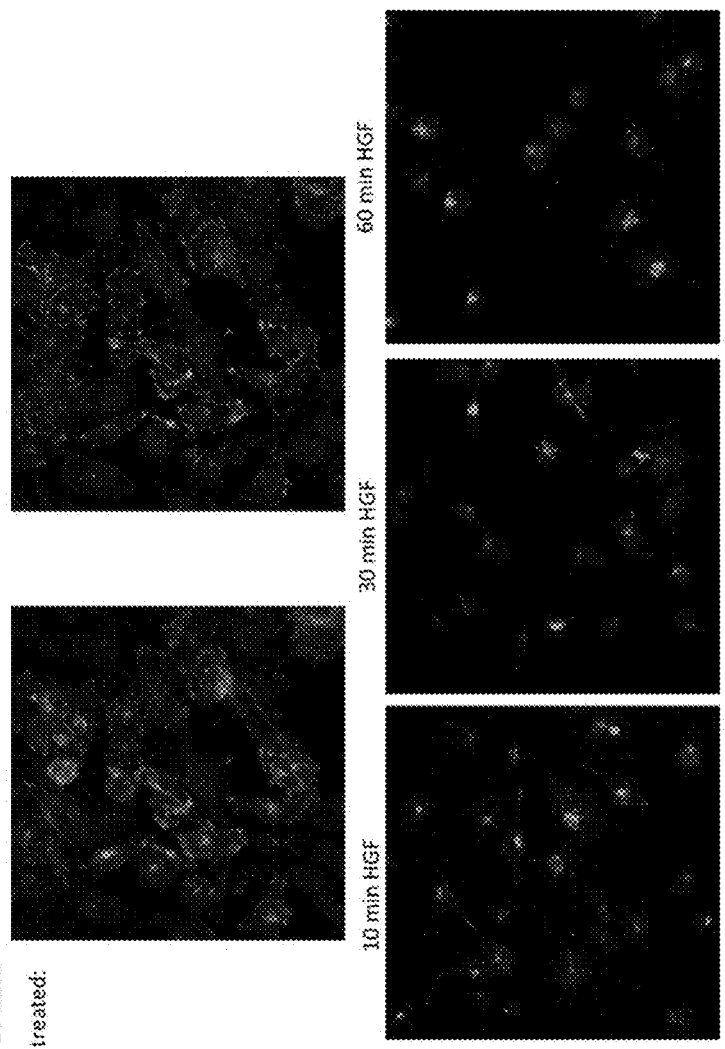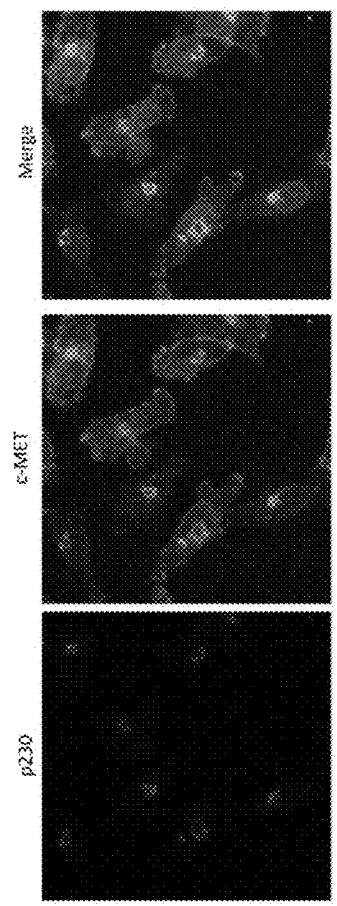
FIG. 12A
FIG. 12C

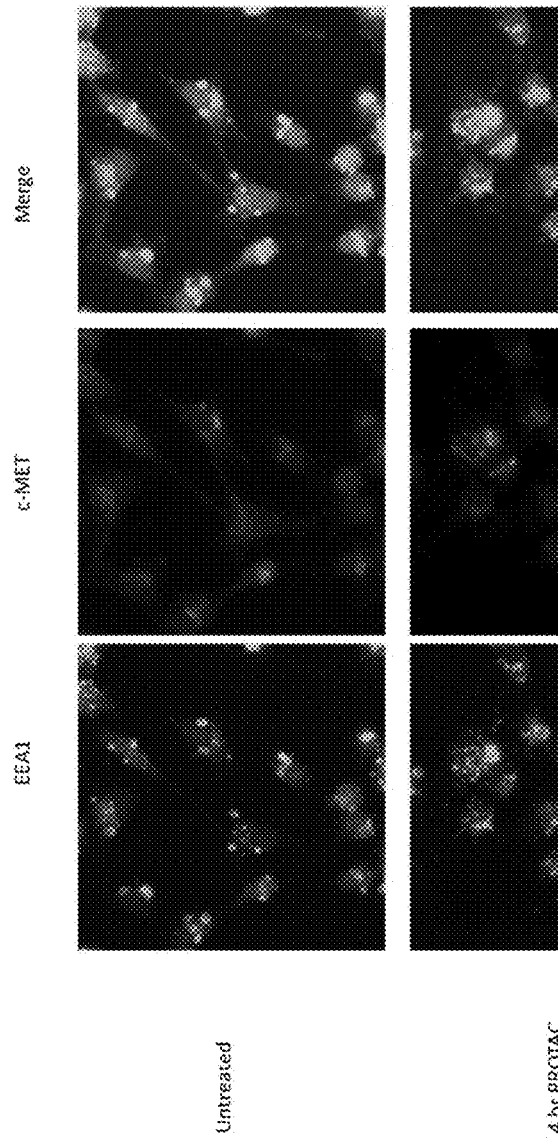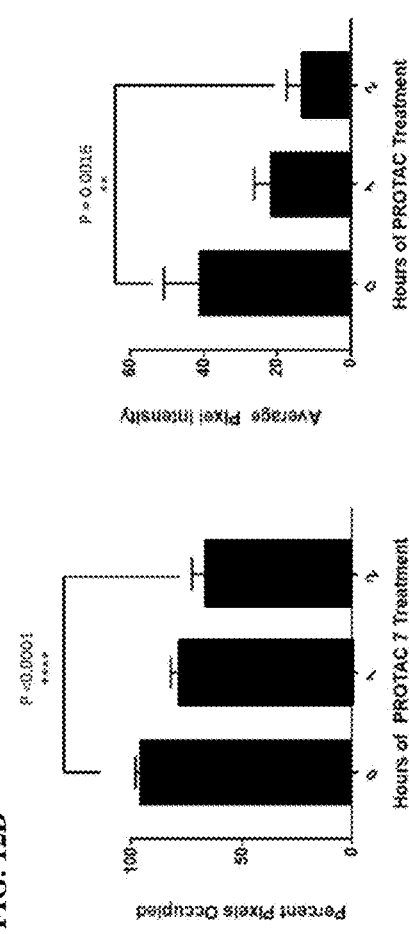
FIG. 12B
FIG. 12D

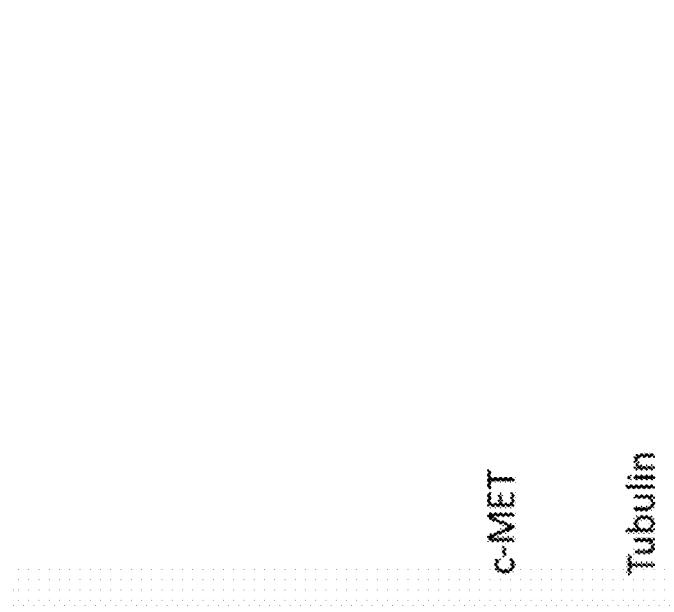
FIG. 13D
FIG. 13E
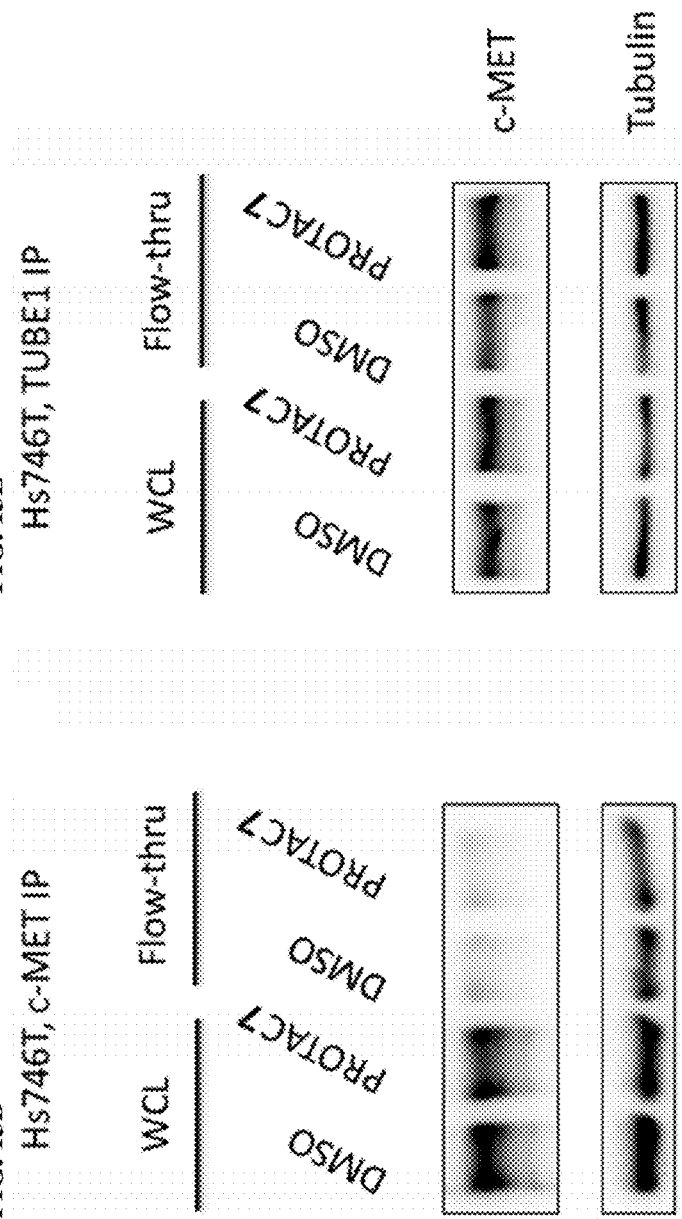
FIG. 15A
| Compound # | HER1 % Deg @ 1uM | HER2 % Deg @ 1 uM | Linker Atoms | Length | Linker Nature | E3 Ub ligase |
|---|---|---|---|---|---|---|
| SJF-1-124 | 70% | 10% | 19 | 21.77 | O-6-Alkyl-3PEG-Acetyl | VHL |
| SJF-1-135 | 65% | 30% | 13 | 14.46 | N-3PEG-O-Propionyl | VHL |
| SJF-1-142 | 40% | 35% | 15 | 16.8 | N-4PEG-O-Acetyl | VHL |
| SJF-1-145 | 65% | 15% | 16 | 18.26 | N-6Alkyl-2PEG-O-Acetyl | VHL |
| SJF-1-150 | 30% | 5% | 22 | 25.39 | N-6Alkyl-4PEG-O-Acetyl | VHL |
| SJF-1-154 | 10% | 0% | 19 | 21.82 | N-6Alkyl-3PEG-O-Acetyl | VHL |
| SJF-77714 | 35% | 0% | 19 | 22.02 | N-6Alkyl-2PEG-O-Pentanoyl | VHL |
| SJF-77174 | 70% | 10% | 20 | 23.27 | N-6Alkyl-2PEG-O-Hexanoyl | VHL |
| SJF-7724 | 80% | 0% | 17 | 19.7 | N-6Alkyl-O-PEG-O-Hexanoyl | VHL |

SJF-8272 (compound 321)
SJF-110 (compound 320)
SJF-7785 (compound 337)

EGFR PROTEOLYSIS TARGETING CHIMERIC MOLECULES AND ASSOCIATED METHODS OF USE

CROSS-REFERENCE TO RELATED APPLICATIONS

The present application claims priority to U.S. Provisional Patent Application Ser. No. 62/438,901, titled: EGFR Proteolysis Targeting Chimeric Molecules and Associated Methods of Use, filed 23 Dec. 2016, and U.S. Provisional Patent Application Ser. No. 62/563,494, titled: EGFR Proteolysis Targeting Chimeric Molecules and Associated Methods of Use, filed 26 Sep. 2017, which are incorporated by reference herein in their entirety.

STATEMENT OF FEDERAL SUPPORT

This invention was made with government support under grant number: R35CA197589 from the National Institutes of Health. The government has certain rights in the invention.

FIELD

The description provides bifunctional compounds comprising a target protein binding moiety and a E3 ubiquitin ligase binding moiety, and associated methods of use. The bifunctional compounds are useful as modulators of ubiquitination and subsequent degradation of targeted polypeptides, in particular EGFR, which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1a, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death.

The discovery of small molecule receptor tyrosine kinase (RTK) inhibitors greatly enabled the study of these key proteins in normal and oncogenic signalling. Eukaryotic cell proliferation is driven by RTK activation following binding of cognate growth factors, and many forms of cancer are driven by the hyperactivation of specific RTKs due either to overexpression of the protein to super-physiological levels, or to mutations that confer growth factor-independent activation. For example, epidermal growth factor receptor (EGFR) is implicated in cancers and inflammatory diseases. Activated EGFR elicits downstream activation and signaling by several other proteins leading to DNA synthesis and cell proliferation.

In order to obtain RTK inhibition over an extended time, exposure to small molecule kinase inhibitors at sustained and saturating concentrations is required. Studies have shown that cancerous cells can co-opt other existing RTK signalling pathways in order to permit the inhibited RTK to continue to exist as a node, thereby restoring downstream oncogenic signalling.

Degradation of the RTK, as opposed to inhibition of the kinase activity, is a strategy with the potential to yield a more complete and lasting inactivation of downstream signalling and circumvent the problem of "kinome re-wiring", whereby inhibition of receptor signalling leads to compensatory feedback activation via alternate kinases. Indeed, RTK elimination would prevent the inactive kinase from persisting as a scaffolding node for oncogenic signalling. For example, Small molecule-mediated degradation of the protein itself rather than inhibition of the kinase domain could provide advantages, such as reduced drug exposure time required to suppress signalling and the ability to target kinase-independent functions.

Bifunctional compounds such as those that are described in U.S. Patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and proteins, which are then degraded and/or otherwise inhibited by the bifunctional compounds. Through the specific degradation of the target proteins, the bifunctional compounds provide a therapeutic effect.

An outstanding question, however, has been whether the PROTAC methodology is able to induce degradation of transmembrane-spanning proteins, given their restricted cellular localization and the questionable accessibility of membrane-bound receptors for ubiquitination by the cytosolic machinery. PROTACs could provide key advantages such as improved physicochemical properties, reduced toxicity, facile modular design, and a defined mechanism of degradation.

There exists in the art an ongoing need for effective treatments for disease associated with overexpression or hyperactivation of RTK, e.g., EGFR, IGFR, and HGFR. As such, small-molecule therapeutic agents that target RTKs are highly desired for the treatment of RTK-related diseases.

SUMMARY

The present disclosure describes bifunctional compounds which function to recruit endogenous RTK proteins to an E3 ubiquitin ligase for ubiquitination and subsequent degradation, and methods of using the same. The sustained loss of RTK function can be accomplished using Proteolysis Targeting Chimeras (PROTACs)), a technology for post-translational protein degradation. By chemically tethering ligands for two different proteins—an E3 ubiquitin ligase and a protein of interest—a new pharmacological entity is created that facilitates the ubiquitination and proteasomal degradation of the protein of interest. Its net effect on target protein levels is similar to that achievable using RNAi technology; however, the small-molecule approach of PROTACs does not have the inherent liabilities of proposed nucleic-based modalities. Indeed, PROTACs are comparable to RTK inhibitors, in that both are amenable to adjustable dosing and can offer temporal control to achieve the desired level of signal inactivation, nor does it require any genetic manipulations/modification of cells in order to work.

Thus, the present disclosure provides bifunctional proteolysis targeting chimeric (PROTAC) compounds, which find utility as modulators of target protein ubiquitination and subsequent degradation. An advantage of the PROTAC compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer.

In one aspect the disclosure provides bifunctional or PROTAC compounds, which comprise an E3 ubiquitin ligase binding moiety (i.e., a ligand for an E3 ubqutin ligase or "ULM" group), and a moiety that binds a RTK, e.g., the epidermal growth factor receptor (EGFR) protein (i.e., a protein/polypeptide targeting moiety or "PTM" group), such that the RTK protein is placed in proximity to the ubiquitin ligase to effect degradation (and inhibition) of that protein.

In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

[PTM]-[ULM], wherein PTM is a RTK (e.g., EGFR) binding moiety, and ULM is an E3 ubiquitin ligase binding moiety.

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

[PTM]-L-[ULM], wherein PTM is a RTK (e.g., EGFR) binding moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

[PTM]-L-[VLM or CLM or MLM or ILM]

wherein PTM is a RTK (e.g., EGFR) binding moiety, L is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones. In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In certain embodiments, the description provides a compound having the structure selected from compound 1-351 as described in FIG. 2. In certain embodiments, the description provides a therapeutic composition comprising an effective amount of at least one compound selected from compound 1-351 as described in FIG. 2, and a pharmaceutically acceptable carrier or excipient. In certain embodiments, the description provides a combination for co-administration (e.g., either separately or in a single dosage form) comprising an effective amount of at least one compound as described herein, at least one additional bioactive agent, and a pharmaceutically acceptable carrier or exceipient. In certain embodiments, the additional bioactive agent is an anti-oncologic agent.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer.

In yet another aspect, the present disclosure provides a method of ubiquitinating/degrading a target RTK protein, e.g., EGFR, in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

Figure 2:
Figure 2:
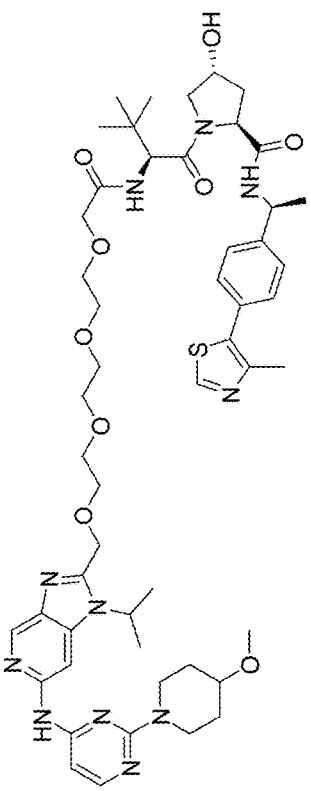
Figure 2:
Figure 2:
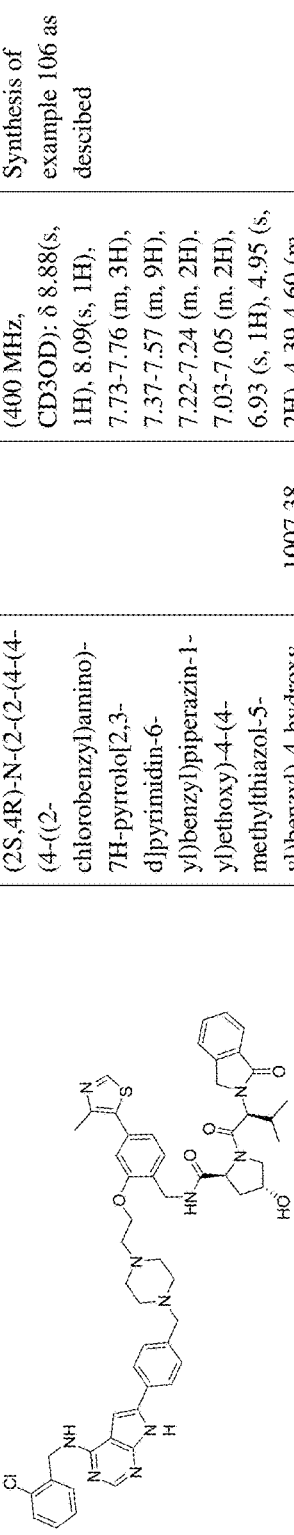
Figure 2:
Figure 2:
Figure 2:
Figure 2:
Figure 2:
Figure 2:
Figure 2:
Figure 2:
Figure 2:
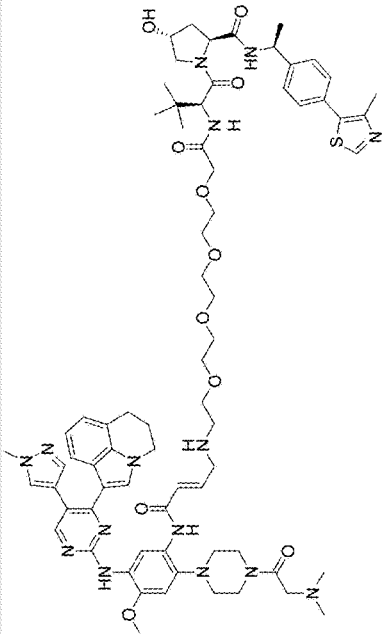
Figure 2:
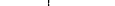
Figure 2:
Figure 2:
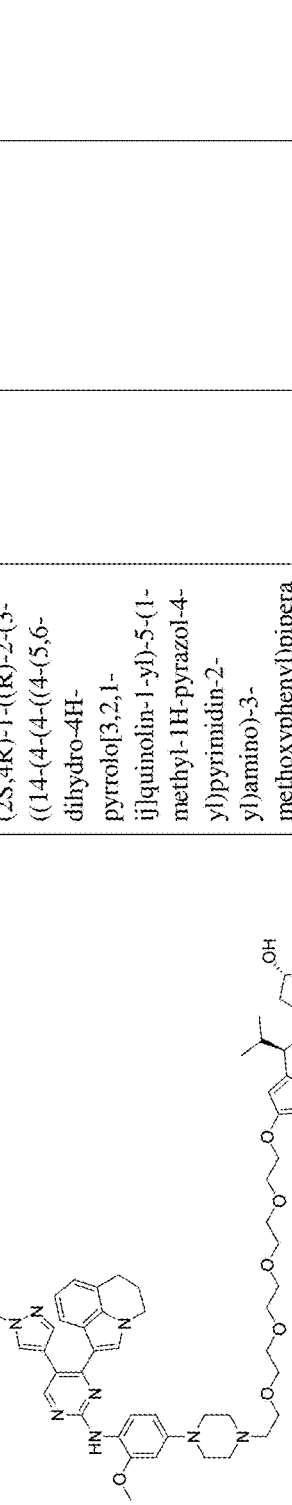
Figure 2:
Figure 2:
Figure 2:
Figure 2:
Figure 2:
Figure 2:
Figure 2:
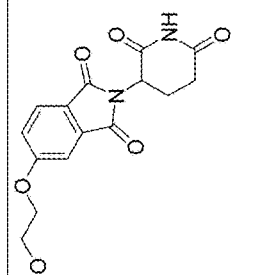
Figure 2:
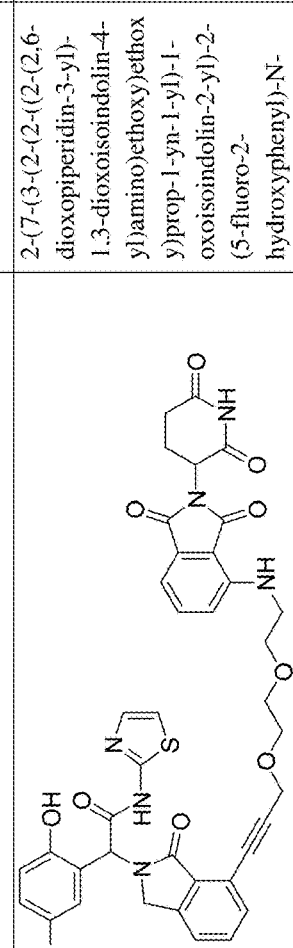
Figure 2:
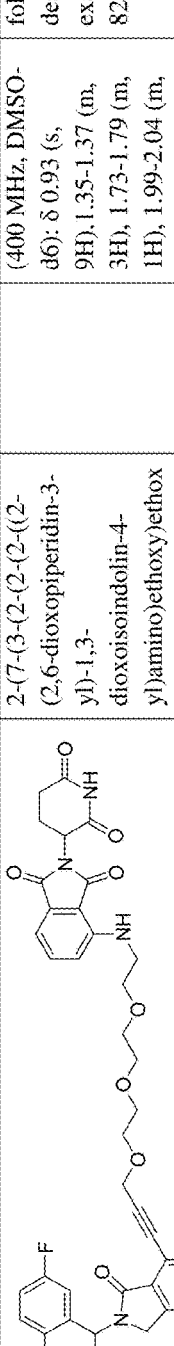
Figure 2:
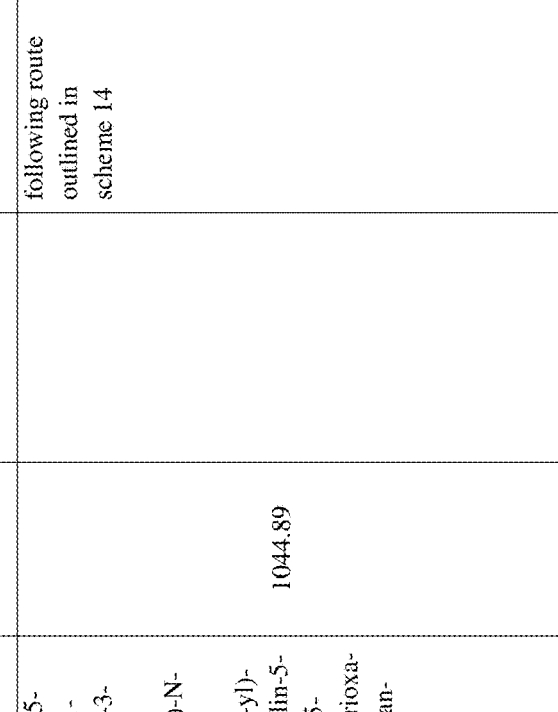
Figure 2:
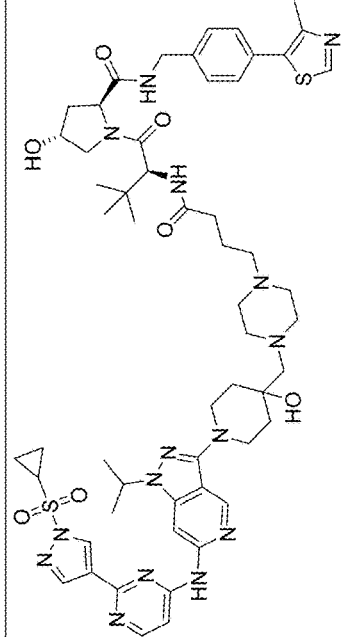

FIG. 2. Table of Exemplary PROTAC compounds as described herein.

Figure 3:
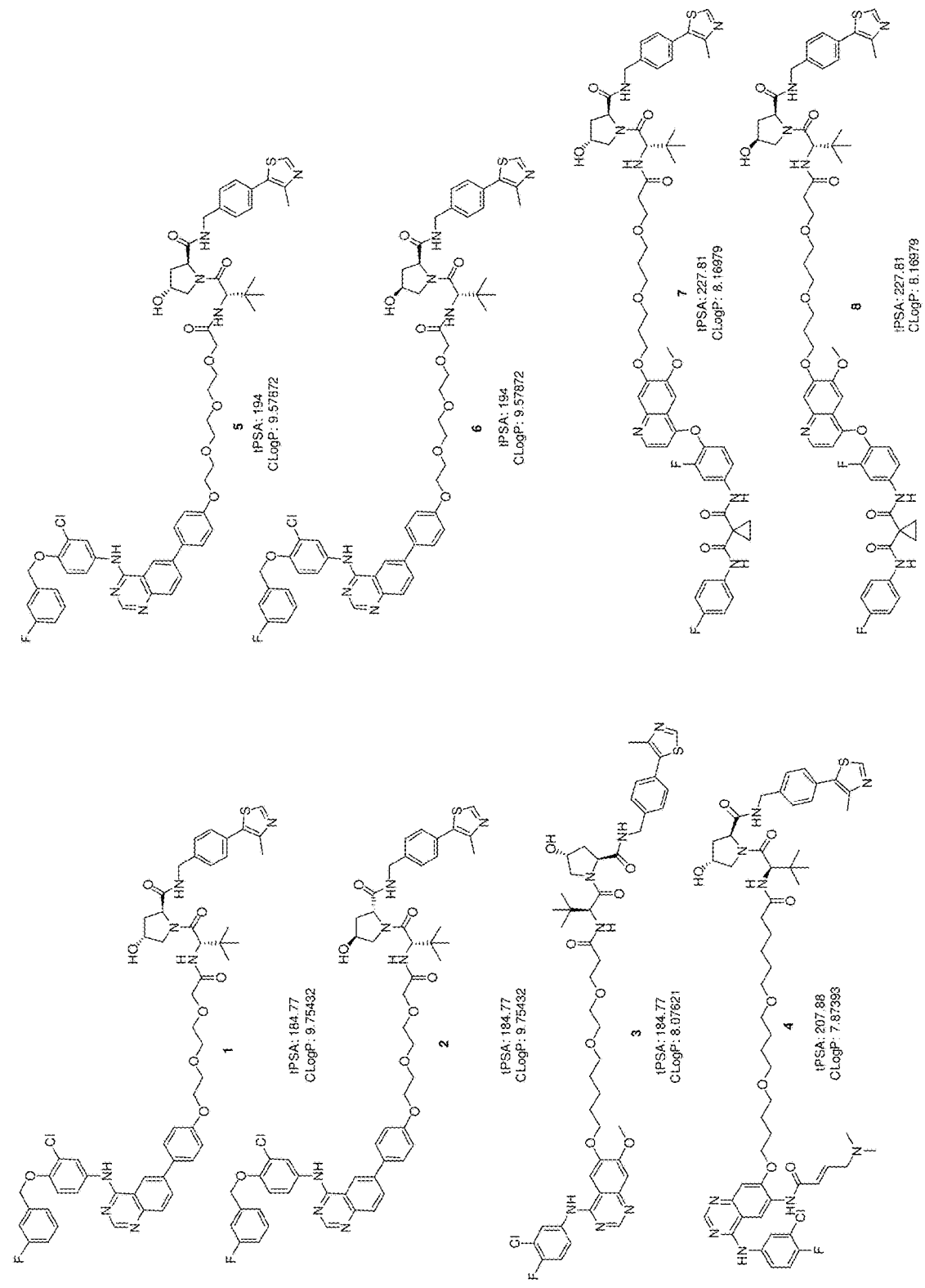

FIG. 3. Structures of exemplary PROTAC compounds as described herein. (tPSA=total surface area). 1-Lapatinib-based PROTAC (2 PEG linker); 2—Lapatinib-based PROTAC diastereomer (2 PEG linker); 3—Gefitinib-based PROTAC; 4—Afatinib-based PROTAC; 5—Lapatinib-based PROTAC (3 PEG linker); 6—Lapatinib-based PROTAC diastereomer (3 PEG linker); 7—Foretinib-based PROTAC; 8—Foretinib-based PROTAC diastereomer.

Figure 4B:
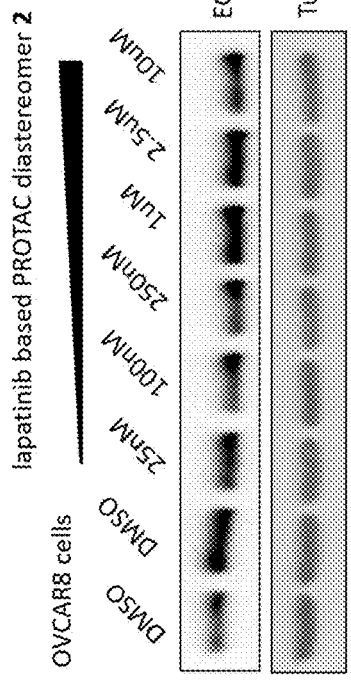
Figure 4A:
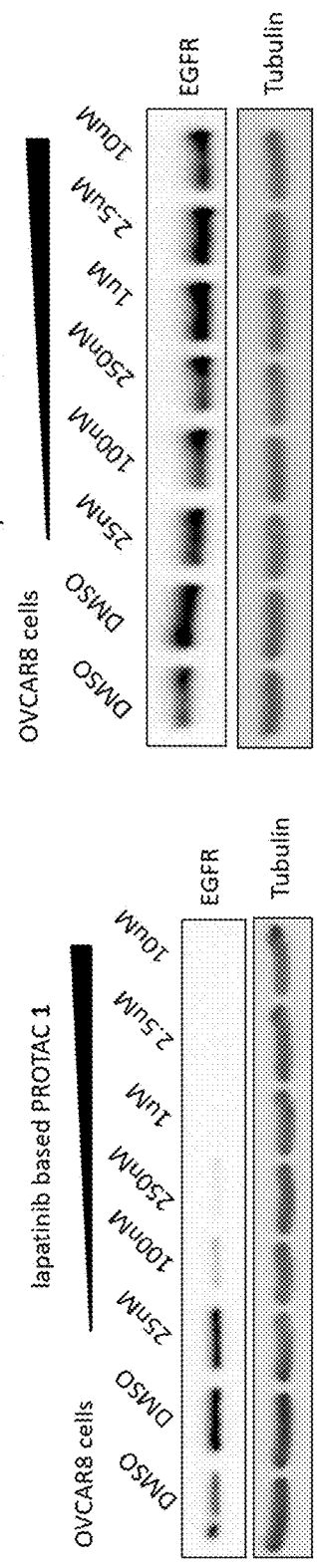
Figure 4D:
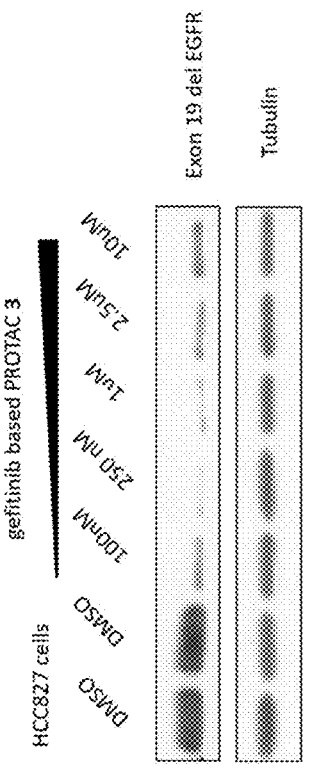
Figure 4C:
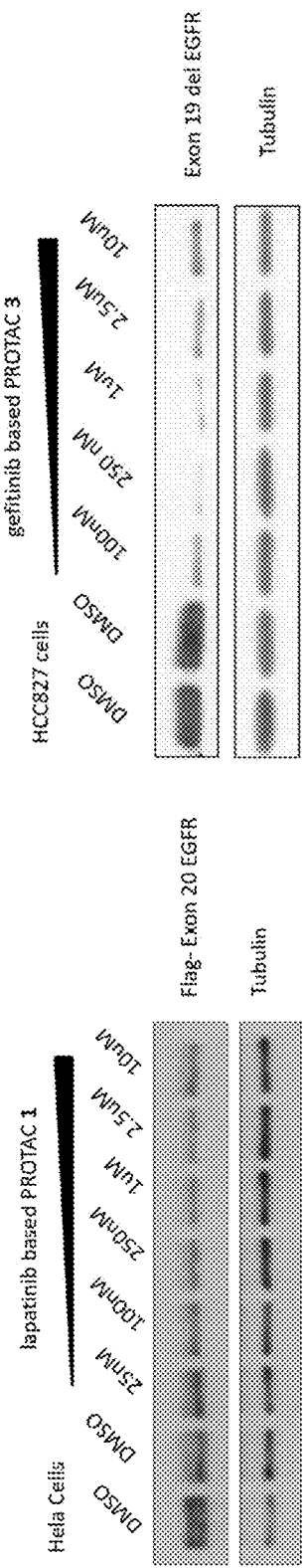
Figure 4F:
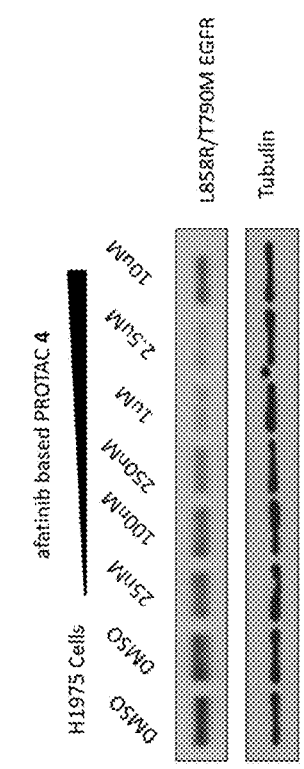
Figure 4E:
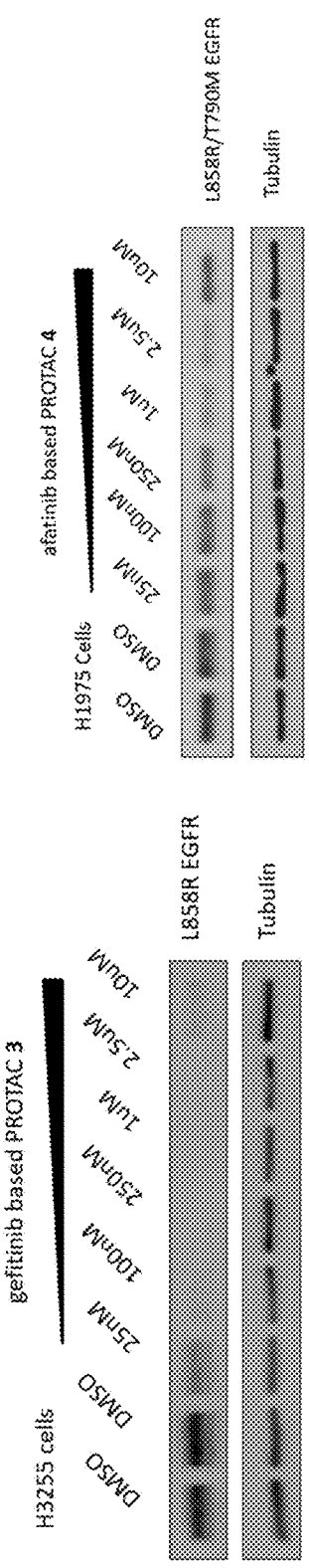

FIGS. 4A, 4B, 4C, 4D, 4E, 4F, and 4G. Degradation activity of EGFR and mutants by PROTACs of FIG. 3. FIG. 4A-4F—Immunoblots of cells expressing different EGFR variants treated with increasing doses of the indicated compound for 24 hours. FIG. 4A—OVCAR8 cells treated with lapatinib-based PROTAC 1. FIG. 4B—OVCAR8 cells treated with compound 2, an inactive diastereomer of lapatinib-based PROTAC 1. FIG. 4C—HeLa cells expressing FLAG-tagged exon 20 insertion (ASV duplication) EGFR treated with lapatinib-based PROTAC 1. FIG. 4D—HCC827 cells expressing exon 19 deletion EGFR treated with gefitinib-based PROTAC 2. FIG. 4E—H3255 cells expressing L858R EGFR treated with gefitinib-based PROTAC 3. FIG. 4F—H1975 cells expressing double mutant (L858R/T790M) EGFR treated with afatinib-based PROTAC 4. FIG. 4G—Summary table of $DC_{50}$ (the concentration at which half-maximal degradation is achieved) and $D_{max}$ (the maximum percentage of degradation) values.

FIGS. 5A, 5B, 5C, and 5D. Selective PROTAC-mediated degradation of HER2 with the compounds of FIG. 3. FIG. 5A—Employing different linker lengths imparts PROTAC selectivity for EGFR over HER2. OVCAR8 cells were treated with PROTAC 1 or 5 for 24 hours before being lysed and probed for EGFR, HER2 and tubulin (as a loading control). FIG. 5B—Cell proliferation assay in SKBr3 cells after 72 hours of treatment with the indicated compound concentrations. FIG. 5C—Treatment of SKBr3 cells with sub-lethal concentrations (500 nM) of PROTAC 1 or diastereomer 2 over 48 hours shows a gradual increase in downstream signalling consistent with kinome re-wiring, previously observed in SKBr3 cells, with diastereomer but not with PROTAC. FIG. 5D—Immunoblotting analysis of c-Met phosphorylation after 48 hours with 500 nM PROTAC 1 or diastereomer 2.

FIGS. 6A, 6B, and 6C. FIG. 6A—Gefitinib-based PROTAC 3 spares WT EGFR. OVCAR8 Cells were treated for 24 hours with increasing doses of PROTAC 3 or with DMSO control before immunoblotting. FIG. 6B/6C—Characterization of PROTAC 1 (6B) and diastereomer 2 (6C) in SKBr3 cells. Cells were treated for 24 hours in full serum with increasing doses of PROTAC 1 or with diastereomer 2 before immunoblotting.

Figure 7D:
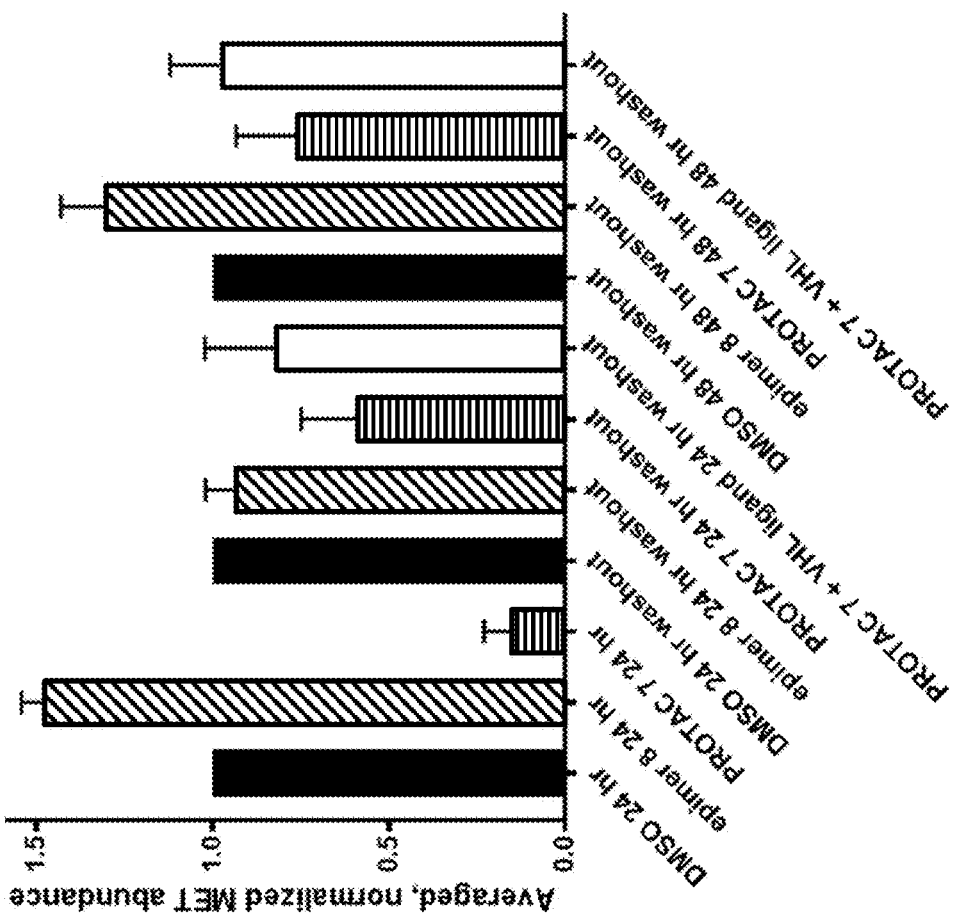
Figure 7C:
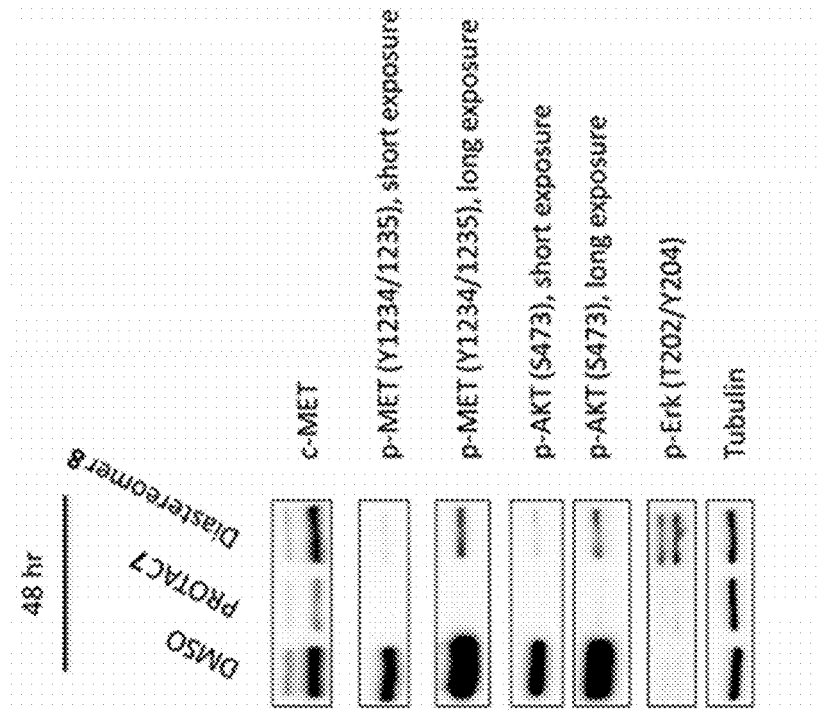

FIGS. 7A, 7B, 7C, 7D, 7E, and 7F. Characterization of Foretinib-based PROTACs in GTL16 cells. FIG. 7A/7B—GTL16 cells were treated with increasing concentrations of PROTAC 7 (7A) or diastereomer 8 (7B) in media containing full serum for 24 hours before immunoblotting analysis. FIG. 7C—Representative blot of cells treated with 500 nM PROTAC 7 or 500 nM diastereomer 8 for 48 hr before immunoblotting analysis FIG. 7D—Quantitation of washout experiments. c-MET levels normalized to tubulin after treatment with the indicated compounds at the indicated time points. Average of 3 independent repeats and error bars represent S.E.M. FIG. 7E—Structure of VHL-Ligand 9 used in competition experiments. FIG. 7F—Co-treatment competition of PROTAC 7 with VHL-Ligand 9 in MDA-MB-231 cells for 24 hours.

Figure 8D:
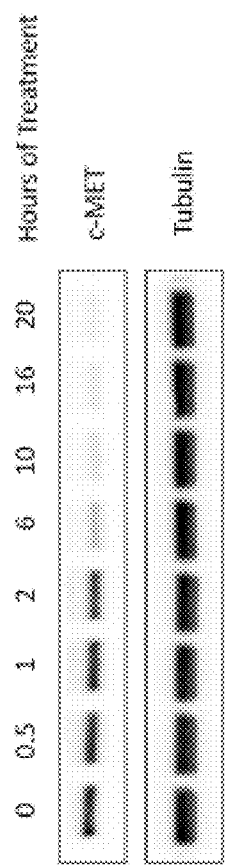
Figure 8C:
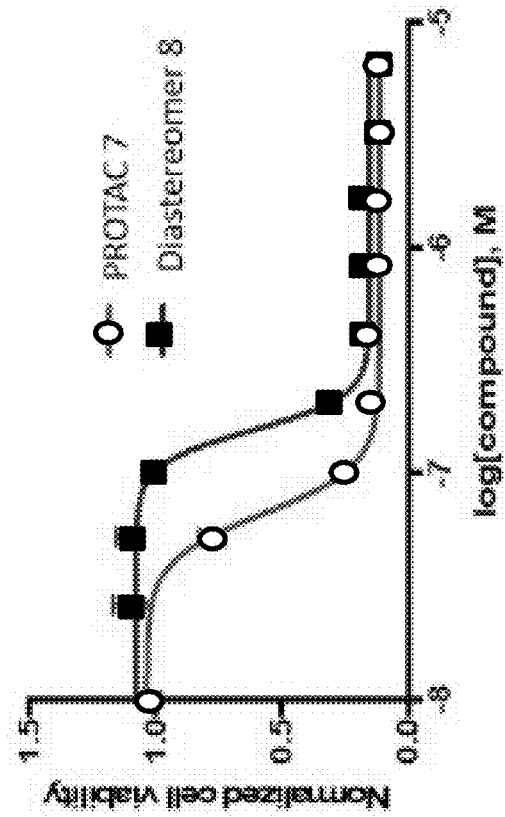
Figure 8E:
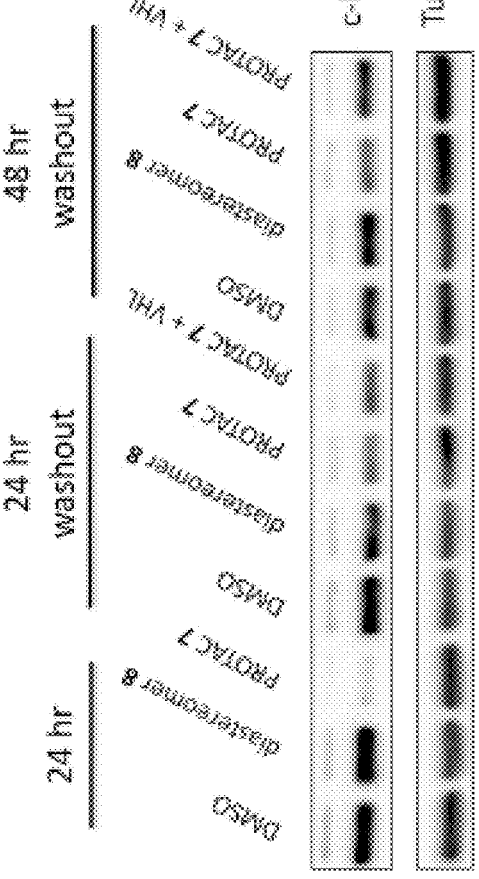

FIGS. 8A, 8B, 8C, 8D, and 8E. PROTAC-mediated degradation of c-Met. FIGS. 8A and 8B—MDA-MB-231 cells treated for 24 hr with increasing concentrations of foretinib-based PROTAC 7 (8A) or diastereomer 8 (8B). FIGS. 8C and 8D—Cell-proliferation assay in GTL16 cells (PROTAC 7 IC50=66.7 nM, diastereomer 8 IC50=156 nM) (8C) and time course of c-Met degradation by foretinib based PROTAC (500 nM) 7 (8D). (8E) PROTAC effects are longer lasting in cell culture. Cells were treated for 24 hr with 500 nM PROTAC 7 or diastereomer 8 before replating on new plastic, in fresh medium for 24 or 48 hr. Excess VHL (25 mM) ligand was added to the indicated wells.

Figure 9A:
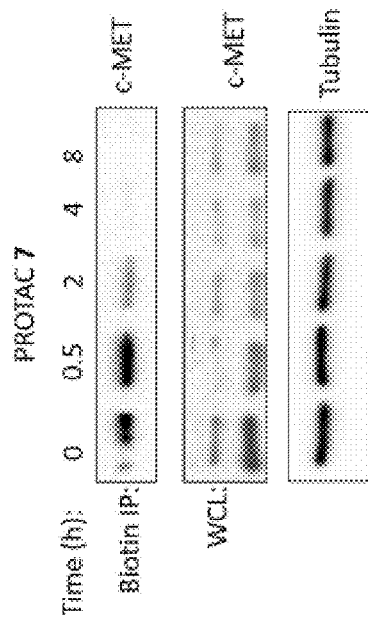
Figure 9B:
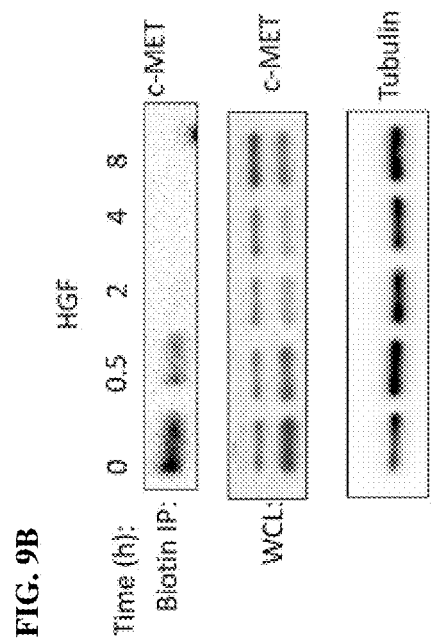
Figure 9C:
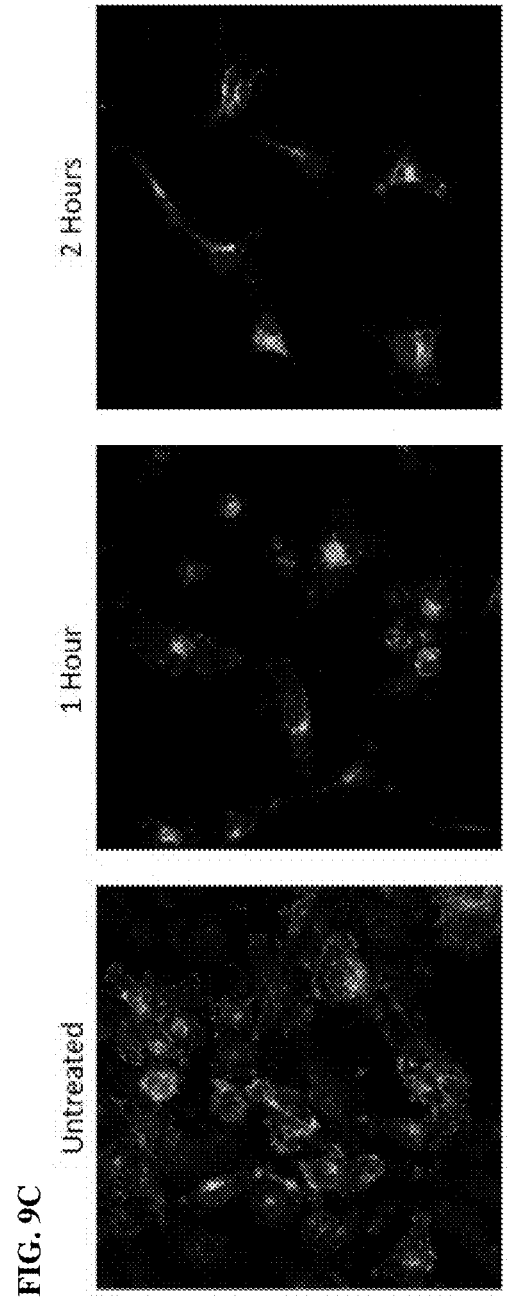

FIGS. 9A, 9B, and 9C. PROTAC-mediated internalization. FIGS. 9A and 9B—Cell-surface proteins were labeled with a cell membrane impermeant biotin reagent prior to treatment with 500 nM foretinib-based PROTAC 7 (9A) or 100 ng/mL HGF (9B) for the indicated times and lysed. Biotinylated proteins were enriched by streptavidin pull-down and immunoblotted for c-Met. Biotinylated proteins represent the cell-surface fraction. Corresponding whole-cell lysates are also shown. (9C) Representative confocal microscopy images of c-Met (green) internalization in response to PROTAC 7 (500 nM) treatment for the indicated times (DAPI nuclear stain in blue).

Figure 10E:
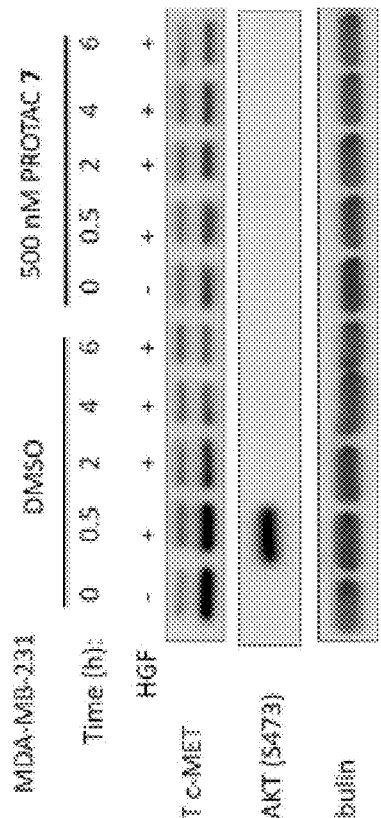
Figure 10F:
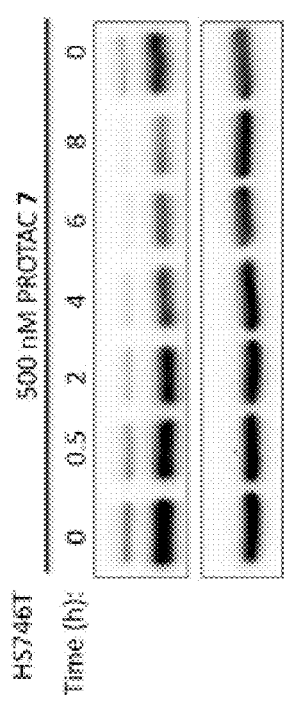
Figure 10G:
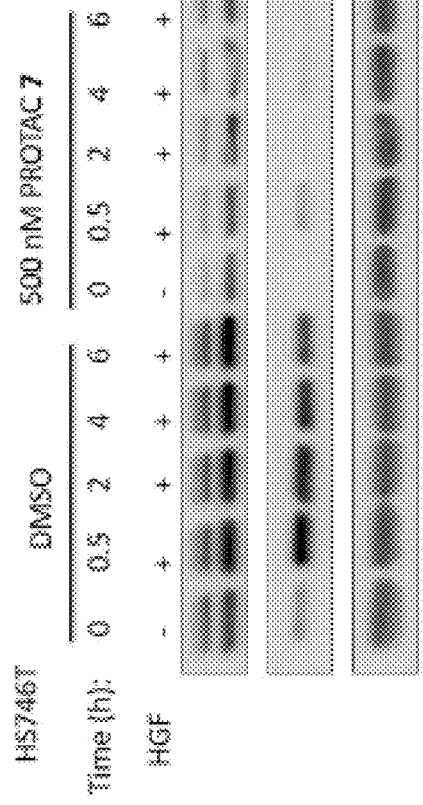
Figure 10H:
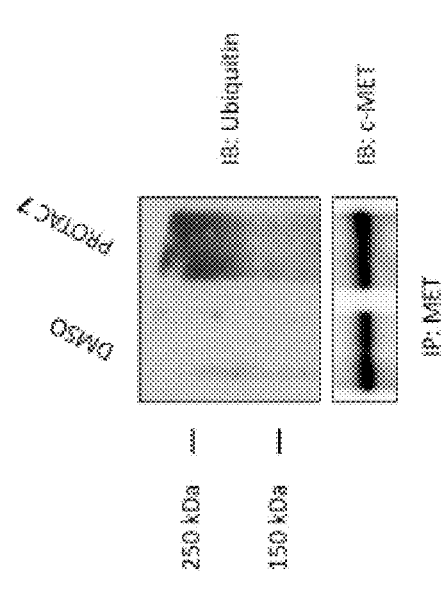

FIGS. 10A, 10B, 10C, 10D, 10E, 10F, 10G, 10H, and 10I. Exon 14-deleted c-Met has increased stability and resistance to HGF-mediated degradation that can be combated by foretinib-based PROTAC 7. FIG. 10A—Quantitation of WT c-Met or exon 14-deleted c-Met degradation upon treatment with HGF, PROTAC 7, or DMSO control in the presence of cycloheximide (CHX). FIG. 10B—Table of calculated half-lives. FIG. 10C—Representative CHX time course of WT c-Met degradation and signaling in MDA-MB-231 cells treated with HGF. FIG. 10D—Representative CHX time course of exon 14-deleted c-Met degradation and signaling in Hs746T cells treated with HGF. FIG. 10E—Representative CHX time course of exon 14-deleted c-Met degradation in Hs746T cells treated with PROTAC 7. FIGS. 10F and 10G—MDA-MB-231 (10F) and Hs746T (10G) cells were treated with either DMSO or PROTAC for 18 hr before the addition of HGF and lysis at the indicated time points following stimulation. FIG. 10H—Immunoprecipitation of c-Met from PROTAC 7-treated (1 mM) or DMSO-treated Hs746T cells followed by immunoblotting for ubiquitin. FIG. 10I—Tandem ubiquitin binding entity 1 (TUBE1) pull-down from PROTAC 7 (1 mM) or DMSO-treated Hs746T cells followed by immunoblotting for c-Met.

Figure 11D:
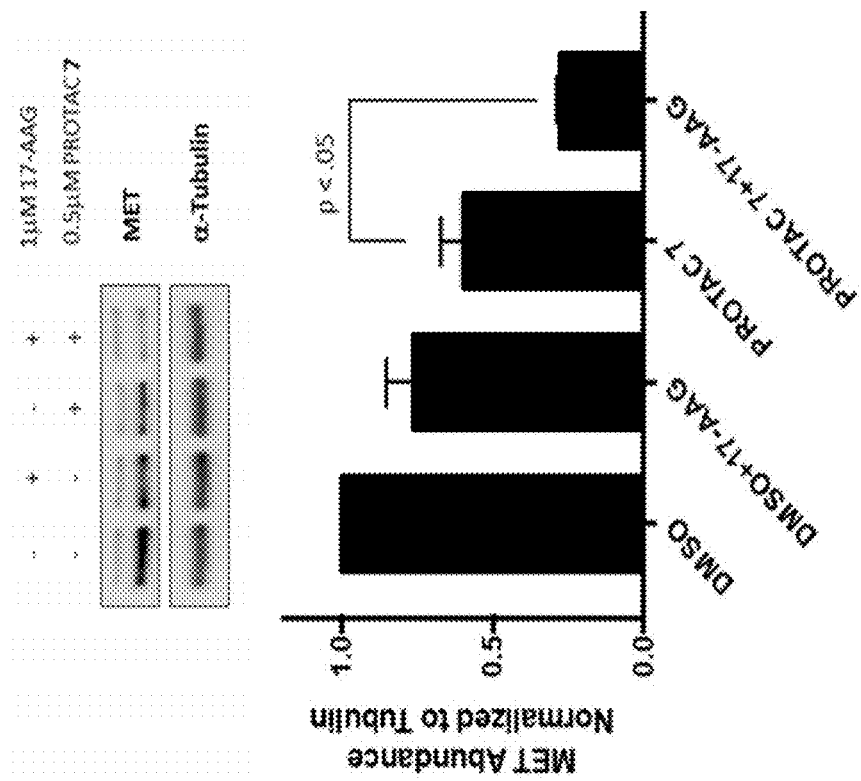

FIGS. 11A, 11B, 11C, and 11D. FIG. 11A—Quantitative real time PCR was performed at the indicated timepoints after PROTAC treatment (500 nM). Data is normalized to beta-Tubulin. FIG. 11B-11D Representative Western blots and quantitation for cotreatment experiments. FIG. 11B—Co-treatment of PROTAC 7 (500 nM) with proteasome inhibitor epoxomicin (500 nM) for 6 hours in MDA-MB-231 cells. Quantified data represent average of 2 repeats. FIG. 11C—Co-treatment of PROTAC 7 (500 nM) with neddylation inhibitor MLN-4924 (1 μM) for 6 hours in MDA-MB-231 cells. Quantified data represent average of 2 repeats. FIG. 11D—Co-treatment of PROTAC 7 (500 nM) with HSP90 inhibitor 17-AAG (1 μM) for 6 hours in MDA-MB-231 cells. Quantified data represent average of 2 repeats.

Figure 12E:
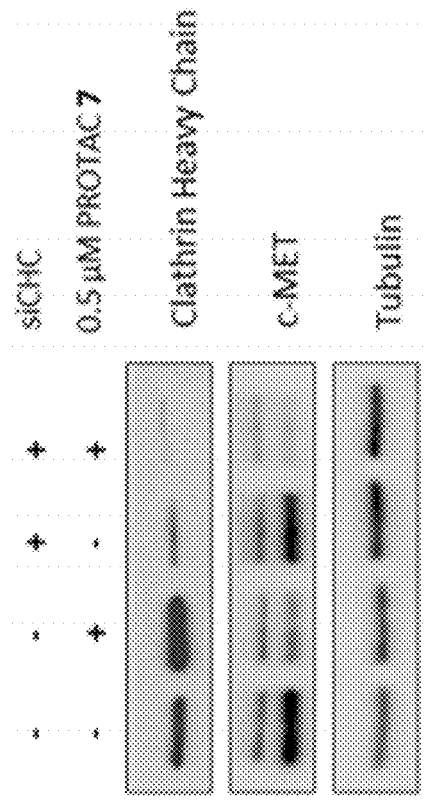

FIGS. 12A, 12B, 12C, 12D, and 12E. Representative confocal microscopy images of HGF-mediated internalization of c-Met. FIG. 12A—MDA-MB-231 cells treated with 100 ng/ml HGF for the indicated times before fixing, permeabilizing, and immunostaining for c-Met. FIG. 12B—Representative confocal microscopy images demonstrating PROTAC-mediated colocalization with early endosome antigen 1 (EEA1). MDA-MB-231 cells treated with 500 nM PROTAC 7 for the indicated times before fixing, permeabilizing, and immunostaining for c-Met and EEA1. FIG. 12C—Representative confocal microscopy images demonstrating c-Met co-localization with p230 (a trans-Golgi marker). FIG. 12D—Quantification of images from FIG. 12C. Percentage of cellular pixels occupied by c-Met immunofluorescence and average cellular pixel intensity were used as a proxy for puncta formation and reduction in cell surface c-Met. FIG. 12E—Clathrin heavy chain (CHC) siRNA experiment. MDA-MB-231 cells were transfected with CHC siRNA before treatment with PROTAC 7 for 24 hours prior to lysis and immunoblotting.

Figure 13A:
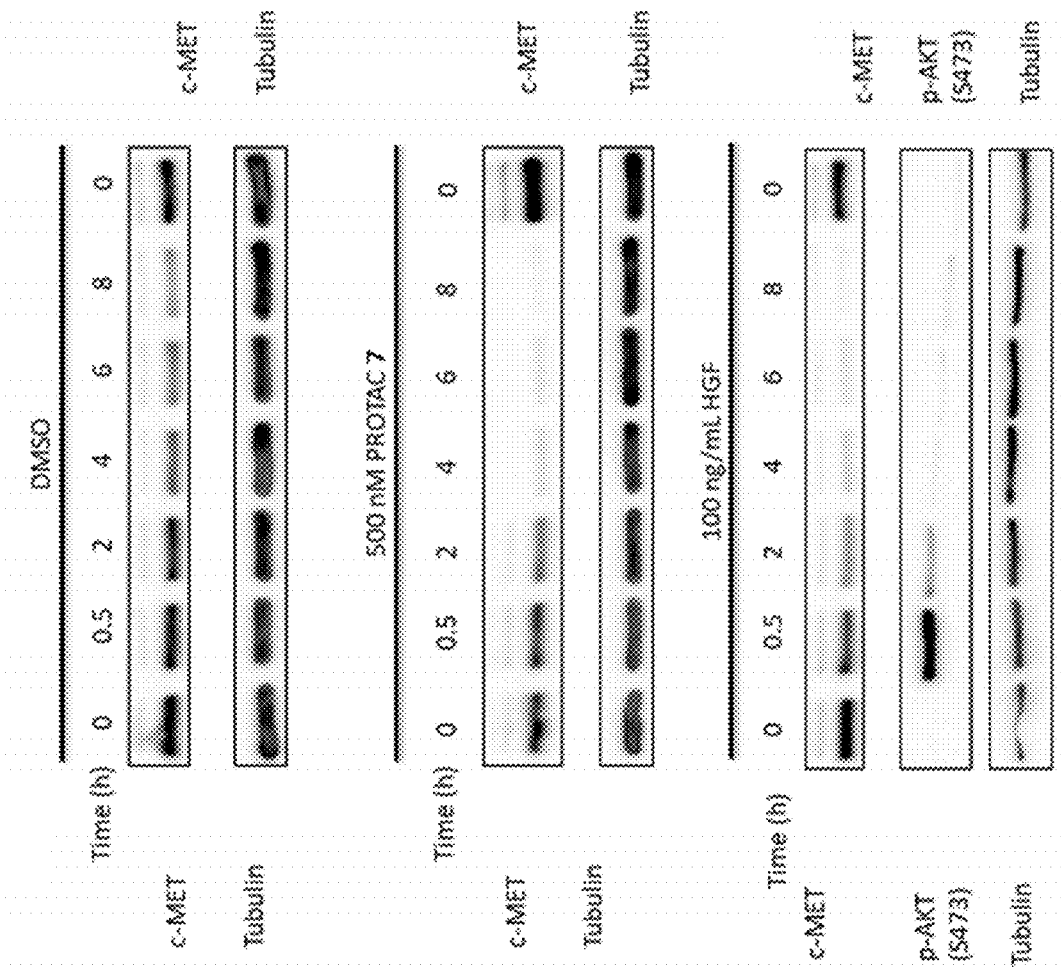
Figure 13B:
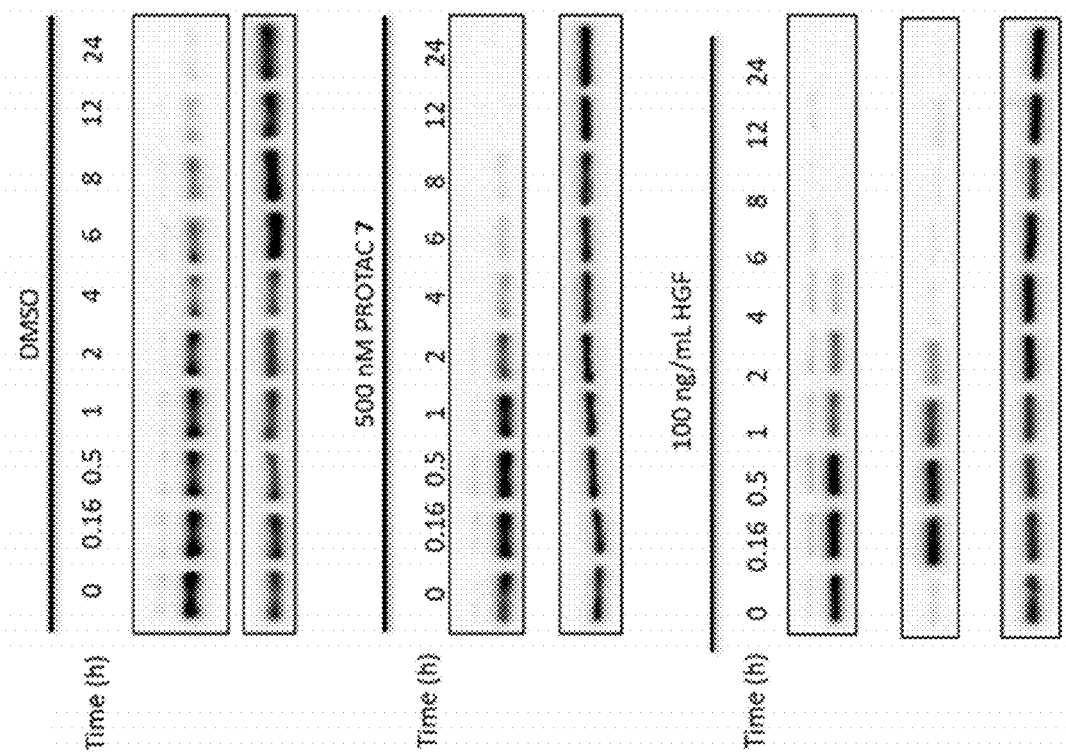
Figure 13C:
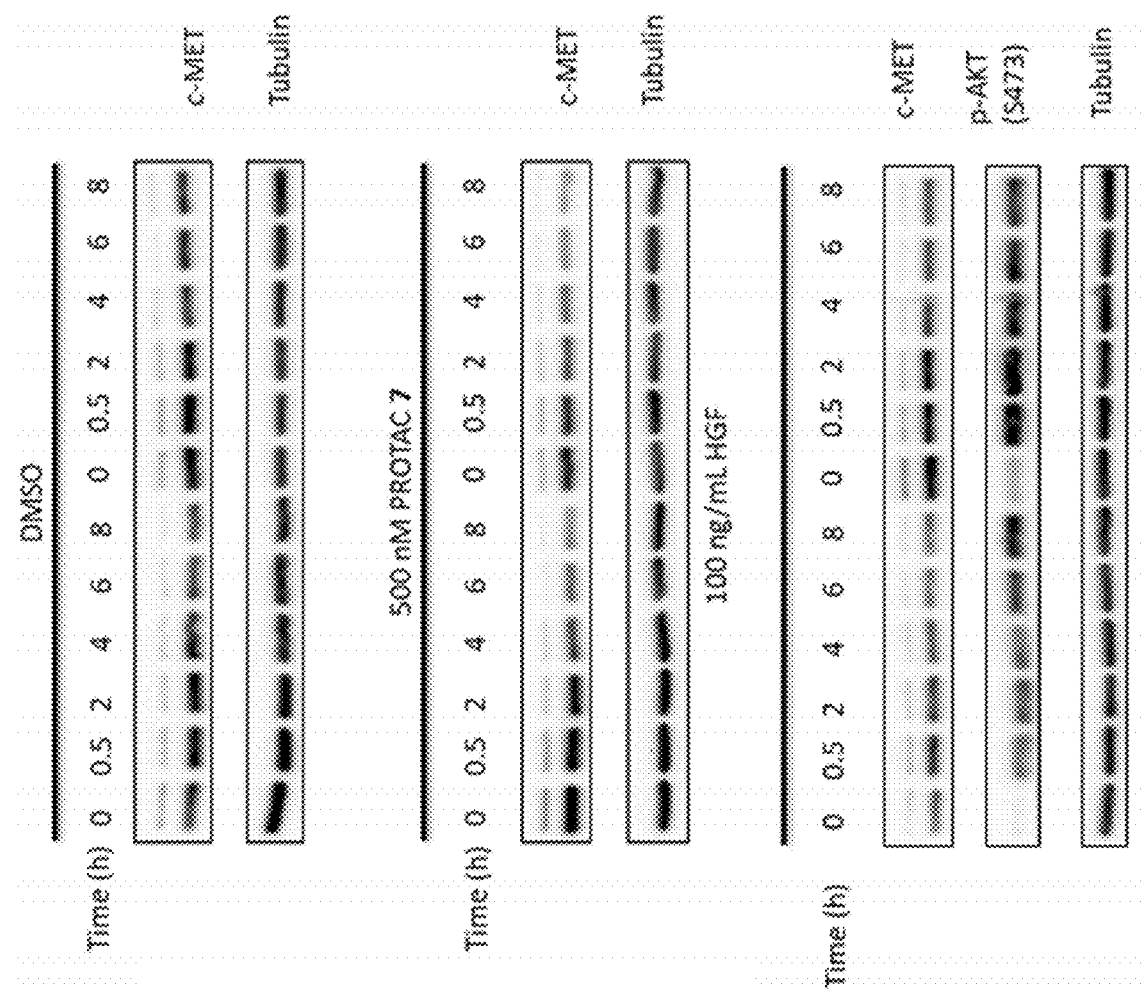

FIGS. 13A, 13B, 13C, 13D, and 13E. Cycloheximide pulse-chase western blots. FIG. 13A—MDA-MB-231 cells were treated with cycloheximide followed by DMSO, PROTAC 7 or HGF and lysed at the indicated incubation times—Set 1. FIG. 13B—MDA-MB231 cells were treated with cycloheximide followed by DMSO, PROTAC 7 or HGF and lysed at the indicated incubation times—Set 2. FIG. 13C—Hs746T cells were treated with cycloheximide followed by DMSO, PROTAC 7 or HGF and lysed at the indicated incubation times. FIG. 13D—c-Met immunoprecipitation experiments.Hs746T cells were treated with 2 uM epoxomicin for 30 minutes before the addition of PROTAC 7 for 4 hours prior to c-Met immunoprecipitation. (WCL=Whole-cell lysate). FIG. 13E—Hs746T cells were treated as in D prior to TUBE1 immunoprecipitation experiments.

Figure 14:
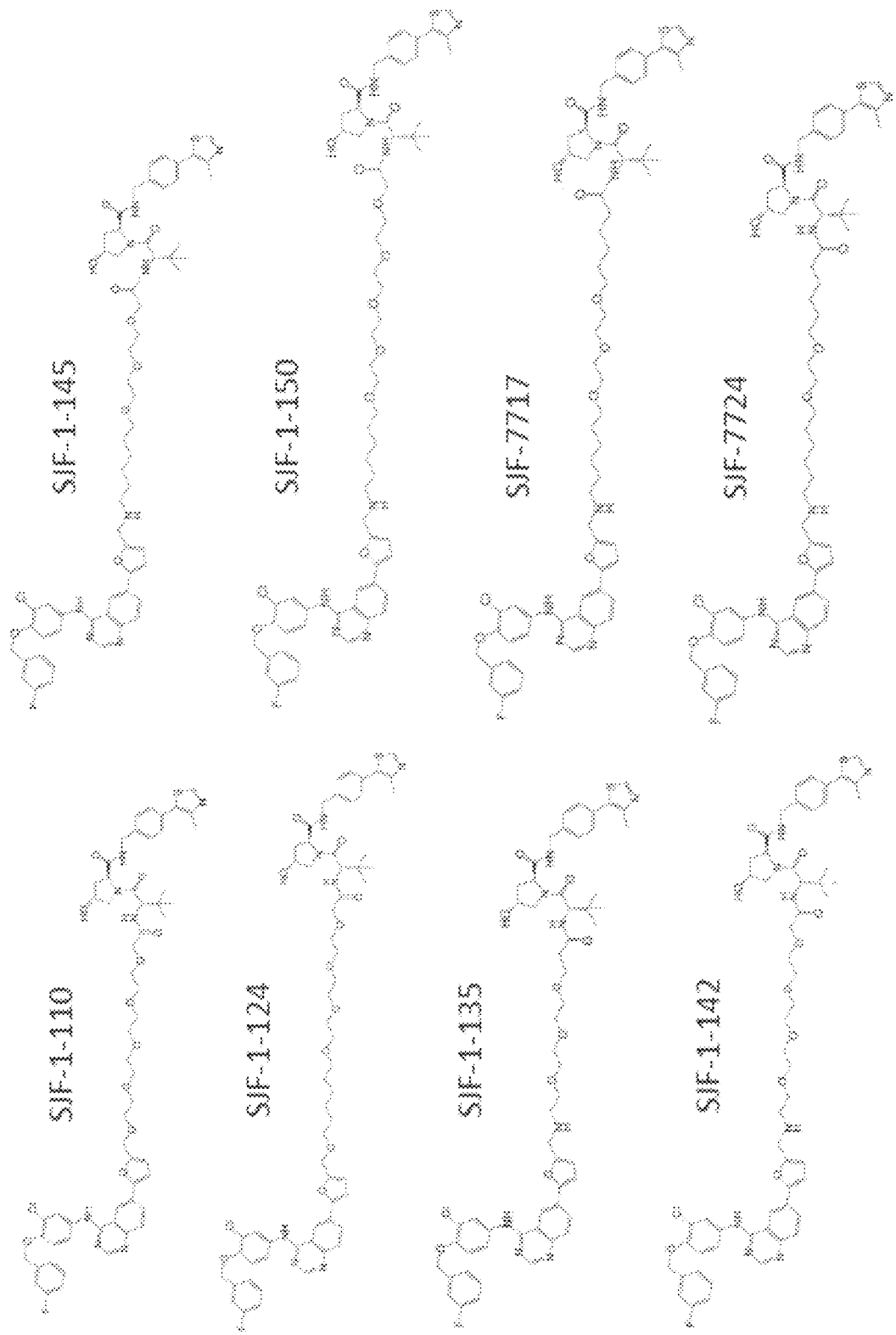

FIG. 14. Structures of exemplary PROTAC compounds as described herein (Lapatinib-based (furan) PROTACs).

Figure 15B:
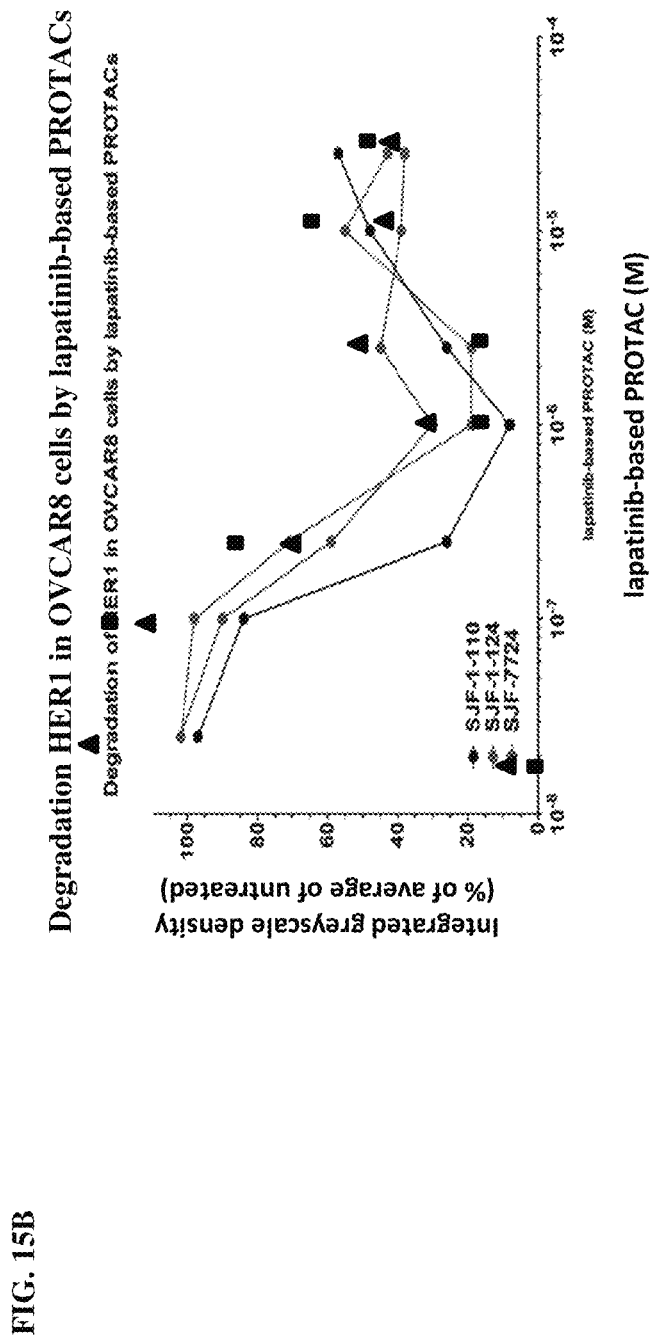

FIGS. 15A and 15B. Degradation activity of exemplary PROTAC compounds of FIG. 14. FIG. 15A—the percent degraded HER1 and HER2 protein at 1 uM, linker atoms, linker length (in Angstroms), linker type and E3 ligase binding moiety (ULM) is indicated. FIG. 15B—demonstrates the degradation activity (dose-response) of HER1 in OVCAR8 cells by lapatinib-based PROTACS as indicated.

Figure 16A:
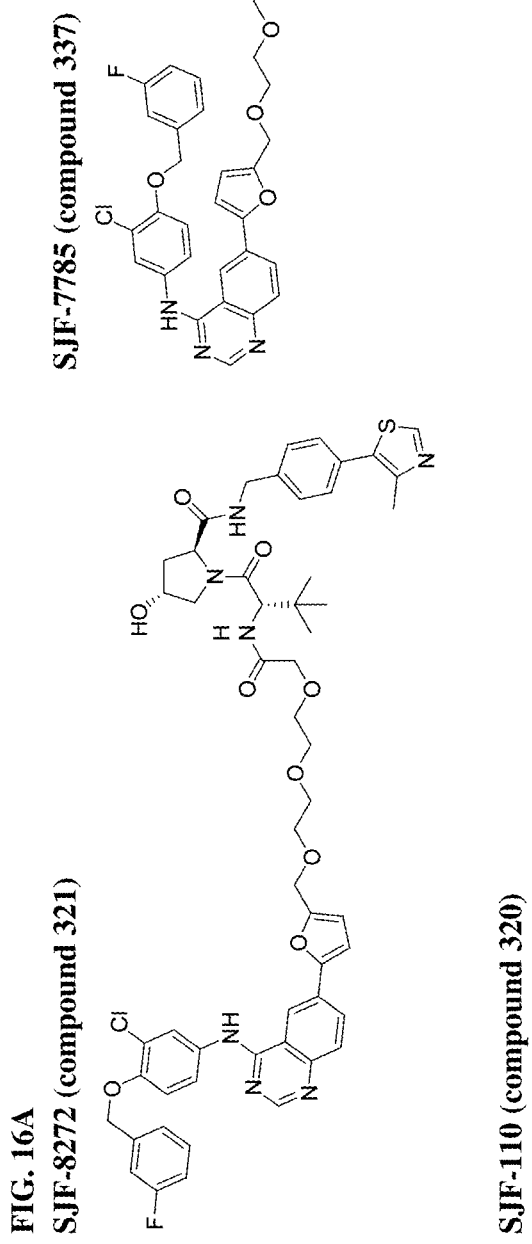
Figure 16A:
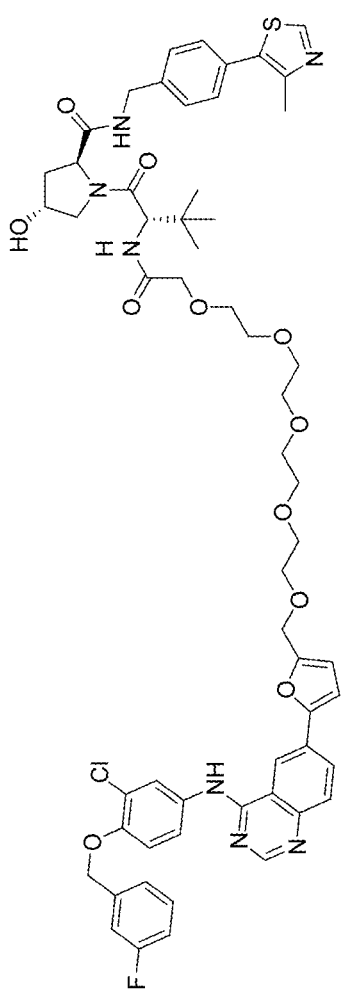
Figure 16B:
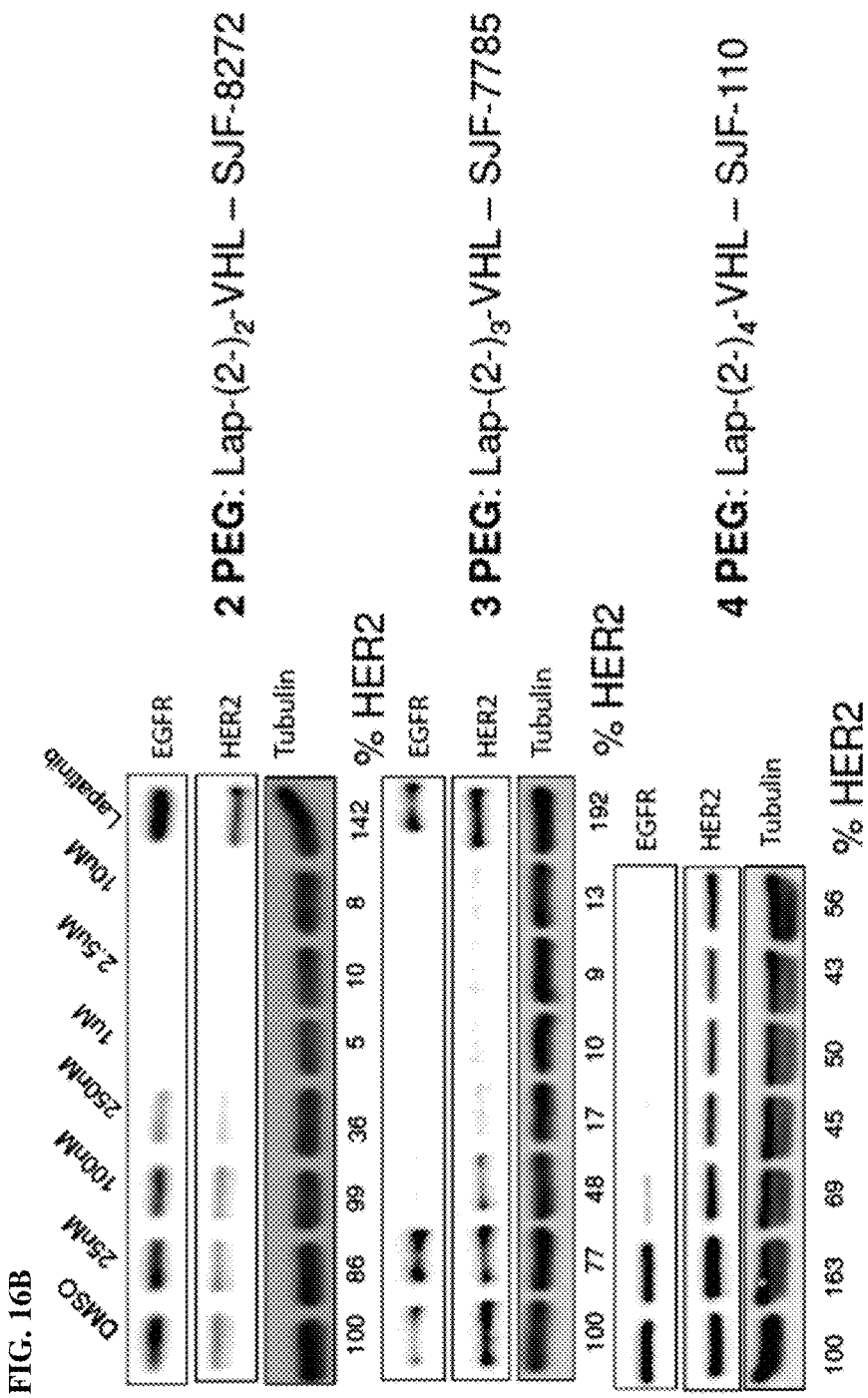

FIGS. 16A and 16B. Degradation activity of exemplary PROTAC compounds. FIG. 16A—shows structures of exemplary lapatinib (furan)-based PROTACs. FIG. 16B—Western blot demonstrating degradation activity of compounds of FIG. 13A. OVCAR8 treated cells for 24 hours. NRG (5 ng/mL) stimulation for the last 5 minutes. Anti-EGFR rabbit (CST), anti-HER2 (Santa Cruz Biotechnologies), and anti-tubulin (Sigma-Aldrich) were used for detection of proteins.

Figure 17A:
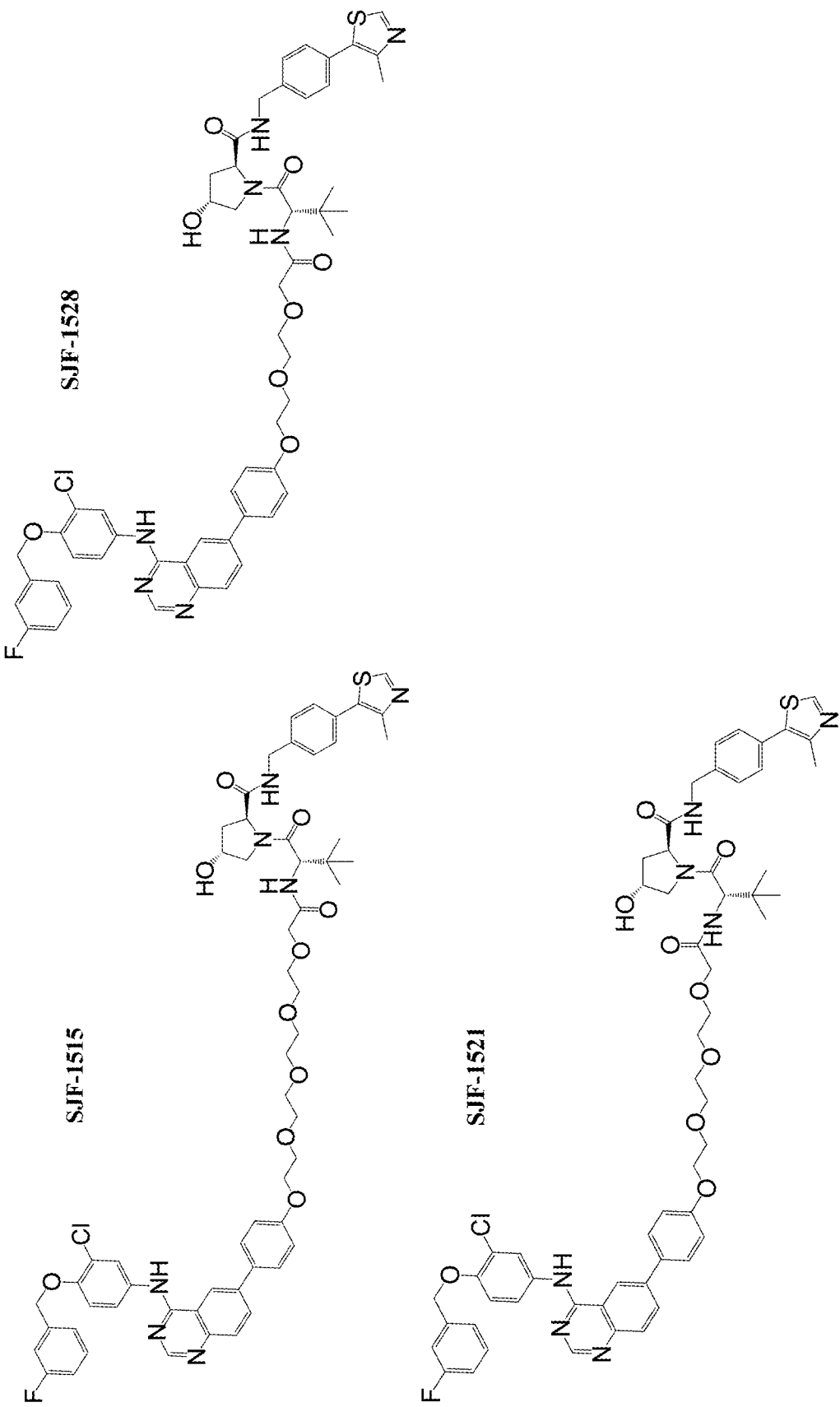
Figure 17B:
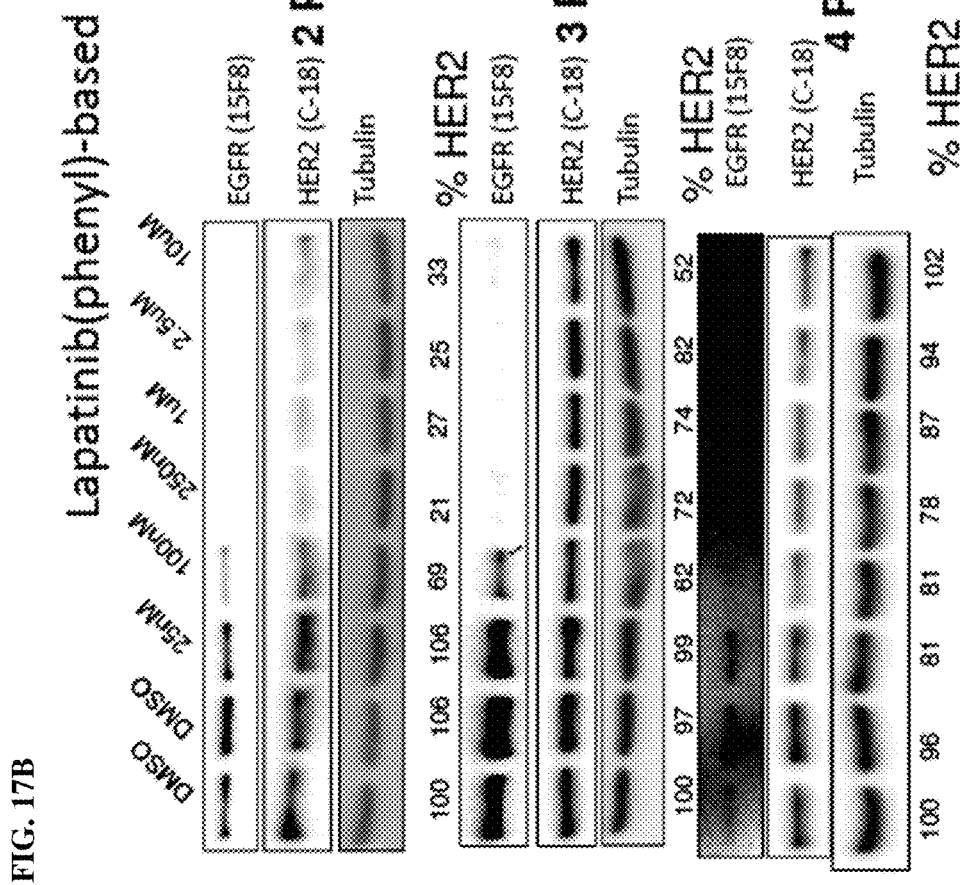

FIGS. 17A and 17B. Degradation activity of exemplary PROTAC compounds. FIG. 17A—shows structures of exemplary lapatinib (phenyl)-based PROTACs. FIG. 17B—Western blot demonstrating degradation activity of compounds of FIG. 17A. OVCAR8 treated cells for 24 hours. NRG (5 ng/mL) stimulation for the last 5 minutes. Anti-EGFR rabbit (CST), anti-HER2 (Santa Cruz Biotechnologies), and anti-tubulin (Sigma-Aldrich) were used for detection of proteins.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety, e.g., a small molecule, that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

U.S. patent application Ser. No. 15/230,354, filed on Aug. 5, 2016; and U.S. patent application Ser. No. 15/206,497 filed 11 Jul. 2016; and U.S. patent application Ser. No. 15/209,648 filed 13 Jul. 2016; and U.S. Patent Application Ser. No. 62/406,888, filed on Oct. 11, 2016; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

As some of the most compelling anti-cancer targets are RTKs, the demonstration of their susceptibility to PROTAC-mediated degradation has remained an important question. Given their well-defined role in human cancers and the broad understanding of their regulation and downstream signalling pathways, EGFR, HER2 and c-Met represent potential PROTAC targets of interest.

Herein, we show effective PROTAC-mediated degradation of these RTKs, including a number of relevant oncogenic mutant isoforms. The described results demonstrate that not only are RTKs viable substrates for post-translational degradation, but also that the signalling inactivation and growth inhibition achieved by PROTACs is more potent, more sustained, and less susceptible to kinome re-wiring than that achieved via RTK inhibition.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a RTK target protein binding moiety (PTM) via a chemical linker (L) according to the structure:

(A) PTM-L-ULM wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

(B) PTM-ILM
(C) PTM-CLM
(D) PTM-VLM
(E) PTM-MLM

In certain embodiments, the bifunctional compound further comprises a chemical linker ("L"). For example, the bifunctional compound can be depicted as:

(F) PTM-L-ILM
(G) PTM-L-CLM
(H) PTM-L-VLM
(I) PTM-L-MLM wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 µM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 μM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects of embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ILMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

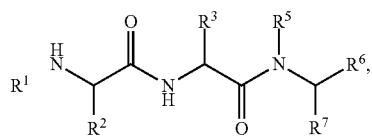
(I)

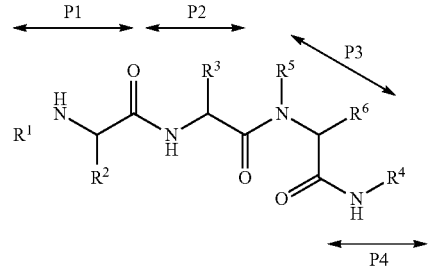
(II)

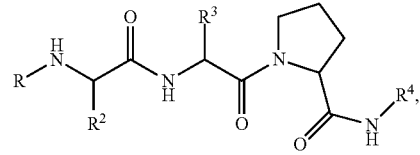
(III)

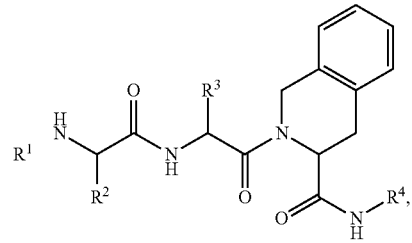
(IV)

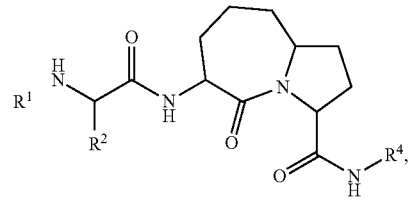
(V)

wherein:
  $R^1$ for Formulas (I), (II), (III), (IV), and (V) is selected from H or alkyl;
  $R^2$ for Formulas (I), (II), (III), (IV), and (V) is selected from H or alkyl;
  $R^3$ for Formulas (I), (II), (III), (IV), and (V) is selected from H, alkyl, cycloalkyl and heterocycloalkyl;
  $R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;

R³ and R⁵ for Formulas (I), (II), (III), (IV), and (V) taken together can form a 5-8-membered ring further optionally fused to 1-2 cycloalkyl, heterocycloalkyl, aryl or heteroaryl rings;

R⁷ for Formulas (I), (II), (III), (IV), and (V) is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or R⁷ is —C(O)NH—R⁴; and R⁴ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

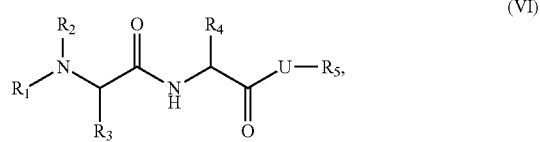

(VI)

wherein:
R₁ of Formula (VI) is, independently selected from H, $C_1$-$C_4$-alky, $C_1$-$C_4$-alkenyl, $C_1$-$C_4$-alkynyl or $C_3$-$C_{10}$-cycloalkyl which are unsubstituted or substituted;

R₂ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;

R₃ of Formula (VI) is, independently selected from H, —CF₃, —C₂H₅, $C_1$-$C_4$-alkyl, $C_1$-$C_4$-alkenyl, $C_1$-$C_4$-alkynyl, —CH₂—Z or any R₂ and R₃ together form a heterocyclic ring; each Z of Formula (VI) is, independently selected from H, —OH, F, Cl, —CH₃, —CF₃, —CH₂Cl, —CH₂F or —CH₂OH;

R₄ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, —(CH₂)₀₋₆—Z₁, —(CH₂)₀₋₆-aryl, and —(CH₂)₀₋₆-het, wherein alkyl, cycloalkyl, and phenyl are unsubstituted or substituted;

R₅ of Formula (VI) is, independently selected from H, $C_{1-10}$-alkyl, aryl, phenyl, $C_{3-7}$-cycloalkyl, —(CH₂)₁₋₆—$C_{3-7}$— cycloalkyl, —$C_{1-10}$-alkyl-aryl, —(CH₂)₀₋₆—$C_{3-7}$-cycloalkyl-(CH₂)₀₋₆-phenyl, —(CH₂)₀₋₄—CH[(CH₂)₁₋₄— phenyl]₂, indanyl, —C(O)—$C_{1-10}$-alkyl, —C(O)—(CH₂)₁₋₆—$C_{3-7}$-cycloalkyl, —C(O)—(CH₂)₀₋₆-phenyl, —(CH₂)₀₋₆—C(O)-phenyl, —(CH₂)₀₋₆-het. —C(O)—(CH₂)₁₋₆-het, or R₅ is selected from a residue of an amino acid, wherein the alkyl. cycloalkyl, phenyl, and aryl substituents are unsubstituted or substituted;

Z₁ of Formula (VI) is, independently selected from —N(R₁₀)—C(O)—$C_{1-10}$-alkyl, —N(R₁₀)—C(O)—(CH₂)₀₋₆—$C_{3-7}$-cycloalkyl, —N(R₁₀)—C(O)—(CH₂)₀₋₆-phenyl, —N(R₁₀)—C(O)(CH₂)₁₋₆-het, —C(O)—N(R₁₁)(R₁₂), —C(O)—O—$C_{1-10}$-alkyl, —C(O)—O—(CH₂)₁₋₆—$C_{3-7}$-cycloalkyl, —C(O)—O—(CH₂)₀₋₆-phenyl, —C(O)—O—(CH₂)₁₋₆-het, —O—C(O)—$C_{1-10}$-alkyl, —O—C(O)—(CH₂)₁₋₆—$C_{3-7}$-cycloalkyl, —O—C(O)—(CH₂)₀₋₆-phenyl, —O—C(O)—(CH₂)₁₋₆-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

R₁₀ of Formula (VI) is selected from H, —CH₃, —CF₃, —CH₂OH, or —CH₂Cl;

R₁₁ and R₁₂ of Formula (VI) are independently selected from H, $C_{1-4}$-alkyl, $C_{3-7}$-cycloalkyl, —(CH₂)₁₋₆—$C_{3-7}$— cycloakyl. (CH₂)₀₋₆-phenyl, wherein alkyl. cycloalkyl, and phenyl are unsubstituted or substituted; or R₁₁ and R₁₂ together with the nitrogen form het, and U of Formula (VI) is, independently, as shown in Formula (VII):

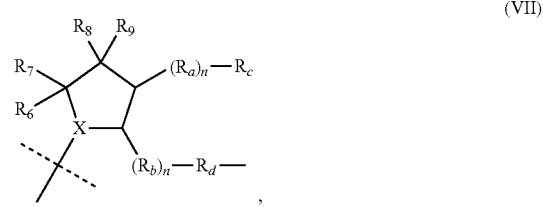

(VII)

wherein:
each n of Formula (VII) is, independently selected from 0 to 5;

X of Formula (VII) is selected from the group —CH and N;

R_a and R_b, of Formula (VII) are independently selected from the group O, S, or N atom or $C_{0-8}$-alkyl wherein one or more of the carbon atoms in the alkyl chain are optionally replaced by a heteroatom selected from O, S, or N, and where each alkyl is, independently, either unsubstituted or substituted;

R_d of Formula (VII) is selected from the group Re-Q-(R_f)_p(R_g)_q, and Ar₁-D-Ar₂;

R_c of Formula (VII) is selected from the group H or any R_c and R_d together form a cycloalkyl or het; where if R_c and R_d form a cycloalkyl or het. R₅ is attached to the formed ring at a C or N atom;

p and q of Formula (VII) are independently selected from 0 or 1;

$R_e$ of Formula (VII) is selected from the group $C_{1-8}$-alkyl and alkylidene, and each Re is either unsubstituted or substituted;

Q is selected from the group N, O, S. S(O), and S(O)$_2$;

$Ar_1$ and $Ar_2$ of Formula (VII) are independently selected from the group of substituted or unsubstituted aryl and het;

$R_f$ and $R_g$ of Formula (VII) are independently selected from H, —C1-10-alkyl, $C_{1-10}$-alkylaryl. —OH, —O—$C_{1-10}$-alkyl, —(CH$_2$)$_{0-6}$—$C_{3-7}$-cycloalky, —O—(CH$_2$)$_{0-6}$aryl, phenyl, aryl, phenyl-phenyl, —(CH$_2$)$_{1-6}$-het, —O—(CH$_2$)$_{1-6}$-het, —OR$_{13}$, —C(O)—R$_{13}$, —C(O)—N(R$_{13}$)(R$_{14}$). —N(R$_{13}$)(R$_{14}$), —S—R$_{13}$, —S(O)—R$_{13}$, —S(O)$_2$—R$_{13}$, —S(O)$_2$—NR$_{13}$R$_{14}$, —NR$_{13}$—S(O)$_2$—R$_{14}$, —S—C$_{t-10}$-alkyl, aryl-$C_{1-4}$-alkyl, or het-$C_{1-4}$-alkyl, wherein alkyl, cycloalkyl, het, and aryl are unsubstituted or substituted, —SO$_2$—$C_{1-2}$-alkyl, —SO$_2$—$C_{1-2}$-alkylphenyl, —O—$C_{1-4}$-alkyl, or any $R_g$ and $R_f$ together form a ring selected from het or aryl;

D of Formula (VII) is selected from the group —CO—, —C(O)—$C_{1-7}$-alkylene or arylene, —CF$_2$—, —O—, —S(O)$_r$ where r is 0-2, 1,3-dioxalane, or $C_{1-7}$-alkyl-OH: where alkyl, alkylene, or arylene are unsubstituted or substituted with one or more halogens, OH, —O—$C_{1-6}$-alkyl, —S—$C_{1-6}$-alkyl, or —CF$_3$: or each D is, independently selected from N(R$_b$);

Rh is selected from the group H, unsubstituted or substituted $C_{1-7}$-alkyl, aryl, unsubstituted or substituted —O—($C_{1-7}$-cycloalkyl). —C(O)—$C_{1-10}$-alkyl, —C(O)—$C_{0-10}$-alkyl-aryl, —C—O—$C_{01-10}$-alkyl, —C—O—$C_{0-10}$-alkyl-aryl, —SO$_2$—$C_{1-10}$-alkyl, or —SO$_2$—($C_{0-10}$-alkylaryl);

$R_6$, $R_7$, $R_8$, and $R_9$ of Formula (VII) are, independently, selected from the group H, —$C_{1-10}$-alkyl, —$C_{1-10}$-alkoxy, aryl-$C_{1-10}$-alkoxy. —OH. —O—$C_{1-10}$-alkyl, —(CH$_2$)$_{0-6}$—$C_{3-7}$-cycloalkyl, —O—(CH$_2$)$_{0-6}$-aryl, phenyl, —(CH$_2$)$_{1-6}$-het. —O—(CH$_2$)$_{1-6}$-het. —OR$_{13}$, —C(O)—R$_{13}$, —C(O)—N(R$_{13}$)(R$_{14}$). —N(R$_{13}$)(R$_{14}$), —S—R$_{13}$, —S(O)—R$_{13}$, —S(O)$_2$— R$_{13}$, —S(O)$_2$—NR$_{13}$R$_{14}$, or —NR$_{13}$—S(O)$_2$—R$_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H. $C_{1-10}$-alkyl, —(CH$_2$)$_{0-6}$— $C_{3-7}$-cycloalkyl, —(CH$_2$)$_{0-6}$— (CH)$_{0-1}$-(aryl)$_{1-2}$, —C(O)—$C_{1-10}$-alkyl, —C(O)—(CH$_2$)$_{1-6}$—$C_{3-7}$-cycloalkyl, —C(O)—O—(CH$_2$)$_{0-6}$-aryl, —C(O)—(CH$_2$)$_{0-6}$—O-fluorenyl, —C(O)—NH—(CH$_2$)$_{0-6}$-aryl, —C(O)—(CH$_2$)$_{0-6}$-aryl, —C(O)—(CH$_2$)$_{0-6}$-het, —C(S)—$C_{1-10}$-alkyl, —C(S)—(CH$_2$)$_{1-6}$—$C_{3-7}$-cycloalkyl, —C(S)—O—(CH$_2$)$_{0-6}$-aryl, —C(S)—(CH$_2$)$_{0-6}$—O-fluorenyl, —C(S)—NH—(CH$_2$)$_{0-6}$-aryl, —C(S)—(CH$_2$)$_{0-6}$-aryl, or —C(S)—(CH$_2$)$_{1-6}$-het, wherein each alkyl, cycloalkyl, and aryl is unsubstituted or substituted: or any $R_{13}$ and $R_{14}$ together with a nitrogen atom form het;

wherein alkyl substituents of $R_{13}$ and $R_{14}$ of Formula (VII) are unsubstituted or substituted and when substituted, are substituted by one or more substituents selected from $C_{1-10}$-alkyl, halogen, OH, —O—$C_{1-6}$-alkyl, —S—$C_{1-6}$-alkyl, and —CF$_3$: and substituted phenyl or aryl of $R_{13}$ and $R_{14}$ are substituted by one or more substituents selected from halogen. hydroxyl, $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from $R_4$ and $R_5$. For example, an ILM of Formula (VI) and a second ILM of Formula (VI), or an unnatural mimetic thereof, can be linked as shown below:

(A)

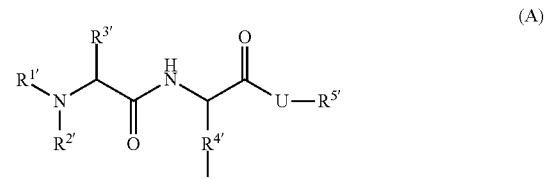

(B)

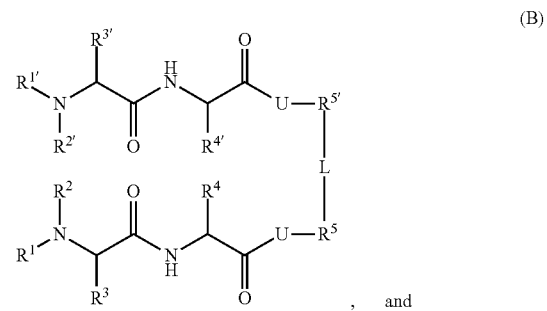

, and (C)

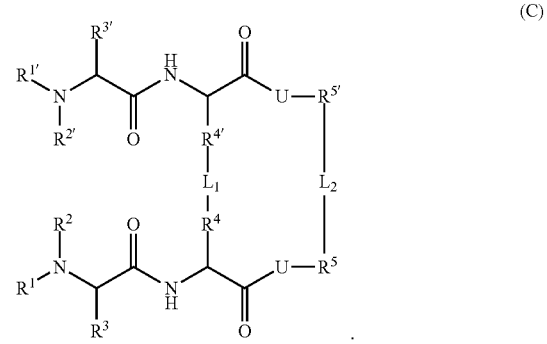

In certain embodiments, the ILM, the at least one additional independently selected linker group L, and the second ILM has a structure selected from the group consisting of:
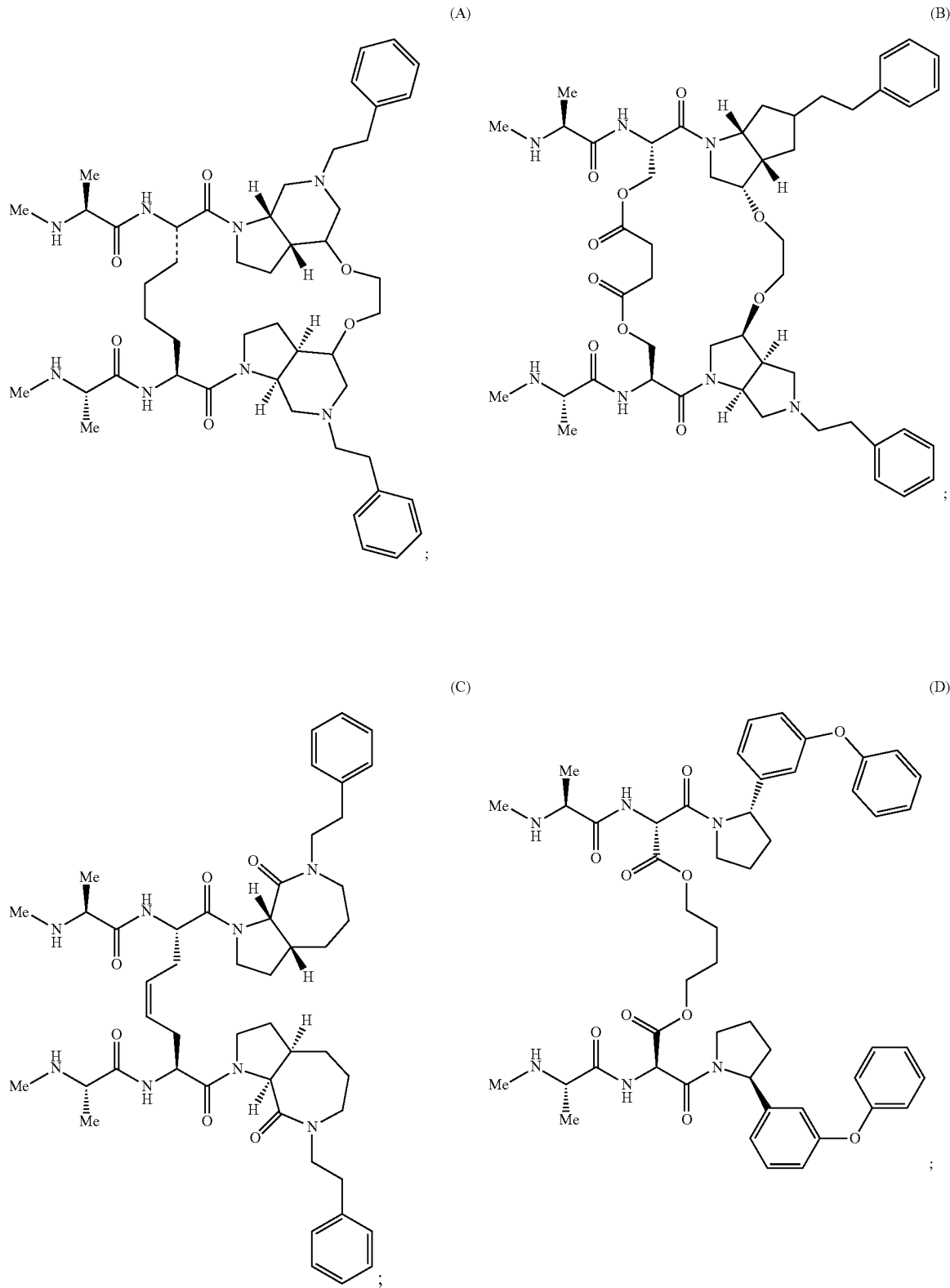

(E)

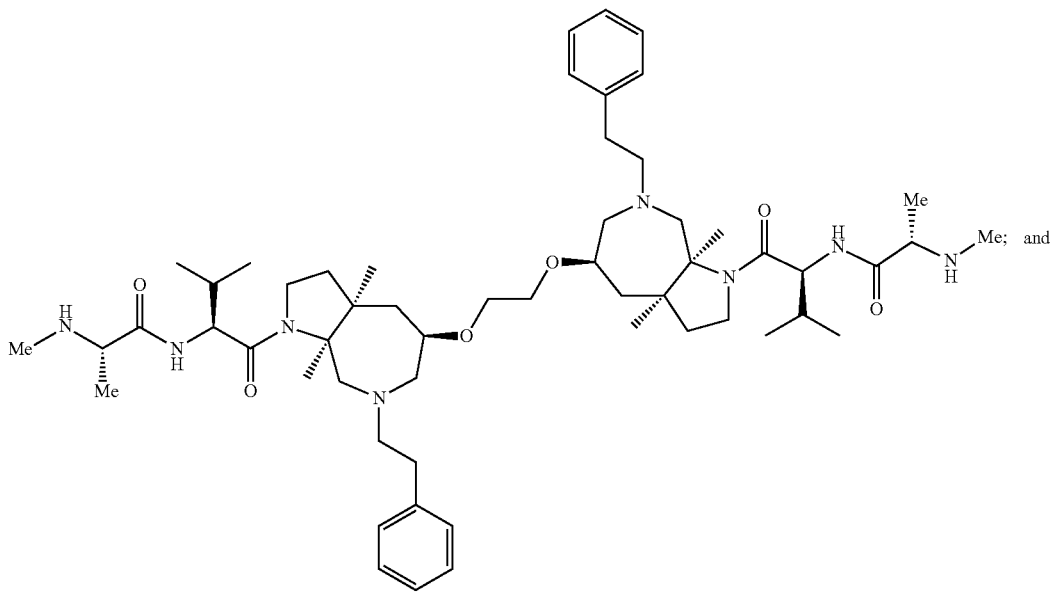

(F)

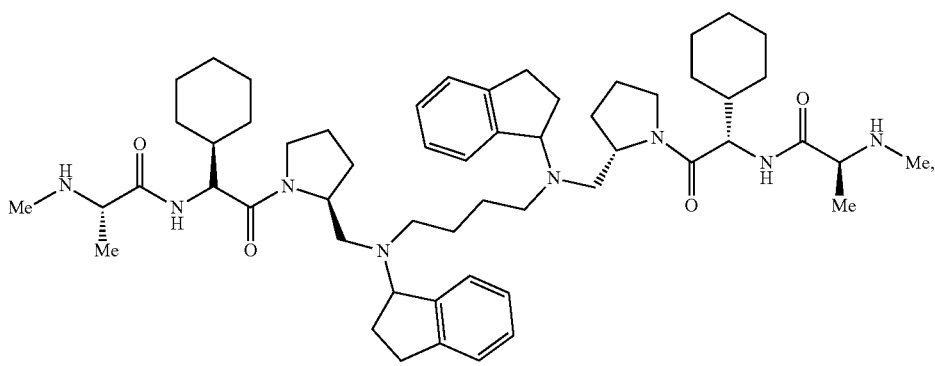

which are derivatives of IAP antagonists described in WO Pub. No. 2008/014236.

In any of the compounds described herein, the ILM can have the structure of Formula (VIII), which is based on the IAP ligrands described in Ndubaku, C., et al. Antagonism of c-IAP and XIAP proteins is required for efficient induction of cell death by small-molecule IAP antagonists, *ACS Chem. Biol.*, 557-566, 4 (7) (2009), or an unnatural mimetic thereof:

(VIII)

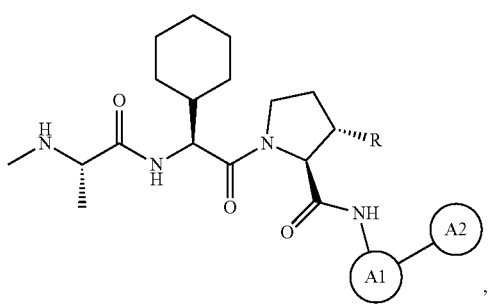

wherein each of A1 and A2 of Formula (VIII) is independently selected from optionally substituted monocyclic, fused rings, aryls and hetoroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of (A)

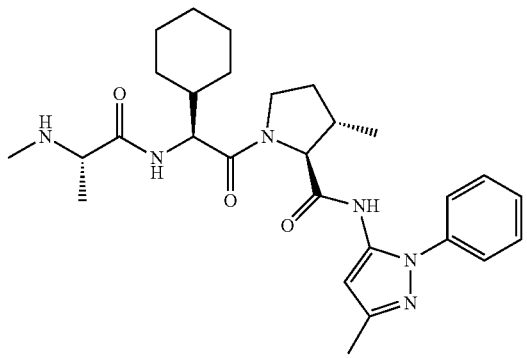

and

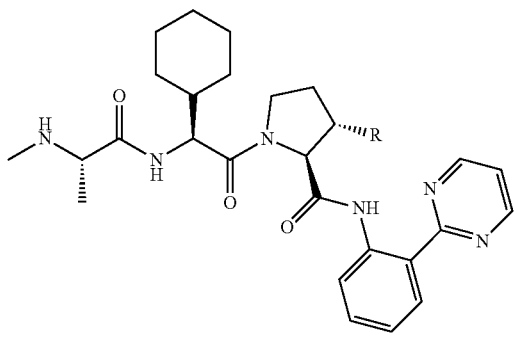

(B)

In any of the compounds described herein, the ILM can have the structure of Formula (IX), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

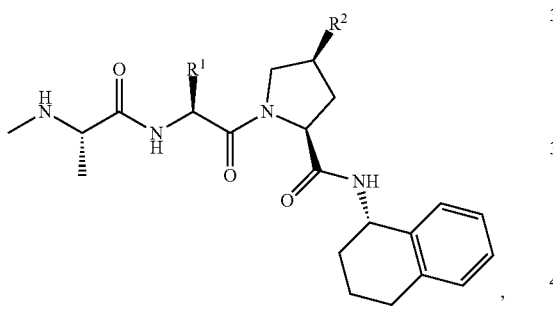

(IX)

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

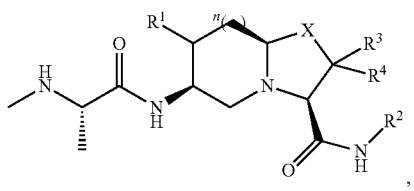

(X)

n = 1, 2, 3 wherein:
$R^1$ of Formula (X) is selected from H, —CH$_2$OH, —CH$_2$CH$_2$OH, —CH$_2$NH$_2$, —CH$_2$CH$_2$NH$_2$;
X of Formula (X) is selected from S or CH$_2$;
$R^2$ of Formula (X) is selected from:

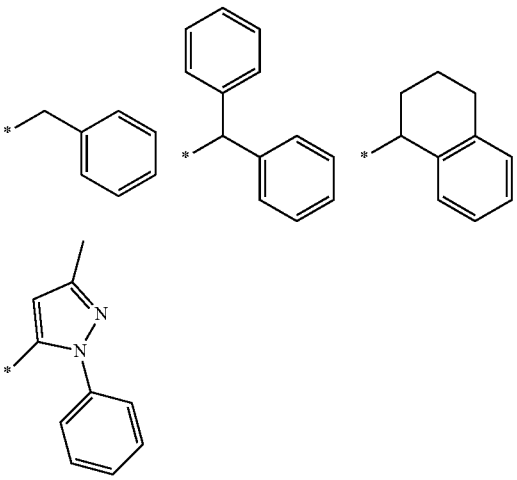

$R^3$ and $R^4$ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

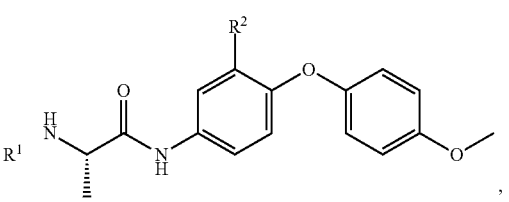

(XI)

wherein $R^1$ of Formula (XI) is selected from H or Me, and $R^2$ of Formula (XI) is selected from H or

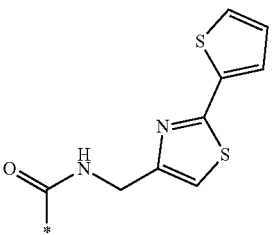

In any of the compounds described herein, the ILM can have the structure of Formula (XII), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:
(XII)
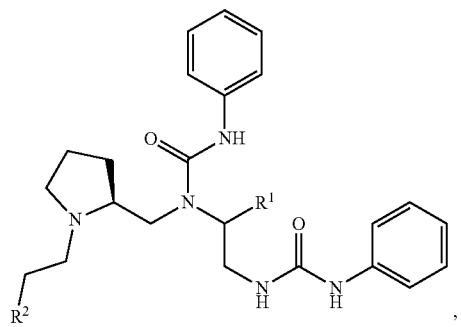
wherein:
$R^1$ of Formula (XII) is selected from:
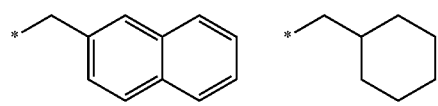
and
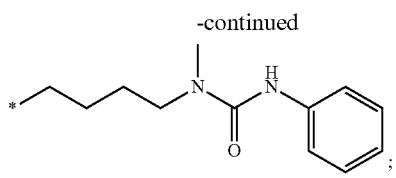
;
and
$R^2$ of Formula (XII) is selected from:
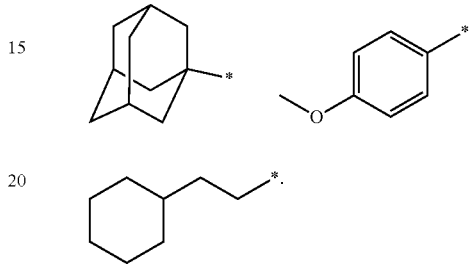
In any of the compounds described herein, the IAP E3 ubiquitin ligase binding moiety is selected from the group consisting of:
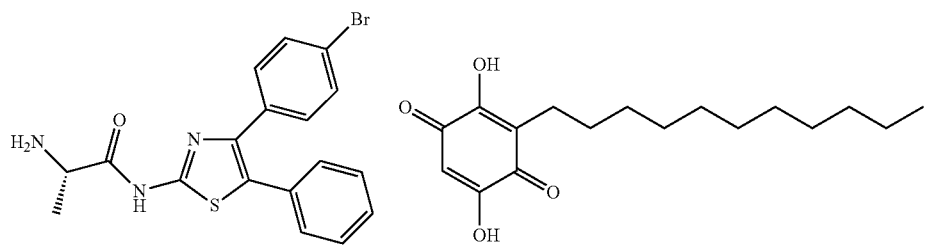
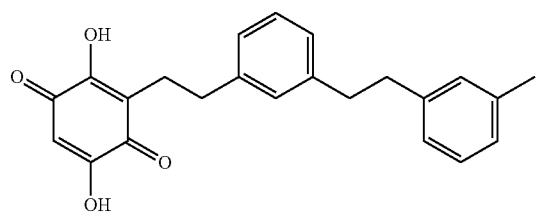
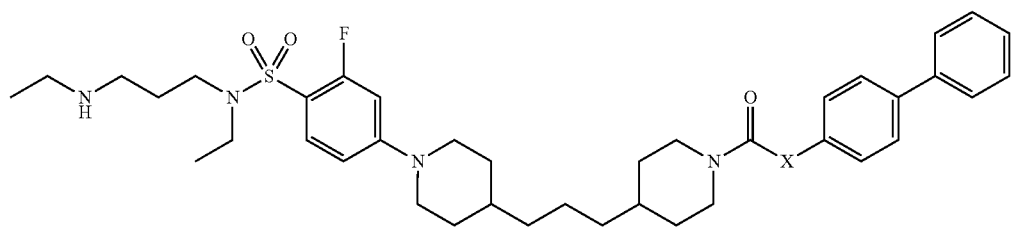

-continued
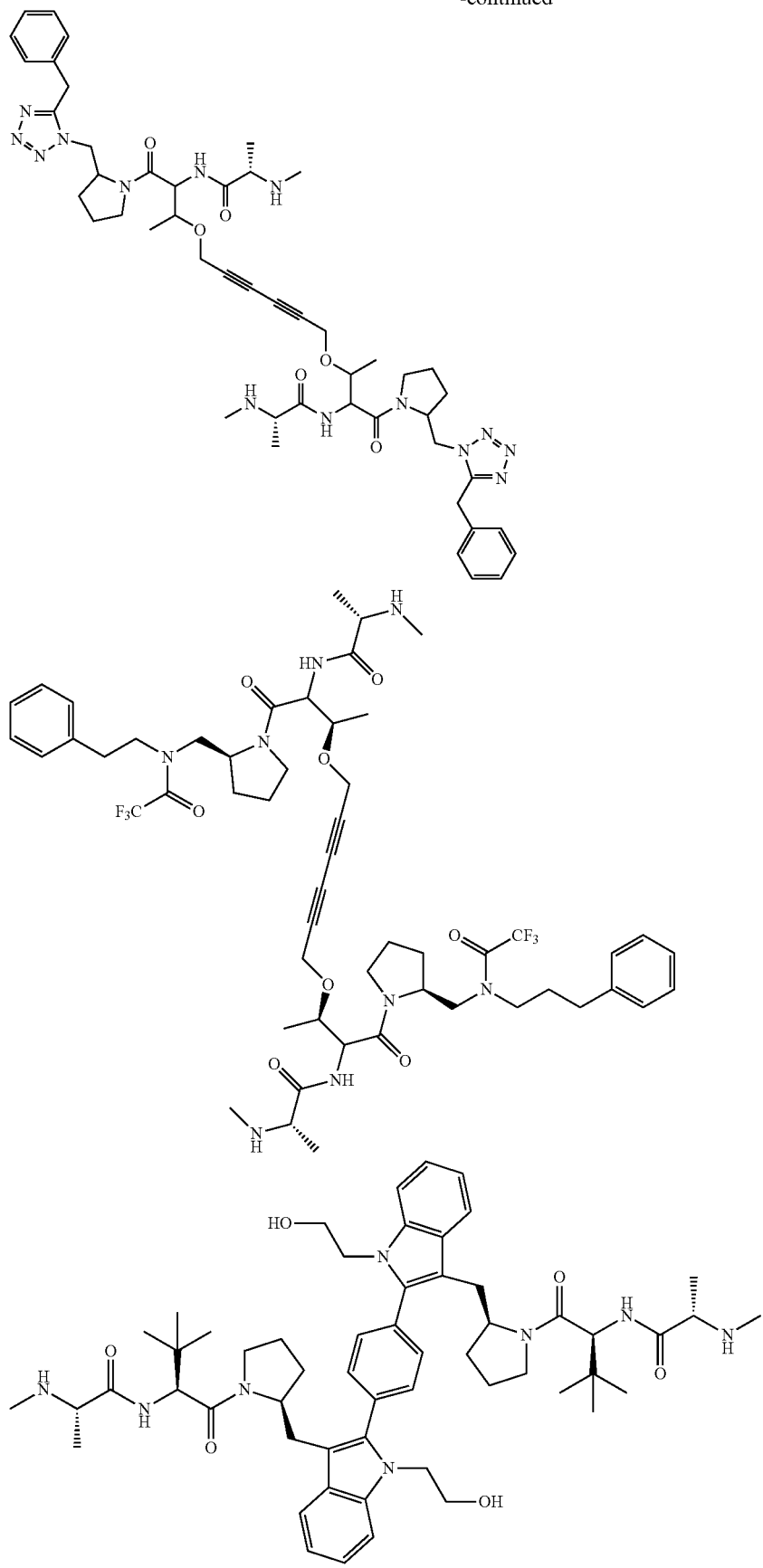

31 32
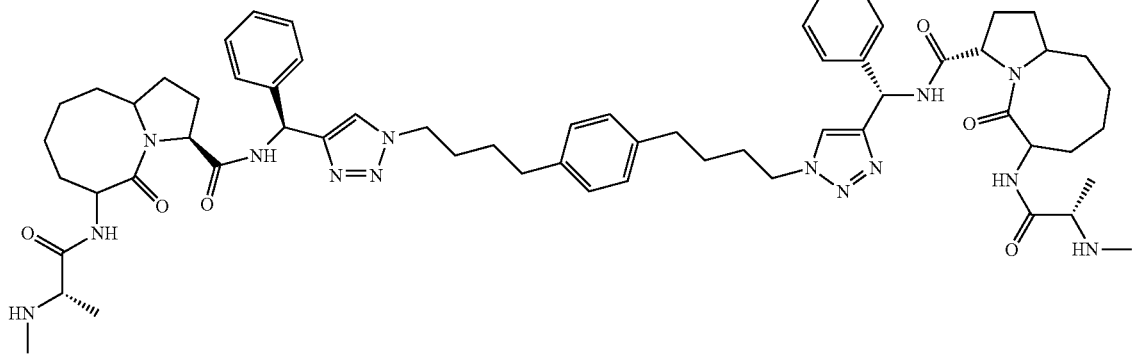
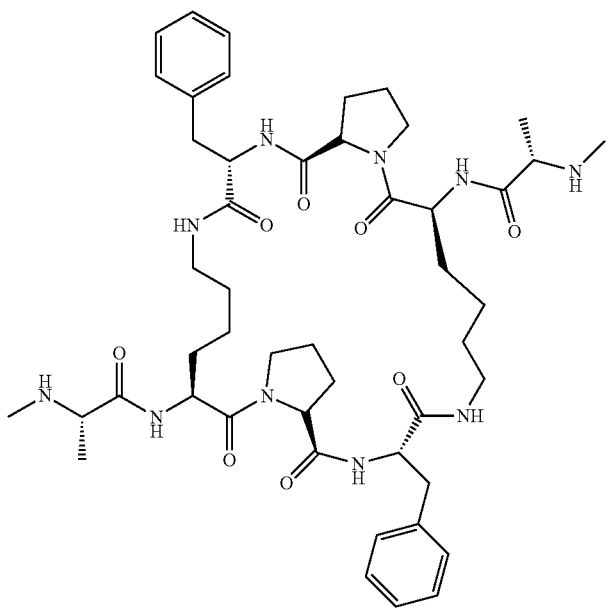
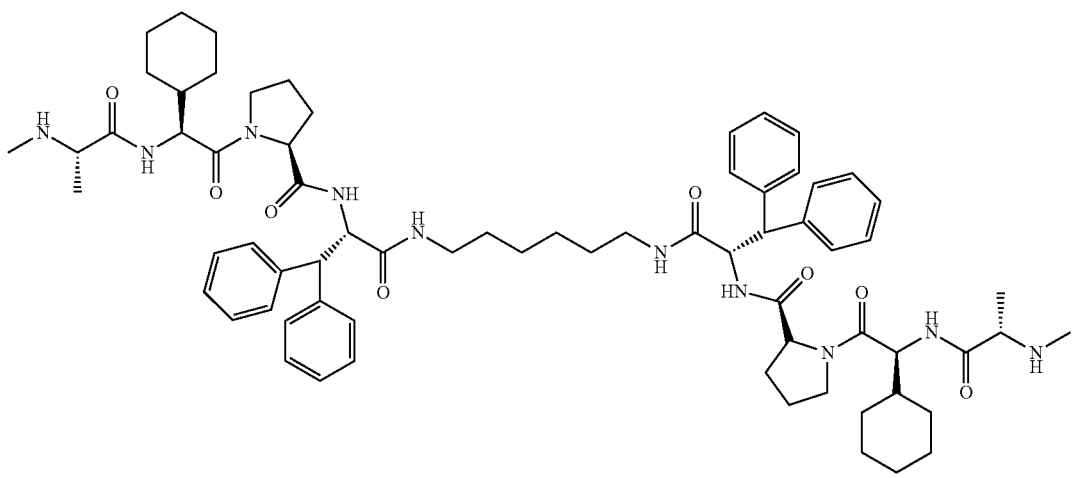
and

-continued

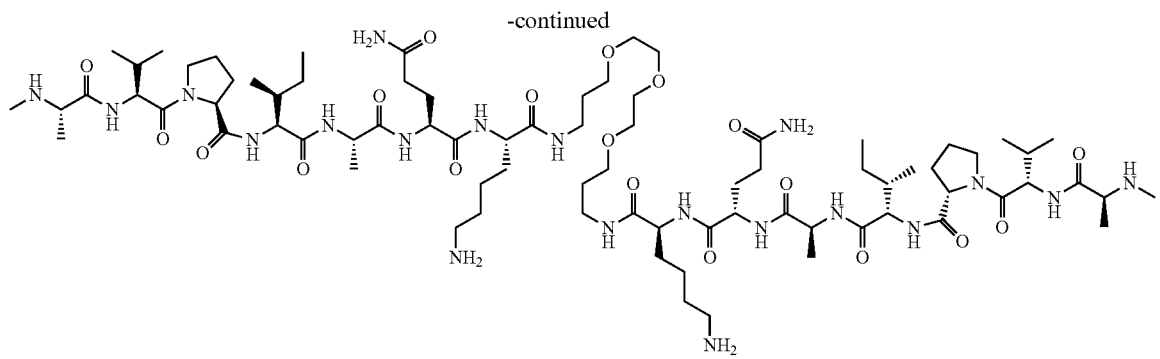

X = NH, bond

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

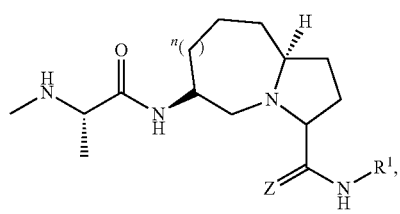
(XIII)

n = 0, 2 or, preferably, 1 wherein:
Z of Formula (XIII) is absent or O;
R¹ of Formula (XIII) is selected from:

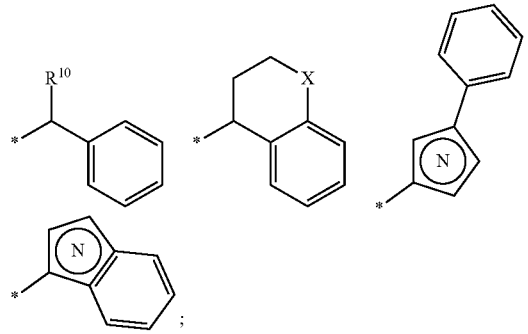

R¹⁰ of

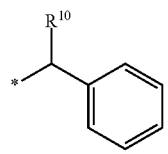

is selected from H, alkyl, or aryl;

X is selected from CH2 and O; and

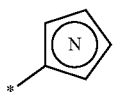

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

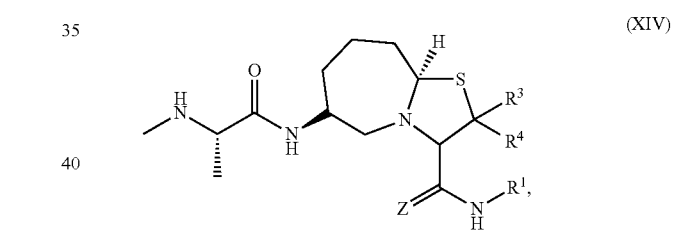
(XIV)

wherein:
Z of Formula (XIV) is absent or O;
R³ and R⁴ of Formula (XIV) are independently selected from H or Me;
R¹ of Formula (XIV) is selected from:

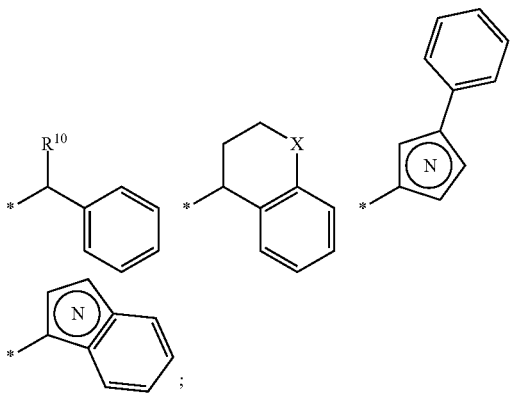

R[10] of

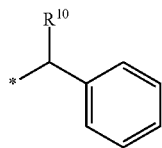

is selected from H, alkyl, or aryl;

X of

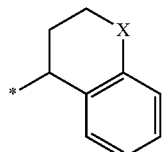

is selected from CH2 and O; and

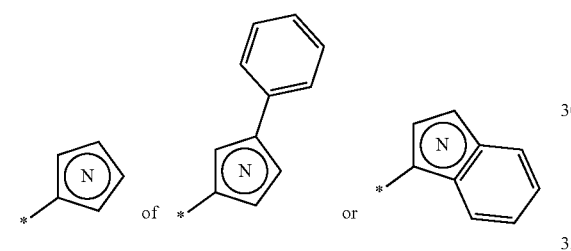

is a nitrogen-containing heteraryl.

In any of the compounds described herein, the ILM is selected from the group consisting of:

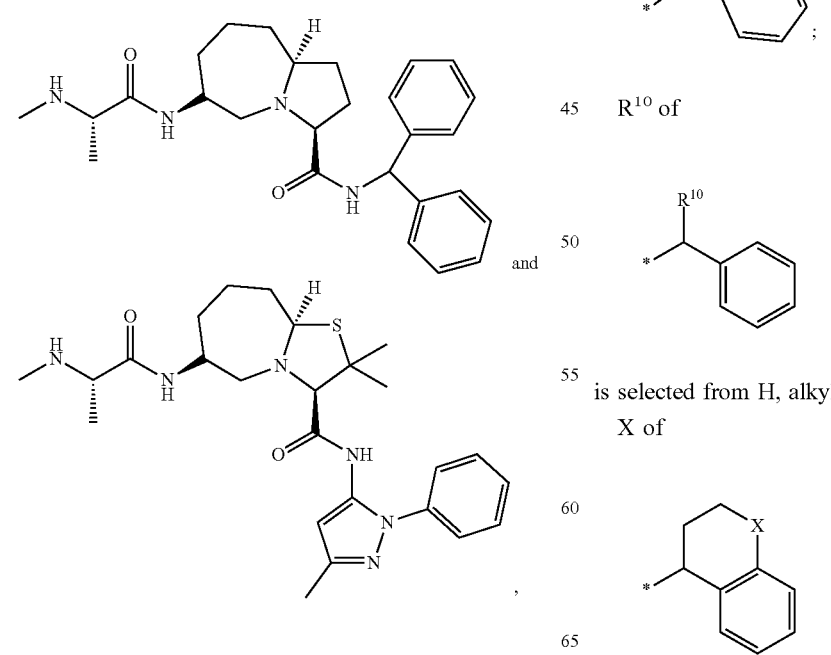

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

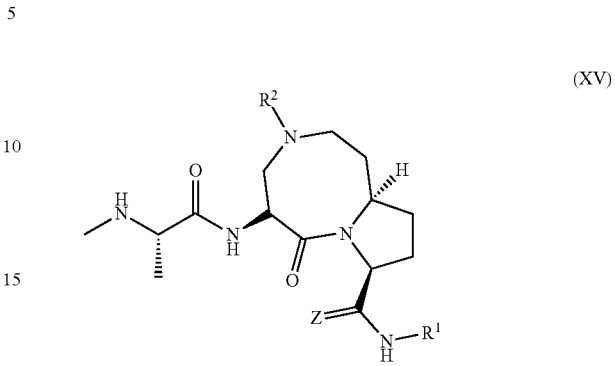

(XV)

wherein:

Z of Formula (XV) is absent or O;

R[1] of Formula (XV) is selected from:

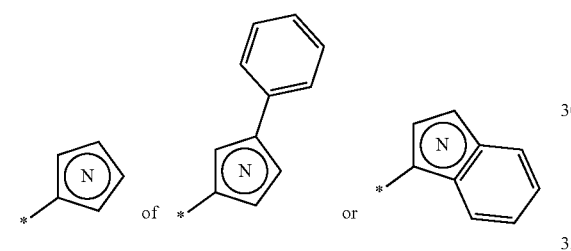

;

R[10] of

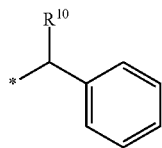

is selected from H, alkyl, or aryl;

X of

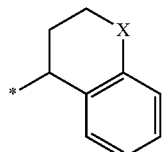

is selected from CH2 and O; and

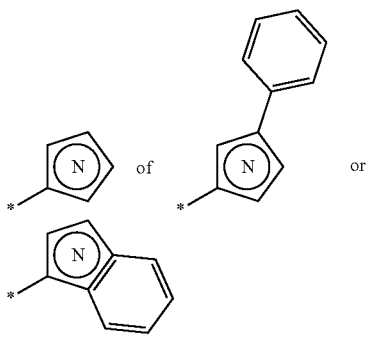

is a nitrogen-containing heteraryl; and

R² of Formula (XV) selected from H, alkyl, or acyl;

In a particular embodiment, the ILM has the following structure:

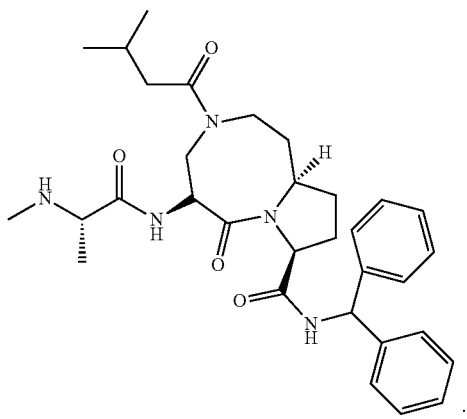

In any of the compounds described herein, the ILM can have the structure of Formula (XVI), which is based on the IAP ligand described in WO Pub. No. 2006/069063, or an unnatural mimetic thereof:

(XVI)

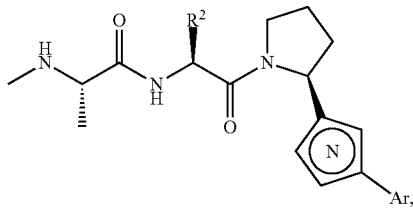

wherein:

R² of Formula (XVI) is selected from alkyl, cycloalkyl and heterocycloalkyl; more preferably, from isopropyl, tert-butyl, cyclohexyl and tetrahydropyranyl, most preferably from cyclohexyl;

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVII)

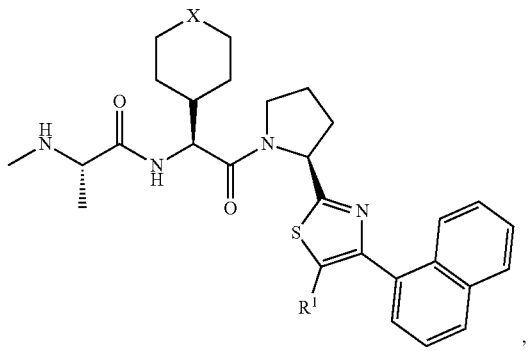

wherein:

R¹ of Formula (XVII) is selected from the group halogen (e.g. fluorine), cyano,

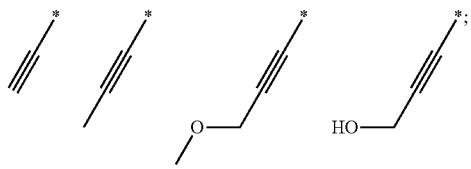

X of Formula (XVII) is selected from the group O or CH2.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVIII)

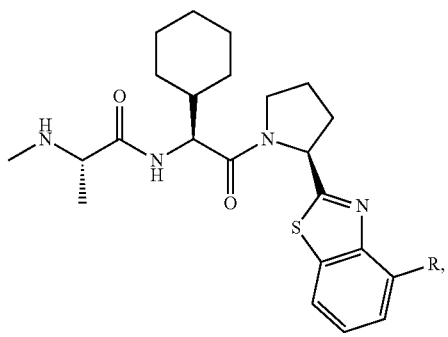

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antogonists of inhibitors of apoptosis proteins based on thiazole amide isosteres*, Bioorg. Med. Chem. Lett., 20(7), 2229-33 (2010), or an unnatural mimetic thereof:

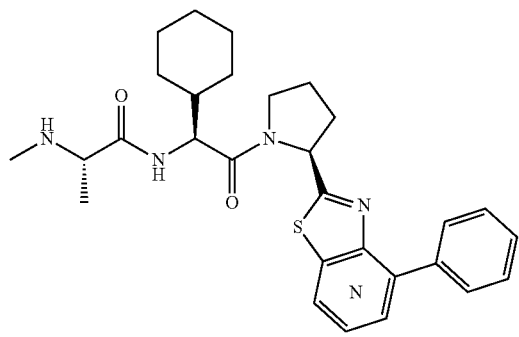
(XIX)

wherein

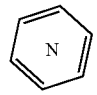

is a 6-member nitrogen heteroaryl.

In a certain embodiment, the ILM of the composition is selected from the group consisting of:

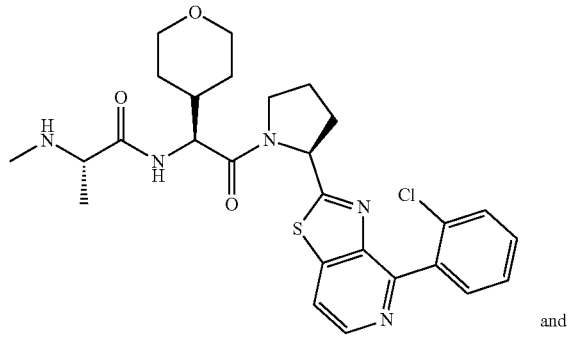
and

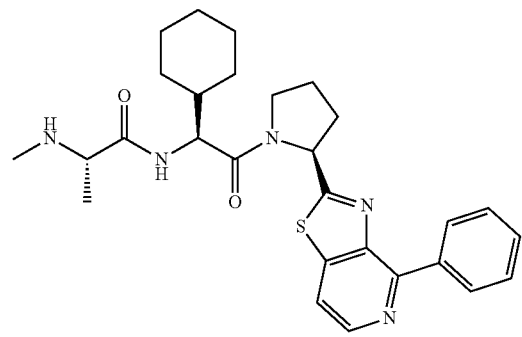
,

In certain embodiments, the ILM of the composition is selected from the group consisting of:

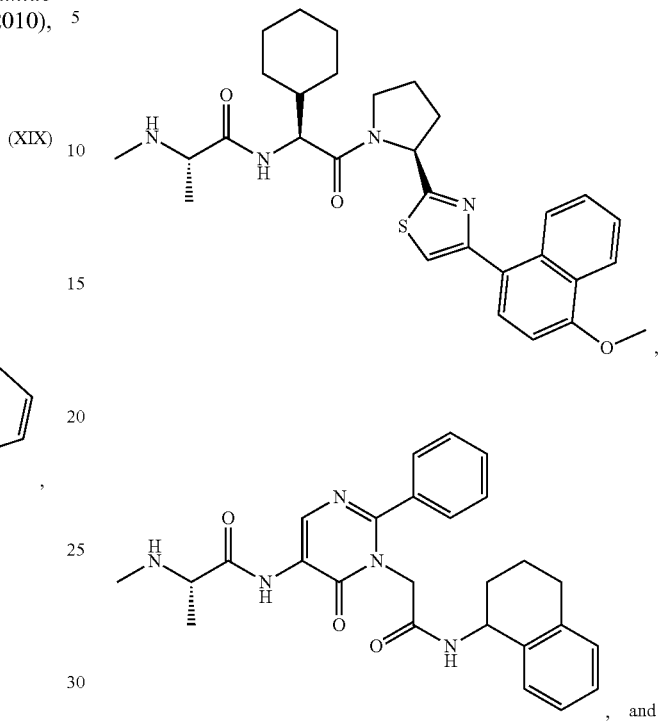

In any of the compounds described herein, the ILM can have the structure of Formula (XX), which is based on the IAP ligands described in WO Pub. No. 2007/101347, or an unnatural mimetic thereof:

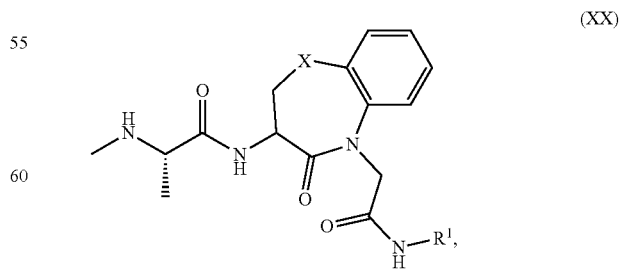
(XX)

wherein X of Formula (XX) is selected from $CH_2$, O, NH, or S.

In any of the compounds described herein, the ILM can have the structure of Formula (XXI), which is based on the AP ligands described in U.S. Pat. Nos. 7,345,081 and 7,419,975, or an unnatural mimetic thereof:

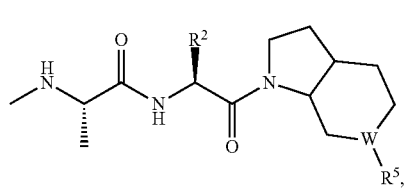
(XXI)

wherein:
R² of Formula (XXI) is selected from:

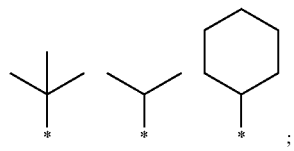

R⁵ of Formula (XXI) is selected from:

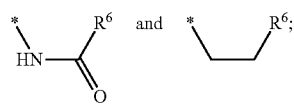

and
W of Formula (XXI) is selected from CH or N; and R⁶ of

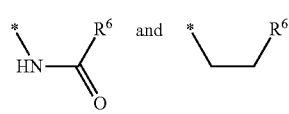

are independently a mono- or bicyclic fused aryl or heteroaryl.

In certain embodiments, the ILM of the compound is selected from the group consisting of:

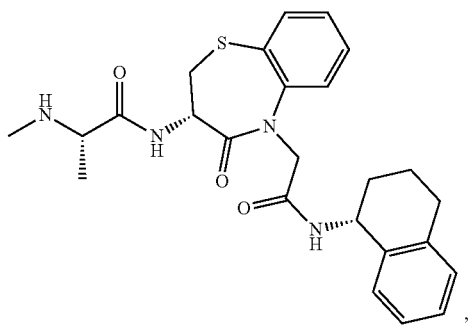
,

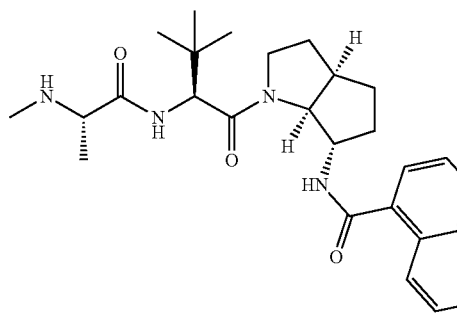
, and

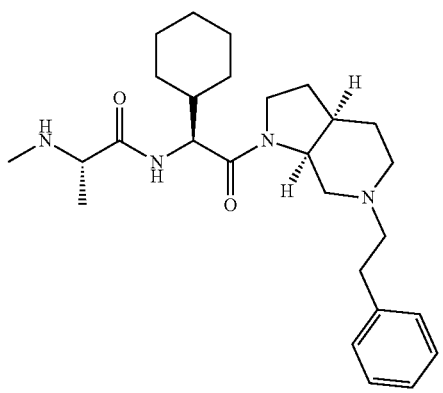

In certain embodiments, the ILM of the compound is selected from the group consisting of:
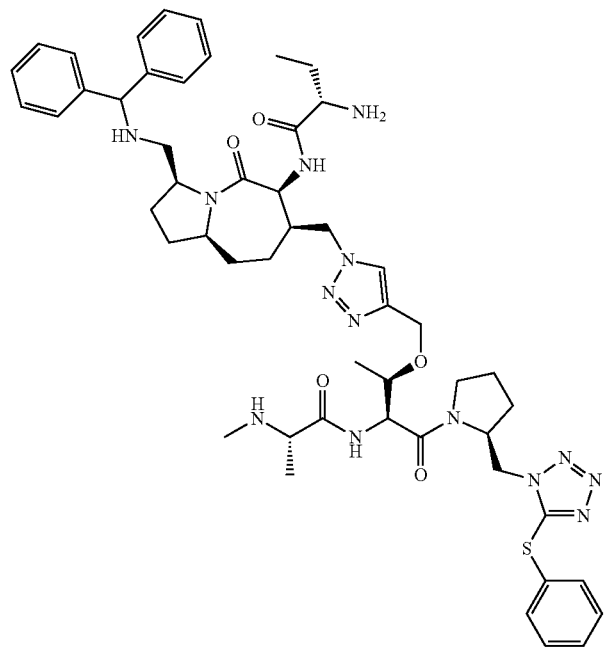
,
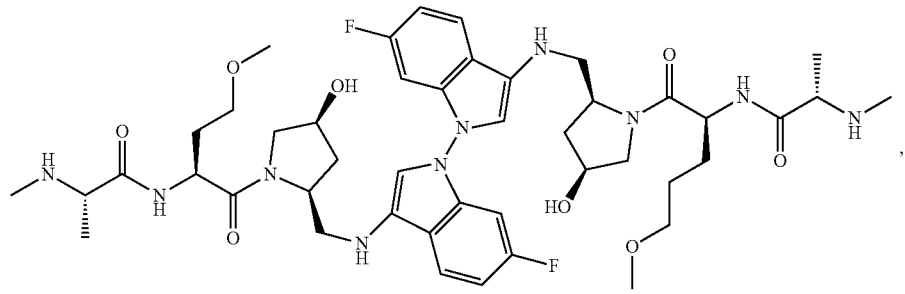
,
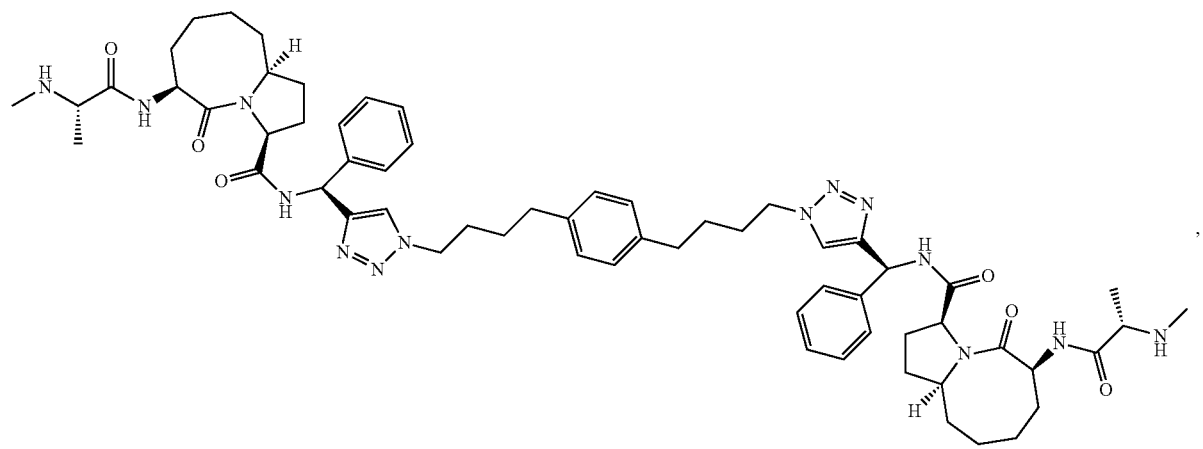
,

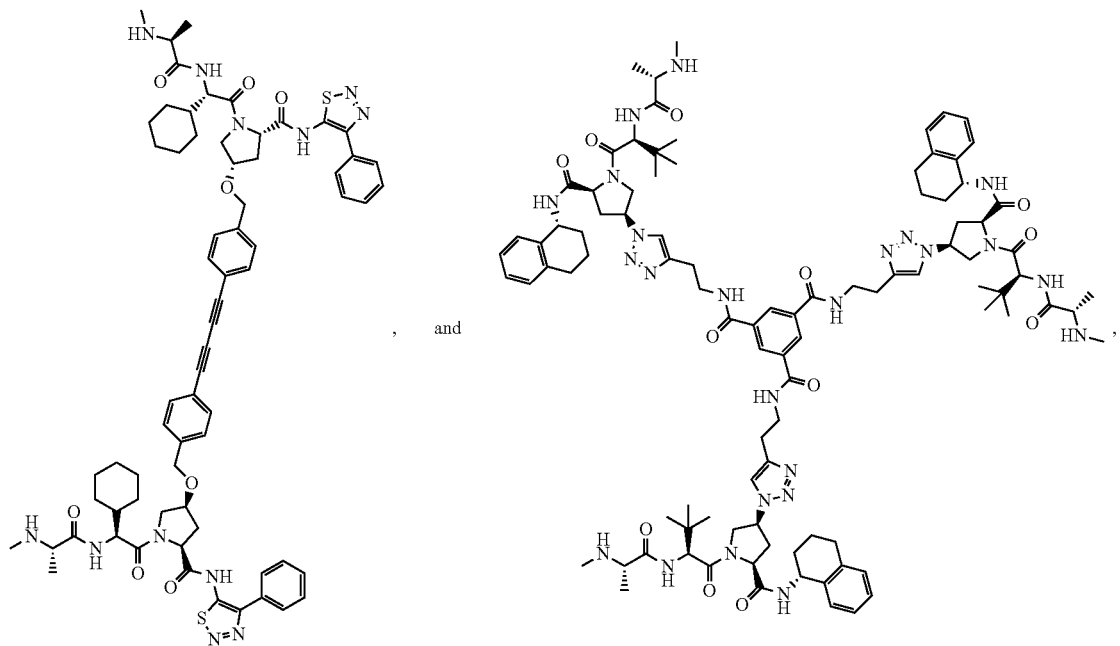 [SMILES: CN[C@@H](C)C(=O)N[C@H](C(=O)N1C[C@@H](OCc2ccc(C#CC#Cc3ccc(CO[C@H]4C[C@@H](C(=O)Nc5snnc5-c5ccccc5)N(C(=O)[C@@H](NC(=O)[C@H](C)NC)C5CCCCC5)C4)cc3)cc2)C[C@H]1C(=O)Nc1snnc1-c1ccccc1)C1CCCCC1 ; CN[C@@H](C)C(=O)N[C@H](C(=O)N1C[C@@H](n2cc(CCNC(=O)c3cc(C(=O)NCCc4cn([C@H]5C[C@@H](C(=O)N[C@@H]6CCCc7ccccc76)N(C(=O)[C@@H](NC(=O)[C@H](C)NC)C(C)(C)C)C5)nn4)cc(C(=O)NCCc4cn([C@H]5C[C@@H](C(=O)N[C@@H]6CCCc7ccccc76)N(C(=O)[C@@H](NC(=O)[C@H](C)NC)C(C)(C)C)C5)nn4)c3)nn2)C[C@H]1C(=O)N[C@@H]1CCCc2ccccc21)C(C)(C)C]

, and which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

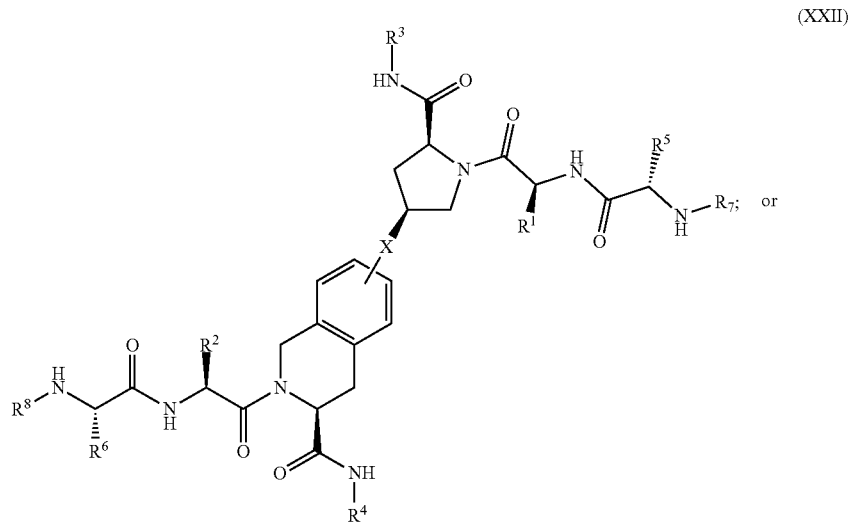

(XXII)

-continued

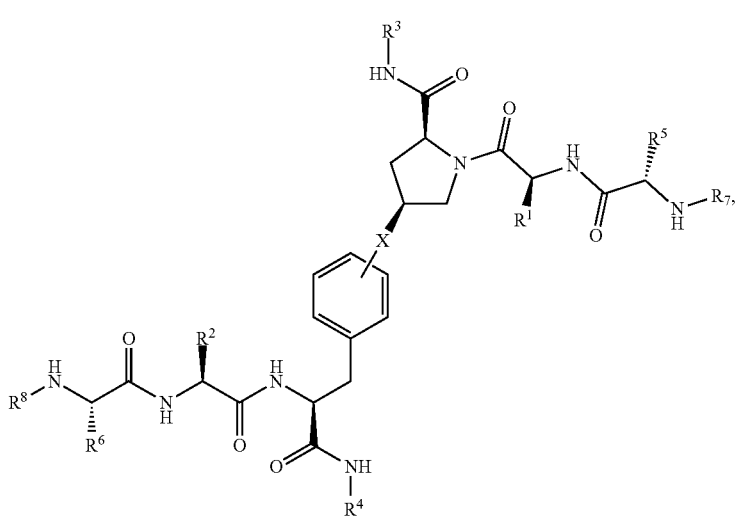

(XXIII)

wherein:
- R[1] of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;
- R[2] of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;
- or alternatively, R[1] and R[2] of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, —(CH$_2$)$_v$COR[20], —CH$_2$CHR[21]COR[22] or —CH$_2$R[23];

wherein:
- v is an integer from 1-3;
- R[20] and R[22] of —(CH$_2$)$_v$COR[20] and —CH$_2$R[23] are independently selected from OH, NR[24]R[25] or OR[26];
- R[21] of —CH$_2$CHR[21]COR[2] is selected from the group NR[24]R[25];
- R[23] of —CH$_2$R[23] is selected from optionally substituted aryl or optionally substituted heterocyclyl, where the optional substituents include alkyl and halogen;
- R[24] of NR[24]R[25] is selected from hydrogen or optionally substituted alkyl;
- R[25] of NR[24]R[25] is selected from hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine;
- R[26] of OR[26] is selected from optionally substituted alkyl, wherein the optional substituents are OH, halogen or NH$_2$; and
- m is an integer from 1-8;
- R[3] and R[4] of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
- R[5], R[6], R[7] and R[8] of Formula (XXII) or (XXIII) are independently selected from hydrogen, optionally substituted alkyl or optionally substituted cycloalkyl; and
- X is selected from a bond or a chemical linker group, and/or a pharmaceutically acceptable salt, tautomer or stereoisomer thereof.

In certain embodiments, X is a bond or is selected from the group consisting of:

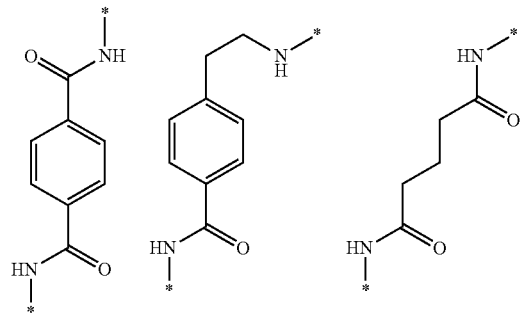

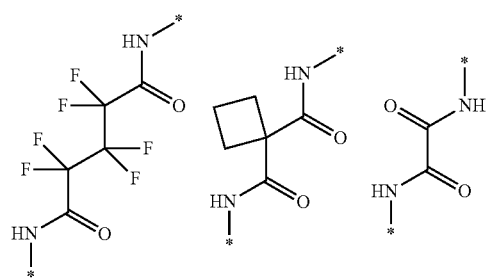

-continued

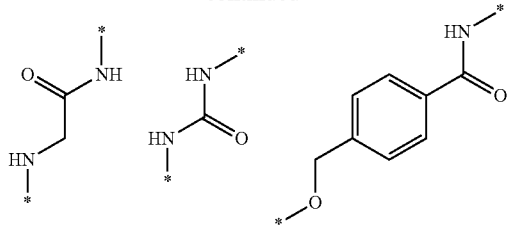

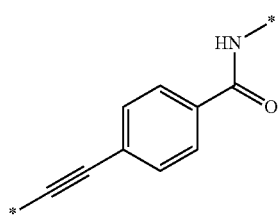

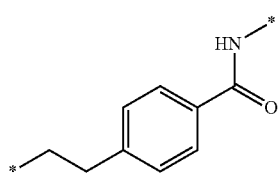

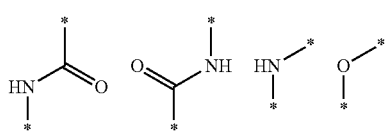

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof, and the chemical linker to linker group L as shown:

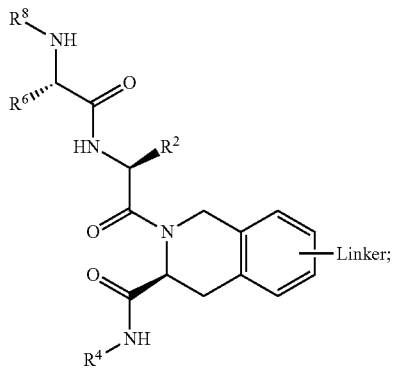

wherein:

$R^1$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

R² of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

or alternatively,

R¹ and R² of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, —(CH₂)ᵥCOR²⁰, —CH₂CHR²¹COR²² or —CH₂R²³, wherein:

v is an integer from 1-3;

R²⁰ and R²² of —(CH₂)ᵥCOR²⁰ and —CH₂R²³ are independently selected from OH, NR²⁴R²⁵ or OR²⁶;

R²¹ of —CH₂CHR²¹COR² is selected from NR²⁴R²⁵;

R²³ of —CH₂R²³ is selected from optionally substituted aryl or optionally substituted heterocyclyl, wherein the optional substituents include alkyl and halogen;

R²⁴ of NR²⁴R²⁵ is selected from hydrogen or optionally substituted alkyl;

R²⁵ of NR²⁴R²⁵ is selected from hydrogen, optionally substituted alkyl, optionally substituted branched alkyl, optionally substituted arylalkyl, optionally substituted heterocyclyl, —CH₂(OCH₂CH₂O)ₘCH₃, or a polyamine chain, such as spermine or spermidine;

R²⁶ of OR²⁶ is selected from optionally substituted alkyl, wherein the optional substituents are OH, halogen or NH₂; and m is an integer from 1-8;

R³ and R⁴ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R⁵, R⁶, R⁷ and R⁸ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):

R⁷ and R⁸ are selected from the H or Me;

R⁵ and R⁶ are selected from the group comprising:

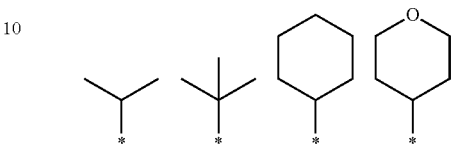

R³ and R⁴ are selected from the group comprising:

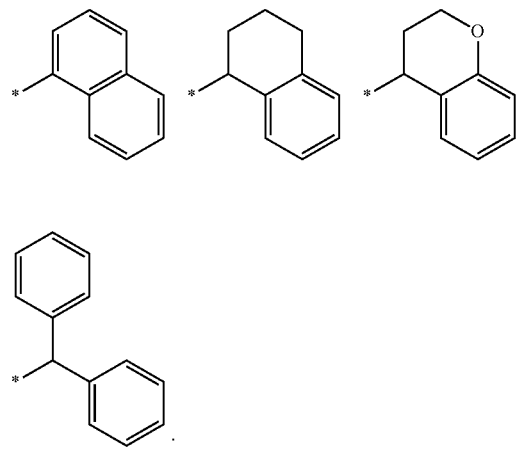

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof:

(XXVII)

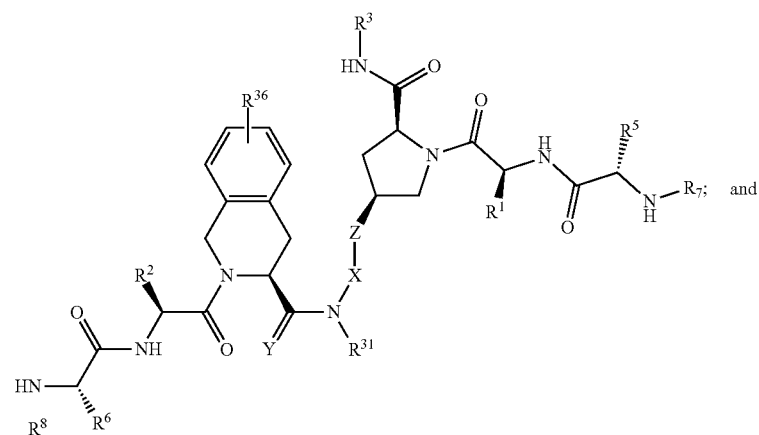

(XXVIII)

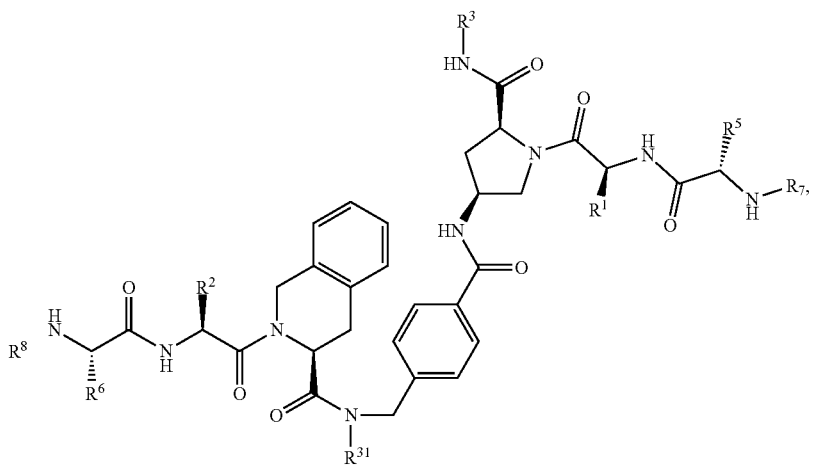

wherein:
R$^{35}$ is 1-2 substituents selected from alkyl, halogen, alkoxy, cyano and haloalkoxy;

R$^1$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

R$^2$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

or alternatively,

R$^1$ and R$^2$ of Formula (XXVII) and (XXVIII) are independently selected from an optionally substituted thioalkyl —CR$^{60}$R$^{61}$SR$^{70}$, wherein R$^{60}$ and R$^{61}$ are selected from H or methyl, and R$^{70}$ is selected from an optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$, wherein:

v is an integer from 1-3;

R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;

R$^{21}$ of —CH$_2$CHR$^{21}$COR$^{22}$ is selected from NR$^{24}$R$^{25}$;

R$^{23}$ of —CH$_2$R$^{23}$ is selected from an optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$CH$_2$(OCH$_2$CH$_2$)$_m$CH$_3$, or a polyamine chain —[CH$_2$CH$_2$(CH$_2$)$_\delta$NH]$_\psi$CH$_2$CH$_2$(CH$_2$)$_{\overline{\omega}}$NH$_2$, such as spermine or spermidine;

wherein $\delta$=0-2, $\psi$=1-3, $\overline{\omega}$=0-2;

R$^{26}$ of OR$^{26}$ is an optionally substituted alkyl, wherein the optional substituents are OH, halogen or NH$_2$; and m is an integer from 1-8, R$^3$ and R$^4$ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$, R$^6$, R$^7$ and R$^8$ of Formula (XXVII) and (XXVIII) are independently selected from hydrogen, optionally substituted alkyl or optionally substituted cycloalkyl;

R$^{31}$ of Formulas (XXVII) and (XXVIII) is selected from alkyl, aryl, arylalkyl, heteroaryl or heteroarylalkyl optionally further substituted, preferably selected form the group consisting of:

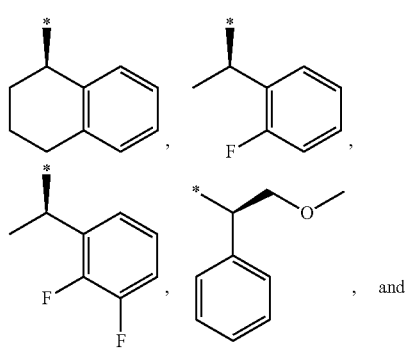

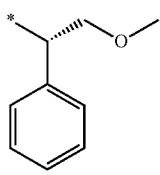

X of Formulas (XXVII) and (XXVIII) is selected from —(CR$^{81}$R$^{82}$)$_m$—, optionally substituted heteroaryl or heterocyclyl,

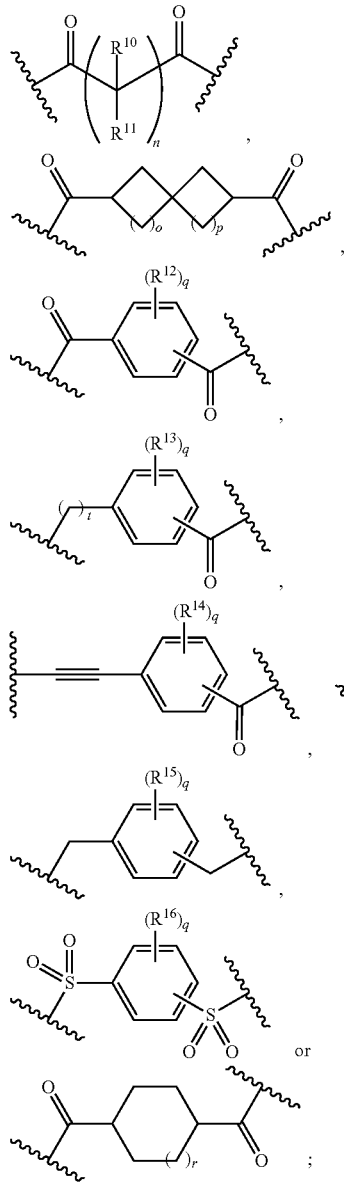

Z of Formulas (XXVII) is selected from C=O, —O—, —NR, —CONH—, —NHCO—, or may be absent;

R$^{81}$ and R$^{82}$ of —(CR$^{81}$R$^{82}$)$_m$— are independently selected from hydrogen, halogen, alkyl or cycloalkyl, or R$^{81}$ and R$^{82}$ can be taken together to form a carbocyclic ring;

R$^{10}$ and R$^{11}$ of

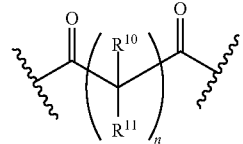

are independently selected from hydrogen, halogen or alkyl;

R$^{12}$, R$^{13}$, R$^{14}$, R$^{15}$ and R$^{16}$ of

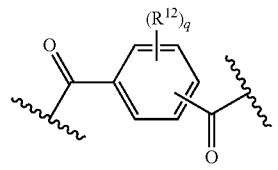

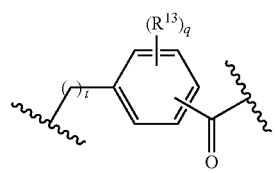

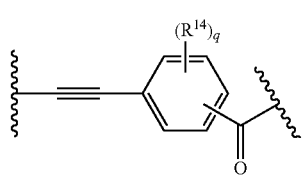

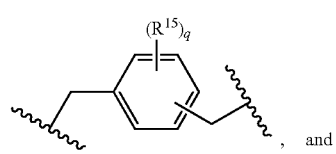, and

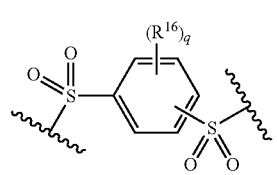

are independently selected from hydrogen, halogen or optionally substituted alkyl or OR$^{17}$;

$R^{17}$ is selected from hydrogen, optionally substituted alkyl or optionally substituted cycloalkyl;

m and n of $-(CR^{21}R^{22})_m-$ and

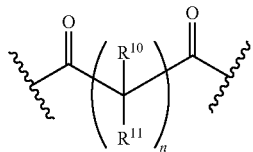

are independently 0, 1, 2, 3, or 4;
o and p of

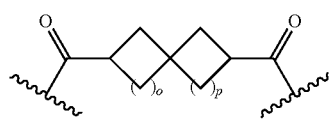

are independently 0, 1, 2 or 3;
q and t of

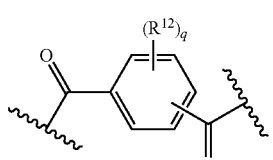

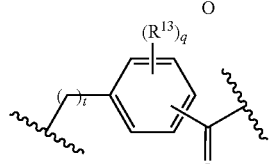

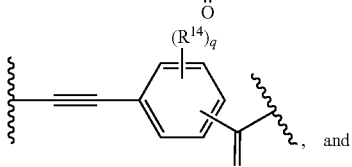

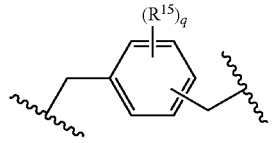

are independently 0, 1, 2, 3, or 4;
r of

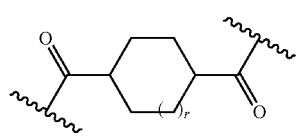

is 0 or 1;
and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

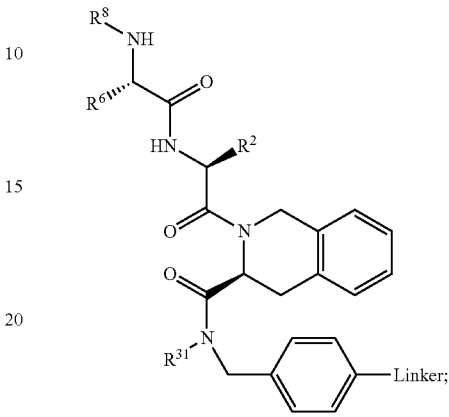

(XXIX)

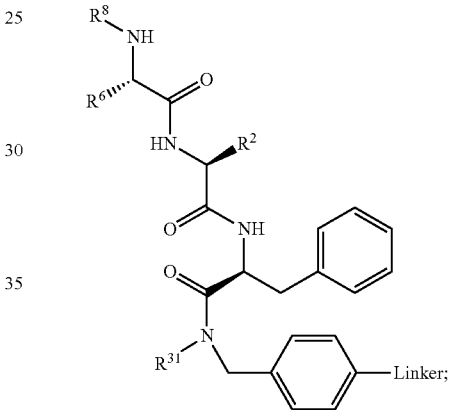

(XXX)

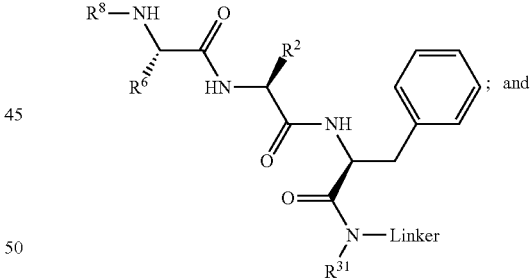

(XXXI)

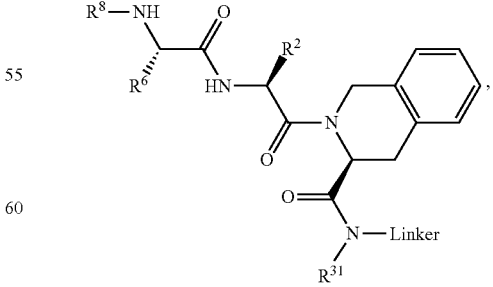

(XXXII)

wherein:
$R^2$ of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl;

or alternatively;

$R^1$ and $R^2$ of Formula (XXVII) and (XXVIII) are independently selected from H, an optionally substituted thioalkyl —$CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{25}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^2$ of $NR^{24}R^{25}$ is selected from hydrogen, optionally substituted alkyl, optionally substituted branched alkyl, optionally substituted arylalkyl, optionally substituted heterocyclyl, ——$CH_2CH_2(OCH_2CH_2)_mCH_3$, or a polyamine chain —$[CH_2CH_2(CH_2)_\delta NH]CH_2CH_2(CH_2)\overline{\omega}_\psi NH_2$, such as spermine or spermidine, wherein $\delta$=0-2, $\psi$=1-3, $\overline{\omega}$=0-2;

$R^{26}$ of $OR^{26}$ is an optionally substituted alkyl, wherein the optional substituents are OH, halogen or $NH_2$;

m is an integer from 1-8;

$R^6$ and $R^8$ of Formula (XXIX) through (XXXII) are independently selected from hydrogen, optionally substituted alkyl or optionally substituted cycloalkyl; and $R^{31}$ of Formulas (XXIX) through (XXXII) is selected from alkyl, aryl, arylalkyl, heteroaryl or heteroarylalkyl optionally further substituted, preferably selected form the group consisting of:

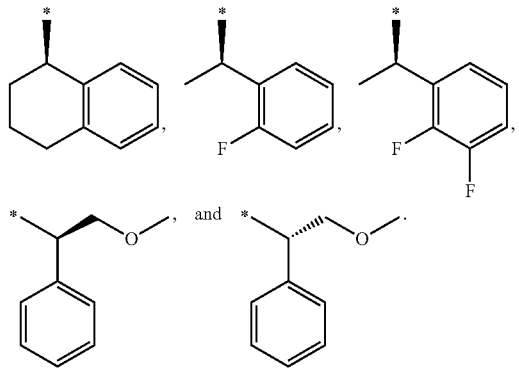

In certain embodiments, the ILM of the compound is:

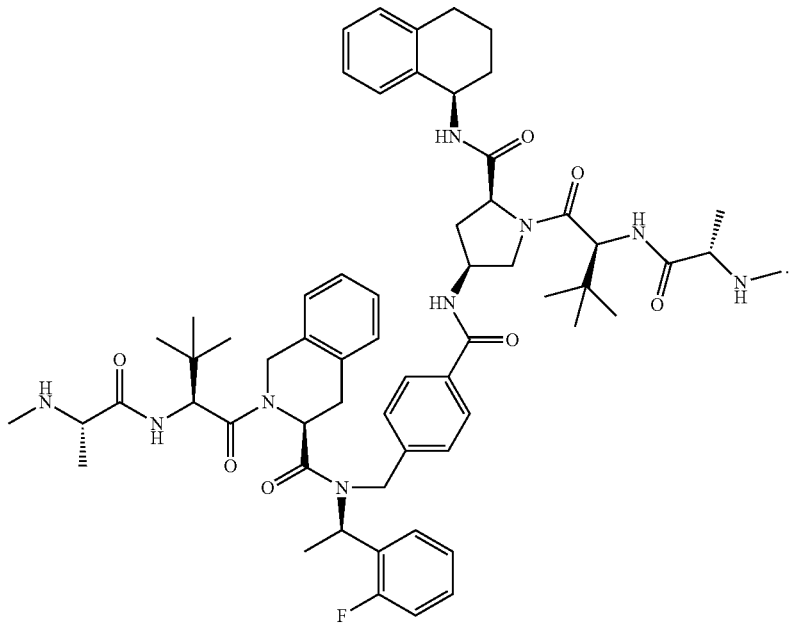

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

(XXXIII)

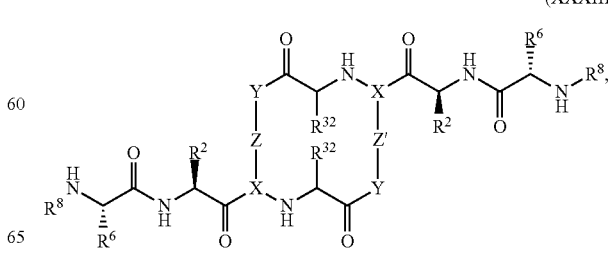

wherein:

R² of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

R⁶ and R⁸ of Formula (XXXIII) are independently selected from hydrogen, optionally substituted alkyl or optionally substituted cycloalkyl;

R³² of Formula (XXXIII) is selected from (C1-C4 alkylene)-R³³ wherein R³³ is selected from hydrogen, aryl, heteroaryl or cycloalkyl optionally further substituted;

X of Formula (XXXIII) is selected from:

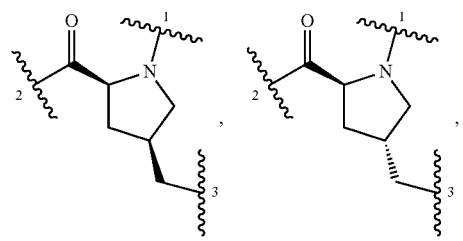

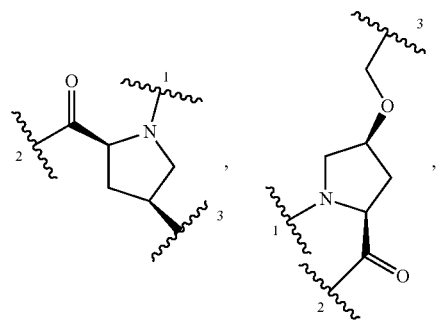

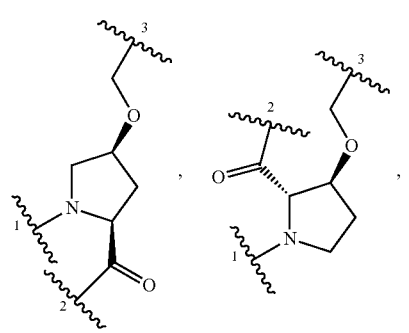

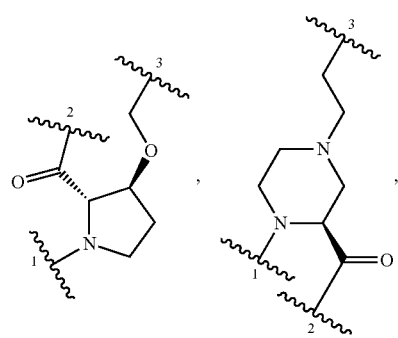

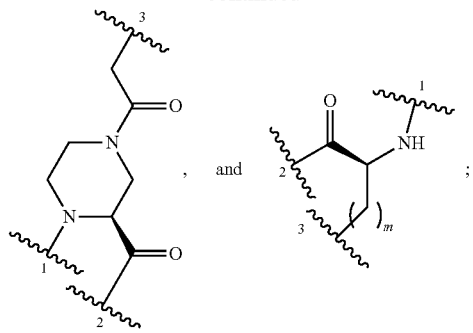

Z and Z' of Formula (XXXIII) are independently selected from:

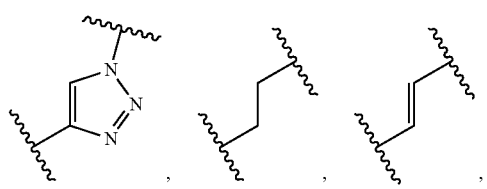

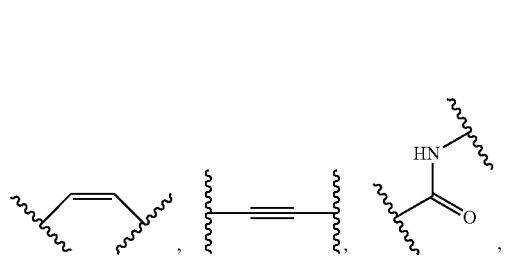

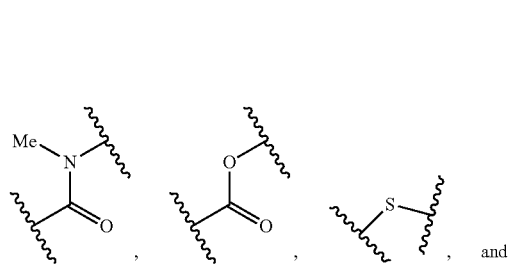

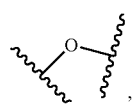

wherein each

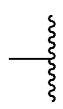

represents a point of attachment to the compound, and Z and Z' cannot both be
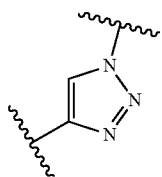 [SMILES: *c1cn(*)nn1]
in any given compound;
Y of Formula (XXXIII) is selected from:
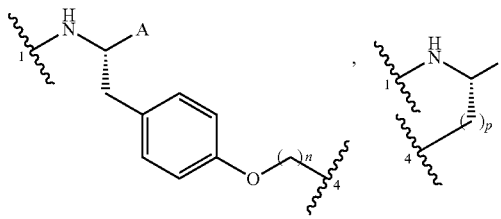
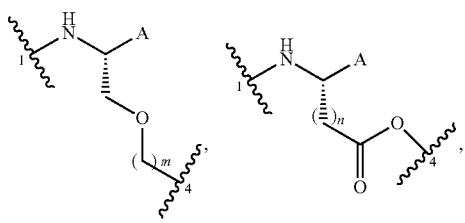
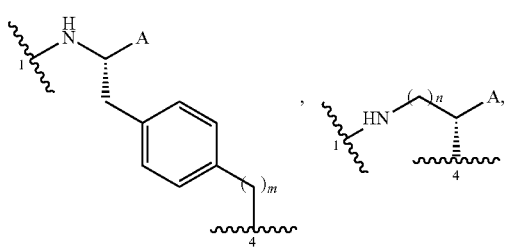
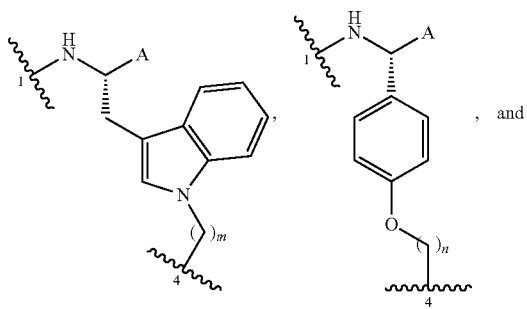, and
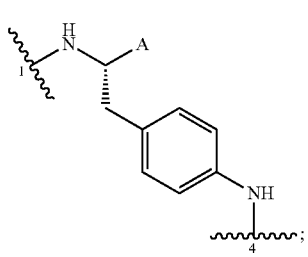
wherein Z and Z' of Formula (XXXIII) are the same and Z is
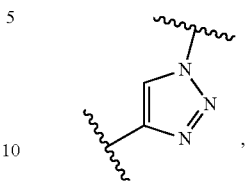,
wherein each
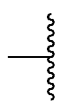
represents a point of attachment to the compound,
X is selected from:
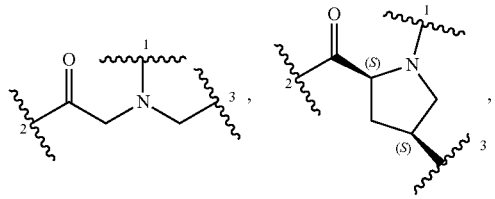
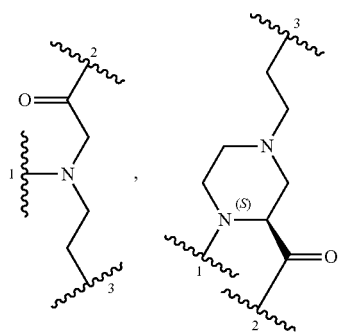

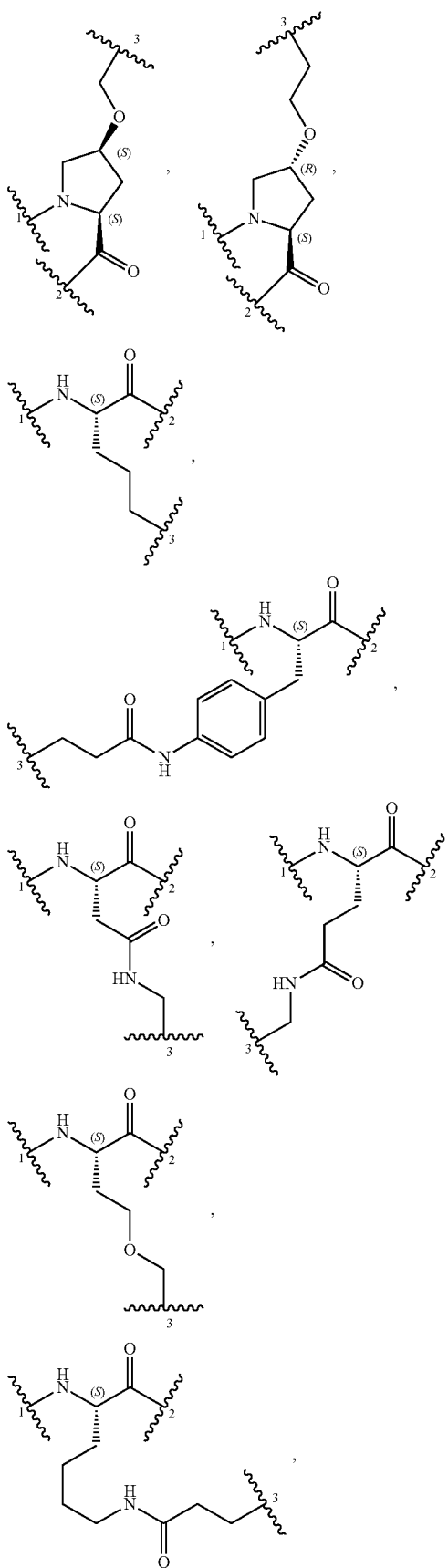
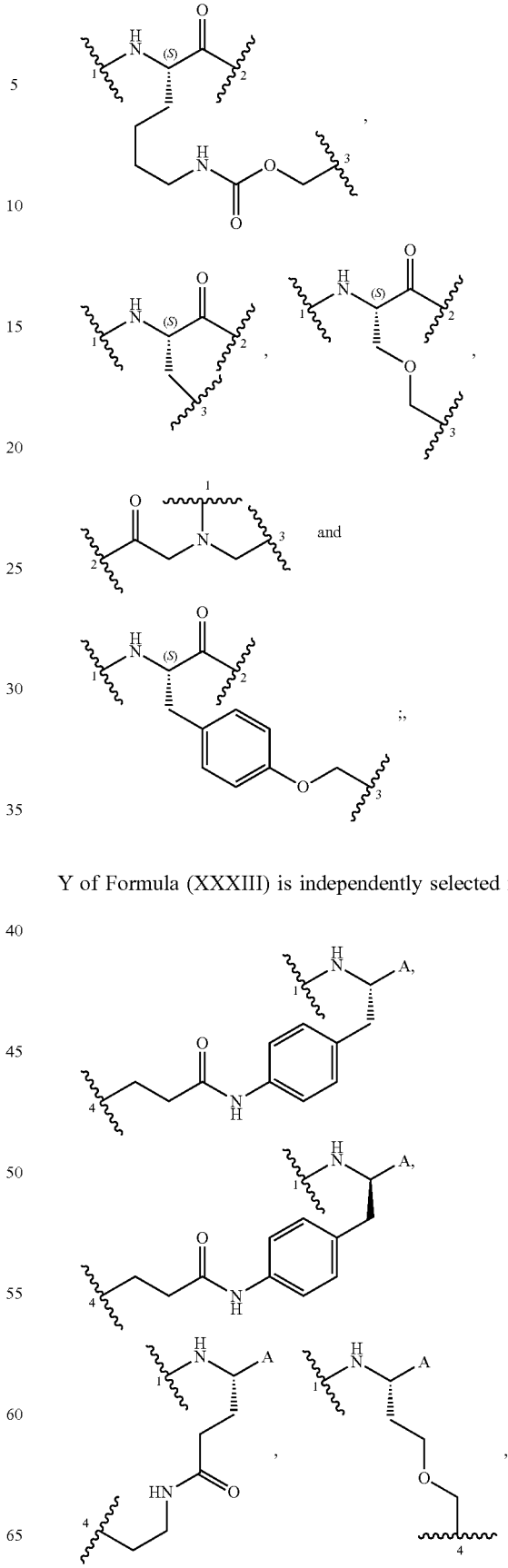
Y of Formula (XXXIII) is independently selected from:
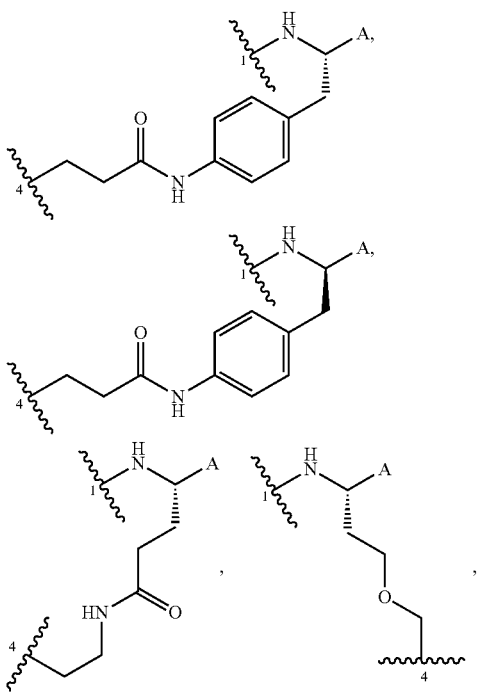

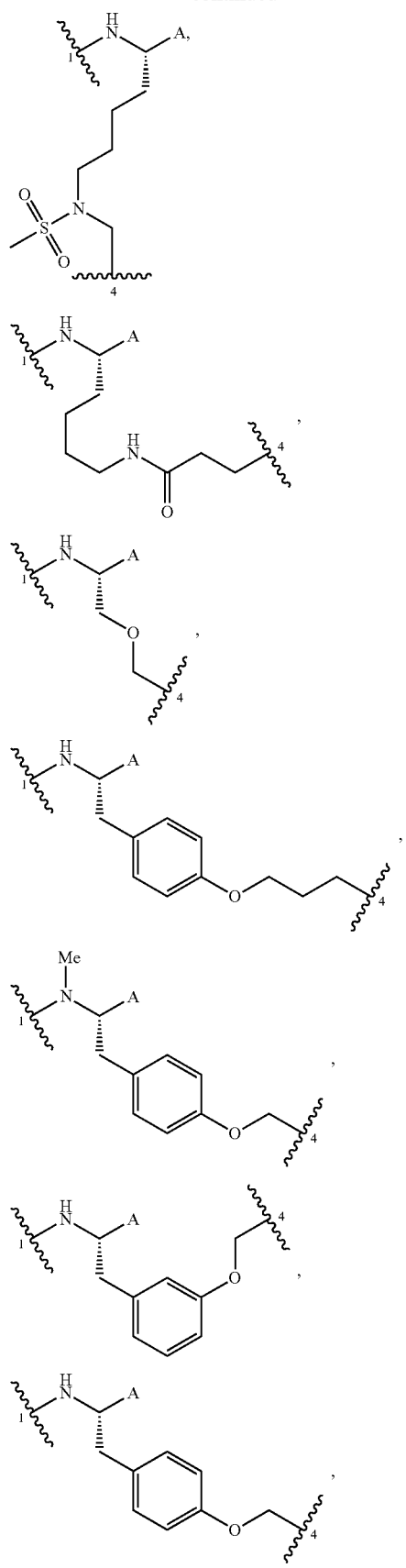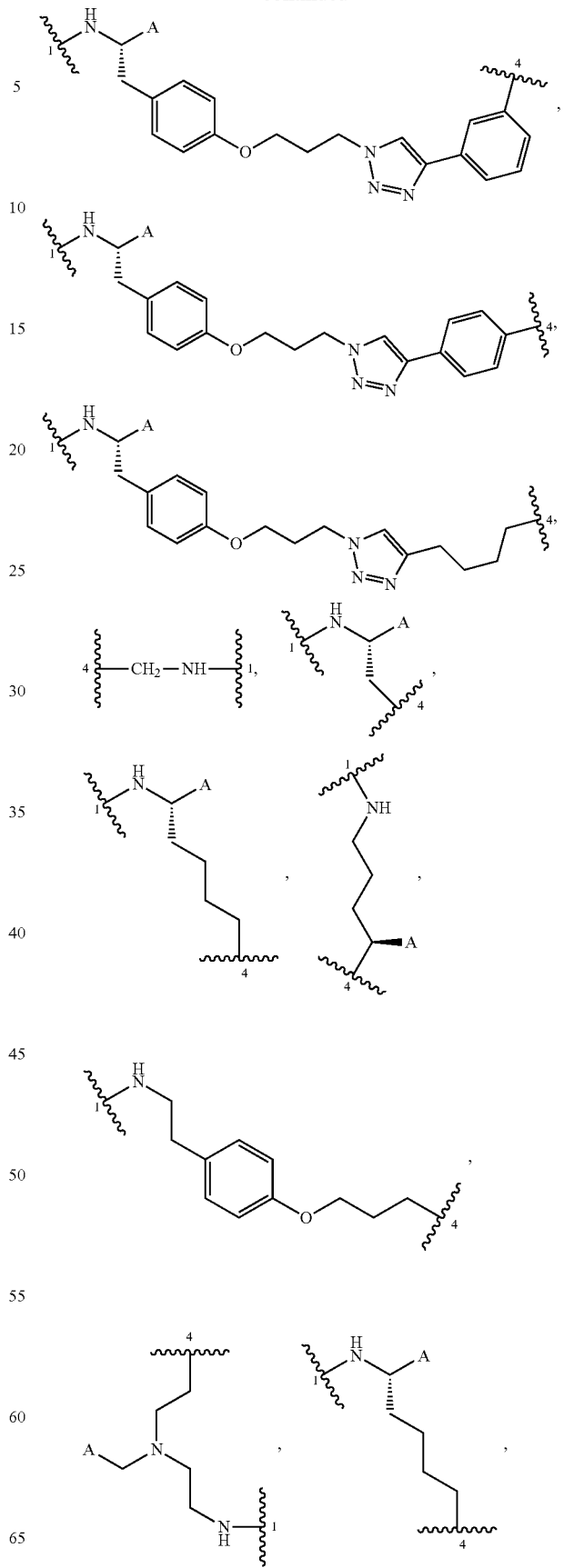

-continued wherein:

represents a point of attachment to a —C=O portion of the compound;

represents a point of attachment to a —NH portion of the compound;

represents a first point of attachment to Z;

represents a second point of attachment to Z;
m is an integer from 0-3;
n is an integer from 1-3;
p is an integer from 0-4; and
A is —C(O)R$^3$;
R$^3$ is selected from —C(O)R$^3$ is OH, NHCN, NHSO$_2$R$^{10}$, NHOR$^{11}$ or N(R$^{12}$)(R$^{13}$);
R$^{10}$ and F$^{11}$ of NHSO$_2$R$^{10}$ and NHOR$^{11}$ are independently selected from hydrogen, optionally substituted —C$_1$-C$_4$ alkyl, cycloalkyl, aryl, heteroaryl, heterocyclyl or heterocycloalkyl;
R$^{12}$ and R$^{13}$ of N(R$^{12}$)(R$^{13}$) are independently selected from hydrogen, —C$_1$-C$_4$ alkyl, —(C$_1$-C$_4$) alkylene)-NH—(C$_1$-C$_4$ alkyl), and —(C$_1$-C$_4$ alkylene)-O—(C$_1$-C$_4$ hydroxyalkyl), or R$^{12}$ and R$^{13}$ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

(XXXIV)

(XXXV)

wherein:
X of Formula (XXXIV) or (XXXV) is absent or a group selected from —(CR$^{10}$NR$^{11}$)$_m$—, optionally substituted heteroaryl or optionally substituted heterocyclyl,

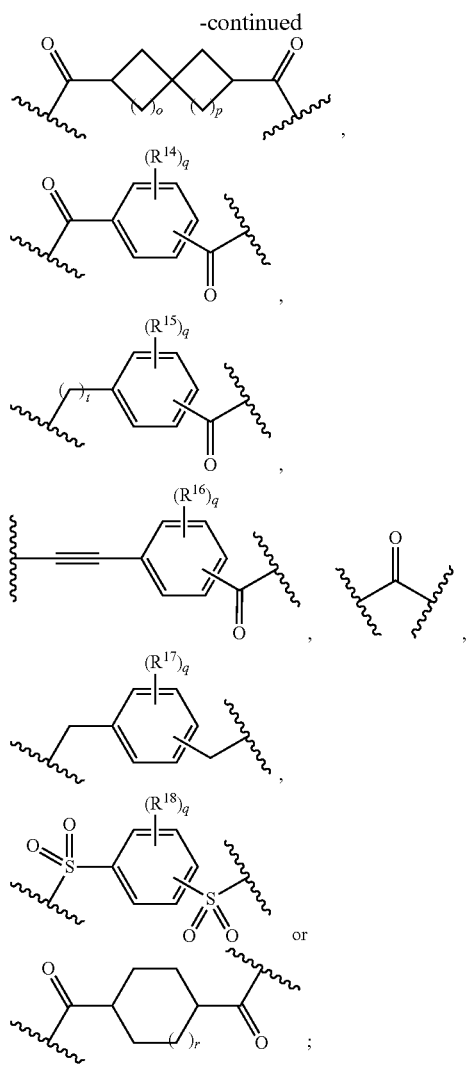

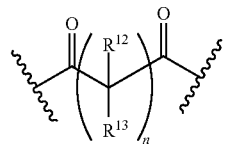

Y and ZX of Formula (XXXIV) or (XXXV) is absent or a group selected from C=O, —O—, —NR$^9$—, —CONH—, —NHCO— or may be absent;

R$^1$ and R$^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or R$^1$ and R$^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$; wherein v is an integer from 1-3;

R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;

R$^{21}$ of —CH$_2$CHR$^{21}$COR$^{22}$ is selected from NR$^{24}$R$^{25}$;

R$^{23}$ of —CH$_2$R$^{23}$ are selected from an optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$^{20}$)mCH3, or a polyamine chain;

R$^{26}$ is an optionally substituted alkyl, wherein the optional substituents are OH, halogen or NH$_2$;

m of —(CR$^{10}$R$^{11}$)$_m$— is an integer from 1-8;

R$^3$ and R$^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$, R$^6$, R$^7$ and R of Formula (XXXIV) or (XXXV) are independently selected from hydrogen, optionally substituted alkyl or optionally substituted cycloalkyl;

R$^{10}$ and R$^{11}$ of —(CR$^{10}$R$^{11}$)$_m$— are independently selected from hydrogen, halogen or optionally substituted alkyl;

R$^{12}$ and R$^{13}$ of

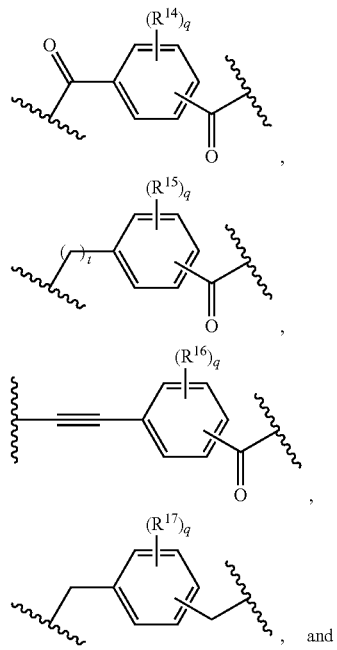

are independently selected from hydrogen, halogen or optionally substituted alkyl, or R$^{12}$ and R$^{13}$ can be taken together to form a carbocyclic ring;

R$^{14}$, R$^{15}$, R$^{16}$, R$^{17}$ and R$^{18}$ of

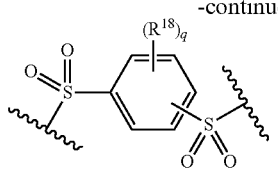

and are independently selected from hydrogen, halogen, optionally substituted alkyl or OR$^{19}$;

R$^{19}$ of OR$^{19}$ is selected from hydrogen, optionally substituted alkyl or optionally substituted cycloalkyl;

m and n of —(CR$^{10}$R$^{11}$)$_m$— are independently 0, 1, 2, 3, or 4;

o and p of —(CR$^{10}$R$^{11}$)$_m$— are independently 0, 1, 2 or 3;

q of —(CR$^{10}$R$^{11}$)$_m$— is 0, 1, 2, 3, or 4; r is 0 or 1;

t of —(CR$^{10}$R$^{11}$)$_m$— is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

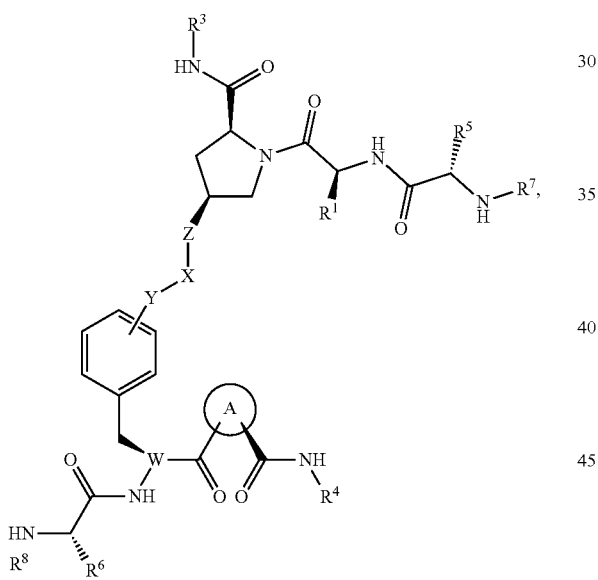

(XXXVI)

where:

A of Formula (XXXVI) is selected from:

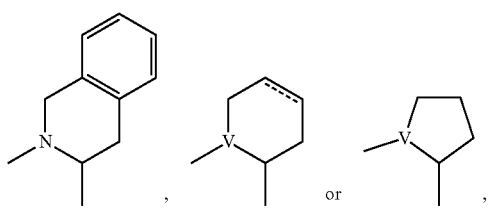

where the dotted line represents an optional double bond;

X of Formula (XXXVI) is selected from: —(CR$^{21}$R$^{22}$)$_m$—,

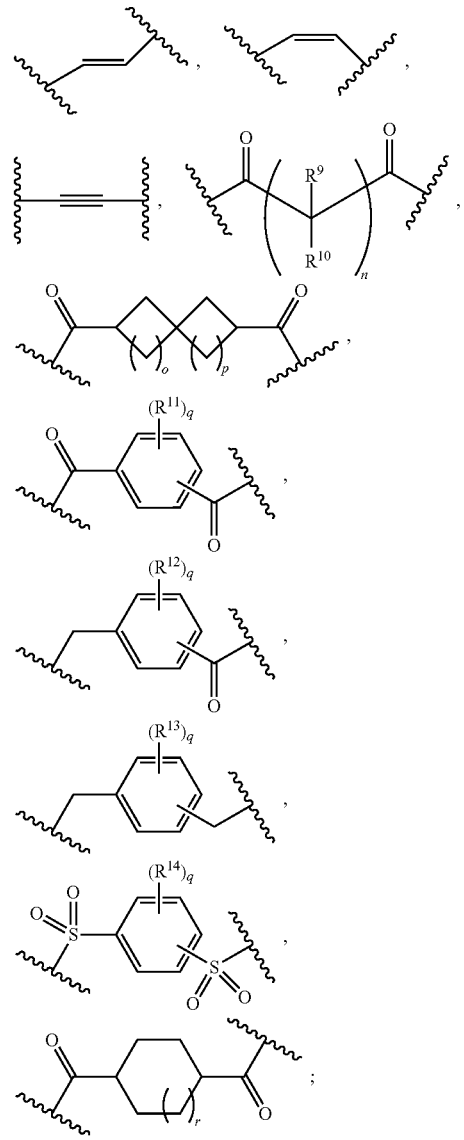

Y and Z of Formula (XXXVI) are independently selected from —O—, —NR$^6$— or are absent;

V of Formula (XXXVI) is selected from —N— or —CH—;

W of Formula (XXXVI) is selected from —CH— or —N—;

R$^1$ of Formula (XXXVI) is selected from an optionally substituted alkyl, optionally substituted cycloalkyl, optionally substituted cycloalkylalkyl, optionally substituted arylalkyl or optionally substituted aryl;

R$^3$ and R$^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R$^5$, R$^6$, R$^7$ and R$^8$ of Formula (XXIV), (XXV) or (XXVI) are independently selected from hydrogen, optionally substituted alkyl or optionally substituted cycloalkyl, or preferably methyl;

$R^9$ and $R^{10}$ of

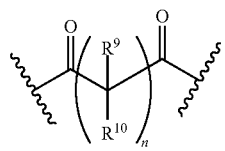

are independently selected from hydrogen, halogen or optionally substituted alkyl, or $R^9$ and $R^{10}$ can be taken together to form a ring;

$R^{11}$, $R^{12}$, $R^{13}$ and $R^{14}$ of

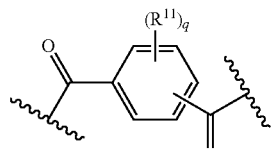

,

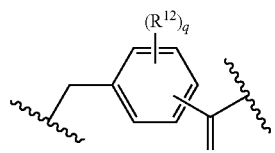

,

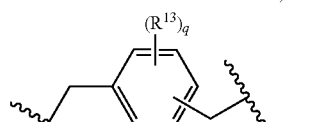

, and

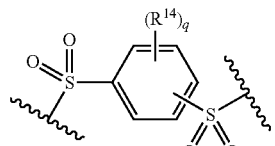

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

m and n of —$(CR^{21}R^{22})_m$— and

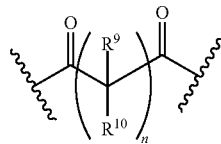

are independently selected from 0, 1, 2, 3, or 4;

o and p of

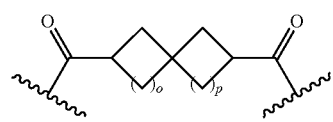

and are independently selected from 0, 1, 2 or 3;

q of

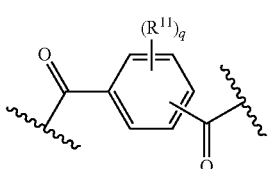

,

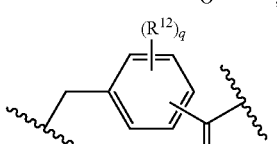

,

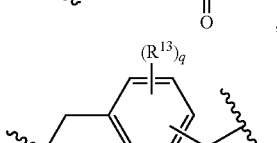

, or

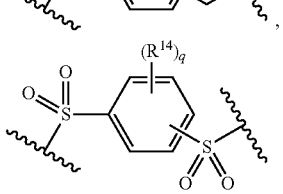

is selected from 0, 1, 2, 3, or 4;

r of

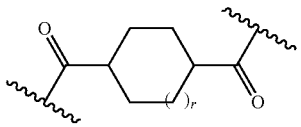

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

(XXXVII)

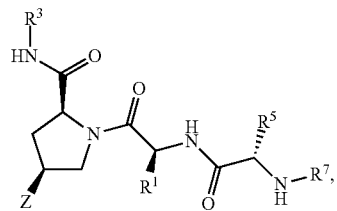

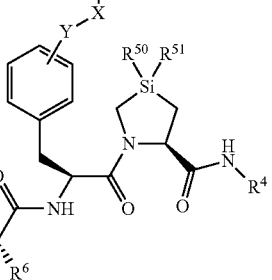

(XXXVIII)

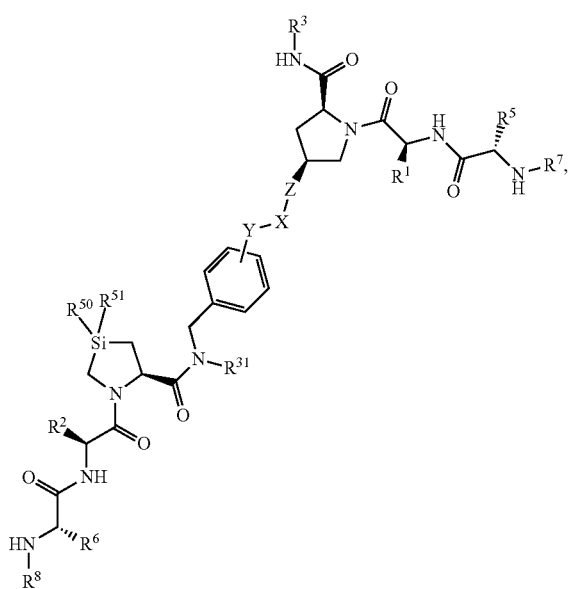

wherein:

X of Formulas (XXXVII) and (XXXVIII) is —(CR$^{16}$R$^{17}$)$_m$—,

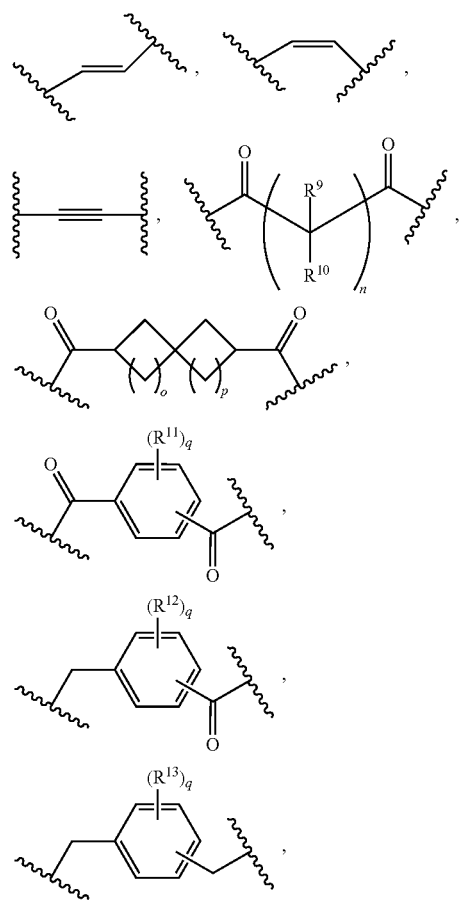

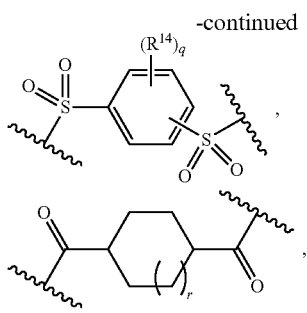

or absent;

Y and Z of Formula (XXXVII) and (XXXVIII) are independently selected from —O—, C═O, NR$^6$ or are absent;

R$^1$ and R$^2$ of Formula (XXXVII) and (XXXVIII) are selected from optionally substituted alkyl, optionally substituted cycloalkyl, optionally substituted alkylaryl or optionally substituted aryl;

R$^3$ and R$^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

R$^5$ and R$^6$ of Formula (XXXVII) and (XXXVIII) are independently selected from optionally substituted alkyl or optionally substituted cycloalkyl;

R$^7$ and R$^8$ of Formula (XXXVII) and (XXXVIII) are independently selected from hydrogen, optionally substituted alkyl or optionally substituted cycloalkyl, or preferably methyl;

R$^9$ and R$^{10}$ of

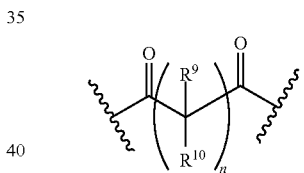

are independently selected from hydrogen, optionally substituted alkyl, or R$^9$ and R$^{10}$ may be taken together to form a ring;

R$^{11}$ to R$^{14}$ of

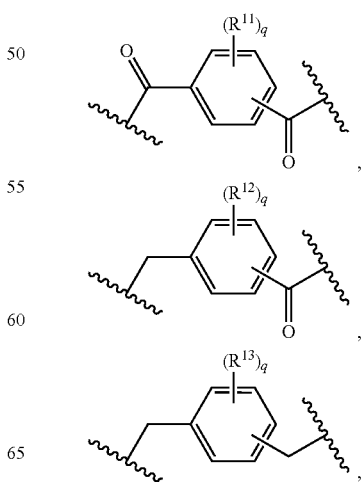

-continued

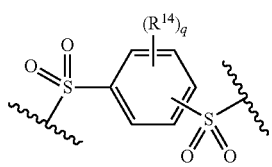

are
independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

$R^{16}$ and $R^{17}$ of $-(CR^{16}R^{17})_m-$ are independently selected from hydrogen, halogen or optionally substituted alkyl;

$R^{50}$ and $R^{51}$ of Formula (XXXVII) and (XXXVIII) are independently selected from optionally substituted alkyl, or $R^{50}$ and $R^{51}$ are taken together to form a ring;

m and n of $-(CR^{16}R^{17})_m-$ and

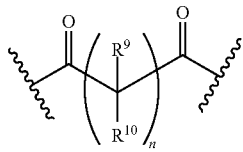

are independently an integer from 0-4;
o and p of

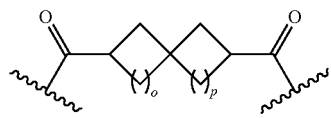

are independently an integer from 0-3;
q of

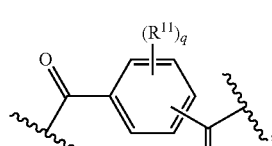

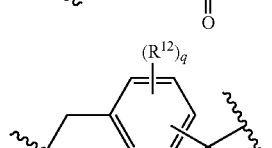

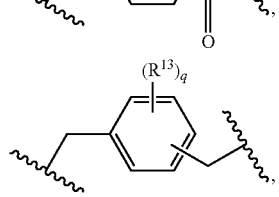

-continued

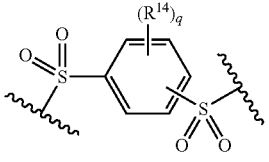

is an integer from 0-4; and
r of

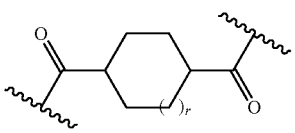

is an integer from 0-1;
or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

(XXXIX)

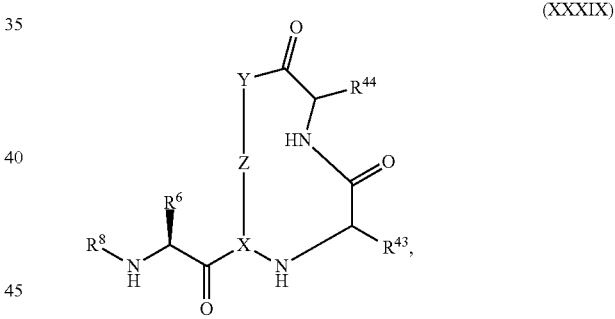

(XL)

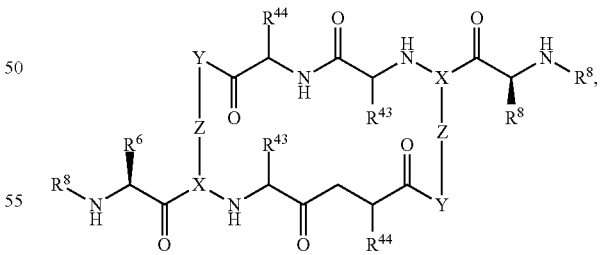

wherein:
$R^{43}$ and $R^{44}$ of Formulas (XXXIX) and (XL) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXXIX) and (XL) are independently selected from hydrogen, optionally substituted alkyl or optionally substituted cycloalkyl.

each X of Formulas (XXXIX) and (XL) is independently selected from:
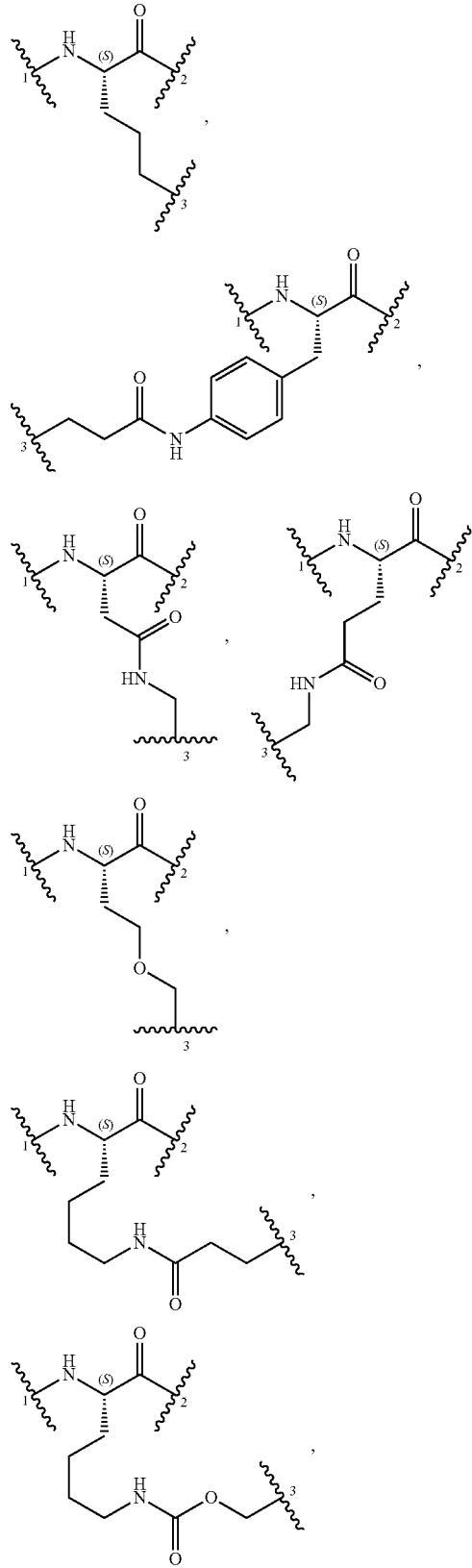
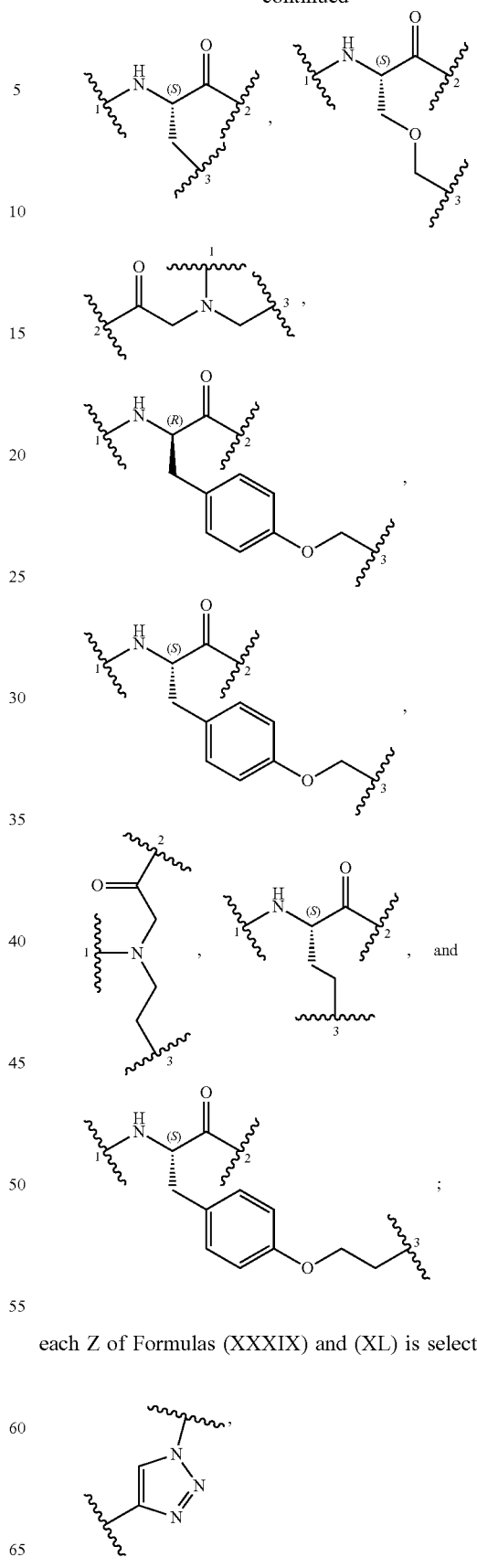
each Z of Formulas (XXXIX) and (XL) is selected from wherein each
represents a point of attachment to the compound; and each Y is selected from:
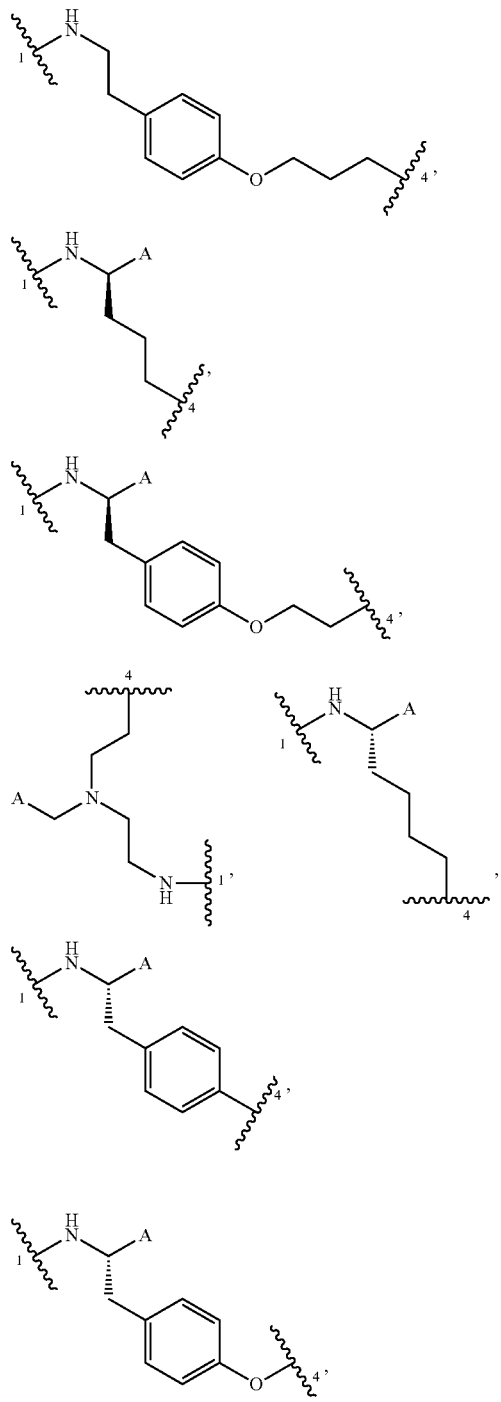
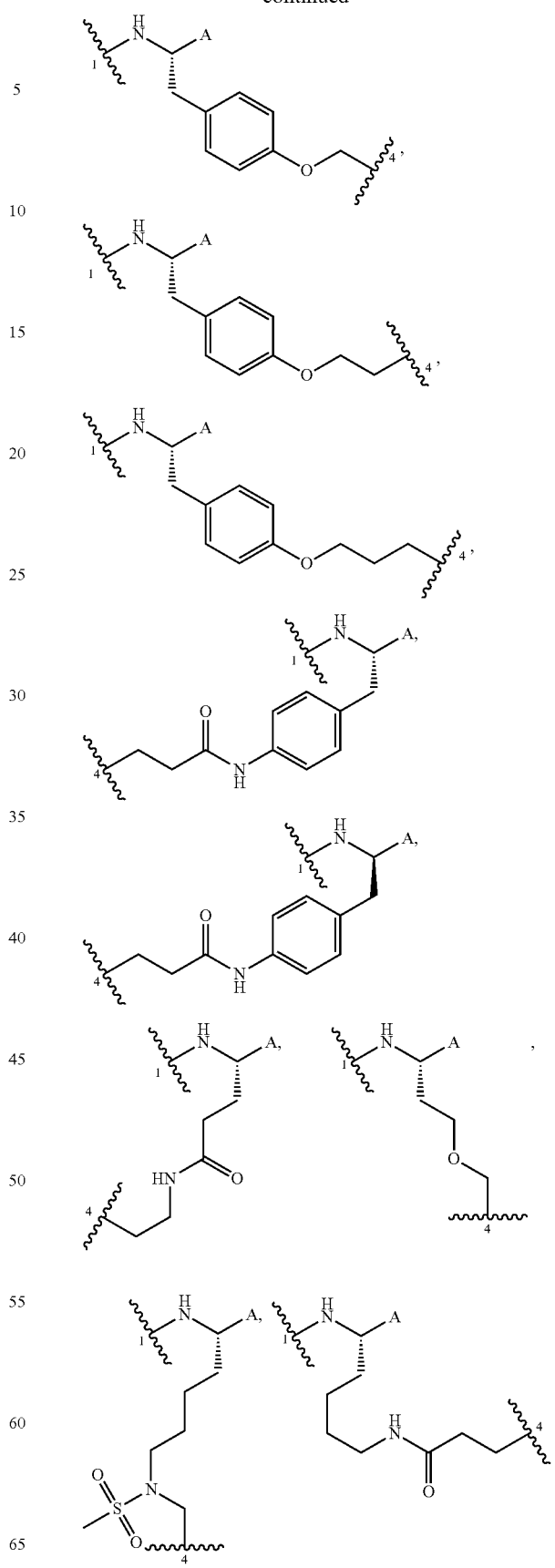

-continued

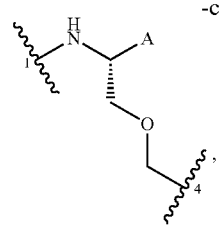

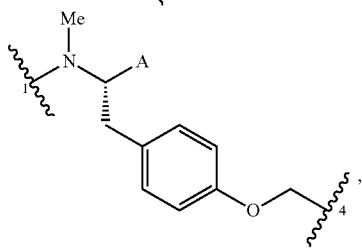

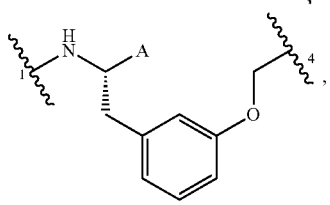

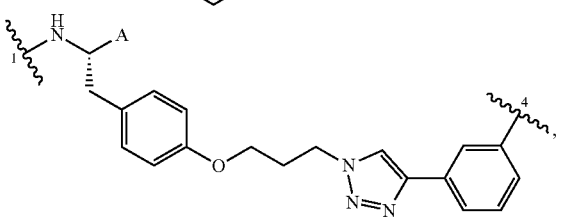

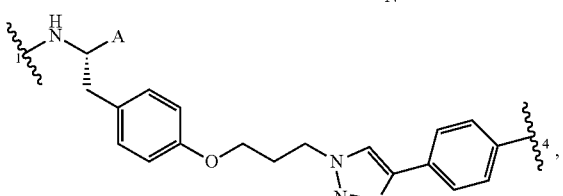

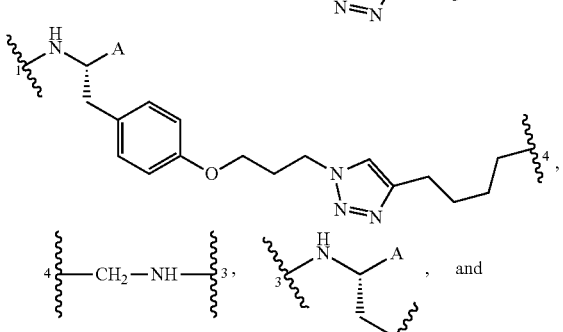

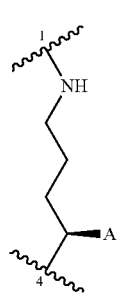

wherein:

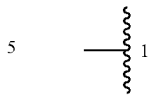

represents a point of attachment to a —C=O portion of the compound;

represents a point of attachment to an amino portion of the compound;

represents a first point of attachment to Z;

represents a second point of attachment to Z; and
A is selected from —C(O)R$^3$ or

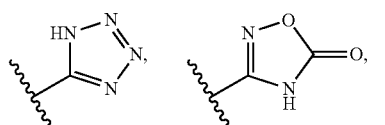

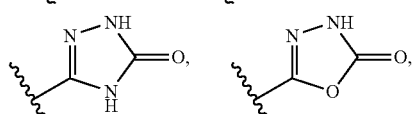

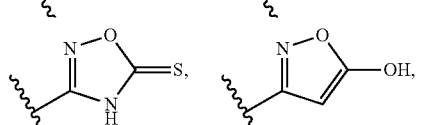

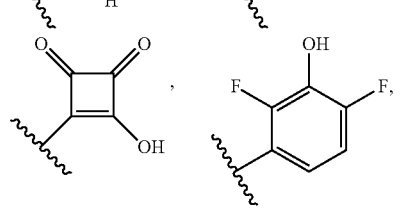

or a tautomeric form of any of the foregoing, wherein:
R$^3$ of —C(O)R$^3$ is selected from OH, NHCN, NHSO$_2$R$^{10}$, NHOR$^{11}$ or N(R$^{12}$)(R$^{13}$);
R$^{10}$ and R$^{11}$ of NHSO$_2$R$^{10}$ and NHOR$^{11}$ are independently selected from —C$_1$-C$_4$ alkyl, cycloalkyl, aryl, heteroaryl, or heterocycloalkyl, any of which are optionally substituted, and hydrogen;

each of $R^{12}$ and $R^{13}$ of $N(R^{12})(R^{13})$ are independently selected from hydrogen, —$C_1$-$C_4$ alkyl, —($C_1$-$C_4$ alkylene)-NH—($C_1$-$C_4$ alkyl), benzyl, —($C_1$-$C_4$ alkylene)-C(O)OH, —($C_1$-$C_4$ alkylene)-C(O)CH$_3$, —CH(benzyl)-COOH, —$C_1$-$C_4$ alkoxy, and —($C_1$-$C_4$ alkylene)-O—($C_1$-$C_4$ hydroxyalkyl); or $R^{12}$ and $R^{13}$ of $N(R^{12})(R^{13})$ are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

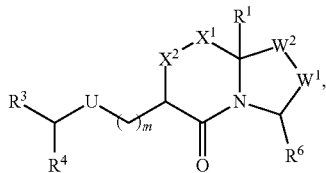

(XLI)

wherein:
$W^1$ of Formula (XLI) is selected from O, S, N—$R^A$, or $C(R^{8a})(R^{8b})$;
$W^2$ of Formula (XLI) is selected from O, S, N—$R^A$, or $C(R^{8c})(R^{8d})$; provided that $W^1$ and $W^2$ are not both O, or both S;
$R^1$ of Formula (XLI) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when $X^1$ is selected from O, N—$R^A$, S, S(O), or S(O)$_2$, then $X^2$ is $C(R^{2a}R^{2b})$;
or:
$X^1$ of Formula (XLI) is selected from $CR^{2c}R^{2d}$ and $X^2$ is $CR^{2a}R^{2b}$, and $R^{2c}$ and $R^{2a}$ together form a bond;
or:
$X^1$ and $X^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
$X^1$ of Formula (XLI) is selected from CH$_2$ and $X^2$ is C=O, C=C($R^C$)$_2$, or C=NR$^C$; where each R$^c$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^A$ of N—$R^A$ is selected from H, $C_1$-$C_6$alkyl, —C(=O)$C_1$-$C_2$alkyl, substituted or unsubstituted aryl, or substituted or unsubstituted heteroaryl;

$R^{2a}$, $R^{2b}$, $R^{2c}$, $R^{2d}$ of $CR^{2c}R^{2d}$ and $CR^{2a}R^{2b}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;

$R^D$ and $R^E$ of NR$^D$R$^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLI) is selected from 0, 1 or 2;
—U— of Formula (XLI) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLI) is selected from $C_1$-$C_3$alkyl, or $C_1$-$C_3$fluoroalkyl;

$R^4$ of Formula (XLI) is selected from —NHR$^5$, —N($R^5$)2, —N+($R^5$)3 or —OR$^5$;

each $R^5$ of —NHR$^5$, —N($R^5$)2, —N+($R^5$)3 and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
$R^3$ and $R^5$ of Formula (XLI) together with the atoms to which they are attached form a substituted or unsubstituted 5-7 membered ring;

or:
$R^3$ of Formula (XLI) is bonded to a nitrogen atom of U to form a substituted or unsubstituted 5-7 membered ring;

$R^6$ of Formula (XLI) is selected from —NHC(=O)R$^7$, —C(=O)NHR$^7$, —NHS(=O)2R$^7$, S(=O)$_2$NHR$^7$; —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^7$, —($C_1$-$C_3$alkyl)-NHS(=O)2R$^7$, —($C_1$-$C_3$alkyl)-S(=O)2NHR$^7$; —($C_1$-$C_3$alkyl)-NHC(=O)NHR$^7$, —($C_1$-$C_3$alkyl)-NHS(=O)2NHR$^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, NHS(=O)$_2$NH$R^7$, —(C$_1$-C$_3$alkyl)-NHC(=O)$R^7$, —(C$_1$-C$_3$alkyl)-C(=O)NH$R^7$, —(C$_1$-C$_3$alkyl)-NHS(=O)2$R^7$, —(C$_1$-C$_3$alkyl)-S(=O)2NH$R^7$; —(C$_1$-C$_3$alkyl)-NHC(=O)NH$R^7$, —(C$_1$-C$_3$alkyl)-NHS(=O)2NH$R^7$ is independently selected from C$_1$-C$_6$alkyl, C$_1$-C$_6$haloalkyl, C$_1$-C$_6$heteroalkyl, a substituted or unsubstituted C3-C10cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C2-C10heterocycloalkyl), —C1-C6alkyl-(substituted or unsubstituted aryl), —C$_1$-C$_6$alkyl-(substituted or unsubstituted heteroaryl), —(CH2)p-CH(substituted or unsubstituted aryl)2, —(CH$_2$)p-CH(substituted or unsubstituted heteroaryl)2, —(CH$_2$)$_P$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of C($R^{8a}$)($R^{8b}$) and C($R^{8C}$)($R^{8d}$) are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, C$_1$-C$_4$alkyl, C1-C4fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(=O)OH, —C(=O)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O—(C—C$_4$alkyl), —O(C$_1$-C$_4$alkyl)-NH2; —O(C$_1$-C$_4$alkyl)-NH—(C$_1$-C$_4$alkyl), and —O(C$_1$-C$_4$alkyl)-N—(C$_1$-C$_4$alkyl)$_2$, or two $R^9$ together with the atoms to which they are attached form a methylene dioxy or ethylene dioxy ring substituted or unsubstituted with halogen, —OH, or C$_1$-C$_3$alkyl.

In any of the compounds described herein, the ILM can have the structure of Formula (XLII), which are derived from the IAP ligands described in WO Pub. No. 2013/071039, or an unnatural mimetic thereof:

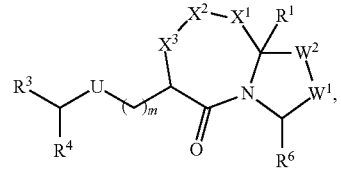

(XLII)

wherein:
$W^1$ of Formula (XLII) is O, S, N—$R^A$, or C($R^{8a}$)($R^{8b}$);
$W^2$ of Formula (XLII) is O, S, N—$R^A$, or C($R^{8c}$)($R^{8d}$);
provided that $W^1$ and $W^2$ are not both O, or both S;
$R^1$ of Formula (XLII) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);
when $X^1$ of Formula (XLII) is N—$R^A$, then $X^2$ is C=O, or CR$^{2C}$R$^{2d}$, and $X^3$ is CR$^{2a}$R$^{2b}$
or:
when $X^1$ of Formula (XLII) is selected from S, S(O), or S(O)$_2$, then $X^2$ is CR$^{2C}$R$^{2d}$, and $X^3$ is CR$^{2a}$R$^{2b}$;
or:
when $X^1$ of Formula (XLII) is O, then $X^2$ is CR$^{2C}$R$^{2d}$ and N—$R^A$ and $X^3$ is CR$^{2a}$R$^{2b}$;
or:
when $X^1$ of Formula (XLII) is CH$_3$, then $X^2$ is selected from O, N—$R^A$, S, S(O), or S(O)$_2$, and $X^3$ is CR$^{2a}$R$^{2b}$;
when $X^1$ of Formula (XLII) is CR$^{2e}$R$^{2f}$ and X2 is CR$^{2c}$R$^{2d}$, and R$^{2e}$ and R$^{2c}$ together form a bond, and $X^3$ of Formula (VLII) is CR$^{2a}$R$^{2b}$;
or:
$X^1$ and $X^3$ of Formula (XLII) are both CH$_2$ and $X^2$ of Formula (XLII) is C=O, C=C($R^C$)2, or C=N$R^C$; where each $R^C$ is independently selected from H, —CN, —OH, alkoxy, substituted or unsubstituted C1-C6alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
or:
$X^1$ and $X^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and XI of Formula (VLII) is $CR^{2e}R^{2f}$;

$R^A$ of N—$R^A$ is selected from H, $C_1$-$C_6$alkyl, —C(=O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLII) is selected from 0, 1 or 2;

—U— of Formula (XLII) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLII) is selected from $C_1$-$C_3$alkyl, or $C_1$-$C_3$fluoroalkyl;

$R^4$ of Formula (XLII) is selected from —$NHR^5$, —$N(R^5)_2$, —$N+(R^5)_3$ or —$OR^5$; each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLII) together with the atoms to which they are attached form a substituted or unsubstituted 5-7 membered ring;

or:

$R^3$ of Formula (XLII) is bonded to a nitrogen atom of U to form a substituted or unsubstituted 5-7 membered ring;

$R^6$ of Formula (XLII) is selected from —NHC(=O)$R^7$, —C(=O)NH$R^7$, —NHS(=O)2$R^7$, S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)p-CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —$NH_2$, —$NH(C_1$-$C_4$alkyl), —$NH(C_1$-$C_4$alkyl)$_2$, —C(=O)OH, —C(=O)$NH_2$, —C(=O)$C_1$-$C_3$alkyl, —S(=O)$_2CH_3$, —$NH(C_1$-$C_4$alkyl)-OH, —$NH(C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIII), which is derived from the IAP ligands described in WO Pub. No. 2013/071039, or an unnatural mimetic thereof:

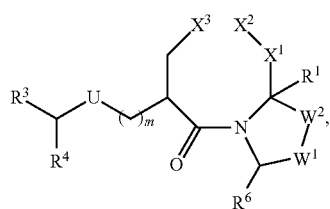

(XLIII)

wherein:
- $W^1$ of Formula (XLIII) is selected from O, S, N—$R^A$, or C($R^{8a}$)($R^{8b}$);
- $W^2$ of Formula (XLIII) is selected from O, S, N—$R^A$, or C($R^{8c}$)($R^{8d}$); provided that $W^1$ and $W^2$ are not both O, or both S;
- $R^1$ of Formula (XLIII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
- when $X^1$ of Formula (XLIII) is selected from N—$R^A$, S, S(O), or S(O)$_2$, then $X^2$ of Formula (XLIII) is $CR^{2c}R^{2d}$, and $X^3$ of Formula (XLIII) is $CR^{2a}R^{2b}$ or:
- when $X^1$ of Formula (XLIII) is O, then $X^2$ of Formula (XLIII) is selected from O, N—$R^A$, S, S(O), or S(O)$_2$, and $X^3$ of Formula (XLIII) is $CR^{2a}R^{2b}$;

or:
- when $X^1$ of Formula (XLIII) is $CR^{2e}R^{2f}$ and $X^2$ of Formula (XLIII) is $CR^{2c}R^{2d}$, and $R^{2e}$ and $R^{2c}$ together form a bond, and $X^3$ of Formula (XLIII) is $CR^{2a}R^{2b}$;

or:
- $X^1$ and $X^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIII) is $CR^{2a}R^{2b}$;

or:
- $X^2$ and $X^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;
- $R^A$ of N—$R^A$ is H, $C_1$-$C_6$alkyl, —C(=O)$C_1$-$C_2$alkyl, substituted or unsubstituted aryl, or substituted or unsubstituted heteroaryl;
- $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
- $R^B$ of —C(=O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
- $R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
- m of Formula (XLIII) is 0, 1 or 2;
- —U— of Formula (XLIII) is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
- $R^3$ of Formula (XLIII) is $C_1$-$C_3$alkyl, or $C_1$-$C_3$fluoroalkyl;
- $R^4$ of Formula (XLIII) is —$NHR^5$, —$N(R^5)_2$, —$N+(R^5)_3$ or —$OR^5$;
- each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
- $R^3$ and $R^5$ of Formula (XLIII) together with the atoms to which they are attached form a substituted or unsubstituted 5-7 membered ring;

or:
- $R^3$ of Formula (XLIII) is bonded to a nitrogen atom of U to form a substituted or unsubstituted 5-7 membered ring;
- $R^6$ of Formula (XLIII) is selected from —NHC(=O)$R^7$, —C(=O)$NHR^7$, —NHS(=O)2$R^7$, S(=O)$_2NHR^7$; —NHC(=O)$NHR^7$, —NHS(=O)$_2NHR^7$, —($C_1$-

$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_P$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIV), which is derived from the IAP ligands described in WO Pub. No. 2013/071039, or an unnatural mimetic thereof:

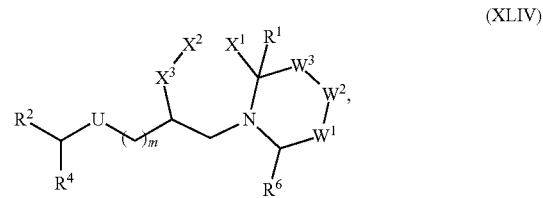

(XLIV)

wherein:

$W^1$ of Formula (XLIV) is selected from O, S, N—$R^A$, or C($R^{8a}$)($R^{8b}$);

$W^2$ of Formula (XLIV) is selected from O, S, N—$R^A$, or C($R^{8c}$)($R^{8d}$); provided that $W^1$ and $W^2$ are not both O, or both S;

$W^3$ of Formula (XLIV) is selected from O, S, N—$R^A$, or C($R^{8e}$)($R^{8f}$), providing that the ring comprising $W^1$, $W^2$, and $W^3$ does not comprise two adjacent oxygen atoms or sulfur atoms;

$R^1$ of Formula (XLIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XLIV) is O, then $X^2$ of Formula (XLIV) is selected from $CR^{2c}R^{2d}$ and N—$R^A$, and $X^3$ of Formula (XLIV) is $CR^{2a}R^{2b}$;

or:

when $X^1$ of Formula (XLIV) is CH$_2$, then $X^2$ of Formula (XLIV) is selected from O, N—$R^A$, S, S(O), or S(O)$_2$, and $X^3$ of Formula (XLIV) is $CR^{2a}R^{2b}$;

or:

when $X^1$ of Formula (XLIV) is $CR^{2e}R^{2f}$ and $X^2$ of Formula (XLIV) is $CR^{2c}R^{2d}$, and $R^{2e}$ and $R^{2c}$ together form a bond, and $X^3$ of Formula (VLIV) is $CR^{2a}R^{2b}$;

or:

$X^1$ and $X^3$ of Formula (XLIV) are both CH$_2$ and $X^2$ of Formula (XLII) is C=O, C=C($R^C$)2, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:
- $X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;

or:
- $X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2e}R^{2f}$;
- $R^A$ of $N-R^A$ is selected from H, $C_1$-$C_6$alkyl, $-C(=O)C_1$-$C_2$alkyl, substituted or unsubstituted aryl, or substituted or unsubstituted heteroaryl;
- $R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —$C(=O)R^B$;
- $R^B$ of —$C(=O)R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
- $R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
- m of Formula (XLIV) is selected from 0, 1 or 2;
- —U— of Formula (XLIV) is selected from —NHC(=O)—, —C(=O)NH—, —NHS(=O)$_2$—, —S(=O)$_2$NH—, —NHC(=O)NH—, —NHC(C=O)O—, —OC(=O)NH—, or —NHS(=O)$_2$NH—;
- $R^3$ of Formula (XLIV) is selected from $C_1$-$C_3$alkyl, or $C_1$-$C_3$fluoroalkyl;
- $R^4$ of Formula (XLIV) is selected from —$NHR^5$, —$N(R^5)_2$, —$N+(R^5)_3$ or —$OR^5$;
- each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
- $R^3$ and $R^5$ of Formula (XLIV) together with the atoms to which they are attached form a substituted or unsubstituted 5-7 membered ring;

or:
- $R^3$ of Formula (XLIII) is bonded to a nitrogen atom of U to form a substituted or unsubstituted 5-7 membered ring;
- $R^6$ of Formula (XLIII) is selected from —NHC(=O)$R^7$, —C(=O)NH$R^7$, —NHS(=O)2$R^7$, S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;
- each $R^7$ of —NHC(=O)$R^7$, —C(=O)NH$R^7$, —NHS(=O)2$R^7$, —S(=O)$_2$NH$R^7$; —NHC(=O)NH$R^7$, NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-C10heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);
- p of $R^7$ is selected from 0, 1 or 2;
- $R^{8a}$, $R^{8b}$, $R^{8c}$, $R^{8d}$, $R^{8e}$, and $R^{8f}$ of $C(R^{8a})(R^{8b})$, $C(R^{8c})(R^{8d})$ and $C(R^{8e})(R^{8f})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:
- $R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8e}$ together form a bond;

or:
- $R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together form a bond;

or:
- $R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$, and $R^{8f}$ of $C(R^{8a})(R^{8d})$ and $C(R^{8e})(R^{8f})$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of $C(R^{8a})(R^{8b})$ and $C(R^{8e})(R^{8f})$ are as defined above, and $R^{8e}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ of $C(R^{8a})(R^{8b})$ and $C(R^{8c})(R^{8d})$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$, $R^{8d}$, $R^{8e}$, and $R^{8f}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

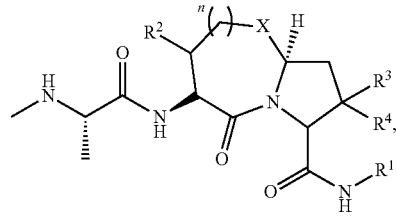

(XLV)

n = 0, 1

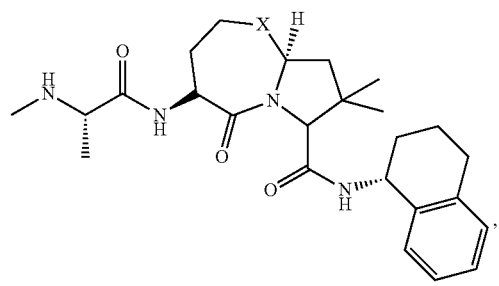

(XLVI)

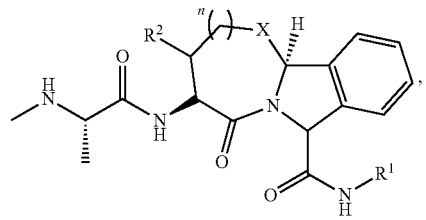

(XLVII)

n = 0, 1 wherein:

$R^2$, $R^3$ and $R^4$ of Formula (XLV) are independently selected from H or ME;

X of Formula (XLV) is independently selected from O or S; and $R^1$ of Formula (XLV) is selected from:

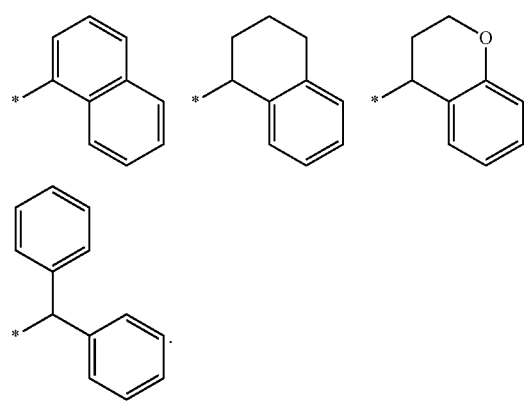

In a particular embodiment, the ILM has a structure according to Formula (XLVIII):

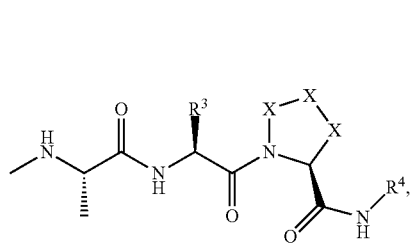

(XLVIII)

wherein $R^3$ and $R^4$ of Formula (XLVIII) are independently selected from H or ME;

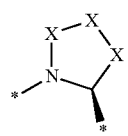

is a 5-member heterocycle selected from:

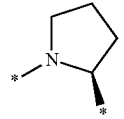 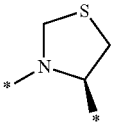 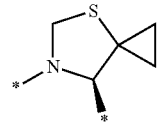

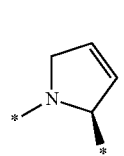 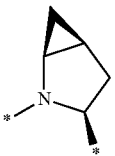

In a particular embodiment, the

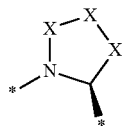

of Formula XLVIII) is

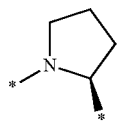

In a particular embodiment, the ILM has a structure and attached to a linker group L as shown below:

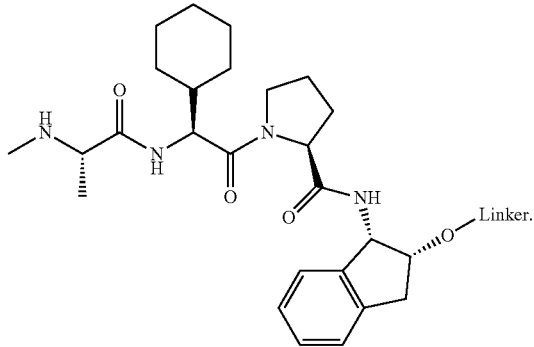

In a particular embodiment, the ILM has a structure according to Formula (XLIX), (L), or (LI):

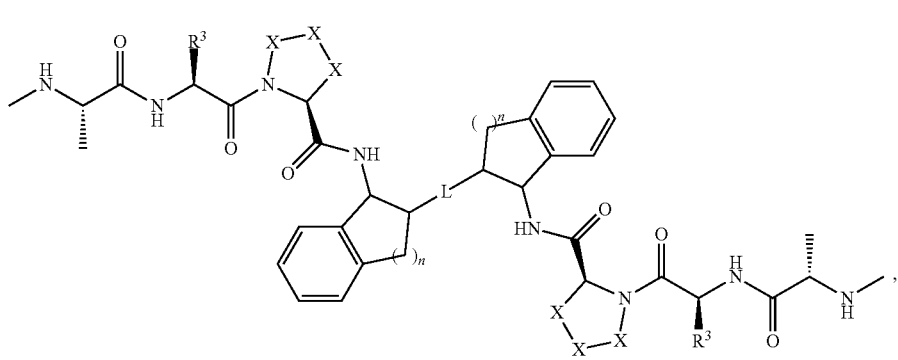

(XLIX)

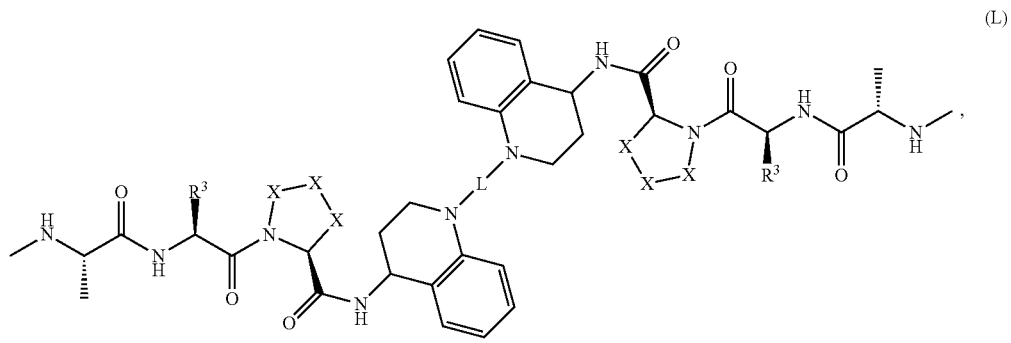
(L)
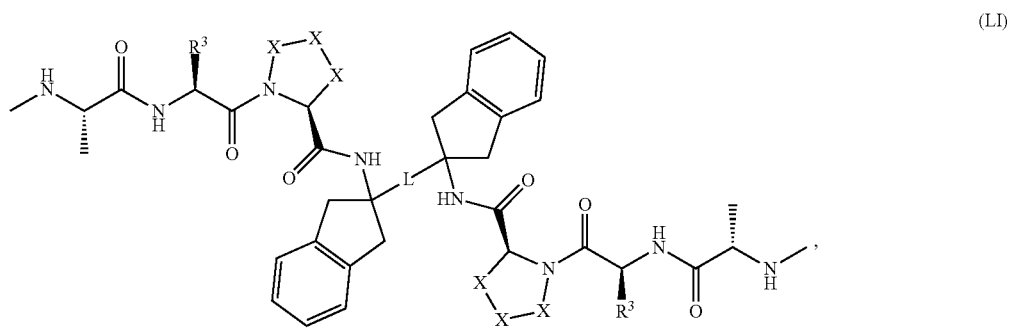
(LI)
n = 1, 2
wherein:
R³ of Formula (XLIX), (L) or (LI) are independently selected from H or ME;
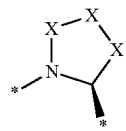
is a 5-member heterocycle selected from:
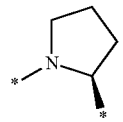 [SMILES: *[C@@H]1CCCN1*] 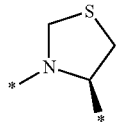 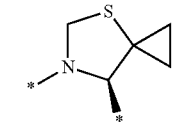
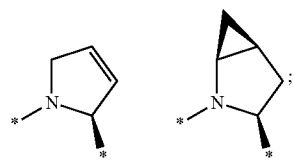
and
L of Formula (XLIX), (L) or (LI) is selected from:
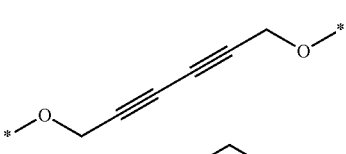
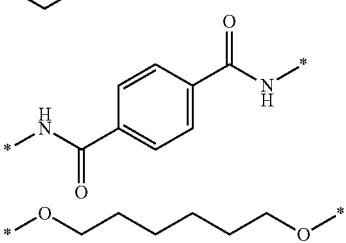
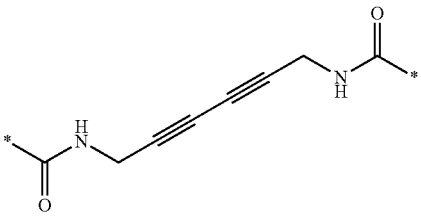

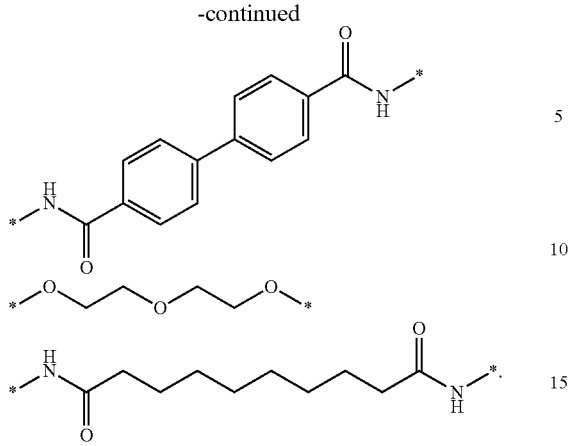

In a particular embodiment, L of Formula (XLIX), (L), or (LI)

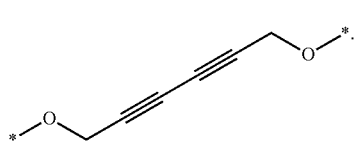

In a particular embodiment, the ILM has a structure according to Formula (LII):

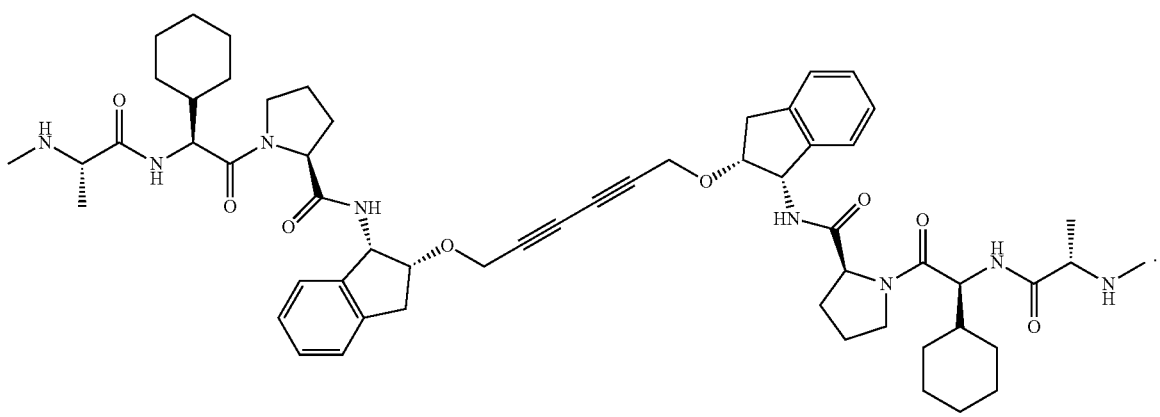

In a particular embodiment, the ILM according to Formula (LII) is chemically linked to the linker group L in the area denoted with and as shown below:

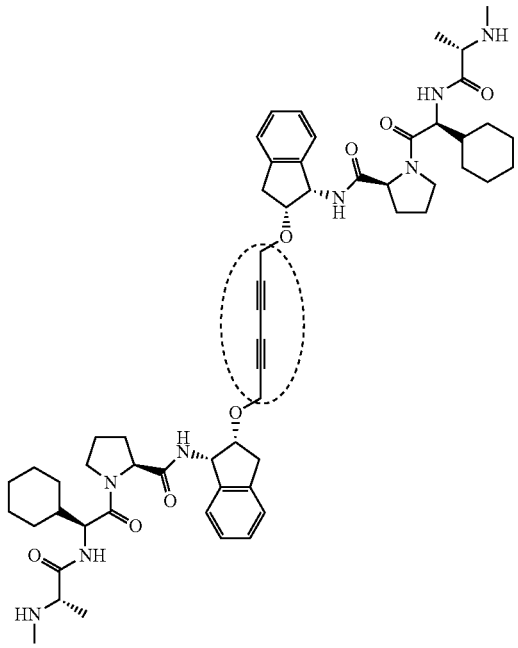 [SMILES: CN[C@@H](C)C(=O)N[C@H](C(=O)N1CCC[C@H]1C(=O)N[C@H]1c2ccccc2C[C@H]1OCC#CC#CCO[C@@H]1Cc2ccccc2[C@@H]1NC(=O)[C@@H]1CCCN1C(=O)[C@@H](NC(=O)[C@H](C)NC)C1CCCCC1)C1CCCCC1]

In any of the compounds described herein, the ILM can have the structure of Formula (LIII) or (LIV), which is based on the IAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

(LIV)

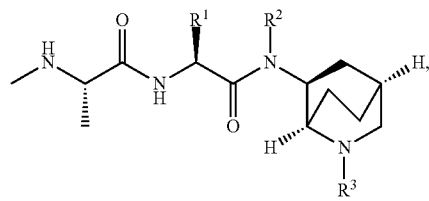

n = 0, 1, 2 wherein:

R¹ of Formulas (LIII) and (LIV) is selected from:

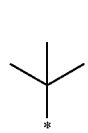 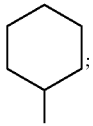;

R² of Formulas (LIII) and (LIV) is selected from H or Me;
R³ of Formulas (LIII) and (LIV) is selected from:

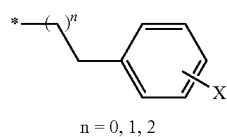 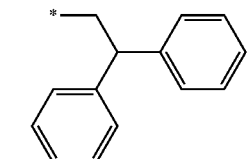

n = 0, 1, 2

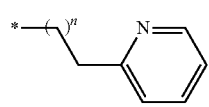 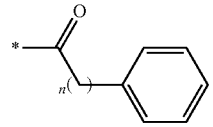

n = 0, 1, 2    n = 0, 1

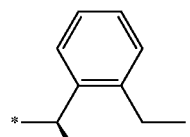 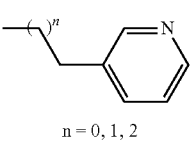

n = 0, 1, 2

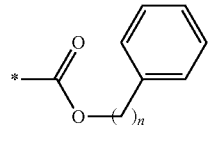

n = 0, 1

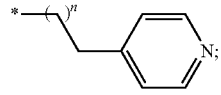

n = 0, 1, 2

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

(LV)

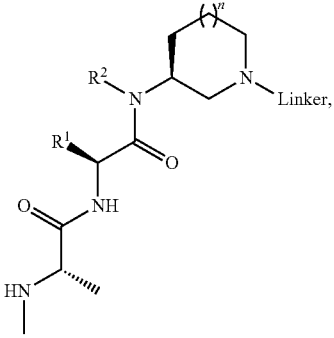

(LVI)

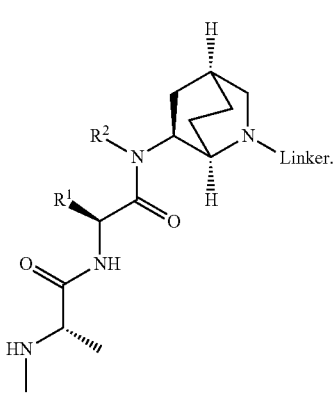

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

(LVII)

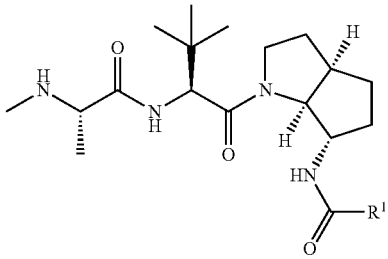

wherein:

R1 of Formulas (LVII) is selected from:

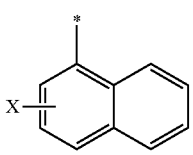 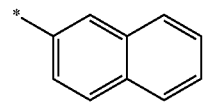

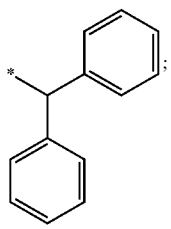

X of

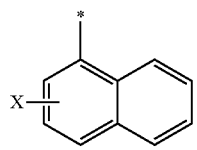

is selected from H, fluoro, methyl or methoxy.

In a particular embodiment, the ILM is represented by the following structure:

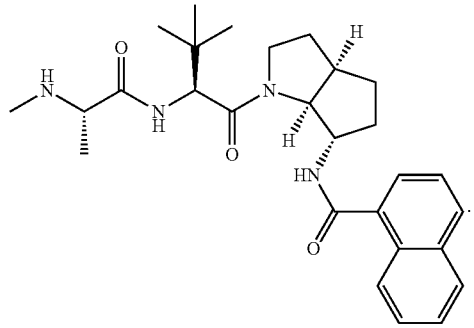 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM is selected from the group consisting of, and which the chemical link between the ILM and linker group L is shown:

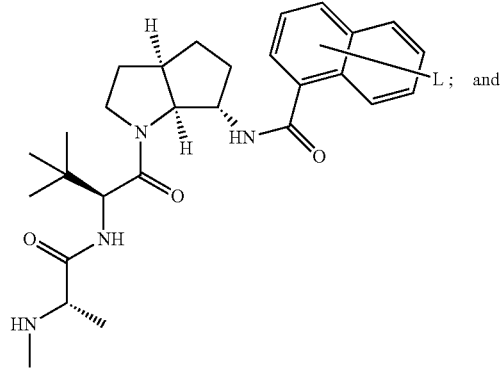

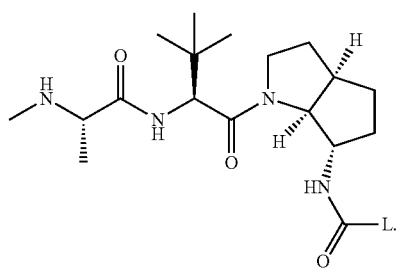

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

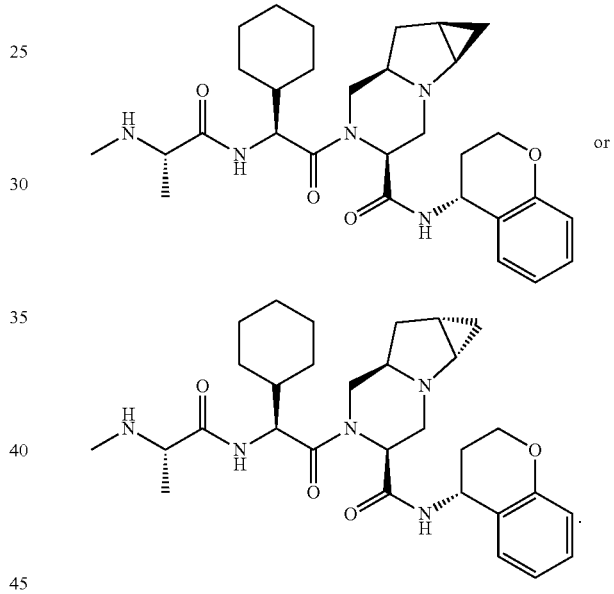

In a particular embodiment, the ILM is selected from the group consisting of, and which the chemical link between the ILM and linker group L is shown:

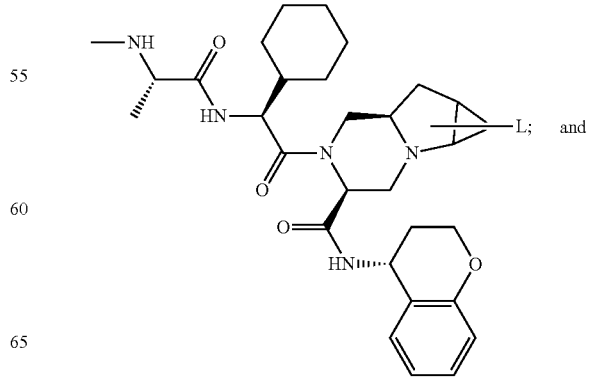

-continued

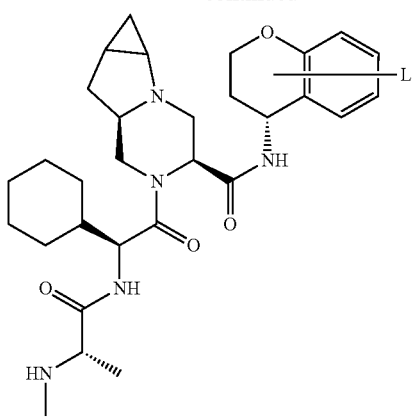

In any of the compounds described herein, the ILM can have the structure of Formula (LVIII), which is based on the IAP ligands described in Asano, M, et al., *Design, steriose-lective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

(LVIII)

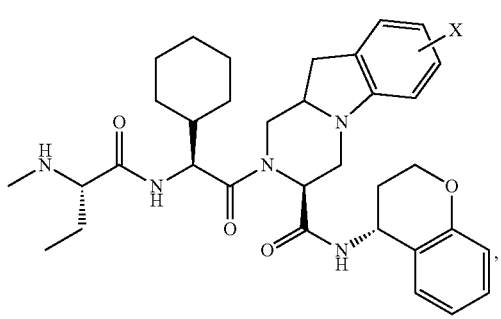

wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:

(LIX)

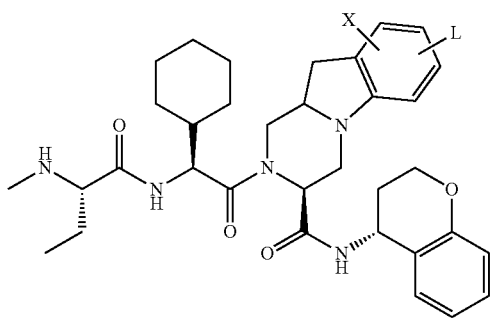

-continued (LX)

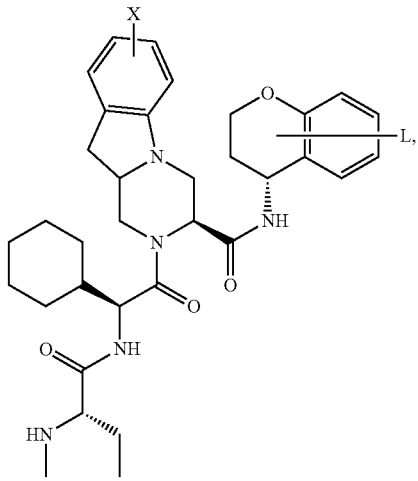

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, synthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

(LXI)

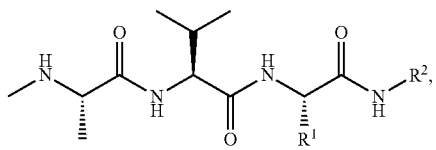

wherein:

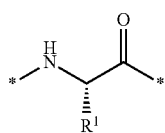

of Formula (LXI) is a natural or unnatural amino acid; and R² of Formula (LXI) is selected from:

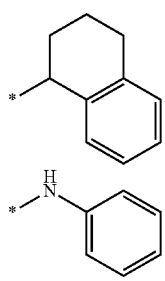

In any of the compounds described herein, the ILM can have the structure of and be chemically linked to the linker group L as shown in Formula (LXII) or (LLXIII), or an unnatural mimetic thereof:

(LXII)

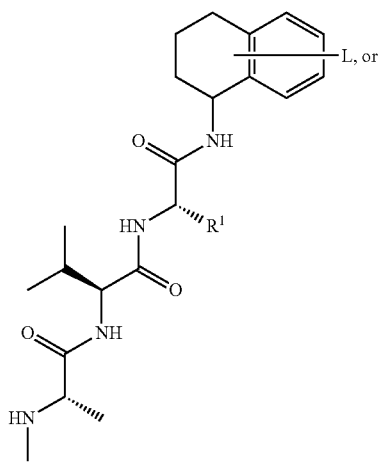

(LXIII)

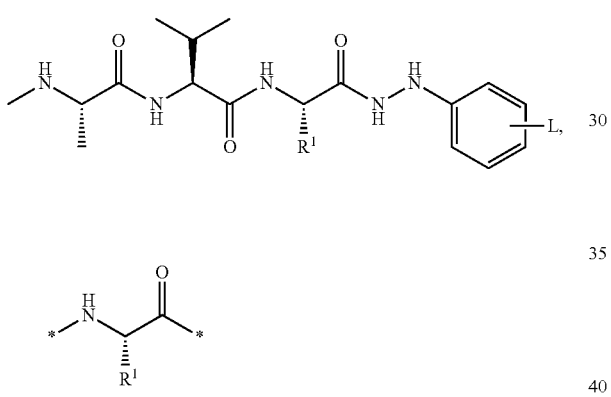

of Formula (LXI) is a natural or unnatural amino acid; and L of Formula (LXI) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

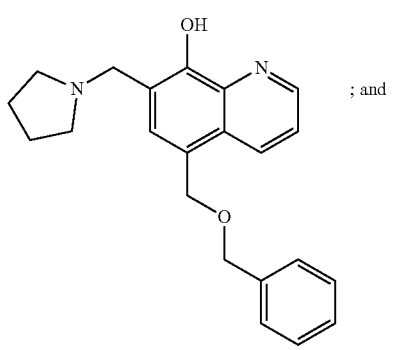

; and

-continued

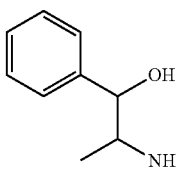

In any of the compounds described herein, the ILM has a structure according to Formula (LXIX), which is based on the IAP ligands described in Hird, A W, et al., Structure-based design and synthesis of tricyclic IAP (*Inhibitors of Apoptosis Proteins*) inhibitors, Bioorg. Med. Chem. Lett., 24(7): 1820-4 (2014), or an unnatural mimetic thereof:

(LXIX)

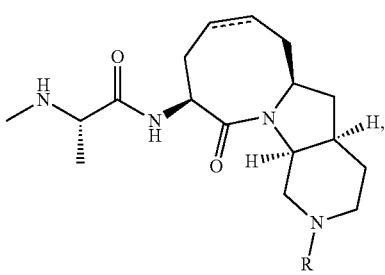

wherein R of Formula LIX is selected from the group consisting of:

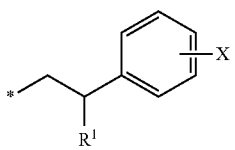

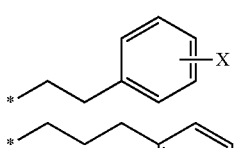

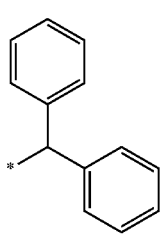

-continued

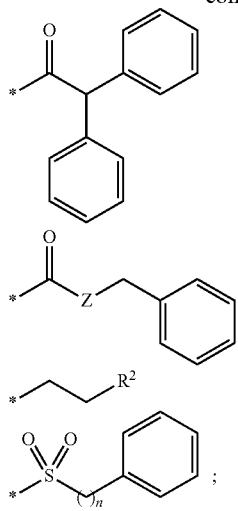

R1 of

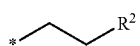

is selected from H or Me;
R2 of

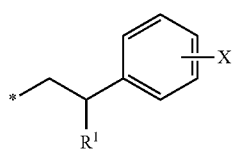

is selected from alkyl or cycloalkyl;

X of

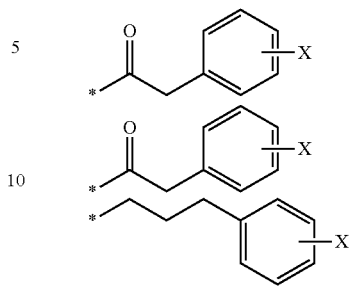

is 1-2 substitutents independently selected from halogen, hydroxy, methoxy, nitro and trifluoromethyl
Z of

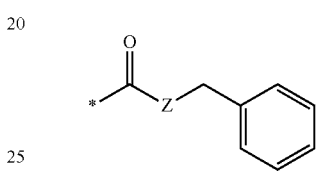

is O or NH;
HET of

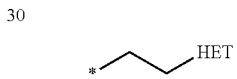

is mono- or fused bicyclic heteroaryl; and
--- of Formula (LIX) is an optional double bond.

In a particular embodiment, the ILM of the compound has a chemical structure as represented by:

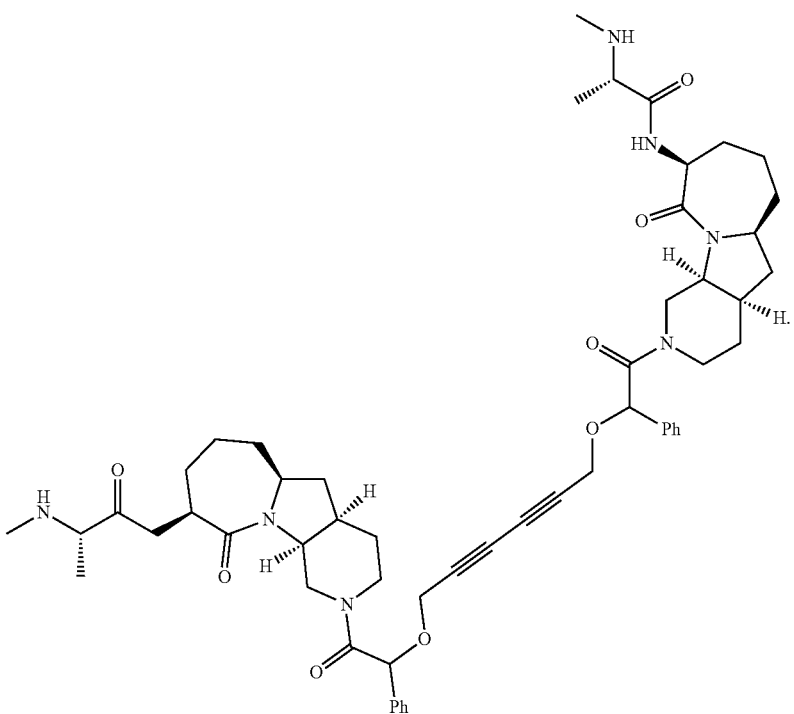

In a particular embodiment, the ILM of the compound has a chemical structure selected from the group consisting of:

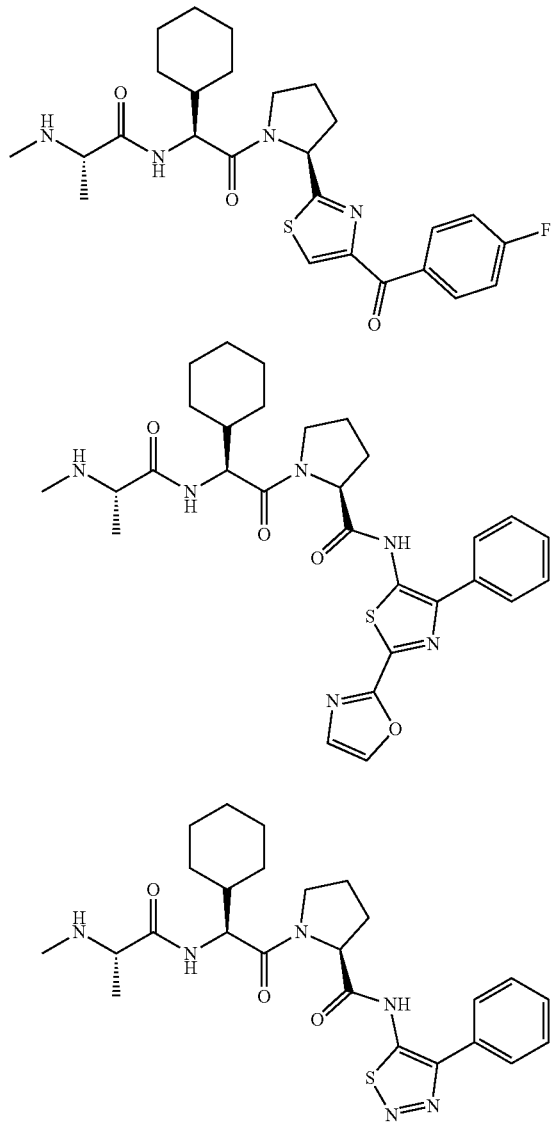

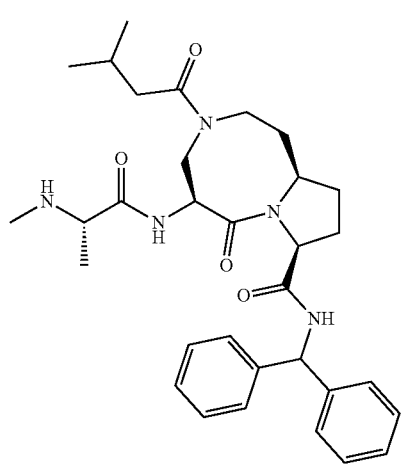

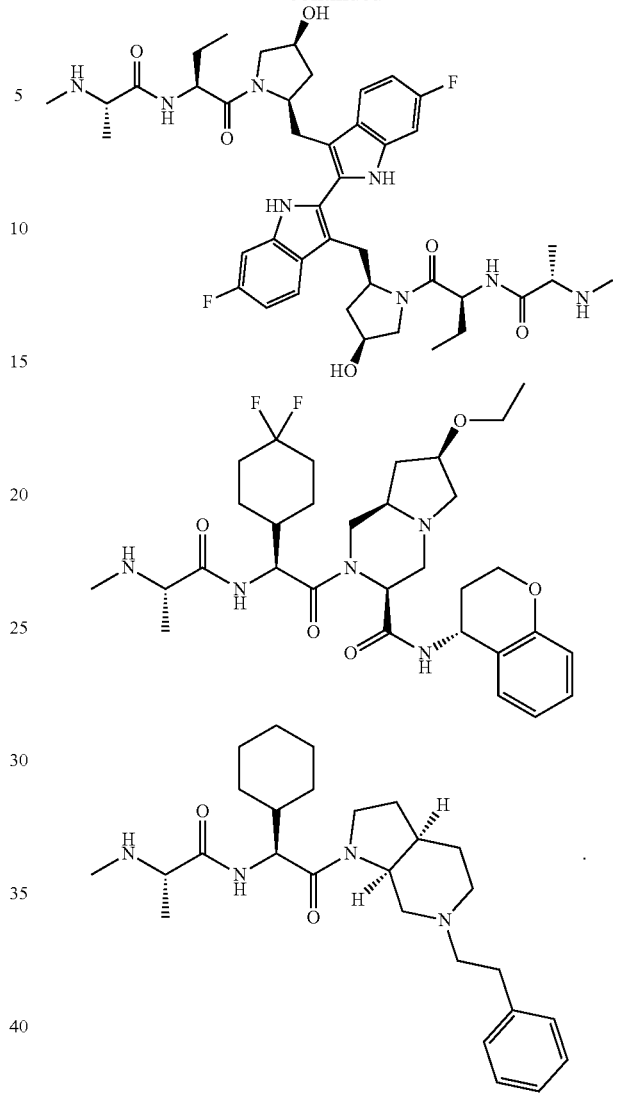

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a C1-$C_6$, alternatively a C1-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C—C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$ or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—$(C_1$-$C_6)$alkyl, —$(CH_2)$—O—$(CH_2)$—$(C_1$-$C_6)$alkyl, —$(CH_2)_n$—C(O)$(C_0$-$C_6)$ alkyl, —$(CH_2)$—C(O)O$(C_0$-$C_6)$ alkyl, —$(CH_2)_n$—OC(O)$(C_0$-$C_6)$alkyl, amine, mono- or di-$(C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

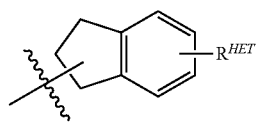

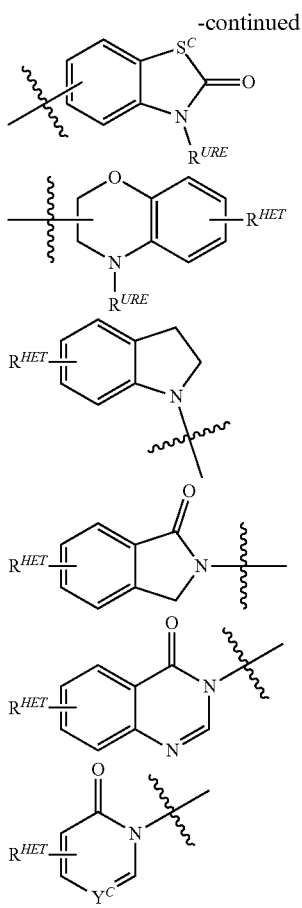

wherein:
S$^c$ is CHR$^{SS}$, NR$^{URE}$, or O;
R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);
R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
Y$^c$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO—heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl.

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrrolopyrimidine/imidazolopyridine represented as Formula (A-7), or pyrrolopyrrolidinone/imidazolopyrrolidinone represented as Formula (A-8).

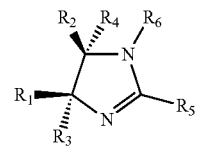

Formula (A-1)

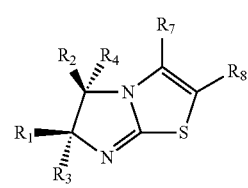

Formula (A-2)

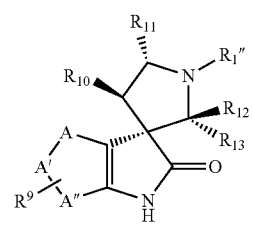

Formula (A-3)

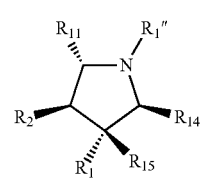

Formula (A-4)

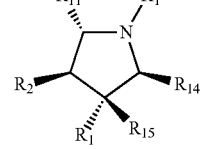

Formula (A-5)

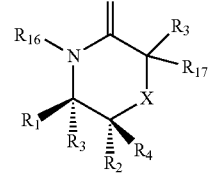

Formula (A-6)

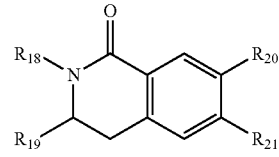

Formula (A-7)

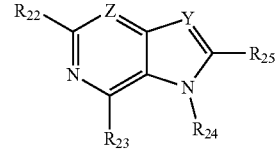

Formula (A-8)

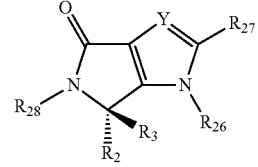

wherein above Formula (A-1) through Formula (A-8),

X of Formula (A-1) through Formula (A-8) is selected from the group consisting of carbon, oxygen, sulfur, sulfoxide, sulfone, and N—$R^a$;

$R^a$ is independently H or an alkyl group with carbon number 1 to 6;

Y and Z of Formula (A-1) through Formula (A-8) are independently carbon or nitrogen;

A, A' and A" of Formula (A-1) through Formula (A-8) are independently selected from C, N, O or S, can also be one or two atoms forming a fused bicyclic ring, or a 6,5- and 5,5-fused aromatic bicyclic group;

$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ of Formula (A-1) through Formula (A-8) are independently selected from the group consisting of H, methyl and C1 to C6 alkyl;

$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ of Formula (A-1) through Formula (A-8) is H or —C(=O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—SO$_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the one group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:

H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ of Formula (A-1) through Formula (A-8) are independently selected from the group consisting of H, connected to form a ring, 4-hydroxycyclohehexane; mono- and di-hydroxy substituted alkyl (C3 to C6); 3-hydroxycyclobutane; phenyl-4-carboxylic acid, and substituted phenyl-4-carboxylic acid;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, $R^{12}$ and $R^{13}$ can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one CH$_2$ replaced by S(=O), —S, or —S(=O)$_2$, alkyl or cycloalkyl with terminal CH$_3$ replaced by S(=O)$_2$N(alkyl)(alkyl), —C(=O)N(alkyl)(alkyl), —N(alkyl)S(=O)$_2$(alkyl), —C(=O)2(alkyl), —O(alkyl), C1-6 alkyl or alkyl-cycloalkyl with hydron replaced by hydroxyl group, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of $(CH_2)nC(O)NR^kR^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mono- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)— heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydroxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ of Formula (A-1) through Formula (A-8) is selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L" is a connector (i.e. a linker group), and "PTM" is a ligand binding to a target protein.

In certain embodiments, the description provides a bifunctional molecule comprising a structure selected from the group consisting of:

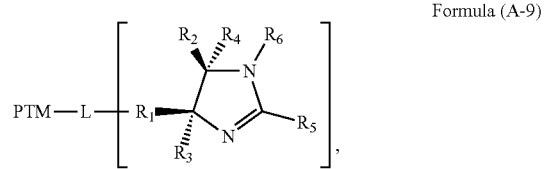

Formula (A-9)

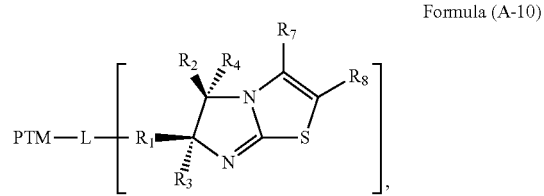

Formula (A-10)

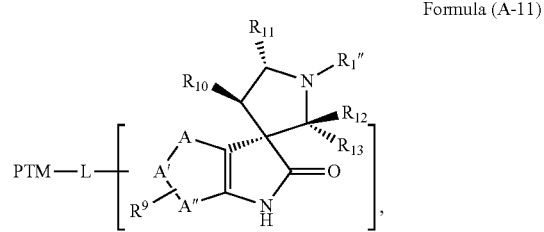

Formula (A-11)

-continued

Formula (A-12)
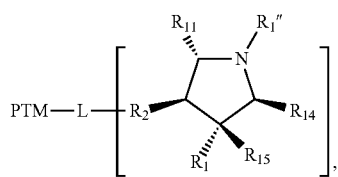

Formula (A-13)
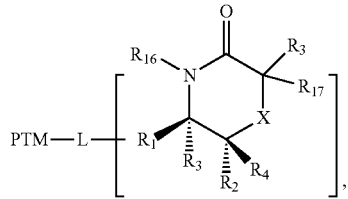

Formula (A-14)
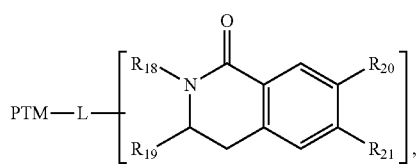

Formula (A-15)
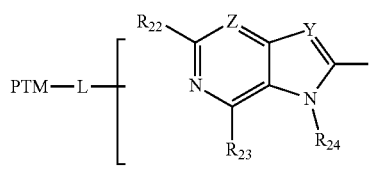

Formula (A-16)
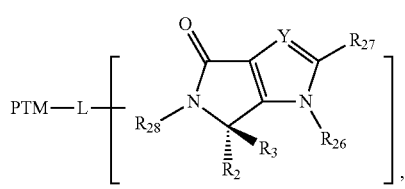

wherein X, $R^a$, Y, Z, A, A', A'', $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_1$, are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1
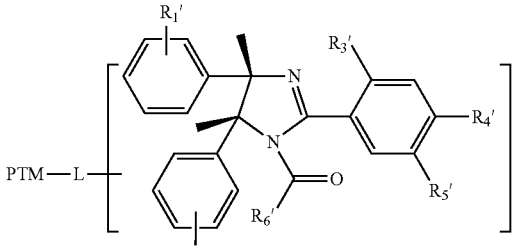

A-1-2
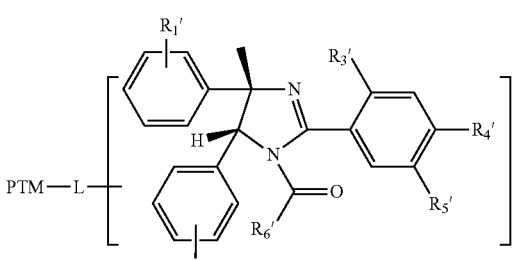

A-1-3
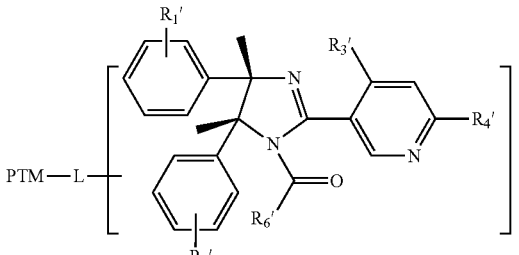

A-1-4
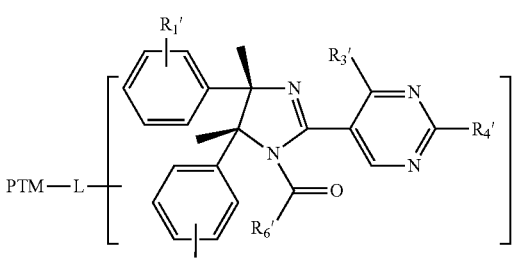

wherein:
R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$;
R3' is selected from the group consisting of —$OCH_3$, —$OCH_2CH_3$, —$OCH_2CH_2F$, —$OCH_2CH_2OCH_3$, and —$OCH(CH_3)_2$;
R4' of Formulas A-1-1 through A-1-4 is selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2OCH_2CH_3$, —$C(CH_3)_2CH_2OH$, —$C(CH_3)_2CH_2OCH_2CH_3$, —$C(CH_3)_2CH_2OCH_2CH_2OH$, —$C(CH_3)_2CH_2OCH_2CH_3$, —$C(CH_3)_2CN$, —$C(CH_3)_2C(O)CH_3$, —$C(CH_3)_2C(O)NHCH_3$, —$C(CH_3)_2C(O)N(CH_3)_2$, —SCH$_3$, —SCH$_2$CH$_3$, —S(O)$_2$CH$_3$, —S(O$_2$)CH$_2$CH$_3$, —NHC(CH$_3$)$_3$, —N(CH$_3$)$_2$, pyrrolidinyl, and 4-morpholinyl;

R5' of Formulas A-1-1 through A-1-4 is selected from the group consisting of halogen, -cyclopropyl, —S(O)$_2$CH$_3$, —S(O)$_2$CH$_2$CH$_3$, 1-pyrrolidinyl, —NH$_2$, —N(CH$_3$)$_2$, and —NHC(CH$_3$)$_3$; and R6' of Formulas A-1-1 through A-1-4 is selected from the structures presented below where the linker connection point is indicated as "*"

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H,

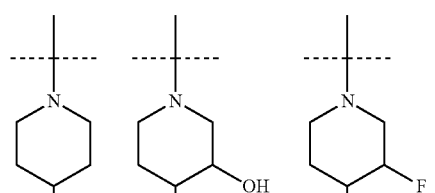

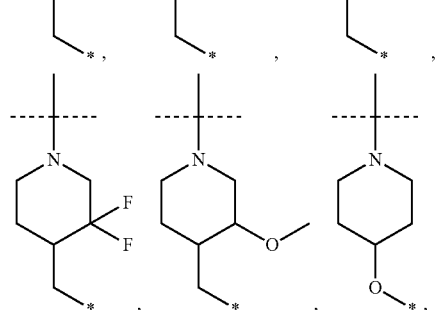

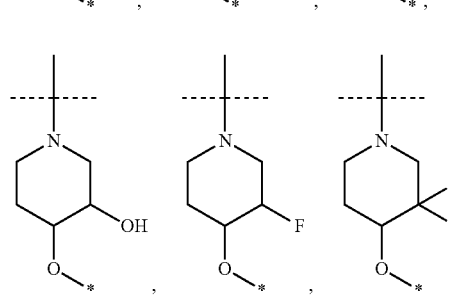

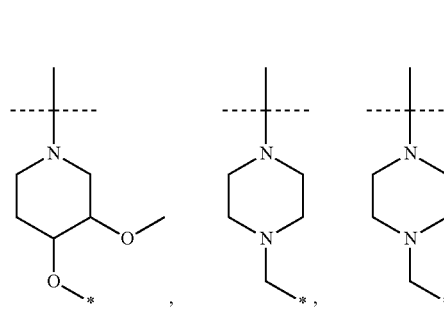

-continued

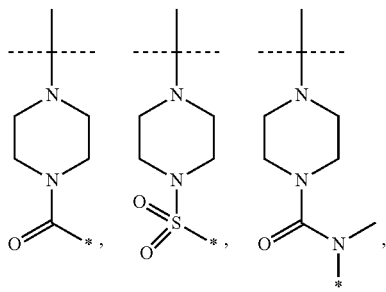

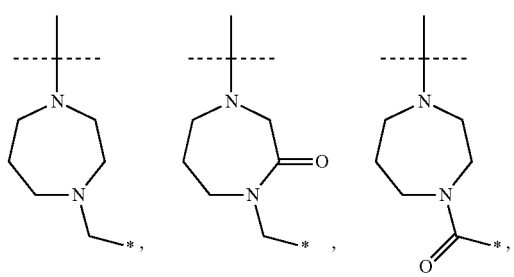

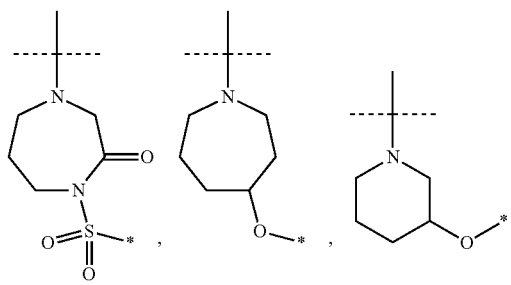

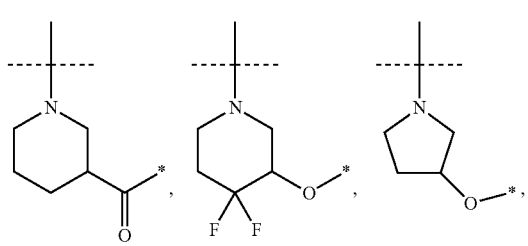

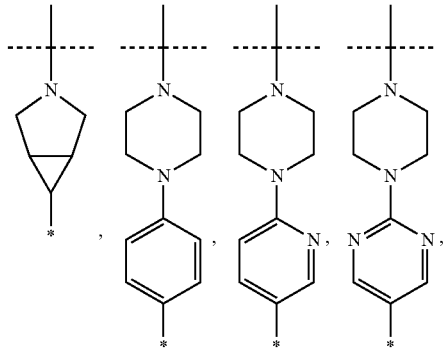

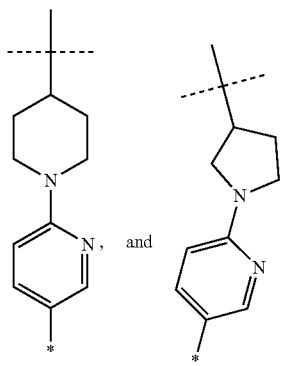

and wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

A-4-1
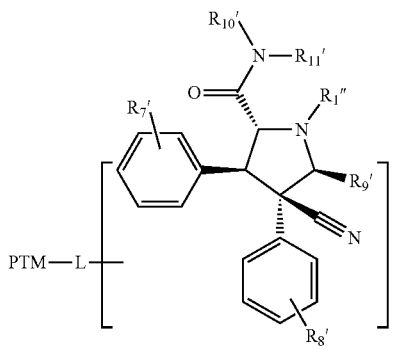

A-4-2
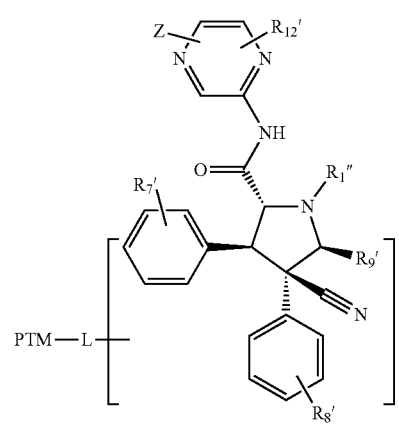

A-4-3
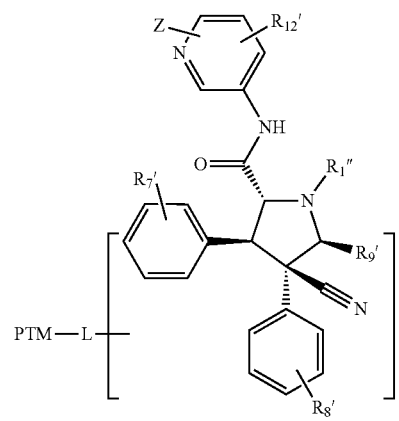

A-4-4
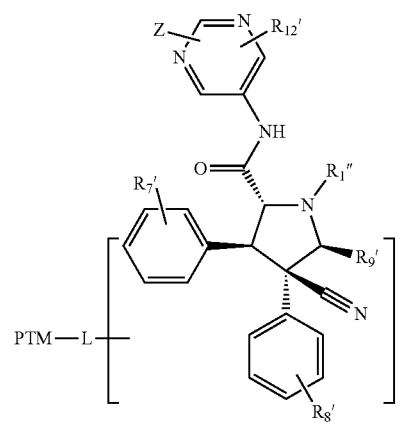

A-4-5

-continued

A-4-6

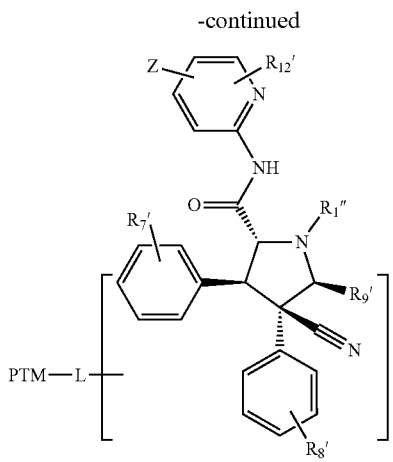

wherein:
R7' of Formula A-4-1 through A-4-6 (i.e., A-4-1, A-4-2, A-4-3, A-4-4, A-4-5, and A-4-6) is a member selected from the group consisting of halogen, mono-, and di- or tri-substituted halogen;
R8' of Formula A-4-1 through A-4-6 is selected from the group consisting of H, —F, —Cl, —Br, —I, —CN, —NO$_2$, ethylenyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;
R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;
Z of Formula A-4-1 through A-4-6 is selected from the group consisting of H, —OCH$_3$, —OCH$_2$CH$_3$, and halogen;
R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$(CH$_2$)$_n$—COOR', (CH$_2$CH$_2$O)$_m$—(CH$_2$)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)$_n$—OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)$_m$—(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)$_p$—(CH$_2$CH$_2$O)$_m$—(CH$_2$)$_n$—SO$_2$R', (CH$_2$)$_p$—(CH$_2$CH$_2$O)$_m$(CH$_2$)$_n$—COR', (CH$_2$)$_p$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR';
wherein R' and R" are selected from H, alkyl, alkyl substituted with halogen, hydroxyl, NH2, NH(alkyl), N(alkyl)$_2$, oxo, carboxy, cycloalkyl and heteroaryl;
m, n, and p are independently 0 to 6;
R12' of Formula A-4-1 through A-4-6 is selected from the group consisting of —O-(alkyl), —O-(alkyl)-alkoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)-(cyclic amine), and —O-aryl-(alkyl), —O-aryl-(alkoxy);
R1" of Formula A-4-1 through A-4-6 is selected from the group consisting of alkyl, aryl substituted alkyl, aloxy substituted alkyl, cycloalkyl, aryl-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

the HDM2/MDM2 inhibitors identified in Vassilev, et al., In vivo activation of the p53 pathway by small-molecule antagonists of MDM2, SCIENCE vol:303, pag:844-848 (2004), and Schneekloth, et al., Targeted intracellular protein degradation induced by a small molecule: En route to chemical proteomics, Bioorg. Med. Chem. Lett. 18 (2008) 5904-5908, including (or additionally) the compounds nutlin-3, nutlin-2, and nutlin-1 (derivatized) as described below, as well as all derivatives and analogs thereof:

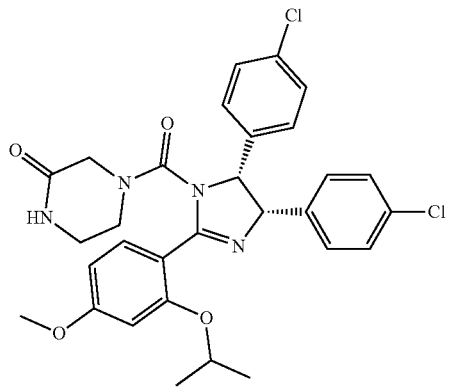 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

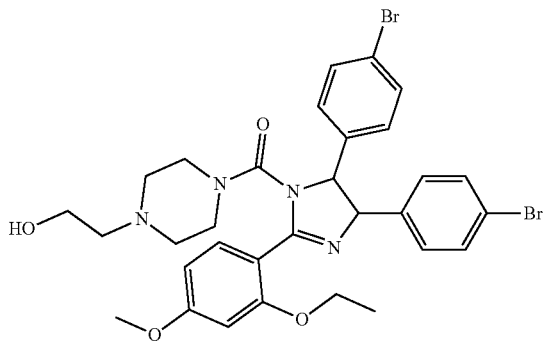 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group); and

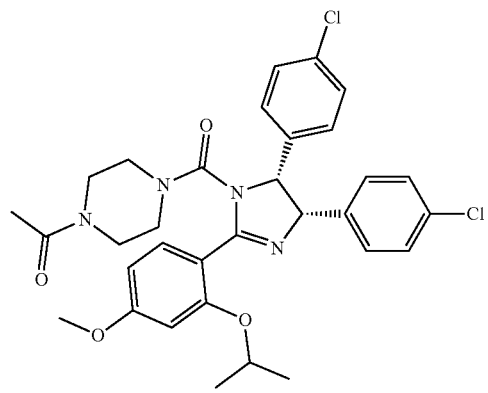 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group).

Exemplary CLMs

Neo-Imide Compounds

In one aspect the description provides compounds useful for binding and/or inhibiting cereblon. In certain embodiments, the compound is selected from the group consisting of chemical structures:

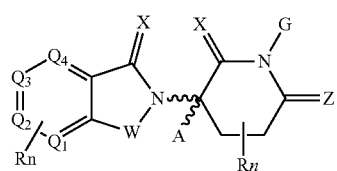
(a)

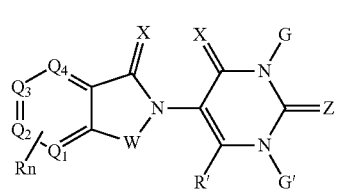
(b)

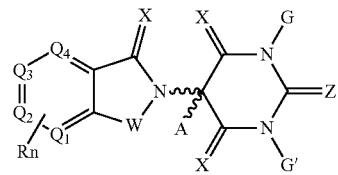
(c)

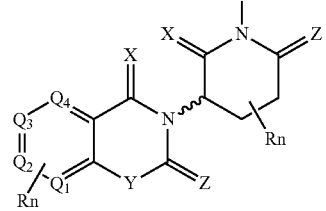
(d)

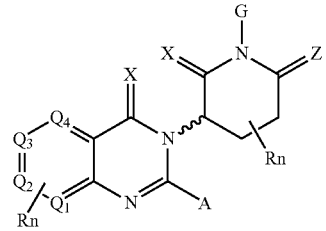
(e)

and

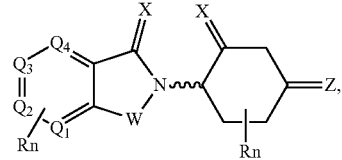
(f)

wherein:
W of Formulas (a) through (e) is independently selected from the group CH$_2$, CHR, C=O, SO$_2$, NH, and N-alkyl;
X of Formulas (a) through (e) is independently selected from the group O, S and H$_2$;
Y of Formulas (a) through (e) is independently selected from the group CH$_2$, —C=CR', NH, N-alkyl, N-aryl, N-hetaryl, N-cycloalkyl, N-heterocyclyl, O, and S;
Z of Formulas (a) through (e) is independently selected from the group O, and S or H$_2$ except that both X and Z cannot be H$_2$;
G and G' of Formulas (a) through (e) are independently selected from the group H, alkyl (linear, branched, optionally substituted), OH, R'OCOOR, R'OCONRR", CH$_2$-heterocyclyl optionally substituted with R', and benzyl optionally substituted with R';
Q1-Q4 of Formulas (a) through (e) represent a carbon C substituted with a group independently selected from R', N or N-oxide;
A of Formulas (a) through (e) is independently selected from the group H, alkyl (linear, branched, optionally substituted), cycloalkyl, Cl and F;
R of Formulas (a) through (e) comprises, but is not limited to: —CONR'R", —OR', —NR'R", —SR', —SO$_2$R', —SO$_2$NR'R", —CR'R"—, —CR'NR'R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO₂)NR'R", —SO₂NR'COR", —NO₂, —CO₂R', —C(C=N—OR')R", —CR'=CR'R", —CCR', —S(C=O)(C=N—R')R", —SF₅ and —OCF₃

R' and R" of Formulas (a) through (e) are independently selected from a bond, H, alkyl, cycloalkyl, aryl, heteroaryl, heterocyclic, —C(=O)R, heterocyclyl, each of which is optionally substituted;

n of Formulas (a) through (e) is an integer from 1-10 (e.g., 1-4, 1, 2, 3, 4, 5, 6, 7, 8, 9, or 10);

~~~ of Formulas (a) through (e) represents a bond that may be stereospecific ((R) or (S)) or non-stereospecific; and R$_n$ of Formulas (a) through (e) comprises 1-4 independent functional groups or atoms.

Exemplary CLMs

In any of the compounds described herein, the CLM comprises a chemical structure selected from the group:

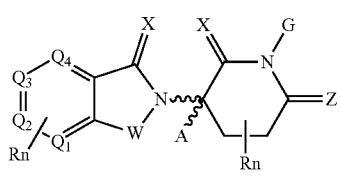
(a)

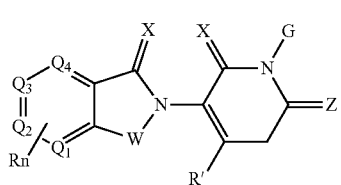
(b)

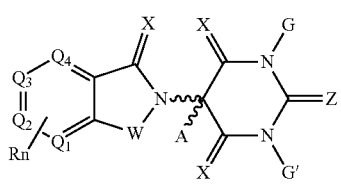
(c)

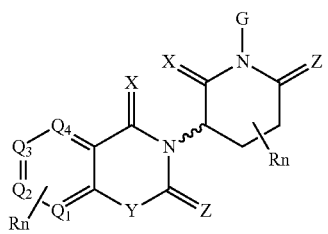
(d)

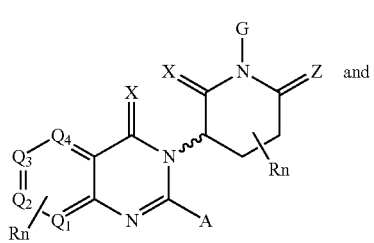
(e) and

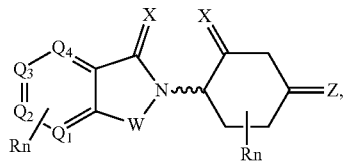
(f)

wherein:
W of Formulas (a) through (e) is independently selected from the group CH₂, CHR, C=O, SO₂, NH, and N-alkyl;
X of Formulas (a) through (e) is independently selected from the group O, S and H2;
Y of Formulas (a) through (e) is independently selected from the group CH₂, —C=CR', NH, N-alkyl, N-aryl, N-heteroaryl, N-cycloalkyl, N-heterocyclyl, O, and S;
Z of Formulas (a) through (e) is independently selected from the group O, and S or H2 except that both X and Z cannot be H2;
G and G' of Formulas (a) through (e) are independently selected from the group H, alkyl (linear, branched, optionally substituted), OH, R'OCOOR, R'OCONRR", CH₂-heterocyclyl optionally substituted with R', and benzyl optionally substituted with R';
Q1-Q4 of Formulas (a) through (e) represent a carbon C substituted with a group independently selected from R', N or N-oxide;
A of Formulas (a) through (e) is independently selected from the group H, alkyl (linear, branched, optionally substituted), cycloalkyl, Cl and F;
R of Formulas (a) through (e) comprises, but is not limited to: —CONR'R", —OR', —NR'R", —SR', —SO2R', —SO2NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3

R' and R" of Formulas (a) through (e) are independently selected from a bond, H, alkyl, cycloalkyl, aryl, heteroaryl, heterocyclic, —C(=O)R, heterocyclyl, each of which is optionally substituted;

n of Formulas (a) through (e) is an integer from 1-10;

~~~ of Formulas (a) through (e) represents a bond that may be stereospecific ((R) or (S)) or non-stereospecific; and Rn of Formulas (a) through (e) comprises 1-4 independent functional groups or atoms, for example, O, N or S, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

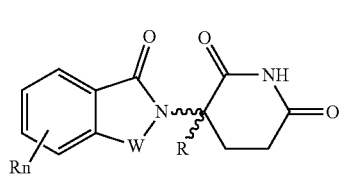
Formula (g)

wherein:

W of Formula (g) is independently selected from the group $CH_2$, $C=O$, NH, and N-alkyl;

R of Formula (g) is independently selected from a H, methyl, or optionally substituted alkyl (e.g., C1-C6 alkyl (linear, branched, optionally substituted));

~~~ of Formula (g) represents a bond that may be stereospecific ((R) or (S)) or non-stereospecific; and Rn of Formula (g) comprises 1-4 independently selected functional groups or atoms, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

In any of the aspects or embodiments described herein, Rn comprises from 1 to 4 functional groups or atoms, for example, O, OH, N, C1-C6 alkyl, C1-C6 alkoxy, amine, amide, or carboxy, and optionally, one of which is modified to be covalently joined to a PTM, a chemical linker group (L), a ULM, CLM (or CLM') or combination thereof.

More specifically, non-limiting examples of CLMs include those shown below as well as those "hybrid" molecules that arise from the combination of 1 or more of the different features shown in the molecules below.

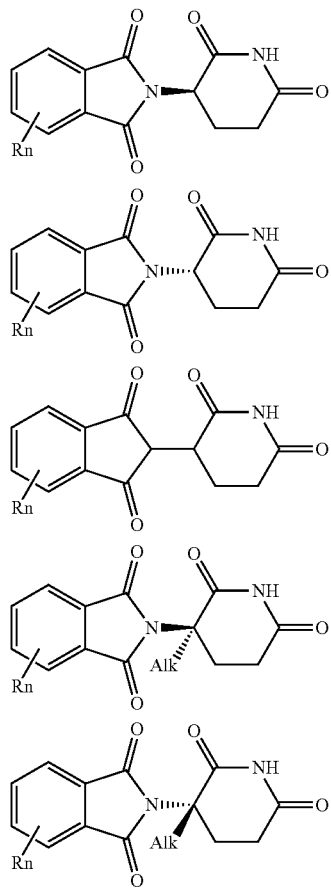

-continued

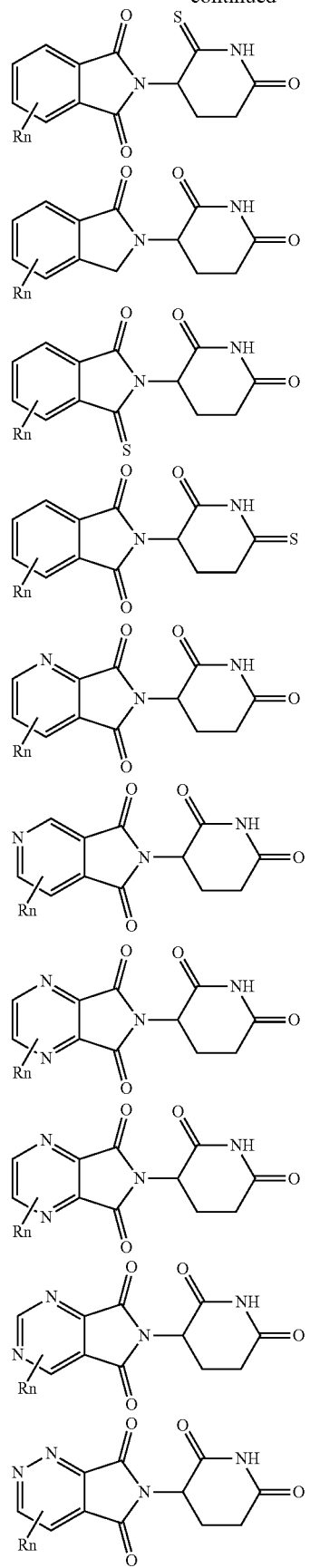

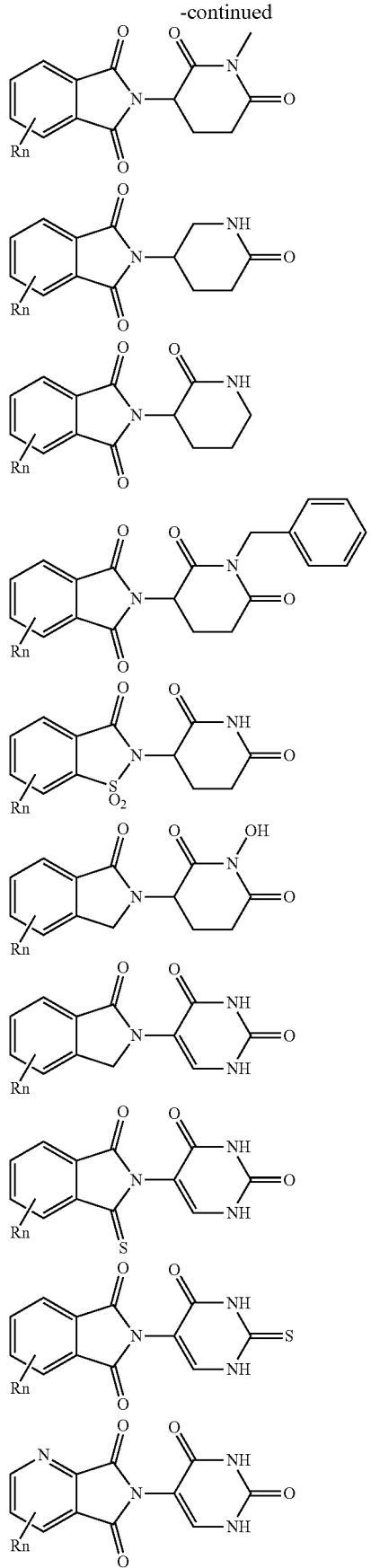
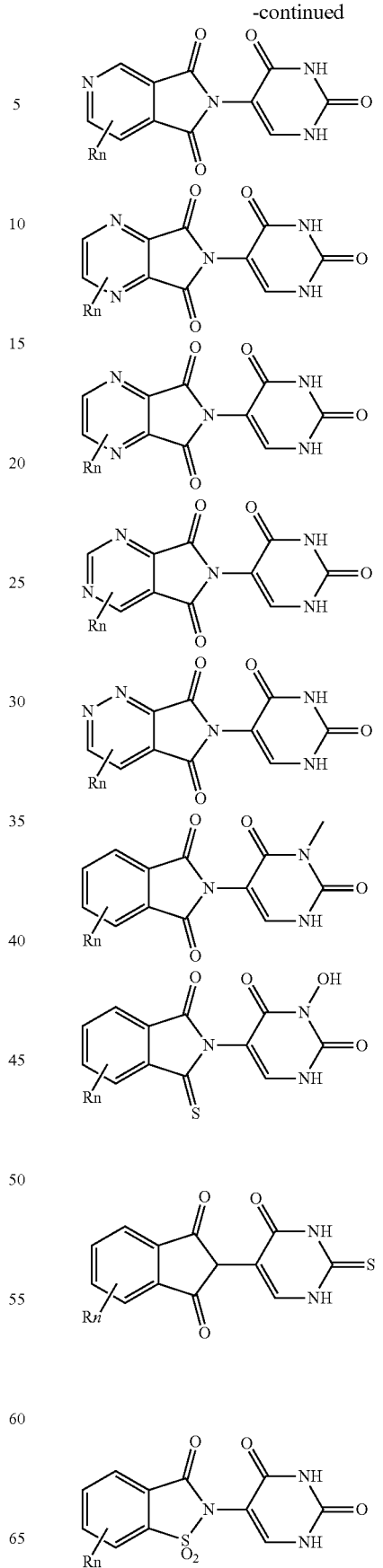

147
-continued
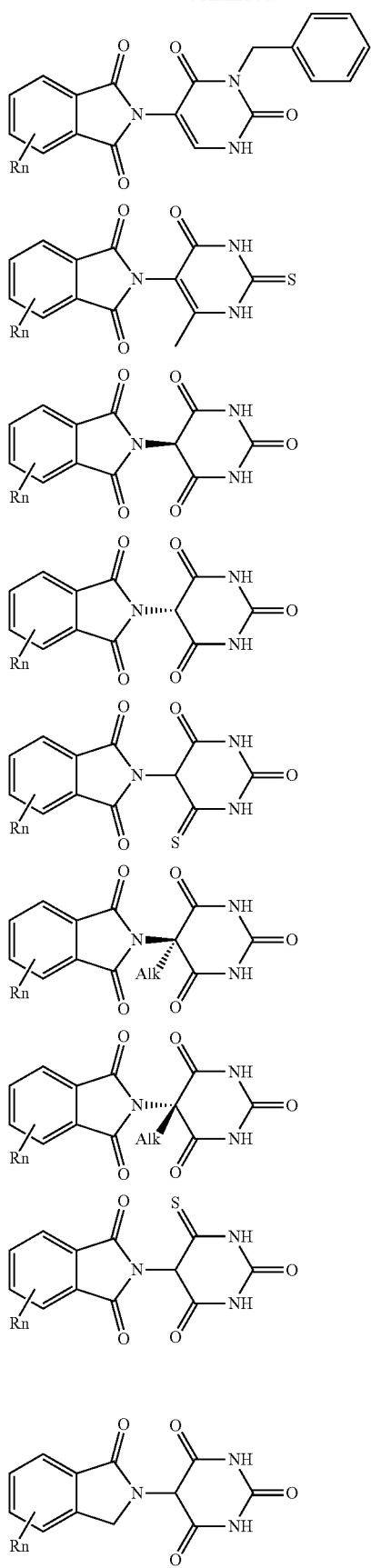
148
-continued
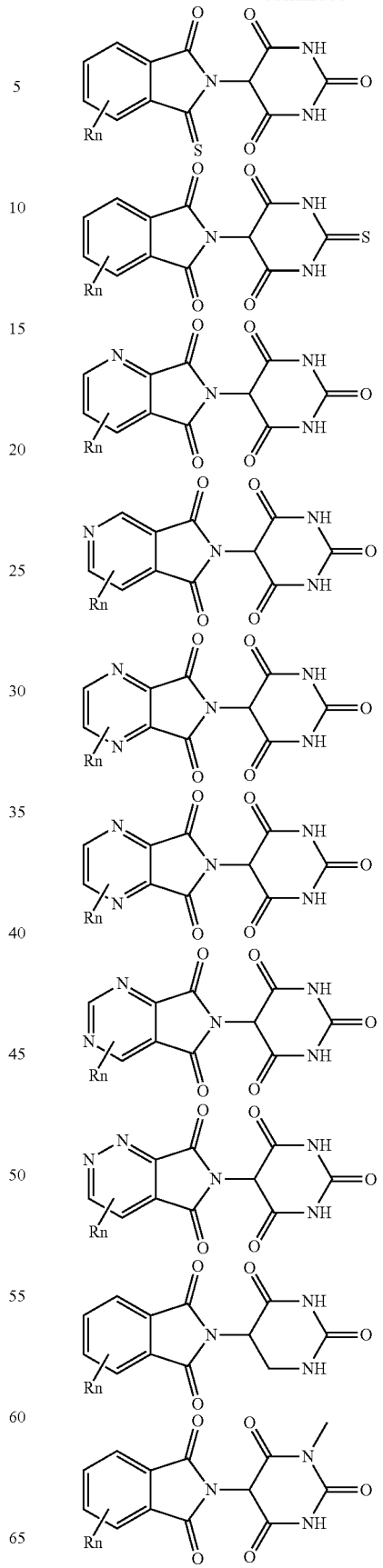

149
-continued
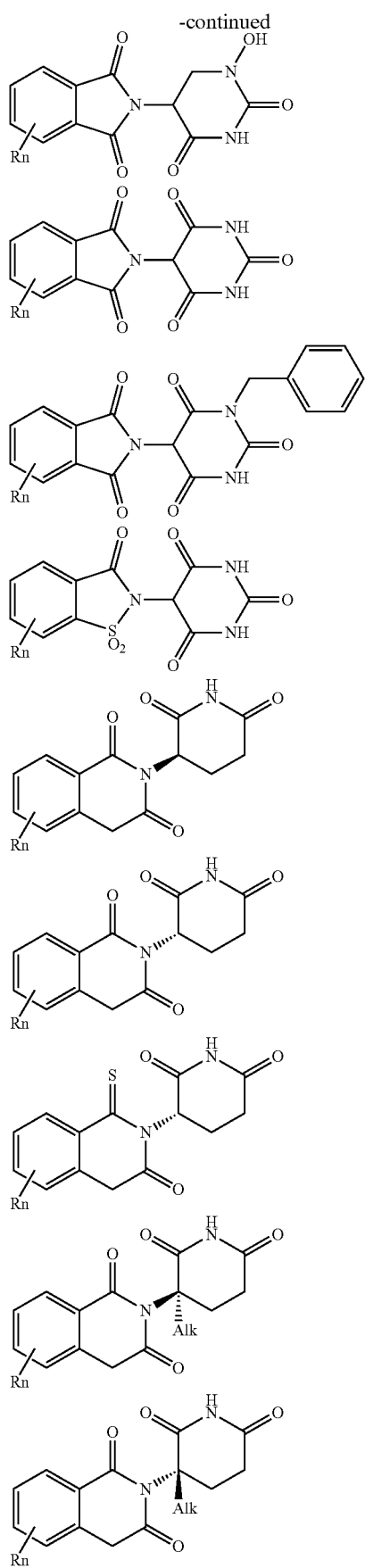
150
-continued
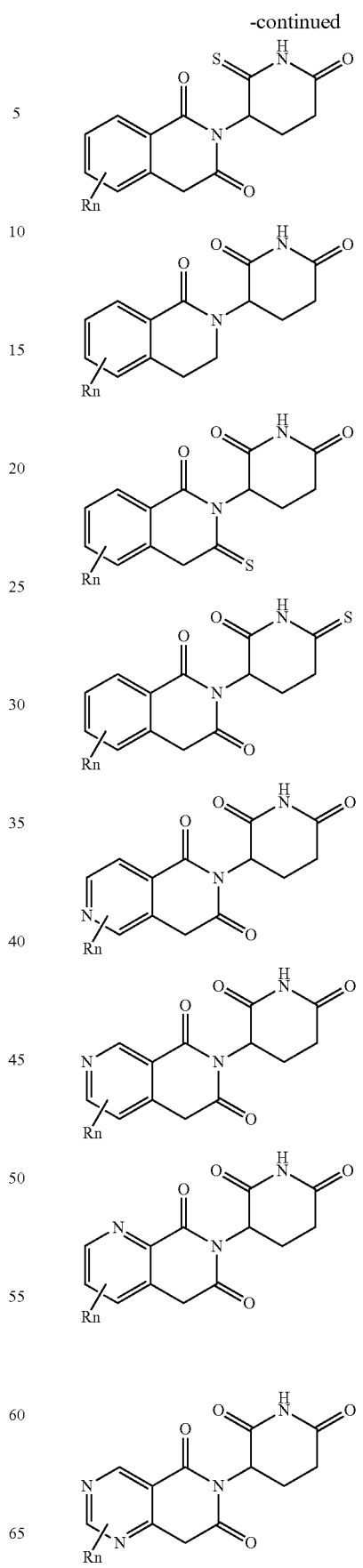

-continued
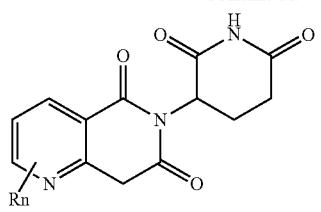
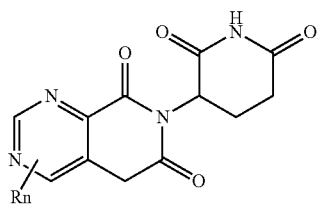
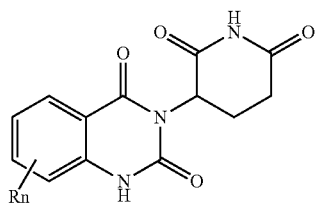
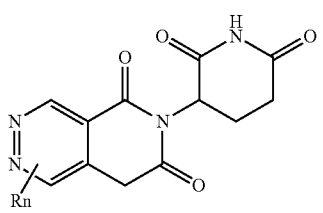
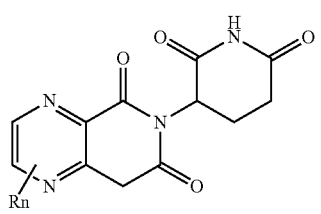
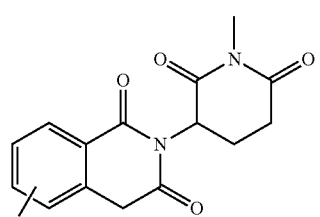
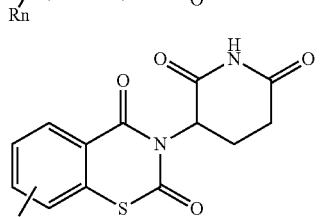
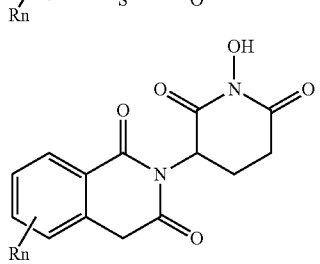
-continued
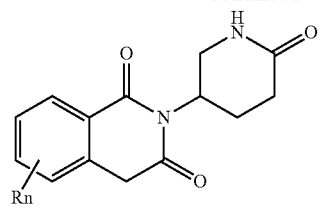
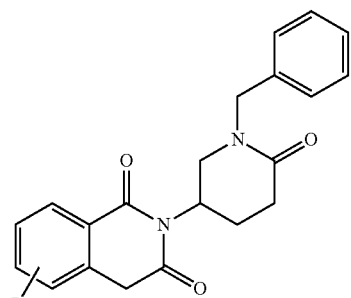
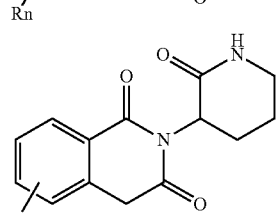
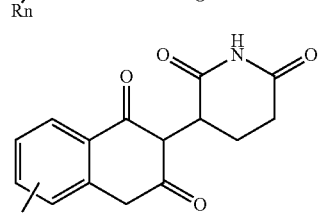
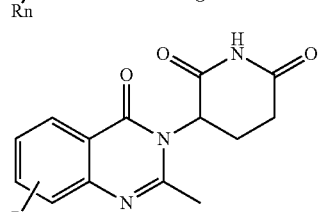
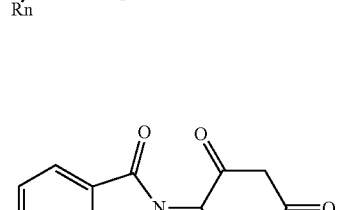
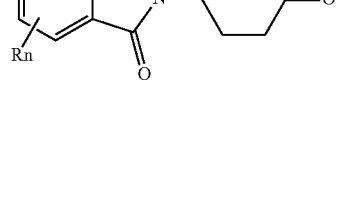
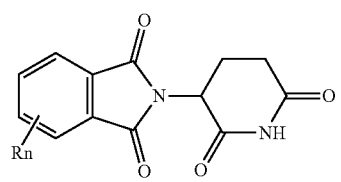

153
-continued
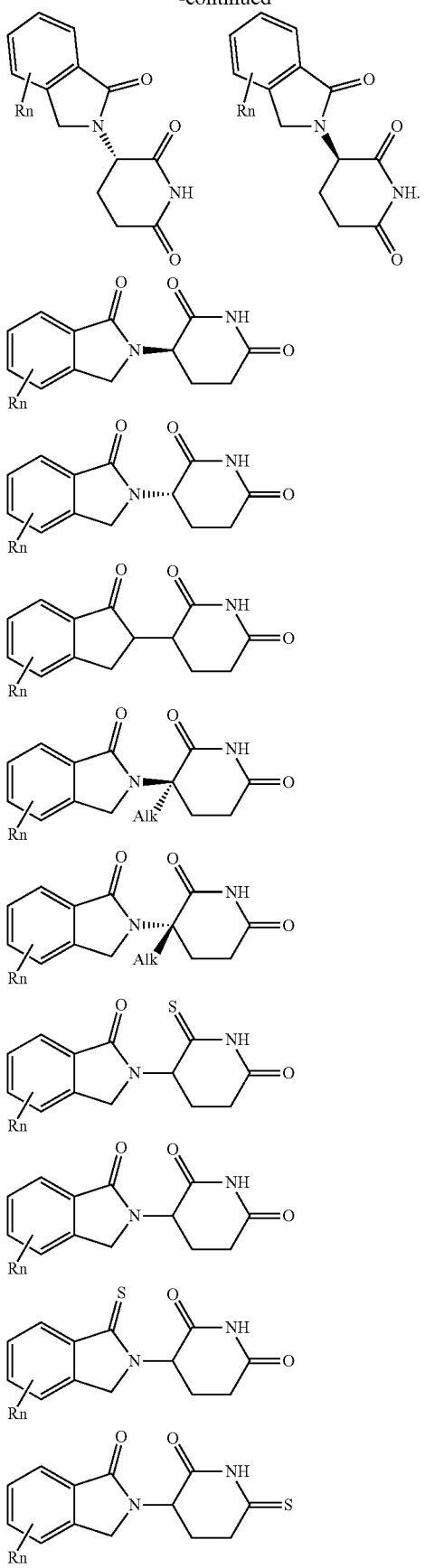
154
-continued
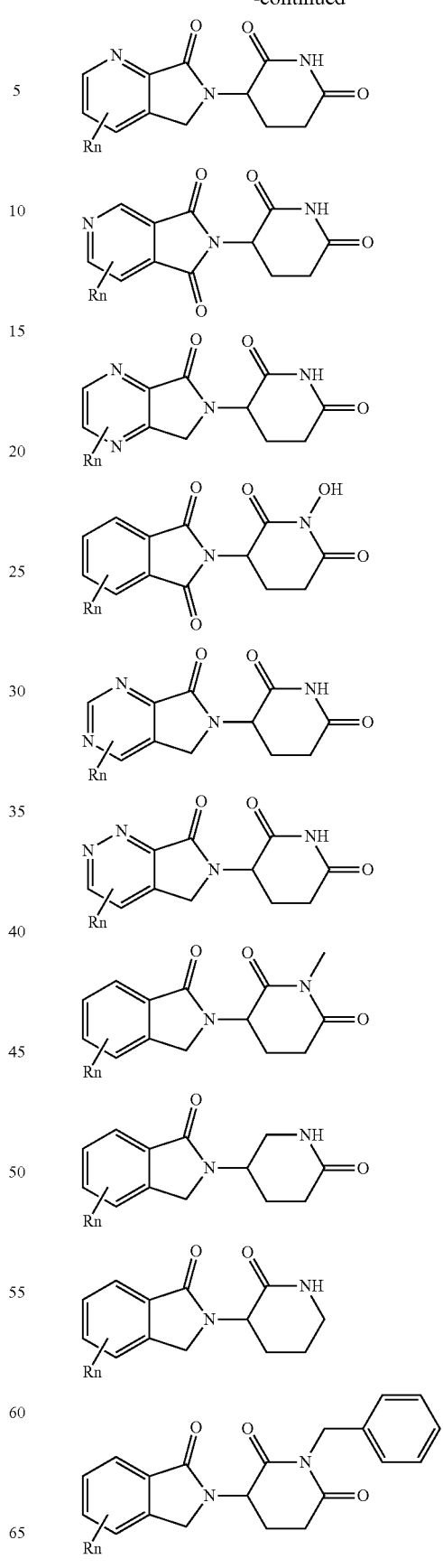

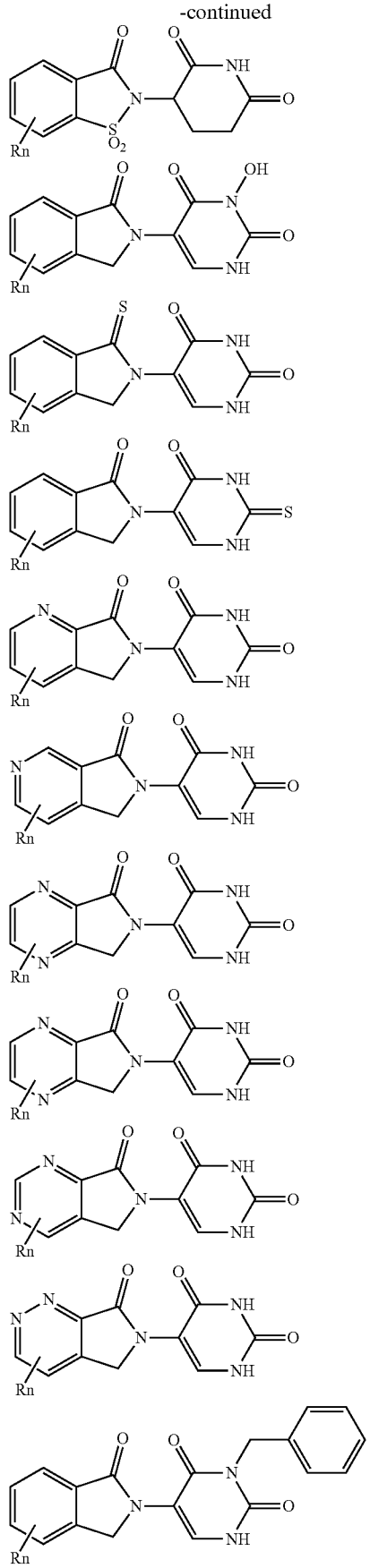
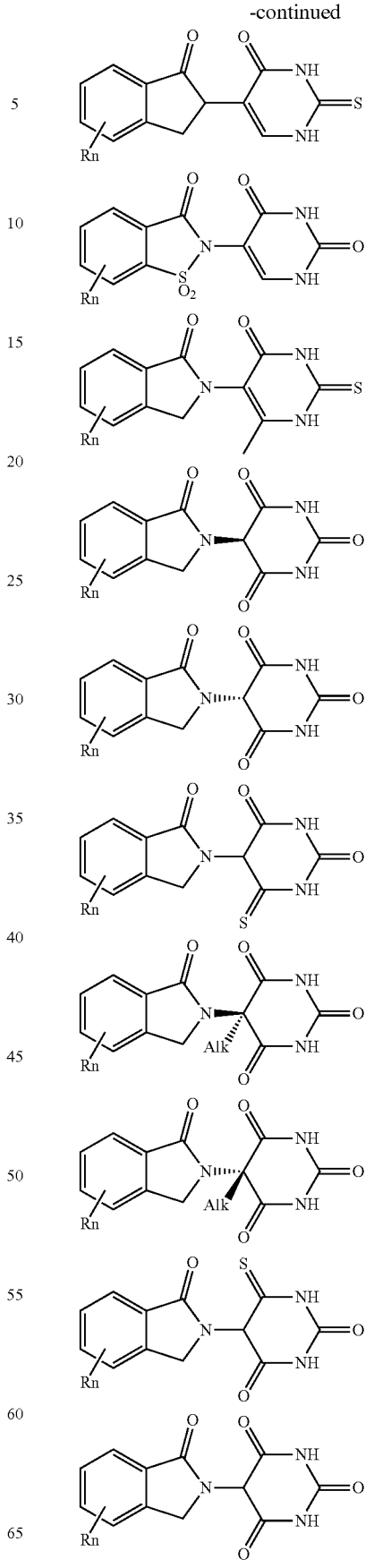

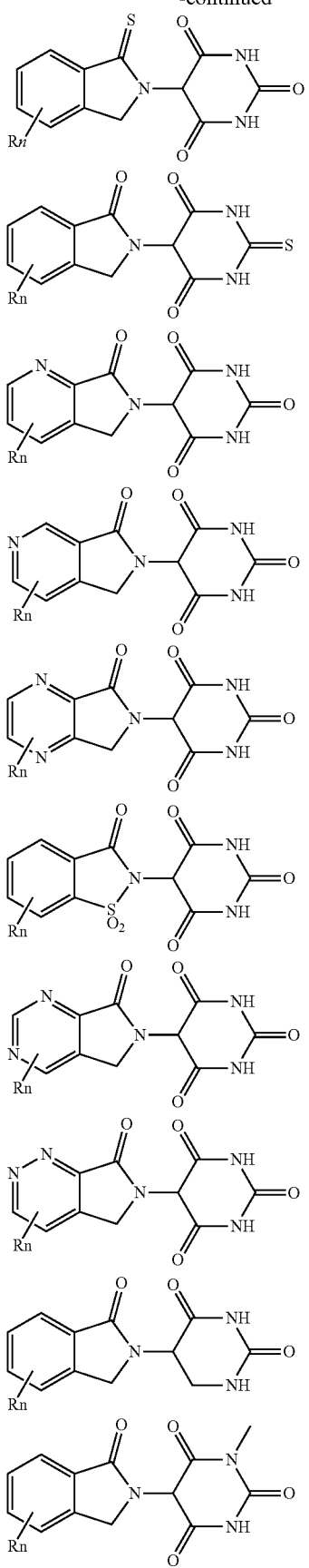
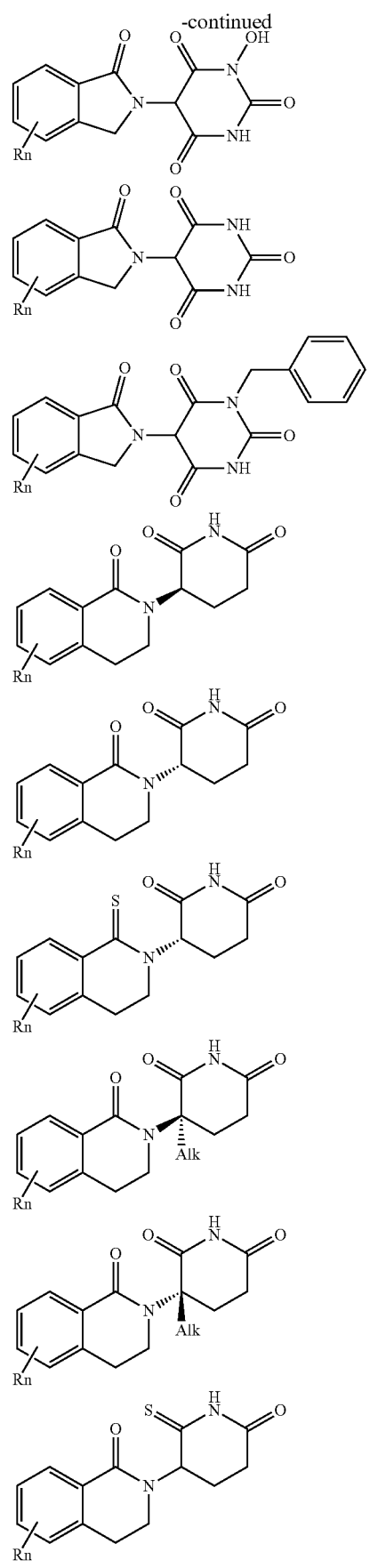

-continued
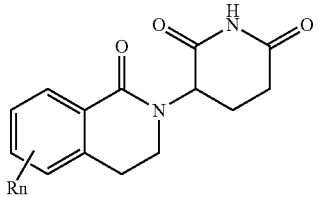
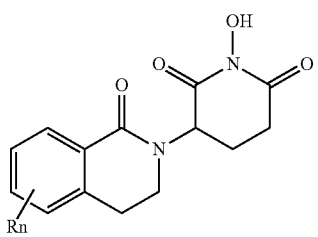
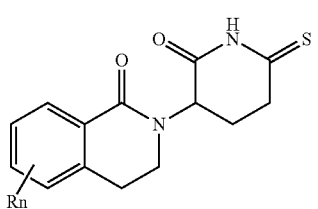
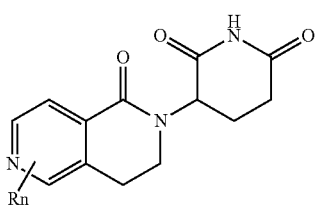
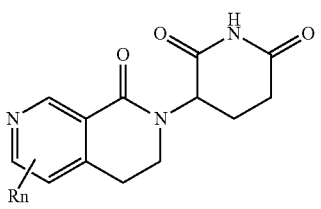
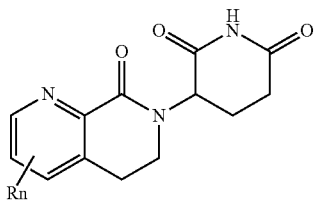
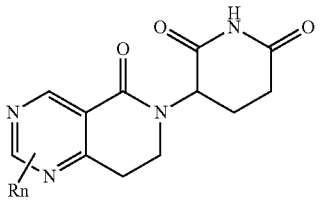
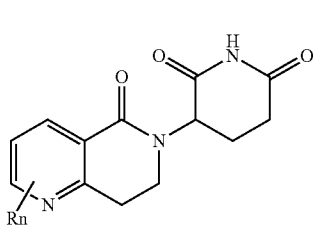
-continued
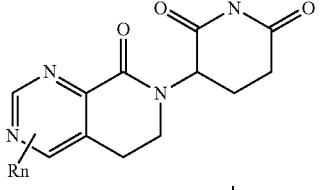
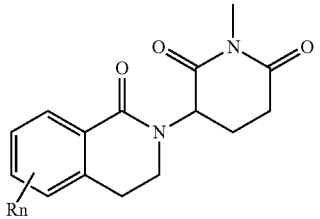
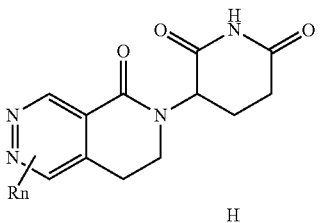
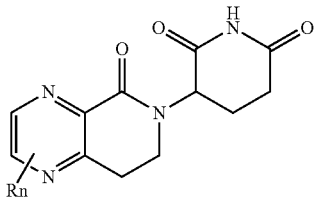
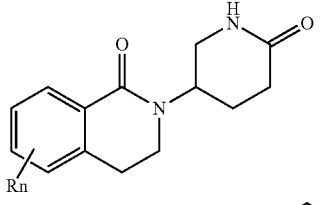
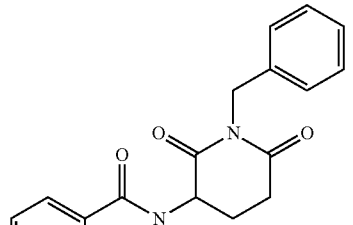
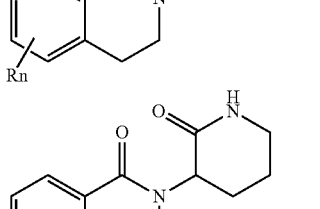
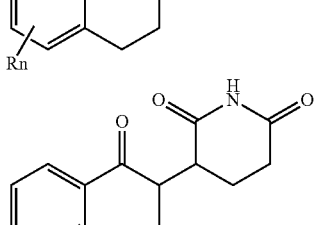

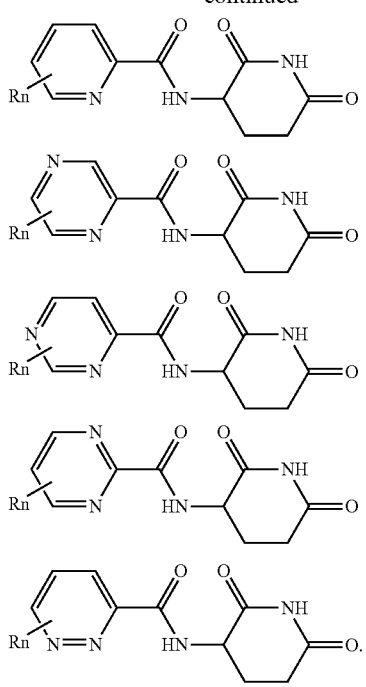
In any of the compounds described herein, the CLM comprises a chemical structure selected from the group:
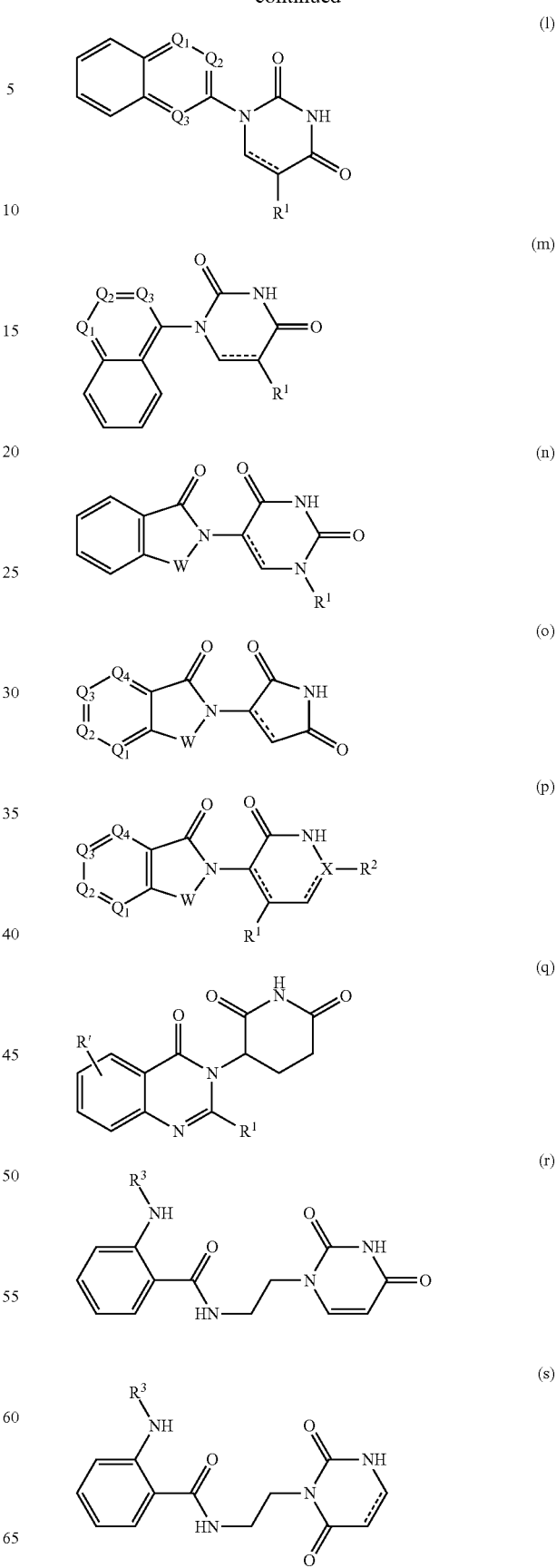

-continued (t) 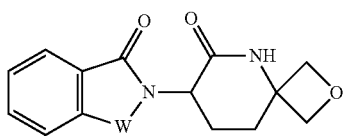

(u) 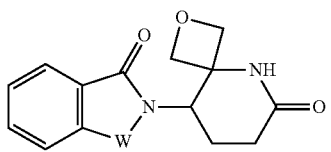

(v) 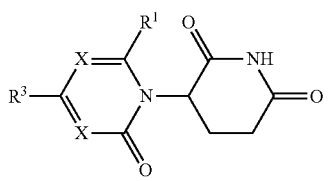

(w) 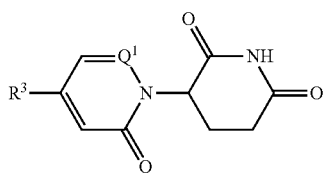

(x) 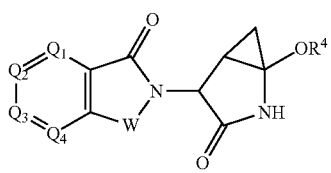

(y) 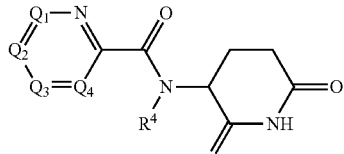

(z) 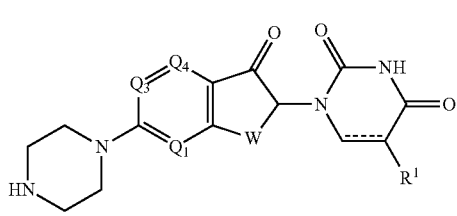

(aa) 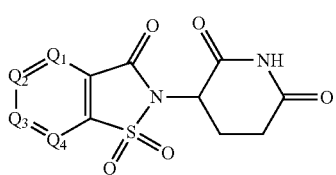

(ab) 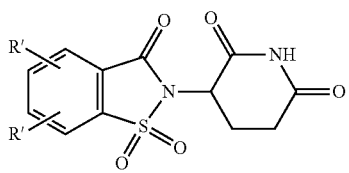

(ac) 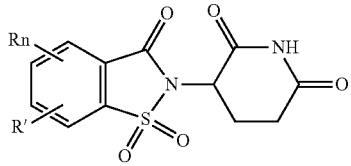

(ad) 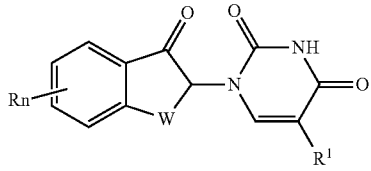

wherein:
W of Formulas (h) through (ab) is independently selected from $CH_2$, CHR, C=O, $SO_2$, NH, and N-alkyl;

$Q_1$, $Q_2$, $Q_3$, $Q_4$, $Q_5$ of Formulas (h) through (ab) are independently represent a carbon C substituted with a group independently selected from R', N or N-oxide;

$R^1$ of Formulas (h) through (ab) is selected from H, CN, C1-C3 alkyl;

$R^2$ of Formulas (h) through (ab) is selected from the group H, CN, C1-C3 alkyl, $CHF_2$, $CF_3$, CHO;

$R^3$ of Formulas (h) through (ab) is selected from H, alkyl, substituted alkyl, alkoxy, substituted alkoxy;

$R^4$ of Formulas (h) through (ab) is selected from H, alkyl, substituted alkyl;

$R^5$ of Formulas (h) through (ab) is H or lower alkyl;

X of Formulas (h) through (ab) is C, CH or N;

R' of Formulas (h) through (ab) is selected from H, halogen, alkyl, substituted alkyl, alkoxy, substituted alkoxy;

R of Formulas (h) through (ab) is H, OH, lower alkyl, lower alkoxy, cyano, halogenated lower alkoxy, or halogenated lower alkyl ⌇ of Formulas (h) through (ab) is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

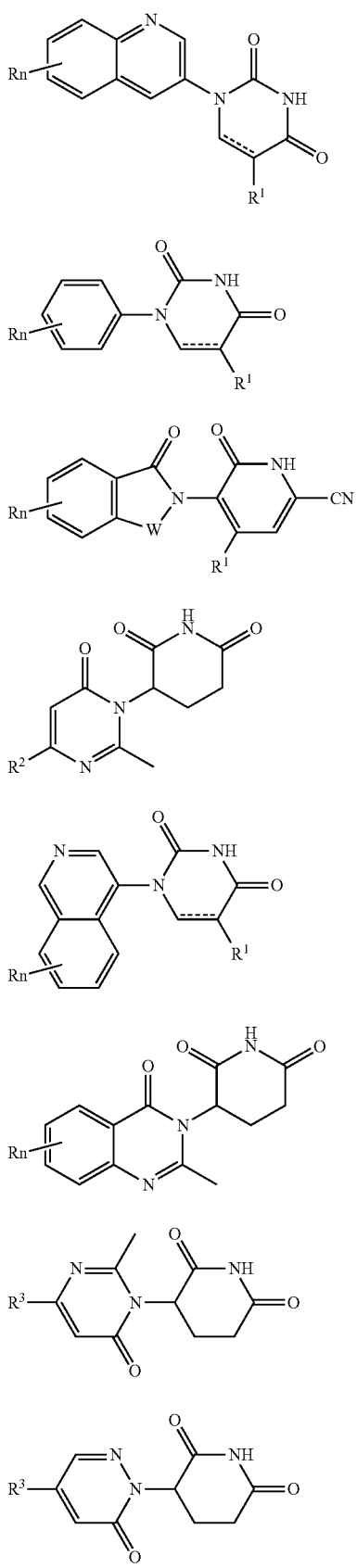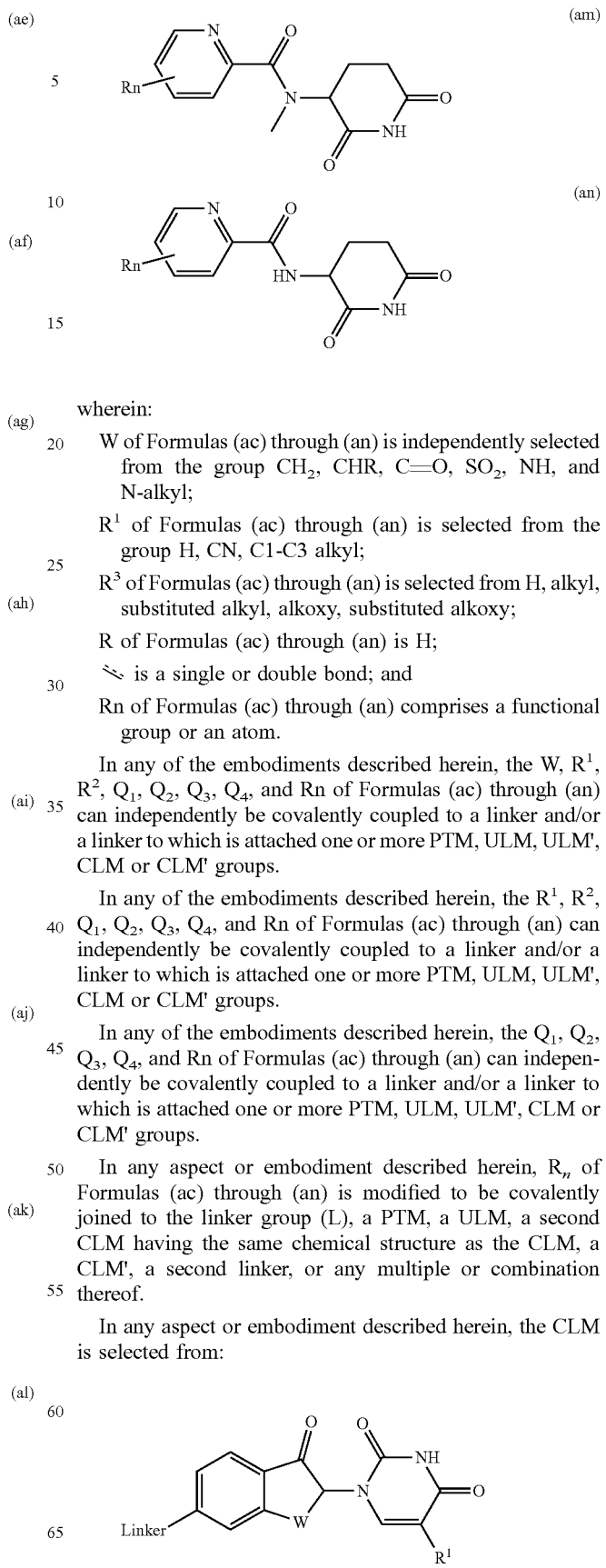

wherein:

W of Formulas (ac) through (an) is independently selected from the group $CH_2$, CHR, C=O, $SO_2$, NH, and N-alkyl;

$R^1$ of Formulas (ac) through (an) is selected from the group H, CN, C1-C3 alkyl;

$R^3$ of Formulas (ac) through (an) is selected from H, alkyl, substituted alkyl, alkoxy, substituted alkoxy;

R of Formulas (ac) through (an) is H;

⸺ is a single or double bond; and

Rn of Formulas (ac) through (an) comprises a functional group or an atom.

In any of the embodiments described herein, the W, $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any aspect or embodiment described herein, $R_n$ of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

-continued
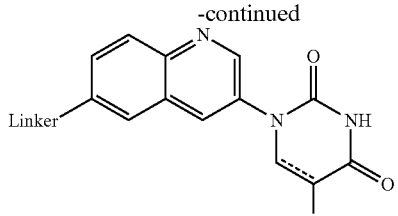
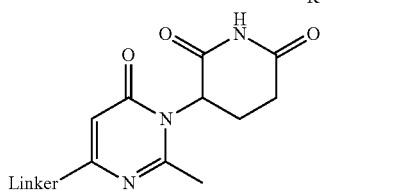
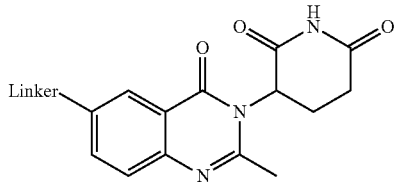
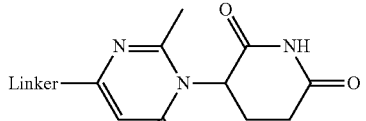
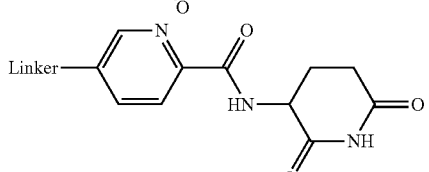
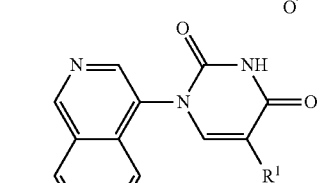
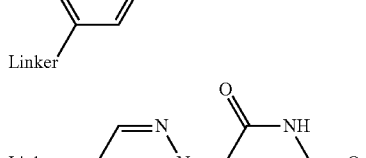
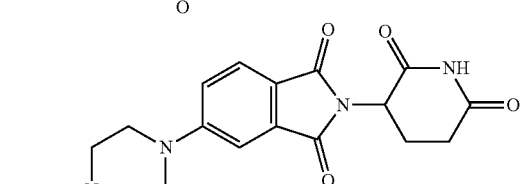
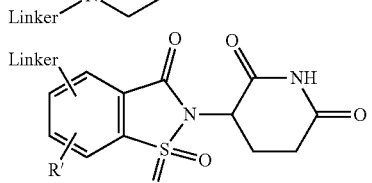
-continued
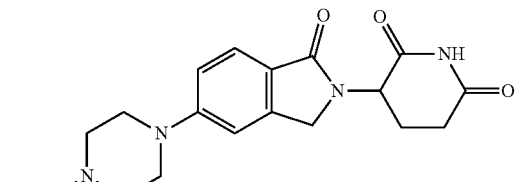
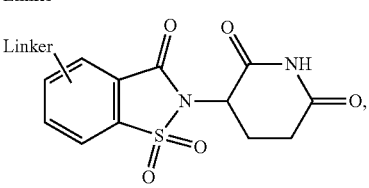
wherein R' is a halogen and $R^1$ is as described above with regard to Formulas (h) through (ab) or (ac) through (an).
In certain cases, the CLM can be imides that bind to cereblon E3 ligase. These imides and linker attachment point can be but not limited to the following structures:
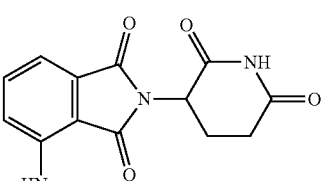
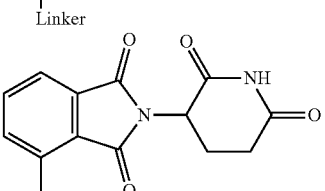
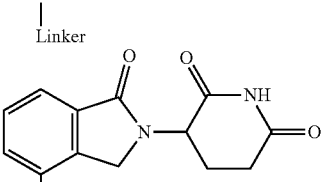
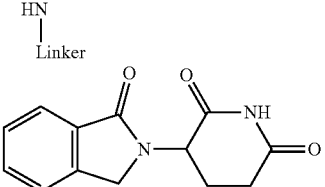
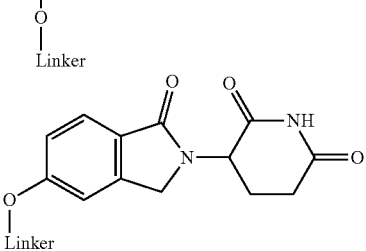

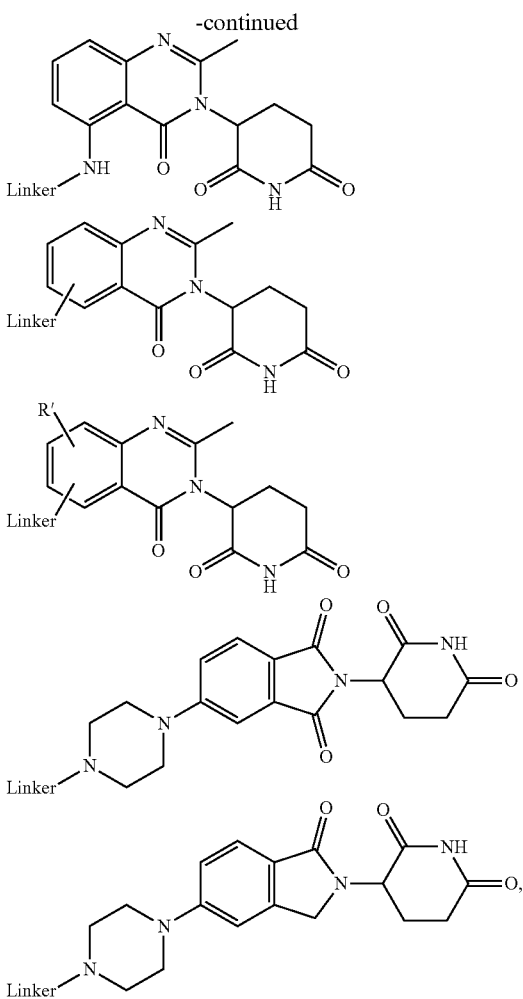

wherein R' is a halogen.

Exemplary VLMs

In certain embodiments of the compounds as described herein, ULM is VLM and comprises a chemical structure selected from the group ULM-a:

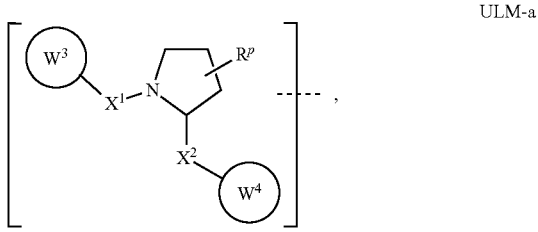

ULM-a wherein:

a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;

$X^1$, $X^2$ of Formula ULM-a are each independently selected from the group of a bond, O, $NR^{Y3}$, $CR^{Y3}R^{Y4}$, C=O, C=S, SO, and $SO_2$;

$R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);

$R^P$ of Formula ULM-a is 0, 1, 2, or 3 groups, each independently selected from the group H, halo, —OH, $C_{1-3}$ alkyl, C=O;

$W^3$ of Formula ULM-a is selected from the group of an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle;

$X^3$ of Formula ULM-a is C=O, $R^1$, $R^{1a}$, $R^{1b}$ each $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}$SO$_2$, N($R^{Y3}R^{Y4}$)C=O, N($R^{Y3}R^{Y4}$)C=S, N($R^{Y3}R^{Y4}$)SO, and N($R^{Y3}R^{Y4}$)SO$_2$;

T of Formula ULM-a is covalently bonded to $X^1$;

$W^4$ of Formula ULM-a is an optionally substituted —NR1-T-Aryl, an optionally substituted —NR1-T-Heteroaryl group or an optionally substituted —NR1-T-Heterocycle, where —NR1 is covalently bonded to $X^2$ and $R^1$ is H or $CH_3$, preferably H.

In any of the embodiments described herein, T is selected from the group of an optionally substituted alkyl, —(CH$_2$)$_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments, $W^4$ of Formula ULM-a is

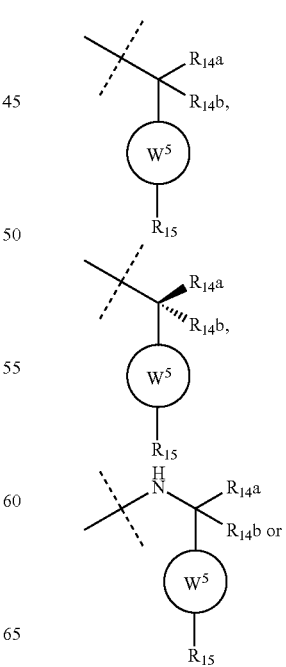

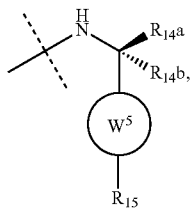

wherein $R_{14a}$, $R_{14b}$, are each independently selected from the group of H, haloalkyl, or optionally substituted alkyl.

In any of the embodiments, $W^5$ of Formula ULM-a is selected from the group of a phenyl or a 5-10 membered heteroaryl, $R_{15}$ of Formula ULM-a is selected from the group of H, halogen, CN, OH, $NO_2$, $NR^{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; optionally substituted aryl; optionally substituted heteroaryl; optionally substituted cycloalkyl; or optionally substituted cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C=O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

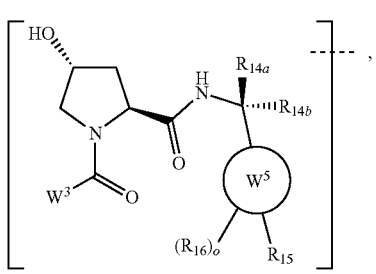

ULM-b wherein $W^3$ of Formula ULM-b is selected from the group of an optionally substituted aryl, optionally substituted heteroaryl, or

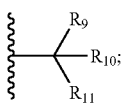

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

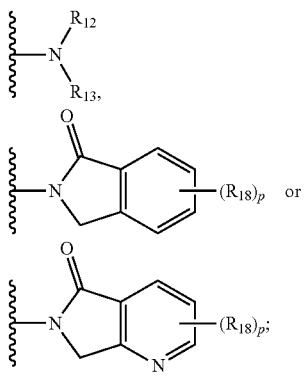

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl, or optionally substituted alkyl;

$W^5$ of Formula ULM-b is selected from the group of a phenyl or a 5-10 membered heteroaryl, $R_{15}$ of Formula ULM-b is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each optionally substituted);

$R_{16}$ of Formula ULM-b is independently selected from the group of H, halo, optionally substituted alkyl, optionally substituted haloalkyl, hydroxy, or optionally substituted haloalkoxy;

o of Formula ULM-b is 0, 1, 2, 3, or 4;

$R_{18}$ of Formula ULM-b is independently selected from the group of halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

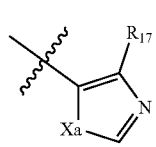

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

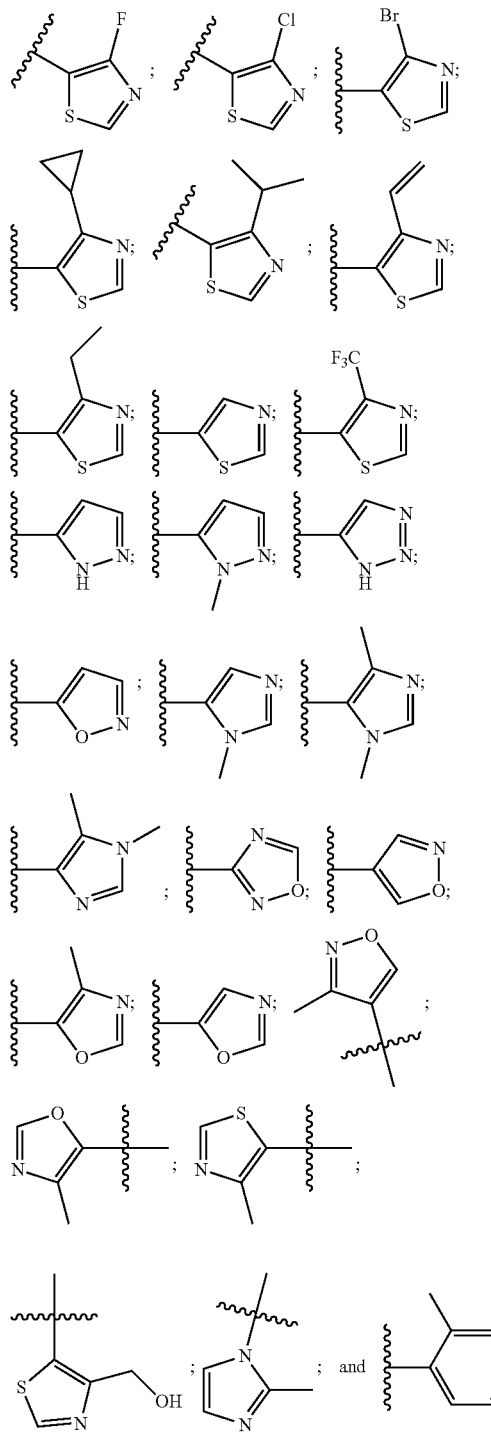

In certain embodiments, $R_{11}$ of Formula ULM-b is selected from the group consisting of:

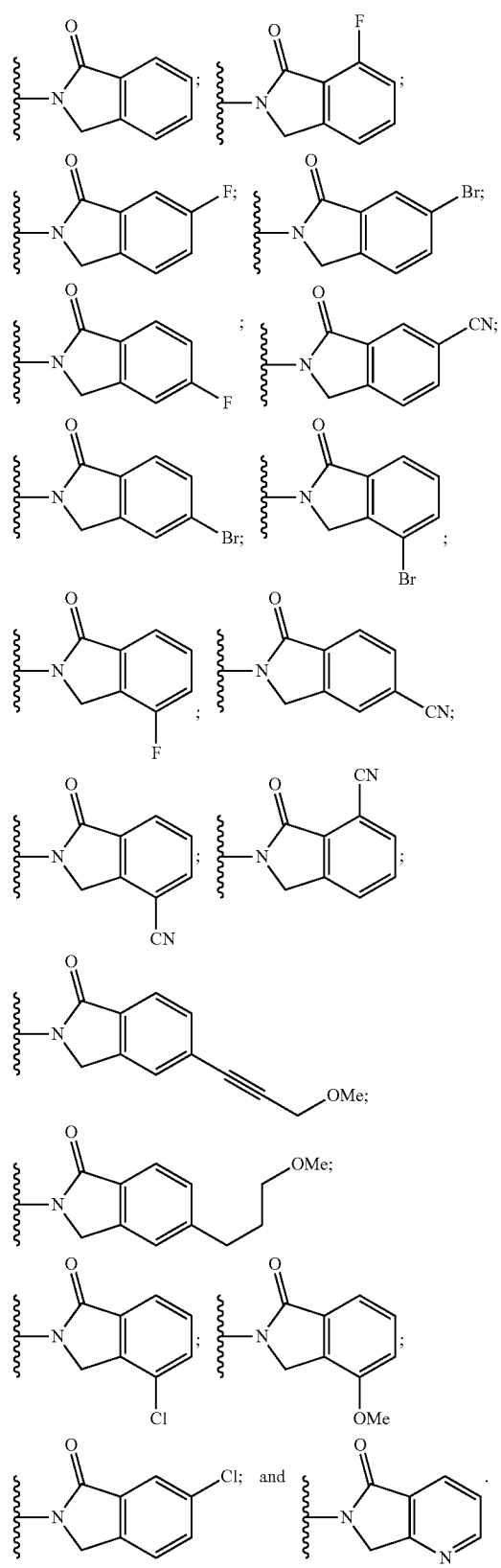

In certain embodiments, ULM has a chemical structure selected from the group of:

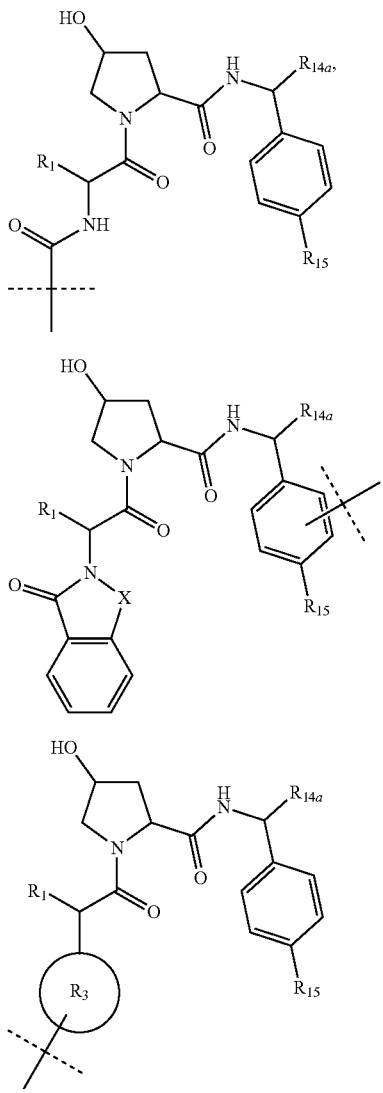

wherein:

R₁ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl (each optionally substituted);

X of Formulas ULM-c, ULM-d, and ULM-e is C, CH₂, or C=O

R₃ of Formulas ULM-c, ULM-d, and ULM-e is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

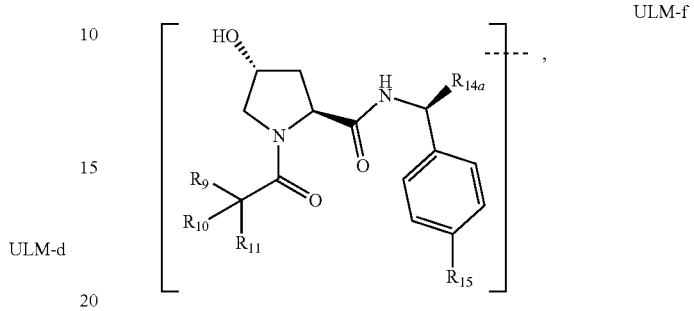

wherein $R_{14a}$ of Formula ULM-f is H, haloalkyl, optionally substituted alkyl, methyl, fluoromethyl, hydroxymethyl, ethyl, isopropyl, or cyclopropyl;

R₉ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl;

$R_{11}$ of Formula ULM-f is

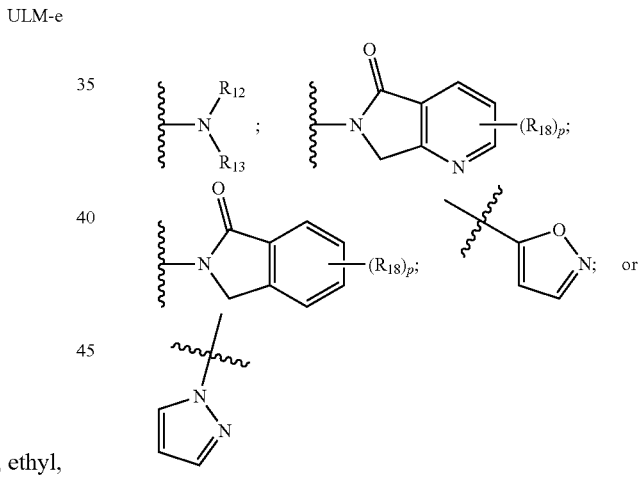

or optionally substituted heteroaryl;

p of Formula ULM-f is 0, 1, 2, 3, or 4;

each $R_{18}$ of Formula ULM-f is independently halo, optionally substituted alkoxy, cyano, optionally substituted alkyl, haloalkyl, haloalkoxy or a linker;

$R_{12}$ of Formula ULM-f is H, C=O;

$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula ULM-f is selected from the group consisting of H, halogen, Cl, CN, OH, NO₂, optionally substituted heteroaryl, optionally substituted aryl;

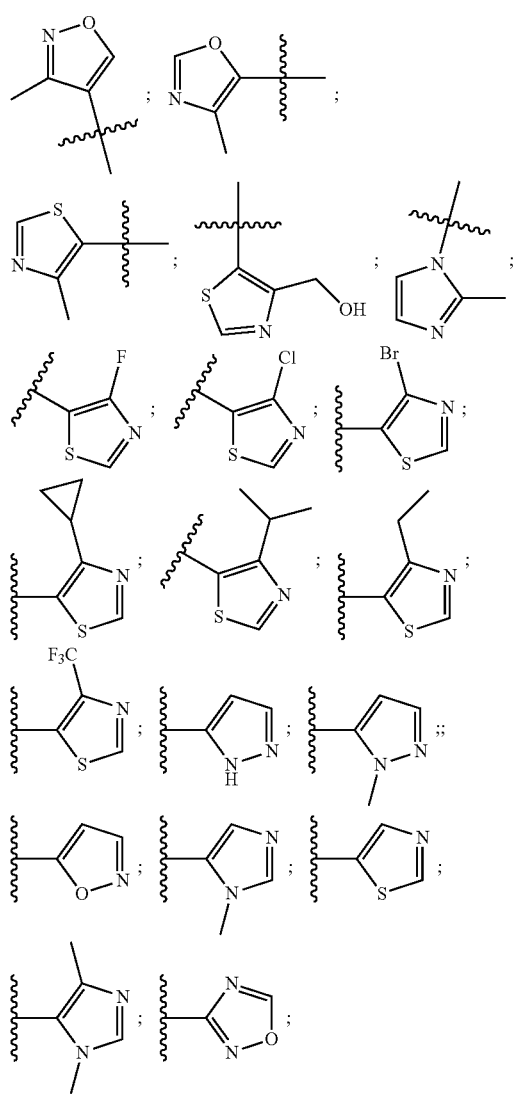
and
wherein the dashed line of Formula ULM-f indicates the site of attachment of at least one PTM, another ULM (ULM') or a chemical linker moiety coupling at least one PTM or a ULM' or both to ULM.
In certain embodiments, the ULM is selected from the following structures:
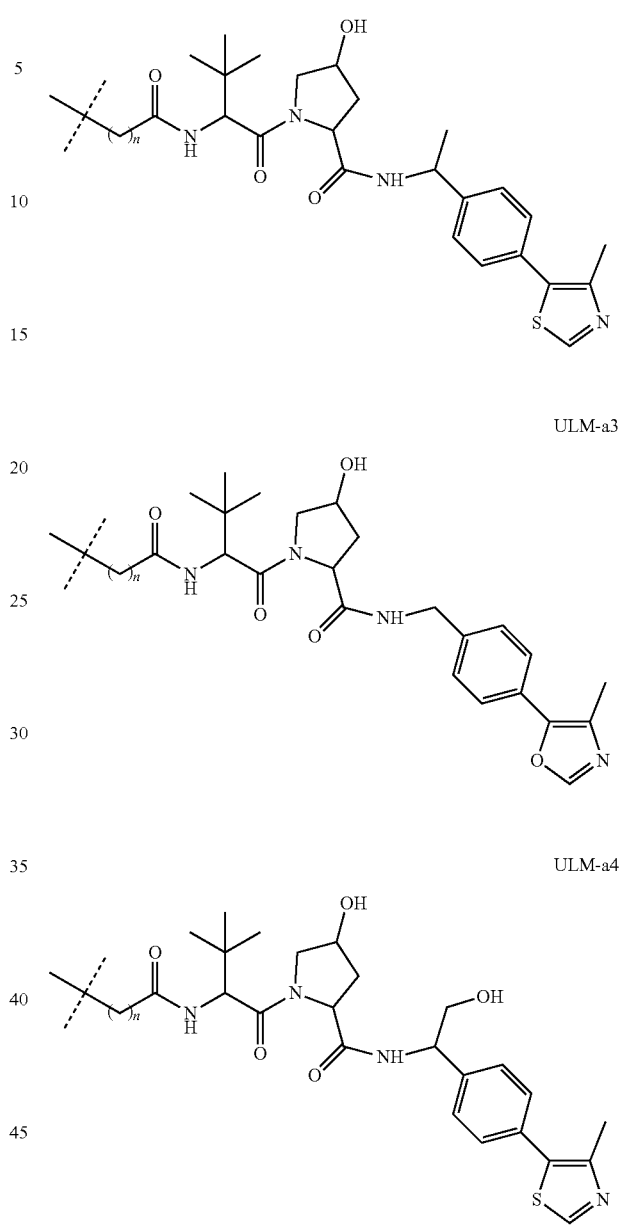
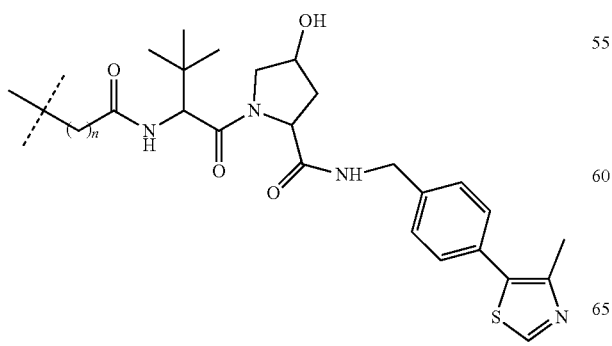
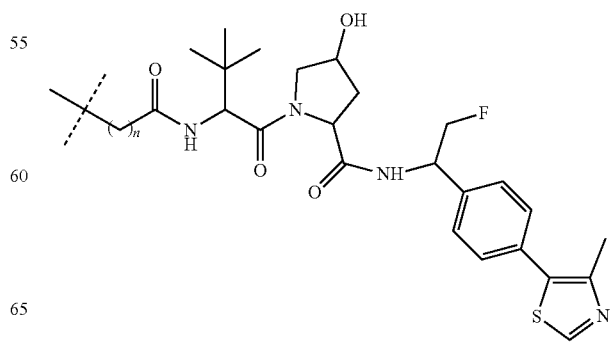

-continued
ULM-a6
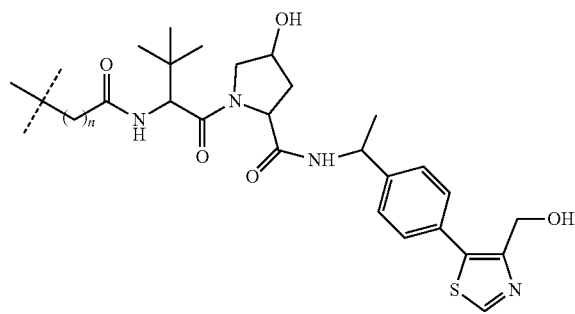
ULM-a7
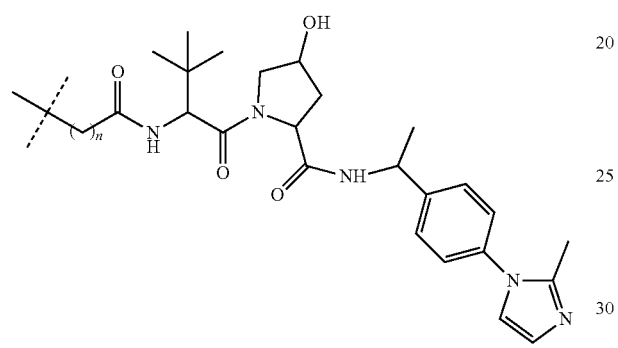
ULM-a8
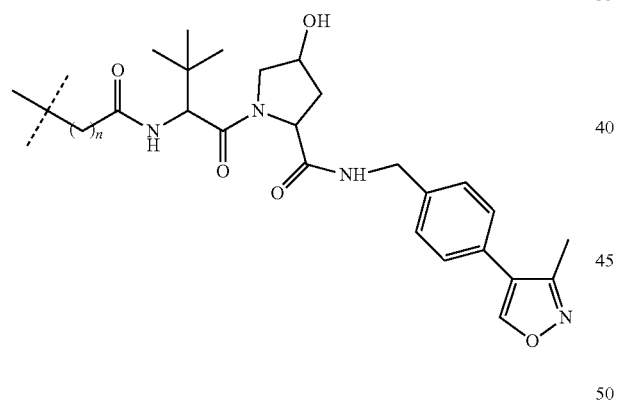
ULM-a9
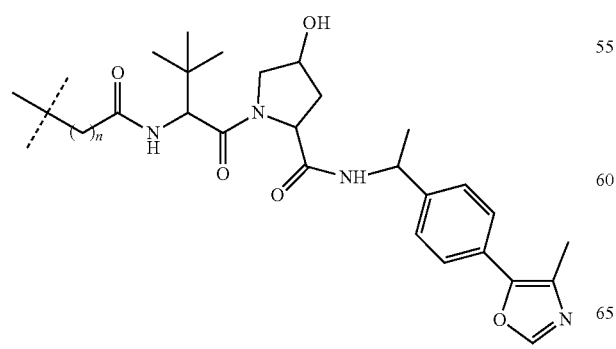
-continued
ULM-a10
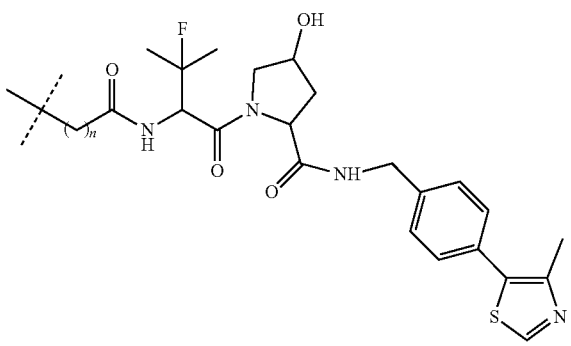
ULM-a11
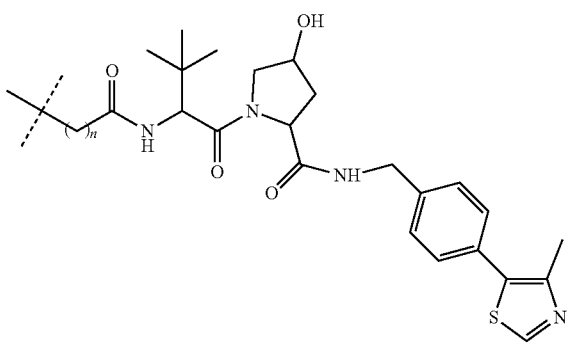
ULM-a12
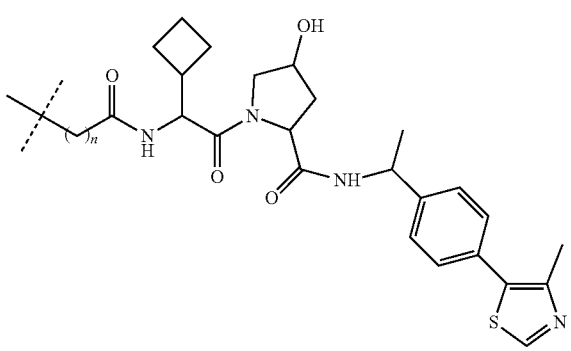
ULM-a13
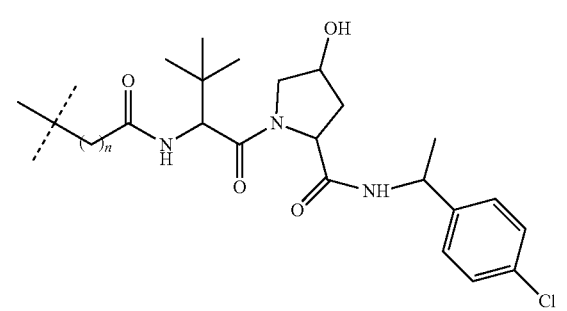

ULM-a14
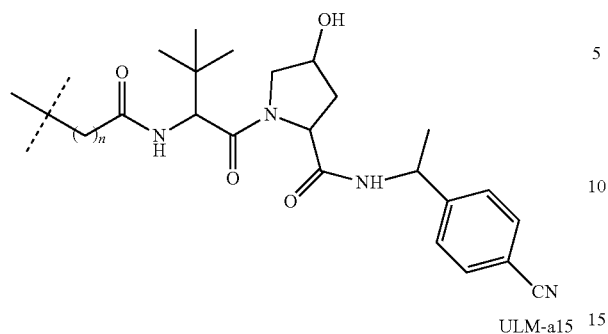
ULM-b3
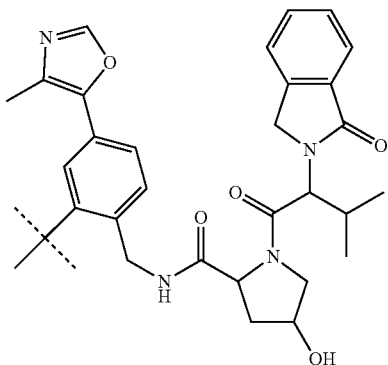
ULM-a15
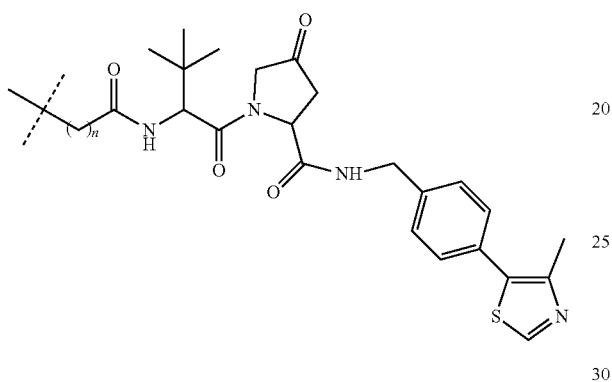
where n is 0 or 1.
In certain embodiments, the ULM is selected from the following structures:
ULM-b1
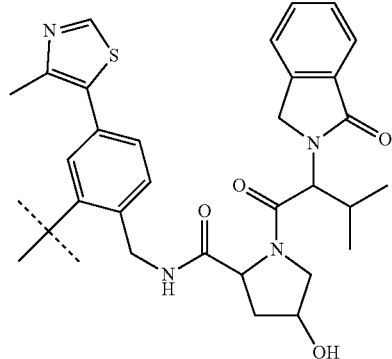
ULM-b4
ULM-b5
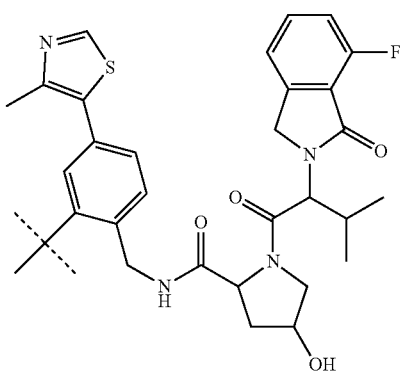
ULM-b2
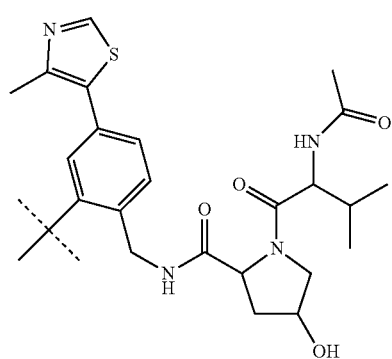
ULM-b6
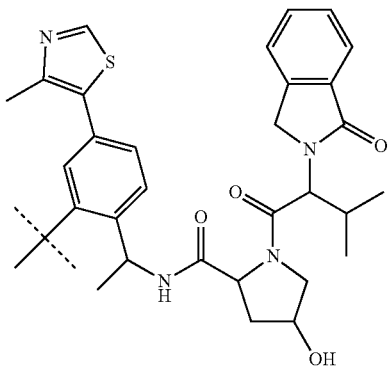

ULM-b7
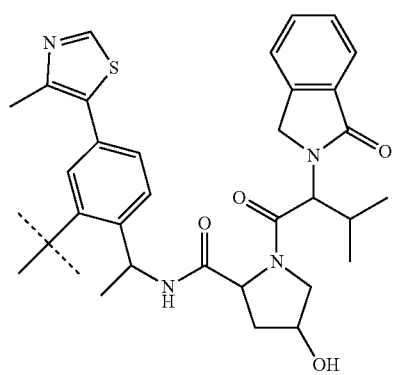
ULM-b8
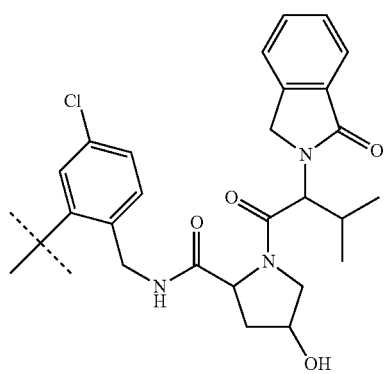
ULM-b9
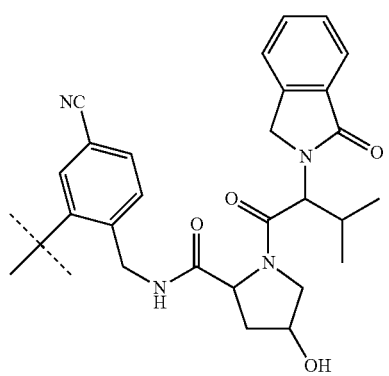
ULM-b10
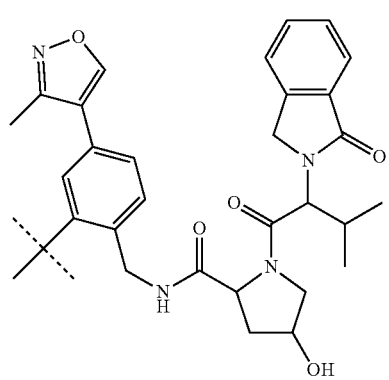
ULM-b11
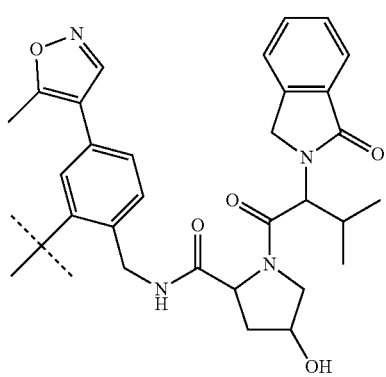
ULM-b12
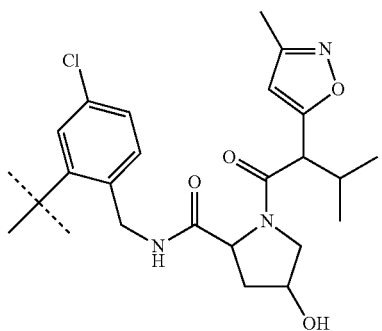
ULM-c1
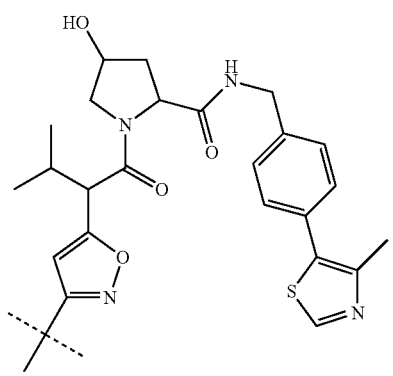
ULM-c2

ULM-c3
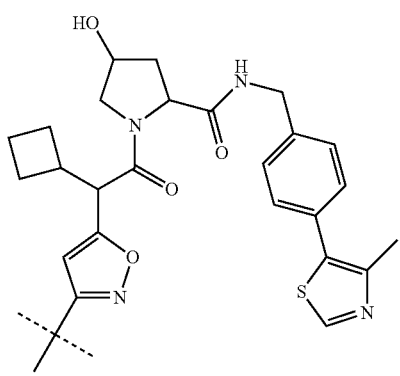
ULM-c4
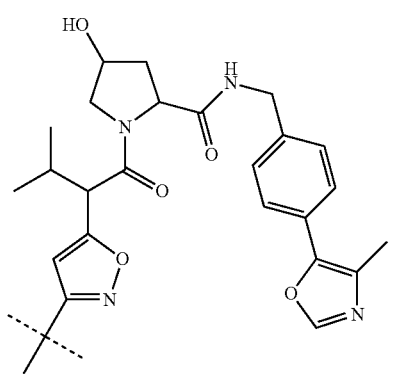
ULM-c5
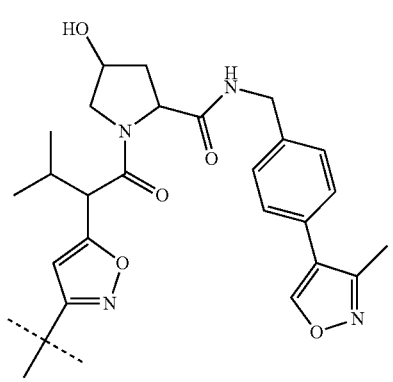
ULM-c6
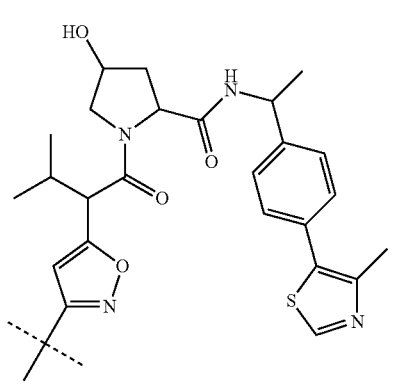
ULM-c7
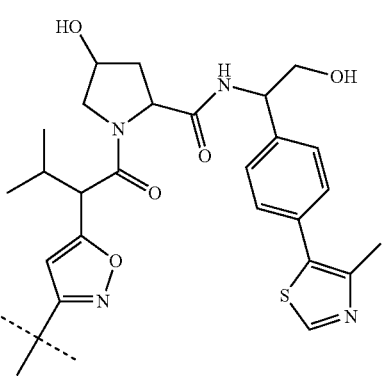
ULM-c8
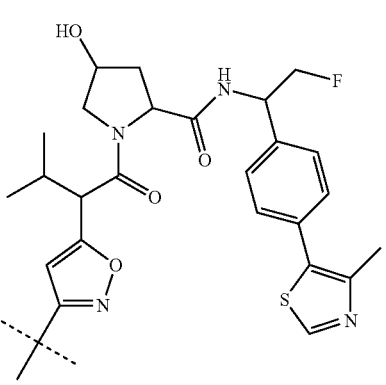
ULM-C9
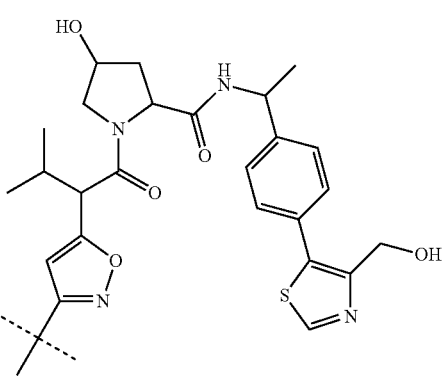
ULM-c10
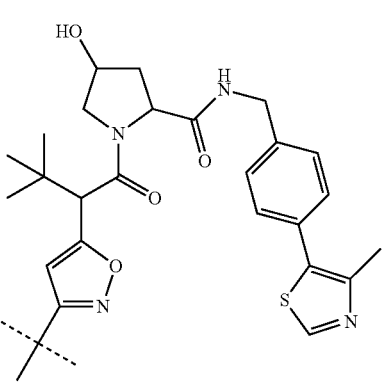

ULM-c11
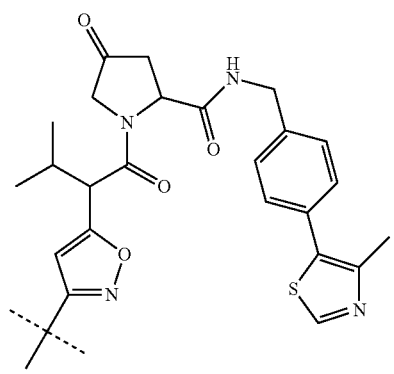
ULM-c12
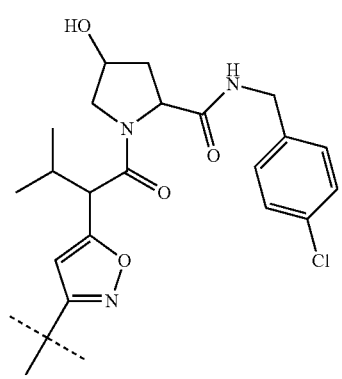
ULM-c13
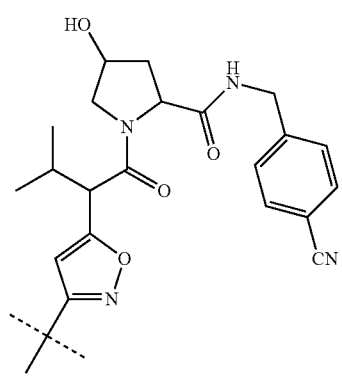
ULM-c14
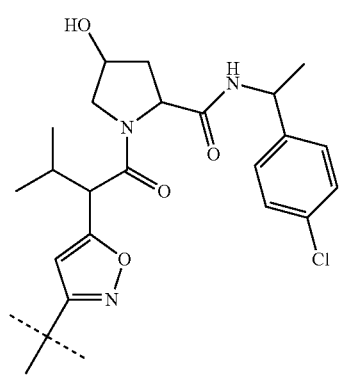
ULM-c15
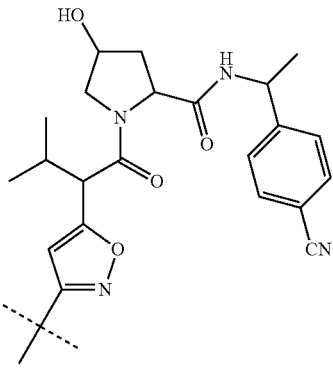
ULM-d1
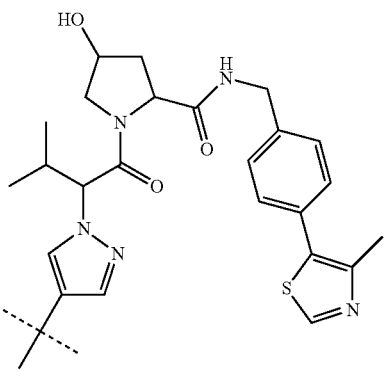
ULM-d2
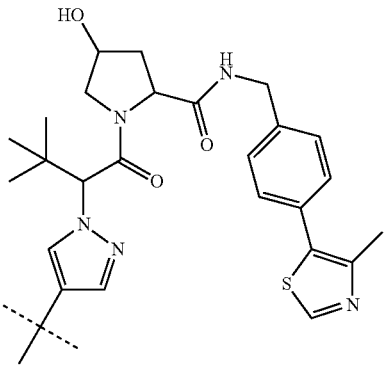
ULM-d3
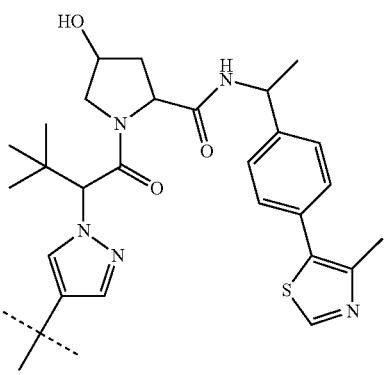

ULM-d4
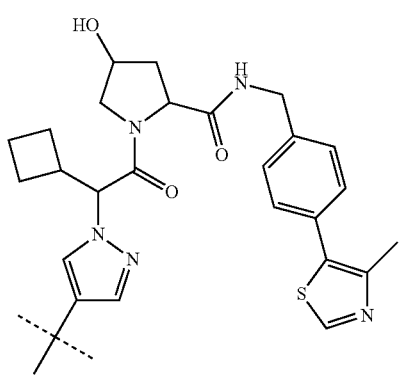

ULM-d5
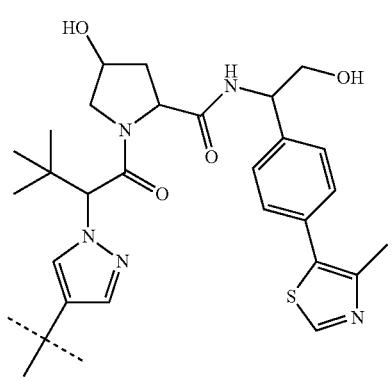

ULM-d6
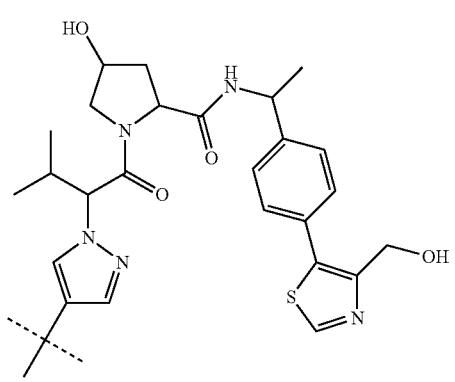

ULM-d7
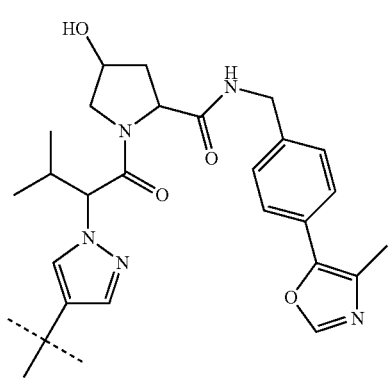

ULM-d8
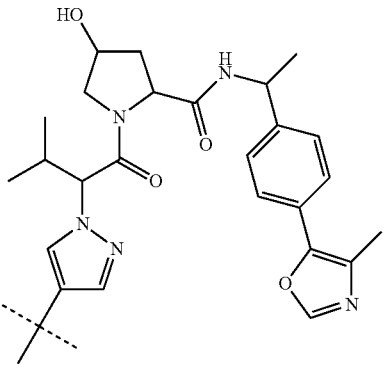

ULM-d9

wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

ULM-g
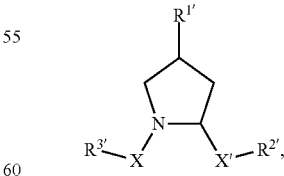

wherein:
$R^{1'}$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_nC(O)$—($C_1$-$C_6$ alkyl), an optionally substituted —$(CH_2)_n$NHC(O)—$R_1$, an optionally substituted —$(CH_2)_nC(O)$—$NR_1R_2$, an optionally substituted —$(CH_2)_nOC(O)$—$NR_1R_2$, —$(CH_2O)_nH$, an optionally substituted —$(CH_2)_nOC(O)$—($C_1$-$C_6$ alkyl), an optionally substituted —$(CH_2)_nC(O)$—O—($C_1$-$C_6$ alkyl), an optionally substituted —$(CH_2O)$COOH, an optionally substituted —$(OCH_2)_n$O—($C_1$-$C_6$ alkyl), an optionally substituted —$(CH_2O)_nC(O)$—($C_1$-$C_6$ alkyl), an optionally substituted —$(OCH_2)_n$NHC(O)—$R_1$, an optionally substituted —$(CH_2O)_nC(O)$—$NR_1R_2$, —$(CH_2CH_2O)_nH$, an optionally substituted —$(CH_2CH_2O)$COOH, an optionally substituted —$(OCH_2CH_2)_n$O—($C_1$-$C_6$ alkyl), an optionally substituted —$(CH_2CH_2O)_nC(O)$—($C_1$-$C_6$ alkyl), an optionally substituted —$(OCH_2CH_2)_n$NHC(O)—$R_1$, an optionally substituted —$(CH_2CH_2O)_nC(O)$—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —$(CH_2)_mNR_1R_2$ group;

X and X' of ULM-g are each independently C=O, C=S, —S(O), $S(O)_2$, (preferably X and X' are both C=O);

$R^2$ of ULM-g is an optionally substituted —$(CH_2)_n$—$(C=O)_u(NR_1)_v(SO_2)_w$alkyl group, an optionally substituted —$(CH_2)_n$—$(C=O)_u(NR_1)_v(SO_2)_wNR_{1N}R_{2N}$ group, an optionally substituted —$(CH_2)_n$—$(C=O)_u(NR_1)_v(SO_2)_w$-Aryl, an optionally substituted —$(CH_2)_n$—$(C=O)_u(NR_1)_v(SO_2)_w$-Heteroaryl, an optionally substituted —$(CH_2)_n$—$(C=O)_vNR_1(SO_2)_w$-Heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_{1N}R_{2N}$, an optionally substituted —$NR^1$—$(CH_2)_n$—$C(O)_u(NR_1)_v(SO_2)_w$—$NR_1C(O)R_{1N}$, an optionally substituted —$NR^1$—$(CH_2)_n$—$(C=O)_u(NR^1)_v(SO_2)_w$-Aryl, an optionally substituted —$NR^1$—$(CH_2)_n$—$(C=O)_u(NR^1)_v(SO_2)_w$-Heteroaryl or an optionally substituted —$NR^1$—$(CH_2)_n$—$(C=O)_vNR_1(SO_2)_w$-Heterocycle, an optionally substituted —$X^{R2'}$-alkyl group; an optionally substituted —$X^{R2'}$-Aryl group; an optionally substituted —$X^{R2'}$-Heteroaryl group; an optionally substituted —$X^{R2'}$-Heterocycle group; an optionally substituted;

$R^{3'}$ of ULM-g is an optionally substituted alkyl, an optionally substituted —$(CH_2)_n$—$(O)_u(NR_1)_v(SO_2)_w$-alkyl, an optionally substituted —$(CH_2)_n$—$C(O)_u(NR_1)_v(SO_2)_w$—$NR^1_NR^2_N$, an optionally substituted —$(CH_2)_n$—$C(O)_u(NR_1)_v(SO_2)_w$—$NR_1C(O)R_{1N}$, an optionally substituted —$(CH_2)_n$—$C(O)_u(NR_1)_v(SO_2)_w$—$C(O)NR_1R_2$, an optionally substituted —$(CH_2)_n$—$C(O)_u(NR_1)_v(SO_2)_w$-Aryl, an optionally substituted —$(CH_2)_n$—$C(O)_u(NR_1)_v(SO_2)_w$-Heteroaryl, an optionally substituted —$(CH_2)_n$—$C(O)_u(NR_1)_v(SO_2)_w$-Heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w^-$ $NR_{1N}R^2_N$, an optionally substituted —$NR^1$—$(CH_2)_n$—$C(O)_u(NR_1)_v(SO_2)_w$—$NR_1C(O)R_{1N}$, an optionally substituted —$NR^1$—$(CH_2)_n$—$C(O)_u(NR_1)_v(SO_2)_w$-Aryl, an optionally substituted —$NR^1$—$(CH_2)_n$—$C(O)_u(NR_1)_v(SO_2)_w$-Heteroaryl, an optionally substituted —$NR^1$—$(CH_2)_n$—$C(O)_u(NR_1)_v(SO_2)_w$-Heterocycle, an optionally substituted —O—$(CH_2)_n$—$(C=O)_u(NR_1)_v(SO_2)_w$-alkyl, an optionally substituted —O—$(CH_2)_n$—$(C=O)_u(NR)_v(SO_2)_w$—$NR_{1N}R_{2N}$, an optionally substituted —O—$(CH_2)_n$—$(C=O)_u(NR_1)_v(SO_2)_w$—$NR_1C(O)R_{1N}$, an optionally substituted —O—$(CH_2)_n$—$(C=O)_u(NR_1)_v(SO_2)_w$-Aryl, an optionally substituted —O—$(CH_2)_n$—$(C=O)_u(NR_1)_v(SO_2)_w$-Heteroaryl or an optionally substituted —O—$(CH_2)_n$—$(C=O)_u(NR_1)_v(SO_2)_w$-Heterocycle; —$(CH_2)_n$—$(V)_{n'}$—$(CH_2)_n$—$(V)_{n'}$-alkyl group, an optionally substituted —$(CH_2)_n$—$(V)_{n'}$—$(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$—$(V)_{n'}$-Heterocycle group, an optionally substituted —$(CH_2)_n$—$N(R_{1'})(C=O)_{m'}$—$(V)_{n'}$-alkyl group, an optionally substituted —$(CH_2)_n$—$N(R_{1'})(C=O)_{m'}$—$(V)_{n'}$-Aryl group, an optionally substituted —$(CH_2)$—$N(R_{1'})(C=O)_{m'}$—$(V)_{n'}$-Heteroaryl group, an optionally substituted —$(CH_2)_n$—$N(R_{1'})(C=O)_{m'}$—$(V)_{n'}$-Heterocycle group, an optionally substituted —$X^{R3'}$-alkyl group; an optionally substituted —$X^{R3'}$-Aryl group; an optionally substituted —$X^{R3'}$-Heteroaryl group; an optionally substituted —$X^{R3}$— Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted —$CH_2)_n$—, —$(CH_2)_n$—$CH(X_v)$ =$CH(X_v)$— (cis or trans), —$(CH_2)_n$—CH=CH—, —$(CH_2CH_2O)_n$— or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

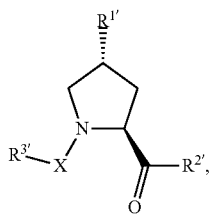

ULM-h wherein:
each of $R^{1'}$, $R^{2'}$ and $R^{3'}$ of ULM-h are the same as above and X is C=O, C=S, —S(O) group or a S(O)$_2$ group, more preferably a C=O group, and
any one or more of $R^{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or
a pharmaceutically acceptable salt, enantiomer, diastereomer, solvate or polymorph thereof.

In any of the aspects or embodiments described herein, the ULM, and when present, ULM', are each independently according to the chemical structure:

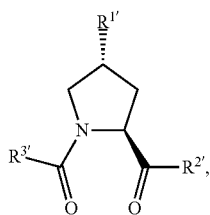

ULM-i wherein:
any one or more of $R^{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or
a pharmaceutically acceptable salt, enantiomer, diastereomer, solvate or polymorph thereof.

In further preferred aspects of the disclosure, $R^1$ of ULM-g through ULM-i is preferably a hydroxyl group or a group which may be metabolized to a hydroxyl or carboxylic group, such that the compound represents a prodrug form of an active compound. Exemplary preferred $R^1$ groups include, for example, —(CH$_2$)$_n$OH, (CH$_2$)$_n$—O—(C$_1$-C$_6$) alkyl group, —(CH$_2$)$_n$COOH, —(CH$_2$O)$_n$H, an optionally substituted —(CH$_2$)$_n$OC(O)—(C$_1$-C$_6$ alkyl), or an optionally substituted —(CH$_2$)$_n$C(O)—O—(C$_1$-C$_6$ alkyl), wherein n is 0 or 1. Where $R^1$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a S(O)$_2$ group, more preferably a C=O group;

$R^2$ of ULM-g through ULM-i is preferably an optionally substituted —NR$^1$-T-Aryl, an optionally substituted —NR$^1$-T-Heteroaryl group or an optionally substituted —NR$^1$-T-Heterocycle, where $R^1$ is H or CH$_3$, preferably H and T is an optionally substituted —(CH$_2$)$_n$— group, wherein each one of the methylene groups may be optionally substituted with one or two substituents, preferably selected from halogen, an amino acid sidechain as otherwise described herein or a C$_1$-C$_3$ alkyl group, preferably one or two methyl groups, which may be optionally substituted; and n is 0 to 6, often 0, 1, 2 or 3, preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, all of which groups are optionally substituted.

Preferred Aryl groups for $R^{2'}$ of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

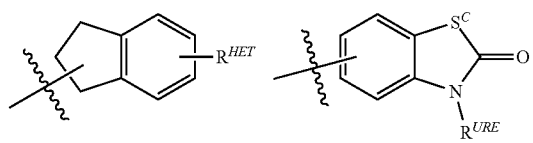

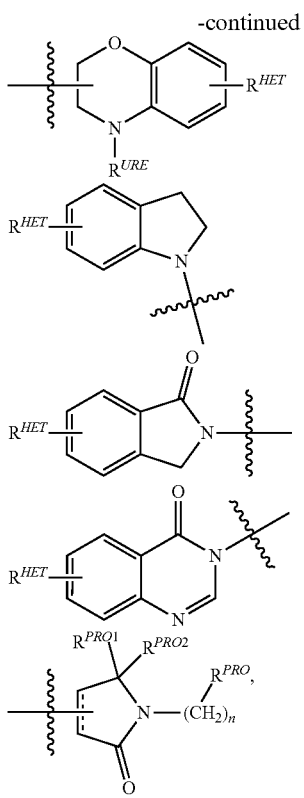

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects,

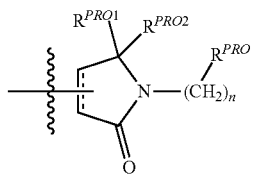

of ULM-g through ULM-i is a

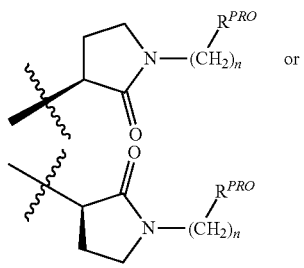

group, where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

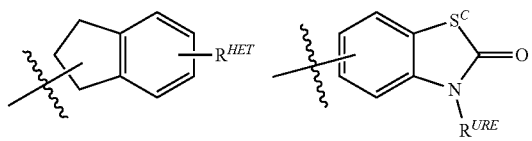

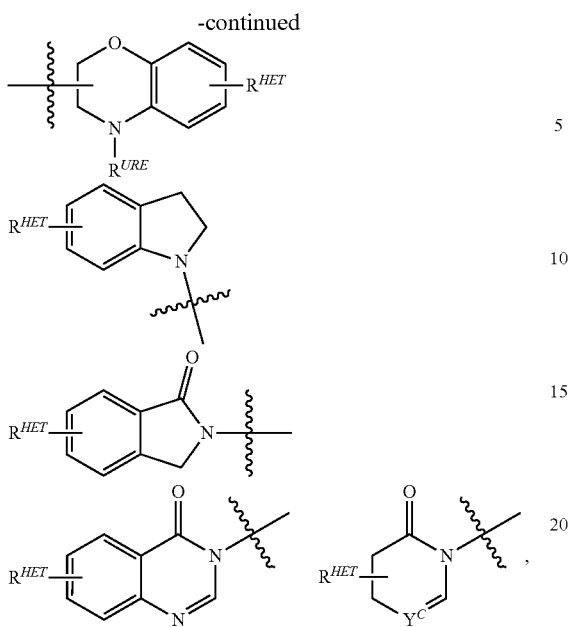

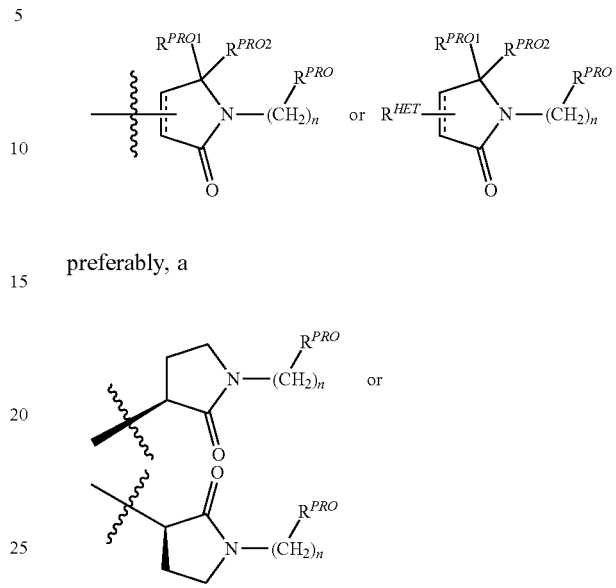

preferably, a group, wherein:

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ of ULM-g through ULM-i is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl), each of which groups may be optionally connected to a PTM group (including a ULM' group) via a linker group.

Preferred heterocycle groups for R$^{2'}$ of ULM-g through ULM-i include tetrahydrofuran, tetrahydrothiene, tetrahydroquinoline, piperidine, piperazine, pyrrolidine, morpholine, oxane or thiane, each of which groups may be optionally substituted, or a group according to the chemical structure:

wherein:

R$^{PRO}$ of ULM-g through ULM-i is H, optionally substituted C$_1$-C$_6$ alkyl or an optionally substituted aryl, heteroaryl or heterocyclic group;

R$^{PRO1}$ and R$^{PRO2}$ of ULM-g through ULM-i are each independently H, an optionally substituted C$_1$-C$_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred R$^{2'}$ substituents of ULM-g through ULM-i also include specifically (and without limitation to the specific compound disclosed) the R$^{2'}$ substituents which are found in the identified compounds disclosed herein (which includes the specific compounds which are disclosed in the present specification, and the figures which are attached hereto). Each of these R$^{2'}$ substituents may be used in conjunction with any number of R$^{3'}$ substituents which are also disclosed herein.

R$^{3'}$ of ULM-g through ULM-i is preferably an optionally substituted -T-Aryl, an optionally substituted-T-Heteroaryl, an optionally substituted -T-Heterocycle, an optionally substituted-NR$^1$-T-Aryl, an optionally substituted —NR$^1$-T-Heteroaryl or an optionally substituted-NR$^1$-T-Heterocycle, where R$^1$ is H or a C$_1$-C$_3$ alkyl group, preferably H or CH$_3$, T is an optionally substituted —(CH$_2$)$_n$— group, wherein each one of the methylene groups may be optionally substituted with one or two substituents, preferably selected from halogen, a C$_1$-C$_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a $C_1$-$C_6$ alkyl group, an optionally substituted aryl, heteroaryl or heterocycle group or a —$(CH_2)_m NR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—$C(O)$—O—$C_1$-$C_6$ alkyl group), an optionally substituted pyridine (2-, 3, or 4-pyridine) or a group according to the chemical structure:

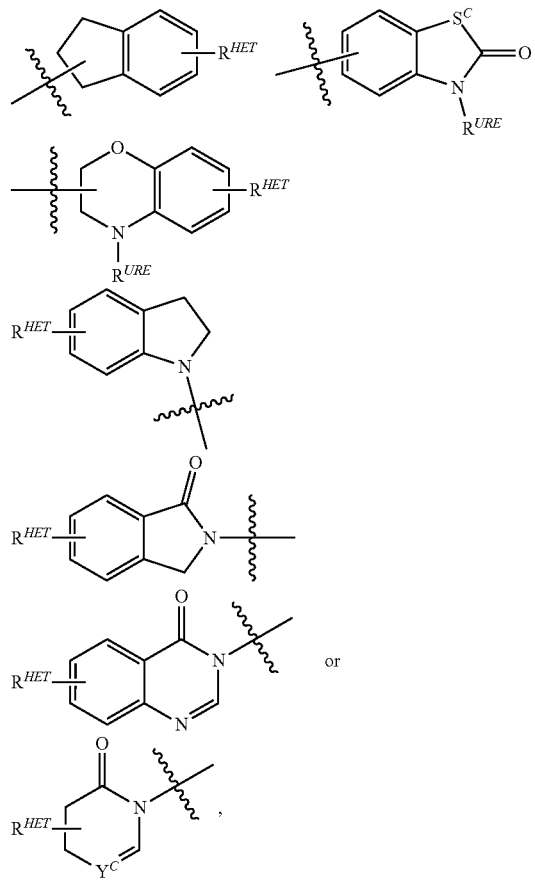

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —$C(O)(C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —$C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrolidine, morpholine, tetrahydrofuran, tetrahydrothiophene, oxane and thiane, each of which groups may be optionally substituted or a group according to the chemical structure:

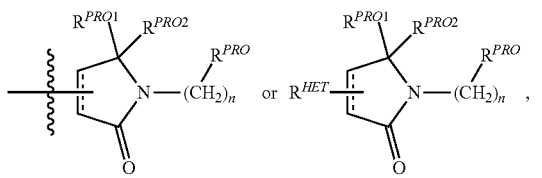

preferably, a

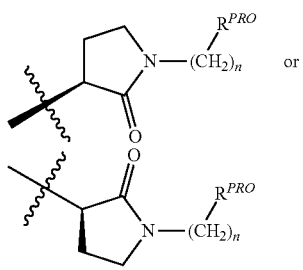

group,
wherein:
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group, and
each n of ULM-g through ULM-i is 0, 1, 2, 3, 4, 5, or 6 (preferably 0 or 1), wherein each of said Heterocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:
$R_1$ of ULM-g through ULM-i is H or a $C_1$-$C_3$ alkyl group (preferably H);
$X^{R2'}$ of ULM-g through ULM-i is an optionally substituted —$(CH_2)_n$—, —$(CH_2)_n$—CH($X_v$)=CH($X_v$)— (cis or trans), —$(CH_2)_n$—CH≡CH—, —$(CH_2CH_2O)_n$— or a $C_3$-$C_6$ cycloalkyl group; and
$X_v$ of ULM-g through ULM-i is H, a halo or a $C_1$-$C_3$ alkyl group which is optionally substituted with one or two hydroxyl groups or up to three halogen groups;
Alkyl of ULM-g through ULM-i is an optionally substituted C1-$C_{10}$ alkyl (preferably a $C_1$-$C_6$ alkyl) group (in certain preferred embodiments, the alkyl group is end-capped with a halo group, often a Cl or Br);
Aryl of ULM-g through ULM-i is an optionally substituted phenyl or naphthyl group (preferably, a phenyl group); and
HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

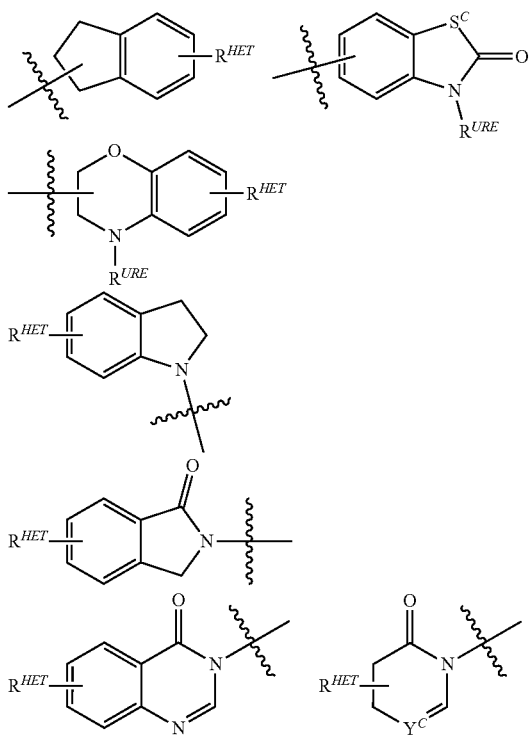

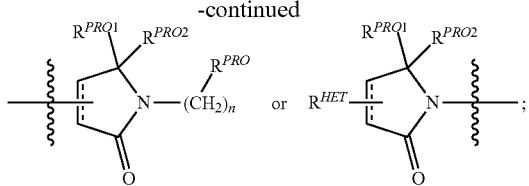

S^c of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present disclosure, $R^{3'}$ of ULM-g through ULM-i is an optionally substituted —$(CH_2)_n$—$(V)_{n'}$—$(CH_2)_n$—$(V)_{n'}$—$R^{S3'}$ group, an optionally substituted-$(CH_2)_n$—$N(R_{1'})(C=O)_{m'}$—$(V)_{n'}$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group, wherein:

$R^{S3}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is —$(CH_2)_n$—, —$(CH_2CH_2O)_n$—, —$CH_2)_n$—CH($X_v$)=CH($X_v$)— (cis or trans), —$CH_2)_n$—CH≡CH—, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

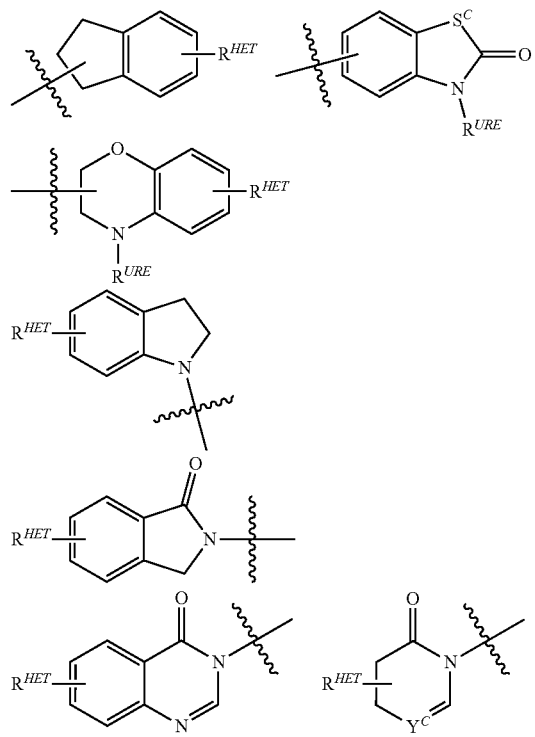

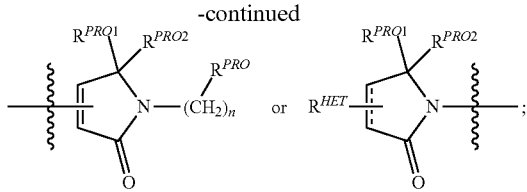

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$—HET, wherein:
said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—($C_1$-$C_6$)alkyl group, a —$(V)_{m'}$—$(CH_2CH_2O)_n$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

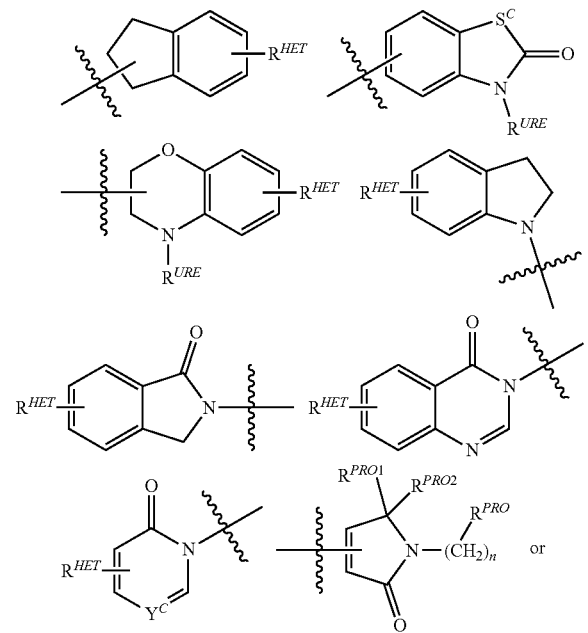

-continued

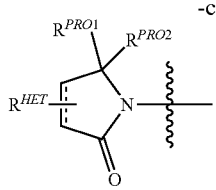

$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—$(C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group;
HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

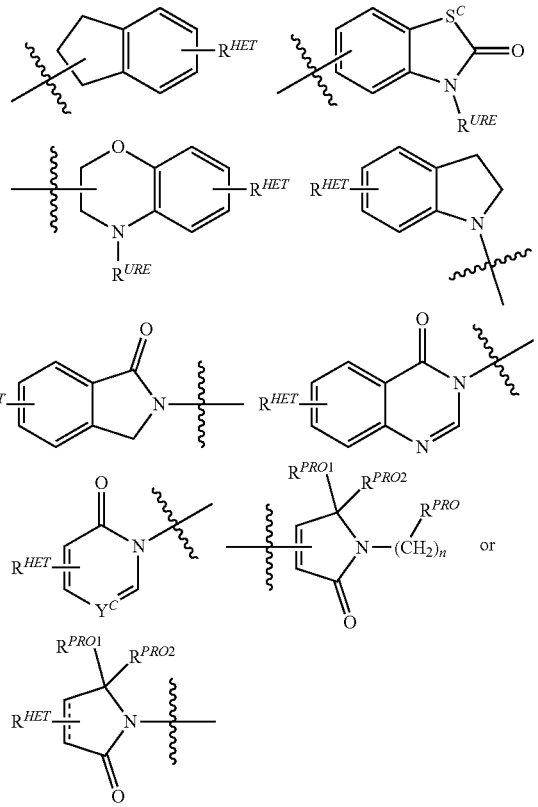

$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—$(C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1-C_6$ alkyl) (preferably substituted with one or two hydroxyl groups or up to three halo groups) or an optionally substituted acetylenic group —C≡C—$R_a$ where $R_a$ is H or a $C_1-C_6$ alkyl group (preferably $C_1-C_3$ alkyl);

$R^{PRO}$ of ULM-g through ULM-i is H, optionally substituted $C_1-C_6$ alkyl or an optionally substituted aryl, heteroaryl or heterocyclic group;

$R^{PRO1}$ and $R^{PRO2}$ of ULM-g through ULM-i are each independently H, an optionally substituted $C_1-C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

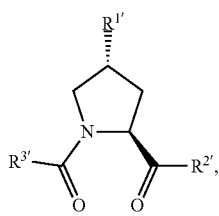

ULM-i wherein:
R¹' of ULM-i is OH or a group which is metabolized in a patient or subject to OH;

R²' of ULM-i is a —NH—$CH_2$-Aryl-HET (preferably, a phenyl linked directly to a methyl substituted thiazole);

R³' of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1-C_4$ alkyl group, preferably methyl, isopropyl or tert-butyl;

$R^{3P1}$ of ULM-i is $C_1-C_3$ alkyl (preferably methyl), an optionally substituted oxetane group (preferably methyl substituted, a —$(CH_2)_nOCH_3$ group where n is 1 or 2 (preferably 2), or a

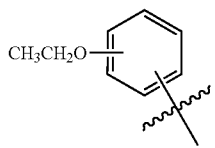

group (the ethyl ether group is preferably meta-substituted on the phenyl moiety), a morpholino group (linked to the carbonyl at the 2- or 3-position;

$R^{3P2}$ of ULM-i is a

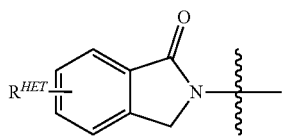

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

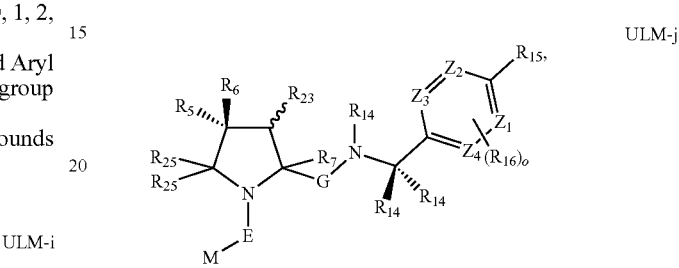

ULM-j wherein:
each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C=O, or C=S;

G of ULM-j is a bond, optionally substituted alkyl, —COOH or C=J;

J of ULM-j is O or N—$R_8$;

$R_8$ of ULM-j is H, CN, optionally substituted alkyl or optionally substituted alkoxy;

M of ULM-j is optionally substituted aryl, optionally substituted heteroaryl, optionally substituted heterocyclic or

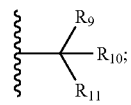

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

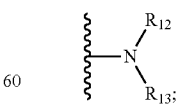

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate, each $R_{14}$ of ULM-j is independently H, haloalkyl, optionally substituted cycloalkyl, optionally substituted alkyl or optionally substituted heterocycloalkyl;

$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

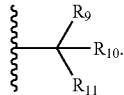

In certain embodiments, wherein E of ULM-j is C=O, $R_{11}$ is optionally substituted heterocyclic or

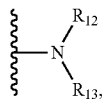

and M is

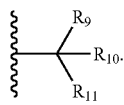

In certain embodiments, wherein E of ULM-j is C=O, M is

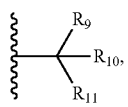

and $R_{11}$ is

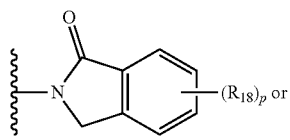

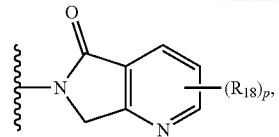

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

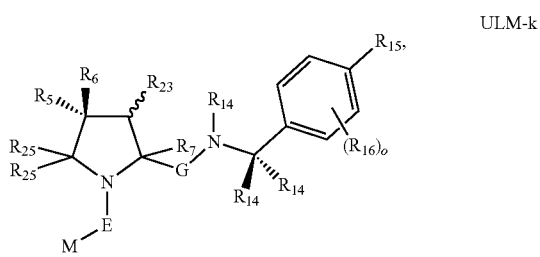

wherein:
G of ULM-k is C=J, J is O;
$R_7$ of ULM-k is H;
each $R_{14}$ of ULM-k is H;
o of ULM-k is 0;
$R_{15}$ of ULM-k is

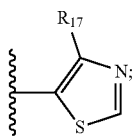

and
$R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

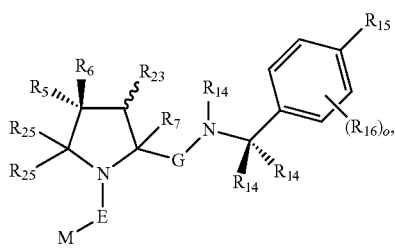

wherein:
G of ULM-k is C=J, J is O;
$R_7$ of ULM-k is H;
each $R_{14}$ of ULM-k is H;
o of ULM-k is 0; and $R_{15}$ of ULM-k is selected from the group consisting of:
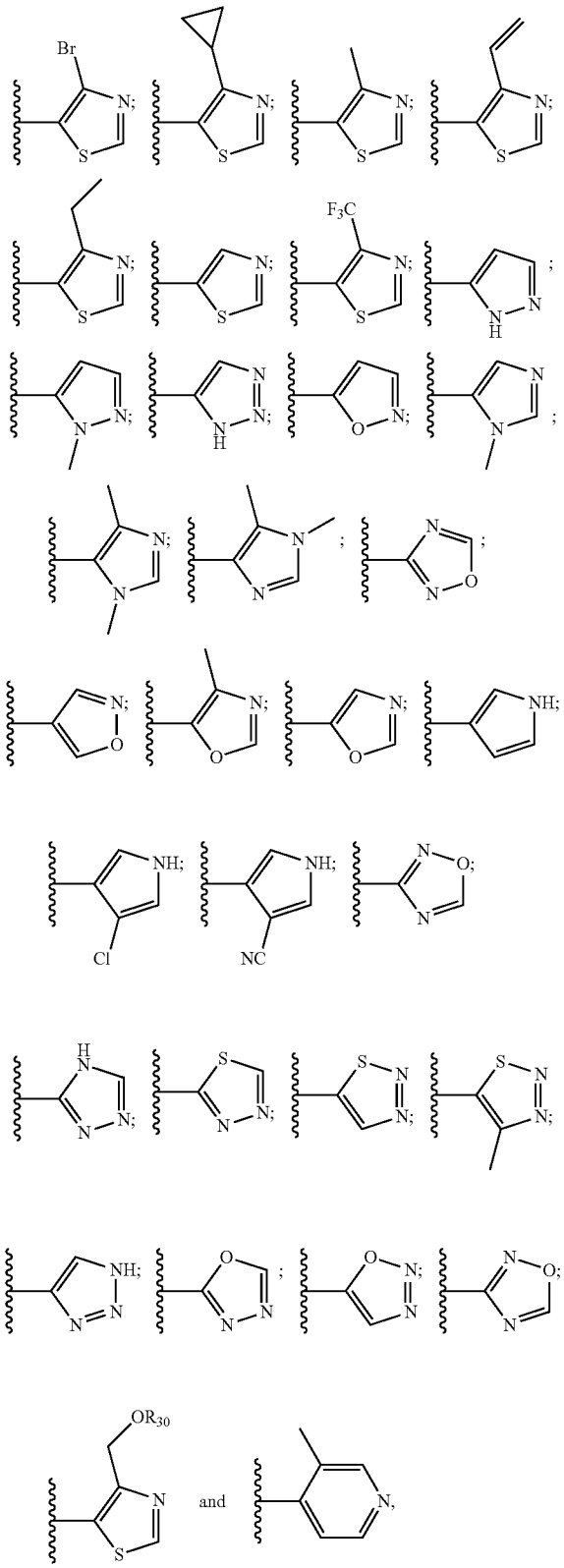
wherein $R_{30}$ of ULM-k is H or an optionally substituted alkyl.
In other embodiments, ULM and where present, ULM', are each independently a group according to the chemical structure:
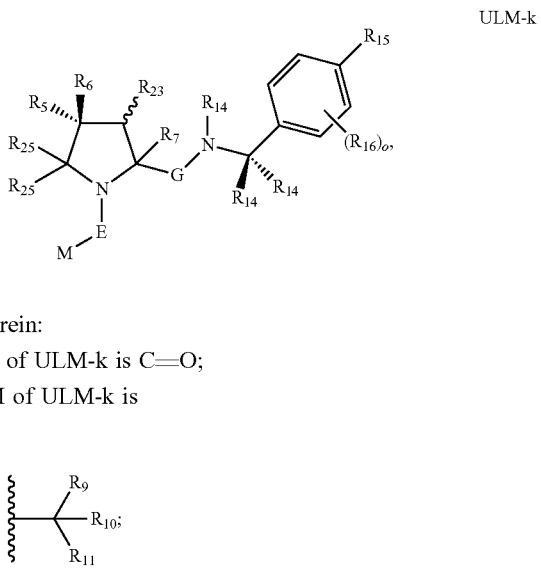
wherein:
E of ULM-k is C=O;
M of ULM-k is
and
$R_{11}$ of ULM-k is selected from the group consisting of:
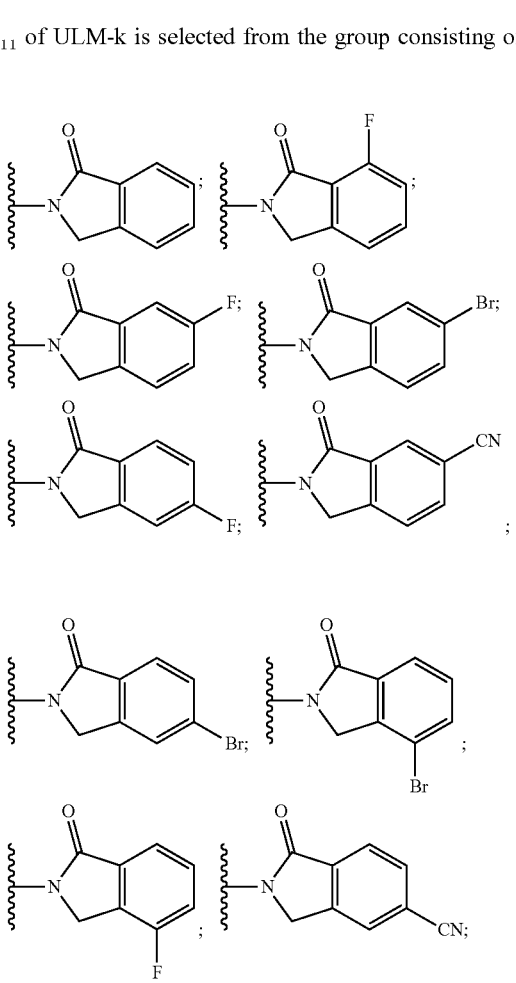

-continued

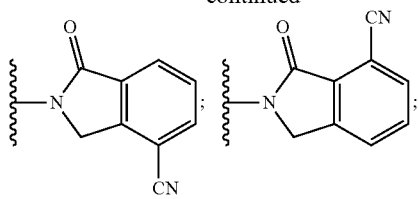

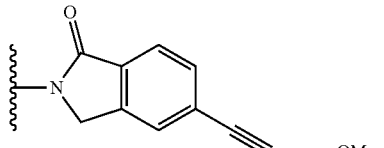

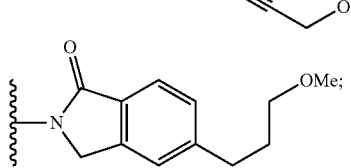

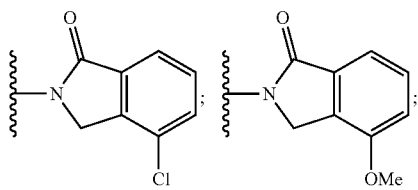

In still other embodiments, a compound of the chemical structure,

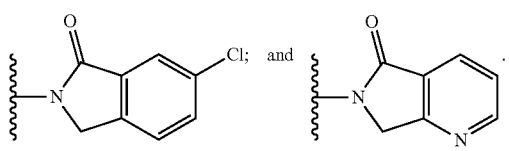
ULM-k wherein E of ULM-k is C=O;
$R_{11}$ of ULM-k is

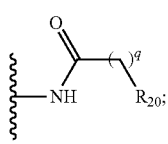

and
M of ULM-k is

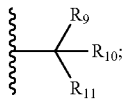

q of ULM-k is 1 or 2;
$R_{20}$ of ULM-k is H, optionally substituted alkyl, optionally substituted cycloalkyl, optionally substituted aryl, or

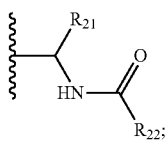

$R_{21}$ of ULM-k is H or optionally substituted alkyl; and
$R_{22}$ of ULM-k is H, optionally substituted alkyl, optionally substituted alkoxy, or haloalkyl.

In any embodiment described herein, $R_{11}$ of ULM-j or ULM-k is selected from the group consisting of:

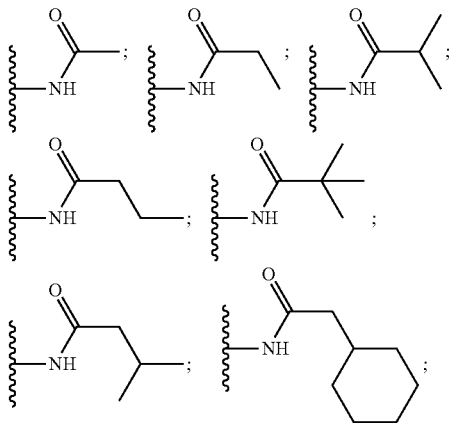

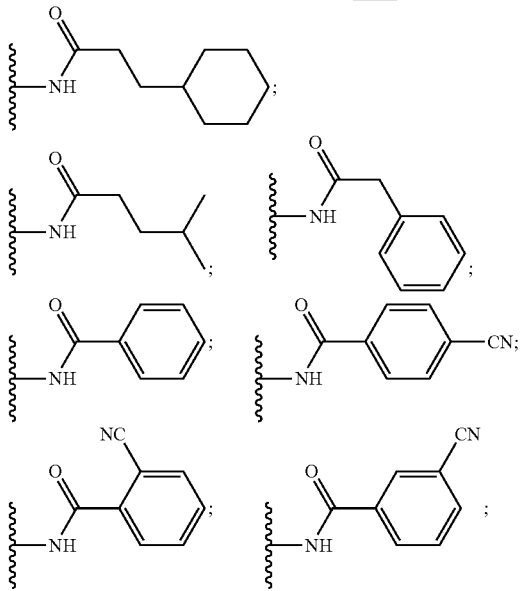

217
-continued
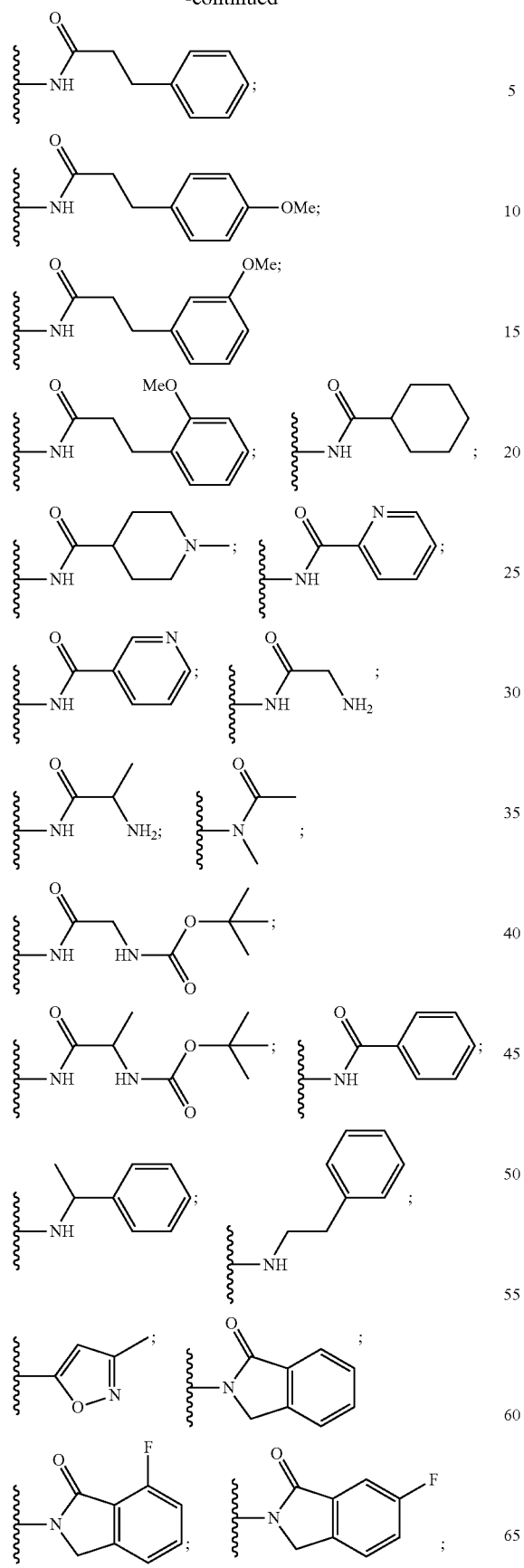
218
-continued
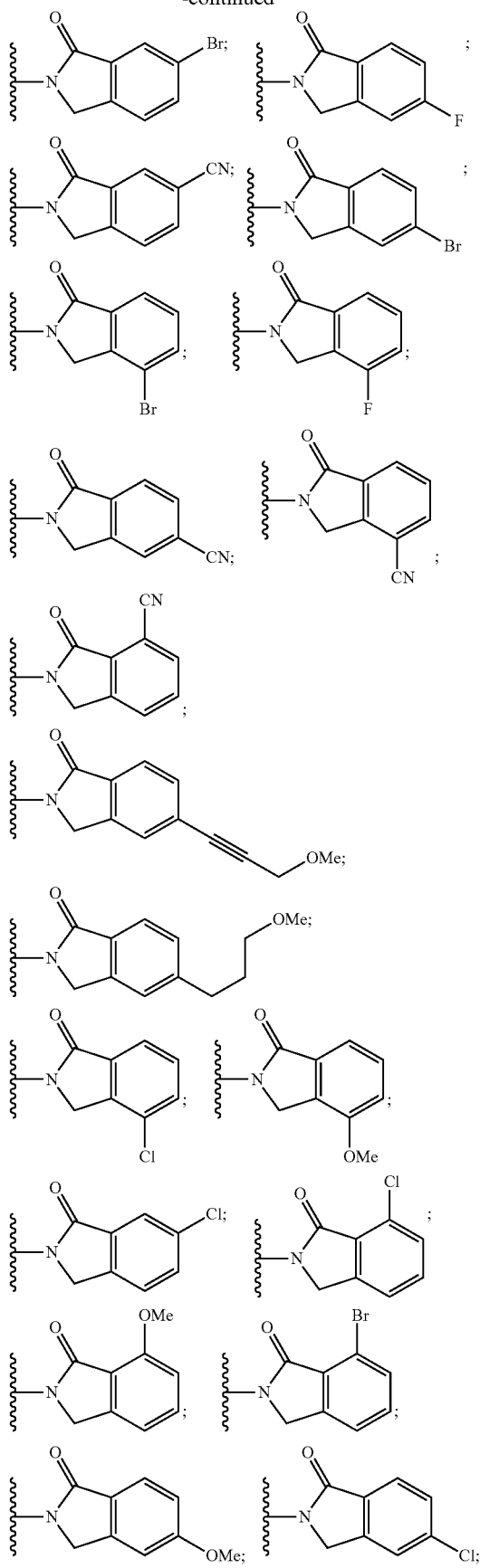

-continued
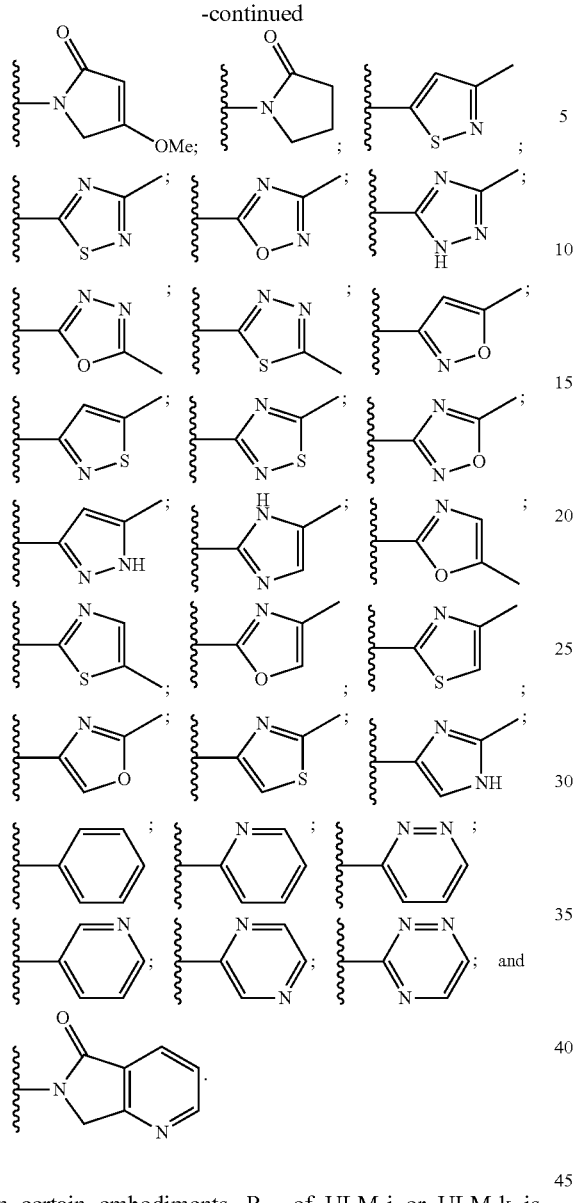
In certain embodiments, $R_{11}$ of ULM-j or ULM-k is selected from the group consisting of:
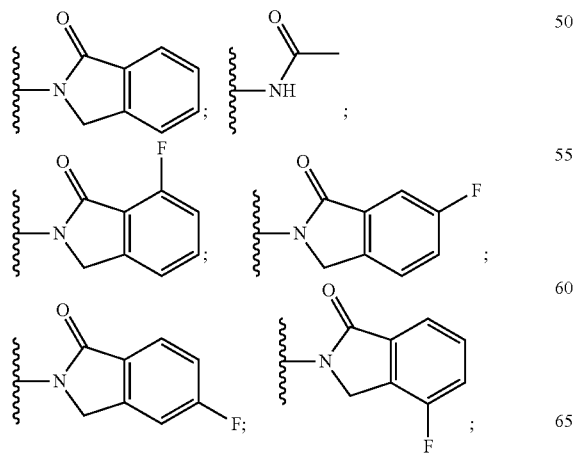
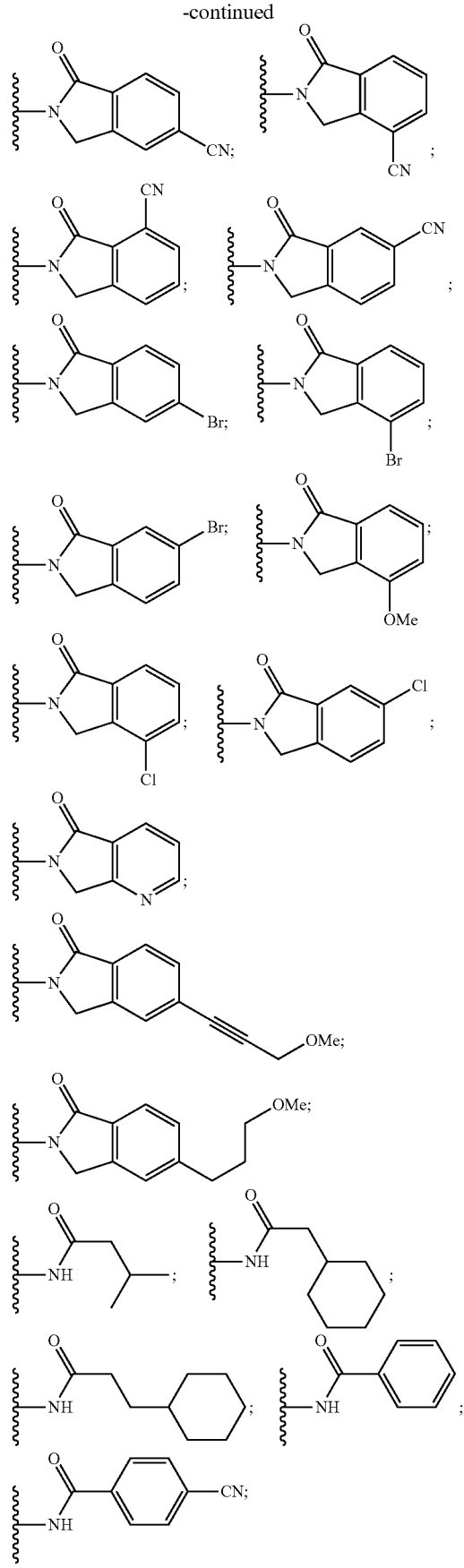

-continued

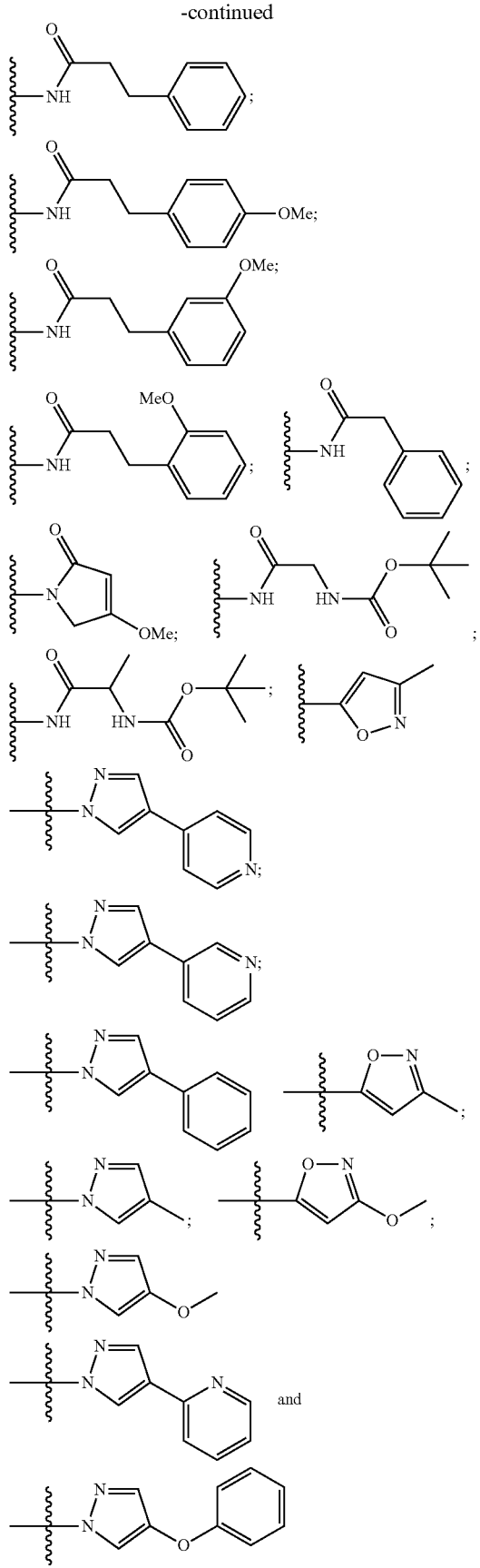

In certain embodiments, ULM (or when present ULM') is a group according to the chemical structure:

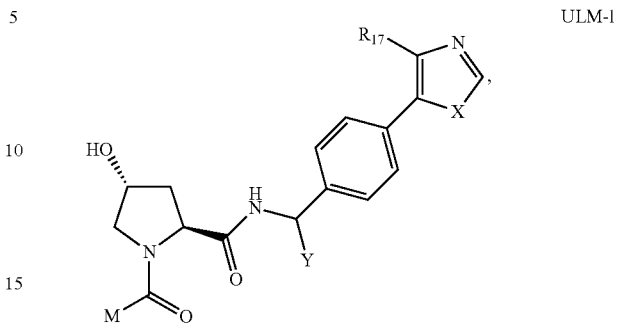

wherein:

X of ULM-1 is O or S;

Y of ULM-1 is H, methyl or ethyl;

$R_{17}$ of ULM-1 is H, methyl, ethyl, hydroxymethyl or cyclopropyl;

M of ULM-1 is optionally substituted aryl, optionally substituted heteroaryl, or

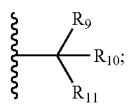

$R_9$ of ULM-1 is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclic, optionally substituted aryl or

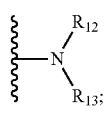

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

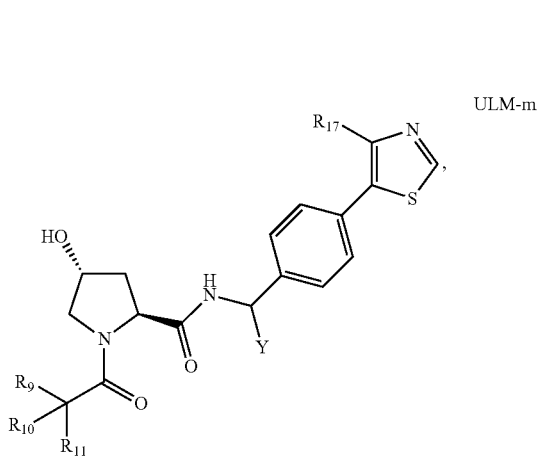

wherein:
Y of ULM-m is H, methyol or ethyl
$R_9$ of ULM-m is H;
$R_{10}$ is isopropyl, tert-butyl, sec-butyl, cyclopentyl, or cyclohexyl;
$R_{11}$ of ULM-m is optionally substituted amide, optionally substituted isoindolinone, optionally substituted isooxazole, optionally substituted heterocycles.

In other preferred embodiments of the disclosure, ULM and where present, ULM', are each independently a group according to the chemical structure:

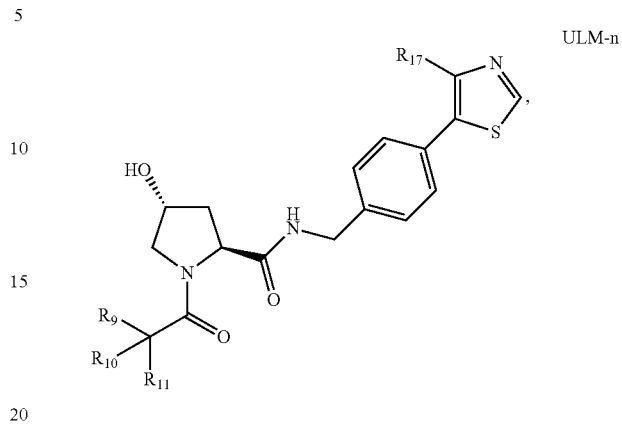

wherein:
$R_{17}$ of ULM-n is methyl, ethyl, or cyclopropyl; and
$R_9$, $R_{10}$, and $R_{11}$ of ULM-n are as defined above. In other instances, $R_9$ is H; and
$R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

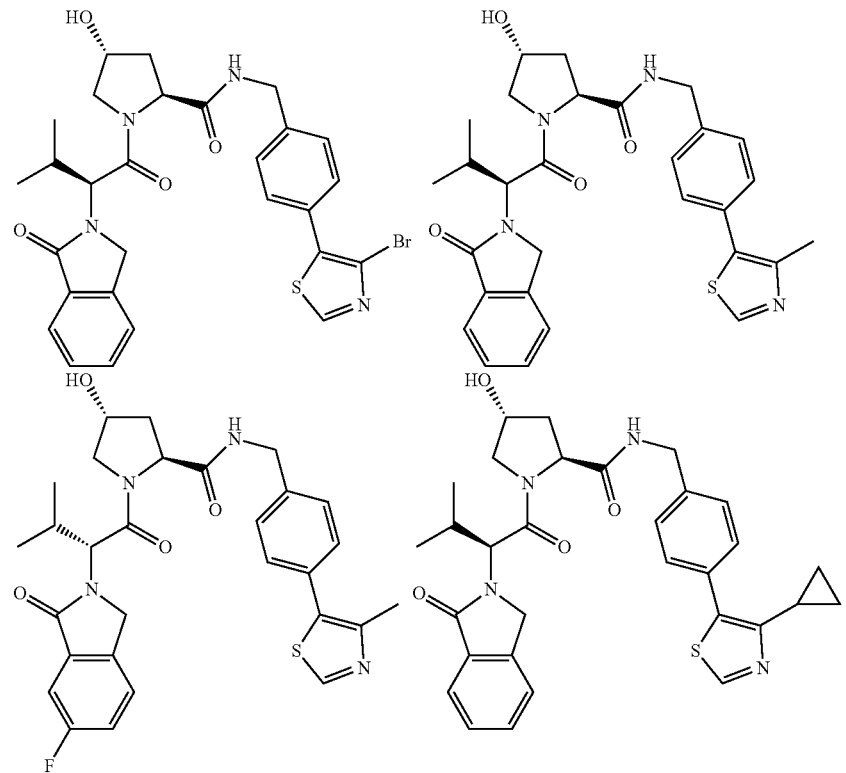

-continued
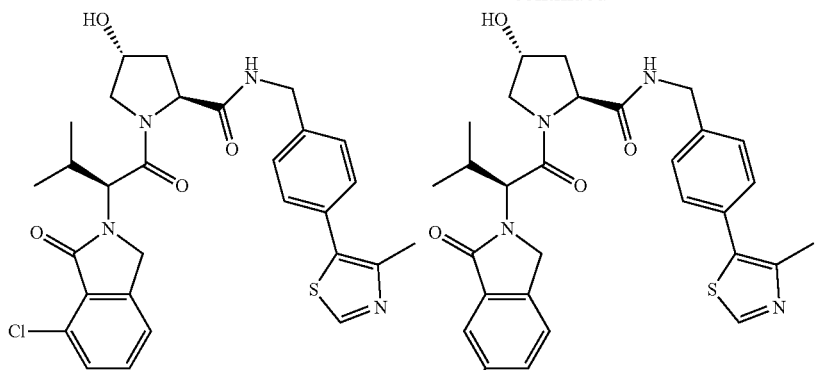
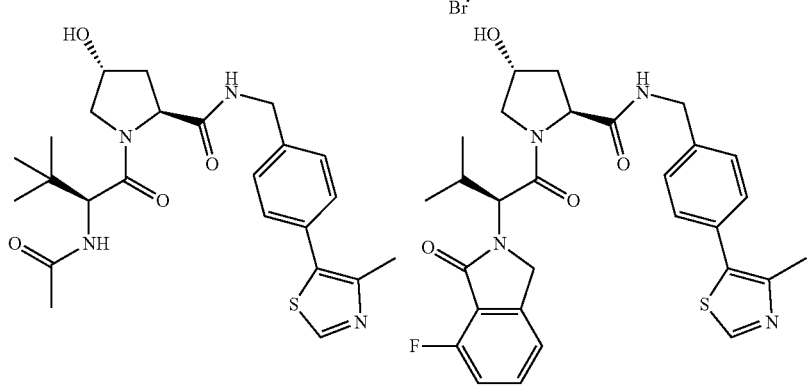
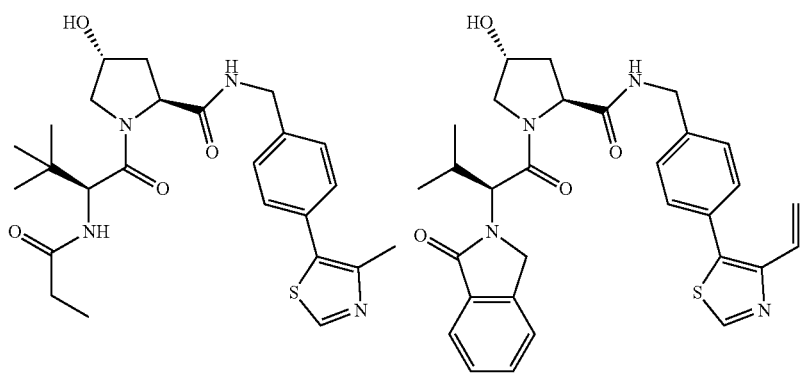
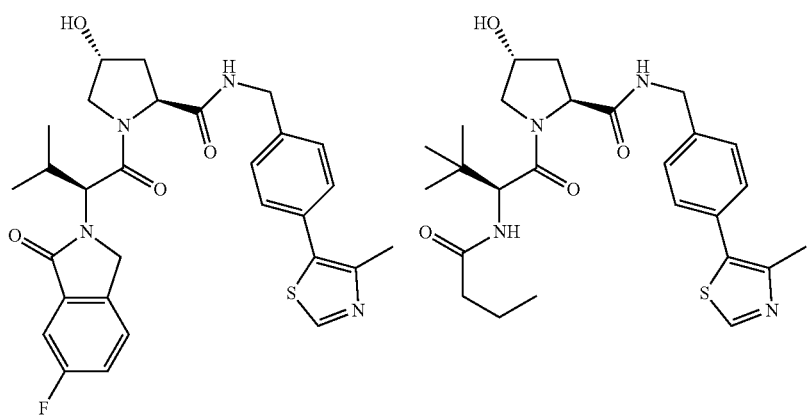

-continued
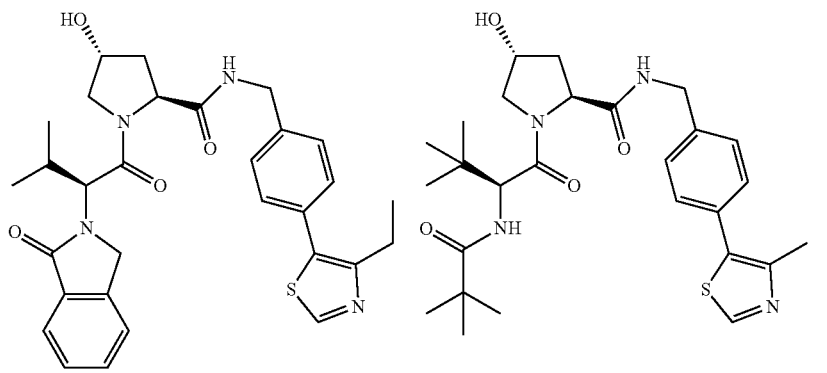
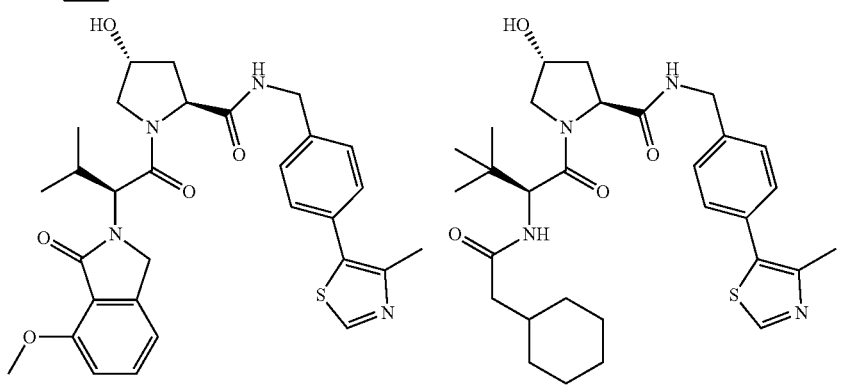
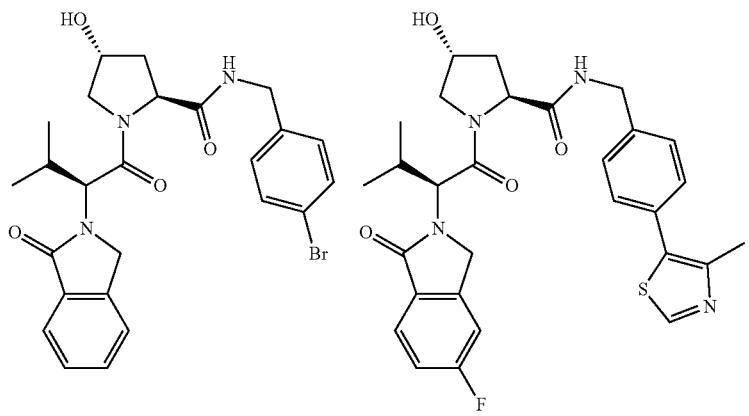
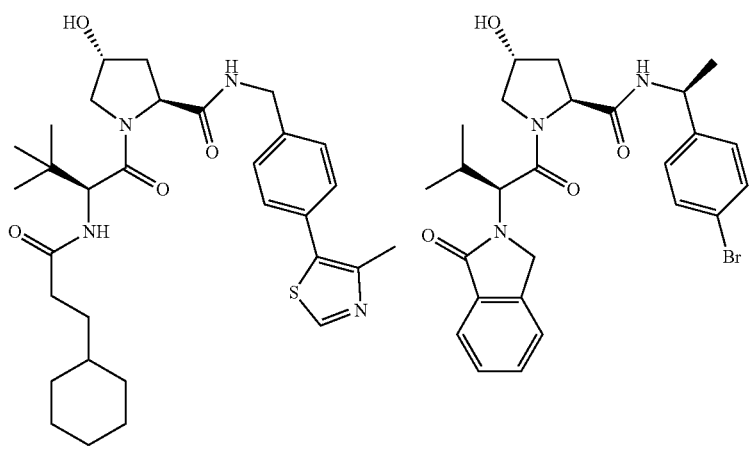

-continued
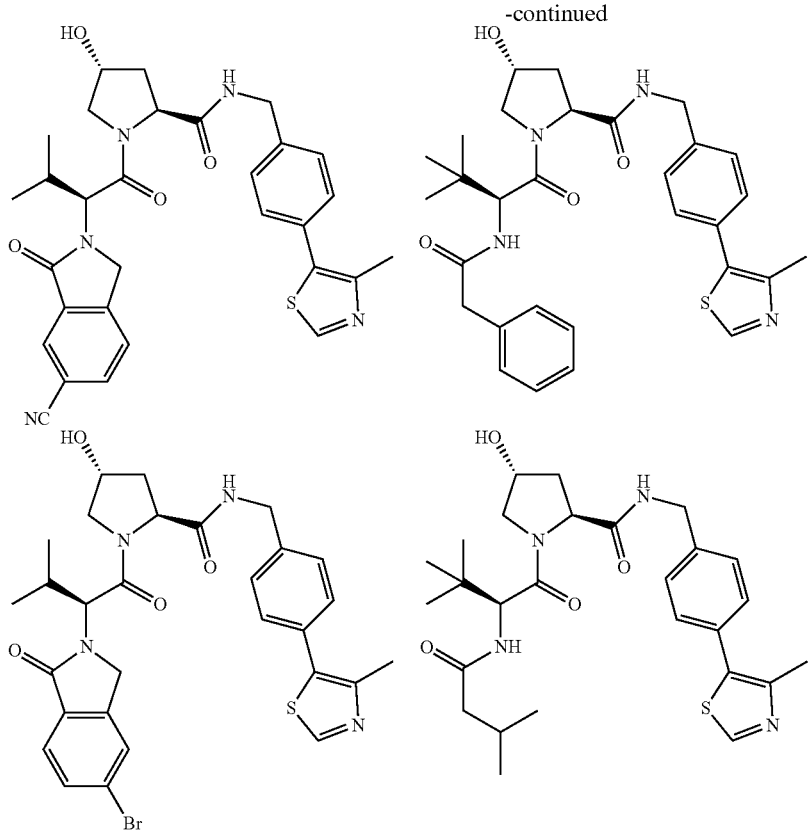
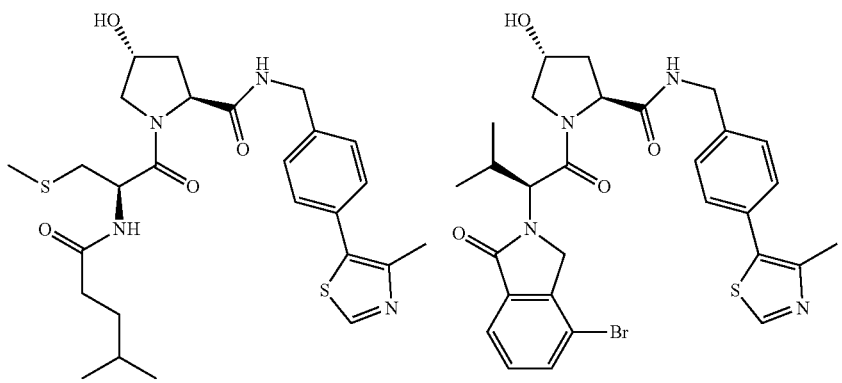
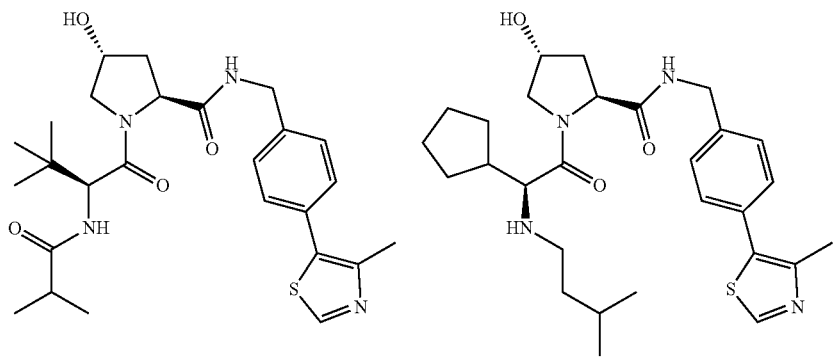

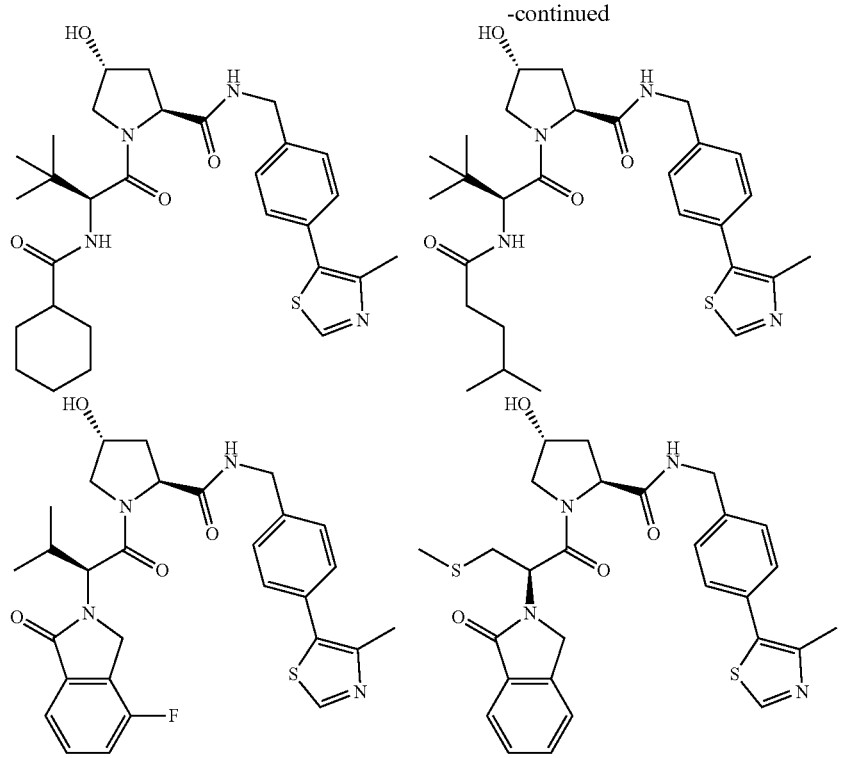
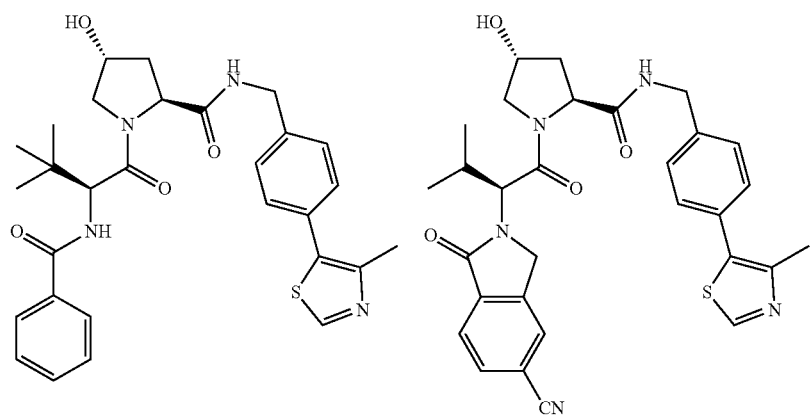
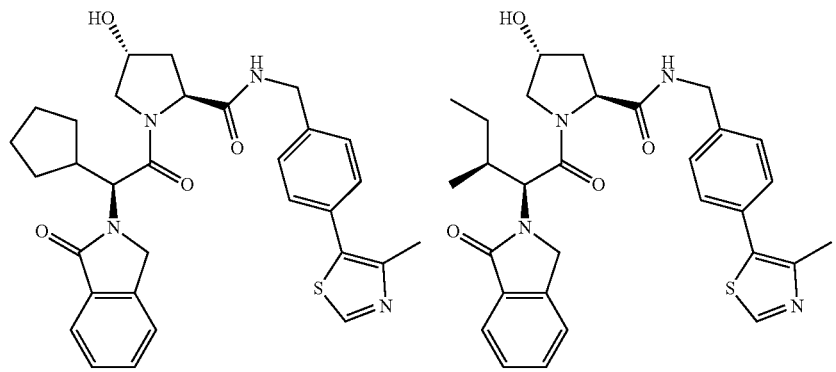

-continued
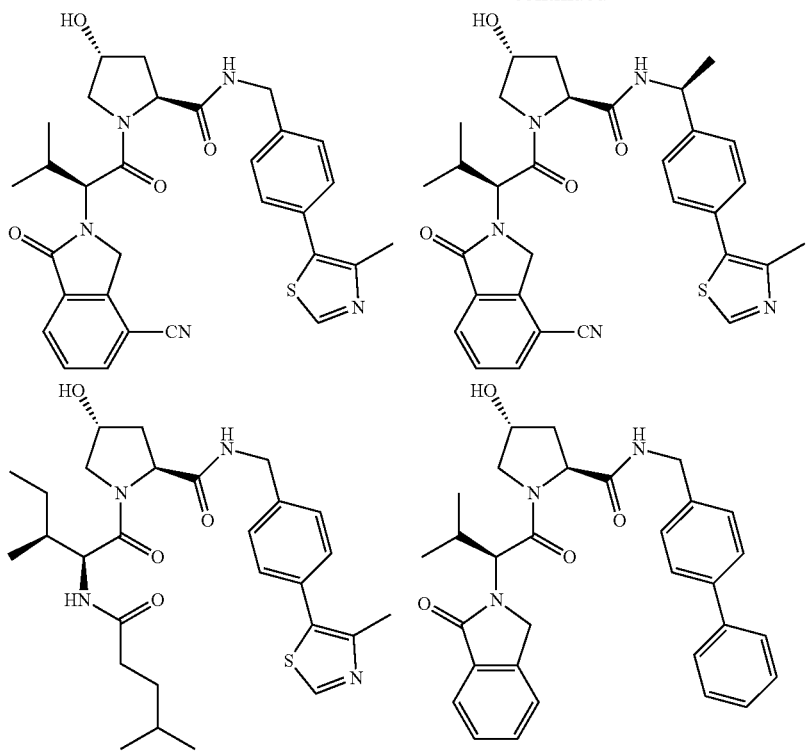
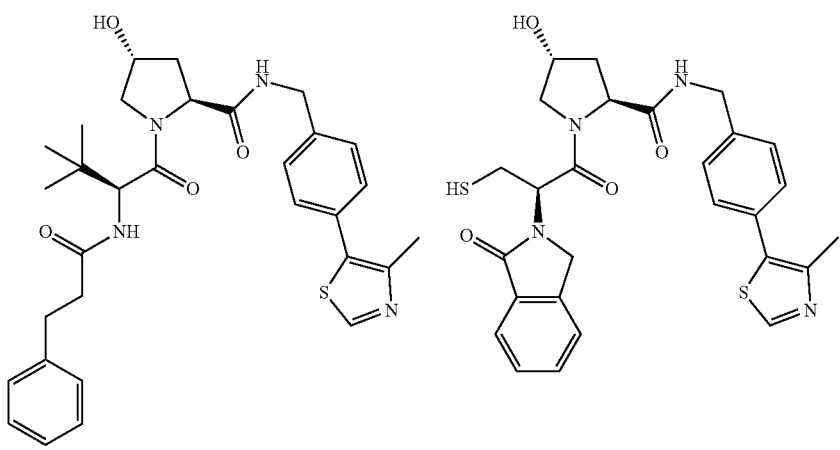
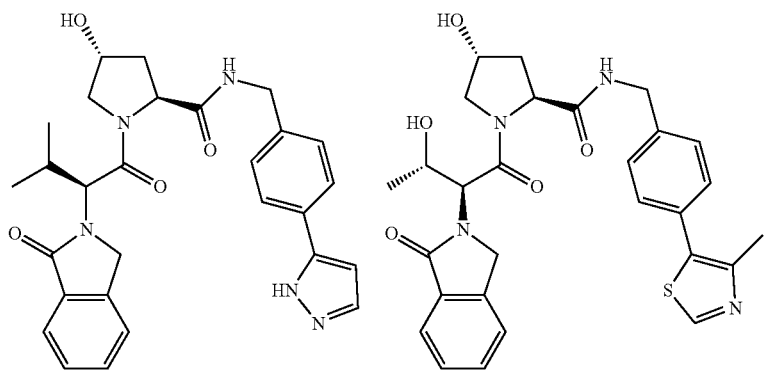

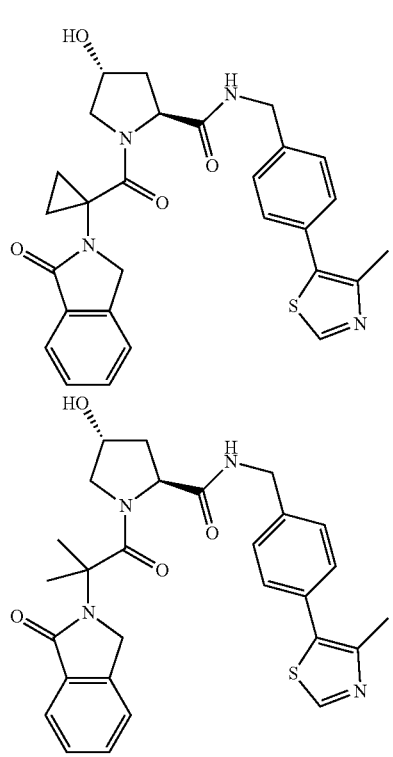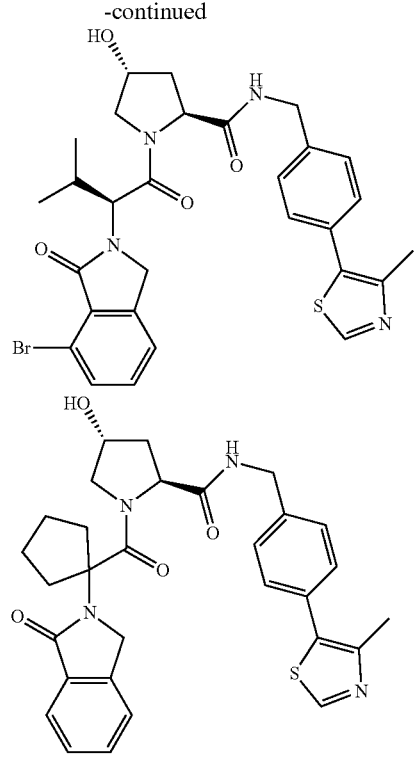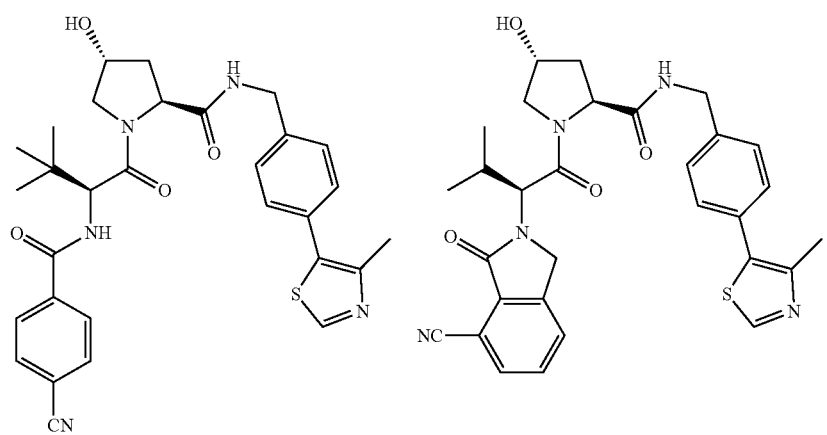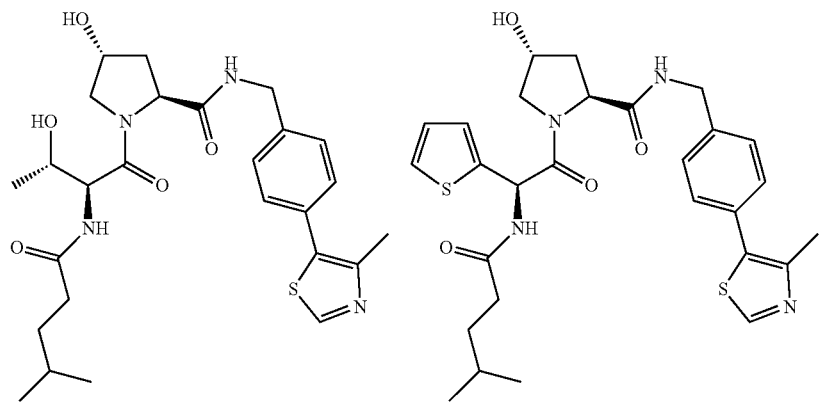

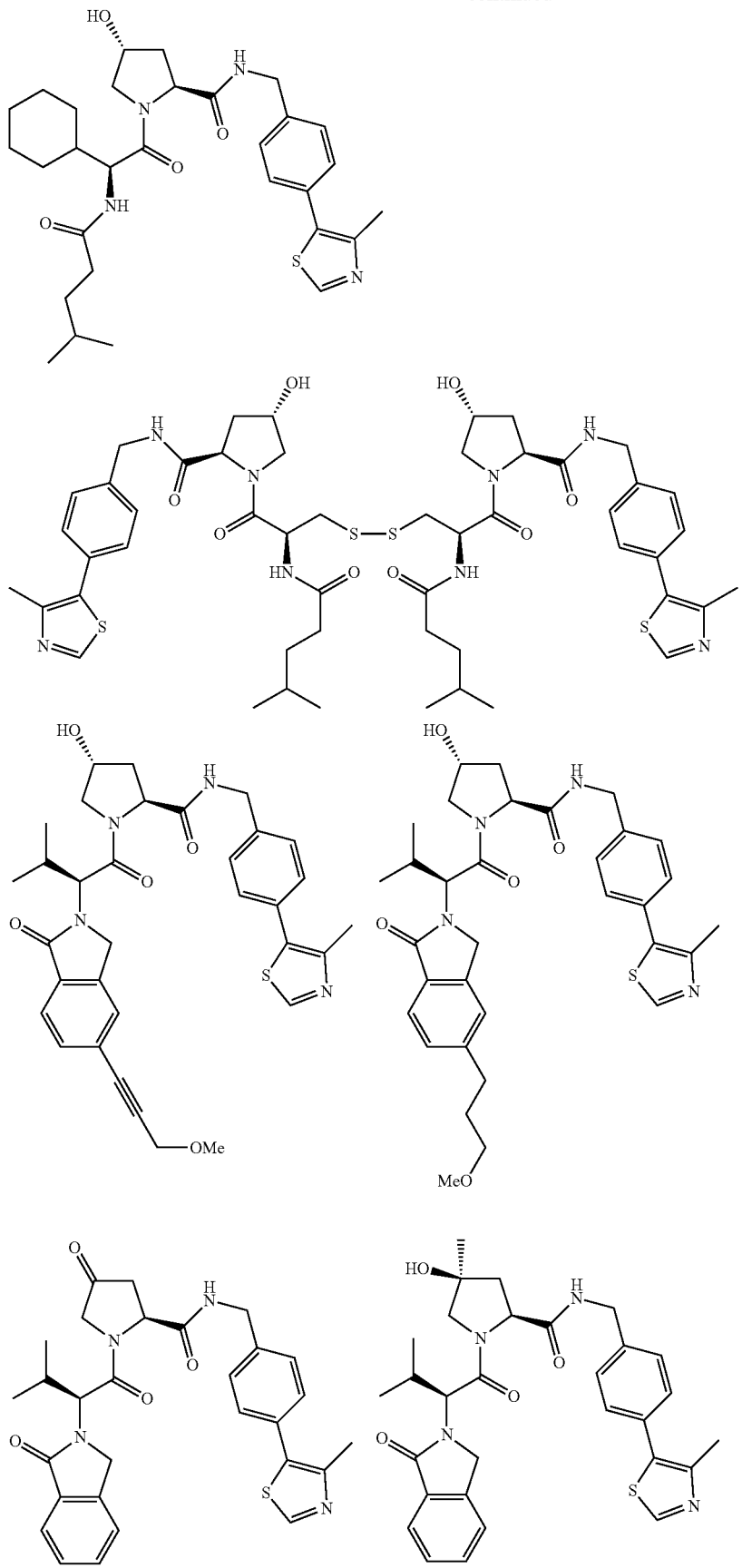

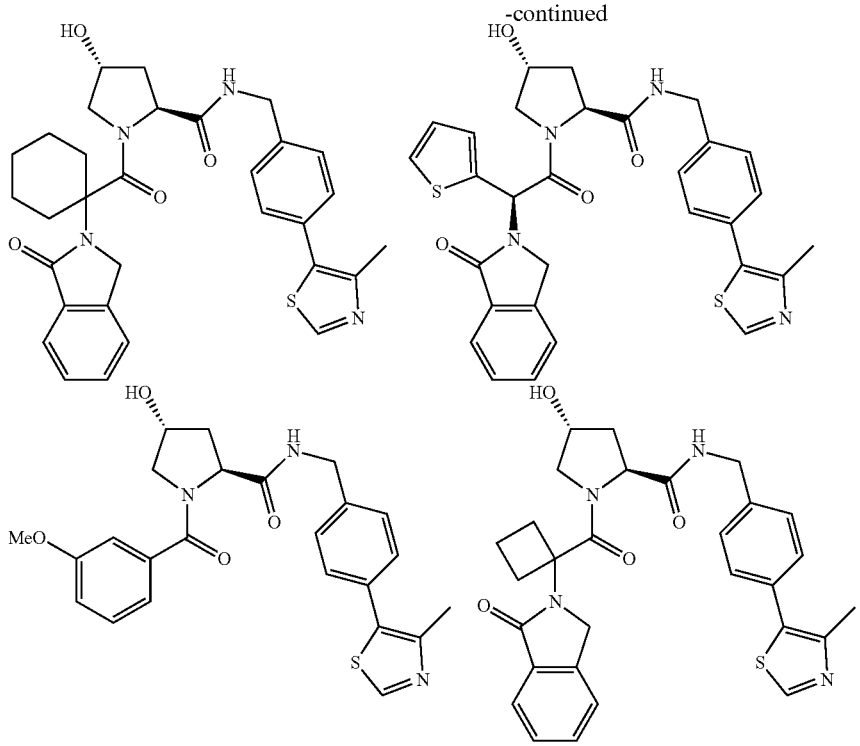
-continued
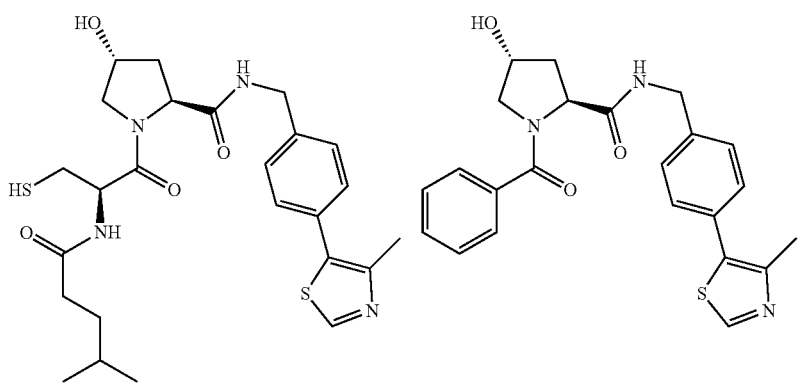
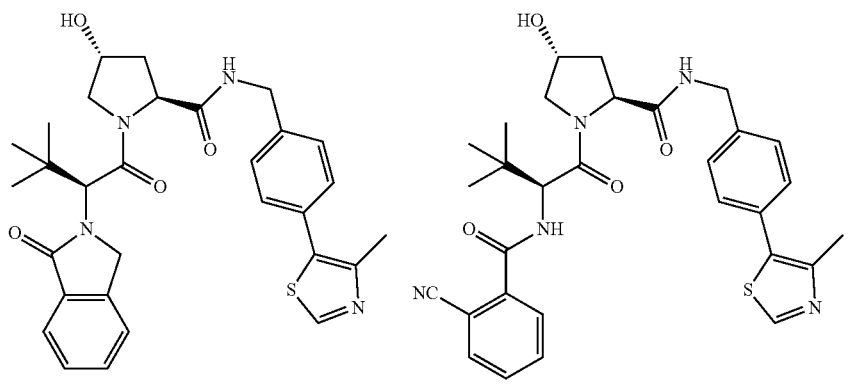

-continued
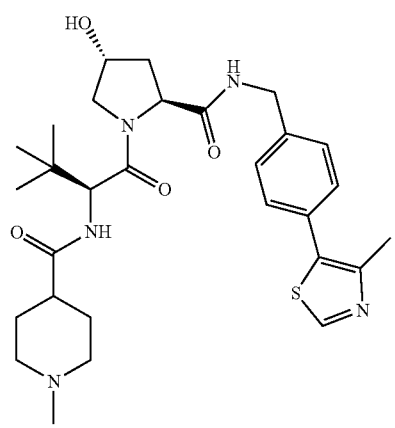
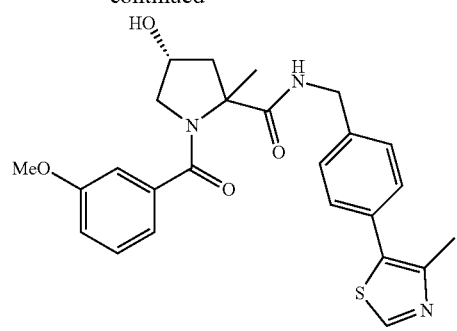
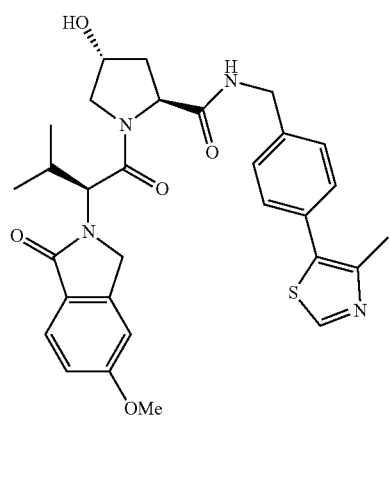
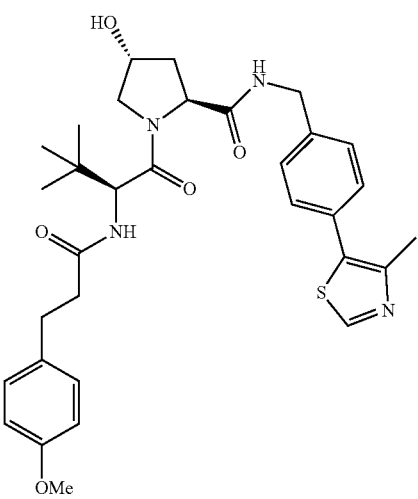
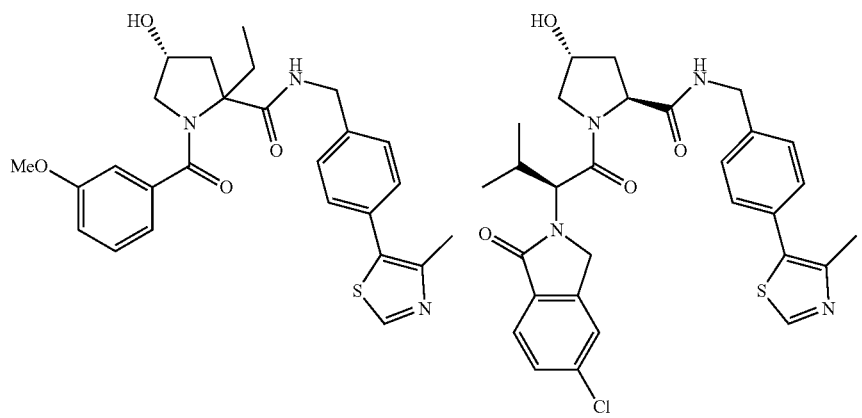

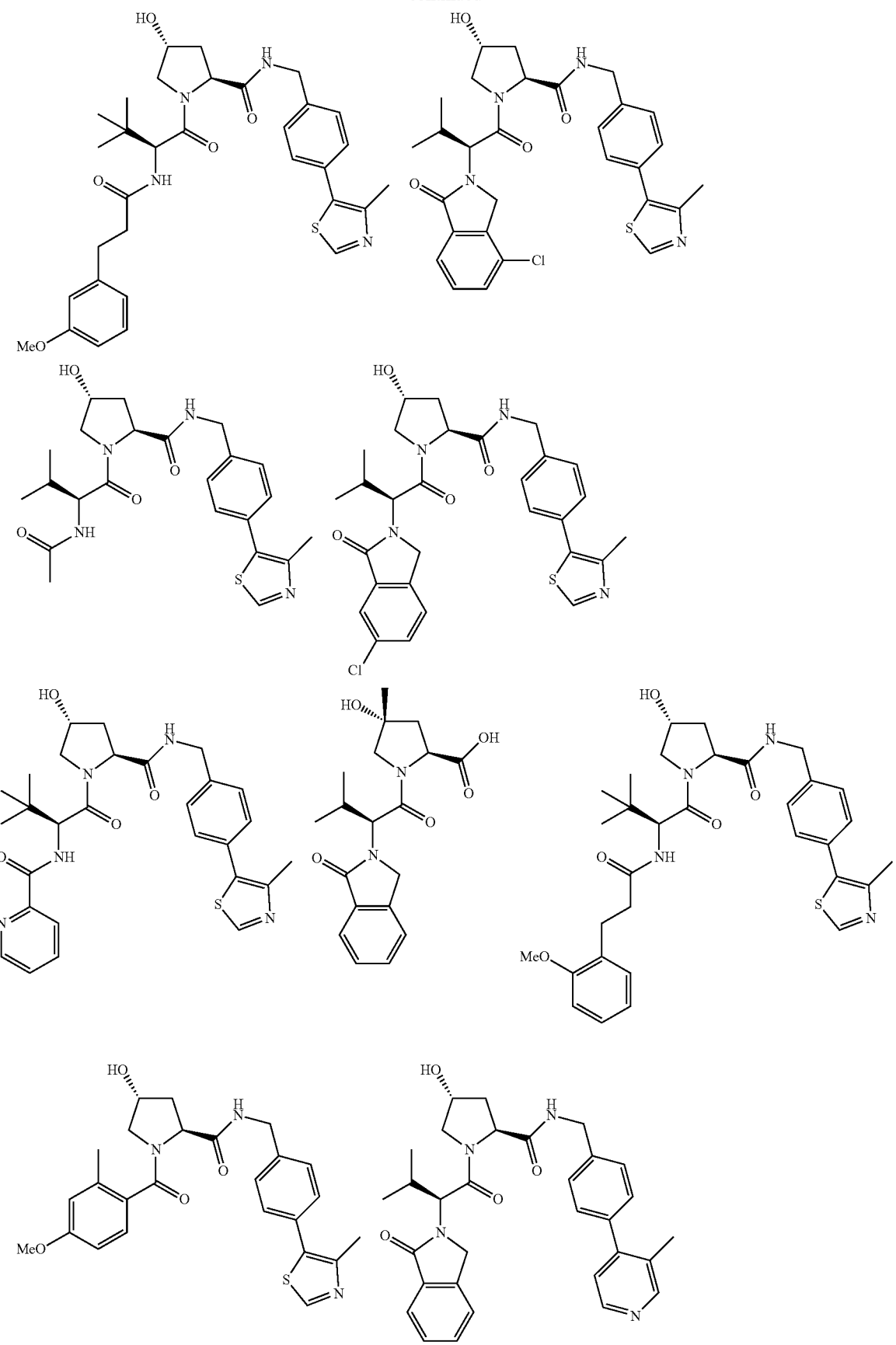

245
-continued
246
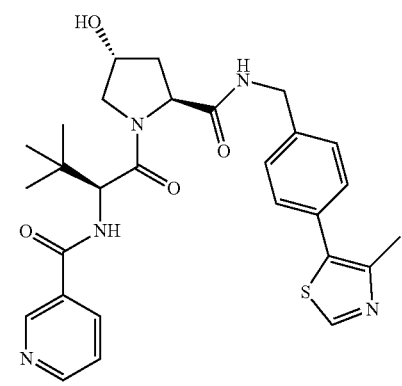
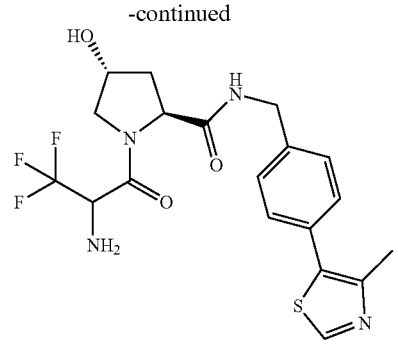
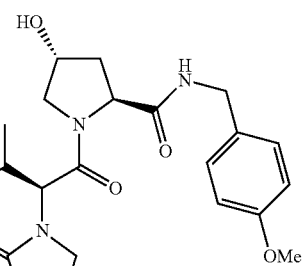
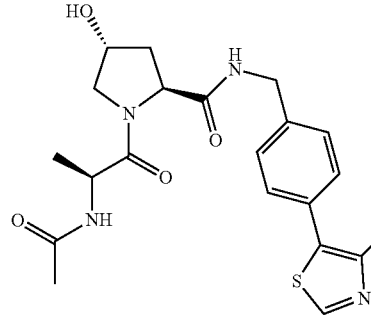
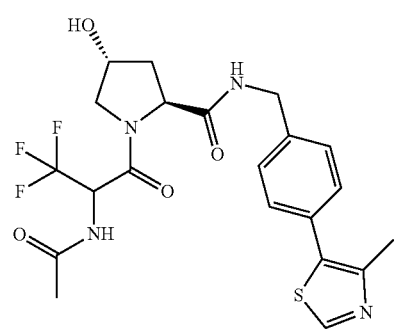
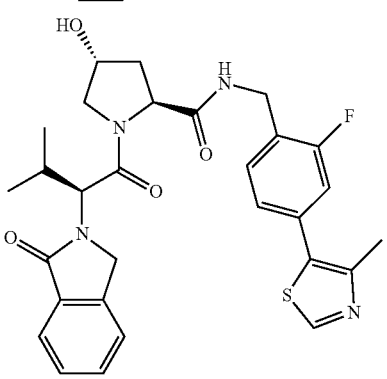
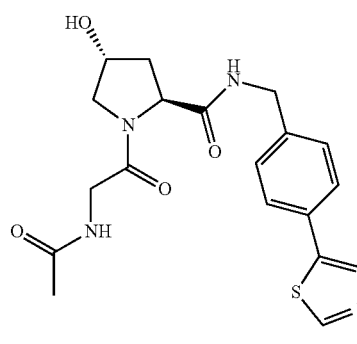
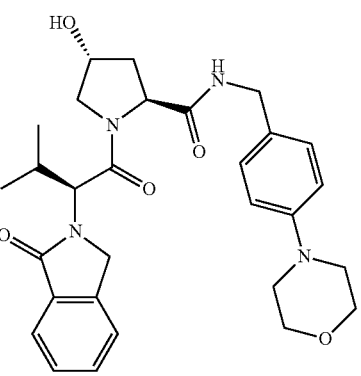
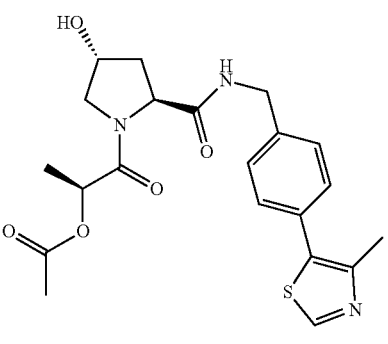
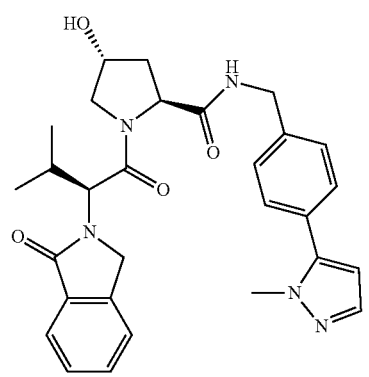
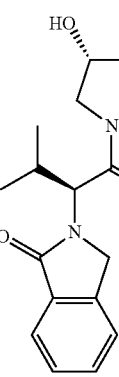
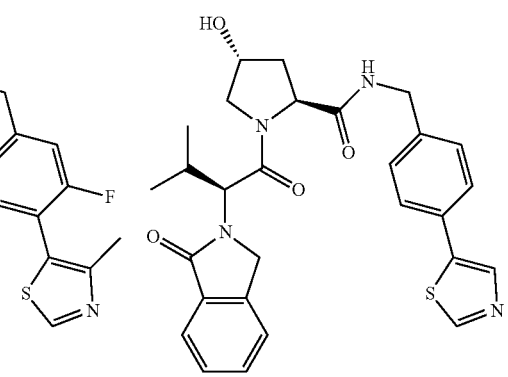

247
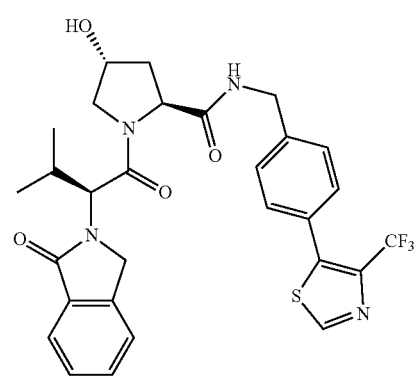
248
-continued
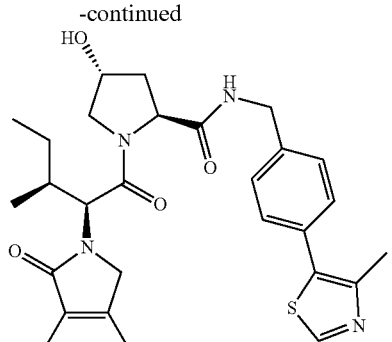
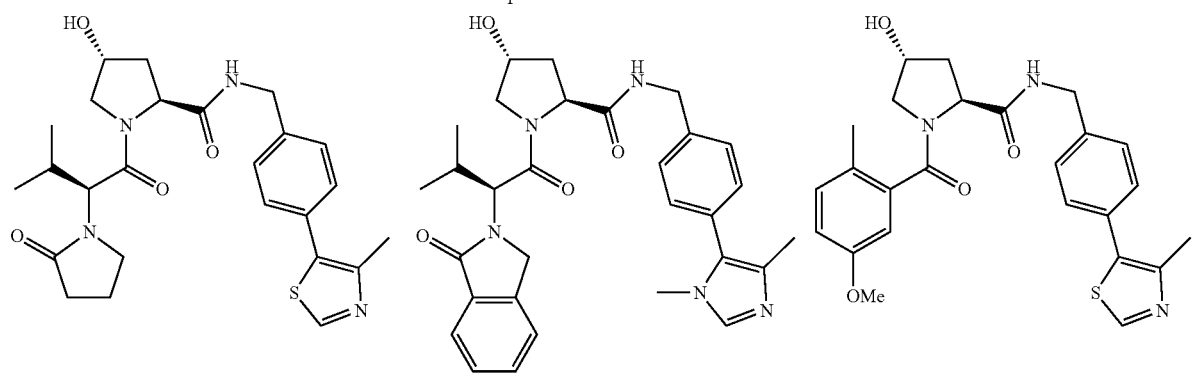
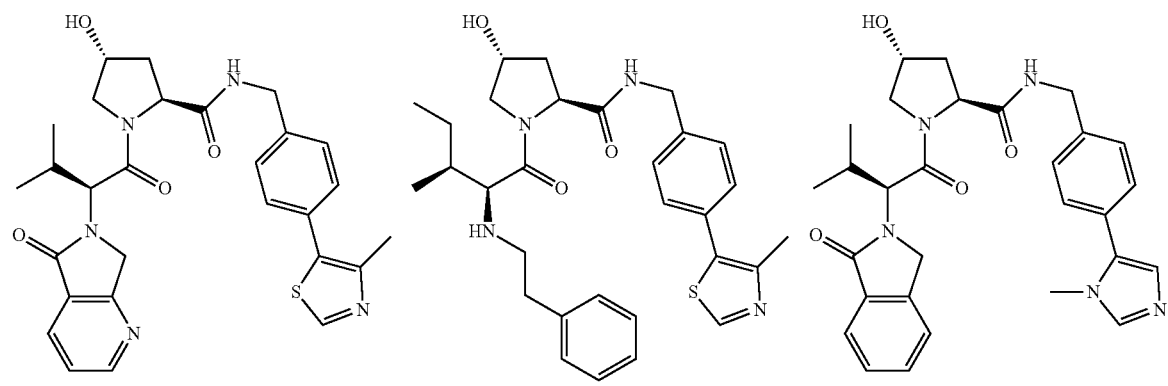
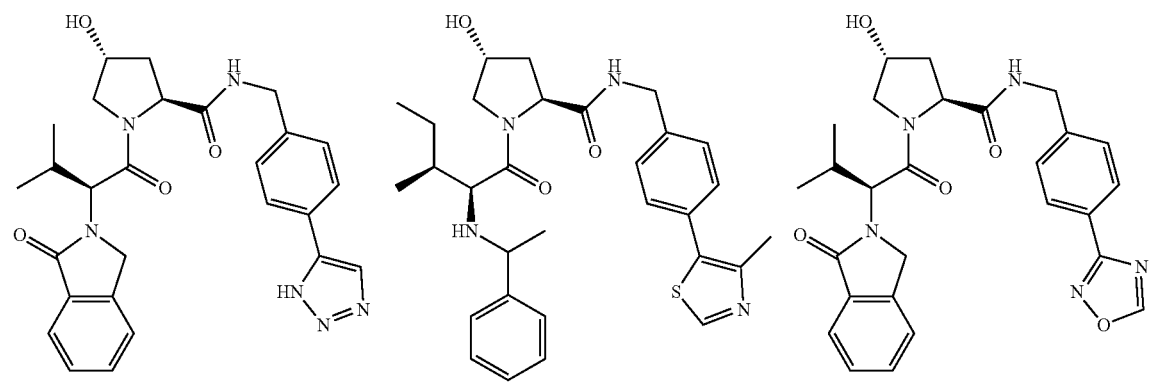

249
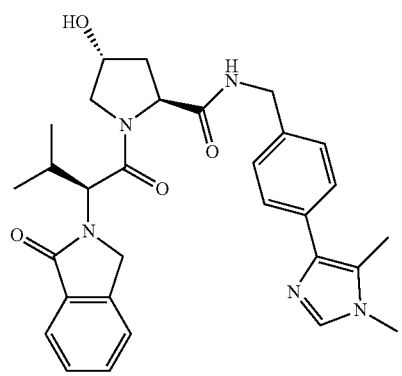 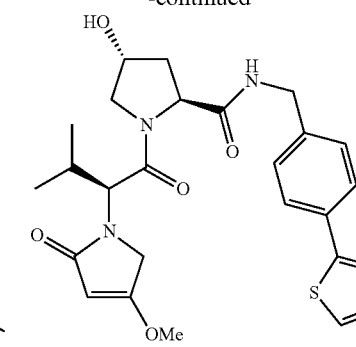 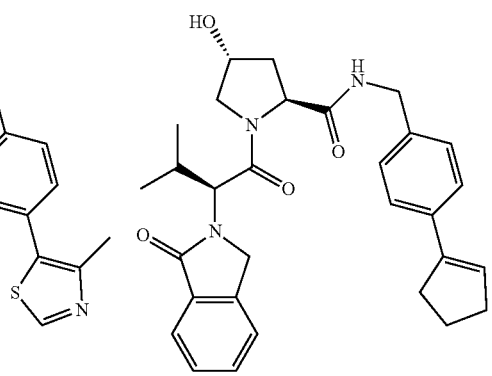
250
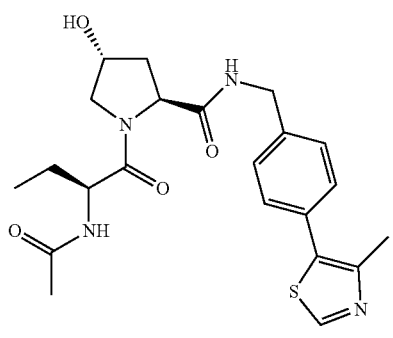 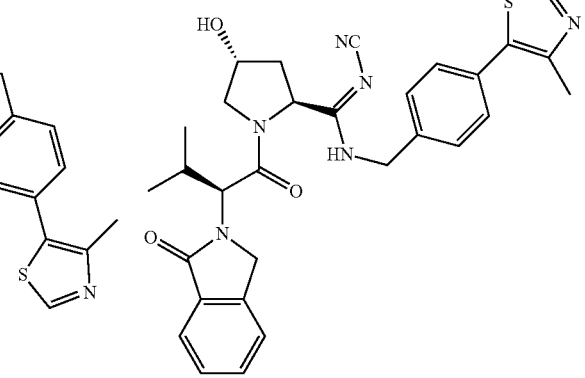
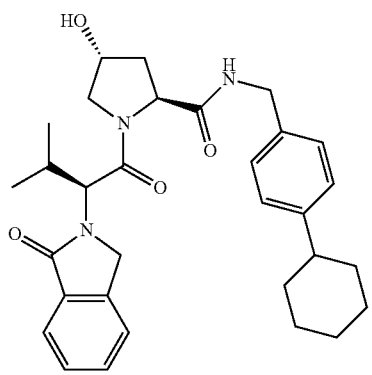  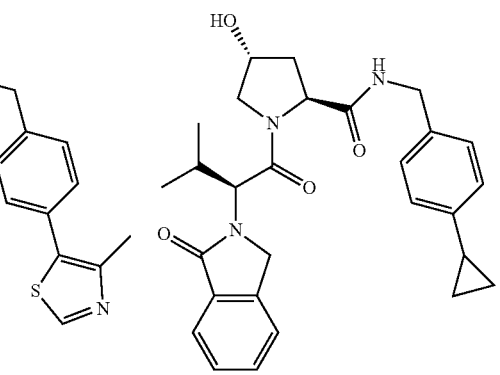
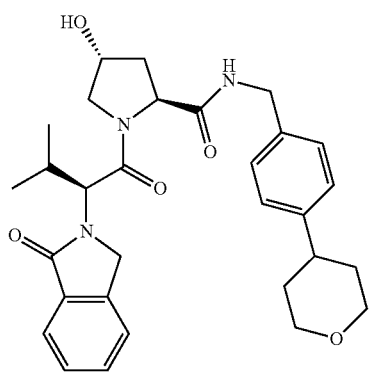 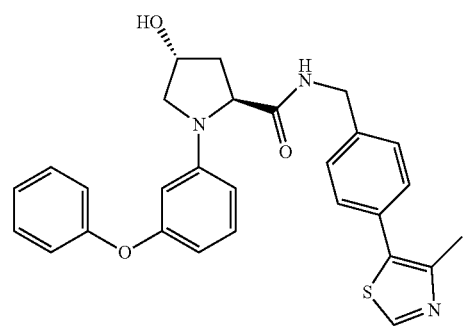

-continued
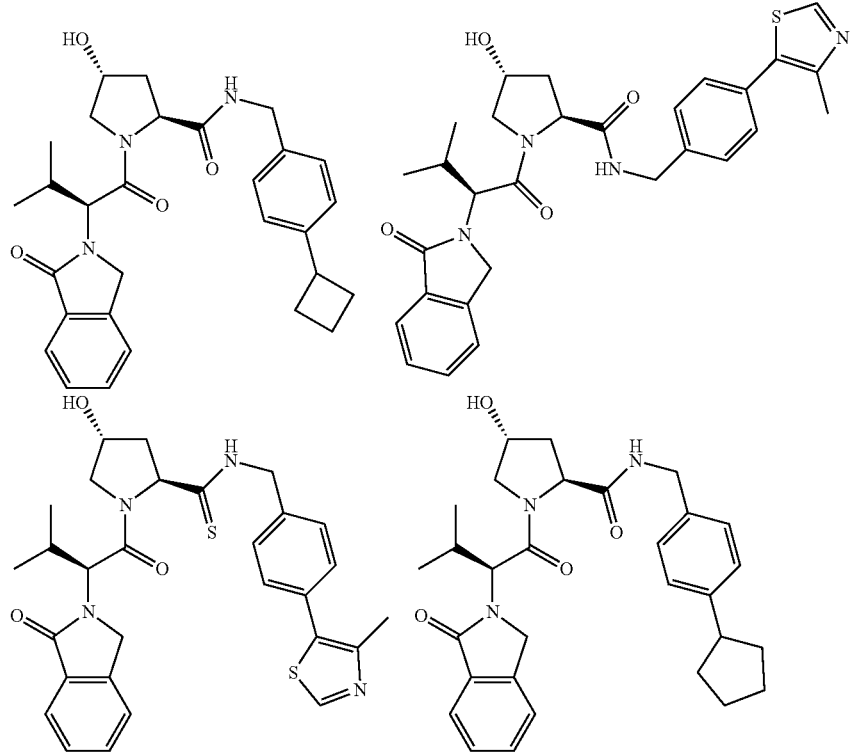
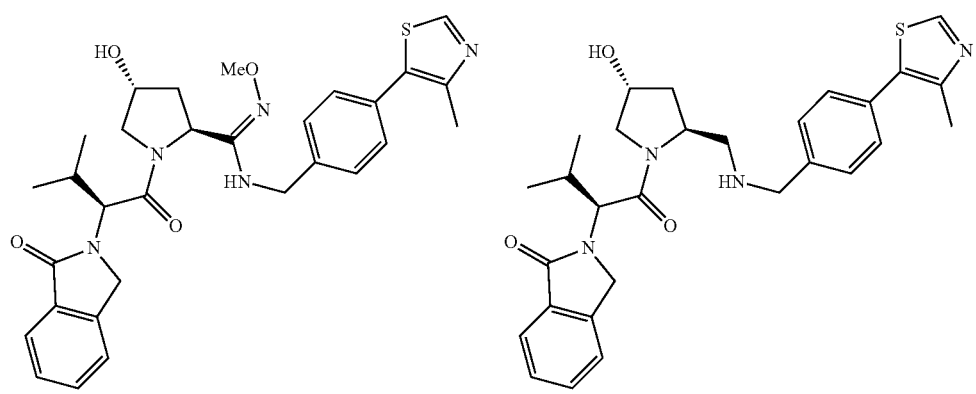
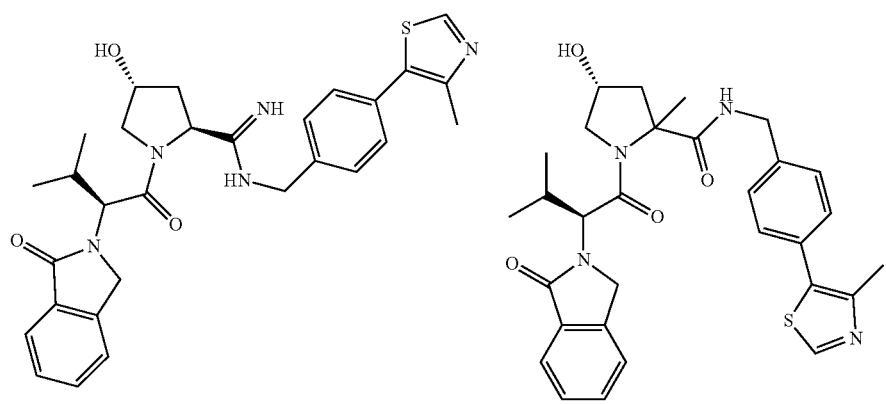

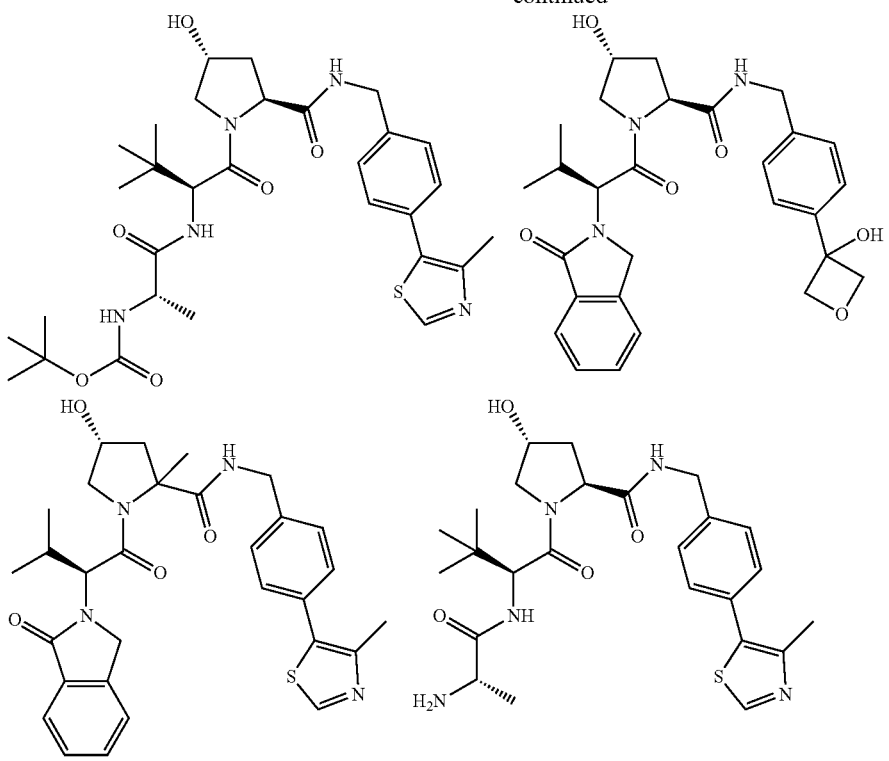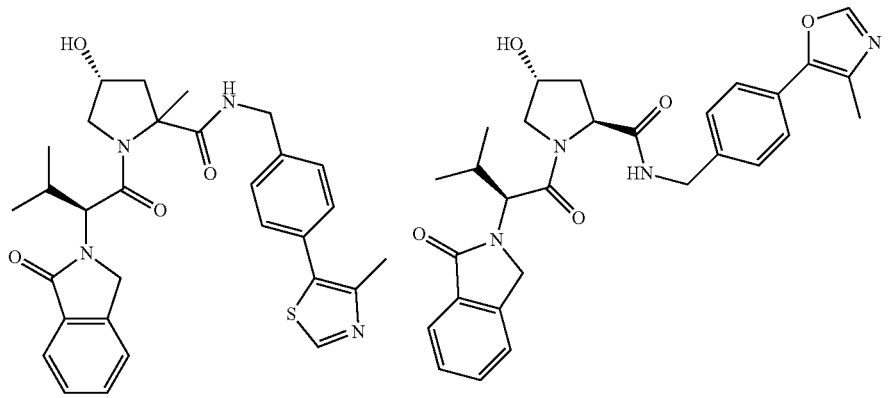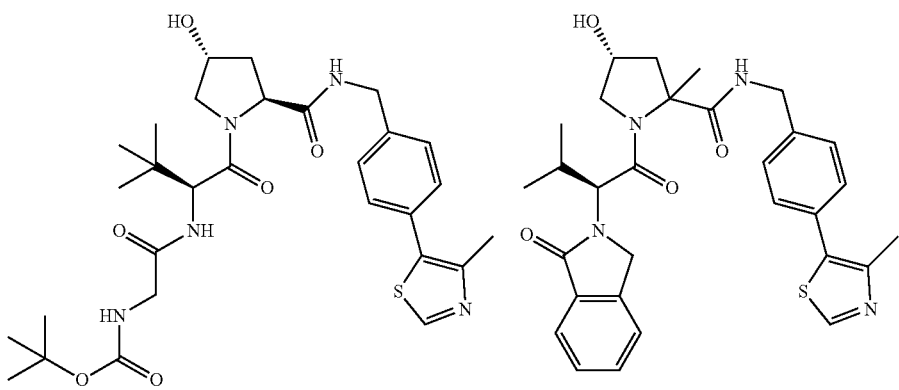

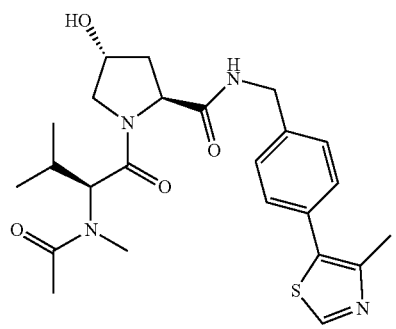
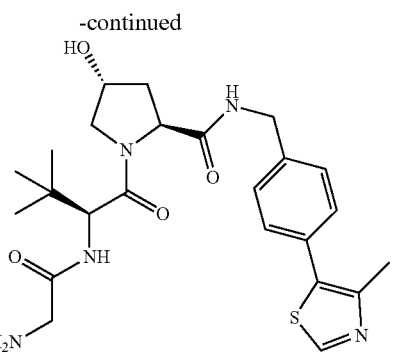
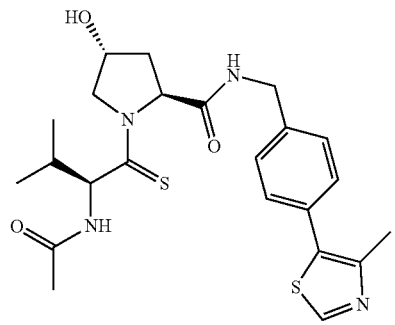
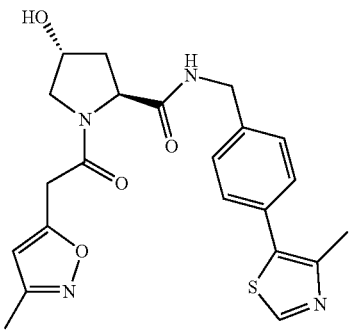
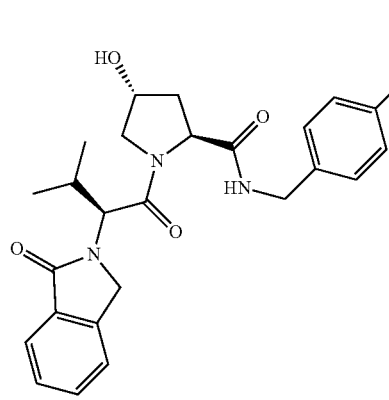
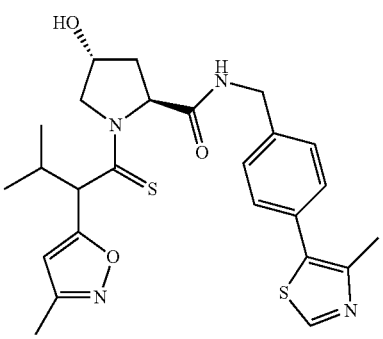
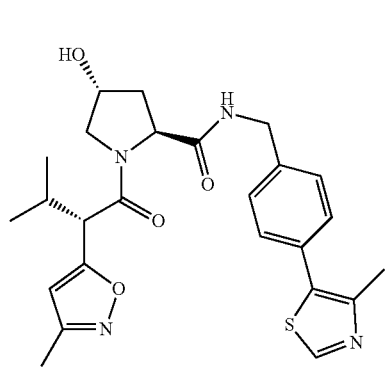
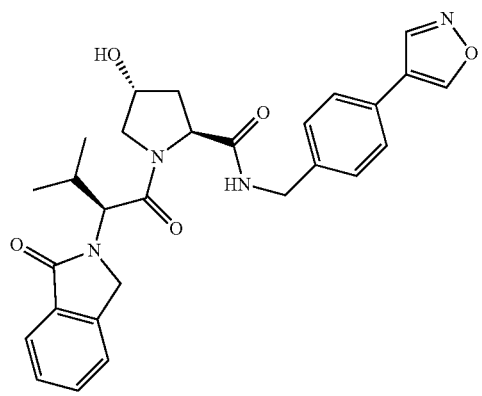

257
-continued
258
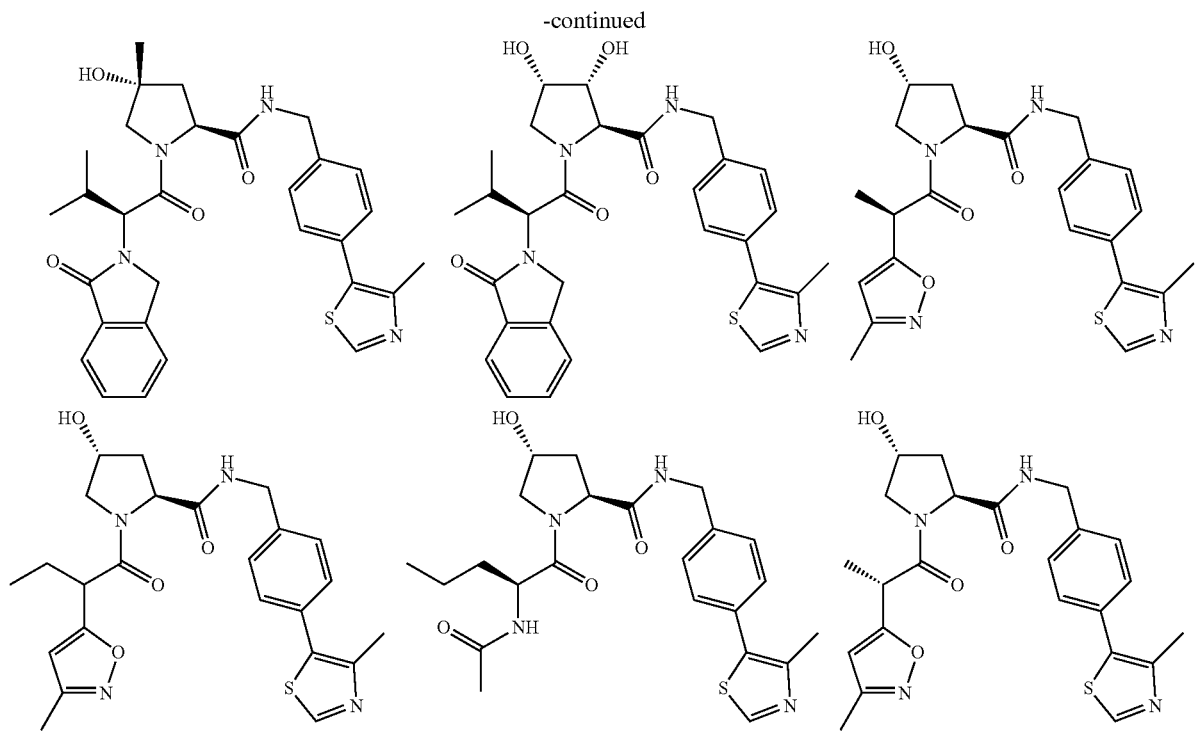
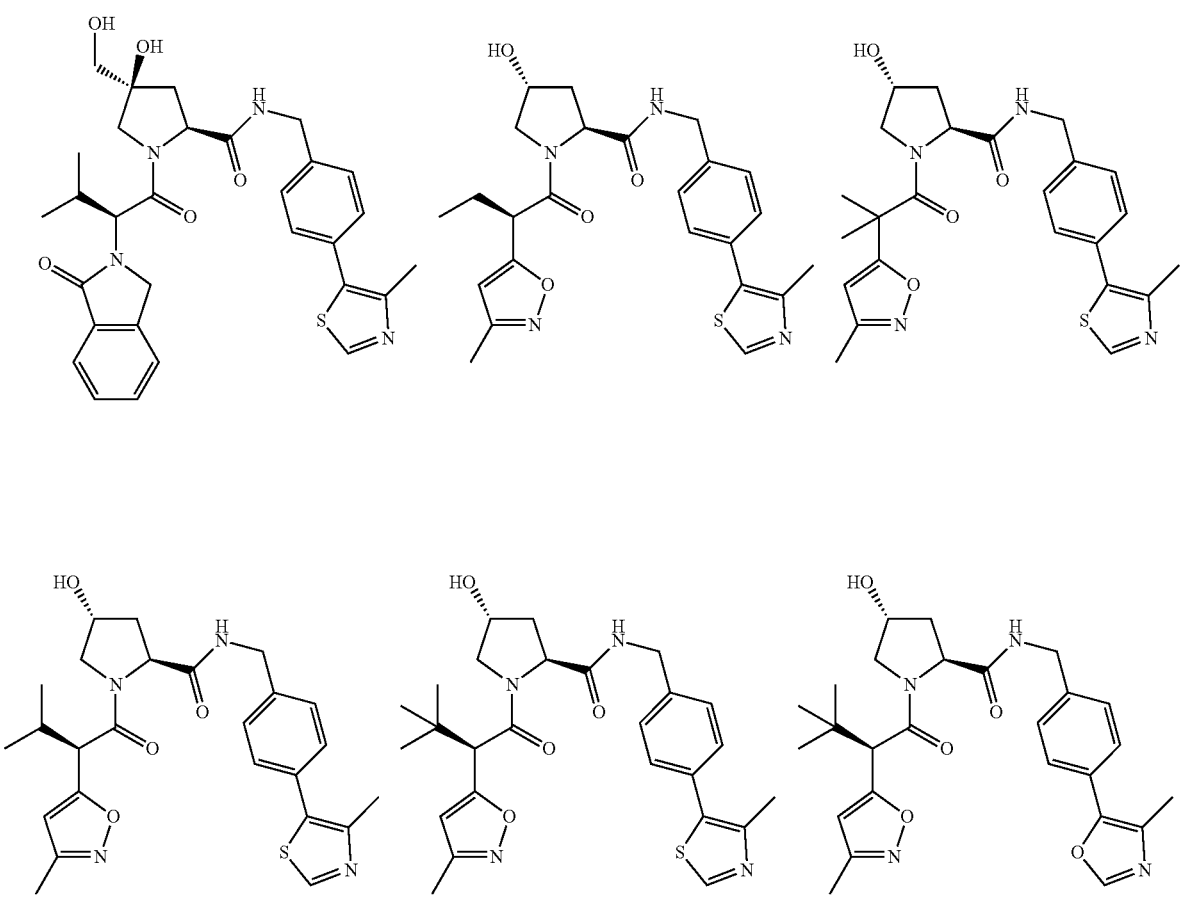

259
-continued
260
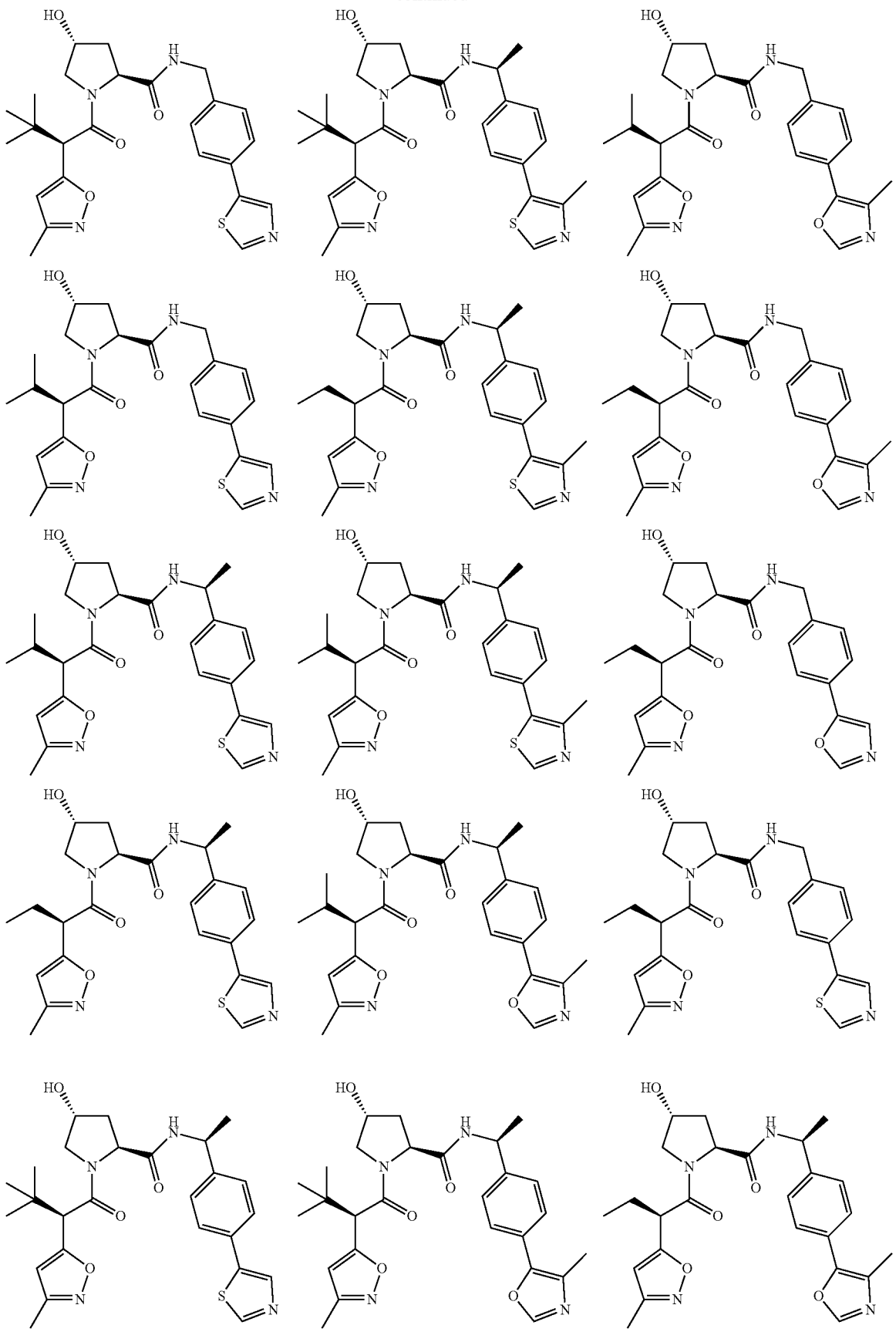

-continued
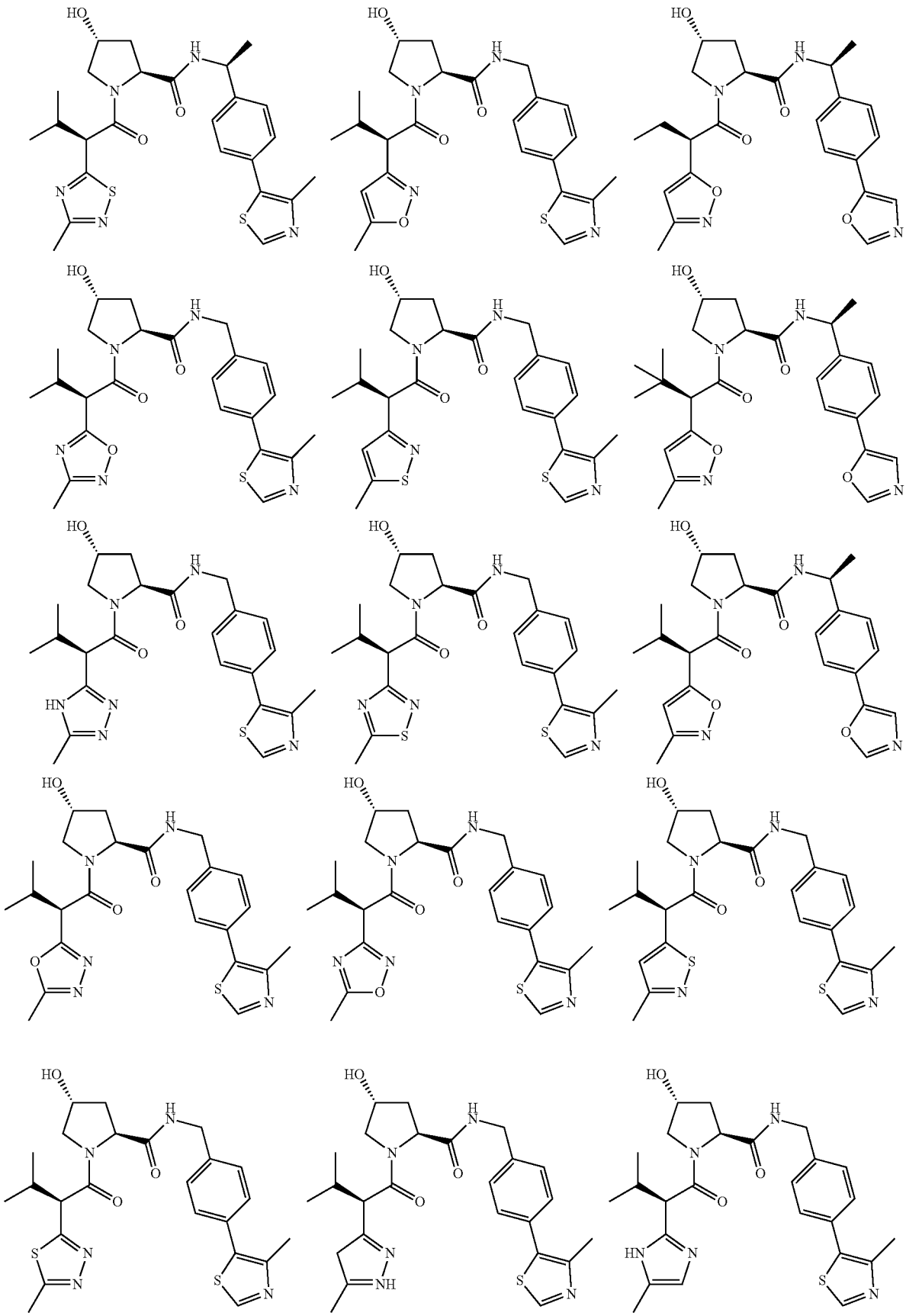

263    -continued    264
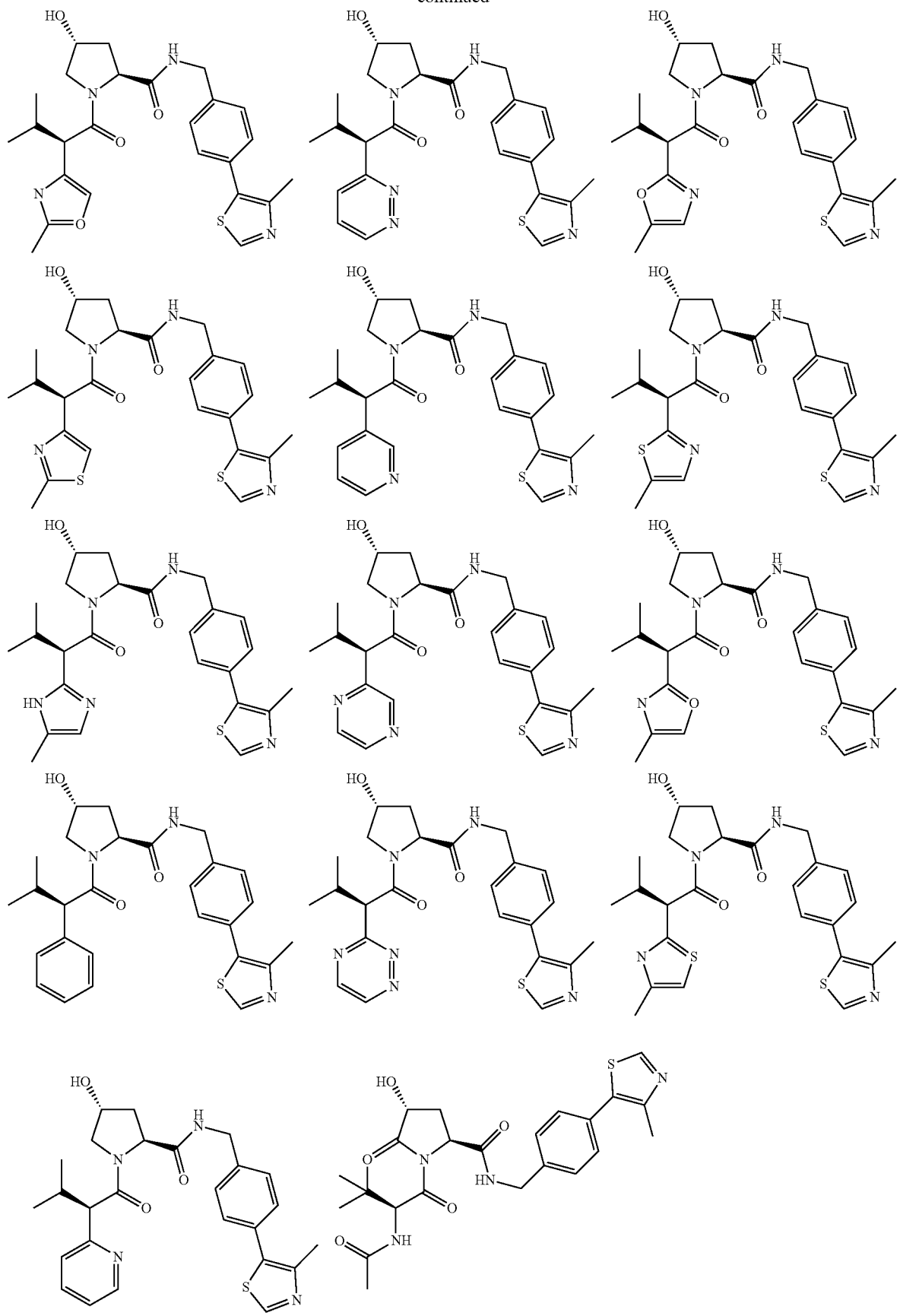

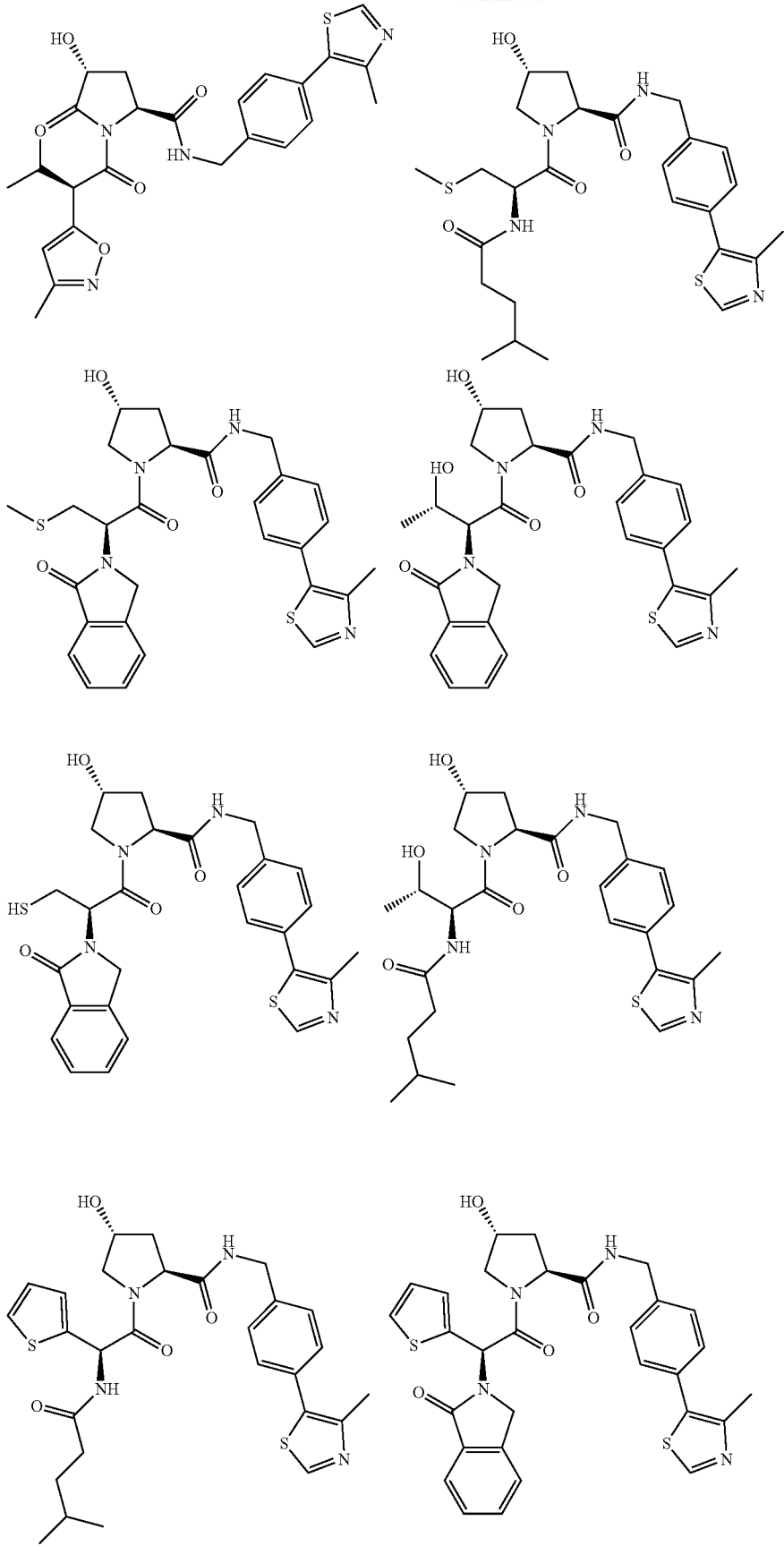

267
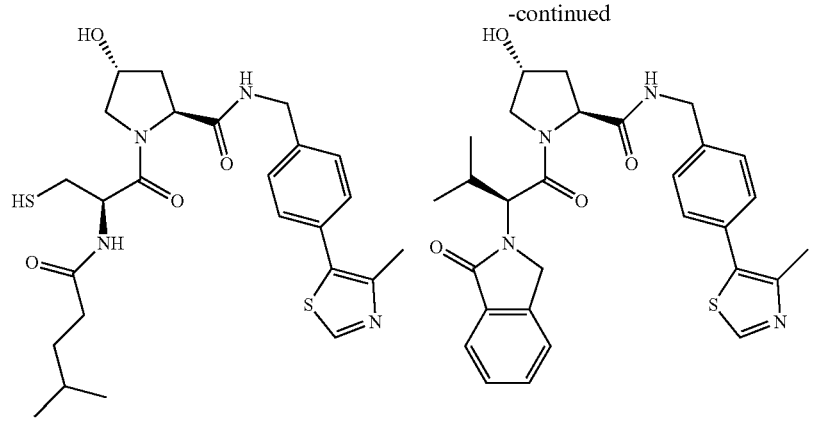
-continued
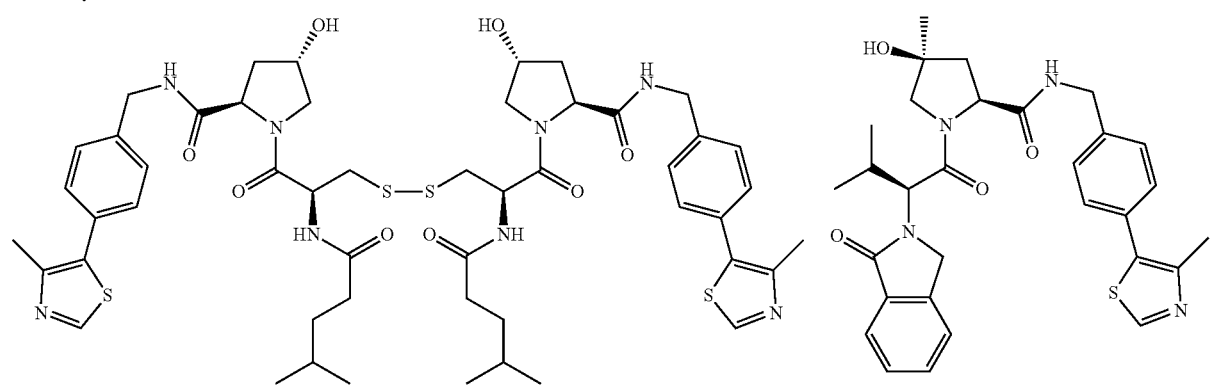
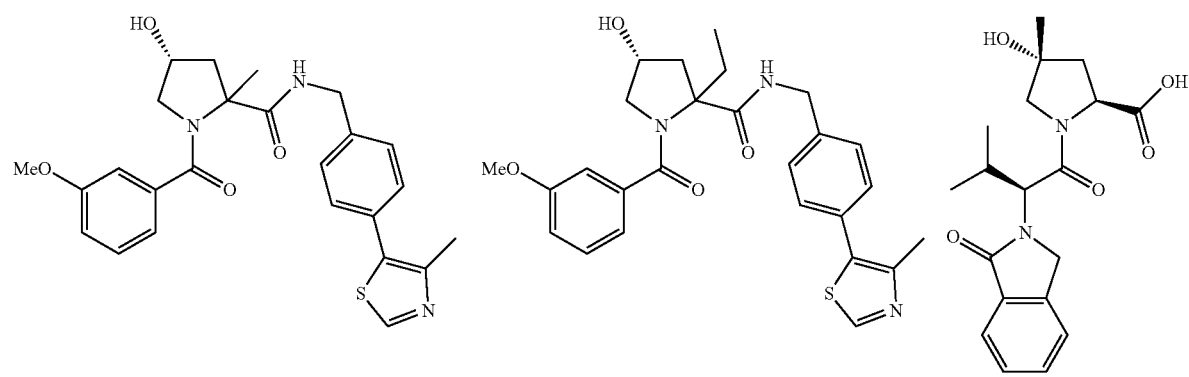
268
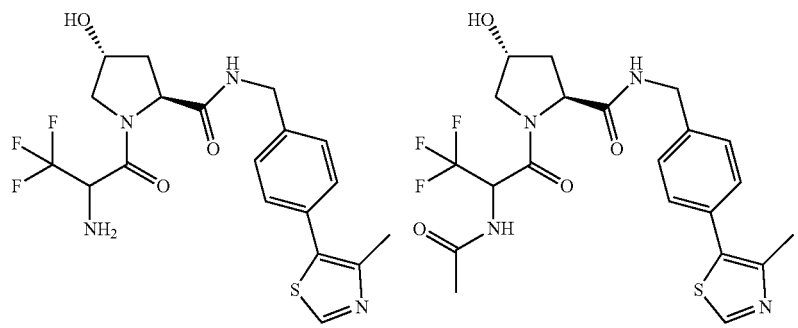

-continued
269
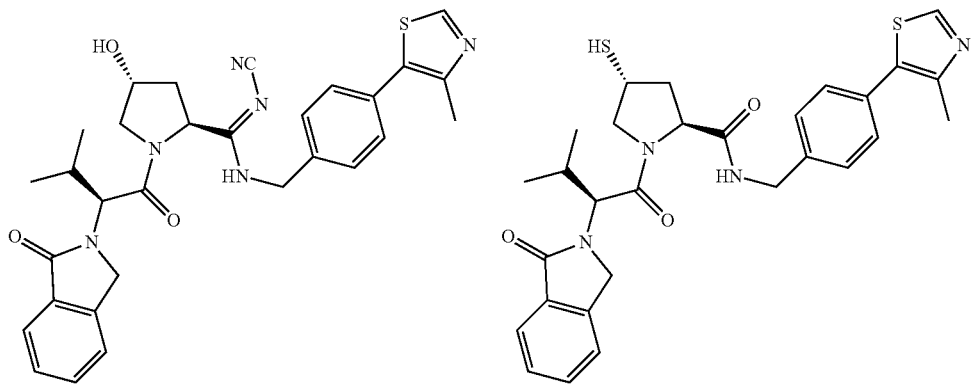
270
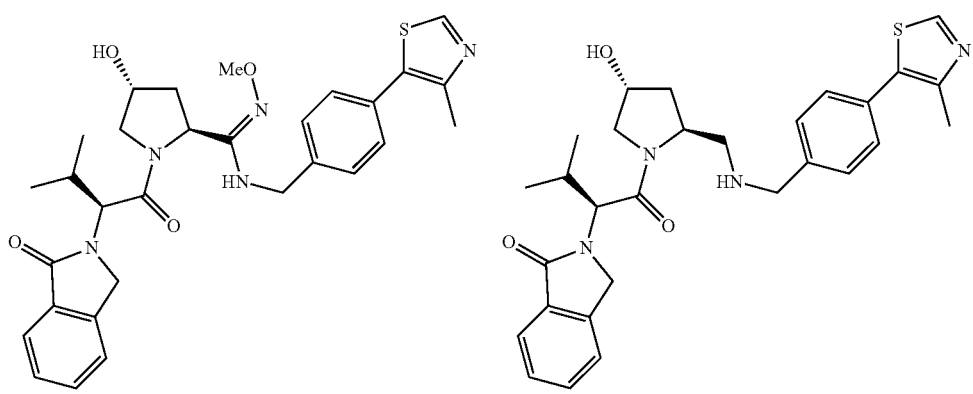
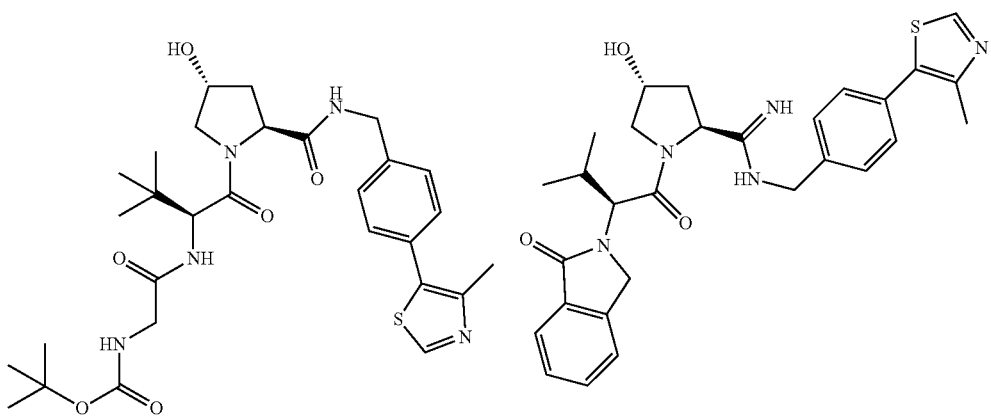
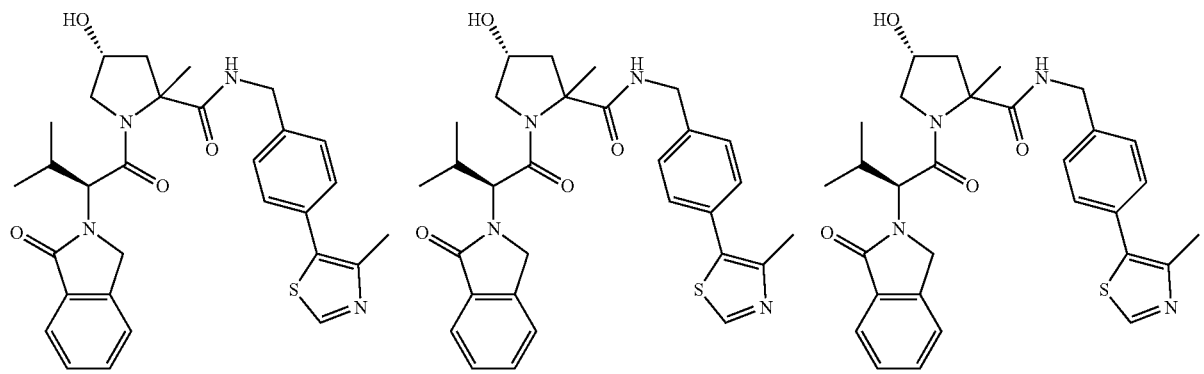

271
-continued
272
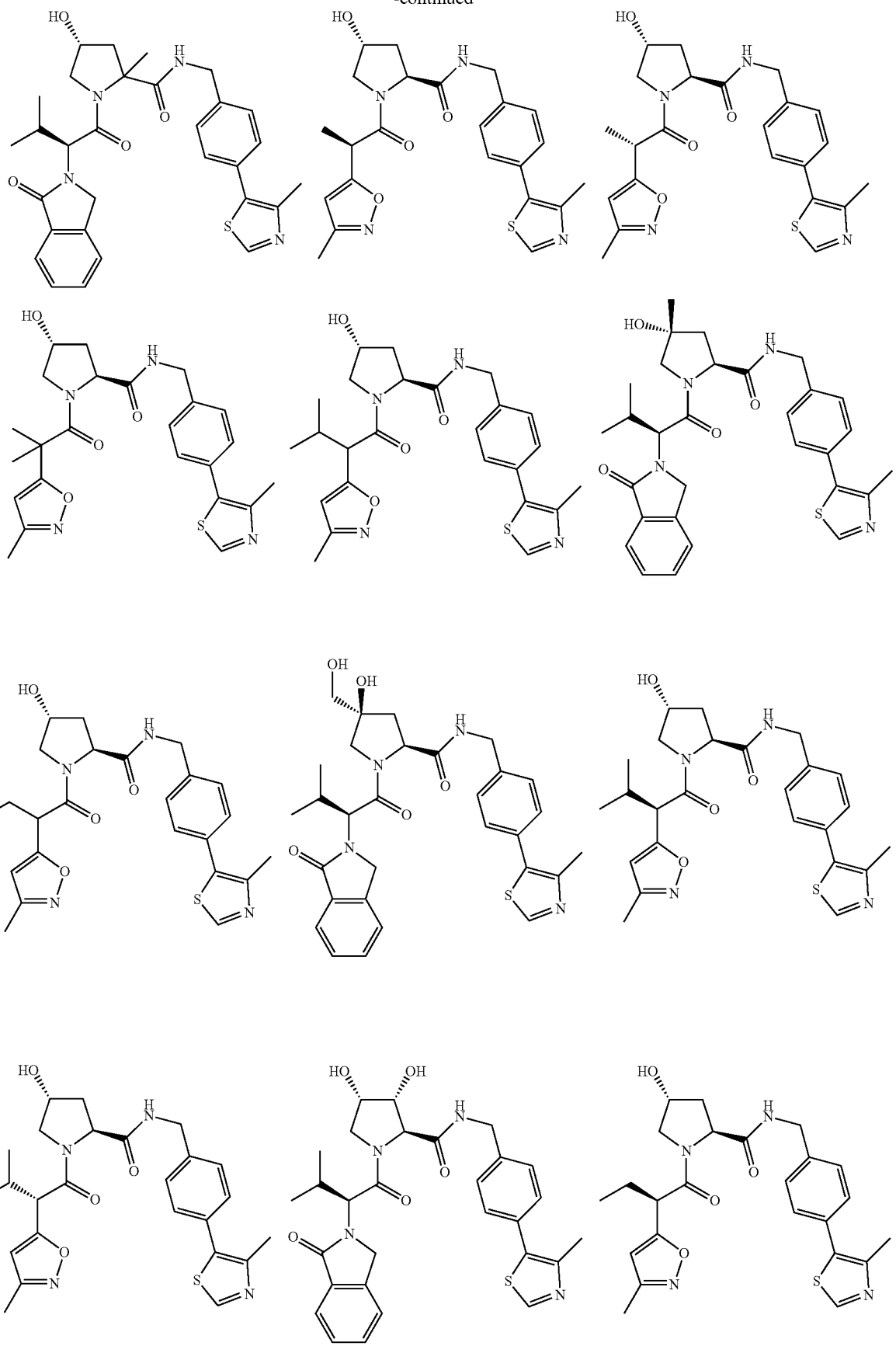

273
274
-continued
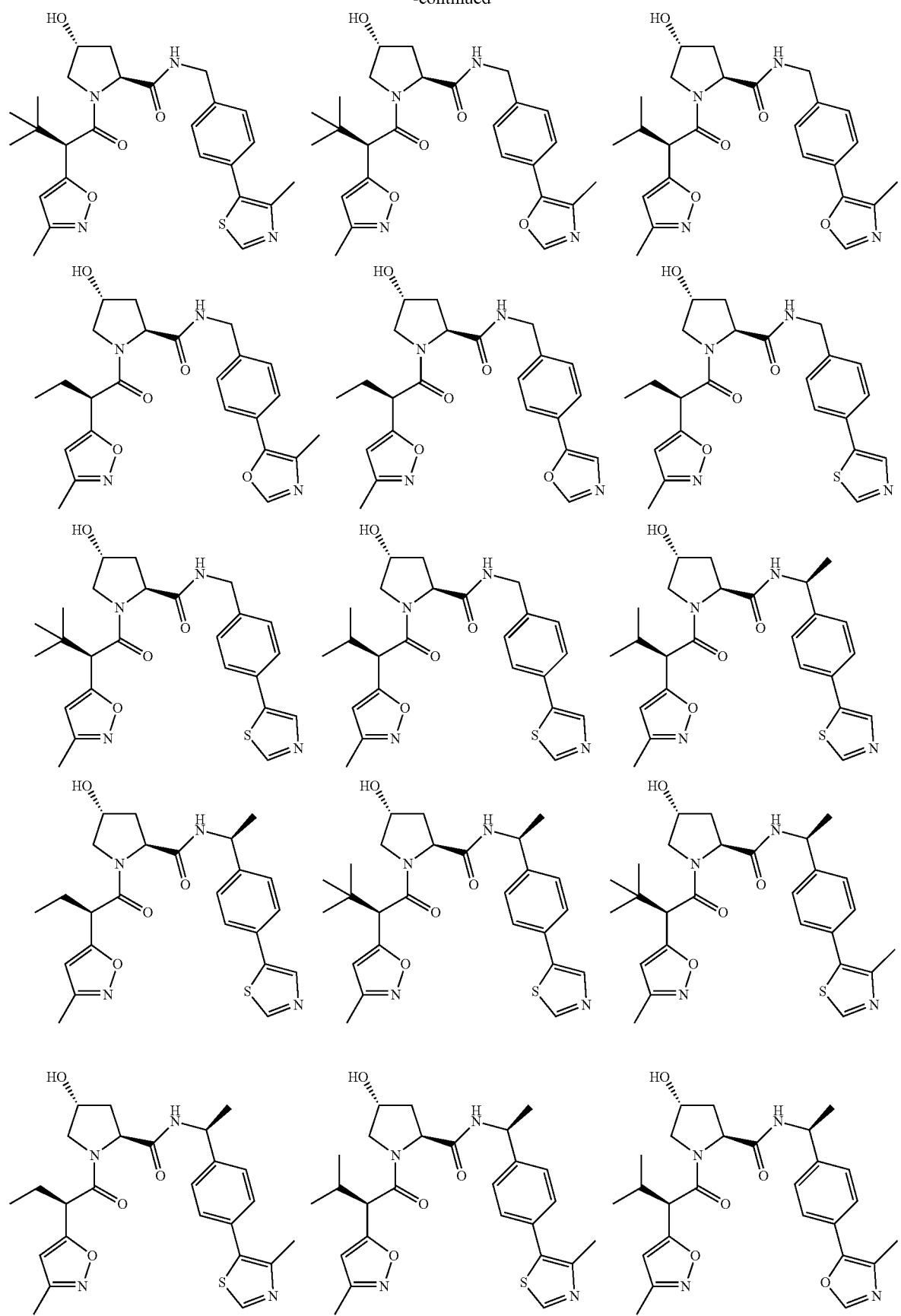

275
-continued
276
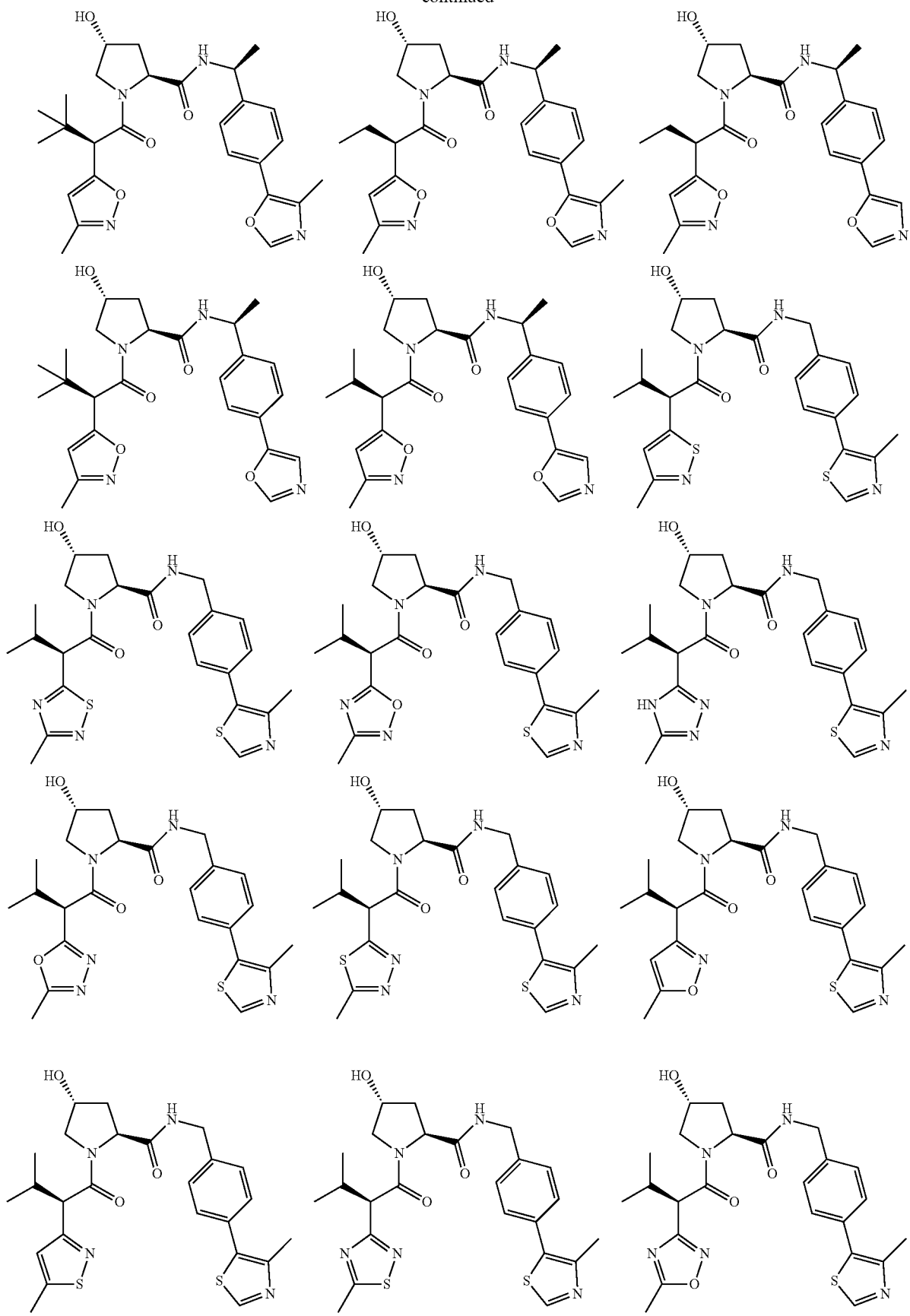

277 278
-continued
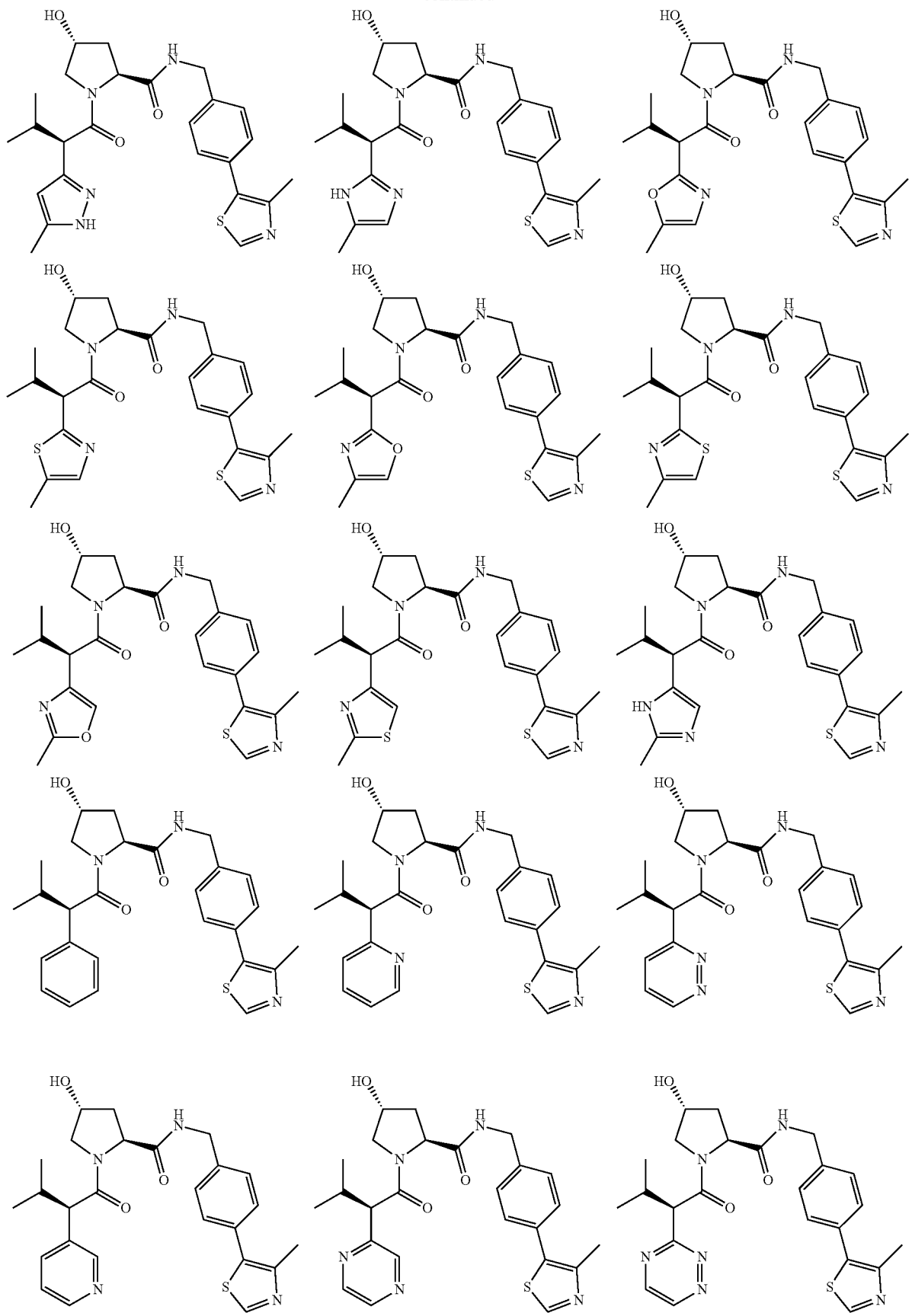

-continued
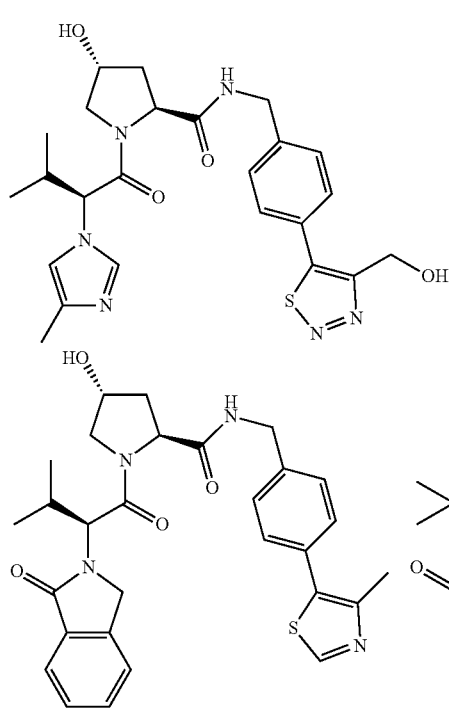
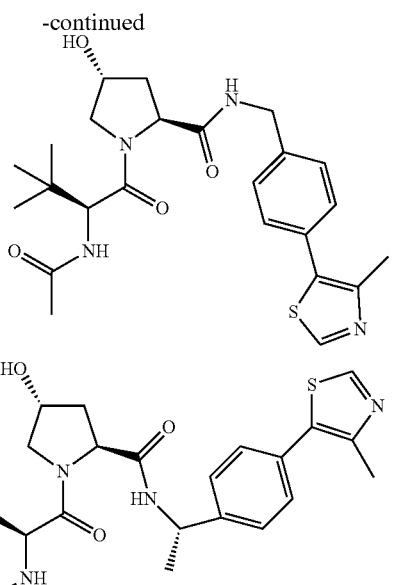
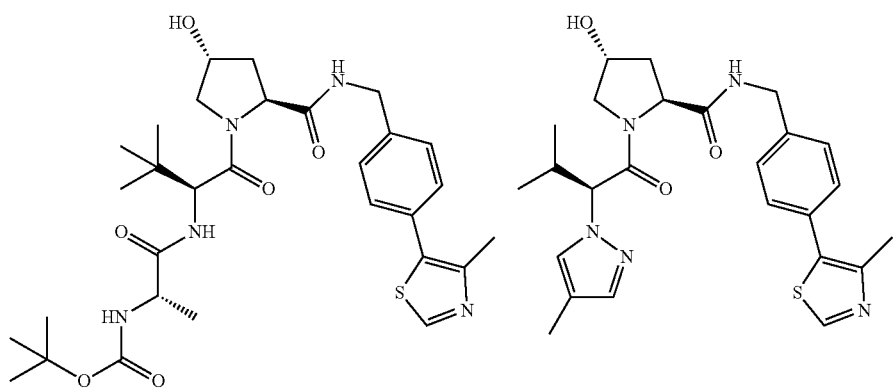
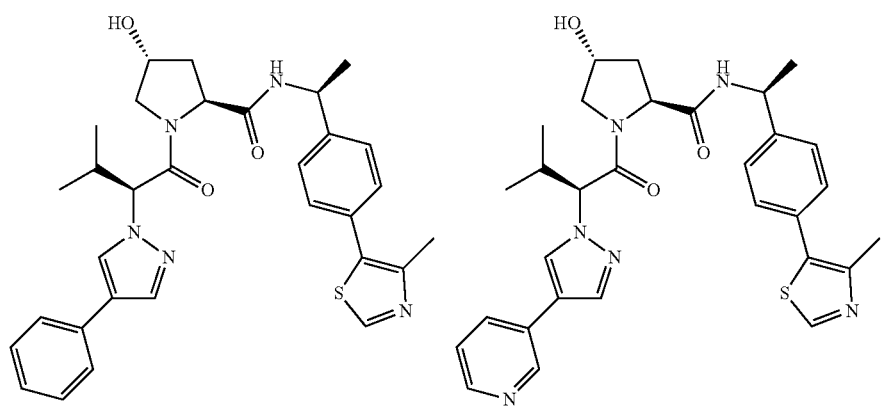

-continued
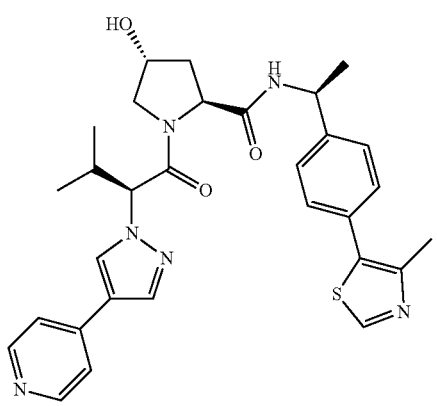
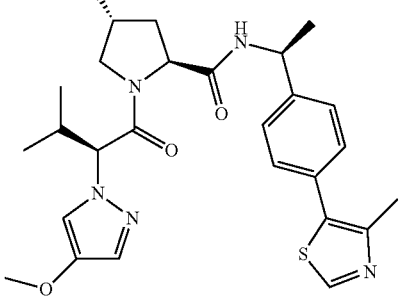
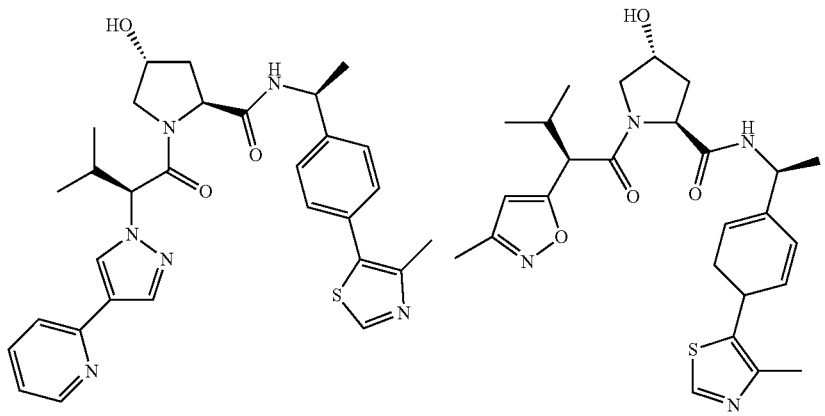
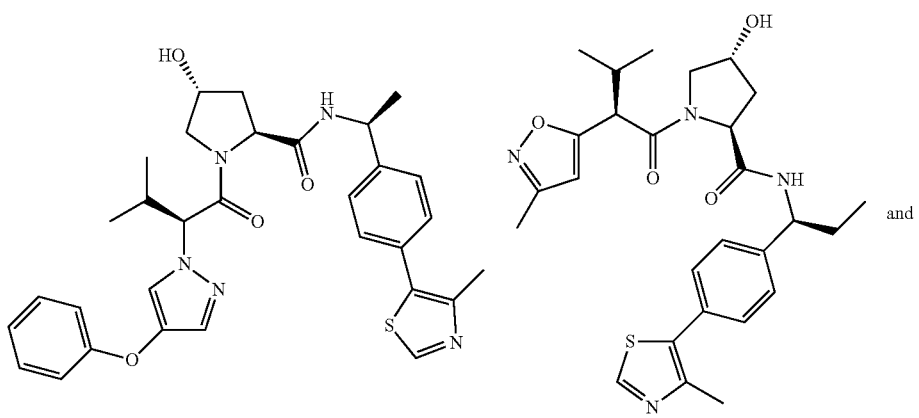
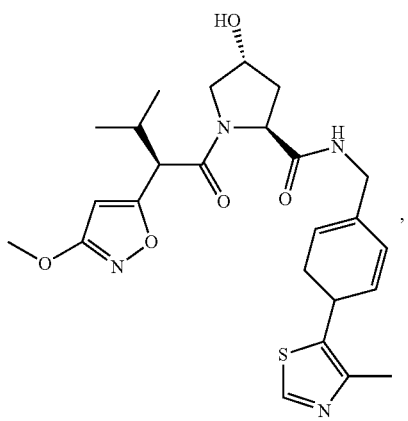
and wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., -$A^L_1$ . . . $(A^L)_q$- or -$(A^L)_q$-), wherein $A_1$ is a group coupled to PTM, and $(A^L)_q$ is a group coupled to ULM.

In certain embodiments, the linker group L is selected from -$(A^L)_q$-:

$(A^L)_q$ is a group which is connected to at least one of a ULM, a PTM moiety, or a combination thereof;

q of the linker is an integer greater than or equal to 1;

each $A^L_q$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, P(O)$R^{L1}$, P(O)O$R^{L1}$, $NR^{L3}$C(=NCN)$NR^{L4}$, $NR^{L3}$C(=NCN), $NR^{L3}$C(=$CNO_2$)$NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, O$C_{1-8}$alkyl, S$C_{1-8}$alkyl, NH$C_{1-8}$alkyl, N($C_{1-8}$alkyl)$_2$, $C_{3-11}$cycloalkyl, aryl, heteroaryl, $C_{3-11}$heterocyclyl, O$C_{1-8}$cycloalkyl, S$C_{1-8}$cycloalkyl, NH$C_{1-8}$cycloalkyl, N($C_{1-8}$cycloalkyl)$_2$, N($C_{1-8}$cycloalkyl)($C_{1-8}$alkyl), OH, $NH_2$, SH, $SO_2C_{1-8}$alkyl, P(O)(O$C_{1-8}$alkyl)($C_{1-8}$alkyl), P(O)(O$C_{1-8}$alkyl)$_2$, CC-$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl)$_2$, Si(OH)$_3$, Si($C_{1-8}$alkyl)$_3$, Si(OH)($C_{1-8}$alkyl)$_2$, CO$C_{1-8}$alkyl, $CO_2$H, halogen, CN, $CF_3$, $CHF_2$, $CH_2$F, $NO_2$, $SF_5$, $SO_2$NH$C_{1-8}$alkyl, $SO_2$N($C_{1-8}$alkyl)$_2$, SONH$C_{1-8}$alkyl, SON($C_{1-8}$alkyl)$_2$, CONH$C_{1-8}$alkyl, CON($C_{1-8}$alkyl)$_2$, N($C_{1-8}$alkyl)CONH($C_{1-8}$alkyl), N($C_{1-8}$alkyl)CON($C_{1-8}$alkyl)$_2$, NHCONH($C_{1-8}$alkyl), NHCON($C_{1-8}$alkyl)$_2$, NHCON$H_2$, N($C_{1-8}$alkyl)$SO_2$NH($C_{1-8}$alkyl), N($C_{1-8}$alkyl) $SO_2$N($C_{1-8}$alkyl)$_2$, NH $SO_2$NH($C_{1-8}$alkyl), NH $SO_2$N($C_{1-8}$alkyl)$_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and $A^L_1$ and $(A^L)_q$ are connected via structural units of the linker (L).

In certain embodiments, e.g., where q of the linker is 2, $(A^L)_q$ is a group which is connected to $A^L_1$ and to a ULM.

In certain embodiments, e.g., where q of the linker is 1, the structure of the linker group L is -$A^L_1$-, and $A^L_1$ is a group which is connected to a ULM moiety and a PTM moiety.

In certain embodiments, the linker (L) comprises a group represented by a general structure selected from the group consisting of:

—NR($CH_2$)$_n$-(lower alkyl)-, —NR($CH_2$)$_n$-(lower alkoxyl)-, —NR($CH_2$)$_n$-(lower alkoxyl)-O$CH_2$—, —NR($CH_2$)$_n$-(lower alkoxyl)-(lower alkyl)-O$CH_2$—, —NR($CH_2$)$_n$-(cycloalkyl)-(lower alkyl)-O$CH_2$-, —NR($CH_2$)$_n$-(hetero cycloalkyl)-, —NR($CH_2CH_2$O)$_n$-(lower alkyl)-O—$CH_2$—, NR($CH_2CH_2$O)$_n$-(hetero cycloalkyl)-O—$CH_2$—, —NR($CH_2CH_2$O)$_n$-Aryl-O—$CH_2$—, —NR($CH_2CH_2$O)$_n$-(hetero aryl)-O—$CH_2$—, —NR($CH_2CH_2$O)$_n$-(cyclo alkyl)-O-(hetero aryl)-O—$CH_2$—, —NR($CH_2CH_2$O)$_n$-(cyclo alkyl)-O-Aryl-O—$CH_2$—, —NR($CH_2CH_2$O)$_n$-(lower alkyl)-NH-Aryl-O—$CH_2$—, NR($CH_2CH_2$O)$_n$-(lower alkyl)-O-Aryl-$CH_2$, —NR($CH_2CH_2$O)$_n$-cycloalkyl-O-Aryl-, NR($CH_2CH_2$O)$_n$-cycloalkyl-O-(hetero aryl)l-, —NR($CH_2CH_2$)$_n$-(cycloalkyl)-O-(heterocycle)-$CH_2$, —NR($CH_2CH_2$)$_n$-(heterocycle)-(heterocycle)-$CH_2$, —N(R1R2)-(heterocycle)-$CH_2$; where n of the linker can be 0 to 10;

R of the linker can be H, lower alkyl;

$R^1$ and $R^2$ of the linker can form a ring with the connecting N.

In certain embodiments, the linker (L) comprises a group represented by a general structure selected from the group consisting of:

—N(R)—(CH2)$_m$—O(CH2)$_n$—O(CH2)$_o$—O(CH2)$_p$—O(CH2)$_q$—O(CH2)$_r$—OCH2—,

—O—(CH2)$_m$—O(CH2)$_n$—O(CH2)$_o$—O(CH2)$_p$—O(CH2)$_q$—O(CH2)$_r$—OCH2—,

—O—(CH2)$_m$—O(CH2)$_n$—O(CH2)$_o$—O(CH2)$_p$—O(CH2)$_q$—O(CH2)$_r$—O—,

—N(R)—(CH2)$_m$—O(CH2)$_n$—O(CH2)$_o$—O(CH2)$_p$—O(CH2)$_q$—O(CH2)$_r$—O—,

—(CH2)$_m$—O(CH2)$_n$—O(CH2)$_o$—O(CH2)$_p$—O(CH2)$_q$—O(CH2)$_r$—O—,

—(CH2)$_m$—O(CH2)$_n$—O(CH2)$_o$—O(CH2)$_p$—O(CH2)$_q$—O(CH2)$_r$—OCH2—;

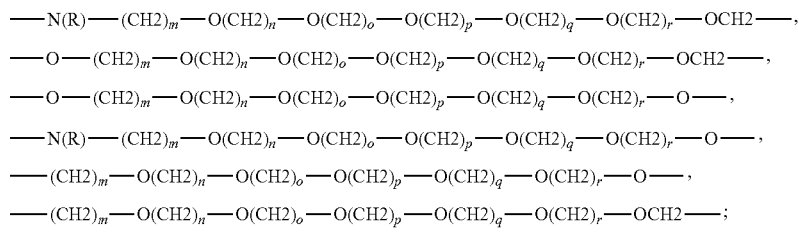

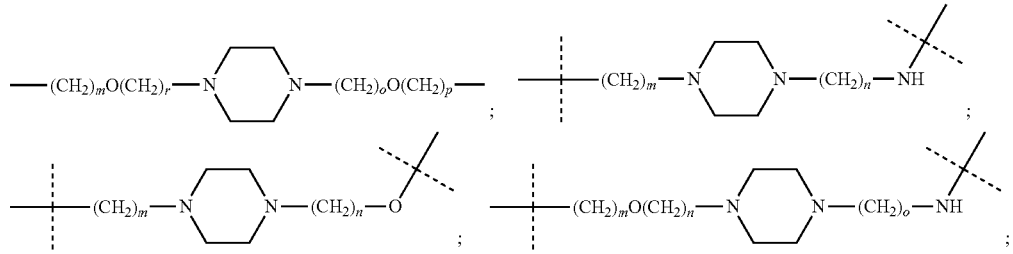

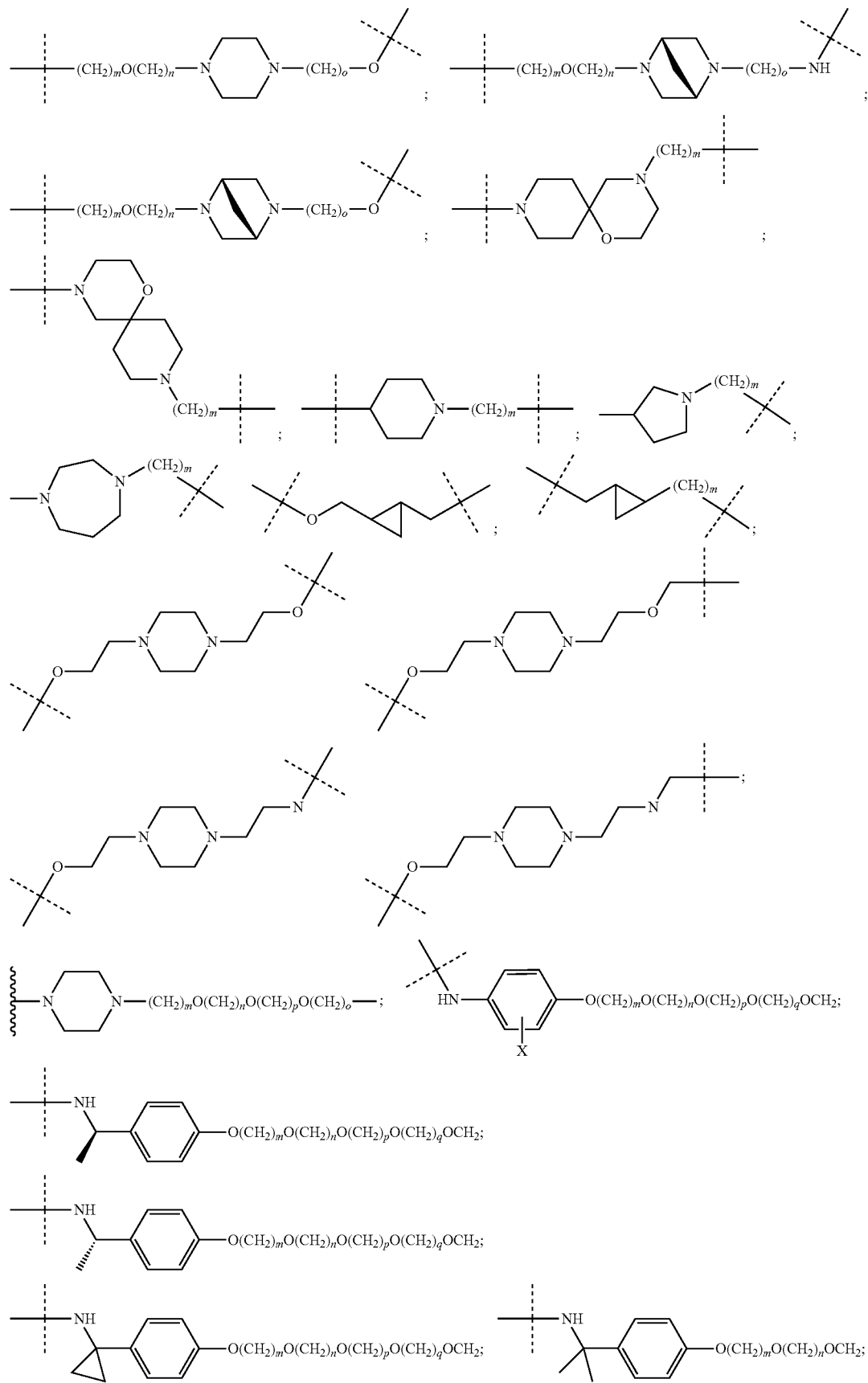

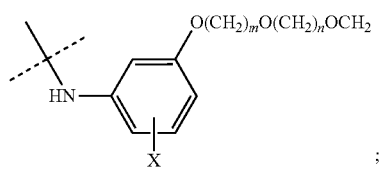 ; and 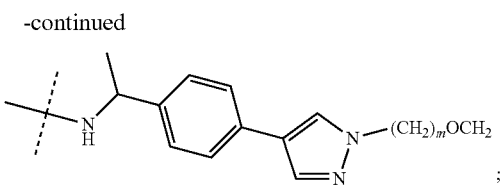 ;
wherein
m, n, o, p, q, and r of the linker are independently 0, 1, 2, 3, 4, 5, 6, 7, 8, 9, 10, 11, 12, 13, 14, 15, 16, 17, 18, 19, 20;
when the number is zero, there is no N—O or O—O bond
R of the linker is H, methyl and ethyl;
X of the linker is H and F
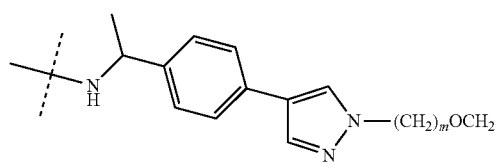
where m of the linker can be 2, 3, 4, 5
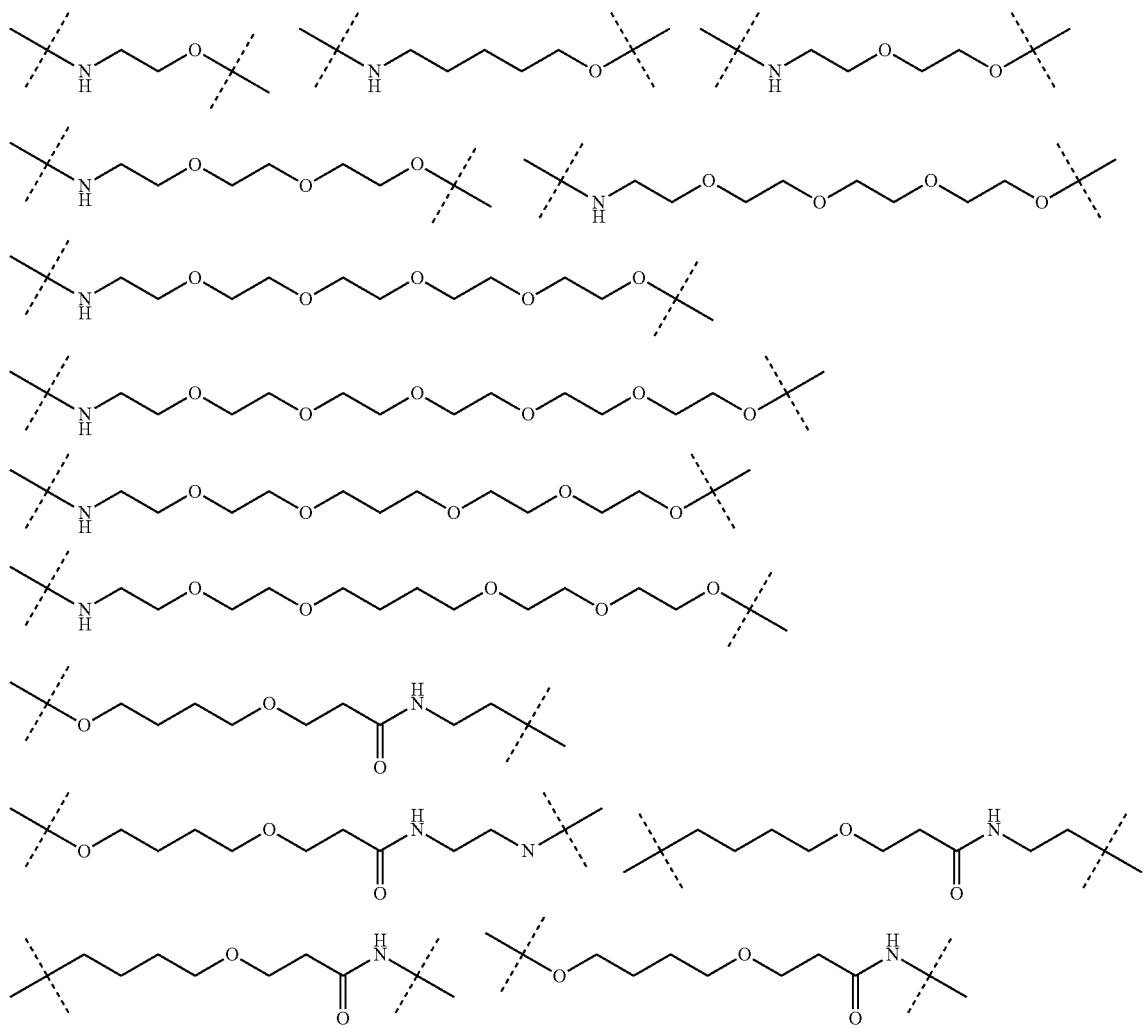

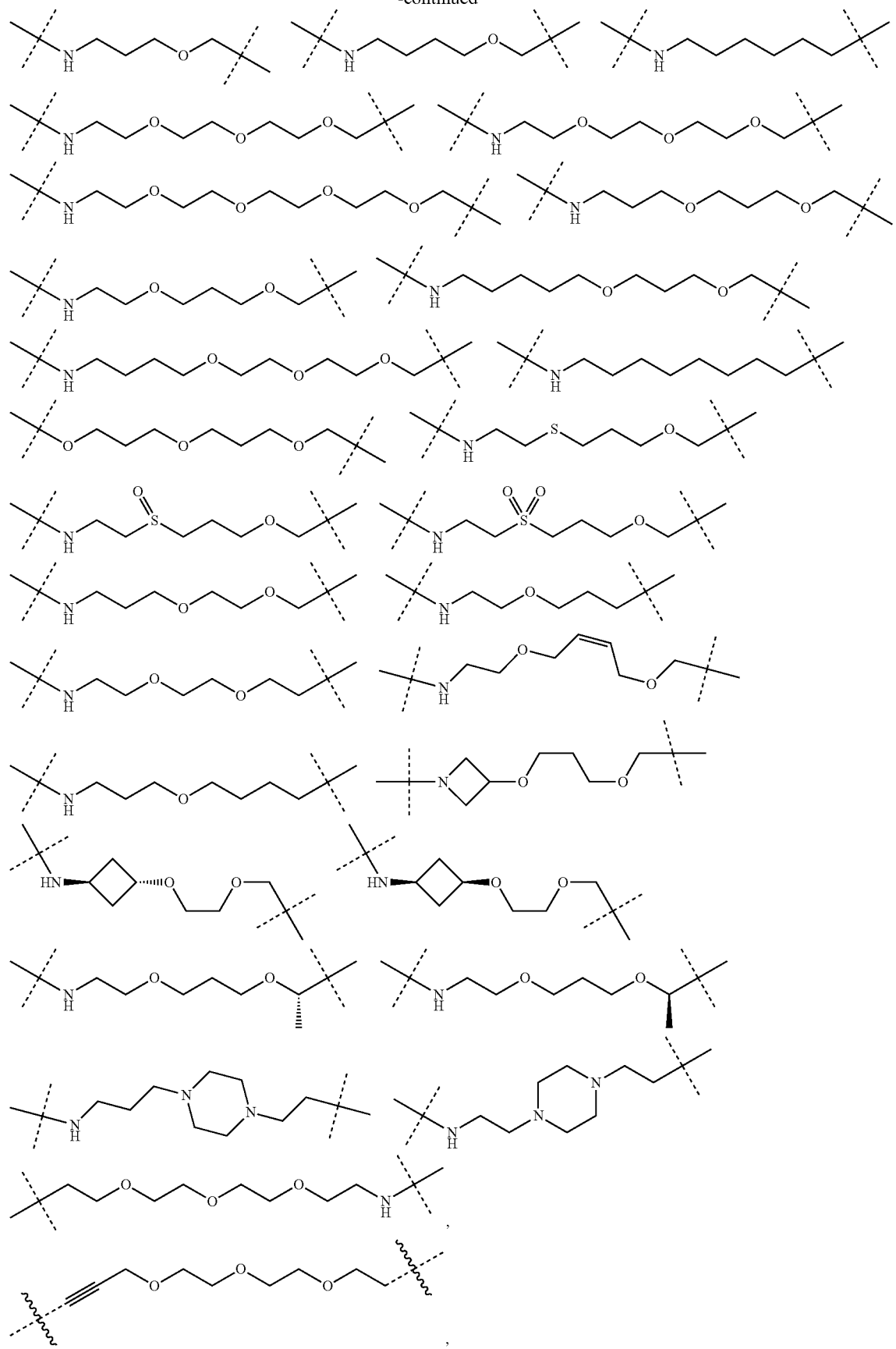

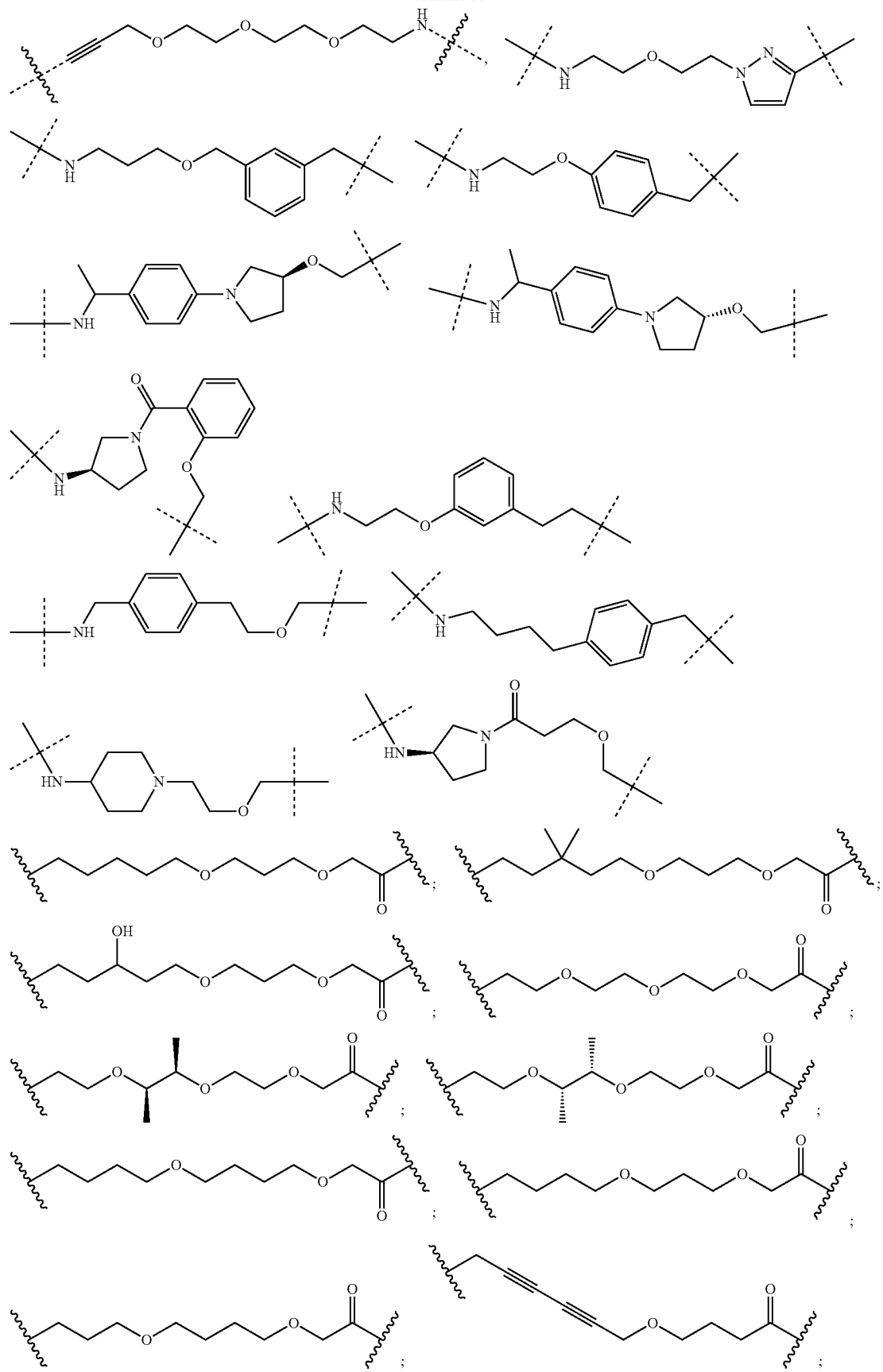
-continued

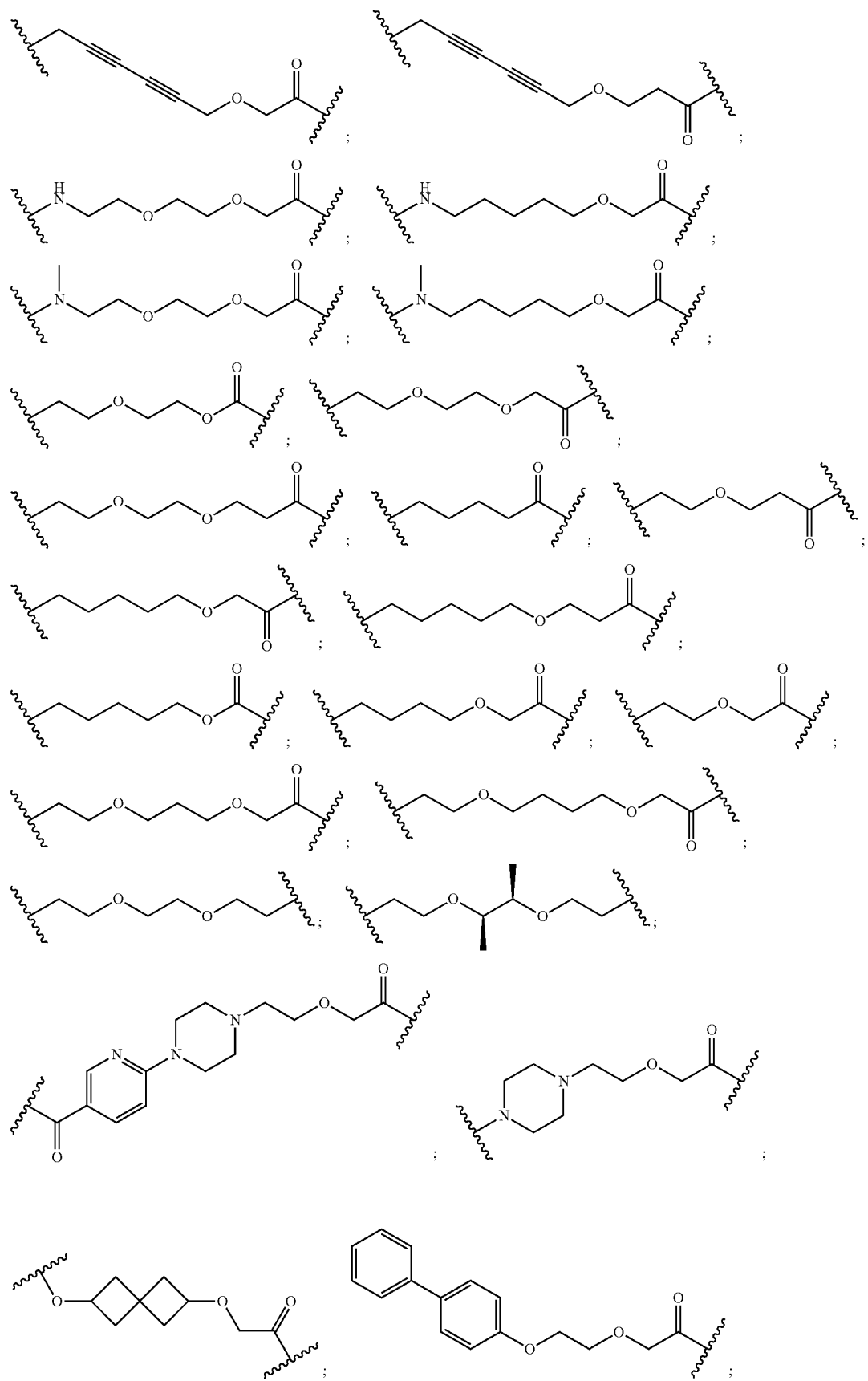

295
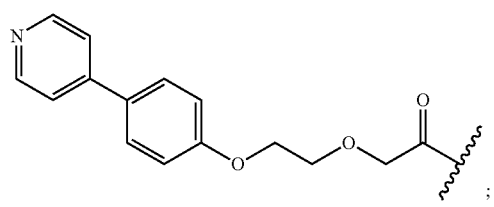
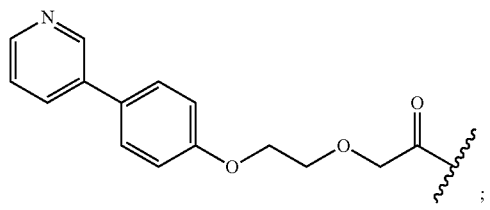
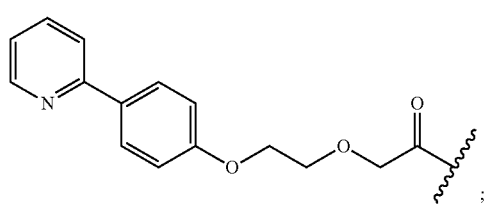
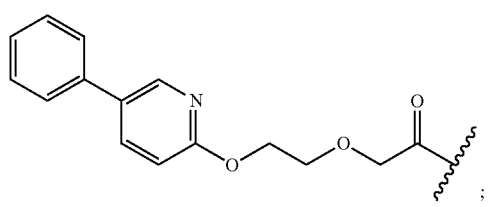
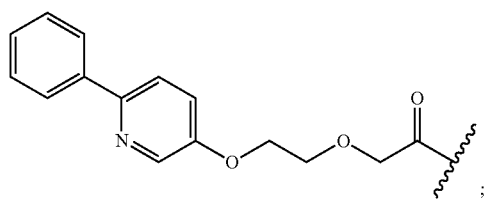
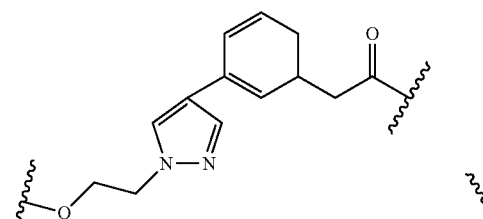
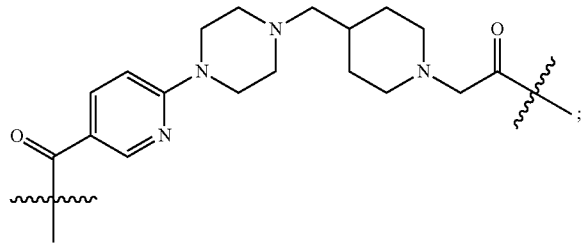
296
-continued
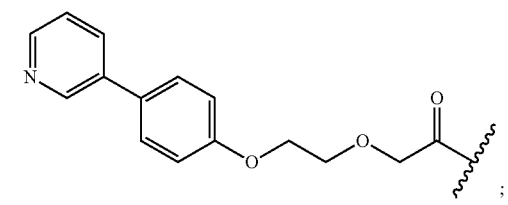
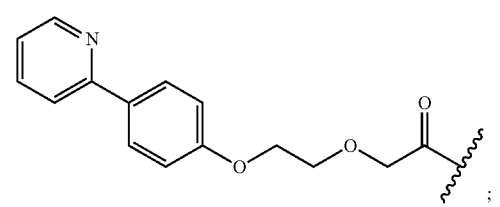
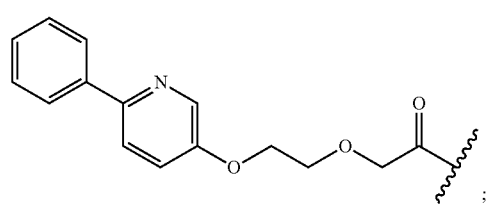
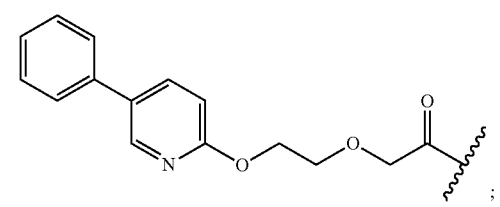
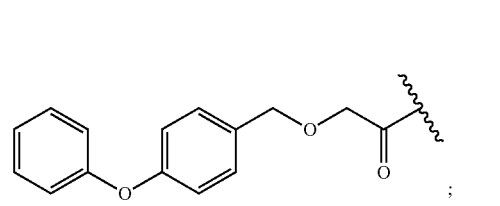
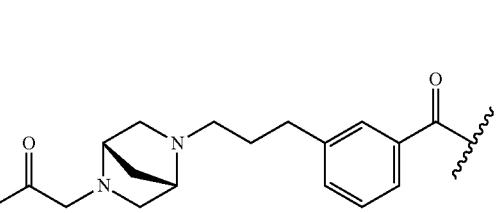

-continued
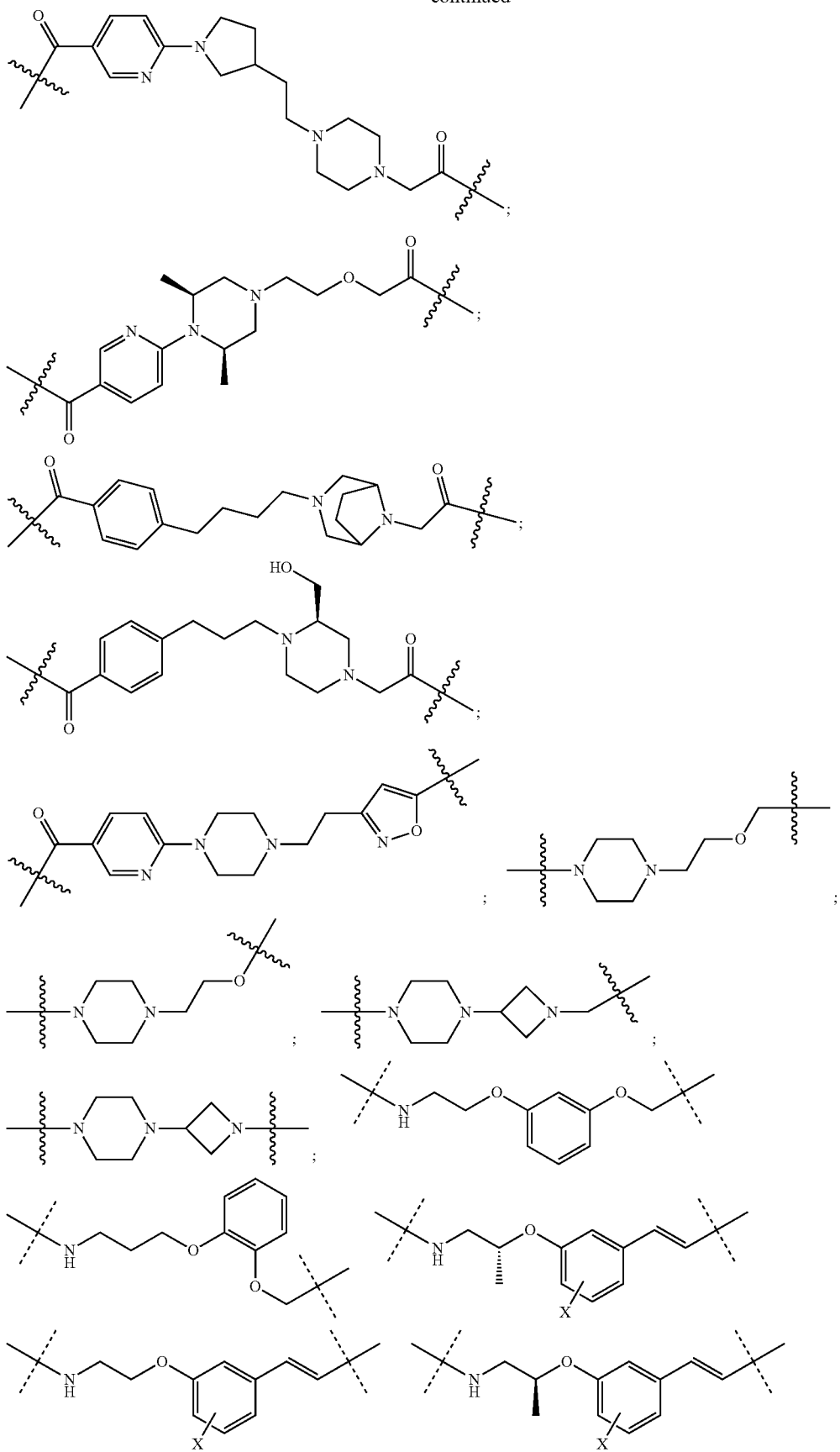

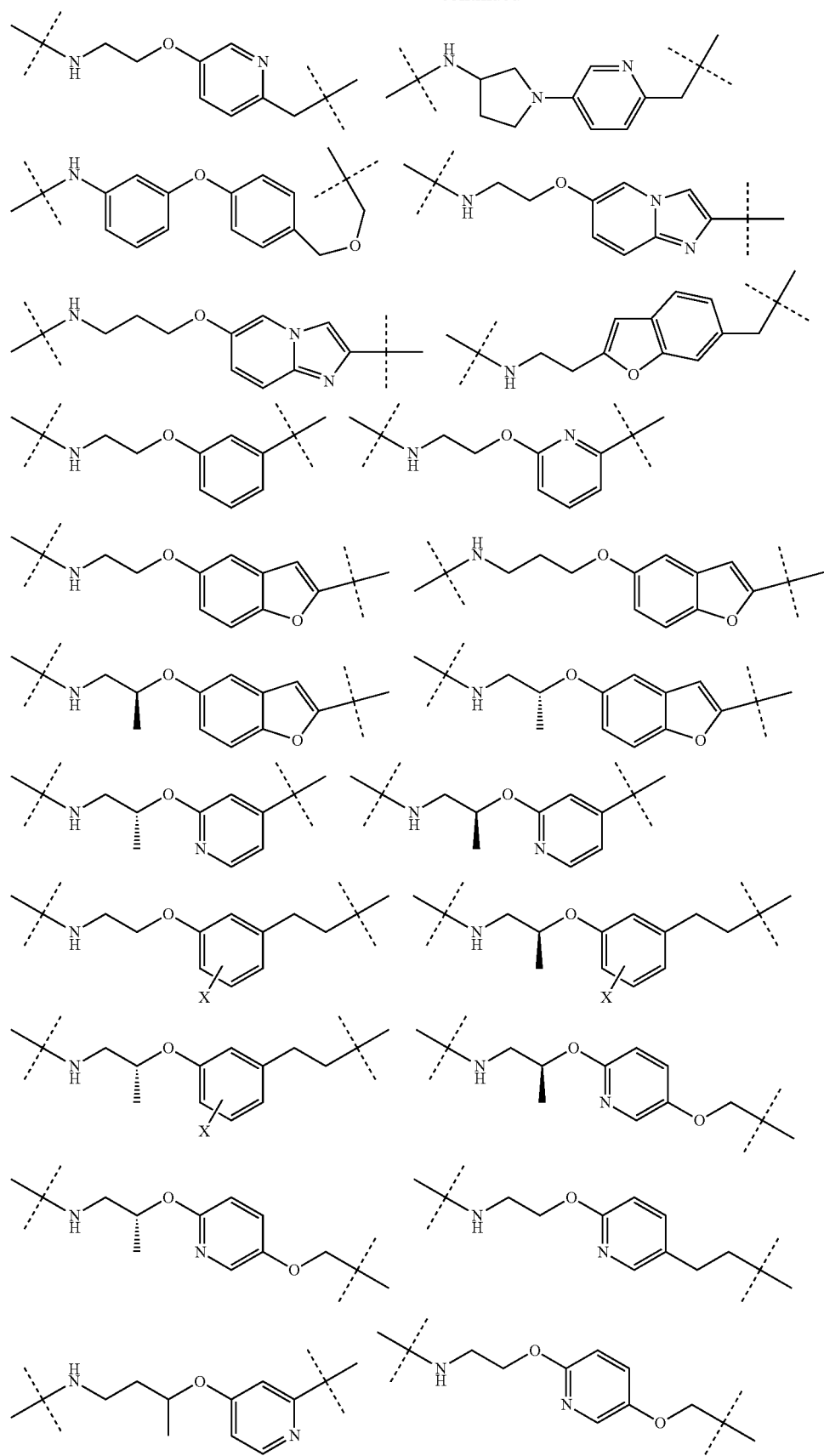

-continued
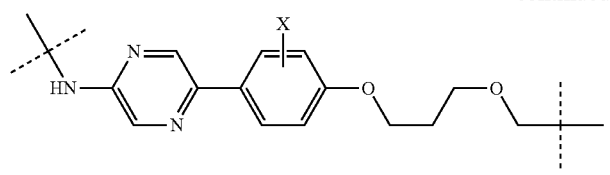
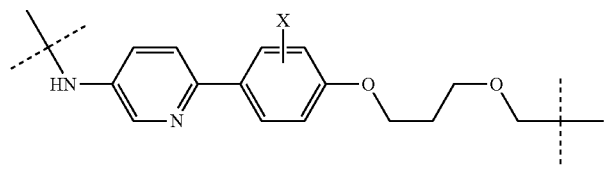
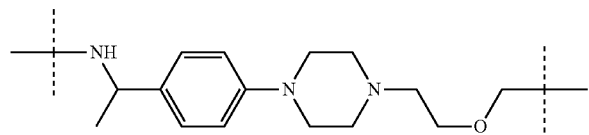
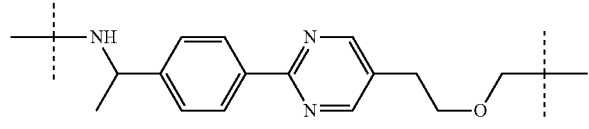
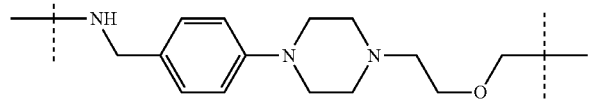
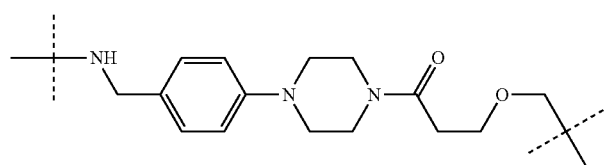
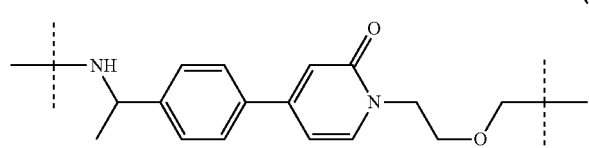
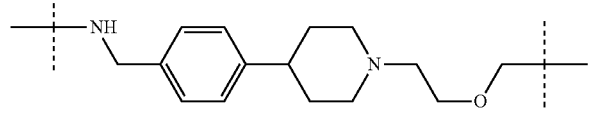
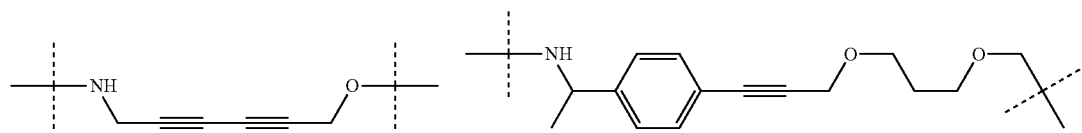
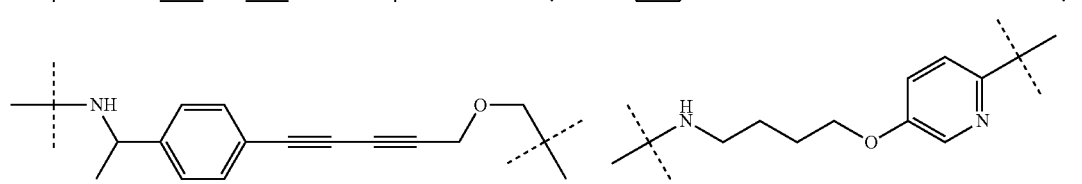
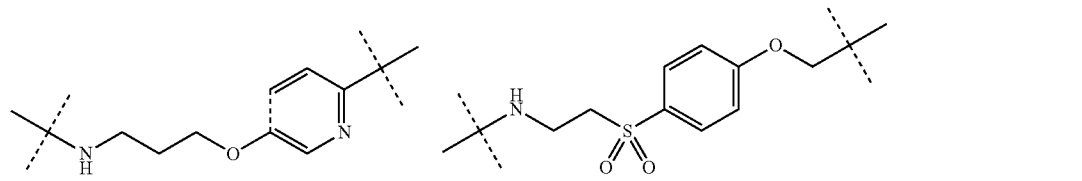

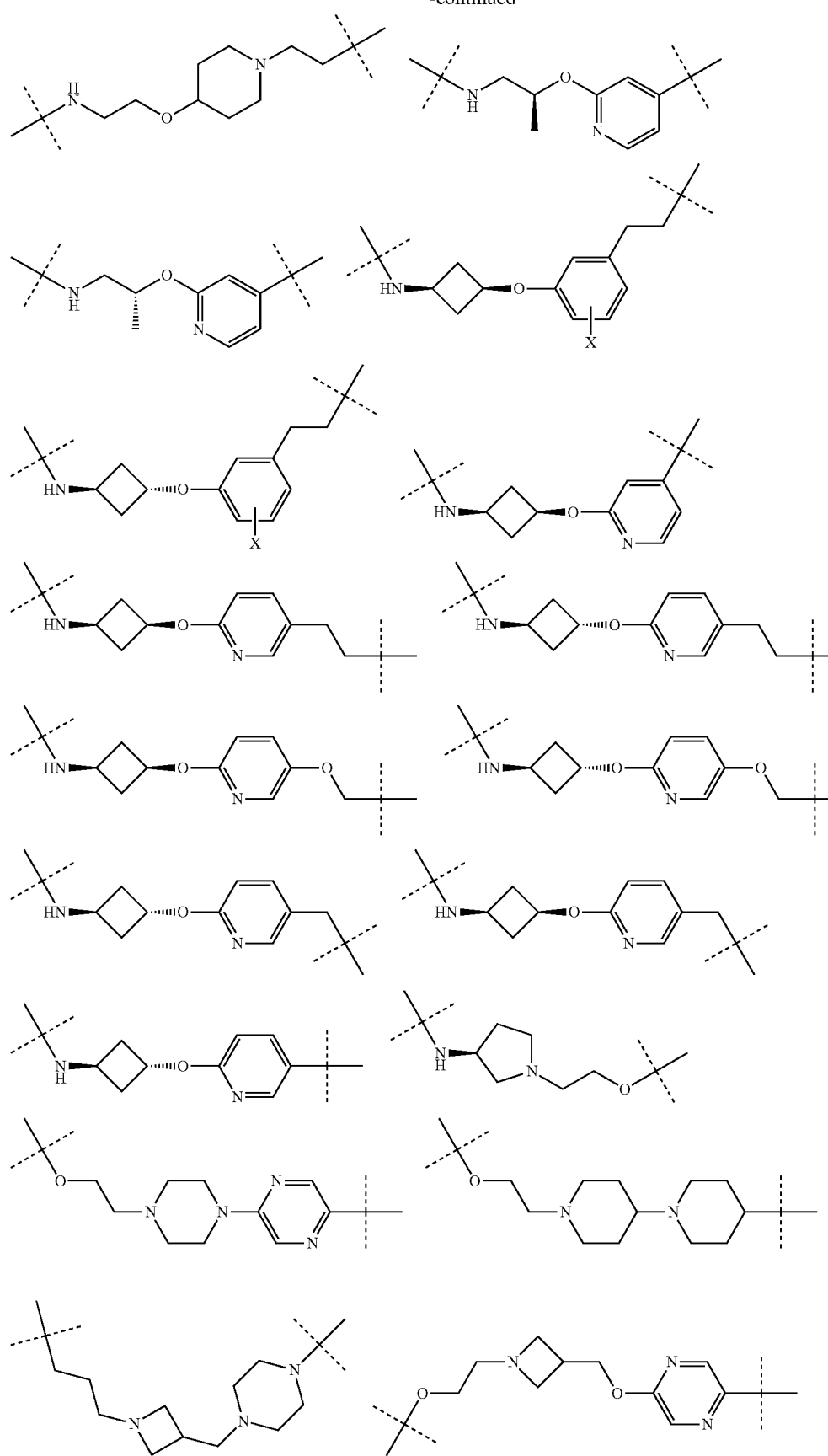

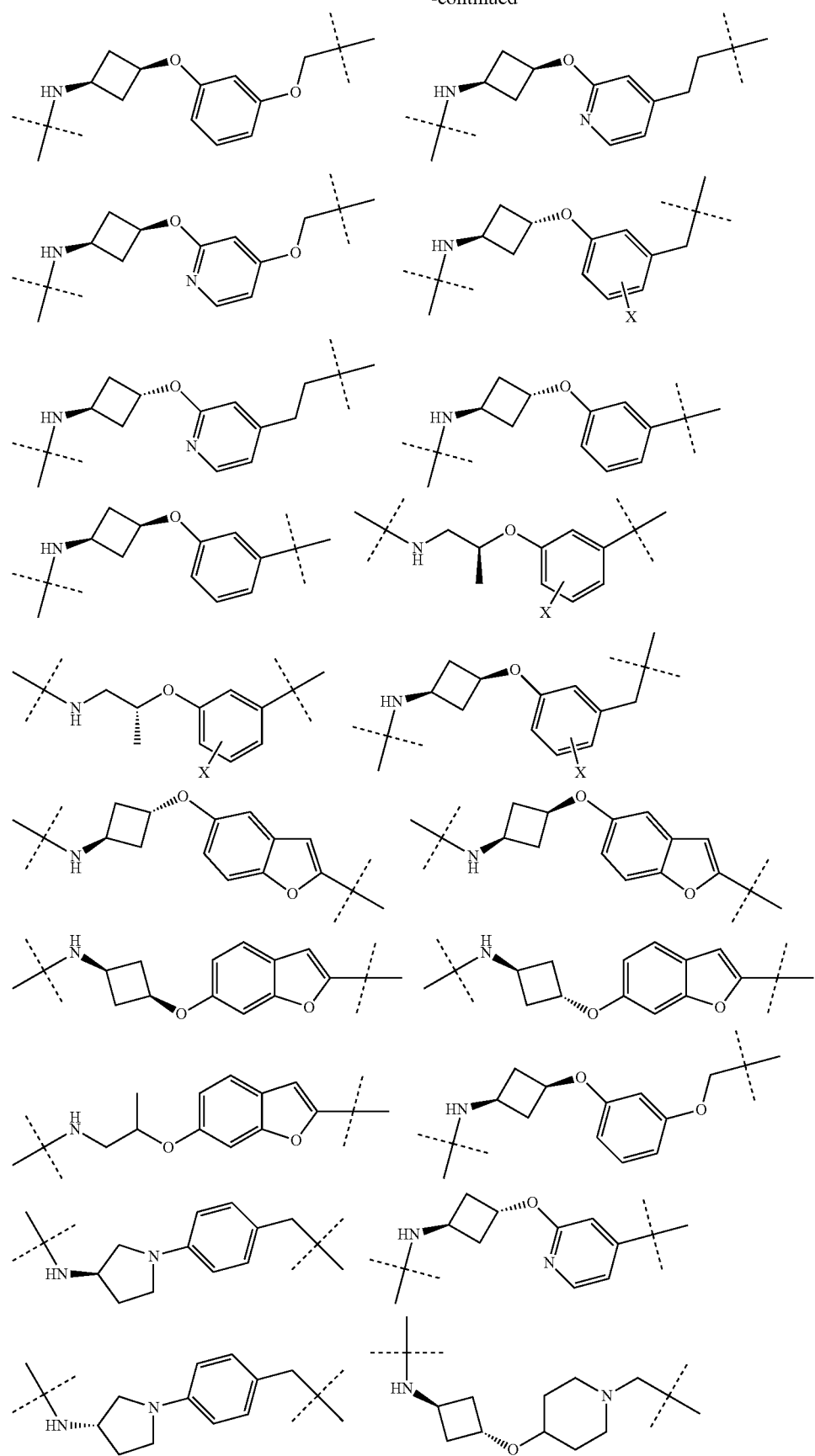

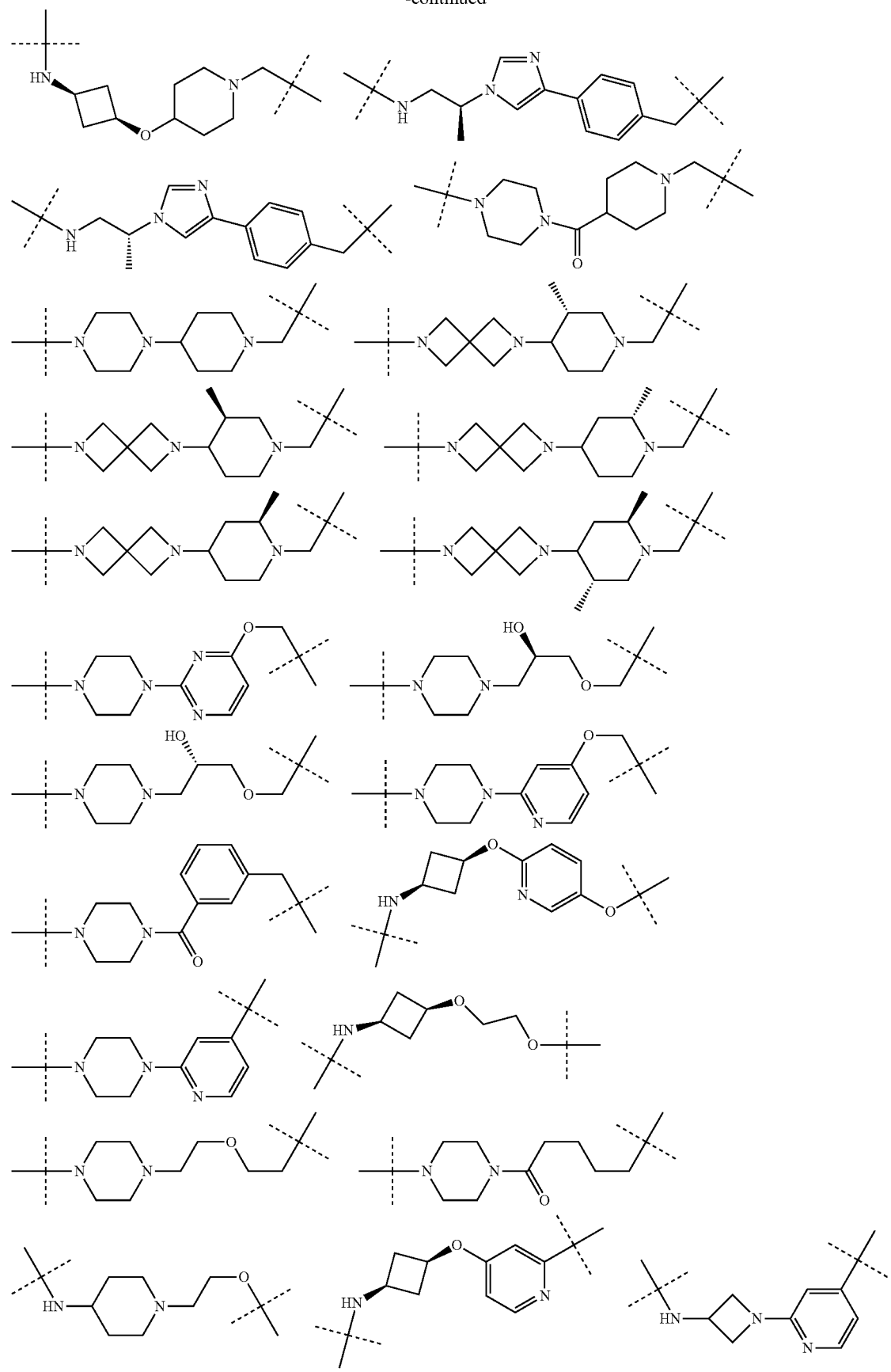

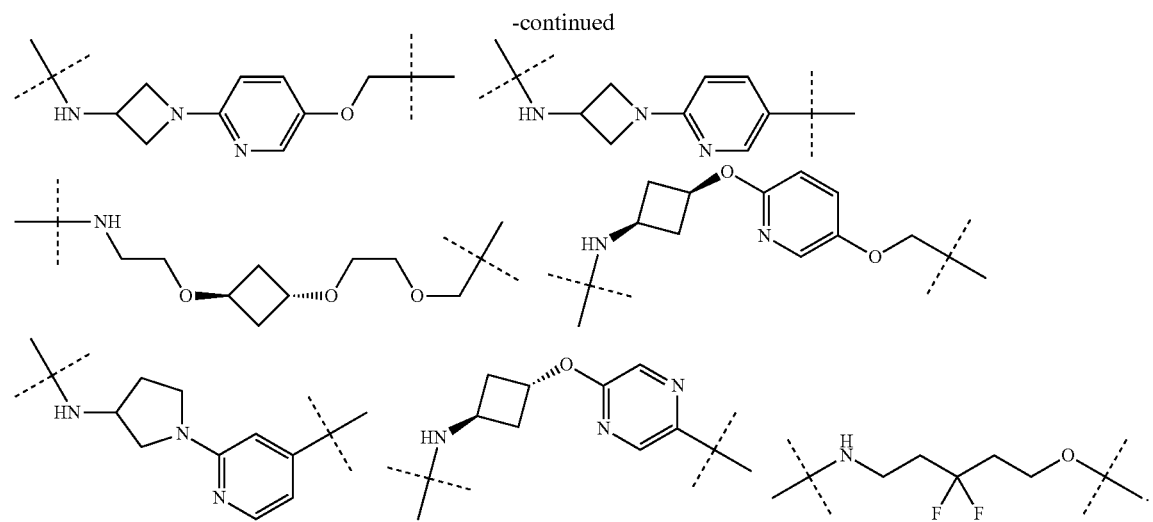
X = H, F
In any aspect or embodiment described herein, the linker (L) is selected from the group consisting of:
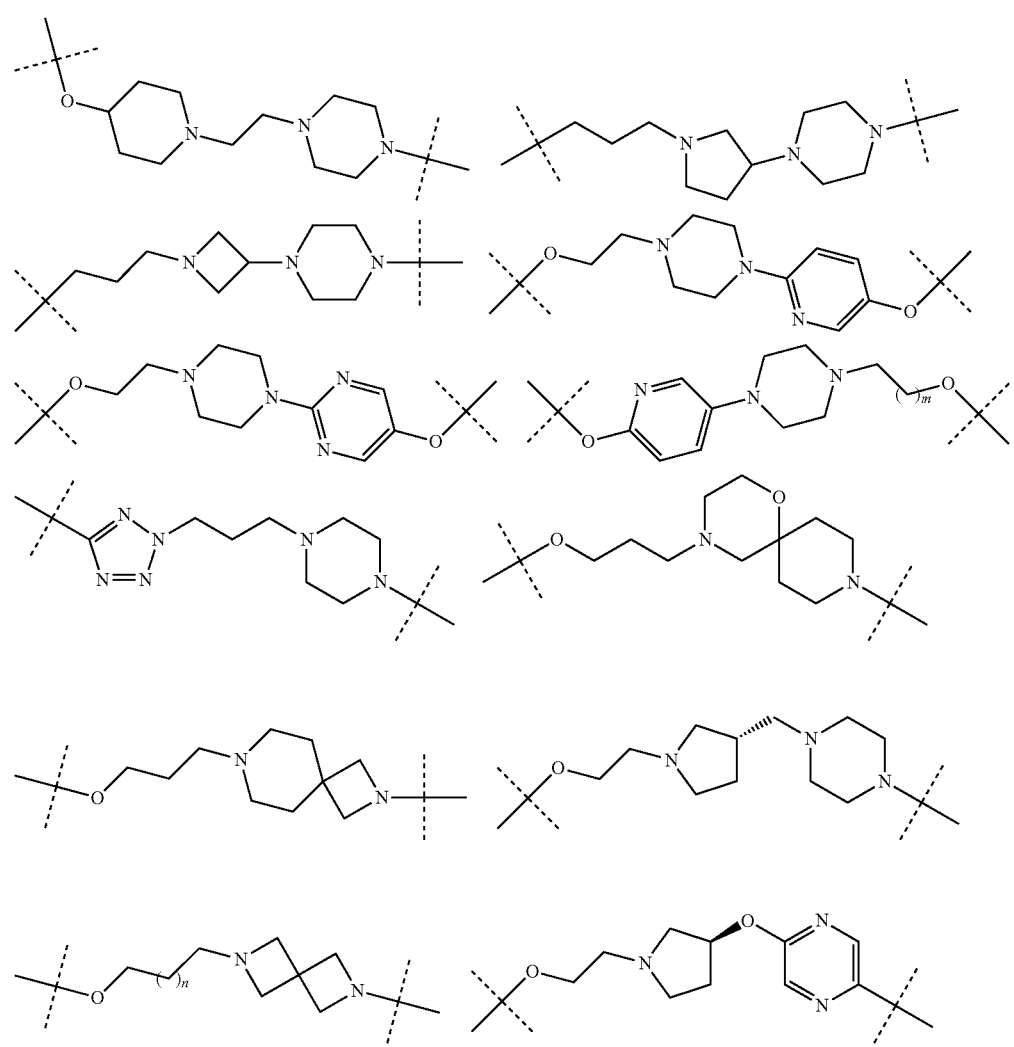

-continued
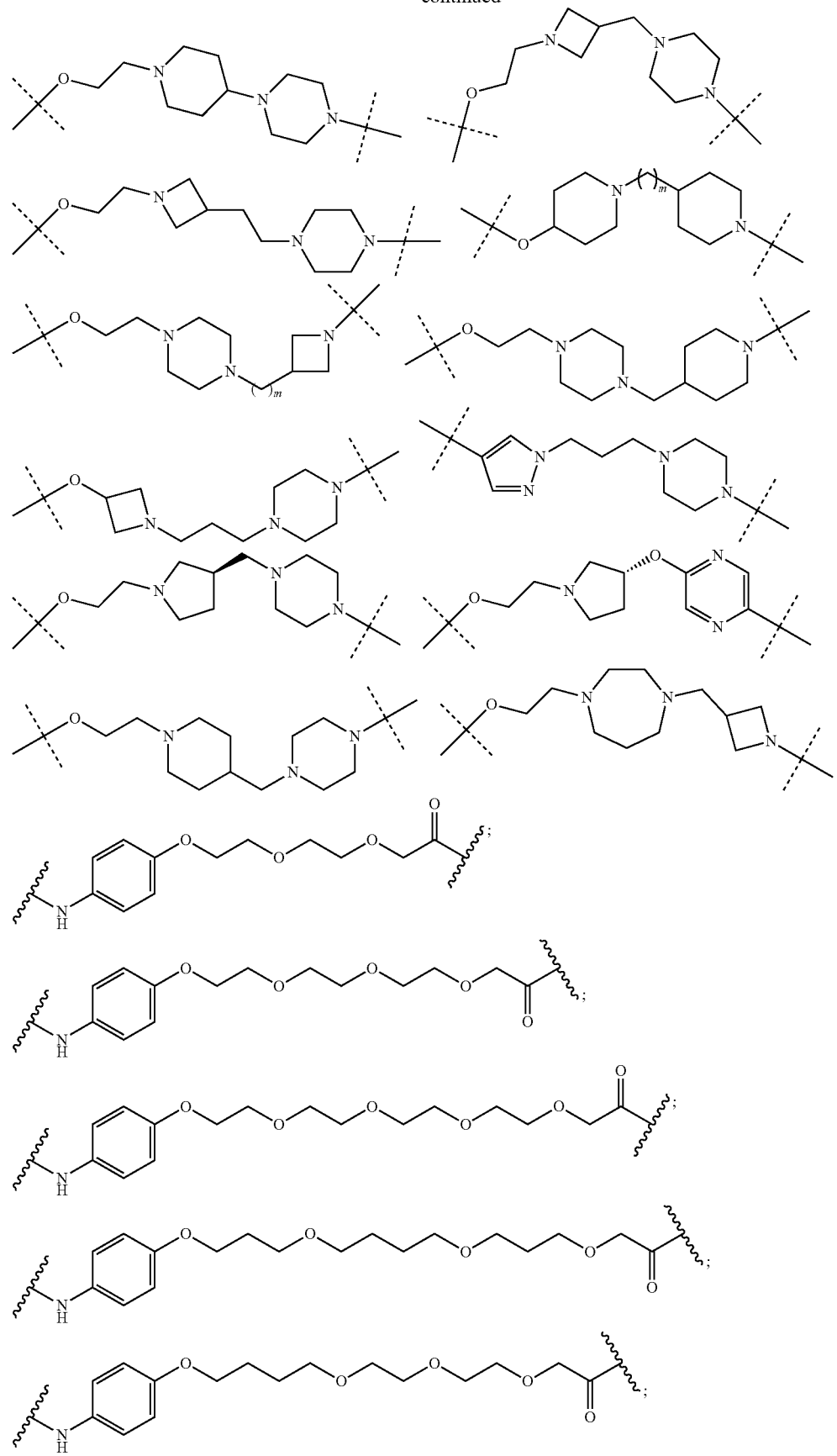

-continued
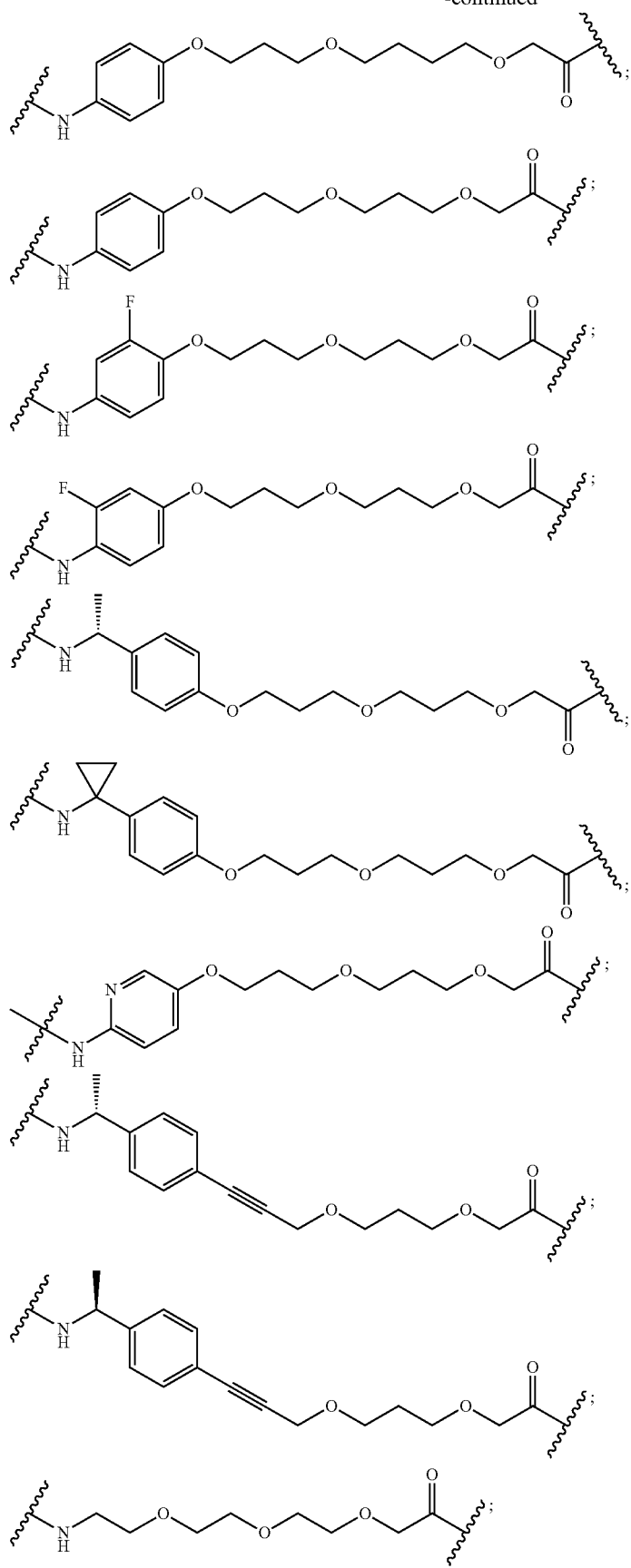

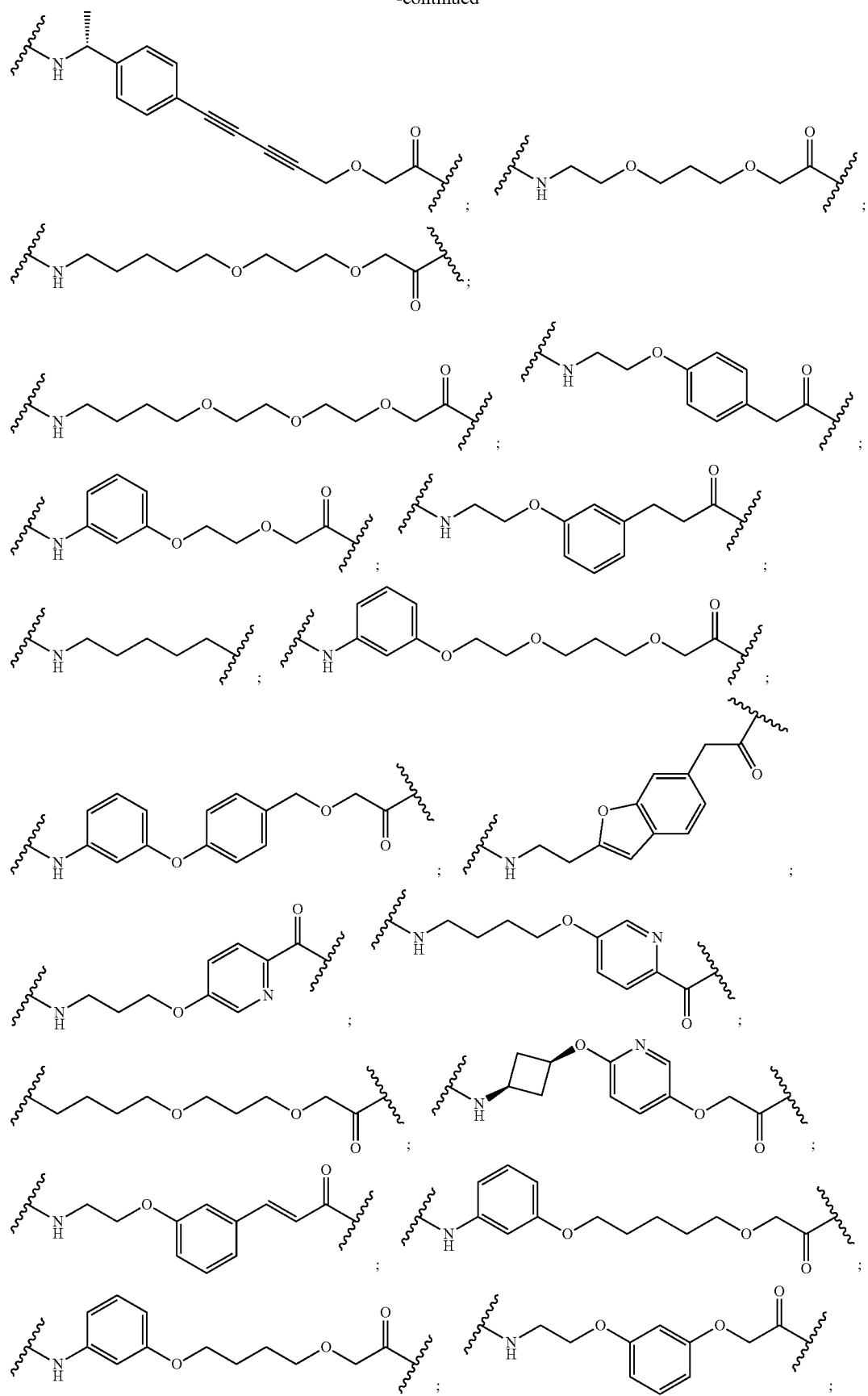

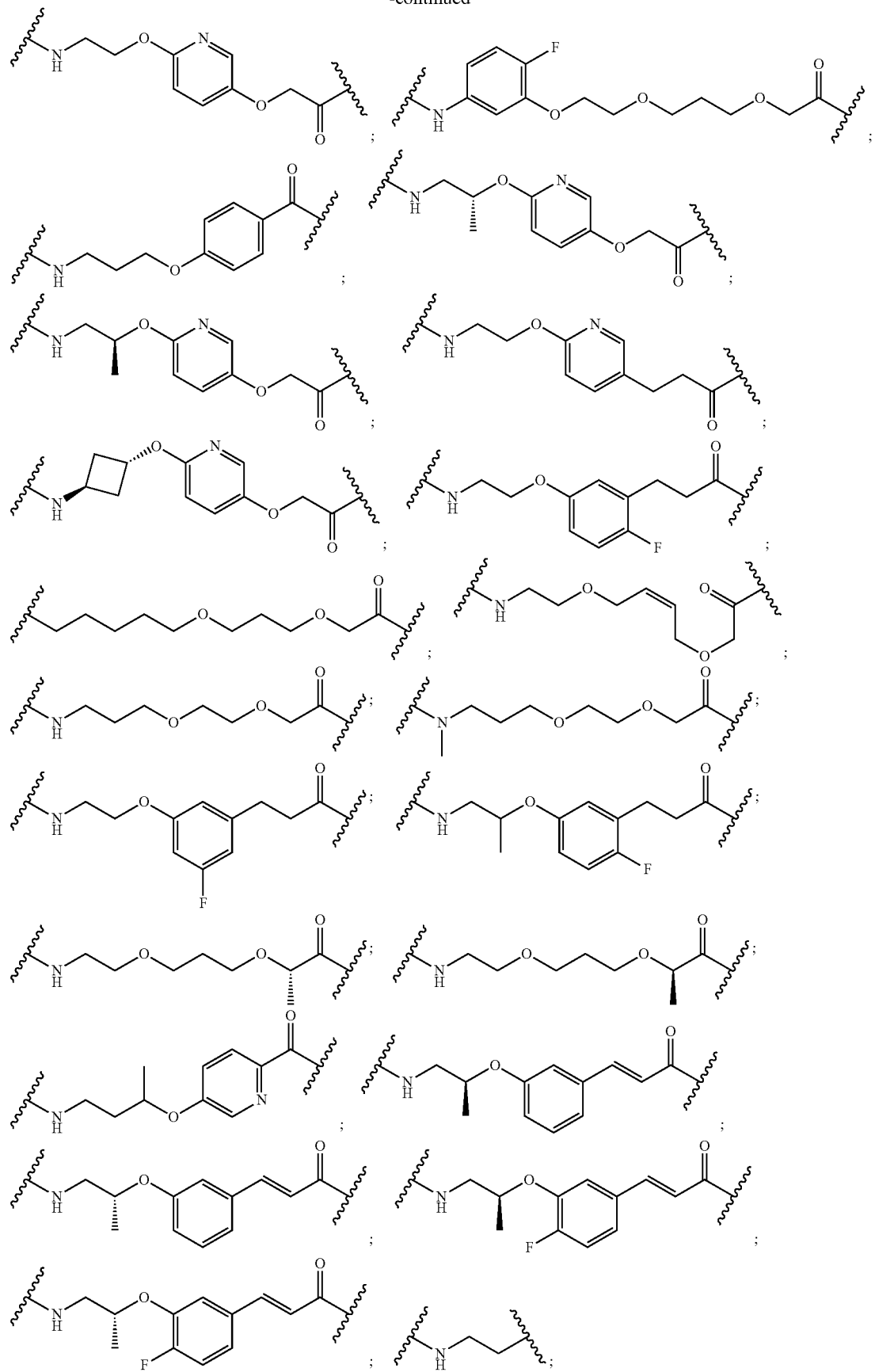

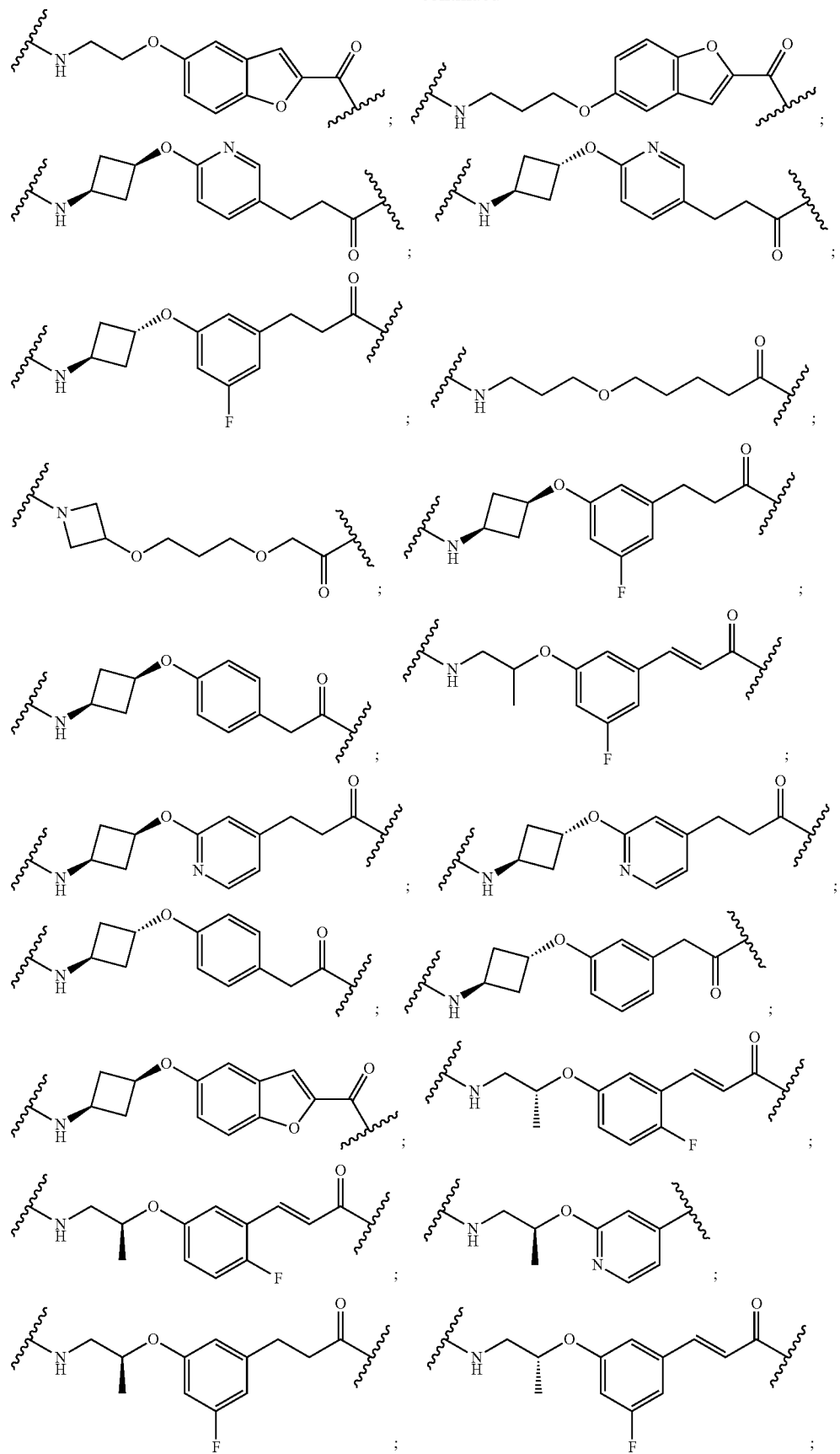

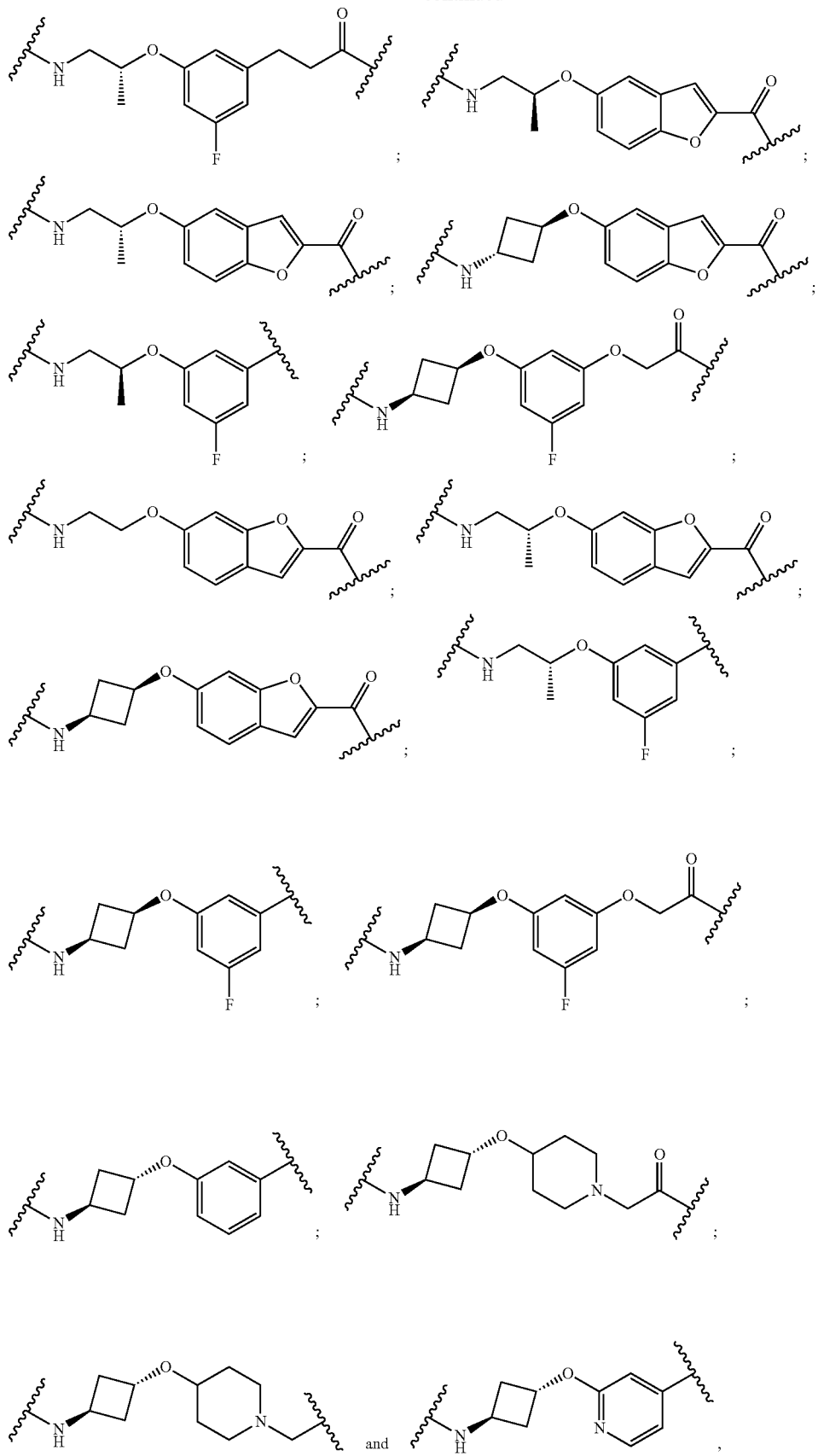

wherein each m and n is independently selected from 0, 1, 2, 3, 4, 5, or 6.
In any aspect or embodiment described herein, the linker (L) is selected from the group consisting of:
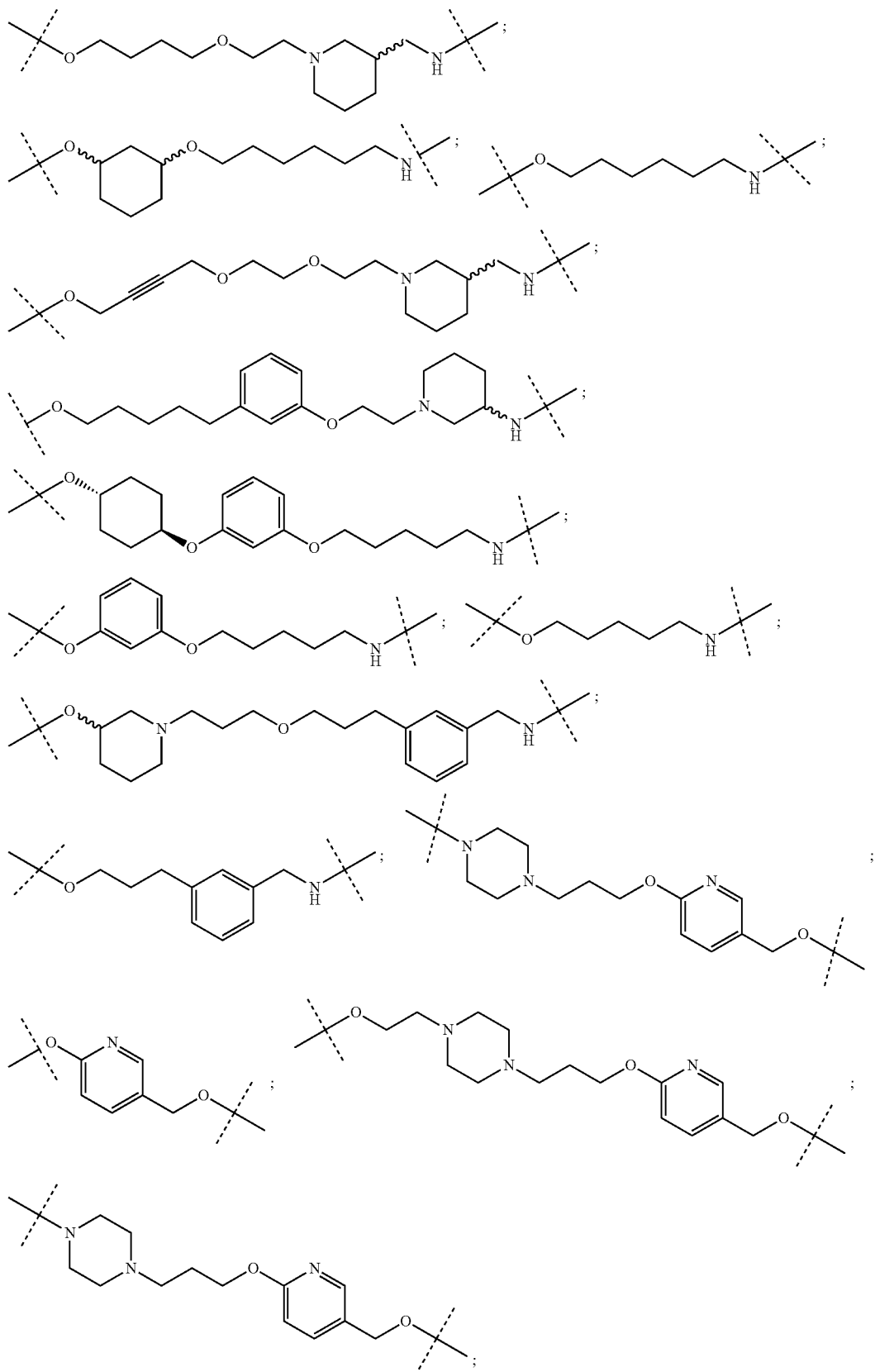

-continued
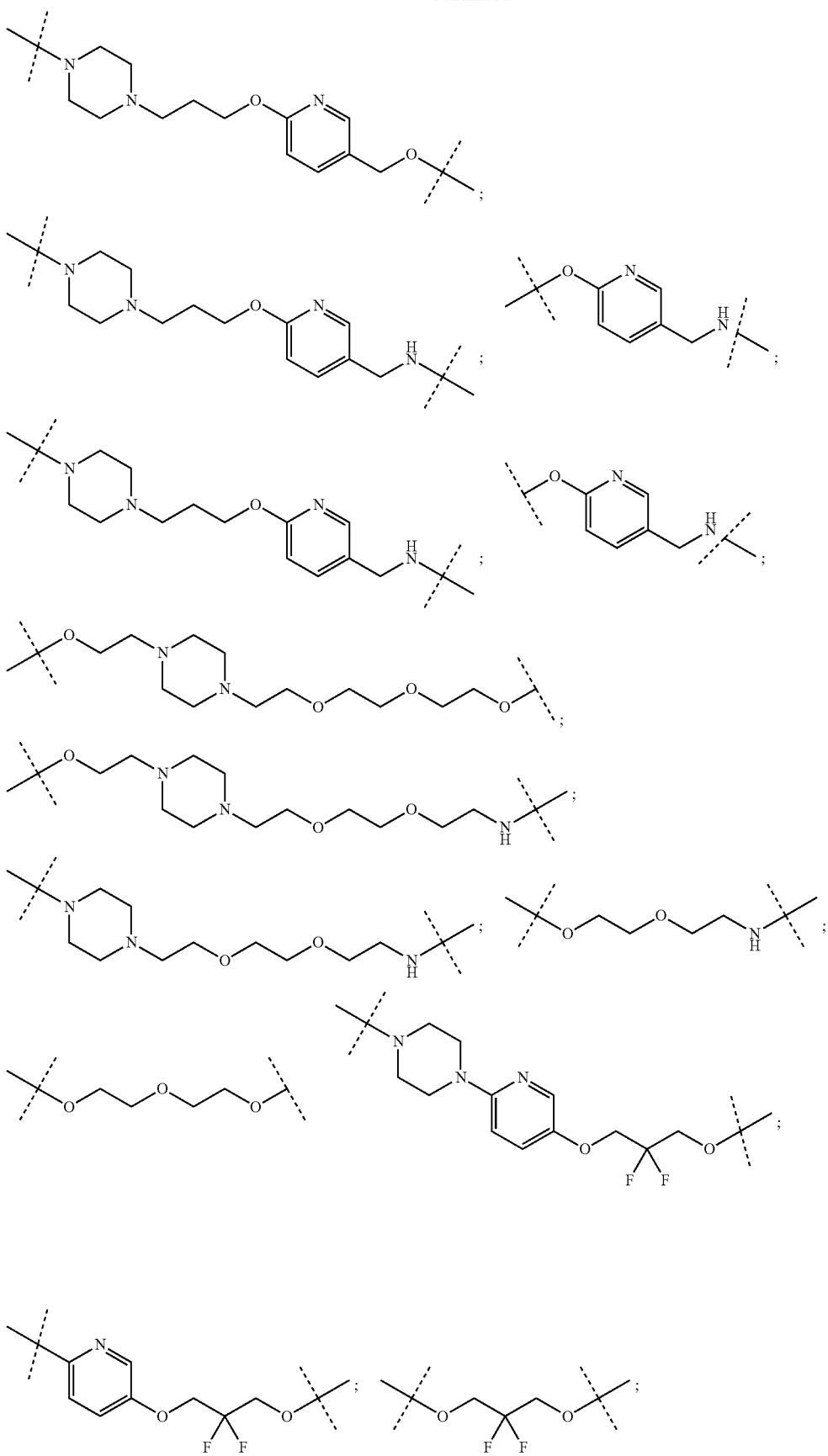

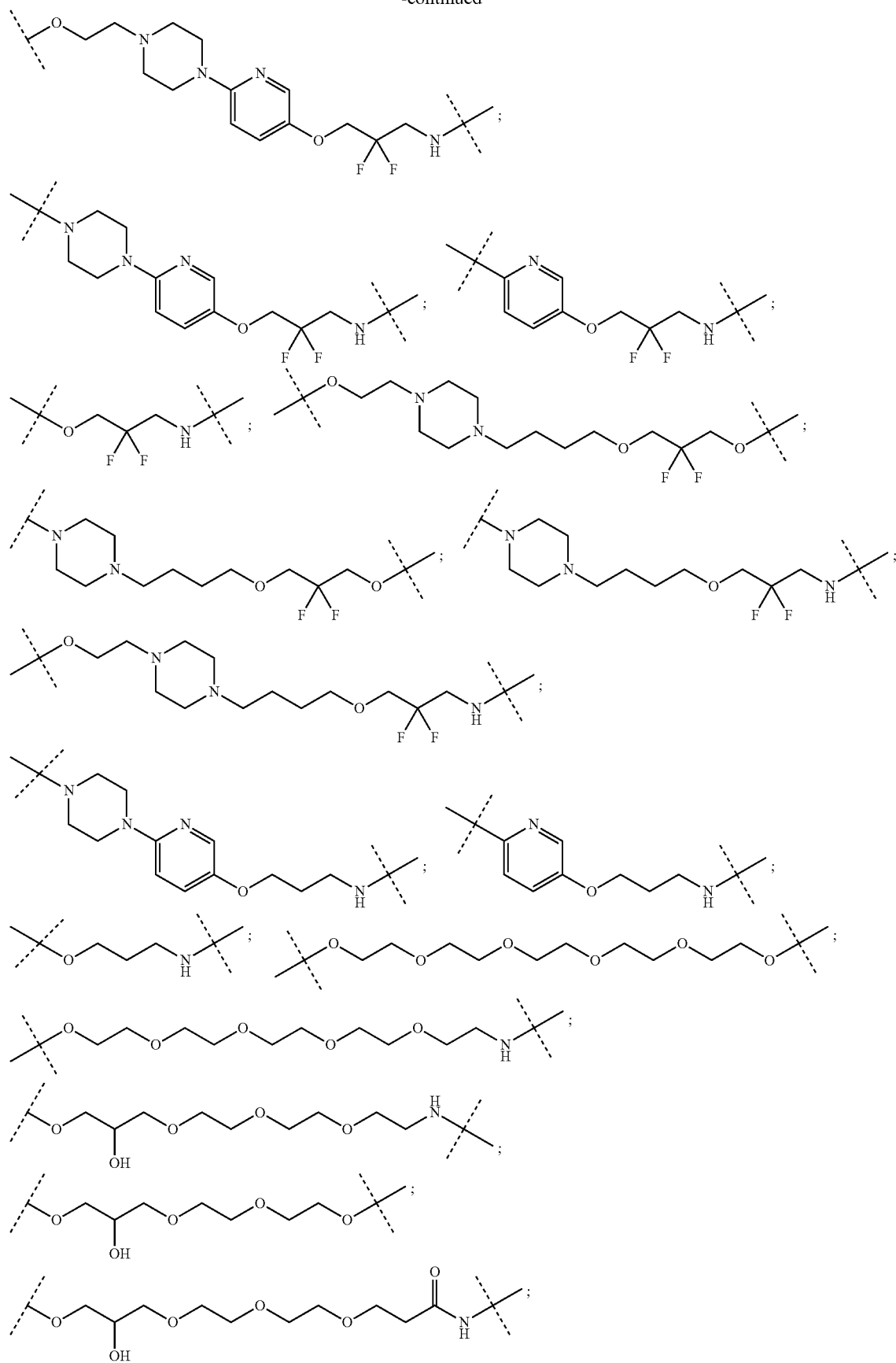

-continued
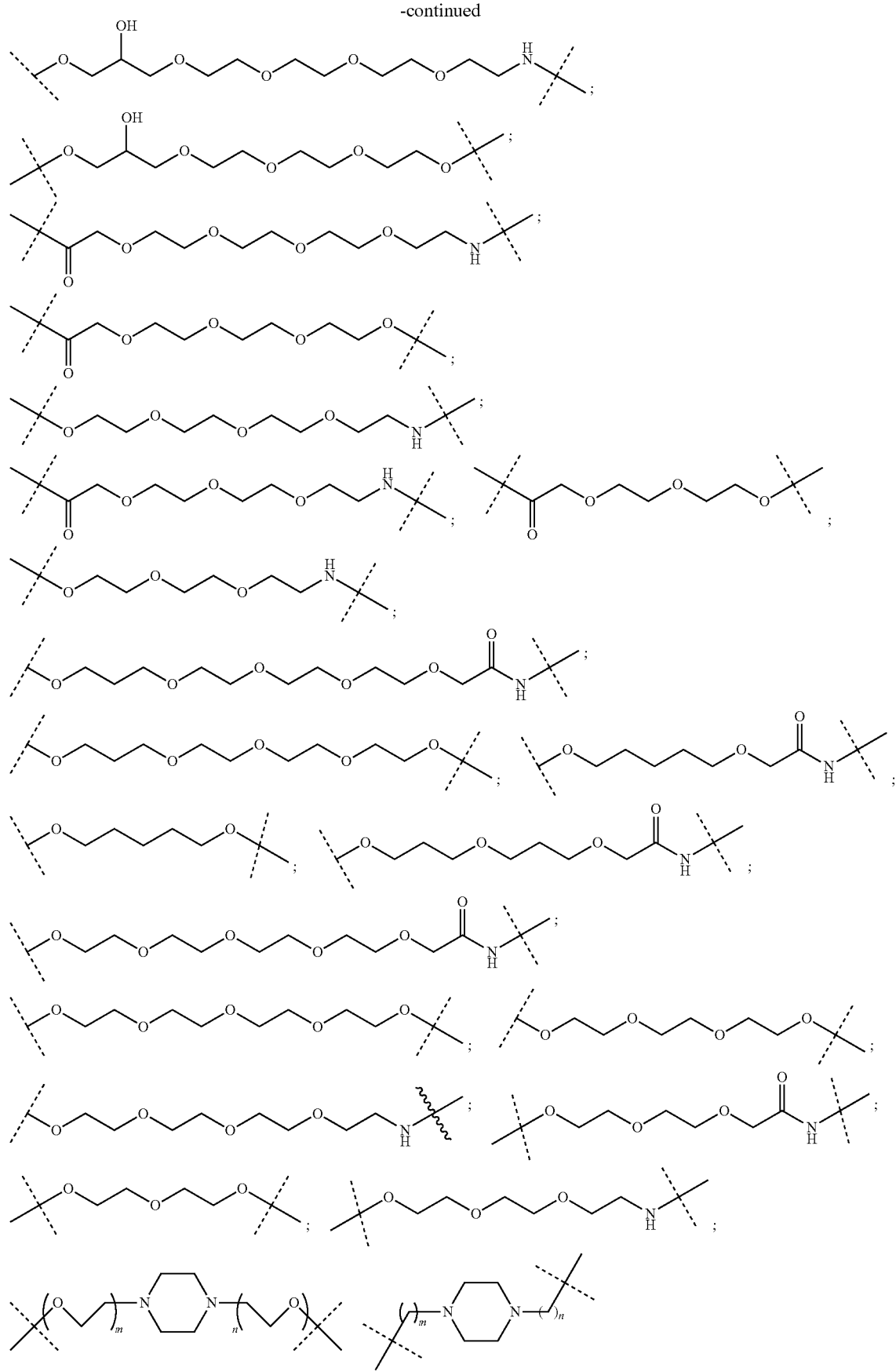

-continued
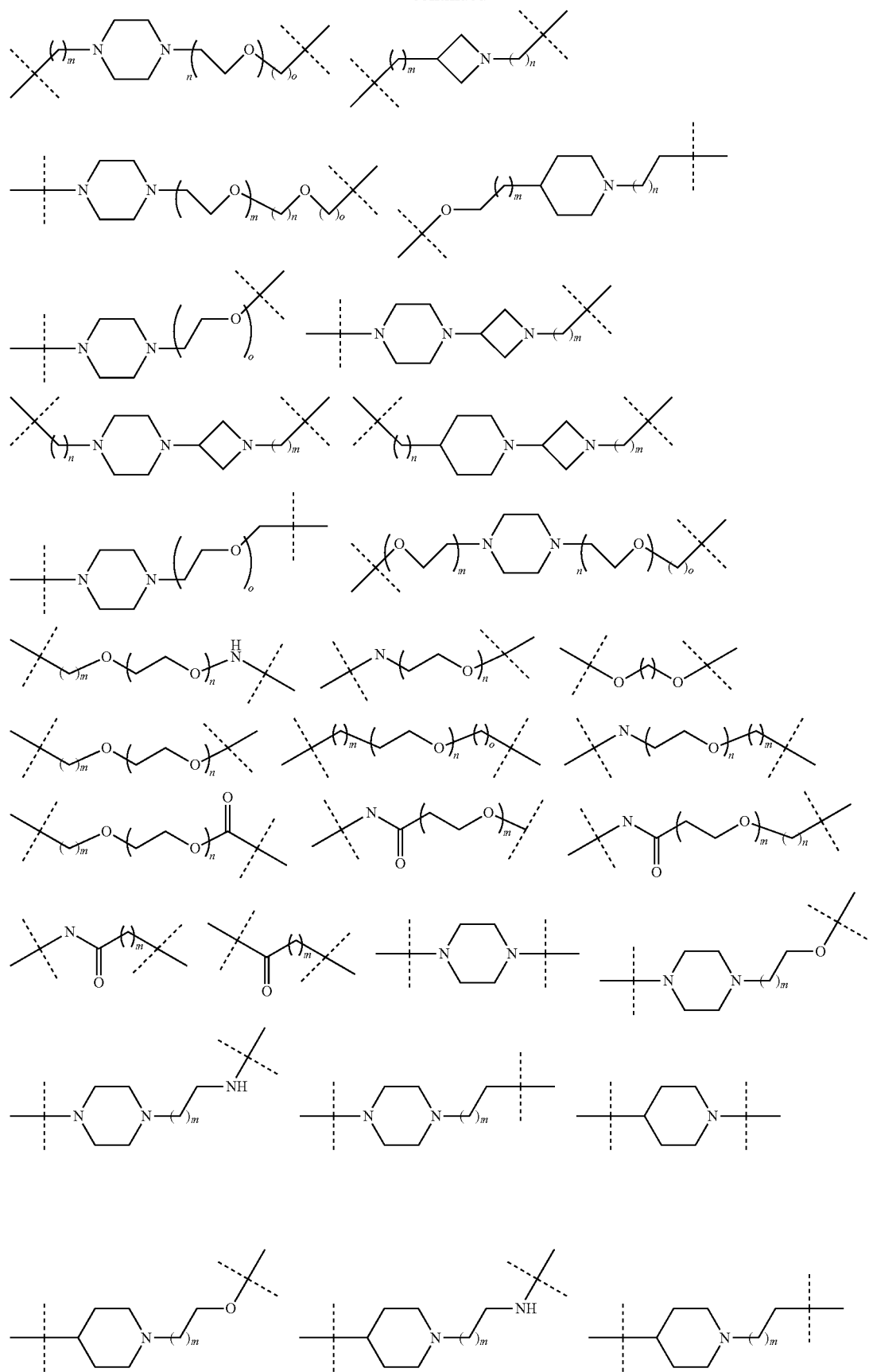

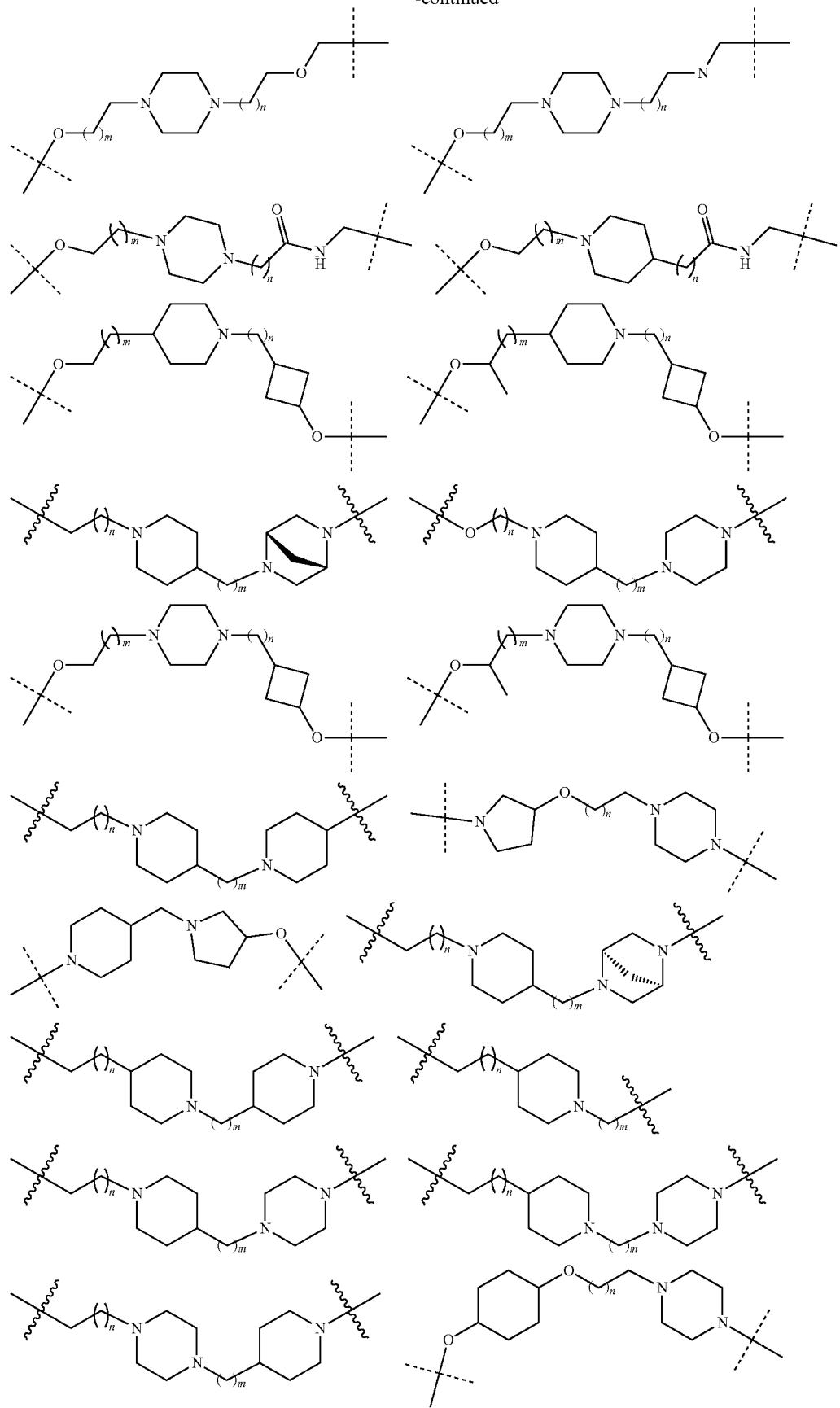

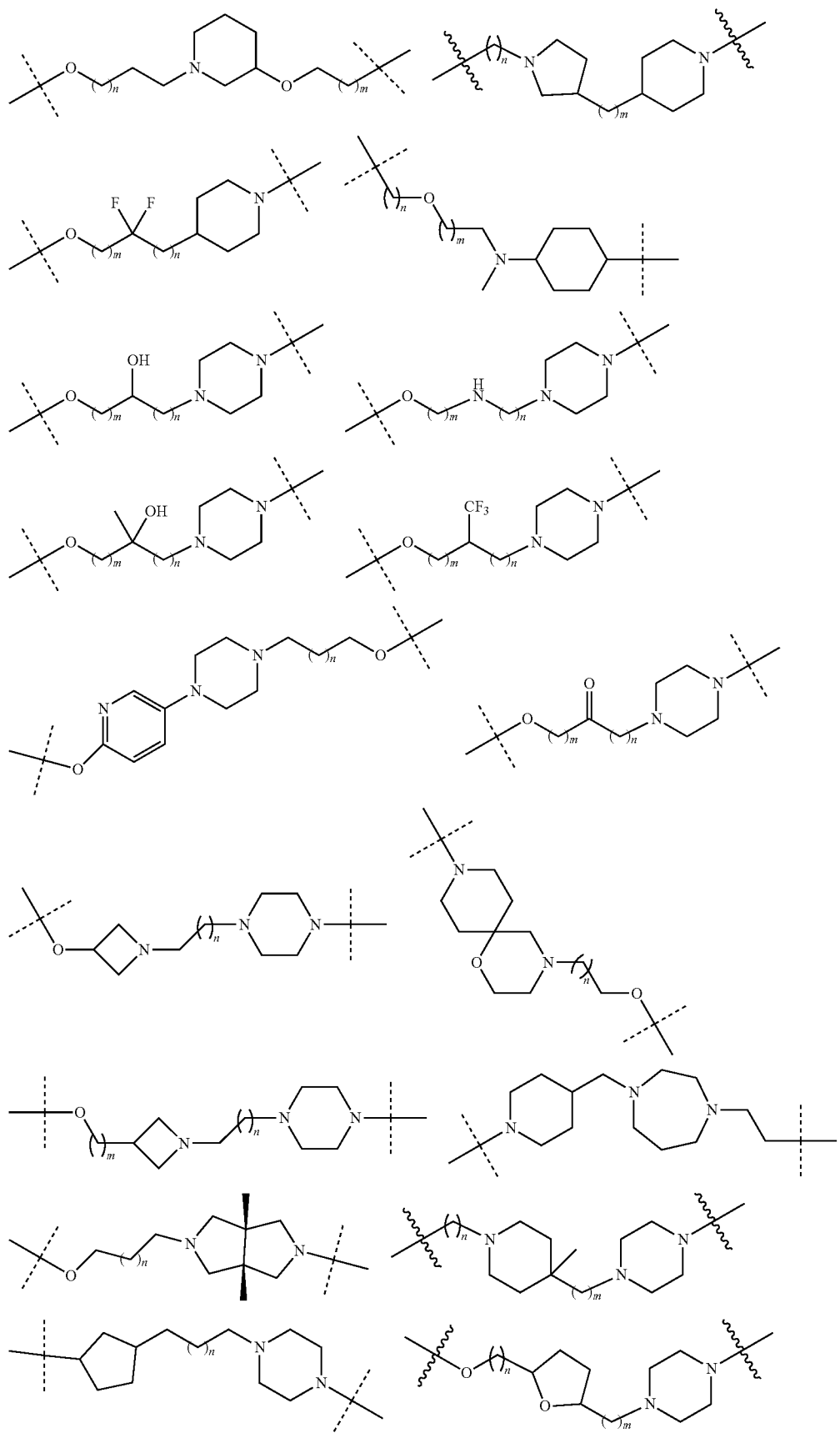

-continued
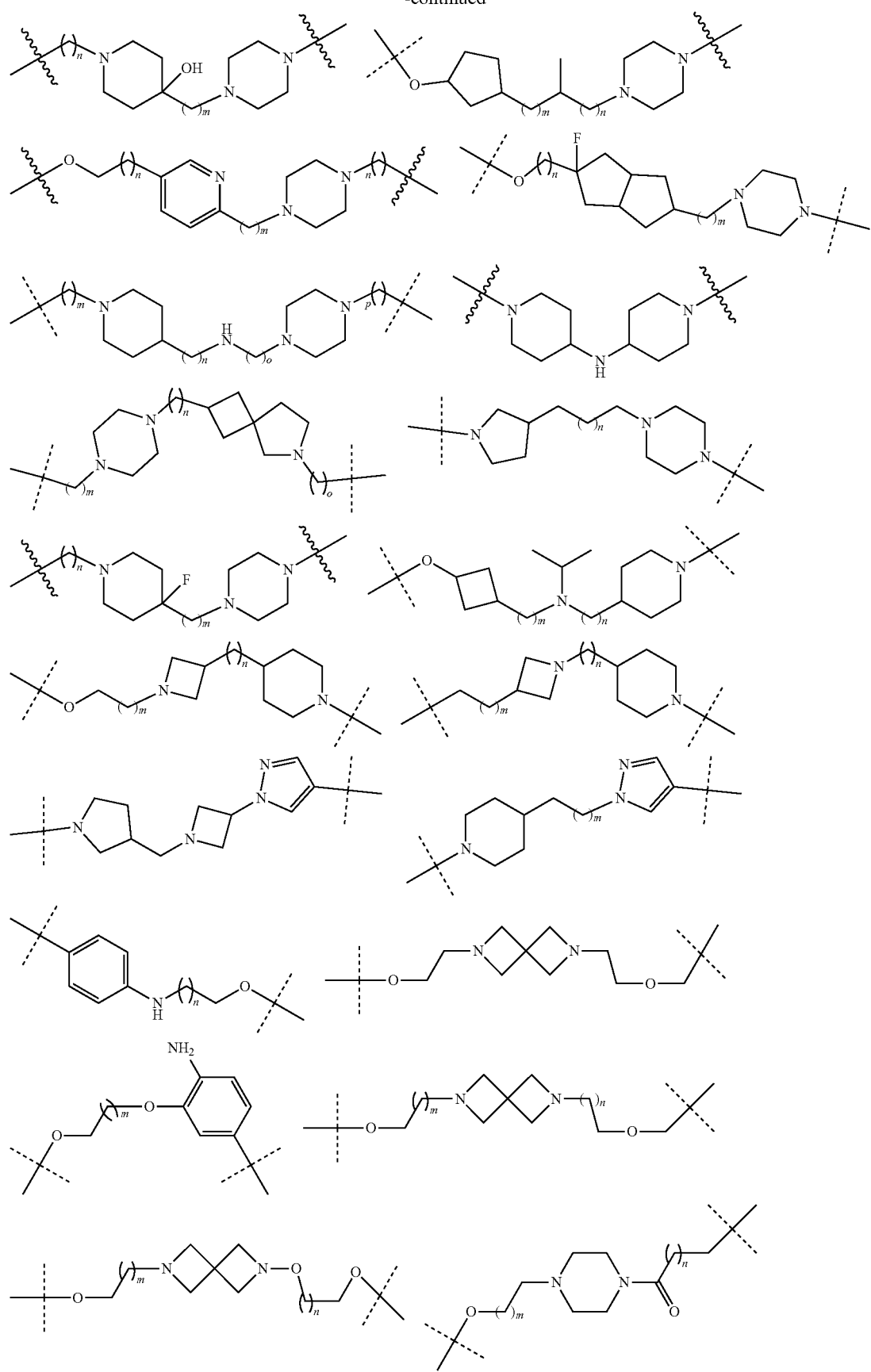

-continued
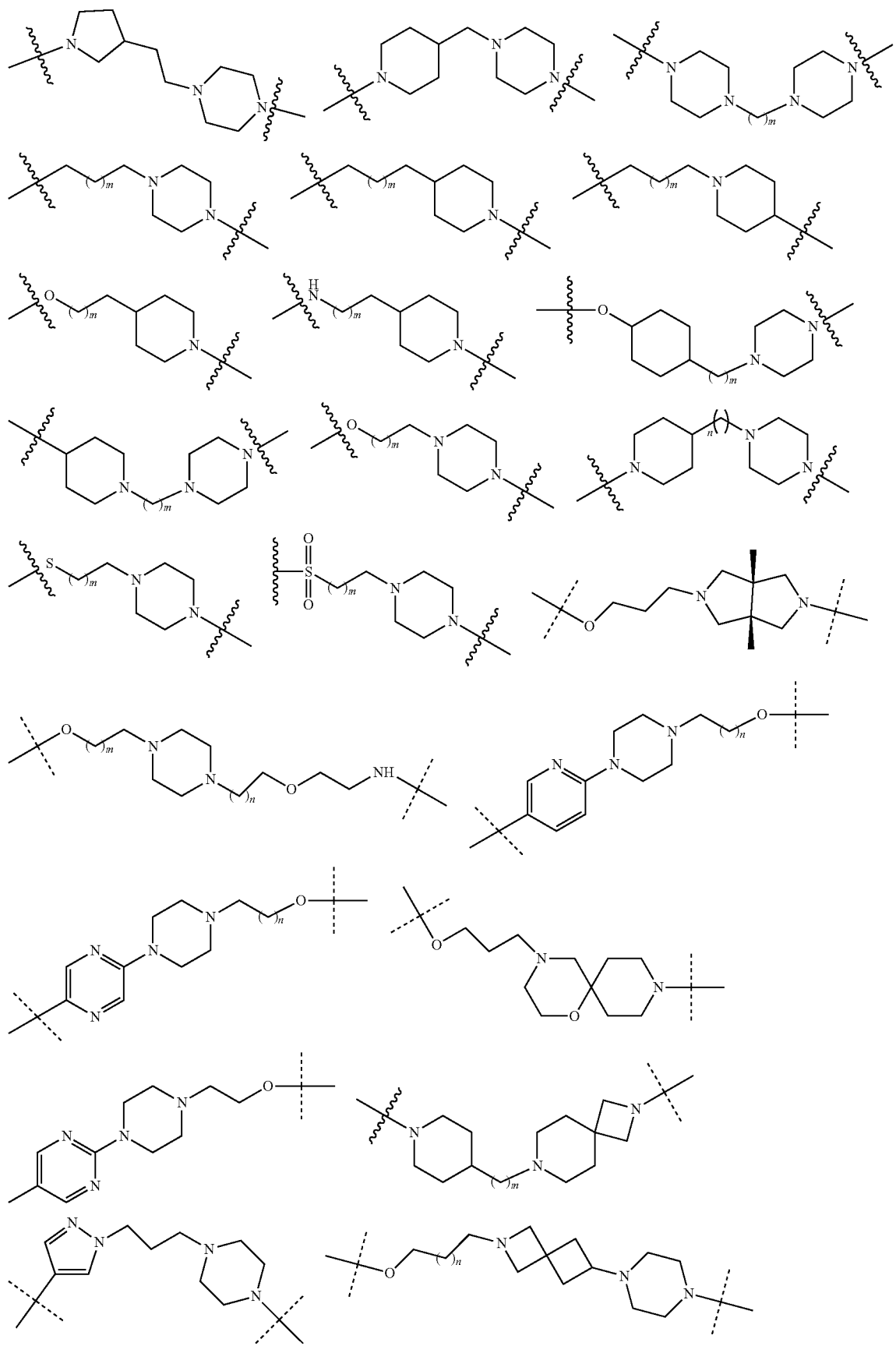

-continued
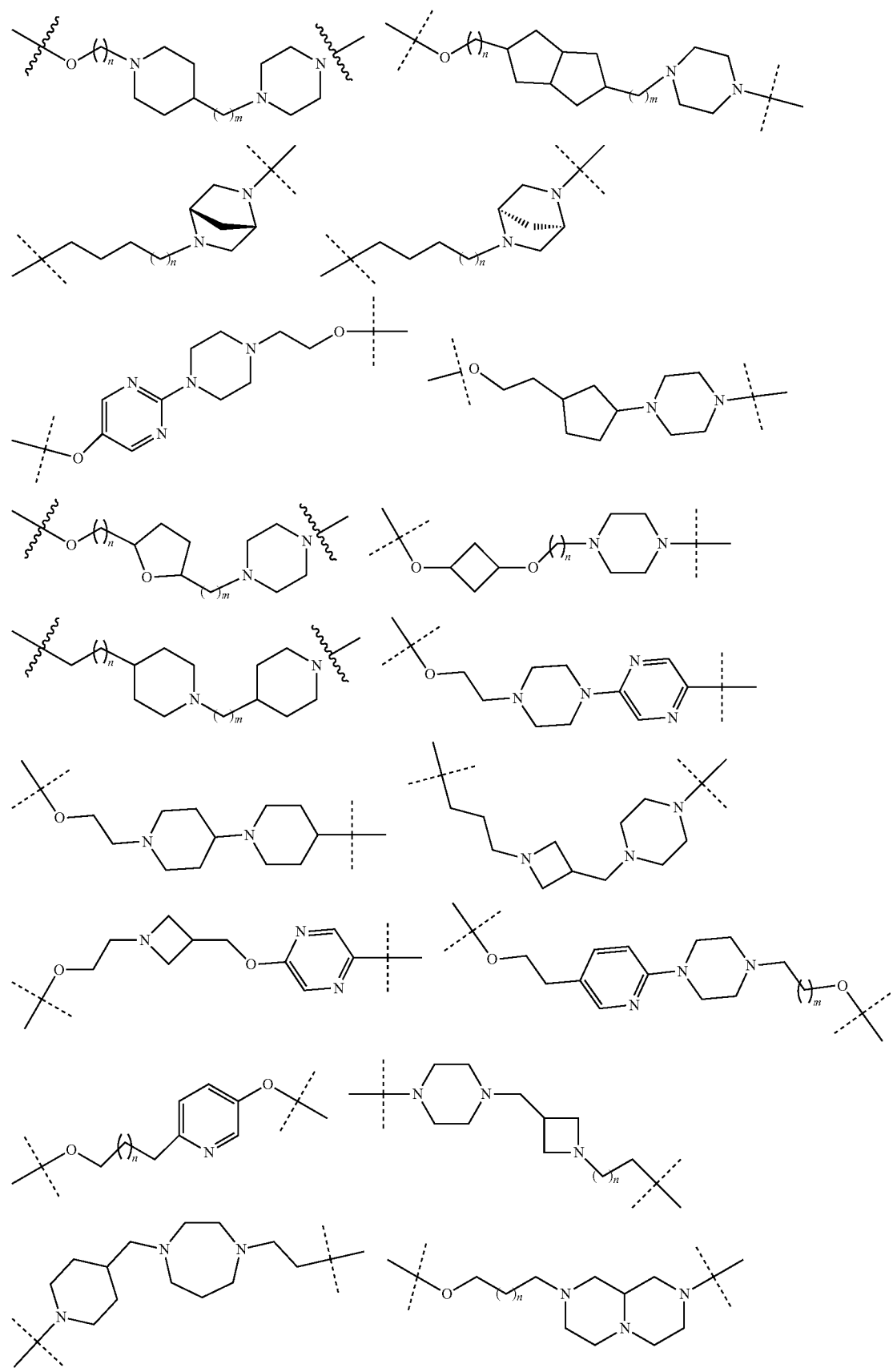

-continued
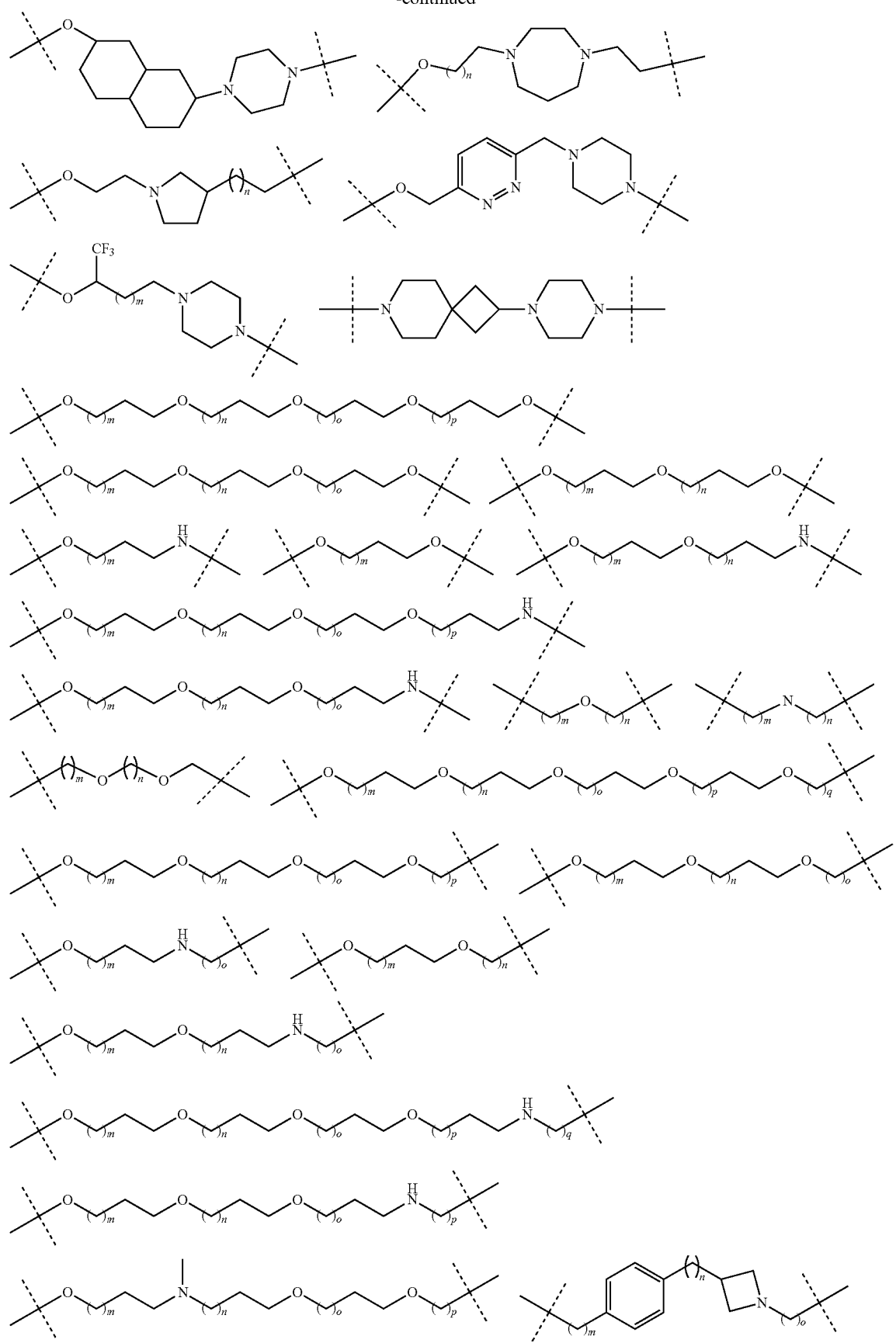

-continued
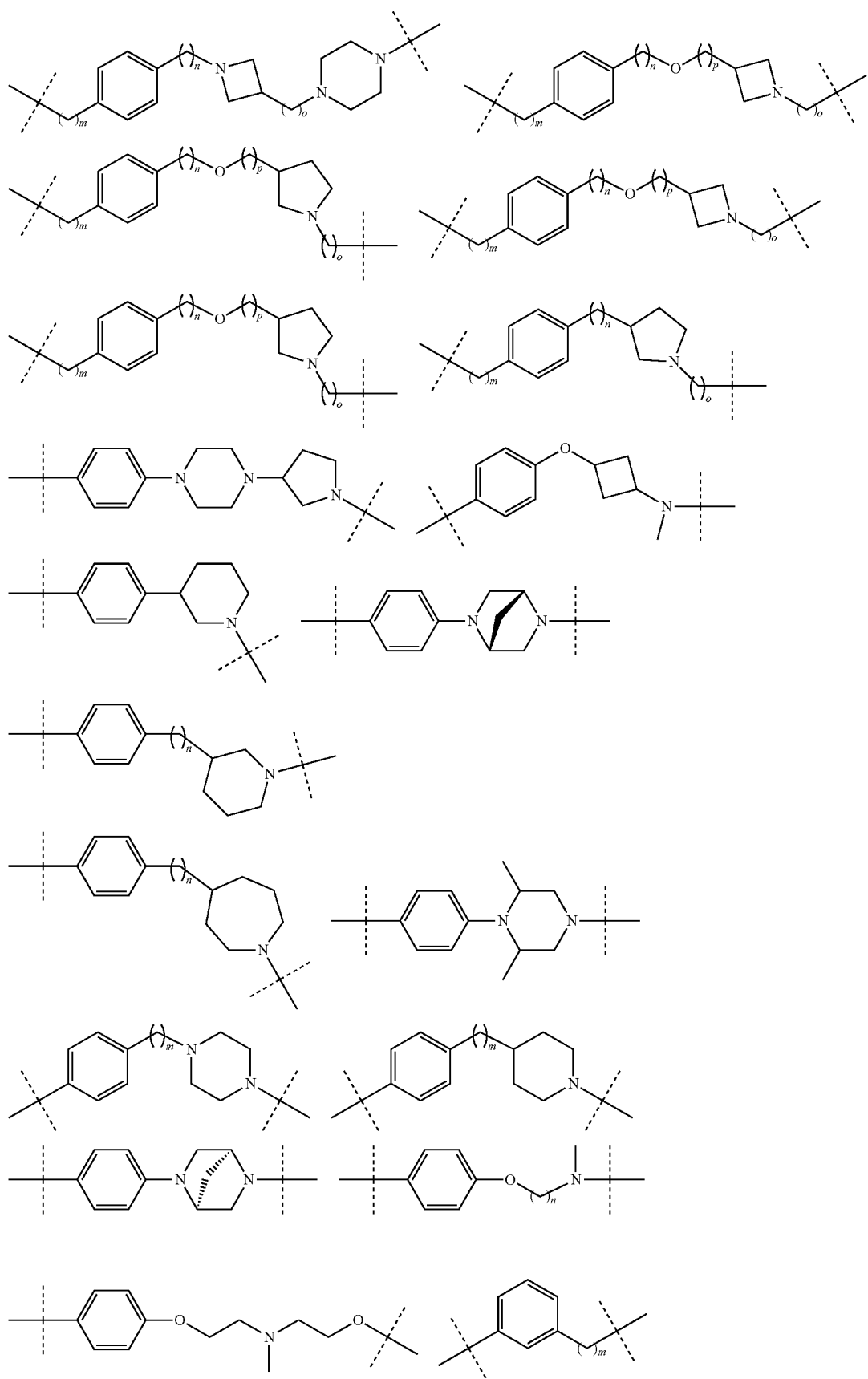

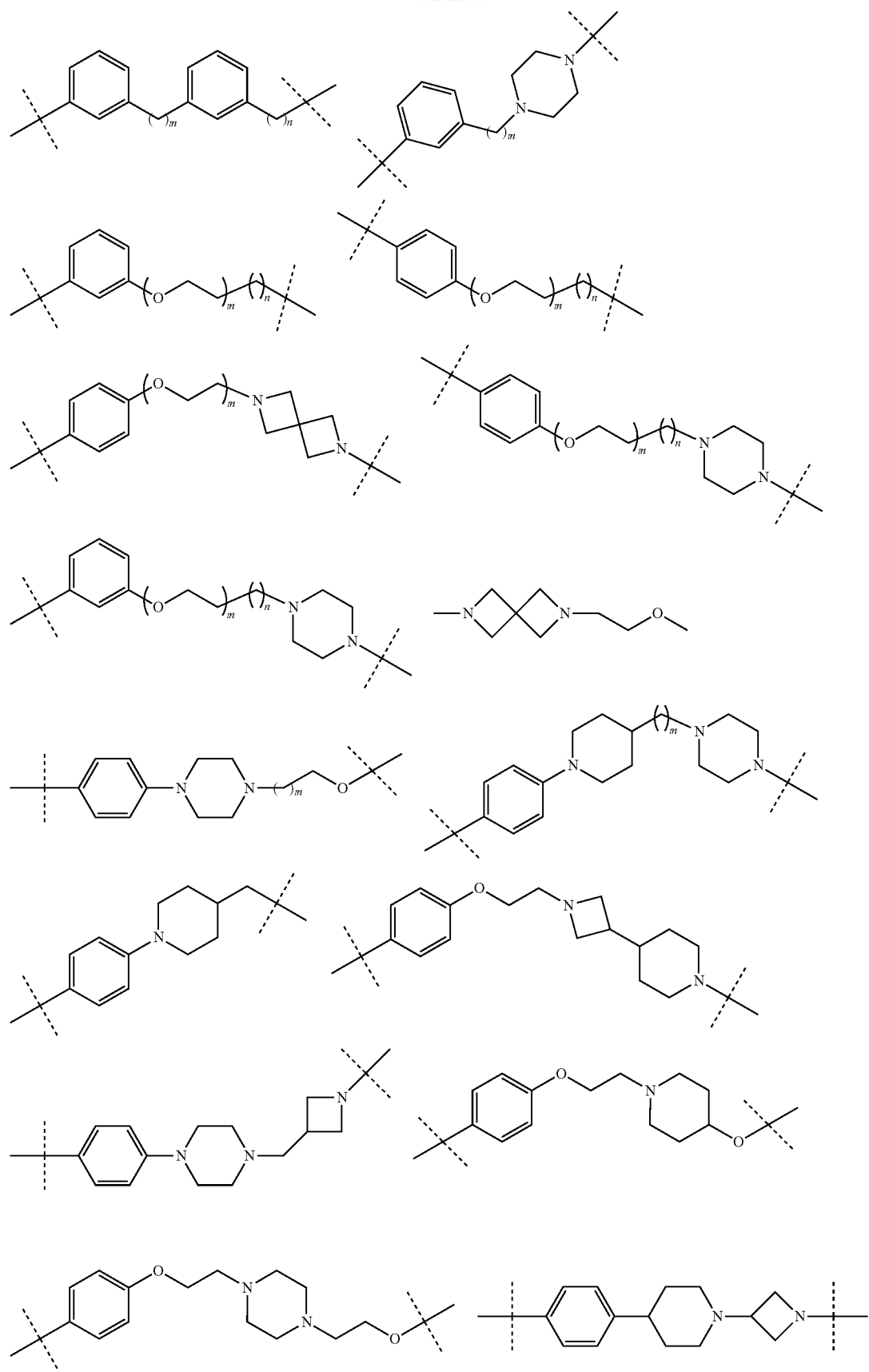

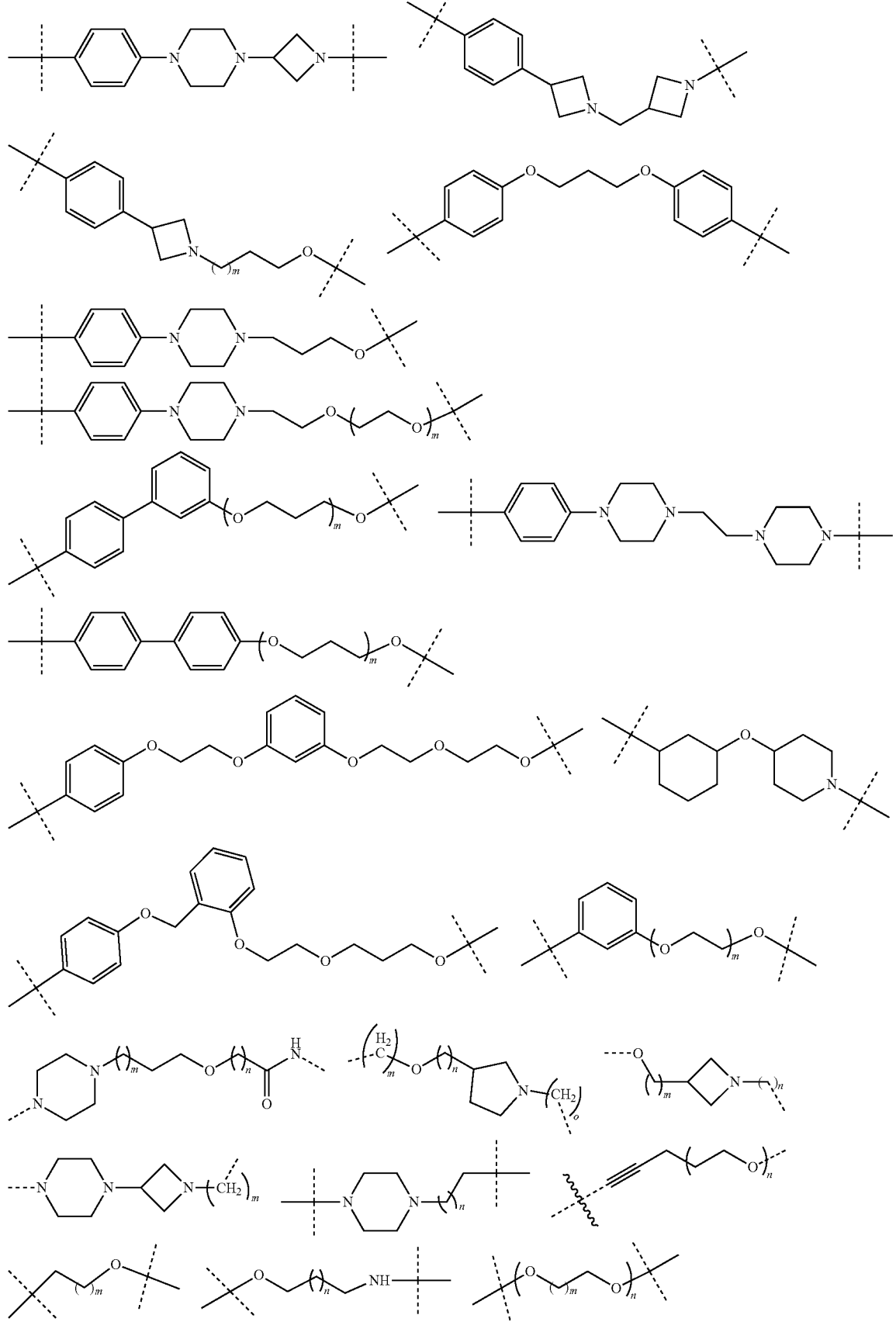

-continued
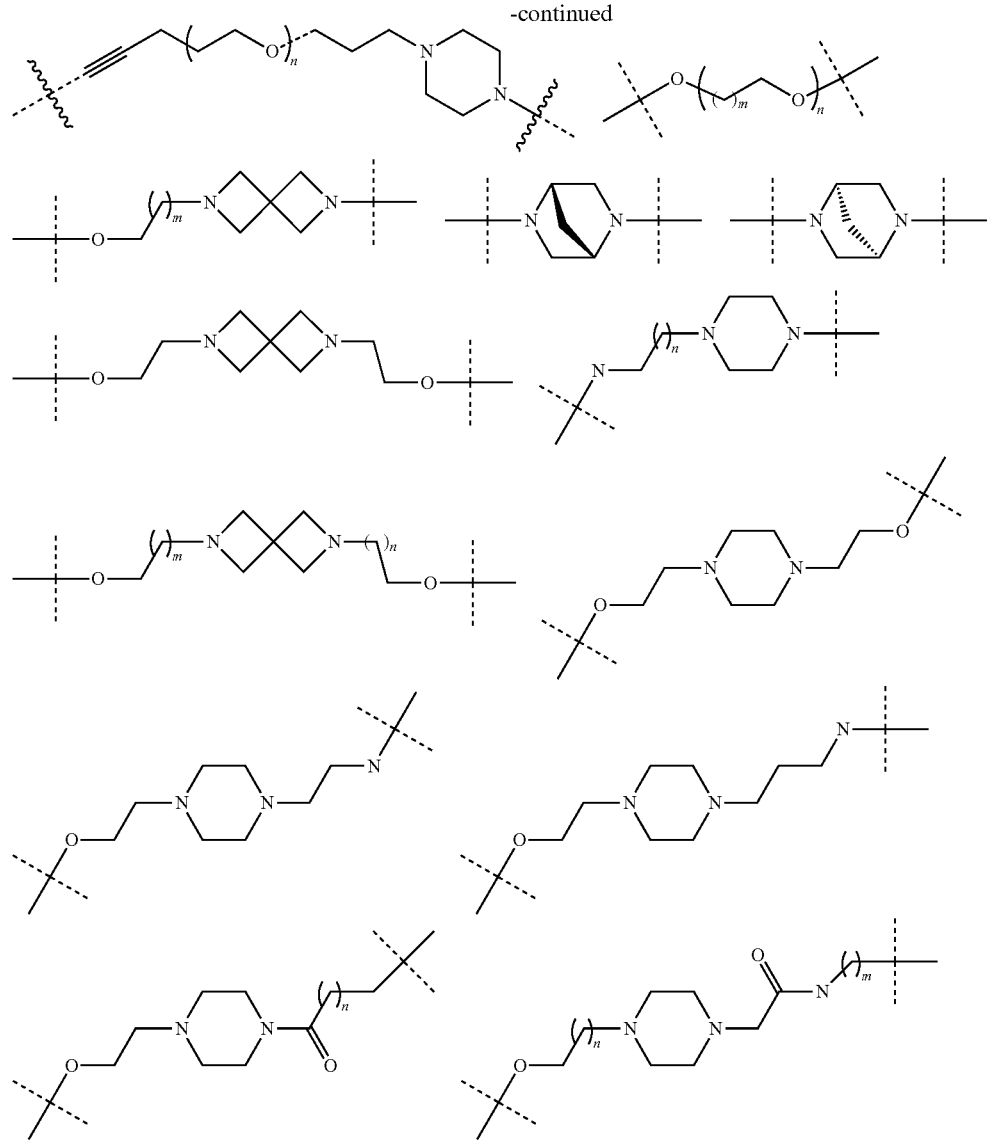
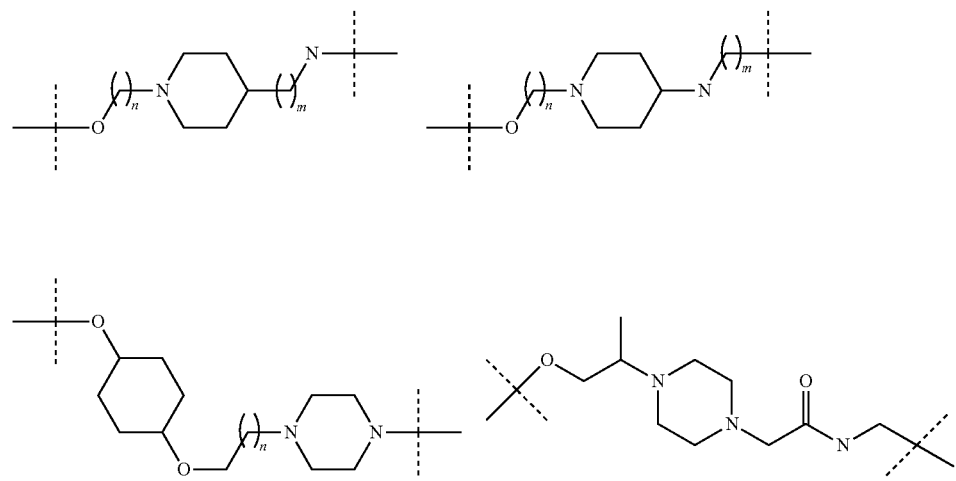

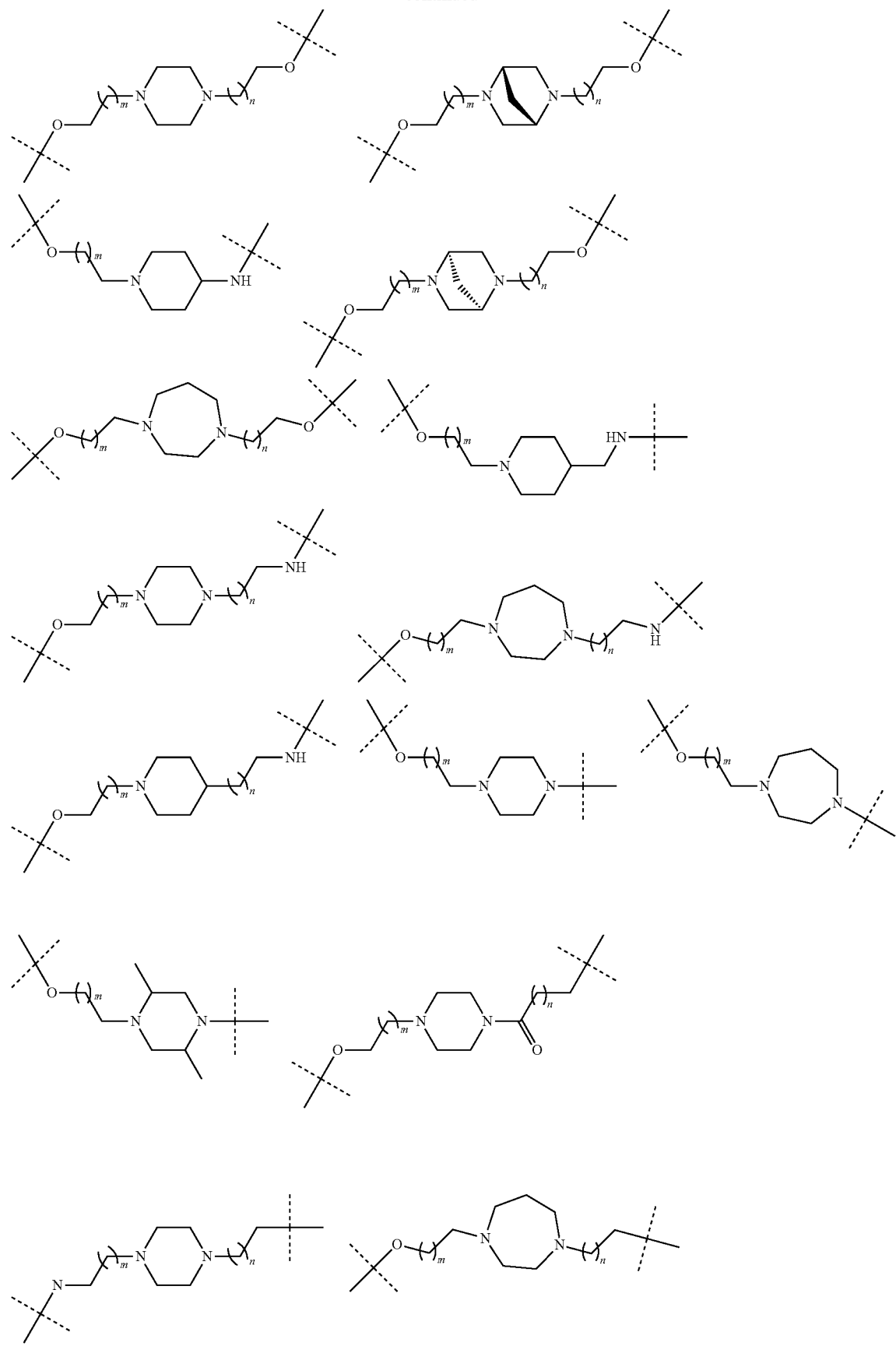

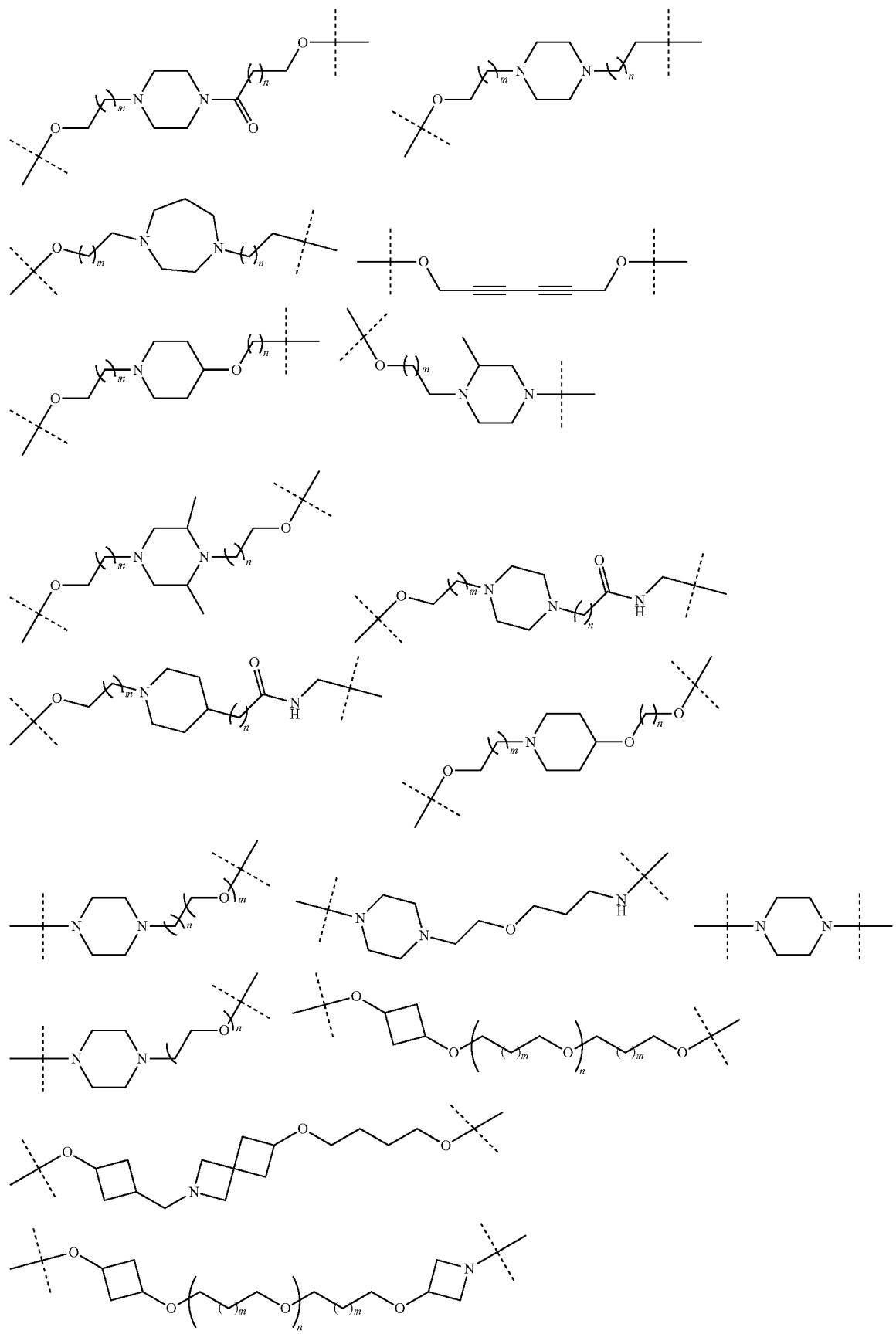

-continued
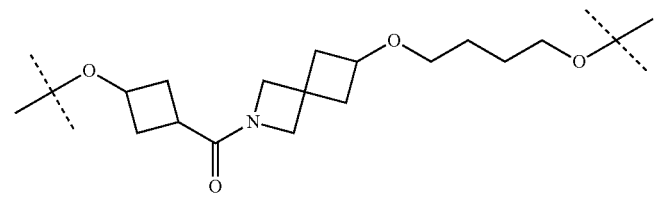
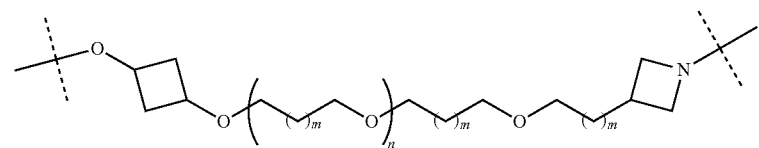
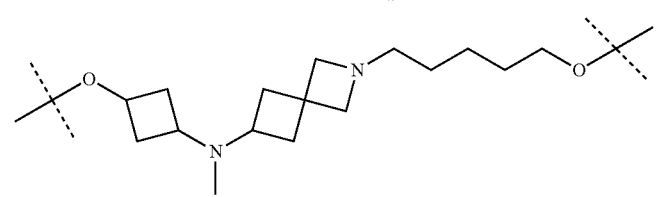
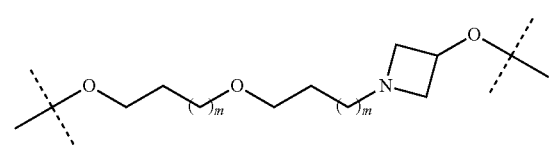
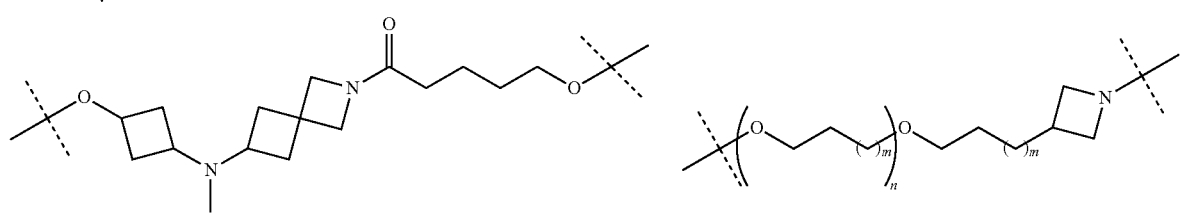
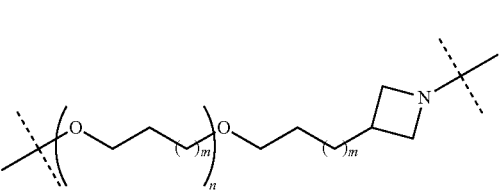
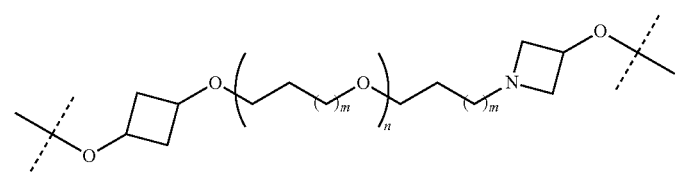
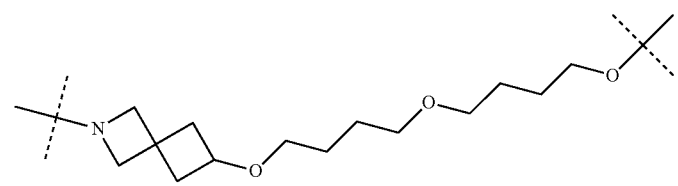
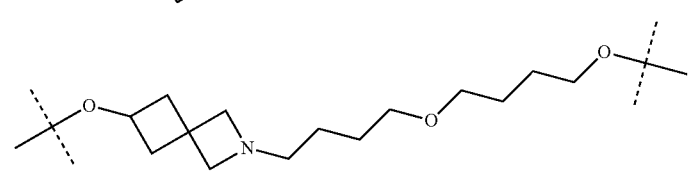
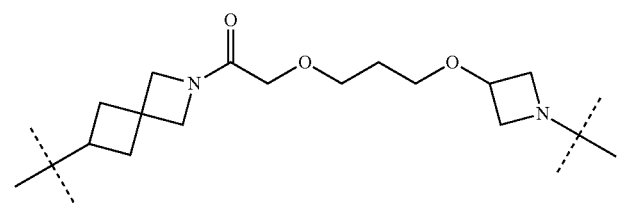

-continued
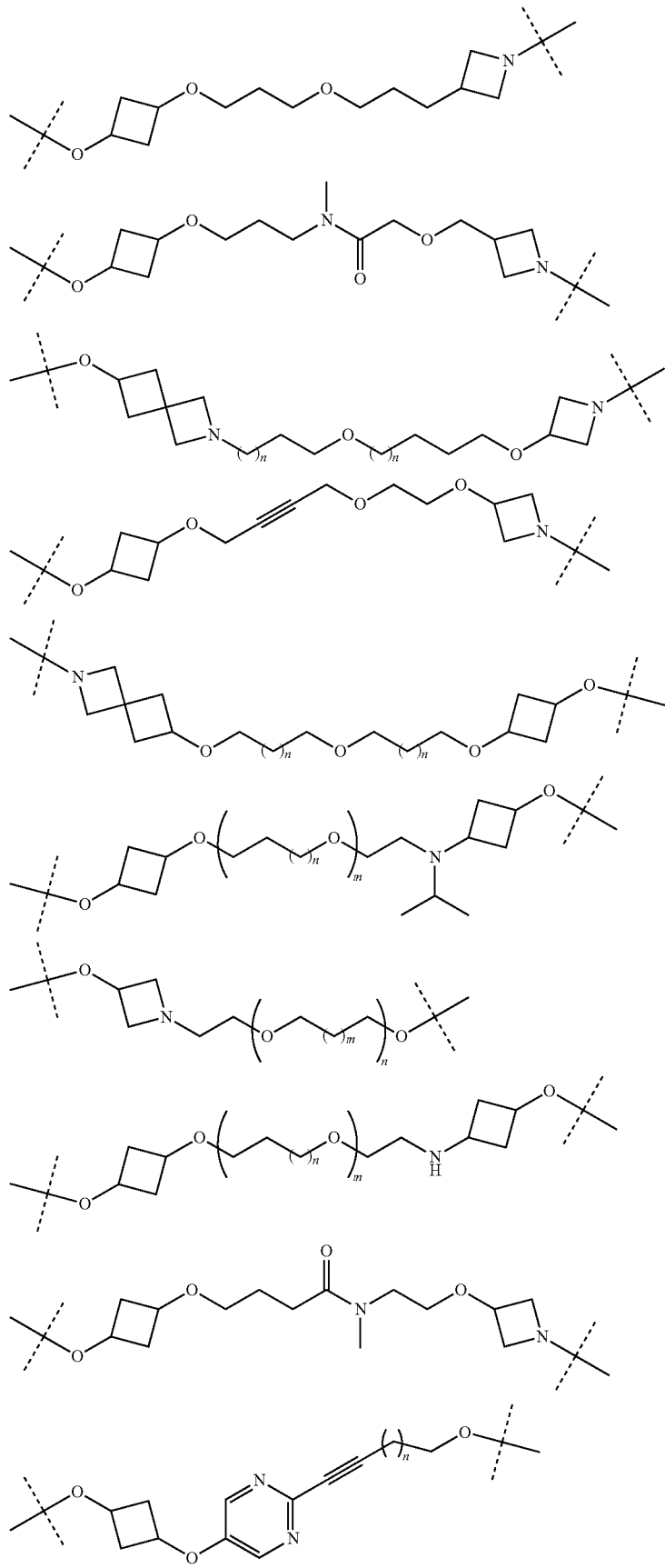

-continued
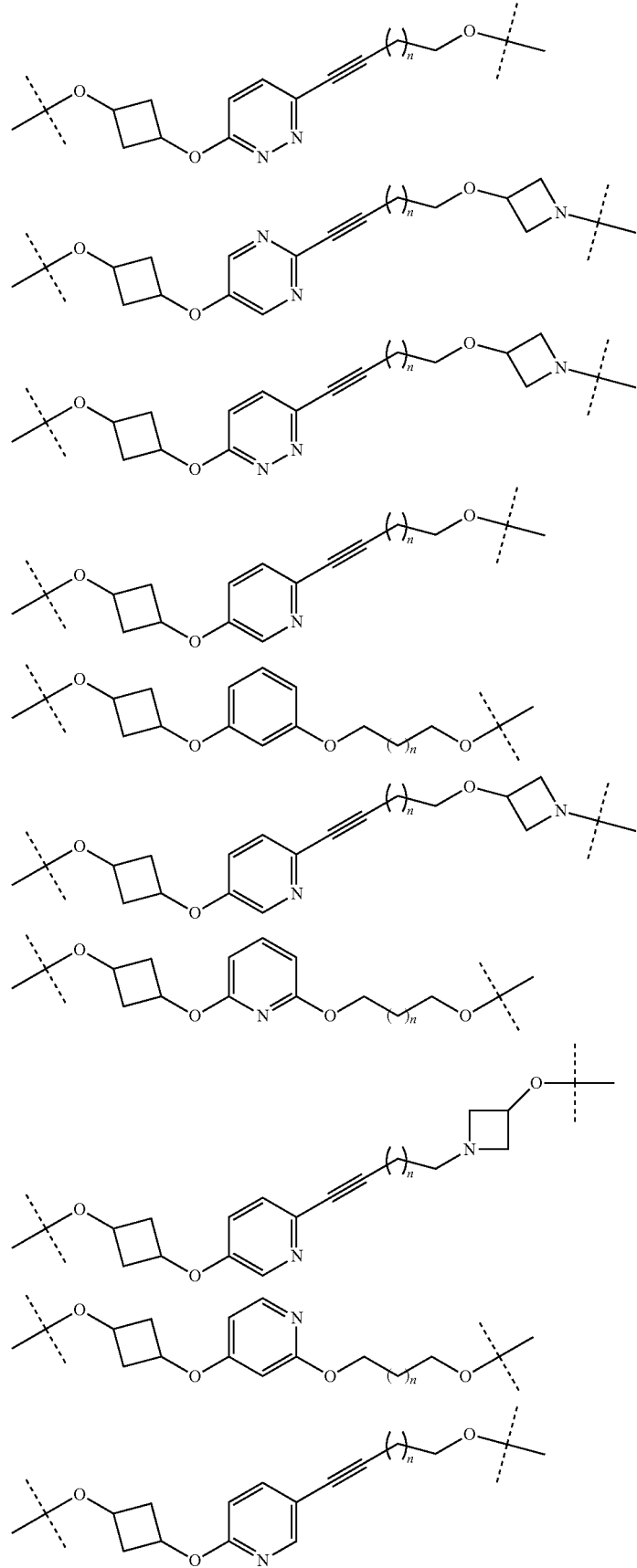

-continued
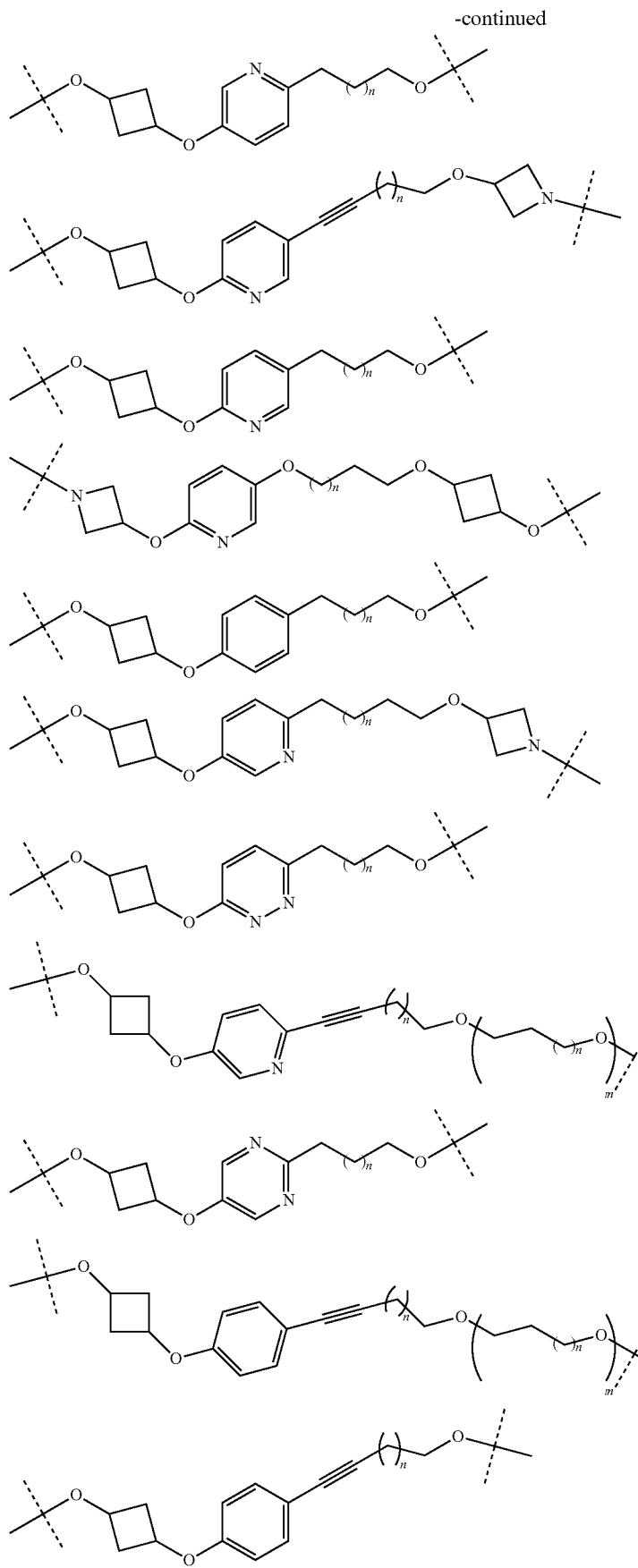

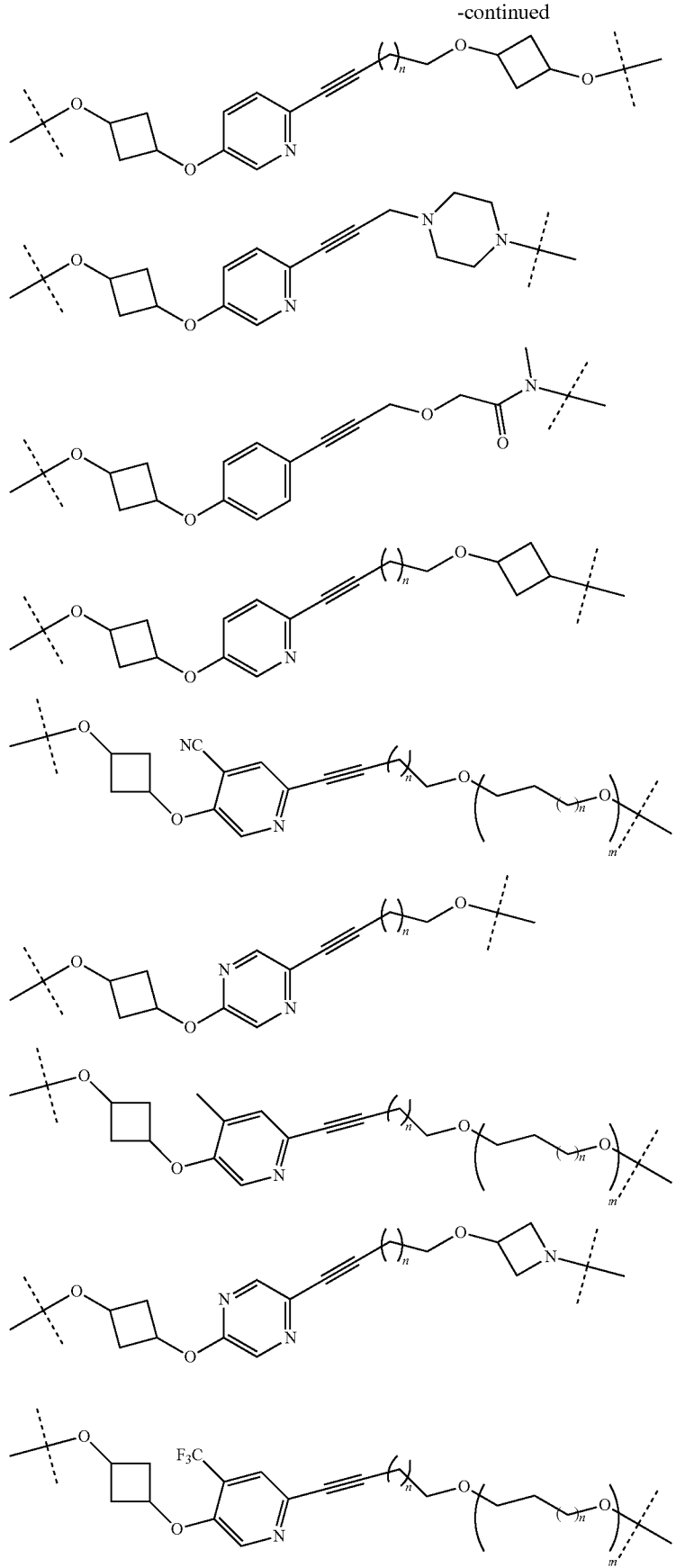

-continued
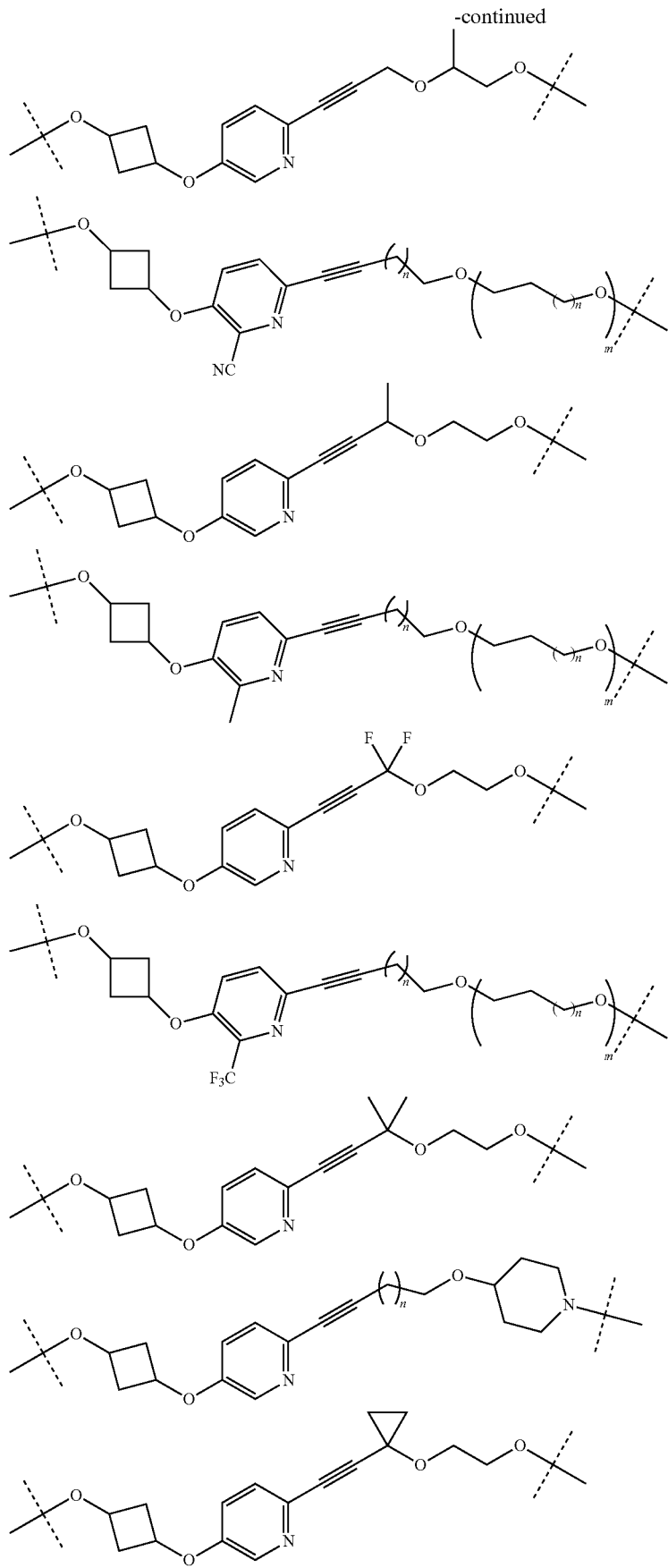

-continued
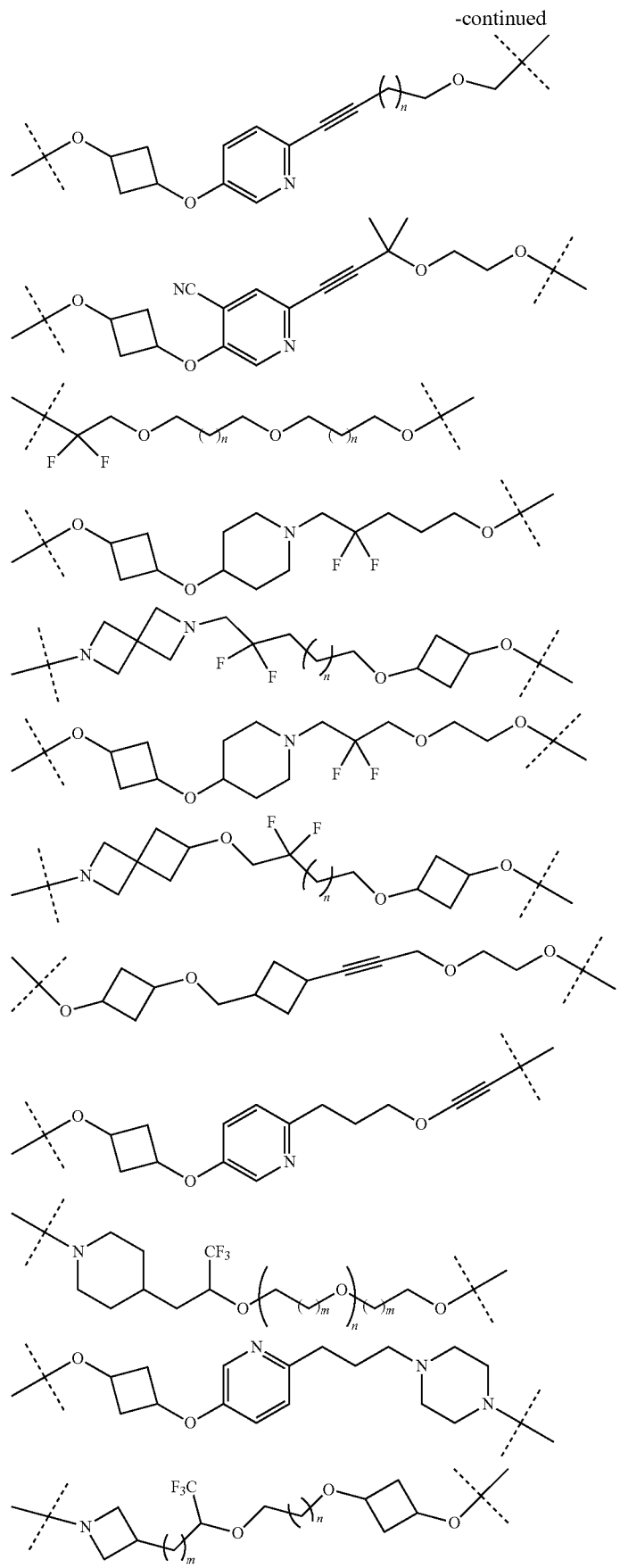

-continued
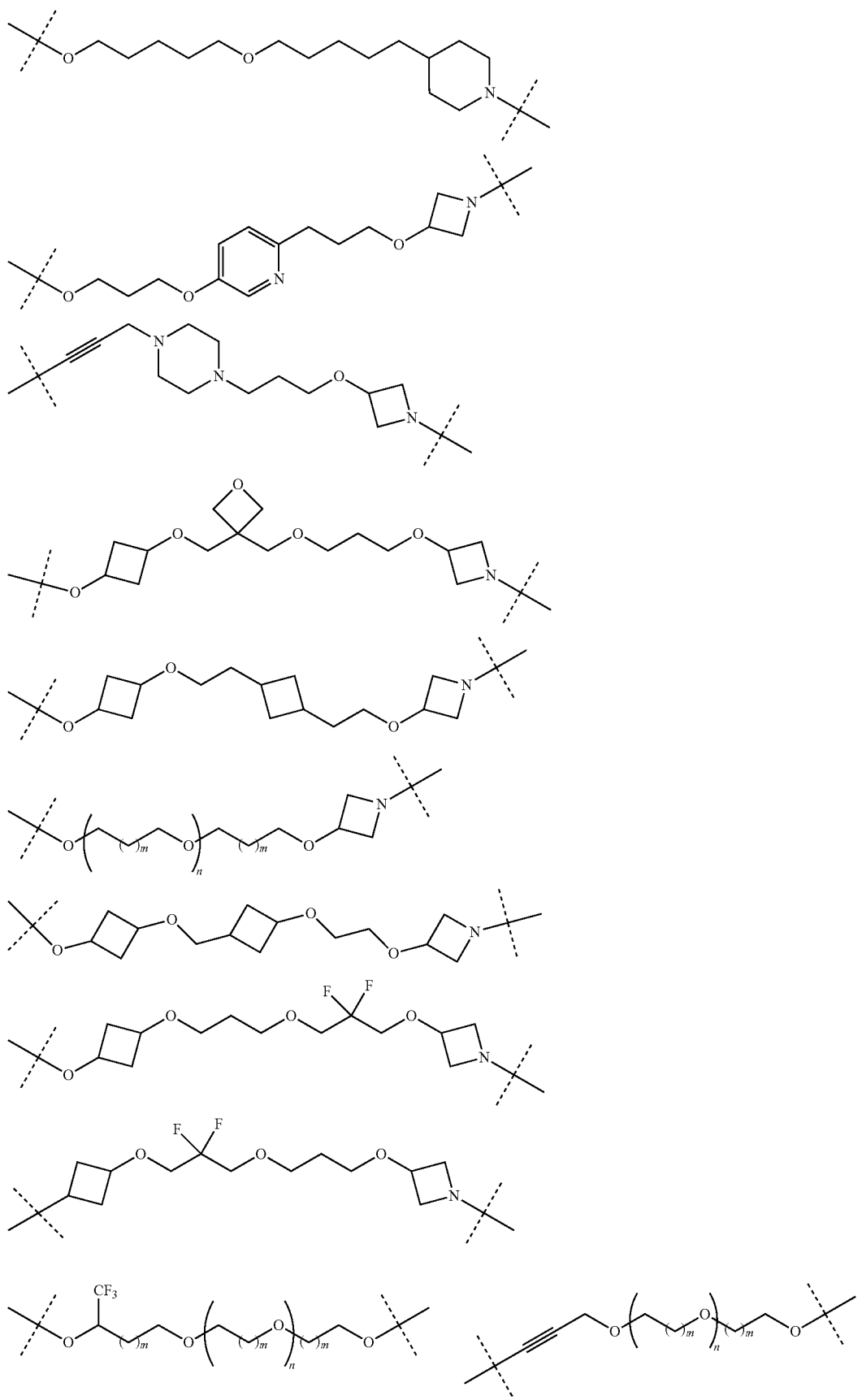

-continued
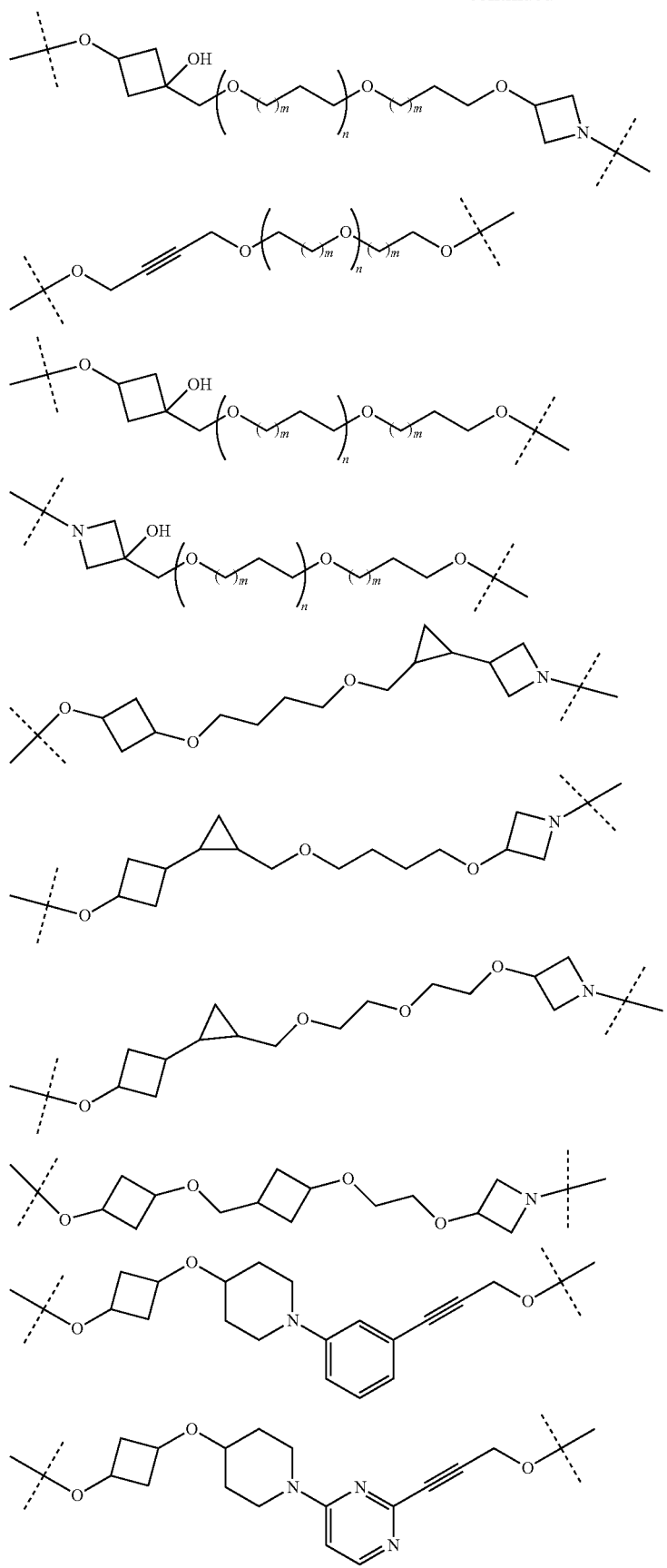

-continued
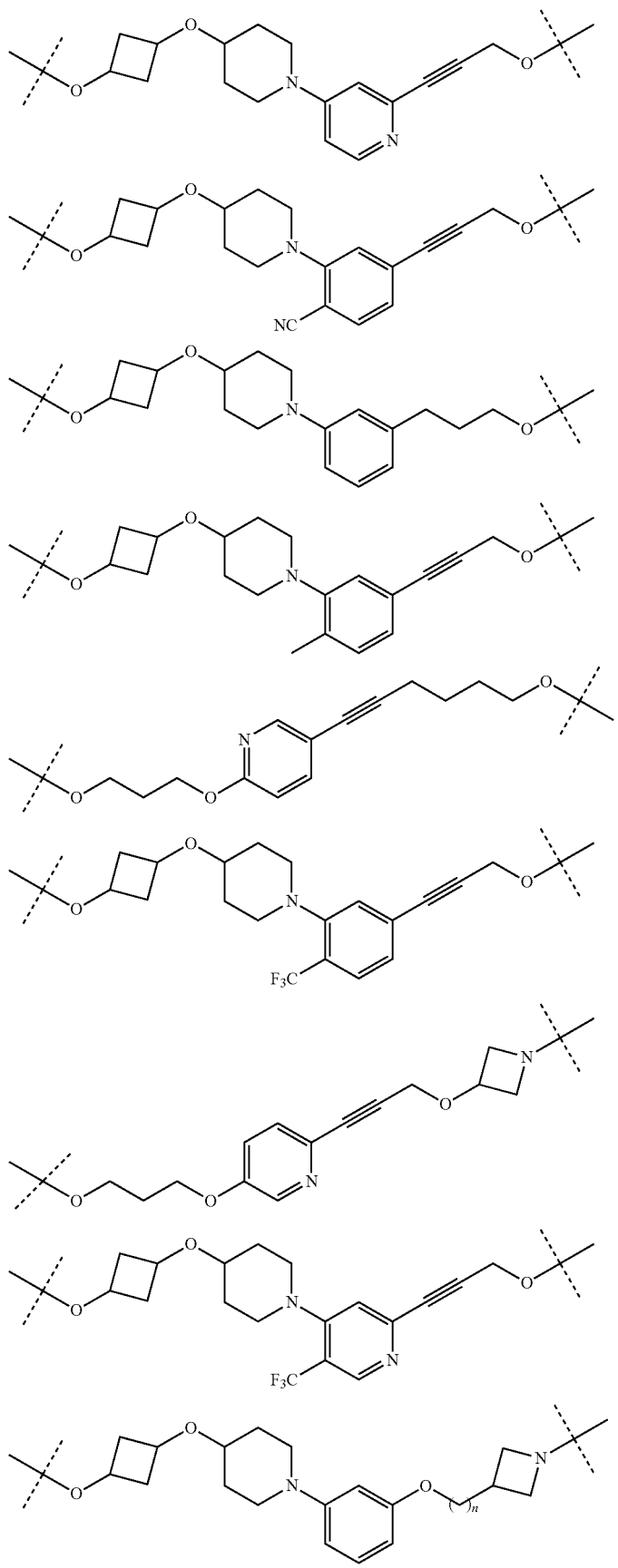

-continued
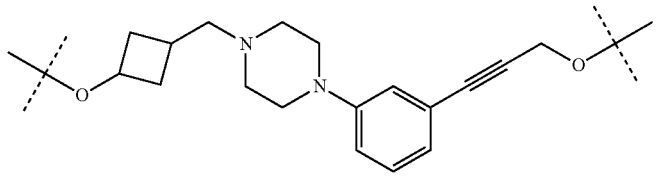
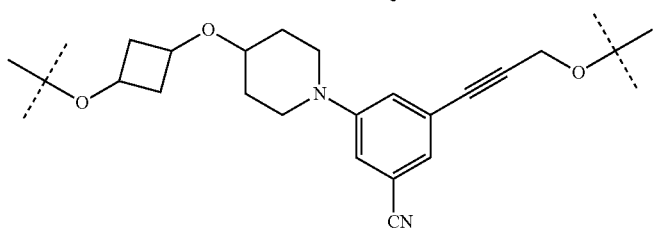
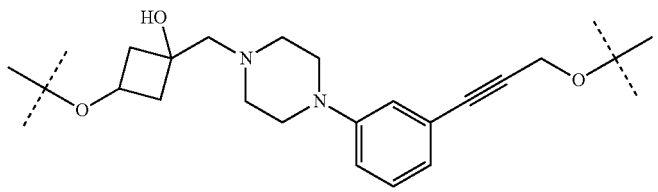
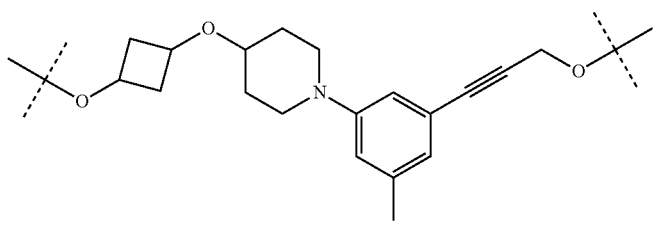
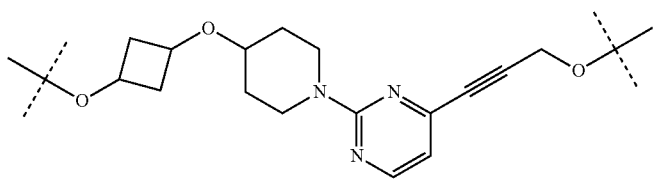
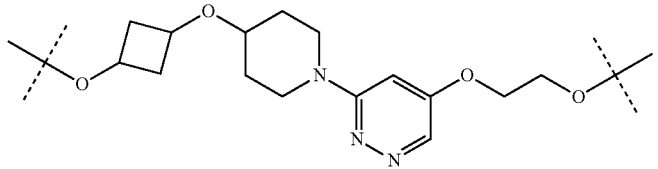
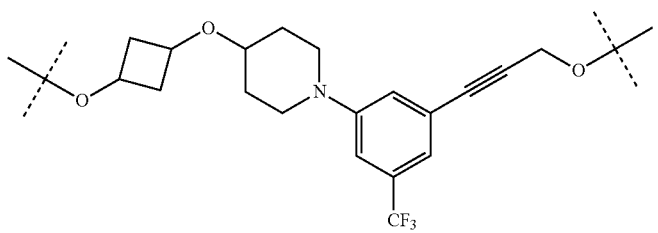
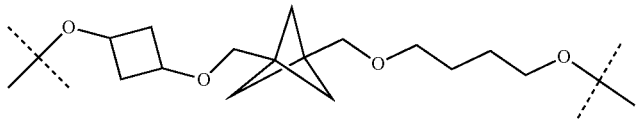

-continued
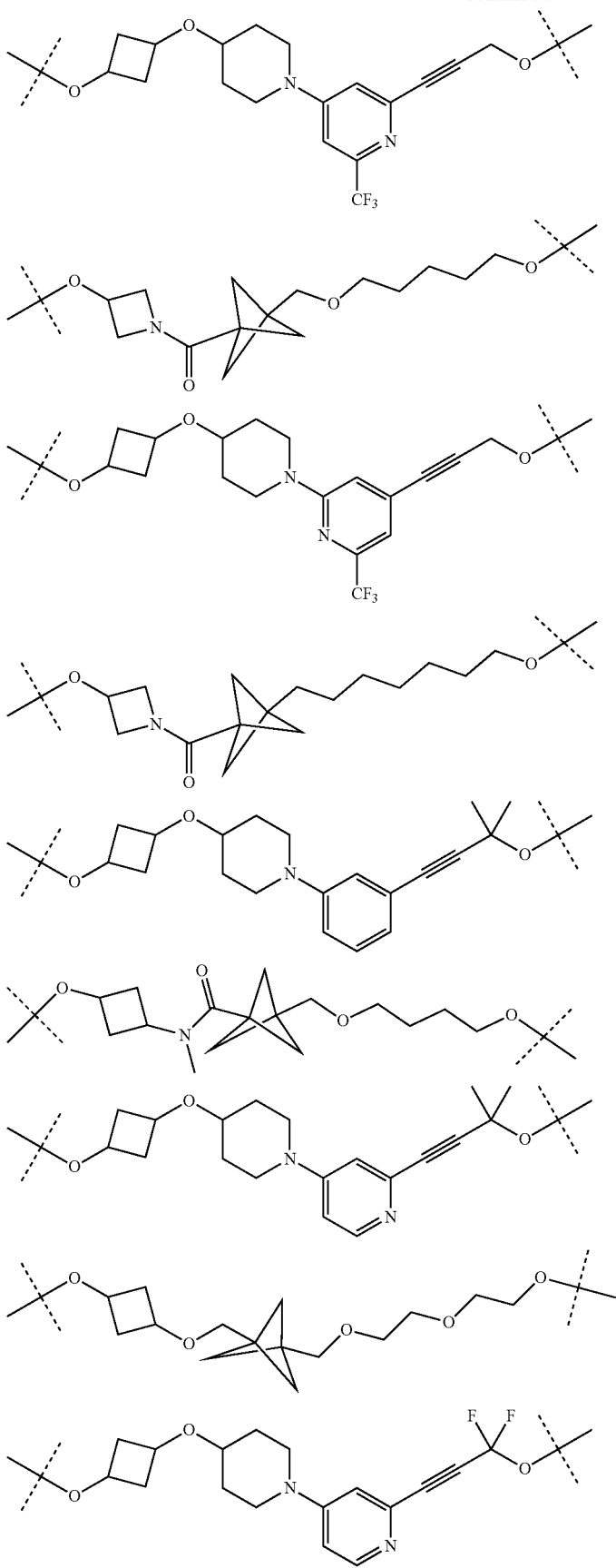

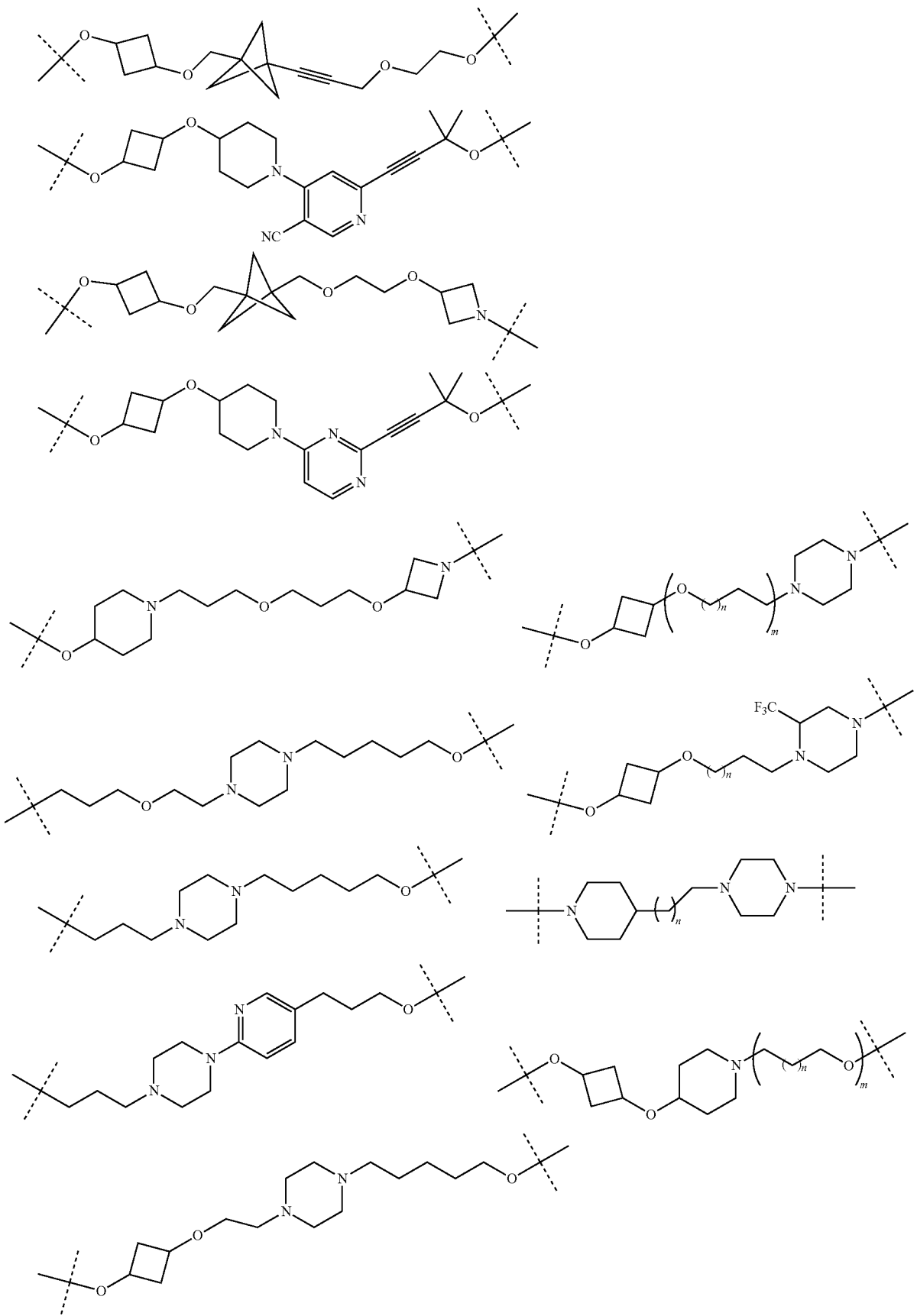

-continued
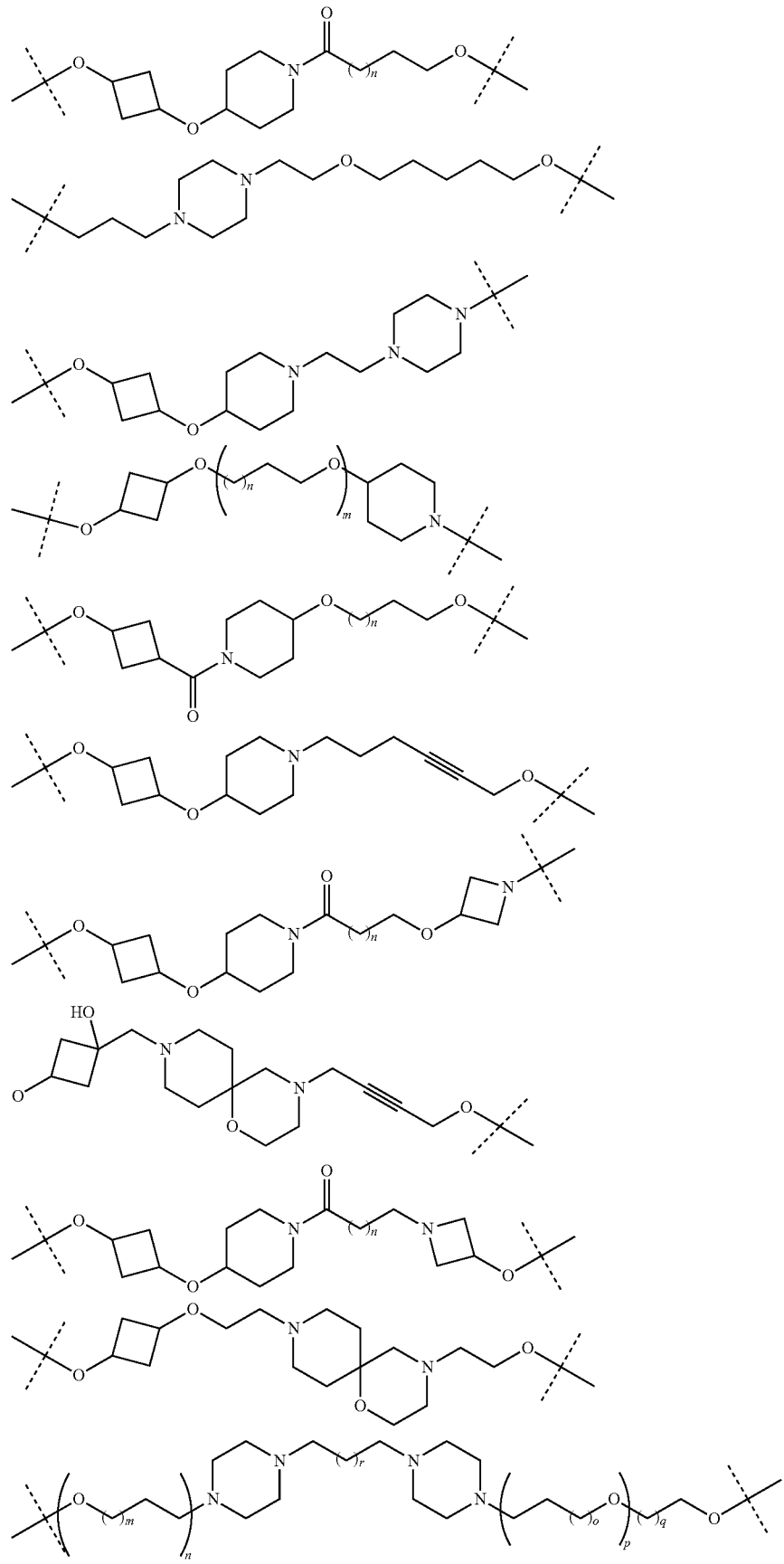

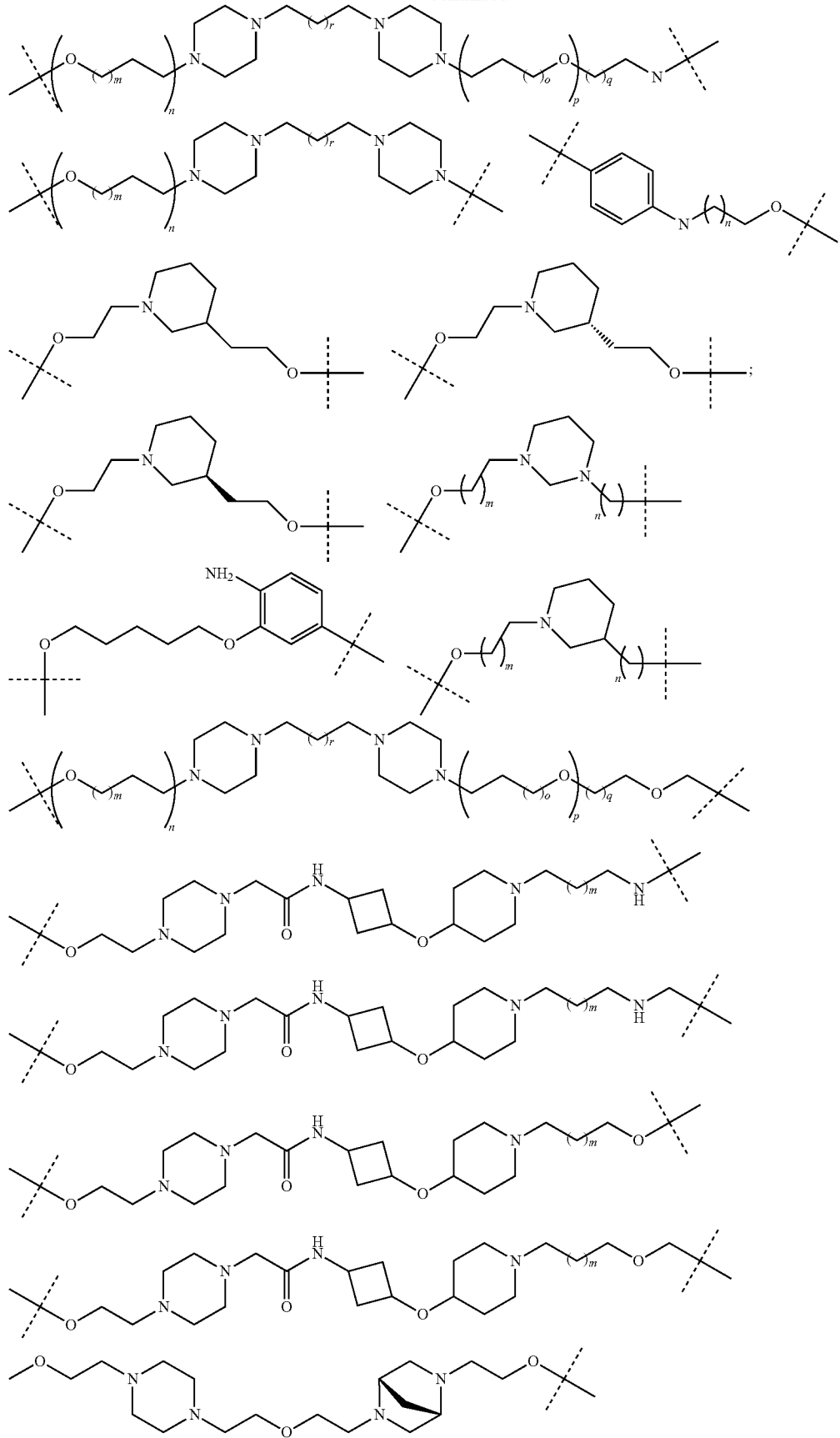

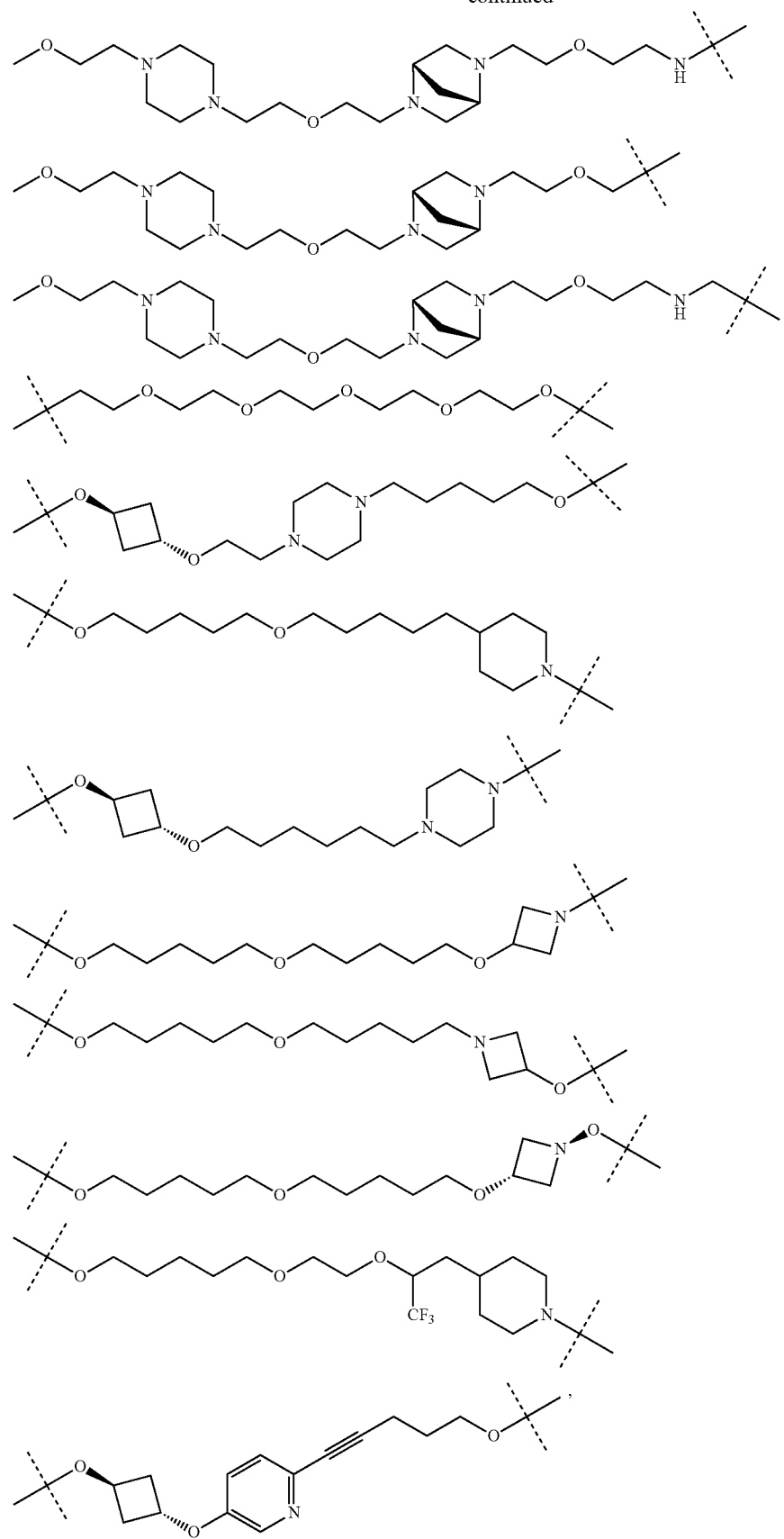

wherein each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, L is selected from the group consisting of:
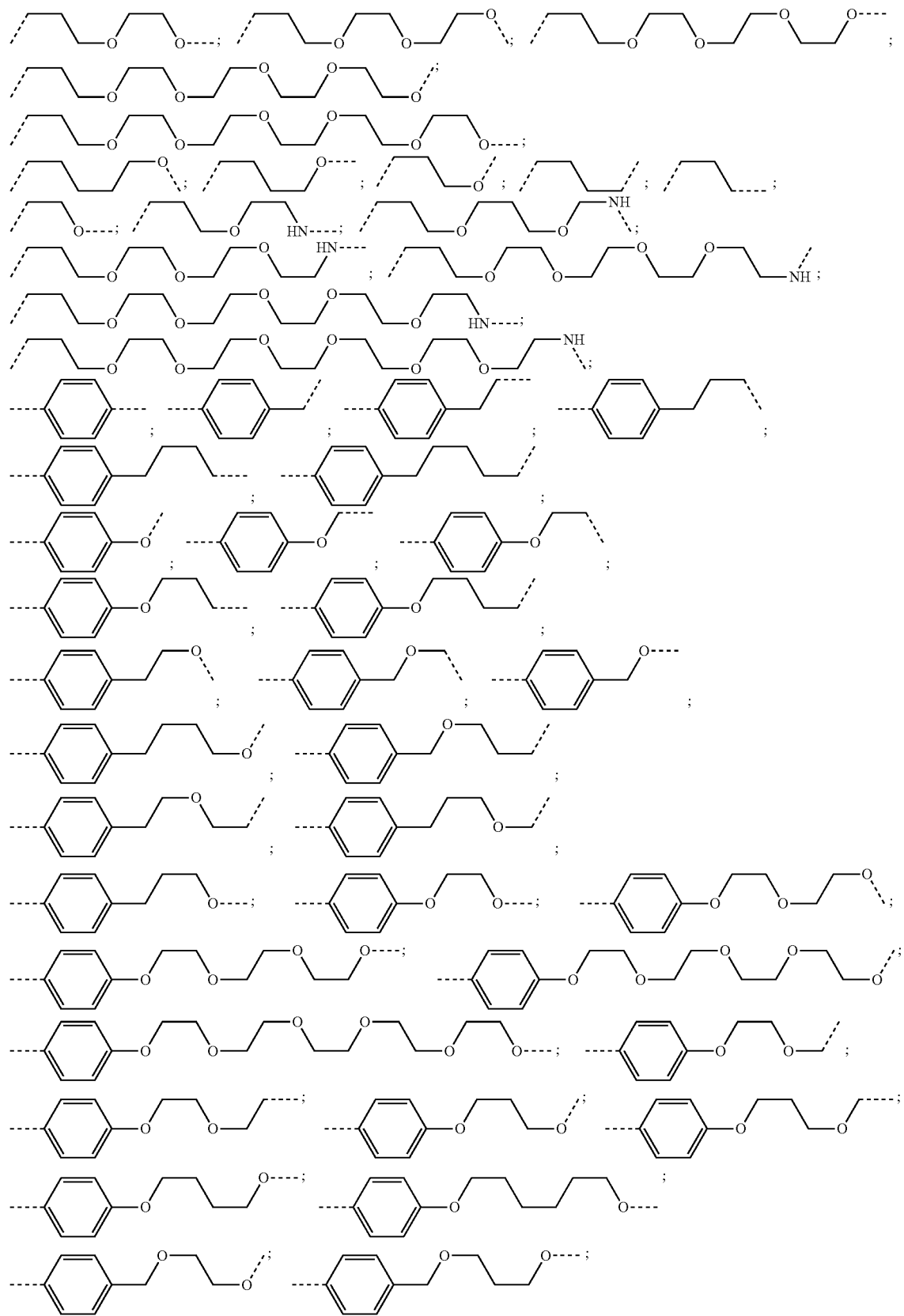

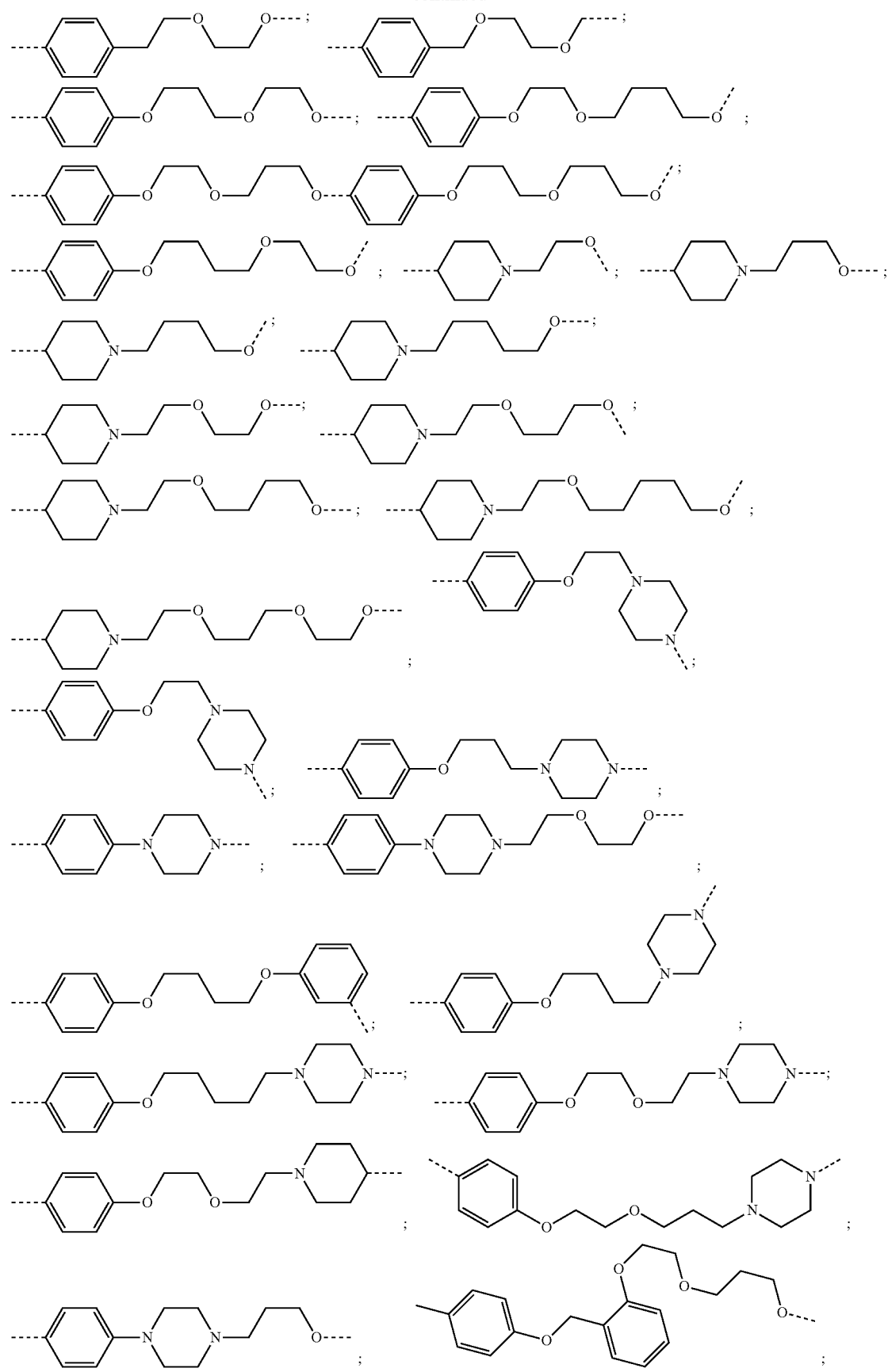

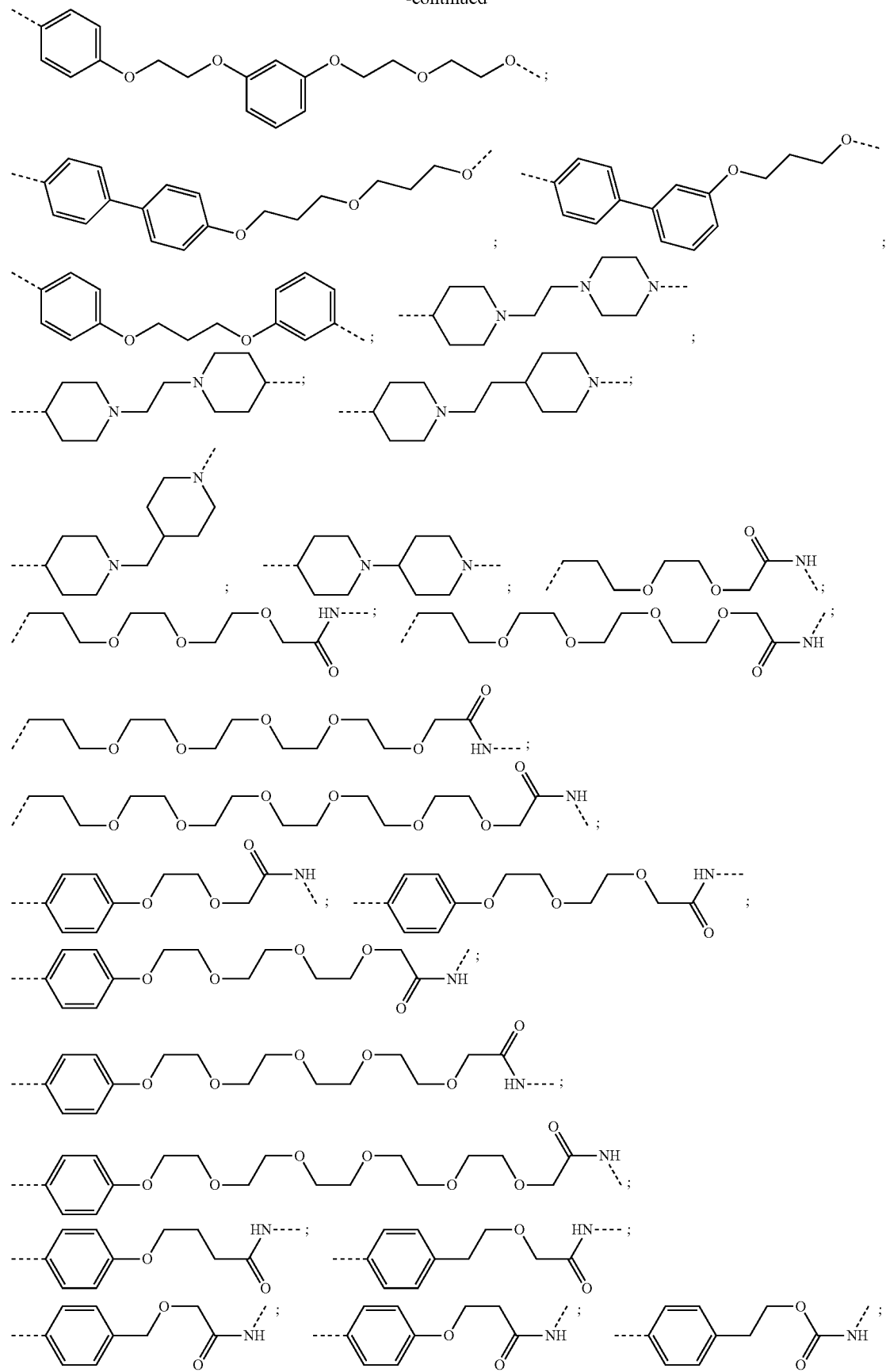

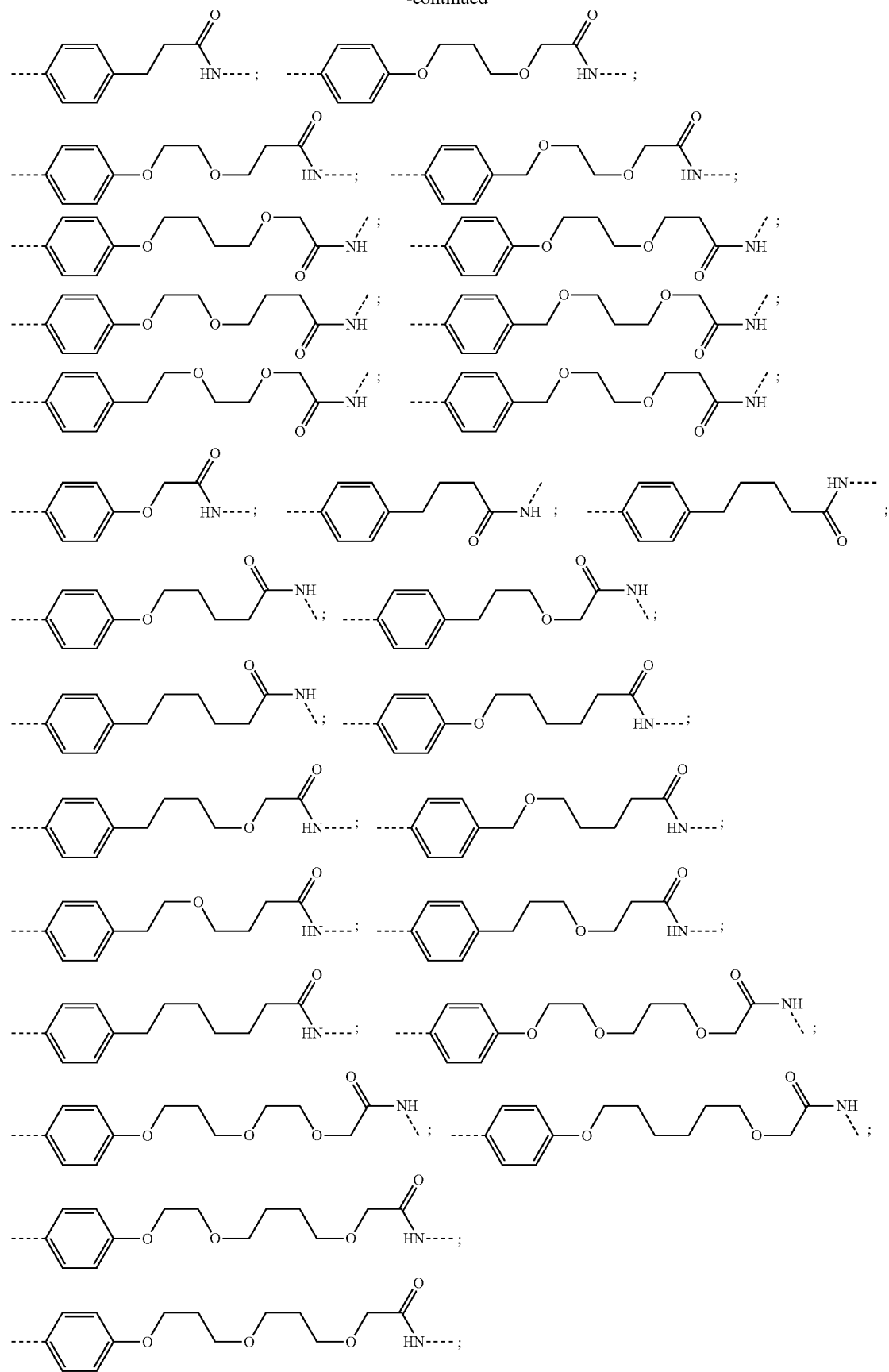

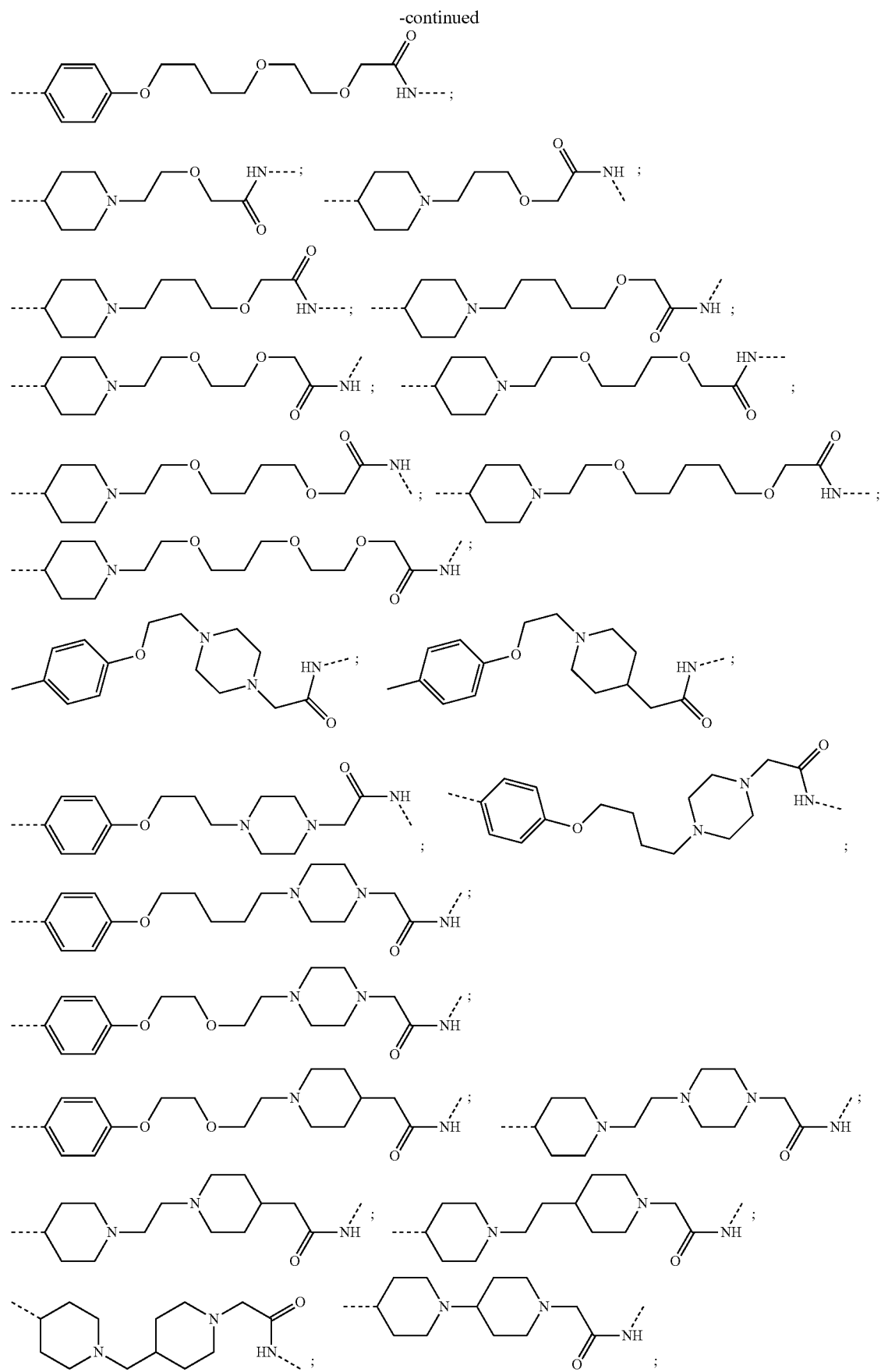

399 400
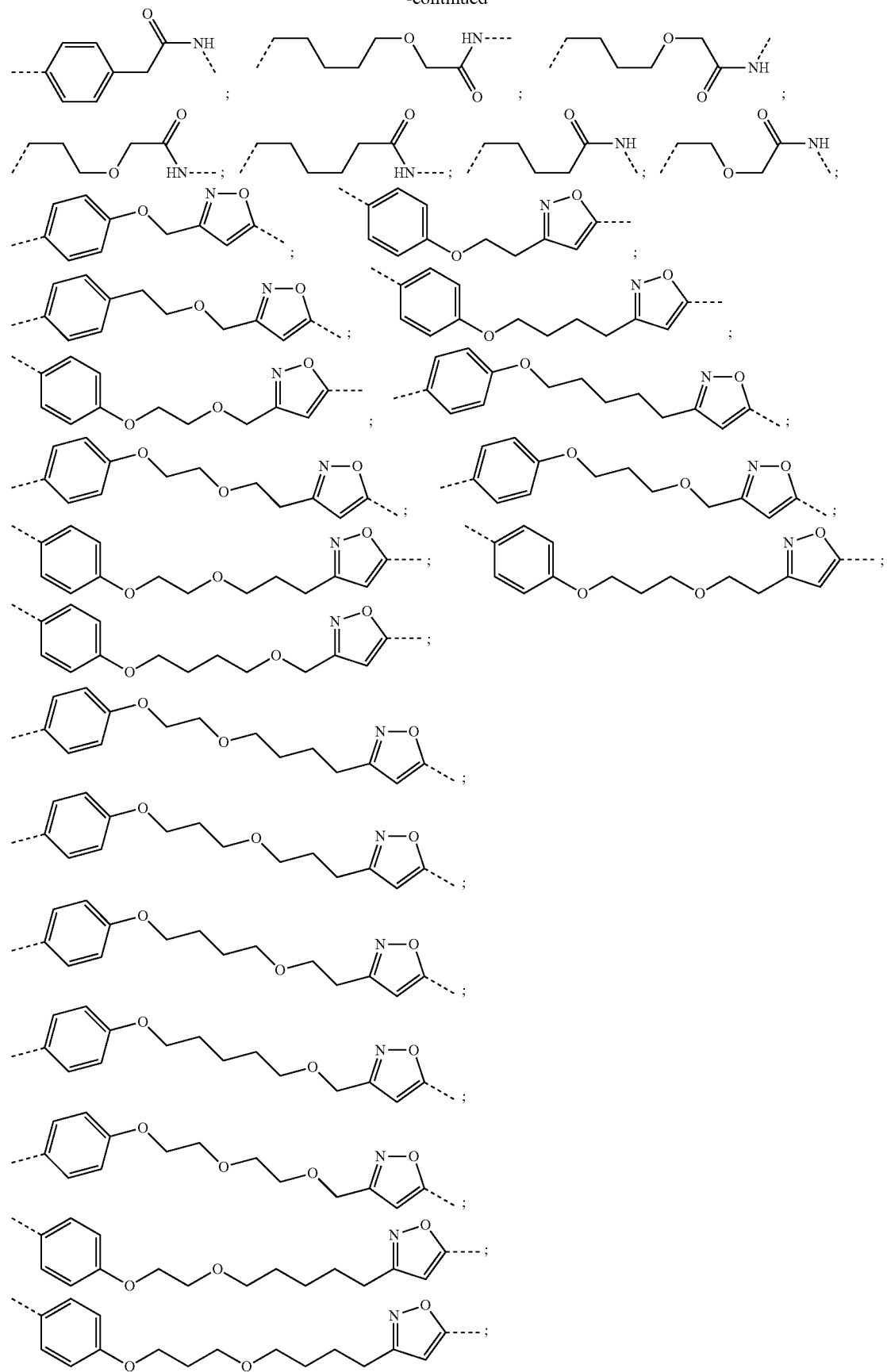

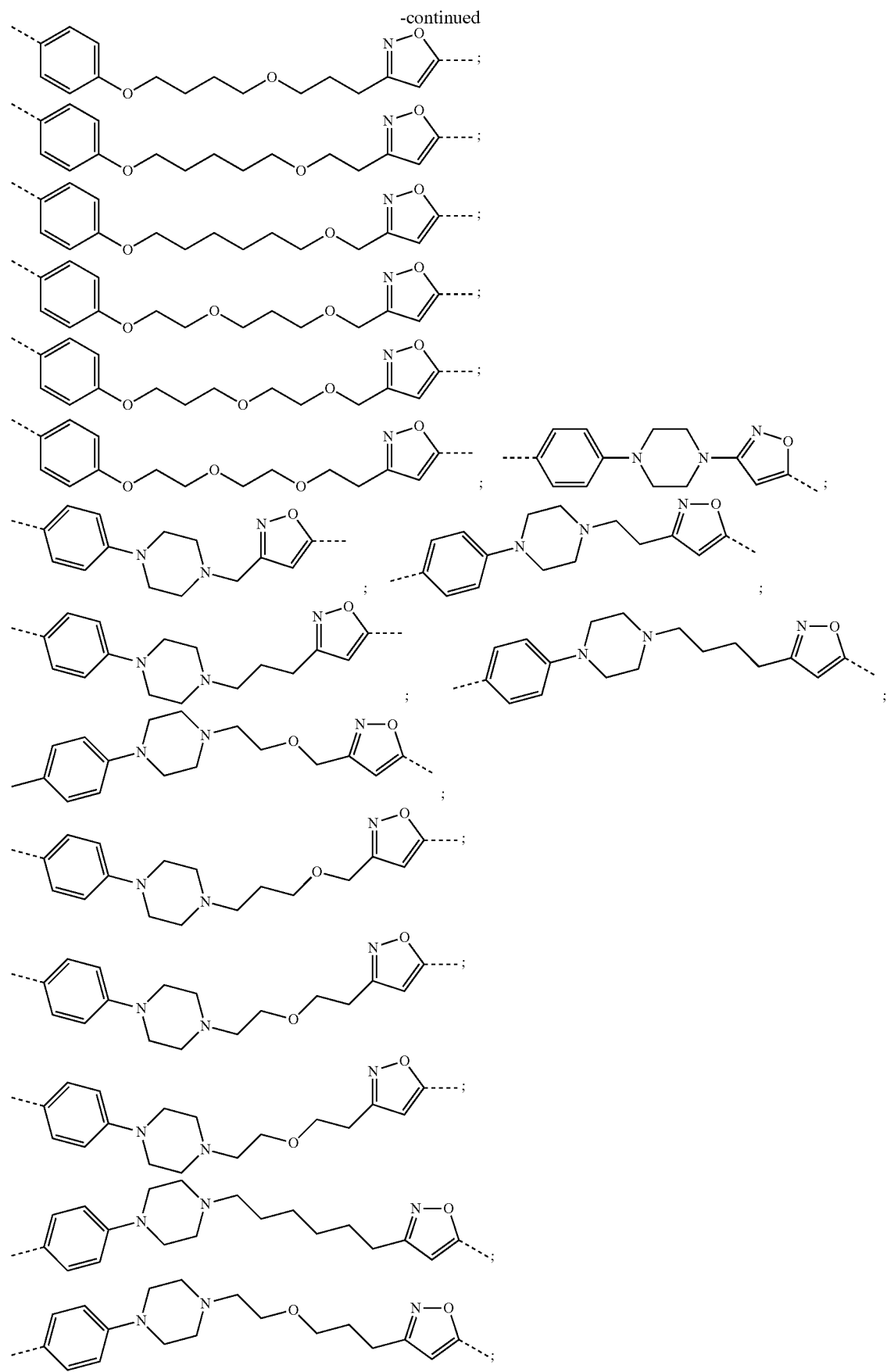

-continued
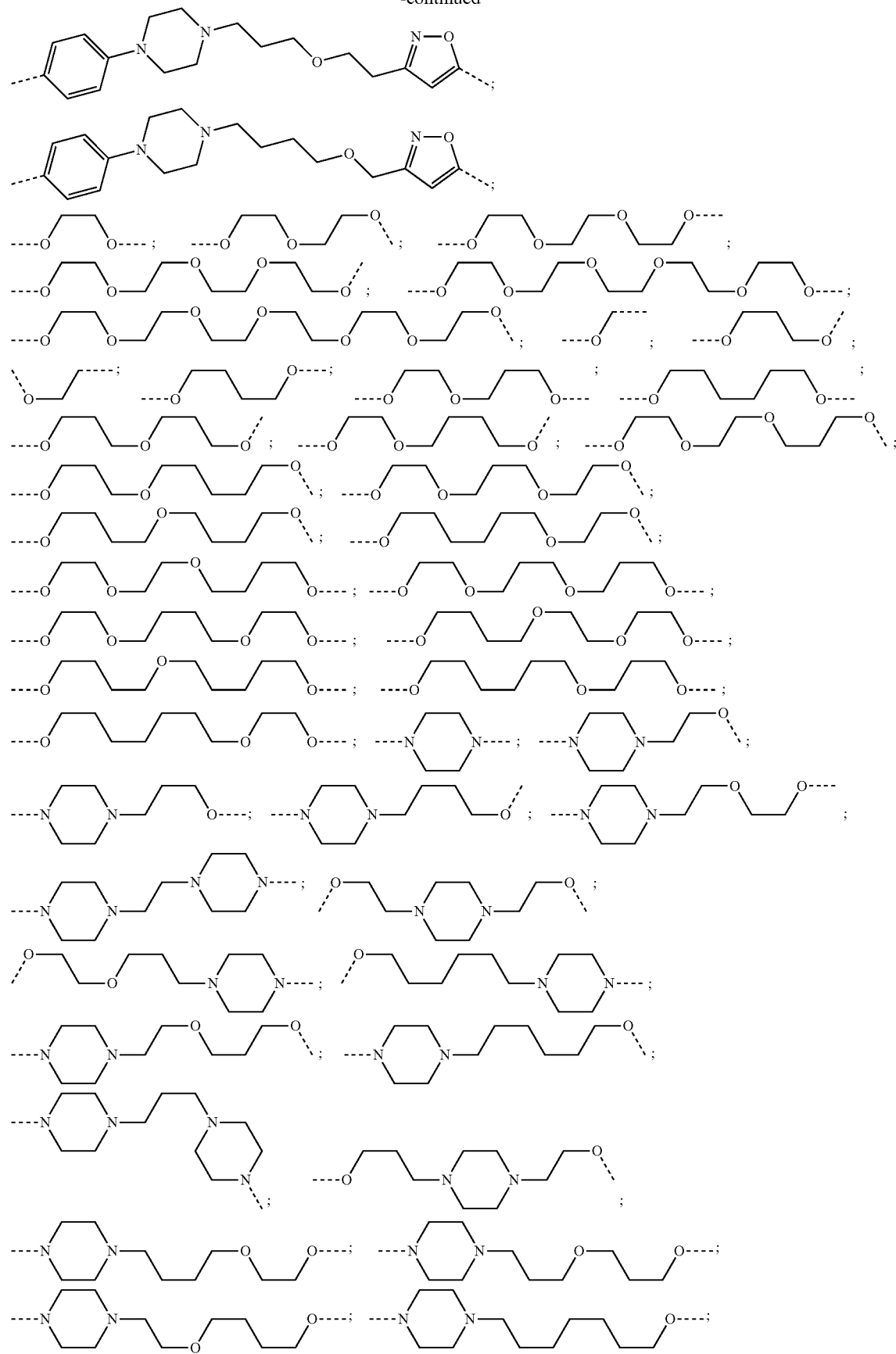

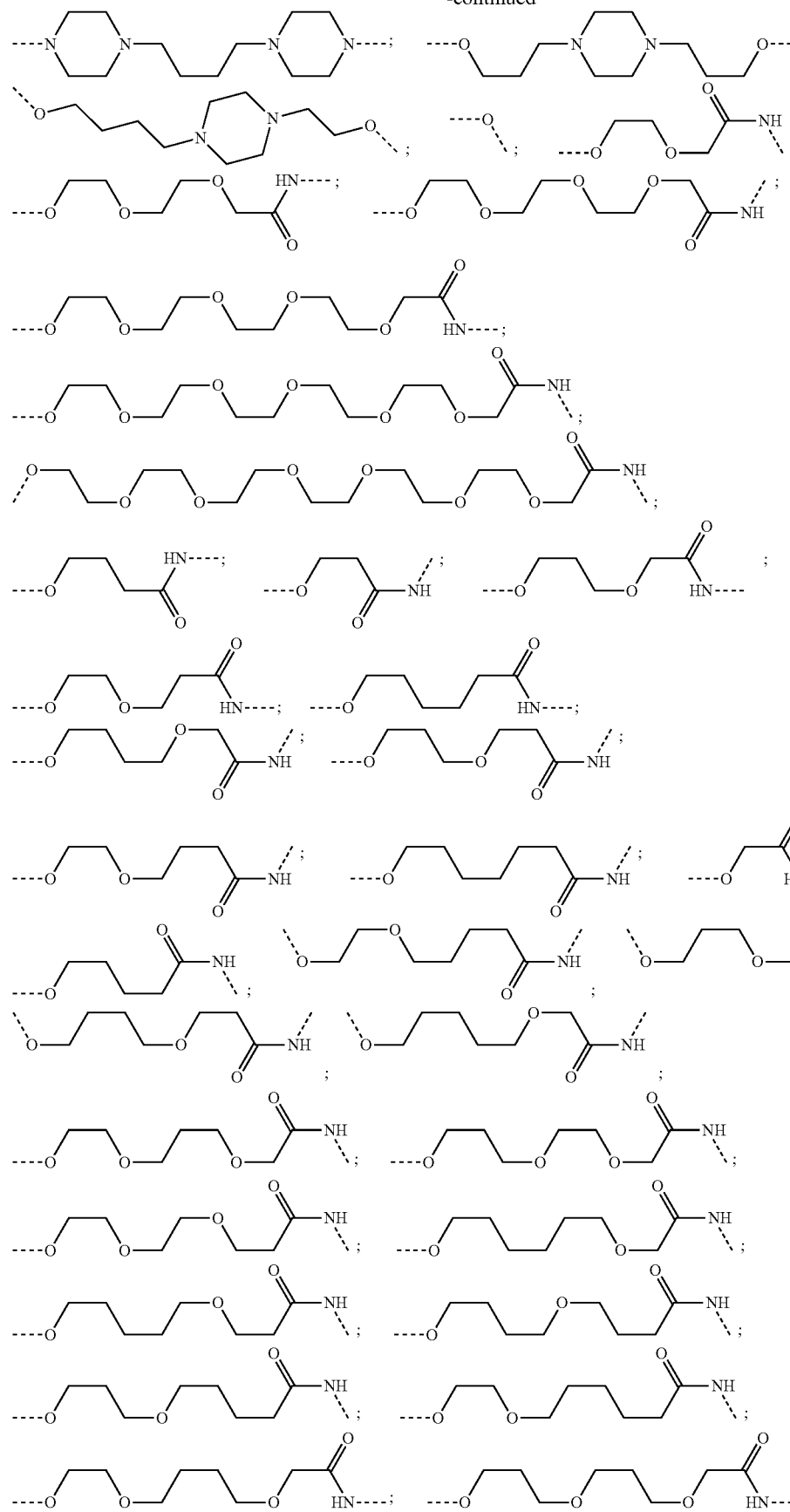

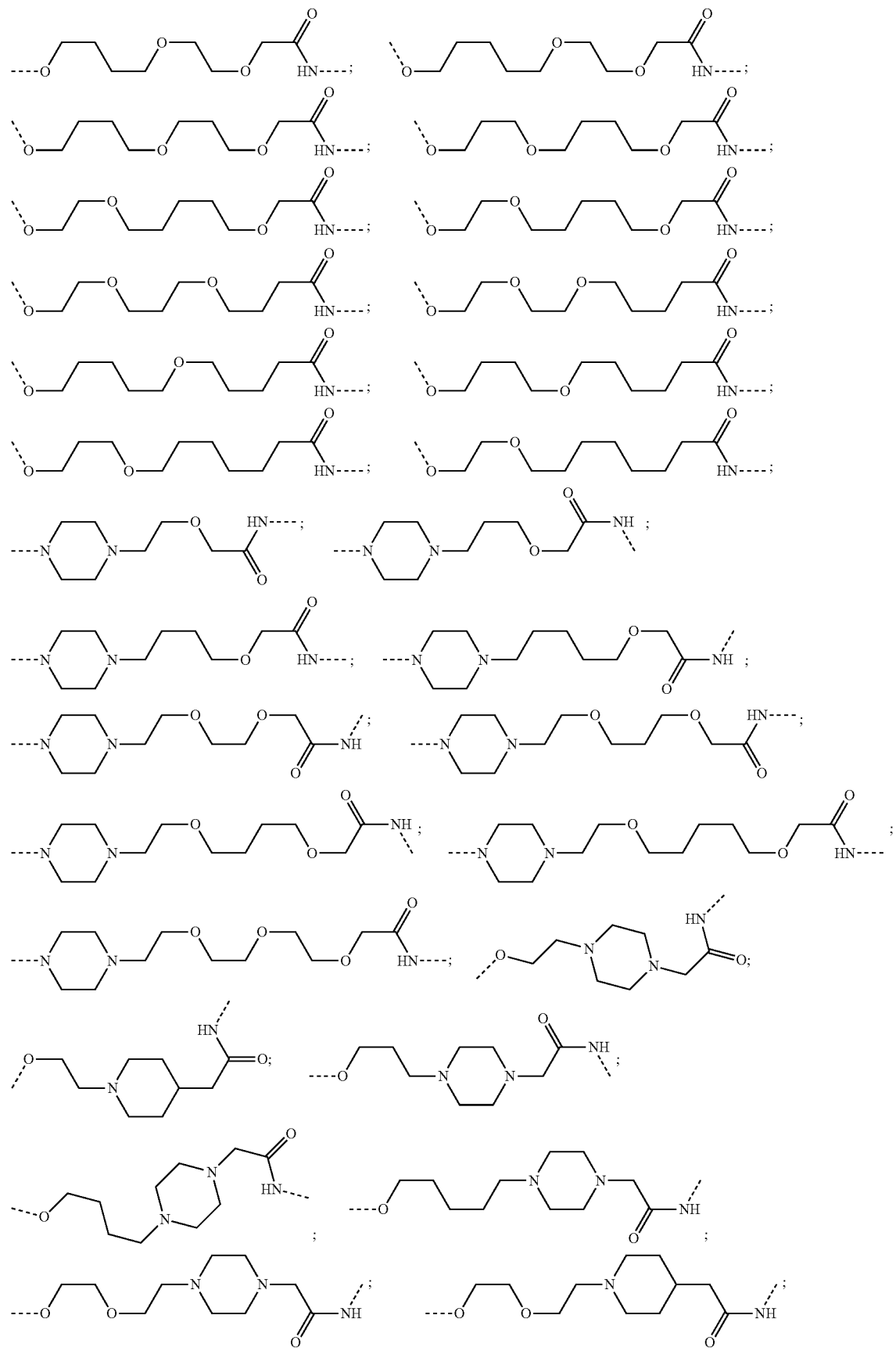

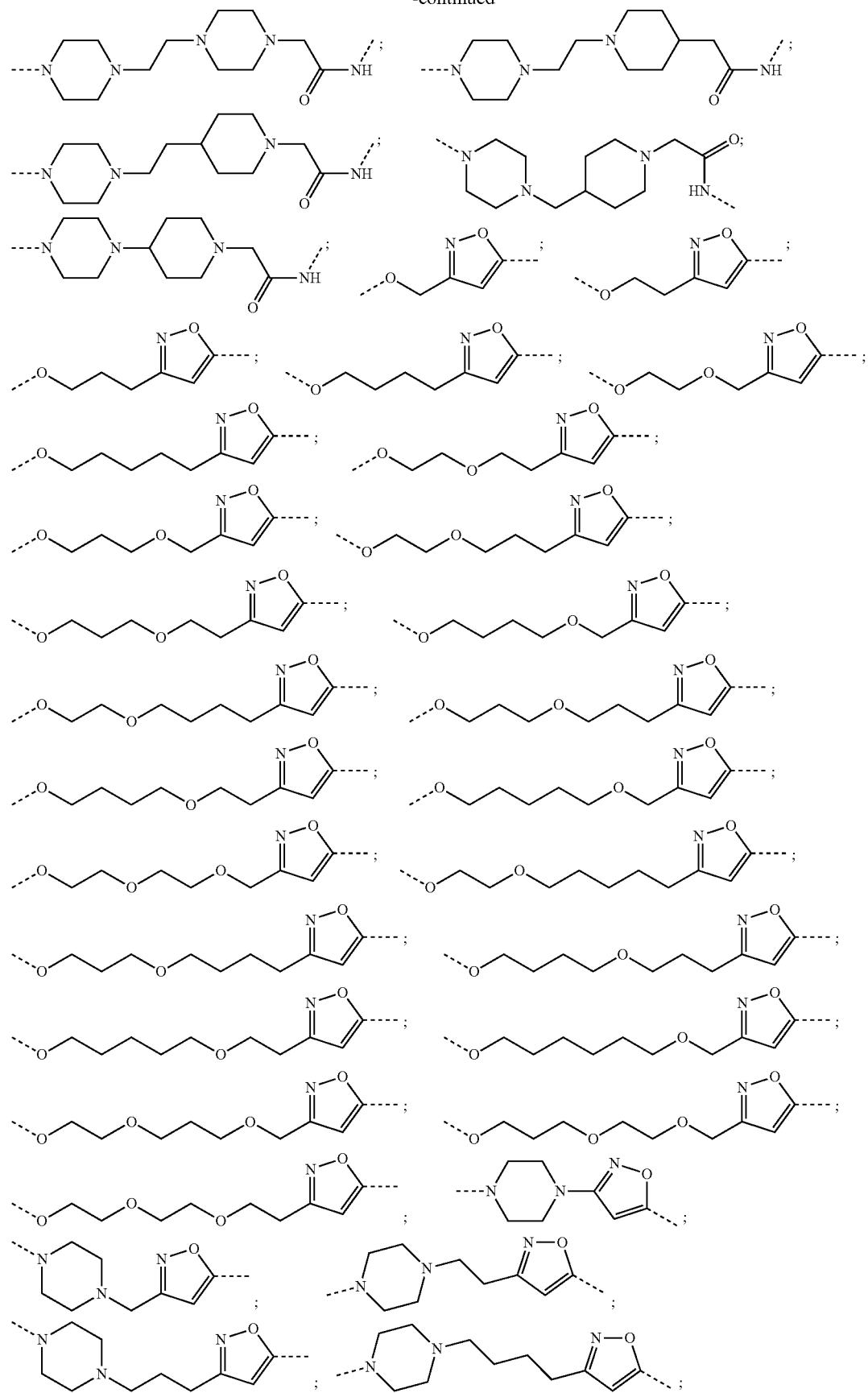

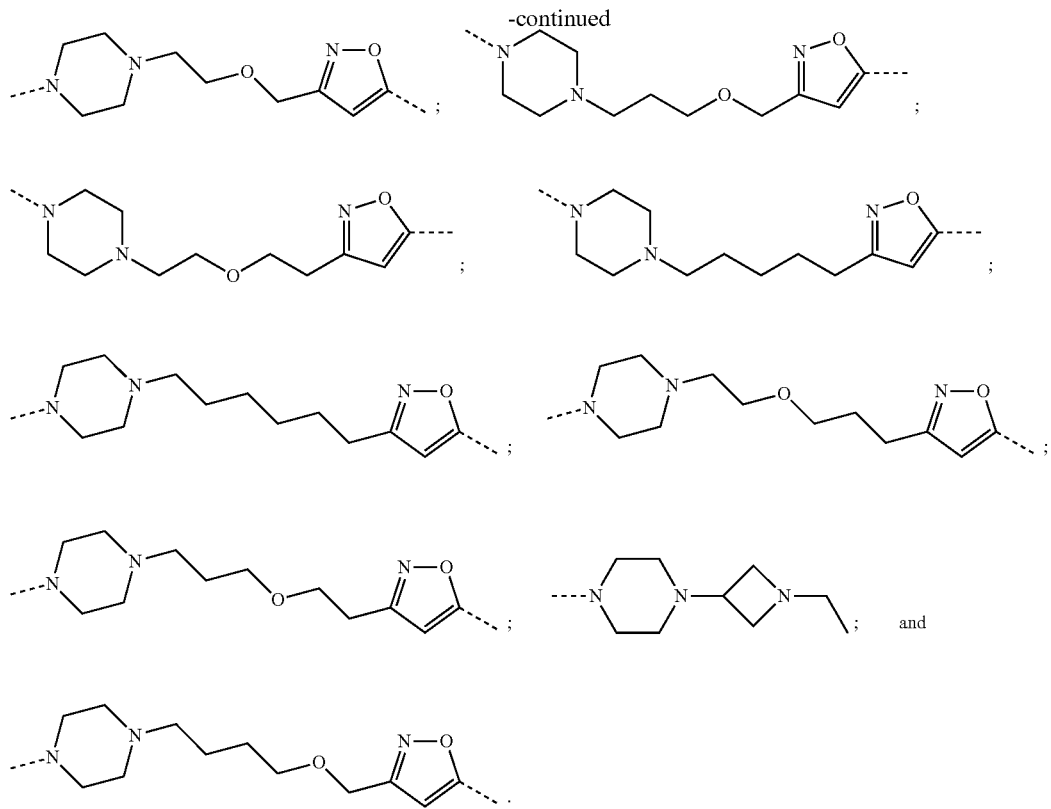

In additional embodiments, the linker (L) comprises a structure selected from, but not limited to, the structure shown below, where a dashed line indicates the attachment point to the PTM or ULM moieties:

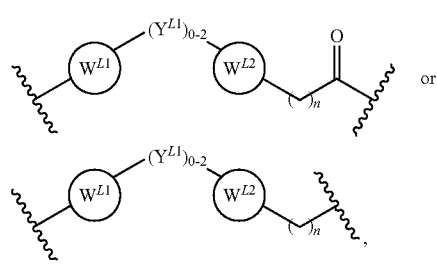

wherein:
W$^{L1}$ and W$^{L2}$ are each independently a 4-8 membered ring with 0-4 heteroatoms, optionally substituted with R$^Q$, each R$^Q$ is independently a H, halo, OH, CN, CF$_3$, C$_1$-C$_6$ alkyl (linear, branched, optionally substituted), C$_1$-C$_6$ alkoxy (linear, branched, optionally substituted), or 2 R$^Q$ groups taken together with the atom they are attached to, form a 4-8 membered ring system containing 0-4 heteroatoms;
Y$^{L1}$ is each independently a bond, C$_1$-C$_6$ alkyl (linear, branched, optionally substituted) and optionally one or more C atoms are replaced with O; or C$_1$-C$_6$ alkoxy (linear, branched, optionally substituted);
n is 0-10; and
a dashed line indicates the attachment point to the PTM or ULM moieties.

In additional embodiments, the linker (L) comprises a structure selected from, but not limited to, the structure shown below, where a dashed line indicates the attachment point to the PTM or ULM moieties:

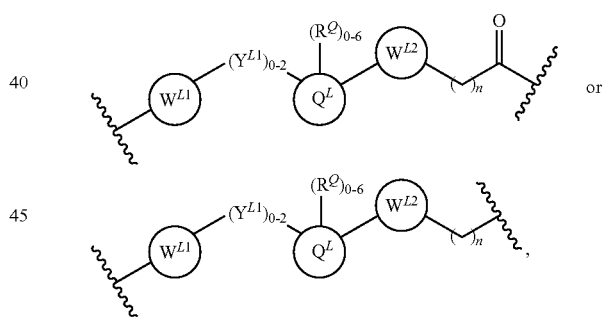

wherein:
W$^{L1}$ and W$^{L2}$ are each independently aryl, heteroaryl, cyclic, heterocyclic, C$_{1-6}$ alkyl, bicyclic, biaryl, biheteroaryl, or biheterocyclic, each optionally substituted with R$^Q$, each R$^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 R$^Q$ groups taken together with the atom they are attached to, form a 4-8 membered ring system containing 0-4 heteroatoms;
Y$^{L1}$ is each independently a bond, NR$^{YL1}$, O, S, NR$^{YL2}$, CR$^{YL1}$R$^{YL2}$, C═O, C═S, SO, SO$_2$, C$_1$-C$_6$ alkyl (linear, branched, optionally substituted) and optionally one or more C atoms are replaced with O; C$_1$-C$_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described herein, which binds to a target protein, e.g., EGFR or polypeptide derived therefrom, which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

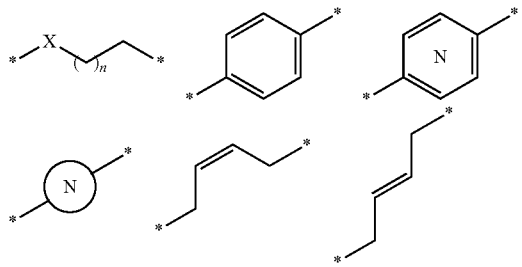

-continued

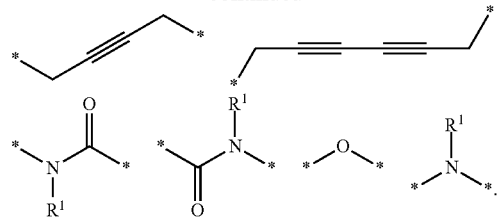

The X is selected from the group consisting of O, N, S, S(O) and $SO_2$; n is integer from 1-5, 5;

$R^{L1}$ is hydrogen or alkyl,

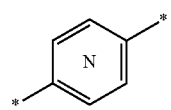

is a mono- or bicyclic aryl or heteroaryl optionally substituted with 1-3 substituents selected from alkyl, halogen, haloalkyl, hydroxy, alkoxy or cyano;

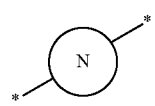

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Without being limited by any particular theory, the inventors believe that the composition and structure of the linker, although unlimited in principal, can have significant effects on the efficacy and potency of the bifunctional compound as described herein; perhaps due to modulation of the interaction between the ULM and the PTM. However, the linker can be optimized according to the present teachings without undue experimentation.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a moiety that binds to a target protein of interest. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to an RTK target protein, including, by way of non-limiting example, EGFR, HER2, c-MET, IGFR. The compositions described below exemplify some of the members of small molecule target protein binding moieties. Such small molecule target protein binding moieties also include pharmaceutically acceptable salts, enantiomers, solvates and polymorphs, prodrug and deuterated forms of the compounds. These binding moieties are linked to the ubiquitin ligase binding moiety preferably through a linker as described herein in order to present the RTK (to which the protein target moiety is bound) in proximity to the ubiquitin ligase for ubiquitination and degradation.

The present disclosure may be used to treat a number of disease states and/or conditions, including any disease state and/or condition in which RTK proteins are dysregulated, e.g., cancer and/or inflammatory disorders, where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is an inflammatory disorder.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer and/or an inflammatory disorder, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

As used herein, unless the context indicates otherwise, the term "target protein" is used to describe a protein or polypeptide, e.g., an RTK, such as EGFR, HER2, c-MET, IGFR, which is a target for binding to a compound according to the present disclosure and degradation by ubiquitin ligase hereunder. Such small molecule target protein binding moieties also include pharmaceutically acceptable salts, enantiomers, solvates and polymorphs, prodrugs and deuterated forms of these compounds, as well as other small molecules that may target a protein of interest. These binding moieties are linked to at least one ULM group (e.g. VLM, CLM, ILM, and/or MLM) through at least one linker group L. In certain aspects, target proteins, which may be bound to the protein target moiety and degraded by the ligase to which the ubiquitin ligase binding moiety is bound, include any protein or peptide, including fragments thereof, analogues thereof, and/or homologues thereof.

Epidermal growth factor receptor (EGFR) exists on the cell surface and is activated by binding of its specific ligands, including epidermal growth factor and transforming growth factor α (TGFα). Upon activation by its growth factor ligands, EGFR undergoes a transition from an inactive monomeric form to an active homodimer—although there is some evidence that preformed inactive dimers may also exist before ligand binding. In addition to forming homodimers after ligand binding, EGFR may pair with another member of the ErbB receptor family, such as ErbB2/Her2/neu, to create an activated heterodimer. There is also evidence to suggest that clusters of activated EGFRs form, although it remains unclear whether this clustering is important for activation itself or occurs subsequent to activation of individual dimers.

EGFR dimerization stimulates its intrinsic intracellular protein-tyrosine kinase activity. As a result, autophosphorylation of several tyrosine (Y) residues in the C-terminal domain of EGFR occurs. These include Y992, Y1045, Y1068, Y1148 and Y1173, as shown in the adjacent diagram. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. Such proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

Mutations that lead to EGFR overexpression (known as upregulation) or overactivity have been associated with a number of cancers, including squamous-cell carcinoma of the lung, anal cancers, glioblastoma, and epithelial tumors of the head and neck. These somatic mutations involving EGFR lead to its constant activation, which produces uncontrolled cell division. In glioblastoma a more or less specific mutation of EGFR, called EGFRvIII is often observed. Mutations, amplifications or misregulations of EGFR or family members are implicated in about 30% of all epithelial cancers. Aberrant EGFR signaling has been implicated in inflammatory disorders, e.g., psoriasis, eczema and atherosclerosis.

In certain embodiments, the description provides compositions and methods for treating an EGFR-related disease or disorder. In certain embodiments, the EGFR-related disease or disorder is at least one of squamous-cell carcinoma of the lung, colon and anal cancers, glioblastoma, and epithelial tumors of the head and neck, psoriasis, eczema and atherosclerosis or a combination thereof.

The identification of EGFR as an oncogene has led to the development of anticancer therapeutics directed against EGFR (called "EGFR inhibitors"), including gefitinib, erlotinib, afatinib, brigatinib and icotinib for lung cancer, and cetuximab for colon cancer. More recently AstraZeneca has developed Osimertinib, a third generation tyrosine kinase inhibitor.

Many therapeutic approaches are aimed at the EGFR. Cetuximab and panitumumab are examples of monoclonal antibody inhibitors. However the former is of the IgG1 type, the latter of the IgG2 type. Other monoclonals in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method is using small molecules to inhibit the EGFR tyrosine kinase, which is on the cytoplasmic side of the receptor. Without kinase activity, EGFR is unable to activate itself, which is a prerequisite for binding of downstream adaptor proteins. By halting the signaling cascade in cells that rely on this pathway for growth, tumor proliferation and migration is diminished or inhibited. Gefitinib, erlotinib, brigatinib and lapatinib (mixed EGFR and ERBB2 inhibitor) are examples of small molecule kinase inhibitors.

CimaVax-EGF, an active vaccine targeting EGF as the major ligand of EGFR, uses a different approach, raising antibodies against EGF itself, thereby denying EGFR-dependent cancers of a proliferative stimulus; it is in use as a cancer therapy against non-small-cell lung carcinoma (the most common form of lung cancer).

The protein target may be used in screens that identify compound moieties which bind to the protein and by incorporation of the moiety into compounds according to the present disclosure, the level of activity of the protein may be altered for therapeutic end result.

The compositions described below exemplify some of the members of EGFR-binding PTMs that can be incorporated into PROTAC compounds as described herein. Such small molecule target protein binding moieties also include pharmaceutically acceptable salts, enantiomers, solvates and polymorphs, prodrugs and deuterated forms of these compounds, as well as other small molecules that may target a protein of interest.

In certain exemplary embodiments, the PTM (protein-targeting moiety) of the PROTAC compound as described herein is selected from EAI045, afatinib, brigatinib, cabozantinib, crizotinib, dacomitinib, erlotinib, foretinib, gefitinib, icotinib, imatinib, lapatinib, lenvatinib, motesanib, neratinib, osimertinib, pazopanib, suntinib, tivantinib, vandetanib, INCB28060, AMG-458, PF-04217903, PF-02341066, E7050, MK-2461, MBS-777607, JNJ-38877605, ARQ197, GSK/1363089/XL880, XL184, analogs, derivatives, polymorphs or solvates thereof.

In certain exemplary embodiments, the PTM (protein-targeting moiety) of the PROTAC compound as described herein is represented by the general formulas I through XVII, and embodiments described. As described herein, the PTMs are coupled via a linker moiety to a ULM. It is contemplated that the linker moiety can be conjugated at any location desired on the PTM. In certain preferred embodiments, the linker moiety is conjugated to at least one R group of the structures as shown and described below.

In one embodiment, PTMs of the PROTACs as described herein comprise the moiety represented by the formula I:

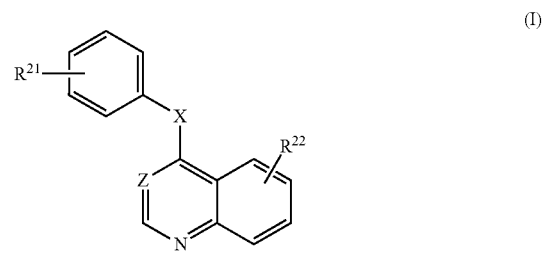

wherein Z is selected from N, CH or C—CN;

X is N-alkyl, amido, NH, or O;

$R^{21}$ is 1 to 3 substituents independently selected from H, halogen, alkyl, e.g., C1-C6 alkyl, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkoxy, amino, alkylamino, e.g., C1-C6 alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprises 1 or more heteroatoms selected from O, N, and S, aryloxy, e.g., C5-C10 aryloxy, and heteroaryloxy, e.g., C5-C10 heteroaryloxy wherein the heteroaryl comprises 1 or more heteroatoms selected from O, N, and S, arylalkyl, heteroarylalkyl, arylalkyloxy and heteroarylalkyloxy, wherein the said aryl, heteroaryl, aryloxy and heteroaryloxy can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano;

$R^{22}$ is 1 to 2 substituents independently selected from H, halogen, alkyl, e.g., C1-C6 alkyl, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkoxy, amino, alkylamino, e.g., C1-C6 alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, furanyl, alkyl or alkylamino substituted furanyl or heterocycloalkyl, wherein the said aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino, cyano or $R^{99}SO_2(CH_2)_sNHCH_2$—, where $R^{99}$ is an alkyl, e.g., C1-C6 alkyl, and s is an integer between 0 and 3, or one or both of the $R^{22}$ substituents can be further selected from —$OR^{23}$ or —$NHC(O)R^{24}$, where $R^{23}$ is selected from hydroxyalkyl, e.g., C1-C6 hydroxyalkyl, alkoxyalkyl, e.g., C1-C6 alkoxyalkyl, aminoalkyl, alkylaminoalkyl, dialkylaminoalkyl, aryl, e.g., C5-C10 aryl, toluene optionally substituted with an alkyl or halogen, heteroaryl, e.g., C5-C10 heteroaryl, cycloalkyl, e.g., C3-C10 cycloalkyl, heterocycloalkyl, C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, arylalkyl, e.g., C5-C10 arylalkyl, cycloalkylalkyl, or heterocycloalkylalkyl as described herein, with the proviso that the two heteroatoms are not attached to the same carbon atom, and $R^{24}$ is selected from alkyl or from the groups below:

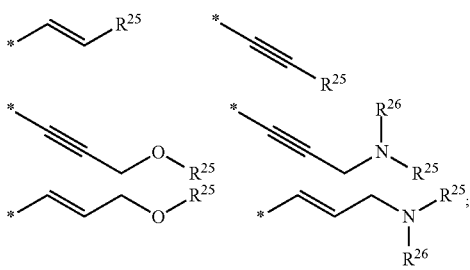

and $R^{25}$ and $R^{26}$ are independently selected from hydrogen or alkyl, e.g., C1-C6 alkyl, with the proviso that $R^{25}$ and $R^{26}$ taken together with the N atom, to which they are connected, may form a heterocycloalkyl.

In certain embodiments, the PTM of formula I comprises a linker, wherein the linker is a chemical moiety as described herein coupling the PTM to the ULM group. In certain additional embodiments, one or more of the R groups of formula I comprises a linker, wherein the linker is a chemical moiety as described herein coupling the PTM to the ULM group.

In certain additional embodiments, one or more of $R^{21}$, $R^{22}$, $R^{23}$, $R^{24}$, $R^{25}$ or $R^{26}$ groups of formula I is coupled to a linker, wherein the linker is a chemical moiety as described herein coupling the PTM to the ULM group.

In certain embodiments, formula I has the structure:

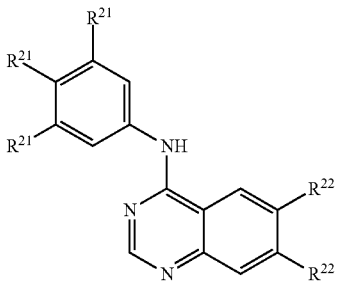

I-2 wherein each $R^{21}$ is independently selected from H, halogen, Cl, F, alkyl, e.g., C1-C6 alkyl, haloalkyl, e.g., C1-C6 haloalkyl, alkynyl, e.g., C1-C6 alkynyl, alkoxy, e.g., C1-C6 alkoxy, arylmethoxy and heteroarylmethoxy, wherein the said aryl and heteroaryl can be further substituted with 1 to 2 substituents selected from alkyl, halogen and haloalkyl; and each $R^{22}$ is independently selected from H, N, halogen, alkyl, e.g., C1-C6 alkyl, haloalkyl, e.g., C1-C6 haloalkyl, alkoxy, e.g., C1-C6 alkoxy, methoxy, ethoxy, amino, amido, alkylamino, dialkylamino, cyano, aryl, e.g., C5-C10 aryl, heteroaryl, e.g., C5-C10 heteroaryl comprising from 1 or more heteroatoms selected from N, O and S, furan, pyrrole, imidazole, oxazole, isoxazole, thazole, cycloalkyl, e.g., C3-C10 cycloalkyl, heterocycloalkyl, e.g., C3-C10 heterocycloalkyl wherein the heterocycle comprises from 1 or more heteroatoms selected from N, O, and S, wherein the said aryl or heteroaryl can be further substituted with 1 to 2 substituents selected from alkyl, e.g., C1-C6 alkyl, halogen, haloalkyl, cyano or $R^{99}SO2(CH_2)sNHCH2$-, where $R^{99}$ is an alkyl, e.g., C1-C6 alkyl, and s is an integer between 0 and 3, —$OR^{23}$ or —$NHC(O)R^{24}$, where $R^{23}$ is selected from hydroxyalkyl, alkoxyalkyl, aminoalkyl, alkylaminoalkyl, or dialkylaminoalkyl, with the proviso that the two heteroatoms are not attached to the same carbon atom, and $R^{24}$ is selected from the groups below:

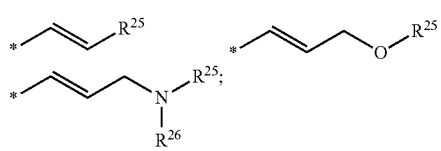

and $R^{25}$ and $R^{26}$ are independently selected from hydrogen or alkyl with the proviso that $R^{25}$ and $R^{26}$ taken together with the N atom, to which they are connected, may form a heterocycloalkyl.

In certain embodiments, the PTM of formula I comprises a linker, wherein the linker is a chemical moiety as described herein coupling the PTM to the ULM group. In certain additional embodiments, one or more of the R groups of formula I comprises a linker, wherein the linker is a chemical moiety as described herein coupling the PTM to the ULM group.

In certain additional embodiments, one or more of $R^{21}$, $R^{22}$, $R^{23}$, $R^{24}$, $R^{25}$ or $R^{26}$ groups of formula I is coupled to a linker, wherein the linker is a chemical moiety as described herein coupling the PTM to the ULM group.

In certain embodiments, formula I has the structure:

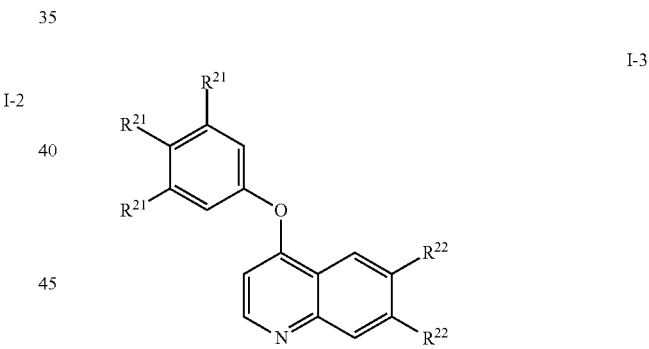

I-3 wherein each $R^{21}$ s independently selected from H, halogen, Cl, F, alkyl, e.g., C1-C6 alkyl, haloalkyl, e.g., C1-C6 haloalkyl, alkynyl, e.g., C1-C6 alkynyl, alkoxy, e.g., C1-C6 alkoxy, arylmethoxy, e.g., C5-C10 arylmethoxy, heteroarylmethoxy, e.g., C5-C10 heteroarylmethoxy wherein the heteroaryl comprises from 1 or more heteroatoms selected from N, O, and S, or

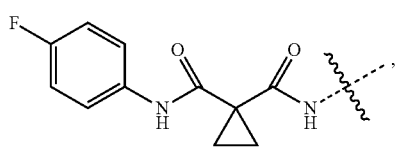

wherein the said aryl and heteroaryl can be further substituted with 1 to 2 substituents selected from alkyl, halogen and haloalkyl; and each $R^{22}$ is independently selected from H, N, halogen, alkyl, e.g., C1-C6 alkyl, haloalkyl, alkoxy, methoxy, amino, amido, alkylamino, dialkylamino, cyano, aryl, heteroaryl, furan, pyrrole, imidazole, oxazole, isoxazole, thiazole, cycloalkyl, heterocycloalkyl—wherein the said aryl or heteroaryl can be further substituted with 1 to 2 substituents selected from alkyl, halogen, haloalkyl, cyano or $R^{99}SO2(CH2)sNHCH2$-, where $R^{99}$ is an alkyl, and s is an integer between 0 and 3, —$OR^{23}$ or —$NHC(O)R^{24}$, where $R^{23}$ is selected from hydroxyalkyl, alkoxyalkyl, aminoalkyl, alkylaminoalkyl, or dialkylaminoalkyl, with the proviso that the two heteroatoms are not attached to the same carbon atom, and $R^{24}$ is selected from the groups below:

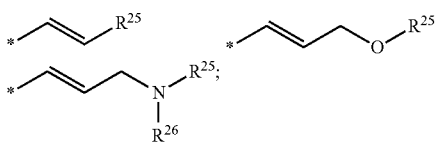

and $R^{25}$ and $R^{26}$ are independently selected from hydrogen or alkyl with the proviso that $R^{25}$ and $R^{26}$ taken together with the N atom, to which they are connected, may form a heterocycloalkyl.

In certain additional embodiments, one or more of $R^{21}$, $R^{22}$, $R^{23}$, $R^{24}$, $R^{25}$ or $R^{26}$ groups of formula I is coupled to a linker, wherein the linker is a chemical moiety as described herein coupling the PTM to the ULM group.

In certain embodiments, PTMs of the PROTACs as described herein comprise the moiety represented by formula I as above:

wherein Z is N or C—CN, most preferably N;

$R^{21}$ is 1 to 2 substituents independently selected from H, halogen, alkyl, haloalkyl, alkynyl, alkoxy, arylmethyloxy and heteroarylmethyloxy, wherein the said aryl and heteroaryl can be further substituted with 1 to 2 substituents selected from alkyl, halogen and haloalkyl.

$R^{22}$ is 1 or 2 substituents each independently selected from H, halogen, alkyl, haloalkyl, alkoxy, amino, alkylamino, dialkylamino, cyano, aryl, heteroaryl, cycloalkyl, heterocycloalkyl—wherein the said aryl or heteroaryl can be further substituted with 1 to 2 substituents selected from alkyl, halogen, haloalkyl, cyano or $R^{99}SO2(CH2)sNHCH2$-, where $R^{99}$ is an alkyl, and s is an integer between 0 and 3—or R22 is 1 to 2 substituents selected from —OR23 or —NHC(O)$R^{24}$ where $R_{23}$ is selected from hydroxyalkyl, alkoxyalkyl, aminoalkyl, alkylaminoalkyl, or dialkylaminoalkyl, with the proviso that the two heteroatoms are not attached to the same carbon atom, and $R^{24}$ is selected from the groups below:

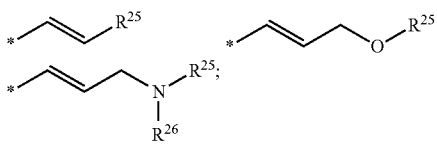

and $R^{25}$ and $R^{26}$ are independently selected from hydrogen or alkyl with the proviso that $R^{25}$ and $R^{26}$ taken together with the N atom, to which they are connected, may form a heterocycloalkyl.

In certain embodiments, the PTM of formula I comprises the structure:

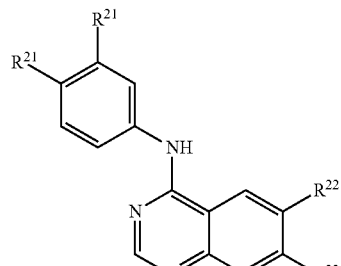

I-4 wherein each $R^{21}$ is independently selected from H, a halogen, Cl, or F; and each $R^{22}$ is independently selected from H, O, N, C1-C6 alkoxy, or methoxy, amine, amido or

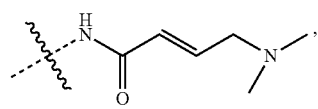

O-linked 5- or 7-membered ring, e.g., ozaxole, isoxazole, imidazole, pyrrole, pyrrolidinyl, pyrazole, furan, or thiazole, and wherein at least one $R^{22}$ group is coupled to a linker group, wherein linker is a chemical moiety coupling the PTM to a ULM group.

In certain additional embodiments, one or more of $R^{21}$, $R^{22}$, $R^{23}$, $R^{24}$, $R^{25}$ or $R^{26}$ groups of formula I is coupled to a linker, wherein the linker is a chemical moiety as described herein coupling the PTM to the ULM group.

In certain embodiments, the PTM of formula I has the structure:

-continued

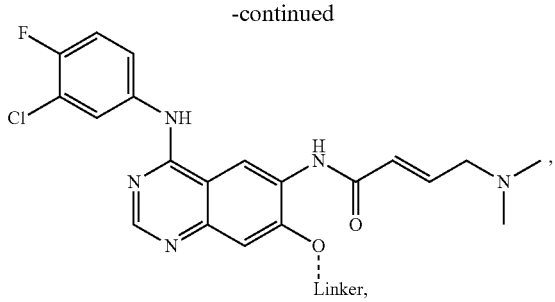
Linker, wherein the linker (L) is a chemical moiety coupling the PTM to a ULM group.

In certain embodiments, the PTM of formula I comprises the structure selected from:

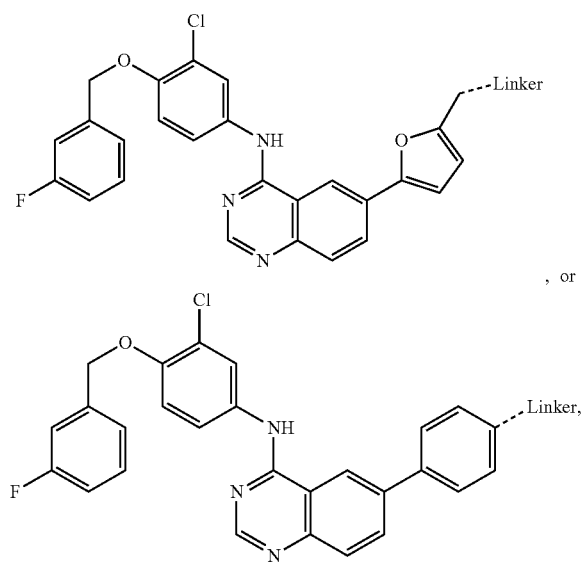

wherein linker (L) is a chemical moiety coupling the PTM to a ULM group.

In one embodiment, PTMs of the PROTACs as described herein comprise the moiety represented by the formula II:

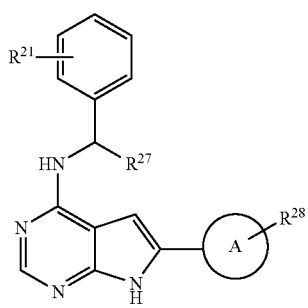

II wherein $R^{21}$ is 1 to 3 substituents independently selected from H, halogen, Cl, F, alkyl, e.g., C1-C6 alkyl, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkoxy, amino, alkylamino, dialkylamino, cyano, aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, aryloxy and heteroaryloxy, arylalkyl, arylalkyl, e.g., C5-C10 arylalkyl, heteroarylalkyl, heteroarylalkyl, e.g., C5-C10 heteroarylalkyl wherein the heteroaryl comprises 1 or more heteroatoms selected from O, N, and S, arylalkyloxy and heteroarylalkyloxy, wherein the said aryl, heteroaryl, aryloxy and heteroaryloxy can be further substituted with 1 to 2 substituents selected from alkyl, e.g., C1-C6 alkyl, halogen, haloalkyl, haloalkyl, e.g., C1-C6 haloalkyl, hydroxyl, alkoxy, alkoxy, e.g., C1-C6 alkoxy, amino, alkylamino, dialkylamino and cyano;

$R^{27}$ is selected from H, alkyl, e.g., C1-C6 alkyl, hydroxyalkyl and alkoxyalkyl;

A is an aryl, aryl, e.g., C5-C10 aryl, a phenyl, or a heteroaryl, e.g., C3-C10 heteroaryl comprising 1 or more heteroatoms selected from O, N, and S; and $R^{28}$ is 1 to 2 substituents independently selected from H, O, N, halogen, alkyl, e.g., C1-C6 alkyl, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkoxy, alkylamino, e.g., C1-C6 alkylamino, dialkylamino, cyano, aryl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano.

In certain embodiments, the PTM of formula II comprises a linker, wherein the linker is a chemical moiety as described herein coupling the PTM to the ULM group. In certain additional embodiments, one or more of the R groups of formula II comprises a linker, wherein the linker is a chemical moiety as described herein coupling the PTM to the ULM group.

In certain additional embodiments, one or more of $R^{21}$, $R^{27}$ or $R^{28}$ groups of formula II is coupled to a linker, wherein the linker is a chemical moiety as described herein coupling the PTM to the ULM group.

In certain embodiments, PTMs of the PROTACs as described herein comprise the moiety represented by the formula II as above:

wherein $R^{21}$ is 1 to 2 substituents independently selected from H, halogen, Cl, F, alkyl, e.g., C1-C6 alkyl, haloalkyl, e.g., C1-C6 haloalkyl, alkynyl, e.g., C1-C6 alkynyl, alkoxy, e.g., C1-C6 alkoxy, arylmethoxy, e.g., a 5-7 membered ring arylmethoxy, cyano, and heteroarylmethoxy, wherein the said aryl and heteroaryl can be further substituted with 1 to 2 substituents selected from alkyl, e.g., C1-C6 alkyl, halogen and haloalkyl, e.g., C1-C6 haloalkyl;

$R^{27}$ is selected from H, methyl, ethyl, hydroxymethyl and methoxymethyl;

A is phenyl or a pyridyl, most preferably phenyl; and $R^{28}$ is 1 to 2 substituents independently selected from H, O, N, halogen, alkyl, e.g., C1-C6 alkyl, haloalkyl, e.g., C1-C6 haloalkyl, and cyano.

In certain embodiments of formula II, the PTM has the structure:

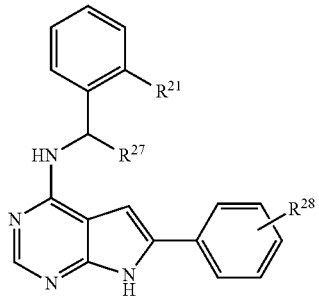

II-2 wherein $R^{21}$ is H, halogen, Cl, F, alkyl, e.g., C1-C6 alkyl, haloalkyl, alkynyl, alkoxy, arylmethyloxy, cyano, and heteroarylmethyloxy, wherein the said aryl and heteroaryl can be further substituted with 1 to 2 substituents selected from alkyl, halogen and haloalkyl;

$R^{27}$ is selected from H, methyl, ethyl, hydroxymethyl and methoxymethyl; $R^{28}$ is selected from H, O, N, halogen, C1-C6 alkyl, haloalkyl, e.g., C1-C6 haloalkyl, alkenyl, e.g., C2-C6 alkenyl, alkynyl, e.g., C2-C6 alkynyl, alkoxy, e.g., C1-C6 alkoxy, alkylamino, e.g., C1-C6 alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said aryl or heteroaryl can be further substituted with 1 to 2 substituents selected from alkyl, e.g., C1-C6 alkyl, halogen, haloalkyl, hydroxyl, alkoxy, amino, alkylamino, dialkylamino and cyano as defined above.

In certain embodiments, $R^{28}$ is coupled to a linker, wherein the linker is a chemical moiety coupling the PTM to the ULM group.

In certain additional embodiments, one or more of $R^{21}$, $R^{27}$ or $R^{28}$ groups of formula II is coupled to a linker, wherein the linker is a chemical moiety as described herein coupling the PTM to the ULM group.

In one embodiment, PTMs of the PROTACs as described herein comprise the moiety represented by the formula III:

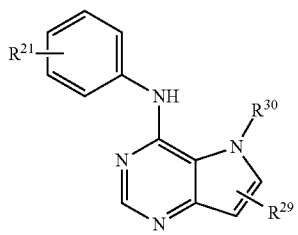

III wherein $R^{21}$ is as described above;
$R^{29}$ is 1 to 2 substituents independently selected from H, halogen, aryl alkyl, haloalkyl, alkoxy and cyano; and
$R^{30}$ is selected from H, hydroxyalkyl, e.g., C1-C6 hydroxyalkyl, alkoxyalkyl, e.g., C1-C6 alkoxyalkyl, aminoalkyl, alkylaminoalkyl, dialkylaminoalkyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, cycloalkylalkyl, or heterocycloalkylalkyl, wherein the said alkyl could be optionally interrupted by —NHC(O)— or —C(O)NH— groups, with the proviso that two heteroatoms are not attached to the same carbon atom.

In certain embodiments, the PTM of formula III, comprises a linker, wherein the linker is a chemical moiety as described herein coupling the PTM to the ULM group. In certain additional embodiments, one or more of the R groups of formula III comprises a linker, wherein the linker is a chemical moiety as described herein coupling the PTM to the ULM group.

In certain additional embodiments, one or more of $R^{21}$, $R^{29}$ or $R^{30}$ groups of formula III is coupled to a linker, wherein the linker is a chemical moiety as described herein coupling the PTM to the ULM group.

In certain embodiments, the PTMs of the PROTACs as described herein comprise the moiety represented by the formula III:

wherein $R^{21}$ is 1 to 2 substituents independently selected from H, halogen, alkyl, e.g., C1-C6 alkyl, haloalkyl, e.g., C1-C6 haloalkyl, alkynyl, e.g., C1-C6 alkynyl, alkoxy, e.g., C1-C6 alkoxy, arylmethyloxy and heteroarylmethyloxy as described herein, wherein the said aryl and heteroaryl can be further substituted with 1 to 2 substituents selected from alkyl, e.g., C1-C6 alkyl, halogen and haloalkyl, e.g., C1-C6 haloalkyl;

$R^{29}$ is 1 substituent selected from H, halogen, alkyl, e.g., C1-C6 alkyl, or haloalkyl, e.g., C1-C6 haloalkyl; and $R^{30}$ is selected from H, hydroxyalkyl, e.g., C1-C6 hydroxyalkyl, alkoxyalkyl, e.g., C1-C6 alkoxyalkyl, aminoalkyl, alkylaminoalkyl, dialkylaminoalkyl, wherein the said alkyl could be optionally interrupted by —NHC(O)— or —C(O)NH— groups, with the proviso that two heteroatoms are not attached to the same carbon atom.

In certain embodiments of formula III, the PTM has the structure:

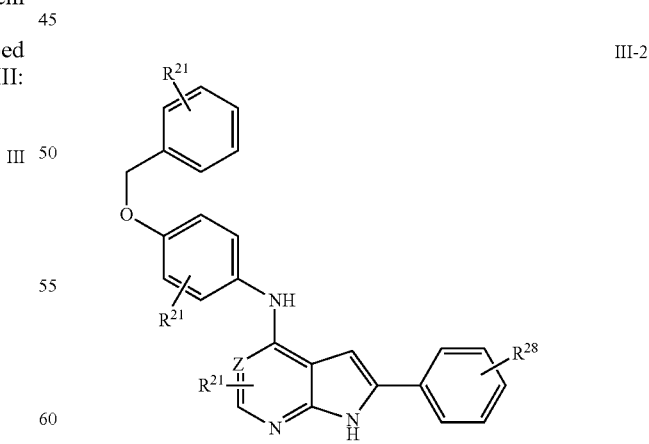

III-2 wherein each $R^{21}$ is independently H, halogen, Cl, F, alkyl, e.g., C1-C6 alkyl, haloalkyl, e.g., C1-C6 haloalkyl, alkenyl, e.g., C2-C6 alkenyl, alkynyl, e.g., C2-C6 alkynyl, alkoxy, e.g., C1-C6 alkoxy, arylmethyloxy, cyano, and heteroarylmethyloxy, wherein the said aryl and heteroaryl can be further substituted with 1 to 2 substituents selected from alkyl, e.g., C1-C6 alkyl, halogen, or haloalkyl, e.g., C1-C6 haloalkyl;

Z is C or N; and $R^{28}$ is defined as above.

In certain additional embodiments, one or more of $R^{21}$ or $R^{28}$ groups of formula III is coupled to a linker, wherein the linker is a chemical moiety as described herein coupling the PTM to the ULM group.

In one embodiment, PTMs of the PROTACs as described herein comprise the moiety represented by the formula IV:

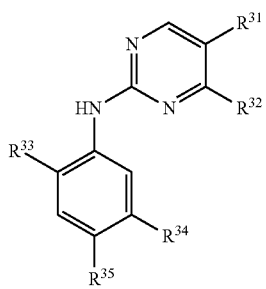

IV wherein $R^{31}$ is selected from H, halogen, Cl, alkyl, e.g., C1-C6 alkyl, haloalkyl, e.g., C1-C6, haloalkyl, $CF_3$, alkoxy, e.g., C1-C6 alkoxy, hydroxyl, cyano, amino, alkylamino, dialkylamino, aryl, e.g., C5-C10 aryl, heteroaryl, e.g., C3-C10 heteroaryl comprising 1 or more heteroatoms selected from O, N, and S, indole, pyrazole, imidazole, cycloalkyl, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said aryl and heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, or cyano;

$R^{32}$ is selected from H, a 5- or 6-membered aryl or heteroaryl, a bicyclic fused aryl or heteroaryl and a bicyclic fused aryl or heteroaryl additionally optionally fused to a cycloalkyl, e.g., C3-C10 cycloalkyl, or a heterocycloalkyl, e.g., C3-C10 heterocycloalkyl wherein the heterocycle comprising 1 or more heteroatoms selected from O, N, and S, wherein the said aryl or heteroaryl is optionally substituted with 1-2 substituents selected from alkyl, e.g., C1-C6 alkyl, halogen, or haloalkyl, e.g., C1-C6 haloalkyl;

$R^{33}$ is selected from H, alkyl, haloalkyl, halogen, alkoxy, hydroxyl, amino, alkylamino, dialkylamino and cyano;

$R^{34}$ is selected from H, O, alkyl, e.g., C1-C6 alkyl, haloalkyl, e.g., C1-C6 haloalkyl, halogen, amino, amido, alkyne, e.g., C2-C6 alkyne, alkoxy, cyano or —NHC(O)$R^{24}$, where $R^{24}$ is $R^{24}$ is selected from the groups below:

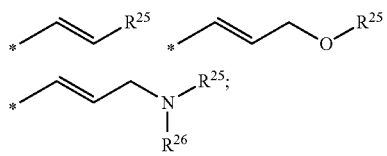

and $R^{25}$ and $R^{26}$ are independently selected from H, N, N(CH$_2$)$_{1-3}$, or alkyl, C1-C6 alkyl, with the proviso that $R^{25}$ and $R^{26}$ taken together with the N atom, to which they are connected, may form a heterocycloalkyl; and $R^{35}$ is selected from —OR$^{36}$ and —NR$^{37}$R$^{38}$, wherein R$^{36}$ is selected from hydroxyalkyl, e.g., C1-C6 hydroxyalkyl, alkoxyalkyl, e.g., C1-C6 alkoxyalkyl, aminoalkyl, alkylaminoalkyl, dialkylaminoalkyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, cycloalkylalkyl or heterocycloalkylalkyl with the proviso that the two heteroatoms are not attached to the same carbon atom, and R$^{37}$ and R$^{38}$ are independently selected from H or alkyl, e.g., C1-C6 alkyl, —NR$^{37}$R$^{38}$, or —NR$^{37}$R$^{38}$ taken together represent a heterocycloalkyl ring, wherein R$^{35}$, R$^{37}$ or R$^{38}$ further optionally substituted with alkyl, e.g., C1-C6 alkyl, hydroxyl, alkoxy, e.g., C1-C6 alkoxy, amino, alkylamino, dialkylamino, heterocycloalkyl, e.g., C3-C10 heterocycloalkyl wherein the heterocycle comprising 1 or more heteroatoms selected from O, N, and S, aminoalkyl, alkylaminoalkyl, dialkylaminoalkyl, heterocycloalkylalkyl or —C(O)R$^{39}$ where R$^{39}$ is an alkyl, e.g., C1-C6 alkyl.

In certain embodiments, the PTM of formula IV comprises a linker, wherein the linker is a chemical moiety as described herein coupling the PTM to the ULM group. In certain additional embodiments, one or more of the R groups of formula IV is coupled to a linker, wherein the linker is a chemical moiety as described herein coupling the PTM to the ULM group.

In certain additional embodiments, one or more of $R^{24}$, $R^{25}$, $R^{26}$, $R^{31}$, $R^{32}$, $R^{33}$, $R^{34}$, $R^{35}$, $R^{36}$, $R^{37}$, $R^{38}$ or $R^{39}$ groups of formula IV is coupled to a linker, wherein the linker is a chemical moiety as described herein coupling the PTM to the ULM group.

In certain embodiments, $R^{32}$ is selected from:

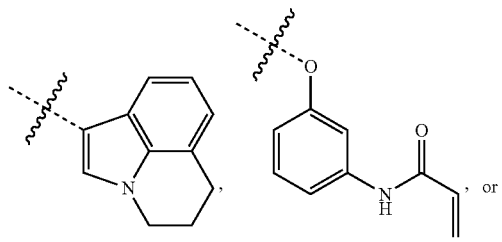

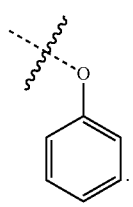

In certain embodiment, the $R^{32}$ group comprises a linker, wherein the linker is a chemical moiety coupling the PTM to the ULM group. For example, in certain embodiments, $R^{32}$ is:

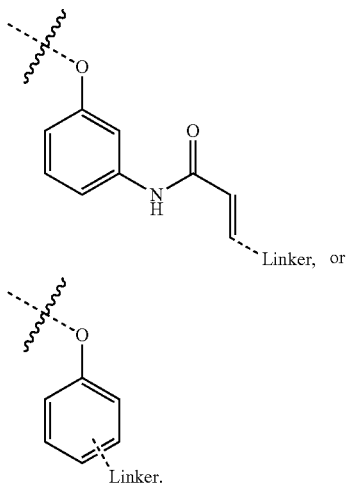

In certain embodiments, $R^{33}$ is selected from C1-C6 alkyoxy.

In certain embodiments, $R^{35}$ is selected from:

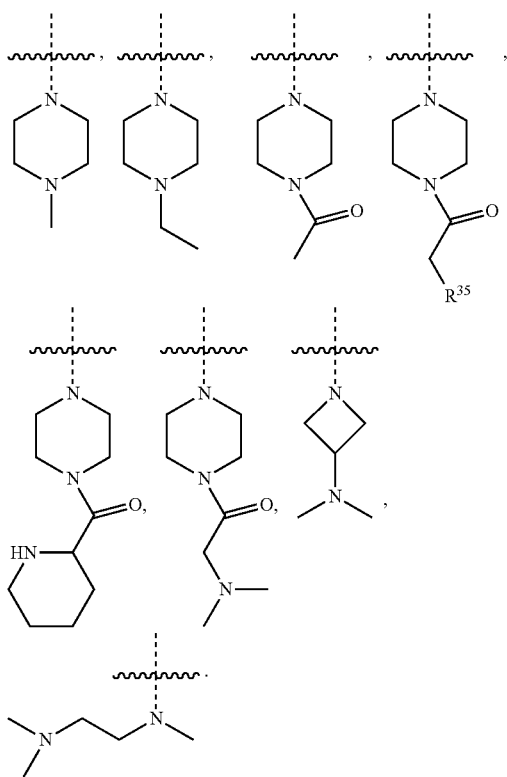

In certain embodiments, $R^{35}$ group is coupled to a linker, wherein the linker is a chemical moiety coupling the PTM to the ULM group.

In certain embodiments, the PTMs of the PROTACs as described herein comprise the moiety represented by the formula IV above:

wherein $R^{31}$ is selected from H, halogen, alkyl, e.g., C1-C6 alkyl, haloalkyl, e.g., C1-C6 haloalkyl, 5- or 6-membered heteroaryl, wherein the said heteroaryl can be further substituted with 1 substituent selected from alkyl, e.g., C1-C6 alkyl, halogen or haloalkyl, e.g., C1-C6 haloalkyl;

$R^{32}$ is selected from H, a 5- or 6-membered aryl or heteroaryl, a bicyclic fused aryl or heteroaryl, e.g., each ring has 4- to 6-members, or a bicyclic fused aryl or heteroaryl additionally fused to a cycloalkyl or a heterocycloalkyl wherein the said aryl or heteroaryl is optionally substituted with 1-2 substituents selected from alkyl, e.g., C1-C6 alkyl, halogen, or haloalkyl, e.g., C1-C6 haloalkyl;

$R^{33}$ is selected from methoxy or ethoxy;

$R^{34}$ is selected from H or —NHC(O)$R^{24}$, where $R^{24}$ is selected from the groups below:

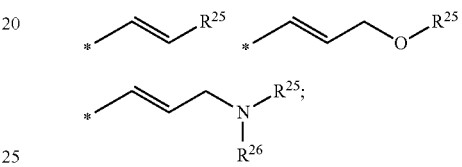

and $R^{25}$ and $R^{26}$ are independently selected from hydrogen or alkyl, e.g., C1-C6 alkyl, with the proviso that $R^{25}$ and $R^{26}$ taken together with the N atom, to which they are connected, may form a heterocycloalkyl;

$R^{35}$ is —$NR^{37}R^{38}$ where $R^{37}$ and $R^{38}$ are independently selected from H or alkyl, e.g., C1-C6 alkyl, or —$NR^{37}R^{38}$ taken together represent a heterocycloalkyl ring, most preferably piperazine, further optionally substituted with alkyl, e.g., C1-C6 alkyl, amino, alkylamino, dialkylamino, aminoalkyl, or —C(O)$R^{39}$ where $R^{39}$ is an alkyl, e.g., C1-C6 alkyl.

In a further embodiment, $R^{32}$ of formula IV is an indole or an indole further fused to a cyclohexane or a piperidine ring through the positions 1 and 7 of the indole ring with the proviso that N atoms are not attached to the same C atom.

In certain embodiments, PTM of formula IV has the structure:

IV-2

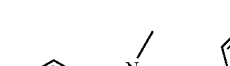

wherein $R^{37}$ and $R^{38}$ are as described.

In certain additional embodiments, one or more of $R^{37}$ or $R^{38}$ groups of formula IV is coupled to a linker, wherein the linker is a chemical moiety as described herein coupling the PTM to the ULM group.

In certain embodiments, PTM of formula IV has the structure:

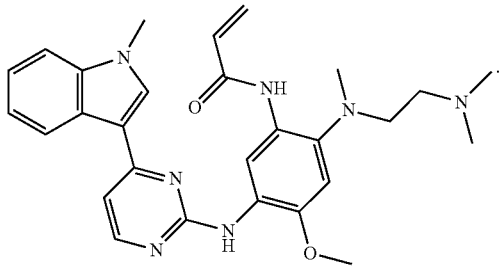 [SMILES: C=CC(=O)Nc1cc(Nc2nccc(-c3cn(C)c4ccccc34)n2)c(OC)cc1N(C)CCN(C)C ; "."]

In certain embodiments, PTM of formula IV has the structure selected from the group:

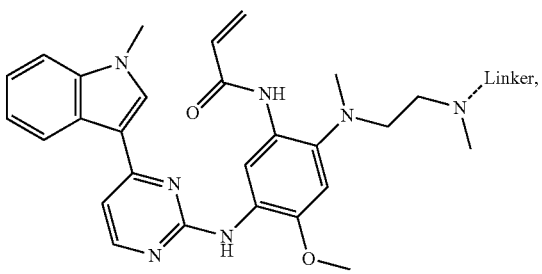

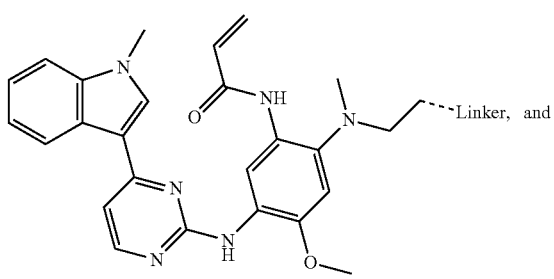

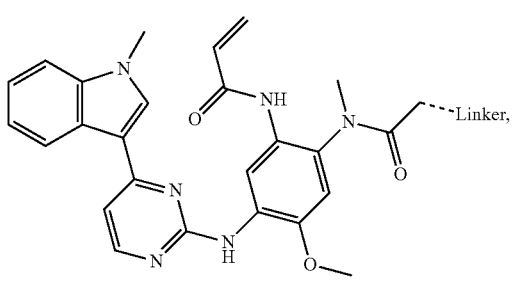

wherein Linker (L) is a chemical moiety coupling the PTM to a ULM group.

In one embodiment, PTMs of the PROTACs as described herein comprise the moiety represented by the formula V:

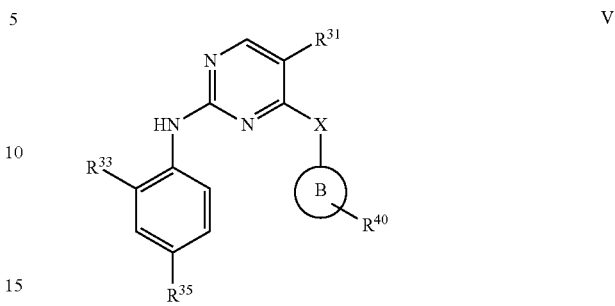

wherein $R^{31}$, $R^{33}$ and $R^{35}$ are as described above;

B is selected from an aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, provided that in the latter case the heteroatom of the said heterocycloalkyl is separated from X by at least two carbon atoms;

X is O, S or NH; and $R^{40}$ is —NHC(O)$R^{24}$, or —C(O)$R^{24}$ if attached to a ring nitrogen of B where $R^{24}$ is as described above.

In certain embodiments, PTMs of the PROTACs as described herein comprise the moiety represented by the formula V above:

wherein $R^{31}$ is selected from H, halogen, alkyl, e.g., C1-C6 alkyl, haloalkyl, e.g., C1-C6 haloalkyl, or 5- or 6-membered heteroaryl, wherein the said heteroaryl can be further substituted with 1 substituent selected from alkyl, e.g., C1-C6 alkyl, halogen, or haloalkyl, e.g., C1-C6 haloalkyl;

$R^{33}$ is selected from methoxy or ethoxy;

$R^{35}$ is —NR$^{37}$R$^{38}$ where $R^{37}$ and $R^{38}$ are independently selected from H or alkyl, e.g., C1-C6 alkyl, or —NR$^{37}$R$^{38}$ taken together represent a heterocycloalkyl ring, most preferably piperazine, further optionally substituted with alkyl, e.g., C1-C6 alkyl, amino, alkylamino, dialkylamino, aminoalkyl, or —C(O)$R^{39}$ where $R^{39}$ is an alkyl, e.g., C1-C6 alkyl;

B is phenyl or a pyridyl, most preferably phenyl;

X is O or NH, most preferably NH;

$R^{40}$ is —NHC(O)$R^{24}$, where $R^{24}$ is selected from the groups below:

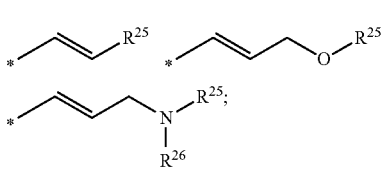

and $R^{25}$ and $R^{26}$ are independently selected from hydrogen or alkyl, e.g., C1-C6 alkyl, with the proviso that $R^{25}$ and $R^{26}$ taken together with the N atom, to which they are connected, may form a heterocycloalkyl.

In certain embodiments, the PTM of formula V comprises a linker, wherein the linker is a chemical moiety as described herein coupling the PTM to the ULM group. In certain additional embodiments, one or more of the R groups of formula V is coupled to a linker, wherein the linker is a chemical moiety as described herein coupling the PTM to the ULM group.

In certain additional embodiments, one or more of $R^{24}$, $R^{25}$, $R^{26}$, $R^{31}$, $R^{33}$, $R^{35}$, $R^{37}$, $R^{38}$, $R^{39}$ or $R^{40}$ groups of formula V is coupled to a linker, wherein the linker is a chemical moiety as described herein coupling the PTM to the ULM group.

In one embodiment, PTMs of the PROTACs as described herein comprise the moiety represented by the formula VI:

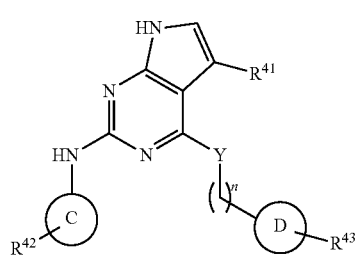

VI $R^{41}$ is selected from H, alkyl, e.g., C1-C6 alkyl, halogen, or haloalkyl, e.g., C1-C6 haloalkyl, alkoxy, e.g., C1-C6 alkoxy, and cyano;

$R^{42}$ is 1 to 2 substituents independently selected from H, halogen, alkyl, e.g., C1-C6 alkyl, alkoxy, e.g., C1-C6 alkoxy, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkoxy, amino, alkylamino, dialkylamino, cyano, aryl, e.g., C5-C10 aryl, heteroaryl, e.g., C3-C10 heteroaryl comprising 1 or more heteroatoms selected from O, N, and S, imidazole, pyrazole, pyrrole, cycloalkyl, e.g., C3-C10 cycloalkyl, heterocycloalkyl, e.g., C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, cycloalkylalkyl, heterocycloalkylalkyl—wherein the said aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano;

C is an aryl or a heteroaryl, e.g., C3-C10 heteroaryl comprising 1 or more heteroatoms selected from O, N, and S;

D is an aryl, e.g., C5-C10 aryl, heteroaryl, e.g., C3-C10 heteroaryl comprising 1 or more heteroatoms selected from O, N, and S, cycloalkyl or heterocycloalkyl, e.g., 3-8 membered aryl or heteroaryl comprising at least one heteroatom selected from S, O, or N;

Y is a bond, O, S, or NH;

n is selected from 0, 1 or 2;

$R^{43}$ is 1 to 2 substituents independently selected from H, halogen, alkyl, e.g., C1-C6 alkyl, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkyoxy, amino, alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano—or one of the $R^{43}$ substituents can be —NHC(O)$R^{24}$, or —C(O)$R^{24}$ if attached to a ring nitrogen of D; and $R^{24}$ is as described above.

In certain embodiments, the PTM of formula VI comprises a linker, wherein the linker is a chemical moiety as described herein coupling the PTM to the ULM group. In certain additional embodiments, one or more of the R groups of formula VI is coupled to a linker, wherein the linker is a chemical moiety as described herein coupling the PTM to the ULM group.

In certain additional embodiments, one or more of $R^{24}$, $R^{25}$, $R^{26}$, $R^{41}$, $R^{42}$ or $R^{43}$ groups of formula VI is coupled to a linker, wherein the linker is a chemical moiety as described herein coupling the PTM to the ULM group.

In certain embodiments, PTMs of the PROTACs as described herein comprise the moiety represented by the formula VI:

wherein $R^{41}$ is selected from H, halogen, or alkyl, e.g., C1-C6 alkyl;

$R^{42}$ is 1 substituent independently selected from H, halogen, alkyl, e.g., C1-C6 alkyl, or haloalkyl, e.g., C1-C6 haloalkyl;

C is a 5- or 6-membered heteroaryl, most preferably 5-membered heteroaryl;

D is a heterocycloalkyl, most preferably pyrrolidine;

Y is a bond, O, or NH, most preferably O;

n is 1 or 2;

$R^{43}$ is 1 to 2 substituents where one substituent is —NHC(O)$R^{24}$, or —C(O)$R^{24}$ if attached to a ring nitrogen of D, and the other is optionally selected from H, halogen, alkyl, e.g., C1-C6 alkyl, haloalkyl, e.g., C1-C6 haloalkyl, or alkoxy, e.g., C1-C6 alkoxy;

$R^{24}$ is selected from the groups below:

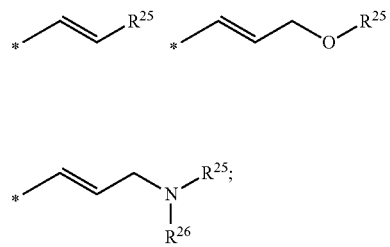

and $R^{25}$ and $R^{26}$ are independently selected from hydrogen or alkyl with the proviso that $R^{25}$ and $R^{26}$ taken together with the N atom, to which they are connected, may form a heterocycloalkyl.

In certain embodiments, at least one R group comprises a linker, wherein the linker is a chemical moiety coupling the PTM to the ULM group.

In one embodiment, PTMs of the PROTACs as described herein comprise the moiety represented by the formula VII:

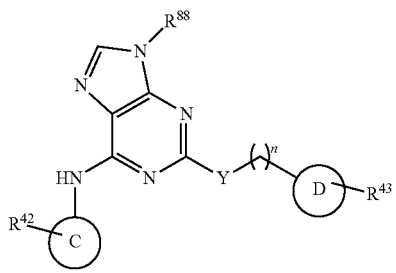

VII wherein $R^{42}$ is 1 to 2 substituents independently selected from H, halogen, alkyl, e.g., C1-C6 alkyl, haloalkyl, e.g., C1-C6 haloalkyl, alkenyl, e.g., C2-C6 alkenyl, alkynyl, e.g., C2-C6 alkynyl, hydroxy, alkoxy, e.g., C1-C6 alkoxy, amino, alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, cycloalkylalkyl, heterocycloalkylalkyl—wherein the said aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano;

C is an aryl or a heteroaryl, e.g., imidazole, pyrazole, pyrrole;

D is an aryl, heteroaryl, cycloalkyl or heterocycloalkyl, e.g., pyrrolidinyl;

Y is a bond, O, S, or NH;

n is selected from 0, 1 or 2;

$R^{43}$ is 1 to 2 substituents independently selected from H, halogen, Cl, F, alkyl, e.g., C1-C6 alkyl, haloalkyl, e.g., C1-C6 haloalkyl, alkenyl, e.g., C2-C6 alkenyl, alkynyl, e.g., C2-C6 alkynyl, alkoxy, e.g., C1-C6 alkoxy, amino, amido, alkylamino, e.g., C1-C6 alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano, or one of the $R^{43}$ substituents can be —NHC(O)$R^{24}$, or —C(O)$R^{24}$ if attached to a ring nitrogen of D;

$R^{24}$ is as described above; and $R^{88}$ is a hydrogen or alkyl, e.g., C1-C6 alkyl.

In certain embodiments, PTMs of the PROTACs as described herein comprise the moiety represented by the formula VII:

wherein $R^{42}$ is 1 to 2 substituents independently selected from H, halogen, alkyl, e.g., C1-C6 alkyl, haloalkyl, e.g., C1-C6 haloalkyl, and alkoxy, e.g., C1-C6 alkoxy;

C is a 5- or 6-membered heteroaryl, most preferably 5-membered heteroaryl;

D is a heterocycloalkyl, most preferably pyrrolidine;

Y is a bond;

n is 0;

$R^{43}$ is 1 to 2 substituents where one substituent is —NHC(O)$R^{24}$, or —C(O)$R^{24}$ if attached to a ring nitrogen of D, and the other is optionally selected from H, halogen, alkyl, e.g., C1-C6 alkyl, haloalkyl, e.g., C1-C6 haloalkyl, alkoxy, e.g., C1-C6 alkoxy;

$R^{24}$ is selected from the groups below:

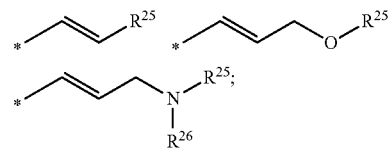

$R^{25}$ and $R^{26}$ are independently selected from hydrogen or alkyl with the proviso that $R^{25}$ and $R^{26}$ taken together with the N atom, to which they are connected, may form a heterocycloalkyl; and $R^{88}$ is methyl or ethyl.

In certain embodiments, the PTM of formula VII comprises a linker, wherein the linker is a chemical moiety as described herein coupling the PTM to the ULM group. In certain additional embodiments, one or more of the R groups of formula VII is coupled to a linker, wherein the linker is a chemical moiety as described herein coupling the PTM to the ULM group.

In certain additional embodiments, one or more of $R^{24}$, $R^{25}$, $R^{26}$, $R^{42}$, $R^{43}$ or $R^{88}$ groups of formula VII is coupled to a linker, wherein the linker is a chemical moiety as described herein coupling the PTM to the ULM group.

In one embodiment, PTMs of the PROTACs as described herein comprise the moiety represented by the formula VIII:

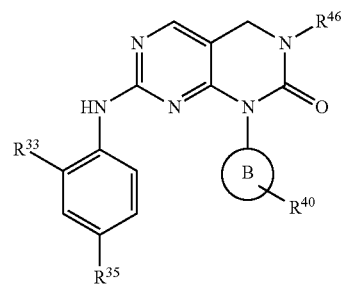

VIII wherein $R^{33}$, $R^{35}$, $R^{40}$ and B are as described above; and $R^{46}$ is selected from H, alkyl, e.g., C1-C6 alkyl, hydroxyalkyl, e.g., C1-C6 hydroxyalkyl, alkoxyalkyl, aminoalkyl, alkylaminoalkyl, dialkylaminoalkyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, cycloalkylalkyl or heterocycloalkylalkyl with the proviso that the two heteroatoms are not attached to the same carbon atom and wherein the said aryl and heteroaryl can be further substituted with 1-2 substituents selected from alkyl, e.g., C1-C6 alkyl, halogen, alkoxy, e.g., C1-C6 alkoxy, and cyano.

In certain embodiments, PTMs of the PROTACs as described herein comprise the moiety represented by the formula VIII:

wherein $R^{33}$ is selected from methoxy or ethoxy;

$R^{35}$ is $-NR^{37}R^{38}$ where $R^{37}$ and $R^{38}$ are independently selected from H or alkyl, e.g., C1-C6 alkyl, or $-NR^{37}R^{38}$ taken together represent a heterocycloalkyl ring, most preferably piperazine, further optionally substituted with alkyl, e.g., C1-C6 alkyl, amino, alkylamino, dialkylamino, aminoalkyl, or $-C(O)R^{39}$ where $R^{39}$ is an alkyl, e.g., C1-C6 alkyl;

B is phenyl or a pyridyl, most preferably phenyl;

$R^{40}$ is $-NHC(O)R^{24}$, where $R^{24}$ is selected from the groups below:

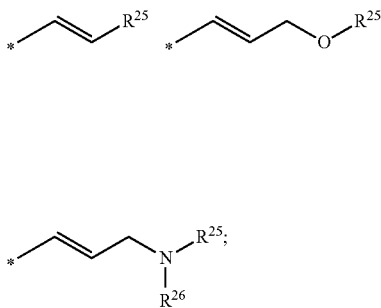

$R^{25}$ and $R^{26}$ are independently selected from hydrogen or alkyl with the proviso that $R^{25}$ and $R^{26}$ taken together with the N atom, to which they are connected, may form a heterocycloalkyl; and $R^{46}$ is selected from H, alkyl, e.g., C1-C6 alkyl, alkoxyalkyl, aminoalkyl, alkylaminoalkyl, dialkylaminoalkyl, aryl, e.g., C5-C10 aryl, heteroaryl, e.g., C3-C10 heteroaryl comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, with the proviso that the two heteroatoms are not attached to the same carbon atom and wherein the said aryl and heteroaryl can be further substituted with 1-2 substituents selected from alkyl, e.g., C1-C6 alkyl, and halogen.

In certain embodiments, the PTM of formula VIII comprises a linker, wherein the linker is a chemical moiety as described herein coupling the PTM to the ULM group. In certain additional embodiments, one or more of the R groups of formula VIII is coupled to a linker, wherein the linker is a chemical moiety as described herein coupling the PTM to the ULM group.

In certain additional embodiments, one or more of $R^{24}$, $R^{25}$, $R^{26}$, $R^{33}$, $R^{35}$, $R^{37}$, $R^{38}$, $R^{39}$, $R^{40}$ or $R^{46}$ groups of formula VIII is coupled to a linker, wherein the linker is a chemical moiety as described herein coupling the PTM to the ULM group.

In one embodiment, PTMs of the PROTACs as described herein comprise the moiety represented by the formula IX:

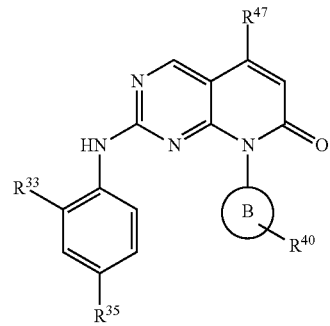

wherein $R^{33}$, $R^{35}$, $R^{40}$ and B are as described above; and $R^{47}$ is selected from H or alkyl, e.g., C1-C6 alkyl.

In certain embodiments, at least one R group comprises a linker, wherein the linker is a chemical moiety coupling the PTM to the ULM group.

In certain embodiments, PTMs of the PROTACs as described herein comprise the moiety represented by the formula IX:

wherein $R^{33}$ is selected from methoxy or ethoxy;

$R^{35}$ is $-NR^{37}R^{38}$ where $R^{37}$ and $R^{38}$ are independently selected from H or alkyl, e.g., C1-C6 alkyl, or $-NR^{37}R^{38}$ taken together represent a heterocycloalkyl ring, most preferably piperazine, further optionally substituted with alkyl, e.g., C1-C6 alkyl, amino, alkylamino, dialkylamino, aminoalkyl, or $-C(O)R^{39}$ where $R^{39}$ is an alkyl, e.g., C1-C6 alkyl;

B is phenyl or a pyridyl, most preferably phenyl;

$R^{40}$ is $-NHC(O)R^{24}$, where $R^{24}$ is selected from the groups below:

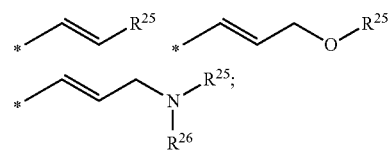

and $R^{25}$ and $R^{26}$ are independently selected from hydrogen or alkyl with the proviso that $R^{25}$ and $R^{26}$ taken together with the N atom, to which they are connected, may form a heterocycloalkyl, heterocycloalkyl, e.g., C3-C10 heterocycloalkyl wherein the heterocycle comprising 1 or more heteroatoms selected from O, N, and S; and $R^{47}$ is selected from H or alkyl, e.g., C1-C6 alkyl.

In certain embodiments, the PTM of formula IX comprises a linker, wherein the linker is a chemical moiety as described herein coupling the PTM to the ULM group. In certain additional embodiments, one or more of the R groups of formula IX is coupled to a linker, wherein the linker is a chemical moiety as described herein coupling the PTM to the ULM group.

In certain additional embodiments, one or more of $R^{24}$, $R^{25}$, $R^{26}$, $R^{33}$, $R^{35}$, $R^{37}$, $R^{38}$, $R^{39}$, $R^{40}$ or $R^{47}$ groups of formula IX is coupled to a linker, wherein the linker is a chemical moiety as described herein coupling the PTM to the ULM group.

In one embodiment, PTMs of the PROTACs as described herein comprise the moiety represented by the formula X:

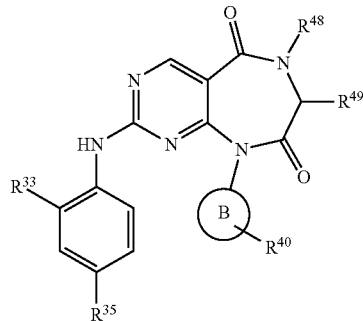

X wherein $R^{33}$, $R^{35}$, $R^{40}$ and B are as described above;

$R^{48}$ is selected from H or alkyl, e.g., C1-C6 alkyl; and $R^{49}$ is selected from H, alkyl, e.g., C1-C6 alkyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, arylalkyl, e.g., C5-C10 arylalkyl, heteroarylalkyl, e.g., C5-C10 heteroarylalkyl wherein the heteroaryl comprises 1 or more heteroatoms selected from O, N, and S, cycloalkylalkyl or heterocycloalkylalkyl.

In a more preferred embodiment, PTMs of the PROTACs as described herein comprise the moiety represented by the formula X:

wherein $R^{33}$ is selected from methoxy or ethoxy;

$R^{35}$ is —$NR^{37}R^{38}$ where $R^{37}$ and $R^{38}$ are independently selected from H or alkyl, e.g., C1-C6 alkyl, or —$NR^{37}R^{38}$ taken together represent a heterocycloalkyl ring, most preferably piperazine, further optionally substituted with alkyl, e.g., C1-C6 alkyl, amino, alkylamino, dialkylamino, aminoalkyl, or —$C(O)R^{39}$ where $R^{39}$ is an alkyl, e.g., C1-C6 alkyl;

B is phenyl or a pyridyl, most preferably phenyl;

$R^{40}$ is —$NHC(O)R^{24}$, where $R^{24}$ is selected from the groups below:

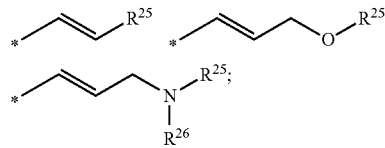

$R^{25}$ and $R^{26}$ are independently selected from hydrogen or alkyl with the proviso that $R^{25}$ and $R^{26}$ taken together with the N atom, to which they are connected, may form a heterocycloalkyl;

$R^{48}$ is selected from H or alkyl, e.g., C1-C6 alkyl; and $R^{49}$ is selected from H or alkyl, e.g., C1-C6 alkyl; and.

In certain embodiments, the PTM of formula X comprises a linker, wherein the linker is a chemical moiety as described herein coupling the PTM to the ULM group. In certain additional embodiments, one or more of the R groups of formula X is coupled to a linker, wherein the linker is a chemical moiety as described herein coupling the PTM to the ULM group.

In certain additional embodiments, one or more of $R^{24}$, $R^{25}$, $R^{26}$, $R^{33}$, $R^{35}$, $R^{37}$, $R^{38}$, $R^{39}$, $R^{40}$, $R^{48}$ or $R^{49}$ groups of formula X is coupled to a linker, wherein the linker is a chemical moiety as described herein coupling the PTM to the ULM group.

In one embodiment, PTMs of the PROTACs as described herein comprise the moiety represented by the formula XI:

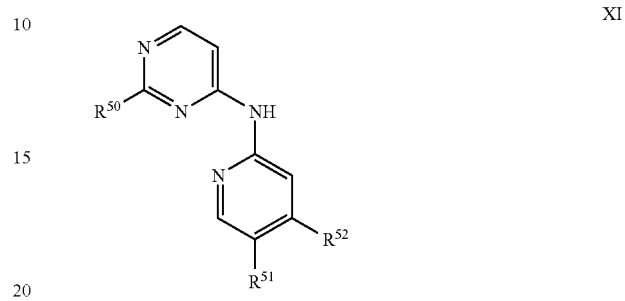

XI wherein $R^{50}$ is an alkyl, e.g., C1-C6 alkyl, alkylamino, dialkylamino, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said cycloalkyl or heterocycloalkyl are further optionally substituted with halogen, alkoxy, e.g., C1-C6 alkoxy, amino, alkylamino, dialkylamino or cyano with the proviso that any two heteroatoms are separated by at least two carbon atoms; and $R^{51}$ is a hydrogen and $R^{52}$ is —$NHC(O)R^{53}$ where $R^{53}$ is an aryl or a heteroaryl optionally substituted with 1-2 substituents independently selected from alkyl, e.g., C1-C6 alkyl, halogen, or haloalkyl, e.g., C1-C6 haloalkyl, alkoxy, e.g., C1-C6 alkoxy, and cyano, or $R^{51}$ and $R^{52}$ taken together constitute a 5-6-membered aryl or heteroaryl ring further optionally substituted with 1-2 substituents independently selected from alkyl, e.g., C1-C6 alkyl, halogen, or haloalkyl, e.g., C1-C6 haloalkyl, alkoxy, e.g., C1-C6 alkoxy, cyano, amino, alkylamino, dialkylamino, aryl, e.g., C5-C10 aryl, or heteroaryl, e.g., C3-C10 heteroaryl comprising 1 or more heteroatoms selected from O, N, and S.

In certain embodiments, the PTM of formula XI comprises a linker, wherein the linker is a chemical moiety as described herein coupling the PTM to the ULM group. In certain additional embodiments, one or more of the R groups of formula XI is coupled to a linker, wherein the linker is a chemical moiety as described herein coupling the PTM to the ULM group.

In certain additional embodiments, one or more of $R^{50}$, $R^{51}$ or $R^{52}$ groups of formula XI is coupled to a linker, wherein the linker is a chemical moiety as described herein coupling the PTM to the ULM group.

In one embodiment, PTMs of the PROTACs as described herein comprise the moiety represented by the formula XII:

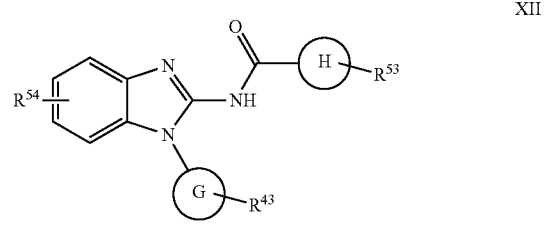

XII wherein G is a cycloalkyl, e.g., C3-C10 cycloalkyl, or heterocycloalkyl, e.g., C3-C10 heterocycloalkyl wherein the heterocycle comprising 1 or more heteroatoms selected from O, N, and S;

H is an aryl, e.g., C5-C10 aryl, heteroaryl, e.g., C3-C10 heteroaryl comprising 1 or more heteroatoms selected from O, N, and S;

$R^{43}$ is as described above; and $R^{53}$ and $R^{54}$ are each independently 1-2 substituents independently selected from H, halogen, Cl, F, alkyl, e.g., C1-C6 alkyl, haloalkyl, e.g., C1-C6 haloalkyl, alkenyl, e.g., C2-C6 alkenyl, alkynyl, e.g., C2-C6 alkynyl, alkoxy, e.g., C1-C6 alkoxy, amino, alkylamino, e.g., C1-C6 alkylamino, dialkylamino, cyano, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, heterocycloalkyl, e.g., C3-C10 heterocycloalkyl wherein the heterocycle comprising 1 or more heteroatoms selected from O, N, and S, wherein the said aryl or heteroaryl can be further substituted with 1 to 2 substituents selected from alkyl, e.g., C1-C6 alkyl, halogen, or haloalkyl, e.g., C1-C6 haloalkyl, hydroxyl, alkoxy, e.g., C1-C6 alkoxy, amino, alkylamino, dialkylamino and cyano.

In certain embodiments, the PTM of formula XII comprises a linker, wherein the linker is a chemical moiety as described herein coupling the PTM to the ULM group. In certain additional embodiments, one or more of the R groups of formula XII is coupled to a linker, wherein the linker is a chemical moiety as described herein coupling the PTM to the ULM group.

In certain embodiments, PTMs of the PROTACs as described herein comprise the moiety represented by the formula XII:

wherein G is a heterocycloalkyl, heterocycloalkyl, e.g., C3-C10 heterocycloalkyl wherein the heterocycle comprising 1 or more heteroatoms selected from O, N, and S most preferably 6- or 7-membered heterocycloalkyl, most preferably hexahydroazepine;

H is phenyl or a pyridyl;

$R^{43}$ is 1 to 2 substituents where one substituent is —NHC(O)$R^{24}$, or —C(O)$R^{24}$ if attached to a ring nitrogen of D, and the other is optionally selected from H, alkyl, e.g., C1-C6 alkyl, halogen, or haloalkyl, e.g., C1-C6 haloalkyl, alkoxy, e.g., C1-C6 alkoxy, wherein $R^{24}$ is selected from the groups below:

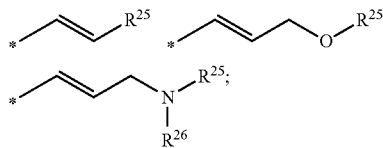

$R^{25}$ and $R^{26}$ are independently selected from hydrogen or alkyl, e.g., C1-C6 alkyl, with the proviso that $R^{25}$ and $R^{26}$ taken together with the N atom, to which they are connected, may form a heterocycloalkyl; and $R^{53}$ and $R^{54}$ are each independently 1-2 substituents independently selected from H, halogen, alkyl, e.g., C1-C6 alkyl, and haloalkyl, e.g., C1-C6 haloalkyl.

In certain additional embodiments, one or more of $R^{24}$, $R^{25}$, $R^{26}$, $R^{43}$, $R^{53}$ or $R^{54}$ groups of formula XII is coupled to a linker, wherein the linker is a chemical moiety as described herein coupling the PTM to the ULM group.

In one embodiment, PTMs of the PROTACs as described herein comprise the moiety represented by the formula XIII:

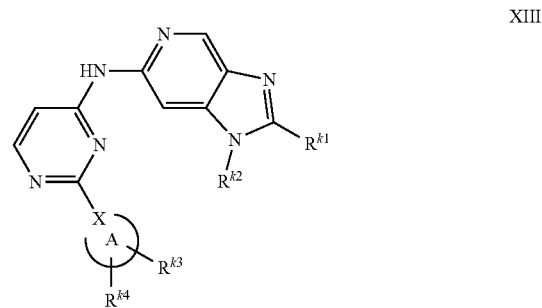

XIII wherein A is a saturated or unsaturated 4-8 atom carbocyclic or heterocyclic ring comprising 1-7 heteroatoms, e.g., O, S or N;

$R^{k1}$ is selected from H, alkyl, e.g., C1-C6 alkyl, alkenyl, e.g., C2-C6 alkenyl, alkynyl, e.g., C2-C6 alkynyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, wherein the said alkyl, aryl or heteroaryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, alkoxy, hydroxyl, amino, alkylamino, dialkylamino and cyano;

$R^{k2}$ is selected from H, alkyl, e.g., C1-C6 alkyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, wherein the said alkyl, aryl or heteroaryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano;

$R^{k3}$ and $R^{k4}$ are independently selected from H, hydroxyl, alkyl, e.g., C1-C6 alkyl, alkoxy, e.g., C1-C6 alkoxy, aryl, e.g., C5-C10 aryl, —SO$^2$R$^{k2}$, or halogen—wherein the said hydroxyl, alkyl, aryl or alkoxy can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano;

X is N or CH or C with a double bond to the neighbor atom in the ring.

In certain embodiments, the PTM of formula XIII comprises a linker, wherein the linker is a chemical moiety as described herein coupling the PTM to the ULM group. In certain additional embodiments, one or more of the R groups of formula XIII is coupled to a linker, wherein the linker is a chemical moiety as described herein coupling the PTM to the ULM group.

In certain additional embodiments, one or more of $R^{k1}$, $R^{k2}$, $R^{k3}$ or $R^{k4}$ groups of formula XIII is coupled to a linker, wherein the linker is a chemical moiety as described herein coupling the PTM to the ULM group.

In certain embodiments of formula XIII, A is substituted with an alkyl, e.g., C1-C6 alkyl, alkoxy, e.g., C1-C6 alkoxy.

In certain embodiments of formula XIII, A is pyrazole, imidazole, pyrrole, oxazole, or thiazole.

In certain embodiments of formula XIII, A is a pyrazole and at least one of $R^{k3}$ or $R^{k4}$ is:

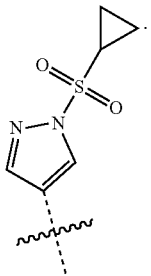

In certain embodiments, an R group of formula XIII comprises a linker, wherein the linker is a chemical moiety coupling the PTM to the ULM group.

In certain embodiments, the PTM of formula XIII comprises the structure:

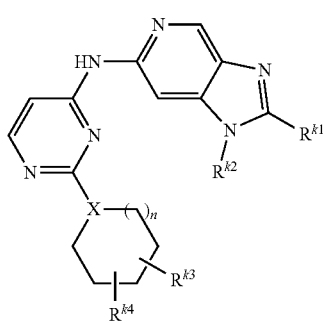

XIII-2 wherein, X, $R^{k1}$, $R^{k2}$, $R^{k3}$, $R^{k4}$, and $R^{k1}$ are as above; and n=0, 1 or 2.

In certain additional embodiments, one or more of $R^{k1}$, $R^{k2}$, $R^{k3}$ or $R^{k4}$ groups of formula XIII is coupled to a linker, wherein the linker is a chemical moiety as described herein coupling the PTM to the ULM group.

In certain embodiments, the PTM of formula XIII comprises the structure:

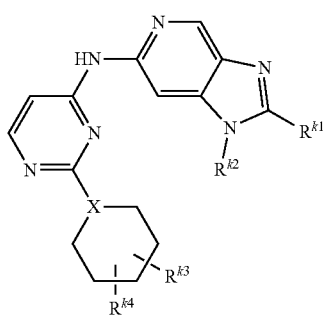

XIII-3 wherein X, $R^{k1}$, $R^{k2}$, $R^{k3}$, and $R^{k4}$ are as above.

In certain additional embodiments, one or more of $R^{k1}$, $R^{k2}$, $R^{k3}$ or $R^{k4}$ groups of formula XIII is coupled to a linker, wherein the linker is a chemical moiety as described herein coupling the PTM to the ULM group.

In certain embodiments, the PTM of formula XIII comprises the structure:

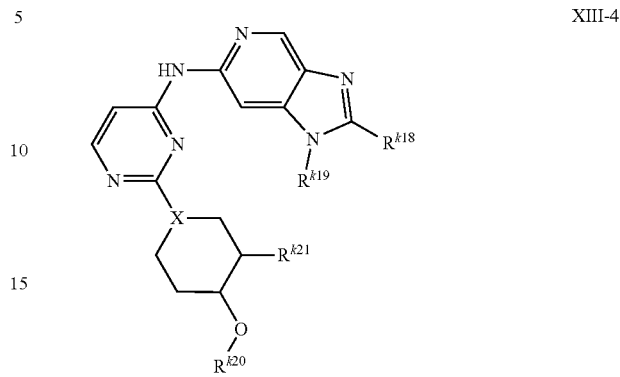

XIII-4 wherein $R^{k18}$ is selected from H, alkyl, e.g., C1-C6 alkyl, haloalkyl, e.g., C1-C6 haloalkyl, alkenyl, e.g., C2-C6 alkenyl, alkynyl, e.g., C2-C6 alkynyl, aryl, e.g., C5-C10 aryl, heteroaryl, e.g., C3-C10 heteroaryl comprising 1 or more heteroatoms selected from O, N, and S, wherein the said alkyl, aryl or heteroaryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano;

$R^{k19}$ is either H, alkyl (linear or branched) or halogen substituted alkyl with 1-6 C atoms $R^{k20}$ is either H, alkyl (linear or branched) or halogen substituted alkyl with 1-6 C atoms $R^{k21}$ is either H, CN, halogen or alkyl (linear or branched) or halogen substituted alkyl with 1-3 C atoms; and X=CH or N.

In certain additional embodiments, one or more of $R^{k18}$, $R^{k19}$, $R^{k20}$ or $R^{k21}$ groups of formula XIII is coupled to a linker, wherein the linker is a chemical moiety as described herein coupling the PTM to the ULM group.

In certain embodiments, the PTM of formula XIII comprises the structure:

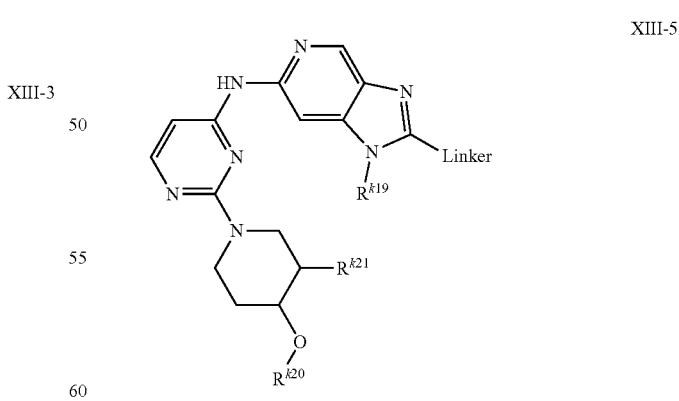

XIII-5 wherein $R^{k19}$ is either H, alkyl (linear or branched) or halogen substituted alkyl with 1-6 C atoms;

$R^{k20}$ is either H, alkyl (linear or branched) or halogen substituted alkyl with 1-6 C atoms;

$R^{k21}$ is either H, halogen or alkyl (linear or branched) or halogen substituted alkyl with 1-3 C atoms; and Linker (L) is a bond or a chemical linker coupling the PTM to a ULM.

In certain additional embodiments, one or more of $R^{k19}$, $R^{k20}$ or $R^{k21}$ groups of formula XIII is coupled to a linker, wherein the linker is a chemical moiety as described herein coupling the PTM to the ULM group.

In certain embodiments, the PTM of formula XIII comprises the structure:

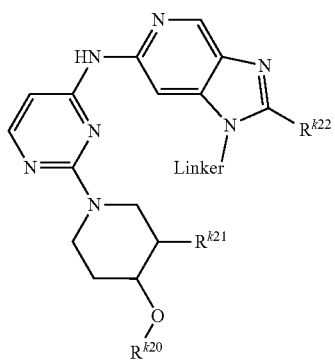

XIII-6 wherein $R^{k20}$ and $R^{k21}$ are as above;

$R^{k22}$ is either H, alkyl (linear or branched) or halogen substituted alkyl with 1-6 C atoms; and Linker (L) is a bond or chemical linker coupling the PTM to a ULM.

In certain additional embodiments, one or more of $R^{k20}$, $R^{k21}$ or $R^{k22}$ groups of formula XIII is coupled to a linker, wherein the linker is a chemical moiety as described herein coupling the PTM to the ULM group.

In certain embodiments, the PTM of formula XIII comprises the structure:

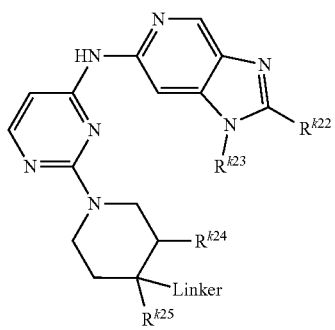

XIII-7 wherein $R^{k22}$ is either H, alkyl (linear or branched) or halogen substituted alkyl with 1-6 C atoms;

$R^{k23}$ is either H, alkyl (linear, branched or cyclic) with up to 6 carbon atoms, optionally substituted with halogen;

$R^{k24}$ is either H, halogen, cyano or alkyl (linear or branched) or halogen substituted alkyl with 1-3 C atoms;

$R^{25}$ is either H, alkyl (linear or branched), alkoxy (linear or branched) or hydroxyl; and Linker (L) is a bond or chemical linker coupling the PTM to a ULM.

In certain embodiments of formula XIII, the linker moiety is conjugated to at least one of $R^{k1}$, $R^{k2}$, $R^{k3}$, and $R^{k4}$ groups of formula XIII, wherein the linker is a chemical moiety as described herein coupling the PTM to the ULM group.

In certain embodiments, the PTM of formula XIII comprises the structure:

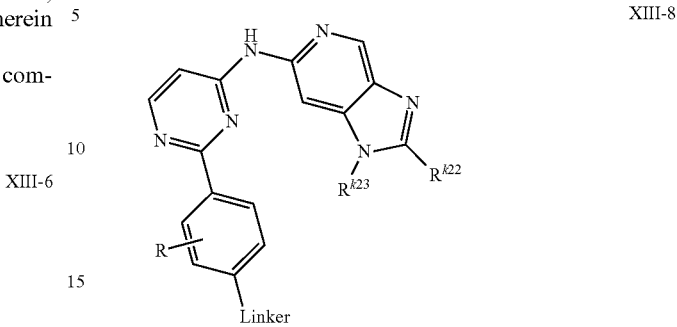

XIII-8 wherein R and $R^{k23}$ are as defined above; and

R is 1-3 substituents independently selected from H, halogen, C1-C6 alkyl, cyano, or haloalkyl, wherein linker (L) is a bond or chemical linker coupling PTM to a ULM.

In certain additional embodiments, one or more of R, $R^{k22}$ or $R^{k33}$ groups of formula XIII is coupled to a linker, wherein the linker is a chemical moiety as described herein coupling the PTM to the ULM group.

In certain embodiments, the PTM of formula XIII comprises the structure:

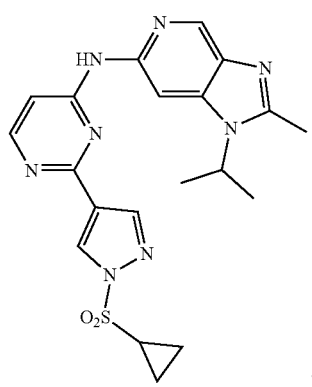

In certain embodiments, the PTM includes a linker, wherein the linker is a chemical moiety coupling the PTM to the ULM group.

In certain embodiments, PTMs of the PROTACs as described herein comprise the moiety represented by the formula XIV:

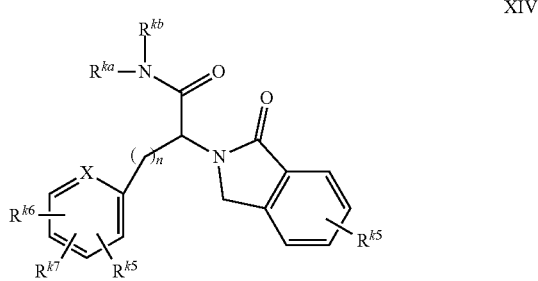

XIV wherein $R^{ka}$ is H, alkyl, e.g., C1-C6 alkyl, alkoxy, e.g., C1-C6 alkoxy;

$R^{kb}$ is aryl, e.g., C5-C10 aryl, or heteroaryl comprising one or two 5-7 membered rings and 1-4 heteroatoms selected from N, O, and S, wherein the aryl and heteroaryl are each optionally substituted with one or more groups selected from alkyl, e.g., C1-C6 alkyl, haloalkyl, e.g., C1-C6 haloalkyl, alkoxy, e.g., C1-C6 alkoxy, haloalkoxy, e.g., C1-C6 haloalkoxy, halogen, $NO_2$, OH, CN, $C(O)Y^1$, $C(O)OY^1$, $C(O)NY^1Y^2$, $NY^1Y^2$, cycloalkyl, e.g., C3-C10 cycloalkyl, heterocycle comprising 5-7 membered ring and 1-3 heteroatoms selected from N, O, and S, C6-C10 aryl, and heteroaryl comprising one or two 5-7 membered rings and 1-4 heteroatoms selected from N, O, and S, wherein the alkyl cycloalkyl, heterocyclyl, aryl or heteroaryl are each optionally substituted with one or more $Y^1$;

each $Y^1$ and $Y^2$ is independently selected from H, alkyl, e.g., C1-C6 alkyl, haloalkyl, e.g., C1-C6 haloalkyl, alkoxy, e.g., C1-C6 alkoxy, haloalkoxy, e.g., C1-C6 haloalkoxy, halogen, $NO_2$, OH, or CN;

wherein $R^k$, $R^{k6}$ and $R^{k7}$ are independently selected from H, alkyl, e.g., C1-C6 alkyl, a alkyne, e.g., C1-C6 alkyne, alkoxy, e.g., C1-C6 alkoxy, hydroxyl, cyano, haloalkyl, e.g., C1-C6 haloalkyl, haloalkoxy, e.g., C1-C6 haloalkoxy, $NO_2$, or halogen, Cl, F—wherein the said alkyl or alkoxy can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano; and X is N, CH, C(C1-C6 alkyl), C(C1-C6) haloalkyl, C(C1-6) alkoxy, C(C1-C6) haloalkyl, halogen, $C(NO_2)$, $C(NH_2)$, C(OH), or C(CN).

In certain embodiments, the PTM of formula XIV comprises a linker, wherein the linker is a chemical moiety as described herein coupling the PTM to the ULM group. In certain additional embodiments, one or more of the R groups of formula XIV is coupled to a linker, wherein the linker is a chemical moiety as described herein coupling the PTM to the ULM group.

In certain additional embodiments, one or more of $R^{ka}$, $R^{kb}$, $R^{k5}$, $R^{k6}$ or $R^{k7}$ groups of formula XIV is coupled to a linker, wherein the linker is a chemical moiety as described herein coupling the PTM to the ULM group.

In one embodiment of formula XIV, PTMs of the PROTACs as described herein comprise the moiety represented by the formula:

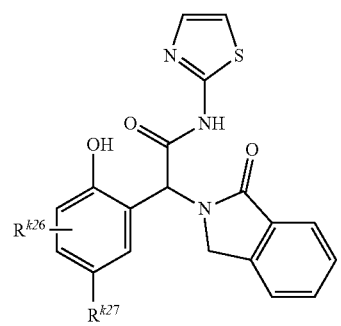

XIV-2 wherein $R^k$, $R^{k6}$ and $R^{k7}$ are independently selected from H, alkyl, e.g., C1-C6 alkyl, a alkyne, e.g., C1-C6 alkyne, alkoxy, e.g., C1-C6 alkoxy, hydroxyl, cyano, haloalkyl, e.g., C1-C6 haloalkyl, haloalkoxy, e.g., C1-C6 haloalkoxy, $NO_2$, or halogen, Cl, F, wherein the said alkyl or alkoxy can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano; and X is N, CH, C(C1-C6 alkyl), C(C1-C6) haloalkyl, C(C1-6) alkoxy, C(C1-C6) haloalkyl, halogen, $C(NO_2)$, $C(NH_2)$, C(OH), or C(CN).

In certain additional embodiments, one or more of $R^{k5}$, $R^{k6}$, or $R^{k7}$ groups of formula XIV is coupled to a linker, wherein the linker is a chemical moiety as described herein coupling the PTM to the ULM group.

In certain embodiments, the PTM of formula XIV is linked to a ULM via an unsaturated chemical linker. In certain embodiments, the unsaturated linker is substituted.

In certain embodiments, the PTM of formula XIV comprises the structure:

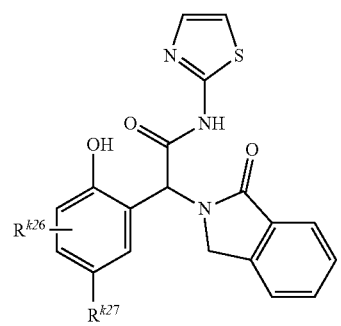

XIV-3 wherein $R^{k26}$ and $R^{k27}$ are independently selected from H, alkyl, e.g., C1-C6 alkyl, alkoxy, e.g., C1-C6 alkoxy, hydroxyl, cyano or halogen, wherein the said alkyl or alkoxy can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano.

In certain additional embodiments, one or more of $R^{k26}$ or $R^{k27}$ groups of formula XIV is coupled to a linker, wherein the linker is a chemical moiety as described herein coupling the PTM to the ULM group.

In certain embodiments, the PTM of formula XIV comprises the structure:

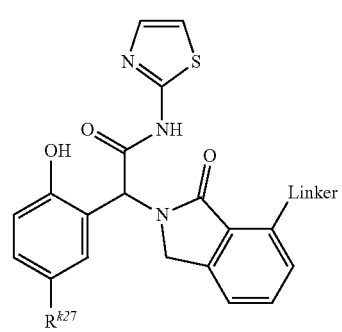

XIV-4 wherein $R^{k27}$ is selected from H, cyano or halogen, wherein Linker (L) is a bond or a chemical linker coupling the PTM to a ULM.

In certain embodiments, the PTM of formula XIV comprises the structure:

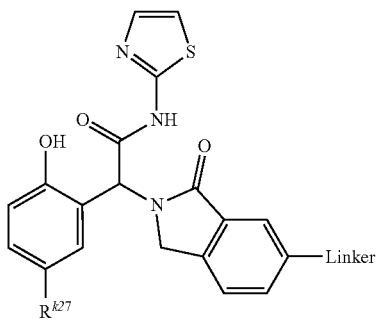

XIV-5 wherein $R^{k27}$ is selected from H, cyano or halogen, wherein Linker (L) is a bond or a chemical linker coupling the PTM to a ULM.

In certain additional embodiments, $R^{k27}$ of formula XIV is coupled to a linker, wherein the linker is a chemical moiety as described herein coupling the PTM to the ULM group.

In certain embodiments, the PTM of formula XIV comprises the structure:

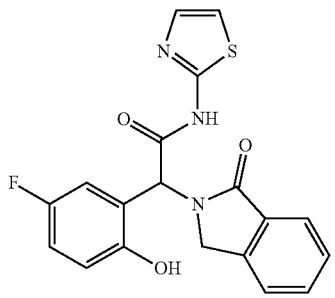

In one embodiment, PTMs of the PROTACs as described herein comprise the moiety represented by the formula XV:

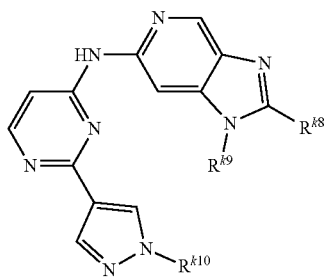

XV wherein $R^{k8}$ is selected from H, alkyl, e.g., C1-C6 alkyl, haloalkyl, e.g., C1-C6 haloalkyl, alkenyl, e.g., C2-C6 alkenyl, alkynyl, e.g., C2-C6 alkynyl, alkoxy, e.g., C1-C6 alkoxy, aryl, e.g., C5-C10 aryl, heteroaryl, e.g., C3-C10 heteroaryl comprising 1 or more heteroatoms selected from O, N, and S, wherein the said alkyl, aryl or heteroaryl can be further substituted with 1 to 2 substituents selected from alkyl, e.g., C1-C6 alkyl, halogen, haloalkyl, e.g., C1-C6 haloalkyl, hydroxyl, alkoxy, e.g., C1-C6 alkoxy, amino, alkylamino, dialkylamino and cyano;

$R^{k9}$ is selected from H, alkyl, e.g., C1-C6 alkyl or cycloalkyl, e.g., C3-C10 cycloalkyl, wherein the said alkyl or cycloalkyl can be further substituted with 1 to 3 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano; and $R^{k10}$ is selected from H, alkyl, e.g., C1-C6 alkyl, alkylsulfone, alkylcarboxamide or aryl, wherein the said alkyl or aryl can be further substituted with 1 to 2 substituents selected from alkyl, e.g., C1-C6 alkyl, halogen, alkylsulfone, alkylsulfonamide, amide, carboxamide, haloalkyl, e.g., C1-C6 haloalkyl, hydroxyl, alkoxy, e.g., C1-C6 alkoxy, amino, amide, alkylamino, dialkylamino and cyano.

In certain embodiments, the PTM of formula XV comprises a linker, wherein the linker is a chemical moiety as described herein coupling the PTM to the ULM group. In certain additional embodiments, one or more of the R groups of formula XV is coupled to a linker, wherein the linker is a chemical moiety as described herein coupling the PTM to the ULM group.

In certain additional embodiments, one or more of $R^{k8}$, $R^{k9}$, or $R^{k10}$ groups of formula XV is coupled to a linker, wherein the linker is a chemical moiety as described herein coupling the PTM to the ULM group.

In certain embodiments of formula XV, $R^{k10}$ is:

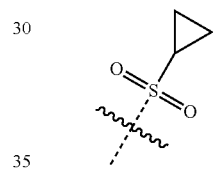

In certain embodiments, the PTM of formula XV comprises the structure:

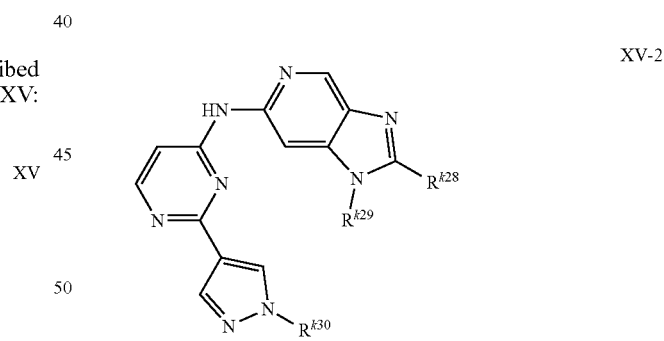

XV-2 wherein $R^{k28}$ is selected from H, alkyl, e.g., C1-C6 alkyl, haloalkyl, e.g., C1-C6 haloalkyl, alkenyl, e.g., C2-C6 alkenyl, alkynyl, e.g., C2-C6 alkynyl, alkoxy, e.g., C1-C6 alkoxy, aryl, e.g., C5-C10 aryl, heteroaryl, e.g., C3-C10 heteroaryl comprising 1 or more heteroatoms selected from O, N, and S, wherein the said alkyl, aryl or heteroaryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano;

$R^{k29}$ is selected from H, alkyl, e.g., C1-C6 alkyl, or cycloalkyl, e.g., C3-C10 cycloalkyl, wherein the said alkyl or cycloalkyl can be further substituted with 1-3 halogen substituents; and $R^{k30}$ is selected from H, alkyl, e.g., C1-C6 alkyl, cycloalkyl, e.g., C3-C10 cycloalkyl, alkylsulfone, cycloalkylsulfone or —COR—wherein the said alkyl or aryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, amide, alkylamino, dialkylamino and cyano.

In certain additional embodiments, one or more of $R^{k28}$, $R^{29}$, or $R^{k30}$ groups of formula XV is coupled to a linker, wherein the linker is a chemical moiety as described herein coupling the PTM to the ULM group.

In one embodiment, PTMs of the PROTACs as described herein comprise the moiety represented by the formula XVI:

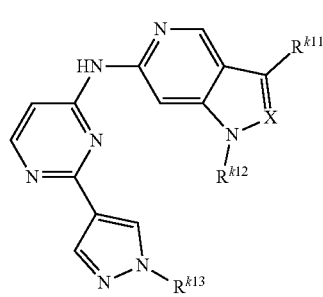

XVI wherein $R^{k11}$ is selected from H, alkyl, e.g., C1-C6 alkyl, alkoxy, e.g., C1-C6 alkoxy, C(O)NHR where R is selected from H, alkyl, e.g., C1-C6 alkyl, cycloalkyl, e.g., C3-C10 cycloalkyl or a saturated heterocycle with 4-6 ring atoms;

$R^{k12}$ is selected from H, alkyl (linear or branched), e.g., C1-C6 alkyl, aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, wherein the said alkyl, aryl or heteroaryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano;

$R^{k13}$ is selected from H, alkyl, —C(O)NHR, C(O)R, S(O)$_2$R where R is H, alkyl, e.g., C1-C6 alkyl, or cycloalkyl, e.g., C3-C10 cycloalkyl, which can be further substituted with 1 to 2 substituents selected from alkyl, e.g., C1-C6 alkyl, halogen, alkylsulfone, alkylsulfonamide, amide, carboxamide, haloalkyl, e.g., C1-C6 haloalkyl, alkoxy, e.g., C1-C6 alkoxy, hydroxyl, amino, amide, alkylamino, dialkylamino and cyano; and X is N or CH.

In certain embodiments, the PTM of formula XVI comprises a linker, wherein the linker is a chemical moiety as described herein coupling the PTM to the ULM group. In certain additional embodiments, one or more of the R groups of formula XVI is coupled to a linker, wherein the linker is a chemical moiety as described herein coupling the PTM to the ULM group.

In certain additional embodiments, one or more of $R^{k11}$, $R^{k12}$, or $R^{k13}$ groups of formula XVI is coupled to a linker, wherein the linker is a chemical moiety as described herein coupling the PTM to the ULM group.

In certain embodiments of formula XVI, $R^{k13}$ is:

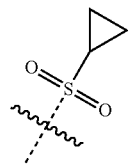

In certain embodiments, an R group of formula XVI comprises a linker, wherein the linker is a chemical moiety coupling the PTM to the ULM group.

In certain embodiments, the PTM of formula XVI comprises the structure:

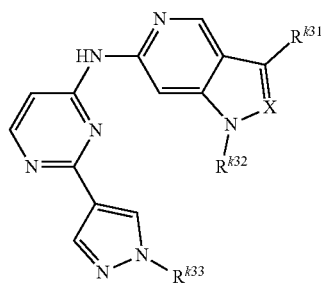

XVI-2 wherein $R^{k31}$ is selected from H, alkyl, e.g., C1-C6 alkyl, alkoxy, C(O)NHR where R is selected from H, alkyl, e.g., C1-C6 alkyl, cycloalkyl, e.g., C3-C10 cycloalkyl or a saturated heterocycle with 4-6 ring atoms;

$R^{k32}$ is selected from H, alkyl (linear or branched), e.g., C1-C6 alkyl, or halogen substituted alkyl with 1-6 C atoms;

$R^{k33}$ is selected from H, alkyl, —C(O)NHR, C(O)R, S(O)$_2$R where R is H, alkyl, e.g., C1-C6 alkyl, or cycloalkyl, which can be further substituted with 1 to 2 substituents selected from alkyl, e.g., C1-C6 alkyl, halogen, alkylsulfone, alkylsulfonamide, amide, carboxamide, haloalkyl, e.g., C1-C6 haloalkyl, hydroxyl, alkoxy, e.g., C1-C6 alkoxy, amino, amide, alkylamino, dialkylamino and cyano; and X is N or CH.

In certain additional embodiments, one or more of $R^{k31}$, $R^{k32}$, or $R^{k33}$ groups of formula XVI is coupled to a linker, wherein the linker is a chemical moiety as described herein coupling the PTM to the ULM group.

In certain embodiments of formula XVI, $R^{k33}$ is:

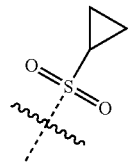

In one embodiment, PTMs of the PROTACs as described herein comprise the moiety represented by the formula XVII:

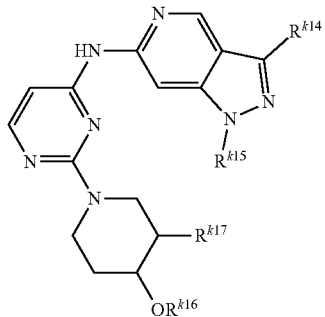

XVII wherein $R^{k14}$ is selected from H, alkyl, e.g., C1-C6 alkyl, alkoxy, e.g., C1-C6 alkoxy, —C(O)NHR where R is selected from H, alkyl, e.g., C1-C6 alkyl, cycloalkyl, e.g., C3-C10 cycloalkyl, or a saturated heterocycle with 4-6 ring atoms;

$R^{k15}$ is selected from H, alkyl (linear or branched), aryl, e.g., C5-C10 aryl, heteroaryl, e.g., C3-C10 heteroaryl comprising 1 or more heteroatoms selected from O, N, and S, cycloalkyl, e.g., C3-C10 cycloalkyl, wherein the said alkyl, aryl or heteroaryl can be further substituted with 1 to 2 substituents selected from alkyl, e.g., C1-C6 alkyl, halogen, or haloalkyl, e.g., C1-C6 haloalkyl, alkoxy, e.g., C1-C6 alkoxy, hydroxyl, amino, alkylamino, dialkylamino and cyano;

$R^{k16}$ is selected from H, alkyl, e.g., C1-C6 alkyl, or cycloalkyl, e.g., C3-C10 cycloalkyl, which can be further substituted with 1 to 2 substituents selected from alkyl, e.g., C1-C6 alkyl, halogen, alkylsulfone, alkylsulfonamide, amide, carboxamide, haloalkyl, e.g., C1-C6 haloalkyl, alkoxy, e.g., C1-C6 alkoxy, hydroxyl, amino, amide, alkylamino, dialkylamino and cyano; and $R^{k17}$ is selected from H, halogen, CN.

In certain embodiments, the PTM of formula XVII comprises a linker, wherein the linker is a chemical moiety as described herein coupling the PTM to the ULM group. In certain additional embodiments, one or more of the R groups of formula XVII is coupled to a linker, wherein the linker is a chemical moiety as described herein coupling the PTM to the ULM group.

In certain additional embodiments, one or more of $R^{k14}$, $R^{k15}$, $R^{k16}$ or $R^{k17}$ groups of formula XVII is coupled to a linker, wherein the linker is a chemical moiety as described herein coupling the PTM to the ULM group.

In certain embodiments, the PTM of formula XVII comprises the structure:

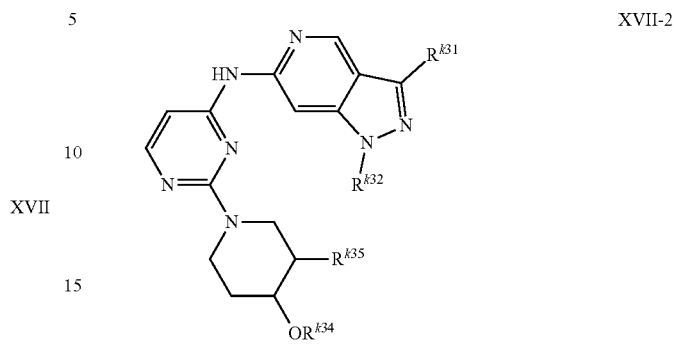

XVII-2 wherein $R^{k31}$ is selected from H, alkyl, alkoxy, C(O)NHR where R is selected from H, alkyl, cycloalkyl or a saturated heterocycle with 4-6 ring atoms;

$R^{k32}$ is selected from H, alkyl (linear or branched) or halogen substituted alkyl with 1-6 C atoms;

$R^{k34}$ is selected from H, alkyl (linear or branched) or halogen substituted alkyl with 1-3 C atoms; and $R^{35}$ is selected from H, F, Cl, Br or cyano.

In certain additional embodiments, one or more of $R^{k31}$, $R^{k32}$, $R^{k34}$ or $R^{k35}$ groups of formula XVII is coupled to a linker, wherein the linker is a chemical moiety as described herein coupling the PTM to the ULM group.

In certain embodiments, the PTM of formula XVII comprises the structure:

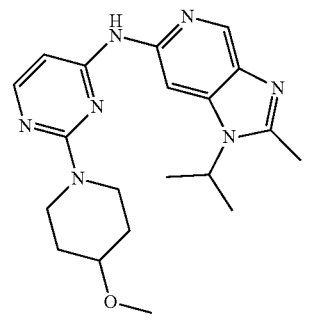

As described herein, the PTMs are coupled via a linker moiety to a ULM. It is contemplated that the linker moiety can be conjugated at any location desired on the PTM. In certain embodiments, the PTM comprises a structure selected from the group consisting of:

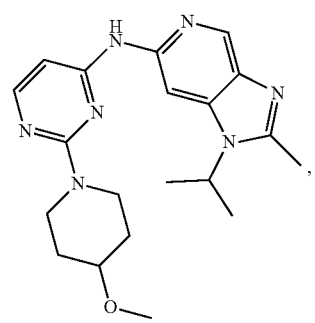 [SMILES: COC1CCN(c2nccc(Nc3cc4c(cn3)nc(C)n4C(C)C)n2)CC1]

,

-continued
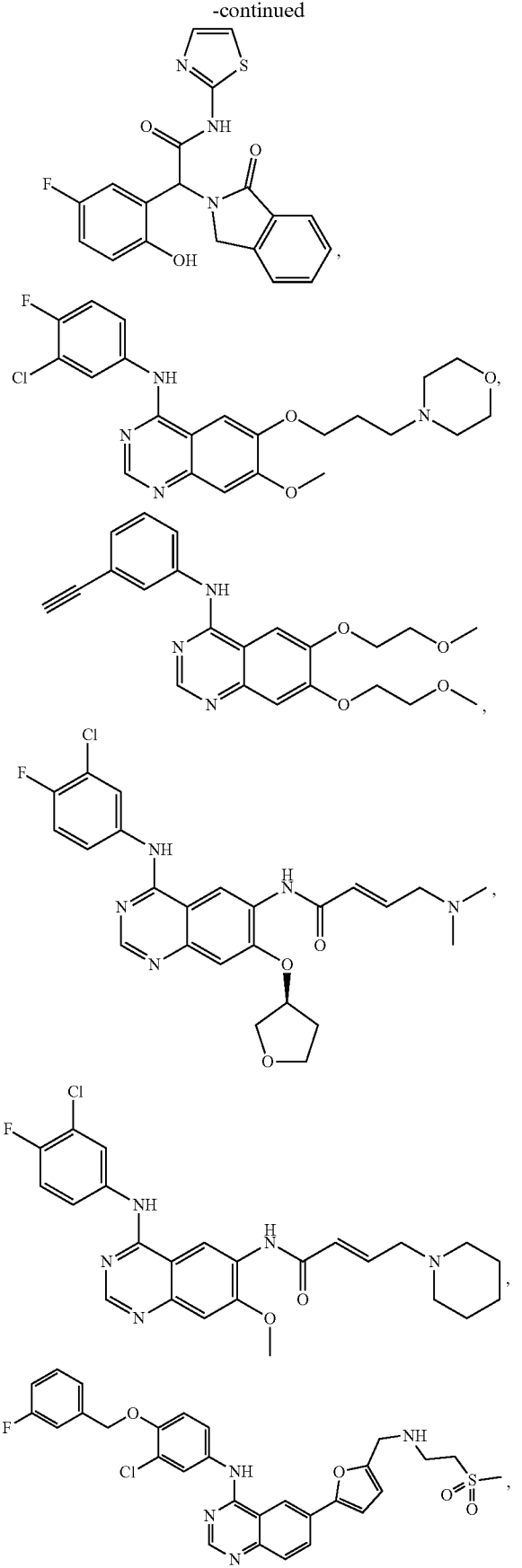
-continued
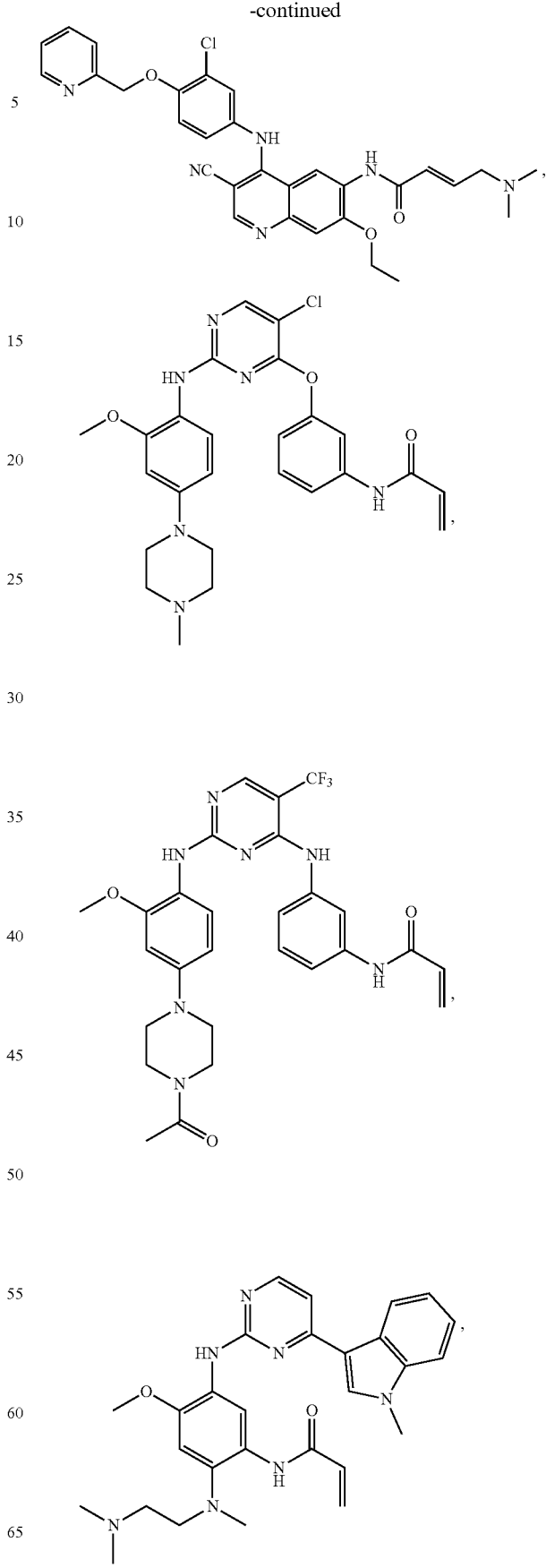

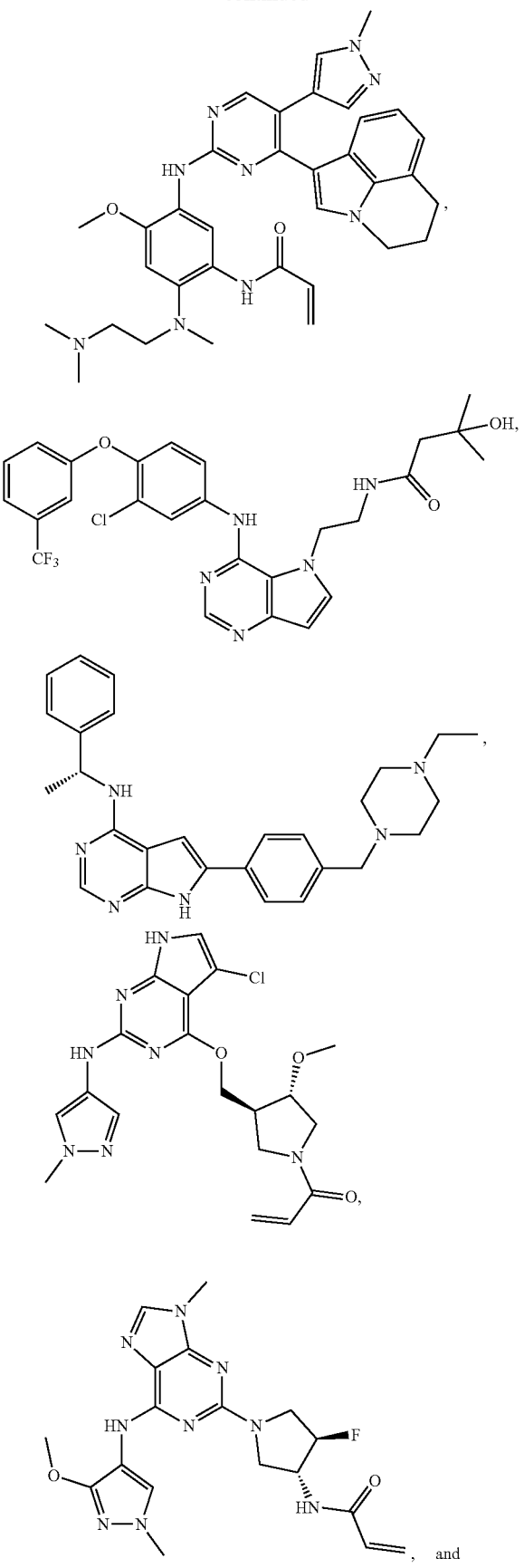

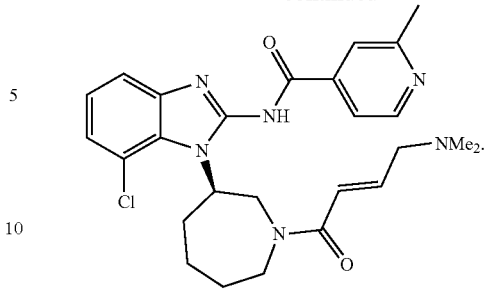

In certain embodiments, the description provides a compound having the structure selected from compound 1-351 as described in FIG. 2.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

In certain embodiments, the description provides a therapeutic composition comprising an effective amount of at least one compound selected from compound 1-351 as described in FIG. 2, and a pharmaceutically acceptable carrier or excipient. In certain embodiments, the description provides a combination for co-administration (e.g., either separately or in a single dosage form) comprising an effective amount of at least one compound as described herein, at least one additional bioactive agent, and a pharmaceutically acceptable carrier or excipient. In certain embodiments, the additional bioactive agent is an anti-oncologic agent.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

In another aspect, the disclosure provides therapeutic compositions comprising an effective and/or synergistic amount of a compound as described herein, and at least one additional bioactive agent (i.e., a combination therapeutic), e.g., another EGFR PROTAC as described herein, an anti-cancer, and anti-inflammatory, and/or an EGFR inhibitor. In certain embodiments, the EGFR inhibitor includes at least one of gefitinib, erlotinib, afatinib, brigatinib, icotinib, lapatinib, cetuximab, panitumumab, osimertinib, zalutumumab, nimotuzumab, matuzumab or combinations thereof. In certain embodiments, the combination therepay composition an effective amount of the EGFR inhibitor.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, e.g., EGFR-related diseases or disorders, which may be treated using compounds according to the present disclosure are contemplated.

The description provides therapeutic compositions as described herein for effectuating the degradation of proteins of interest for the treatment or amelioration of an EGFR-related disease, e.g., cancer and/or an inflammatory disorder, and/or hair growth. As such, in another aspect, the description provides a method of ubiquitinating/degrading a target protein in a cell.

In certain embodiments, the description provides compositions and methods for treating an EGFR-related disease or disorder. In certain embodiments, the EGFR-related disease or disorder is at least one of cancer and/or an inflammatory disorder. In certain embodiments, the EGFR-related disease or disorder is at least one of squamous-cell carcinoma of the lung, colon and anal cancers, glioblastoma, and epithelial tumors of the head and neck, psoriasis, eczema and atherosclerosis or a combination thereof.

In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through EGFR protein where the degradation of that protein will produce a therapeutic effect in the patient, the method comprising administering to a patient in need an effective amount of a compound according to the present disclosure. In certain embodiments, the compound as described herein is administered in combination with another bioactive agent, e.g., an EGFR inhibitor, as described herein.

The term "disease state or condition" is used to describe any disease state or condition wherein EGFR protein dysregulation (i.e., the amount of EGFR protein expressed in a patient is elevated) occurs and where degradation of EGFR proteins in a patient may provide beneficial therapy or relief of symptoms to a patient in need thereof. In certain instances, the disease state or condition may be cured.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiaryl-methane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

PTM embodiments of the current invention can be prepared according to the synthetic routes previously described in the literature and/or detailed in schemes 1-6 below. These routes can be modified and adapted to the synthesis of the particular PTM embodiment using general methods known to those skilled in the art. In particular, synthetic approaches to the PTMs represented by the general formula I have been previously described (see, for example, Barker, A. J. et al. WO199730034 and Barker, A. J. et al. *Bioorganic and Medicinal Chemistry Letters* 2001, 11(14), 1911-1914) and can be generalized as shown in Scheme 1 and 2, where $R^{22'}$ is a synthetic precursor of the targeted substitution $R^{22}$ into which in can be converted using general synthetic methods known to those skilled in the art.

Experimental Procedures
Synthesis of Example 1
(2S,4R)-1-((S)-2-(tert-butyl)-14-(4-(4-(4-((2-chlorobenzyl)amino)-7H-pyrrolo[2,3-d]pyrimidin-6-yl)benzyl)piperazin-1-yl)-4-oxo-6,9,12-trioxa-3-azatetradecanoyl)-4-hydroxy-N-(4-(4-methylthiazol-5-yl)benzyl)pyrrolidine-2-carboxamide
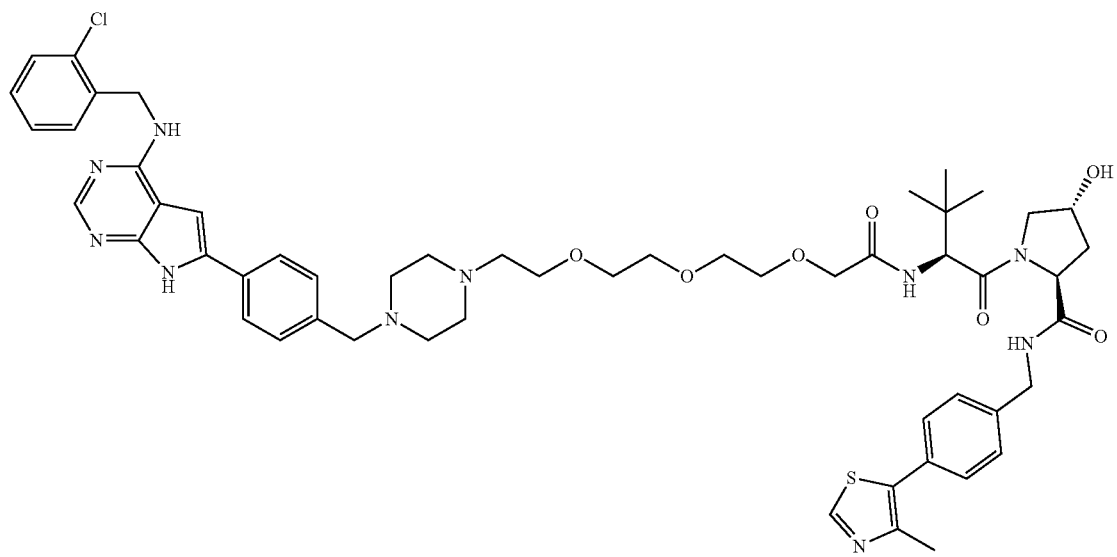 [SMILES: Cc1ncsc1-c1ccc(CNC(=O)[C@@H]2C[C@@H](O)CN2C(=O)[C@@H](NC(=O)COCCOCCOCCN2CCN(Cc3ccc(-c4cc5c(NCc6ccccc6Cl)ncnc5[nH]4)cc3)CC2)C(C)(C)C)cc1]
Synthetic scheme:
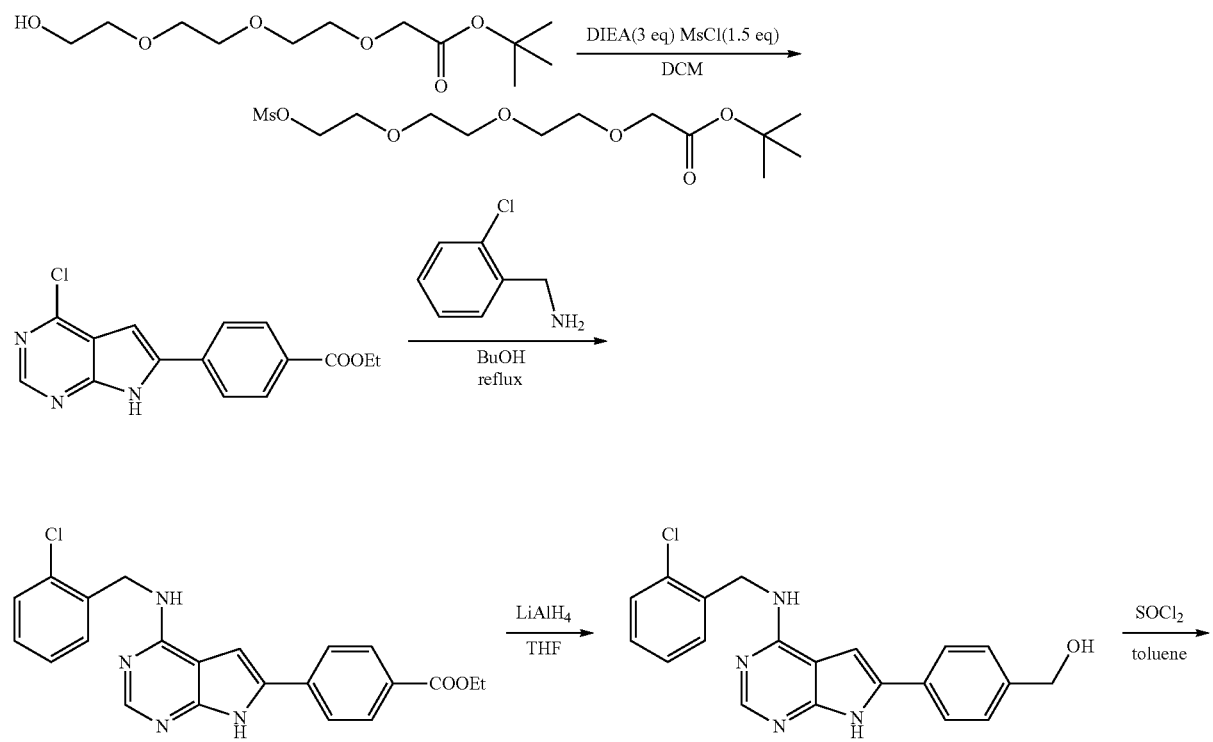

-continued
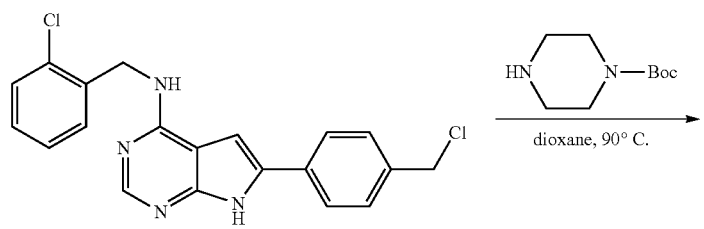
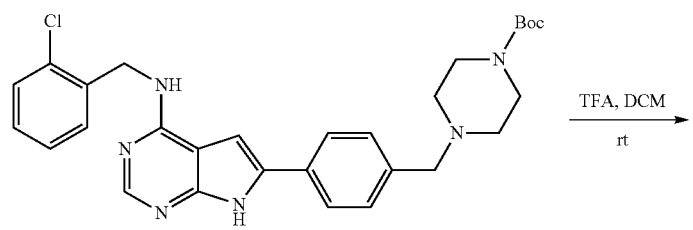
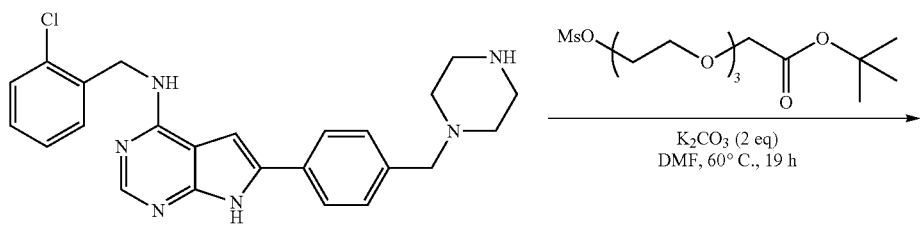
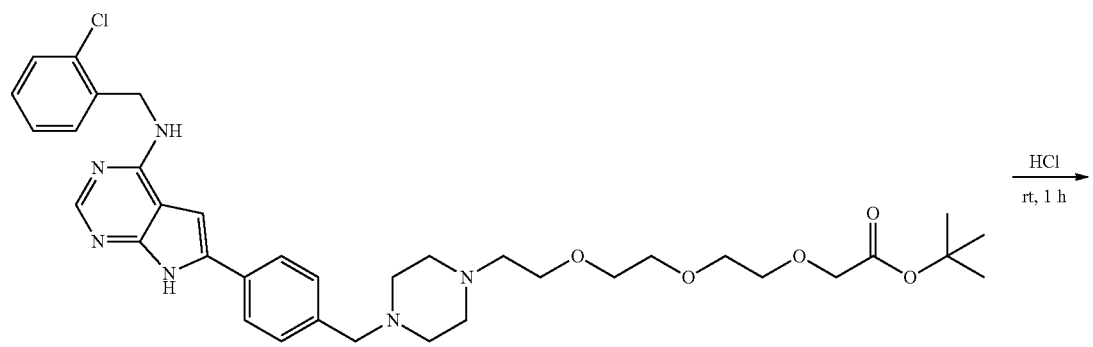
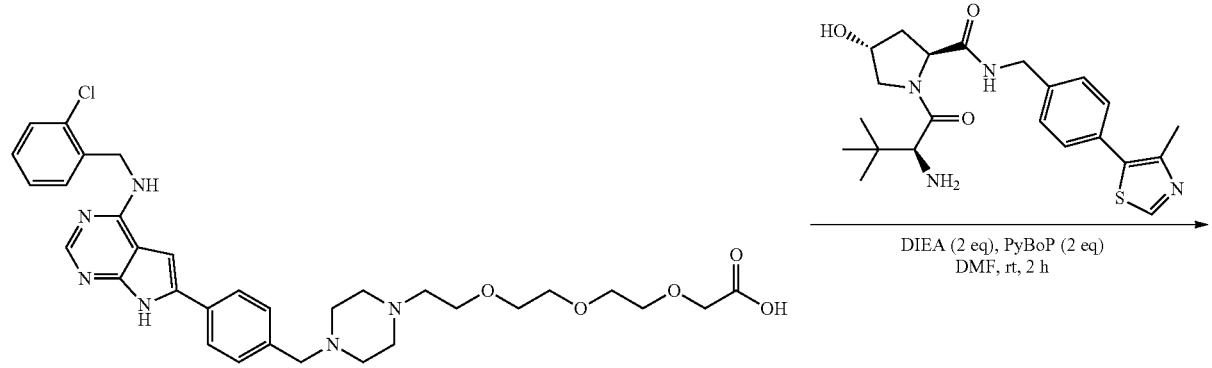

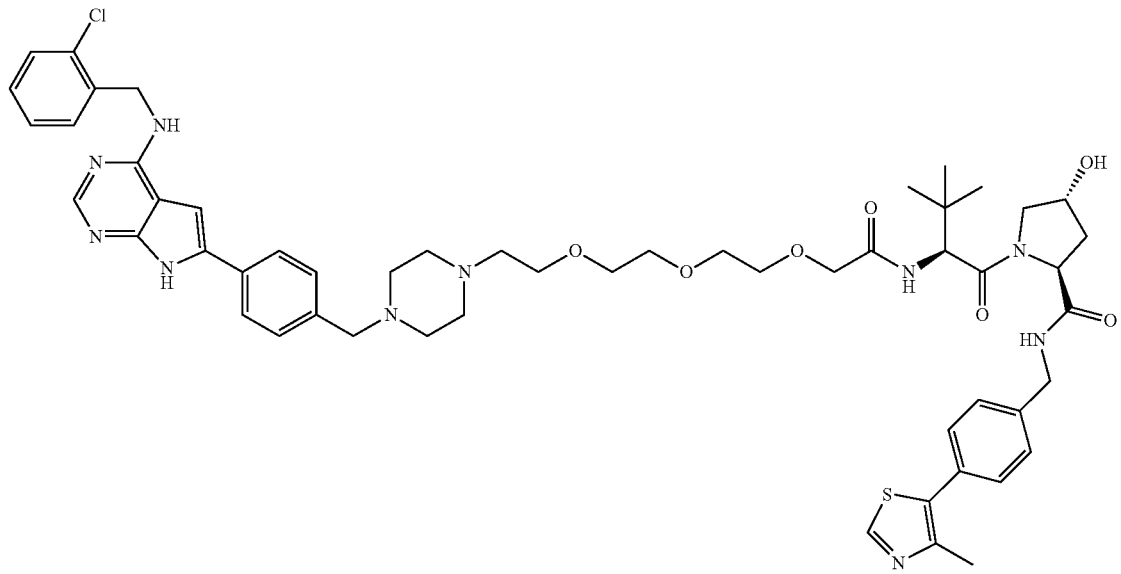

1. Step—Synthesis of tert-Butyl 2-(2-(2-(2-((methylsulfonyl)oxy)ethoxy)ethoxy)ethoxy)acetate

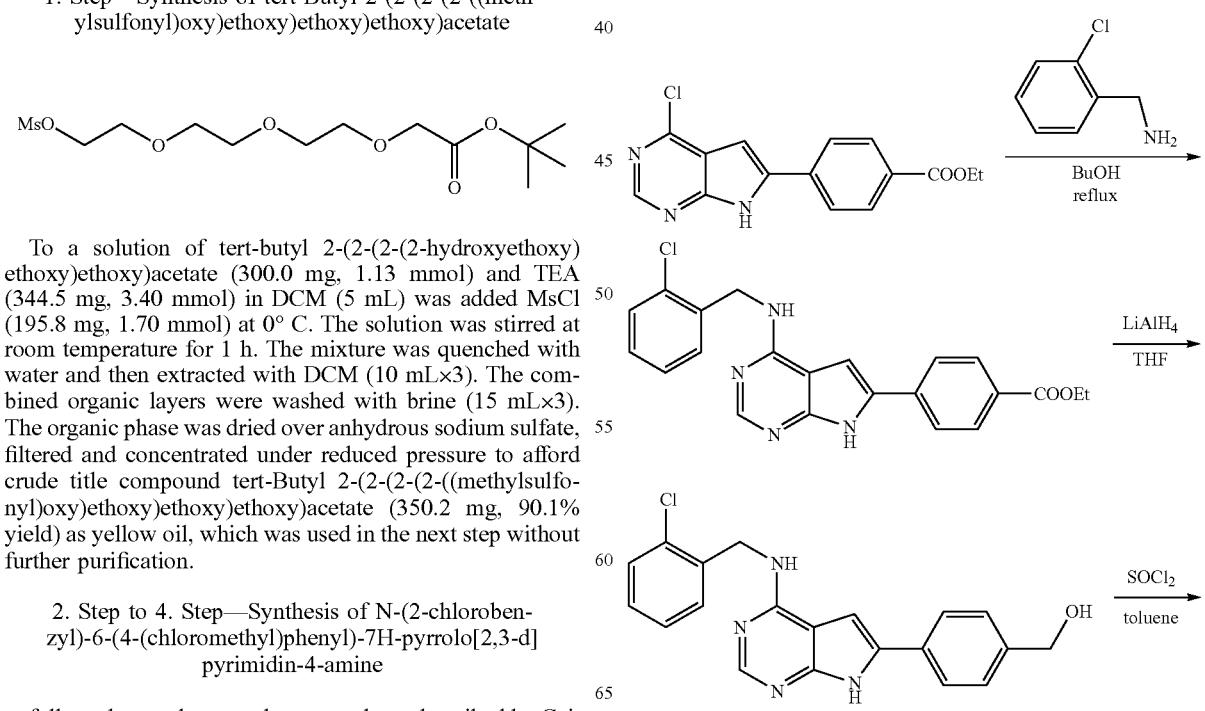

To a solution of tert-butyl 2-(2-(2-(2-hydroxyethoxy)ethoxy)ethoxy)acetate (300.0 mg, 1.13 mmol) and TEA (344.5 mg, 3.40 mmol) in DCM (5 mL) was added MsCl (195.8 mg, 1.70 mmol) at 0° C. The solution was stirred at room temperature for 1 h. The mixture was quenched with water and then extracted with DCM (10 mL×3). The combined organic layers were washed with brine (15 mL×3). The organic phase was dried over anhydrous sodium sulfate, filtered and concentrated under reduced pressure to afford crude title compound tert-Butyl 2-(2-(2-(2-((methylsulfonyl)oxy)ethoxy)ethoxy)ethoxy)acetate (350.2 mg, 90.1% yield) as yellow oil, which was used in the next step without further purification.

2. Step to 4. Step—Synthesis of N-(2-chlorobenzyl)-6-(4-(chloromethyl)phenyl)-7H-pyrrolo[2,3-d]pyrimidin-4-amine followed procedures analogous to those described by Cai, X. et al. in WO 2008033747.

-continued

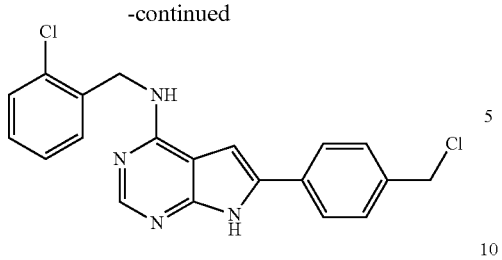

5. Step—Synthesis of tert-Butyl 4-(4-(4-((2-chlorobenzyl)amino)-7H-pyrrolo[2,3-d]pyrimidin-6-yl)benzyl)piperazine-1-carboxylate

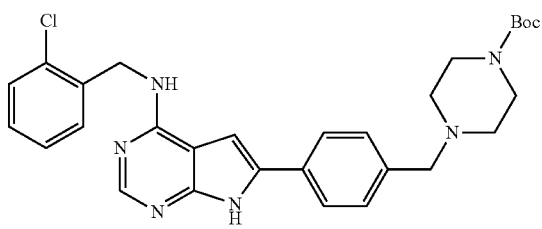 [SMILES: CC(C)(C)OC(=O)N1CCN(Cc2ccc(-c3cc4c(NCc5ccccc5Cl)ncnc4[nH]3)cc2)CC1]

To a solution of N-(2-chlorobenzyl)-6-(4-(chloromethyl)phenyl)-7H-pyrrolo[2,3-d]pyrimidin-4-amine (3.93 g, 10.3 mmol) in dioxane (80 mL) was added tert-butyl piperazine-1-carboxylate (3.92 g, 21.0 mmol). The solution was stirred at 90° C. for 7 h. The mixture was concentrated under reduced pressure. The residue was recrystallized from CH₃OH to give tert-Butyl 4-(4-(4-((2-chlorobenzyl)amino)-7H-pyrrolo[2,3-d]pyrimidin-6-yl)benzyl)piperazine-1-carboxylate (4.08 g, 91.9% yield) as a light yellow solid.

6. Step—Synthesis of N-(2-Chlorobenzyl)-6-(4-(piperazin-1-ylmethyl)phenyl)-7H-pyrrolo[2,3-d]pyrimidin-4-amine

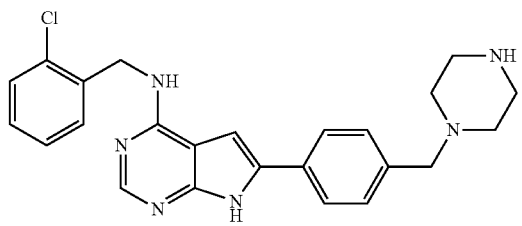 [SMILES: Clc1ccccc1CNc1ncnc2[nH]c(-c3ccc(CN4CCNCC4)cc3)cc12]

To a solution of tert-butyl 4-(4-(4-((2-chlorobenzyl)amino)-7H-pyrrolo[2,3-d]pyrimidin-6-yl)benzyl)piperazine-1-carboxylate (3.98 g, 7.5 mmol) in DCM (30 mL) was added trifluoroacetic acid (9.0 mL). The mixture was stirred at RT for 3 h. The solvent was removed under reduced pressure. The residue was dissolved in water (50 mL). The pH of the solution was adjusted to 9 by solid NaHCO₃. The mixture was extracted with DCM (50 mL×3). The combined organic layers were washed with brine. The organic phase was dried over anhydrous sodium sulfate, filtered and evaporated under reduced pressure to afford crude product N-(2-Chlorobenzyl)-6-(4-(piperazin-1-ylmethyl)phenyl)-7H-pyrrolo[2,3-d]pyrimidin-4-amine (2.0 g, 61.9% yield), which was used in the next step without further purification.

7. Step—Synthesis of 2-(2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethoxy)acetic acid

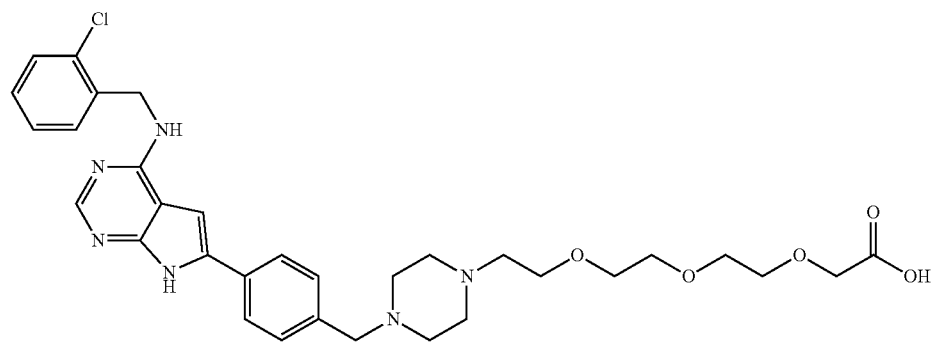 [SMILES: O=C(O)COCCOCCOCCN1CCN(Cc2ccc(-c3cc4c(NCc5ccccc5Cl)ncnc4[nH]3)cc2)CC1]

To a solution of tert-butyl 2-(2-(2-(2-(4-(4-(4-((2-chlorobenzyl)amino)-7H-pyrrolo[2,3-d]pyrimidin-6-yl)benzyl)piperazin-1-yl)ethoxy)ethoxy)ethoxy)acetate (136.2 mg, 0.20 mmol) in dioxane (2.0 mL) was added dioxane/HCl (0.5 mL). The mixture was stirred at RT for 1.5 h. The solvent was removed in vacuo to afford crude title product 2-(2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethoxy)acetic acid (121.5 mg), which was used in the next step without further purification.

8. Step—Synthesis of (2S,4R)-1-((S)-2-(tert-butyl)-14-(4-(4-(4-((2-chlorobenzyl)amino)-7H-pyrrolo[2,3-d]pyrimidin-6-yl)benzyl)piperazin-1-yl)-4-oxo-6,9,12-trioxa-3-azatetradecanoyl)-4-hydroxy-N-(4-(4-methylthiazol-5-yl)benzyl)pyrrolidine-2-carboxamide

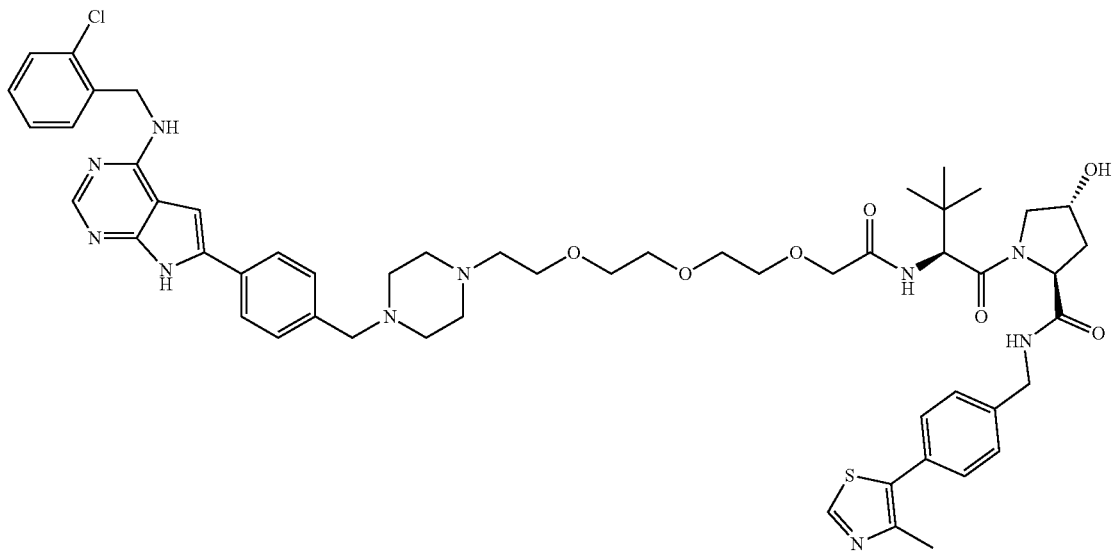 [SMILES: Cc1ncsc1-c1ccc(CNC(=O)[C@@H]2C[C@@H](O)CN2C(=O)[C@@H](NC(=O)COCCOCCOCCN2CCN(Cc3ccc(-c4cc5c(NCc6ccccc6Cl)ncnc5[nH]4)cc3)CC2)C(C)(C)C)cc1]

To a solution of 2-(2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethoxy)acetic acid (121.5 mg, 0.19 mmol) and (2S,4R)-1-((S)-2-amino-3,3-dimethylbutanoyl)-4-hydroxy-N-(4-(4-methylthiazol-5-yl)benzyl)pyrrolidine-2-carboxamide (87.9 mg, 0.19 mmol) in dry DMF (6.0 mL) were added DIEA (76.7 mg, 0.57 mmol) and PyBop (197.8 mg, 0.38 mmol). The mixture was stirred at RT for 1.5 h. The solution was quenched with water (20 mL) and then extracted with EA (20 mL×3). The combined organic layers were washed with brine. The organic phase was dried over anhydrous sodium sulfate, filtered and evaporated in vacuo. The residue was purified by silica gel column chromatography (dichloromethane/methanol=25/1) to afford crude title product (60.2 mg). Then it was further purified by prep-HPLC to afford the title product of (2S,4R)-1-((S)-2-(tert-butyl)-14-(4-(4-(4-((2-chlorobenzyl)amino)-7H-pyrrolo[2,3-d]pyrimidin-6-yl)benzyl)piperazin-1-yl)-4-oxo-6,9,12-trioxa-3-azatetradecanoyl)-4-hydroxy-N-(4-(4-methylthiazol-5-yl)benzyl)pyrrolidine-2-carboxamide (19.0 mg, 9.5% yield).

$^1$H NMR (400 MHz, MeOD): δ 8.85 (s, 1H), 8.10 (s, 1H), 7.74 (d, J=8.0 Hz, 2H), 7.37-7.44 (m, 8H), 7.23-7.25 (m, 2H), 6.92 (s, 1H), 4.69 (s, 1H), 4.48-4.59 (m, 5H), 4.30 (s, 1H), 4.00 (d, J=5.60 Hz, 2H), 3.87 (d, J=11.08 Hz, 1H), 3.80 (d, J=3.80 Hz, 1H), 3.63-3.68 (m, 12H), 2.90 (s, 4H), 2.65 (s, 3H), 2.45 (s, 3H), 2.22 (m, 1H), 2.21 (m, 1H), 1.03 (s, 9H).

Synthesis of Example 8
4-((17-(4-(4-(4-((2-chlorobenzyl)amino)-7H-pyrrolo[2,3-d]pyrimidin-6-yl)benzyl)piperazin-1-yl)-3,6,9,12,15-pentaoxaheptadecyl)amino)-2-(2,6-dioxopiperidin-3-yl)isoindoline-1,3-dione
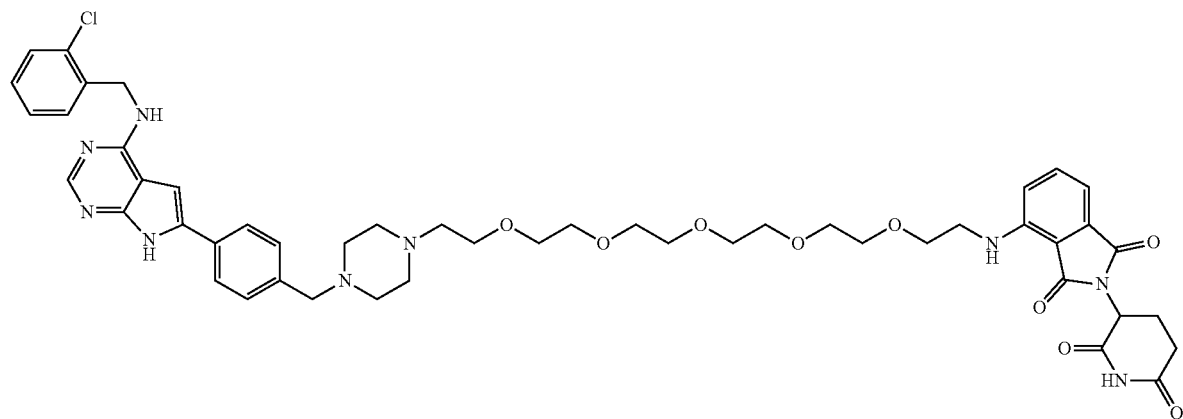 [SMILES: O=C1CCC(N2C(=O)c3cccc(NCCOCCOCCOCCOCCOCCN4CCN(Cc5ccc(-c6cc7c(NCc8ccccc8Cl)ncnc7[nH]6)cc5)CC4)c3C2=O)C(=O)N1]
Synthetic scheme:
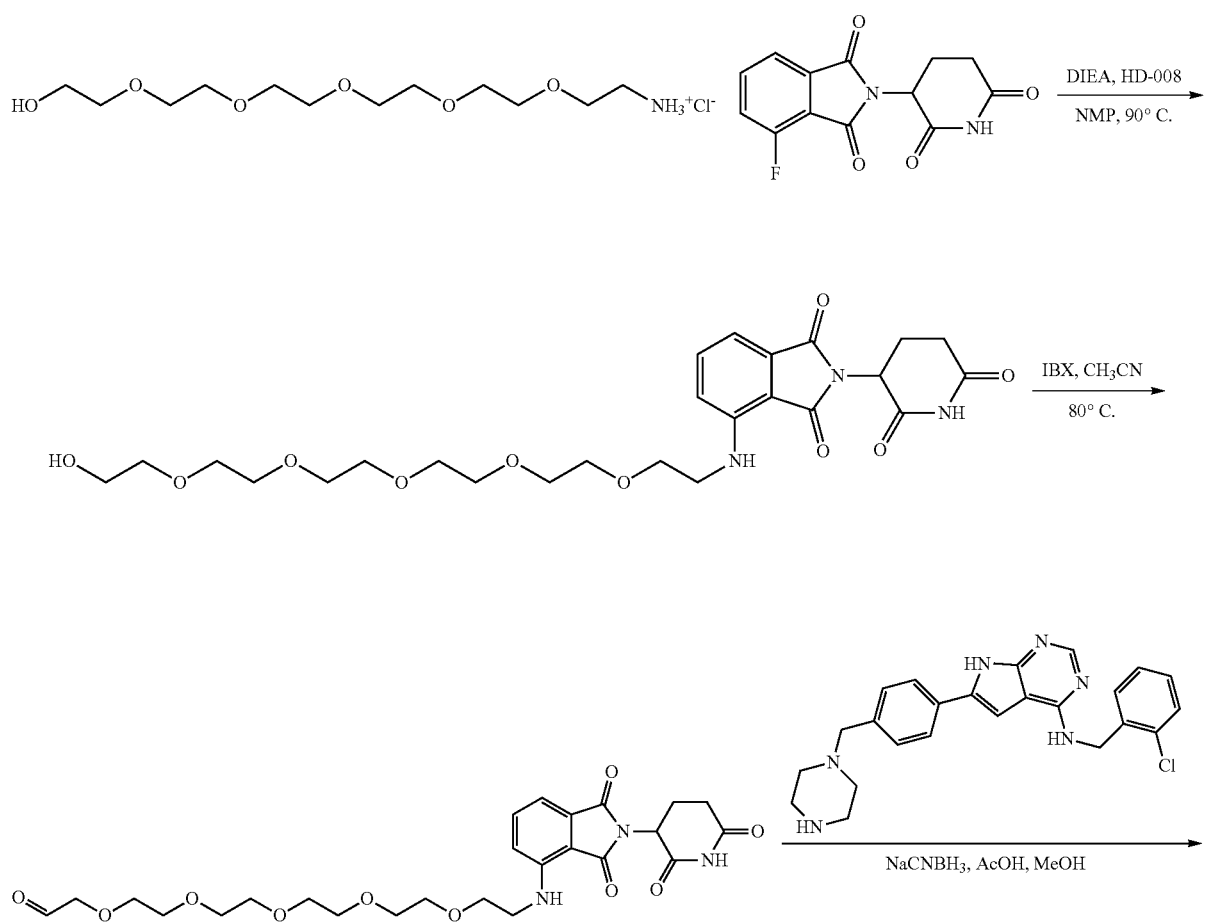

-continued

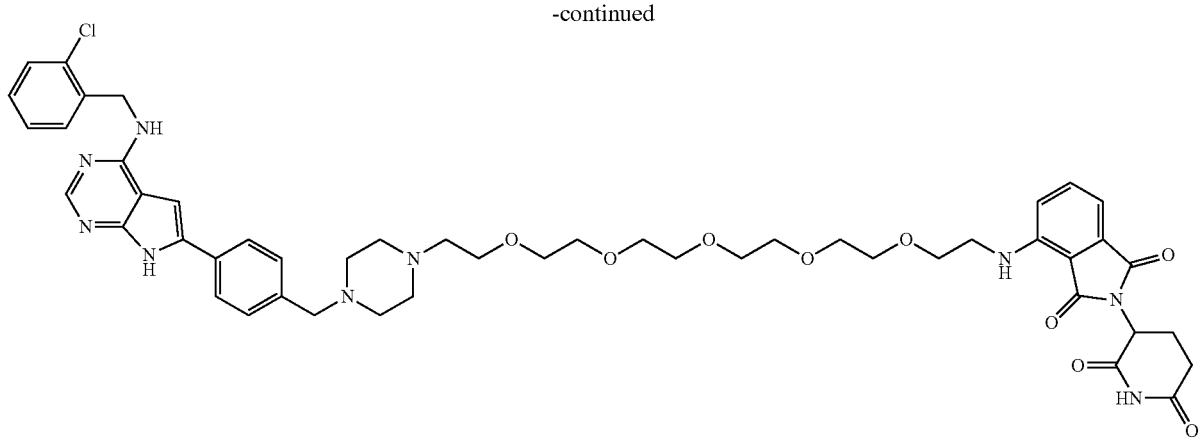

1. Step—Synthesis of 2-(2,6-Dioxopiperidin-3-yl)-4-((17-hydroxy-3,6,9,12,15-pentaoxaheptadecyl)amino)isoindoline-1,3-dione

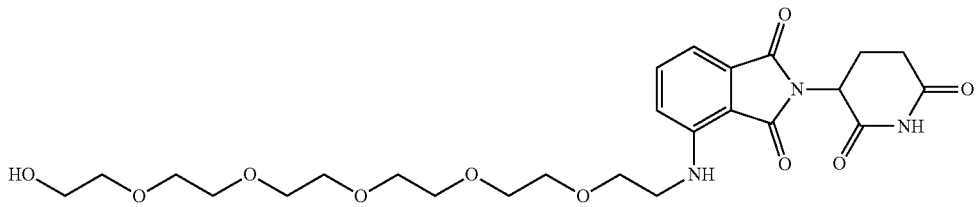 [SMILES: O=C1CCC(N2C(=O)c3cccc(NCCOCCOCCOCCOCCOCCO)c3C2=O)C(=O)N1]

To a solution of 17-amino-3,6,9,12,15-pentaoxaheptadecan-1-ol hydrochloride (2.00 g, 7.1 mmol) and 2-(2,6-dioxopiperidin-3-yl)-4-fluoroisoindoline-1,3-dione (2.94 g, 10.65 mmol) in NMP (10 mL) was added DIEA (3.67 g, 28.4 mmol). The solution was stirred at 90° C. for 2.5 h. Then it was cooled to rt and quenched with water (20 mL). The mixture was extracted with DCM (50 mL×3). The combined organic layers were dried over anhydrous sodium sulfate, filtered and concentrated under vacuum. The residue was purified by silica gel column chromatography (DCM/MeOH=25/1) to afford the title compound 2-(2,6-Dioxopiperidin-3-yl)-4-((17-hydroxy-3,6,9,12,15-pentaoxaheptadecyl)amino)isoindoline-1,3-dione (300.2 mg, 9.9% yield).

2. Step—Synthesis of 17-((2-(2,6-Dioxopiperidin-3-yl)-1,3-dioxoisoindolin-4-yl)amino)-3,6,9,12,15-pentaoxaheptadecanal

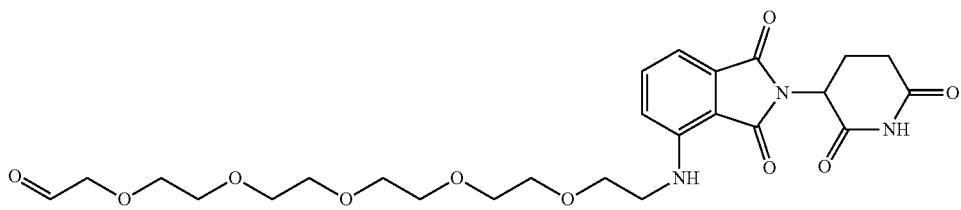 [SMILES: O=CCOCCOCCOCCOCCOCCNc1cccc2c1C(=O)N(C1CCC(=O)NC1=O)C2=O]

To a solution of 2-(2,6-Dioxopiperidin-3-yl)-4-((17-hydroxy-3,6,9,12,15-pentaoxaheptadecyl)amino)isoindoline-1,3-dione (300.0 mg, 0.56 mmol) in CH$_3$CN (15.0 mL) was added IBX (234.4 mg, 0.84 mmol). The mixture was stirred at 80° C. for 2 h. Then it was filtered through Celite and the filtrate was concentrated under reduced pressure to afford the crude title product 17-((2-(2,6-Dioxopiperidin-3-yl)-1,3-dioxoisoindolin-4-yl)amino)-3,6,9,12,15-pentaoxaheptadecanal (230.6 mg, 77.2% yield), which was used in the next reaction without further purification.

3. Step—Synthesis of 4-((17-(4-(4-(4-((2-chlorobenzyl)amino)-7H-pyrrolo[2,3-d]pyrimidin-6-yl)benzyl)piperazin-1-yl)-3,6,9,12,15-pentaoxaheptadecyl)amino)-2-(2,6-dioxopiperidin-3-yl)isoindoline-1,3-dione

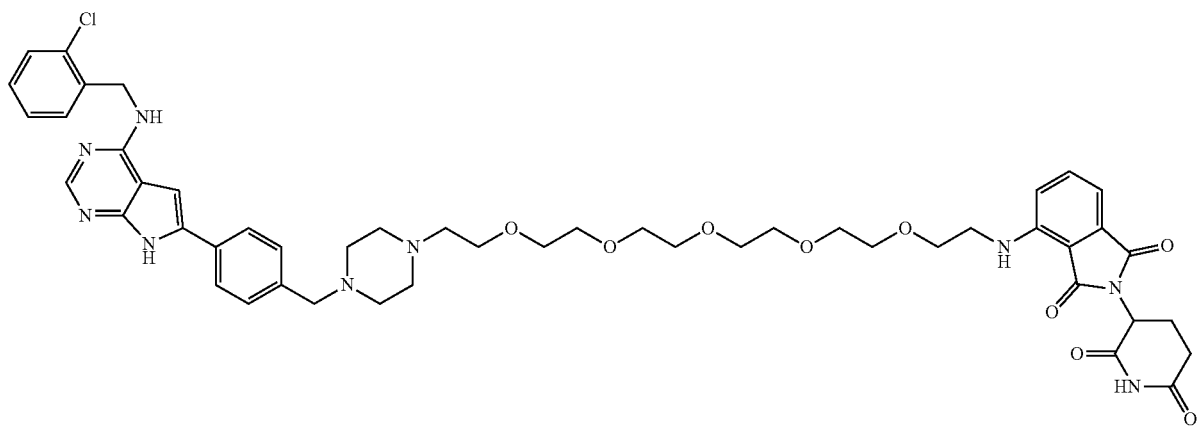 [SMILES: O=C1CCC(N2C(=O)c3cccc(NCCOCCOCCOCCOCCOCCN4CCN(Cc5ccc(-c6cc7c(NCc8ccccc8Cl)ncnc7[nH]6)cc5)CC4)c3C2=O)C(=O)N1]

To a solution of 17-((2-(2,6-dioxopiperidin-3-yl)-1,3-dioxoisoindolin-4-yl)amino)-3,6,9,12,15-pentaoxaheptadecanal (150.0 mg, 0.33 mmol) and N-(2-chlorobenzyl)-6-(4-(piperazin-1-ylmethyl)phenyl)-7H-pyrrolo[2,3-d]pyrimidin-4-amine (145.0 mg, 0.33 mmol) in MeOH (10 mL) were added NaCNBH$_3$ (98.0 mg, 1.0 mmol) and two drops of AcOH. The mixture was stirred at rt for 16 h. Then the solvent was removed in vacuo. The residue was purified by prep-HPLC to afford the title compound 4-((17-(4-(4-(4-((2-chlorobenzyl)amino)-7H-pyrrolo[2,3-d]pyrimidin-6-yl)benzyl)piperazin-1-yl)-3,6,9,12,15-pentaoxaheptadecyl)amino)-2-(2,6-dioxopiperidin-3-yl)isoindoline-1,3-dione (45.9 mg, 17.2% yield).
$^1$H NMR (400 MHz, CD$_3$OD): δ 8.26 (s, 1H), 7.77 (d, J=7.6 Hz, 2H), 7.47-7.51 (m, 5H), 7.36-7.39 (m, 2H), 7.15 (s, 1H), 6.99-7.02 (m, 2H), 5.00-5.04 (m, 1H), 4.93 (s, 2H), 3.81 (s, 4H), 3.42-3.69 (m, 24H), 2.69-3.00 (m, 8H), 2.03-2.09 (m, 1H), 1.25-1.32 (m, 1H).

Synthesis of Example 10

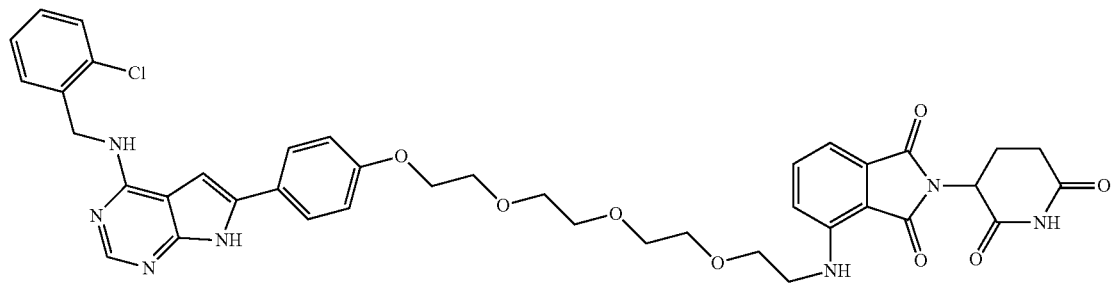 [SMILES: O=C1CCC(N2C(=O)c3cccc(NCCOCCOCCOCCOc4ccc(-c5cc6c(NCc7ccccc7Cl)ncnc6[nH]5)cc4)c3C2=O)C(=O)N1]

4-((2-(2-(2-(2-(4-(4-((2-chlorobenzyl)amino)-7H-pyrrolo[2,3-d]pyrimidin-6-yl)phenoxy)ethoxy)ethoxy)ethoxy)ethyl)amino)-2-(2,6-dioxopiperidin-3-yl)isoindoline-1,3-dione Synthetic Scheme:

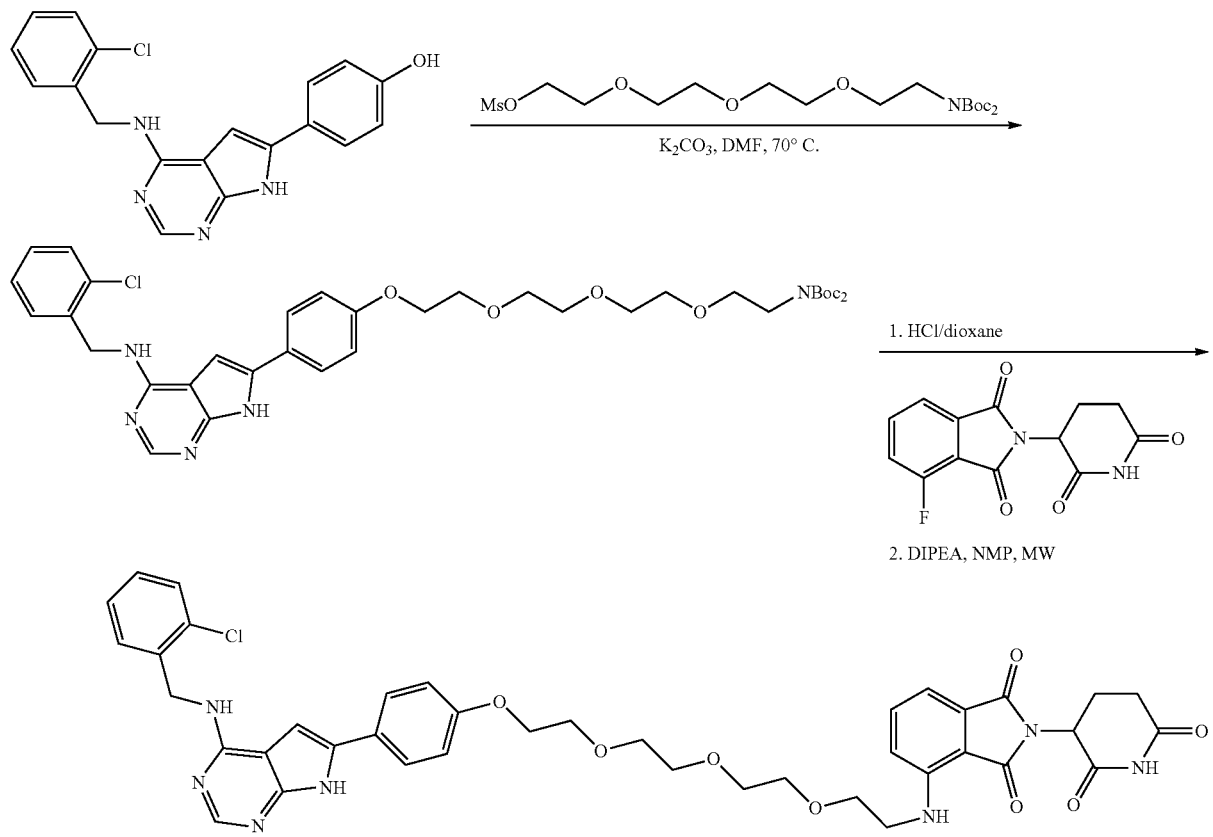

1. Step—Synthesis of 6-(4-(2-(2-(2-(2-(N,N-di-tert-butoxycarbonyl-amino)ethoxy)ethoxy)ethoxy)ethoxy)phenyl)-N-(2-chlorobenzyl)-7H-pyrrolo[2,3-d]pyrimidin-4-amine

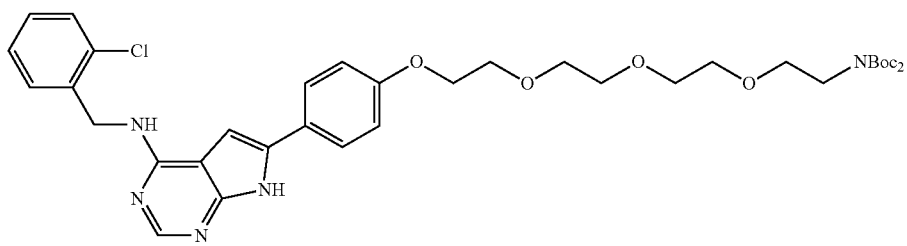

To a solution of 2-(2-(2-(2-(N,N-di-tert-butoxycarbonyl-amino)aminoethoxy)ethoxy)ethoxy)ethyl methanesulfonate (490 mg, 1.04 mmol) in DMF (10 mL) and 4-(4-((2-chlorobenzyl)amino)-7H-pyrrolo[2,3-d]pyrimidin-6-yl)phenol (364 mg, 1.04 mmol) was added $K_2CO_3$ (430 mg, 3.12 mmol) at 25° C. The resulting solution was stirred at 70° C. for 16 h. The resulting solution was cooled to 20° C. The mixture was diluted with $H_2O$ (40 mL). The mixture was extracted with EtOAc (40 mL×2). The combined organic layers were dried over anhydrous sodium sulfate and concentration. The residue was purified with silica gel column to afford the title compound 6-(4-(2-(2-(2-(2-(N,N-di-tert-butoxycarbonyl-amino)ethoxy)ethoxy)ethoxy)ethoxy)phenyl)-N-(2-chlorobenzyl)-7H-pyrrolo[2,3-d]pyrimidin-4-amine (280 mg, 37.1% yield).

2. Step and 3. Step—Synthesis of 4-((2-(2-(2-(2-(4-(4-((2-chlorobenzyl)amino)-7H-pyrrolo[2,3-d]pyrimidin-6-yl)phenoxy)ethoxy)ethoxy)ethoxy)ethyl)amino)-2-(2,6-dioxopiperidin-3-yl)isoindoline-1,3-dione

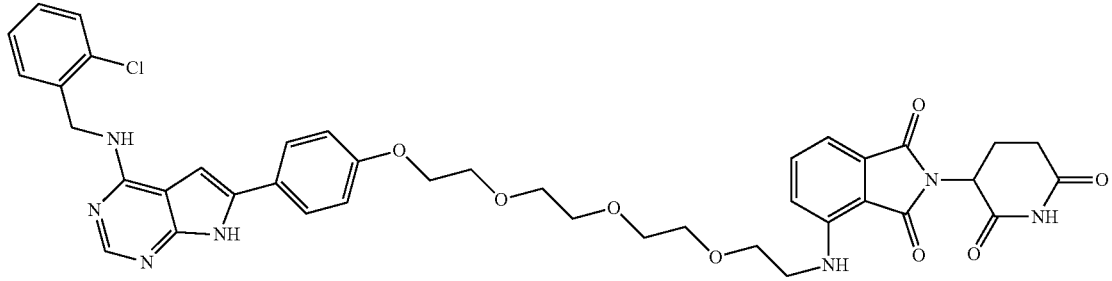 [SMILES: O=C1CCC(N2C(=O)c3cccc(NCCOCCOCCOCCOc4ccc(-c5cc6c(NCc7ccccc7Cl)ncnc6[nH]5)cc4)c3C2=O)C(=O)N1]

To a solution of 6-(4-(2-(2-(2-(2-(N,N-di-tert-butoxycarbonyl-amino)ethoxy)ethoxy)ethoxy)ethoxy)phenyl)-N-(2-chlorobenzyl)-7H-pyrrolo[2,3-d]pyrimidin-4-amine (280 mg, 0.38 mmol) in dioxane (5 mL) was added HCl (g)/dioxane (2 mL) at 0° C., and then the reaction was stirred at 25° C. for 2 h. The solvent was removed under vacuum. The residue was dissolved into NMP (5 mL). To the above mixture were added 2-(2,6-dioxopiperidin-3-yl)-4-fluoroisoindoline-1,3-dione (334.6 mg, 1.16 mmol) and DIPEA (245 mg, 1.9 mmol) at 25° C. subsequently. The reaction was microwave irradiated to 150° C. for 20 min. Then it was cooled to RT and quenched by addition of water (20 mL). The mixture was extracted with DCM (50 mL×3). The combined organic layers were dried over anhydrous sodium sulfate and concentrated under vacuum. The residue was purified with silica gel column to afford the crude product, and it was purified again by prep-HPLC to afford the title compound 4-((2-(2-(2-(2-(4-(4-((2-chlorobenzyl)amino)-7H-pyrrolo [2,3-d]pyrimidin-6-yl)phenoxy)ethoxy)ethoxy)ethoxy)ethyl)amino)-2-(2,6-dioxopiperidin-3-yl)isoindoline-1,3-dione (28 mg, 9.2% yield).

$^1$HNMR (400 MHz, CDCl$_3$): δ 11.38 (br, 1H), 10.29 (s, 1H), 8.34 (s, 1H), 7.49-7.53 (m, 3H), 7.39-7.44 (m, 2H), 7.22-7.24 (m, 2H), 7.05 (d, J=7.2 Hz, 1H), 6.95 (d, J=8.4 Hz, 1H), 6.88 (d, J=8.8 Hz, 2H), 6.47 (s, 1H), 6.39-6.42 (m, 1H), 4.95-4.98 (m, 3H), 4.12 (t, J=5.2 Hz, 2H), 3.85 (t, J=5.2 Hz, 2H), 3.67-3.73 (m, 10H), 3.42-3.46 (m, 2H), 2.65-2.91 (m, 3H), 2.09-2.15 (m, 2H).

Synthesis of Example 14

(2S,4R)-1-((S)-2-(tert-butyl)-14-(4-(4-((2-chlorobenzyl)amino)-7H-pyrrolo[2,3-d]pyrimidin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide

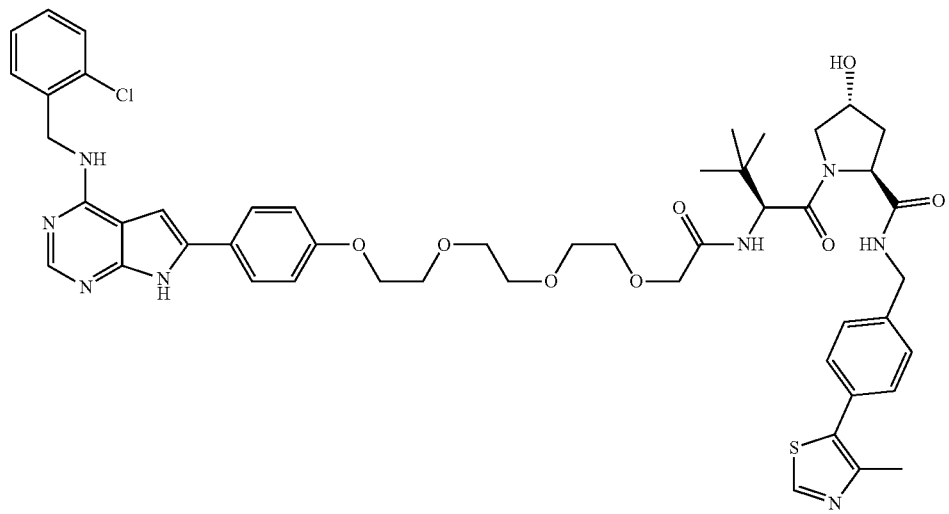 [SMILES: Cc1ncsc1-c1ccc(CNC(=O)[C@@H]2C[C@@H](O)CN2C(=O)[C@@H](NC(=O)COCCOCCOCCOc2ccc(-c3cc4c(NCc5ccccc5Cl)ncnc4[nH]3)cc2)C(C)(C)C)cc1]

Synthetic scheme:
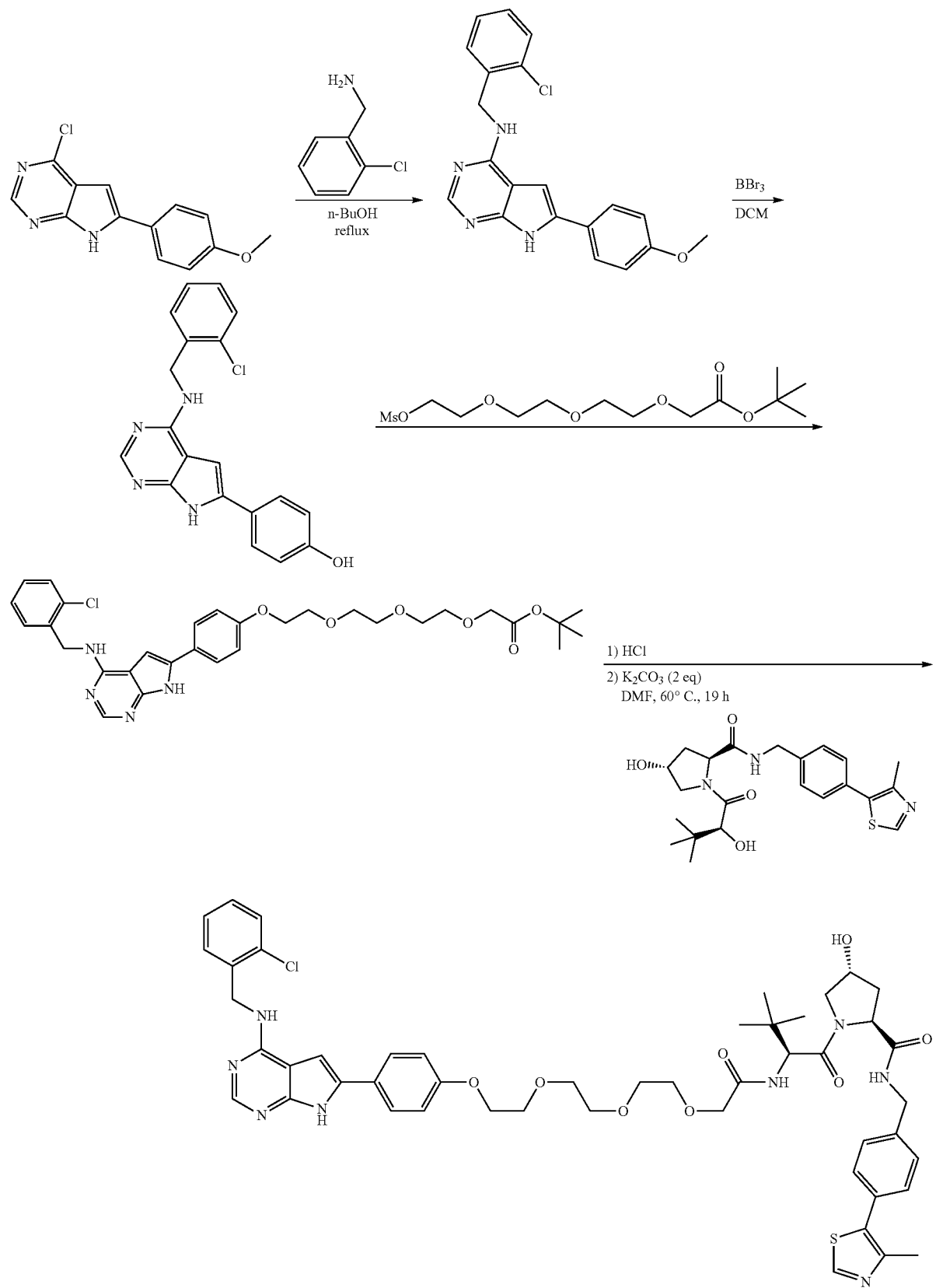

1. Step to 2. Step—Synthesis of 4-(4-((2-chlorobenzyl)amino)-7H-pyrrolo[2,3-d]pyrimidin-6-yl)phenol starting from 4-chloro-6-(4-methoxyphenyl)-7H-pyrrolo[2,3-d]pyrimidine using procedures analogous to those described by Kaspersen, S. et al. in Bioorganic Chemistry 2012, 44, 35-41.

3. Step—Synthesis of tert-Butyl 2-(2-(2-(2-(4-(4-((2-chlorobenzyl)amino)-7H-pyrrolo[2,3-d]pyrimidin-6-yl)phenoxy)ethoxy)ethoxy)ethoxy)acetate

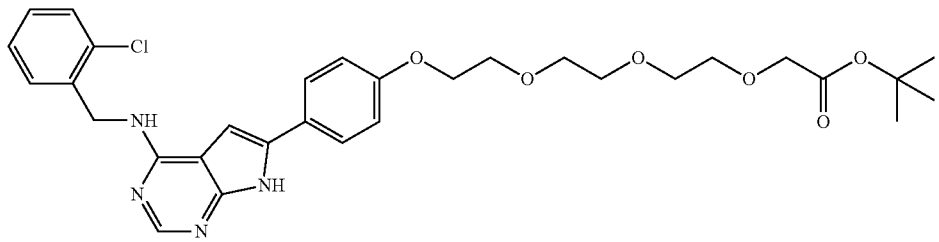 [SMILES: CC(C)(C)OC(=O)COCCOCCOCCOc1ccc(-c2cc3c(NCc4ccccc4Cl)ncnc3[nH]2)cc1]

To a solution of 4-(4-((2-chlorobenzyl)amino)-7H-pyrrolo[2,3-d]pyrimidin-6-yl)phenol (500 mg, 1.16 mmol) in DMF (10 mL) were added tert-butyl 2-(2-(2-(2-((methylsulfonyl)oxy)ethoxy)ethoxy)ethoxy)acetate (515 mg, 1.5 mmol) and K$_2$CO$_3$ (480 mg, 3.48 mmol). The solution was stirred at 80° C. for 20 h. The mixture was extracted with EtOAc (20 mL×3). The combined organic layers were washed with brine. The organic layer was dried over anhydrous sodium sulfate, filtered and concentrated under reduced pressure. The residue was purified by silica gel column chromatography (PE/EA=1/1) to afford the title compound tert-Butyl 2-(2-(2-(2-(4-(4-((2-chlorobenzyl)amino)-7H-pyrrolo [2,3-d]pyrimidin-6-yl)phenoxy)ethoxy)ethoxy)ethoxy)acetate (320 mg) as a yellow solid.

4. Step and 5. Step—Synthesis of (2S,4R)-1-((S)-2-(tert-butyl)-14-(4-(4-((2-chlorobenzyl)amino)-7H-pyrrolo[2,3-d]pyrimidin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide

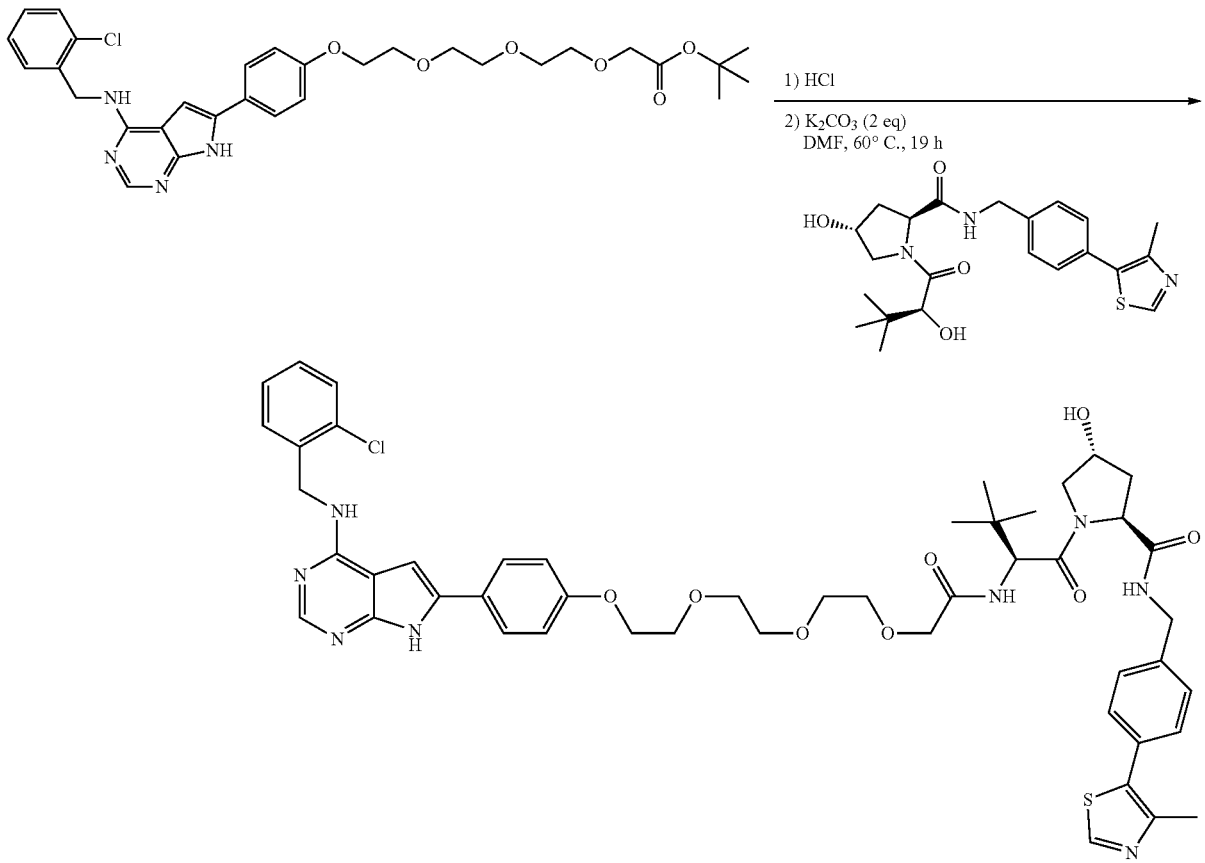

493 tert-Butyl 2-(2-(2-(2-(4-(4-((2-chlorobenzyl)amino)-7H-pyrrolo [2,3-d]pyrimidin-6-yl)phenoxy)ethoxy)ethoxy)ethoxy)acetate was converted to the final compound, (2S, 4R)-1-((S)-2-(tert-butyl)-14-(4-(4-((2-chlorobenzyl)amino)-7H-pyrrolo[2,3-d]pyrimidin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide using as described for the example 1 above.

494

Synthesis of Example 17

5-(2-(2-(2-(4-(4-(4-((2-chlorobenzyl)amino)-7H-pyrrolo[2,3-d]pyrimidin-6-yl)benzyl)piperazin-1-yl)ethoxy)ethoxy)ethoxy)-2-(2,6-dioxopiperidin-3-yl)isoindoline-1,3-dione

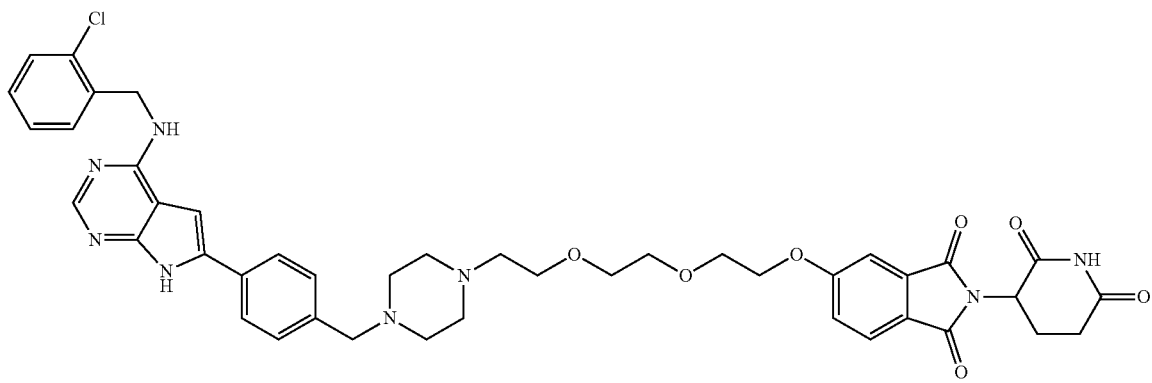

Synthetic scheme:

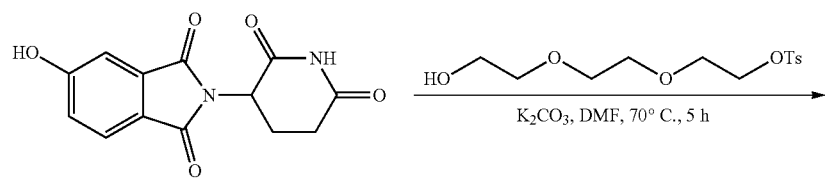

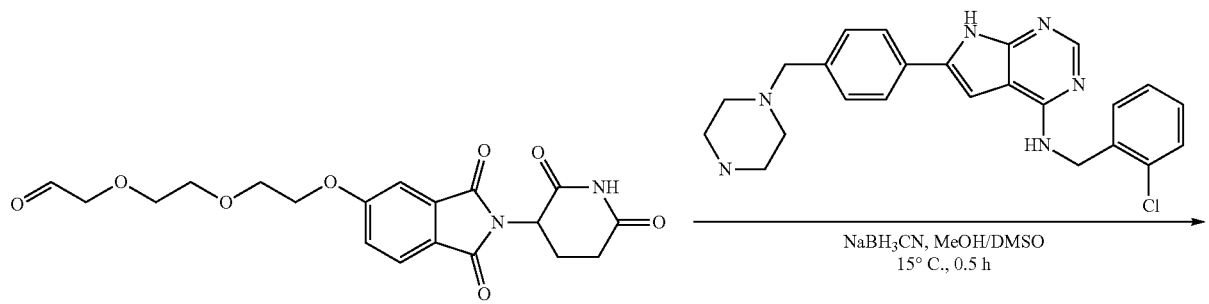

1. Step—Synthesis of 2-(2,6-Dioxopiperidin-3-yl)-5-(2-(2-(2-hydroxyethoxy)ethoxy)ethoxy)isoindoline-1,3-dione

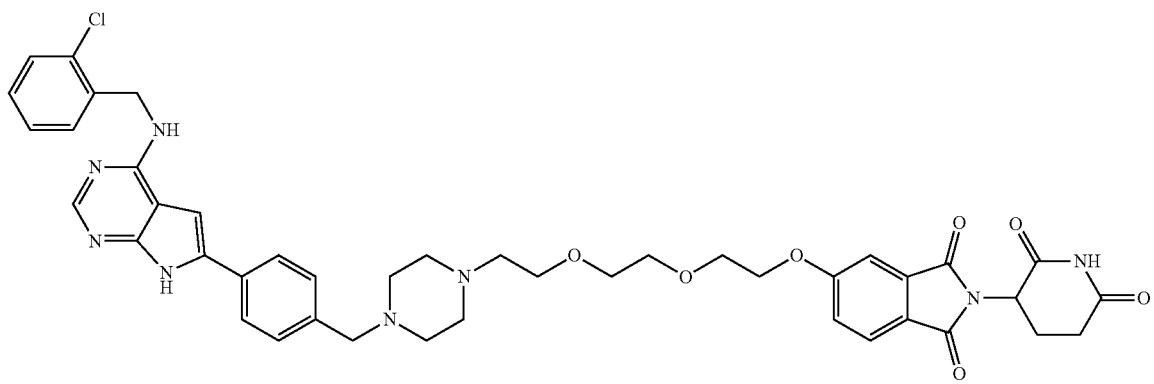 [SMILES: O=C1CCC(N2C(=O)c3ccc(OCCOCCOCCN4CCN(Cc5ccc(-c6cc7c(NCc8ccccc8Cl)ncnc7[nH]6)cc5)CC4)cc3C2=O)C(=O)N1]

To a solution of 2-(2,6-dioxopiperidin-3-yl)-5-hydroxyisoindoline-1,3-dione (500 mg, 1.82 mmol) in DMF (10 mL) were added $K_2CO_3$ (756 mg, 5.47 mmol) and 2-(2-(2-hydroxyethoxy)ethoxy)ethyl 4-methyl-benzenesulfonate (832 mg, 2.73 mmol) at 25° C. The resulting solution was stirred at 70° C. for 5 h. After cooling to rt, the reaction was quenched with $H_2O$ (10 mL), and the mixture was extracted with EtOAc (10 mL×2). The combined organic layers were dried over anhydrous sodium sulfate and concentrated. The residue was purified with silica gel column to afford the title product 2-(2,6-Dioxopiperidin-3-yl)-5-(2-(2-(2-hydroxyethoxy)ethoxy)ethoxy)isoindoline-1,3-dione (95 mg, 13% yield).

2. Step—Synthesis of 2-(2-(2-((2-(2,6-Dioxopiperidin-3-yl)-1,3-dioxoisoindolin-5-yl)oxy)ethoxy)ethoxy)acetaldehyde

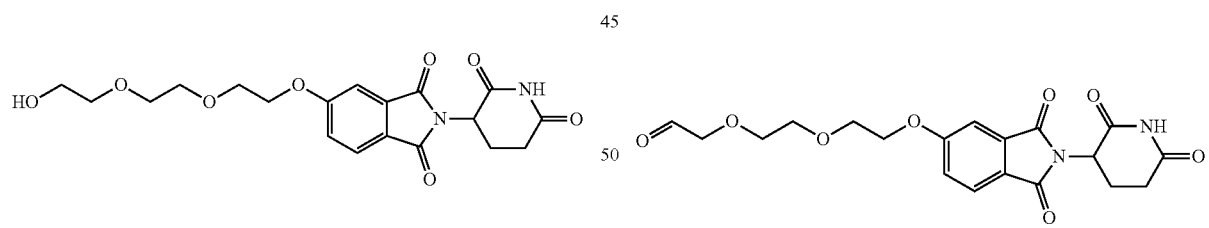

To a solution of 2-(2,6-dioxopiperidin-3-yl)-5-(2-(2-(2-hydroxyethoxy)ethoxy)ethoxy)isoindoline-1,3-dione (95 mg, 0.23 mmol) in $CH_3CN$ (5 mL) was added IBX (130 mg, 0.46 mmol) at 25° C. The reaction was stirred at 80° C. for 2 h. After cooling to rt, the mixture was filtered through Celite, and the filtrate was concentrated to afford title product 2-(2-(2-((2-(2,6-Dioxopiperidin-3-yl)-1,3-dioxoisoindolin-5-yl)oxy)ethoxy)ethoxy)acetaldehyde (90 mg, crude), which was used in next step without further purification.

3. Step—Synthesis of 5-(2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethoxy)-2-(2,6-dioxopiperidin-3-yl)isoindoline-1,3-dione

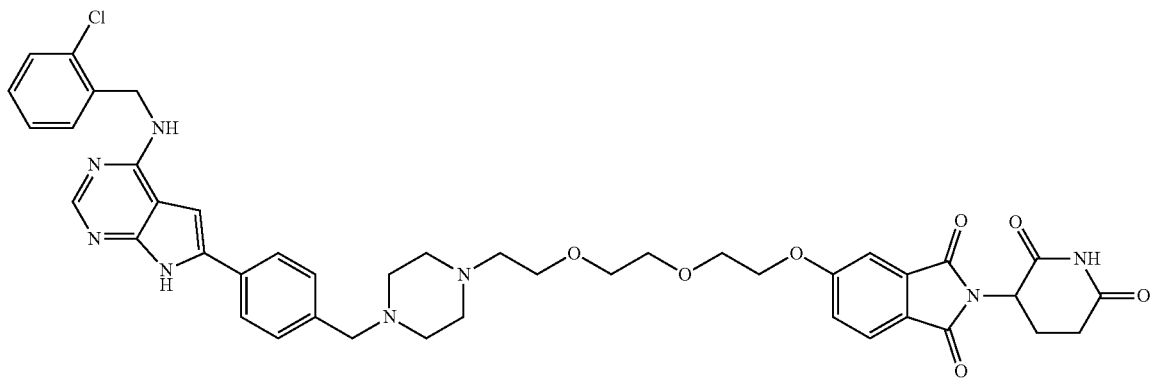 [SMILES: O=C1CCC(N2C(=O)c3ccc(OCCOCCOCCN4CCN(Cc5ccc(-c6cc7c(NCc8ccccc8Cl)ncnc7[nH]6)cc5)CC4)cc3C2=O)C(=O)N1]

To a solution of 2-(2-(2-((2-(2,6-Dioxopiperidin-3-yl)-1,3-dioxoisoindolin-5-yl)oxy)ethoxy)ethoxy)acetaldehyde (90 mg, 0.15 mmol) and N-(2-chlorobenzyl)-6-(4-(piperazin-1-ylmethyl)phenyl)-7H-pyrrolo[2,3-d]pyrimidin-4-amine (79.2 mg, 0.18 mmol) in DMSO/MeOH (2 mL/2 mL) was added NaBH$_3$CN (47.9 mg, 0.76 mmol) at 10° C. The resulting mixture was stirred at 15° C. for 0.5 h. The mixture was quenched with H$_2$O (10 mL), and the mixture was extracted with EtOAc (10 mL×2). The combined organic layers were washed with brine (10 mL×2), dried over anhydrous sodium sulfate and concentrated. The residue was purified with silica gel column and prep-HPLC to afford the title compound 5-(2-(2-(2-(4-(4-(4-((2-Chlorobenzyl)amino)-7H-pyrrolo [2,3-d]pyrimidin-6-yl)benzyl)piperazin-1-yl)ethoxy)ethoxy)ethoxy)-2-(2,6-dioxopiperidin-3-yl)isoindoline-1,3-dione (21 mg, 11% yield).

$^1$H NMR (400 MHz, DMSO-d6): δ 12.09 (s, 1H), 11.14 (s, 1H), 8.06-8.11 (m, 2H), 7.74-7.85 (m, 3H), 7.30-7.46 (m, 8H), 7.01 (s, 1H), 5.13 (d, J=7.6 Hz, 1H), 4.79 (d, J=4.4 Hz, 2H), 4.43 (s, 2H), 3.79 (s, 2H), 3.38-3.59 (m, 10H), 2.06-2.62 (m, 10H), 1.91 (s, 2H).

Synthesis of Example 18

(2S,4R)-1-((S)-2-(tert-butyl)-20-((4-((3-chloro-4-fluorophenyl)amino)-7-methoxyquinazolin-6-yl)oxy)-4-oxo-6,9,12,15,18-pentaoxa-3-azaicosanoyl)-4-hydroxy-N-(4-(4-methylthiazol-5-yl)benzyl)pyrrolidine-2-carboxamide

Reaction Scheme - part 1

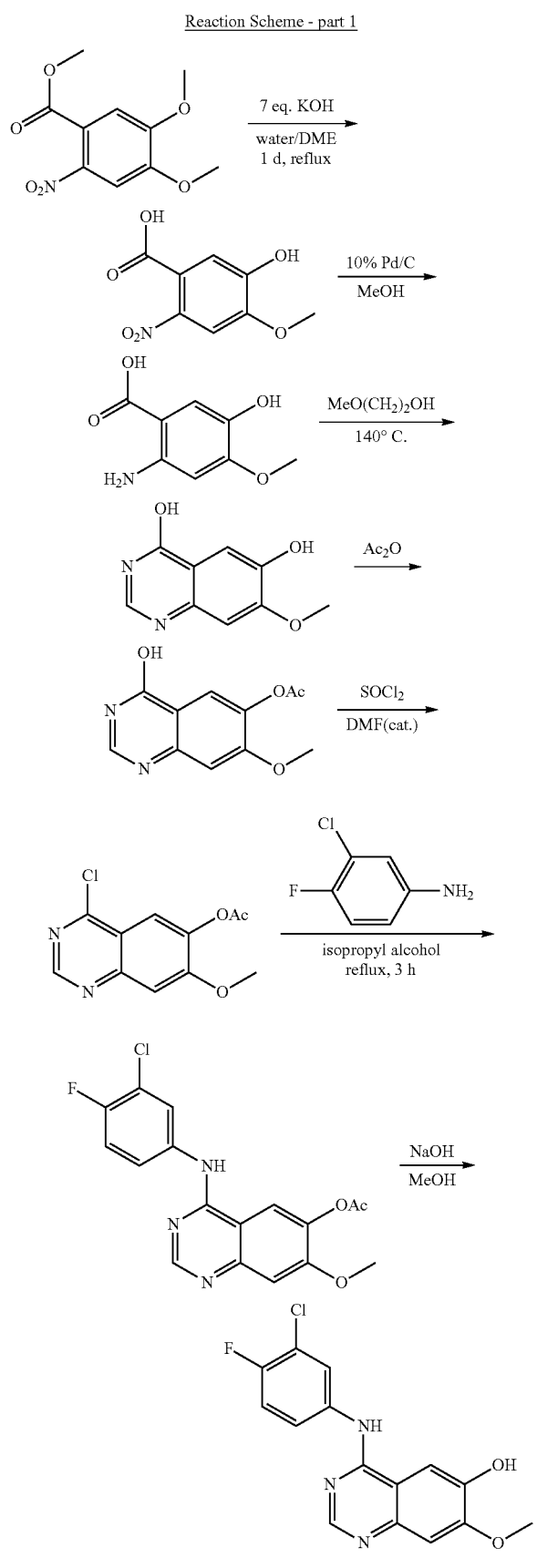

Experimental Details

1. Step—Synthesis of 5-hydroxy-4-methoxy-2-nitrobenzoic acid

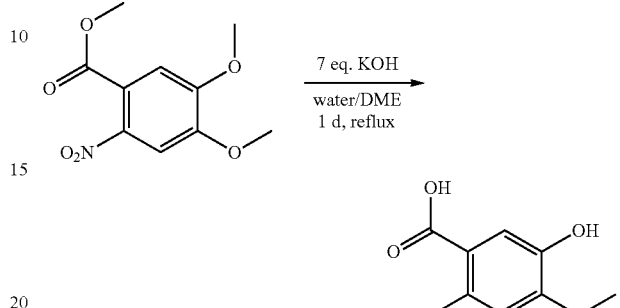

Into a 3-L round-bottom flask, was placed a solution of methyl 4,5-dimethoxy-2-nitrobenzoate (45 g, 186.57 mmol, 1.00 equiv) in water (800 mL) and DME (200 mL), potassium hydroxide (72 g, 1.28 mol, 7.00 equiv). The resulting solution was refluxed for 1 day. The resulting mixture was washed with 2×200 mL of hexane. The pH value of the solution was adjusted to 5 with hydrogen chloride (6 mol/L). The solids were collected by filtration. The resulting mixture was concentrated under vacuum. This resulted in 40 g of 5-hydroxy-4-methoxy-2-nitrobenzoic acid as a yellow solid. LC-MS: (ES, m/z): 214 [M+H]$^+$ Retention time: 0.217 min

2. Step—Synthesis of 2-amino-5-hydroxy-4-methoxybenzoic acid

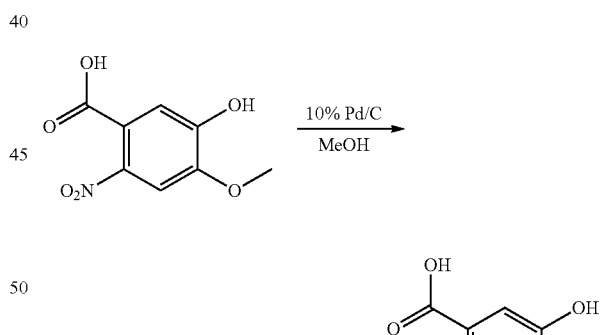

Into a 1-L round-bottom flask, was placed 5-hydroxy-4-methoxy-2-nitrobenzoic acid (41.2 g, 193.30 mmol, 1.00 equiv), 10% Palladium carbon (5 g, 0.10 equiv), methanol (500 mL). H$_2$ was introduced into the reaction mixture. The resulting solution was stirred for overnight at room temperature under H$_2$ atmosphere. The solids were filtered out. The resulting mixture was concentrated under vacuum. This resulted in 21.3 g (60%) of 2-amino-5-hydroxy-4-methoxybenzoic acid as a yellow solid. LC-MS: (ES, m/z): 184 [M+H]$^+$ Retention time: 0.356 min

3. Step—Synthesis of 7-methoxyquinazoline-4,6-diol

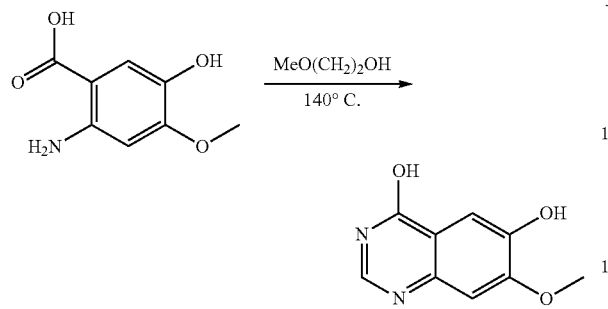

Into a 500-mL round-bottom flask, was placed a solution of 2-amino-5-hydroxy-4-methoxybenzoic acid (21.3 g, 116.29 mmol, 1.00 equiv) in MeO(CH$_2$)$_2$OH (200 mL) and methanimidamide monoacetate (12.6 g, 122.33 mmol, 1.10 equiv). The resulting solution was stirred for 30 min at 140° C. The resulting mixture was concentrated under vacuum. This resulted in 20 g (89%) of 7-methoxyquinazoline-4,6-diol as a black solid.

LC-MS: (ES, m/z): 193 [M+H]$^+$ Retention time: 0.959 min

4. Step—Synthesis of 4-hydroxy-7-methoxyquinazolin-6-yl acetate

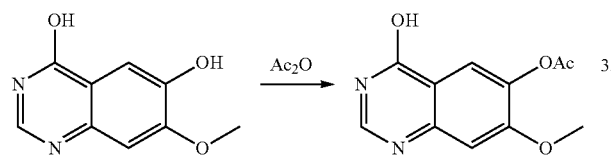

Into a 500-mL round-bottom flask, was placed 7-methoxyquinazoline-4,6-diol (12 g, 62.44 mmol, 1.00 equiv), Ac$_2$O (200 mL), pyridine (20 mL). The resulting solution was stirred for 3 h at 100° C. The resulting mixture was concentrated under vacuum. The residue was purified on combi-flash with MeOH/DCM (1:100-1:10). This resulted in 8.5 g (58%) of 4-hydroxy-7-methoxyquinazolin-6-yl acetate as a brown solid. LC-MS: (ES, m/z): 235 [M+H]$^+$ Retention time: 1.251 min

5. Step—Synthesis of 4-chloro-7-methoxyquinazolin-6-yl acetate

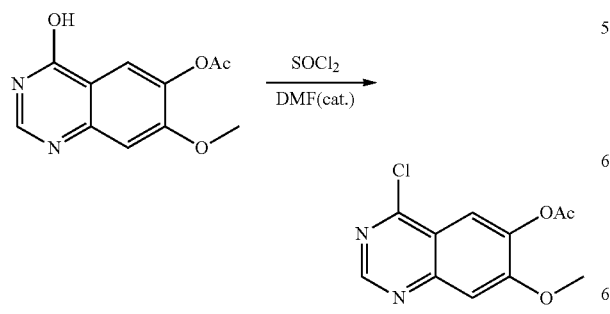

Into a 250-mL round-bottom flask, was placed 4-hydroxy-7-methoxyquinazolin-6-yl acetate (8.5 g, 36.29 mmol, 1.00 equiv), thionyl chloride (100 mL), N,N-dimethylformamide (1 mL). The resulting solution was stirred for 1.5 h at 85° C. The resulting solution was evaporated in vacuum, extracted with 3×100 mL of ethyl acetate and the organic layers combined and dried in an oven under reduced pressure, concentrated under vacuum. The residue was purified on combi-flash with MeOH/DCM (1:100-1:10). This resulted in 9.1 g (99%) of 4-chloro-7-methoxyquinazolin-6-yl acetate as a brown solid. LC-MS: (ES, m/z): 253 [M+H]$^+$ Retention time: 0.744 min

6. Step—Synthesis of 4-[(3-chloro-4-fluorophenyl)amino]-7-methoxyquinazolin-6-yl acetate

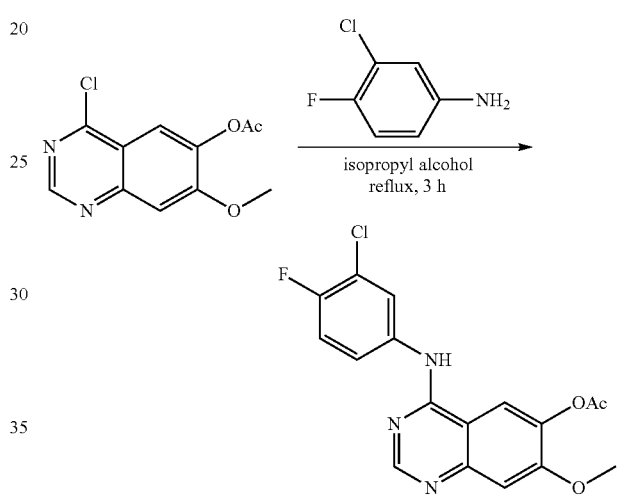

Into a 500-mL round-bottom flask, was placed 4-chloro-7-methoxyquinazolin-6-yl acetate (9.1 g, 36.02 mmol, 1.00 equiv), 3-chloro-4-fluoroaniline (5.23 g, 35.93 mmol, 1.00 equiv) in propan-2-ol (200 mL). The resulting solution was refluxed for 3 hours. The reaction mixture was cooled to room temperature. The solids were collected by filtration. This resulted in 10.1 g (78%) of 4-[(3-chloro-4-fluorophenyl)amino]-7-methoxyquinazolin-6-yl acetate as a brown solid. LC-MS: (ES, m/z): 362 [M+H]$^+$ Retention time: 0.681 min

7. Step—Synthesis of 4-[(3-chloro-4-fluorophenyl)amino]-7-methoxyquinazolin-6-ol

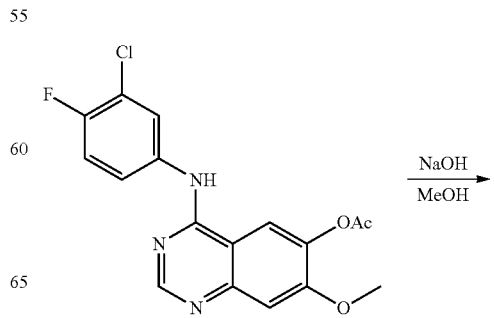

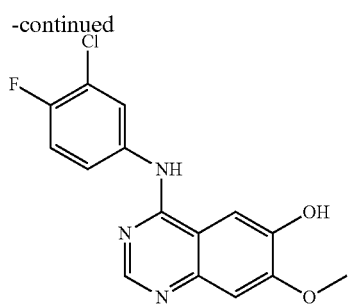

Into a 500-mL round-bottom flask, was placed a solution of 4-[(3-chloro-4-fluorophenyl)amino]-7-methoxyquinazo- lin-6-yl acetate (10.1 g, 27.92 mmol, 1.00 equiv) in methanol (200 mL), a solution of NaOH (4 g, 100.01 mmol, 5.00 equiv) in water(20 mL). The resulting solution was stirred for overnight at room temperature. The pH value of the solution was adjusted to 5 with hydrogen chloride (1 mol/L). The solids were collected by filtration. This resulted in 7.5 g (84%) of 4-[(3-chloro-4-fluorophenyl)amino]-7-methoxyquinazolin-6-ol as a brown solid. LC-MS: (ES, m/z): 320 [M+H]$^+$ Retention time: 0.904 min $^1$H-NMR: (DMSO, ppm): δ=11.15-11.12 (s, 1H), 10.59-10.51 (s, 1H), 9.88-9.82 (s, 1H), 8.25-7.99 (m, 2H), 7.86-7.69 (m, 1H), 7.58-7.47 (m, 1H), 7.37-7.33 (s, 1H), 4.06-3.99 (s, 3H).

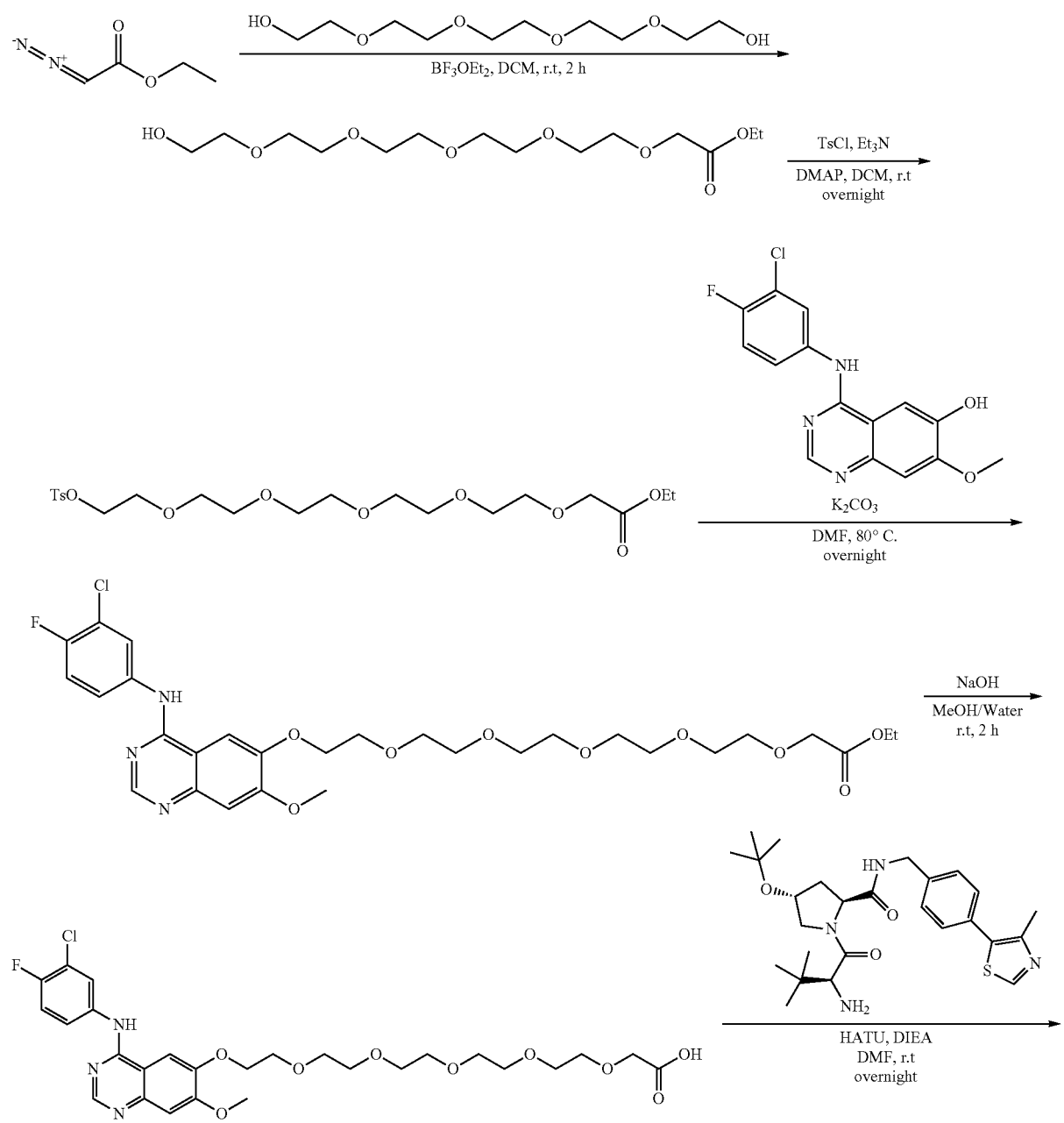

Reaction Scheme - part 2

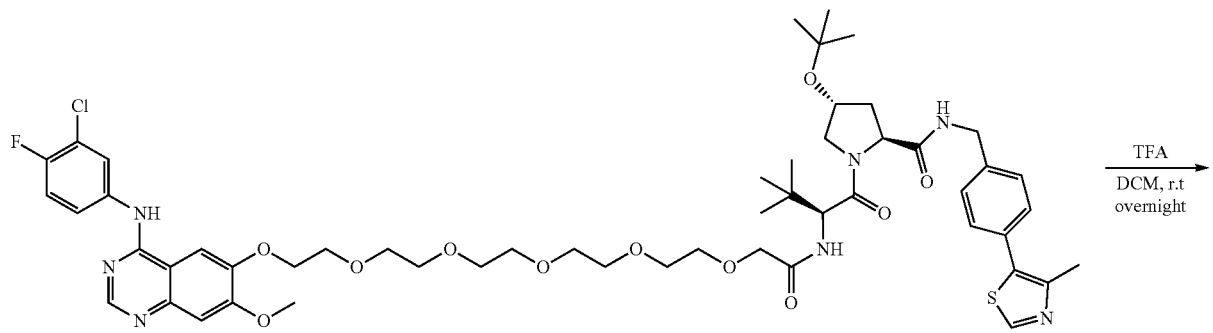

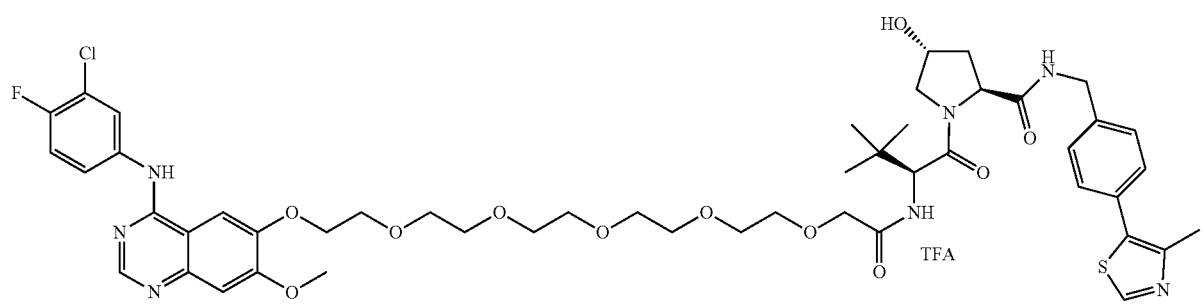

Experimental Details

8. Step—Synthesis of ethyl 17-hydroxy-3,6,9,12,15-pentaoxaheptadecanoate

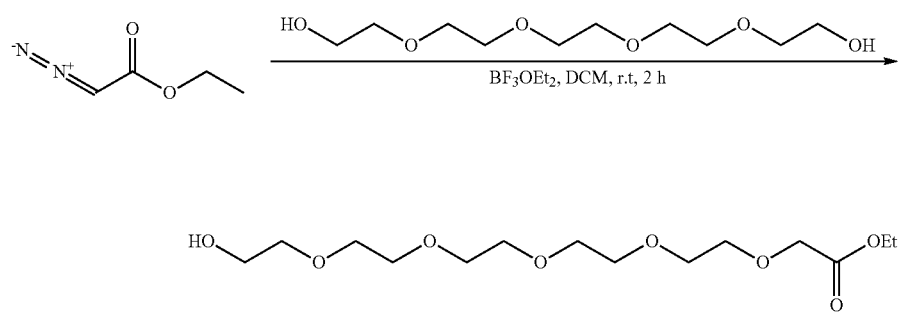

Into a 500-mL 3-necked round-bottom flask, was placed dichloromethane (150 mL), 3,6,9,12-tetraoxatetradecane-1,14-diol (18 g, 75.54 mmol, 2.00 equiv), $BF_3\text{-}Et_2O$ (1 mL). This was followed by the addition of ethyl 2-diazenylacetate (4.3 g, 37.03 mmol, 1.00 equiv) dropwise with stirring at 0° C. in 1 hr. The resulting solution was stirred for 2 h at 25° C. The reaction was then quenched by the addition of 200 mL of water. The resulting solution was extracted with 150 mL of dichloromethane and the organic layers combined and concentrated under vacuum. The residue was applied onto a silica gel column with dichloromethane/methanol (50:1). This resulted in 1.5 g of ethyl 17-hydroxy-3,6,9,12,15-pentaoxaheptadecanoate as white oil. LC-MS: (ES, m/z): 325 $[M+H]^+$ Retention time: 1.285 min 9. Step—Synthesis of ethyl 17-[[(4-methylbenzene)sulfonyl]oxy]-3,6,9,12,15-pentaoxaheptadecanoate

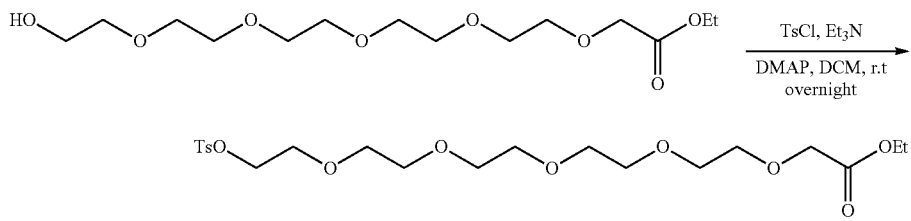

Into a 100-mL round-bottom flask, was placed ethyl 17-hydroxy-3,6,9,12,15-pentaoxaheptadecanoate (3.2 g, 9.87 mmol, 1.00 equiv), dichloromethane (50 mL), triethylamine (1.52 g, 15.02 mmol, 1.50 equiv), 4-dimethylaminopyridine (183 mg, 1.50 mmol, 0.10 equiv). This was followed by the addition of TsCl (2.09 g, 10.96 mmol, 1.10 equiv) in portions. The resulting solution was stirred overnight at 25° C. The reaction was then quenched by the addition of 20 mL of water. The resulting solution was extracted with 2×30 mL of dichloromethane and the organic layers combined and dried over anhydrous sodium sulfate and concentrated under vacuum. The residue was applied onto a silica gel column with dichloromethane/methanol (40:1). This resulted in 1 g (21%) of ethyl 17-[[(4-methylbenzene)sulfonyl]oxy]-3,6,9,12,15-pentaoxaheptadecanoate as light yellow oil. LC-MS: (ES, m/z): 479 [M+H]$^+$ Retention time: 1.480 min 10. Step—Synthesis of ethyl 1-[4-[(3-chloro-4-fluorophenyl)amino]-7-methoxyquinazolin-6-yl]-1,4,7,10,13,16-hexaoxaoctadecan-18-oate Into a 50-mL round-bottom flask purged and maintained with an inert atmosphere of nitrogen, was placed 4-[(3-chloro-4-fluorophenyl)amino]-7-methoxyquinazolin-6-ol (100 mg, 0.31 mmol, 1.00 equiv), N,N-dimethylformamide (10 mL), potassium carbonate (86.4 mg, 0.63 mmol, 2.00 equiv), ethyl 17-[[(4-methylbenzene)sulfonyl]oxy]-3,6,9,12,15-pentaoxaheptadecanoate (224 mg, 0.47 mmol, 1.50 equiv). The resulting solution was stirred overnight at 80° C. The reaction was then quenched by the addition of 10 mL of water. The resulting solution was extracted with 2×10 mL of ethyl acetate and the organic layers combined and dried over anhydrous sodium sulfate and concentrated under vacuum. The residue was applied onto a silica gel column with ethyl acetate/petroleum ether (1:1). This resulted in 157 mg (80%) of ethyl 1-[4-[(3-chloro-4-fluorophenyl)amino]-7-methoxyquinazolin-6-yl]-1,4,7,10,13,16-hexaoxaoctadecan-18-oate as light yellow oil. LC-MS: (ES, m/z): 626 [M+H]$^+$ Retention time: 1.279 min

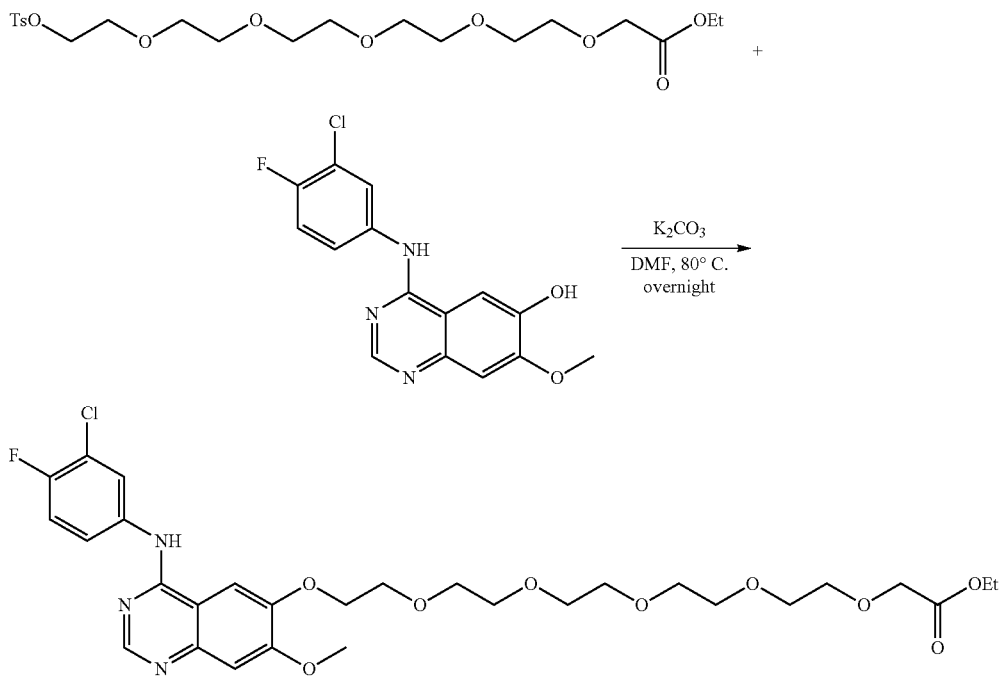

11. Step—Synthesis of 1-[4-[(3-chloro-4-fluorophenyl)amino]-7-methoxyquinazolin-6-yl]-1,4,7,10,13,16-hexaoxaoctadecan-18-oic acid

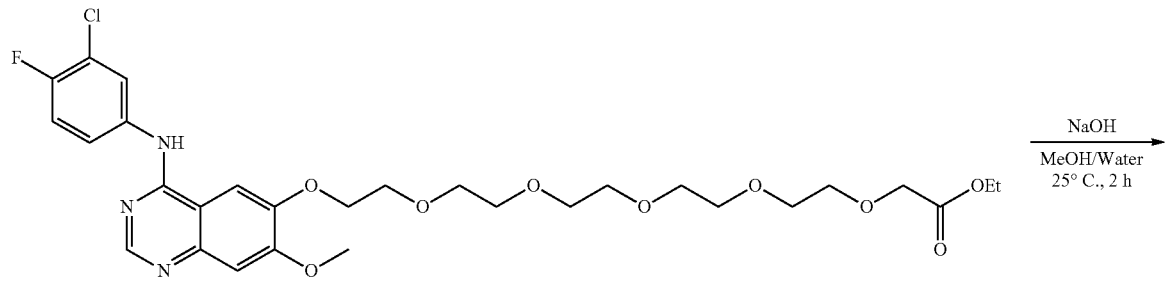

Into a 50-mL round-bottom flask, was placed ethyl 1-[4-[(3-chloro-4-fluorophenyl)amino]-7-methoxyquinazolin-6-yl]-1,4,7,10,13,16-hexaoxaoctadecan-18-oate (158 mg, 0.25 mmol, 1.00 equiv) in methanol (10 mL), sodium hydroxide (50.3 mg, 1.26 mmol, 5.00 equiv) in water(1 mL). The resulting solution was stirred for 2 h at 25° C. The resulting mixture was concentrated under vacuum. The pH value of the solution was adjusted to 5 with hydrogen chloride (1 mol/L). The solids were collected by filtration. This resulted in 67 mg (44%) of 1-[4-[(3-chloro-4-fluorophenyl)amino]-7-methoxyquinazolin-6-yl]-1,4,7,10,13,16-hexaoxaoctadecan-18-oic acid as a white solid. LC-MS: (ES, m/z): 598 [M+H]$^+$ Retention time: 1.192 min 12. Step—Synthesis of (2S,4R)-4-(tert-butoxy)-1-[(2S)-2-(1-[4-[(3-chloro-4-fluorophenyl)amino]-7-methoxyquinazolin-6-yl]-1,4,7,10,13,16-hexaoxaoctadecan-18-amido)-3,3-dimethylbutanoyl]-N-[[4-(4-methyl-1,3-thiazol-5-yl)phenyl]methyl]pyrrolidine-2-carboxamide

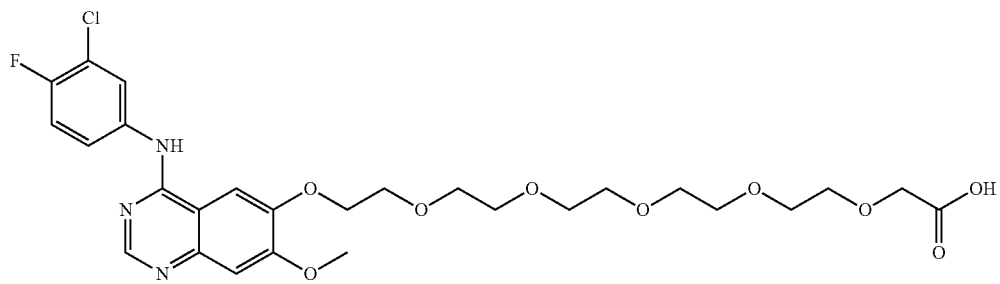

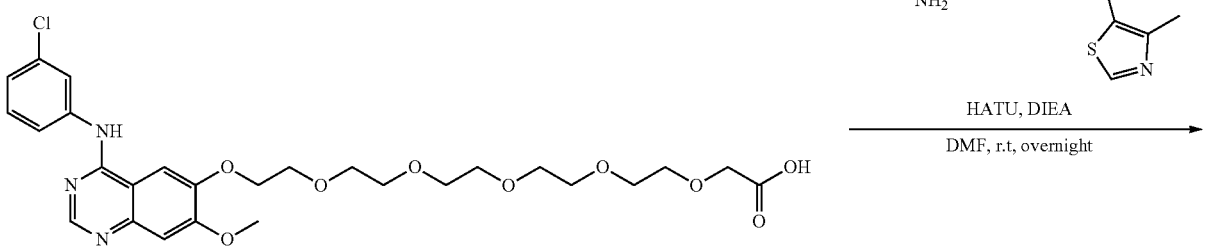

511

-continued

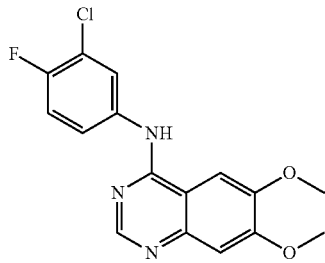 [SMILES: COc1cc2ncnc(Nc3ccc(F)c(Cl)c3)c2cc1O] 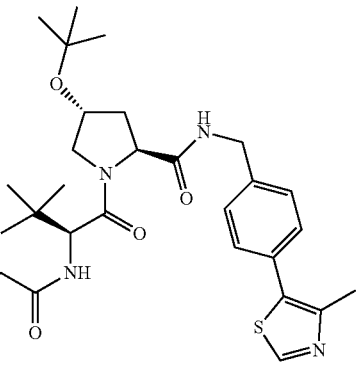

Into a 50-mL round-bottom flask, was placed 1-[4-[(3-chloro-4-fluorophenyl)amino]-7-methoxyquinazolin-6-yl]-1,4,7,10,13,16-hexaoxaoctadecan-18-oic acid (67 mg, 0.11 mmol, 1.00 equiv) in N,N-dimethylformamide (3 mL), DIEA (28.4 mg, 0.22 mmol, 2.00 equiv), HATU (55.4 mg, 0.15 mmol, 1.30 equiv), (2S,4R)-1-[(2S)-2-amino-3,3-dimethylbutanoyl]-4-(tert-butoxy)-N-[[4-(4-methyl-1,3-thiazol-

512

13. Step—Synthesis of (2S,4R)-1-[(2S)-2-(1-[4-[(3-chloro-4-fluorophenyl)amino]-7-methoxyquinazolin-6-yl]-1,4,7,10,13,16-hexaoxaoctadecan-18-amido)-3,3-dimethylbutanoyl]-4-hydroxy-N-[[4-(4-methyl-1,3-thiazol-5-yl)phenyl]methyl]pyrrolidine-2-carboxamide

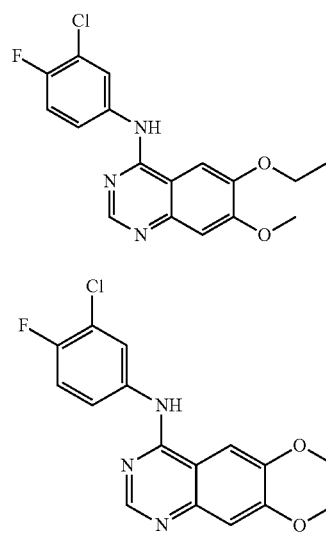 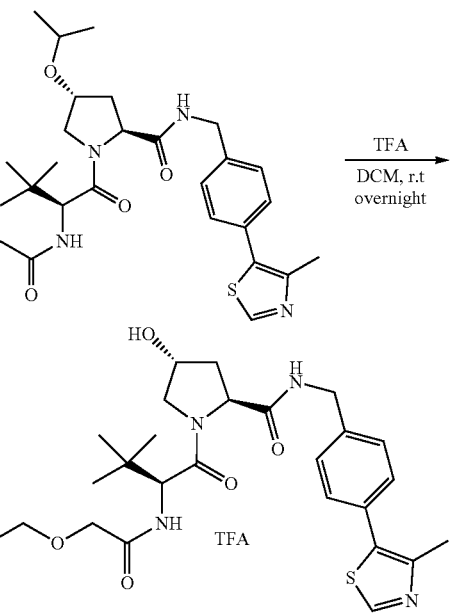

5-yl)phenyl]methyl]pyrrolidine-2-carboxamide (54.5 mg, 0.11 mmol, 1.00 equiv). The resulting solution was stirred overnight at 25° C. The reaction was then quenched by the addition of 20 mL of water. The resulting solution was extracted with 2×50 mL of ethyl acetate and the organic layers combined and dried over anhydrous sodium sulfate and concentrated under vacuum. The residue was applied onto a silica gel column with dichloromethane/methanol (20:1). This resulted in 84 mg (70%) of (2S,4R)-4-(tert-butoxy)-1-[(2S)-2-(1-[4-[(3-chloro-4-fluorophenyl)amino]-7-methoxyquinazolin-6-yl]-1,4,7,10,13,16-hexaoxaoctadecan-18-amido)-3,3-dimethylbutanoyl]-N-[[4-(4-methyl-1,3-thiazol-5-yl)phenyl]methyl]pyrrolidine-2-carboxamide as a light yellow solid. LC-MS: (ES, m/z): 1066 [M+H]$^+$ Retention time: 1.409 min Into a 25-mL round-bottom flask, was placed a solution of (2S,4R)-4-(tert-butoxy)-1-[(2S)-2-(1-[4-[(3-chloro-4-fluorophenyl)amino]-7-methoxyquinazolin-6-yl]-1,4,7,10,13,16-hexaoxaoctadecan-18-amido)-3,3-dimethylbutanoyl]-N-[[4-(4-methyl-1,3-thiazol-5-yl)phenyl]methyl]pyrrolidine-2-carboxamide (81 mg, 0.08 mmol, 1.00 equiv) in dichloromethane (5 mL). This was followed by the addition of CF$_3$COOH (0.5 mL) dropwise with stirring at 0° C. The resulting solution was stirred overnight at 25° C. The resulting mixture was concentrated under vacuum. The crude product was purified by Prep-HPLC with the following conditions (Prep-HPLC-043): Column, XBridge Prep C18 OBD Column, 30*50 mm 5 um 13 nm; mobile phase, WATER with 0.05% TFA and MeCN (35.0% MeCN up to 65.0% in 8 min); Detector, Waters 2489 254&220 nm. This resulted in 20 mg (23%) of (2S,4R)-1-[(2S)-2-(1-[4-[(3- chloro-4-fluorophenyl)amino]-7-methoxyquinazolin-6-yl]-1,4,7,10,13,16-hexaoxaoctadecan-18-amido)-3,3-dimethylbutanoyl]-4-hydroxy-N-[[4-(4-methyl-1,3-thiazol-5-yl)phenyl]methyl]pyrrolidine-2-carboxamide; trifluoroacetic acid as a white solid. LC-MS: (ES, m/z): 1010 [M+H]$^+$ Retention time: 3.344 min $^1$H-NMR: (CD$_3$OD, ppm): δ=8.89 (s, 1H), 8.46 (s, 1H), 8.02-7.99 (dd, J=4.0 Hz, 5.6 Hz, 1H), 7.75 (s, 1H), 7.69-7.65 (m, 1H), 7.41-7.18 (m, 6H), 4.87 (s, 1H), 4.68-4.49 (m, 3H), 4.36-4.31 (m, 3H), 4.10 (m, 9H), 3.80-3.73 (m, 3H), 3.68-3.60 (m, 13H), 3.30 (s, 3H), 0.2.47-2.21 (m, 1H), 2.11-2.07 (m, 1H), 1.56-1.54 (m, 1H), 1.29 (s, 1H), 1.02-1.00 (t, J=8.8 Hz, 9H).

Synthesis of Example 39

(2S,4R)-1-((S)-2-(3-(2-((5-((4-((3-chloro-4-fluorophenyl)amino)-7-methoxyquinazolin-6-yl)oxy)pentyl)oxy)ethoxy)propanamido)-3,3-dimethylbutanoyl)-4-hydroxy-N-(4-(4-methylthiazol-5-yl)benzyl)pyrrolidine-2-carboxamide

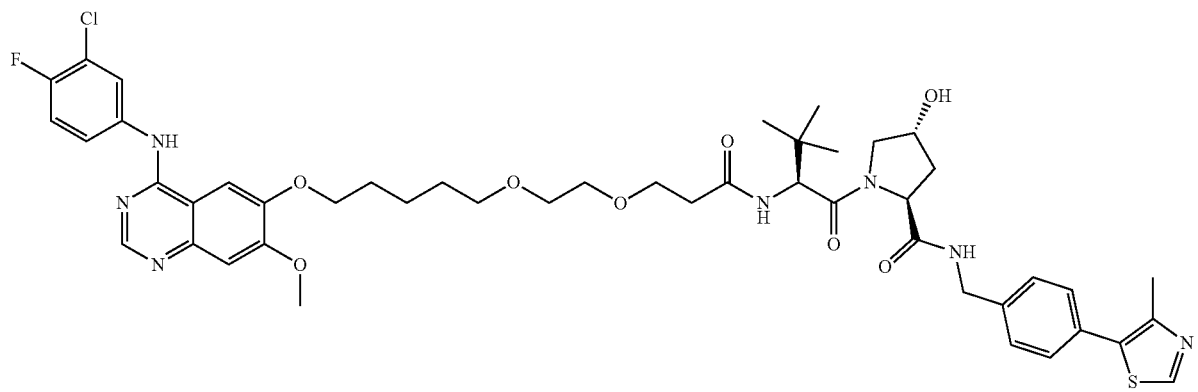 [SMILES: COc1cc2ncnc(Nc3ccc(F)c(Cl)c3)c2cc1OCCCCCOCCOCCC(=O)N[C@H](C(=O)N1C[C@H](O)C[C@H]1C(=O)NCc1ccc(-c2scnc2C)cc1)C(C)(C)C]

Synthetic scheme:

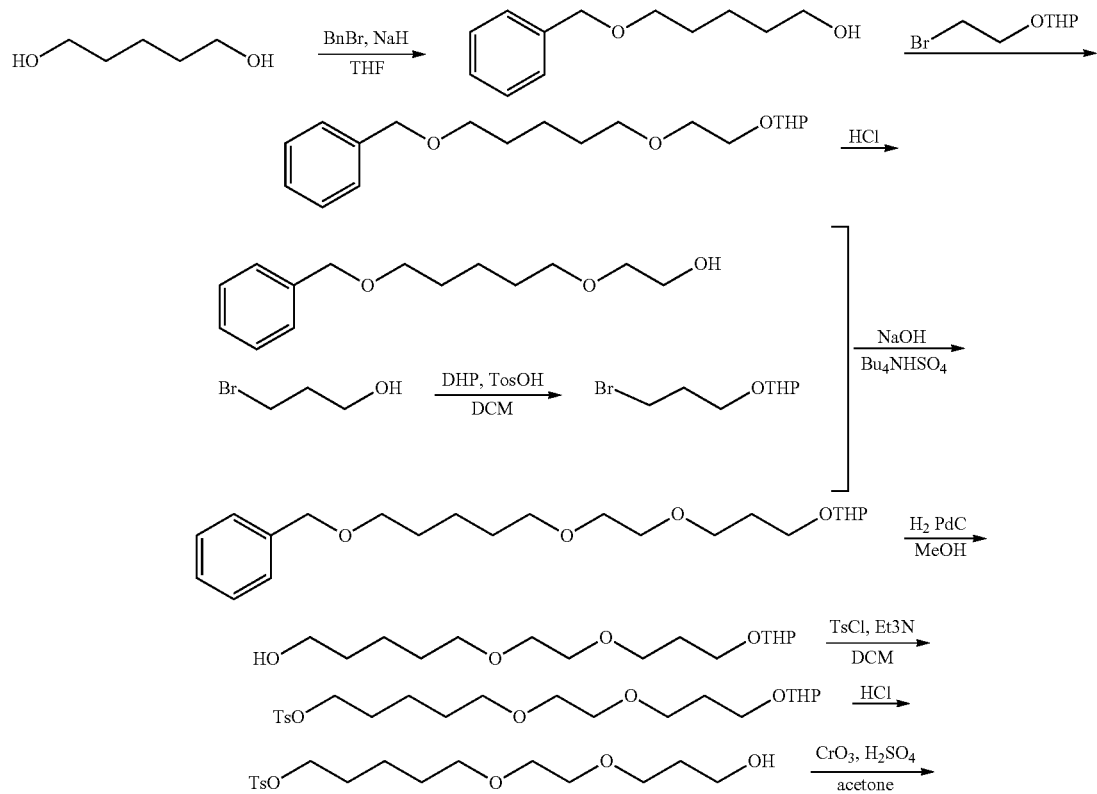

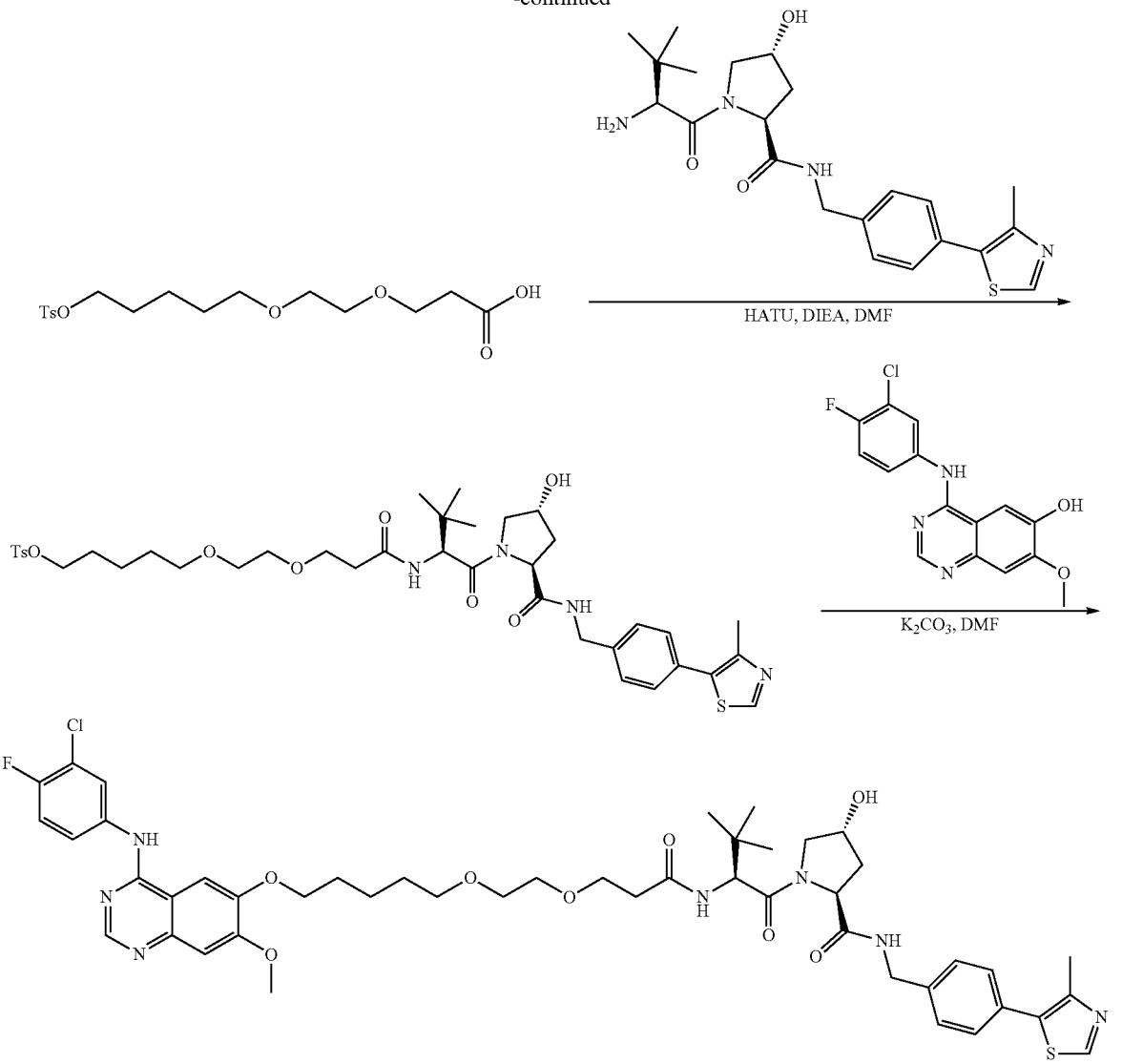

1. Step—Synthesis of 5-(Benzyloxy)pentan-1-ol

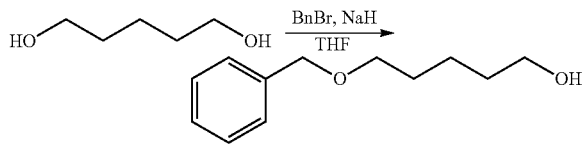

Into a 1000 mL round-bottom flask, was placed pentane-1,5-diol (30 g, 288.05 mmol, 1.00 equiv), tetrahydrofuran (500 mL). This was followed by the addition of sodium hydride (13.8 g, 575.00 mmol, 2.00 equiv) in several batches. The mixture was stirred for 1 h at 25° C. To this was added BnBr (58 g, 339.12 mmol, 1.20 equiv) dropwise with stirring. The resulting solution was stirred overnight at 25° C. The reaction was then quenched by the addition of 50 mL of water. The resulting solution was extracted with 3×500 mL of ethyl acetate and the organic layers were combined and dried over anhydrous sodium sulfate. The solids were filtered out. The resulting mixture was concentrated under vacuum. The residue was applied onto a silica gel column eluted with ethyl acetate/petroleum ether (1:5). This resulted in 28 g (50%) of 5-(benzyloxy)pentan-1-ol as colorless oil.

LC-MS m/z: (ES+) [M+H]+=195; Retention time: 1.01 min;

1H NMR (300 MHz, CDCl3, 25° C.): 7.35 (s, 5H), 4.52 (s, 2H), 3.65 (t, 2H), 3.51 (t, 2H), 1.69-1.40 (m, 6H).

2. Step—Synthesis of 2-(2-[[5-(Benzyloxy)pentyl]oxy]ethoxy)oxane

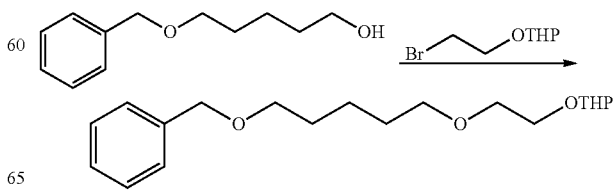

Into a 100 mL round-bottom flask, was placed 5-(benzyloxy)pentan-1-ol (3 g, 15.44 mmol, 1.00 equiv), 50% sodium hydroxide solution (20 mL), 2-(2-bromoethoxy)oxane (12.8 g, 61.22 mmol, 4.00 equiv), Bu4NHSO4 (0.5 g, 0.10 equiv). The resulting solution was stirred for 12 h at 65° C. The reaction mixture was cooled. The resulting mixture was washed with 20 mL of water and 20 mL of brine. The mixture was dried over anhydrous sodium sulfate. The solids were filtered out. The resulting mixture was concentrated under vacuum. This resulted in 4 g (80%) of 2-(2-[[5-(benzyloxy)pentyl]oxy]ethoxy)oxane as red oil. LC-MS m/z: (ES+) [M+H]+=323; Retention time: 1.25 min.

3. Step—Synthesis of 2-[[5-(Benzyloxy)pentyl]oxy]ethan-1-ol

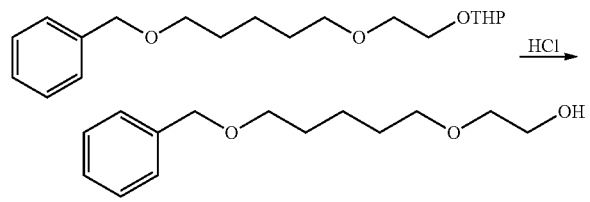

Into a 100 mL round-bottom flask, was placed 2-(2-[[5-(benzyloxy)pentyl]oxy]ethoxy)oxane (4 g, 12.41 mmol, 1.00 equiv), methanol (40 mL), hydrogen chloride (2 mL). The resulting solution was stirred overnight at 50° C. The reaction mixture was cooled. The resulting mixture was washed with water and brine. The mixture was dried over anhydrous sodium sulfate. The solids were filtered out. The resulting mixture was concentrated under vacuum. The residue was applied onto a silica gel column eluted with ethyl acetate/petroleum ether (1:2). This resulted in 3 g (100%) of 2-[[5-(benzyloxy)pentyl]oxy]ethan-1-ol as colorless oil. LC-MS m/z: (ES+) [M+H]+=239; Retention time: 1.12 min.

4. Step—Synthesis of 2-(3-Bromopropoxy)oxane

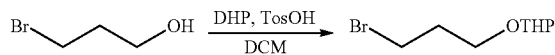

Into a 250 mL round-bottom flask, was placed 3-bromopropan-1-ol (4.75 g, 34.17 mmol, 1.00 equiv), dichloromethane (100 mL), PPTs (10 mg, 0.04 mmol, 0.10 equiv), 3,4-dihydro-2H-pyran (3.32 g, 39.47 mmol, 1.16 equiv). The resulting solution was stirred for 5 h at room temperature. The mixture was dried over anhydrous magnesium sulfate. The solids were filtered out. The resulting mixture was concentrated under vacuum. The residue was applied onto a silica gel column eluted with ethyl acetate/petroleum ether (1:5). This resulted in 5 g (66%) of 2-(3-bromopropoxy)oxane as colorless oil. 1H NMR (300 MHz, CDCl3, 25° C.): 4.62 (t, 1H), 3.95-3.85 (m, 2H), 3.59-3.48 (m, 4H), 2.18-2.10 (m, 2H), 1.90-1.45 (m, 6H).

5. Step—Synthesis of 2-[3-(2-[[5-(benzyloxy)pentyl]oxy]ethoxy)propoxy]oxane

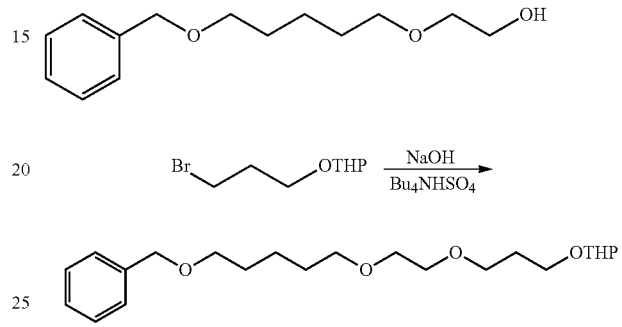

Into a 50 mL round-bottom flask, was placed 2-[[5-(benzyloxy)pentyl]oxy]ethan-1-ol (150 mg, 0.63 mmol, 1.00 equiv), 2 mL of 50% NaOH solution, 4 equivalents of 2-(3-bromopropoxy)oxane, and catalytic amount of Bu4NHSO4 (0.1 eq). The resulting solution was stirred overnight at 65° C. The reaction mixture was cooled. The resulting solution was extracted with 3×50 mL of ethyl acetate and the organic layers were combined and dried over anhydrous sodium sulfate and concentrated under vacuum. The residue was applied onto a silica gel column eluted with ethyl acetate/petroleum ether (1:2). This resulted in 200 mg (84%) of 2-[3-(2-[[5-(benzyloxy)pentyl]oxy]ethoxy)propoxy]oxane as colorless oil. LC-MS m/z: (ES+) [M+Na]+=403; Retention time: 1.53 min; 1H NMR (300 MHz, CDCl3, 25° C.): 7.35 (s, 5H), 4.62 (t, 1H), 4.52 (s, 2H), 3.95-3.85 (m, 4H), 3.59-3.48 (m, 10H), 1.90-1.45 (m, 14H).

6. Step—Synthesis of 5-[2-[3-(Oxan-2-yloxy)propoxy]ethoxy]pentan-1-ol

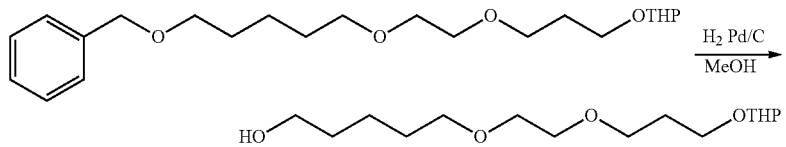

Into a 50 mL round-bottom flask, was placed 2-[3-(2-[[5-(benzyloxy)pentyl]oxy]ethoxy)propoxy]oxane (80 mg, 0.21 mmol, 1.00 equiv), methanol (5 mL), palladium on carbon (200 mg, 0.20 equiv). To this mixture H2(g) was introduced in. The resulting solution was stirred overnight at room temperature. The solids were filtered out. The resulting mixture was concentrated under vacuum. This resulted in 64 mg (crude) of 5-[2-[3-(oxan-2-yloxy)propoxy]ethoxy]pentan-1-ol as colorless oil. LC-MS m/z: (ES+) [M+H]+=291; Retention time: 1.32 min; 1H NMR (300 MHz, CDCl3, 25° C.): 4.62 (t, 1H), 3.98-3.79 (m, 2H), 3.65-3.47 (m, 8H), 1.90-1.45 (m, 14H).

7. Step—Synthesis of 5-[2-[3-(Oxan-2-yloxy) propoxy]ethoxy]pentyl 4-methylbenzene-1-sulfonate

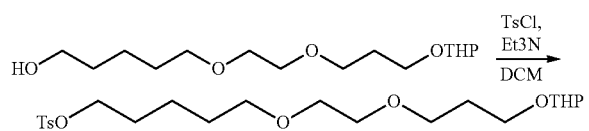

Into a 50 mL round-bottom flask, was placed 5-[2-[3-(oxan-2-yloxy)propoxy]ethoxy]pentan-1-ol (60 mg, 0.21 mmol, 1.00 equiv), dichloromethane (2 mL), triethylamine (47 mg, 0.46 mmol, 3.00 equiv), TsCl (30 mg, 0.16 mmol, 1.50 equiv). The resulting solution was stirred overnight at room temperature. The resulting mixture was washed with water and brine. The mixture was dried over anhydrous sodium sulfate. The solids were filtered out. The resulting mixture was concentrated under vacuum. This resulted in 90 mg (98%) of 5-[2-[3-(oxan-2-yloxy)propoxy]ethoxy]pentyl 4-methylbenzene-1-sulfonate as colorless oil. LC-MS m/z: (ES+) [M+H]+=445, Retention time: 1.25 min.

8. Step—Synthesis of 3-[2-[(5-[[(4-Methylbenzene) sulfonyl]oxy]pentyl)oxy]ethoxy]propan-1-ol

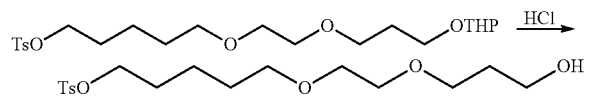

Into a 50 mL round-bottom flask, was placed 5-[2-[3-(oxan-2-yloxy)propoxy]ethoxy]pentyl 4-methylbenzene-1-sulfonate (90 mg, 0.20 mmol, 1.00 equiv), methanol (2 mL), hydrogen chloride (0.5 mL). The resulting solution was stirred for 2 h at room temperature. The resulting mixture was concentrated under vacuum. The resulting solution was extracted with 3×20 mL of ethyl acetate and the organic layers were combined and dried over anhydrous sodium sulfate. The solids were filtered out. The resulting mixture was concentrated under vacuum. This resulted in 45 mg (62%) of 3-[2-[(5-[[(4-methylbenzene)sulfonyl]oxy]pentyl) oxy]ethoxy]propan-1-ol as colorless oil. LC-MS m/z: (ES+) [M+H]+=291; Retention time: 0.93 min; 1H NMR (400 MHz, CDCl3, 25° C.): 7.83 (d, 2H), 7.35 (d, 2H), 4.05 (t, 2H), 3.80 (t, 2H), 3.70 (t, 2H), 3.64 (d, 2H), 3.58 (d, 2H), 3.45 (t, 2H), 2.92 (brs, 1H), 2.47 (s, 3H), 1.91-1.82 (m, 2H), 1.73-1.65 (m, 2H), 1.58-1.52 (m, 2H), 1.45-1.35 (m, 2H).

9. Step—Synthesis of 3-[2-[(5-[[(4-Methylbenzene) sulfonyl]oxy]pentyl)oxy]ethoxy]propanoic acid

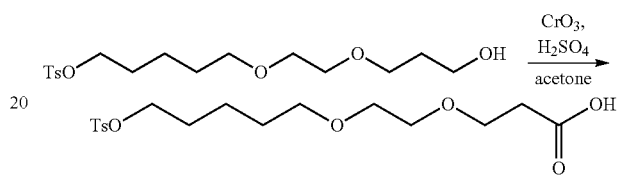

Into a 50 mL round-bottom flask, was placed 3-[2-[(5-[[(4-methylbenzene) sulfonyl]oxy]pentyl)oxy]ethoxy]propan-1-ol (100 mg, 0.28 mmol, 1.00 equiv), acetone (2 mL). To this was added CrO3 (55 mg, 2.00 equiv), sulfuric acid (0.1 mL), water (0.6 mL) under ice bath. The resulting solution was stirred for 2 h at 5-10° C. The reaction was then quenched by the addition of iso-propanol. The resulting solution was extracted with 2×10 mL of ethyl acetate and the organic layers were combined and dried over anhydrous sodium sulfate. The solids were filtered out. The resulting mixture was concentrated under vacuum. This resulted in 90 mg (87%) of 3-[2-[(5-[[(4-methylbenzene)sulfonyl]oxy] pentyl)oxy]ethoxy]propanoic acid as colorless oil.

LC-MS m/z: (ES+) [M+H]+=375; Retention time: 0.92 min.

10. Step—Synthesis of (2S,4R)-1-[(2S)-3,3-Dimethyl-2-(3-[2-[(5-[[(4-methylbenzene)-sulfonyl]oxy] pentyl)oxy]ethoxy]propanamido)butanoyl]-4-hydroxy-N-[[4-(4-methyl-1,3-thiazol-5-yl)phenyl] methyl]pyrrolidine-2-carboxamide

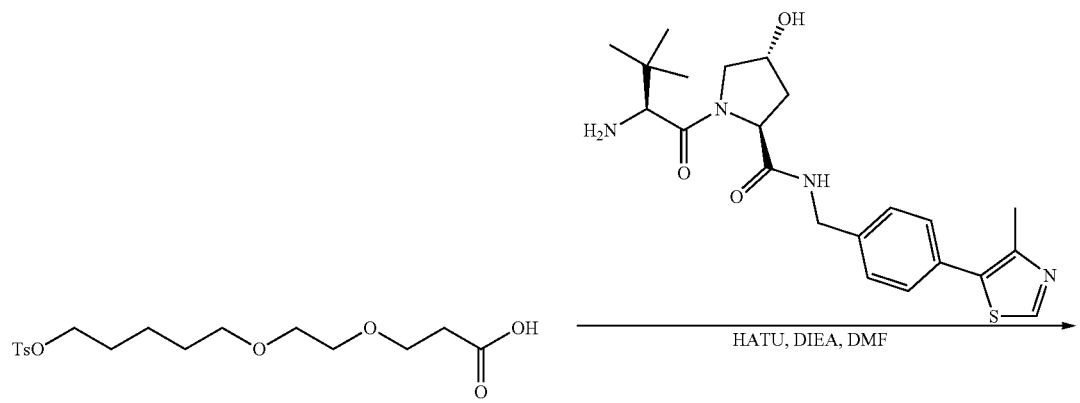

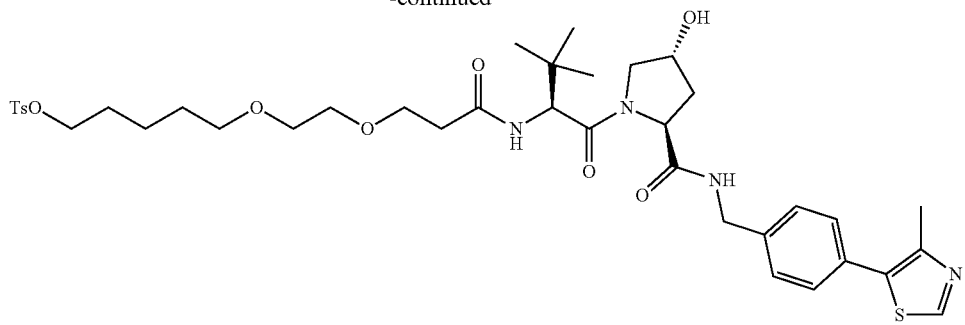

Into a 50 mL round-bottom flask, was placed 3-[2-[(5-[[(4-methylbenzene)sulfonyl]oxy]pentyl)oxy]ethoxy]propanoic acid (112 mg, 0.30 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (90 mg, 0.21 mmol, 1.00 equiv), HATU (137 mg, 0.36 mmol, 1.50 equiv), N,N-dimethylformamide (2 mL), DIEA (124 mg, 0.96 mmol, 4.00 equiv). The resulting solution was stirred for 2 h at room temperature. The resulting solution was extracted with 2×10 mL of ethyl acetate and the organic layers were combined. The resulting mixture was washed with 4×5 mL of water. The mixture was dried over anhydrous sodium sulfate. The solids were filtered out. The resulting mixture was concentrated under vacuum. This resulted in 110 mg (47%) of (2S,4R)-1-[(2S)-3,3-dimethyl-2-(3-[2-[(5-[[(4-methylbenzene)-sulfonyl]oxy]pentyl)oxy]ethoxy]propanamido)butanoyl]-4-hydroxy-N-[[4-(4-methyl-1,3-thiazol-5-yl)phenyl]methyl] pyrrolidine-2-carboxamide as colorless oil. LC-MS m/z: (ES+) [M+H]+=787; Retention time: 1.03 min.

11. Step—Synthesis of (2S,4R)-1-[(2S)-2-[3-(2-[[5-([4-[(3-Chloro-4-fluorophenyl)amino]-7-methoxyquinazolin-6-yl]oxy)pentyl]oxy]ethoxy)propanamido]-3,3-dimethylbutanoyl]-4-hydroxy-N-[[4-(4-methyl-1,3-thiazol-5-yl)phenyl]methyl]pyrrolidine-2-carboxamide

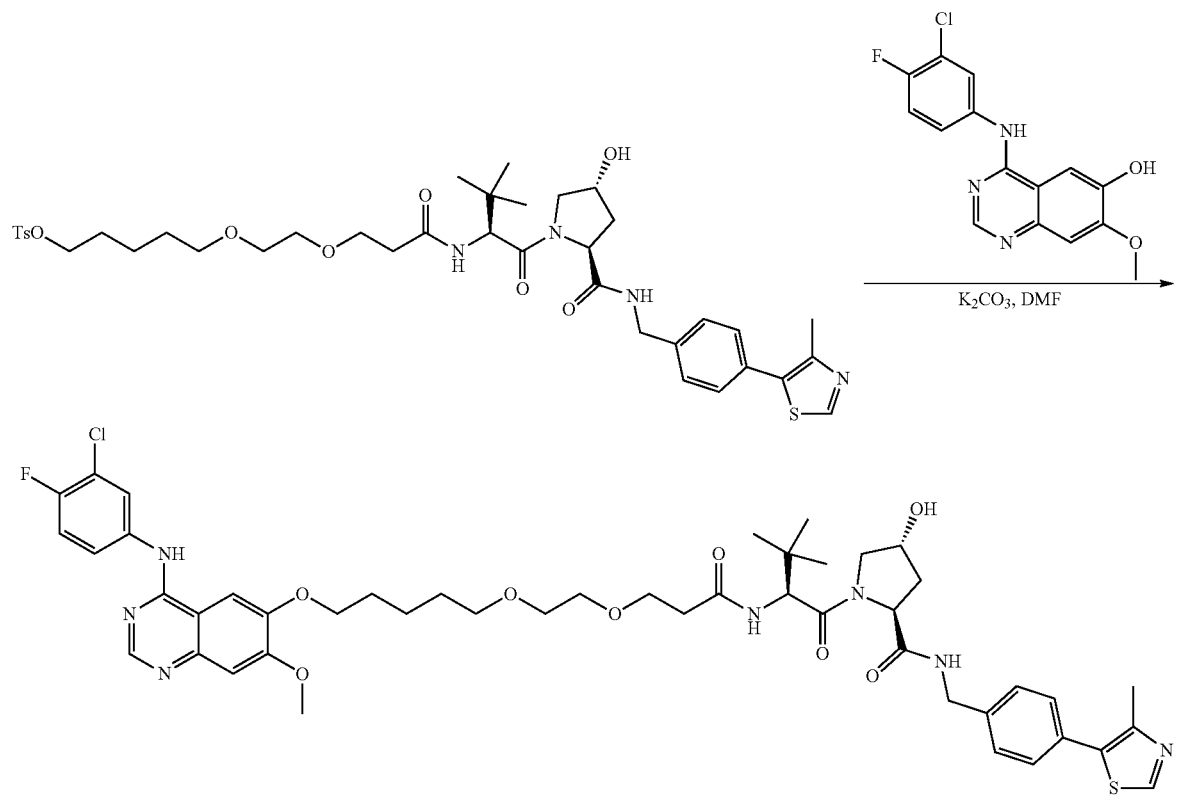

Into a 50 mL round-bottom flask, was placed 4-[(3-chloro-4-fluorophenyl)amino]-7-methoxyquinazolin-6-ol (45 mg, 0.14 mmol, 1.00 equiv), (2S,4R)-1-[(2S)-3,3-dimethyl-2-(3-[2-[(5-[[(4-methylbenzene)sulfonyl]oxy]-pentyl)oxy]ethoxy]propanamido)butanoyl]-4-hydroxy-N-[[4-(4-methyl-1,3-thiazol-5-yl)phenyl]methyl]pyrrolidine-2-carboxamide (110 mg, 0.14 mmol, 1.00 equiv), potassium carbonate (58 mg, 0.42 mmol, 3.00 equiv), N,N-dimethylformamide (2 mL). The resulting solution was stirred for 4 h at 80° C. The solids were filtered out. The crude product was purified by Prep-HPLC with the following conditions: XBridge Prep C18 OBD Column, 19×100 mm, 5 micron; mobile phase, water with 0.1% TFA and MeCN (25.0% MeCN up to 45.0% in 10 min); Detector, UV 254 nm. HPLC purification resulted in 16.3 mg (12%) of (2S,4R)-1-[(2S)-2-[3-(2-[[5-([4-[(3-chloro-4-fluorophenyl)amino]-7-methoxyquinazolin-6-yl]oxy)pentyl]oxy]ethoxy)propanamido]-3,3-dimethylbutanoyl]-4-hydroxy-N-[[4-(4-methyl-1,3-thiazol-5-yl) phenyl]methyl]pyrrolidine-2-carboxamide as a white solid. LC-MS m/z: (ES+) [M+H]+=934; Retention time: 1.97 min; 1H NMR (300 MHz, CD3OD, 25° C.): 8.89 (s, 1H), 8.45 (s, 1H), 7.95-8.05 (d, 1H), 7.65-7.74 (m, 2H), 7.36-7.49 (m, 3H), 7.17-7.31 (m, 2H), 4.68-4.34 (m, 5H), 4.15-4.23 (m, 2H), 4.02 (s, 3H), 3.91-3.72 (m, 4H), 3.62 (s, 4H), 3.52-3.54 (m, 2H), 2.58-2.45 (m, 4H), 2.25-1.52 (m, 8H), 1.05 (s, 9H).

Synthesis of Example 41

(2S,4R)-1-((S,E)-2-(tert-butyl)-16-((4-((4-chloro-3-fluorophenyl)amino)-7-methoxyquinazolin-6-yl)amino)-12-methyl-4,16-dioxo-6,9-dioxa-3,12-diazahexadec-14-enoyl)-4-hydroxy-N-(4-(4-methylthiazol-5-yl)benzyl)pyrrolidine-2-carboxamide

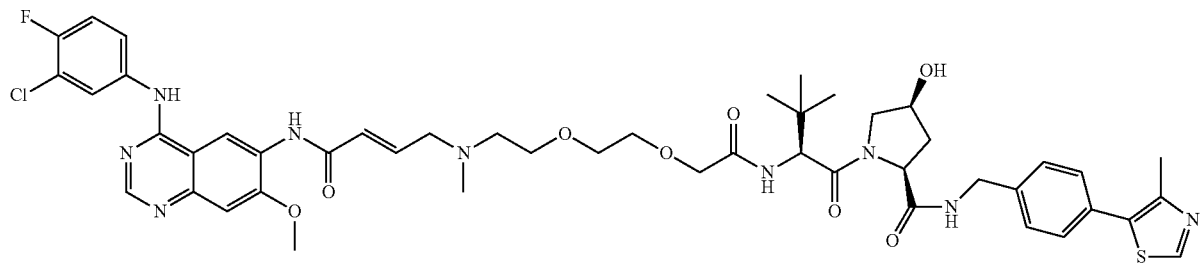 [SMILES: COc1cc2ncnc(Nc3ccc(F)c(Cl)c3)c2cc1NC(=O)/C=C/CN(C)CCOCCOCC(=O)N[C@H](C(=O)N1C[C@@H](O)C[C@H]1C(=O)NCc1ccc(-c2scnc2C)cc1)C(C)(C)C]

Synthesis Scheme part 1

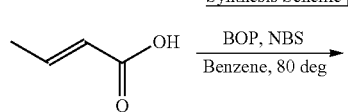

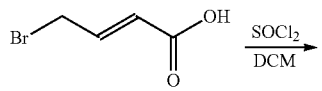

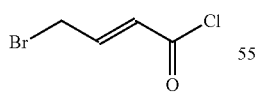

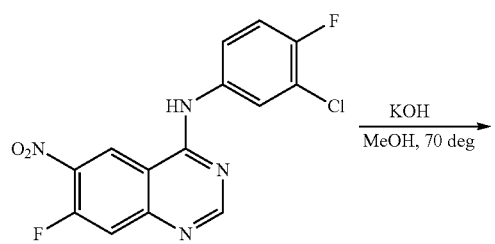

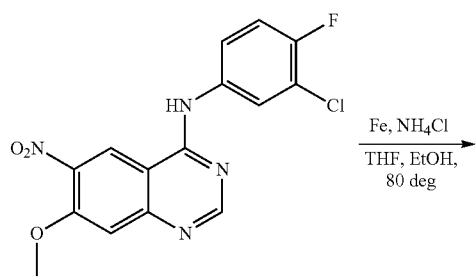

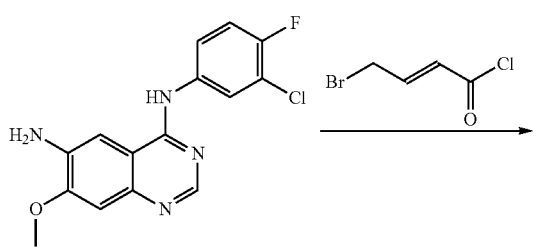

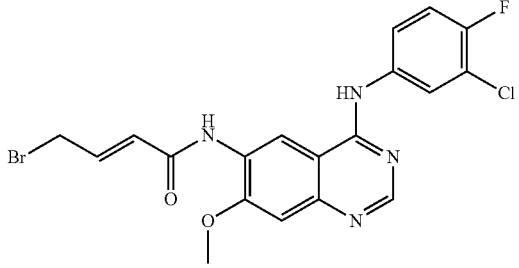

1. Step—Synthesis of (E)-4-bromobut-2-enoic acid

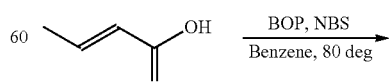

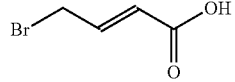

To a solution of (E)-but-2-enoic acid (20 g, 0.23 mol) in CCl$_4$ were added NBS (43 g, 0.24 mol) and benzoyl peroxide (5.6 g, 0.023 mol) under N$_2$. Then the mixture was stirred at 80° C. for 3 h. TLC analysis showed the complete consumption of (E)-but-2-enoic acid. It was cooled to rt. The mixture was filtered through Celite, and the filtrate was concentrated under vacuum. The residue was purified via column (PE:EA=5:1) to afford the desired product (E)-4-bromobut-2-enoic acid (10 g, 26% yield) as yellow white solid. $^1$H-NMR (400 MHz, CDCl$_3$): δ 7.01-7.09 (m, 1H), 5.98 (d, J=15.2 Hz, 1H), 3.96 (d, J=7.2 Hz, 2H).

2. Step—Synthesis of (E)-4-Bromobut-2-enoyl chloride

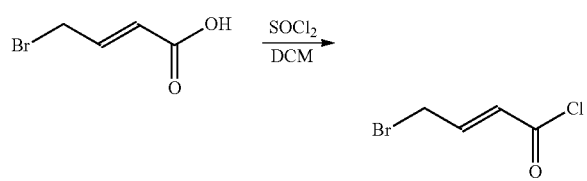

To a solution of compound (E)-4-bromobut-2-enoic acid (5.2 g, 0.03 mol) in DCM was added SOCl$_2$ (10 mL, 0.16 mol) dropwise in an ice-bath. Then the mixture was stirred at rt overnight. The solvent was removed under vacuum to afford the desired product (E)-4-Bromobut-2-enoyl chloride as yellow oil, which was used into next reaction without further purification.

3. Step—Synthesis of N-(3-Chloro-4-fluorophenyl)-7-methoxy-6-nitroquinazolin-4-amine

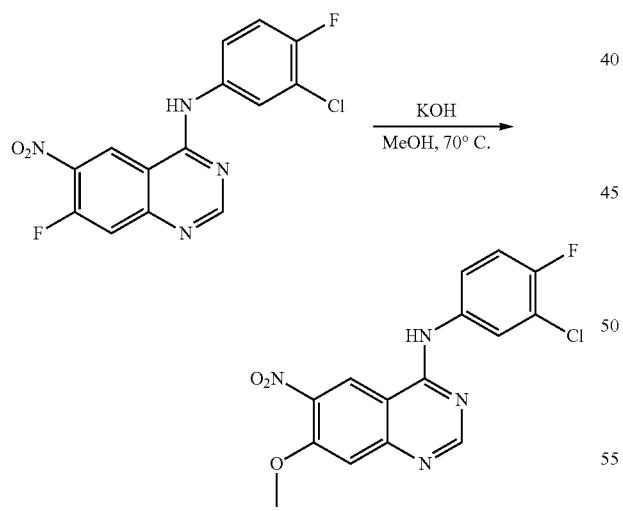

To a solution of N-(3-chloro-4-fluorophenyl)-7-fluoro-6-nitroquinazolin-4-amine (15 g, 44.56 mmol) in MeOH 150 mL, was added 50% KOH (5 g, 89 mmol) at rt. The reaction mixture was stirred at 70° C. for 2 h. Then it was cooled to rt and extracted with ethyl acetate. The combined organic layers were washed with water, and dried over Na$_2$SO$_4$. The organic phase was concentrated under vacuum to afford N-(3-Chloro-4-fluorophenyl)-7-methoxy-6-nitroquinazolin-4-amine (20 g, 96.7% yield). $^1$H NMR (400 MHz, DMSO-d$_6$): δ 10.16 (s, 1H), 9.21 (s, 1H), 8.67 (s, 1H), 8.15 (dd, J=2.4, 6.8 Hz, 1H), 7.79-7.81 (m, 1H), 7.48 (t, J=7.2 Hz, 2H), 4.07 (s, 3H).

4. Step—Synthesis of N$^4$-(3-Chloro-4-fluorophenyl)-7-methoxyquinazoline-4,6-diamine

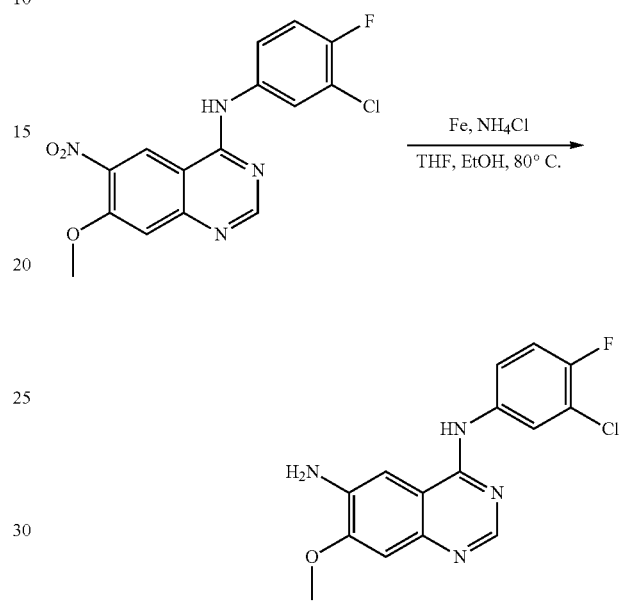

To a solution of N-(3-Chloro-4-fluorophenyl)-7-methoxy-6-nitroquinazolin-4-amine (10 g, 28.6 mmol) in a mixture of ethanol (200 mL), THF (100 mL), H$_2$O (50 mL), and saturated NH$_4$Cl solution (50 mL) was added iron powder (6.5 g, 116 mmol) at rt. Then the mixture was heated to 80° C. for 3 h. The mixture was filtered through Celite, and the cake was washed with ethanol. Water (100 mL) was added to the filtrate, and the yellow white solid was formed. The solid was filtered and dried to obtain the desired compound N$^4$-(3-chloro-4-fluorophenyl)-7-methoxyquinazoline-4,6-diamine (8 g, 88% yield) as yellow solid. $^1$H-NMR (400 MHz, DMSO-d$_6$): δ 9.41 (s, 1H), 8.38 (s, 1H), 8.20-8.17 (m, 1H), 7.82-7.80 (m, 1H), 7.41-7.37 (m, 2H), 5.36 (s, 2H), 3.97 (s, 3H).

5. Step—Synthesis of (E)-4-Bromo-N-(4-(3-chloro-4-fluorophenylamino)-7-methoxyquinazolin-6-yl)but-2-enamide

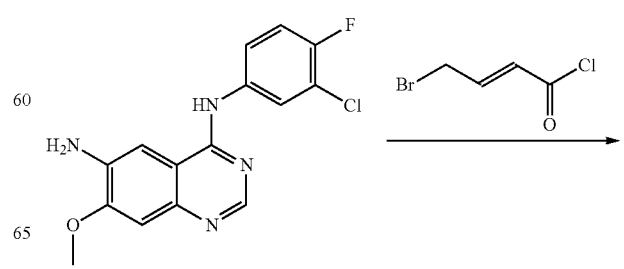

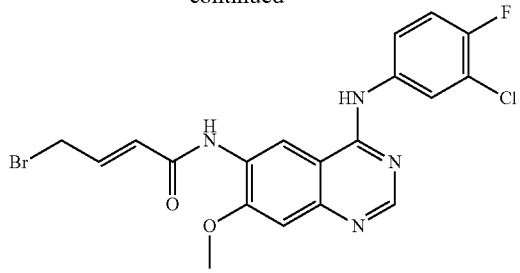

To a solution of N⁴-(3-chloro-4-fluorophenyl)-7-methoxyquinazoline-4,6-diamine (10 g, 31.4 mmol) in THF were added (E)-4-Bromobut-2-enoyl chloride (8.6 g, 47.1 mmol) and TEA (8 g, 78.4 mmol) at 0° C. subsequently. Then the mixture was stirred at room temperature for 2 h. The reaction mixture was quenched with water. The mixture was extracted with EA. The combined organic layers were washed NaHCO₃ solution and brine. The organic phase was dried over Na₂SO₄, and concentrated to afford the desired compound (E)-4-Bromo-N-(4-(3-chloro-4-fluorophenylamino)-7-methoxyquinazolin-6-yl)but-2-enamide (7.6 g, 52% yield) as brown solid.

¹H-NMR (400 MHz, CDCl₃): δ 8.95 (s, 1H), 8.65 (s, 1H), 8.25 (s, 1H), 7.93-7.91 (m, 1H), 7.72 (s, 1H), 7.54-7.51 (m, 1H), 7.14-7.10 (m, 1H), 6.56-6.48 (m, 2H), 4.06 (s, 3H), 3.46 (d, J=6.8 Hz, 2H). LCMS: 465 [M+H]; $t_R$=1.38

Synthetic Scheme part 2:

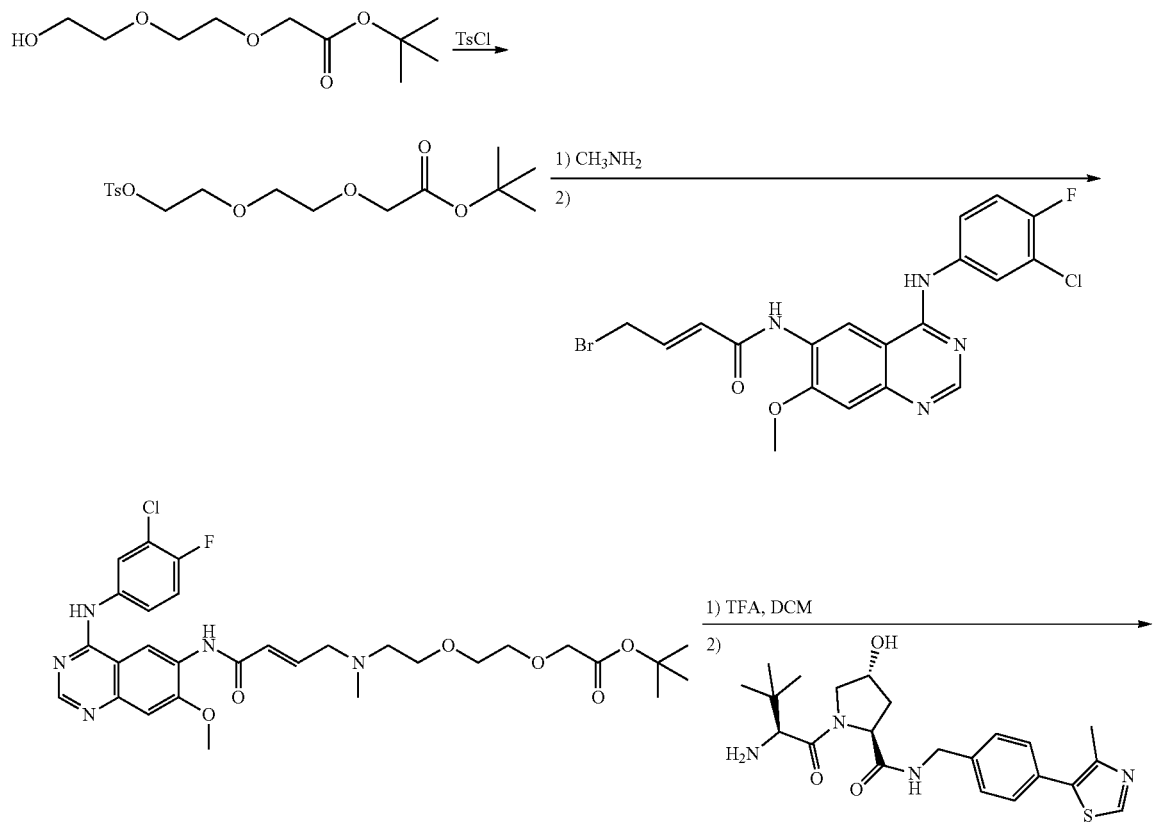

-continued

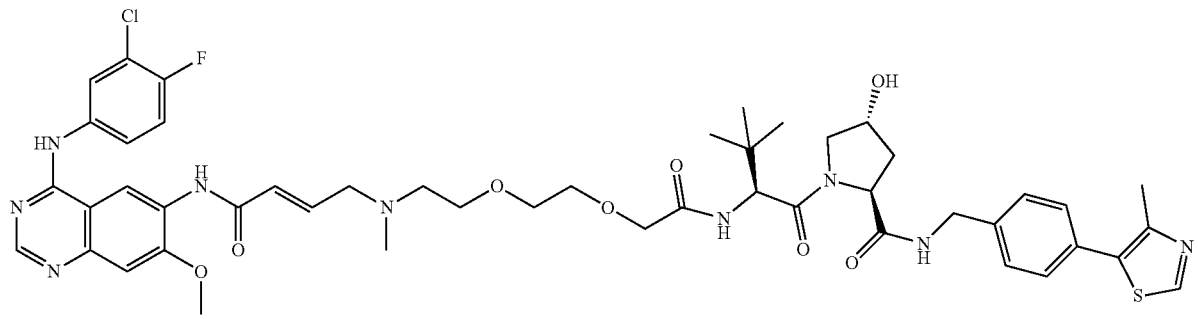

Step 6—Synthesis of tert-butyl 2-(2-(2-(tosyloxy)ethoxy)ethoxy)acetate

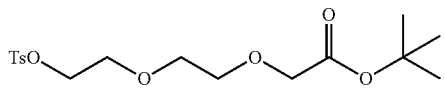 [SMILES: Cc1ccc(S(=O)(=O)OCCOCCOCC(=O)OC(C)(C)C)cc1]

To a stirred solution of tert-butyl 2-(2-(2-hydroxyethoxy) ethoxy)acetate (2.0 g, 9.08 mmol), triethylamine (3.2 g, 31.78 mmol), and 4-dimethylaminopyridine (111 mg, 0.91 mmol) in anhydrous dichloromethane (20 ml) was added a solution of 4-toluenesulfonyl chloride (1.9 g, 3.12 mmol) in anhydrous dichloromethane (10 ml) dropwise at 0° C. The resulting mixture was then allowed to warm up to room temperature and stirred at room temperature for 10 hours. TLC showed formation of desired product. The reaction mixture was diluted with dichloromethane (250 ml), washed with water (50 ml×3) and brine (50 ml), dried over anhydrous sodium sulfate, and concentrated under reduced pressure to give a crude residue which was purified by silica gel flash column chromatography (eluted with 20-30% ethyl acetate in hexane) to afford tert-butyl2-(2-(2-(tosyloxy) ethoxy)ethoxy)acetate (1.7 g, yield 50%) as a colorless oil. LC_MS: (ES+): m/z 397.10 [M+Na+]. $t_R$=2.799 min.

Step 7—Synthesis of (E)-tert-butyl2-(2-(2-((4-(4-(3-chloro-4-fluorophenylamino)-7-methoxyquinazolin-6-ylamino)-4-oxobut-2-enyl)(methyl)amino)ethoxy) ethoxy)acetate

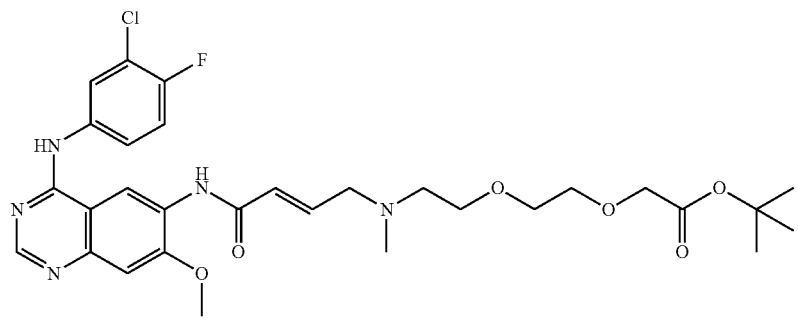 [SMILES: COc1cc2ncnc(Nc3ccc(F)c(Cl)c3)c2cc1NC(=O)/C=C/CN(C)CCOCCOCC(=O)OC(C)(C)C]

A mixture of tert-butyl2-(2-(2-(tosyloxy)ethoxy)ethoxy) acetate (250 mg, 0.67 mmol) in methylamine methanol solution (30%, 5 ml) was stirred at room temperature for 5 hours. TLC showed formation of desired product. The volatiles were removed under reduced pressure; the residue was partitioned between dichloromethane (120 ml) and water (30 ml). The organic layer was collected, washed with brine (30 ml), dried over anhydrous sodium sulfate, and concentrated under reduced pressure. The residue was re-dissolved in anhydrous N-methyl-2-pyrrolidone (3 ml), followed by sequentially addition of N,N-diisopropylethylamine (30 mg, 0.23 mmol) and (E)-4-bromo-N-(4-(3-chloro-4-fluorophenylamino)-7-methoxyquinazolin-6-yl)but-2-enamide (100 mg, 0.21 mmol) at room temperature. The resulting mixture was stirred at room temperature for 5 hours. TLC showed formation of desired product. The reaction mixture was partitioned between ethyl acetate (150 ml) and water (40 ml). The organic layer was collected, washed with brine (30 ml), dried over anhydrous sodium sulfate, and concentrated under reduced pressure to give a crude residue which was purified by pre-TLC to afford (E)-tert-butyl2-(2-(2-((4-(4-(3-chloro-4-fluorophenylamino)-7-methoxyquinazolin-6-ylamino)-4-oxobut-2-enyl)(methyl)amino)ethoxy)ethoxy)acetate (60 mg, yield 45%) as yellow oil. LC_MS: (ES$^+$): m/z 618.30 [M+H$^+$]. t$_R$=1.696 min.

Step 8—Synthesis of (2S,4R)-1-((S,E)-17-(4-(4-chloro-3-fluorophenylamino)-7-methoxyquinazolin-6-ylamino)-2,2,13-trimethyl-5,17-dioxo-7,10-dioxa-4,13-diazaheptadec-15-enecarbonyl)-4-hydroxy-N-(4-(4-methylthiazol-5-yl)benzyl)pyrrolidine-2-carboxamide

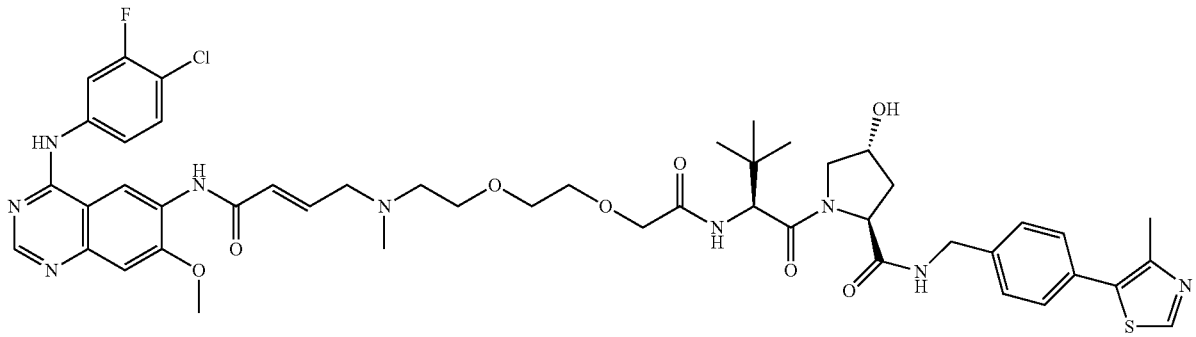 [SMILES: COc1cc2ncnc(Nc3ccc(Cl)c(F)c3)c2cc1NC(=O)/C=C/CN(C)CCOCCOCC(=O)N[C@H](C(=O)N1C[C@H](O)C[C@H]1C(=O)NCc1ccc(-c2scnc2C)cc1)C(C)(C)C]

A mixture of (E)-tert-butyl2-(2-(2-((4-(4-(3-chloro-4-fluorophenylamino)-7-methoxyquinazolin-6-ylamino)-4-oxobut-2-enyl)(methyl)amino)ethoxy)ethoxy)acetate (60 mg, 0.097 mmol) in 2,2,2-trifluoroacetic acid (1 ml) and anhydrous dichloromethane (1 ml) was stirred at room temperature for 2 hours. TLC showed formation of desired product. The volatiles were evaporated under reduced pressure; the residue was re-dissolved in anhydrous N,N-dimethylformamide (2 ml), followed by sequential addition of (2S,4R)-1-((S)-2-amino-3,3-dimethylbutanoyl)-4-hydroxy-N-(4-(4-methylthiazol-5-yl)benzyl)pyrrolidine-2-carboxamide hydrochloric acid salt (46 mg, 0.098 mmol), N,N-diisopropylethylamine (51 mg, 0.388 mmol), and HATU (2-(7-Aza-1H-benzotriazole-1-yl)-1,1,3,3-tetramethyluronium hexafluorophosphate) (74 mg, 0.194 mmol) at 0° C. The resulting mixture was allowed to warm up to room temperature and stirred at room temperature for 20 min. TLC showed formation of desired product. The reaction mixture was partitioned between ethyl acetate (150 ml) and water (30 ml). The organic layer was collected, washed with brine (20 ml), dried over anhydrous sodium sulfate, and concentrated under reduced pressure to give a crude residue which was purified by pre-TLC to afford (2S,4R)-1-((S,E)-17-(4-(4-chloro-3-fluorophenylamino)-7-methoxyquinazolin-6-ylamino)-2,2,13-trimethyl-5,17-dioxo-7,10-dioxa-4,13-diazaheptadec-15-enecarbonyl)-4-hydroxy-N-(4-(4-methylthiazol-5-yl)benzyl)pyrrolidine-2-carboxamide (26.9 mg, yield 28%) as a light yellow solid. LC_MS: (ES$^+$): m/z 974.20 [M+H$^+$]. t$_R$=1.630 min. $^1$H NMR (400 MHz, CD$_3$OD): δ1.04, 1.06 (two singles, 9H), 2.06-2.11 (m, 1H), 2.25-2.30 (m, 1H), 2.44 (s, 3H), 2.83, 2.85 (two singles, 3H), 3.77-4.16 (m, 15H), 4.42-4.63 (m, 4H), 4.76-4.81 (m, 1H), 6.76 (d, J=15.2 Hz, 1H), 7.04-7.08 (m, 1H), 7.24-7.28 (m, 2H), 7.36-7.40 (m, 4H), 7.67-7.68 (m, 1H), 7.99 (br, 1H), 8.37 (br, 1H), 8.49 (s, 1H), 8.85 (s, 1H), 8.93 (s, 1H).

Synthesis of Example 59
(2S,4R)-1-((S)-2-(6-(2-((4-((3-chloro-4-fluorophenyl)amino)-6-((E)-4-(dimethylamino)but-2-enamido)quinazolin-7-yl)oxy)ethoxy)hexanamido)-3,3-dimethylbutanoyl)-4-hydroxy-N-(4-(4-methylthiazol-5-yl)benzyl)pyrrolidine-2-carboxamide
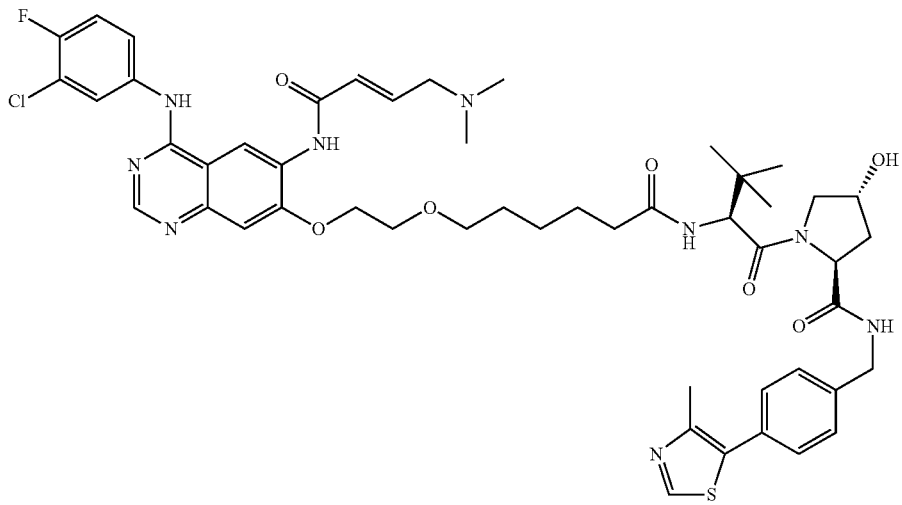 [SMILES: Cc1ncsc1-c1ccc(CNC(=O)[C@@H]2C[C@@H](O)CN2C(=O)[C@@H](NC(=O)CCCCCOCCOc2cc3ncnc(Nc4ccc(F)c(Cl)c4)c3cc2NC(=O)/C=C/CN(C)C)C(C)(C)C)cc1]
Reaction Scheme
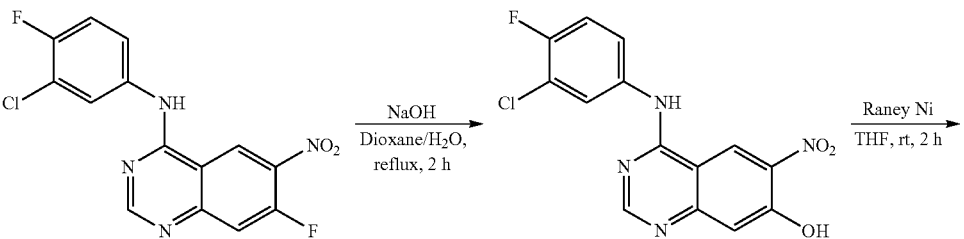
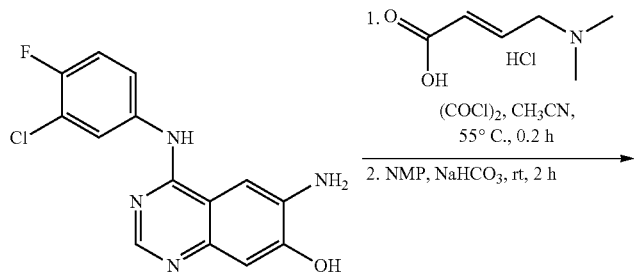
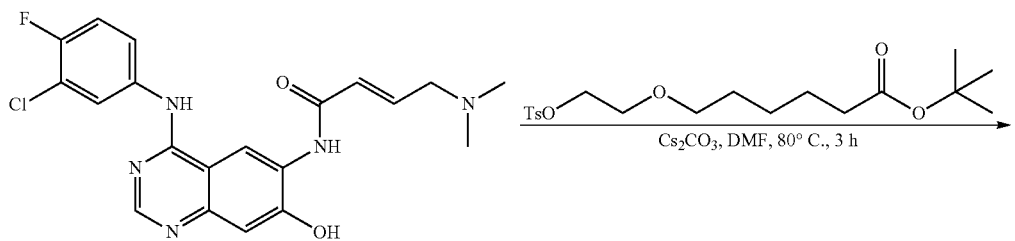

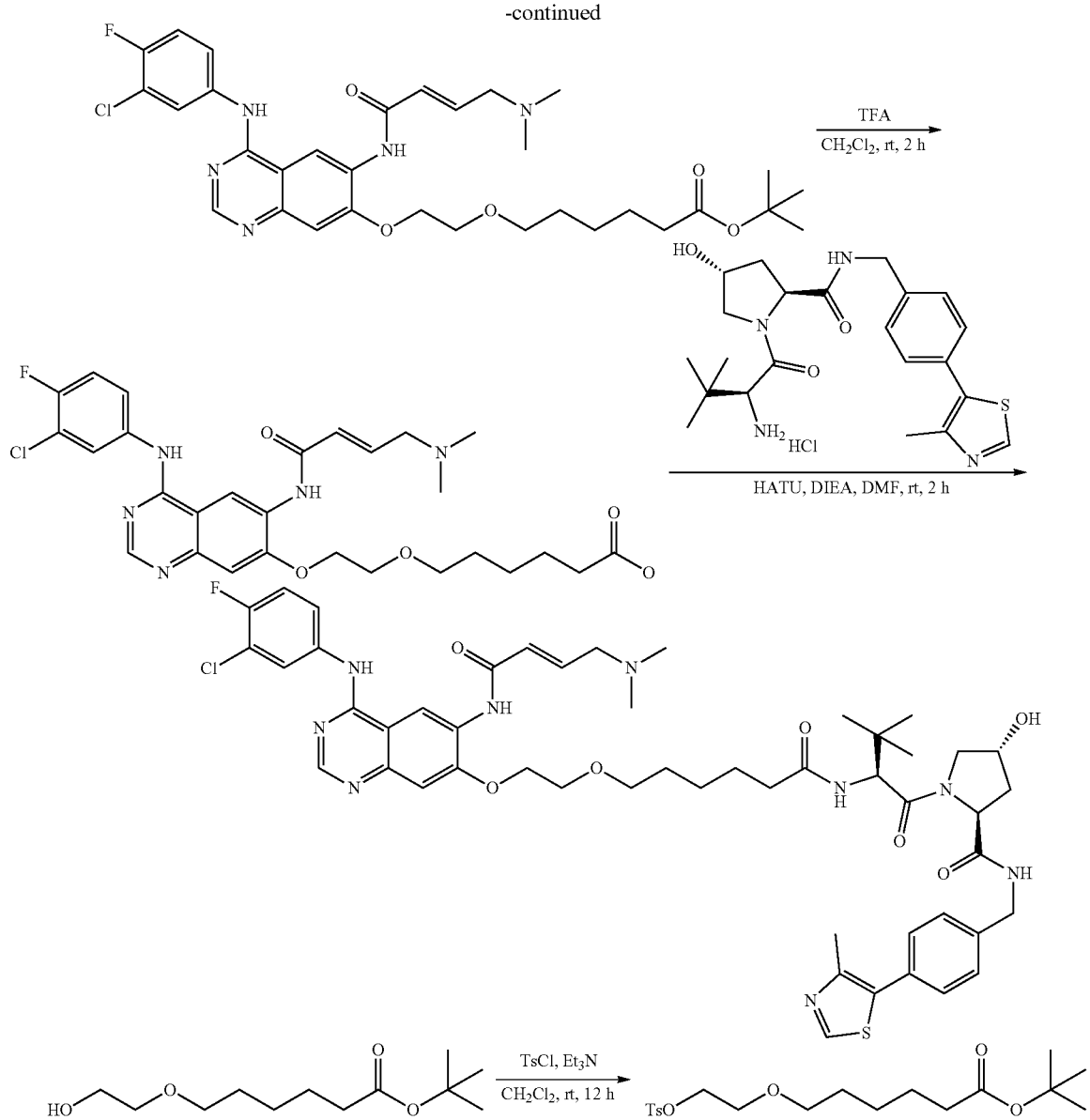

Experimental Details

1. Step—Synthesis of 4-[(3-chloro-4-fluorophenyl)amino]-6-nitroquinazolin-7-ol

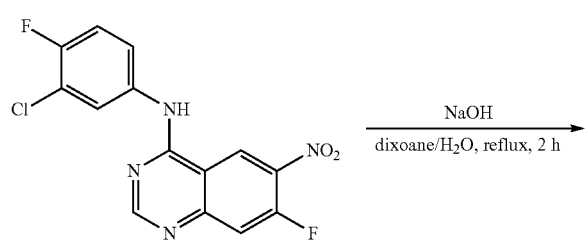

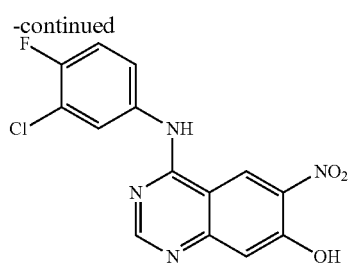

Into a 250-mL round-bottom flask, was placed a solution of N-(3-chloro-4-fluorophenyl)-7-fluoro-6-nitroquinazolin-4-amine (5.0 g, 14.85 mmol, 1.00 equiv) in dixoane/50% sodium hydroxide (aq) (80/15 mL). The resulting solution was heated to reflux for 2 hr. The reaction mixture was cooled. The resulting solution was diluted with water (1000 mL). The pH value of the solution was adjusted to 3 with hydrogen chloride (c). The resulting solution was extracted with ethyl acetate (500 mL×4) and the organic layers combined. The resulting mixture was washed with brine (500 mL×1). The mixture was dried over anhydrous sodium sulfate and concentrated under vacuum. The residue was applied onto a silica gel column with ethyl acetate/petroleum ether (1:2). This resulted in 1.92 g (39%) of 4-[(3-chloro-4-fluorophenyl)amino]-6-nitroquinazolin-7-ol as a orange solid. $^1$H NMR (300 MHz, DMSO) δ 11.94-11.81 (b, 1H), 10.17 (s, 1H), 9.22 (s, 1H), 8.60 (s, 1H), 8.16-8.15 (d, J=4.5 Hz, 1H), 7.81-7.78 (d, J=8.1 Hz, 1H), 7.53-7.44 (m, 2H), 7.26 (s, 1H); LC-MS (ES$^+$): m/z 335.05 [MH$^+$], $t_R$=0.95 min (1.9 minute run).

2. Step—Synthesis of 6-amino-4-[(3-chloro-4-fluorophenyl)amino]quinazolin-7-ol

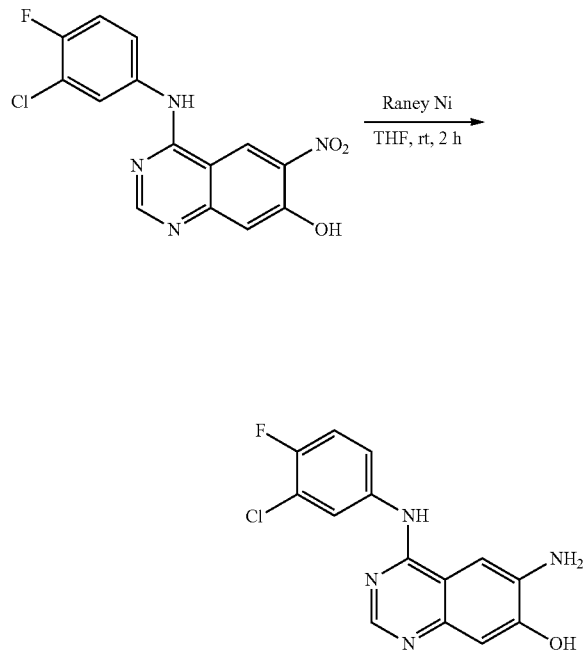

Into a 250-mL round-bottom flask, was placed a solution of 4-[(3-chloro-4-fluorophenyl)amino]-6-nitroquinazolin-7-ol (4.0 g, 11.95 mmol, 1.00 equiv) in tetrahydrofuran (100 mL), Raney Ni (2.0 g) was added in the solution under nitrogen atmosphere. Nitrogen was removed under vacuum, hydrogen was introduced into under hydrogen atmosphere. The resulting solution was stirred for 2 h at room temperature. The solids were filtered out. The resulting mixture was concentrated under vacuum. The residue was applied onto a silica gel column with dichloromethane/methanol (10:1). This resulted in 2.3 g (63%) of 6-amino-4-[(3-chloro-4-fluorophenyl)amino]quinazolin-7-ol as a blue green solid. $^1$H NMR (300 MHz, DMSO) δ 10.80-10.50 (b, 1H), 9.33 (s, 1H), 8.37 (s, 1H), 8.19-8.18 (d, J=4.5 Hz, 1H), 7.81-7.78 (d, J=8.1 Hz, 1H), 7.41-7.35 (m, 2H), 7.00 (s, 1H), 5.30-5.22 (b, 2H); LC-MS (ES$^+$): m/z 305.20 [MH$^+$], $t_R$=0.85 min (1.9 minute run).

3. Step—Synthesis of (2E)-N-[4-[(3-chloro-4-fluorophenyl)amino]-7-hydroxyquinazolin-6-yl]-4-(dimethylamino)but-2-enamide

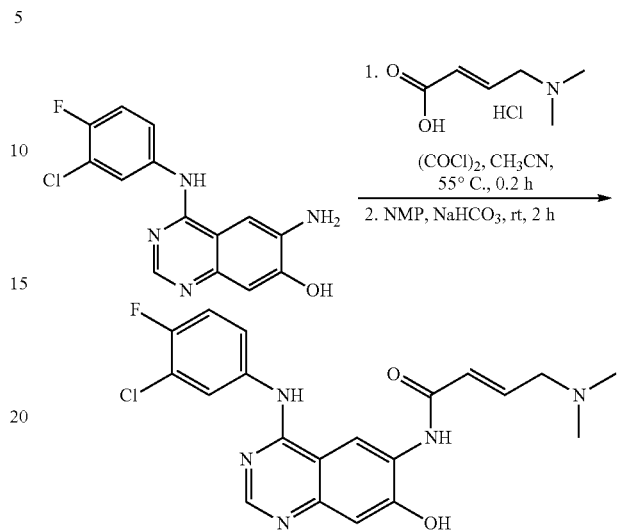

Onto a 100-mL round-bottom flask purged and maintained with an inert atmosphere of nitrogen, was placed a solution of (2E)-4-(dimethylamino)but-2-enoic acid hydrogen chloride (1.27 g, 9.83 mmol, 2.00 equiv) in acetonitrile (25 mL). N,N-dimethylformamide (3 drops) (cat) and oxalic dichloride (10 mL) were added dropwise at room temperature. The resulting solution was stirred for 30 min at 55° C. The solution was concentrated under vacuum. This black oil was dissolved in 1-Methyl-2-pyrrolidinone (10 mL), and was dropwised into another a 100-mL round-bottom flask purged and maintained with an inert atmosphere of nitrogen, that was loaded with a solution of 6-amino-4-[(3-chloro-4-fluorophenyl)amino]quinazolin-7-ol (1.5 g, 4.92 mmol, 1.00 equiv) in 1-Methyl-2-pyrrolidinone (40 mL) and sodium bicarbonate (4.0 g, 37.74 mmol, 7.00 equiv) at 0° C. The resulting solution was allowed to react, with stirring, for 2 h at room temperature. The reaction was then quenched by the addition of 30 mL of water. The solids were removed by filtration. The resulting mixture was concentrated under vacuum. The residue was applied onto C18 column (330 g) with water/methanol (10%-70%) in 90 mins. This resulted in 2.03 g (80% purity) of (2E)-N-[4-[(3-chloro-4-fluorophenyl)amino]-7-hydroxyquinazolin-6-yl]-4-(dimethylamino) but-2-enamide as a brown solid. LC-MS (ES$^+$): m/z 416.05 [MH$^+$], $t_R$=1.05 min (2.6 minute run).

4. Step—Synthesis of tert-butyl 6-(2-[[(4-methylbenzene)sulfonyl]oxy]ethoxy)hexanoate

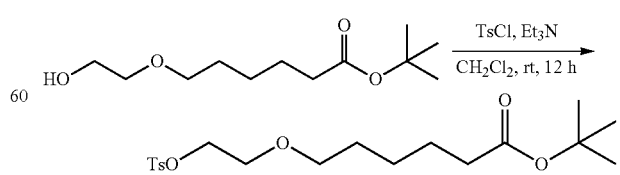

Into a 100-mL round-bottom flask, was placed tert-butyl 6-(2-hydroxyethoxy)hexanoate (500.0 mg, 2.15 mmol, 1.00 equiv), triethylamine (653.0 mg, 6.45 mmol, 3.00 equiv), 4-methylbenzene-1-sulfonyl chloride (614.0 mg, 3.22 mmol, 1.50 equiv), 4-dimethylaminopyridine (26 mg, 0.21 mmol, 0.10 equiv), dichloromethane (25 mL). The resulting solution was stirred for 12 h at room temperature. The resulting mixture was concentrated under vacuum. The residue was applied onto a silica gel column with ethyl acetate/petroleum ether (1:2). This resulted in 650.0 mg (78%) of tert-butyl 6-(2-[[(4-methylbenzene)sulfonyl]oxy]ethoxy)hexanoate as colorless oil.

5. Step—Synthesis of tert-butyl 6-[2-([4-[(3-chloro-4-fluorophenyl)amino]-6-[(2E)-4-(dimethylamino)but-2-enamido]quinazolin-7-yl]oxy)ethoxy]hexanoate

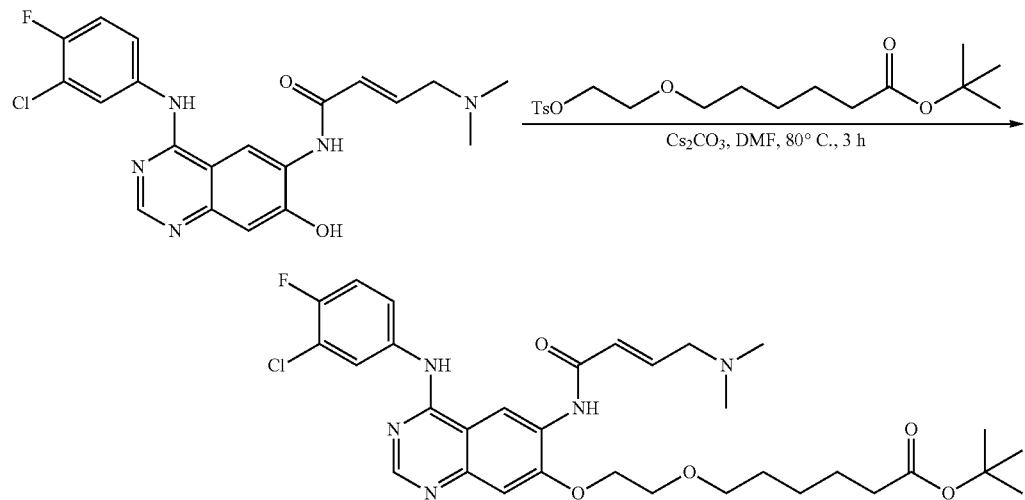

Into a 50-mL round-bottom flask, was placed a solution of (2E)-N-[4-[(3-chloro-4-fluorophenyl)amino]-7-hydroxyquinazolin-6-yl]-4-(dimethylamino)but-2-enamide (160.0 mg, 0.38 mmol, 1.00 equiv) in N,N-dimethylformamide (15.0 mL), $Cs_2CO_3$ (251.0 mg, 0.77 mmol, 2.00 equiv), tert-butyl 6-(2-[(4-methylbenzene) sulfonyl]oxyethoxy)hexanoate (148.0 mg, 0.38 mmol, 1.00 equiv). The resulting solution was stirred for 3 h at 80° C. The reaction was then quenched by the addition of water (10 mL). The resulting solution was extracted with ethyl acetate (20 mL×2) and the organic layers combined. The resulting mixture was washed with brine (30 mL×1). The mixture was dried over anhydrous sodium sulfate and concentrated under vacuum. The residue was applied onto a silica gel column with ethyl acetate/petroleum ether (1:2). The collected fractions were combined and concentrated under vacuum. This resulted in 130.0 mg (54%) of tert-butyl 6-[2-([4-[(3-chloro-4-fluorophenyl)amino]-6-[(2E)-4-(dimethylamino)but-2-enamido]quinazolin-7-yl]oxy)ethoxy]hexanoate as yellow oil. LC-MS (ES$^+$): m/z 630.35 [MH$^+$], $t_R$=1.33 min (1.9 minute run).

6. Step—Synthesis of 6-[2-([4-[(3-chloro-4-fluorophenyl)amino]-6-[(2E)-4-(dimethylamino)but-2-enamido]quinazolin-7-yl]oxy)ethoxy]hexanoic acid

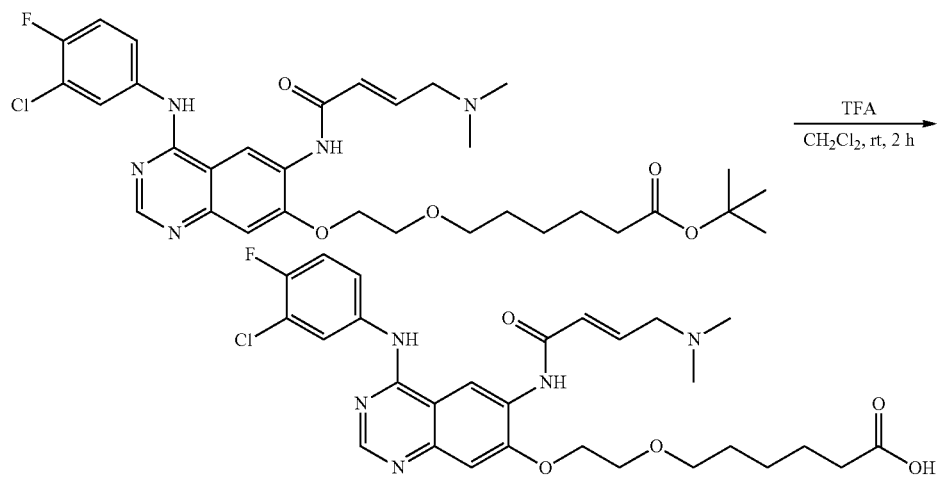

Into a 50-mL round-bottom flask, was placed a solution of tert-butyl 6-[2-([4-[(3-chloro-4-fluorophenyl)amino]-6-[(2E)-4-(dimethylamino)but-2-enamido]quinazolin-7-yl]oxy)ethoxy]hexanoate (130.0 mg, 0.21 mmol, 1.00 equiv) in dichloromethane/trifluoroacetic acid (10/3 mL). The resulting solution was stirred for 2 h at room temperature. The resulting mixture was concentrated under vacuum. This resulted in 100.0 mg (84%) of 6-[2-([4-[(3-chloro-4-fluorophenyl)amino]-6-[(2E)-4-(dimethylamino)but-2-enamido]quinazolin-7-yl]oxy)ethoxy]hexanoic acid as yellow oil. LC-MS (ES+): m/z 574.15[MH+], $t_R$=0.53 min (1.9 minute run).

7. Step—Synthesis of (2S,4R)-1-[(2S)-2-[6-[2-([4-[(3-chloro-4-fluorophenyl)amino]-6-[(2E)-4-(dimethylamino)but-2-enamido]quinazolin-7-yl]oxy)ethoxy]hexanamido]-3,3-dimethylbutanoyl]-4-hydroxy-N-[[4-(4-methyl-1,3-thiazol-5-yl)phenyl]methyl]pyrrolidine-2-carboxamide

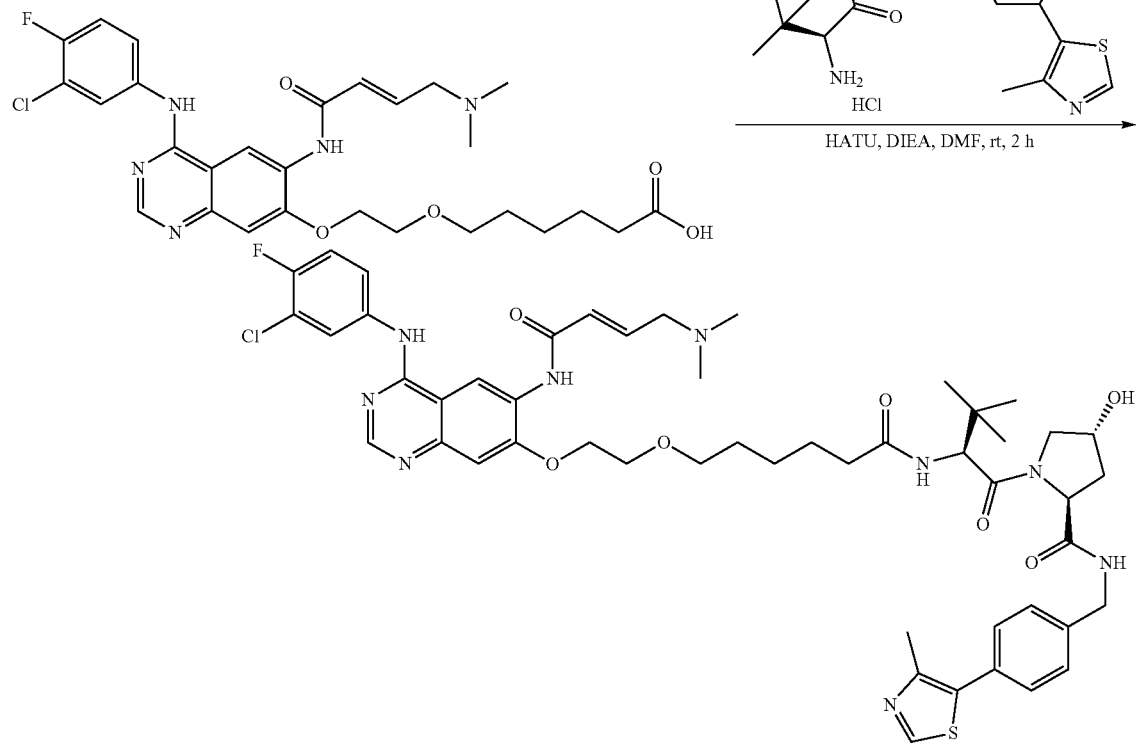

Into a 50-mL round-bottom flask, was placed a solution of 6-[2-([4-[(3-chloro-4-fluorophenyl)amino]-6-[(2E)-4-(dimethylamino)but-2-enamido]quinazolin-7-yl]oxy)ethoxy]hexanoic acid (100.0 mg, 0.17 mmol, 1.00 equiv) in N,N-dimethylformamide (10.0 mL), N-ethyl-N-isopropylpropan-2-amine (90.0 mg, 0.70 mmol, 4.00 equiv). This was followed by the addition of o-(7-Azabenzotriazol-1-yl)-N,N,N',N'-tetramethyluronium hexafluorophosphate (80.0 mg, 0.21 mmol, 1.20 equiv). It was stirred for 5 min at room temperature. To this was added (2S,4R)-1-[(2S)-2-amino-3,3-dimethylbutanoyl]-4-hydroxy-N-[4-(4-methyl-1,3-thiazol-5-yl)phenyl]methylpyrrolidine-2-carboxamide hydrochloride (98.0 mg, 0.21 mmol, 1.20 equiv). The resulting solution was stirred for 2 h at room temperature. The reaction was then quenched by the addition of water (20 mL). The resulting solution was extracted with ethyl acetate (20 mL×3) and the organic layers combined. The resulting mixture was washed with brine (10 mL×1). The solid was dried in an oven under reduced pressure. The crude product was purified by Prep-HPLC with the following conditions: Column: X Bridge C18, 19*150 mm, 5 um; Mobile Phase A: Water/10 mmol/L Ammonium bicarbonate Mobile Phase B: acetonitrile; Flow rate: 20 mL/min; Gradient: 30% B to 65% B in 8 min; 254 nm. This resulted in 12.5 mg (7%) of (2S,4R)-1-[(2S)-2-[6-[2-([4-[(3-chloro-4-fluorophenyl)amino]-6-[(2E)-4-(dimethylamino)but-2-enamido]quinazolin-7-yl]oxy)ethoxy]hexanamido]-3,3-dimethylbutanoyl]-4-hydroxy-N-[[4-(4-methyl-1,3-thiazol-5-yl)phenyl]methyl]pyrrolidine-2-carboxamide as a yellow solid. $^1$H NMR (300 MHz, CD$_3$OD) δ 8.92 (s, 1H), 8.83 (s, 1H), 8.45 (s, 1H), 8.01-7.99 (d, J=8.4 Hz, 1H), 7.70-7.60 (m, 1H), 7.43-7.36 (m, 4H), 7.25-7.19 (m, 2H), 7.02-6.97 (m, 1H), 6.50-6.45 (d, J=15.3 Hz, 1H), 4.58 (s, 1H), 4.52-4.47 (m, 3H), 4.39-4.33 (m, 3H), 3.93-3.92 (m, 2H), 3.90-3.83 (m, 1H), 3.82-3.70 (m, 1H), 3.60-3.56 (m, 2H), 3.20-3.18 (m, 2H), 2.42 (s, 3H), 2.29 (s, 6H), 2.29-2.12 (m, 3H), 2.10-2.00 (m, 1H), 1.65-1.60 (m, 4H), 1.38-1.29 (m, 2H), 0.97 (s, 9H); LC-MS (ES+): m/z 986.40 [MH+], $t_R$=0.82 min (3.0 minute run). Chemical formula: C$_{50}$H$_{61}$ClFN$_9$O$_7$S [985.41]

Synthesis of Example 66
(2S,4R)-1-((S)-2-(6-(4-(4-((4-((3-chloro-4-fluorophenyl)amino)-6-((E)-4-(dimethylamino)but-2-enamido)quinazolin-7-yl)oxy)butoxy)butoxy)hexanamido)-3,3-dimethylbutanoyl)-4-hydroxy-N-(4-(4-methylthiazol-5-yl)benzyl)pyrrolidine-2-carboxamide
5
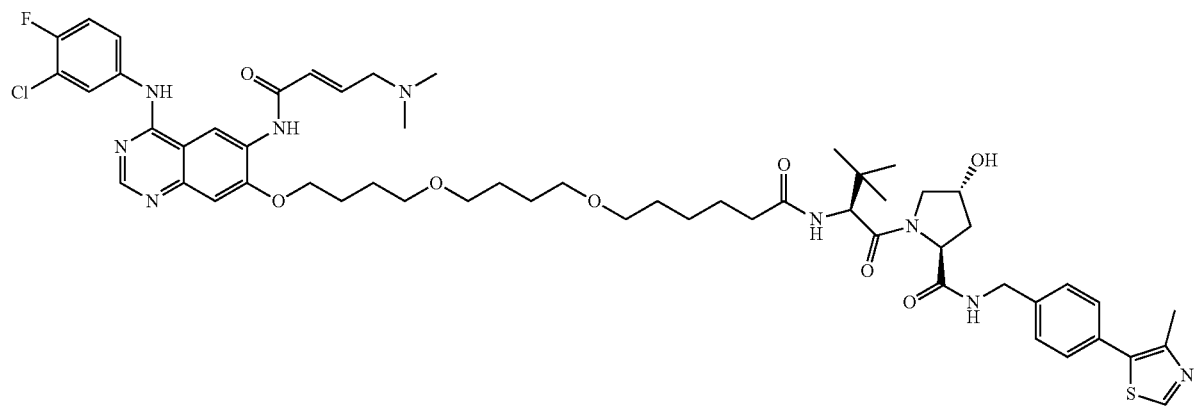 [SMILES: Cc1ncsc1-c1ccc(CNC(=O)[C@@H]2C[C@@H](O)CN2C(=O)[C@@H](NC(=O)CCCCCOCCCCOCCCCOc2cc3ncnc(Nc4ccc(F)c(Cl)c4)c3cc2NC(=O)/C=C/CN(C)C)C(C)(C)C)cc1]
Synthetic scheme:
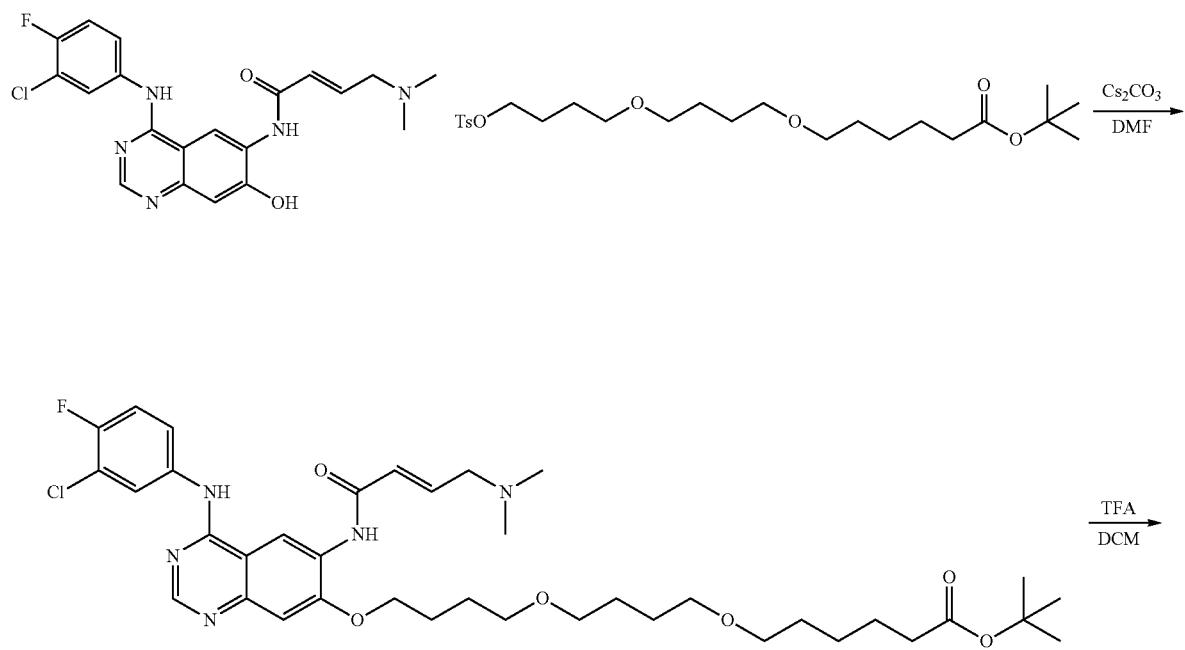

-continued

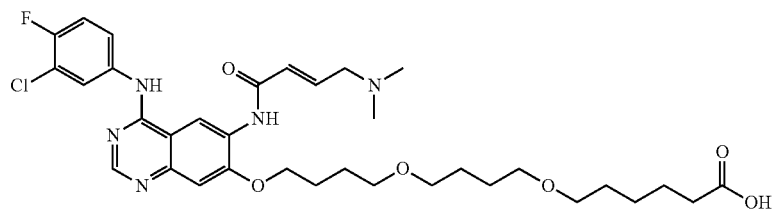
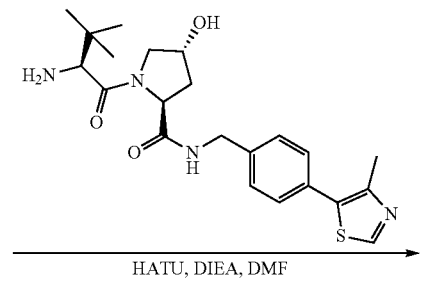

HATU, DIEA, DMF

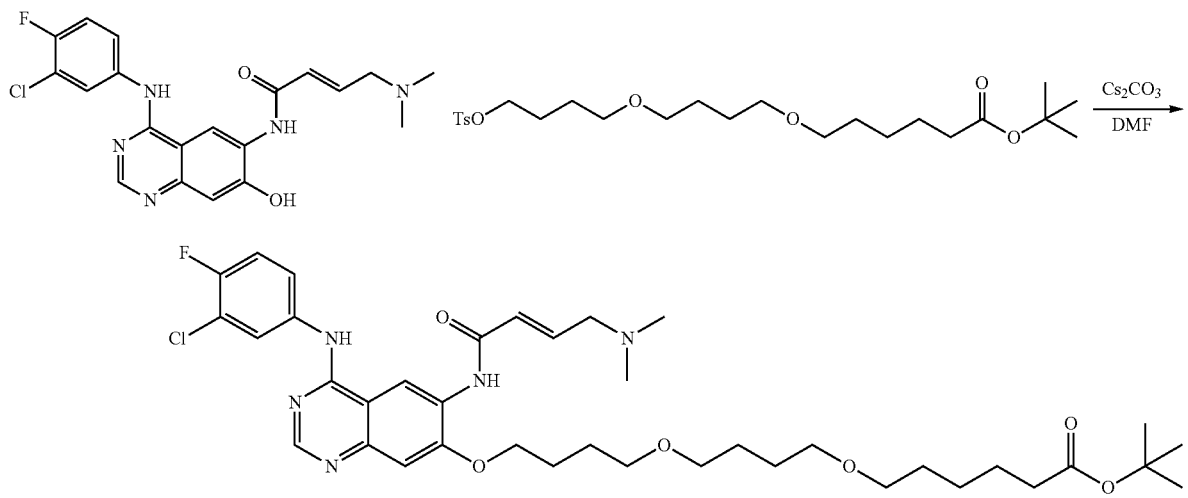

1. Step—Synthesis of tert-Butyl 6-[4-[4-([4-[(3-chloro-4-fluorophenyl)amino]-6-[(2E)-4-(dimethylamino)but-2-enamido]quinazolin-7-yl]oxy)butoxy]butoxy]hexanoate

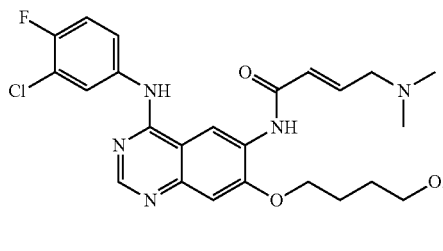
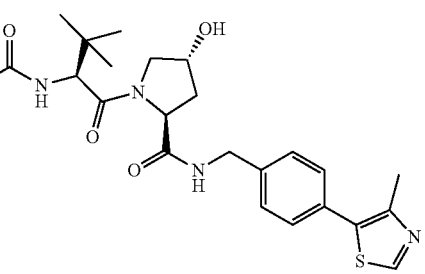

Into a 25 mL round-bottom flask, was placed a solution of (2E)-N-[4-[(3-chloro-4-fluorophenyl)amino]-7-hydroxyquinazolin-6-yl]-4-(dimethylamino)but-2-enamide (200.0 mg, 0.48 mmol, 1.00 equiv) in N,N-dimethylformamide (10 mL), cesium carbonate (314.0 mg, 0.96 mmol, 2.00 equiv), tert-butyl 6-(4-(4-(tosyloxy)butoxy)butoxy)hexanoate (281.0 mg, 1.20 equiv). The resulting solution was stirred for 12 h at 80° C. in an oil bath. The reaction was then quenched by the addition of water (20 mL). The resulting mixture was extracted with ethyl acetate (10 mL×3) and the organic layers were combined. The resulting mixture was washed with brine (10 mL). The mixture was dried over anhydrous sodium sulfate and concentrated under vacuum. The residue was applied onto a silica gel column eluted with dichloromethane/methanol (10:1). This resulted in 77.0 mg (22%) of tert-butyl 6-[4-[4-([4-[(3-chloro-4-fluorophenyl)amino]-6-[(2E)-4-(dimethylamino)but-2-enamido]quinazolin-7-yl]oxy)butoxy]butoxy]hexanoate as a brown solid. LC-MS (ES$^+$): m/z 730.31 [M+H]+

2. Step—Synthesis of 6-[4-[4-([4-[(3-Chloro-4-fluorophenyl)amino]-6-[(2E)-4-(dimethylamino)but-2-enamido]quinazolin-7-yl]oxy)butoxy]butoxy] hexanoic acid

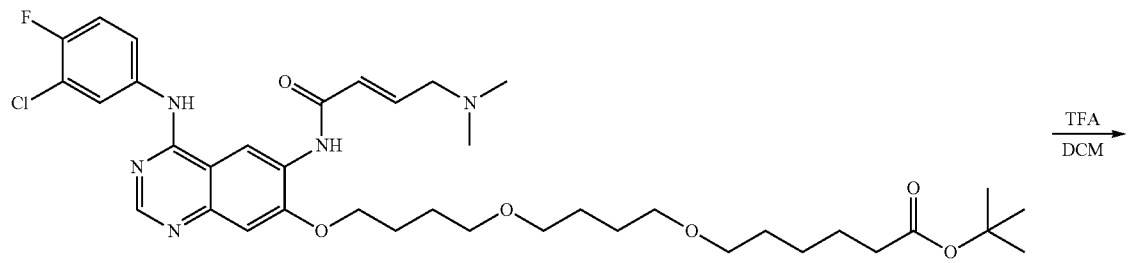

Into a 25 mL round-bottom flask, was placed a solution of tert-butyl 6-[4-[4-([4-[(3-chloro-4-fluorophenyl)amino]-6-[(2E)-4-(dimethylamino)but-2-enamido]quinazolin-7-yl]oxy)butoxy]butoxy]hexanoate (77.0 mg, 0.11 mmol, 1.00 equiv) in dichloromethane/trifluoroacetic acid (10/2 mL). The resulting solution was stirred for 2 h at room temperature. The resulting mixture was concentrated under vacuum. This resulted in 71.0 mg (100%) of 6-[4-[4-([4-[(3-chloro-4-fluorophenyl)amino]-6-[(2E)-4-(dimethylamino)but-2-enamido]quinazolin-7-yl]oxy)butoxy]butoxy]hexanoic acid as brown oil. LC-MS (ES+): m/z 674.30 [M+H]+

3. Step—Synthesis of (2S,4R)-1-[(2S)-2-(6-[4-[4-([4-[(3-chloro-4-fluorophenyl)amino]-6-[(2E)-4-(dimethylamino)but-2-enamido]quinazolin-7-yl]oxy)butoxy]butoxy]hexanamido)-3,3-dimethylbutanoyl]-4-hydroxy-N-[[4-(4-methyl-1,3-thiazol-5-yl)phenyl]methyl]pyrrolidine-2-carboxamide

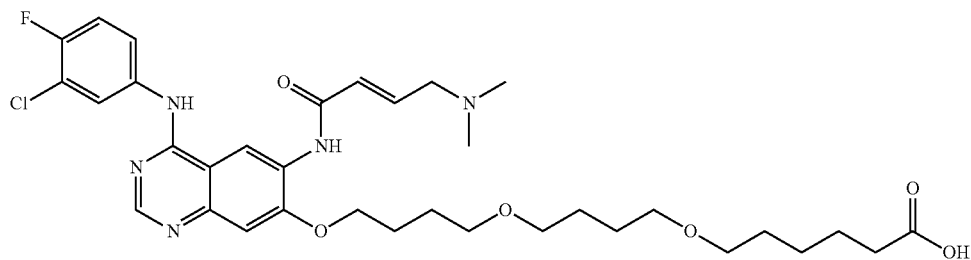

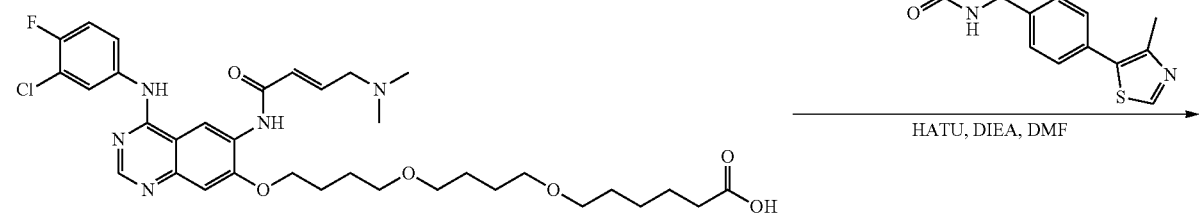

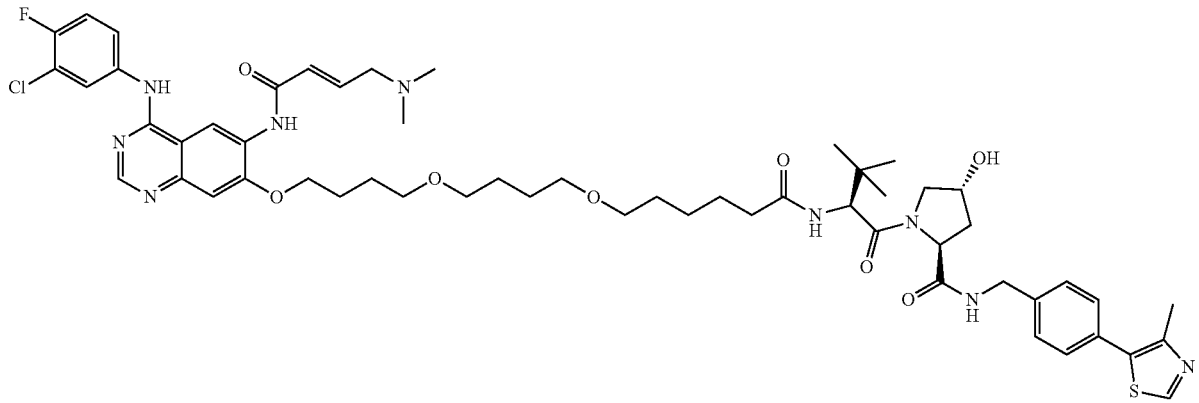

Into a 25 mL round-bottom flask under ice bath, was placed a solution of 6-[4-[4-([4-[(3-chloro-4-fluorophenyl)amino]-6-[(2E)-4-(dimethylamino)but-2-enamido]quinazolin-7-yl]oxy)butoxy]butoxy]hexanoic acid (71.0 mg, 0.11 mmol, 1.00 equiv) in N,N-dimethylformamide (10 mL), N-ethyl-N-isopropylpropan-2-amine (68.0 mg, 0.53 mmol, 5.00 equiv), o-(7-azabenzotriazol-1-yl)-N,N,N',N'-tetramethyluronium hexafluorophosphate (52.0 mg, 0.14 mmol, 1.30 equiv). The mixture was stirred for 20 min. To this was added (2S,4R)-1-[(2S)-2-amino-3,3-dimethylbutanoyl]-4-hydroxy-N-[4-(4-methyl-1,3-thiazol-5-yl)phenyl]methylpyrrolidine-2-carboxamide hydrochloride (64.0 mg, 1.30 equiv) at 0° C. The resulting solution was stirred for 2 h at room temperature. The resulting solution was extracted with ethyl acetate (10 mL×3) and the organic layers were combined. After washing with brine (10 mL), the mixture was dried over anhydrous sodium sulfate, filtered, and concentrated under vacuum. The residue was purified by prep-HPLC under the following condition: X Bridge RP18 column, 19×150 mm, 5 micron; Mobile Phase A: water/0.05% ammonium bicarbonate; Mobile Phase B: acetonitrile; Flow rate: 20 mL/min; Gradient: 38% B to 52% B in 15 min; Detector: 254 nm. This resulted in 27.0 mg (24%) of (2S,4R)-1-[(2S)-2-(6-[4-[4-([4-[(3-chloro-4-fluorophenyl)amino]-6-[(2E)-4-(dimethylamino)but-2-enamido]quinazolin-7-yl]oxy)butoxy]butoxy]hexanamido)-3,3-dimethylbutanoyl]-4-hydroxy-N-[[4-(4-methyl-1,3-thiazol-5-yl)phenyl]methyl]pyrrolidine-2-carboxamide as a white solid. 1H NMR (300 MHz, CD3OD): δ 8.88 (s, 1H), 8.49 (s, 1H), 8.04-8.02 (d, J=6.9 Hz, 1H), 7.75-7.65 (m, 1H), 7.47-7.41 (m, 4H), 7.38-7.26 (m, 2H), 7.05-7.00 (m, 1H), 6.55-6.50 (d, J=15.3 Hz, 1H), 4.63 (s, 1H), 4.56-4.49 (m, 3H), 4.37-4.30 (m, 3H), 3.92-3.78 (m, 2H), 3.57-3.53 (m, 2H), 3.47-3.46 (m, 2H), 3.46-3.40 (m, 4H), 3.24-3.21 (m, 2H), 2.47 (s, 3H), 2.32 (s, 6H), 2.30-2.23 (m, 3H), 2.08-2.01 (m, 3H), 1.84-1.82 (m, 2H), 1.61-1.52 (m, 8H), 1.38-1.25 (m, 2H), 1.00 (s, 9H); LC-MS (ES+): m/z 544.25 [(M+2H+)/2].

Synthesis of Example 70

2-(2,6-dioxopiperidin-3-yl)-5-(2-(2-(2-((1-isopropyl-6-((2-(4-methoxypiperidin-1-yl)pyrimidin-4-yl)amino)-1H-imidazo[4,5-c]pyridin-2-yl)methoxy)ethoxy)ethoxy)ethoxy)isoindoline-1,3-dione

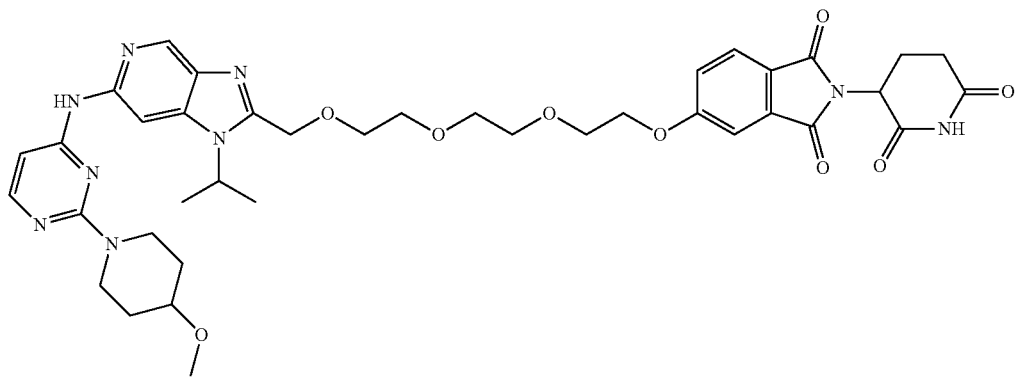 [SMILES: COC1CCN(c2nccc(Nc3cc4c(cn3)nc(COCCOCCOCCOc3ccc5c(c3)C(=O)N(C3CCC(=O)NC3=O)C5=O)n4C(C)C)n2)CC1]

Synthetic Scheme:
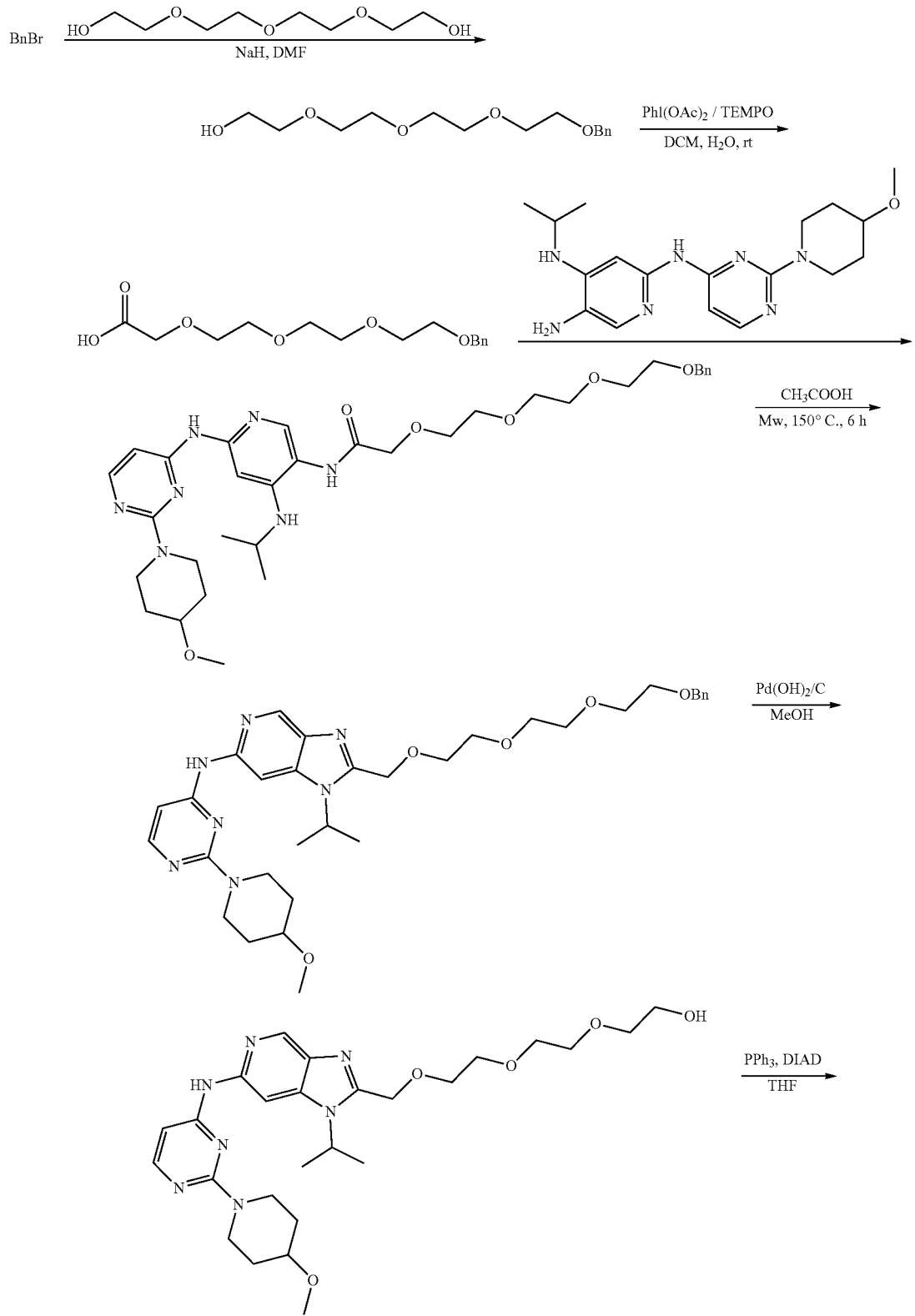

-continued

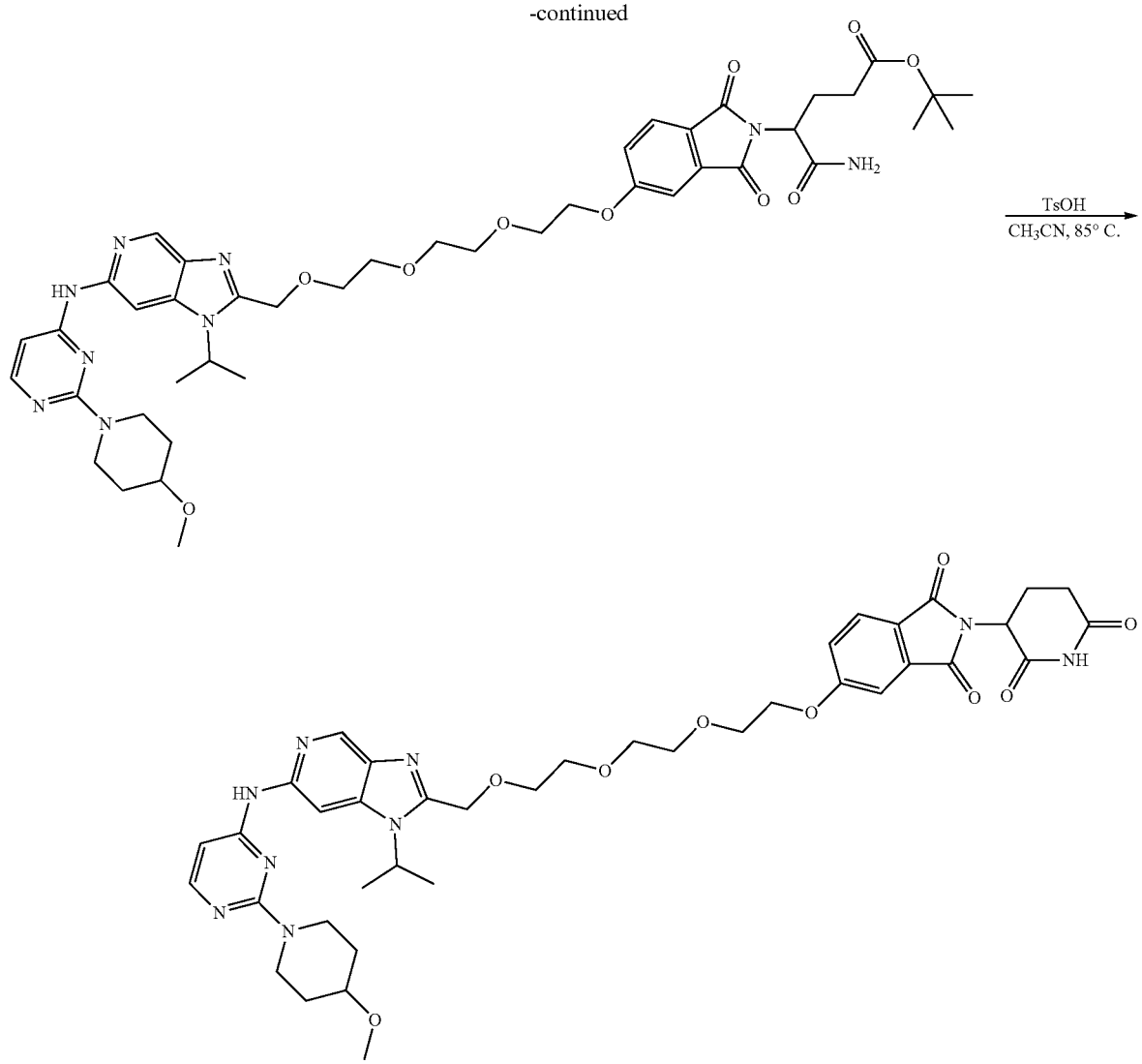

1. Step—Synthesis of
1-Phenyl-2,5,8,11-tetraoxatridecan-13-ol

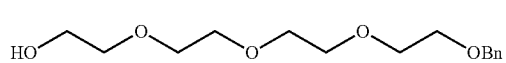 [SMILES: OCCOCCOCCOCCOCc1ccccc1]

To a solution of 3,6,9,12-tetraoxatetradecane-1,14-diol (45 g, 234 mmol) in DMF (100 mL), was added NaH (60%, 2.34 g, 58.5 mmol) at 0° C. After stirring at RT 1 h, BnBr (10 g, 58.5 mmol) was added and the mixture was heated to 60° C. for 3 h. Then the reaction mixture was quenched with water (100 mL) and the resulting reaction mixture was extracted with EtOAc (2×200 mL). The combined organic layers were washed with brine (100 mL), dried over $Na_2SO_4$ and filtered. The solvent was evaporated under reduced pressure. The residue was purified by column chromatography (hexane:EtOAc 1:3) to afford the desired product 1-Phenyl-2,5,8,11-tetraoxatridecan-13-ol (15 g, 52.8 mmol, 90%). $^1$H NMR (400 MHz, $CDCl_3$): δ 7.27-7.34 (m, 5H), 4.57 (s, 2H), 3.59-3.73 (m, 16H). Chemical Formula: $C_{15}H_{24}O_5$; Molecular Weight: 284.35

2. Step—Synthesis of
1-Phenyl-2,5,8,11-tetraoxatridecan-13-oic acid

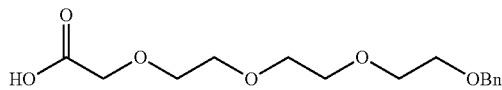 [SMILES: O=C(O)COCCOCCOCCOCc1ccccc1]

To a solution of 1-Phenyl-2,5,8,11-tetraoxatridecan-13-ol (6.3 g, 22.1 mmol) in DCM (60 mL) and $H_2O$ (30 mL) were added $PhI(OAc)_2$ (21.3 g, 66.3 mmol and TEMPO (689 mg, 4.42 mmol) subsequently at 0° C. The mixture was stirred at room temperature for 3 h. The reaction mixture was diluted with water (200 mL) and extracted with DCM. The organic layer was washed with brine, dried over $MgSO_4$, and concentrated in vacuo. The residue was purified by column chromatography (DCM:MeOH=20:1) to afford the desired product 1-Phenyl-2,5,8,11-tetraoxatridecan-13-oic acid (4.0 g, 13.4 mmol, 60.6%). $^1$H NMR (400 MHz, CDCl$_3$): δ 7.27-7.35 (m, 5H), 4.57 (s, 2H), 4.13 (s, 2H), 3.63-3.75 (m, 12H). Chemical Formula: C$_{15}$H$_{22}$O$_6$; Molecular Weight: 298.34

3. Step—Synthesis of N-(4-(Isopropylamino)-6-((2-(4-methoxypiperidin-1-yl)pyrimidin-4-yl)amino)pyridin-3-yl)-1-phenyl-2,5,8,11-tetraoxatridecan-13-amide

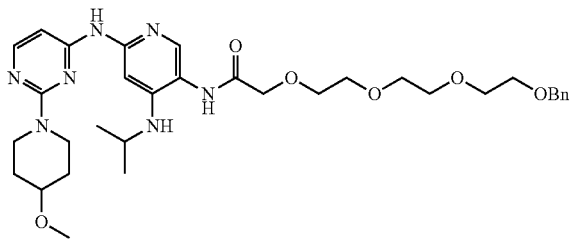 [SMILES: COC1CCN(c2nccc(Nc3cc(NC(C)C)c(NC(=O)COCCOCCOCCOCc4ccccc4)cn3)n2)CC1]

To a solution of 1-Phenyl-2,5,8,11-tetraoxatridecan-13-oic acid (1.05 g, 3.53 mmol), N$^4$-isopropyl-N$^2$-(2-(4-methoxypiperidin-1-yl)pyrimidin-4-yl)pyridine-2,4,5-triamine (1.05 g, 2.94 mmol, J. Med. Chem. 2015, 58, 8877-8895), Et$_3$N (742 mg, 7.35 mmol) and HOBt (595 mg, 4.41 mmol) in DCM (60 mL) was added EDCI (842 mg, 4.41 mol) at RT. The reaction mixture was stirred at rt for 2 h. Then the reaction mixture was diluted with water (20 mL) and the resulting reaction mixture was extracted with DCM (2×50 mL). The combined organic layers were washed with brine (100 mL), dried over Na$_2$SO$_4$ and filtered. The solvent was evaporated under reduced pressure. The residue was purified by column chromatography (DCM:MeOH=20:1) to afford the desired compound N-(4-(Isopropylamino)-6-((2-(4-methoxypiperidin-1-yl)pyrimidin-4-yl)amino)pyridin-3-yl)-1-phenyl-2,5,8,11-tetraoxatridecan-13-amide (1.4 g, 2.19 mmol, 74.8%). LC-MS: (ES$^+$): m/z 638.3 [M+H]. t$_R$=3.46 min. Chemical Formula: C$_{33}$H$_{47}$N$_7$O$_6$; Molecular Weight: 637.78

4. Step—Synthesis of 1-Isopropyl-N-(2-(4-methoxypiperidin-1-yl)pyrimidin-4-yl)-2-(12-phenyl-2,5,8,11-tetraoxadodecyl)-1H-imidazo[4,5-c]pyridin-6-amine

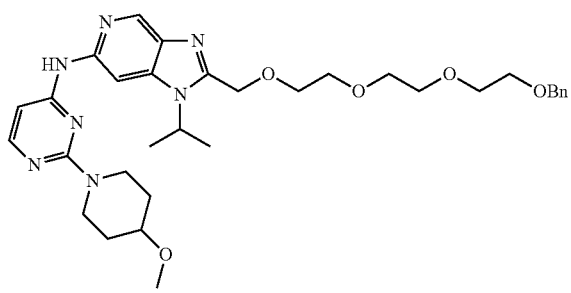 [SMILES: COC1CCN(c2nccc(Nc3cc4c(cn3)nc(COCCOCCOCCOCc3ccccc3)n4C(C)C)n2)CC1]

A solution of N-(4-(Isopropylamino)-6-((2-(4-methoxypiperidin-1-yl)pyrimidin-4-yl)amino)pyridin-3-yl)-1-phenyl-2,5,8,11-tetraoxatridecan-13-amide (1.4 g, 2.19 mmol) in HOAc (5 mL) was irradiated with microwave at 150° C. for 6 h. The solvent was removed in vacuo to afford crude desired product 1-Isopropyl-N-(2-(4-methoxypiperidin-1-yl)pyrimidin-4-yl)-2-(12-phenyl-2,5,8,11-tetraoxadodecyl)-1H-imidazo[4,5-c]pyridin-6-amine (1.4 g, crude), which was used into next reaction without further purification. LC-MS: (ES$^+$): m/z 620.3 [M+H]. t$_R$=3.24 min Chemical Formula: C$_{33}$H$_{45}$N$_7$O$_5$; Molecular Weight: 619.77.

5. Step—Synthesis of 2-(2-(2-((1-Isopropyl-6-((2-(4-methoxypiperidin-1-yl)pyrimidin-4-yl)amino)-1H-imidazo[4,5-c]pyridin-2-yl)methoxy)ethoxy)ethoxy)ethan-1-ol

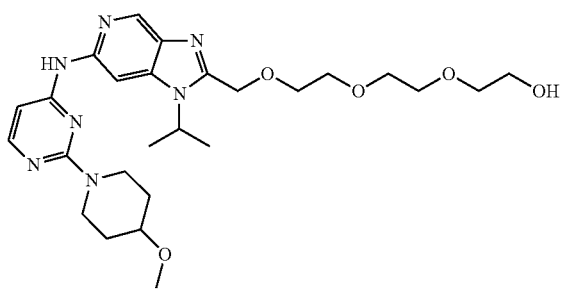 [SMILES: COC1CCN(c2nccc(Nc3cc4c(cn3)nc(COCCOCCOCCO)n4C(C)C)n2)CC1]

To a stirred solution of 1-Isopropyl-N-(2-(4-methoxypiperidin-1-yl)pyrimidin-4-yl)-2-(12-phenyl-2,5,8,11-tetraoxadodecyl)-1H-imidazo[4,5-c]pyridin-6-amine (1.2 g, crude) in methanol (50 mL) was added Pd(OH)$_2$/C (10%, 0.5 g) and cat. conc. HCl (0.1 mL). The mixture was stirred for 2 h under H$_2$ 1 atm. The mixture was filtered through a Celite pad, and the filtrate was concentrated. The residue was dissolved with DCM, and the mixture was washed with aq.NaHCO3, brine and dried with Na$_2$SO$_4$. The solvent was removed under vacuum to afford the desired compound 2-(2-(2-((1-Isopropyl-6-((2-(4-methoxypiperidin-1-yl)pyrimidin-4-yl)amino)-1H-imidazo[4,5-c]pyridin-2-yl)methoxy)ethoxy)ethoxy)ethan-1-ol (1.0 g, crude). LC-MS: (ES$^+$): m/z 530.3 [M+H]. t$_R$=2.59 min. Chemical Formula: C$_{26}$H$_{39}$N$_7$O$_5$; Molecular Weight: 529.64

6. Step—Synthesis of Tert-butyl 5-amino-4-(5-(2-(2-(2-((1-isopropyl-6-((2-(4-methoxypiperidin-1-yl)pyrimidin-4-yl)amino)-1H-imidazo[4,5-c]pyridin-2-yl)methoxy)ethoxy)ethoxy)ethoxy)-1,3-dioxoisoindolin-2-yl)-5-oxopentanoate

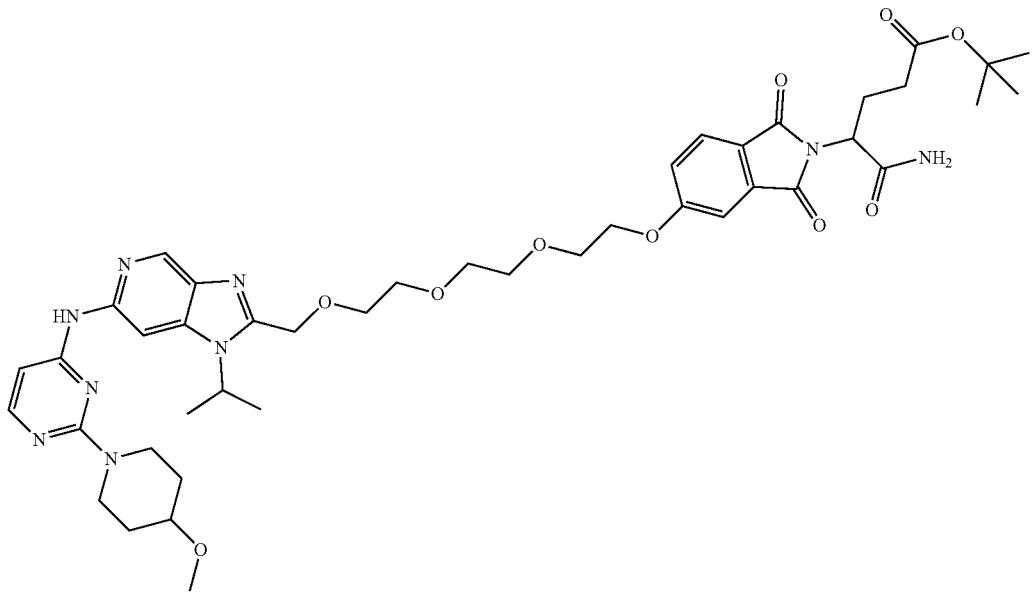 [SMILES: COC1CCN(c2nccc(Nc3cc4c(cn3)nc(COCCOCCOCCOc3ccc5c(c3)C(=O)N(C(CCC(=O)OC(C)(C)C)C(N)=O)C5=O)n4C(C)C)n2)CC1]

To a solution of 2-(2-(2-((1-Isopropyl-6-((2-(4-methoxypiperidin-1-yl)pyrimidin-4-yl)amino)-1H-imidazo[4,5-c]pyridin-2-yl)methoxy)ethoxy)ethoxy)ethan-1-ol (265 mg, 0.50 mmol), PPh$_3$ (655 mg, 2.5 mmol) and tert-butyl 5-amino-4-(5-hydroxy-1,3-dioxoisoindolin-2-yl)-5-oxopentanoate (175 mg, 0.50 mmol) in dry THF (10 mL) was added DIAD (505 mg, 2.5 mmol) dropwise at 0° C. under N$_2$. The mixture was stirred at room temperature for 1 h. Then the reaction mixture was diluted with water (50 mL) and extracted with DCM. The organic phase was washed with brine, dried over MgSO$_4$, and concentrated. The residue was purified by chromatography (silica gel, DCM: MeOH (50:1, v:v)) to afford the desired compound Tert-butyl 5-amino-4-(5-(2-(2-(2-((1-isopropyl-6-((2-(4-methoxypiperidin-1-yl)pyrimidin-4-yl)amino)-1H-imidazo[4,5-c]pyridin-2-yl)methoxy)ethoxy)ethoxy)ethoxy)-1,3-dioxoisoindolin-2-yl)-5-oxopentanoate (90 mg, crude). Chemical Formula: C43H57N9O10; Molecular Weight: 859.98

7. Step—Synthesis of 2-(2,6-Dioxopiperidin-3-yl)-5-(2-(2-(2-((1-isopropyl-6-((2-(4-methoxypiperidin-1-yl)pyrimidin-4-yl)amino)-1H-imidazo[4,5-c]pyridin-2-yl)methoxy)ethoxy)ethoxy)ethoxy)isoindoline-1,3-dione

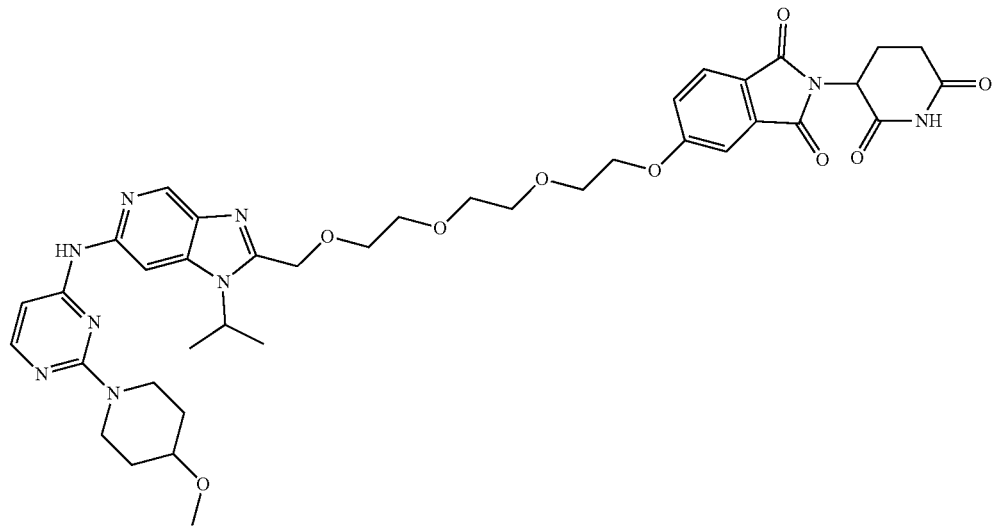 [SMILES: COC1CCN(c2nccc(Nc3cc4c(cn3)nc(COCCOCCOCCOc3ccc5c(c3)C(=O)N(C3CCC(=O)NC3=O)C5=O)n4C(C)C)n2)CC1]

To a solution of Tert-butyl 5-amino-4-(5-(2-(2-(2-((1-isopropyl-6-((2-(4-methoxypiperidin-1-yl)pyrimidin-4-yl)amino)-1H-imidazo [4,5-c]pyridin-2-yl)methoxy)ethoxy)ethoxy)-1,3-dioxoisoindolin-2-yl)-5-oxopentanoate (80 mg, 0.093 mmol) in $CH_3CN$ (5 mL) was added TsOH (62 mg, 0.36 mmol). The solution was stirred at 80° C. for 3 h. Then it was cooled to RT and quenched with aq NaHCO3. The mixture was taken up with DCM. The organic phase was washed with water (10 mL×2) and brine (10 mL). The organic layer was dried over anhydrous sodium sulfate, filtered and concentrated under vacuum. The residue was purified by silica gel column chromatography (DCM/MeOH=20/1) to afford 2-(2,6-dioxopiperidin-3-yl)-5-(2-(2-(2-((1-isopropyl-6-((2-(4-methoxypiperidin-1-yl)pyrimidin-4-yl)amino)-1H-imidazo [4,5-c]pyridin-2-yl)methoxy)ethoxy)ethoxy)ethoxy)isoindoline-1,3-dione (12 mg, 0.015 mmol, 16%). $^1$H NMR (400 MHz, $CDCl_3$): δ 12.59 (s, 1H), 8.65-8.71 (m, 3H), 8.12 (s, 1H), 7.72 (d, J=8.0 Hz, 1H), 7.32 (s, 1H), 7.17 (d, J=8.0 Hz, 1H), 6.60 (s, 1H), 5.30-5.31 (m, 1H), 4.94-4.96 (m, 2H), 4.24 (s, 2H), 3.87-4.03 (m, 2H), 3.72-3.85 (m, 4H), 3.60-3.82 (m, 10H), 3.39 (s, 3H), 2.71-2.92 (m, 3H), 2.09-2.11 (m, 1H), 1.86-2.00 (m, 2H), 1.75-1.86 (m, 2H), 1.66-1.68 (m, 6H). LC-MS: ($ES^+$): m/z 786.2 [M+H]. $t_R$=3.10 min Chemical Formula: $C_{39}H_{47}N_9O_9$; Molecular Weight: 785.86

Synthesis of Example 71

2-(2,6-dioxopiperidin-3-yl)-5-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)isoindoline-1,3-dione

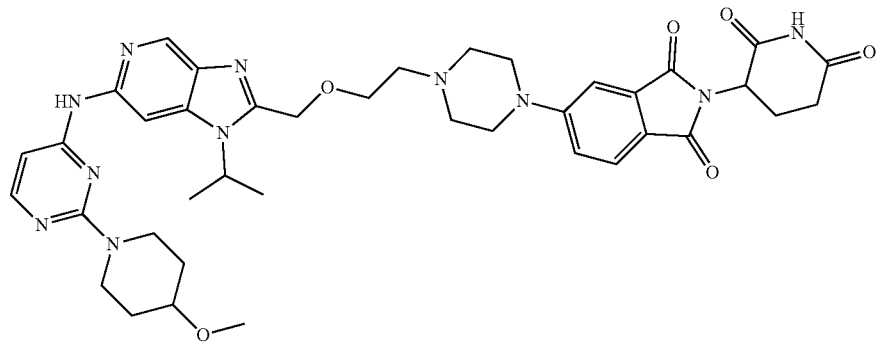 [SMILES: COC1CCN(c2nccc(Nc3cc4c(cn3)nc(COCCN3CCN(c5ccc6c(c5)C(=O)N(C5CCC(=O)NC5=O)C6=O)CC3)n4C(C)C)n2)CC1]

Synthesis Scheme - part 1:

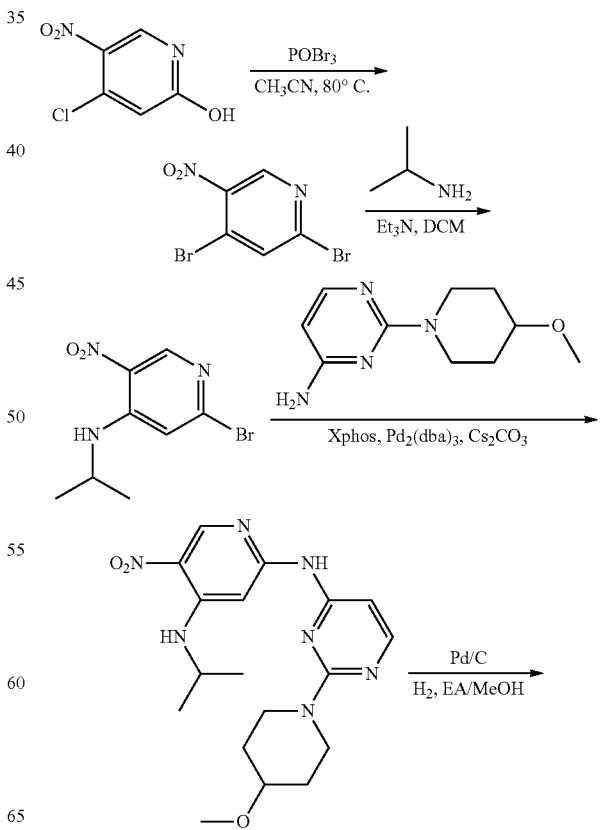

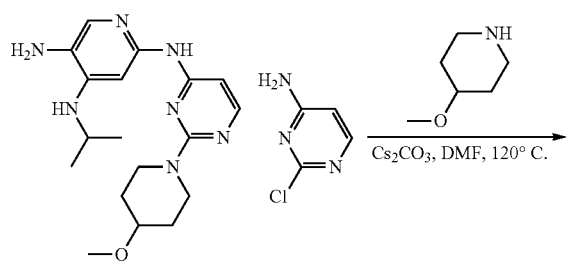
Experimental Section
N[4]-Isopropyl-N[2]-(2-(4-methoxypiperidin-1-yl)pyrimidin-4-yl)pyridine-2,4,5-triamine
was synthesized as described in J. Med. Chem. 2015, 58, 8877-8895.
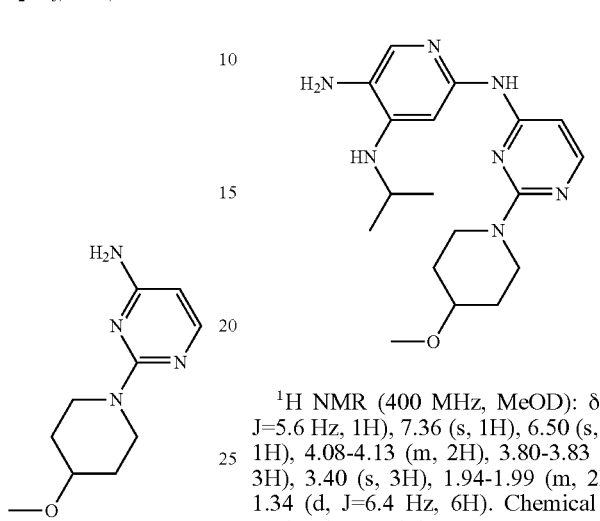
$^1$H NMR (400 MHz, MeOD): δ 8.56 (s, 1H), 8.06 (d, J=5.6 Hz, 1H), 7.36 (s, 1H), 6.50 (s, 1H), 6.13 (d, J=5.6 Hz, 1H), 4.08-4.13 (m, 2H), 3.80-3.83 (m, 1H), 3.41-3.53 (m, 3H), 3.40 (s, 3H), 1.94-1.99 (m, 2H), 1.55-1.60 (m, 2H), 1.34 (d, J=6.4 Hz, 6H). Chemical Formula: $C_{18}H_{27}N_7O$; Molecular Weight: 357.46 LC-MS: (ES$^+$): m/z 358.2 [M+H$^+$]. $t_R$=2.61 min.
Synthesis Scheme - part 2:
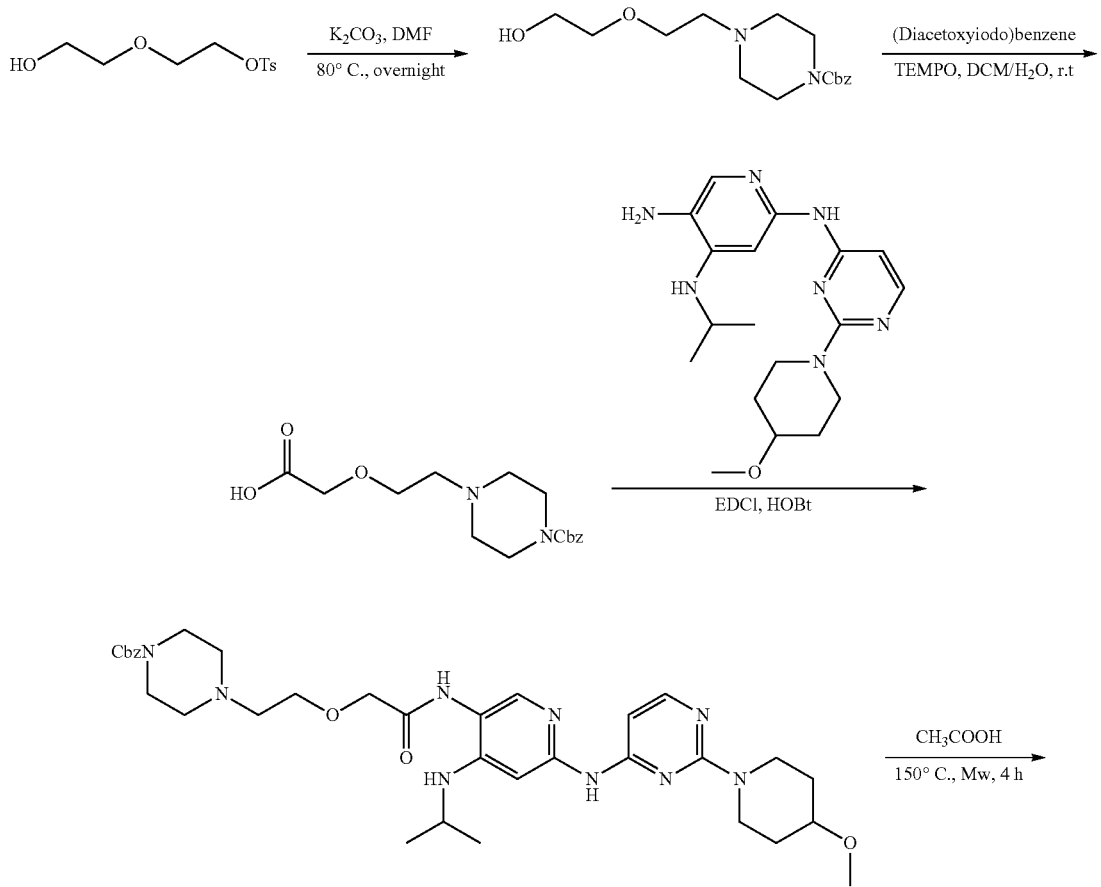

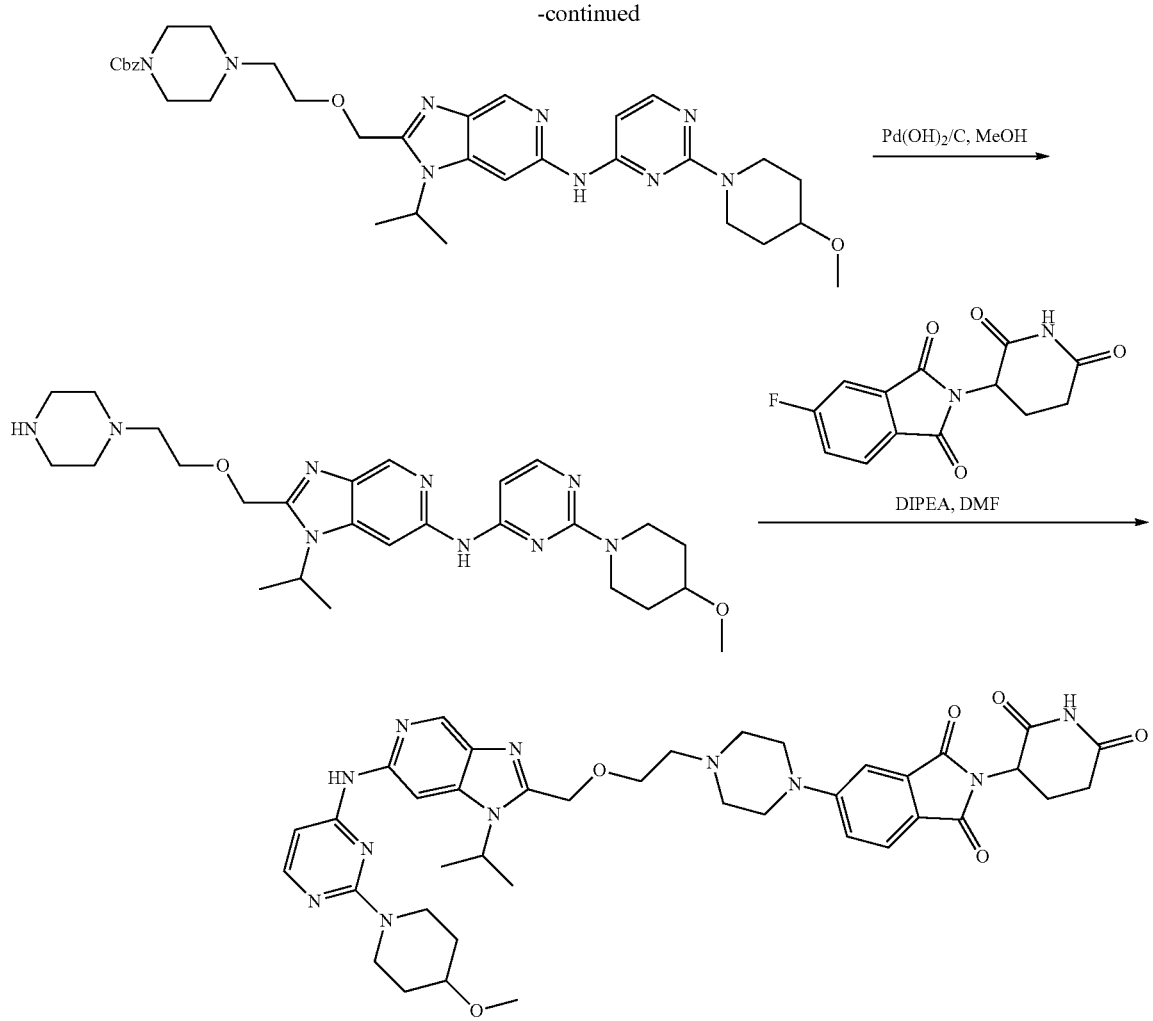

1. Step—Synthesis of Benzyl 4-(2-(2-hydroxy-ethoxy)ethyl)piperazine-1-carboxylate

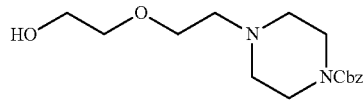 [SMILES: O=C(OCc1ccccc1)N1CCN(CCOCCO)CC1]

To a solution of 2-(2-hydroxyethoxy)ethyl 4-methylbenzenesulfonate (2.7 g, 10.4 mmol) and benzyl piperazine-1-carboxylate (2.3 g, 10.4 mmol) in DMF (10 mL) was added K$_2$CO$_3$ (2.86 g, 20.8 mmol). The solution was stirred at 80° C. overnight. The mixture was extracted with ethyl acetate (50 mL×2). The organic phase was washed with water (10 mL) and brine (8 mL). The organic layer was dried (Na$_2$SO$_4$), filtered and concentrated under reduced pressure to afford the crude Benzyl 4-(2-(2-hydroxyethoxy)ethyl)piperazine-1-carboxylate (4.5 g), which was used in the next reaction without further purification.

2. Step—Synthesis of 2-(2-(4-((Benzyloxy)carbonyl)piperazin-1-yl)ethoxy)acetic acid

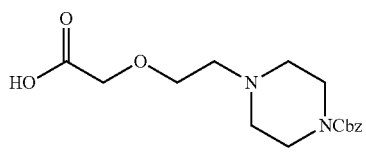 [SMILES: O=C(O)COCCN1CCN(C(=O)OCc2ccccc2)CC1]

To a solution of Benzyl 4-(2-(2-hydroxyethoxy)ethyl)piperazine-1-carboxylate (3.5 g, 11.4 mmol) and (Diacetoxyiodo)benzene (11.0 g, 34.2 mmol) in DCM (70 mL) and water (35 ml) was added TEMPO (350 mg, 2.2 mmol). The solution was stirred at rt for 4 h. The mixture was quenched with saturated Na$_2$S$_2$O$_3$ and stirred for 20 min. The mixture was extracted with DCM (50 mL×2). The combined organic phases were washed with water (10 mL) and brine (8 mL). The organic phase was dried (Na$_2$SO$_4$), filtered and concentrated under reduced pressure. The residue was purified by silica gel column chromatography to afford 2-(2-(4-((Benzyloxy)carbonyl)piperazin-1-yl)ethoxy)acetic acid (300 mg, 0.93 mmol, 8.2% yield).

3. Step—Synthesis of Benzyl 4-(2-(2-((4-(isopropylamino)-6-((2-(4-methoxypiperidin-1-yl)pyrimidin-4-yl)amino)pyridin-3-yl)amino)-2-oxoethoxy)ethyl)piperazine-1-carboxylate

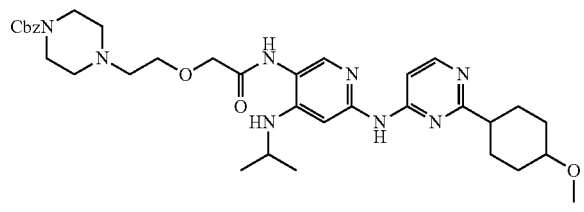 [SMILES: COC1CCC(c2nccc(Nc3cc(NC(C)C)c(NC(=O)COCCN4CCN(C(=O)OCc5ccccc5)CC4)cn3)n2)CC1]

To a solution of 2-(2-(4-((Benzyloxy)carbonyl)piperazin-1-yl)ethoxy)acetic acid (300 mg, 0.93 mmol) and $N^4$-isopropyl-$N^2$-(2-(4-methoxypiperidin-1-yl)pyrimidin-4-yl)pyridine-2,4,5-triamine (365 mg, 1.02 mmol) [J. Med. Chem. 2015, 58, 8877-8895] in DCM (15 mL) were added EDCI (231 mg, 1.2 mmol), HOBt (162 mg, 1.2 mmol) and Et$_3$N (151 mg, 1.5 mmol). The solution was stirred at RT overnight and then diluted with DCM (50 mL). The mixture was washed with water (10 ml) and brine (8 ml). The organic layer was dried (Na$_2$SO$_4$), filtered and concentrated under reduced pressure. The residue was purified by silica gel column chromatography to afford Benzyl 4-(2-(2-((4-(isopropylamino)-6-((2-(4-methoxypiperidin-1-yl)pyrimidin-4-yl)amino)pyridin-3-yl)amino)-2-oxoethoxy)ethyl)piperazine-1-carboxylate (380 mg, 0.57 mmol, 61.3% yield). Chemical Formula: C$_{34}$H$_{47}$N$_9$O$_5$; Molecular Weight: 661.81 LC-MS: (ES$^+$): m/z 662.3 [M+H$^+$]. t$_R$=2.74 min 4. Step—Synthesis of Benzyl 4-(2-((1-isopropyl-6-((2-(4-methoxypiperidin-1-yl)pyrimidin-4-yl)amino)-1H-imidazo[4,5-c]pyridin-2-yl)methoxy)ethyl)piperazine-1-carboxylate

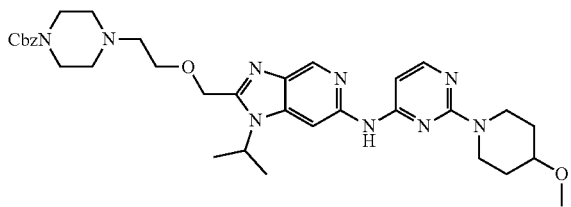 [SMILES: COC1CCN(c2nccc(Nc3cc4c(cn3)nc(COCCN3CCN(C(=O)OCc5ccccc5)CC3)n4C(C)C)n2)CC1]

A solution of Benzyl 4-(2-(2-((4-(isopropylamino)-6-((2-(4-methoxypiperidin-1-yl)pyrimidin-4-yl)amino)pyridin-3-yl)amino)-2-oxoethoxy)ethyl)piperazine-1-carboxylate (380 mg, 0.57 mmol) in CH$_3$COOH (8 mL) was irradiated by microwave at 150° C. for 6 h under nitrogen atmosphere. The mixture was concentrated under reduced pressure to afford the crude Benzyl 4-(2-((1-isopropyl-6-((2-(4-methoxypiperidin-1-yl)pyrimidin-4-yl)amino)-1H-imidazo[4,5-c]pyridin-2-yl)methoxy)ethyl)piperazine-1-carboxylate (400 mg), which was used into the next reaction without further purification. Chemical Formula: C$_{34}$H$_{45}$N$_9$O$_4$; Molecular Weight: 643.79 LC-MS: (ES$^+$): m/z 645.3 [M+H$^+$]. t$_R$=2.75 min.

5. Step—Synthesis of 1-Isopropyl-N-(2-(4-methoxypiperidin-1-yl)pyrimidin-4-yl)-2-((2-(piperazin-1-yl)ethoxy)methyl)-1H-imidazo[4,5-c]pyridin-6-amine

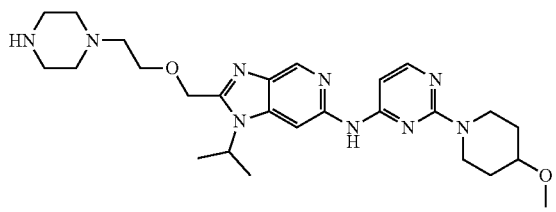 [SMILES: COC1CCN(c2nccc(Nc3cc4c(cn3)nc(COCCN3CCNCC3)n4C(C)C)n2)CC1]

To a solution of crude Benzyl 4-(2-((1-isopropyl-6-((2-(4-methoxypiperidin-1-yl)pyrimidin-4-yl)amino)-1H-imidazo [4,5-c]pyridin-2-yl)methoxy)ethyl)piperazine-1-carboxylate (150 mg, crude) in methanol (12 mL) were added Pd(OH)$_2$ (10%, 70 mg) and conc. HCl (0.01 mL). The mixture was stirred for 2 h under H$_2$ atmosphere. The mixture was filtered through Celite, and the filtrate was concentrated under reduced pressure to afford crude 1-Isopropyl-N-(2-(4-methoxypiperidin-1-yl)pyrimidin-4-yl)-2-((2-(piperazin-1-yl)ethoxy)methyl)-1H-imidazo[4,5-c]pyridin-6-amine (120 mg), which was used into the next reaction without further purification. LC-MS: (ES$^+$): m/z 510.3 [M+H]$^+$. t$_R$=2.31 min. Chemical Formula: C$_{26}$H$_{39}$N$_9$O$_2$; Molecular Weight: 509.66

6. Step—Synthesis of 2-(2,6-Dioxopiperidin-3-yl)-5-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)isoindoline-1,3-dione

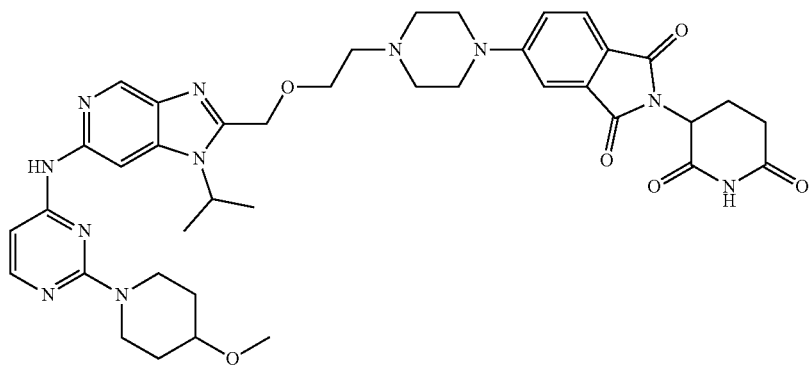 [SMILES: COC1CCN(c2nccc(Nc3cc4c(cn3)nc(COCCN3CCN(c5ccc6c(c5)C(=O)N(C5CCC(=O)NC5=O)C6=O)CC3)n4C(C)C)n2)CC1]

To a solution of 1-Isopropyl-N-(2-(4-methoxypiperidin-1-yl)pyrimidin-4-yl)-2-((2-(piperazin-1-yl)ethoxy)methyl)-1H-imidazo[4,5-c]pyridin-6-amine (110 mg, 0.21 mmol) and 2-(2,6-dioxopiperidin-3-yl)-5-fluoroisoindoline-1,3-dione (80 mg, 0.65 mmol) in NMP (8 mL) was added DIPEA (140 mg, 0.11 mmol). The solution was irradiated by microwave at 150° C. for 15 min under nitrogen atmosphere. The mixture was concentrated under reduced pressure. The residue was purified by silica gel column chromatography to afford the crude desired product, and it was further purified by prep-TLC to afford 2-(2,6-Dioxopiperidin-3-yl)-5-(4-(2-((1-isopropyl-6-((2-(4-methoxypiperidin-1-yl)pyrimidin-4-yl)amino)-1H-imidazo [4,5-c]pyridin-2-yl)methoxy)ethyl)piperazin-1-yl)isoindoline-1,3-dione (20 mg, 0.026 mmol, 12.4% yield). $^1$H NMR (400 MHz, DMSO): δ 11.06 (s, 1H), 9.77 (s, 1H), 8.64 (s, 1H), 8.45 (s, 1H), 7.97 (d, J=6.4 Hz, 1H), 7.67 (d, J=8.4 Hz, 1H), 7.33 (s, 1H), 7.22 (d, J=8.4 Hz, 1H), 6.42 (d, J=6.0 Hz, 1H), 5.05-5.09 (m, 1H), 4.90-4.93 (m, 1H), 4.79 (s, 2H), 4.21-4.24 (m, 1H), 3.65 (s, 2H), 3.30-3.50 (m, 11H), 2.82-2.92 (m, 1H), 2.51-2.55 (m, 7H), 2.00-2.09 (m, 1H), 1.85-1.95 (m, 2H), 1.60 (d, J=6.8 Hz, 6H), 1.44-1.46 (m, 2H). Chemical Formula: $C_{39}H_{47}N_{11}O_6$; Molecular Weight: 765.88 LC-MS: (ES$^+$): m/z 766.3 [M+H]$^+$. $t_R$=2.67 min Synthesis of Example 76

2-(2,6-dioxopiperidin-3-yl)-5-(2-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)ethoxy)isoindoline-1,3-dione

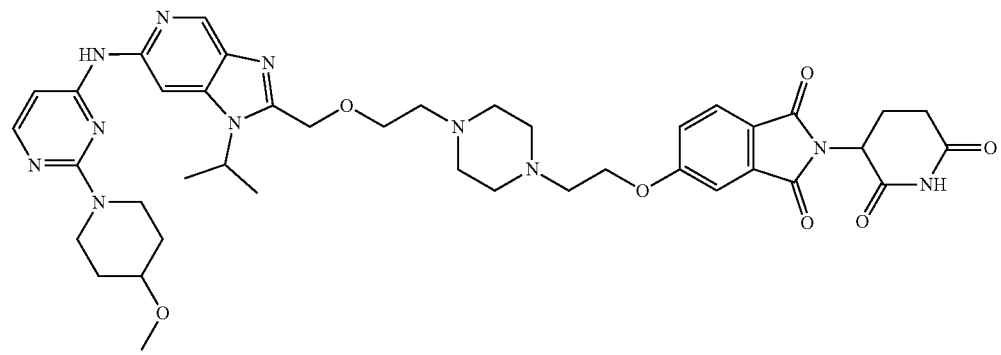 [SMILES: COC1CCN(c2nccc(Nc3cc4c(cn3)nc(COCCN3CCN(CCOc5ccc6c(c5)C(=O)N(C5CCC(=O)NC5=O)C6=O)CC3)n4C(C)C)n2)CC1]

Synthesis Scheme:

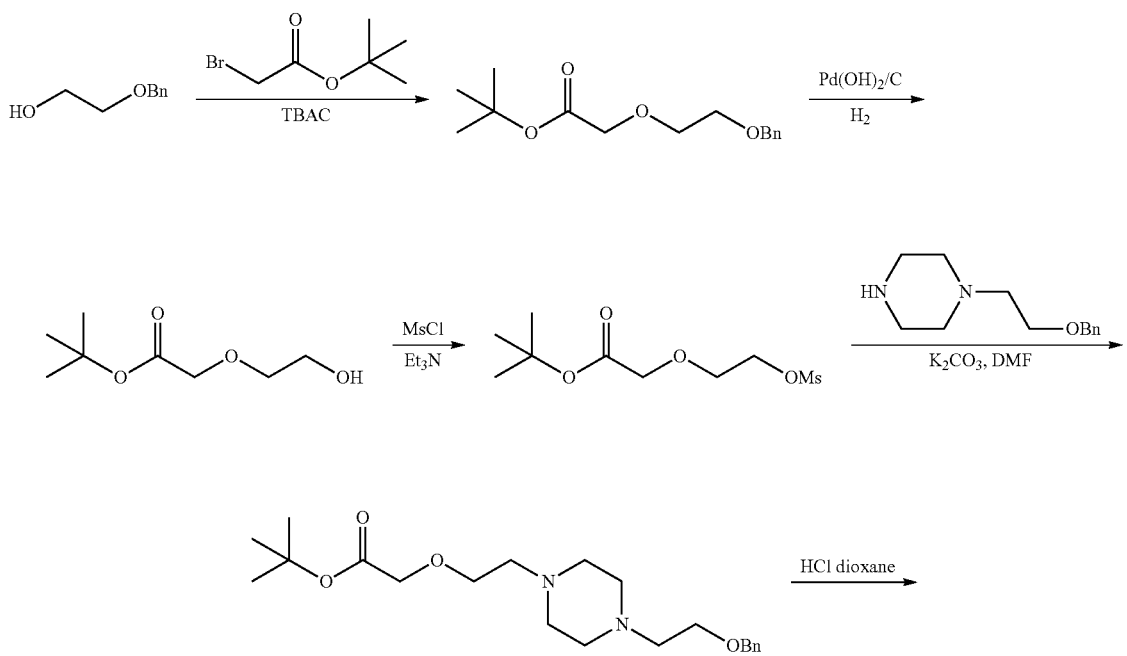

-continued
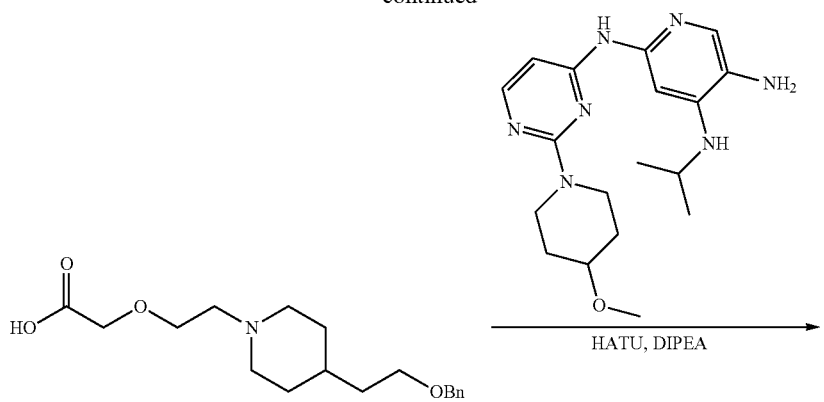
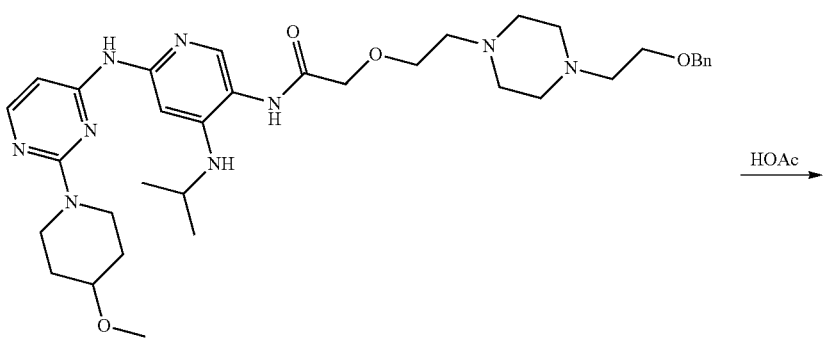
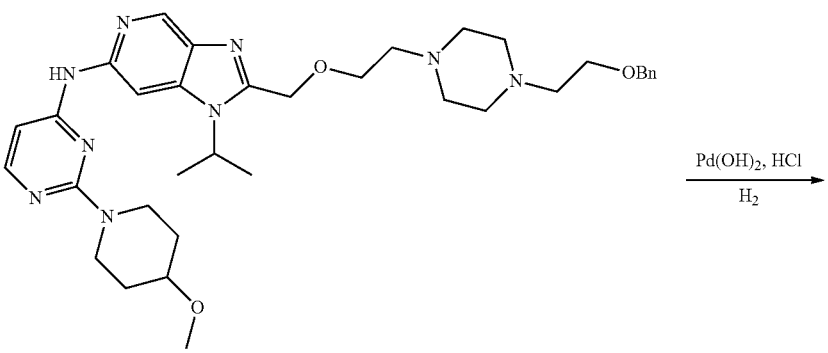
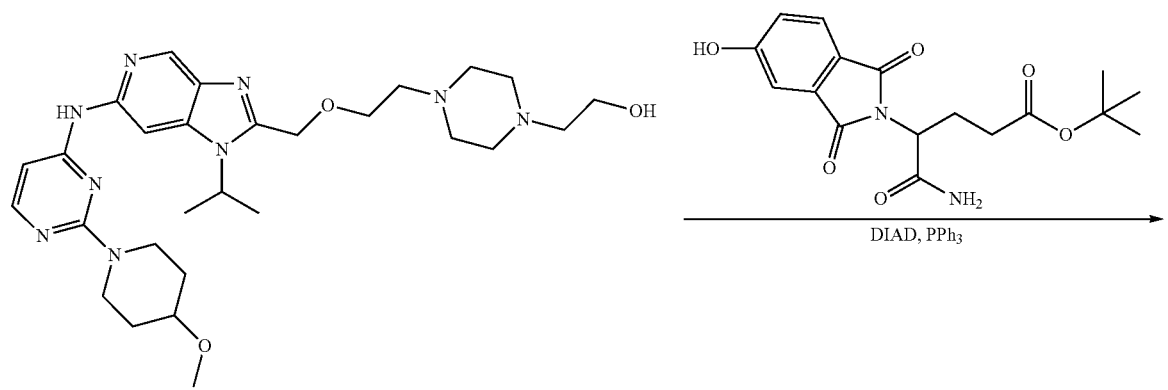

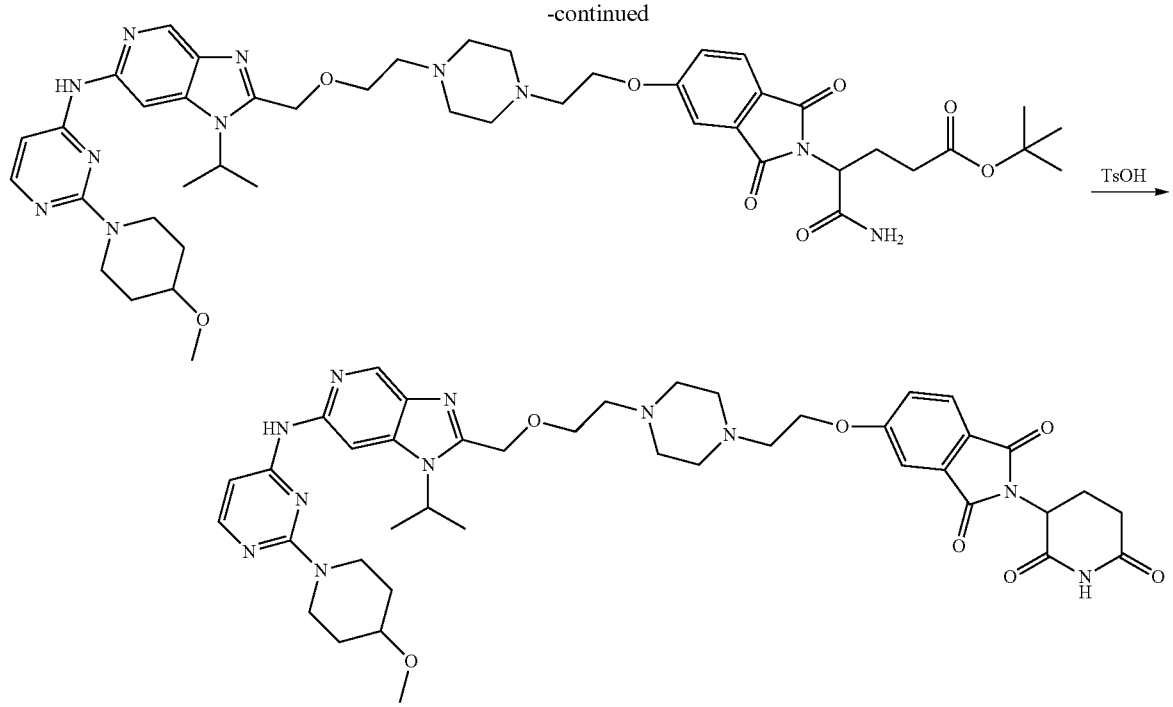

Experimental Section

1. Step—Synthesis of Tert-butyl 2-(2-(benzyloxy)ethoxy)acetate

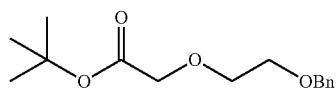 [SMILES: CC(C)(C)OC(=O)COCCOCc1ccccc1]

To a solution of 2-(benzyloxy)ethanol (10.0 g, 0.07 mol) in DCM (150 mL) were added tert-butyl 2-bromoacetate (51.0 g, 0.26 mol), TBACl (18.4 g, 0.07 mol) and 37% NaOH (15 mL) subsequently. The resulting solution was stirred at r.t. overnight. After the reaction was quenched with water (200 mL), the mixture was extracted with DCM (2×200 mL). The combined organic layers were washed with brine (100 mL), dried over $Na_2SO_4$ and filtered. The solvent was removed under reduced pressure. The residue was purified by column chromatography (DCM:MeOH=20:1) to afford the desired product tert-butyl 2-(2-(benzyloxy)ethoxy)acetate (1.5 g, 5.60 mmol, 9%) as colorless oil.

Chemical Formula: $C_{15}H_{22}O_4$; Molecular Weight: 266.33

2. Step—Synthesis of Tert-butyl 2-(2-hydroxyethoxy)acetate

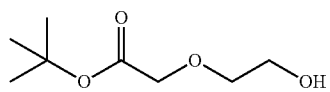

To a solution of product tert-butyl 2-(2-(benzyloxy) ethoxy)acetate (1.50 g, 5.60 mmol) in MeOH (10 mL) was added $Pd(OH)_2/C$ (20%, 0.50 g). The mixture was stirred at room temperature for 4 h under $H_2$ at 1 atm. The reaction mixture was filtered and concentrated in vacuo to afford the desired product Tert-butyl 2-(2-hydroxyethoxy)acetate (1.65 g, crude) as colorless oil. Chemical Formula: $C_8H_{16}O_4$; Molecular Weight: 176.21

3. Step Synthesis of Tert-butyl 2-(2-((methylsulfonyl)oxy)ethoxy)acetate

To a solution of Tert-butyl 2-(2-hydroxyethoxy)acetate (1 g, 5.68 mmol) in DCM and $Et_3N$ (1.15 g, 11.36 mmol) at 0° C., MsCl (0.98 g, 8.52 mmol) was added. The reaction mixture was stirred at r.t for 1 h. Then the reaction mixture was diluted with 20 mL water and the resulting reaction mixture was extracted with DCM (2×50 mL). The combined organic layers were washed with brine (1×100 mL), dried over $Na_2SO_4$ and filtered. The solvent was removed under reduced pressure to afford the desired product Tert-butyl 2-(2-((methylsulfonyl)oxy)ethoxy)acetate (1.46 g, 5.75 mmol, crude) as colorless oil.

$^1$H NMR (400 MHz, $CDCl_3$): δ 4.44 (t, J=4.4 Hz, 2H), 4.05 (s, 2H), 3.85 (t, J=4.4 Hz, 2H), 3.12 (s, 3H), 1.50 (s, 9H). Chemical Formula: $C_9H_{18}O_6S$; Molecular Weight: 254.30

4. Step—Synthesis of Tert-butyl 2-(2-(4-(2-(benzyloxy)ethyl)piperazin-1-yl)ethoxy)acetate

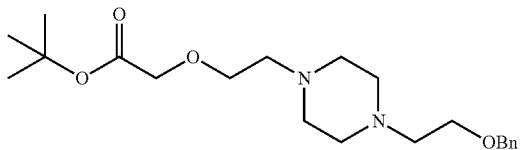 [SMILES: CC(C)(C)OC(=O)COCCN1CCN(CCOCc2ccccc2)CC1]

A mixture of Tert-butyl 2-(2-((methylsulfonyl)oxy)ethoxy)acetate (1.46 g, 5.68 mmol), 1-(2-(benzyloxy)ethyl)piperazine (1.62 g, 7.38 mmol) and K$_2$CO$_3$ (3.14 g, 22.70 mmol) in DMF (10 mL) was heated to 80° C. overnight. After cooling to rt, the reaction was quenched with water (20 mL), and the mixture was extracted with DCM (2×50 mL). The combined organic layers were washed with brine (100 mL), dried over Na$_2$SO$_4$ and filtered. The solvent was removed under reduced pressure to afford the desired compound Tert-butyl 2-(2-(4-(2-(benzyloxy)ethyl)piperazin-1-yl)ethoxy)acetate (1.0 g, 2.65 mmol, crude) as colorless oil.

$^1$H NMR (400 MHz, CDCl$_3$): δ 7.35-7.28 (m, 5H), 4.55 (s, 2H), 4.00 (s, 2H), 3.68 (t, J=5.6 Hz, 2H), 3.61 (t, J=5.6 Hz, 2H), 2.65-2.58 (m, 12H), 1.50 (s, 9H). Chemical Formula: C$_{21}$H$_{34}$N$_2$O$_4$; Molecular Weight: 378.51

5. Step—Synthesis of 2-(2-(4-(2-(Benzyloxy)ethyl)piperazin-1-yl)ethoxy)acetic acid

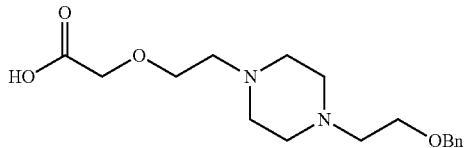 [SMILES: O=C(O)COCCN1CCN(CCOCc2ccccc2)CC1]

A solution of tert-butyl 2-(2-(4-(2-(benzyloxy)ethyl)piperazin-1-yl)ethoxy)acetate (1 g, 2.65 mmol) in HCl/dioxane (4.0 M, 5 mL) was stirred at r.t. for 3 hours. The solvent was removed under reduced pressure to afford the desired compound 2-(2-(4-(2-(Benzyloxy)ethyl)piperazin-1-yl)ethoxy)acetic acid (0.97 g, 3.01 mmol, crude) as colorless oil. Chemical Formula: C$_{17}$H$_{26}$N$_2$O$_4$; Molecular Weight: 322.40

6. Step—Synthesis of 2-(2-(4-(2-(Benzyloxy)ethyl)piperazin-1-yl)ethoxy)-N-(4-(isopropylamino)-6-((2-(4-methoxypiperidin-1-yl)pyrimidin-4-yl)amino)pyridin-3-yl)acetamide

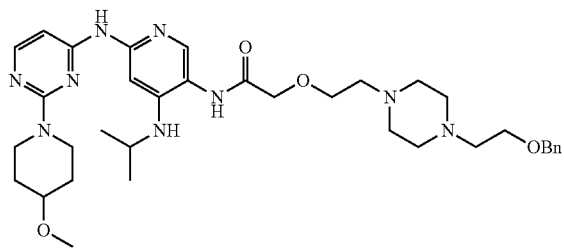 [SMILES: COC1CCN(c2nccc(Nc3cc(NC(C)C)c(NC(=O)COCCN4CCN(CCOCc5ccccc5)CC4)cn3)n2)CC1]

To a solution of 2-(2-(4-(2-(Benzyloxy)ethyl)piperazin-1-yl)ethoxy)acetic acid (0.97 g, 3.01 mmol), N$^4$-isopropyl-N$^2$-(2-(4-methoxypiperidin-1-yl)pyrimidin-4-yl)pyridine-2,4,5-triamine [J. Med. Chem. 2015, 58, 8877-8895] (0.9 g, 2.50 mmol), and DIPEA (0.65 g, 5.01 mmol) in DCM (60 mL) was added HATU (1.9 g, 5.01 mmol). The resulting solution was stirred at r.t. for 2 h. The reaction mixture was quenched with water (20 mL), and the mixture was extracted with DCM (2×50 mL). The combined organic layers were washed with brine (100 mL), dried over Na$_2$SO$_4$ and filtered. The solvent was evaporated under reduced pressure. The residue was purified by column chromatography (DCM:MeOH=20:1) to afford the desired compound 2-(2-(4-(2-(Benzyloxy)ethyl)piperazin-1-yl)ethoxy)-N-(4-(isopropylamino)-6-((2-(4-methoxypiperidin-1-yl)pyrimidin-4-yl)amino)pyridin-3-yl)acetamide (0.63 g, 0.95 mmol, crude) as red solid.

7. Step—Synthesis of 2-((2-(4-(2-(Benzyloxy)ethyl)piperazin-1-yl)ethoxy)methyl)-1-isopropyl-N-(2-(4-methoxypiperidin-1-yl)pyrimidin-4-yl)-1H-imidazo[4,5-c]pyridin-6-amine

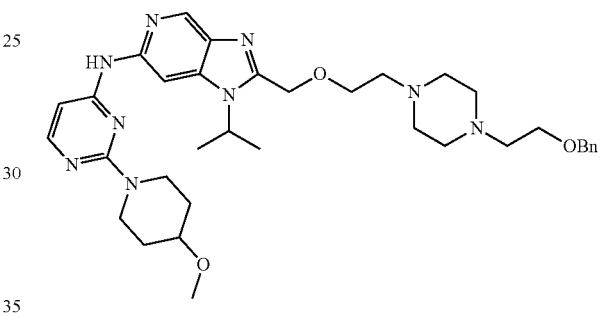

A solution of 2-(2-(4-(2-(Benzyloxy)ethyl)piperazin-1-yl)ethoxy)-N-(4-(isopropylamino)-6-((2-(4-methoxypiperidin-1-yl)pyrimidin-4-yl)amino)pyridin-3-yl)acetamide (0.63 g, 0.95 mmol) in AcOH (5 mL) was irradiated to 150° C. with microwave for 6 h. After cooling to rt, the solvent was removed in vacuo to afford the desired product 2-((2-(4-(2-(Benzyloxy)ethyl)piperazin-1-yl)ethoxy)methyl)-1-isopropyl-N-(2-(4-methoxypiperidin-1-yl)pyrimidin-4-yl)-1H-imidazo[4,5-c]pyridin-6-amine (1.0 g, 1.56 mmol, crude) as red oil. LC-MS: (ES$^+$): m/z 644.4 [M+H]. t$_R$=2.749 min. Chemical Formula: C$_{35}$H$_{49}$N$_9$O$_3$; Molecular Weight: 643.82

8. Step—Synthesis of 2-(4-(2-((1-Isopropyl-6-((2-(4-methoxypiperidin-1-yl)pyrimidin-4-yl)amino)-1H-imidazo[4,5-c]pyridin-2-yl)methoxy)ethyl)piperazin-1-yl)ethanol

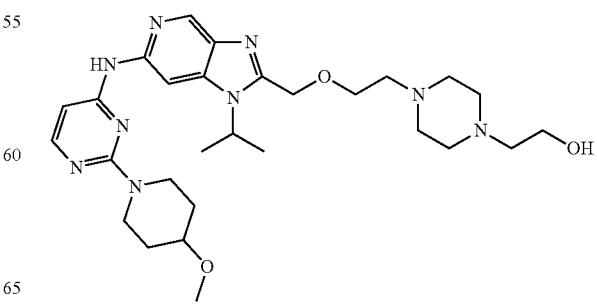

To a solution of 2-((2-(4-(2-(Benzyloxy)ethyl)piperazin-1-yl)ethoxy)methyl)-1-isopropyl-N-(2-(4-methoxypiperidin-1-yl)pyrimidin-4-yl)-1H-imidazo[4,5-c]pyridin-6-amine (1 g, 1.56 mmol) in methanol (20 mL) was added Pd(OH)$_2$/C (20%, 0.50 g) and conc. HCl (0.1 ml) subsequently at rt. The mixture was stirred for 2 h under H$_2$ at 1 atm. The reaction mixture was filtered and the filtrate was concentrated under vacuum to afford the desired product 2-(4-(2-((1-Isopropyl-6-((2-(4-methoxypiperidin-1-yl)pyrimidin-4-yl)amino)-1H-imidazo [4,5-c]pyridin-2-yl)methoxy)ethyl)piperazin-1-yl)ethanol (0.31 g, 0.56 mmol, crude) as red oil. LC-MS: (ES$^+$): m/z 554.3 [M+H]. t$_R$=2.342 min. Chemical Formula: C$_{28}$H$_{43}$N$_9$O$_3$; Molecular Weight: 553.70

9. Step—Synthesis of Tert-butyl 5-amino-4-(5-(2-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)ethoxy)-1,3-dioxoisoindolin-2-yl)-5-oxopentanoate

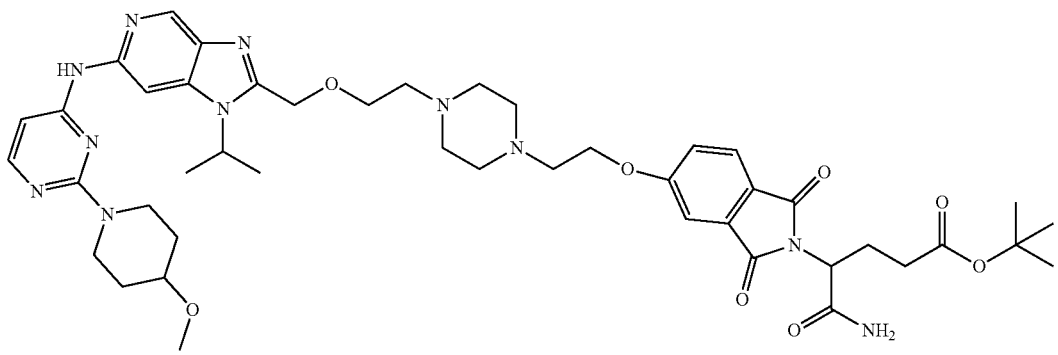 [SMILES: COC1CCN(c2nccc(Nc3cc4c(cn3)nc(COCCN3CCN(CCOc5ccc6c(c5)C(=O)N(C(CCC(=O)OC(C)(C)C)C(N)=O)C6=O)CC3)n4C(C)C)n2)CC1]

To a solution of 2-(4-(2-((1-Isopropyl-6-((2-(4-methoxypiperidin-1-yl)pyrimidin-4-yl)amino)-1H-imidazo [4,5-c]pyridin-2-yl)methoxy)ethyl)piperazin-1-yl)ethanol (55 mg, 0.10 mmol), PPh$_3$ (131 mg, 0.51 mmol) and tert-butyl 5-amino-4-(5-hydroxy-1,3-dioxoisoindolin-2-yl)-5-oxopentanoate (70 mg, 0.21 mmol) in dry THF (5 mL) was added DIAD (101 mg, 0.51 mmol) drop-wise at 0° C. under N$_2$. The mixture was stirred at room temperature for 1 h. The resulting solution was quenched with water (50 mL), and the mixture was extracted with DCM (20 mL×2). The combined organic layers were dried over MgSO$_4$, and concentrated under vacuum. The residue was purified by chromatography (silica gel, DCM/MeOH=1/1) to afford the desired product Tert-butyl 5-amino-4-(5-(2-(4-(2-((1-isopropyl-6-((2-(4-methoxypiperidin-1-yl)pyrimidin-4-yl)amino)-1H-imidazo [4,5-c]pyridin-2-yl)methoxy)ethyl)piperazin-1-yl)ethoxy)-1,3-dioxoisoindolin-2-yl)-5-oxopentanoate (90 mg, 0.10 mmol, crude) as yellow solid. Chemical Formula: C$_{45}$H$_{61}$N$_{11}$O$_8$; Molecular Weight: 884.03

10. Step—Synthesis of 2-(2,6-Dioxopiperidin-3-yl)-5-(2-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)ethoxy) isoindoline-1,3-dione

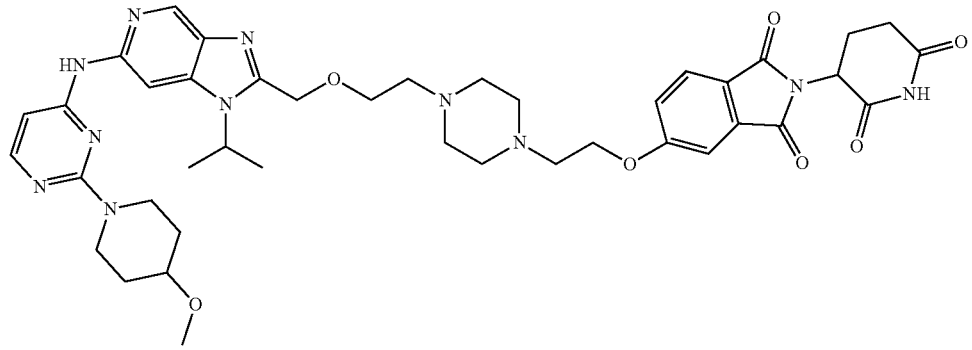 [SMILES: COC1CCN(c2nccc(Nc3cc4c(cn3)nc(COCCN3CCN(CCOc5ccc6c(c5)C(=O)N(C5CCC(=O)NC5=O)C6=O)CC3)n4C(C)C)n2)CC1]

To a solution of Tert-butyl 5-amino-4-(5-(2-(4-(2-((1-isopropyl-6-((2-(4-methoxypiperidin-1-yl)pyrimidin-4-yl)amino)-1H-imidazo [4,5-c]pyridin-2-yl)methoxy)ethyl)piperazin-1-yl)ethoxy)-1,3-dioxoisoindolin-2-yl)-5-oxopentanoate (90 mg, 0.10 mmol) in $CH_3CN$ (10 mL) and was added TsOH (172 mg, 1.01 mmol) at rt. The resulting solution was stirred at 80° C. for 3 h. After cooling to 0° C., the reaction was quenched with aq $NaHCO_3$, and the mixture was extracted with DCM (10 mL×3). The combined organic layers were dried over anhydrous sodium sulfate, filtered and concentrated under vacuum. The residue was purified by silica gel column chromatography (DCM/MeOH=20/1) to afford 2-(2,6-Dioxopiperidin-3-yl)-5-(2-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)ethoxy)isoindoline-1,3-dione (14 mg, 0.02 mmol, 17%) as white solid. $^1H$ NMR (400 MHz, $CDCl_3$): δ 8.73 (br, 1H), 8.71 (s, 1H), 8.47 (s, 1H), 8.04 (d, J=5.6 Hz, 1H), 7.78 (d, J=8.4 Hz, 1H), 7.66 (s, 1H), 7.35 (s, 1H), 7.20-7.18 (m, 1H), 6.06 (d, J=5.6 Hz, 1H), 4.97-4.93 (m, 2H), 4.79 (s, 2H), 4.39-4.36 (m, 2H), 4.21-4.19 (m, 2H), 3.64-3.61 (m, 2H), 3.50-3.48 (m, 3H), 3.41 (s, 3H), 2.88-2.82 (m, 5H), 2.61-2.52 (m, 10H), 2.14-2.11 (m, 5H), 2.09-1.96 (m, 2H), 1.67-1.65 (m, 8H). LC-MS: ($ES^+$): m/z 811.3 [M+H]. $t_R$=2.639 min. Chemical Formula: $C_{41}H_{51}N_{11}O_7$; Molecular Weight: 809.91

Synthesis of Example 78

2-(2,6-dioxopiperidin-3-yl)-5-(4-(2-(1-(4-((1-isopropyl-2-methyl-1H-imidazo[4,5-c]pyridin-6-yl)amino)pyrimidin-2-yl)-4-methoxypiperidin-4-yl)ethyl)piperazin-1-yl)isoindoline-1,3-dione

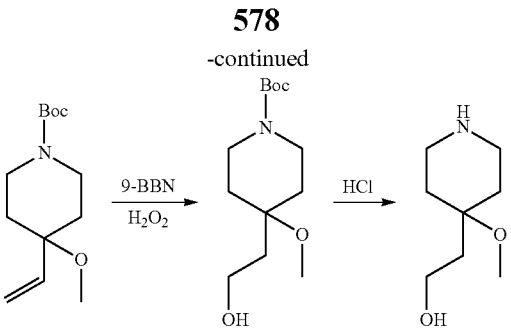

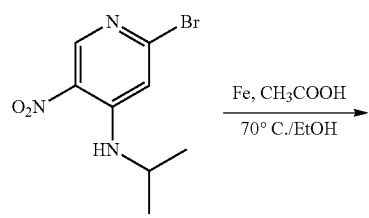

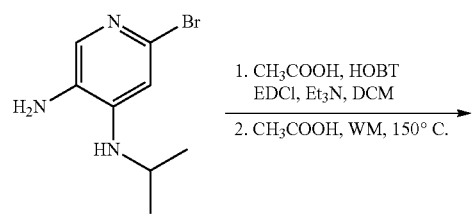

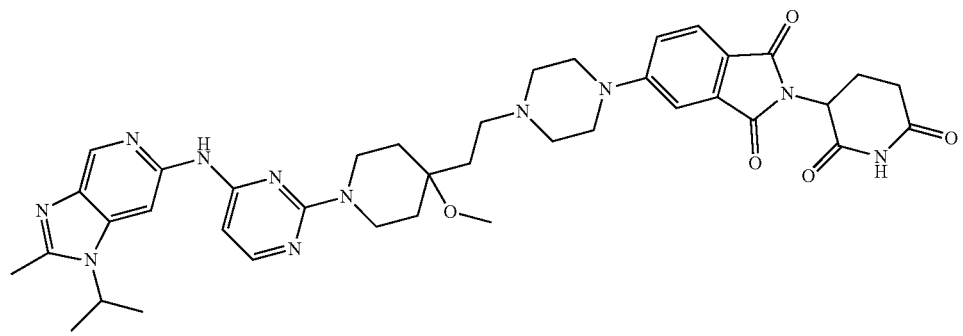 [SMILES: COC1(CCN2CCN(c3ccc4c(c3)C(=O)N(C3CCC(=O)NC3=O)C4=O)CC2)CCN(c2nccc(Nc3cc4c(cn3)nc(C)n4C(C)C)n2)CC1]

Synthetic Scheme - part 1:

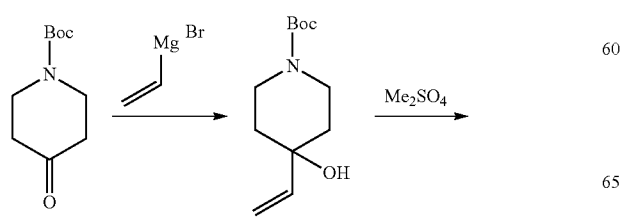

-continued

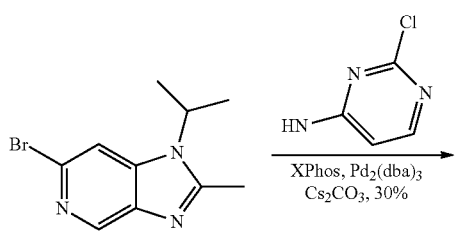

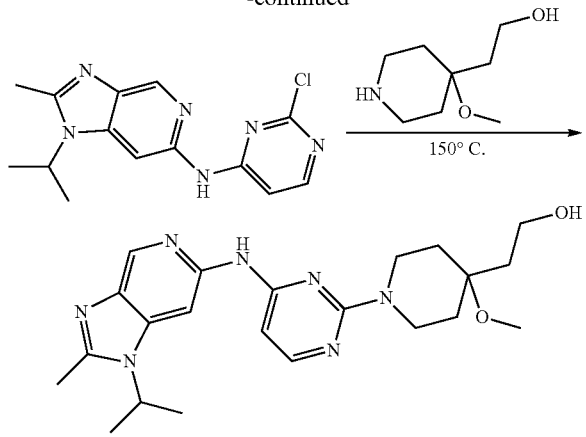

The synthesis of 2-(4-methoxypiperidin-4-yl)ethan-1-ol followed the route described in Monatshefte fuer Chemie, 2004, 135 (7), 899-909

Experimental Section

1. Step—Synthesis of 6-Bromo-N4-isopropylpyridine-3,4-diamine

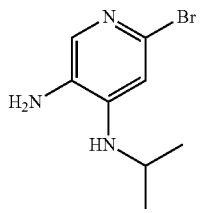

To a solution of 2-bromo-N-isopropyl-5-nitropyridin-4-amine (1 g, 3.85 mmol) in ethanol (30 mL) were added $NH_4Cl$ solution (0.57 g in 10 mL water, 105.6 mmol) and Fe powder (645 mg, 11.55 mmol) subsequently. The resulting reaction was stirred at 70° C. for 3 h. After cooling to rt, the mixture was filtered through Celite, and the filtrate was concentrated under vacuum. The residue was dissolved in sat. sodium bicarbonate solution, and the aqueous was extracted with ethyl acetate (20 mL×3). The combined organic layers were dried over sodium sulfate and concentrated to afford the desired compound 6-Bromo-N4-isopropylpyridine-3,4-diamine (920 mg, 92%), which was used in the next reaction without further purification. $^1$H NMR (400 MHz, CDCl3): δ 7.62 (s, 1H), 6.57 (s, 1H), 4.19 (br, 1H), 3.59-3.64 (m, 1H), 3.00 (br, 2H), 1.26 (d, J=6.4 Hz, 6H). Chemical Formula: $C_8H_{12}BrN_3$; Molecular Weight: 230.11

2. Step—Synthesis of 6-Bromo-1-isopropyl-2-methyl-1H-imidazo[4,5-c]pyridine

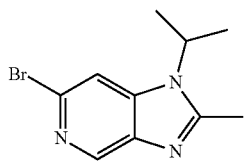

A solution of 6-Bromo-N4-isopropylpyridine-3,4-diamine (900 mg, 3.913 mmol), $CH_3COOH$ (235 mg, 3.913 mmol), EDCI (897 mg, 4.696 mmol), HOBt (634 mg, 4.696 mmol), and $Et_3N$ (593 mg, 5.870 mmol) in DCM (15 mL) was stirred at rt overnight. After the reaction was quenched with water (10 mL), the mixture was extracted with DCM (20 mL×2). The combined organic layers were dried ($Na_2SO_4$), filtered and concentrated under reduced pressure. The residue was purified by silica gel column to afford the desired acet-amide intermediate (1.1 g, crude 100%).

A solution of the acetamide intermediate (1.0 g, 3.67 mmol) in $CH_3COOH$ (10 mL) was irradiated to 150° C. with microwave for 6 h. After cooling to rt, the solvent was removed under vacuum to afford crude desired product 6-Bromo-1-isopropyl-2-methyl-1H-imidazo[4,5-c]pyridine (475 mg, 48%). $^1$H NMR (400 MHz, CDCl3): δ 8.70 (s, 1H), 7.57 (s, 1H), 4.62-4.65 (m, 1H), 2.64 (s, 3H), 1.63 (d, J=6.8 Hz, 6H). Chemical Formula: $C_{10}H_{12}BrN_3$; Molecular Weight: 254.13

3. Step—Synthesis of N-(2-Chloropyrimidin-4-yl)-1-isopropyl-2-methyl-1H-imidazo[4,5-c]pyridin-6-amine

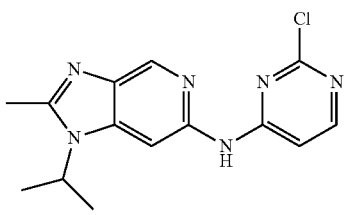 [SMILES: Cc1nc2cnc(Nc3ccnc(Cl)n3)cc2n1C(C)C]

A mixture of 6-Bromo-1-isopropyl-2-methyl-1H-imidazo[4,5-c]pyridine (467 mg, 1.85 mmol), 2-chloropyrimidin-4-amine (266 mg, 2.04 mmol), $Pd_2(dba)_3$ (213 mg, 0.37 mmol), xantphos (429 mg, 0.74 mmol), and $Cs_2CO_3$ (1.8 g, 5.55 mmol) in dioxane (10 mL) was heated to 100° C. overnight in sealed tube with sand-bath. After cooling to rt, the mixture was filtered through Celite, and the filtered cake was washed with EtOAc. The filtrate was concentrated under vacuum. The residue was purified by prep-HPLC to afford the desired product N-(2-Chloropyrimidin-4-yl)-1-isopropyl-2-methyl-1H-imidazo[4,5-c]pyridin-6-amine (150 mg, 27%).

$^1$H NMR (400 MHz, DMSO): δ 8.57 (s, 1H), 8.25 (d, J=5.6 Hz, 1H), 8.12 (br s, 1H), 7.48 (br s, 1H), 4.71-4.75 (m, 1H), 2.58 (s, 3H), 1.58 (d, J=7.2 Hz, 6H).

Chemical Formula: $C_{14}H_{15}ClN_6$; Molecular Weight: 302.77

4. Step—Synthesis of 2-(1-(4-(((1-Isopropyl-2-methyl-1H-imidazo[4,5-c]pyridin-6-yl)amino)pyrimidin-2-yl)-4-methoxypiperidin-4-yl)ethan-1-ol

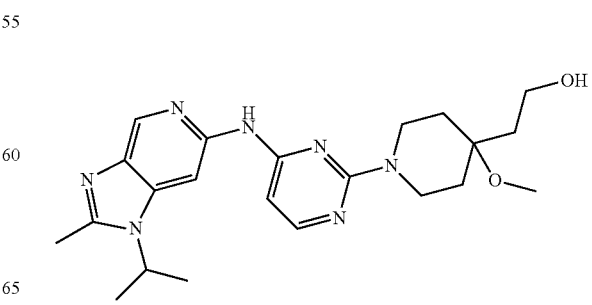

A solution of N-(2-Chloropyrimidin-4-yl)-1-isopropyl-2-methyl-1H-imidazo[4,5-c]pyridin-6-amine (103 mg, 0.341 mmol), 2-(4-methoxypiperidin-4-yl)ethan-1-ol (49 mg, 0.31 mmol), Et$_3$N (157 mg, 1.55 mmol) in isopropanol was irradiated to 150° C. with microwave for 20 min under N$_2$. The mixture was filtered through Celite and the filtrate was concentrated under vacuum. The residue was purified by chromatography column (PE/EA=10/1 to EA) to afford the desired product 2-(1-(4-(((1-Isopropyl-2-methyl-1H-imidazo[4,5-c]pyridin-6-yl)amino)pyrimidin-2-yl)-4-methoxypiperidin-4-yl)ethan-1-ol (66 mg, 50%) as a white solid.

$^1$H NMR (400 MHz, MeOD): δ 8.52 (s, 1H), 8.37 (s, 1H), 7.91 (d, J=6.0 Hz, 1H), 6.36 (d, J=6.0 Hz, 1H), 4.33 (d, J=13.2 Hz, 2H), 3.67 (t, J=7.2 Hz, 2H), 3.30-3.35 (m, 3H), 3.26 (s, 3H), 2.64 (s, 3H), 1.89-1.92 (d, J=13.2 Hz, 2H), 1.82 (t, J=7.2 Hz, 2H), 1.67 (d, J=6.8 Hz, 6H), 1.61-1.64 (m, 2H).

Chemical Formula: C$_{22}$H$_{31}$N$_7$O$_2$; Molecular Weight: 425.54

LC-MS (ES$^+$): m/z 426.3 [MH$^+$]; t$_R$=2.51 min

Synthetic Scheme-part 2

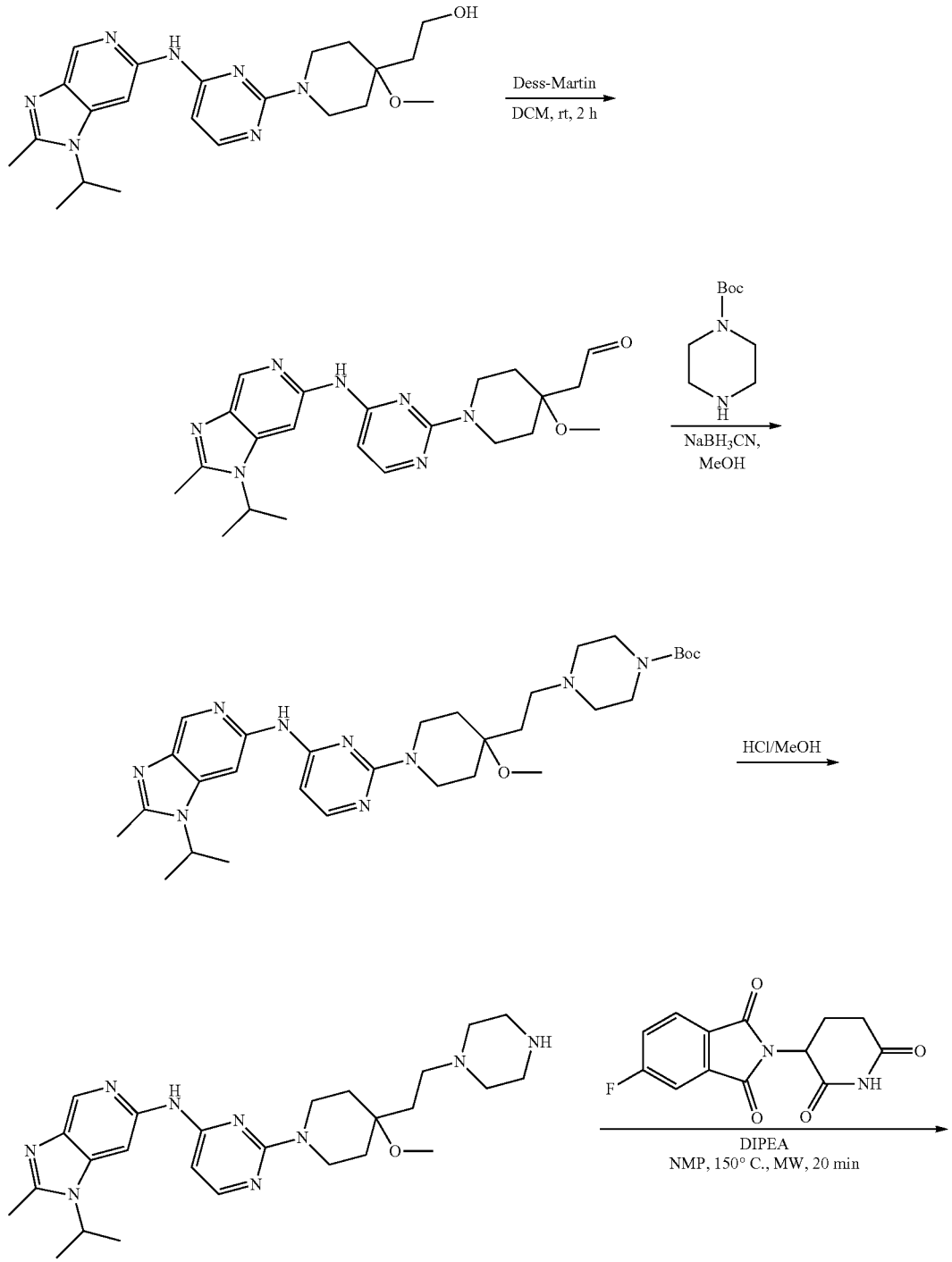

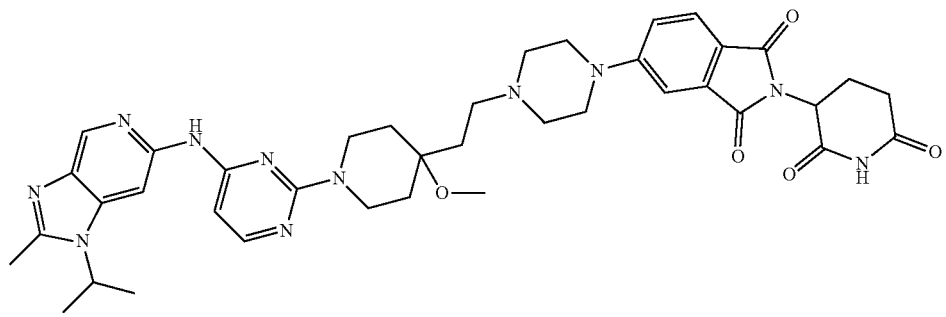

5. Step—Synthesis of 2-(1-(4-((1-Isopropyl-2-methyl-1H-imidazo[4,5-c]pyridin-6-yl)amino)pyrimidin-2-yl)-4-methoxypiperidin-4-yl)acetaldehyde

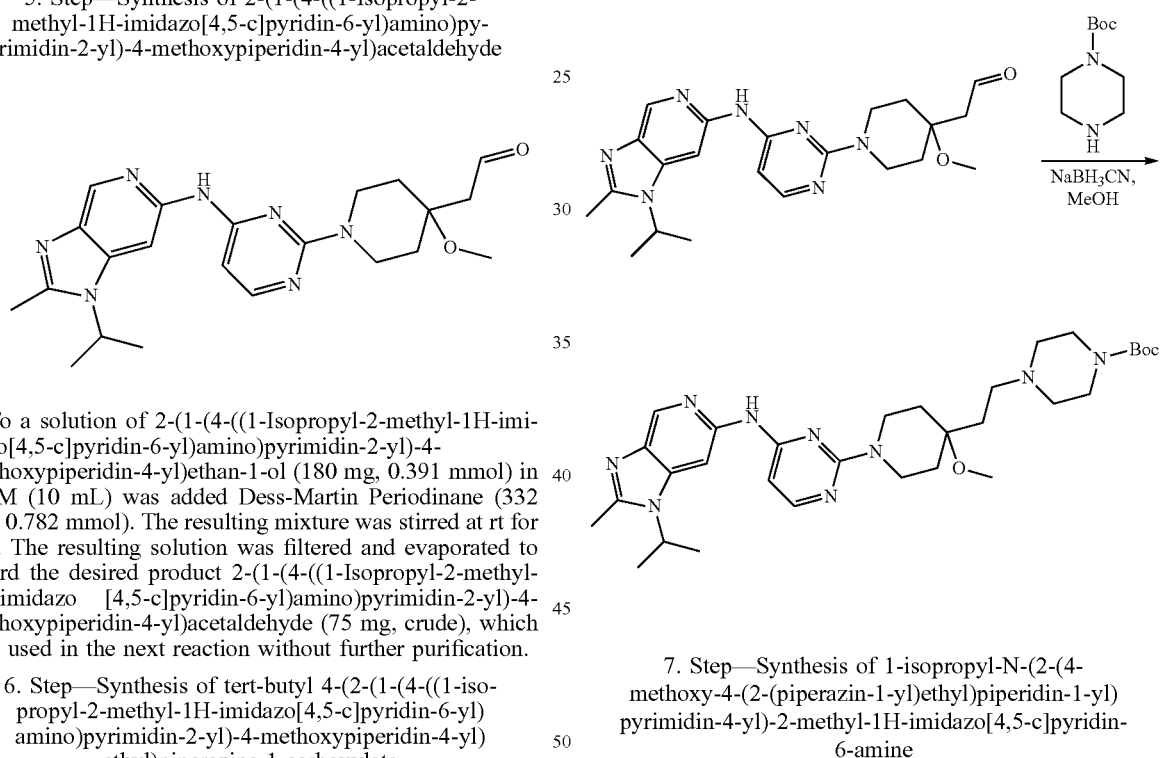

To a solution of 2-(1-(4-((1-Isopropyl-2-methyl-1H-imidazo[4,5-c]pyridin-6-yl)amino)pyrimidin-2-yl)-4-methoxypiperidin-4-yl)ethan-1-ol (180 mg, 0.391 mmol) in DCM (10 mL) was added Dess-Martin Periodinane (332 mg, 0.782 mmol). The resulting mixture was stirred at rt for 2 h. The resulting solution was filtered and evaporated to afford the desired product 2-(1-(4-((1-Isopropyl-2-methyl-1H-imidazo [4,5-c]pyridin-6-yl)amino)pyrimidin-2-yl)-4-methoxypiperidin-4-yl)acetaldehyde (75 mg, crude), which was used in the next reaction without further purification.

6. Step—Synthesis of tert-butyl 4-(2-(1-(4-((1-isopropyl-2-methyl-1H-imidazo[4,5-c]pyridin-6-yl)amino)pyrimidin-2-yl)-4-methoxypiperidin-4-yl)ethyl)piperazine-1-carboxylate followed the reductive amination procedure as described in example 307.

7. Step—Synthesis of 1-isopropyl-N-(2-(4-methoxy-4-(2-(piperazin-1-yl)ethyl)piperidin-1-yl)pyrimidin-4-yl)-2-methyl-1H-imidazo[4,5-c]pyridin-6-amine using HCl in Methanol to cleave BOC protecting group. The crude product was used without further purification.

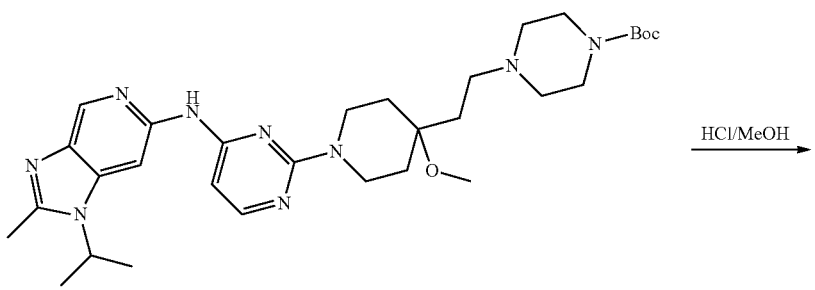

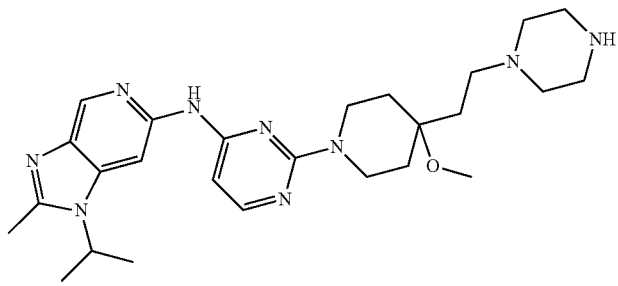
8. Step—Synthesis of 2-(2,6-dioxopiperidin-3-yl)-5-(4-(2-(1-(4-((1-isopropyl-2-methyl-1H-imidazo[4,5-c]pyridin-6-yl)amino)pyrimidin-2-yl)-4-methoxypiperidin-4-yl)ethyl)piperazin-1-yl)isoindoline-1,3-dione
followed the S$_N$Ar reaction conditions described in example 71.
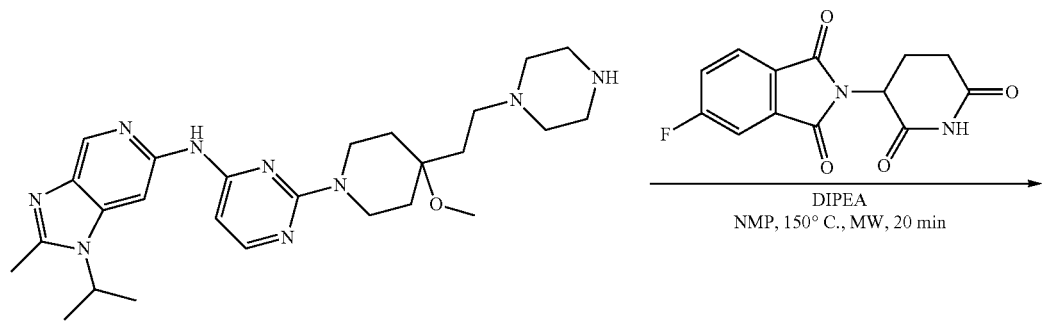
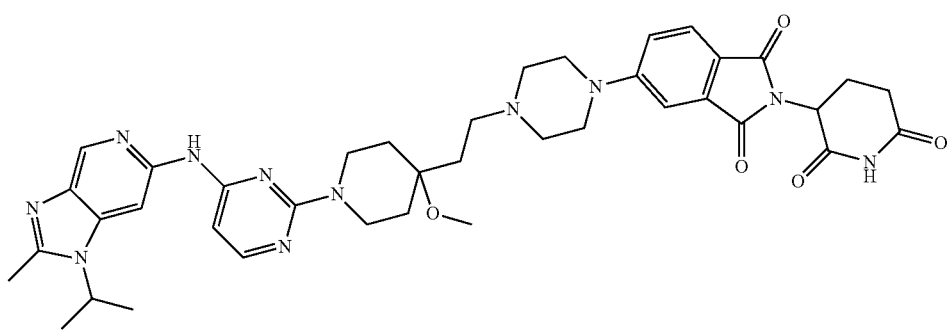

¹HNMR (400 MHz, DMSO-d₆): δ: 11.08 (s, 1H), 9.69 (s, 1H), 8.50 (s, 1H), 8.40 (s, 1H), 7.95 (d, J=5.6 Hz, 1H), 7.67 (d, J=7.2 Hz, 1H), 7.33 (s, 1H), 7.25 (d, J=7.2 Hz, 1H), 6.39 (d, J=4.0 Hz, 1H), 5.04-5.09 (m, 1H), 4.71 (t, J=6.4 Hz, 1H), 4.34 (d, J=12.4 Hz, 2H), 3.42 (s, 4H), 3.21-3.24 (m, 3H), 3.15 (s, 3H), 3.31 (s, 3H), 2.55 (s, 3H), 2.37 (s, 3H), 1.98-2.02 (m, 2H), 1.71-1.78 (m, 4H), 1.51 (s, 6H).

LCMS: m/e=375.8=[M+2H]²⁺, $t_R$=2.60 min.

Chemical Formula: $C_{39}H_{47}N_{11}O_5$; Molecular Weight: 749.9

Synthesis of Example 80

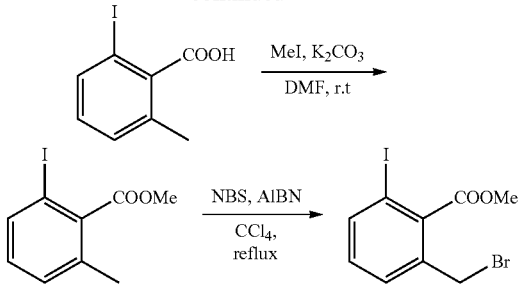

-continued

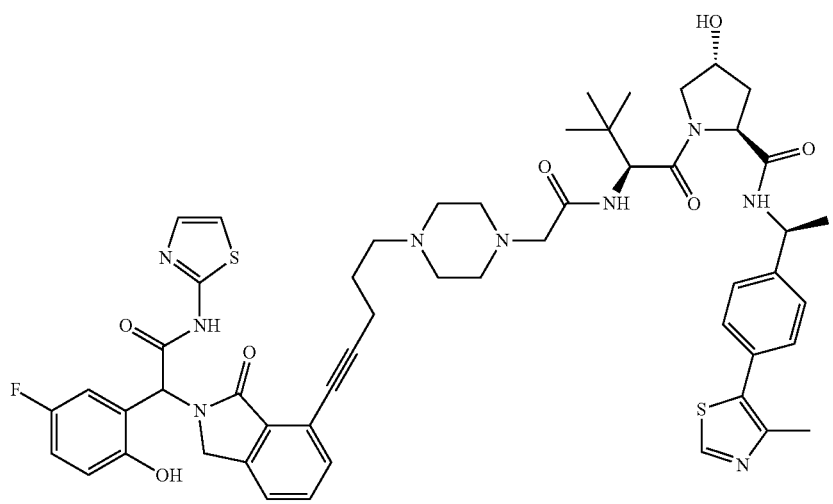 [SMILES: Cc1ncsc1-c1ccc([C@H](C)NC(=O)[C@@H]2C[C@@H](O)CN2C(=O)[C@@H](NC(=O)CN2CCN(CCCC#Cc3cccc4c3C(=O)N(C(C(=O)Nc3nccs3)c3cc(F)ccc3O)C4)CC2)C(C)(C)C)cc1]

(2S,4R)-1-((2S)-2-(2-(4-(5-(2-(1-(5-fluoro-2-hydroxyphenyl)-2-oxo-2-(thiazol-2-ylamino)ethyl)-3-oxoisoindolin-4-yl)pent-4-yn-1-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide Synthesis Scheme - Part 1

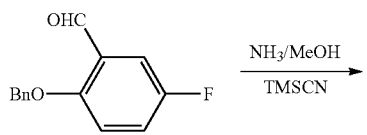

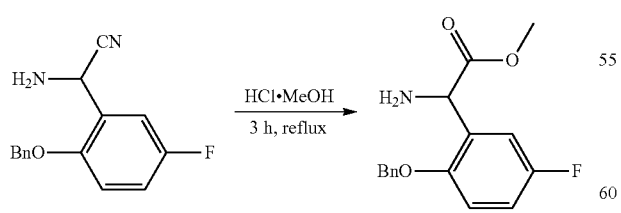

-continued

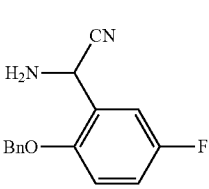 [SMILES: N#CC(N)c1cc(F)ccc1OCc1ccccc1]

Experiments

1. Step—Synthesis of 2-amino-2-(2-(benzyloxy)-5-fluorophenyl)acetonitrile

A mixture of 2-(benzyloxy)-5-fluorobenzaldehyde (80 g, 347 mmol) in ammonia solution (7.0 M in methanol, 500 ml) was stirred at 0° C. for 0.5 hour, then trimethylsilyl cyanide (37.2 g, 375 mmol) was added dropwise at the same temperature. The resulting reaction mixture was stirred at 45° C. for 3 hour. TLC showed the reaction was complete. The volatiles were evaporated under reduced pressure to give 2-amino-2-(2-(benzyloxy)-5-fluorophenyl)acetonitrile (crude) as yellow oil which was used in next step without further purification.

2. Step—Synthesis of methyl 2-amino-2-(2-(benzyloxy)-5-fluorophenyl)acetate hydrochloride

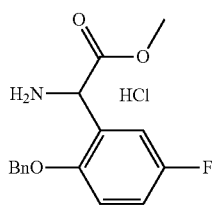 [SMILES: COC(=O)C(N)c1cc(F)ccc1OCc1ccccc1 ; Cl]

Thionyl chloride (60 ml) was added to methanol (400 ml) dropwise at 0° C. and the resulting reaction mixture was stirred at the same temperature for 10 min. to afford crude solution of hydrogen chloride in methanol. The mixture of hydrogen chloride in methanol (400 ml) and 2-amino-2-(2-(benzyloxy)-5-fluorophenyl)acetonitrile (crude, 347 mmol) was stirred at 65° C. overnight. TLC showed the reaction was complete. The volatiles were removed under reduced pressure. The residue was dissolved in methanol (50 ml), and ethyl acetate (500 ml) was added. The resulting mixture was stirred at room temperature for 0.5 hour, and white solid precipitated. The solid was collected by filtration and dried under vacuum to afford methyl 2-amino-2-(2-(benzyloxy)-5-fluorophenyl)acetate hydrochloride (82 g, yield: 72% over 2 steps) as white solid. LC_MS: (ES$^+$): m/z 290.2 [M+H]$^+$. $t_R$=1.852 min. 1H NMR (400 Hz, CD$_3$OD): δ 3.73 (s, 3H), 5.22-5.24 (m, 2H), 5.35 (s, 1H), 7.19-7.26 (m, 3H), 7.36-7.48 (m, 5H). Chemical Formula: C$_{16}$H$_{17}$ClFNO$_3$; Molecular Weight: 289.30;

3. Step—Synthesis of 2-iodo-6-methylbenzoic acid

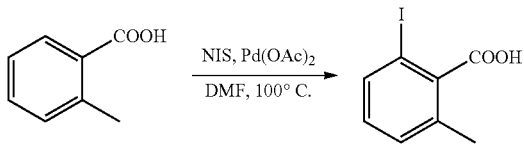

A mixture of 2-methylbenzoic acid (10.0 g, 73.5 mmol), N-Iodosuccinimide (16.0 g, 73.5 mmol) and palladium diacetate (1.6 g, 7.35 mmol) in N,N-dimethylformamide (160 ml) was stirred at 100° C. for 2 hours under nitrogen atmosphere. TLC showed the reaction was complete. The cooled reaction mixture was allowed to cool to room temperature and partitioned between ethyl acetate (300 ml) and water (500 ml). The organic layer was collected, and the aqueous layer was extracted with ethyl acetate (100 ml×2). The combined organic layers were washed with brine (200 ml), dried over anhydrous sodium sulfate, and concentrated under reduced pressure to give 2-iodo-6-methylbenzoic acid (16 g, yield 84%) as yellow solid which was used in next step directly without further purification. 1H NMR (400 Hz, CDCl$_3$): δ 2.29 (s, 3H), 7.06 (t, J=8.0 Hz, 1H), 7.27 (d, J=7.6 Hz, 1H), 7.67 (d, J=8.0 Hz, 1H). Chemical Formula: C$_8$H$_7$IO$_2$; Molecular Weight: 262.04;

4. Step—Synthesis of methyl 2-iodo-6-methylbenzoate

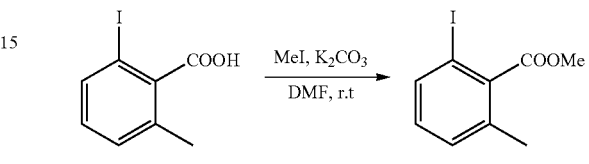

A mixture of 2-iodo-6-methylbenzoic acid (5.6 g, 21.4 mmol), iodomethane (2.5 ml, 40.1 mmol) and potassium carbonate (5.0 g, 35.9 mmol) in N,N-dimethylformamide (40 ml) was a stirred at room temperature overnight. TLC showed the reaction was complete. The reaction mixture was partitioned between ethyl acetate (50 ml) and water (50 ml). The organic layer was collected, and the aqueous layer was extracted with ethyl acetate (100 ml×2). The combined organic layers were washed with brine (200 ml), dried over anhydrous sodium sulfate, and concentrated under reduced pressure to afford a crude residue which was purified by silica gel flash chromatography (eluted with 5% ethyl acetate in hexane) to afford methyl 2-iodo-6-methylbenzoate (3.8 g, yield 63%) as white solid. LC_MS: (ES$^+$): m/z 277.0 [M+H]$^+$. $t_R$=2.863 min. 1H NMR (400 Hz, CDCl$_3$): δ 2.35 (s, 3H), 3.97 (s, 3H), 7.01 (t, J=8.0 Hz, 1H), 7.20 (d, J=7.6 Hz, 1H), 7.67 (d, J=8.0 Hz, 1H). Chemical Formula: C$_9$H$_9$IO$_2$; Molecular Weight: 276.07;

5. Step—Synthesis of methyl 2-(bromomethyl)-6-iodobenzoate

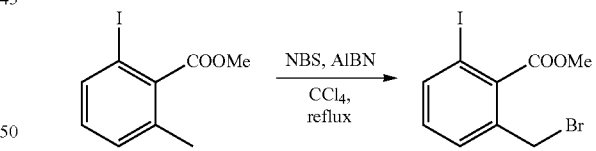

A mixture of methyl 5-iodo-2-methylbenzoate (3.8 g, 13.7 mmol), AIBN (2,2'-Dimethyl-2,2'-azodipropionitrile) (1 g, 6.16 mmol) and N-Bromosuccinimide (2.9 g, 16.5 mmol) in carbon tetrachloride (40 ml) was refluxed overnight. TLC showed the reaction was complete. The cooled reaction mixture was partitioned between dichloromethane (30 ml) and water (20 ml). The organic layer was collected, and the aqueous layer was extracted with dichloromethane (30 ml×2). The combined organic layers were washed with brine (20 ml), dried over anhydrous sodium sulfate, and concentrated under reduced pressure to give a crude residue which was purified by silica gel flash chromatography (eluted with 5% ethyl acetate in hexane) to afford methyl 2-(bromomethyl)-6-iodobenzoate (2.4 g, yield 50%) as white solid. 1H NMR (400 Hz, CDCl$_3$): δ 3.99 (s, 3H), 4.78 (s, 2H), 7.09 (t, J=8.0 Hz, 1H), 7.40 (d, J=7.6 Hz, 1H), 7.80 (d, J=8.0 Hz, 1H). Chemical Formula: $C_9H_8BrIO_2$; Molecular Weight: 354.97;

6. Step—Synthesis of methyl 2-(2-(benzyloxy)-5-fluorophenyl)-2-(7-iodo-1-oxoisoindolin-2-yl)acetate A mixture of methyl methyl 2-amino-2-(2-(benzyloxy)-5-fluorophenyl)acetate (1.2 g, 4.1 mmol), methyl 2-(bromomethyl)-6-iodobenzoate (1.5 g, 4.1 mmol) and triethylamine (0.9 ml, 6.2 mmol) in toluene (10 ml) was stirred at 110° C. overnight under nitrogen atmosphere. TLC showed the reaction was complete. The cooled reaction mixture was partitioned between ethyl acetate (50 ml) and water (30 ml). The organic layer was collected, and the aqueous layer was extracted with ethyl acetate (30 ml×2). The combined organic layers were washed with brine (30 ml), dried over anhydrous sodium sulfate, and concentrated under reduced pressure to give a crude residue which was purified by silica gel flash chromatography (eluted with 10% ethyl acetate in hexane) to afford methyl 2-(2-(benzyloxy)-5-fluorophenyl)-2-(7-iodo-1-oxoisoindolin-2-yl)acetate (1.3 g, yield: 59%) as white solid. LC_MS: (ES$^+$): m/z 532.1 [M+H]$^+$. $t_R$=3.137 min. 1H NMR (400 Hz, CD$_3$OD): δ 3.62 (s, 3H), 3.86 (d, J=17.2 Hz, 1H), 4.58 (d, J=16.2 Hz, 1H), 5.04-5.15 (m, 2H), 6.43 (s, 1H), 6.93-6.97 (m, 1H), 7.00-7.05 (m, 1H), 7.06-7.09 (m, 1H), 7.19 (t, J=7.6 Hz, 1H), 7.27-7.39 (m, 6H), 7.89 (d, J=7.6 Hz, 1H). Chemical Formula: C24H19FINO4; Molecular Weight: 531.31; See also the closely related synthesis of example 307.

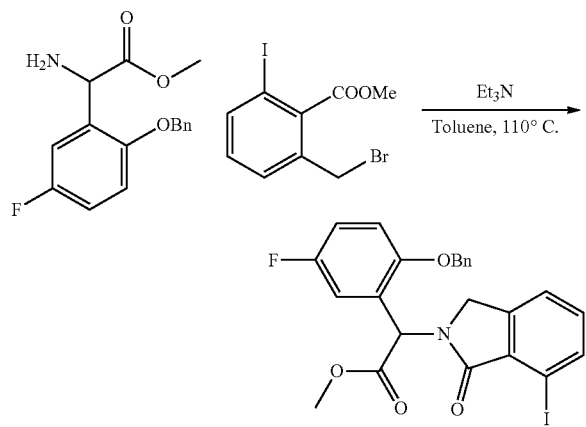

Synthetic Scheme-Part 2:

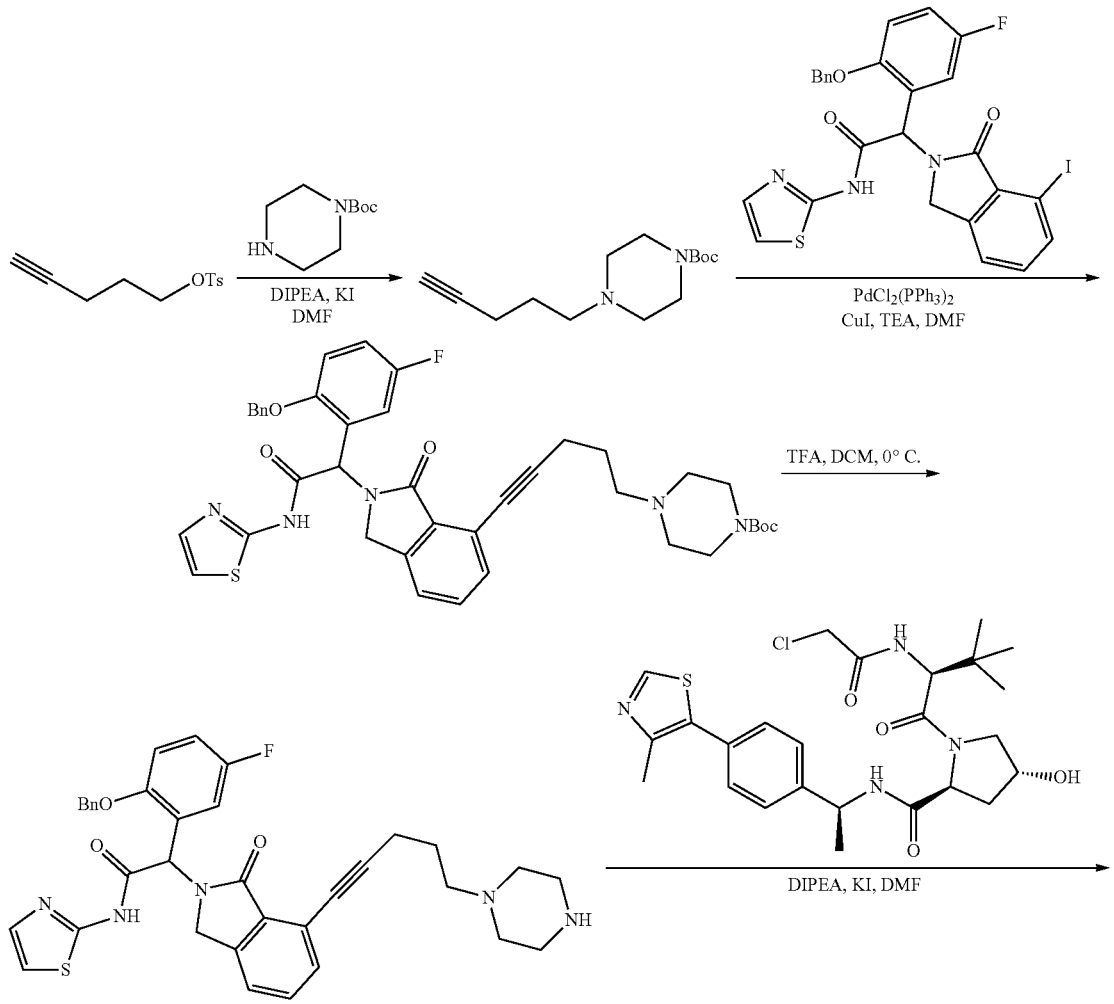

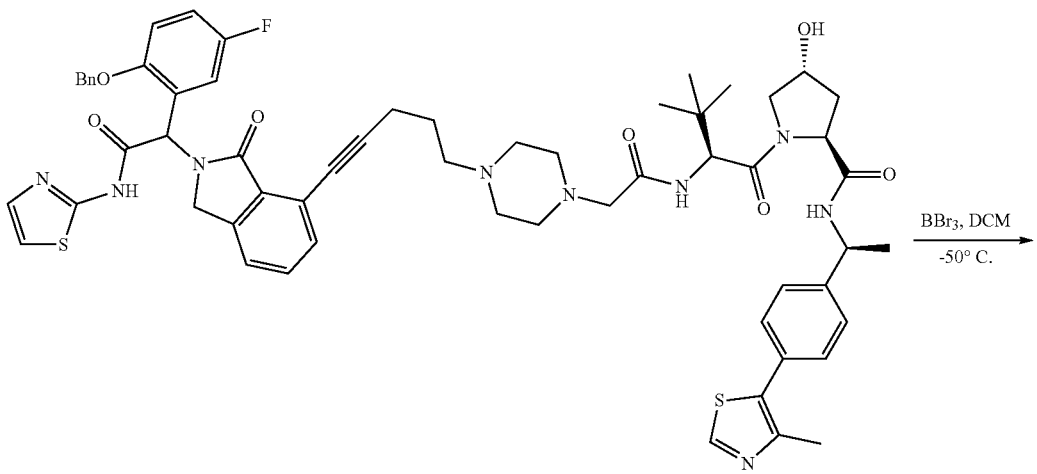

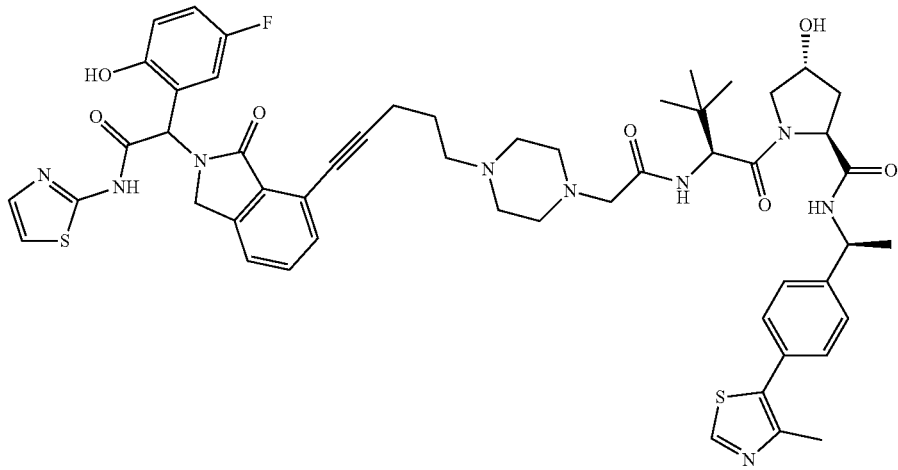 [SMILES: Cc1ncsc1-c1ccc([C@H](C)NC(=O)[C@@H]2C[C@@H](O)CN2C(=O)[C@@H](NC(=O)CN2CCN(CCCC#Cc3cccc4c3C(=O)N(C(C(=O)Nc3nccs3)c3cc(F)ccc3O)C4)CC2)C(C)(C)C)cc1]

7. Step—Synthesis of tert-butyl 4-(pent-4-yn-1-yl)piperazine-1-carboxylate

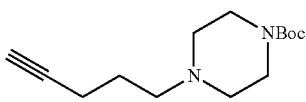 [SMILES: C#CCCCN1CCN(C(=O)OC(C)(C)C)CC1]

To a stirred solution of pent-4-yn-1-yl 4-methylbenzenesulfonate (2.88 mg, 12.09 mmol), N-ethyl-N-isopropylpropan-2-amine (3.12 g, 24.17 mmol) and potassium iodide (201 mg, 1.21 mmol) in N,N-dimethylformamide (30 ml) was added tert-butyl piperazine-1-carboxylate (2.25 mg, 12.09 mmol), and the mixture was stirred at 50° C. overnight under nitrogen. TLC showed the reaction was complete. The reaction mixture was partitioned between ethyl acetate (50 ml) and water (50 ml), the organic layer was washed with brine (50 ml×2), dried over anhydrous sodium sulfate and concentrated under reduced pressure to give a crude residue which was purified by silica gel flash column chromatography (eluted with 20-40% ethyl acetate in hexane) to afford tert-butyl 4-(pent-4-yn-1-yl)piperazine-1-carboxylate (1.7 g, yield 56%) as yellow oil. $^1$H NMR (400 MHz, CDCl$_3$): δ 1.46 (s, 9H), 1.68-1.75 (m, 2H), 1.95 (t, J=2.6 Hz, 1H), 2.22-2.26 (m, 2H), 2.38 (t, J=4.8 Hz, 4H), 2.42-2.46 (m, 2H), 3.42 (t, J=5.0 Hz, 4H). Chemical Formula: C$_{14}$H$_{24}$N$_2$O$_2$; Molecular Weight: 252.35;

8. Step—Synthesis of tert-butyl 4-(5-(2-(1-(2-(benzyloxy)-5-fluorophenyl)-2-oxo-2-(thiazol-2-ylamino)ethyl)-3-oxoisoindolin-4-yl)pent-4-yn-1-yl)piperazine-1-carboxylate

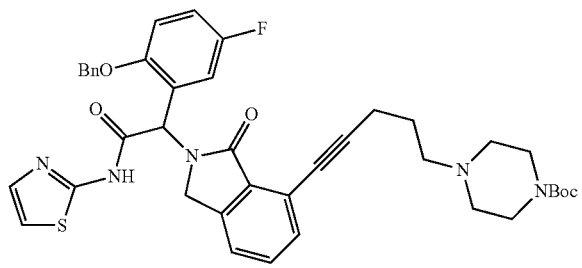 [SMILES: CC(C)(C)OC(=O)N1CCN(CCCC#Cc2cccc3c2C(=O)N(C(C(=O)Nc2nccs2)c2cc(F)ccc2OCc2ccccc2)C3)CC1]

To a solution of 2-(5-(benzyloxy)-2-fluorophenyl)-2-(7-iodo-1-oxoisoindolin-2-yl)-N-(thiazol-2-yl)acetamide (468 mg, 0.78 mmol), 1-methyl-4-(pent-4-yn-1-yl)piperazine (296 mg, 1.17 mmol) and triethylamine (474 mg, 4.68 mmol) in N,N-dimethylformamide (8 ml) was added cuprous iodide (30 mg, 0.16 mmol) and [1,1'-bis(diphenylphosphino)ferrocene]dichloropalladium(II) (109 mg, 0.16 mmol) at room temperature under nitrogen atmosphere; the mixture was degassed with nitrogen three times. The resulting mixture was refluxed for 2 hours. TLC showed the reaction was complete. The reaction mixture was partitioned between ethyl acetate (30 ml) and water (20 ml); the organic layer was collected and the aqueous layer was extracted with ethyl acetate (20 ml×2). The combined organic layers were washed with brine (40 ml), dried over anhydrous sodium sulfate, and concentrated under reduced pressure to give a crude residue which was purified by silica gel flash column chromatography (eluted with 5-10% methanol in dichloromethane) to afford tert-butyl 4-(5-(2-(1-(2-(benzyloxy)-5-fluorophenyl)-2-oxo-2-(thiazol-2-ylamino)ethyl)-3-oxoisoindolin-4-yl)pent-4-yn-1-yl)piperazine-1-carboxylate (348 mg, yield 62%) as black solid. LC_MS: (ES$^+$): m/z 724.3 [M+H]$^+$. $t_R$=2.483 min. Chemical Formula: $C_{40}H_{42}FN_5O_5S$; Molecular Weight: 723.86;

9. Step—Synthesis of 2-(2-(benzyloxy)-5-fluorophenyl)-2-(1-oxo-7-(5-(piperazin-1-yl)pent-1-yn-1-yl)isoindolin-2-yl)-N-(thiazol-2-yl)acetamide TFA salt

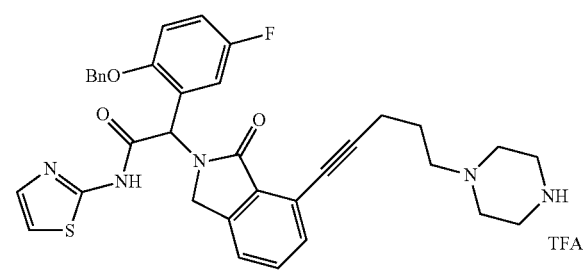 [SMILES: O=C(Nc1nccs1)C(c1cc(F)ccc1OCc1ccccc1)N1Cc2cccc(C#CCCCN3CCNCC3)c2C1=O]

To a stirred solution of tert-butyl 4-(5-(2-(1-(2-(benzyloxy)-5-fluorophenyl)-2-oxo-2-(thiazol-2-ylamino)ethyl)-3-oxoisoindolin-4-yl)pent-4-yn-1-yl)piperazine-1-carboxylate (348 mg, 0.48 mmol) in dichloromethane (3 ml) was added 2,2,2-trifluoroacetic acid (2 ml) at 0° C., the mixture solution was stirred at this temperature for 2 hours. TLC showed the reaction was complete. The volatiles were evaporated under reduced pressure to afford 2-(2-(benzyloxy)-5-fluorophenyl)-2-(1-oxo-7-(5-(piperazin-1-yl)pent-1-yn-1-yl)isoindolin-2-yl)-N-(thiazol-2-yl)acetamide TFA salt (crude) as yellow oil. LC_MS: (ES$^+$): m/z 624.3 [M+H]$^+$. $t_R$=1.958 min. Chemical Formula: $C_{35}H_{34}FN_5O_3S$; Molecular Weight: 623.74;

10. Step—Synthesis of (2S,4R)-1-((2S)-2-(2-(4-(5-(2-(1-(2-(benzyloxy)-5-fluorophenyl)-2-oxo-2-(thiazol-2-ylamino)ethyl)-3-oxoisoindolin-4-yl)pent-4-yn-1-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide

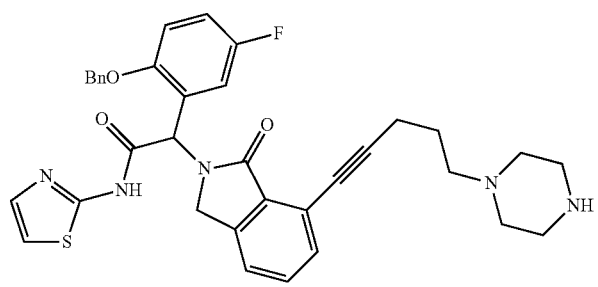

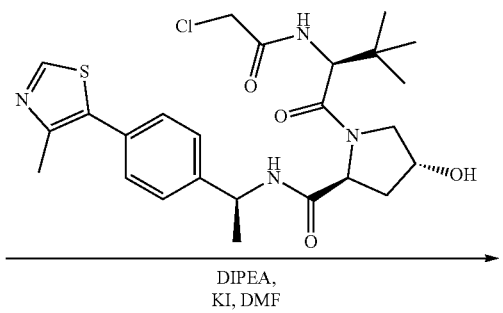

DIPEA,
KI, DMF

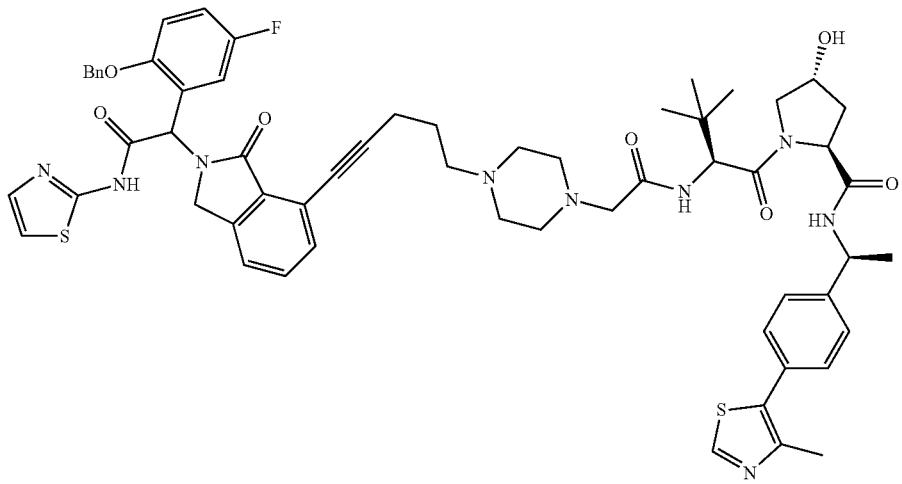

To a stirred solution of 2-(2-(benzyloxy)-5-fluorophenyl)-2-(1-oxo-7-(5-(piperazin-1-yl)pent-1-yn-1-yl)isoindolin-2-yl)-N-(thiazol-2-yl)acetamide (crude, <=0.48 mmol), N-ethyl-N-isopropylpropan-2-amine (124 mg, 0.96 mmol) and potassium iodide (8 mg, 0.05 mmol) in N,N-dimethylformamide (3 ml) was added (2S,4R)-1-((S)-2-(2-chloroacetamido)-3,3-dimethylbutanoyl)-4-hydroxy-N—((S)-1-(4-(4-methylthiazol-5-yl)phenyl)ethyl)pyrrolidine-2-carboxamide (250 mg, 0.48 mmol), and the mixture was stirred at 50° C. overnight under nitrogen. TLC showed the reaction was complete. The reaction mixture was partitioned between ethyl acetate (20 ml) and water (20 ml), the organic layer was washed with brine (20 ml×2), dried over anhydrous sodium sulfate and concentrated under reduced pressure to give a crude residue which was purified by silica gel flash column chromatography (eluted with 2-10% methanol in dichloromethane) to afford (2S,4R)-1-((2S)-2-(2-(4-(5-(2-(1-(2-(benzyloxy)-5-fluorophenyl)-2-oxo-2-(thiazol-2-ylamino)ethyl)-3-oxoisoindolin-4-yl)pent-4-yn-1-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (90 mg, yield 17%) as yellow oil. LC_MS: (ES+): m/z 1108.4 [M+H]+. $t_R$=2.458 min. Chemical Formula: $C_{60}H_{66}FN_9O_7S_2$; Molecular Weight: 1108.35;

11. Step—Synthesis of (2S,4R)-1-((2S)-2-(2-(4-(5-(2-(1-(2-fluoro-5-hydroxyphenyl)-2-oxo-2-(thiazol-2-ylamino)ethyl)-3-oxoisoindolin-4-yl)pent-4-yn-1-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

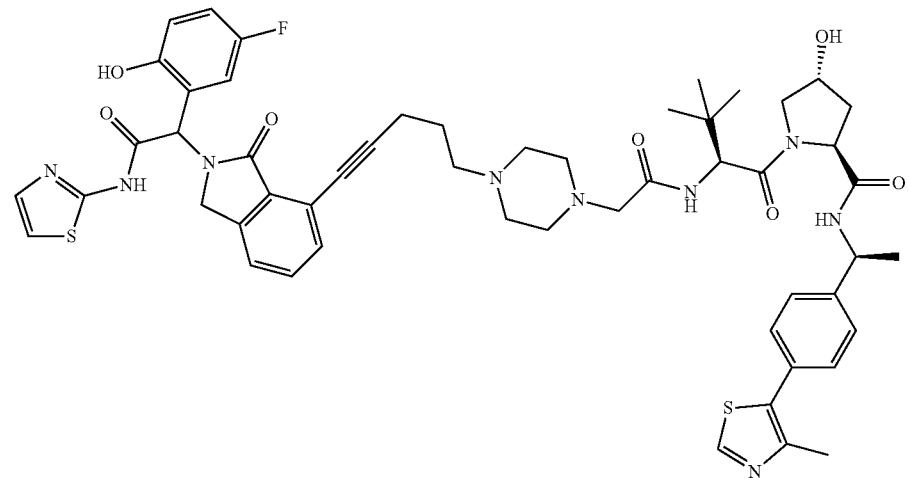 [SMILES: Cc1ncsc1-c1ccc([C@H](C)NC(=O)[C@@H]2C[C@@H](O)CN2C(=O)[C@@H](NC(=O)CN2CCN(CCCC#Cc3cccc4c3C(=O)N(C(C(=O)Nc3nccs3)c3cc(F)ccc3O)C4)CC2)C(C)(C)C)cc1]

To a stirred solution of (2S,4R)-1-((2S)-2-(2-(4-(5-(2-(1-(2-(benzyloxy)-5-fluorophenyl)-2-oxo-2-(thiazol-2-ylamino)ethyl)-3-oxoisoindolin-4-yl)pent-4-yn-1-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (90 mg, 0.08 mmol) in anhydrous dichloromethane (5 ml) was added boron tribromide (102 mg, 0.41 mmol) in dichloromethane (1 ml) dropwise at −40° C. under nitrogen. The mixture solution was stirred at this temperature for 2 hours. TLC showed the reaction was complete. The reaction mixture was quenched with water (3 ml) at −60° C. and aqueous solution of sodium bicarbonate was added till pH 7-8. The mixture was diluted with dichloromethane (20 ml), the organic layer was washed with brine (20 ml×2), dried over anhydrous sodium sulfate and concentrated under reduced pressure to give a crude residue which was purified by preparative TLC (eluted with 5% methanol in dichloromethane) to afford (2S,4R)-1-((2S)-2-(2-(4-(5-(2-(1-(5-fluoro-2-hydroxyphenyl)-2-oxo-2-(thiazol-2-ylamino)ethyl)-3-oxoisoindolin-4-yl)pent-4-yn-1-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (5.6 mg, yield 13% two steps) as white solid. LC_MS: (ES$^+$): m/z 1018.4 [M+H]$^+$. $t_R$=2.402 min. $^1$H NMR (400 MHz, DMSO-d$_6$): δ 0.96 (s, 9H), 1.34-1.36 (m, 3H), 1.45-1.51 (m, 1H), 1.74-1.83 (m, 1H), 1.96-2.06 (m, 2H), 2.11-2.21 (m, 2H), 2.44-2.45 (m, 3H), 3.00-3.16 (m, 6H), 3.61-3.62 (m, 1H), 3.67-3.73 (m, 2H), 3.81-3.98 (m, 4H), 4.23-4.29 (m, 1H), 4.42-4.46 (m, 1H), 4.52-4.65 (m, 2H), 4.88-4.93 (m, 1H), 5.14 (s, 1H), 6.32 (s, 1H), 6.84-6.87 (m, 1H), 6.99-7.02 (m, 1H), 7.13 (s, 2H), 7.26 (s, 2H), 7.36-7.42 (m, 4H), 7.47-7.49 (m, 1H), 7.52-7.54 (m, 1H), 7.59-7.61 (m, 1H), 7.66-7.70 (m, 1H), 7.81-7.83 (m, 1H), 8.18 (s, 1H), 8.39-8.40 (m, 1H), 8.98 (s, 1H), 10.13 (s, 1H), 12.64 (s, 1H). Chemical Formula: $C_{53}H_{60}FN_9O_7S_2$; Molecular Weight: 1018.23;

Synthesis of Example 81

(2S,4R)-1-((S)-18-(tert-butyl)-1-(1-isopropyl-6-((2-(4-methoxypiperidin-1-yl)pyrimidin-4-yl)amino)-1H-imidazo[4,5-c]pyridin-2-yl)-16-oxo-2,5,8,11,14-pentaoxa-17-azanonadecan-19-oyl)-4-hydroxy-N—((S)-1-(4-(4-methylthiazol-5-yl)phenyl)ethyl)pyrrolidine-2-carboxamide

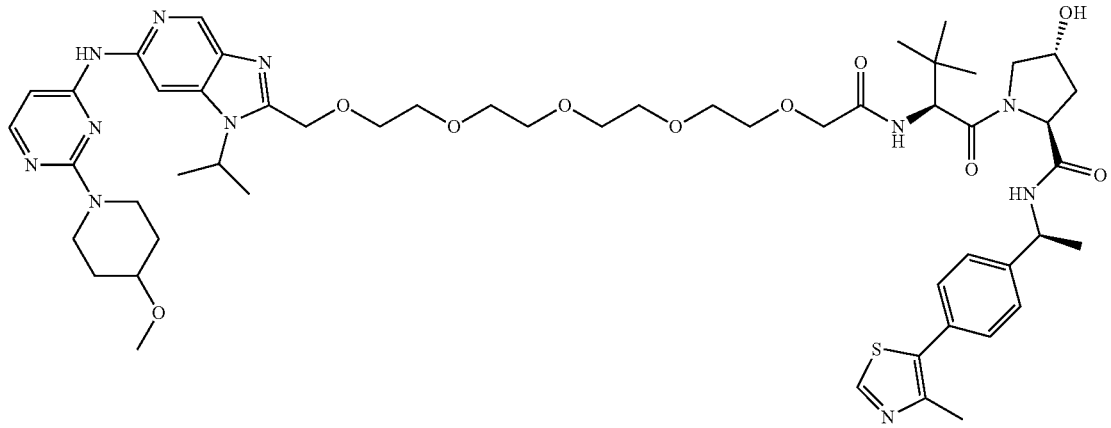 [SMILES: COC1CCN(c2nccc(Nc3cc4c(cn3)nc(COCCOCCOCCOCCOCC(=O)N[C@H](C(=O)N3C[C@H](O)C[C@H]3C(=O)N[C@@H](C)c3ccc(-c5scnc5C)cc3)C(C)(C)C)n4C(C)C)n2)CC1]

Synthesis Scheme:

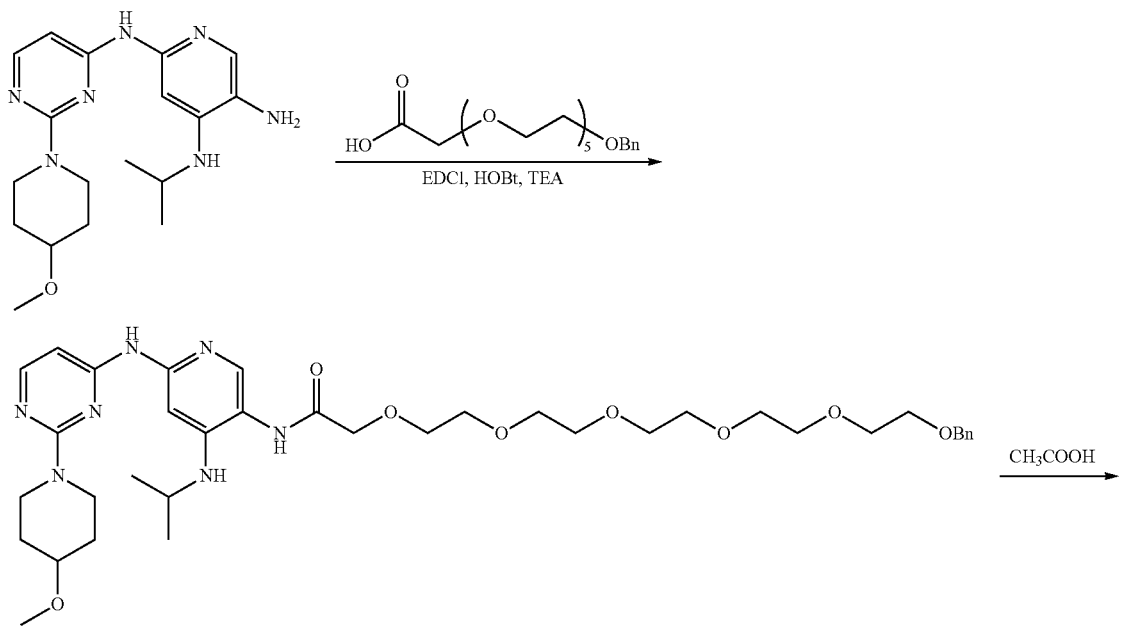

601 602
-continued
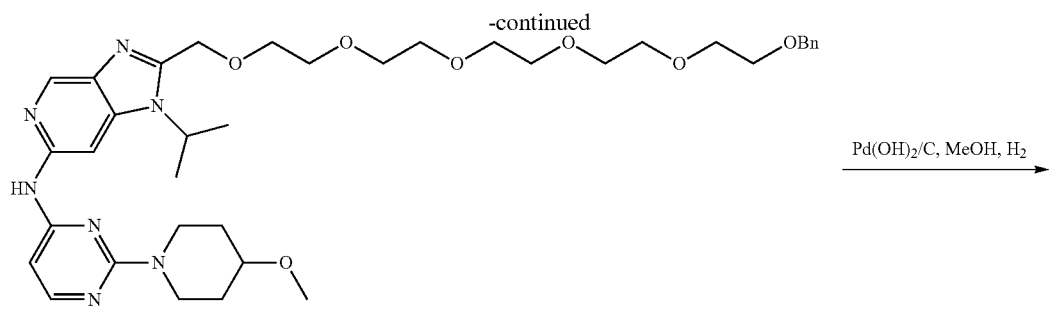
Pd(OH)₂/C, MeOH, H₂ →
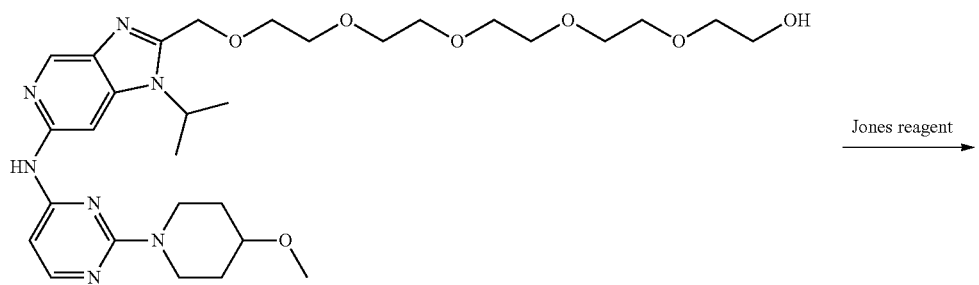
Jones reagent →
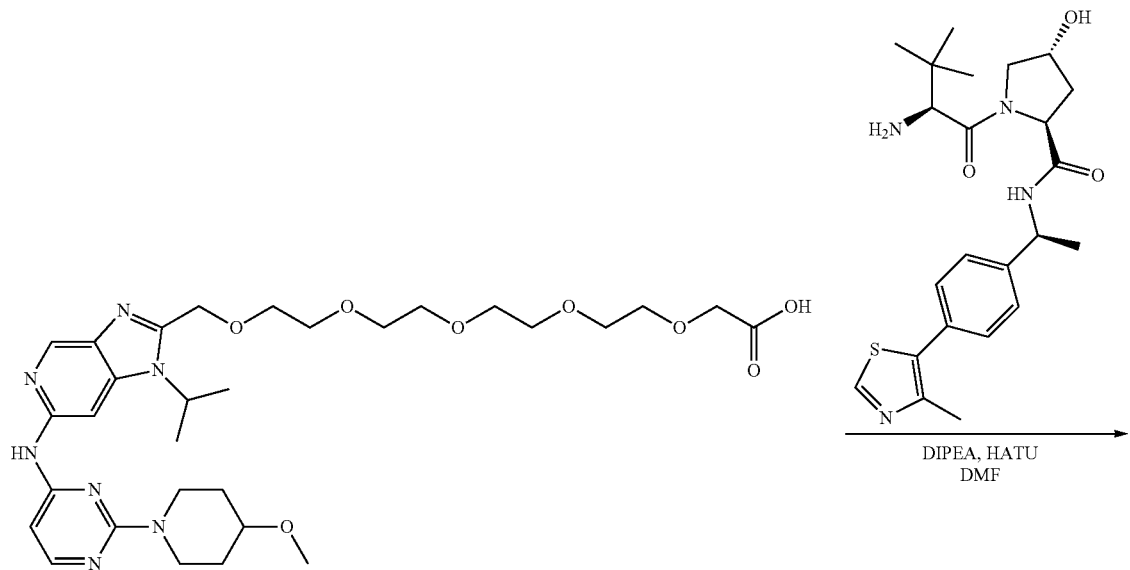
DIPEA, HATU
DMF
→
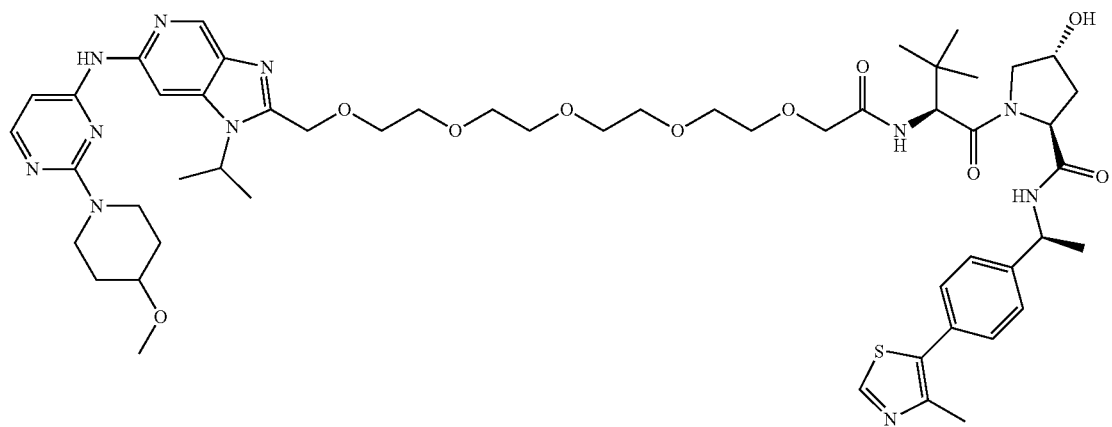

Experimental Section

1. Step—Synthesis of N-(4-(Isopropylamino)-6-((2-(4-methoxypiperidin-1-yl)pyrimidin-4-yl)amino)pyridin-3-yl)-1-phenyl-2,5,8,11,14,17-hexaoxanonadecan-19-amide

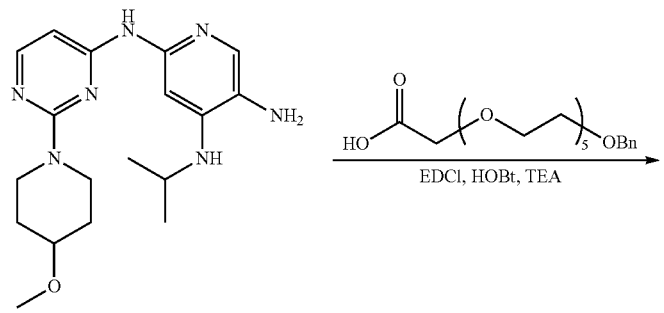

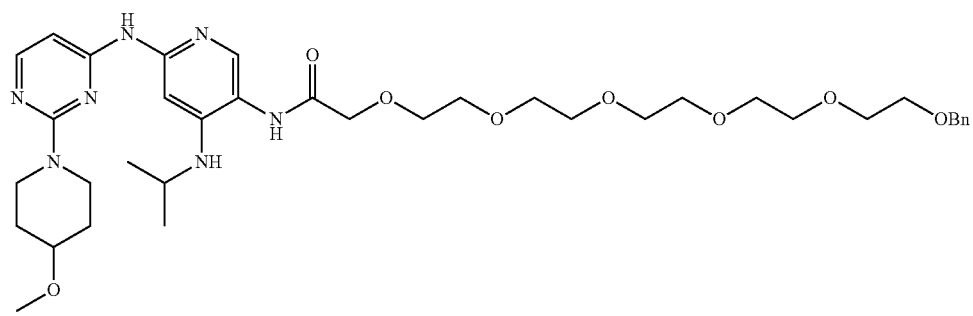

To a solution of $N^4$-isopropyl-$N^2$-(2-(4-methoxypiperidin-1-yl)pyrimidin-4-yl)pyridine-2,4,5-triamine [J. Med. Chem. 2015, 58, 8877-8895] (580 mg, 1.62 mmol) in DCM (10 mL) were added 1-phenyl-2,5,8,11,14,17-hexaoxanonadecan-19-oic acid (689.7 mg, 1.78 mmol, see example 70), TEA (328.4 mg, 3.25 mmol), EDCI (465.8 mg, 2.43 mmol) and HOBt (328.4 mg, 2.43 mmol) at 10° C. The resulting solution was stirred at 20° C. for 16 h. The reaction was diluted with a solution of H₂O (40 mL), the mixture was extracted with DCM (20 mL×2). The combined organic layers were dried over anhydrous sodium sulfate and concentration. The residue was purified with silica gel column to afford the desired product N-(4-(Isopropylamino)-6-((2-(4-methoxypiperidin-1-yl)pyrimidin-4-yl)amino)pyridin-3-yl)-1-phenyl-2,5,8,11,14,17-hexaoxanonadecan-19-amide (480 mg, 41% yield). Chemical Formula: $C_{37}H_{55}N_7O_8$; Molecular Weight: 725.87

2. Step—Synthesis of 1-Isopropyl-N-(2-(4-methoxypiperidin-1-yl)pyrimidin-4-yl)-2-(18-phenyl-2,5,8,11,14,17-hexaoxaoctadecyl)-1H-imidazo[4,5-c]pyridin-6-amine

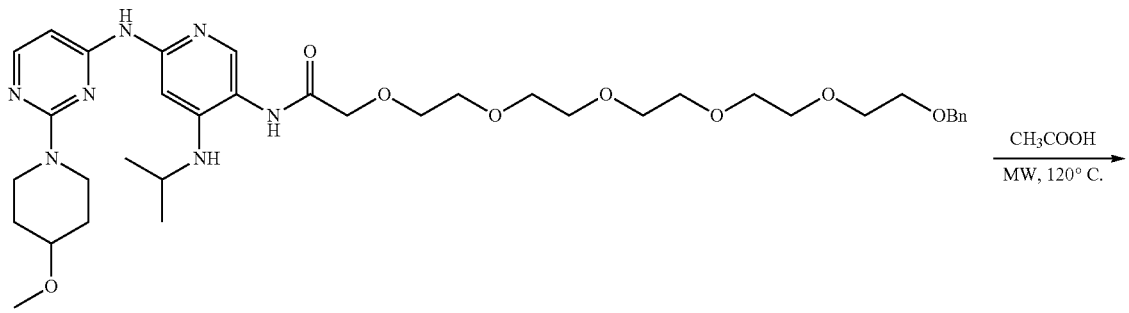

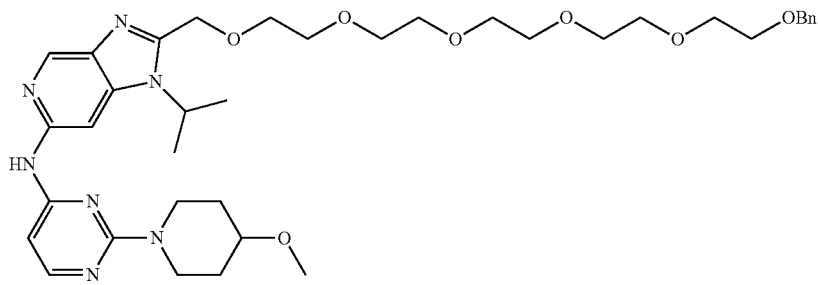

A mixture of N-(4-(Isopropylamino)-6-((2-(4-methoxypiperidin-1-yl)pyrimidin-4-yl)amino)pyridin-3-yl)-1-phenyl-2,5,8,11,14,17-hexaoxanonadecan-19-amide (480 mg, 0.66 mmol) in CH$_3$COOH (5 mL) was radiated at 120° C. for 10 h with microwave. After cooling to rt, the solvent was removed in vacuo to afford crude desired product 1-Isopropyl-N-(2-(4-methoxypiperidin-1-yl)pyrimidin-4-yl)-2-(18-phenyl-2,5,8,11,14,17-hexaoxaoctadecyl)-1H-imidazo[4,5-c]pyridin-6-amine (900 mg, crude), which was used in the next step without further purification. Chemical Formula: C$_{37}$H$_{53}$N$_7$O$_7$; Molecular Weight: 707.86

3. Step—Synthesis of 1-(1-Isopropyl-6-((2-(4-methoxypiperidin-1-yl)pyrimidin-4-yl)amino)-1H-imidazo[4,5-c]pyridin-2-yl)-2,5,8,11,14-pentaoxahexadecan-16-ol

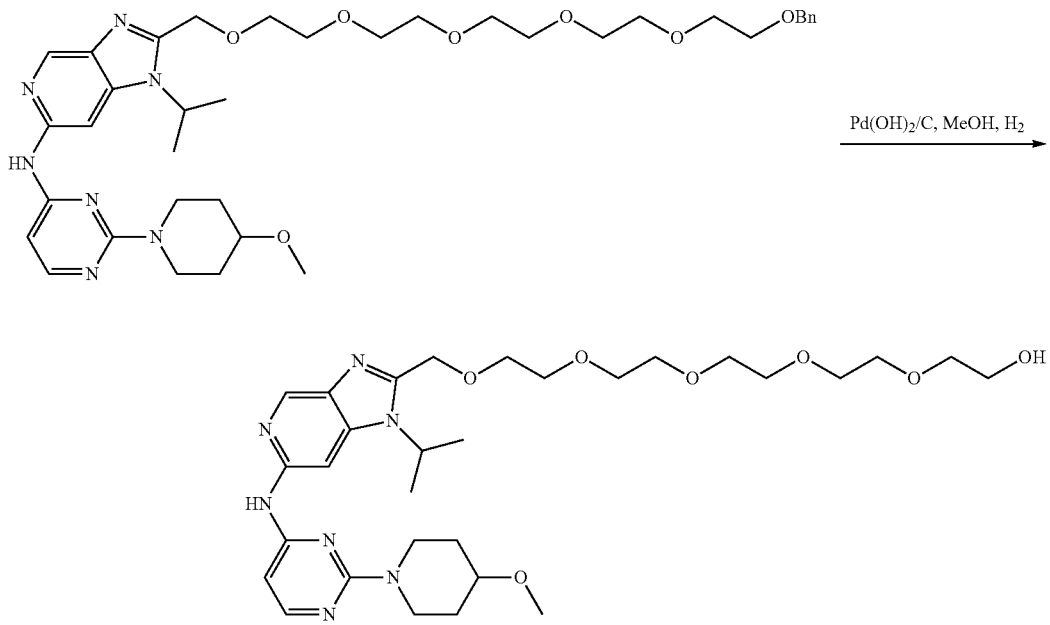 [SMILES: COC1CCN(c2nccc(Nc3cc4c(cn3)nc(COCCOCCOCCOCCOCCOCc3ccccc3)n4C(C)C)n2)CC1 ; COC1CCN(c2nccc(Nc3cc4c(cn3)nc(COCCOCCOCCOCCOCCO)n4C(C)C)n2)CC1]

To a solution of 1-Isopropyl-N-(2-(4-methoxypiperidin-1-yl)pyrimidin-4-yl)-2-(18-phenyl-2,5,8,11,14,17-hexaoxaoctadecyl)-1H-imidazo[4,5-c]pyridin-6-amine (900 mg, crude) in MeOH (50 mL) was added Pd(OH)$_2$/C (180 mg) at 15° C. The mixture was stirred at 15° C. for 2 h under H$_2$ 1 atm. Then the mixture was filtered through Celite, and the filtrate was concentrated to afford the desired product 1-(1-Isopropyl-6-((2-(4-methoxypiperidin-1-yl)pyrimidin-4-yl)amino)-1H-imidazo[4,5-c]pyridin-2-yl)-2,5,8,11,14-pentaoxahexadecan-16-ol (350 mg, crude), which was used into next reaction without further purification. Chemical Formula: C$_{30}$H$_{47}$N$_7$O$_7$; Molecular Weight: 617.74

4. Step—Synthesis of 1-(1-Isopropyl-6-((2-(4-methoxypiperidin-1-yl)pyrimidin-4-yl)amino)-1H-imidazo[4,5-c]pyridin-2-yl)-2,5,8,11,14-pentaoxa-hexadecan-16-oic acid

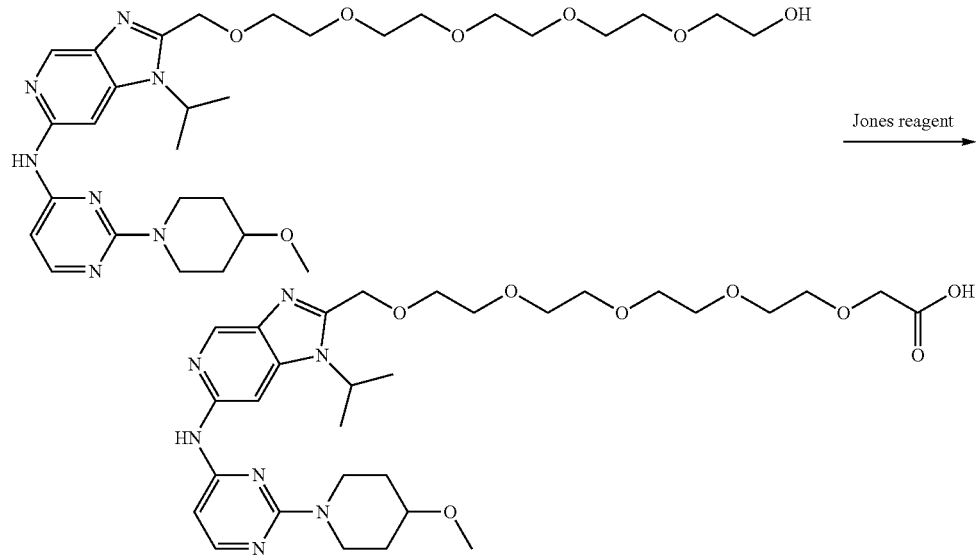

To a solution of 1-(1-Isopropyl-6-((2-(4-methoxypiperidin-1-yl)pyrimidin-4-yl)amino)-1H-imidazo [4,5-c]pyridin-2-yl)-2,5,8,11,14-pentaoxahexadecan-16-ol (130 mg, crude) in DMF (5 mL) was added Jones reagent (2.0 mL) at 0° C. under $N_2$ 1 atm. The mixture was stirred at 15° C. for 2 h. Then the mixture was filtered through Celite, and the filtrate was concentrated to afford the desired product 1-(1-Isopropyl-6-((2-(4-methoxypiperidin-1-yl)pyrimidin-4-yl)amino)-1H-imidazo[4,5-c]pyridin-2-yl)-2,5,8,11,14-pentaoxahexadecan-16-oic acid (210 mg crude), which was used in the next reaction without further purification. Chemical Formula: $C_{30}H_{45}N_7O_8$; Molecular Weight: 631.72

5. Step—Synthesis of (2S,4R)-1-((S)-18-(Tert-butyl)-1-(1-isopropyl-6-((2-(4-methoxypiperidin-1-yl)pyrimidin-4-yl)amino)-1H-imidazo[4,5-c]pyridin-2-yl)-16-oxo-2,5,8,11,14-pentaoxa-17-azanonadecan-19-oyl)-4-hydroxy-N—((S)-1-(4-(4-methylthiazol-5-yl)phenyl)ethyl)pyrrolidine-2-carboxamide

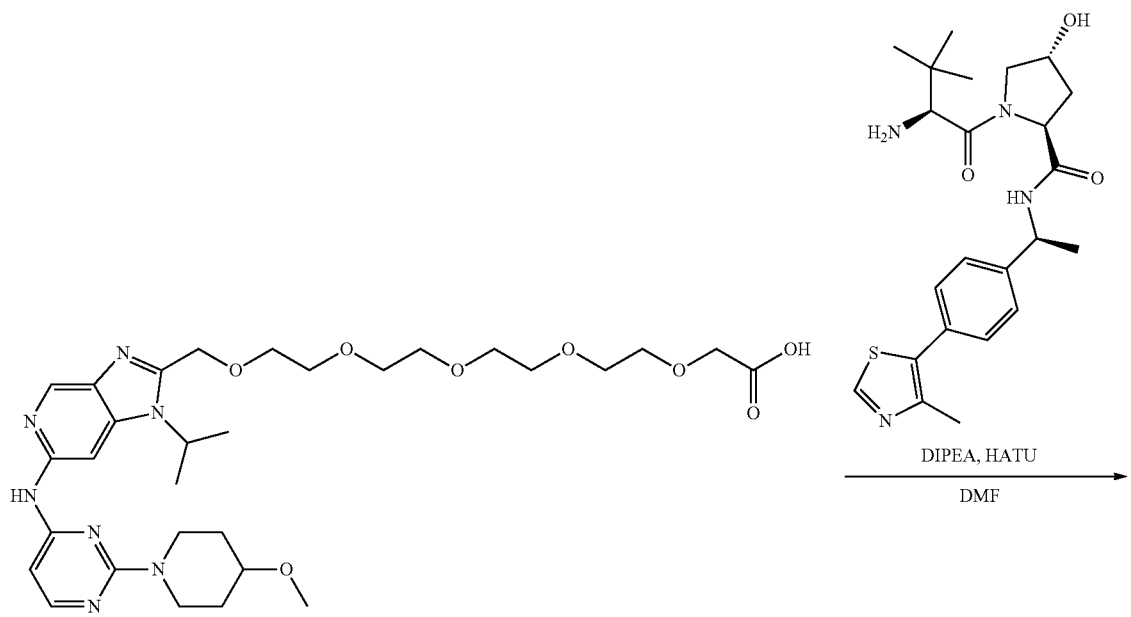

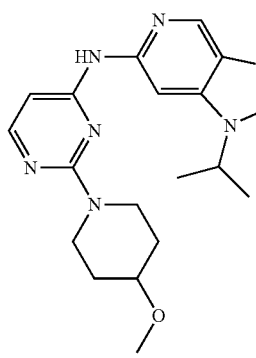
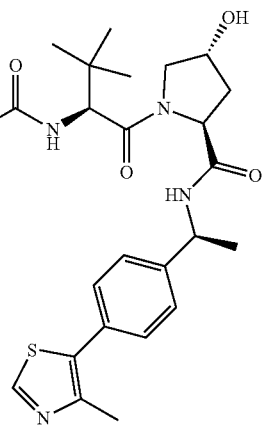

To a solution of 1-(1-Isopropyl-6-((2-(4-methoxypiperidin-1-yl)pyrimidin-4-yl)amino)-1H-imidazo [4,5-c]pyridin-2-yl)-2,5,8,11,14-pentaoxahexadecan-16-oic acid (210 mg crude, ~0.25 mmol) and (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (110 mg, 0.25 mmol) in DMF (15 mL) were added DIPEA (85 mg, 0.66 mmol) and HATU (251 mg, 0.66 mmol) at 15° C. After stirring at 15° C. for 16 h, the reaction was diluted with H₂O (30 mL). The resulting mixture was extracted with DCM (20 mL×2). The combined organic layers were dried over anhydrous sodium sulfate and concentration. The residue was purified with silica gel column and prep-HPLC to afford the desired product (2S,4R)-1-((S)-8-(Tert-butyl)-1-(1-isopropyl-6-((2-(4-methoxypiperidin-1-yl)pyrimidin-4-yl)amino)-1H-imidazo [4,5-c]pyridin-2-yl)-16-oxo-2,5,8,11,14-pentaoxa-17-azanonadecan-19-oyl)-4-hydroxy-N—((S)-1-(4-(4-methylthiazol-5-yl)phenyl)ethyl)pyrrolidine-2-carboxamide (4.3 mg) as a white solid. $^1$H NMR (400 MHz, CD₃OD): δ: 8.77 (s, 1H), 8.60 (s, 1H), 8.45 (s, 1H), 8.24 (br.s, 1H), 7.77 (d, J=4.0 Hz, 1H), 7.52 (d, J=12.0 Hz, 1H), 7.28-7.33 (m, 4H), 4.88-4.94 (m, 3H), 4.76 (d, J=12.0 Hz, 1H), 4.56-4.59 (m, 1H), 4.47 (s, 1H), 3.91-4.00 (m, 2H), 3.51-3.66 (m, 20H), 3.31 (s, 3H), 2.37 (s, 3H), 2.09-2.16 (m, 2H), 1.86-1.89 (m, 3H), 1.60 (s, 1H), 1.58 (s, 1H), 1.39 (d, J=8.0 Hz, 3H), 0.93 (s, 9H). LCMS: m/e=529.8 [M+2H]$^{2+}$, $t_R$=3.35 min. Chemical Formula: C₅₃H₇₅N₁₁O₁₀S; Molecular Weight: 1058.3

Synthesis of Example 82

2-(7-(3-(2-(2-(2-((2-(2,6-dioxopiperidin-3-yl)-1,3-dioxoisoindolin-5-yl)amino)ethoxy)ethoxy)ethoxy)prop-1-yn-1-yl)-1-oxoisoindolin-2-yl)-2-(5-fluoro-2-hydroxyphenyl)-N-(thiazol-2-yl)acetamide

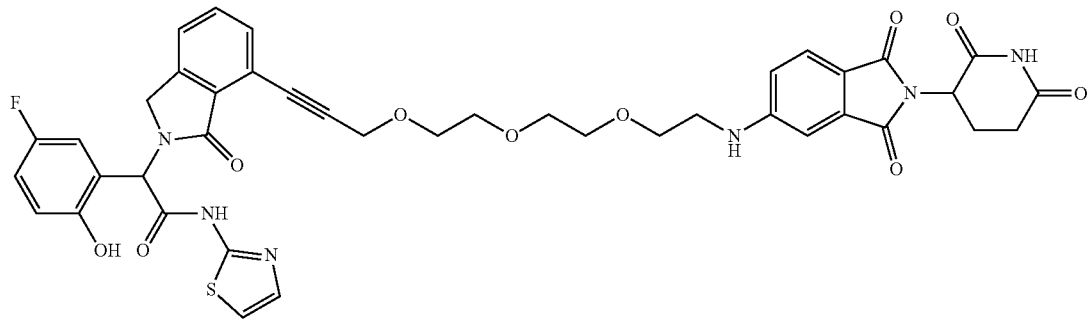 [SMILES: O=C1CCC(N2C(=O)c3ccc(NCCOCCOCCOCC#Cc4cccc5c4C(=O)N(C(C(=O)Nc4nccs4)c4cc(F)ccc4O)C5)cc3C2=O)C(=O)N1]

Synthesis Scheme:

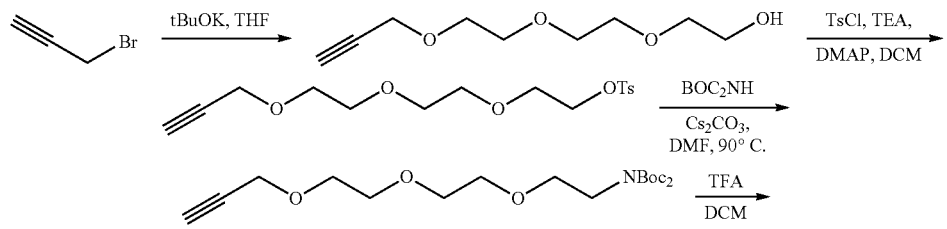

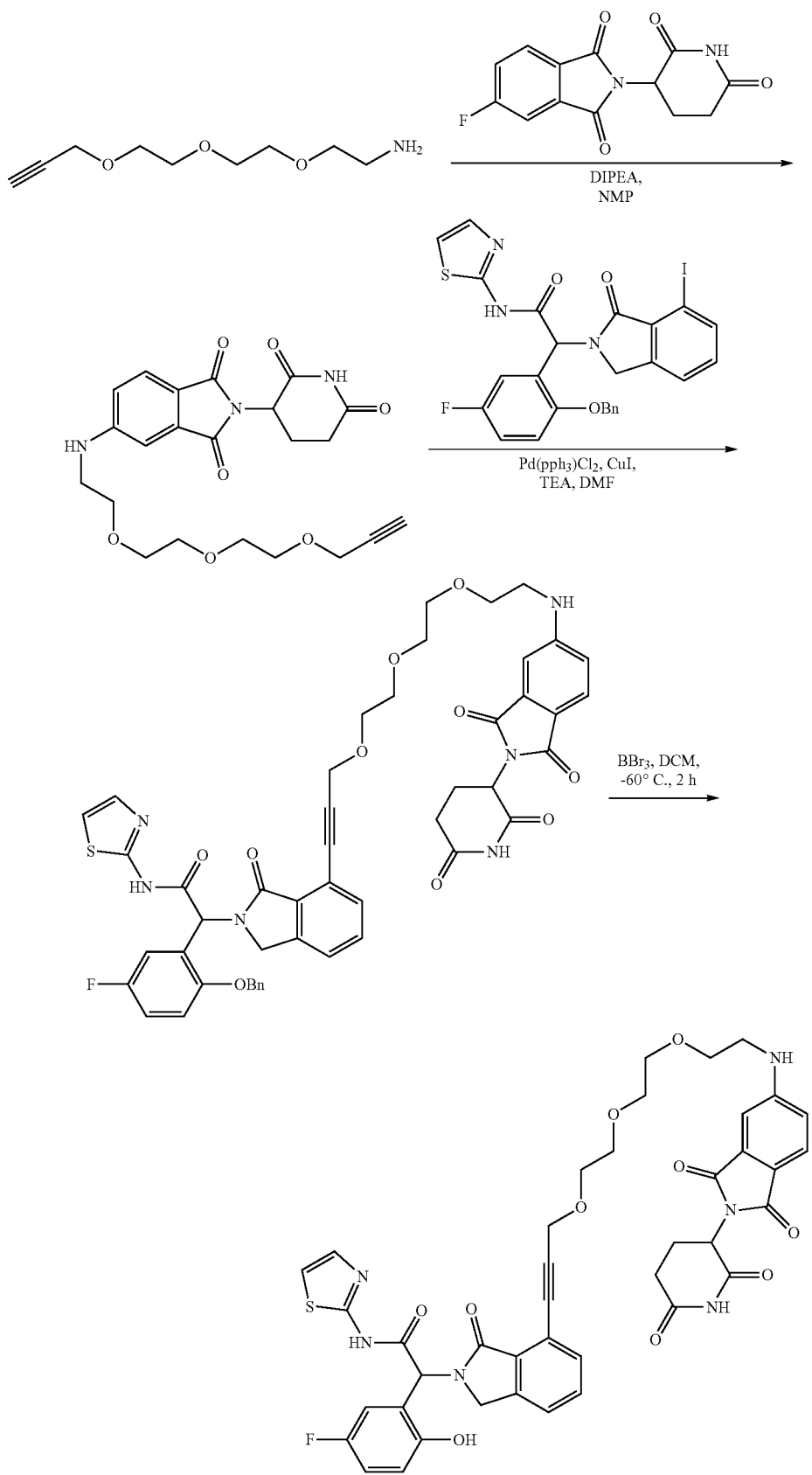

Experiments

1. Step—Synthesis of 2-(2-(2-(prop-2-yn-1-yloxy)ethoxy)ethoxy)ethanol

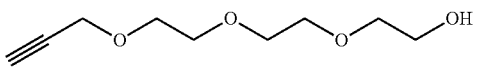

To a stirred solution of potassium tert-butanolate (38 ml, 38 mmol, 1M in tetrahydrofuran) in tetrahydrofuran (100 ml) was added 2,2'-(ethane-1,2-diylbis(oxy))diethanol (10.6 g, 100 mmol) slowly at room temperature, and the reaction mixture was stirred at room temperature for 30 minutes. The reaction mixture was cooled to 0° C., then 3-bromoprop-1-yne (3.6 g, 30 mmol) in tetrahydrofuran (25 ml) was added dropwise, and the resulting reaction mixture was allowed to warm up to room temperature and stirred overnight. TLC showed the reaction was complete. The reaction mixture was quenched with water (50 ml) at 0° C. and extracted with ethyl acetate (100 ml×2). The combined organic layers were washed with brine (50 ml×2), dried over anhydrous sodium sulfate, and concentrated under reduced pressure to give a residue which was purified by silica gel flash chromatography (eluted with 30% ethyl acetate in hexane) to afford 2-(2-(2-(prop-2-yn-1-yloxy)ethoxy)ethoxy)ethanol (4 g, yield 70%) as colorless oil. $^1$H NMR (400 Hz, CDCl$_3$): δ 2.44 (d, J=2.0 Hz, 1H), 2.56-2.86 (m, 1H), 3.60-3.63 (m, 2H), 3.66-3.75 (m, 10H), 4.21 (d, J=2.4 Hz, 2H). Chemical Formula: C$_9$H$_{16}$O$_4$; Molecular Weight: 188.22;

2. Step—Synthesis of 2-(2-(2-(prop-2-yn-1-yloxy)ethoxy)ethoxy)ethyl 4-methylbenzenesulfonate

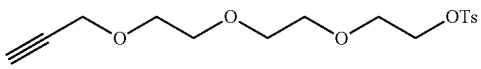 [SMILES: C#CCOCCOCCOCCOS(=O)(=O)c1ccc(C)cc1]

To a stirred solution of 2-(2-(2-(prop-2-yn-1-yloxy)ethoxy)ethoxy)ethanol (1.0 g, 5.3 mmol), triethylamine (1.5 ml, 10 mmol) in dichloromethane (10 ml) was added tosyl-chloride (1.1 g, 5.8 mmol) and 4-dimethylaminopyridine (64 mg, 0.53 mmol) at 0° C. The resulting solution was allowed to warm up to room temperature and stirred for 2 hours. TLC showed the reaction was complete. The mixture was poured into water (20 ml) and extracted with dichloromethane (20 ml×2). The combined organic layers were washed with brine (20 ml), dried over anhydrous sodium sulfate, and concentrated under reduced pressure to give a crude residue which was purified by silica gel flash column chromatography (eluted with 30% ethyl acetate in hexane) to afford 2-(2-(2-(prop-2-yn-1-yloxy)ethoxy)ethoxy)ethyl 4-methylbenzenesulfonate (1 g, yield 55%) as colorless oil.

3. Step—Synthesis of N,N-bis-Boc 2-(2-(2-(prop-2-yn-1-yloxy)ethoxy)ethoxy)ethan-1-amine

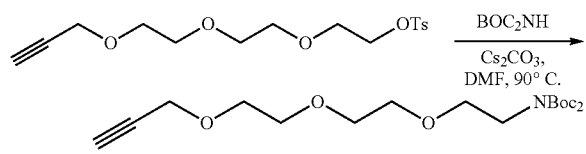

A mixture of di-tert-butyl iminodicarboxylate (0.7 g, 3.2 mmol), 2-(2-(2-(prop-2-yn-1-yloxy)ethoxy)ethoxy)ethyl 4-methylbenzenesulfonate (1.0 g, 2.9 mmol) and cesium carbonate (1.15 g, 3.5 mmol) in N,N-dimethylformamide (10 ml) was stirred at 90° C. overnight under nitrogen atmosphere. TLC showed the reaction was complete. The mixture was partitioned between ethyl acetate (30 ml) and water (30 ml). The organic layer was collected, washed with brine (20 ml), dried over anhydrous sodium sulfate, and concentrated under reduced pressure to give a crude residue which was purified by silica gel flash chromatography (eluted with 25% ethyl acetate in hexane) to afford N,N-bis-Boc 2-(2-(2-(prop-2-yn-1-yloxy)ethoxy)ethoxy)ethan-1-amine (550 mg, yield 48%) as yellow oil. $^1$H NMR (400 Hz, CDCl$_3$): δ 1.50 (s, 18H), 2.42 (d, J=2.0 Hz, 1H), 2.59-3.62 (m, 6H), 3.65-3.71 (m, 4H), 3.79 (t, J=6.0 Hz, 2H), 4.20 (d, J=2.4 Hz, 2H). Chemical Formula: C$_{19}$H$_{33}$NO$_7$; Molecular Weight: 387.47;

4. Step—Synthesis of 2-(2-(2-(prop-2-yn-1-yloxy)ethoxy)ethoxy)ethanamine

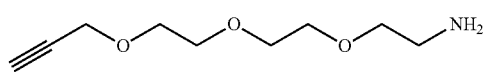

A mixture of N,N-bis-Boc 2-(2-(2-(prop-2-yn-1-yloxy)ethoxy)ethoxy)ethan-1-amine (220 mg, 0.56 mmol) and 2,2,2-trifluoroacetic acid (3 ml) in dichloromethane (5 ml) was stirred at room temperature for 1 hour. TLC showed the reaction was complete. The volatiles were evaporated under reduced pressure. The residue was taken up in ethyl acetate (10 ml) and washed with aqueous sodium bicarbonate solution (sat, 10 ml). The organic layer was collected, dried over anhydrous sodium sulfate, and concentrated under reduced pressure to give a residue which was purified by silica gel flash chromatography (eluted with 5% methanol in dichloromethane) to afford 2-(2-(2-(prop-2-yn-1-yloxy)ethoxy)ethoxy)ethanamine (120 mg, yield 85%) as yellow oil.

5. Step—Synthesis of 2-(2,6-dioxopiperidin-3-yl)-5-((2-(2-(2-(prop-2-yn-1-yloxy)ethoxy)ethoxy)ethyl)amino)isoindoline-1,3-dione

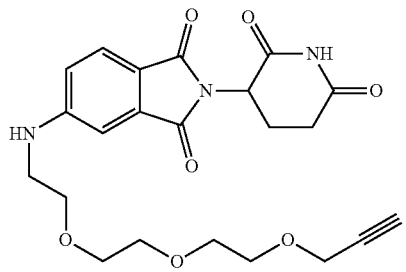 [SMILES: C#CCOCCOCCOCCNc1ccc2c(c1)C(=O)N(C1CCC(=O)NC1=O)C2=O]

A mixture of 2-(2-(2-(prop-2-yn-1-yloxy)ethoxy)ethoxy)ethanamine (120 mg, 0.31 mmol), 2-(2,6-dioxopiperidin-3-yl)-5-fluoroisoindoline-1,3-dione (86 mg, 0.31 mmol), and N-ethyl-N-isopropylpropan-2-amine (0.09 ml, 0.5 mmol) in 1-methylpyrrolidin-2-one (2 ml) was stirred at 90° C. overnight under nitrogen. TLC showed the reaction was complete. The reaction mixture was partitioned between ethyl acetate (50 ml) and water (30 ml). The organic layer was collected, washed with brine (30 ml), dried over anhydrous sodium sulfate, and concentrated under reduced pressure to give a crude residue which was purified by silica gel flash chromatography (eluted with 50% ethyl acetate in dichloromethane) to afford 2-(2,6-dioxopiperidin-3-yl)-5-((2-(2-(2-(prop-2-yn-1-yloxy)ethoxy)ethoxy)ethyl)amino)isoindoline-1,3-dione (55 mg, yield 20%) as yellow solid. LC_MS: (ES⁺): m/z 444.2 [M+H]⁺. $t_R$=2.135 min.

6. Step—Synthesis of 2-(2-(benzyloxy)-5-fluorophenyl)-2-(7-(3-(2-(2-(2-((2-(2,6-dioxopiperidin-3-yl)-1,3-dioxoisoindolin-5-yl)amino)ethoxy)ethoxy)ethoxy)prop-1-yn-1-yl)-1-oxoisoindolin-2-yl)-N-(thiazol-2-yl)acetamide

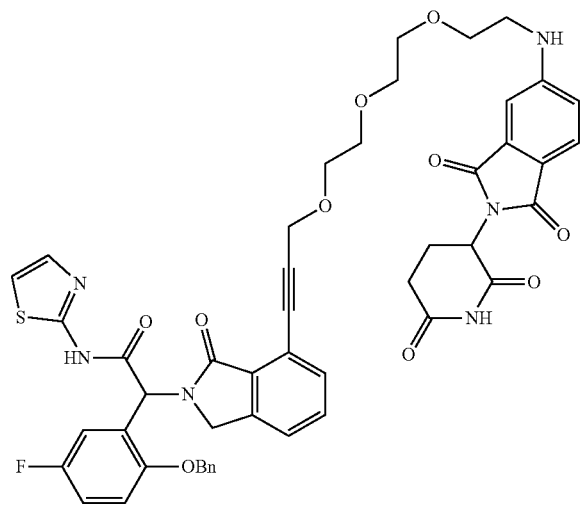 [SMILES: O=C1CCC(N2C(=O)c3ccc(NCCOCCOCCOCC#Cc4cccc5c4C(=O)N(C(C(=O)Nc4nccs4)c4cc(F)ccc4OCc4ccccc4)C5)cc3C2=O)C(=O)N1]

To a solution of 2-(2-(benzyloxy)-5-fluorophenyl)-2-(7-iodo-1-oxoisoindolin-2-yl)-N-(thiazol-2-yl)acetamide (61 mg, 0.10 mmol), 2-(2,6-dioxopiperidin-3-yl)-5-((2-(2-(2-(prop-2-yn-1-yloxy)ethoxy)ethoxy)ethyl)amino)isoindoline-1,3-dione (46 mg, 0.10 mmol) and triethylamine (61 mg, 0.6 mmol) in N,N-dimethylformamide (2 ml) were added cuprous iodide (4 mg, 0.02 mmol) and [1,1'-bis(diphenylphosphino)ferrocene]dichloropalladium(II) (14 mg, 0.02 mmol) at room temperature under nitrogen atmosphere; the mixture was degassed with nitrogen three times. The resulting stirred mixture was refluxed for 2 hours. TLC showed the reaction was complete. The reaction mixture was partitioned between ethyl acetate (20 ml) and water (10 ml). The organic layer was washed with brine (10 ml), dried over anhydrous sodium sulfate, and concentrated under reduced pressure to give a crude residue which was purified by purified by preparative TLC (eluted with 5% methanol in dichloromethane) to afford 2-(2-(benzyloxy)-5-fluorophenyl)-2-(7-(3-(2-(2-(2-((2-(2,6-dioxopiperidin-3-yl)-1,3-dioxoisoindolin-5-yl)amino)ethoxy)ethoxy)ethoxy)prop-1-yn-1-yl)-1-oxoisoindolin-2-yl)-N-(thiazol-2-yl)acetamide (25 mg, yield: 22%) as yellow solid. LC_MS: (ES⁺): m/z 915.3 [M+H]⁺. $t_R$=2.840 min.

7. Step—Synthesis of 2-(7-(3-(2-(2-(2-((2-(2,6-dioxopiperidin-3-yl)-1,3-dioxoisoindolin-5-yl)amino)ethoxy)ethoxy)ethoxy)prop-1-yn-1-yl)-1-oxoisoindolin-2-yl)-2-(5-fluoro-2-hydroxyphenyl)-N-(thiazol-2-yl)acetamide

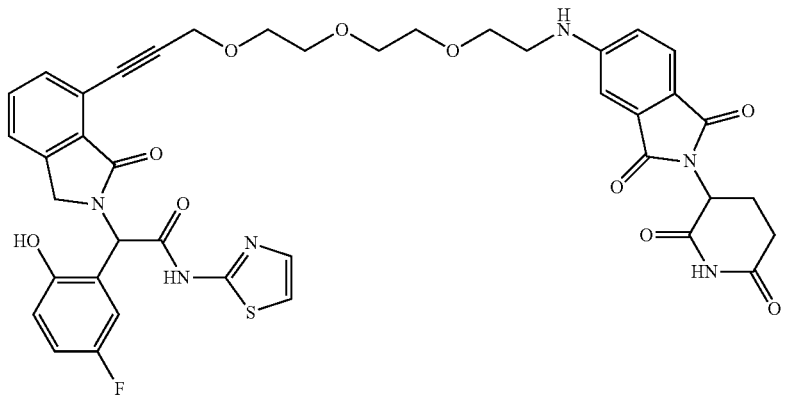 [SMILES: O=C1CCC(N2C(=O)c3ccc(NCCOCCOCCOCC#Cc4cccc5c4C(=O)N(C(C(=O)Nc4nccs4)c4cc(F)ccc4O)C5)cc3C2=O)C(=O)N1]

To a stirred solution of 2-(2-(benzyloxy)-5-fluorophenyl)-2-(7-(3-(2-(2-(2-((2-(2,6-dioxopiperidin-3-yl)-1,3-dioxoisoindolin-5-yl)amino)ethoxy)ethoxy)ethoxy)prop-1-yn-1-yl)-1-oxoisoindolin-2-yl)-N-(thiazol-2-yl)acetamide (25 mg, 0.027 mmol) in anhydrous dichloromethane (5 ml) was added boron tribromide (67 mg, 0.27 mmol in anhydrous dichloromethane (1 ml)) dropwise at −60° C. under nitrogen. The mixture solution was stirred at −60° C. for 2 hours. TLC showed the reaction was complete. The reaction mixture was quenched with water (3 ml) at −60° C. and aqueous solution of sodium bicarbonate was added till pH 7-8. The mixture was diluted with dichloromethane (20 ml), the organic layer was washed with brine (20 ml×2), dried over anhydrous sodium sulfate and concentrated under reduced pressure to give a crude residue which was purified by preparative TLC (eluted with 10% methanol in dichloromethane) to afford 2-(7-(3-(2-(2-(2-((2-(2,6-dioxopiperidin-3-yl)-1,3-dioxoisoindolin-5-yl)amino)ethoxy)ethoxy)ethoxy)prop-1-yn-1-yl)-1-oxoisoindolin-2-yl)-2-(5-fluoro-2-hydroxyphenyl)-N-(thiazol-2-yl)acetamide (6.5 mg, yield 28%) as yellow solid. LC_MS: (ES$^+$): m/z 825.5 [M+H]$^+$. $t_R$=2.580 min. 1H NMR (400 Hz, DMSO-d6): δ 1.41-1.47 (m, 1H) 1.92-2.00 (m, 4H), 2.33 (s, 1H), 2.58-2.68 (m, 1H), 2.83-2.91 (m, 1H), 3.55-3.58 (m, 6H), 3.66-3.76 (m, 2H), 3.91 (d, J=17.6 Hz, 1H), 4.43 (s, 2H), 4.56 (d, J=18.0 Hz, 1H), 5.00-5.05 (m, 1H), 5.31-5.33 (m, 1H), 6.27 (s, 1H), 6.83-6.92 (m, 2H), 6.99 (s, 1H), 7.10-7.41 (m, 4H), 7.47-7.58 (m, 4H), 9.97 (s, 1H), 11.06 (s, 1H), 12.60 (s, 1H). Chemical Formula: $C_{41}H_{37}FN_6O_{10}S$; Molecular Weight: 824.83;

Synthesis of Example 85

(2S,4R)-4-hydroxy-1-((S)-2-(2-(3-(4-(3-((1-isopropyl-6-((2-(4-methoxypiperidin-1-yl)pyrimidin-4-yl)amino)-1H-imidazo[4,5-c]pyridin-2-yl)methoxy)propyl)piperazin-1-yl)propoxy)acetamido)-3,3-dimethylbutanoyl)-N—((S)-1-(4-(4-methylthiazol-5-yl)phenyl)ethyl)pyrrolidine-2-carboxamide

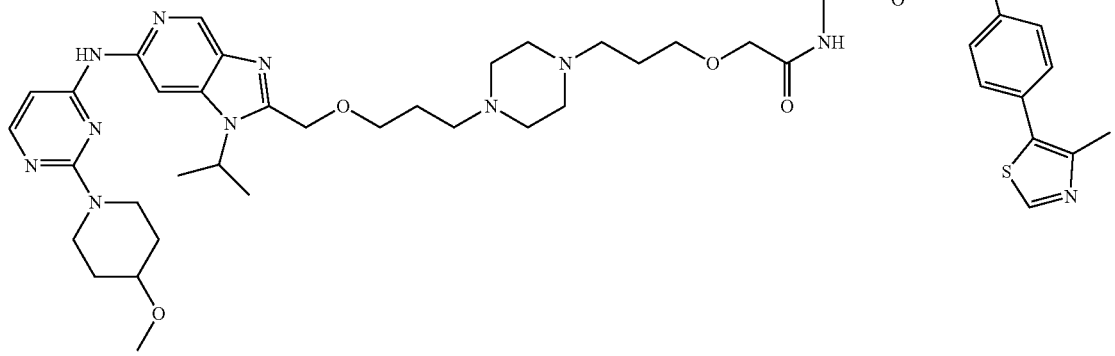

Synthetic Scheme

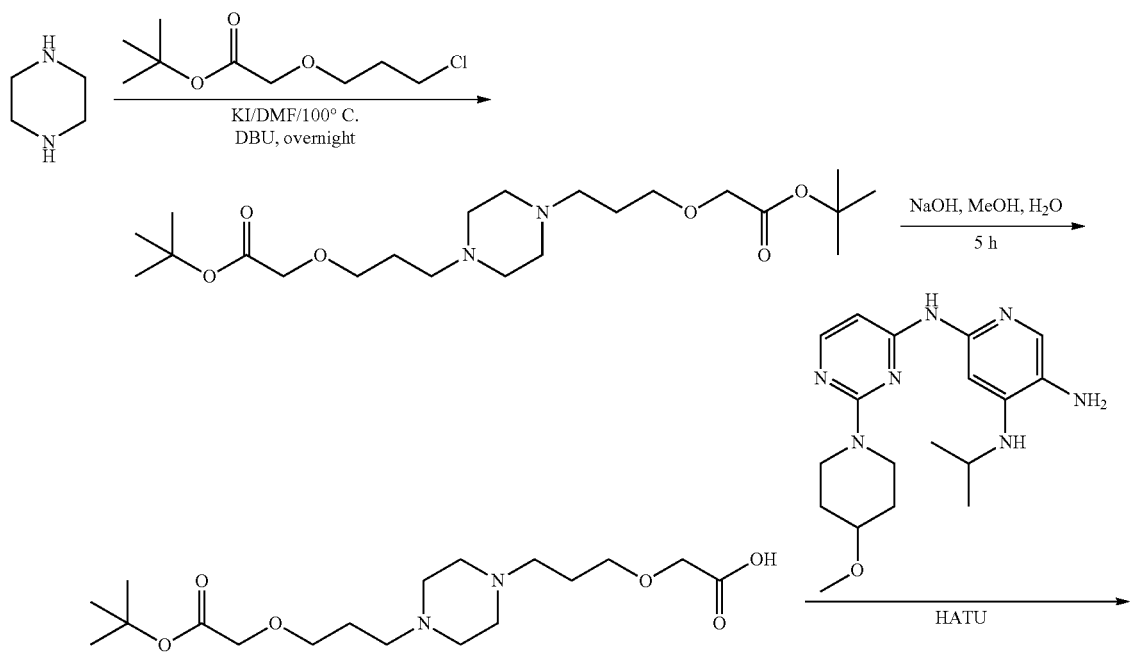

619 620
-continued
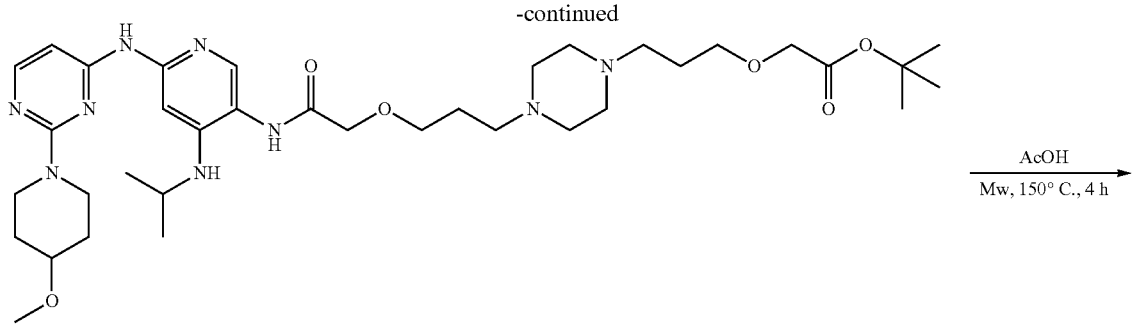
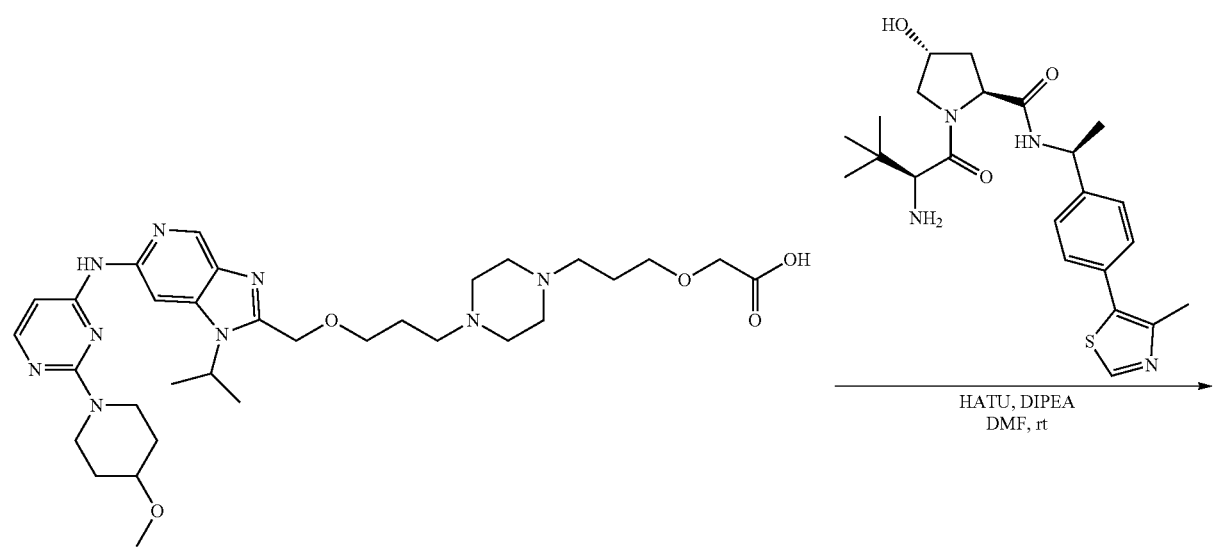
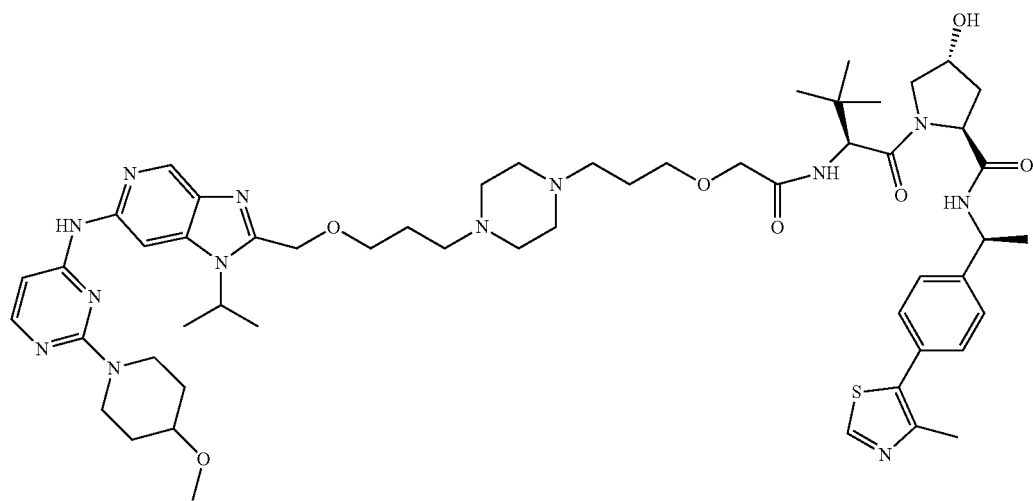

Experimental Section

1. Step—Synthesis of Di-tert-butyl 2,2'-((piperazine-1,4-diylbis(propane-3,1-diyl))bis(oxy))diacetate

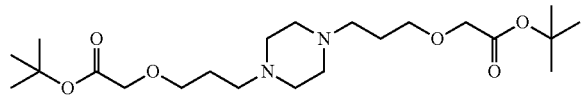 [SMILES: CC(C)(C)OC(=O)COCCCN1CCN(CCCOCC(=O)OC(C)(C)C)CC1]

To a solution of piperazine (86 mg, 1.0 mmol) in CH$_3$CN (10 mL) were added tert-butyl 2-(3-chloropropoxy)acetate (628 mg, 3.0 mmol), DBU (456 mg, 3.0 mmol) and KI (33 mg, 0.2 mmol). The mixture was stirred at 100° C. overnight. After the mixture was cooled to r.t., it was quenched with water (10 mL), and extracted with ethyl acetate (10 mL×3). The combined organic layers were washed with brine (3 mL), dried over anhydrous sodium sulfate and concentrated under vacuum. The residue was purified by silica gel column chromatography using ethyl acetate/petroleum ether (1:1) as eluent to afford the desired product Di-tert-butyl 2,2'-((piperazine-1,4-diylbis(propane-3,1-diyl))bis(oxy))diacetate as a colorless oil (200 mg, 46.5% yield). $^1$H NMR (400 MHz, CDCl$_3$): δ 3.94 (s, 4H), 3.56 (t, J=6.4 Hz, 4H), 2.42-2.47 (m, 12H), 1.79-1.83 (m, 4H), 1.48 (s, 18H). Chemical Formula: C$_{22}$H$_{42}$N$_2$O$_6$; Molecular Weight: 430.59

2. Step—Synthesis of 2-(3-(4-(3-(2-(Tert-butoxy)-2-oxoethoxy)propyl)piperazin-1-yl)propoxy)acetic acid

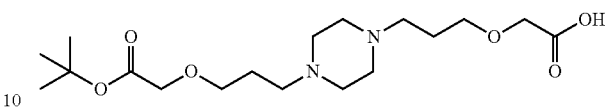

To a solution of Di-tert-butyl 2,2'-((piperazine-1,4-diylbis(propane-3,1-diyl))bis(oxy))diacetate (1.5 g, 4.01 mmol) in MeOH (30 mL) and water (10 mL) was added NaOH (160 mg, 4.01 mmol) at r.t. The resulting mixture was stirred at rt overnight. The pH was adjusted to 6 with 2N HCl, and the mixture was extracted with DCM (30 ml×2). The combined organic layers were dried over anhydrous sodium sulfate and concentrated under vacuum to afford the crude compound 2-(3-(4-(3-(2-(Tert-butoxy)-2-oxoethoxy)propyl)piperazin-1-yl)propoxy)acetic acid as a colorless oil (1.0 g), which was used in next step without further purification. Chemical Formula: C$_{18}$H$_{34}$N$_2$O$_6$; Molecular Weight: 374.48

3. Step—Synthesis of Tert-butyl 2-(3-(4-(3-(2-((4-(isopropylamino)-6-((2-(4-methoxypiperidin-1-yl)pyrimidin-4-yl)amino)pyridin-3-yl)amino)-2-oxoethoxy)propyl)piperazin-1-yl)propoxy)acetate

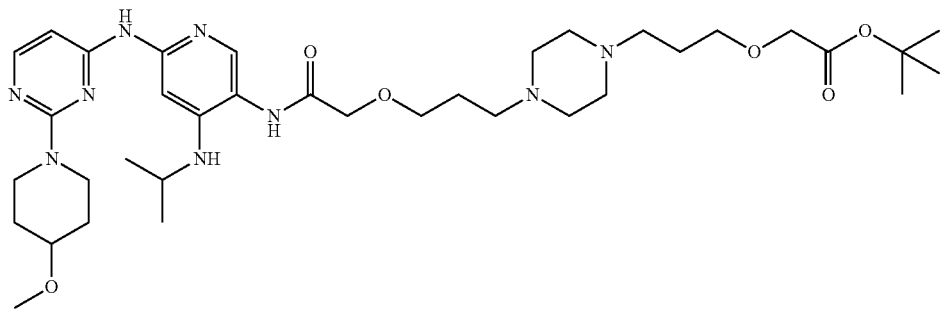 [SMILES: COC1CCN(c2nccc(Nc3cc(NC(C)C)c(NC(=O)COCCCN4CCN(CCCOCC(=O)OC(C)(C)C)CC4)cn3)n2)CC1]

To a mixture of 2-(3-(4-(3-(2-(Tert-butoxy)-2-oxoethoxy)propyl)piperazin-1-yl)propoxy)acetic acid (53 mg, 0.14 mmol), N$^4$—Isopropyl-N$^2$-(2-(4-methoxypiperidin-1-yl)pyrimidin-4-yl)pyridine-2,4,5-triamine (50 mg, 0.14 mmol), and DIPEA (72 mg, 0.56 mmol) in DMF (5 mL) was added HATU (106 mg, 0.28 mmol). The reaction mixture was stirred at rt for 1 h. Then the reaction mixture was diluted with 10 mL water and the resulting reaction mixture was extracted with DCM (2×30 mL). The combined organic layers were washed with brine (10 mL), dried over Na$_2$SO$_4$ and filtered. The solvent was evaporated under reduced pressure. The residue was purified by column chromatography (DCM:MeOH=20:1) to afford the crude desired compound Tert-butyl 2-(3-(4-(3-(2-((4-(isopropylamino)-6-((2-(4-methoxypiperidin-1-yl)pyrimidin-4-yl)amino)pyridin-3-yl)amino)-2-oxoethoxy)propyl)piperazin-1-yl)propoxy)acetate as a colorless oil (50 mg, 0.07 mmol, 50.1%). LC-MS: (ES$^+$): m/z 714.3 [M+H]. $t_R$=2.98 min Chemical Formula: C$_{36}$H$_{59}$N$_9$O$_6$; Molecular Weight: 713.92

4. Step—Synthesis of 2-(3-(4-(3-((1-Isopropyl-6-((2-(4-methoxypiperidin-1-yl)pyrimidin-4-yl)amino)-1H-imidazo[4,5-c]pyridin-2-yl)methoxy)propyl)piperazin-1-yl)propoxy)acetic acid

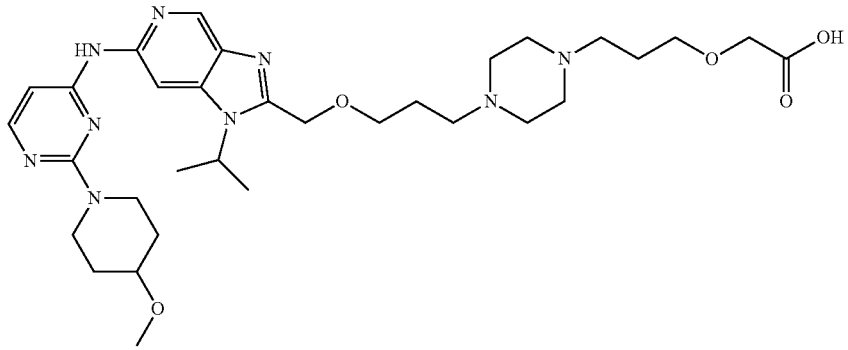 [SMILES: COC1CCN(c2nccc(Nc3cc4c(cn3)nc(COCCCN3CCN(CCCOCC(=O)O)CC3)n4C(C)C)n2)CC1]

A solution of Tert-butyl 2-(3-(4-(3-(2-((4-(isopropylamino)-6-((2-(4-methoxypiperidin-1-yl)pyrimidin-4-yl)amino)pyridin-3-yl)amino)-2-oxoethoxy)propyl)piperazin-1-yl)propoxy)acetate (200 mg, 0.28 mmol) in HOAc (5 mL) was heated to 150° C. under microwave for 6 h. Then it was concentrated in vacuo to afford the crude desired product 2-(3-(4-(3-((1-Isopropyl-6-((2-(4-methoxypiperidin-1-yl)pyrimidin-4-yl)amino)-1H-imidazo [4,5-c]pyridin-2-yl) methoxy)propyl)piperazin-1-yl)propoxy)acetic acid (200 mg, crude). LC-MS: (ES$^+$): m/z 640.3 [M+H]. $t_R$=2.37 min Chemical Formula: $C_{32}H_{49}N_9O_5$; Molecular Weight: 639.80

5. Step—Synthesis of (2S,4R)-4-hydroxy-1-((S)-2-(2-(3-(4-(3-((1-Isopropyl-6-((2-(4-methoxypiperidin-1-yl)pyrimidin-4-yl)amino)-1H-imidazo[4,5-c]pyridin-2-yl)methoxy)propyl)piperazin-1-yl)propoxy)acetamido)-3,3-dimethylbutanoyl)-N—((S)-1-(4-(4-methylthiazol-5-yl)phenyl)ethyl)pyrrolidine-2-carboxamide To a mixture of 2-(3-(4-(3-((1-Isopropyl-6-((2-(4-methoxypiperidin-1-yl)pyrimidin-4-yl)amino)-1H-imidazo [4,5-c]pyridin-2-yl)methoxy)propyl)piperazin-1-yl) propoxy)acetic acid (100 mg, crude), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (45 mg, 0.10 mmol), and DIPEA (48 mg, 0.37 mmol) in DCM (5 mL) was added HATU (80 mg, 0.21 mmol). The reaction mixture was stirred at rt for 1 h. Then the reaction mixture was diluted with water (10 mL), and the resulting reaction mixture was extracted with DCM (30 mL×2). The combined organic layers were washed with brine (10 mL), dried over $Na_2SO_4$ and filtered. The solvent was evaporated under reduced pressure. The residue was purified by prep-TLC (DCM:MeOH=20:1) to afford the desired compound (2S,4R)-4-hydroxy-1-((S)-2-(2-(3-(4-(3-((1-Isopropyl-6-((2-(4-methoxypiperidin-1-yl)pyrimidin-4-yl)amino)-1H-imidazo [4,5-c]pyridin-2-yl)methoxy)propyl)piperazin-1-yl)propoxy)acetamido)-3,3-dimethylbutanoyl)-N—((S)-1-

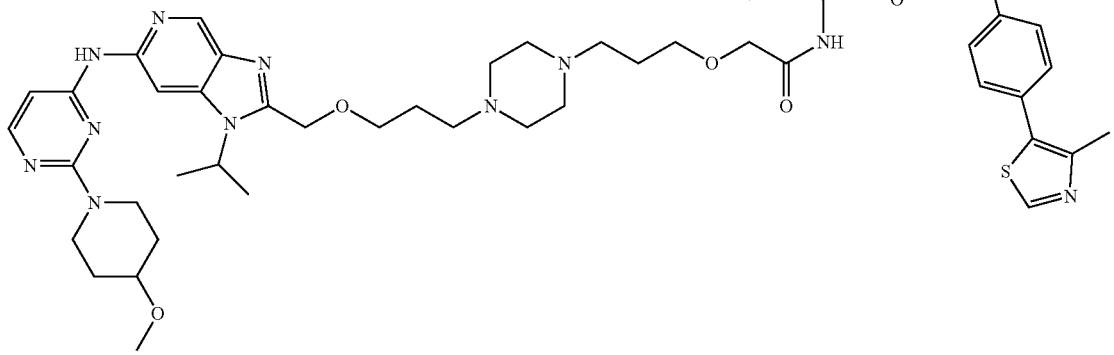

(4-(4-methylthiazol-5-yl)phenyl)ethyl)pyrrolidine-2-carboxamide (10 mg, 0.0094 mmol, 9.4%) as a white solid. $^1$H NMR (400 MHz, CDCl$_3$): δ 8.67 (d, J=4.4 Hz, 2H), 8.45 (s, 1H), 8.04 (d, J=5.6 Hz, 1H), 7.46 (d, J=7.6 Hz, 1H), 7.37-7.42 (m, 6H), 7.18 (d, J=8.4 Hz, 1H), 6.04 (d, J=5.2 Hz, 1H), 5.34-5.35 (m, 1H), 5.02-5.12 (m, 1H), 4.85-4.95 (m, 1H), 4.75 (s, 3H), 4.51-4.53 (m, 2H), 4.36-4.39 (m, 2H), 4.12-4.15 (m, 1H), 3.93-3.95 (m, 2H), 3.46-3.56 (m, 8H), 3.42 (s, 3H), 2.53 (s, 3H), 2.41-2.45 (m, 12H), 2.20-2.22 (m, 1H), 1.65-1.67 (m, 5H), 1.64 (s, 9H), 1.47 (d, J=4.8 Hz, 3H), 1.06 (s, 9H). LC-MS: (ES$^+$): m/z 1066.6 [M+H]. $t_R$=2.88 min Chemical Formula: C$_{55}$H$_{79}$N$_{13}$O$_7$S; Molecular Weight: 1066.38

Synthesis of Examples 97, 98, 99, and 100

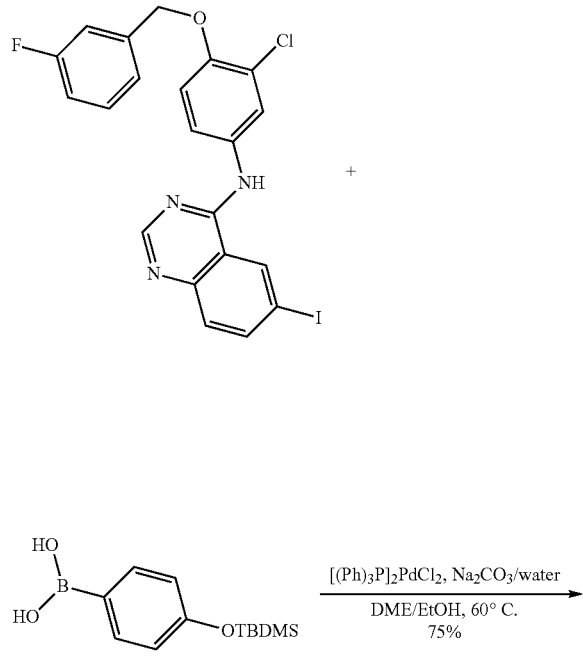

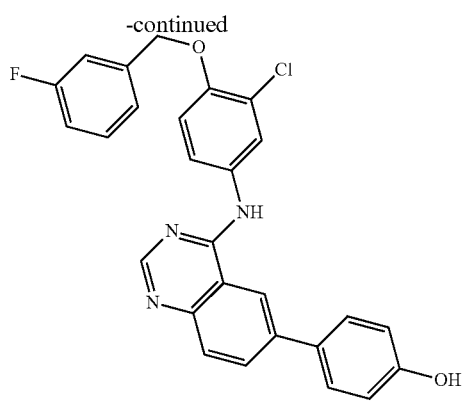

4-(4-((3-Chloro-4-((3-fluorobenzyl)oxy)phenyl)amino)quinazolin-6-yl)phenol

A suspension of N-[3-chloro-4-[(3-fluorophenyl)methoxy]phenyl]-6-iodo-quinazolin-4-amine (300 mg, 0.59 mmol) in a mixture of 1,2-Dimethoxyethane (12 ml) and Ethanol (8 ml) was evacuated in vacuum and purged with argon (5×), then 2M Na$_2$CO$_3$ in water (6.5 ml) was added and the reaction mixture was again evacuated in vacuum and purged with argon (5×), then [4-[tert-butyl(dimethyl)silyl]oxyphenyl]boronic acid (209 mg, 0.831 mmol) was added into, and [(Ph)$_3$P]$_2$PdCl$_2$ (70 mg, 0.08 mmol). The reaction mixture was heated to 60° C. for 3 h. The reaction mixture was cooled to room temperature and the reaction mixture was poured into an aqueous saturated solution of NaHCO$_3$ (30 mL) and product was extracted with AcOEt (2×30 mL). Organic extracts were combined, dried (Na$_2$SO$_4$), filtered over a celite pad, and evaporated under vacuum. Crude product was purified by flash chromatography (SiO$_2$-25 g. dry silica-dispersion loading, gradient Hex:AcOEt, 9:1 to 100% AcOEt in 15 min) to give 210 mg of product 4-(4-((3-Chloro-4-((3-fluorobenzyl)oxy)phenyl)amino)quinazolin-6-yl)phenol (75% yield). $^1$H NMR (400 MHz, DMSO-d6) δ 9.85 (s, 1H), 9.68 (s, 1H), 8.69 (s, 1H), 8.56 (s, 1H), 8.12 (d, J=8.7 Hz, 1H), 8.03 (s, 1H), 7.87-7.67 (m, 4H), 7.48 (td, J=8.0, 6.0 Hz, 1H), 7.39-7.25 (m, 3H), 7.19 (tt, J=7.8, 1.4 Hz, 1H), 6.93 (d, J=8.6 Hz, 2H), 5.27 (s, 2H). $^{13}$C NMR (151 MHz, dmso) δ 163.06, 161.44, 157.66, 157.59, 154.07, 149.69, 148.44, 139.73, 139.69, 138.23, 133.18, 131.45, 130.69, 130.64, 129.86, 128.36, 128.32, 124.20, 123.45, 123.43, 122.38, 121.01, 118.95, 115.88, 115.33, 114.87, 114.73, 114.28, 114.21, 114.07, 69.37. LC-MS (ESI): m/z [M+H]$^+$ Calcd. for C$_{27}$H$_{20}$ClFN$_3$O$_2$, 472.1228. Found 472.1283.

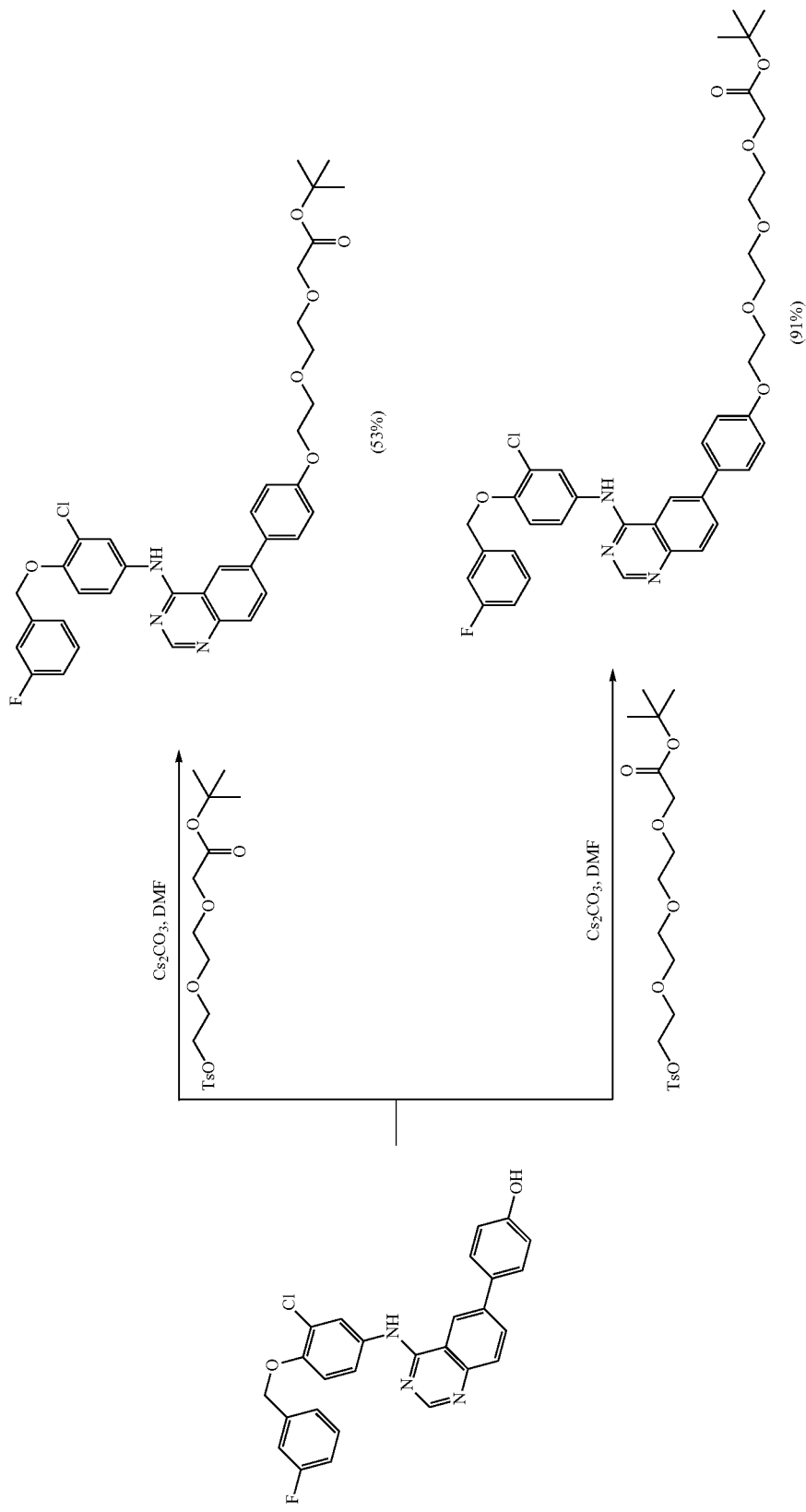

tert-Butyl 2-(2-(2-(4-(4-((3-chloro-4-((3-fluorobenzyl)oxy)phenyl)amino)quinazolin-6-yl)phenoxy)-ethoxy)ethoxy)acetate To a mixture of 4-[4-[3-chloro-4-[(3-fluorophenyl)methoxy]anilino]-quinazolin-6-yl]phenol (10.4 mg, 0.022 mmol) and tert-butyl 2-[2-[2-(p-tolylsulfonyloxy)ethoxy]ethoxy]-acetate (10.8 mg, 0.03 mmol) in N,N-Dimethylformamide (2 mL) was added $Cs_2CO_3$ (21.7 mg, 0.067 mmol). Reaction mixture was heated at 50° C. for 6 h. Reaction mixture was diluted with AcOEt (20 mL), washed with water (4×15 mL), dried $Na_2SO_4$ and evaporated under vacuum. Crude product was purified by PTLC (DCM:MeOH:$NH_4OH$, 92:7:1) to give 8 mg of pure product tert-Butyl 2-(2-(2-(4-(4-((3-chloro-4-((3-fluorobenzyl)oxy)phenyl)amino)quinazolin-6-yl)phenoxy)-ethoxy)ethoxy)acetate (53% yield). $^1H$ NMR (500 MHz, DMSO-d6) δ 9.88 (s, 1H), 8.74 (s, 1H), 8.57 (s, 1H), 8.16 (d, J=8.7 Hz, 1H), 8.03 (s, 1H), 7.83 (dd, J=8.7, 6.6 Hz, 3H), 7.76 (dd, J=8.9, 2.6 Hz, 1H), 7.52-7.40 (m, 1H), 7.38-7.25 (m, 3H), 7.21-7.15 (m, 1H), 7.13 (d, J=8.8 Hz, 2H), 5.26 (s, 2H), 4.26-4.12 (m, 2H), 4.01 (s, 2H), 3.83-3.71 (m, 2H), 3.63 (s, 4H), 1.42 (s, 9H). $^{13}C$ NMR (151 MHz, dmso) δ 169.37, 163.01, 161.39, 158.54, 157.60, 154.15, 149.70, 148.58, 139.69, 139.64, 137.71, 133.15, 131.46, 131.44, 130.60, 130.55, 128.33, 128.25, 124.19, 123.36, 123.34, 122.36, 121.03, 119.29, 115.29, 115.00, 114.78, 114.64, 114.30, 114.12, 113.98, 80.66, 69.88, 69.40, 69.38, 68.91, 68.12, 67.28, 27.77. LC-MS (ESI): m/z [M+H]$^+$ Calcd. for $C_{37}H_{38}ClFN_3O_6$, 674.2433. Found 674.2411.

tert-Butyl 2-(2-(2-(2-(4-(4-((3-chloro-4-((3-fluorobenzyl)oxy)phenyl)amino)quinazolin-6-yl)phenoxy)-ethoxy)ethoxy)ethoxy)acetate To a mixture of 4-[4-[3-chloro-4-[(3-fluorophenyl)methoxy]anilino]-quinazolin-6-yl]phenol (7.2 mg, 0.015 mmol) and tert-butyl 2-[2-[2-[2-(p-tolylsulfonyloxy)ethoxy]ethoxy]-ethoxy]-acetate (8.3 mg, 0.02 mmol) in N,N-Dimethylformamide (2 mL) was added $Cs_2CO_3$ (14.91 mg, 0.05 mmol). Reaction mixture was heated at 50° C. for 2 h. Reaction mixture was diluted with AcOEt (20 mL), washed with water (4×15 mL), dried $Na_2SO_4$ and evaporated under vacuum. Crude product was purified by PTLC (DCM:MeOH:$NH_4OH$, 92:7:1) to give 10 mg of product tert-Butyl 2-(2-(2-(2-(4-(4-((3-chloro-4-((3-fluorobenzyl)oxy)phenyl)amino)quinazolin-6-yl)phenoxy)-ethoxy)ethoxy)ethoxy)acetate (91% yield). $^1H$ NMR (500 MHz, DMSO-d6) δ 9.87 (s, 1H), 8.74 (d, J=2.1 Hz, 1H), 8.57 (s, 1H), 8.16 (dd, J=8.8, 1.9 Hz, 1H), 8.03 (s, 1H), 7.83 (dd, J=8.6, 5.7 Hz, 3H), 7.76 (dd, J=9.0, 2.6 Hz, 1H), 7.47 (td, J=8.0, 6.1 Hz, 1H), 7.38-7.25 (m, 3H), 7.22-7.14 (m, 1H), 7.13 (d, J=8.8 Hz, 2H), 5.27 (s, 2H), 4.23-4.13 (m, 2H), 3.98 (s, 2H), 3.84-3.74 (m, 2H), 3.68-3.46 (m, 8H), 1.41 (s, 9H). $^{13}C$ NMR (151 MHz, DMSO-d6) δ 169.36, 163.01, 161.39, 158.54, 157.60, 154.15, 149.70, 148.57, 139.69, 139.64, 137.72, 133.14, 131.44, 130.61, 130.55, 128.32, 128.25, 124.19, 123.36, 123.34, 122.37, 121.03, 119.29, 115.28, 115.02, 114.78, 114.64, 114.30, 114.13, 113.98, 80.64, 69.95, 69.86, 69.78, 69.72, 69.38, 68.95, 68.09, 67.29, 27.76. LC-MS (ESI): m/z [M+H]$^+$ Calcd. For $C_{39}H_{42}ClFN_3O_7$, 718.2695. Found 718.3026.

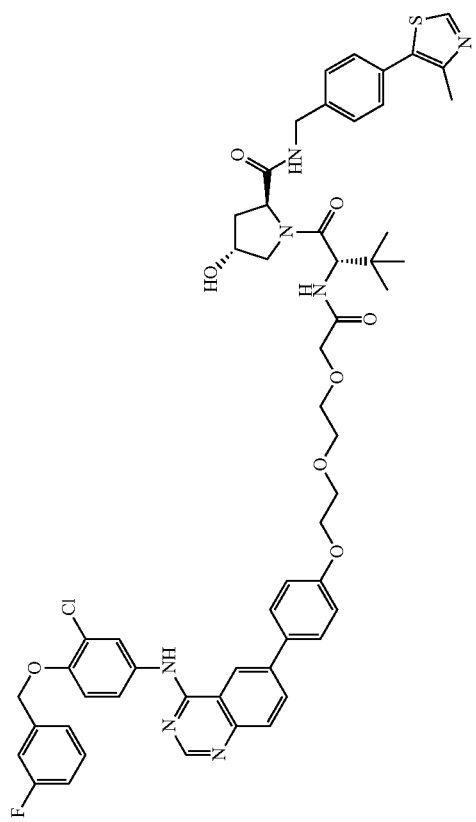
Example 97 (98%)

Example 98 (86%)
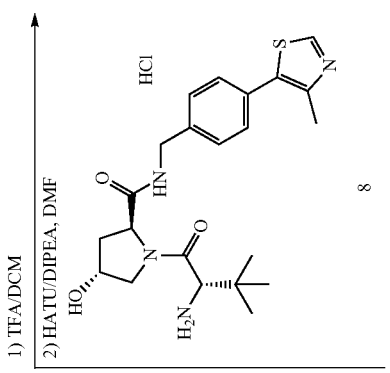
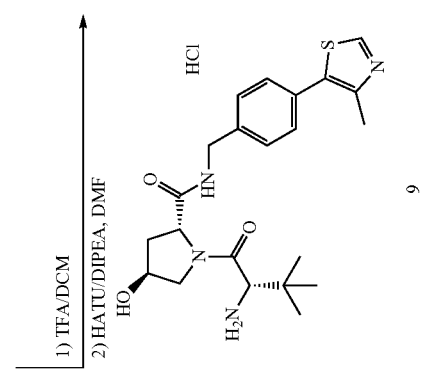
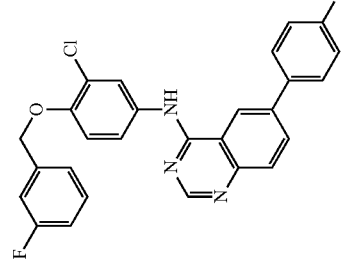

Synthesis of Example 97 and 98

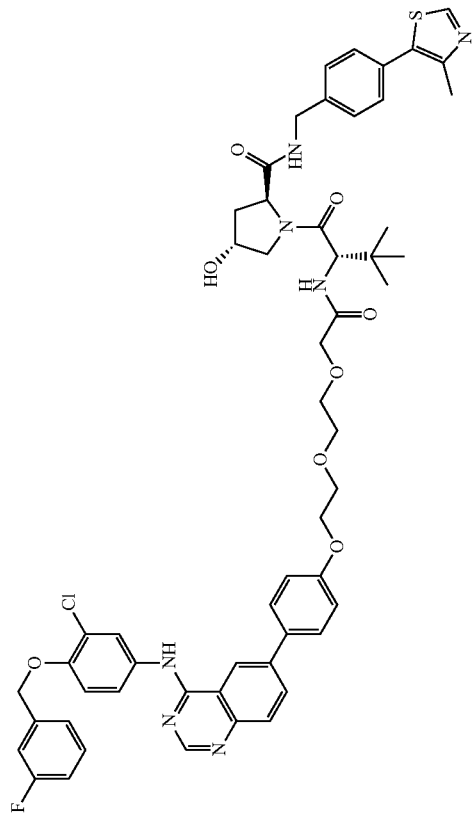
Example 97 (98%)
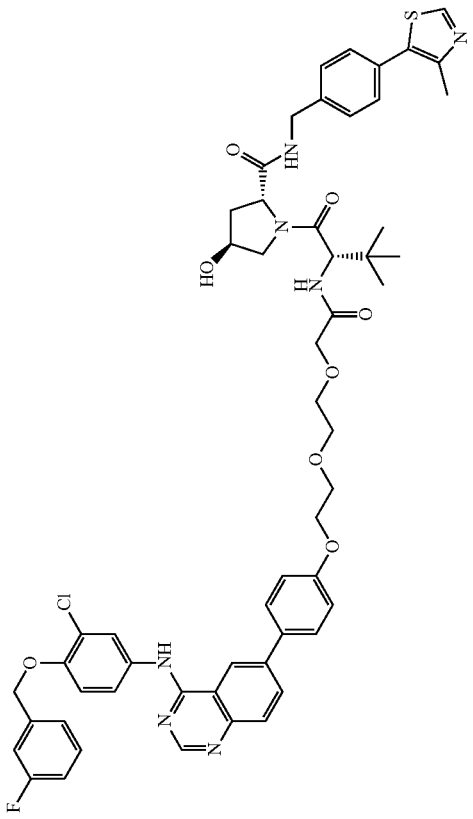
Example 98 (86%)
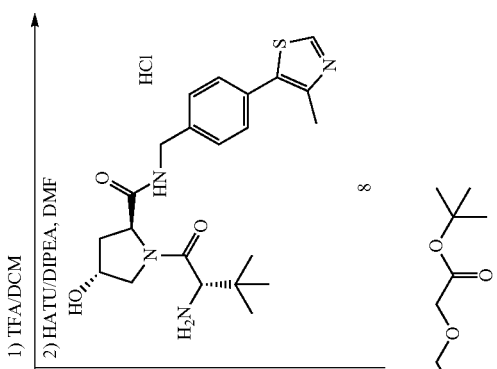
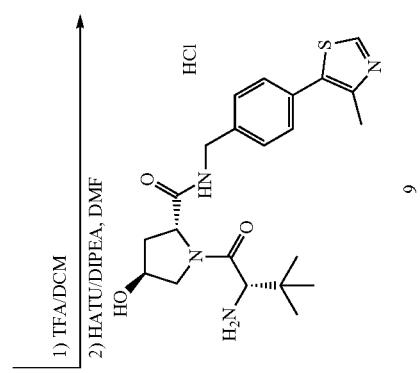
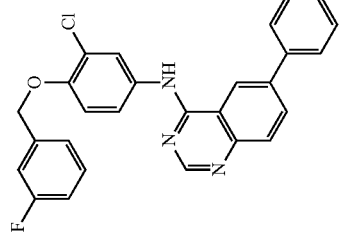

(2S,4R)-1-((S)-2-(2-(2-(2-(4-(4-((3-Chloro-4-((3-fluorobenzyl)oxy)phenyl)amino)quinazolin-6-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide (Example 97)

A solution of tert-butyl 2-[2-[2-[4-[4-[3-chloro-4-[(3-fluorophenyl)methoxy]anilino]quinazolin-6-yl]-phenoxy]ethoxy]ethoxy]acetate (8 mg, 0.01 mmol) in a mixture of TFA (1 ml, 13.46 mmol) and Dichloromethane (3 ml) was stirred for 2 h. Then the solvent was removed under vacuum and crude product was dried under high vacuum for 2 h. The crude product was used in the next step without any further purification (7.3 mg, quantitative yield). LC-MS (ESI): m/z [M+H]$^+$ Calcd. for $C_{33}H_{30}ClFN_3O_6$, 618.1807. Found 618.1917.

To a solution of 2-[2-[2-[4-[4-[3-chloro-4-[(3-fluorophenyl)methoxy]anilino]quinazolin-6-yl]phenoxy]-ethoxy]ethoxy]acetic acid (7.3 mg, 0.01 mmol), and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide hydrochloride (8.27 mg, 0.02 mmol) in N,N-Dimethylformamide (2 ml) was added DIPEA (0.2 ml, 1.14 mmol) and HATU (8.98 mg, 0.02 mmol) at room temperature. The reaction mixture was stirred for 12 h (overnight) at the same temperature. Reaction mixture was diluted with AcOEt (20 mL), washed with water (4×15 mL), dried ($Na_2SO_4$) and evaporated under vacuum. Crude product was purified by PTLC (DCM:MeOH:NH$_4$OH, 92:7:1), to give 12 mg of the expected product (2S,4R)-1-((S)-2-(2-(2-(2-(4-(4-((3-Chloro-4-((3-fluorobenzyl)oxy)phenyl)amino)quinazolin-6-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide (98% yield). $^1$H NMR (500 MHz, DMSO-d6) δ 9.87 (s, 1H), 8.95 (s, 1H), 8.72 (s, 1H), 8.57 (d, J=2.6 Hz, 2H), 8.13 (dd, J=8.7, 1.9 Hz, 1H), 8.02 (d, J=2.4 Hz, 1H), 7.81 (dd, J=8.6, 4.9 Hz, 3H), 7.76 (dd, J=9.0, 2.6 Hz, 1H), 7.55-7.24 (m, 9H), 7.18 (t, J=8.6 Hz, 1H), 7.10 (d, J=8.7 Hz, 2H), 5.26 (s, 2H), 5.15 (d, J=3.4 Hz, 1H), 4.58 (d, J=9.6 Hz, 1H), 4.50-4.22 (m, 5H), 4.19 (t, J=4.6 Hz, 2H), 4.00 (s, 2H), 3.89-3.77 (m, 2H), 3.75-3.54 (m, 6H), 2.41 (s, 3H), 2.11-2.01 (m, 1H), 1.95-1.87 (m, 1H), 0.95 (s, 9H). $^{13}$C NMR (151 MHz, DMSO-d6) δ 171.75, 169.16, 168.62, 163.01, 161.40, 158.51, 157.60, 154.15, 151.43, 149.70, 148.58, 147.72, 139.69, 139.64, 139.40, 137.73, 133.15, 131.43, 131.12, 130.61, 130.56, 129.69, 128.67, 128.32, 128.24, 128.15, 127.43, 124.18, 123.37, 123.35, 122.35, 121.04, 119.28, 115.29, 114.99, 114.79, 114.65, 114.30, 114.13, 113.99, 70.48, 69.79, 69.63, 69.40, 69.02, 68.89, 67.21, 58.76, 56.62, 55.73, 41.69, 37.96, 35.74, 26.21, 15.92. LC-MS (ESI): m/z [M+H]$^+$ Calcd. for $C_{55}H_{58}ClFN_7O_8S$, 1030.3740. Found 1030.4004.

(2R,4S)-1-((S)-2-(2-(2-(2-(4-(4-((3-Chloro-4-((3-fluorobenzyl)oxy)phenyl)amino)quinazolin-6-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide (Example 98)

It was prepared from (2R,4S)-1-((S)-2-amino-3,3-dimethylbutanoyl)-4-hydroxy-N-(4-(4-methylthiazol-5-yl)benzyl)pyrrolidine-2-carboxamide hydrochloride and following the same procedure as describe above for example 97. $^1$H NMR (500 MHz, CDCl$_3$) δ 8.67 (s, 1H), 8.62 (s, 1H), 8.54 (s, 1H), 7.96 (dd, J=8.7, 1.7 Hz, 1H), 7.91 (d, J=8.6 Hz, 1H), 7.84 (dd, J=8.8, 2.6 Hz, 1H), 7.71 (d, J=2.5 Hz, 1H), 7.56 (t, J=6.8 Hz, 3H), 7.34 (dd, J=8.0, 6.2 Hz, 2H), 7.22 (t, J=9.3 Hz, 2H), 7.14 (t, J=8.3 Hz, 4H), 7.07-6.99 (m, 3H), 6.96 (d, J=8.9 Hz, 1H), 5.14 (s, 2H), 4.88 (dd, J=8.7, 5.0 Hz, 1H), 4.62 (p, J=5.4 Hz, 1H), 4.36 (dt, J=15.4, 7.3 Hz, 2H), 4.29 (d, J=6.6 Hz, 1H), 4.17-4.06 (m, 5H), 3.91-3.81 (m, 3H), 3.73-3.58 (m, 4H), 3.47-3.36 (m, 2H), 2.41 (s, 3H), 2.38 (t, J=5.3 Hz, 1H), 2.27 (ddd, J=13.8, 8.7, 5.9 Hz, 1H), 1.12 (s, 9H). $^{13}$C NMR (151 MHz, CDCl$_3$) δ 171.85, 171.65, 170.60, 163.79, 162.16, 158.70, 158.07, 154.36, 150.50, 150.20, 148.29, 139.19, 139.14, 139.01, 137.91, 133.24, 132.47, 131.70, 131.65, 130.41, 130.18, 130.12, 129.14, 128.38, 127.54, 124.48, 122.92, 122.45, 122.44, 122.00, 119.24, 115.69, 115.55, 114.94, 114.80, 114.24, 114.04, 113.89, 71.39, 70.69, 70.44, 70.43, 70.17, 69.68, 67.94, 59.67, 58.55, 54.89, 42.89, 38.16, 33.85, 26.66, 16.10. LC-MS (ESI): m/z [M+H]$^+$: Calcd. for $C_{55}H_{58}ClFN_7O_8S$, 1030.3740. Found 1030.3821.

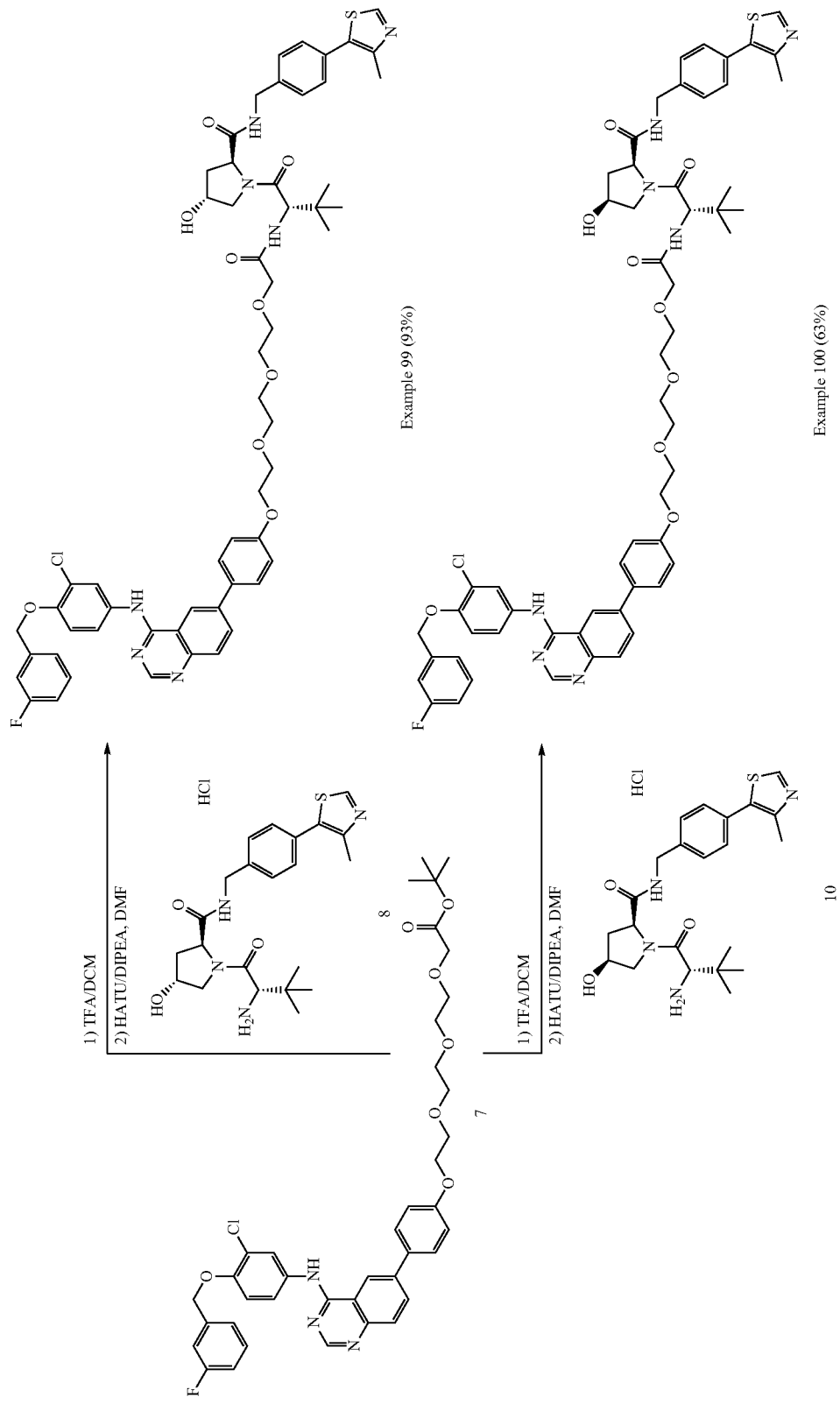

Synthesis of Example 99 and 100

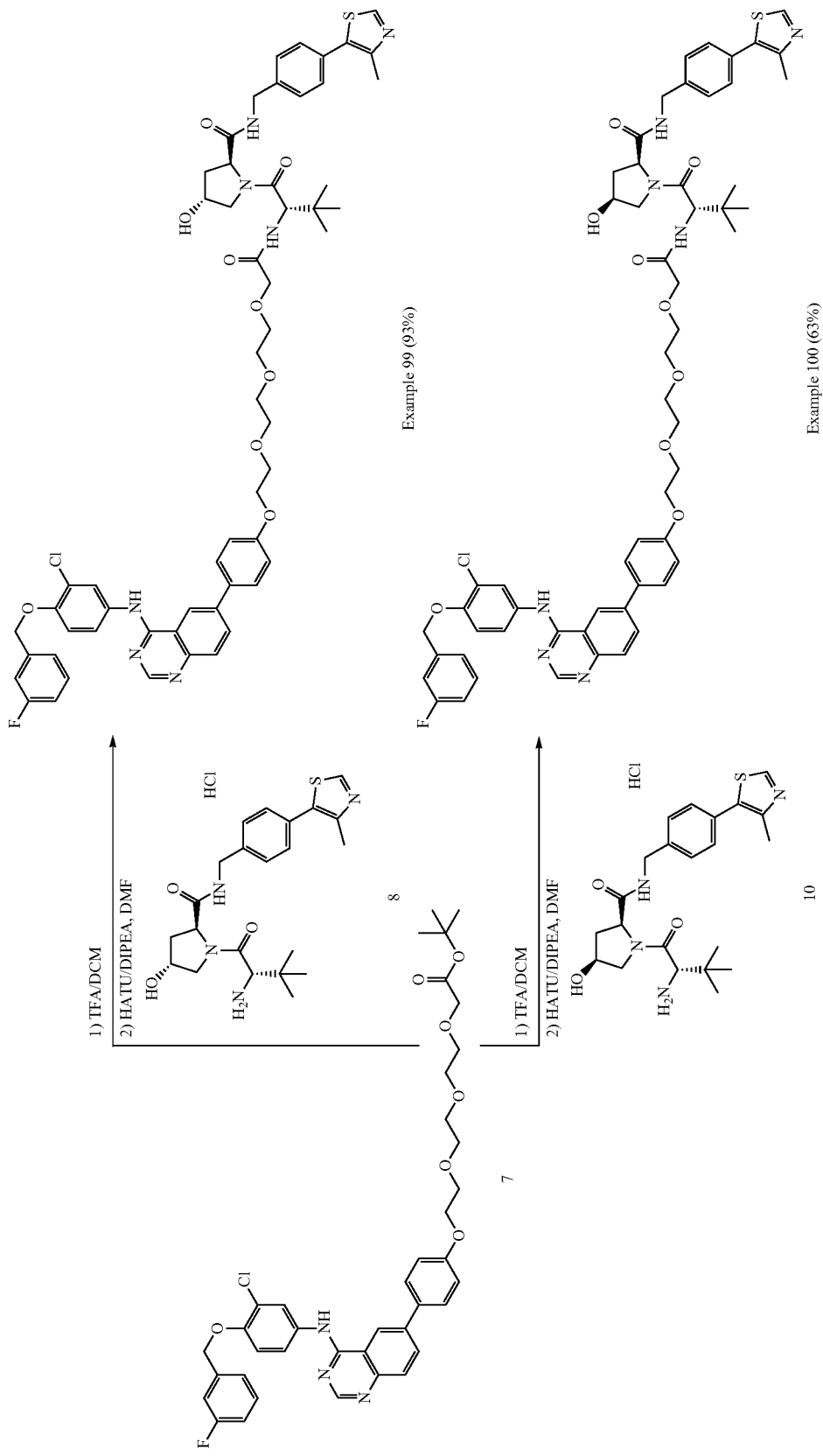

(2S,4R)-1-((S)-2-(tert-Butyl)-14-(4-(4-((3-chloro-4-((3-fluorobenzyl)oxy)phenyl)amino)quinazolin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide It was prepared from (2R,4S)-1-((S)-2-amino-3,3-dimethylbutanoyl)-4-hydroxy-N-(4-(4-methylthiazol-5-yl)benzyl)pyrrolidine-2-carboxamide hydrochloride (8) and tert-butyl 2-(2-(2-(2-(4-(4-((3-chloro-4-((3-fluorobenzyl)oxy)phenyl)amino)-quinazolin-6-yl)phenoxy)ethoxy)ethoxy)ethoxy)acetate, following the same procedure as described above for example 97 (93% yield). $^1$H NMR (400 MHz, DMSO-d6) δ 9.87 (s, 1H), 8.95 (s, 1H), 8.72 (s, 1H), 8.59 (t, J=6.0 Hz, 1H), 8.55 (s, 1H), 8.13 (dd, J=8.7, 1.9 Hz, 1H), 8.00 (d, J=2.5 Hz, 1H), 7.89-7.76 (m, 3H), 7.73 (dd, J=9.0, 2.6 Hz, 1H), 7.54-7.23 (m, 8H), 7.22-7.12 (m, 1H), 7.09 (d, J=8.8 Hz, 2H), 5.24 (s, 2H), 5.15 (d, J=3.5 Hz, 1H), 4.55 (d, J=9.6 Hz, 1H), 4.48-4.18 (m, 5H), 4.18-4.06 (m, 2H), 3.95 (s, 2H), 3.80-3.69 (m, 2H), 3.69-3.51 (m, 8H), 2.41 (s, 3H), 2.08-2.00 (m, 1H), 1.93-1.82 (m, 1H), 0.92 (s, 9H). $^{13}$C NMR (151 MHz, DMSO-d6) δ 171.76, 169.12, 168.59, 163.01, 161.39, 158.53, 157.60, 154.15, 151.45, 149.70, 148.57, 147.73, 139.68, 139.63, 139.42, 137.72, 133.14, 131.44, 131.42, 131.13, 130.60, 130.55, 129.68, 128.68, 128.32, 128.24, 127.44, 124.19, 123.36, 123.34, 122.36, 121.03, 119.27, 115.28, 114.99, 114.78, 114.64, 114.29, 114.13, 113.98, 70.48, 69.97, 69.90, 69.63, 69.59, 69.38, 68.95, 68.88, 67.26, 58.75, 56.60, 55.69, 41.68, 37.94, 35.73, 26.19, 15.93. LC-MS (ESI): m/z [M+H]$^+$: Calcd. for C$_{57}$H$_{62}$ClFN$_7$O$_9$S, 1074.4002. Found 1074.4285.

(2S,4S)-1-((S)-2-(tert-Butyl)-14-(4-(4-((3-chloro-4-((3-fluorobenzyl)oxy)phenyl)amino)quinazolin-6-yl)phenoxy)-4-oxo-6,9,12-trioxa-3-azatetradecanoyl)-4-hydroxy-N-(4-(4-methylthiazol-5-yl)benzyl)pyrrolidine-2-carboxamide (example 100).)

It was prepared from (2S,4S)-1-((S)-2-amino-3,3-dimethylbutanoyl)-4-hydroxy-N-(4-(4-methythiazol-5-yl)benzyl)pyrrolidine-2-carboxamide hydrochloride (10) and tert-butyl 2-(2-(2-(2-(4-(4-((3-chloro-4-((3-fluorobenzyl)oxy)phenyl)amino)-quinazolin-6-yl)phenoxy)ethoxy)ethoxy)ethoxy)acetate, following the same procedure as reported above for example 97 (63% yield). $^1$H NMR (400 MHz, DMSO-d6) δ 9.95 (s, 1H), 9.04 (s, 1H), 8.84-8.77 (m, 1H), 8.73 (t, J=6.0 Hz, 1H), 8.64 (s, 1H), 8.22 (dd, J=8.8, 1.8 Hz, 1H), 8.10 (d, J=2.6 Hz, 1H), 7.89 (dd, J=8.8, 1.8 Hz, 3H), 7.83 (dd, J=9.0, 2.6 Hz, 1H), 7.65-7.30 (m, 9H), 7.25 (td, J=8.8, 8.3, 2.6 Hz, 1H), 7.18 (d, J=8.8 Hz, 2H), 5.51 (d, J=7.2 Hz, 1H), 5.33 (s, 2H), 4.59 (d, J=9.2 Hz, 1H), 4.52-4.41 (m, 2H), 4.40-4.25 (m, 2H), 4.26-4.19 (m, 2H), 4.03 (s, 2H), 3.99-3.91 (m, 1H), 3.88-3.80 (m, 2H), 3.68 (ddt, J=6.7, 5.2, 3.3 Hz, 8H), 3.59-3.44 (m, 1H), 2.50 (s, 3H), 2.44-2.35 (m, 1H), 1.81 (dt, J=12.4, 6.1 Hz, 1H), 1.03 (s, 9H). $^{13}$C NMR (151 MHz, dmso) δ 172.26, 169.38, 168.91, 163.02, 161.40, 158.53, 157.61, 154.16, 151.48, 149.71, 148.58, 147.76, 139.69, 139.64, 139.14, 137.72, 133.15, 131.45, 131.11, 130.61, 130.56, 129.77, 128.70, 128.34, 128.25, 127.47, 124.20, 123.37, 123.35, 122.38, 121.04, 119.29, 115.29, 115.00, 114.79, 114.65, 114.31, 114.13, 113.99, 70.46, 69.96, 69.88, 69.64, 69.52, 69.40, 69.03, 68.97, 67.27, 58.59, 55.84, 55.62, 41.82, 36.92, 35.19, 26.18, 15.94. LC-MS (ESI): m/z [M+H]$^+$: Calcd. for C$_{57}$H$_{62}$ClFN$_7$O$_9$S, 1074.4002. Found 1074.3920.

Synthesis of Example 102

5-(2-(2-(4-(4-(4-((2-chlorobenzyl)amino)-7H-pyrrolo[2,3-d]pyrimidin-6-yl)benzyl)piperazin-1-yl)ethoxy)ethoxy)-2-(2,6-dioxopiperidin-3-yl)isoindoline-1,3-dione

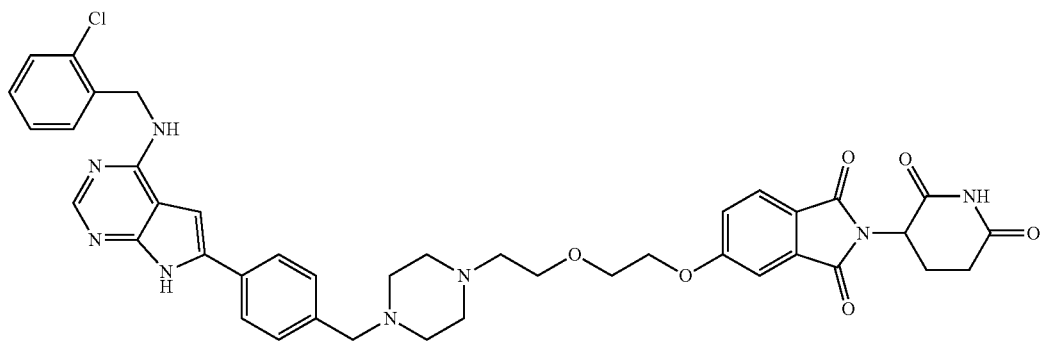 [SMILES: O=C1CCC(N2C(=O)c3ccc(OCCOCCN4CCN(Cc5ccc(-c6cc7c(NCc8ccccc8Cl)ncnc7[nH]6)cc5)CC4)cc3C2=O)C(=O)N1]

Synthetic scheme:
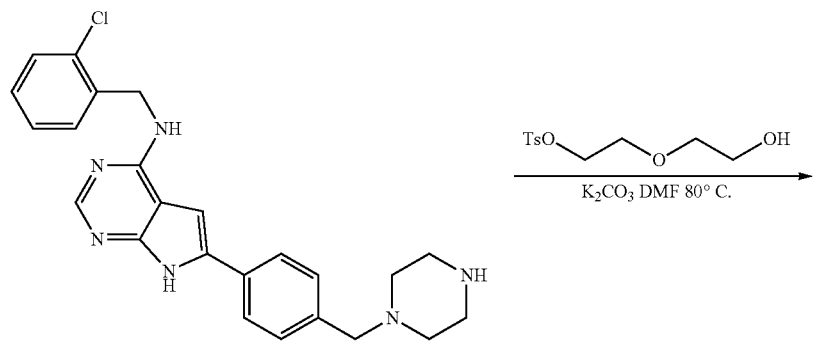
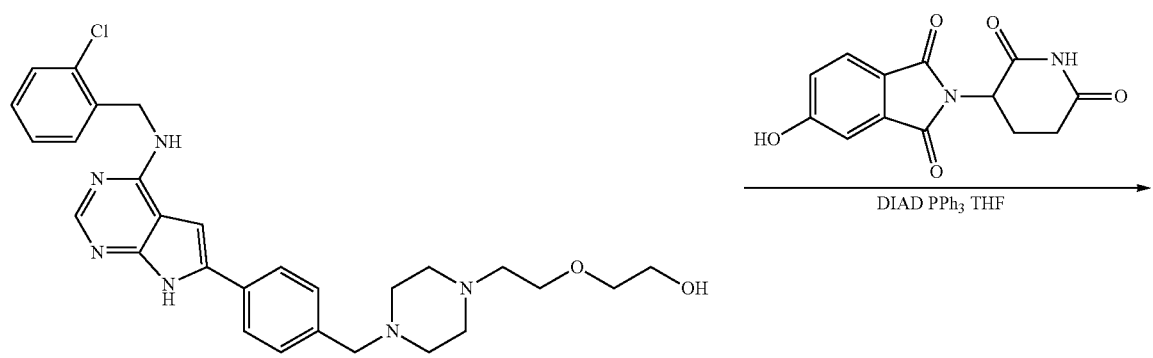
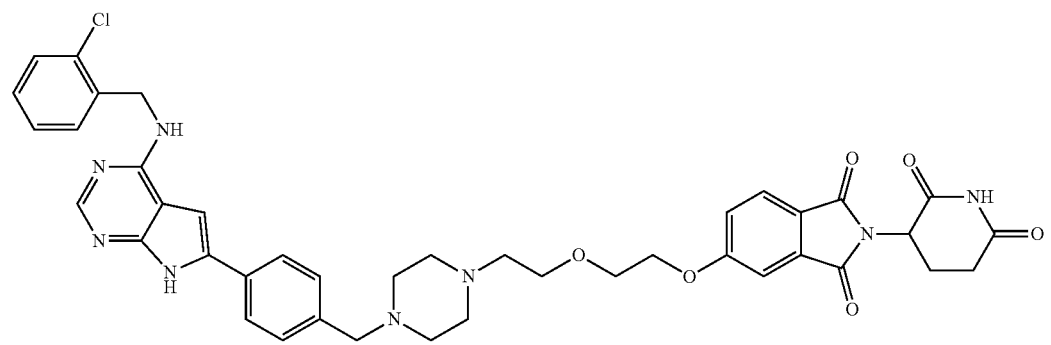 [SMILES: O=C1CCC(N2C(=O)c3ccc(OCCOCCN4CCN(Cc5ccc(-c6cc7c(NCc8ccccc8Cl)ncnc7[nH]6)cc5)CC4)cc3C2=O)C(=O)N1]

1. Step—Synthesis of 2-(2-(4-(4-(4-((2-Chlorobenzyl)amino)-7H-pyrrolo[2,3-d]pyrimidin-6-yl)benzyl)piperazin-1-yl)ethoxy)ethan-1-ol

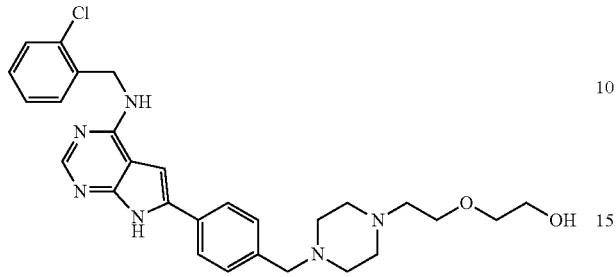

A solution of N-(2-chlorobenzyl)-6-(4-(piperazin-1-ylmethyl)phenyl)-7H-pyrrolo[2,3-d]pyrimidin-4-amine (300 mg, 0.693 mmol), 2-(2-hydroxyethoxy)ethyl 4-methylbenzenesulfonate (900 mg, 3.464 mmol), and $K_2CO_3$ (478 mg, 3.464 mmol) in DMF (8 mL) was stirred at 75° C. overnight. After cooling to rt, the reaction was quenched with water, and the mixture was extracted with ethyl acetate (20 mL×3). The combined organic layers were dried over anhydrous sodium sulfate and concentrated under vacuum to afford crude title compound 2-(2-(4-(4-(4-((2-Chlorobenzyl)amino)-7H-pyrrolo [2,3-d]pyrimidin-6-yl)benzyl)piperazin-1-yl)ethoxy)ethan-1-ol (250 mg), which was used to next step without further purification.

2. Step—Synthesis of 5-(2-(2-(4-(4-(4-((2-Chlorobenzyl)amino)-7H-pyrrolo[2,3-d]pyrimidin-6-yl)benzyl)piperazin-1-yl)ethoxy)ethoxy)-2-(2,6-dioxopiperidin-3-yl)isoindoline-1,3-dione

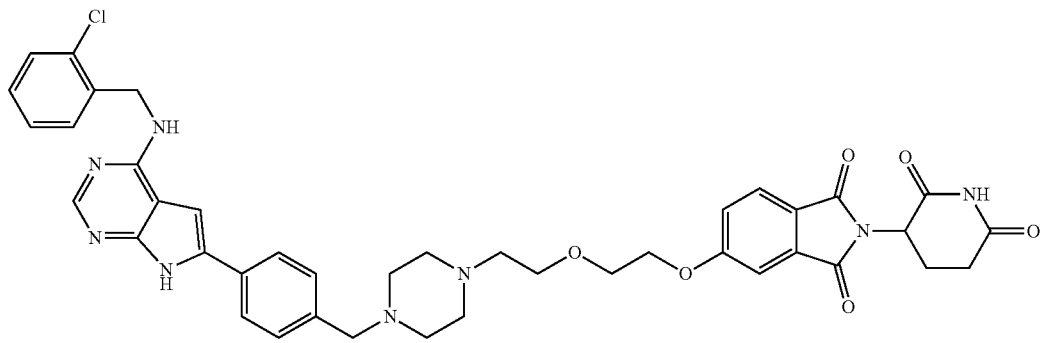

To a solution of 2-(2-(4-(4-(4-((2-chlorobenzyl)amino)-7H-pyrrolo[2,3-d]pyrimidin-6-yl)benzyl)piperazin-1-yl)ethoxy)ethan-1-ol (50 mg, crude, 0.096 mmol), $PPh_3$ (126 mg, 0.480 mmol) and 2-(2,6-dioxopiperidin-3-yl)-5-hydroxyisoindoline-1,3-dione (26 mg, 0.096 mmol) in dry THF (10 mL) was added DIAD (97 mg, 0.480 mmol) dropwise at 0° C. under $N_2$. The mixture was stirred at room temperature for 1 h. The reaction mixture was quenched with water (50 mL), and the mixture was taken up with EA. The combined organic layers were washed with brine, dried over $MgSO_4$, and concentrated. The residue was purified by chromatography (silica gel, DCM: MeOH (10:1, v:v)) to afford the title compound 5-(2-(2-(4-(4-(4-((2-Chlorobenzyl)amino)-7H-pyrrolo[2,3-d]pyrimidin-6-yl)benzyl)piperazin-1-yl)ethoxy)ethoxy)-2-(2,6-dioxopiperidin-3-yl)isoindoline-1,3-dione (6 mg, 0.008 mmol). $^1$H NMR (400 MHz, DMSO-$d_6$): δ 12.09 (s, 1H), 8.18 (s, 1H), 8.10 (s, 1H), 8.05 (s, 1H), 7.74 (d, J=7.2 Hz, 3H), 7.46 (d, J=3.6 Hz, 1H), 7.35 (d, J=8.0 Hz, 3H), 7.28-7.30 (m, 2H), 7.15-7.18 (m, 2H), 7.00 (s, 1H), 5.13-5.18 (m, 1H), 4.78 (d, J=5.2 Hz, 2H), 3.86-3.89 (m, 2H), 3.75-3.79 (m, 2H), 2.72-3.04 (m, 3H), 2.35-2.48 (m, 9H), 2.08-2.13 (m, 1H).

Synthesis of Example 106
(2S,4R)—N-(2-(2-(4-(4-(4-((2-chlorobenzyl)amino)-7H-pyrrolo[2,3-d]pyrimidin-6-yl)benzyl)piperazin-1-yl)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide
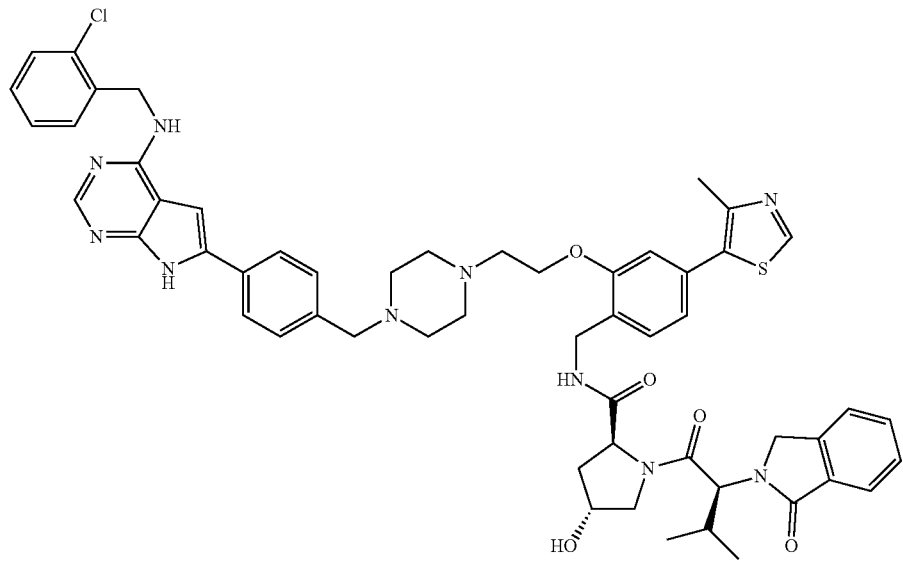
Synthetic scheme:
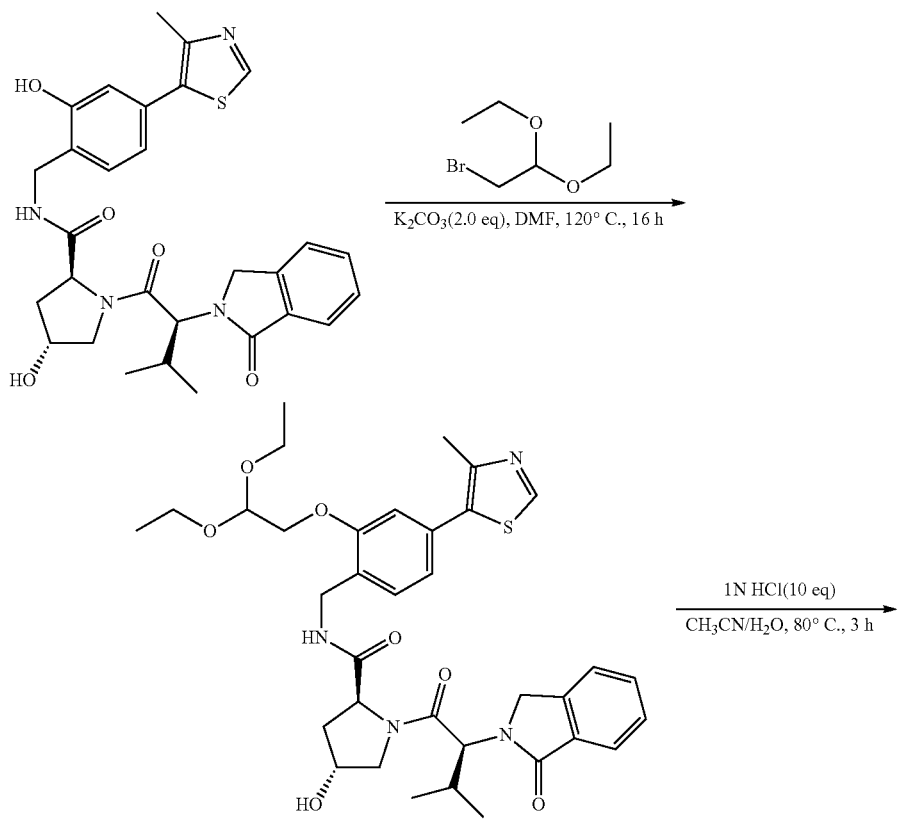

653
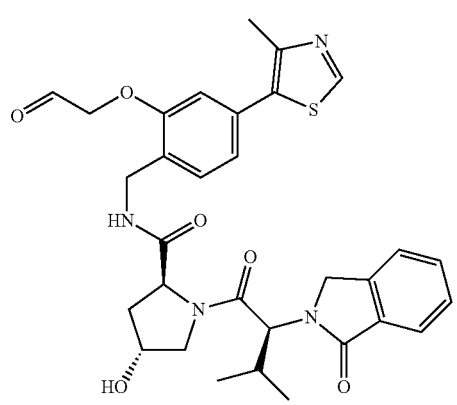
654
-continued
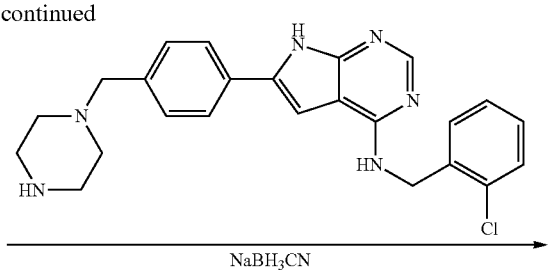
NaBH₃CN
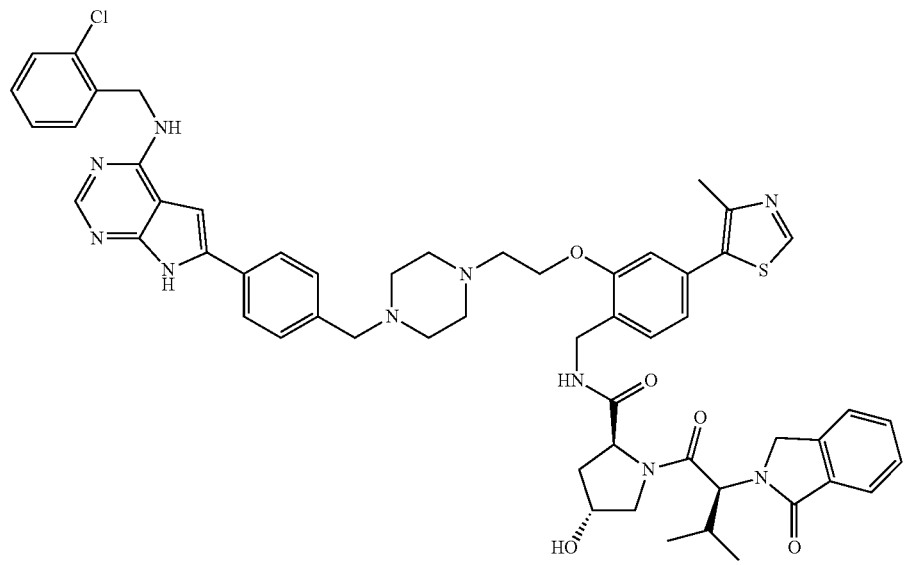 [SMILES: Cc1ncsc1-c1ccc(CNC(=O)[C@@H]2C[C@@H](O)CN2C(=O)[C@H](C(C)C)N2Cc3ccccc3C2=O)c(OCCN2CCN(Cc3ccc(-c4cc5c(NCc6ccccc6Cl)ncnc5[nH]4)cc3)CC2)c1]
1. Step—Synthesis of (2S,4R)—N-(2-(2,2-Diethoxyethoxy)-4-(4-methylthiazol-5-yl)benzyl)-4-hydroxy-1-((S)-3-methyl-2-(1-oxoisoindolin-2-yl)butanoyl)pyrrolidine-2-carboxamide
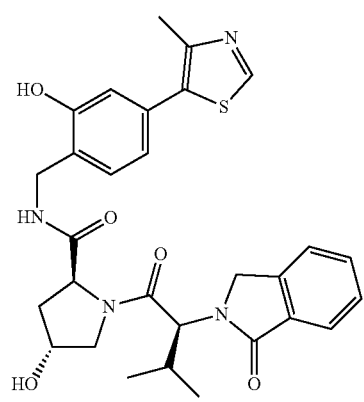
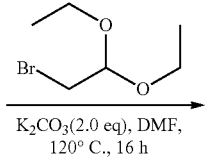
K₂CO₃(2.0 eq), DMF,
120° C., 16 h
-continued
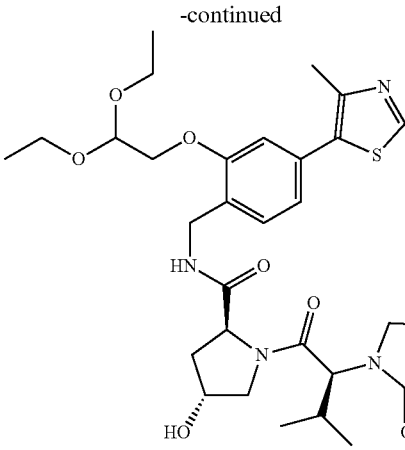
To a solution of (2S,4R)-4-hydroxy-N-(2-hydroxy-4-(4-methylthiazol-5-yl)benzyl)-1-((S)-3-methyl-2-(1-oxoisoin dolin-2-yl)butanoyl)pyrrolidine-2-carboxamide (100 mg, 0.18 mmol) in DMF (5 mL) was added K$_2$CO$_3$ (75.6 mg, 0.55 mmol) and 2-bromo-1,1-diethoxyethane (53.9 mg, 0.27 mmol) at 25° C. The resulting solution was stirred at 110° C. for 16 h. After cooling to rt, the reaction was quenched with H$_2$O (10 mL), and the mixture was extracted with EtOAc (10 mL×2). The combined organic layers were dried over anhydrous sodium sulfate and concentration to give the title product (2S,4R)—N-(2-(2,2-Diethoxyethoxy)-4-(4-methyl-thiazol-5-yl)benzyl)-4-hydroxy-1-((S)-3-methyl-2-(1-oxoi-soindolin-2-yl)butanoyl)pyrrolidine-2-carboxamide (90 mg, crude), which was used in the next step without further purification.

2. Step—Synthesis of (2S,4R)-4-Hydroxy-1-((S)-3-methyl-2-(1-oxoisoindolin-2-yl)butanoyl)-N-(4-(4-methylthiazol-5-yl)-2-(2-oxoethoxy)benzyl)pyrrolidine-2-carboxamide

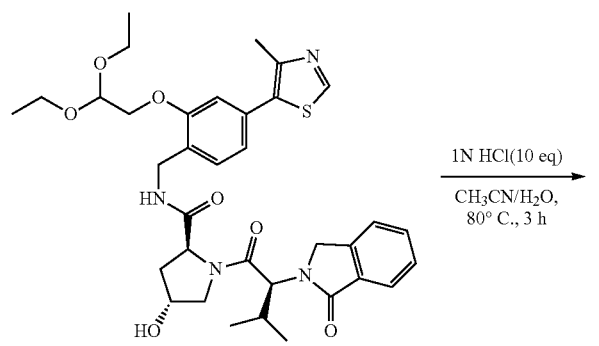

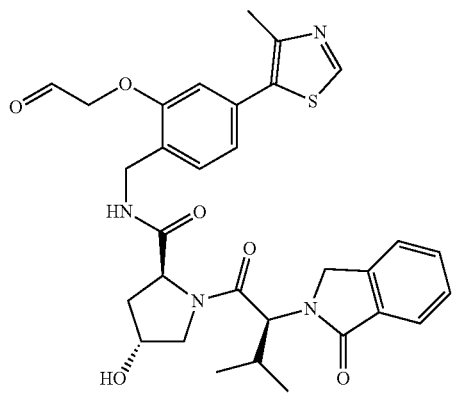

To a solution (2S,4R)—N-(2-(2,2-Diethoxyethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (90 mg, 0.14 mmol) in CH$_3$CN/H$_2$O (5 mL/2 mL) was added 1 N HCl (2 mL) at 25° C. The reaction was stirred at 80° C. for 2 h. After cooling to 25° C., the reaction was quenched with NaHCO$_3$ (10 mL), and the mixture was extracted with EtOAc (10 mL×2). The combined organic layers were washed with brine (10 mL×2), dried over anhydrous sodium sulfate and concentration to afford the title product (2S,4R)-4-Hydroxy-1-((S)-3-methyl-2-(1-oxoisoindolin-2-yl)butanoyl)-N-(4-(4-methylthiazol-5-yl)-2-(2-oxoethoxy)benzyl)pyrrolidine-2-carboxamide (90 mg, crude), which was used in the next step without further purification.

3. Step—Synthesis of (2S,4R)—N-(2-(2-(4-(4-(4-((2-Chlorobenzyl)amino)-7H-pyrrolo[2,3-d]pyrimidin-6-yl)benzyl)piperazin-1-yl)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide

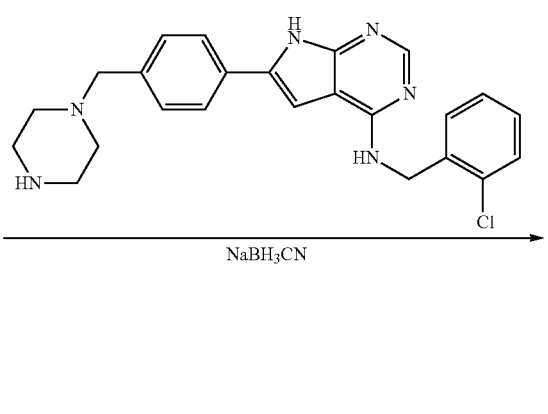

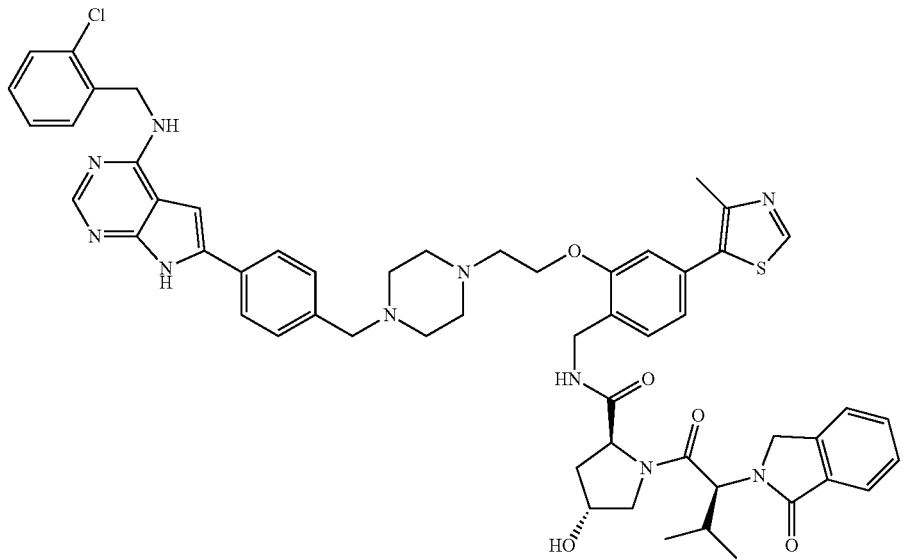 [SMILES: Cc1ncsc1-c1ccc(CNC(=O)[C@@H]2C[C@@H](O)CN2C(=O)[C@H](C(C)C)N2Cc3ccccc3C2=O)c(OCCN2CCN(Cc3ccc(-c4cc5c(NCc6ccccc6Cl)ncnc5[nH]4)cc3)CC2)c1]

To a solution of (2S,4R)-4-hydroxy-1-((S)-3-methyl-2-(1-oxoisoindolin-2-yl)butanoyl)-N-(4-(4-methylthiazol-5-yl)-2-(2-oxoethoxy)benzyl)pyrrolidine-2-carboxamide (90 mg, 0.15 mmol) and N-(2-chlorobenzyl)-6-(4-(piperazin-1-ylmethyl)phenyl)-7H-pyrrolo[2,3-d]pyrimidin-4-amine (79.2 mg, 0.18 mmol) in DMSO/MeOH (2 mL/2 mL) was added NaBH$_3$CN (47.9 mg, 0.76 mmol) at 10° C. The resulting mixture was stirred at 40° C. for 3 h. After cooling to 20° C., the reaction was quenched with H$_2$O (10 mL), and the mixture was extracted with EtOAc (10 mL×2). The combined organic layers were washed with brine (10 mL×2), dried over anhydrous sodium sulfate and concentrated. The residue was purified with silica gel column and prep-HPLC to afford the title product (2S,4R)—N-(2-(2-(4-(4-(-methyl-(2-Chlorobenzyl)amino)-7H-pyrrolo[2,3-d]pyrimidin-6-yl)benzyl)piperazin-1-yl)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (3 g: 99% purity and 6.5 mg: 86% purity, 3 steps 7.6%). $^1$H NMR (400 MHz, CD$_3$OD): δ 8.88 (s, 1H), 8.09 (s, 2H), 7.73-7.76 (m, 3H), 7.37-7.57 (m, 9H), 7.22-7.24 (m, 2H), 7.03-7.05 (m, 2H), 6.93 (s, 1H), 4.95 (s, 2H), 4.39-4.60 (m, 7H), 4.24 (s, 2H), 3.82-3.96 (m, 2H), 3.57 (s, 1H), 2.96 (s, 2H), 2.60-2.77 (m, 8H), 2.49 (s, 3H), 2.01-2.33 (m, 3H), 0.98 (d, J=6.4 Hz, 3H), 0.78 (d, J=6.4 Hz, 3H). Chemical Formula: C$_{55}$H$_{59}$ClN$_{10}$O$_5$S; Molecular Weight: 1007.64 LCMS: m/e+=504.3 [M+2H]2+; t$_R$=3.33 min Synthesis of Example 108

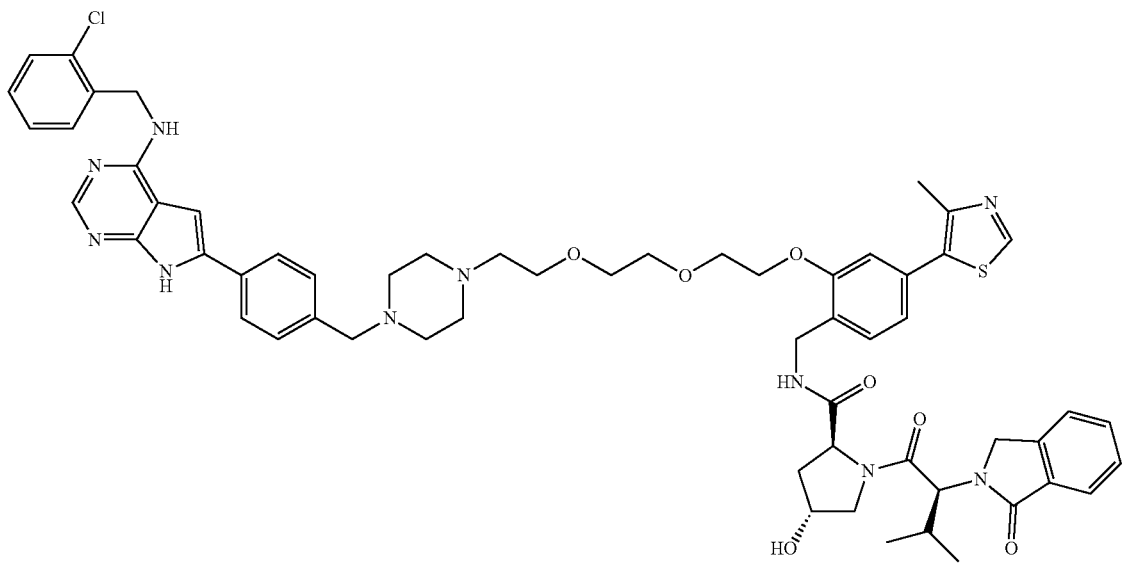 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCN2CCN(Cc3ccc(-c4cc5c(NCc6ccccc6Cl)ncnc5[nH]4)cc3)CC2)c1]

Synthetic Route:
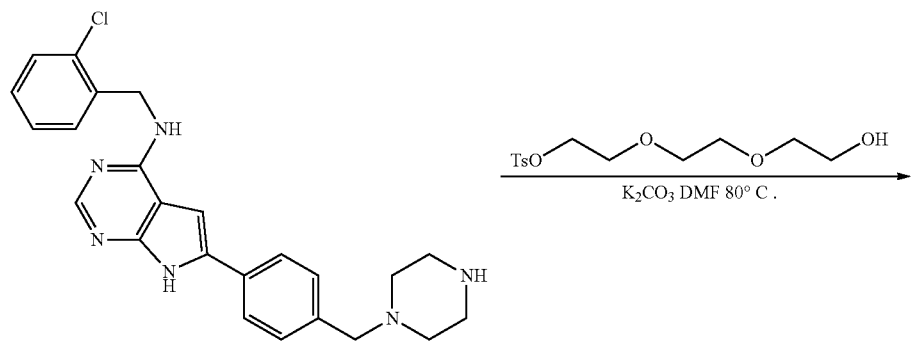
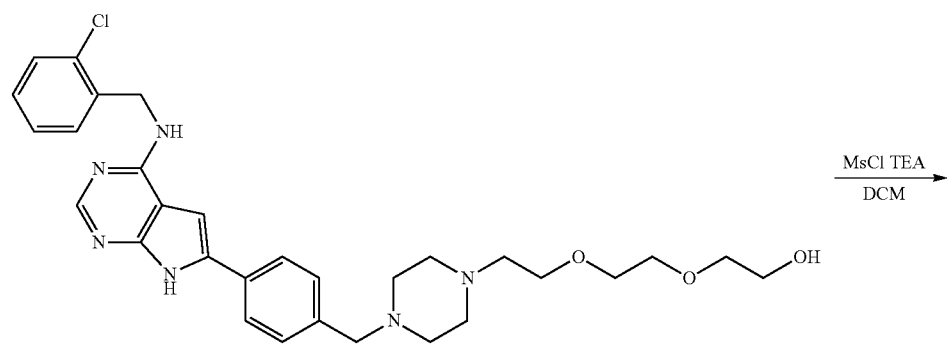
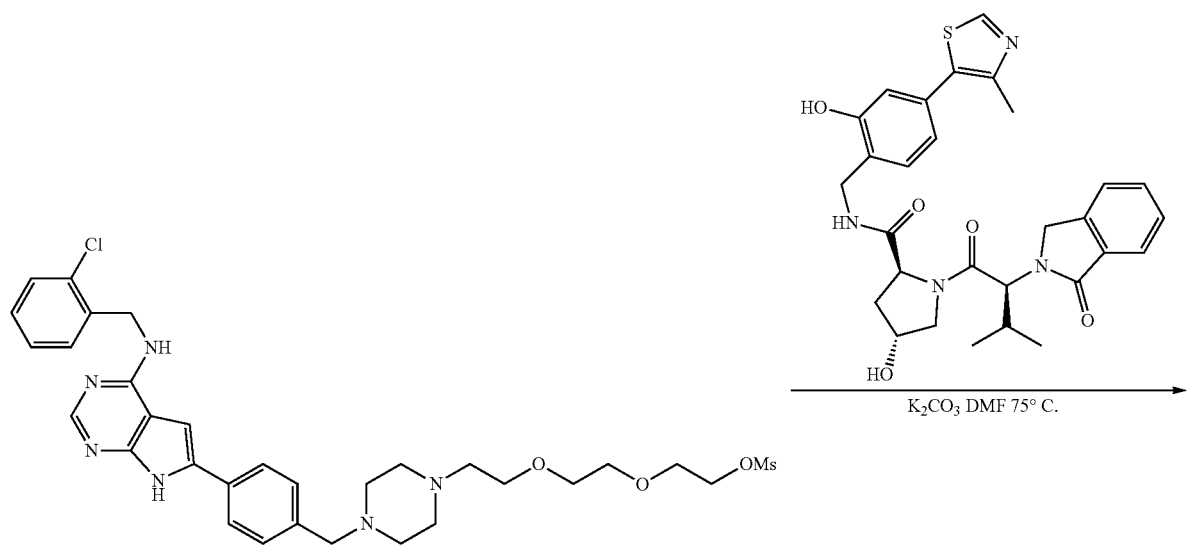

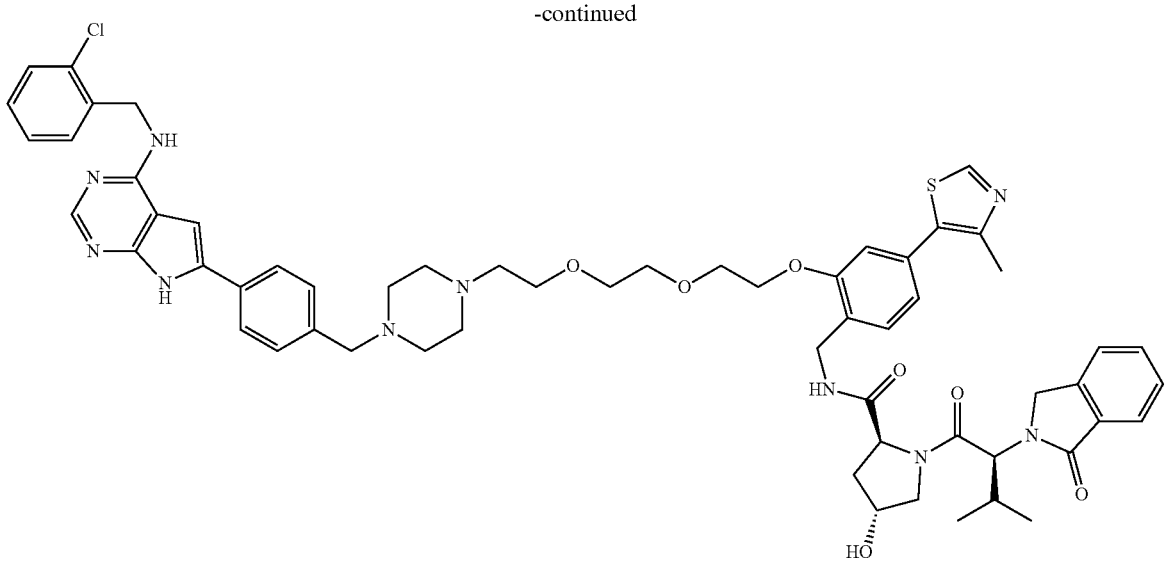

1. Step—Synthesis of 2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethan-1-ol

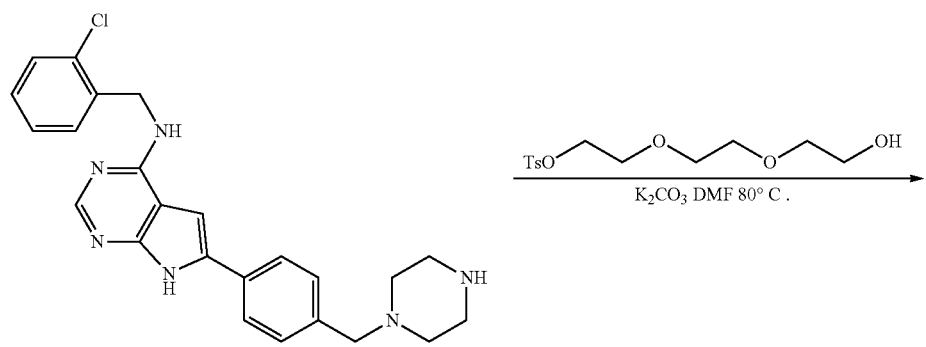

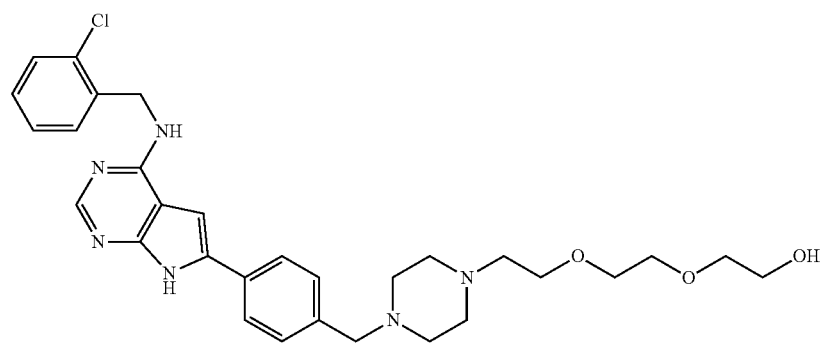

A solution of N-(2-chlorobenzyl)-6-(4-(piperazin-1-ylmethyl)phenyl)-7H-pyrrolo[2,3-d]pyrimidin-4-amine (300 mg, 0.693 mmol), 2-(2-(2-hydroxyethoxy)ethoxy)ethyl 4-methylbenzenesulfonate (900 mg, 3.464 mmol), and K$_2$CO$_3$ (478 mg, 3.464 mmol) in dry DMF (8 mL) was stirred at 80° C. overnight. After cooling to room temperature, the reaction was quenched with water (20 mL), and the mixture was extracted with ethyl acetate (20 mL×3). The combined organic layers were dried over anhydrous Na$_2$SO$_4$ and concentrated to give title product 2-(2-(2-(4-(4-(4-((2-Chlorobenzyl)amino)-7H-pyrrolo [2,3-d]pyrimidin-6-yl)benzyl)piperazin-1-yl)ethoxy)ethoxy)ethan-1-ol (300 mg, crude) as light yellow solid, which was used to next step without further purification.

2. Step—Synthesis of 2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethyl methanesulfonate

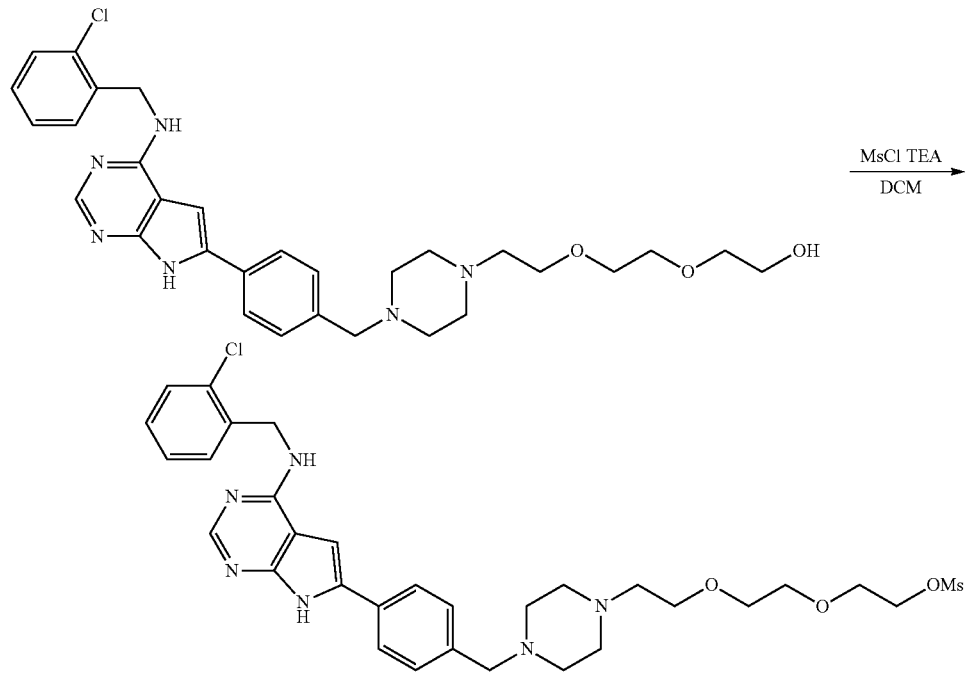

To a solution of 2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethan-1-ol (300 mg, crude, 0.531 mmol) in DCM (10 mL) were added TEA (265 mg, 2.653 mmol) and MsCl (182 mg, 1.593 mmol) at room temperature. After stirring for 20 min, the reaction was quenched with water, and the mixture was extracted with DCM (30 mL×3). The combined organic layers were dried over anhydrous $Na_2SO_4$ and concentrated to give the title product 2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethyl methanesulfonate (350 mg, crude) as faint yellow solid, which was used in the next step without further purification.

2. Step—Synthesis of (2S,4R)—N-(2-(2-(2-(2-(4-(4-(4-((2-Chlorobenzyl)amino)-7H-pyrrolo[2,3-d]pyrimidin-6-yl)benzyl)piperazin-1-yl)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide

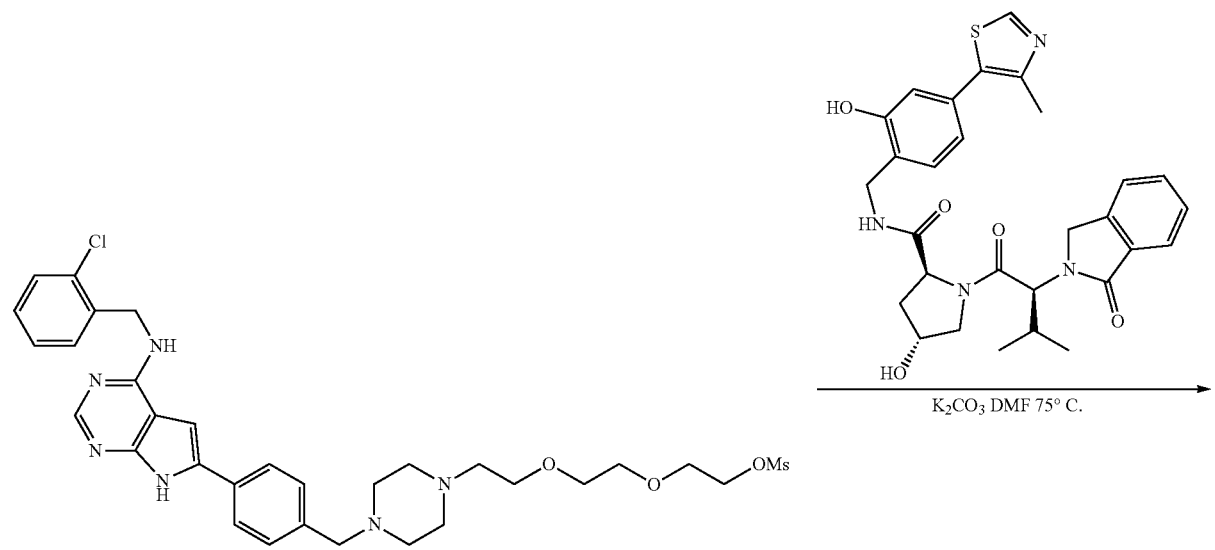

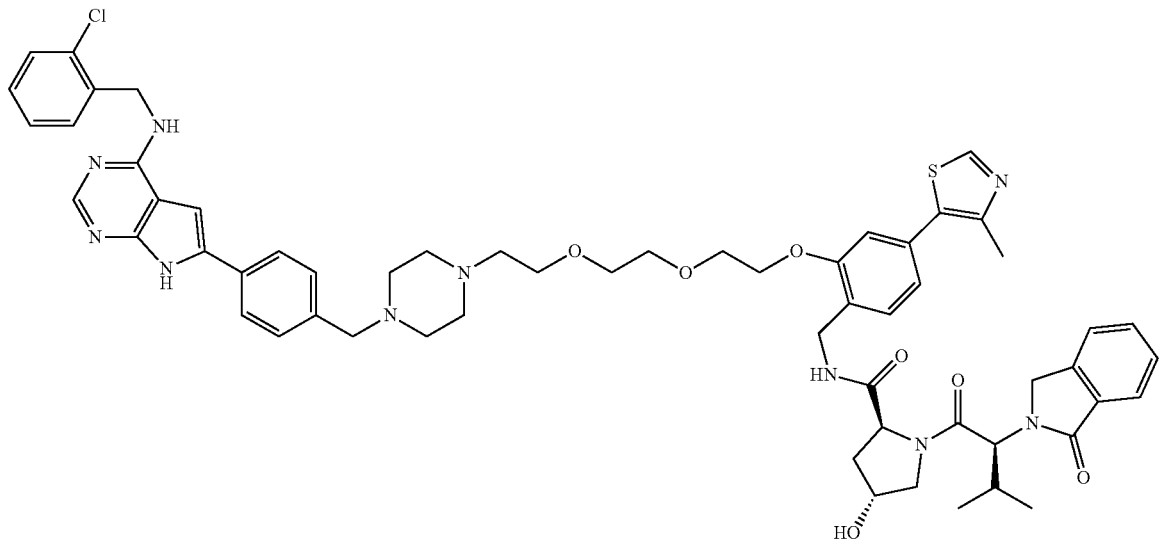

To a solution of 2-(2-(2-(4-((4-(4-((2-chlorobenzyl)amino)-7H-pyrrolo [2,3-d]pyrimidin-6-yl)benzyl)piperazin-1-yl)ethoxy)ethoxy)ethyl methanesulfonate (250 mg, crude, 0.39 mmol) in dry DMF (5 ml) were added K$_2$CO$_3$ (108 mg, 0.78 mmol) and (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (215 mg, 0.39 mmol). The resulting solution was stirred at 75° C. overnight. After cooling to rt, the reaction mixture was quenched with water, and the mixture was extracted with EA (30 mL×2). The combined organic layers were dried over anhydrous sodium sulfate and concentrated under vacuum. The residue was purified by column chromatography to afford the title product (2S,4R)—N-(2-(2-(2-(2-(4-(4-(4-((2-Chlorobenzyl)amino)-7H-pyrrolo [2,3-d]pyrimidin-6-yl)benzyl)piperazin-1-yl)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (17 mg). 1H NMR (400 MHz, CDCl$_3$): δ 8.64 (s, 1H), 8.31 (s, 1H), 7.67 (d, J=7.2 Hz, 3H), 7.46-7.47 (m, 1H), 7.30-7.41 (m, 8H), 7.20 (s, 2H), 6.94 (d, J=5.6 Hz, 1H), 6.84 (s, 1H), 6.63 (s, 1H), 6.04 (s, 1H), 4.95 (d, J=4.4 Hz, 2H), 4.14-4.79 (m, 10H), 3.46-3.85 (m, 13H), 2.48-2.65 (m, 16H), 1.99 (d, J=6.0 Hz, 3H), 0.82 (d, J=6.4 Hz, 3H).

Synthesis of Examples 256 and 257

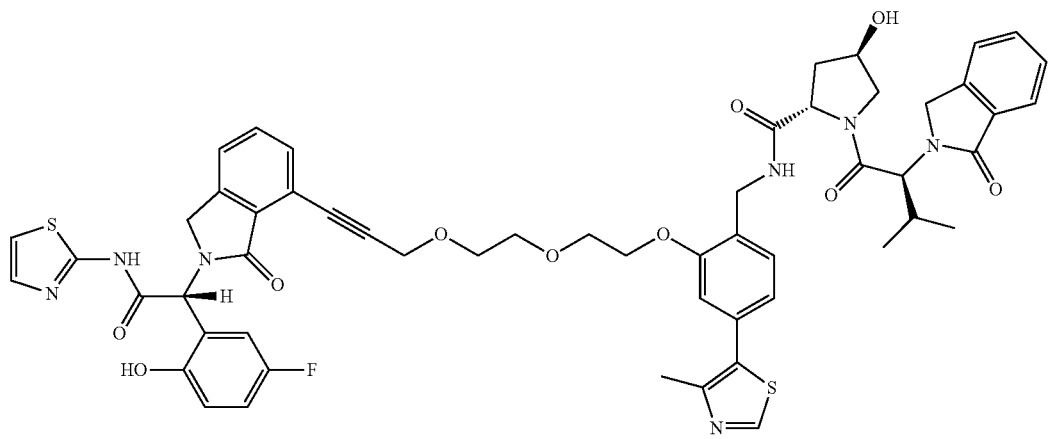

Diastereoisomeres were separated but configuration not determined

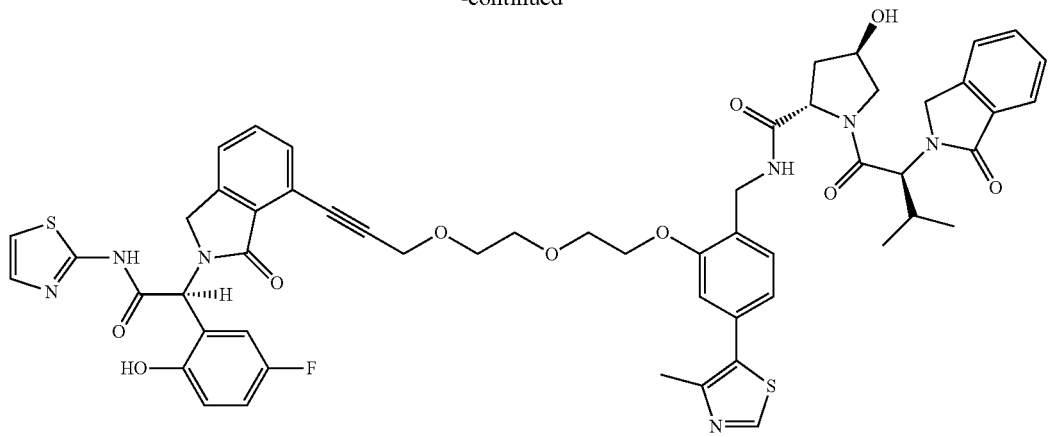

(2S,4R)—N-(2-(2-(2-((3-(2-((R)-1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide and (2S,4R)—N-(2-(2-(2-((3-(2-((R)-1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide Synthetic Scheme - Part 1

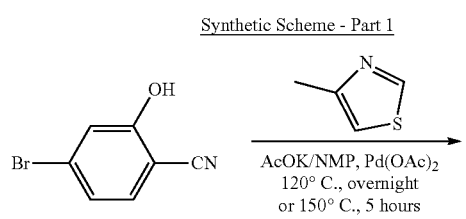

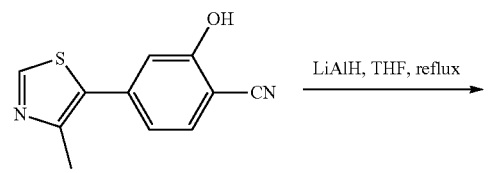

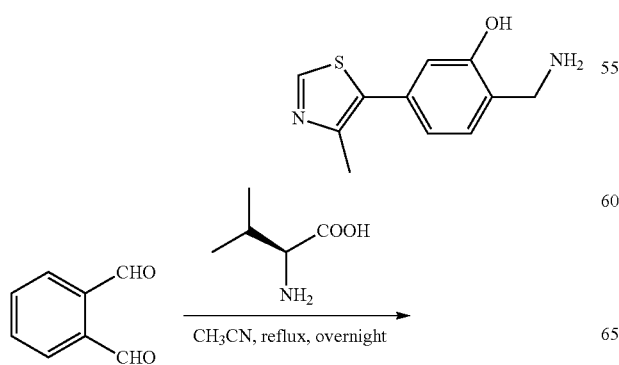

-continued

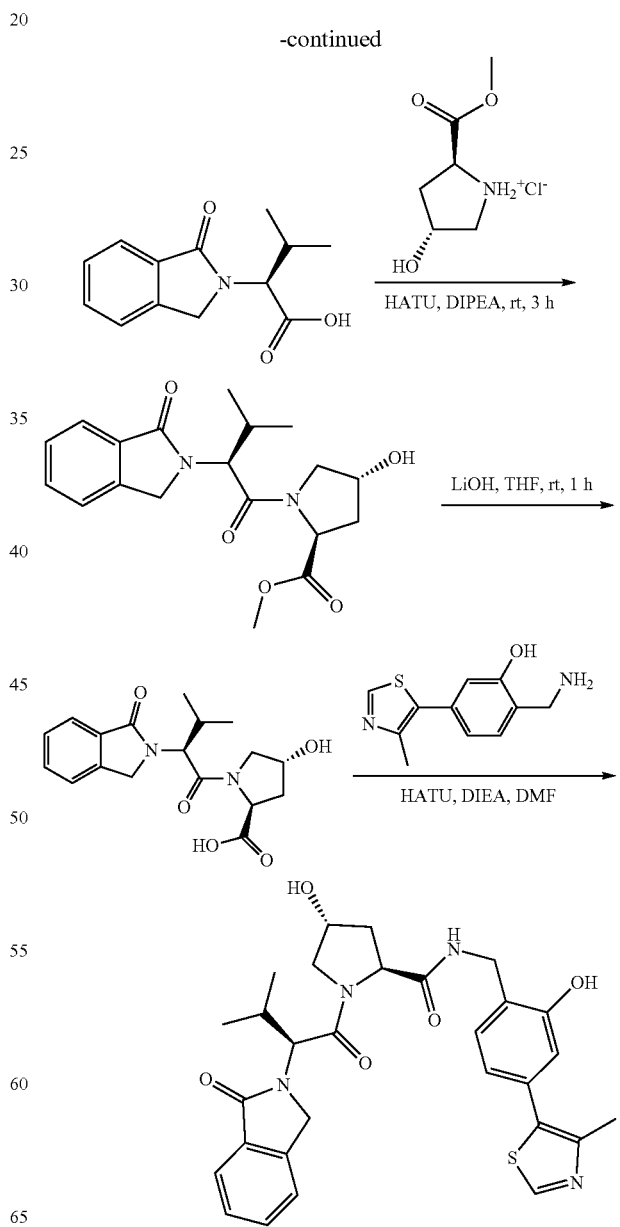

Experimental Procedures

1. Step—Synthesis of 2-hydroxy-4-(4-methylthiazol-5-yl)benzonitrile

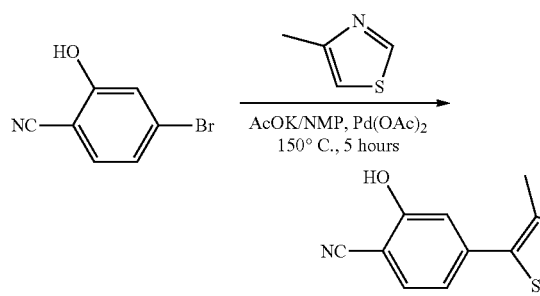

Into a 500-ml-3-necked round-bottom flask with an inert atmosphere of nitrogen were loaded 4-bromo-2-hydroxybenzonitrile (26 g, 131.3 mmol, 1.00 equiv), DMA (300 ml), 4-methylthiazole (26 g, 262.6 mmol, 2.00 equiv), KOAc (26 g, 262.6 mmol, 2.00 equiv), Pd(OAc)$_2$ (884.3 mg, 3.94 mmol, 0.03 equiv). The resulting solution was stirred for 5 hour at 150° C. The reaction was then quenched by the addition of 1000 mL of water. The resulting mixture was washed with 3×500 mL of ethyl acetate and the organic layers combined, and washed with 3×500 mL of H$_2$O. The mixture was dried over anhydrous sodium sulfate and concentrated under vacuum. The residue was applied onto a silica gel column with ethyl acetate/petroleum ether (1:1). This resulted in 14.4 g (66.66 mmol, 50.77%) of 2-hydroxy-4-(4-methylthiazol-5-yl) benzonitrile as a yellow solid. $^1$HNMR (400 MHz, DMSO-d6): δ 2.49 (s, 3H), 7.08 (d, J=8.0 Hz, 1H), 7.13 (s, 1H), 7.71 (d, J=8.0 Hz, 1H), 9.07 (s, 1H), 11.35 (s, 1H).

2. Step—Synthesis of 2-(aminomethyl)-5-(4-methylthiazol-5-yl)phenol

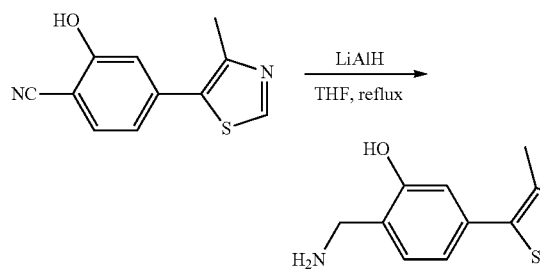

Into a 1000-ml-3-necked round-bottom flash purged and maintained with an inert atmosphere of nitrogen, was placed a solution of 2-hydroxy-4-(4-methylthiazol-5-yl) benzonitrile (14.4 g, 66.66 mmol) in THF 400 ml. This was followed by the addition of LiAlH$_4$ (6.34 g, 166.67 mmol, 2.50 equiv) in several batches at 0° C. The resulting mixture heated to reflux overnight, then allowed to cool to room temperature. The mixture was filtered and the filter cake was washed with 10% MeOH in DCM for four times. The combined filtrates were concentrated to afford the crude product 2-(aminomethyl)-5-(4-methylthiazol-5-yl)phenol 10.4 g (47.27 mmol, 71% yield). It was used to next step without further purification. $^1$H NMR (400 MHz, DMSO-d6): δ 2.40 (s, 3H), 3.62 (br, 1H), 6.33 (d, J=6.0 Hz, 1H), 6.56 (s, 1H), 6.96 (d, J=7.6 Hz, 1H), 8.82 (s, 1H).

3. Step—Synthesis of (S)-3-methyl-2-(1-oxoisoindolin-2-yl)butanoic acid

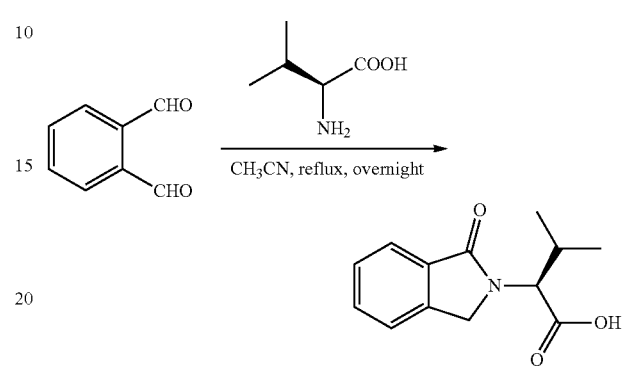

(S)-2-amino-3-methylbutanoic acid (43.7 g, 373 mmol) was added to a solution of phthalaldehyde (50 g, 373 mmol) in acetonitrile (1000 mL). The resulting mixture was refluxed for overnight. The reaction mixture was cooled to r.t then filtered and dried to afford the desired compound (S)-3-methyl-2-(1-oxoisoindolin-2-yl)butanoic acid (72 g, 83%).

4. Step—Synthesis of methyl (2S,4R)-4-hydroxy-1-((S)-3-methyl-2-(1-oxoisoindolin-2-yl)butanoyl) pyrrolidine-2-carboxylate

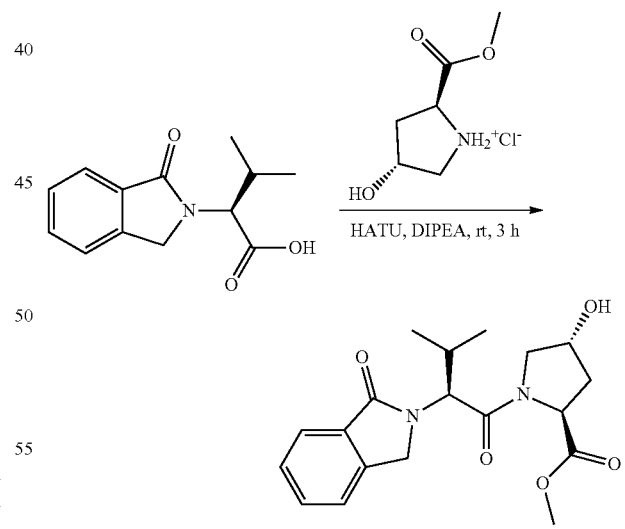

A solution of (S)-3-methyl-2-(1-oxoisoindolin-2-yl) butanoic acid (5 g, 21.44 mmol), (2S,4R)-methyl 4-hydroxypyrrolidine-2-carboxylate, HCl (4.67 g, 25.7 mmol) DIPEA (8.98 ml, 51.4 mmol) in DMF (Volume: 30 ml) was added HATU (9.78 g, 25.7 mmol) at 0° C., The resulting mixture was stirred at room temperature for 2 hours. The mixture was partitioned between EtOAc and water. The organic phase was washed with water, brine and dried over anhydrous Na$_2$SO$_4$. The residue was purified with column chromatography to afford the desired compound methyl (2S,4R)-4-hydroxy-1-((S)-3-methyl-2-(1-oxoisoindolin-2-yl)butanoyl)pyrrolidine-2-carboxylate (5.41 g, 70%). $^1$H-NMR (400 MHz, CDCl$_3$): δ 0.84 (d, J=5.6 Hz, 3H), 1.09 (d, J=5.2 Hz, 3H), 2.00 (m, 1H), 2.31-2.41 (m, 2H), 3.76 (s, 3H), 3.84 (d, J=11.2 Hz, 1H), 4.30-4.38 (m, 2H), 4.56-4.71 (m, 3H), 4.78 (m, 1H), 7.27-7.42 (m, 3H), 7.69 (d, J=7.2 Hz, 1H).

5. Step—Synthesis of (2S,4R)-4-hydroxy-1-((S)-3-methyl-2-(1-oxoisoindolin-2-yl)butanoyl)pyrrolidine-2-carboxylic acid

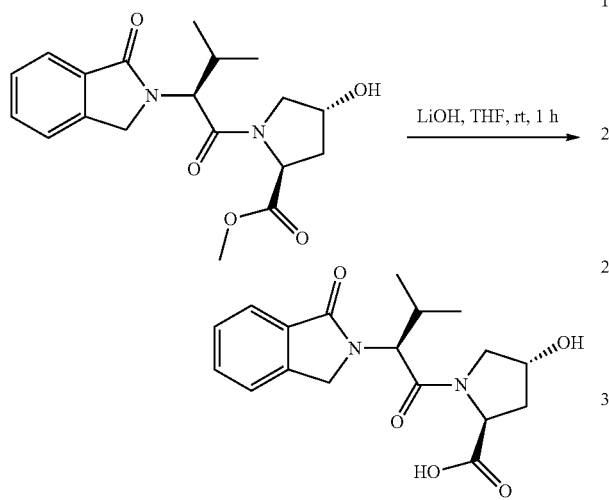

A solution of methyl (2S,4R)-methyl 4-hydroxy-1-((S)-3-methyl-2-(1-oxoisoindolin-2-yl) butanoyl) pyrrolidine-2-carboxylate (5 g, 13.87 mmol) in Water (Volume: 50 ml), THF (Volume: 100 ml), was added lithium hydroxide, H$_2$O (1.164 g, 27.7 mmol), at 0° C. The reaction was stirred at room temperature for 2 h. The reaction mixture was acidified with 1N HCl to pH1-2, and extracted with EtOAc. The combined organic layer was washed with brine, dried over Na$_2$SO$_4$ and concentrated to afford the desired compound (2S,4R)-4-hydroxy-11-((S)-3-methyl-2-(1-oxoisoindolin-2-yl)butanoyl)pyrrolidine-2-carboxylic acid (4.42 g, 92%). $^1$HNMR (400 MHz, CDCl$_3$): δ 0.87 (d, J=6.4 Hz, 3H), 1.05 (d, J=5.6 Hz, 3H), 2.21 (m, 1H), 2.31 (m, 1H), 2.43 (m, 1H), 3.80 (d, J=6.4 Hz, 1H), 4.37-4.44 (m, 2H), 4.55 (s, 1H), 4.64 (t, J=8.0 Hz, 7.6 Hz, 1H), 4.73 (d, J=17.6 Hz, 1H), 4.83 (d, J=10.8 Hz, 1H), 7.38-7.42 (m, 2H), 7.49 (d, J=7.2 Hz, 1H), 7.74 (d, J=7.6 Hz, 1H).

6. Step—Synthesis of (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide

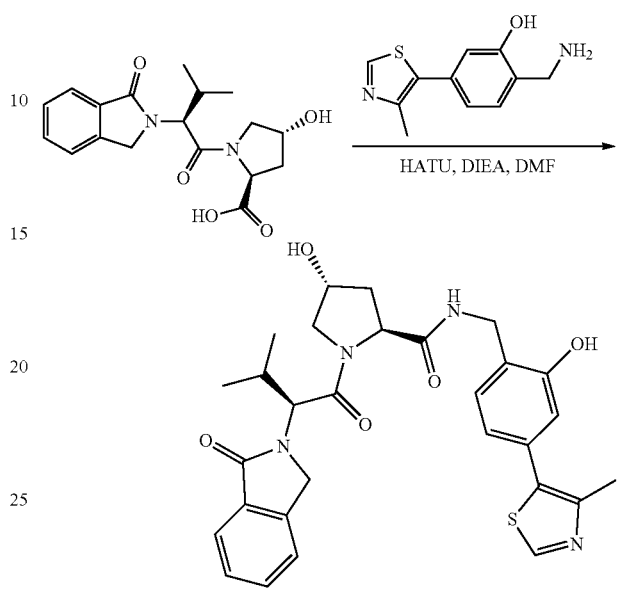

To a solution of 2-(aminomethyl)-5-(4-methylthiazol-5-yl)phenol (6.00 g, 27.3 mmol, 1.10 equiv), (2S,4R)-4-hydroxy-1-((S)-3-methyl-2-(1-oxoisoindolin-2-yl)butanoyl)pyrrolidine-2-carboxylic acid (8.58 g, 24.79 mmol, 1.00equiv), EDCI (5.70 g, 29.75 mmol, 1.20equiv), HOBT (4.02 g, 29.75 mmol, 1.20equiv) in CH$_2$Cl$_2$ (100 mL), was added Et$_3$N (6.0 g, 10.75 mmol). The resulting solution was stirred at room temperature for 1 hour. The mixture was partitioned between CH$_2$Cl$_2$ and water. The organic phase was washed with water, brine and dried over anhydrous Na$_2$SO$_4$. The residue was purified with column chromatography to give the title compound (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (6.3 g, 11.49 mmol, 46.3% yield) $^1$HNMR (400 MHz, CDCl$_3$): δ 0.81 (d, J=6.4 Hz, 3H), 0.86 (d, J=6.8 Hz, 3H), 1.96-2.01 (m, 1H), 2.34-2.40 (m, 1H), 2.44-2.53 (m, 4H), 3.63 (dd, J=3.6, 12.0 Hz 1H), 4.27-4.2 (m, 1H), 4.38-4.43 (m, 2H), 4.53 (s, 2H), 4.68-4.71 (m, 3H), 6.91 (d, J=8.0 Hz, 1H), 7.01 (s, 1H), 7.13 (d, J=7.6 Hz, 1H), 7.42-7.44 (m, 2H), 7.52 (d, J=7.2 Hz, 1H), 7.78 (d, J=7.2 Hz, 1H), 8.01 (s, 1H), 8.66 (s, 1H), 9.20 (br, H). LC-MS (ESI): calcd. 548.21; Found, 549.3 (M+H).

Synthetic Scheme - Part 2:

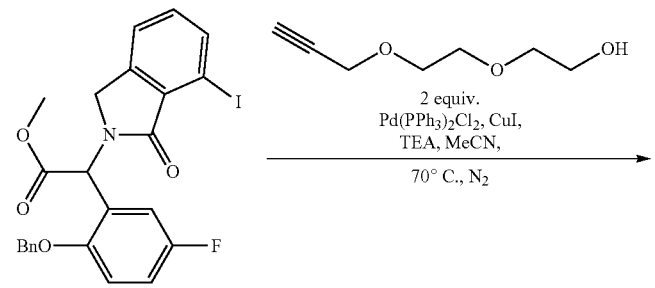

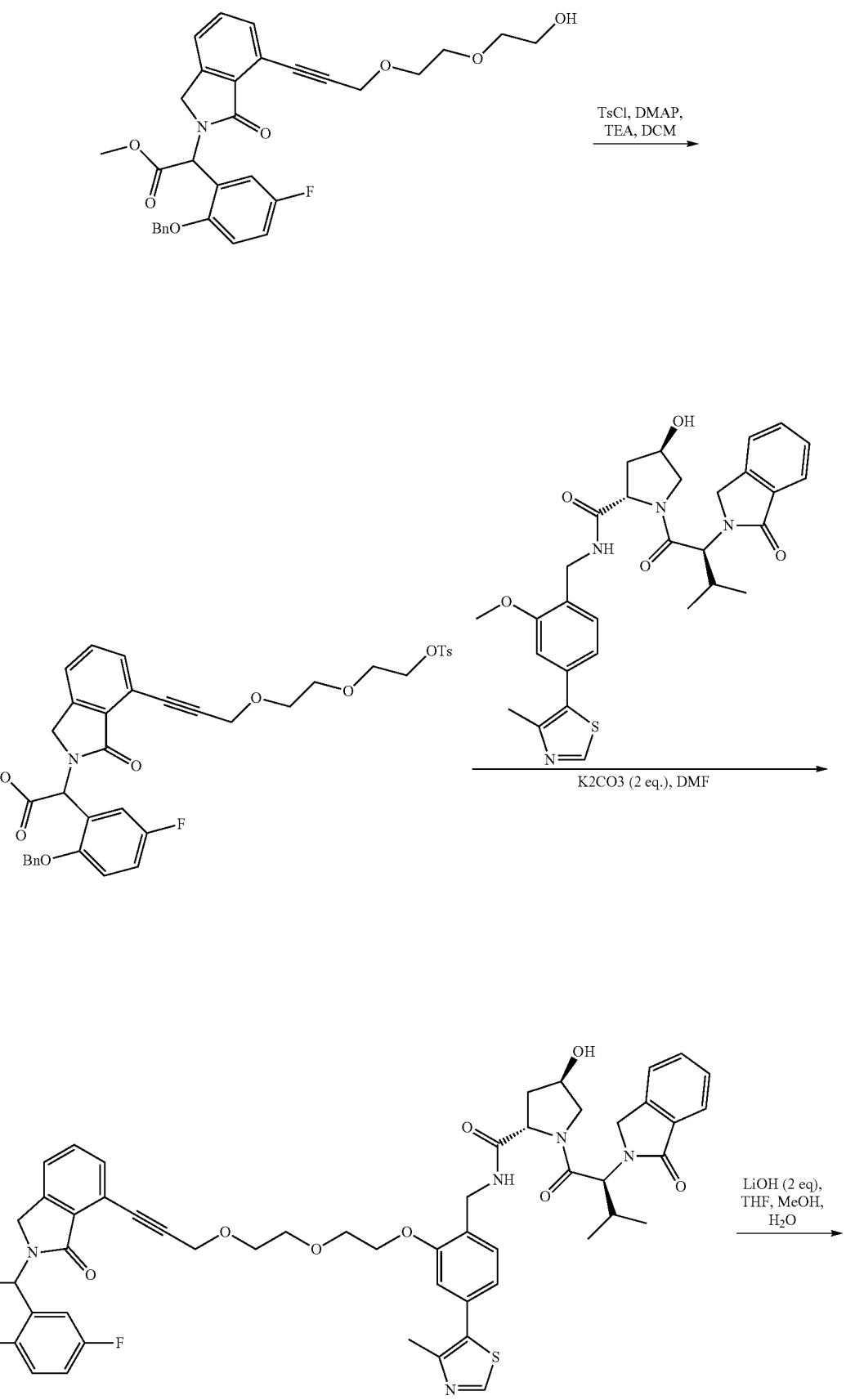

675
676
-continued
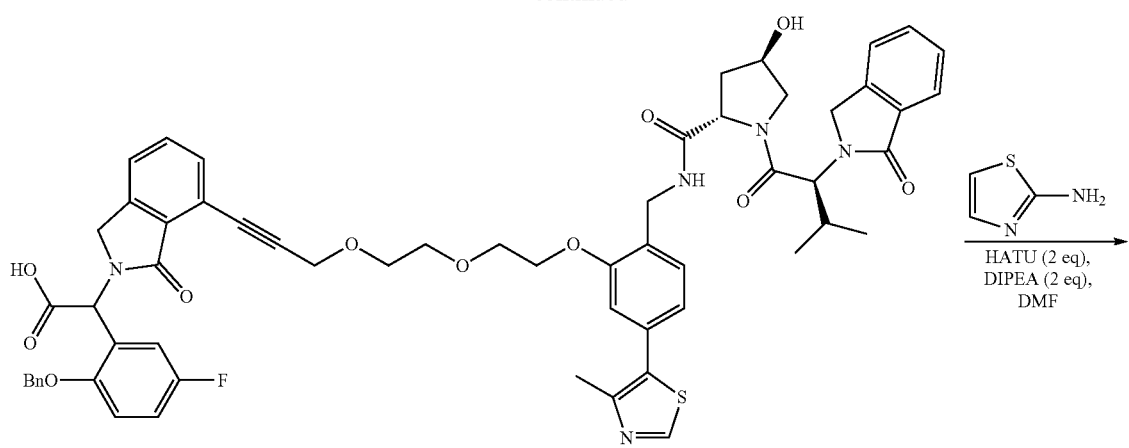
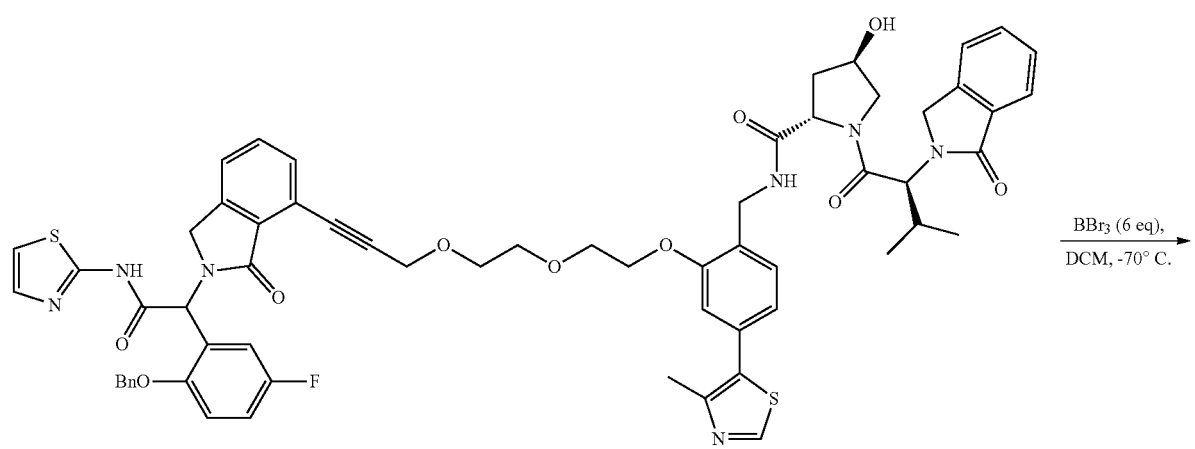
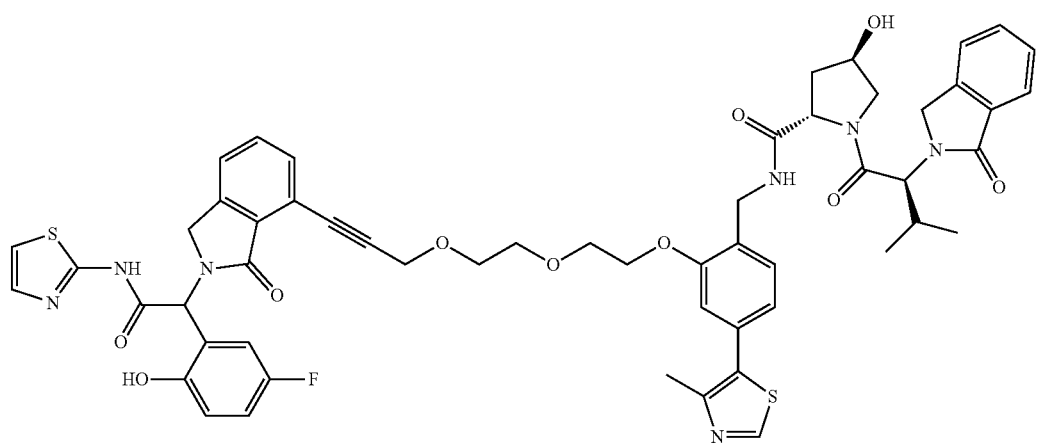

7. Step—Synthesis of methyl 2-(2-(benzyloxy)-5-fluorophenyl)-2-(7-(3-(2-(2-hydroxyethoxy)ethoxy)prop-1-yn-1-yl)-1-oxoisoindolin-2-yl)acetate

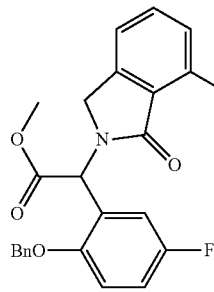

8. Step—Synthesis of methyl 2-(2-(benzyloxy)-5-fluorophenyl)-2-(1-oxo-7-(3-(2-(2-(tosyloxy)ethoxy)ethoxy)prop-1-yn-1-yl)isoindolin-2-yl)acetate

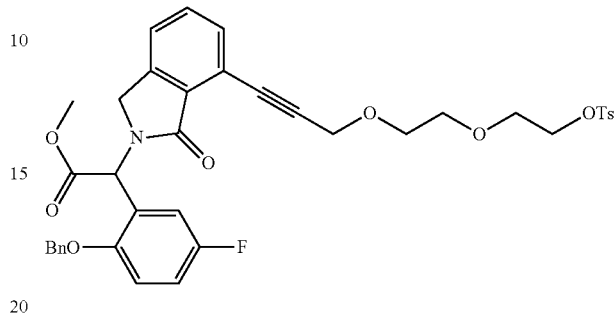

To a stirred mixture of methyl 2-(2-(benzyloxy)-5-fluorophenyl)-2-(7-iodo-1-oxoisoindolin-2-yl)acetate (531 mg, 1.0 mmol), 2-(2-(prop-2-yn-1-yloxy)ethoxy)ethanol (288 mg, 2.0 mmol) and triethylamine (607 mg, 6.00 mmol) in acetonitrile (5 ml) were added copper(I) iodide (38 mg, 0.20 mmol) and bis(triphenylphosphine)palladium(II) chloride (140 mg, 0.20 mmol) under nitrogen atmosphere; the mixture was degassed with nitrogen three times. The mixture was stirred at 65C for 16 hours. TLC showed the reaction was complete. The reaction mixture was partitioned between ethyl acetate (50 ml) and water (20 ml). The organic layer was collected, washed with brine (20 ml×2), dried over anhydrous sodium sulfate and concentrated under reduced pressure to give a crude residue which was purified by silica gel flash column chromatography (eluted with 4% methanol in dichloromethane) to afford methyl 2-(2-(benzyloxy)-5-fluorophenyl)-2-(7-(3-(2-(2-hydroxyethoxy)ethoxy)prop-1-yn-1-yl)-1 1-oxoisoindolin-2-yl)acetate (450 mg, yield 82%) as brown oil. LC_MS: (ES$^+$): m/z 548.3 [M+H]$^+$. $t_R$=2.848 min.

A mixture of methyl 2-(2-(benzyloxy)-5-fluorophenyl)-2-(7-(3-(2-(2-hydroxyethoxy)ethoxy)prop-1-yn-1-yl)-1-oxoisoindolin-2-yl)acetate (450 mg, 0.82 mmol), 4-toluenesulfonyl chloride (235 mg, 1.23 mmol), N,N-dimethylpyridin-4-amine (10 mg, 0.08 mmol), and triethylamine (166 mg, 1.64 mmol) in dichloromethane (15 ml) was stirred at room temperature overnight. TLC showed the reaction was complete. The reaction mixture was diluted with dichloromethane (40 ml) and washed with brine (40 ml×2), dried over anhydrous sodium sulfate and concentrated under reduced pressure to give a crude residue which was purified by silica gel flash column chromatography (eluted with 4% methanol in dichloromethane) to afford methyl 2-(2-(benzyloxy)-5-fluorophenyl)-2-(1-oxo-7-(3-(2-(2-(tosyloxy)ethoxy)ethoxy)prop-1-yn-1-yl)isoindolin-2-yl)acetate (360 mg, yield 61%) as white solid. LC_MS: (ES$^+$): m/z 702.5 [M+H]$^+$. $t_R$=3.282 min.

9. Step—Synthesis of methyl 2-(2-(benzyloxy)-5-fluorophenyl)-2-(7-(3-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)prop-1-yn-1-yl)-1-oxoisoindolin-2-yl)acetate

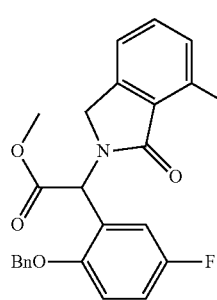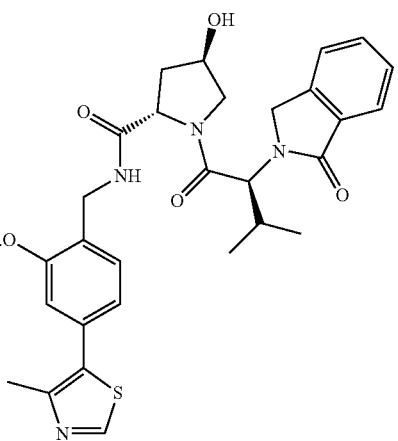

A mixture of methyl 2-(2-(benzyloxy)-5-fluorophenyl)-2-(1-oxo-7-(3-(2-(2-(tosyloxy)ethoxy)ethoxy)prop-1-yn-1-yl)isoindolin-2-yl)acetate (383 mg, 0.55 mmol), (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (250 mg, 0.46 mmol) and potassium carbonate (127 mg, 0.92 mmol) in N,N-dimethylformamide (8 ml) was stirred at 80° C. under nitrogen overnight. TLC showed the reaction was complete. The reaction mixture was partitioned between ethyl acetate (50 ml) and water (30 ml). The organic layer was collected, washed with brine (20 ml×2), dried over anhydrous sodium sulfate and concentrated under reduced pressure to give a crude residue which was purified by silica gel flash column chromatography (eluted with 3% methanol in dichloromethane) to afford methyl 2-(2-(benzyloxy)-5-fluorophenyl)-2-(7-(3-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)prop-1-yn-1-yl)-1-oxoisoindolin-2-yl)acetate (360 mg, yield 73%) as white solid. LC_MS: (ES$^+$): m/z 1078.4 [M+H]$^+$. $t_R$=3.027 min.

10. Step—Synthesis of 2-(2-(benzyloxy)-5-fluorophenyl)-2-(7-(3-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)prop-1-yn-1-yl)-1-oxoisoindolin-2-yl)acetic acid

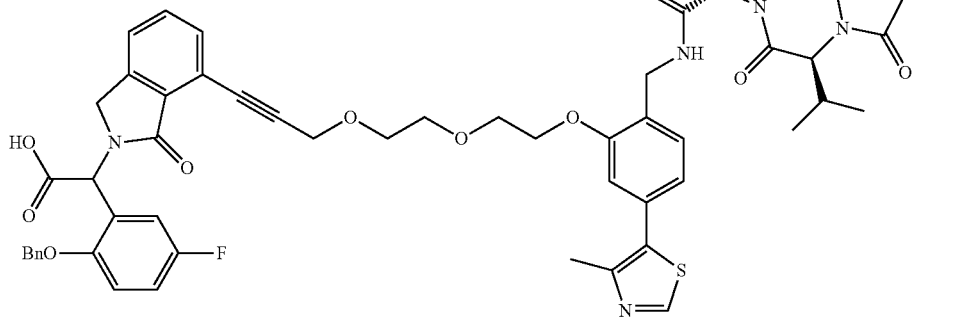

A mixture of methyl 2-(2-(benzyloxy)-5-fluorophenyl)-2-(7-(3-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)prop-1-yn-1-yl)-1-oxoisoindolin-2-yl)acetate (360 mg, 0.33 mmol) and lithium hydroxide monohydrate (28 mg, 0.67 mmol) in tetrahydrofuran (8 ml)-methanol (2 ml)-water (2 ml) was stirred at room temperature for 16 hours. TLC showed the reaction was complete. The reaction mixture was acidified with diluted hydrochloride acid (1N) till pH 5-6, and extracted with ethyl acetate (30 ml×2). The combined organic layers were dried over sodium sulfate and concentrated under reduced pressure to give 2-(2-(benzyloxy)-5-fluorophenyl)-2-(7-(3-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)prop-1-yn-1-yl)-1-oxoisoindolin-2-yl)acetic acid (400 mg, crude) as white solid which was used in next step directly without further purification. LC_MS: (ES$^+$): m/z 1064.6 [M+H]$^+$. $t_R$=2.882 min.

11. Step—Synthesis of (2S,4R)—N-(2-(2-(2-((3-(2-(1-(2-(benzyloxy)-5-fluorophenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide

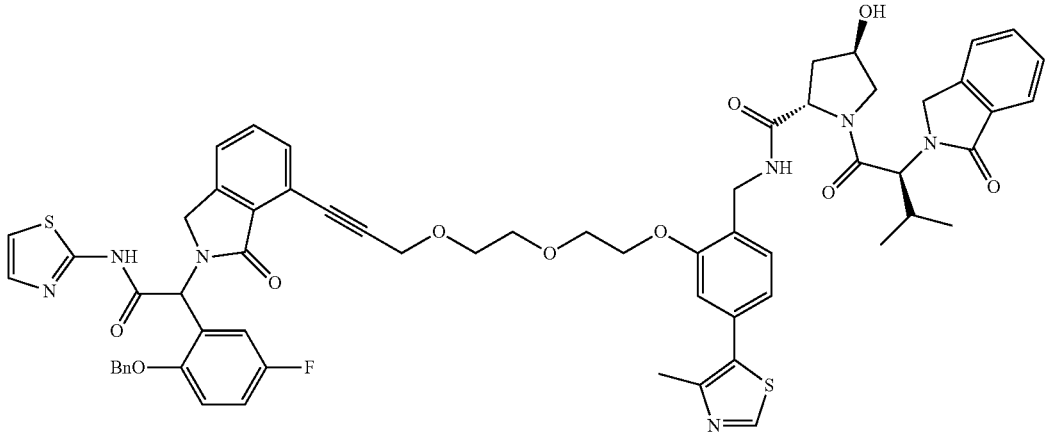 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCC#Cc2cccc3c2C(=O)N(C(C(=O)Nc2nccs2)c2cc(F)ccc2OCc2ccccc2)C3)c1]

To a stirred solution of 2-(2-(benzyloxy)-5-fluorophenyl)-2-(7-(3-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)prop-1-yn-1-yl)-1-oxoisoindolin-2-yl)acetic acid (400 mg, crude), N-ethyl-N-isopropylpropan-2-amine (85 mg, 0.66 mmol) and thiazol-2-amine (33 mg, 0.33 mmol) in N,N-dimethylformamide (5 ml) was added 2-(7-Aza-1H-benzotriazole-1-yl)-1,1,3,3-tetramethyluronium hexafluorophosphate (HATU) (250 mg, 0.66 mmol) at 0° C., the resulting mixture was allowed to warm to room temperature and stirred for 20 min. TLC showed the reaction was complete. The reaction mixture was partitioned between ethyl acetate (30 ml) and water (20 ml). The organic layer was collected, washed with brine (20 ml×2), dried over anhydrous sodium sulfate and concentrated under reduced pressure to give a crude residue which was purified by silica gel flash column chromatography (eluted with 5% methanol in dichloromethane) to afford (2S,4R)—N-(2-(2-(2-((3-(2-(1-(2-(benzyloxy)-5-fluorophenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (200 mg, yield 53%) as white solid. LC_MS: (ES$^+$): m/z 1146.5 [(M+1)/2+H]$^+$. $t_R$=3.010 min.

12. Step—Synthesis of (2S,4R)—N-(2-(2-(2-((3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide

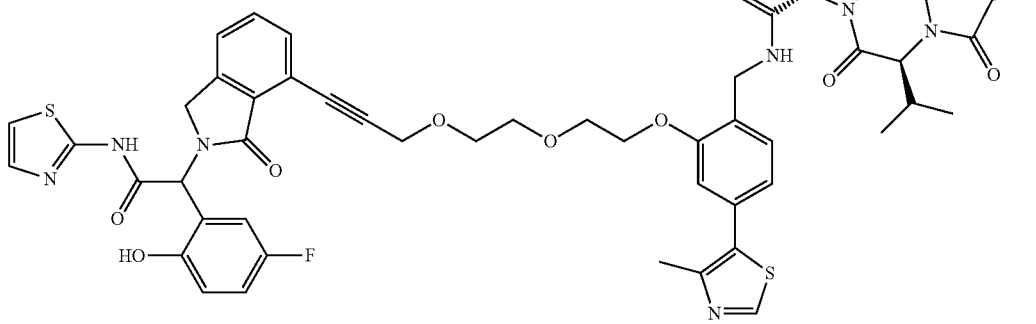

To a stirred solution of (2S,4R)—N-(2-(2-(2-((3-(2-(1-(2-(benzyloxy)-5-fluorophenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (100 mg, 0.09 mmol) in dichloromethane (8 ml) was added boron tribromide (131 mg, 0.52 mmol) in dichloromethane (1 ml) at −70° C. over 30 minutes. The resulting mixture was stirred at −70° C. for 1 hour. TLC showed the reaction was complete. The reaction mixture was diluted with dichloromethane (15 ml) and quenched with saturated sodium bicarbonate solution (8 ml) at −70° C. The organic layer was collected and the aqueous layer was extracted with dichloromethane (15 ml×2). The combined organic layers were washed with brine (20 ml), dried over anhydrous sodium sulfate, and concentrated under reduced pressure to give a crude residue which was purified by preparative TLC (eluted with 5% methanol in dichloromethane) to afford (2S,4R)—N-(2-(2-(2-((3-(2-(1-(5-fluoro-2-hydroxyphenyl)-2-oxo-2-(thiazol-2-ylamino)ethyl)-3-oxoisoindolin-4-yl)prop-2-yn-1-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (8.5 mg, yield 9%) as white solid. LC_MS: (ES$^+$): m/z 1056.5 [M+H]$^+$. t$_R$=2.790 min. $^1$H NMR (400 MHz, DMSO-d6): δ 0.72 (d, J=6.8 Hz, 3H), 0.95 (d, J=6.4 Hz, 3H), 1.88-1.95 (m, 1H), 2.01-2.07 (m, 1H), 2.29-2.35 (m, 1H), 2.46 (s, 3H), 3.69-3.71 (m, 3H), 3.75-3.77 (m, 3H), 3.80-3.82 (m, 2H), 3.95 (d, J=18.4 Hz, 1H), 4.18 (t, J=4.0 Hz, 2H), 4.25-4.33 (m, 3H), 4.38-4.47 (m, 4H), 4.52-4.59 (m, 2H), 4.70 (d, J=10.8 Hz, 1H), 6.26 (s, 1H), 6.84-6.91 (m, 2H), 7.00 (d, J=4.0 Hz, 1H), 7.04 (s, 1H), 7.07-7.12 (m, 1H), 7.23 (d, J=3.2 Hz, 1H), 7.33 (d, J=7.6 Hz, 1H), 7.46-7.53 (m, 3H), 7.55-7.57 (m, 2H), 7.60-7.62 (m, 2H), 7.70 (d, J=7.6 Hz, 1H), 8.38 (t, J=6.0 Hz, 1H), 8.98 (s, 1H). Chemical Formula: $C_{56}H_{54}FN_7O_{10}S_2$; Molecular Weight: 1055.34;

The two diastereoisomerc compounds Example 256 and Example 257 could be separated by reversed phase preparative HPLC.

Synthesis of Examples 268-271 and 273

General Procedure

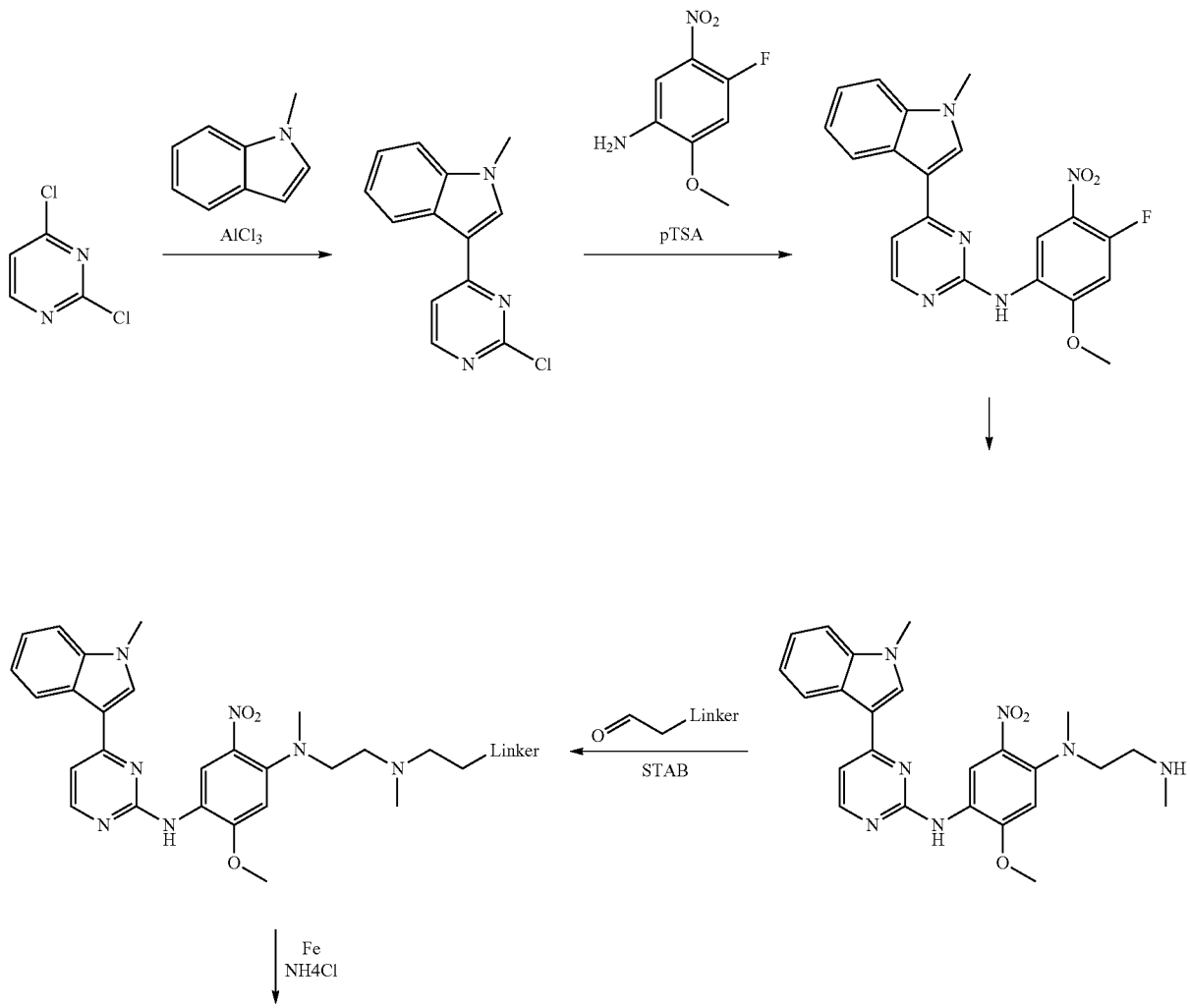

-continued

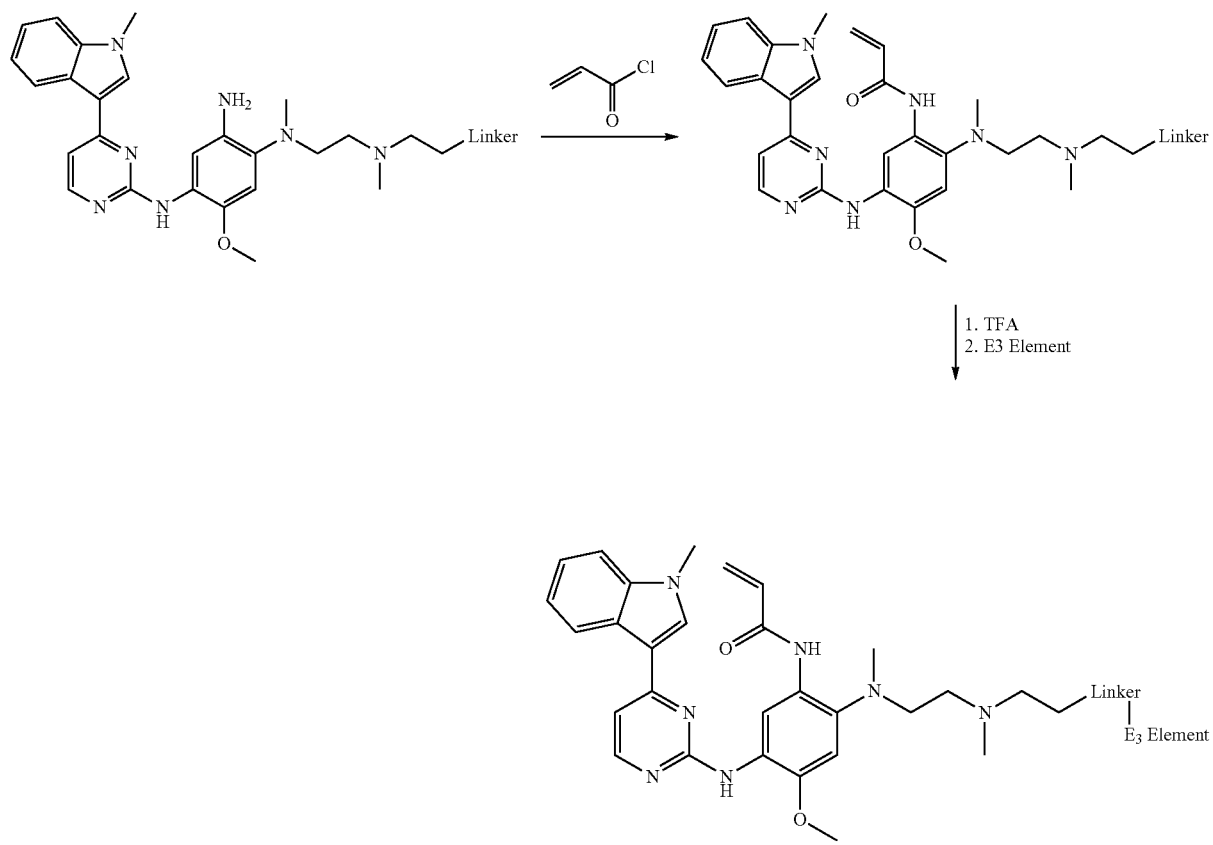

1. TFA
2. E3 Element 3-(2-chloropyrimidin-4-yl)-1-methyl-indole

N-(4-fluoro-2-methoxy-5-nitro-phenyl)-4-(1-methyl-indol-3-yl)pyrimidin-2-amine

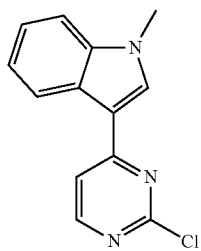 [SMILES: Cn1cc(-c2ccnc(Cl)n2)c2ccccc21]

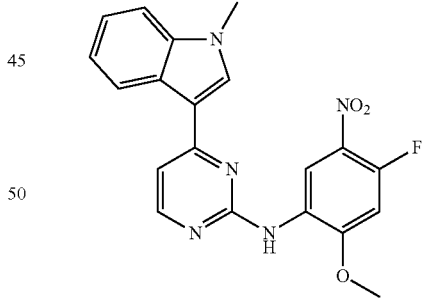

2,4-dichloropyrimidine (3 g, 20.1 mmol) was dissolved in DME (50 ml) and heated to 60° C. FeCl$_3$ (2953 mg, 22.1 mmol) added followed by 1-methylindole (2642 mg, 20.1 mmol) and reaction stirred at 60° C. overnight. Cooled to r.t. and poured into ice water, stirred for 30 minutes and the resulting precipitate collected by filtration. Purified by column chromatography eluting with DCM to provide 2.4 g (49%) of 3-(2-chloropyrimidin-4-yl)-1-methyl-indole. NMR and LC-MS conform to structure and match literature reports.

3-(2-chloropyrimidin-4-yl)-1-methyl-indole (2 g, 8.21 mmol) and 4-fluoro-2-methoxy-5-nitro-aniline (1833 mg, 9.85 mmol) were suspended in 2-pentanol. Para-toluene-sulfonic acid (1873 mg, 9.85 mmol) was added and the reaction heated to 110° C. for 2 hours under microwave conditions. The reaction mixture was allowed to cool to r.t. and the resulting precipitate collected by filtration, washed with 2-pentanol, triturated with acetonitrile and dried in vacuo to a yellow solid (2453 mg, 76%). NMR and LC-MS conform to structure and match literature reports.

2-methoxy-N4-methyl-N4-[2-(methylamino)ethyl]-N1-[4-(1-methylindol-3-yl)pyrimidin-2-yl]-5-nitro-benzene-1,4-diamine

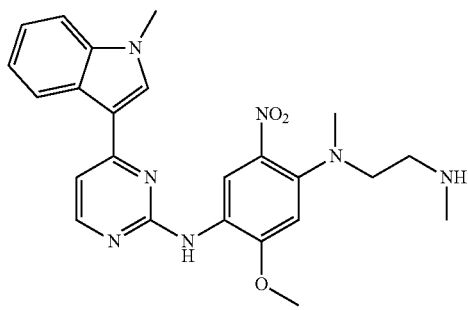 [SMILES: CNCCN(C)c1cc(OC)c(Nc2nccc(-c3cn(C)c4ccccc34)n2)cc1[N+](=O)[O-]]

N-(4-fluoro-2-methoxy-5-nitro-phenyl)-4-(1-methylindol-3-yl)pyrimidin-2-amine (1300 mg, 3.3 mmol) dissolved in DMA (10 ml) and N-(4-fluoro-2-methoxy-5-nitro-phenyl)-4-(1-methylindol-3-yl)pyrimidin-2-amine (1.07 ml, 9.91 mmol) added followed by TEA (0.92 ml, 6.61 mmol) and the reaction heated to 140° C. for 30 minutes under microwave conditions and quenched with water (20 ml). The reaction mixture was extracted with ethyl acetate (3×20 ml). The combined organics were washed with water, dried over $MgSO_4$ and concentrated in vacuo to a red solid. Used in subsequent steps with no further purification.

General Procedure for Linker Introduction Via Reductive Amination

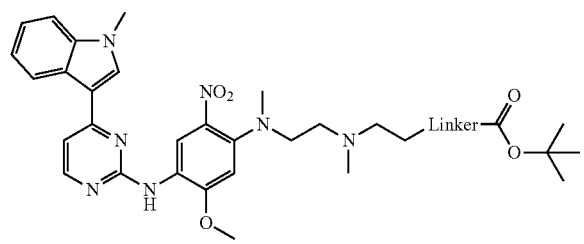

2-methoxy-N4-methyl-N4-[2-(methylamino)ethyl]-N1-[4-(1-methylindol-3-yl)pyrimidin-2-yl]-5-nitro-benzene-1,4-diamine (1 eq.) dissolved in DCM and aldehyde-t-butyl ester (2.2 eq.) added followed by sodium triacetoxyborohydride (1.2 eq.) and the reaction stirred for 1 hour at r.t. Reaction mixture concentrated in vacuo and purified by column chromatography eluting with 0-10% methanol in DCM.

General Procedure for Nitro Group Reduction

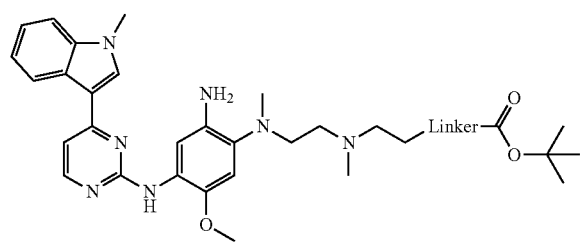

Nitro containing compound (1 eq.) suspended in 1:1 ethanol/water and iron (6 eq.) added followed by ammonium chloride (0.75 eq.). Reaction heated to reflux for 2 hours, allowed to cool to r.t. and filtered through celite, eluting with 10% methanol/DCM. Filtrate extracted with DCM (3×), dried over MgSO4 and concentrated in vacuo. If necessary compounds were purified by column chromatography eluting with 0-10% methanol in DCM.

General Procedure for Aniline Acylation

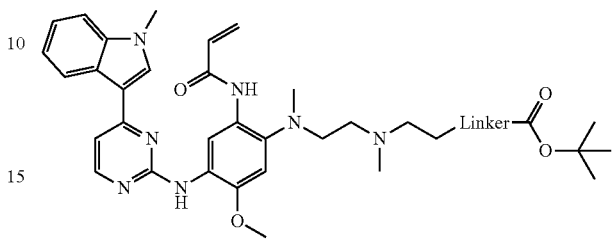

Acryloyl chloride (1.1 eq.) was added dropwise to a vigorously stirred solution of aniline compound (1 eq.) and TEA (5 eq.) in DCM. Reaction stirred for 1 hour at r.t. Excess acryloyl chloride was quenched with methanol (excess) and the reaction mixture concentrated in vacuo. Residue purified by column chromatography eluting with 0-10% methanol in DCM.

General Procedure for t-Butyl Ester Deprotection

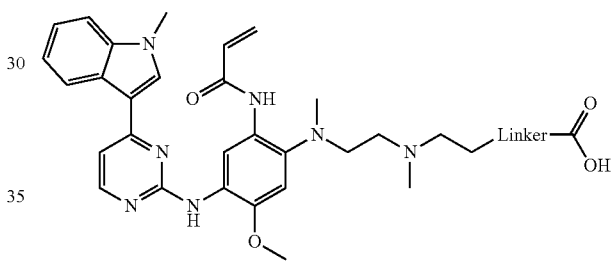

T-butyl ester (1 eq.) dissolved in 20% TFA in DCM and stirred at r.t. for 1 hour. Reaction mixture concentrated in vacuo and used immediately in the next step.

General Procedure for Coupling of E3 Recruiting Element

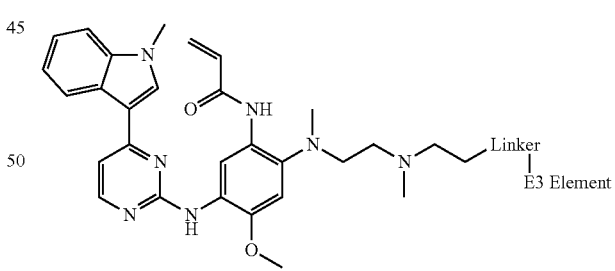

Crude acid component (1 eq.) dissolved in DMF. HATU (1.1 eq.) added followed by TEA (5 eq.) and reaction stirred for 10 minutes. Amine coupling component (either VHL ligand, (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide or 5-(2-aminoethylamino)-2-(2,6-dioxo-3-piperidyl)isoindoline-1,3-dione) (1.1 eq.) added and reaction stirred overnight at r.t. Reaction mixture diluted with water and extracted with ethyl acetate (3×). Organics combined, washed with water, brine and 10% LiCl(aq.), dried over $MgSO_4$ and concentrated in vacuo. Purified by chromatography eluting with 0-10% methanol in DCM.

Synthesis of Example 276
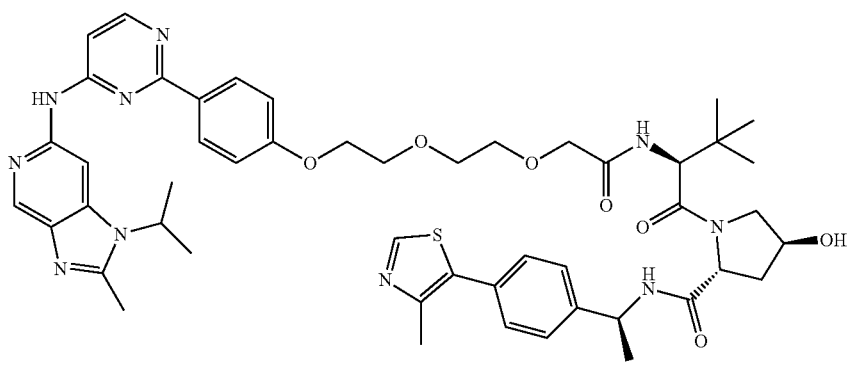 [SMILES: Cc1ncsc1-c1ccc([C@H](C)NC(=O)[C@H]2C[C@H](O)CN2C(=O)[C@@H](NC(=O)COCCOCCOc2ccc(-c3nccc(Nc4cc5c(cn4)nc(C)n5C(C)C)n3)cc2)C(C)(C)C)cc1]
(2R,4S)-4-hydroxy-1-((S)-2-(2-(2-(2-(4-(4-((1-isopropyl-2-methyl-1H-imidazo[4,5-c]pyridin-6-yl)amino)pyrimidin-2-yl)phenoxy)ethoxy)ethoxy)acetamido)-3,3-dimethylbutanoyl)-N—((S)-1-(4-(4-methylthiazol-5-yl)phenyl)ethyl)pyrrolidine-2-carboxamide
Synthetic scheme
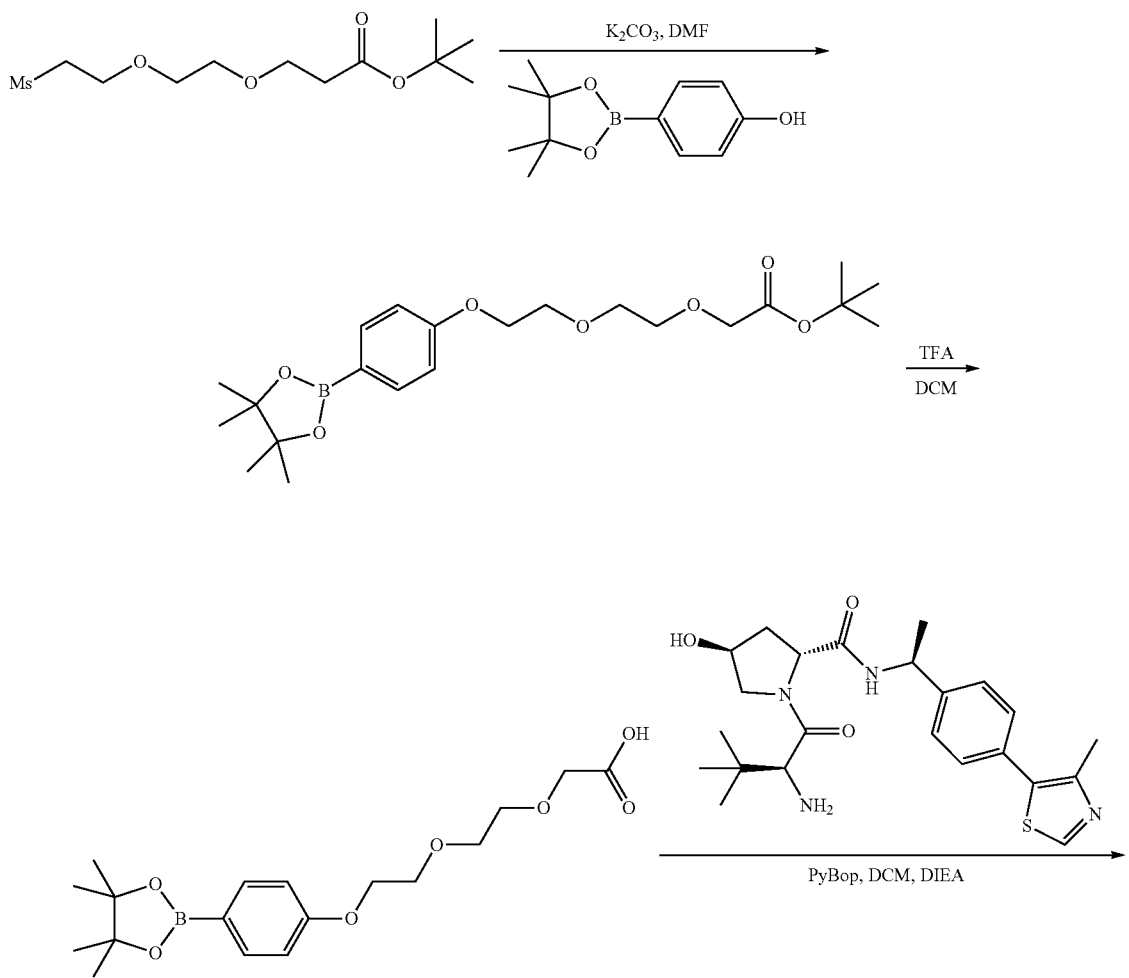

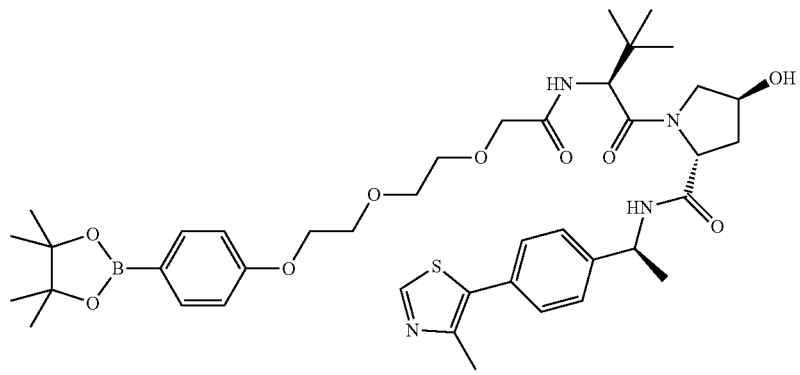

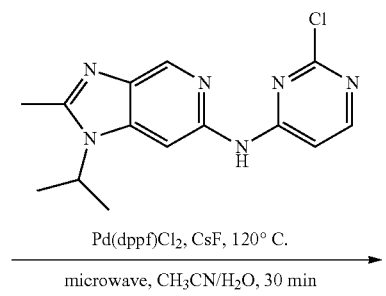

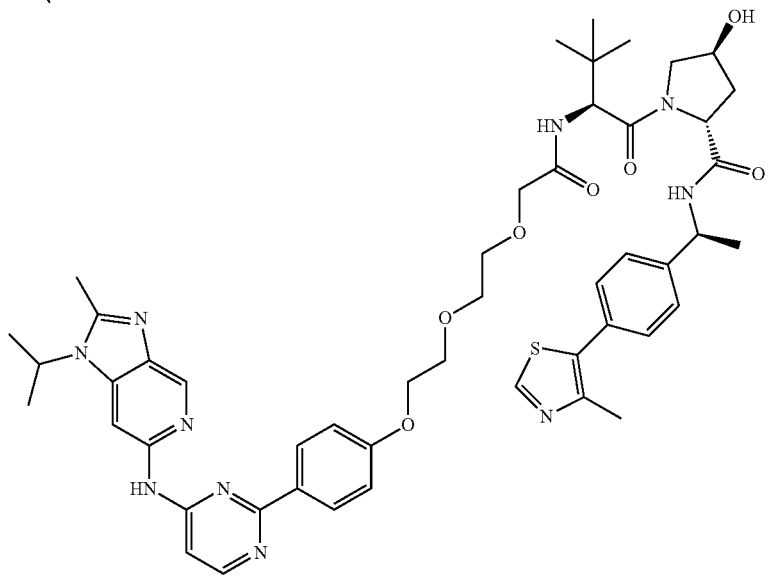

1. Step—Synthesis of tert-butyl 2-(2-(2-(4-(4,4,5,5-tetramethyl-1,3,2-dioxaborolan-2-yl)phenoxy)ethoxy)ethoxy)acetate

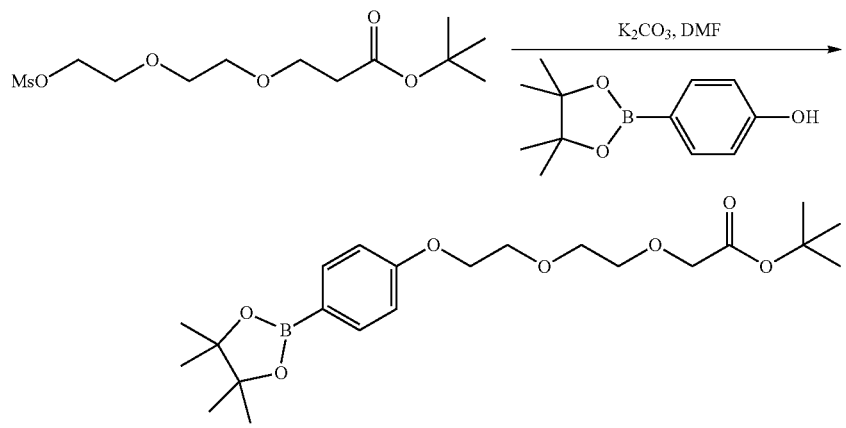

The solution of tert-butyl 3-(2-(2-((methylsulfonyl)oxy)ethoxy)ethoxy)propanoate (275 mg, 0.88 mmol), 4-(4,4,5, 5-tetramethyl-1,3,2-dioxaborolan-2-yl)phenol (194 mg, 0.88 mmol) and Cs₂CO₃(574 mg, 1.76 mmol) was stirred in DMF at 70° C. for 1 hour, and then, after cooling to r.t, water was added. The mixture was extracted with EA. The organic layer was dried and concentrated. Filtered through a silica gel pad (PE:EA=5:1) to get tert-butyl 2-(2-(2-(4-(4,4,5,5- tetramethyl-1,3,2-dioxaborolan-2-yl)phenoxy)ethoxy)ethoxy)acetate (282 mg, 0.67 mmol, 76% yield).

2. Step—Synthesis of 2-(2-(2-(4-(4,4,5,5-tetramethyl-1,3,2-dioxaborolan-2-yl)phenoxy)ethoxy)ethoxy)acetic acid

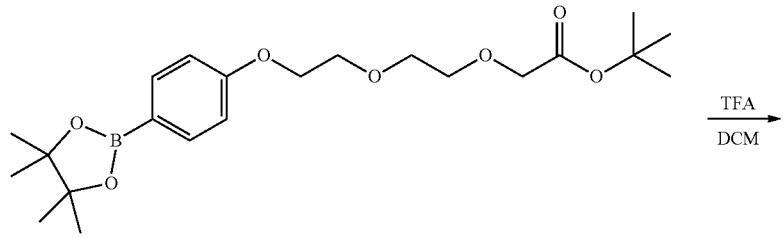

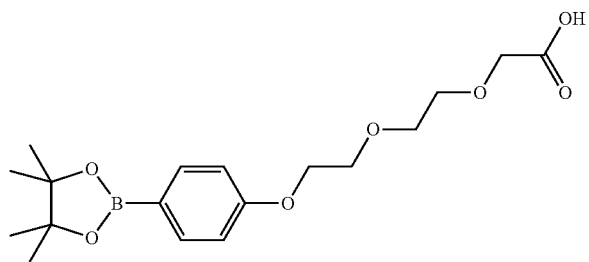

tert-butyl 2-(2-(2-(4-(4,4,5,5-tetramethyl-1,3,2-dioxaborolan-2-yl)phenoxy)ethoxy)ethoxy)acetate (282 mg, 0.67 mmol) was stirred in DCM (8 mL). TFA (2 mL) was added and continued to stir at r.t (18° C.) for 1 hour. Then concentrated to get 282 mg crude product 2-(2-(2-(4-(4,4,5,5-tetramethyl-1,3,2-dioxaborolan-2-yl)phenoxy)ethoxy)ethoxy)acetic acid.

3. Step—Synthesis of (2R,4S)-1-((S)-3,3-dimethyl-2-(2-(2-(2-(4-(4,4,5,5-tetramethyl-1,3,2-dioxaborolan-2-yl)phenoxy)ethoxy)ethoxy)acetamido)butanoyl)-4-hydroxy-N—((S)-1-(4-(4-methylthiazol-5-yl)phenyl)ethyl)pyrrolidine-2-carboxamide

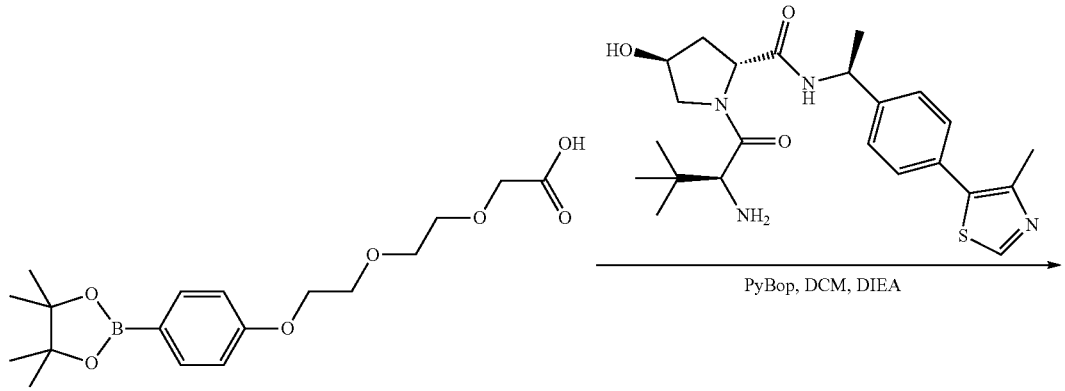

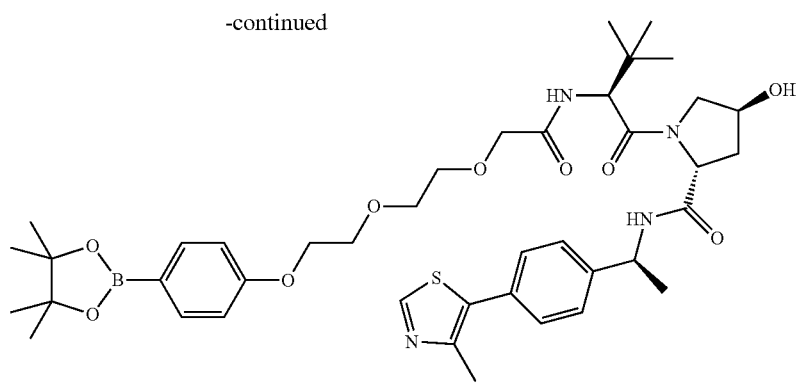

To a solution of (crude) 2-(2-(2-(4-(4,4,5,5-tetramethyl-1,3,2-dioxaborolan-2-yl)phenoxy)ethoxy)ethoxy)acetic acid (157 mg, <=0.43 mmol) in DCM at r.t. (18° C.), (2R,4S)-1-((S)-2-amino-3,3-dimethylbutanoyl)-4-hydroxy-N—((S)-1-(4-(4-methylthiazol-5-yl)phenyl)ethyl)pyrrolidine-2-carboxamide (150 mg, 0.35 mmol), DIPEA (135 mg, 1.04 mmol) and PyBOP (217 mg, 0.42 mmol) were added. The mixture was stirred at r.t (18° C.) for 1 hour. Water was added. The mixture was extracted with DCM. Filtered through a silica gel pad (DCM:MeOH=20:1) to get (2R,4S)-1-((S)-3,3-dimethyl-2-(2-(2-(2-(4-(4,4,5,5-tetramethyl-1,3,2-dioxaborolan-2-yl)phen oxy)ethoxy)acetamido)bu-tanoyl)-4-hydroxy-N—((S)-1-(4-(4-methylthiazol-5-yl)phenyl)ethyl)pyrrolidine-2-carboxamide (189 mg, 0.24 mmol, 68% yield).

4. Step—Synthesis of (2R,4S)-4-hydroxy-1-((S)-2-(2-(2-(2-(4-(4-((1-isopropyl-2-methyl-1H-imidazo[4,5-c]pyridin-6-yl)amino)pyrimidin-2-yl)phenoxy)ethoxy)ethoxy)acetamido)-3,3-dimethylbutanoyl)-N—((S)-1-(4-(4-methylthiazol-5-yl)phenyl)ethyl)pyrrolidine-2-carboxamide

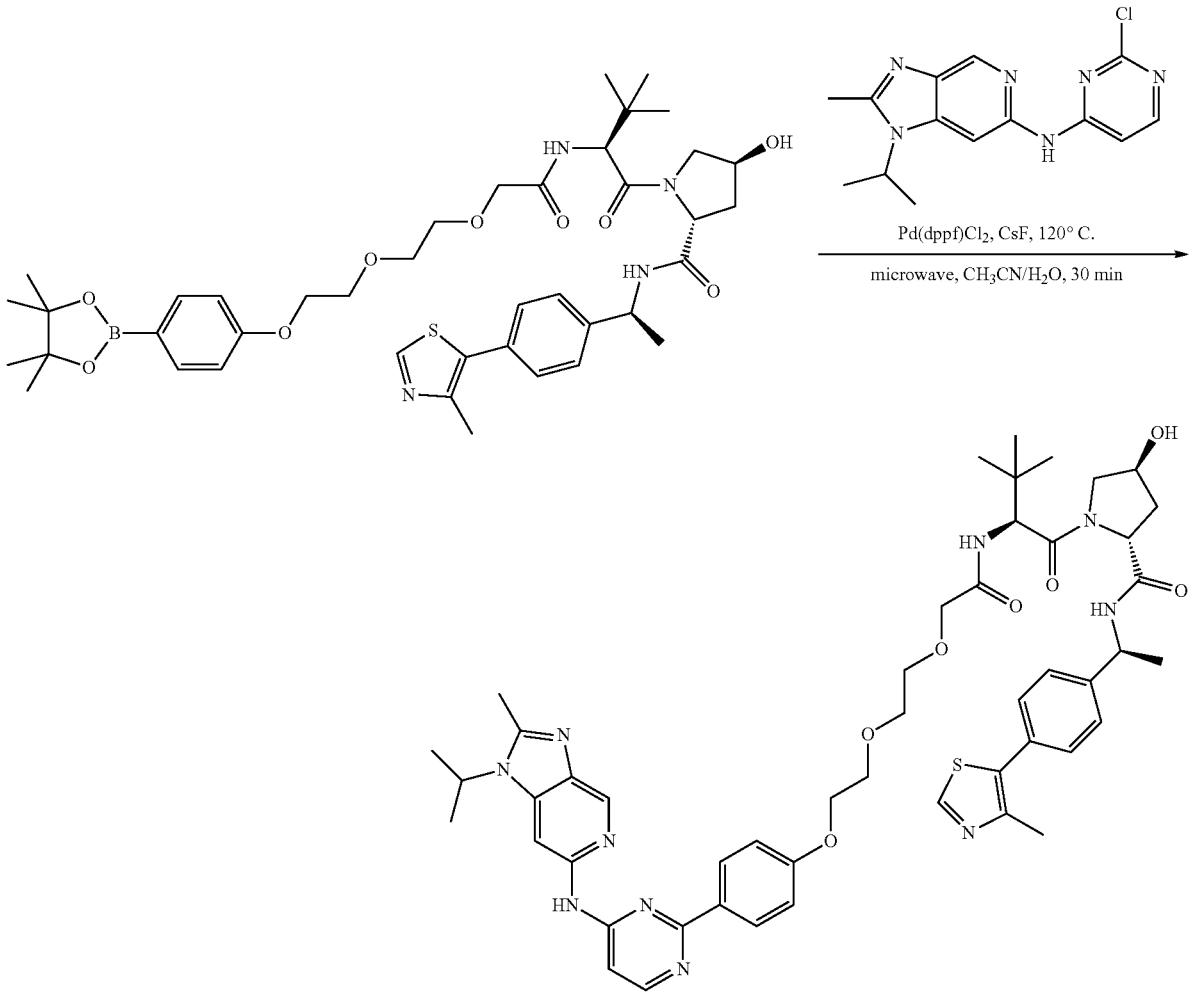

A mixture of N-(2-chloropyrimidin-4-yl)-1-isopropyl-2-methyl-1H-imidazo[4,5-c]pyridin-6-amine (28.7 mg, 0.095 mol), (2R,4S)-1-((S)-3,3-dimethyl-2-(2-(2-(2-(4-(4,4,5,5-tetramethyl-1,3,2-dioxaborolan-2-yl)phenoxy)ethoxy)ethoxy)acetamido)butanoyl)-4-hydroxy-N—((S)-1-(4-(4-methylthiazol-5-yl)phenyl)ethyl)pyrrolidine-2-carboxamide (75.0 mg, 0.095 mol), Pd(dppf)Cl$_2$ (13.9 mg, 0.019 mol) and CsF (57.7 mg, 0.380 mol) in CH$_3$CN/H$_2$O (v/v=5/1, 3 mL) was heated to 120° C. in a microwave reactor for 30 min under N$_2$. After cooling to rt, the reaction was diluted with water (5 mL) and the mixture was taken up with DCM. The organic phase was washed with brine, dried over MgSO$_4$, and concentrated under vacuum. The residue was purified by chromatography (silica gel, DCM: MeOH (10:1, v:v)) to afford the desired compound (2R,4S)-4-hydroxy-1-((S)-2-(2-(2-(2-(4-(4-((1-isopropyl-2-methyl-1H-imidazo[4,5-c]pyridin-6-yl)amino)pyrimidin-2-yl)phenoxy)ethoxy)ethoxy)acetamido)-3,3-dimethylbutanoyl)-N—((S)-1-(4-(4-methylthiazol-5-yl)phenyl)ethyl)pyrrolidine-2-carboxamide (7.6 mg, 9% as white solid). $^1$H NMR (400 MHz, CDCl$_3$): δ 8.63 (s, 3H), 8.42-8.39 (m, 4H), 7.46 (d, J=8.0 Hz, 1H), 7.35-7.31 (m, 5H), 6.99 (d, J=8.0 Hz, 2H), 6.81 (d, J=8.0 Hz, 1H), 5.09-5.05 (m, 1H), 4.71-4.67 (m, 2H), 4.49-4.48 (m, 1H), 4.31-4.30 (m, 1H), 4.18 (s, 2H), 4.08-4.07 (m, 1H), 4.01 (s, 1H), 3.96 (s, 1H), 3.81-3.79 (m, 2H), 3.75-3.73 (m, 4H), 3.62 (dd, J=5.6 Hz, 1H), 2.65 (s, 3H), 2.42-2.40 (m, 4H), 2.09-2.06 (t, J=8.0 Hz, 1H), 1.73 (d, J=8.0 Hz, 6H), 1.38 (d, J=8.0 Hz, 3H), 1.08 (s, 9H). LC-MS: (ES$^+$): m/z 933.4 [M+H]. t$_R$=3.389 min Chemical Formula: C49H60N10O7S; Molecular Weight: 933.13

Synthesis of Example 282

(2S,4R)-4-hydroxy-1-((S)-2-(2-(3-(3-(9-(4-((1-isopropyl-2-methyl-1H-imidazo[4,5-c]pyridin-6-yl)amino)pyrimidin-2-yl)-3,9-diazaspiro[5.5]undecan-3-yl)propoxy)propoxy)acetamido)-3,3-dimethylbutanoyl)-N—((S)-1-(4-(4-methylthiazol-5-yl)phenyl)ethyl)pyrrolidine-2-carboxamide

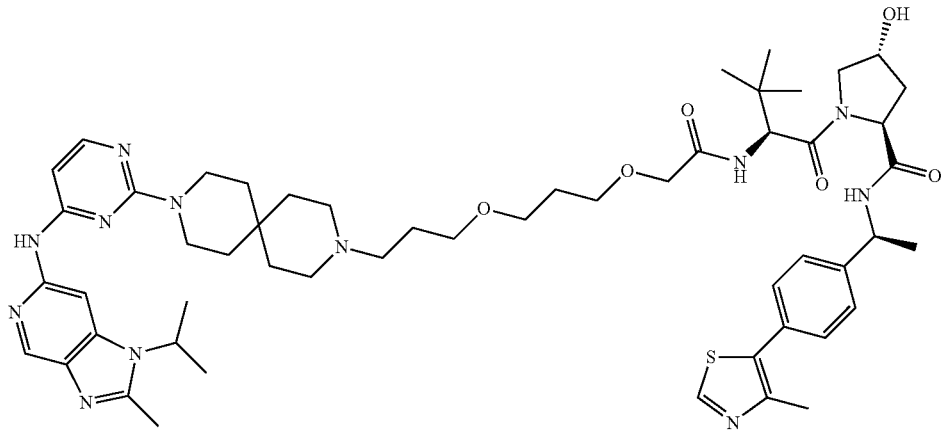 [SMILES: Cc1ncsc1-c1ccc([C@H](C)NC(=O)[C@@H]2C[C@@H](O)CN2C(=O)[C@@H](NC(=O)COCCCOCCCN2CCC3(CC2)CCN(c2nccc(Nc4cc5c(cn4)nc(C)n5C(C)C)n2)CC3)C(C)(C)C)cc1]

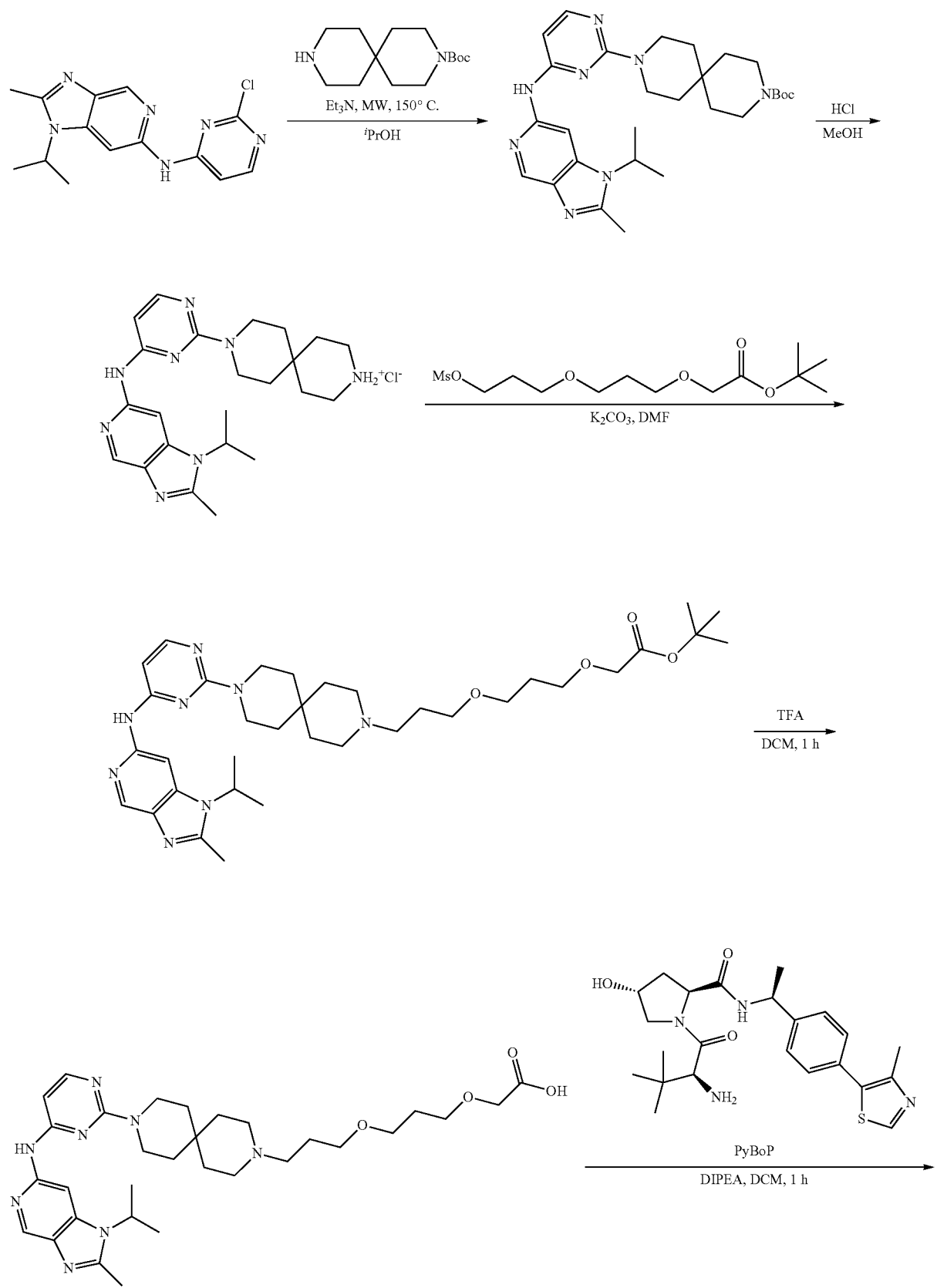
Synthetic Scheme

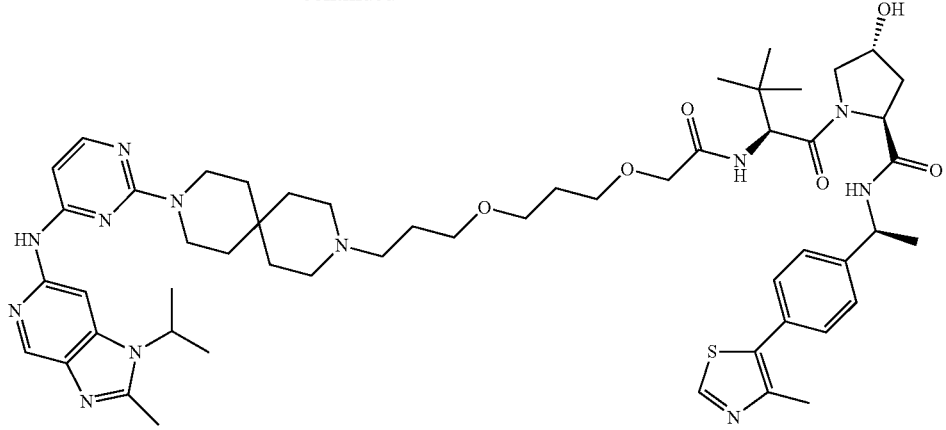 [SMILES: Cc1ncsc1-c1ccc([C@H](C)NC(=O)[C@@H]2C[C@@H](O)CN2C(=O)[C@@H](NC(=O)COCCCOCCCN2CCC3(CC2)CCN(c2nccc(Nc4cc5c(cn4)nc(C)n5C(C)C)n2)CC3)C(C)(C)C)cc1]

Experimental Section

1. Step—Synthesis of Tert-butyl 9-(4-((1-isopropyl-2-methyl-1H-imidazo[4,5-c]pyridin-6-yl)amino)pyrimidin-2-yl)-3,9-diazaspiro[5.5]undecane-3-carboxylate

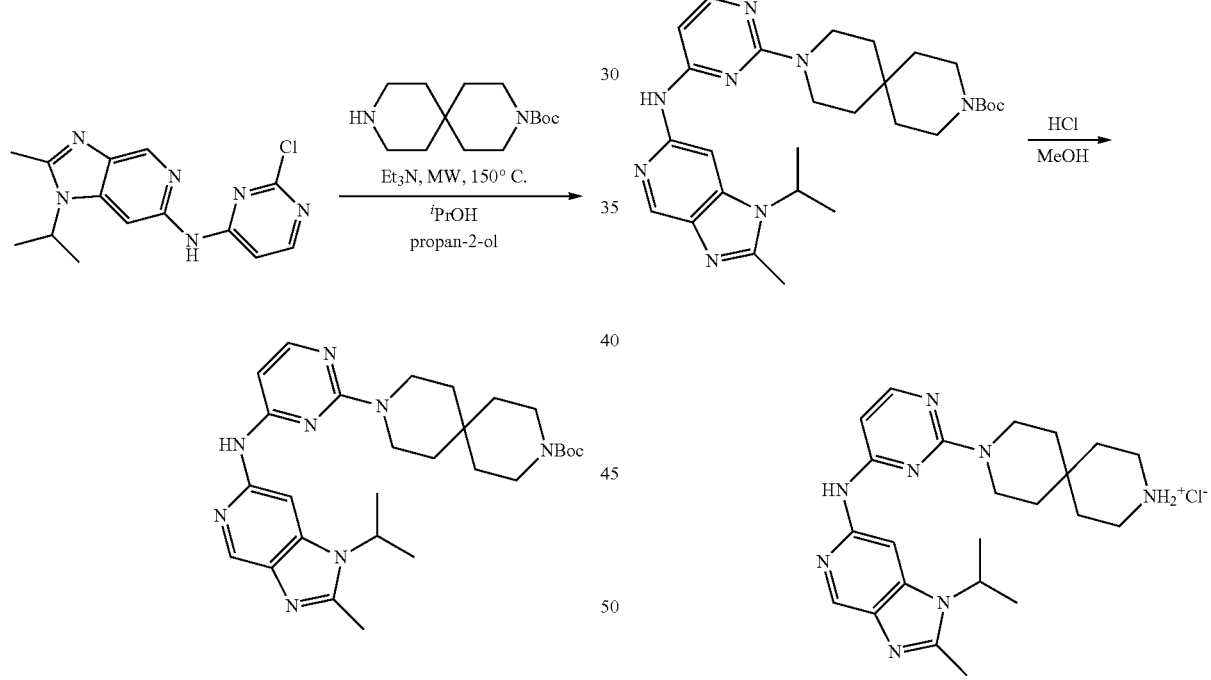

A mixture of N-(2-chloropyrimidin-4-yl)-1-isopropyl-2-methyl-1H-imidazo[4,5-c]pyridin-6-amine (150 mg, 0.47 mmol), tert-butyl 3,9-diazaspiro[5.5]undecane-3-carboxylate (125 mg, 0.49 mmol) and $Et_3N$ (142 mg, 1.4 mmol) in iPrOH (5 mL) was stirred at 150° C. for 1 h. After cooling to rt, the solvent was removed under vacuum. The residue was purified by silica gel column chromatography with MeOH/DCM (1:20) as eluent to afford the desired product Tert-butyl 9-(4-((1-isopropyl-2-methyl-1H-imidazo [4,5-c]pyridin-6-yl)amino)pyrimidin-2-yl)-3,9-diazaspiro[5.5]undecane-3-carboxylate as a yellow solid (200 mg, 0.38 mmol, 80.8% yield). Chemical Formula: $C_{28}H_{40}N_8O_2$; Molecular Weight: 520.68. LC-MS: ($ES^+$): m/z 521.3 [M+H]. $t_R$=3.33 min

2. Step—Synthesis of N-(2-(3,9-Diazaspiro[5.5]undecan-3-yl)pyrimidin-4-yl)-1-isopropyl-2-methyl-1H-imidazo[4,5-c]pyridin-6-amine hydrochloride

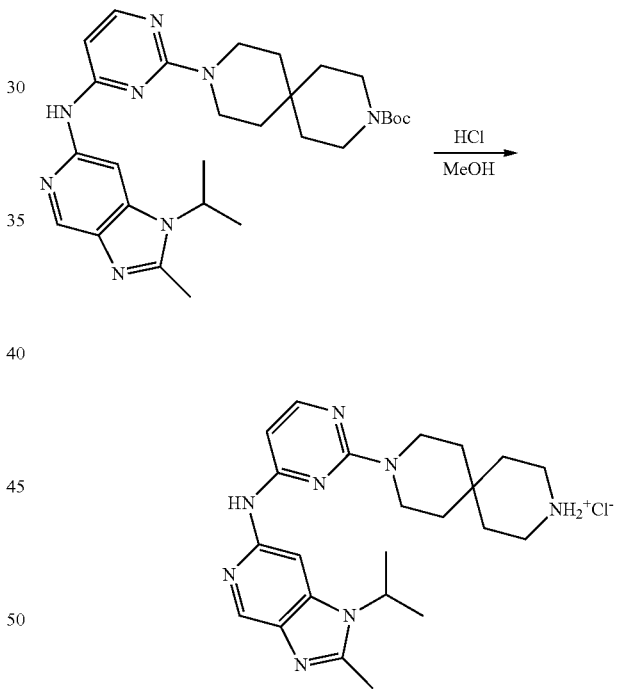

To a solution of Tert-butyl 9-(4-((1-isopropyl-2-methyl-1H-imidazo[4,5-c]pyridin-6-yl)amino)pyrimidin-2-yl)-3,9-diazaspiro[5.5]undecane-3-carboxylate (200 mg, 0.38 mmol) in MeOH (8 mL) was added 6N HCl in dioxane (4 ml, 24 mmol) at rt. After stirring 30 min, the mixture was concentrated under vacuum to afford the crude N-(2-(3,9-Diazaspiro[5.5]undecan-3-yl)pyrimidin-4-yl)-1-isopropyl-2-methyl-1H-imidazo[4,5-c]pyridin-6-amine hydrochloride as a yellow solid (200 mg), which was used in next step without further purification. Chemical Formula: $C_{23}H_{33}ClN_8$; Molecular Weight: 457.02 LC-MS: ($ES^+$): m/z 421.3 [M+H]. $t_R$=2.19 min 3. Step—Synthesis of Tert-butyl 2-(3-(3-(9-(4-((1-isopropyl-2-methyl-1H-imidazo[4,5-c]pyridin-6-yl)amino)pyrimidin-2-yl)-3,9-diazaspiro[5.5]undecan-3-yl)propoxy)propoxy)acetate

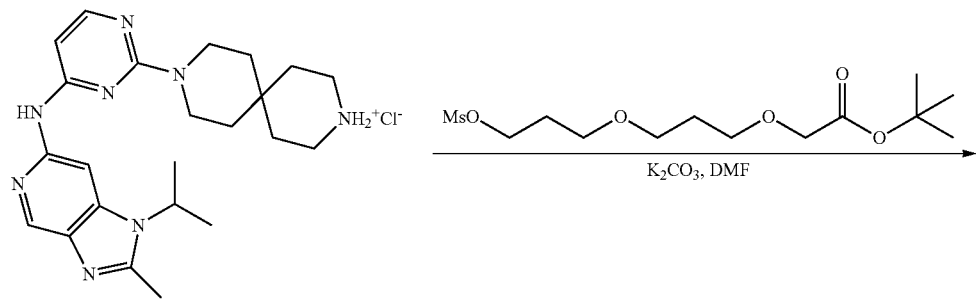

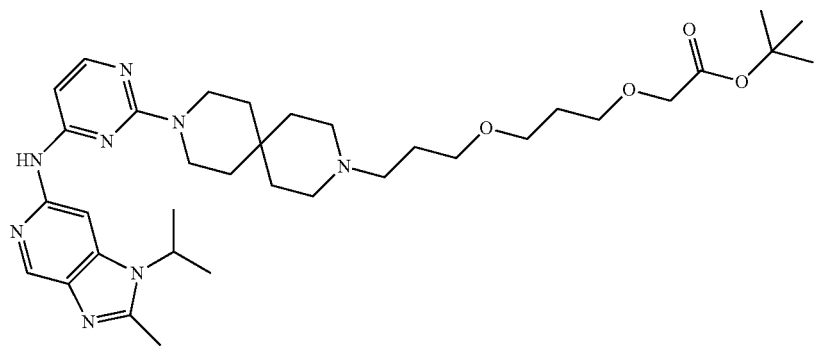

To a mixture of N-(2-(3,9-Diazaspiro[5.5]undecan-3-yl)pyrimidin-4-yl)-1-isopropyl-2-methyl-1H-imidazo[4,5-c]pyridin-6-amine hydrochloride (190 mg crude, <=0.38 mmol), tert-butyl 2-(3-(3-((methylsulfonyl)oxy)propoxy)propoxy)acetate (186 mg, 0.57 mmol) in DMF (10 ml) was added $K_2CO_3$ (209 mg, 1.51 mmol). The resulting solution was stirred at 80° C. for 1 h. After cooling to rt, the reaction was diluted with 10 mL water, and the mixture was extracted with ethyl acetate (2×30 mL). The combined organic layers were washed with brine (10 mL), dried over $Na_2SO_4$ and filtered. The solvent was evaporated under reduced pressure. The residue was purified by pre-TLC (DCM:MeOH=20:1) to afford the desired compound Tert-butyl 2-(3-(3-(9-(4-((1-isopropyl-2-methyl-1H-imidazo[4,5-c]pyridin-6-yl)amino)pyrimidin-2-yl)-3,9-diazaspiro[5.5]undecan-3-yl)propoxy)propoxy)acetate as a white solid (65 mg, 0.10 mmol, 26.3% yield). LC-MS: ($ES^+$): m/z 651.4 [M+H]. $t_R$=2.79 min Chemical Formula: $C_{35}H_{54}N_8O_4$; Molecular Weight: 650.87

4. Step—Synthesis of 2-(3-(3-(9-(4-((1-Isopropyl-2-methyl-1H-imidazo[4,5-c]pyridin-6-yl)amino)pyrimidin-2-yl)-3,9-diazaspiro[5.5]undecan-3-yl)propoxy)propoxy)acetic acid

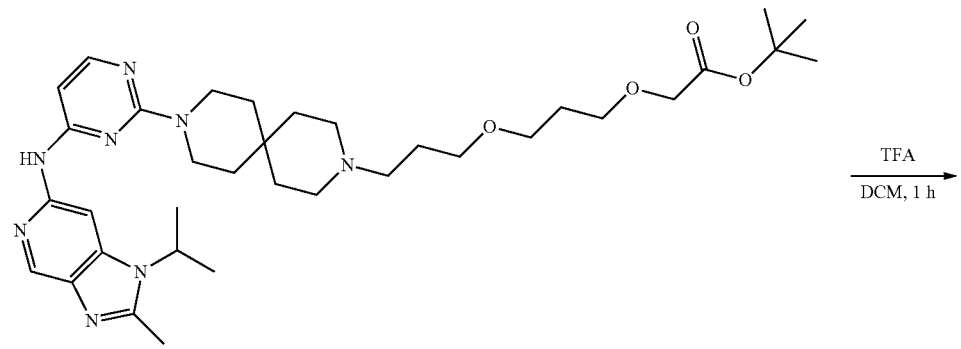

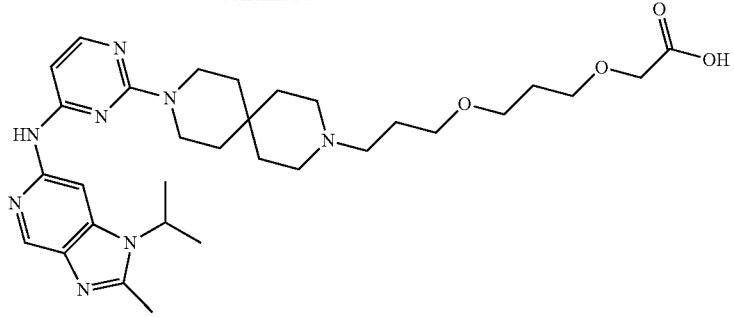

To a solution of Tert-butyl 2-(3-(3-(9-(4-((1-isopropyl-2-methyl-1H-imidazo[4,5-c]pyridin-6-yl)amino)pyrimidin-2-yl)-3,9-diazaspiro[5.5]undecan-3-yl)propoxy)propoxy)acetate (65 mg, 0.10 mmol) in DCM (2 mL) were added TFA (2 ml), After stirring 1 h, the solvent was removed in vacuo to afford the crude desired product 2-(3-(3-(9-(4-((1-Isopropyl-2-methyl-1H-imidazo[4,5-c]pyridin-6-yl)amino)pyrimidin-2-yl)-3,9-diazaspiro[5.5]undecan-3-yl)propoxy)propoxy)acetic acid (100 mg, crude), which was used into next reaction without further purification. LC-MS: (ES+): m/z 595.4 [M+H]. $t_R$=2.36 min Chemical Formula: $C_{31}H_{46}N_8O_4$; Molecular Weight: 594.76

5. Step—Synthesis of (2S,4R)-4-Hydroxy-1-((S)-2-(2-(3-(3-(9-(4-((1-Isopropyl-2-methyl-1H-imidazo[4,5-c]pyridin-6-yl)amino)pyrimidin-2-yl)-3,9-diazaspiro[5.5]undecan-3-yl)propoxy)propoxy)acetamido)-3,3-dimethylbutanoyl)-N—((S)-1-(4-(4-methylthiazol-5-yl)phenyl)ethyl)pyrrolidine-2-carboxamide

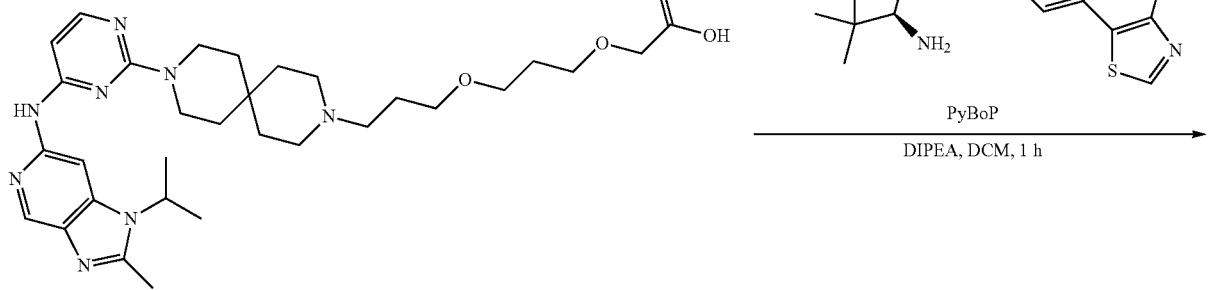

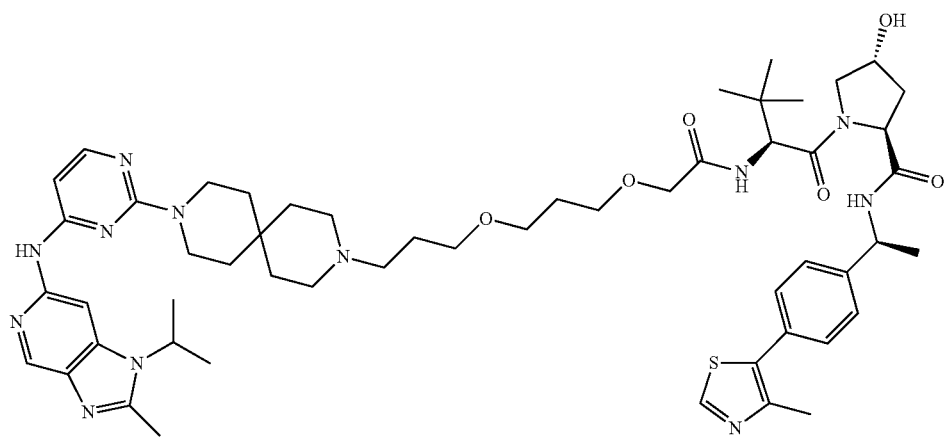

To a solution of 2-(3-(3-(9-(4-((1-Isopropyl-2-methyl-1H-imidazo[4,5-c]pyridin-6-yl)amino)pyrimidin-2-yl)-3,9-diazaspiro[5.5]undecan-3-yl)propoxy)propoxy)acetic acid (100 mg, crude, <=0.10 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (72 mg, 0.15 mmol), DIPEA (77 mg, 0.60 mmol) in DCM (5 mL) was added PyBop (78 mg, 0.15 mmol). The resulting solution was stirred at rt for 1 h. After quenched with water (10 mL), the mixture was extracted with DCM (2×30 mL). The combined organic layers were washed with brine (10 mL), dried over $Na_2SO_4$, filtered and concentrated under vacuum, The residue was purified by prep-HPLC to afford (2S,4R)-4-Hydroxy-1-((S)-2-(2-(3-(3-(9-(4-((1-Isopropyl-2-methyl-1H-imidazo[4,5-c]pyridin-6-yl)amino)pyrimidin-2-yl)-3,9-diazaspiro[5.5]undecan-3-yl)propoxy)propoxy)acetamido)-3,3-dimethylbutanoyl)-N—((S)-1-(4-(4-methylthiazol-5-yl)phenyl)ethyl)pyrrolidine-2-carboxamide as a white solid (45 mg, 0.044 mmol, 44.0% yield, 2 steps).

$^1$H NMR (400 MHz, $CDCl_3$): δ 13.15 (bs, 1H), 11.30 (s, 1H), 8.88 (s, 1H), 8.65 (s, 1H), 8.54 (s, 1H), 7.99 (s, 1H), 7.44 (d, J=7.2 Hz, 1H), 7.42 (s, 4H), 8.67 (d, J=8.7 Hz, 1H), 6.69 (s, 1H), 5.08-5.10 (m, 1H), 4.71-4.77 (m, 2H), 4.60-4.62 (m, 1H), 4.51 (s, 1H), 3.91-4.02 (m, 6H), 3.53-3.64 (m, 9H), 3.10-3.13 (m, 2H), 2.85-2.88 (m, 2H), 2.88 (s, 3H), 2.55 (m, 3H), 2.33-2.34 (m, 1H), 2.10-2.12 (m, 1H), 1.86-2.00 (m, 11H), 1.69 (d, J=6.8 Hz, 6H), 1.59-1.61 (m, 2H), 1.48 (d, J=6.8 Hz, 3H), 1.06 (s, 9H). LC-MS: ($ES^+$): m/z 1021.5 [M+H]. $t_R$=2.84 min Chemical Formula: $C_{54}H_{76}N_{12}O_6S$; Molecular Weight: 1021.34

Synthesis of Example 283

2-(7-(3-(2-(2-(2-((2-(2,6-dioxopiperidin-3-yl)-1,3-dioxoisoindolin-5-yl)oxy)ethoxy)ethoxy)ethoxy)propyl)-1-oxoisoindolin-2-yl)-2-(5-fluoro-2-hydroxyphenyl)-N-(thiazol-2-yl)acetamide

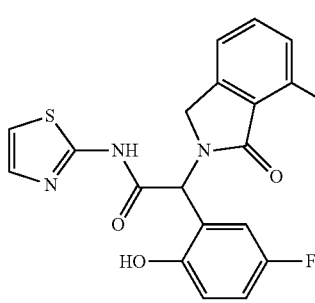

35

Synthetic Scheme:

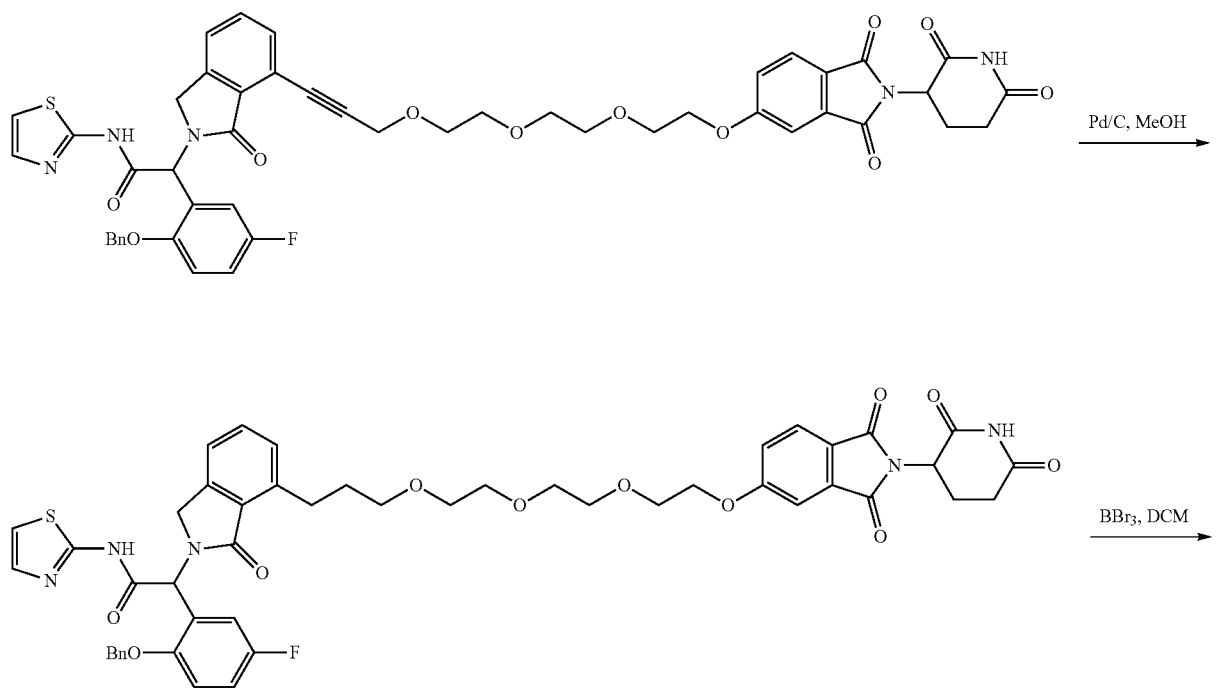

-continued

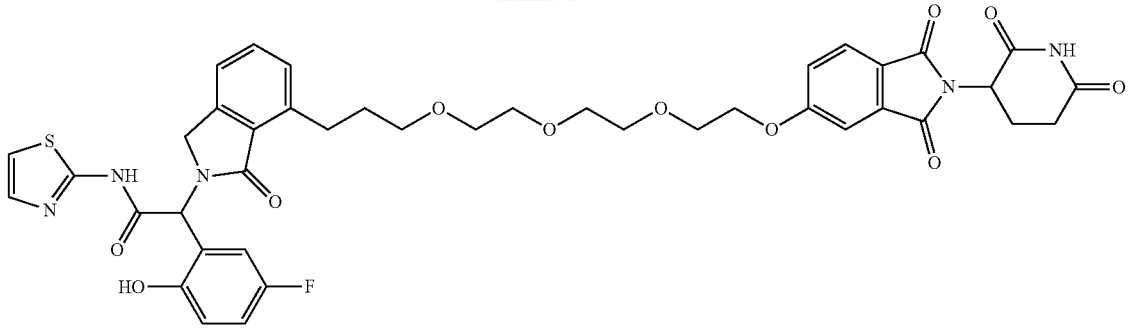 [SMILES: O=C1CCC(N2C(=O)c3ccc(OCCOCCOCCOCCCc4cccc5c4C(=O)N(C(C(=O)Nc4nccs4)c4cc(F)ccc4O)C5)cc3C2=O)C(=O)N1]

1. Step—Synthesis of 2-(2-(benzyloxy)-5-fluorophenyl)-2-(7-(3-(2-(2-(2-((2-(2,6-dioxopiperidin-3-yl)-1,3-dioxoisoindolin-5-yl)oxy)ethoxy)ethoxy)ethoxy)propyl)-1-oxoisoindolin-2-yl)-N-(thiazol-2-yl)acetamide

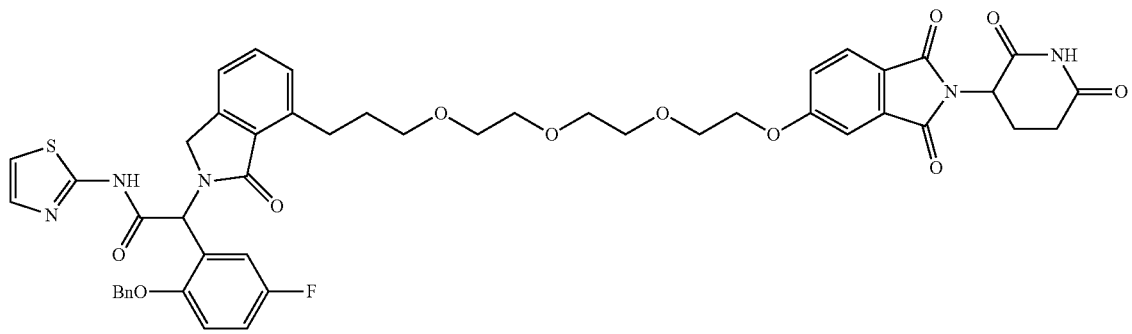 [SMILES: O=C1CCC(N2C(=O)c3ccc(OCCOCCOCCOCCCc4cccc5c4C(=O)N(C(C(=O)Nc4nccs4)c4cc(F)ccc4O)C5)cc3C2=O)C(=O)N1]

A mixture of palladium on carbon (10%, 40 mg) and 2-(2-(benzyloxy)-5-fluorophenyl)-2-(7-(3-(2-(2-(2-((2-(2,6-dioxopiperidin-3-yl)-1,3-dioxoisoindolin-5-yl)oxy)ethoxy)ethoxy)ethoxy)prop-1-yn-1-yl)-1-oxoisoindolin-2-yl)-N-(thiazol-2-yl)acetamide (80 mg, 0.087 mmol) in methanol (20 ml) was stirred at room temperature overnight under hydrogen atmosphere (hydrogen balloon). TLC showed the reaction was complete. Palladium on carbon was removed through filtration and washed with methanol (5 ml×2). The combined filtrates were concentrated under reduced pressure to afford 2-(2-(benzyloxy)-5-fluorophenyl)-2-(7-(3-(2-(2-(2-((2-(2,6-dioxopiperidin-3-yl)-1,3-dioxoisoindolin-5-yl)oxy)ethoxy)ethoxy)ethoxy)propyl)-1-oxoisoindolin-2-yl)-N-(thiazol-2-yl)acetamide (70 mg, crude) as yellow oil. LC_MS: (ES+): m/z 920.5 [M+H]+. $t_R$=3.010 min.

2. Step—Synthesis of 2-(7-(3-(2-(2-(2-((2-(2,6-dioxopiperidin-3-yl)-1,3-dioxoisoindolin-5-yl)oxy)ethoxy)ethoxy)ethoxy)propyl)-1-oxoisoindolin-2-yl)-2-(5-fluoro-2-hydroxyphenyl)-N-(thiazol-2-yl)acetamide

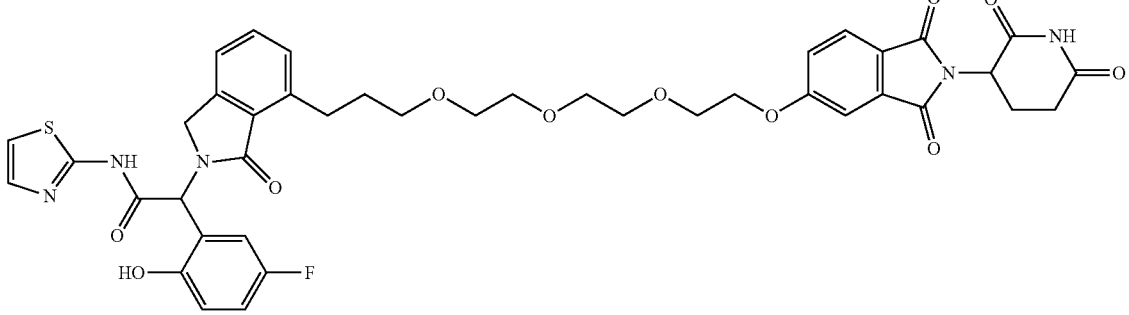

To a stirred solution of 2-(2-(benzyloxy)-5-fluorophenyl)-2-(7-(3-(2-(2-(2-((2-(2,6-dioxopiperidin-3-yl)-1,3-dioxoisoindolin-5-yl)oxy)ethoxy)ethoxy)ethoxy)propyl)-1-oxoisoindolin-2-yl)-N-(thiazol-2-yl)acetamide (70 mg, 0.076 mmol) in dichloromethane (8 ml) was drop wise boron tribromide (95 mg, 0.38 mmol) in dichloromethane (1 ml) at −70° C. dropwise. The resulting mixture was stirred at −70° C. for 1 hour. TLC showed the reaction was complete. The reaction mixture was diluted with dichloromethane (15 ml) and quenched with saturated sodium bicarbonate solution (8 ml) at −40° C. The organic layer was collected and the aqueous layer was extracted with dichloromethane (15 ml×2). The combined organic layers were washed with brine (20 ml), dried over anhydrous sodium sulfate, and concentrated under reduced pressure to give a crude residue which was purified by preparative TLC (eluted with 5% methanol in dichloromethane) to afford 2-(7-(3-(2-(2-(2-((2-(2,6-dioxopiperidin-3-yl)-1,3-dioxoisoindolin-5-yl)oxy)ethoxy)ethoxy)ethoxy)propyl)-1-oxoisoindolin-2-yl)-2-(5-fluoro-2-hydroxyphenyl)-N-(thiazol-2-yl)acetamide (25 mg, yield 27%) as white solid. LC_MS: (ES+): m/z 830.4 [M+H]+. $t_R$=2.645 min. $^1$H NMR (400 MHz, DMSO-d6): δ 1.97-2.03 (m, 4H), 2.54-2.68 (m, 1H), 3.07 (t, J=7.2H, 1H), 3.38-3.41 (m, 4H), 3.47-3.48 (m, 2H), 3.52-3.56 (m, 4H), 3.58-3.60 (m, 2H), 3.78 (t, J=4.0 Hz, 2H), 3.89-3.93 (m, 1H), 4.29 (t, J=4.0 Hz, 2H), 4.52-4.56 (m, 1H), 5.09-5.14 (m, 1H), 5.36 (d, J=4.8 Hz, 1H), 6.26 (s, 1H), 6.82-6.85 (m, 1H), 6.88-6.91 (m, 1H), 7.07-7.12 (m, 1H), 7.24-7.26 (m, 2H), 7.34-7.37 (m, 2H), 7.43-7.48 (m, 3H), 7.80 (d, J=12.0 Hz, 1H), 8.32 (s, 1H), 11.14 (s, 1H). Chemical Formula: $C_{41}H_{40}FN_5O_{11}S$; Molecular Weight: 829.85;

Synthesis of Example 286

2-(2,6-dioxopiperidin-3-yl)-5-(2-(4-(4-(1-isopropyl-6-((2-(4-methoxypiperidin-1-yl)pyrimidin-4-yl)amino)-1H-imidazo[4,5-c]pyridin-2-yl)benzyl)piperazin-1-yl)ethoxy)isoindoline-1,3-dione

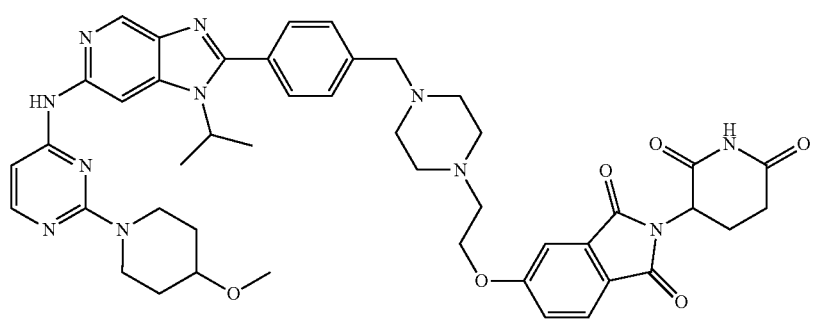 [SMILES: COC1CCN(c2nccc(Nc3cc4c(cn3)nc(-c3ccc(CN5CCN(CCOc6ccc7c(c6)C(=O)N(C6CCC(=O)NC6=O)C7=O)CC5)cc3)n4C(C)C)n2)CC1]

Synthetic Route:

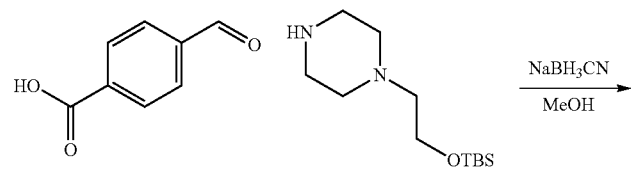

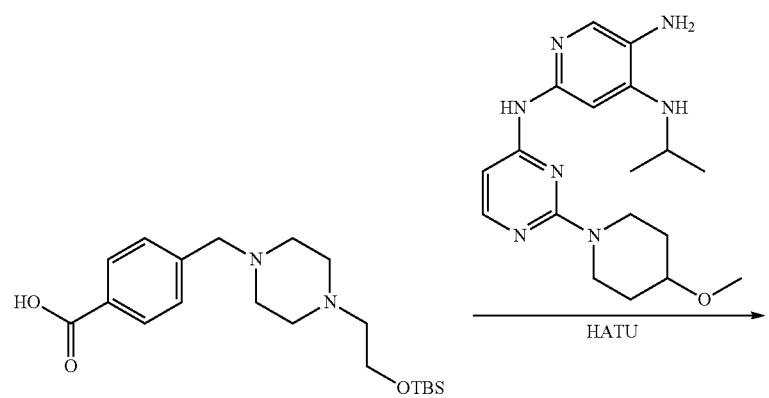

713
714
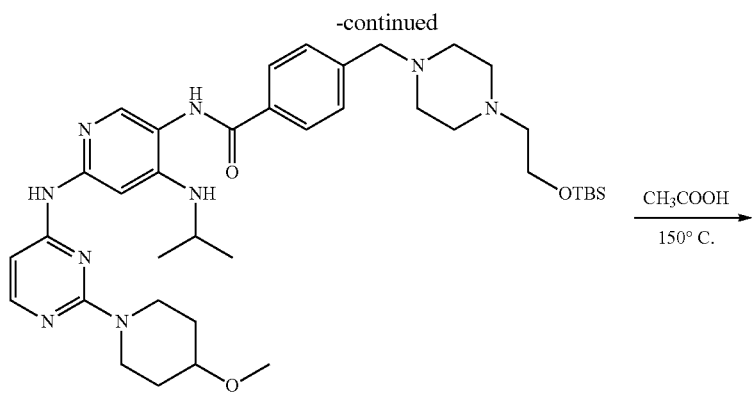
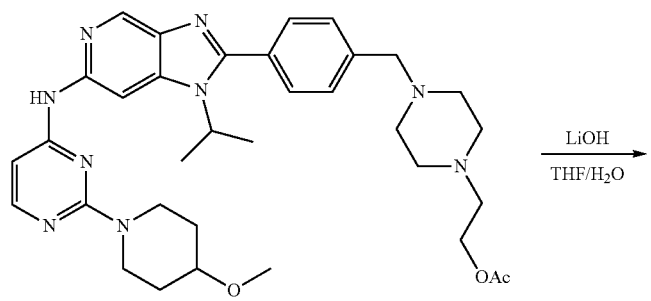
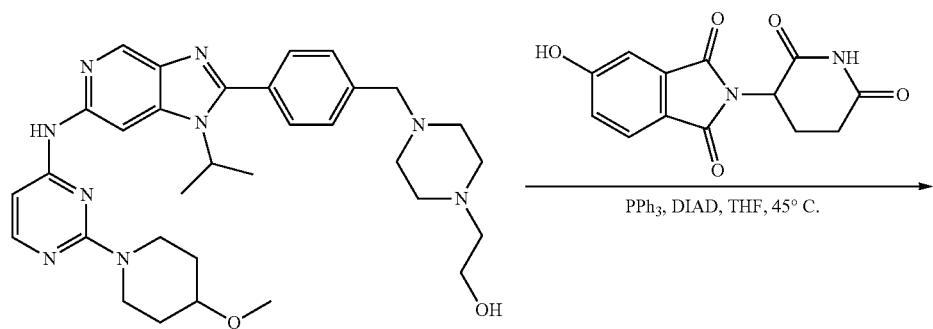
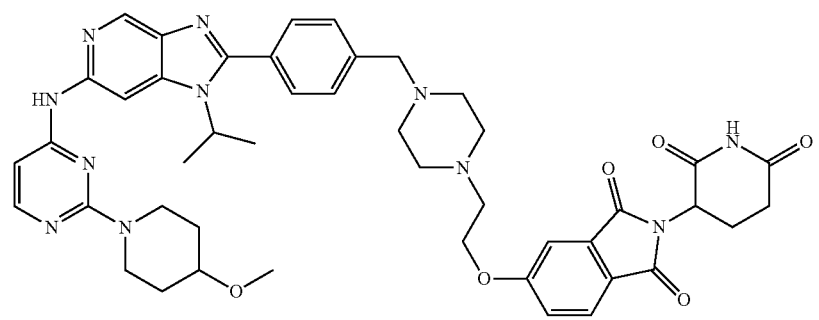

Experimental Section

1. Step—Synthesis of 4-((4-(2-((Tert-butyldimethylsilyl)oxy)ethyl)piperazin-1-yl)methyl)benzoic acid

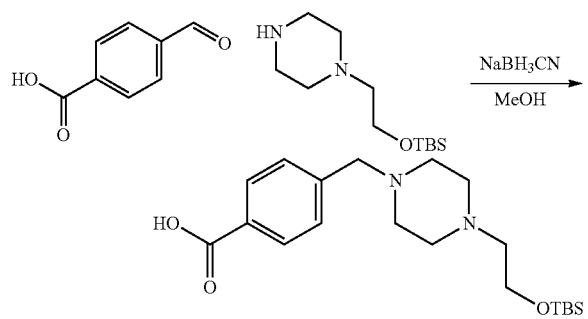

To a solution of 1-(2-((tert-butyldimethylsilyl)oxy)ethyl)piperazine (500 mg, 2.00 mmol) in MeOH (10 mL) were added 4-formylbenzoic acid (300 mg, 2.00 mmol) and $NaBH_3CN$ (151 mg, 2.4 mmol). The solution was stirred at rt for 3 h. Then the solution was diluted with water (10 mL). The resulting mixture was extracted with DCM (2×30 mL). The combined organic layers were washed with brine (20 mL). The organic phase was dried over anhydrous sodium sulfate, filtered and concentrated under vacuum. The residue was purified by silica gel column chromatography (DCM:MeOH=10:1) to afford 4-((4-(2-((Tert-butyldimethylsilyl)oxy)ethyl)piperazin-1-yl)methyl)benzoic acid as a white solid (120 mg, 0.31 mmol, 15.8% yield). Chemical Formula: $C_{20}H_{34}N_2O_3Si$; Molecular Weight: 378.59.

2. Step—Synthesis of 4-((4-(2-((Tert-butyldimethylsilyl)oxy)ethyl)piperazin-1-yl)methyl)-N-(4-(isopropylamino)-6-((2-(4-methoxypiperidin-1-yl)pyrimidin-4-yl)amino)pyridin-3-yl)benzamide

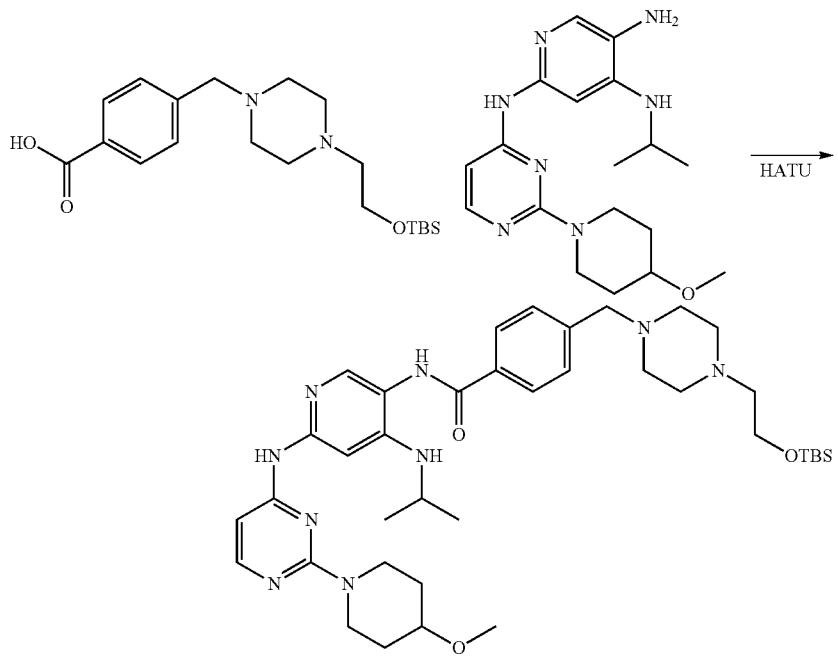

To a solution of N4-isopropyl-N2-(2-(4-methoxypiperidin-1-yl)pyrimidin-4-yl)pyridine-2,4,5-triamine (400 mg, 1.12 mmol) and 4-((4-(2-((Tert-butyldimethylsilyl)oxy)ethyl)piperazin-1-yl)methyl)benzoic acid (677 mg, 1.80 mmol) in DCM (20 mL) were added DIPEA (578 mg, 4.48 mmol) and HATU (851 mg, 2.24 mmol) at rt. The solution was stirred at rt overnight. The solution was diluted with water (5 mL) and the resulting mixture was extracted with DCM (2×20 mL). The combined organic layers were washed with brine (10 mL). The organic phase was dried over anhydrous sodium sulfate, filtered and concentrated under vacuum. The residue was purified by silica gel column chromatography (DCM:MeOH=10:1) to afford 4-((4-(2-((Tert-butyldimethylsilyl)oxy)ethyl)piperazin-1-yl)methyl)-N-(4-(isopropylamino)-6-((2-(4-methoxypiperidin-1-yl)pyrimidin-4-yl)amino)pyridin-3-yl)benzamide as a white solid (100 mg, 0.14 mmol, 12.4% yield). Chemical Formula: $C_{38}H_{59}N_9O_3Si$; Molecular Weight: 718.03

717

3. Step—Synthesis of 2-(4-(4-(1-Isopropyl-6-((2-(4-methoxypiperidin-1-yl)pyrimidin-4-yl)amino)-1H-imidazo[4,5-c]pyridin-2-yl)benzyl)piperazin-1-yl) ethyl acetate

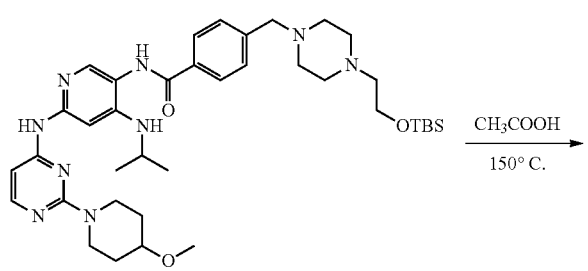

A solution of 4-((4-(2-((Tert-butyldimethylsilyl)oxy)ethyl)piperazin-1-yl)methyl)-N-(4-(isopropylamino)-6-((2-(4-methoxypiperidin-1-yl)pyrimidin-4-yl)amino)pyridin-3-yl)benzamide (150 mg, 0.21 mmol) in CH₃COOH (5 ml) was stirred at 150° C. for 10 h under microwave. Then the reaction mixture was evaporated under reduced pressure. The pH of the solution was adjusted to 8 with saturated NaHCO₃. The resulting mixture was extracted with DCM (2×10 mL). The combined organic layers were washed with brine (5 mL). The organic phase was dried over anhydrous sodium sulfate, filtered and concentrated under vacuum. The residue was purified by prep-TLC (DCM:MeOH=10:1) to afford 2-(4-(4-(1-Isopropyl-6-((2-(4-methoxypiperidin-1-yl)pyrimidin-4-yl)amino)-1H-imidazo [4,5-c]pyridin-2-yl)benzyl)piperazin-1-yl)ethyl acetate as a white solid (42 mg, 0.064 mmol, 31.8% yield). Chemical Formula: C₃₄H₄₅N₉O₃; Molecular Weight: 627.79

718

4. Step—Synthesis of 2-(4-(4-(1-Isopropyl-6-((2-(4-methoxypiperidin-1-yl)pyrimidin-4-yl)amino)-1H-imidazo[4,5-c]pyridin-2-yl)benzyl)piperazin-1-yl) ethan-1-ol

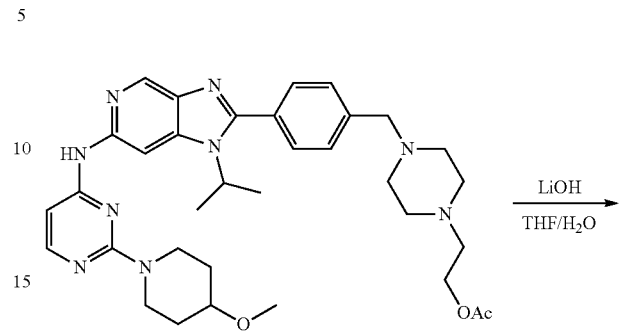

To a solution of 2-(4-(4-(1-Isopropyl-6-((2-(4-methoxypiperidin-1-yl)pyrimidin-4-yl)amino)-1H-imidazo[4,5-c]pyridin-2-yl)benzyl)piperazin-1-yl)ethyl acetate (40 mg, 0.064 mmol) in THF (2 mL) and H₂O (1 ml) was added LiOH.H₂O (16 mg, 0.38 mmol). The mixture was stirred at rt for 1 h. The resulting reaction mixture was extracted with EA (2×5 mL). The combined organic layers were washed with brine (5 mL). The organic phase was dried over anhydrous sodium sulfate, filtered and concentrated under vacuum to afford 2-(4-(4-(1-Isopropyl-6-((2-(4-methoxypiperidin-1-yl)pyrimidin-4-yl)amino)-1H-imidazo [4,5-c]pyridin-2-yl)benzyl)piperazin-1-yl)ethan-1-ol (40 mg, crude), which was used in the next step without further purification. LC-MS: (ES⁺): m/z 586.3 [M+H]⁺. t_R=2.51 min Chemical Formula: C₃₂H₄₃N₉O₂; Molecular Weight: 585.76

5. Step—2-(2,6-Dioxopiperidin-3-yl)-5-(2-(4-(4-(1-isopropyl-6-((2-(4-methoxypiperidin-1-yl)pyrimidin-4-yl)amino)-1H-imidazo[4,5-c]pyridin-2-yl)benzyl)piperazin-1-yl)ethoxy)isoindoline-1,3-dione

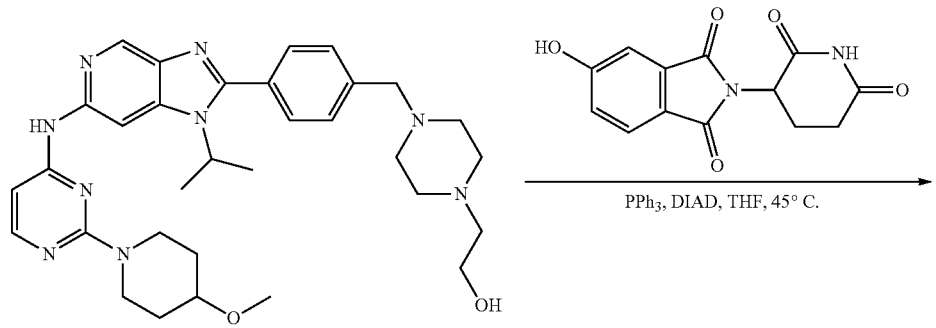 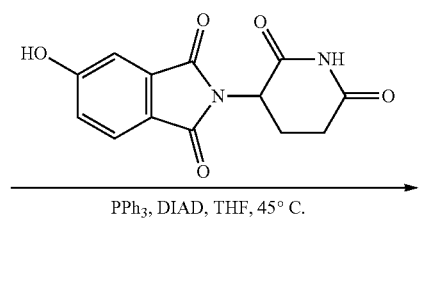

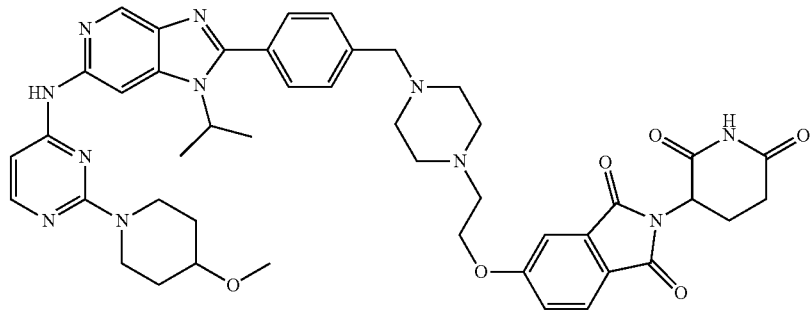 [SMILES: COC1CCN(c2nccc(Nc3cc4c(cn3)nc(-c3ccc(CN5CCN(CCOc6ccc7c(c6)C(=O)N(C6CCC(=O)NC6=O)C7=O)CC5)cc3)n4C(C)C)n2)CC1]

To a mixture of 2-(4-(4-(1-Isopropyl-6-((2-(4-methoxypiperidin-1-yl)pyrimidin-4-yl)amino)-1H-imidazo[4,5-c]pyridin-2-yl)benzyl)piperazin-1-yl)ethan-1-ol (30 mg, 0.051 mmol), 2-(2,6-dioxopiperidin-3-yl)-5-hydroxyisoindoline-1,3-dione (18 mg, 0.066 mmol) and PPh$_3$ (78 mg, 0.31 mmol) in THF (5 mL) was added DIAD (60 mg, 0.31 mmol) dropwise at 45° C. The solution was stirred at 45° C. for 10 min. Then the reaction mixture was diluted with water (10 mL). The mixture was extracted with DCM (2×10 mL). The combined organic layers were washed with brine (5 mL). The organic phase was dried over anhydrous sodium sulfate, filtered and concentrated under vacuum. The residue was purified by prep-TLC to afford 2-(2,6-Dioxopiperidin-3-yl)-5-(2-(4-(4-(1-isopropyl-6-((2-(4-methoxypiperidin-1-yl)pyrimidin-4-yl)amino)-1H-imidazo[4,5-c]pyridin-2-yl)benzyl)piperazin-1-yl)ethoxy)isoindoline-1,3-dione as a white solid (4.5 mg, 0.0053 mmol, 10.0% yield). $^1$H NMR (400 MHz, CD$_3$OD): δ 8.65 (s, 1H), 8.57 (s, 1H), 7.95 (d, J=6.0 Hz, 1H), 7.80 (d, J=8.0 Hz, 1H), 7.65 (d, J=8.0 Hz, 2H), 7.59 (d, J=8.0 Hz, 2H), 7.58 (s, 1H), 7.43 (d, J=2.0 Hz, 1H), 6.32 (d, J=5.6 Hz, 1H), 5.31-5.34 (m, 2H), 5.05-5.15 (m, 1H), 4.29-4.32 (m, 4H), 3.67 (s, 2H), 3.34-3.36 (m, 4H), 3.30 (m, 3H), 2.82-2.83 (m, 3H), 2.65-2.80 (m, 4H), 2.15-2.20 (m, 2H), 2.10-2.12 (m, 1H), 1.95-1.98 (m, 6H), 1.68 (d, J=6.8 Hz, 6H). LC-MS: (ES$^+$): m/z 842.4 [M+H]$^+$. t$_R$=2.71 min Chemical Formula: C$_{45}$H$_{51}$N$_{11}$O$_6$; Molecular Weight: 841.97

Synthesis of Example 291

(2S,4R)-1-((S)-2-(Tert-butyl)-14-(4-((1-(4-((1-isopropyl-2-methyl-1H-imidazo[4,5-c]pyridin-6-yl)amino)pyrimidin-2-yl)piperidin-4-yl)oxy)phenyl)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide

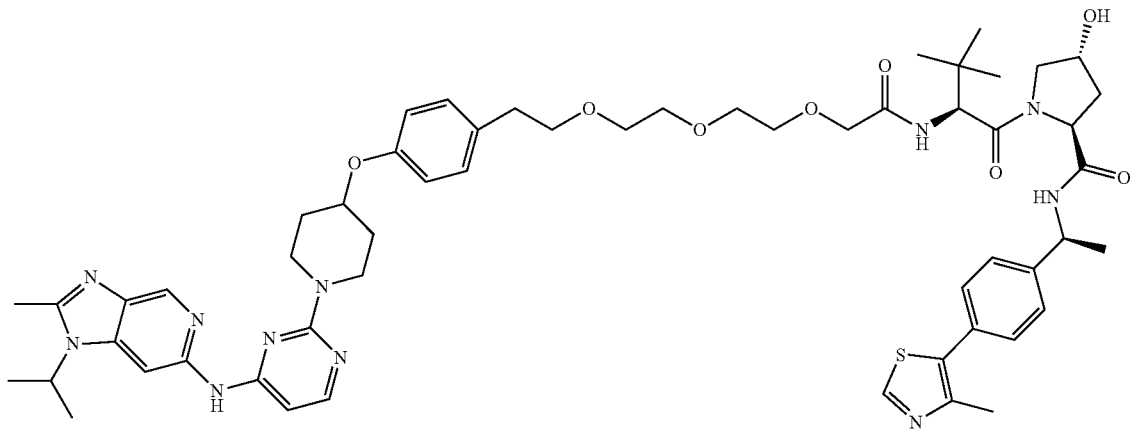 [SMILES: Cc1ncsc1-c1ccc([C@H](C)NC(=O)[C@@H]2C[C@@H](O)CN2C(=O)[C@@H](NC(=O)COCCOCCOCCc2ccc(OC3CCN(c4nccc(Nc5cc6c(cn5)nc(C)n6C(C)C)n4)CC3)cc2)C(C)(C)C)cc1]

The synthesis of example 291 followed the route and methods described for example 282 using the building blocks shown in the scheme below.
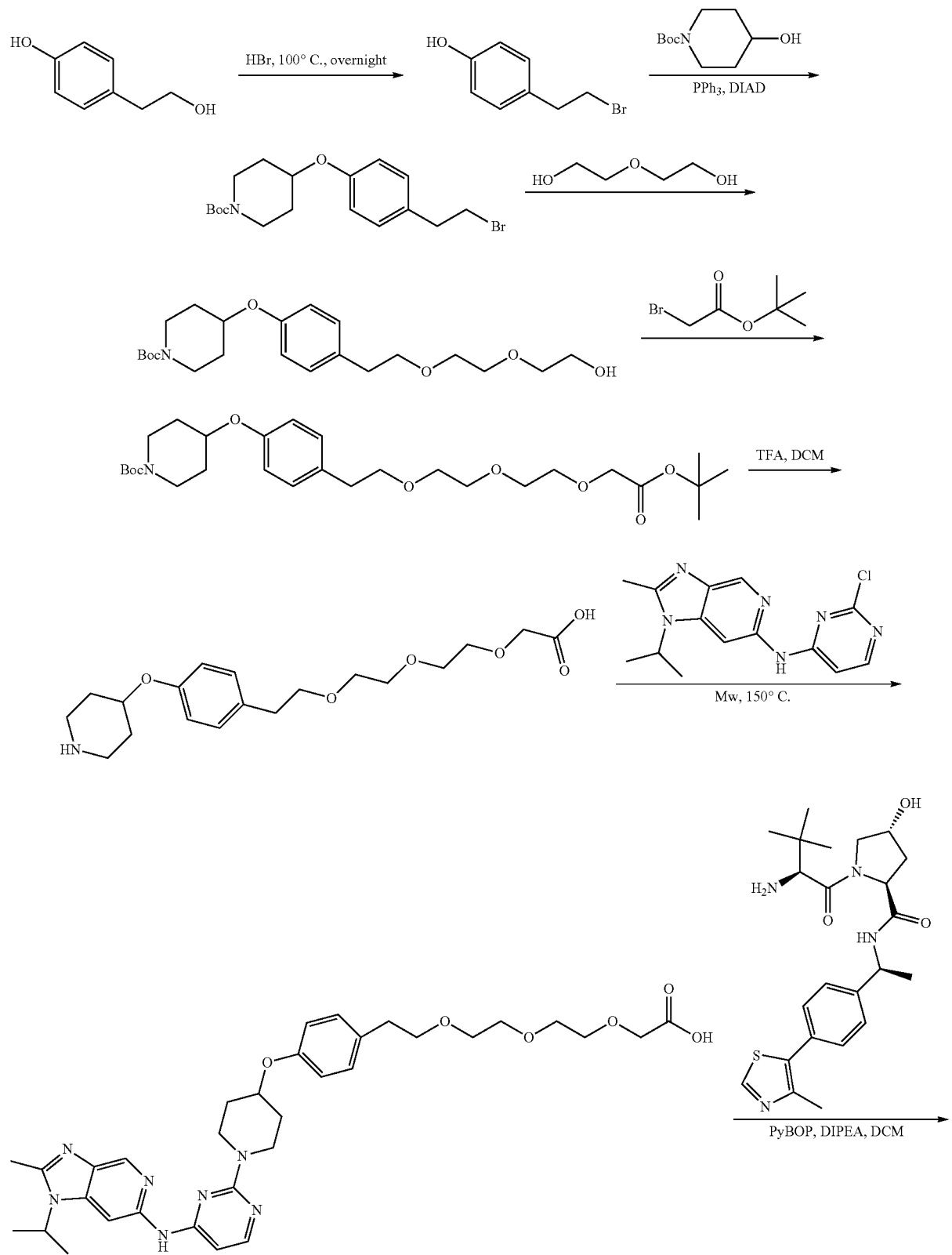

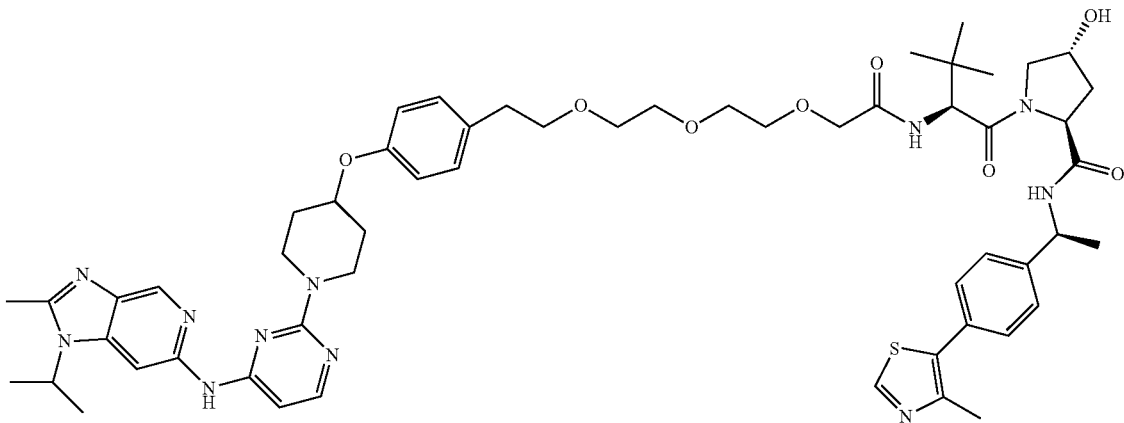 [SMILES: Cc1ncsc1-c1ccc([C@H](C)NC(=O)[C@@H]2C[C@@H](O)CN2C(=O)[C@@H](NC(=O)COCCOCCOCCc2ccc(OC3CCN(c4nccc(Nc5cc6c(cn5)nc(C)n6C(C)C)n4)CC3)cc2)C(C)(C)C)cc1]

¹H NMR (400 MHz, CDCl₃): δ 8.66 (s, 1H), 8.61 (s, 1H), 8.30 (s, 1H), 8.03 (d, J=5.6 Hz, 1H), 7.32-7.41 (m, 7H), 7.14 (d, J=8.4 Hz, 2H), 6.87 (d, J=8.4 Hz, 2H), 6.09 (d, J=5.6 Hz, 1H), 5.10 (t, J=7.2 Hz, 1H), 4.73-4.76 (m, 1H), 4.62-4.66 (m, 1H), 4.50-4.52 (m, 3H), 4.22-4.28 (m, 2H), 4.12-4.15 (m, 1H), 3.95-4.10 (m, 2H), 3.63-3.75 (m, 13H), 2.84 (t, J=7.2 Hz, 2H), 2.61 (s, 3H), 2.60-2.62 (m, 1H), 2.52 (m, 3H), 1.98-2.04 (m, 4H), 1.80-1.85 (m, 2H), 1.63 (d, J=6.8 Hz, 6H), 1.53 (d, J=6.4 Hz, 3H), 1.07 (s, 9H). LC-MS: (ES⁺): m/z 1060.5 [M+H]. $t_R$=3.42 min Chemical Formula: $C_{56}H_{73}N_{11}O_8S$; Molecular Weight: 1060.33.

Synthesis of Example 292

(2S,4R)-4-hydroxy-1-((S)-2-(2-(3-(3-(4-(2-(1-(4-((1-isopropyl-2-methyl-1H-imidazo[4,5-c]pyridin-6-yl)amino)pyrimidin-2-yl)-4-methoxypiperidin-4-yl)ethyl)piperazin-1-yl)propoxy)propoxy)acetamido)-3,3-dimethylbutanoyl)-N—((S)-1-(4-(4-methylthiazol-5-yl)phenyl)ethyl)pyrrolidine-2-carboxamide

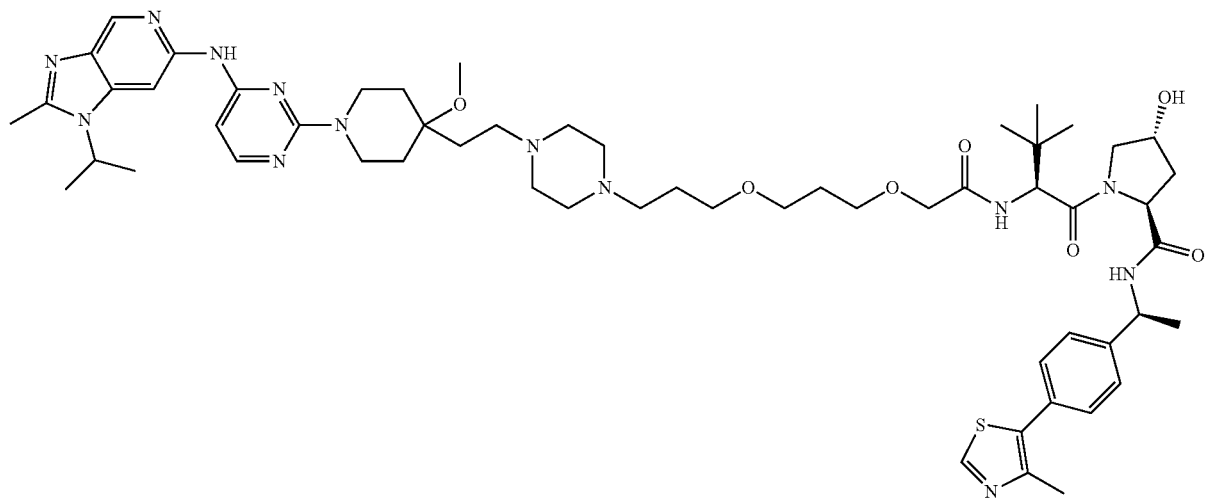 [SMILES: COC1(CCN2CCN(CCCOCCCOCC(=O)N[C@H](C(=O)N3C[C@H](O)C[C@H]3C(=O)N[C@@H](C)c3ccc(-c4scnc4C)cc3)C(C)(C)C)CC2)CCN(c2nccc(Nc3cc4c(cn3)nc(C)n4C(C)C)n2)CC1]

The synthesis of example 292 followed the general strategy and methods used for examples 78 and 282, using the building blocks shown in the scheme below.
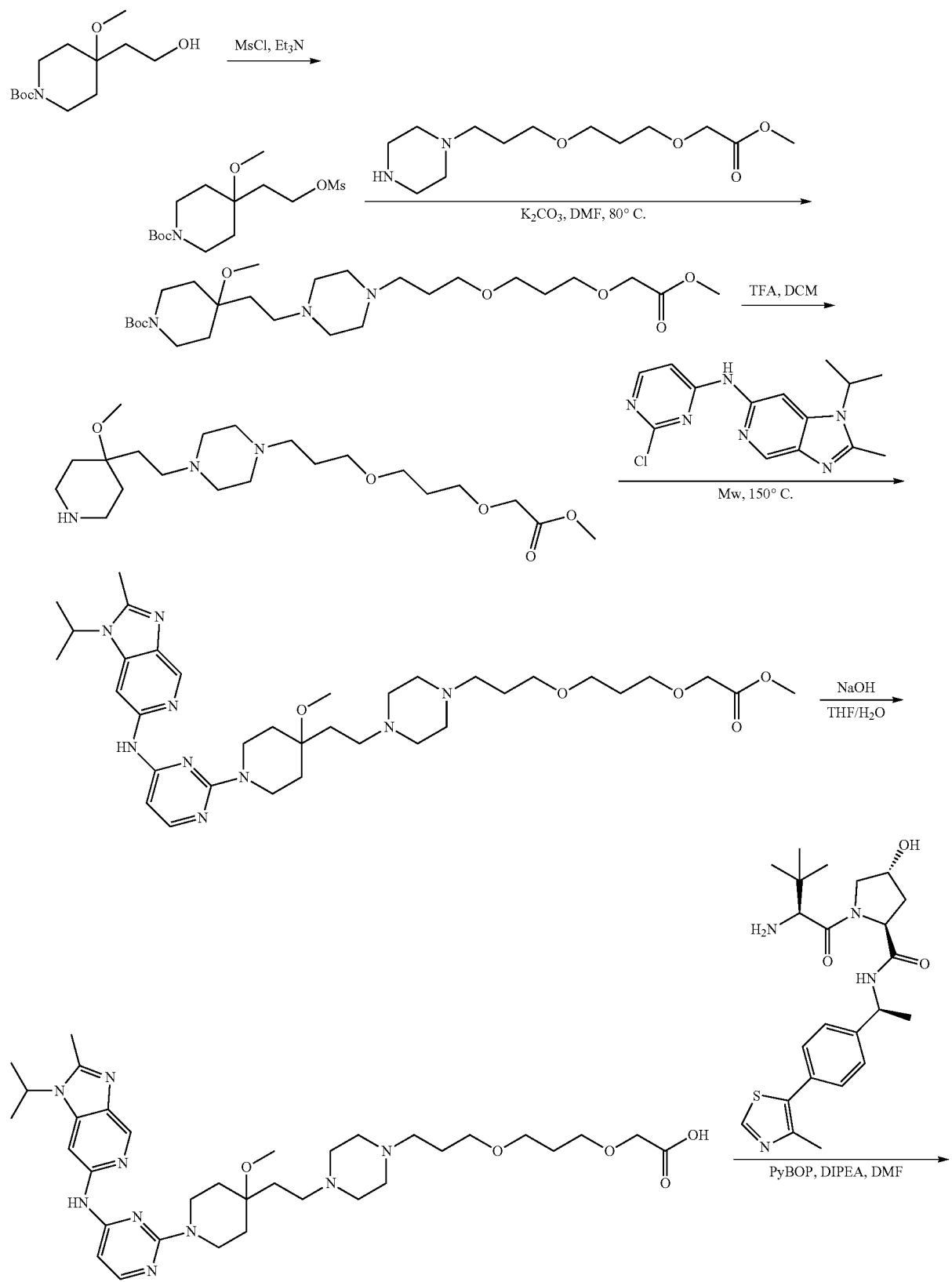

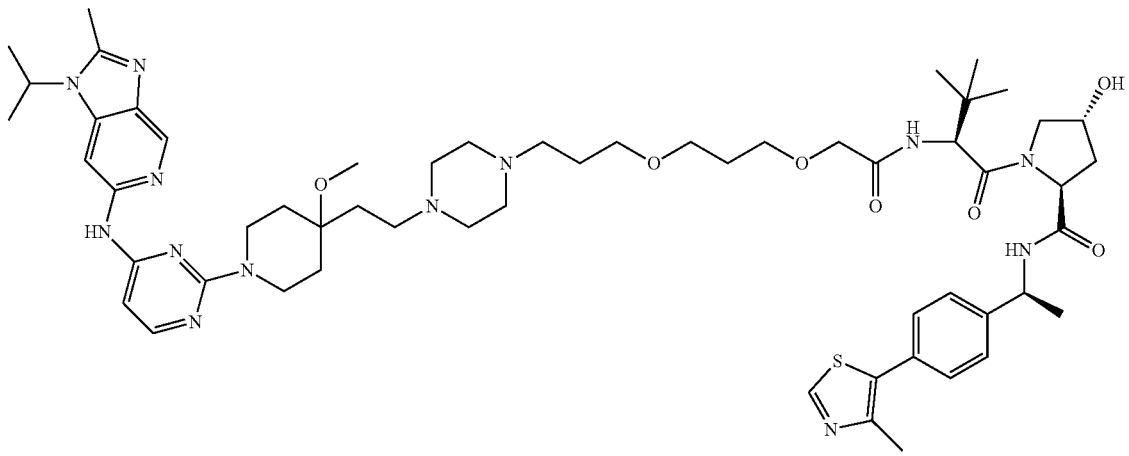 [SMILES: COC1(CCN2CCN(CCCOCCCOCC(=O)N[C@H](C(=O)N3C[C@H](O)C[C@H]3C(=O)N[C@@H](C)c3ccc(-c4scnc4C)cc3)C(C)(C)C)CC2)CCN(c2nccc(Nc3cc4c(cn3)nc(C)n4C(C)C)n2)CC1]

(2S,4R)-4-Hydroxy-1-((S)-2-(2-(3-(3-(4-(2-(1-(4-((1-isopropyl-2-methyl-1H-imidazo[4,5-c]pyridin-6-yl)amino)pyrimidin-2-yl)-4-methoxypiperidin-4-yl)ethyl)piperazin-1-yl)propoxy)propoxy)acetamido)-3,3-dimethylbutanoyl)-N—((S)-1-(4-(4-methylthiazol-5-yl)phenyl)ethyl)pyrrolidine-2-carboxamide

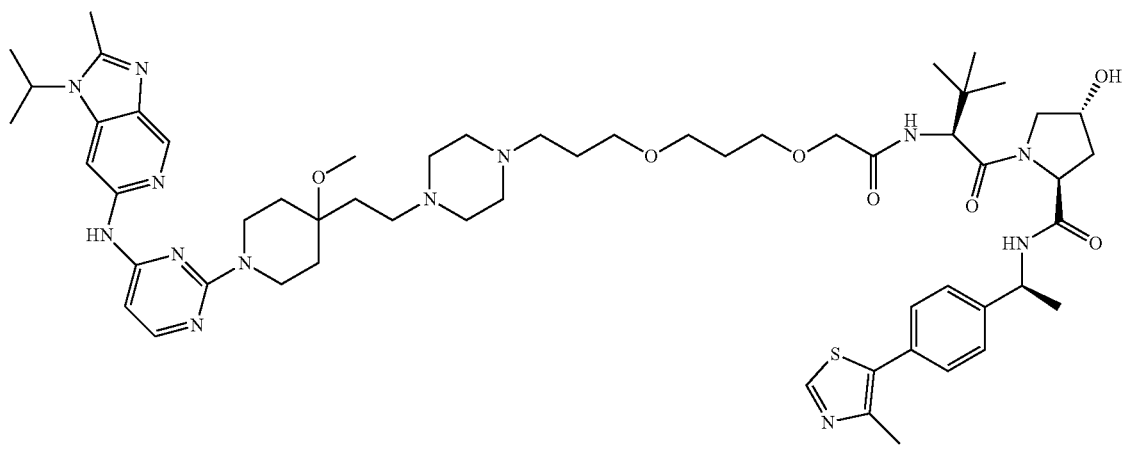 [SMILES: COC1(CCN2CCN(CCCOCCCOCC(=O)N[C@H](C(=O)N3C[C@H](O)C[C@H]3C(=O)N[C@@H](C)c3ccc(-c4scnc4C)cc3)C(C)(C)C)CC2)CCN(c2nccc(Nc3cc4c(cn3)nc(C)n4C(C)C)n2)CC1]

$^1$H NMR (400 MHz, CDCl$_3$): δ 8.59 (s, 1H), 8.53 (s, 1H), 8.31 (s, 1H), 7.94 (d, J=5.6 Hz, 1H), 7.69 (s, 1H), 7.35-7.36 (m, 1H), 7.29-7.33 (m, 4H), 7.15-7.17 (m, 1H), 5.98 (d, J=5.2 Hz, 1H), 4.95-5.05 (m, 1H), 4.36-4.38 (m, 2H), 4.32-4.35 (m, 4H), 3.95-4.02 (m, 1H), 3.86 (d, J=4.0 Hz, 2H), 3.51-3.54 (m, 3H), 3.42-3.43 (m, 4H), 3.25-3.27 (m, 2H), 3.16 (s, 3H), 2.54 (s, 3H), 2.43-2.46 (m, 9H), 2.35-2.38 (m, 6H), 1.98-2.02 (m, 2H), 1.76-1.78 (m, 5H), 1.67-1.69 (m, 3H), 1.65 (d, J=6.8 Hz, 6H), 1.48-1.51 (m, 3H), 1.40 (d, J=6.8 Hz, 3H), 0.98 (s, 9H). LC-MS: (ES$^+$): m/z 1094.3 [M+H]$^+$. t$_R$=2.98 min Chemical Formula: C$_{57}$H$_{83}$N$_{13}$O$_7$S; Molecular Weight: 1094.43

Synthesis of Example 301
2-(2,6-dioxopiperidin-3-yl)-5-(4-(3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)propyl)piperazin-1-yl)isoindoline-1,3-dione
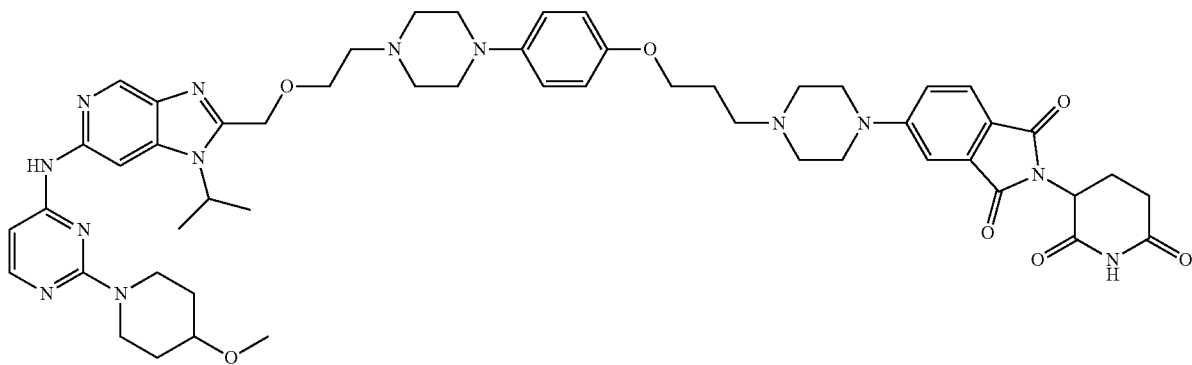 [SMILES: COC1CCN(c2nccc(Nc3cc4c(cn3)nc(COCCN3CCN(c5ccc(OCCCN6CCN(c7ccc8c(c7)C(=O)N(C7CCC(=O)NC7=O)C8=O)CC6)cc5)CC3)n4C(C)C)n2)CC1]
Synthetic Route:
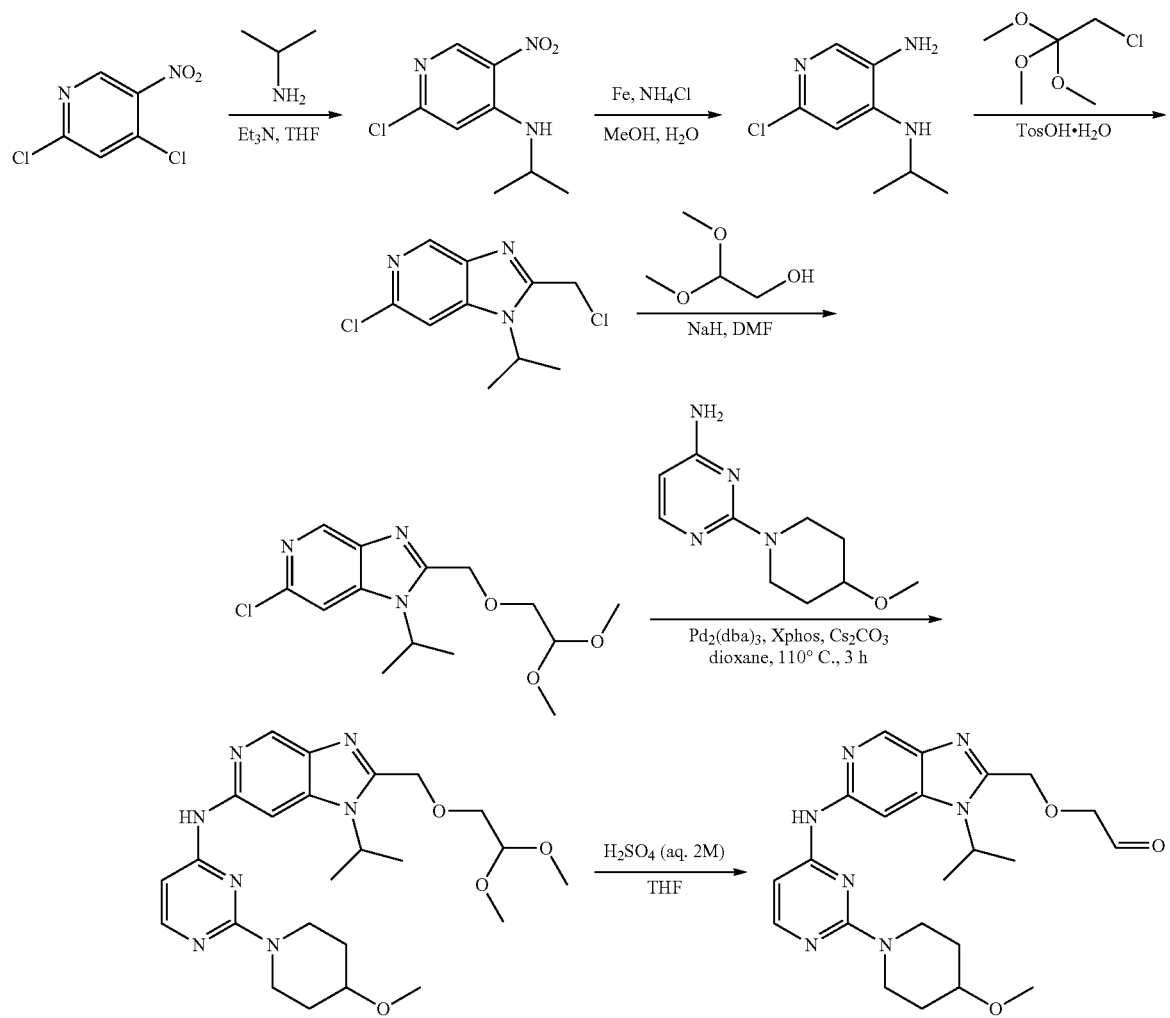

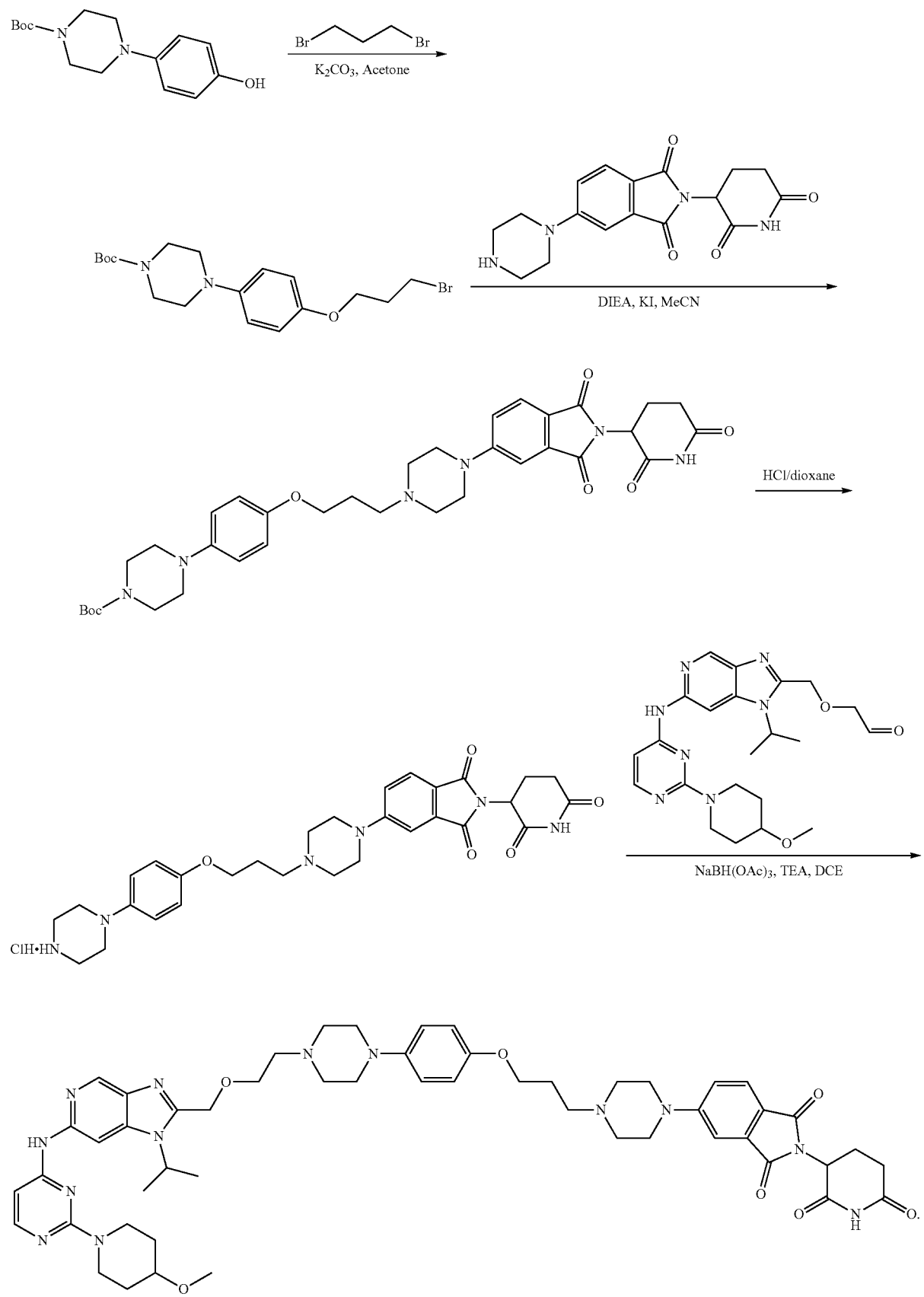

1. Step—Synthesis of 2-chloro-N-isopropyl-5-nitro-pyridin-4-amine

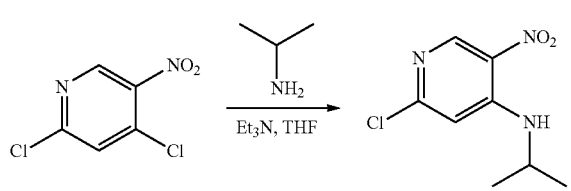

To a solution of 2,4-dichloro-5-nitro-pyridine (14 g, 72.5 mmol, 1 eq) and propan-2-amine (4.29 g, 72.5 mmol, 1 eq) in tetrahydrofuran (100 mL) was added triethylamine (14.68 g, 145.09 mmol, 2 eq), the mixture was stirred at 25° C. for 6 hours. Thin Layer Chromatography (petroleum ether/ethyl acetate=5/1) showed the starting material was consumed completely and one major new spot with higher polarity was detected. The mixture was diluted with water (200 mL), then extracted with ethyl acetate (100 mL×3), the organic layer was dried over anhydrous sodium sulfate, filtered and concentrated under reduced pressure to afford 2-chloro-N-isopropyl-5-nitro-pyridin-4-amine (15.5 g, 71.88 mmol, 99% yield) as a yellow solid. $^1$H NMR (400 MHz, CDCl$_3$) δ: 9.02 (s, 1H), 8.08 (s, 1H), 6.74 (s, 1H), 3.79-3.87 (m, 1H), 1.37 (d, J=6.4 Hz, 6H). Chemical Formula: C$_8$H$_{10}$ClN$_3$O$_2$, Molecular Weight: 215.64

2. Step—Synthesis of 6-chloro-N-4-isopropyl-pyridine-3,4-diamine

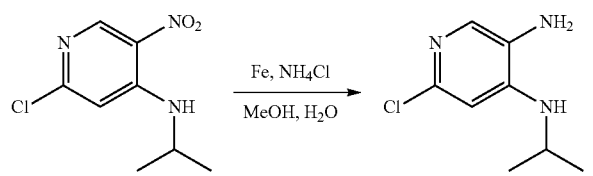

To a mixture of 2-chloro-N-isopropyl-5-nitro-pyridin-4-amine (10 g, 46.37 mmol, 1 eq) and iron (6.47 g, 115.94 mmol, 2.5 eq) in methanol (80 mL) was added ammonium chloride (6.20 g, 115.94 mmol, 2.5 eq) in water (20 mL). The mixture was stirred at 65° C. for 12 hours. Thin Layer Chromatography (petroleum ether/ethyl acetate=1/1) showed the starting material was consumed completely and one major new spot was formed. The mixture was concentrated under reduced pressure to give a residue. The residue was diluted with ethyl acetate (30 mL), filtered and the filtrate was concentrated under reduced pressure to give a residue. The residue was purified by silica gel chromatography (petroleum ether/ethyl acetate=10/1 to 1/1) to afford 6-chloro-N-4-isopropyl-pyridine-3,4-diamine (5.6 g, 30.16 mmol, 65% yield) as a gray solid. $^1$H NMR (400 MHz, CDCl$_3$) δ: 7.62 (s, 1H), 6.43 (s, 1H), 4.23 (s, 1H), 3.56-3.67 (m, 1H), 3.02 (s, 2H), 1.25 (d, J=6.4 Hz, 6H). Chemical Formula: C$_8$H$_{12}$ClN$_3$, Molecular Weight: 185.65

3. Step—Synthesis of 6-chloro-2-(chloromethyl)-1-isopropyl-imidazo [4,5-c]pyridine

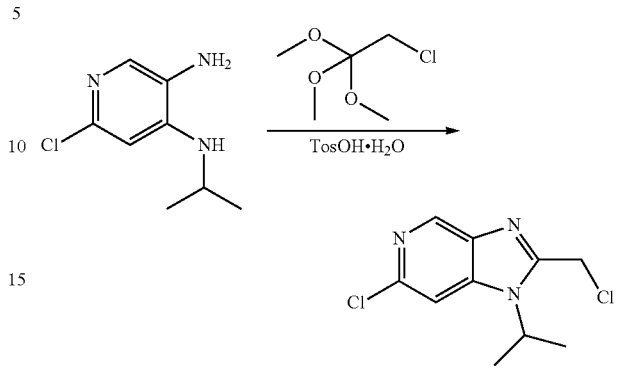

To a solution of 6-chloro-N4-isopropyl-pyridine-3,4-diamine (1.3 g, 7.00 mmol, 1 eq) in 2-chloro-1,1,1-trimethoxy-ethane (4.60 g, 29.76 mmol, 4.0 mL, 4.25 eq) was added p-toluenesulfonic acid monohydrate (133 mg, 0.70 mmol, 0.1 eq), the mixture was stirred at 100° C. for 1 hour. Thin layer chromatography (petroleum ether/ethyl acetate=3/1) showed one major new spot with lower polarity was detected. The mixture was concentrated under reduced pressure. The residue was purified by silica gel chromatography (petroleum ether/ethyl acetate=3/1) to afford 6-chloro-2-(chloromethyl)-1-isopropyl-imidazo[4,5-c]pyridine (0.82 g, 3.36 mmol, 48% yield) as a light yellow solid. $^1$H NMR: (400 MHz, CDCl$_3$) δ: 8.76 (s, 1H), 7.98 (s, 1H), 5.14 (s, 2H), 4.85-4.93 (m, 1H), 1.58 (d, J=6.8 Hz, 6H). Chemical Formula: C$_{10}$H$_{11}$Cl$_2$N3, Molecular Weight: 244.12

4. Step—Synthesis of 6-chloro-2-(2,2-dimethoxy-ethoxymethyl)-1-isopropyl-imidazo[4,5-c]pyridine

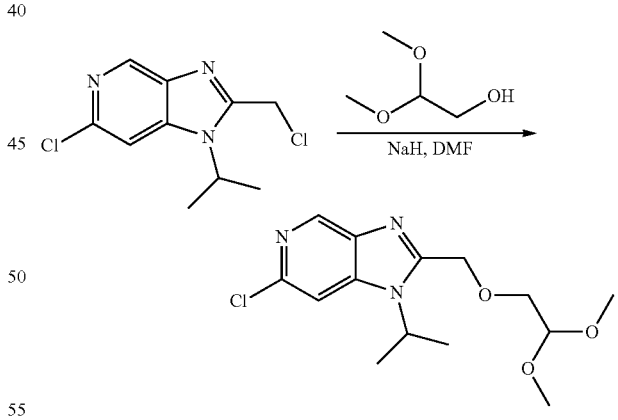

To a solution of 2,2-dimethoxyethanol (469 mg, 4.42 mmol, 1.5 eq) in N,N-dimethylformamide (20 mL) was added sodium hydride (177 mg, 4.42 mmol, 60% purity, 1.5 eq), the mixture was stirred at 50° C. for 1 hour, then 6-chloro-2-(chloromethyl)-1-isopropyl-imidazo[4,5-c]pyridine (0.72 g, 2.95 mmol, 1 eq) was added, the mixture was stirred at 50° C. for 2 hours. The desired MS was detected by LCMS. The mixture was diluted with water (100 mL), then extracted with ethyl acetate (50 mL×3), the organic layer was washed with brine (100 mL×2), dried over anhydrous sodium sulfate, filtered and concentrated under reduced pressure. The residue was purified by silica gel chromatography (petroleum ether/ethyl acetate=10/1 to 1/1) to afford 6-chloro-2-(2,2-dimethoxyethoxymethyl)-1-isopropyl-imidazo[4,5-c]pyridine (0.7 g, 2.23 mmol, 75% yield) as a light yellow oil. LCMS: MS (ESI) m/z: 314.1 [M+1]+. $^1$H NMR: (400 MHz, CDCl$_3$) δ: 8.80 (d, J=0.8 Hz, 1H), 7.49 (d, J=0.8 Hz, 1H), 4.90-4.97 (m, 1H), 4.85 (s, 2H), 4.51 (t, J=5.2 Hz, 1H), 3.57 (d, J=5.2 Hz, 2H), 3.37 (s, 6H), 1.64 (d, J=6.8 Hz, 6H). Chemical Formula: $C_{14}H_{20}ClN_3O_3$, Molecular Weight: 313.78

5. Step—Synthesis of 2-(2,2-dimethoxyethoxymethyl)-1-isopropyl-N-[2-(4-methoxy-1-piperidyl)pyrimidin-4-yl]imidazo[4,5-c]pyridin-6-amine

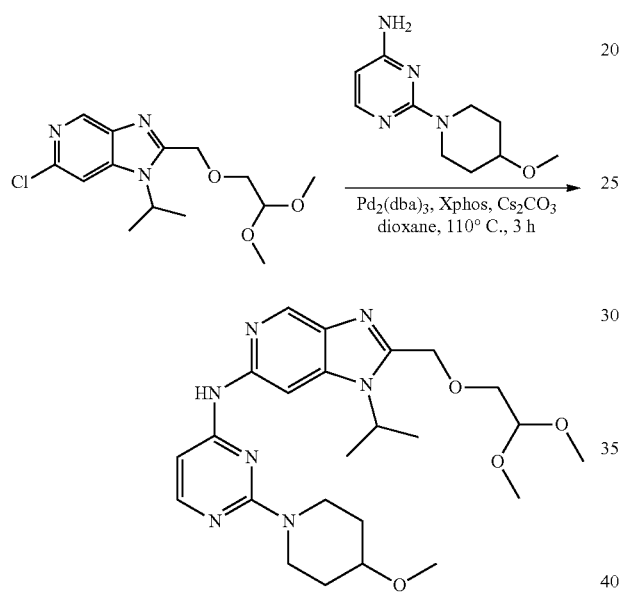

To a solution of 6-chloro-2-(2,2-dimethoxyethoxymethyl)-1-isopropyl-imidazo[4,5-c]pyridine (500 mg, 1.59 mmol, 1 eq) and 2-(4-methoxy-1-piperidyl)pyrimidin-4-amine (331 mg, 1.59 mmol, 1 eq) in 1,4-dioxane (10 mL) was added 2-(dicyclohexylphosphino)-2',4',6'-triisopropylbiphenyl (152 mg, 0.32 mmol, 0.2 eq), tris(dibenzylideneacetone)dipalladium (146 mg, 0.16 mmol, 0.1 eq) and cesium carbonate (1.04 g, 3.19 mmol, 2 eq), the mixture was degassed and purged with nitrogen several times, then stirred at 100° C. for 3 hours under nitrogen atmosphere. The desired MS was detected by LCMS. The mixture was concentrated under reduced pressure. The residue was purified by silica gel chromatography (dichloromethane/methanol=20/1) to afford 2-(2,2-dimethoxyethoxymethyl)-1-isopropyl-N-[2-(4-methoxy-1-piperidyl)pyrimidin-4-yl]imidazo[4,5-c]pyridin-6-amine (0.7 g, 1.44 mmol, 90% yield) as a light yellow oil. LCMS: MS (ESI) m/z: 486.2 [M+1]$^+$. $^1$H NMR: (400 MHz, CDCl$_3$) δ: 8.70 (s, 1H), 8.46 (s, 1H), 8.05 (d, J=5.6 Hz, 1H), 7.37 (s, 1H), 6.04 (d, J=5.6 Hz, 1H), 4.93-4.98 (m, 1H), 4.84 (s, 2H), 4.51 (t, J=5.2 Hz, 1H), 4.36-4.41 (m, 1H), 3.57 (d, J=5.2 Hz, 2H), 3.44-3.54 (m, 4H), 3.42 (s, 3H), 3.38 (s, 6H), 1.95-2.03 (m, 2H), 1.68 (d, J=7.2 Hz, 6H), 1.64-1.66 (m, 2H). Chemical Formula: $C_{24}H_{35}N_7O_4$, Molecular Weight: 485.58

6. Step—Synthesis of 2-[[1-isopropyl-6-[[2-(4-methoxy-1-piperidyl) pyrimidin-4-yl]amino]imidazo[4,5-c]pyridin-2-yl]methoxy]acetaldehyde

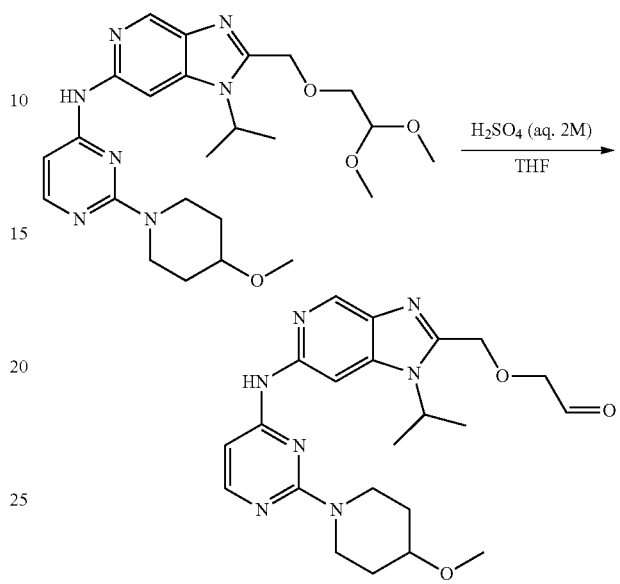

To a solution of 2-(2,2-dimethoxyethoxymethyl)-1-isopropyl-N-[2-(4-methoxy-1-piperidyl) pyrimidin-4-yl]imidazo[4,5-c]pyridin-6-amine (0.6 g, 1.24 mmol, 1 eq) in tetrahydrofuran (20 mL) was added sulfuric acid (2 molar, aqueous, 20 mL, 40 mmol, 32 equiv.), the mixture was stirred at 100° C. for 30 minutes. Thin layer chromatography (dichloromethane/methanol=20/1) showed the starting material was consumed completely and one major new spot with larger polarity was detected. The pH of the mixture was adjusted to 8 by saturated solution of sodium carbonate, then extracted with ethyl acetate (30 mL×3), the organic layer was dried over anhydrous sodium sulfate, filtered and concentrated under reduced pressure. The residue purified by silica gel chromatography (dichloromethane/methanol=50/1 to 20/1) to afford 2-[[1-isopropyl-6-[[2-(4-methoxy-1-piperidyl)pyrimidin-4-yl]amino]imidazo[4,5-c]pyridin-2-yl]methoxy]acetaldehyde (0.5 g, 1.14 mmol, 92% yield) as a light yellow oil. $^1$H NMR: (400 MHz, CDCl$_3$) δ: 9.68 (s, 1H), 8.70 (s, 1H), 8.49 (s, 1H), 8.06 (d, J=5.6 Hz, 1H), 7.50-7.53 (m, 1H), 6.05 (d, J=5.6 Hz, 1H), 4.98-5.05 (m, 1H), 4.90 (s, 2H), 4.38-4.40 (m, 2H), 4.27 (s, 2H), 3.51-3.54 (m, 2H), 3.47-3.49 (m, 1H), 3.42 (s, 3H), 1.96-2.00 (m, 2H), 1.70 (d, J=7.2 Hz, 6H), 1.65-1.67 (m, 2H). Chemical Formula: $C_{22}H_{29}N_7O_3$, Molecular Weight: 439.51

7. Step—Synthesis of tert-butyl 4-[4-(3-bromopropoxy)phenyl]piperazine-1-carboxylate

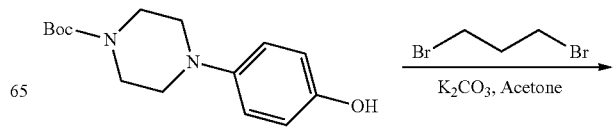

-continued

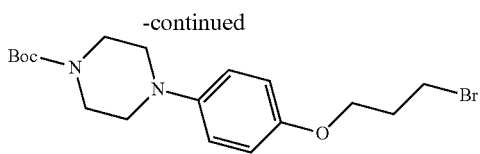

To a solution of tert-butyl 4-(4-hydroxyphenyl)piperazine-1-carboxylate (500 mg, 1.80 mmol, 1 eq) in acetone (10 mL) was added potassium carbonate (745 mg, 5.39 mmol, 3 eq) and 1,3-dibromopropane (1.09 g, 5.39 mmol, 3 eq). The mixture was stirred at 80° C. for 12 hr. LCMS showed the reaction was completed. The reaction mixture was diluted with water (30 mL) and extracted with ethyl acetate (10 mL×2). The combined organic phase was washed with saturated brine (10 mL×2), dried with anhydrous sodium sulfate, filtered and concentrated in vacuum. The residue was purified by silica gel chromatography (Petroleum ether/Ethyl acetate=30:1 to 10:1). tert-butyl 4-[4-(3-bromopropoxy)phenyl]piperazine-1-carboxylate (620 mg, 1.55 mmol, 86% yield) was obtained as a white solid. LCMS: MS (ESI) m/z: 399.0 [M+1]. Chemical Formula: $C_{17}H_{27}N_2O_3Br$, Molecular Weight: 398.12

8. Step—Synthesis of tert-butyl 4-[4-[3-[4-[2-(2,6-dioxo-3-piperidyl)-1,3-dioxo-isoindolin-5-yl]piperazin-1-yl]propoxy]phenyl]piperazine-1-carboxylate To a solution of tert-butyl 4-[4-(3-bromopropoxy)phenyl]piperazine-1-carboxylate (400 mg, 1.00 mmol, 1 eq) and 2-(2,6-dioxo-3-piperidyl)-5-piperazin-1-yl-isoindoline-1,3-dione (379 mg, 1.00 mmol, 1 eq, HCl) in acetonitrile (10 mL) was added potassium iodide (17 mg, 0.10 mmol, 0.1 eq) and diisopropylethylamine (518 mg, 4.01 mmol, 0.7 mL, 4 eq). The mixture was stirred at 100° C. for 12 hr. LCMS showed the reaction was completed. The reaction mixture was diluted with water (30 mL) and extracted with ethyl acetate (20 mL×2). The combined organic phase was washed with saturated brine (20 mL×2), dried with anhydrous sodium sulfate, filtered and concentrated in vacuum. The residue was purified by silica gel chromatography (dichloromethane:methanol=1:0 to 50:1). Tert-butyl 4-[4-[3-[4-[2-(2,6-dioxo-3-piperidyl)-1,3-dioxo-isoindolin-5-yl]piperazin-1-yl]propoxy]phenyl]piperazine-1-carboxylate (480 mg, 0.73 mmol, 72% yield) was obtained as a yellow solid. LCMS:MS (ESI) m/z: 661.2 [M+1]+. $^1$H NMR: (400 MHz, CHLOROFORM-d) δ 8.26 (s, 1H), 7.70 (d, J=8.4 Hz, 1H), 7.29 (d, J=2.0 Hz, 1H), 7.07-7.05 (m, 1H), 6.91-6.81 (m, 4H), 4.94 (dd, J=12.0, 6.2 Hz, 1H), 4.02-3.99 (m, 2H), 3.59-3.56 (m, 4H), 3.45-3.43 (m, 4H), 3.02-3.00 (m, 4H), 2.87-2.86 (m, 4H), 2.62-2.59 (m, 4H), 2.15-2.05 (m, 1H), 2.01-1.98 (m, 2H), 1.56-1.54 (m, 1H), 1.48 (s, 9H). Chemical Formula: $C_{35}H_{44}N_6O_7$, Molecular Weight: 660.76

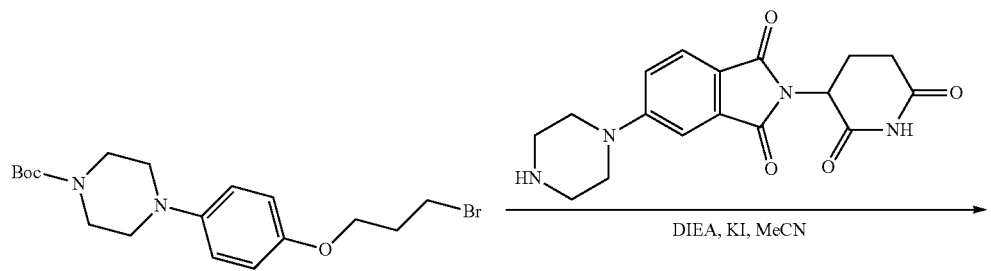

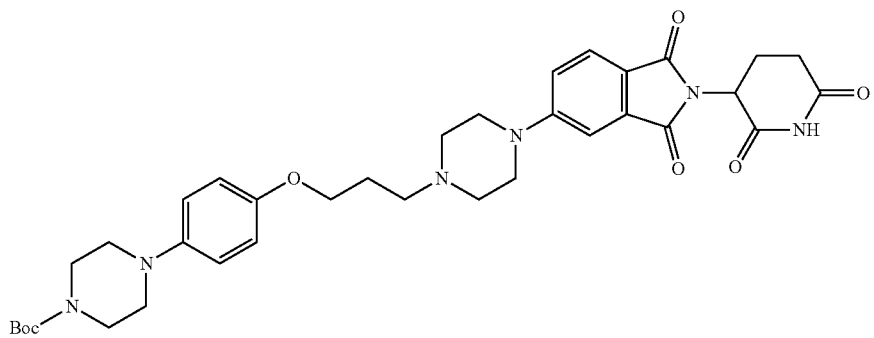

9. Step—Synthesis of 2-(2,6-dioxopiperidin-3-yl)-5-(4-(3-(4-(piperazin-1-yl)phenoxy)propyl)piperazin-1-yl)isoindoline-1,3-dione HCl salt

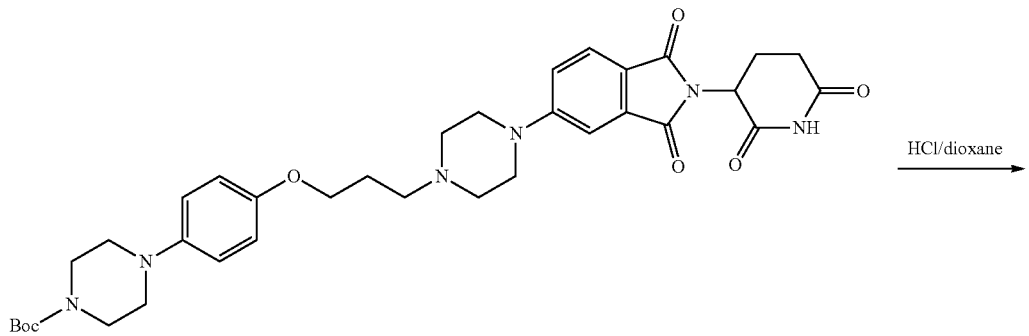

A mixture of tert-butyl 4-[4-[3-[4-[2-(2,6-dioxo-3-piperidyl)-1,3-dioxo-isoindolin-5-yl]piperazin-1-yl]propoxy]phenyl]piperazine-1-carboxylate (480 mg, 0.73 mmol, 1 eq) in hydrochloride/dioxane (8 mL, 4 M) was stirred at 25° C. for 1 hr. LCMS showed starting material was consumed completely and one main peak with desired mass was detected. The mixture was concentrated under reduced pressure. Crude compound 2-(2,6-dioxo-3-piperidyl)-5-[4-[3-(4-piperazin-1-ylphenoxy)propyl]piperazin-1-yl]isoindoline-1,3-dione (500 mg, crude, hydrochloride) was obtained as a yellow solid, which was confirmed by HNMR. LCMS: MS (ESI) m/z: 561.3 [M+1]$^+$. $^1$H NMR: (400 MHz, MeOD) δ 7.80 (d, J=8.8 Hz, 1H), 7.51 (d, J=2.4 Hz, 1H), 7.39 (dd, J=8.4, 2.4 Hz, 1H), 7.12 (d, J=9.2 Hz, 2H), 6.99-6.97 (m, 2H), 5.14-5.09 (m, 1H), 4.22-4.15 (m, 2H), 4.14-4.13 (m, 4H), 3.75-3.73 (m, 4H), 3.48-3.45 (m, 1H), 3.44-3.41 (m, 8H), 3.40-3.26 (m, 1H), 2.79-2.78 (m, 1H), 2.75-2.76 (m, 2H), 2.35-2.34 (m, 2H), 2.33-2.12 (m, 1H). Chemical Formula: $C_{30}H_{36}N_6O_5$, Molecular Weight: 560.64

10. Step—Synthesis of 2-(2,6-dioxo-3-piperidyl)-5-[4-[3-[4-[4-[2-[[1-isopropyl-6-[[2-(4-methoxy-1-piperidyl)pyrimidin-4-yl]amino]imidazo[4,5-c]pyridin-2-yl]methoxy]ethyl]piperazin-1-yl]phenoxy]propyl]piperazin-1-yl]isoindoline-1,3-dione

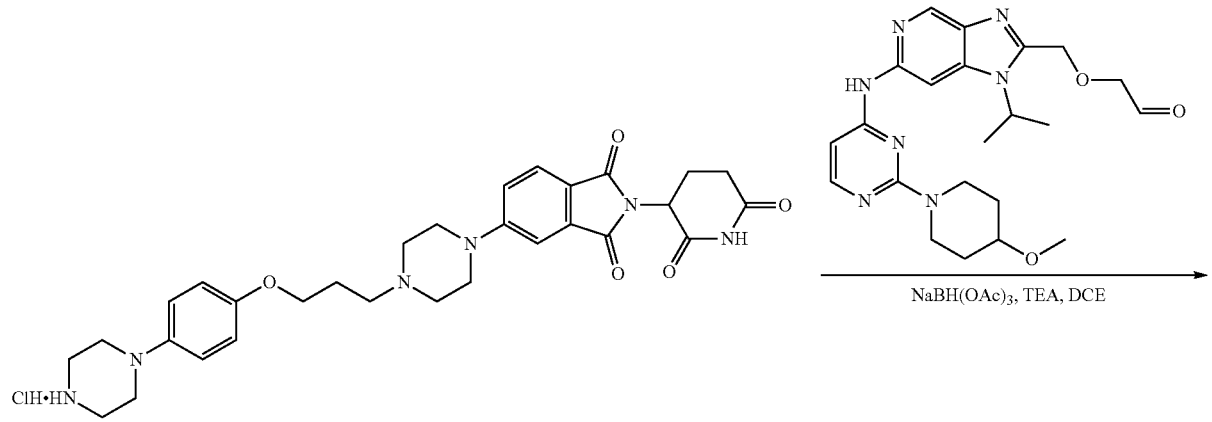

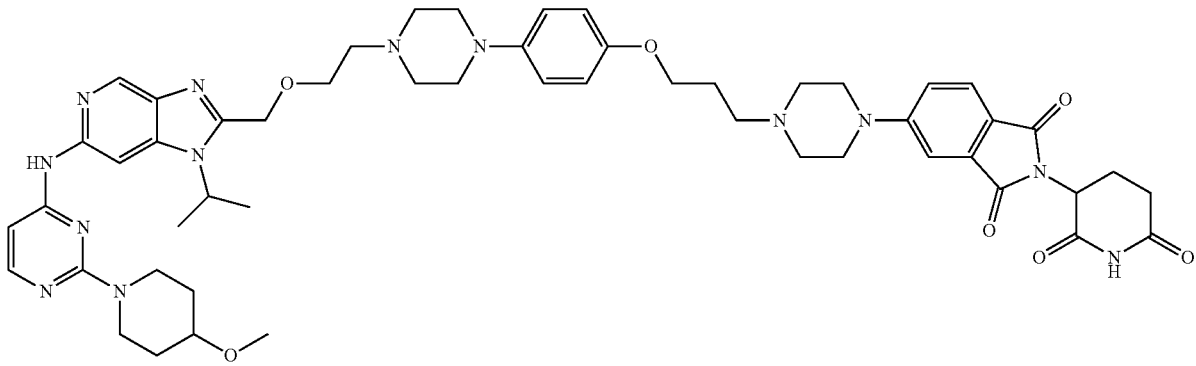

To the mixture of 2-(2,6-dioxo-3-piperidyl)-5-[4-[3-(4-piperazin-1-ylphenoxy)propyl]piperazin-1-yl]isoindoline-1,3-dione (136 mg, 0.23 mmol, 1 eq, hydrochloride) and 2-[[1-isopropyl-6-[[2-(4-methoxy-1-piperidyl)pyrimidin-4-yl]amino]imidazo[4,5-c]pyridin-2-yl]methoxy]acetaldehyde (100 mg, 0.23 mmol, 1 eq) in dichloroethane (5 mL) was added triethylamine (46 mg, 0.46 mmol, 2 eq). The mixture was stirred at 25° C. for 2 hours. Then sodium triacetoxy borohydride (96 mg, 0.46 mmol, 2 eq) was added to the mixture and was stirred at 25° C. for 10 hours. LCMS showed formation of a new peak with the desired mass. The mixture was concentrated under reduced pressure. The residue was purified by prep-Thin-Layer chromatography (dichloromethane:methanol=10:1, $R_f$=0.15). Then it was purified by prep-HPLC [FA]. 2-(2,6-dioxo-3-piperidyl)-5-[4-[3-[4-[4-[2-[[1-isopropyl-6-[[2-(4-methoxy-1-piperidyl)pyrimidin-4-yl]amino]imidazo[4,5-c]pyridin-2-yl]methoxy]ethyl]piperazin-1-yl]phenoxy]propyl]piperazin-1-yl]isoindoline-1,3-dione (13.7 mg, 0.01 mmol, 5% yield, 93% purity) was obtained as a yellow solid, which was confirmed by HNMR and LCMS. LCMS: MS (ESI) m/z: 984.4 [M+1]$^+$. $^1$H NMR: (400 MHz, MeOD) δ 8.67 (s, 1H), 8.50 (s, 1H), 7.96 (d, J=6.0 Hz, 1H), 7.73 (d, J=8.8 Hz, 1H), 7.43 (d, J=2.0 Hz, 1H), 7.30 (d, J=8.4, 2.4 Hz, 1H), 6.98 (d, J=9.2 Hz, 2H), 6.89 (d, J=8.8 Hz, 2H), 6.42-6.38 (m, 1H), 5.10-5.08 (m, 1H), 4.94 (s, 2H), 4.31-4.26 (m, 2H), 4.07-4.04 (m, 2H), 3.94-3.85 (m, 2H), 3.60-3.58 (m, 4H), 3.43-3.42 (m, 1H), 3.42 (s, 3H), 3.25-3.24 (m, 4H), 3.23-3.20 (m, 6H), 2.96-2.95 (m, 4H), 2.89-2.87 (m, 3H), 2.82-2.75 (m, 2H), 2.12-2.10 (m, 3H), 2.05-1.95 (m, 2H), 1.73 (d, J=6.8 Hz, 6H), 1.61-1.51 (m, 2H). Chemical Formula: $C_{52}H_{65}N_{13}O_7$, Molecular Weight: 984.16

Synthesis of Example 302

(2S,4R)-4-hydroxy-1-((S)-2-(2-(((1r,3s)-3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)cyclobutoxy)acetamido)-3,3-dimethylbutanoyl)-N-(4-(4-methylthiazol-5-yl)benzyl)pyrrolidine-2-carboxamide

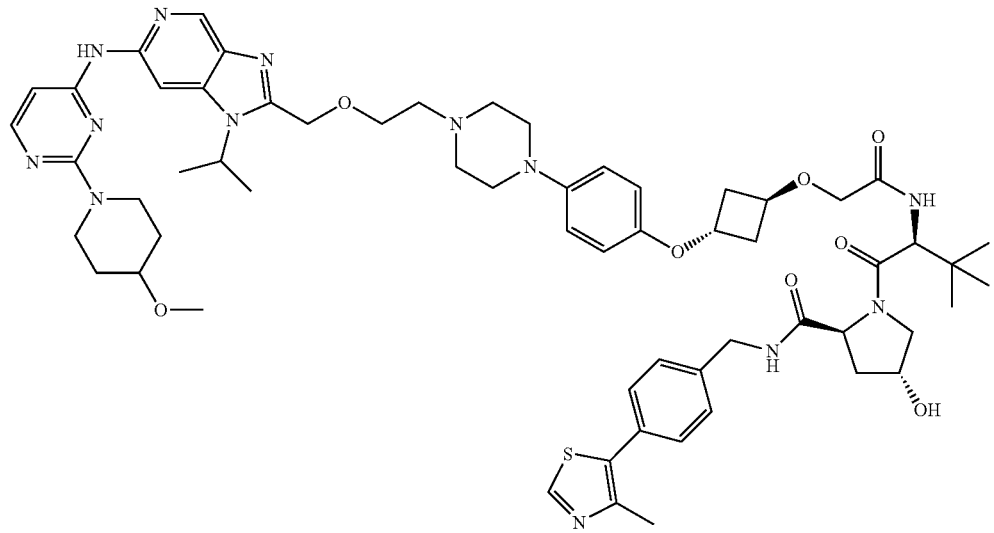 [SMILES: COC1CCN(c2nccc(Nc3cc4c(cn3)nc(COCCN3CCN(c5ccc(O[C@H]6C[C@H](OCC(=O)N[C@H](C(=O)N7C[C@H](O)C[C@H]7C(=O)NCc7ccc(-c8scnc8C)cc7)C(C)(C)C)C6)cc5)CC3)n4C(C)C)n2)CC1]

Synthetic Route:
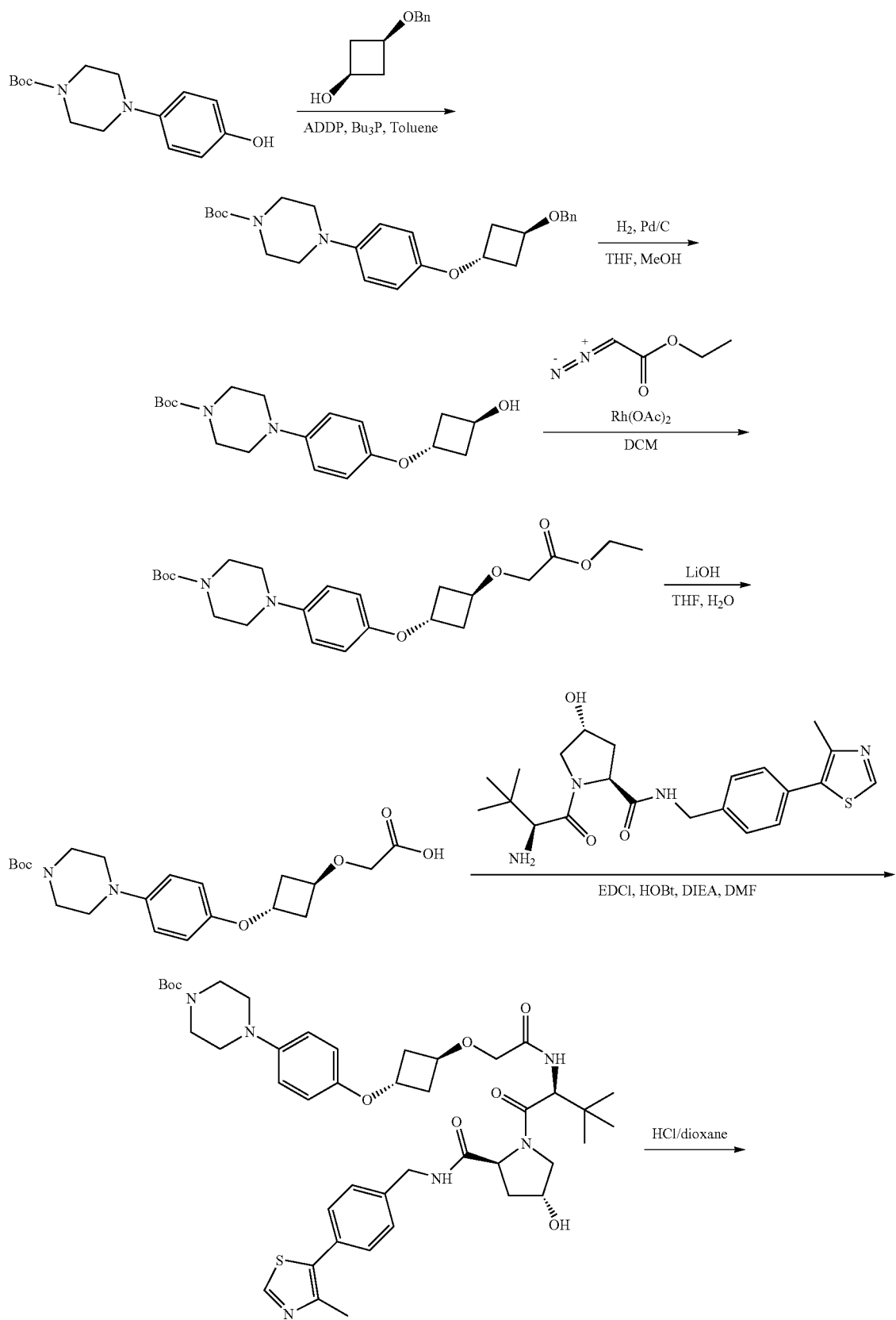

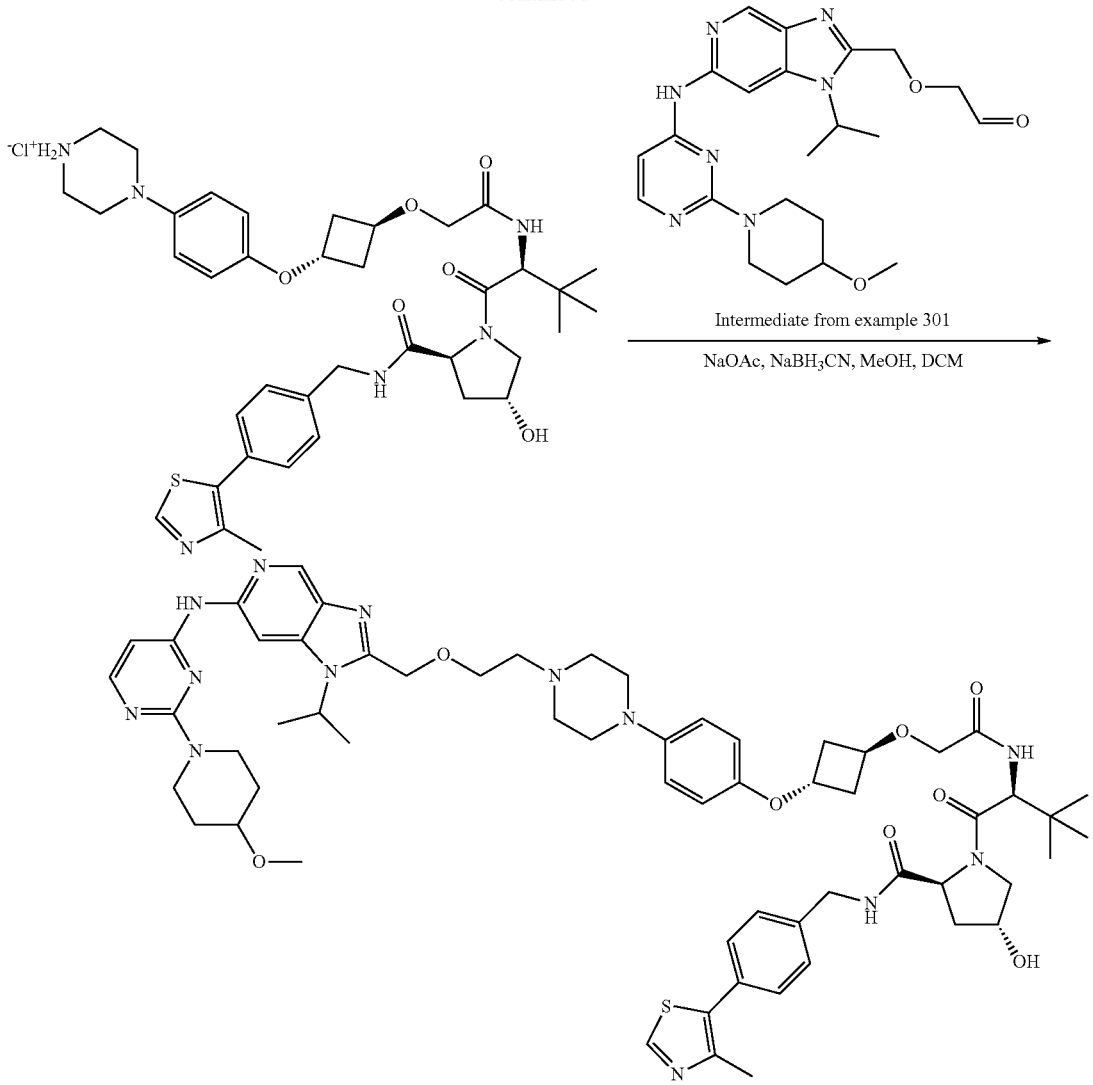

1. Step—Synthesis of tert-butyl 4-(4-((1r,3r)-3-(benzyloxy)cyclobutoxy)phenyl)piperazine-1-carboxylate

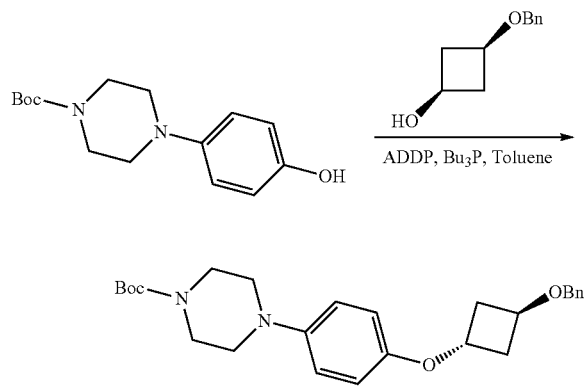

To a solution of tert-butyl 4-(4-hydroxyphenyl)piperazine-1-carboxylate (1.5 g, 5.39 mmol, 1 eq) and cis-3-benzyloxycyclobutanol (1.44 g, 8.08 mmol, 1.5 eq) in toluene (15 mL) was added 1,1'-(azodicarbonyl)dipiperidine (2.72 g, 10.78 mmol, 2 eq) and tributylphosphine (2.18 g, 10.78 mmol, 2.66 mL, 2 eq). The mixture was stirred at 100° C. for 12 hours. LCMS showed the reaction was completed. The reaction mixture was diluted with water (50 mL) and extracted with ethyl acetate (30 mL×2). The combined organic phase was washed with saturated brine (30 mL×2), dried with anhydrous sodium sulfate, filtered and concentrated in vacuum. The residue was purified by preparative High Performance Liquid Chromatography (Formic acid buffered eluent) to afford tert-butyl 4-(4-((1r,3r)-3-(benzyloxy)cyclobutoxy)phenyl)piperazine-1-carboxylate (750 mg, 1.71 mmol, 31% yield) as a brown solid. LCMS: MS (ESI) m/z: 439.2 [M+1]$^+$. $^1$H NMR: (400 MHz, CDCl$_3$) δ: 7.28-7.36 (m, 5H), 6.89 (d, J=7.2 Hz, 2H), 6.73 (d, J=7.2 Hz, 2H), 4.80-4.83 (m, 1H), 4.45 (s, 2H), 4.32-4.35 (m, 1H), 3.57-3.60 (m, 4H), 3.00-3.03 (m, 4H), 2.42-2.49 (m, 4H), 1.49 (s, 9H). Chemical Formula: $C_{26}H_{34}N_2O_4$, Molecular Weight: 438.56

2. Step—Synthesis of tert-butyl 4-(4-((1r,3r)-3-hydroxycyclobutoxy)phenyl)piperazine-1-carboxylate

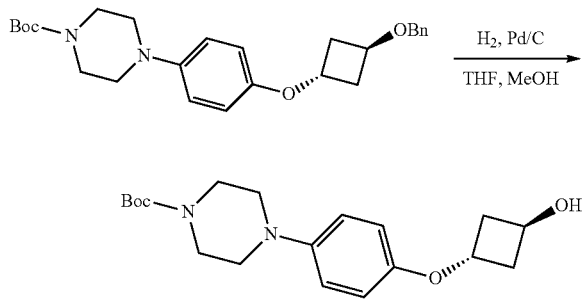 [SMILES: CC(C)(C)OC(=O)N1CCN(c2ccc(O[C@H]3C[C@H](OCc4ccccc4)C3)cc2)CC1 ; CC(C)(C)OC(=O)N1CCN(c2ccc(O[C@H]3C[C@H](O)C3)cc2)CC1]

To a solution of tert-butyl 4-(4-((1r,3r)-3-(benzyloxy)cyclobutoxy)phenyl)piperazine-1-carboxylate (0.9 g, 2.05 mmol, 1 eq) in methanol (20 mL) and tetrahydrofuran (20 mL) was added palladium on activated carbon catalyst (0.2 g, 10% purity), the mixture was degassed and purged with hydrogen several times, then stirred at 25° C. for 12 hours under hydrogen (15 psi) atmosphere. The desired MS was observed by LCMS, thin layer chromatography (petroleum ether/ethyl acetate=3/1) showed one major new spot was detected. The mixture was filtered; the filtrate was concentrated under reduced pressure. The residue was purified by silica gel chromatography (petroleum ether/ethyl acetate=10/1 to 3/1) to afford tert-butyl 4-(4-((1r,3r)-3-hydroxycyclobutoxy)phenyl)piperazine-1-carboxylate (0.62 g, 1.78 mmol, 86% yield) as a light yellow solid. LCMS: MS (ESI) m/z: 349.1 [M+1]$^+$. $^1$H NMR: (400 MHz, CDCl$_3$) δ: 6.86-6.91 (m, 2H), 6.71-6.76 (m, 2H), 4.80-4.88 (m, 1H), 4.58-4.69 (m, 1H), 3.54-3.62 (m, 4H), 2.97-3.05 (m, 4H), 2.46-2.55 (m, 2H), 2.34-2.44 (m, 2H), 1.49 (s, 9H). Chemical Formula: $C_{19}H_{28}N_2O_4$, Molecular Weight: 348.44

3. Step—Synthesis of tert-butyl 4-(4-((1r,3r)-3-(2-ethoxy-2-oxoethoxy)cyclobutoxy)phenyl)piperazine-1-carboxylate

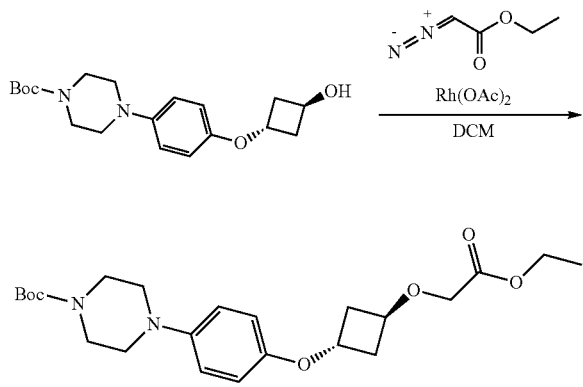

To a solution of tert-butyl 4-(4-((1r,3r)-3-hydroxycyclobutoxy)phenyl)piperazine-1-carboxylate (0.56 g, 1.61 mmol, 1 eq) and ethyl 2-diazoacetate (733 mg, 6.43 mmol, 4 eq) in dichloromethane (20 mL) was added rhodium(II) acetate (18 mg, 0.08 mmol, 0.05 eq), the mixture was stirred at 25° C. for 2 hours. Thin layer chromatography (petroleum ether/ethyl acetate=3/1) showed the starting material was consumed completely and one major new spot was detected. The mixture was concentrated under reduced pressure. The residue was purified by silica gel chromatography (petroleum ether/ethyl acetate=5/1) to afford tert-butyl 4-(4-((1r,3r)-3-(2-ethoxy-2-oxoethoxy)cyclobutoxy)phenyl)piperazine-1-carboxylate (0.42 g, 0.96 mmol, 60% yield) as a light yellow solid. $^1$H NMR: (400 MHz, CDCl$_3$) δ: 6.85-6.92 (m, 2H), 6.67-6.76 (m, 2H), 4.76-4.85 (m, 1H), 4.32-4.37 (m, 1H), 4.24 (q, J=7.2 Hz, 1H), 4.02 (s, 2H), 3.57 (t, J=4.8 Hz, 4H), 3.00 (t, J=4.8 Hz, 4H), 2.40-2.56 (m, 4H), 1.49 (s, 9H), 1.30 (t, J=7.2 Hz, 3H). Chemical Formula: $C_{23}H_{34}N_2O_6$, Molecular Weight: 434.53

4. Step—Synthesis of 2-((1r,3r)-3-(4-(4-(tert-butoxycarbonyl)piperazin-1-yl)phenoxy)cyclobutoxy)acetic acid

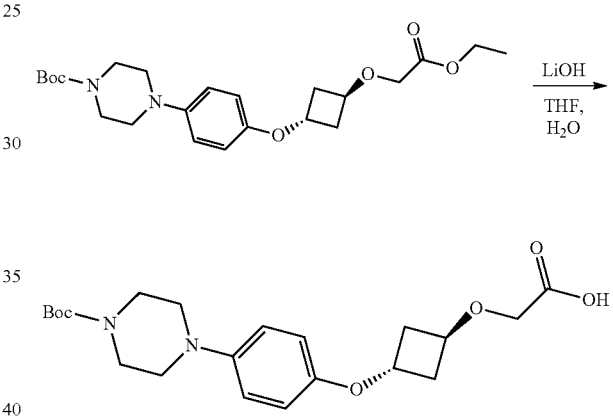

To a solution of tert-butyl 4-(4-((1r,3r)-3-(2-ethoxy-2-oxoethoxy)cyclobutoxy)phenyl)piperazine-1-carboxylate (0.42 g, 0.96 mmol, 1 eq) in tetrahydrofuran (10 mL) and water (1 mL) was added lithium hydroxide (69 mg, 2.90 mmol, 3 eq), the mixture was stirred at 50° C. for 2 hours. Thin layer chromatography (petroleum ether/ethyl acetate=3/1) showed the starting material was consumed completely and the desired MS was detected by LCMS. The mixture was concentrated under reduced pressure, the residue was diluted with water (20 mL), the pH of aqueous phase was adjusted to 6 by hydrochloric acid (1 M), then extracted with ethyl acetate (20 mL×3), the organic layer was dried over anhydrous sodium sulfate, filtered and concentrated under reduced pressure to afford 2-((1r,3r)-3-(4-(4-(tert-butoxycarbonyl)piperazin-1-yl)phenoxy)cyclobutoxy)acetic acid (0.32 g, 0.79 mmol, 81% yield) as a light yellow oil. LCMS: MS (ESI) m/z: 407.1 [M+1]$^+$. $^1$H NMR: (400 MHz, CDCl$_3$) δ: 6.89 (d, J=8.8 Hz, 2H), 6.71 (d, J=8.8 Hz, 2H), 4.69-4.79 (m, 1H), 4.19-4.29 (m, 1H), 3.94 (s, 2H), 3.41-3.45 (m, 4H), 2.74-3.00 (m, 4H), 2.37-2.42 (m, 2H), 2.21-2.29 (m, 2H), 1.41 (s, 9H). Chemical Formula: $C_{21}H_{30}N_2O_6$, Molecular Weight: 406.47

5. Step—Synthesis of tert-butyl 4-[4-[(1s,3r)-3-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]cyclobutoxy]phenyl]piperazine-1-carboxylate

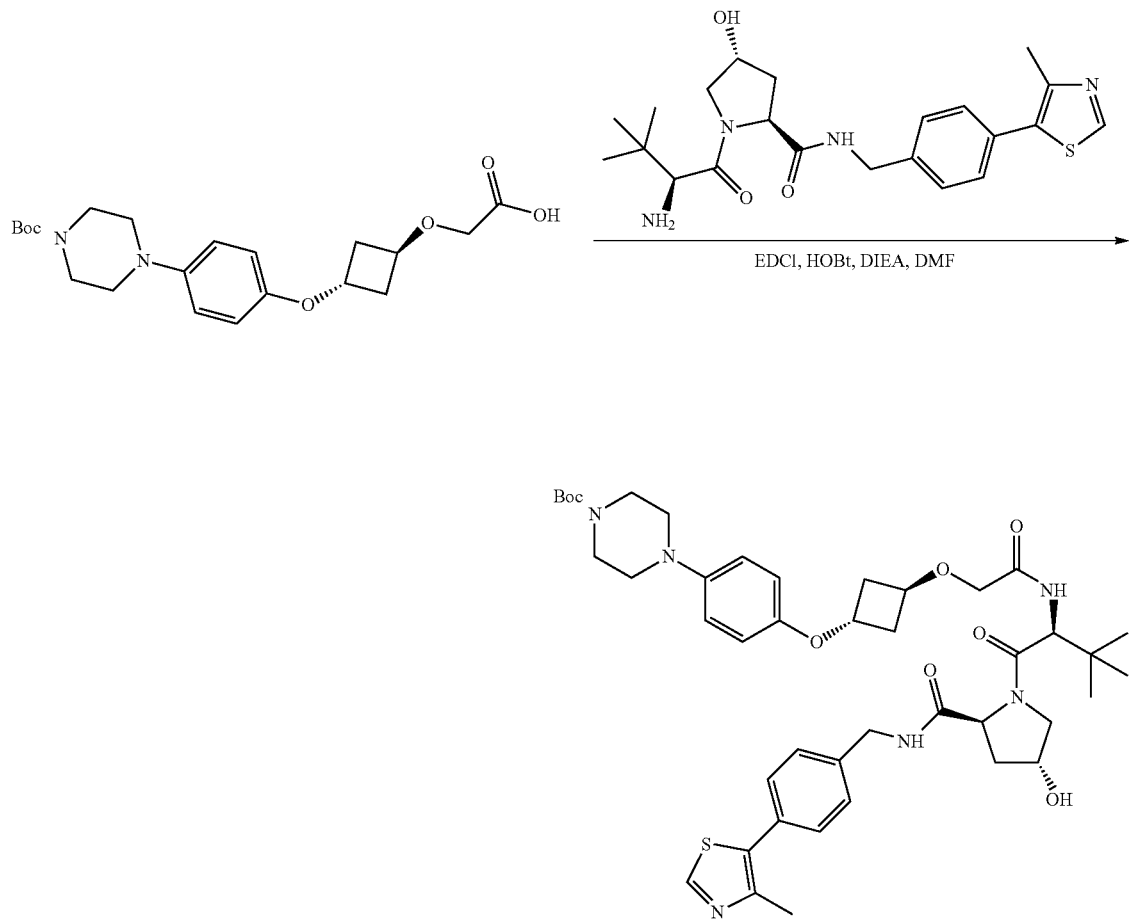

To a solution of 2-[(1r,3r)-3-[4-(4-tert-butoxycarbonylpiperazin-1-yl)phenoxy]cyclobutoxy]acetic acid (0.31 g, 0.76 mmol, 1 eq) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (328 mg, 0.76 mmol, 1 eq) in N,N-dimethylformamide (5 mL) was added 1-hydroxybenzotriazole (154 mg, 1.14 mmol, 1.5 eq), 1-(3-dimethylaminopropyl)-3-ethylcarbodiimide hydrochloride (219 mg, 1.14 mmol, 1.5 eq) and N,N-diisopropylethylamine (295 mg, 2.29 mmol, 0.4 mL, 3 eq), the mixture was stirred at 25° C. for 4 hours. The desired MS was observed by LCMS. The mixture was diluted with water (50 mL), and then extracted with ethyl acetate (30 mL×3), the organic layer was washed with brine (50 mL×2), dried over anhydrous sodium sulfate, filtered and concentrated under reduced pressure. The residue was purified by silica gel chromatography (ethyl acetate/methanol=10/1) to afford tert-butyl 4-[4-[(1 s,3r)-3-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]cyclobutoxy]phenyl]piperazine-1-carboxylate (0.4 g, 0.49 mmol, 64% yield) as a light yellow oil. LCMS: MS (ESI) m/z: 819.3 [M+1]$^+$. $^1$H NMR: (400 MHz, CDCl$_3$) δ: 8.68 (s, 1H), 7.31-7.40 (m, 5H), 6.87 (d, J=8.8 Hz, 2H), 6.72 (d, J=8.8 Hz, 2H), 4.71-4.83 (m, 2H), 4.52-4.56 (m, 2H), 4.24-4.38 (m, 2H), 4.07-4.12 (m, 1H), 3.80-3.90 (m, 2H), 3.56 (t, J=5.2 Hz, 4H), 2.99 (t, J=5.2 Hz, 4H), 2.55-2.59 (m, 1H), 2.52 (s, 3H), 2.42-2.47 (m, 4H), 2.08-2.17 (m, 2H), 2.05 (d, J=4.8 Hz, 1H), 1.48 (s, 9H), 0.95 (s, 9H). Chemical Formula: C$_{43}$H$_{58}$N$_6$O$_8$S, Molecular Weight: 819.02

6. Step—Synthesis of (2S,4R)-1-((S)-3,3-dimethyl-2-(2-(((1r,3s)-3-(4-(piperazin-1-yl)phenoxy)cyclobutoxy)acetamido)butanoyl)-4-hydroxy-N-(4-(4-methylthiazol-5-yl)benzyl)pyrrolidine-2-carboxamide HCl salt

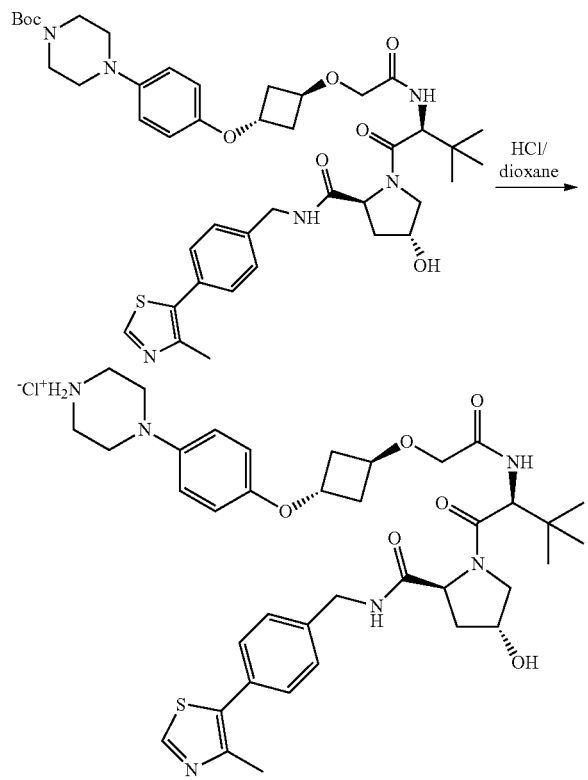

A solution of tert-butyl 4-[4-[(1s,3r)-3-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]cyclobutoxy]phenyl]piperazine-1-carboxylate (0.4 g, 0.49 mmol, 1 eq) in hydrochloric acid/dioxane (4 M, 5 mL) was stirred at 25° C. for 1 hour. The desired MS was observed by LCMS. The mixture was concentrated under reduced pressure. The residue was purified by preparative High Performance Liquid Chromatography (column: Phenomenex Synergi C18 150*25*10 um; mobile phase: [water(0.05% HCl)-ACN]; B %: 15%-42%, 9 min) to afford (2S,4R)-1-((S)-3,3-dimethyl-2-(2-(((1r,3s)-3-(4-(piperazin-1-yl)phenoxy)cyclobutoxy)acetamido)butanoyl)-4-hydroxy-N-(4-(4-methylthiazol-5-yl)benzyl)pyrrolidine-2-carboxamide (200 mg, 0.26 mmol, 54% yield, hydrochloride) as a colorless oil. LCMS: MS (ESI) m/z: 719.1 [M+1]$^+$. $^1$H NMR: (400 MHz, CDCl$_3$) δ: 9.01 (s, 3H), 8.61 (s, 1H), 7.37-7.48 (m, 5H), 6.93 (d, J=7.8 Hz, 2H), 6.75 (d, J=8.8 Hz, 2H), 4.73-4.82 (m, 1H), 4.56 (d, J=9.6 Hz, 1H), 4.33-4.49 (m, 3H), 4.24-4.29 (m, 2H), 3.85-3.92 (m, 2H), 3.59-3.65 (m, 4H), 3.16-3.25 (m, 8H), 2.44 (s, 3H), 2.22-2.30 (m, 2H), 2.03-2.10 (m, 1H), 1.85-1.92 (m, 1H), 0.94 (s, 9H). Chemical Formula: C$_{38}$H$_{51}$ClN$_6$O$_6$S, Molecular Weight: 755.37

7. Step—Synthesis of (2S,4R)-4-hydroxy-1-((S)-2-(2-(((1r,3s)-3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)cyclobutoxy)acetamido)-3,3-dimethylbutanoyl)-N-(4-(4-methylthiazol-5-yl)benzyl)pyrrolidine-2-carboxamide

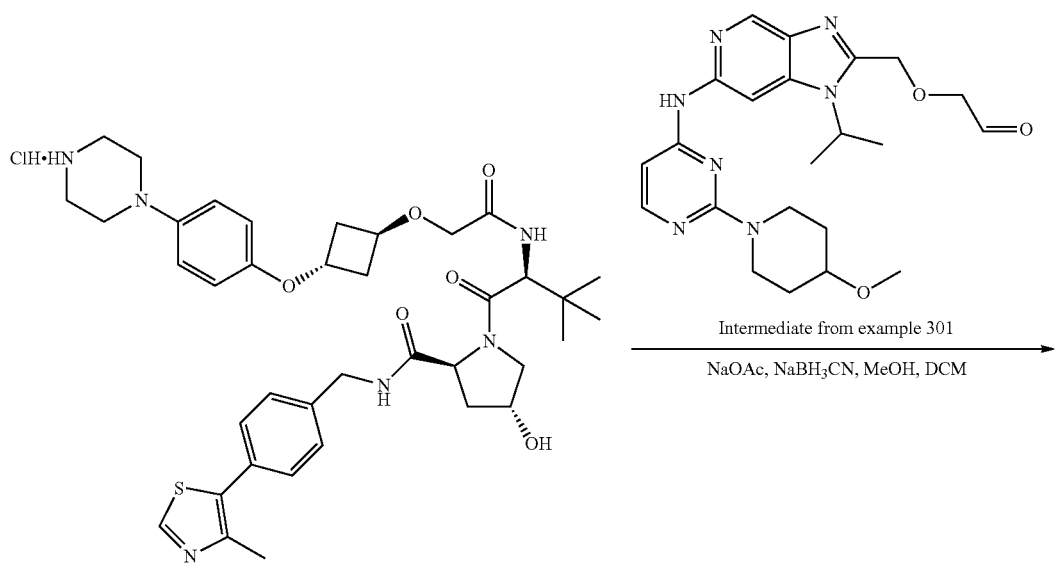

Intermediate from example 301

NaOAc, NaBH$_3$CN, MeOH, DCM

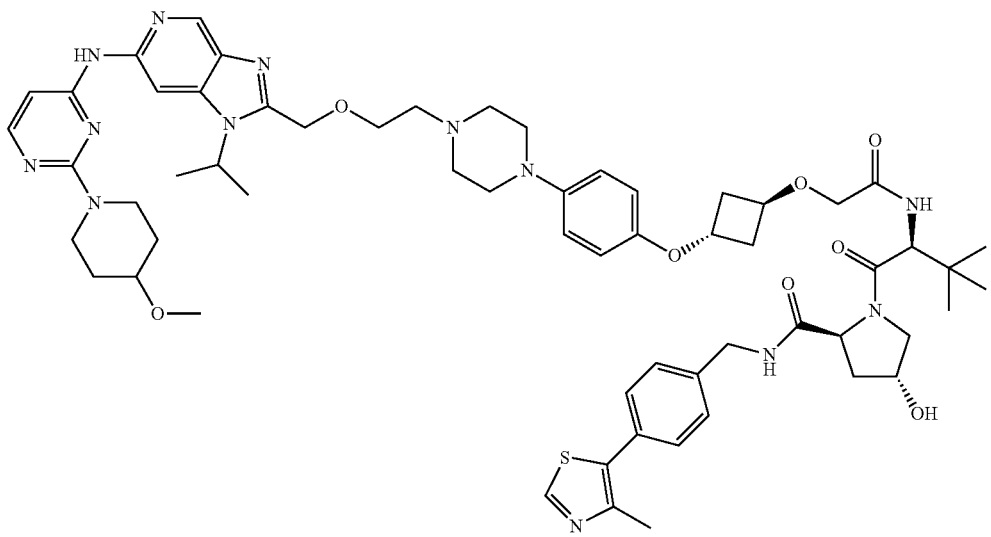

To a solution of (2S,4R)-1-((S)-3,3-dimethyl-2-(2-((1r,3s)-3-(4-(piperazin-1-yl)phenoxy)cyclobutoxy)acetamido)butanoyl)-4-hydroxy-N-(4-(4-methylthiazol-5-yl)benzyl)pyrrolidine-2-carboxamide (50 mg, 0.07 mmol, 1 eq, hydrochloride) in methanol (1 mL) and dichloromethane (1 mL) was added sodium acetate (22 mg, 0.26 mmol, 4 eq), the mixture was stirred at 25° C. for 0.5 hour, then 2-[[1-isopropyl-6-[[2-(4-methoxy-1-piperidyl)pyrimidin-4-yl]amino]imidazo[4,5-c]pyridin-2-yl]methoxy]acetaldehyde (29 mg, 0.07 mmol, 1 eq) was added, the mixture was stirred at 25° C. for 1 hour, then sodium cyanoborohydride (8 mg, 0.13 mmol, 2 eq) was added, the mixture was stirred at 25° C. for 0.5 hour. The desired MS was observed by LCMS. The mixture was concentrated under reduced pressure. The residue was purified by preparative High Performance Liquid Chromatography (column: Boston Green ODS 150*30 5u; mobile phase: [water(0.225% FA)-ACN]; B %: 18%-45%, 10 min) to afford (2S,4R)-4-hydroxy-1-((S)-2-(2-((1r,3s)-3-(4-(4-(2-((1-isopropyl-6-((2-(4-methoxypiperidin-1-yl)pyrimidin-4-yl)amino)-1H-imidazo[4,5-c]pyridin-2-yl)methoxy)ethyl)piperazin-1-yl)phenoxy)cyclobutoxy)acetamido)-3,3-dimethylbutanoyl)-N-(4-(4-methylthiazol-5-yl)benzyl)pyrrolidine-2-carboxamide (29.6 mg, 0.02 mmol, 37% yield, 98.8% purity, formate) as a off-white solid. LCMS: MS (ESI) m/z: 1142.6 [M+1]$^+$. $^1$H NMR: (400 MHz, MeOD) δ: 8.84 (m, 1H), 8.64 (s, 1H), 8.47 (s, 1H), 8.37 (brs, 1H), 7.94 (d, J=6.0 Hz, 1H), 7.38-7.48 (m, 4H), 6.88-6.94 (m, 2H), 6.70-6.76 (m, 2H), 6.36 (d, J=6.0 Hz, 1H), 4.90-4.95 (m, 3H), 4.70-4.82 (m, 2H), 4.46-4.62 (m, 3H), 4.21-4.39 (m, 4H), 3.79-4.02 (m, 6H), 3.43-3.57 (m, 3H), 3.38 (s, 3H), 3.08-3.20 (m, 9H), 2.66 (s, 1H), 2.43-2.55 (m, 5H), 2.32-2.41 (m, 2H), 2.18-2.28 (m, 1H), 2.04-2.15 (m, 1H), 1.93-2.01 (m, 2H), 1.69 (d, J=6.8 Hz, 6H), 1.51-1.62 (m, 2H), 1.04 (m, 9H). Chemical Formula: $C_{60}H_{79}N_{13}O_8S$, Molecular Weight: 1142.42

Synthesis of Example 307

2-(7-((4-(3-(4-(4-(2-(2,6-dioxopiperidin-3-yl)-1,3-dioxoisoindolin-5-yl)piperazin-1-yl)piperidin-1-yl)propoxy)butyl)amino)-1-oxoisoindolin-2-yl)-2-(5-fluoro-2-hydroxyphenyl)-N-(thiazol-2-yl)acetamide

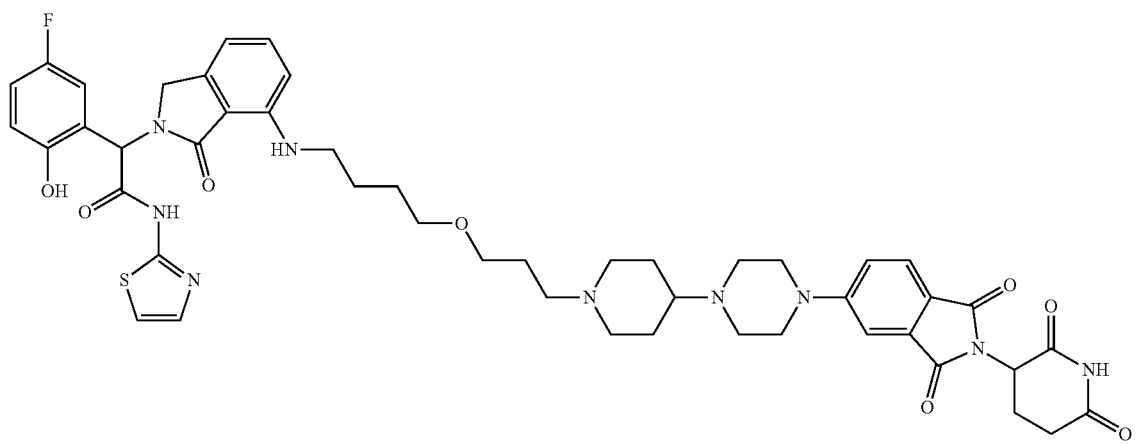 [SMILES: O=C1CCC(N2C(=O)c3ccc(N4CCN(C5CCN(CCCOCCCCNc6cccc7c6C(=O)N(C(C(=O)Nc6nccs6)c6cc(F)ccc6O)C7)CC5)CC4)cc3C2=O)C(=O)N1]

Synthetic Route:
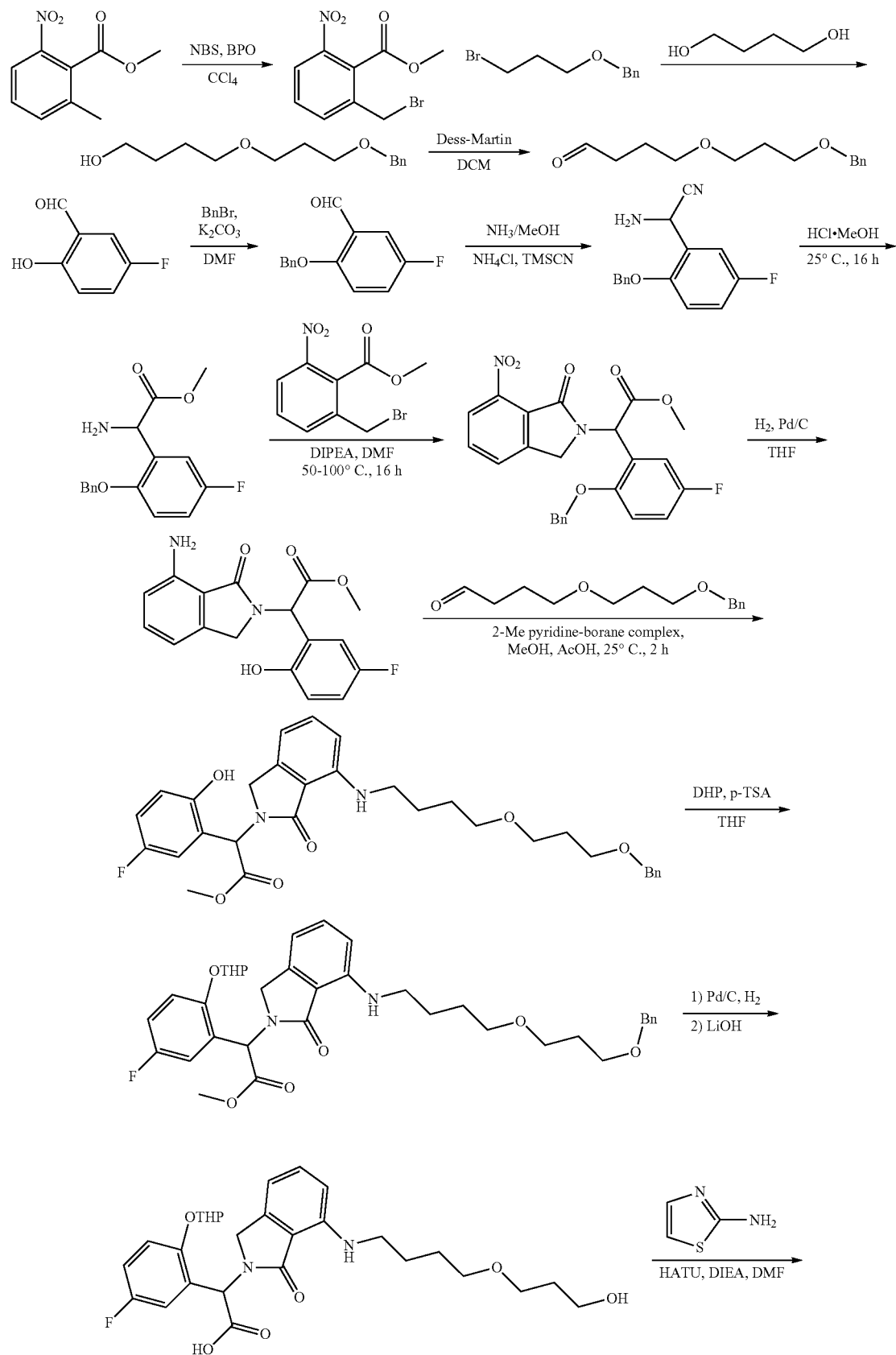

757
758
-continued
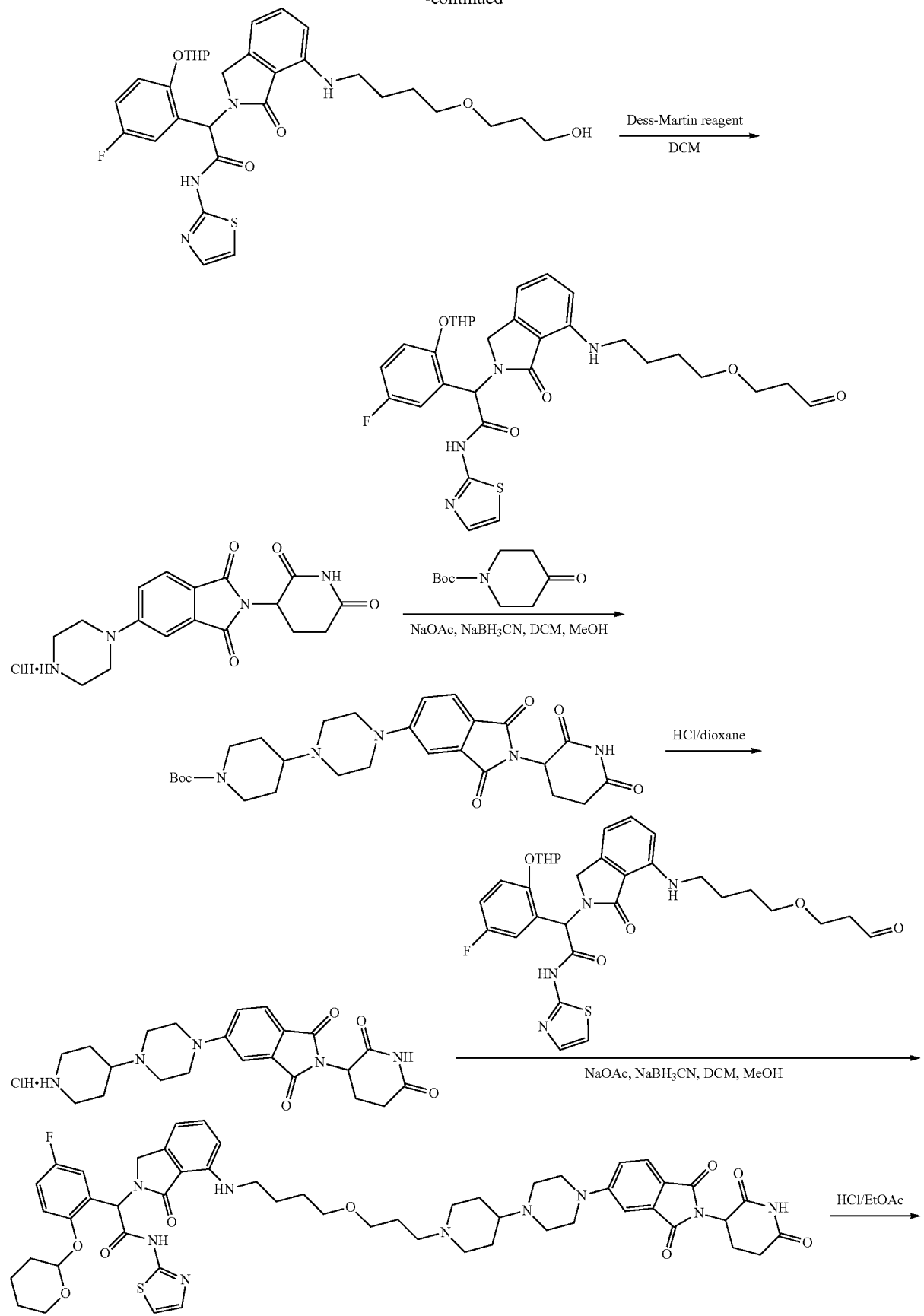

-continued

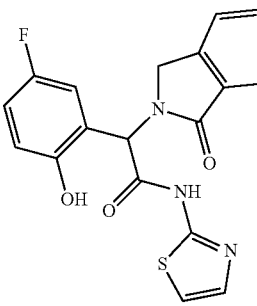

1. Step—Synthetic of methyl 2-(bromomethyl)-6-nitro-benzoate

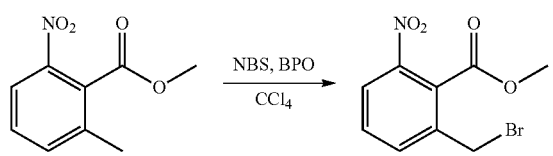

To a solution of methyl 2-methyl-6-nitro-benzoate (2.6 g, 13.32 mmol, 1 eq) in carbon tetrachloride (25 mL) was added benzoyl peroxide (322 mg, 1.33 mmol, 0.1 eq) and NBS (2.49 g, 13.99 mmol, 1.05 eq). The mixture was stirred at 80° C. for 10 hours. Thin layer chromatography (Petroleum ether/Ethyl acetate=10/1) showed the starting material was consumed completely. The reaction mixture was concentrated under reduced pressure. The residue was diluted with water (20 mL), then extracted with ethyl acetate (50 mL×3). The combined organic layers were washed with brine (100 mL×3), dried over anhydrous sodium sulfate, filtered and concentrated under reduced pressure to give a residue. The residue was purified by silica gel chromatography (Petroleum ether/Ethyl acetate=30/1) to give the product methyl 2-(bromomethyl)-6-nitro-benzoate (2.2 g, 8.03 mmol, 60% yield) as a white solid. $^1$H NMR: (400 MHz, CDCl$_3$) δ: 8.08 (d, J=8.0 Hz, 1H), 7.77 (d, J=8.0 Hz, 1H), 7.60 (t, J=8.0 Hz, 1H), 4.58 (s, 2H), 3.99 (s, 3H). Chemical Formula: C$_9$H$_8$BrNO$_4$, Molecular Weight: 274.07

2. Step—Synthesis of 4-(3-benzyloxypropoxy)butan-1-ol

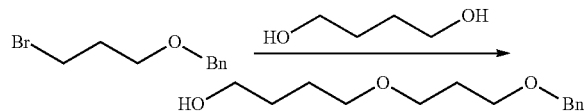

A mixture of butane-1,4-diol (2.36 g, 26.19 mmol, 2.3 mL, 1.2 eq), sodium hydride (960 mg, 24.01 mmol, 60% in mineral oil, 1.1 eq), in tetrahydrofuran (50 mL) was degassed and purged with nitrogen for 3 times and stirred at 25° C. for 2 hours, then to this mixture was added 3-bromopropoxymethylbenzene (5 g, 21.82 mmol, 3.8 mL, 1 eq) and stirred at 70° C. for 10 hours under nitrogen atmosphere. Thin layer chromatography (Petroleum ether/Ethyl acetate=3/1) indicated the starting material was consumed completely and one new spot was formed. The reaction mixture was concentrated under reduced pressure. The residue was diluted with water (40 mL), then extracted with ethyl acetate (100 mL×3). The combined organic layers were washed with brine (200 mL×3), dried over anhydrous sodium sulfate, filtered and concentrated under reduced pressure to give a residue. The residue was purified by silica gel chromatography (Petroleum ether/Ethyl acetate=5/1) to give 4-(3-benzyloxypropoxy)butan-1-ol (1.2 g, 5.04 mmol, 23% yield) as a colorless oil. $^1$H NMR: (400 MHz, CDCl$_3$) δ: 7.30-7.40 (m, 5H), 4.51 (s, 2H), 3.64 (t, J=5.6 Hz, 2H), 3.54-3.57 (m, 4H), 3.47 (t, J=5.6 Hz, 2H), 1.88-1.91 (m, 2H), 1.65-1.70 (m, 4H). Chemical Formula: C$_{14}$H$_{22}$O$_3$, Molecular Weight: 238.32

3. Step—Synthesis of 4-(3-benzyloxypropoxy)butanal

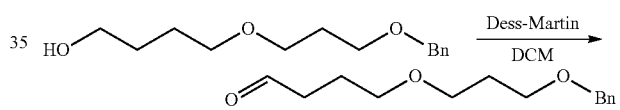

To a solution of 4-(3-benzyloxypropoxy)butan-1-ol (1.2 g, 5.04 mmol, 1 eq) in dichloromethane (50 mL) was added 1,1,1-triacetoxy-1,1-dihydro-1,2-benziodoxol-3(1H)-one (3.20 g, 7.55 mmol, 1.5 eq). The mixture was stirred at 25° C. for 1 hour. Thin layer chromatography (Petroleum ether/Ethyl acetate=3/1) showed the starting material was consumed completely and one new spot was detected. The mixture was filtered, the filtrate was concentrated under reduced pressure to give a residue. The residue was purified by silica gel chromatography (Petroleum ether/Ethyl acetate=5/1) to give 4-(3-benzyloxypropoxy)butanal (0.9 g, 3.81 mmol, 75% yield) as a yellow oil. $^1$H NMR: (400 MHz, CDCl$_3$) δ: 9.76 (s, 1H), 7.28-7.38 (m, 5H), 4.51 (s, 2H), 3.53 (dt, J=16.4, 6.4 Hz, 4H), 3.44 (t, J=6.4 Hz, 2H), 2.47-2.51 (m, 2H), 1.81-1.94 (m, 4H). Chemical Formula: C$_{14}$H$_{20}$O$_3$, Molecular Weight: 236.31

4. Step—Synthesis of 2-(benzyloxy)-5-fluorobenzaldehyde

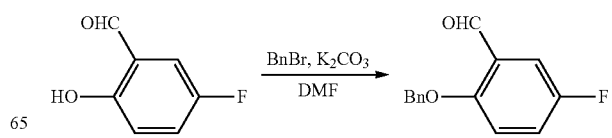

To a solution of 5-fluoro-2-hydroxy-benzaldehyde (25 g, 178.43 mmol, 1 eq) in N,N-dimethylformamide (250 mL) was added potassium carbonate (49.32 g, 356.86 mmol, 2 eq) and bromoethylbenzene (36.62 g, 214.12 mmol, 25.4 mL, 1.2 eq). The mixture was stirred at 50° C. for 2 hours. Thin layer chromatography (Petroleum ether/Ethyl acetate=5/1) indicated the starting material was consumed completely and one new spot was formed. The reaction mixture was concentrated under reduced pressure. The residue was diluted with water (500 mL), then extracted with ethyl acetate (400 mL×3). The combined organic layers were washed with brine (500 mL×3), dried over anhydrous sodium sulfate, filtered and concentrated under reduced pressure to give a residue. The residue was purified by silica gel chromatography (Petroleum ether/Ethyl acetate=5/1) to give the product 2-benzyloxy-5-fluoro-benzaldehyde (40 g, 173.74 mmol, 97% yield) as a white solid. $^1$H NMR: (400 MHz, DMSO-$d_6$) δ: 10.37 (s, 1H), 7.49-7.57 (m, 3H), 7.35-7.44 (m, 5H), 5.29 (s, 2H). Chemical Formula: $C_{14}H_{11}FO_2$, Molecular Weight: 230.07

5. Step—Synthesis of 2-amino-2-(2-benzyloxy-5-fluoro-phenyl)acetonitrile

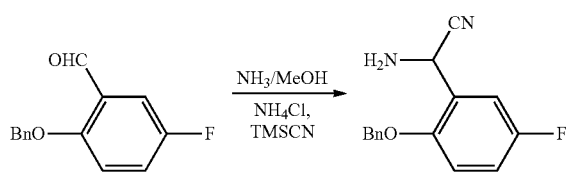

To a solution of ammonium chloride (18.59 g, 347.47 mmol, 2 eq) in methanol (200 mL) was added trimethylsilyl cyanide (25.85 g, 260.60 mmol, 32.6 mL, 1.5 eq) and ammonium hydroxide (1.95 mol, 300 mL, 25% purity, 11.21 eq), after 30 min then this solution was added to a solution of 2-benzyloxy-5-fluoro-benzaldehyde (40 g, 173.74 mmol, 1 eq) in methanol (400 mL). The mixture was stirred at 25° C. for 20 hours. Thin layer chromatography (Petroleum ether/Ethyl acetate=5/1) showed the starting material was consumed completely and one new spot was detected. The reaction mixture was concentrated under reduced pressure. The residue was diluted with water (200 mL), then extracted with ethyl acetate (400 mL×3). The combined organic layers were washed with brine (300 mL×3), dried over anhydrous sodium sulfate, filtered and concentrated under reduced pressure to give a residue 2-amino-2-(2-benzyloxy-5-fluoro-phenyl)acetonitrile (50 g, crude) as a black oil. $^1$H NMR: (400 MHz, DMSO-$d_6$) δ: 7.52 (d, J=7.2 Hz, 2H), 7.31-7.43 (m, 4H), 7.13-7.20 (m, 2H), 5.20 (s, 2H), 5.08 (s, 1H), 2.89 (brs, 2H). Chemical Formula: $C_{15}H_{13}N_2FO$, Molecular Weight: 256.27

6. Step—Synthesis of methyl 2-amino-2-(2-benzyloxy-5-fluoro-phenyl)acetate

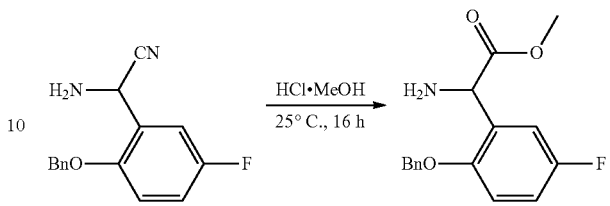

A solution of 2-amino-2-(2-benzyloxy-5-fluoro-phenyl)acetonitrile (50 g, 195.10 mmol, 1 eq) in hydrochloric acid/methanol (4 M, 500 mL) was stirred at 25° C. for 10 hours. LCMS showed the starting material was consumed completely and one main peak with desired m/z was detected. The reaction mixture was concentrated under reduced pressure. The residue was diluted with water (400 mL), the pH of the aqueous phase was adjusted to 7-8 by ammonium hydroxide (25%), then extracted with ethyl acetate (500 mL×3). The combined organic layers were washed with brine (400 mL×3), dried over anhydrous sodium sulfate, filtered and concentrated under reduced pressure to give a residue. The residue was purified by silica gel chromatography (Petroleum ether/Ethyl acetate=5/1) to give the product methyl 2-amino-2-(2-benzyloxy-5-fluoro-phenyl)acetate (45 g, 155.55 mmol, 79% yield) as a brown oil. $^1$H NMR: (400 MHz, DMSO-$d_6$) δ: 7.38-7.46 (m, 4H), 7.31-7.36 (m, 1H), 7.22-7.27 (m, 1H), 7.05-7.10 (m, 2H), 5.10 (s, 2H), 4.71 (s, 1H), 3.52 (s, 3H), 3.34 (brs, 2H). Chemical Formula: $C_{16}H_{16}FNO_3$, Molecular Weight: 289.30.

7. Step—Synthesis of methyl 2-(2-benzyloxy-5-fluoro-phenyl)-2-(7-nitro-1-oxo-isoindolin-2-yl)acetate

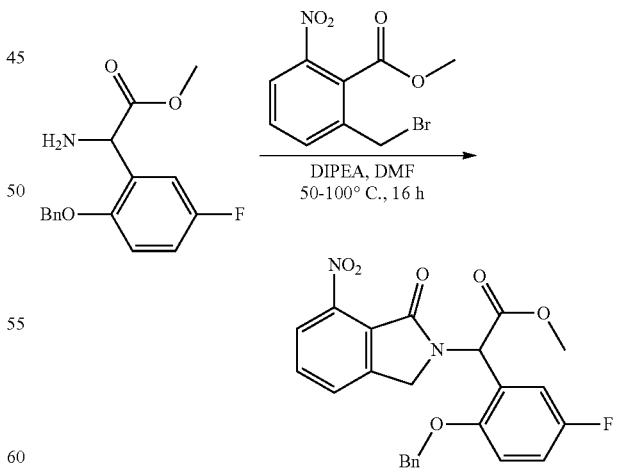

To a solution of methyl 2-amino-2-(2-benzyloxy-5-fluoro-phenyl)acetate (3.2 g, 11.06 mmol, 1 eq) in N,N-dimethylformamide (20 mL) was added diisopropylethylamine (2.86 g, 22.12 mmol, 3.8 mL, 2.0 eq) and methyl 2-(bromomethyl)-6-nitro-benzoate (3.03 g, 11.06 mmol, 1

8. Step—Synthesis of methyl 2-(7-amino-1-oxo-isoindolin-2-yl)-2-(5-fluoro-2-hydroxy-phenyl)acetate

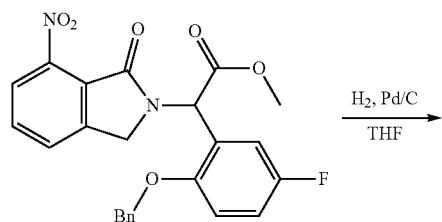

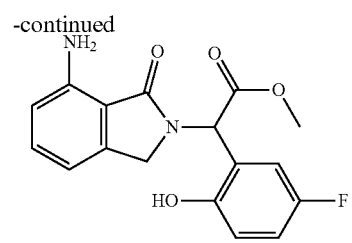

To a solution of methyl 2-(2-benzyloxy-5-fluoro-phenyl)-2-(7-nitro-1-oxo-isoindolin-2-yl)acetate (4 g, 8.88 mmol, 1 eq) in tetrahydrofuran (150 mL) was added palladium on activated carbon catalyst (0.5 g, 10% purity) and purged with hydrogen for 3 times, and then the mixture was stirred at 25° C. for 10 hours under hydrogen (15 Psi). LCMS showed the starting material was consumed completely and one main peak with desired m/z was detected. The reaction mixture was filtered by diatomite and concentrated under reduced pressure to give methyl 2-(7-amino-1-oxo-isoindolin-2-yl)-2-(5-fluoro-2-hydroxy-phenyl) acetate (3.8 g, crude) as a yellow oil, which was used into the next step without further purification. LCMS: MS (ESI) m/z: 331.2 [M+1]$^+$. $^1$H NMR: EW8426-36-P1A, (400 MHz, DMSO-d$_6$) δ: 9.99 (s, 1H), 7.21 (t, J=8.0 Hz, 1H), 6.98-7.10 (m, 2H), 6.83-6.90 (m, 1H), 6.59 (t, J=8.0 Hz, 2H), 6.04-6.07 (m, 3H), 4.49 (d, J=17.6 Hz, 1H), 3.87 (d, J=17.6 Hz, 1H), 3.70 (s, 3H). Chemical Formula: C$_{17}$H$_{15}$FN$_2$O$_4$, Molecular Weight: 330.31.

9. Step—Synthesis of methyl 2-[7-[4-(3-benzyloxy-propoxy)butylamino]-1-oxo-isoindolin-2-yl]-2-(5-fluoro-2-hydroxy-phenyl)acetate

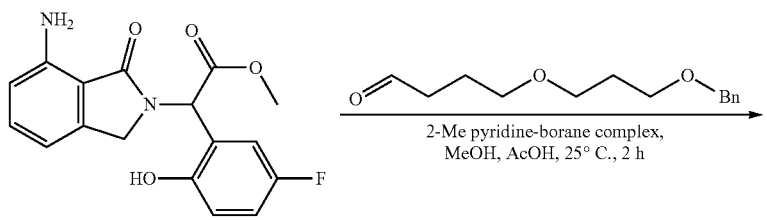

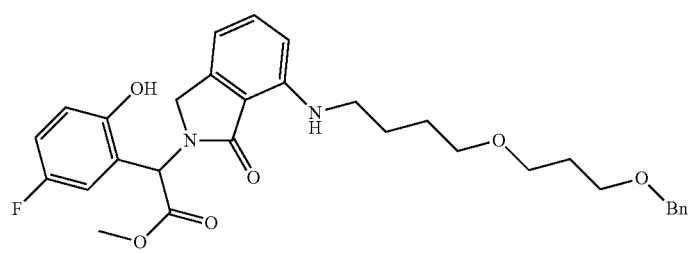

To a solution of methyl 2-(7-amino-1-oxo-isoindolin-2-yl)-2-(5-fluoro-2-hydroxy-phenyl)acetate (1.40 g, 4.23 mmol, 1 eq) in acetic acid (2 mL) and methanol (20 mL) was added 4-(3-benzyloxypropoxy)butanal (1.0 g, 4.23 mmol, 1 eq), the mixture was stirred at 25° C. for 1 hour. Then borane; 2-methylpyridine (905 mg, 8.46 mmol, 2 eq) was added, the mixture was stirred at 25° C. for 1 hour. LCMS showed one main peak with desired m/z was detected. The mixture was concentrated under reduced pressure. The residue was diluted with water (20 mL), then extracted with ethyl acetate (50 mL×3). The combined organic layers were washed with brine (50 mL×3), dried over anhydrous sodium sulfate, filtered and concentrated under reduced pressure to give a residue. The residue was purified by preparative High Performance Liquid Chromatography (Formic acid condition) to give methyl 2-[7-[4-(3-benzyloxypropoxy)butylamino]-1-oxo-isoindolin-2-yl]-2-(5-fluoro-2-hydroxy-phenyl) acetate (1.5 g, 2.72 mmol, 64% yield) as a yellow oil. LCMS: MS (ESI) m/z: 551.2 [M+1]$^{+1}$H NMR: (400 MHz, CDCl$_3$) δ: 10.00 (s, 1H), 7.23-7.37 (m, 6H), 6.99-7.10 (m, 2H), 6.88 (dd, J=8.8, 4.8 Hz, 1H), 6.52-6.66 (m, 3H), 6.04 (s, 1H), 4.50 (d, J=17.6 Hz, 1H), 4.43 (s, 2H), 3.88 (d, J=17.6 Hz, 1H), 3.68 (s, 3H), 3.36-3.49 (m, 6H), 3.06-3.25 (m, 2H), 1.74-1.77 (m, 2H), 1.51-1.63 (m, 4H). Chemical Formula: C$_{31}$H$_{35}$FN$_2$O$_6$, Molecular Weight: 550.62.

10. Step—Synthesis of methyl 2-[7-[4-(3-benzyloxypropoxy)butylamino]-1-oxo-isoindolin-2-yl]-2-(5-fluoro-2-tetrahydropyran-2-yloxy-phenyl)acetate

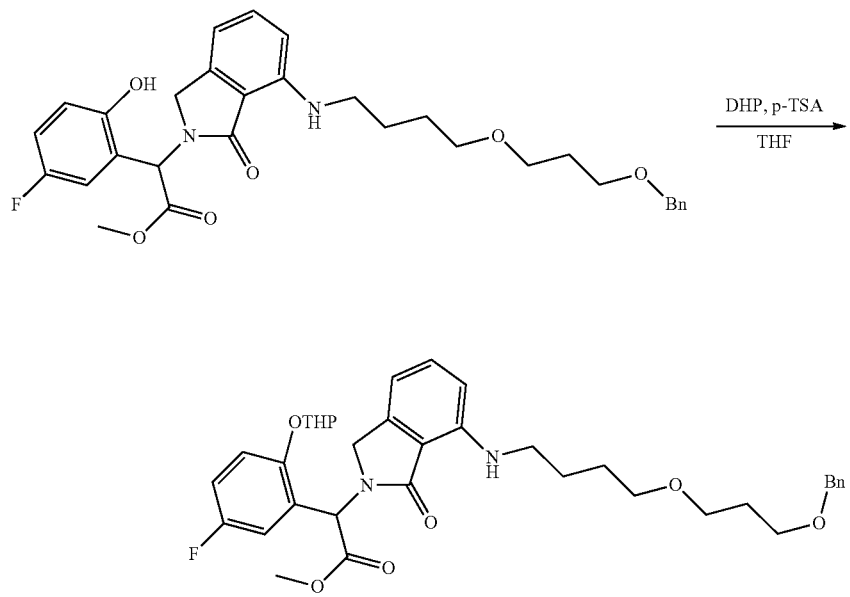

To a solution of methyl 2-[7-[4-(3-benzyloxypropoxy)butylamino]-1-oxo-isoindolin-2-yl]-2-(5-fluoro-2-hydroxy-phenyl)acetate (1.2 g, 2.18 mmol, 1 eq) in tetrahydrofuran (12 mL) was added 3,4-dihydro-2H-pyran (366 mg, 4.36 mmol, 0.4 mL, 2 eq) and p-toluenesulfonic acid (41 mg, 0.22 mmol, 0.1 eq), the mixture was stirred at 25° C. for 4 hours. Thin Layer Chromatography (petroleum ether/ethyl acetate=2/1) showed the starting material remained; one major new spot with lower polarity was detected. The mixture was concentrated under reduced pressure. The residue was purified by silica gel chromatography (petroleum ether/ethyl acetate=10/1 to 3/1) to afford methyl 2-[7-[4-(3-benzyloxypropoxy)butylamino]-1-oxo-isoindolin-2-yl]-2-(5-fluoro-2-tetrahydropyran-2-yloxy-phenyl)acetate (0.8 g, 1.26 mmol, 57% yield) as a light yellow oil. $^1$H NMR: (400 MHz, CDCl$_3$) δ: 7.28-7.34 (m, 4H), 7.11-7.25 (m, 2H), 6.91-7.08 (m, 2H), 6.43-6.74 (m, 3H), 6.31-6.36 (m, 1H), 5.19-5.55 (m, 1H), 4.88-4.96 (m, 1H), 4.57-4.73 (m, 1H), 4.51 (s, 2H), 4.01-4.05 (m, 1H), 3.92-3.95 (m, 1H), 3.76-3.80 (m, 3H), 3.51-3.59 (m, 6H), 3.20-3.29 (m, 2H), 1.86-1.91 (m, 2H), 1.68-1.75 (m, 4H), 1.60-1.65 (m, 4H), 1.53-1.57 (m, 2H). Chemical Formula: C$_{36}$H$_{43}$FN$_2$O$_7$, Molecular Weight: 634.73.

11. Step—Synthesis of methyl 2-(5-fluoro-2-tetra-hydropyran-2-yloxy-phenyl)-2-[7-[4-(3-hydroxy-propoxy)butylamino]-1-oxo-isoindolin-2-yl]acetate

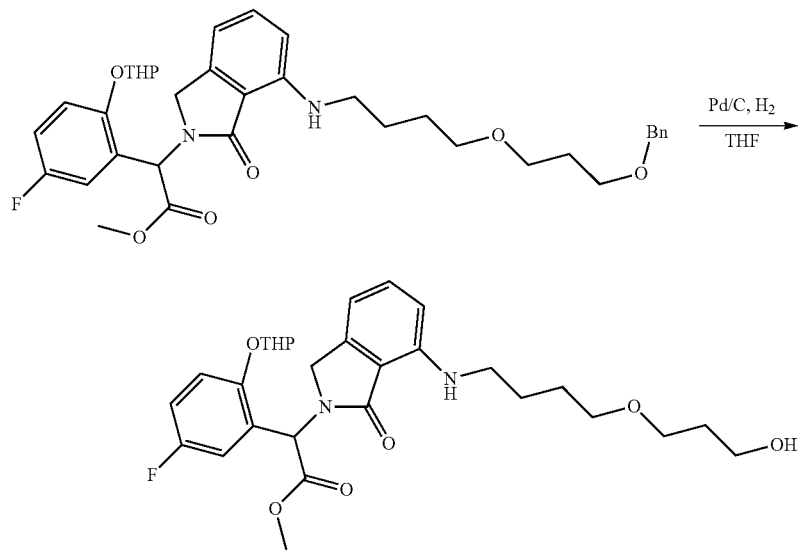

A mixture of methyl 2-[7-[4-(3-benzyloxypropoxy)buty-lamino]-1-oxo-isoindolin-2-yl]-2-(5-fluoro-2-tetrahydropy-ran-2-yloxyphenyl) acetate (0.8 g, 1.26 mmol, 1 eq), palladium on activated carbon catalyst (0.1 g, 10% purity) in tetrahydrofuran (10 mL) was degassed and purged with hydrogen for 3 times, and then the mixture was stirred at 25° C. for 3 hours under hydrogen (15 Psi) atmosphere. Thin layer chromatography (Petroleum ether/Ethyl acetate=1/1) showed the starting material was consumed completely and one new spot was detected. The mixture was filtered, the filtrate was concentrated under reduced pressure to give methyl 2-(5-fluoro-2-tetrahydropyran-2-yloxy-phenyl)-2-[7-[4-(3-hydroxypropoxy)butylamino]-1-oxo-isoindolin-2-yl]acetate (0.5 g, 0.92 mmol, 72% yield) as a yellow oil. $^1$H NMR: (400 MHz, CDCl$_3$) δ: 7.28-7.31 (m, 1H), 7.12-7.23 (m, 1H), 6.97-7.03 (m, 2H), 6.64 (s, 1H), 6.48-6.57 (m, 2H), 6.32 (s, 1H), 5.23-5.51 (m, 1H), 4.54-4.71 (m, 1H), 3.92-4.01 (m, 1H), 3.76-3.81 (m, 5H), 3.66-3.72 (m, 1H), 3.61-3.64 (m, 2H), 3.45-3.57 (m, 3H), 3.24-3.26 (m, 2H), 1.82-1.94 (m, 3H), 1.61-1.80 (m, 9H). Chemical Formula: C$_{29}$H$_{37}$FN$_2$O$_7$, Molecular Weight: 544.61

12. Step—Synthesis of 2-(5-fluoro-2-tetrahydropy-ran-2-yloxy-phenyl)-2-[7-[4-(3-hydroxypropoxy) butylamino]-1-oxo-isoindolin-2-yl]acetic acid

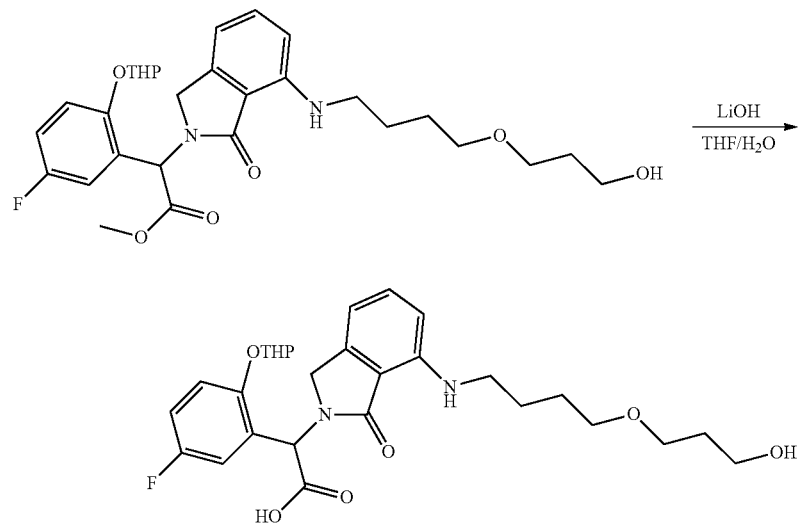

To a solution of methyl 2-(5-fluoro-2-tetrahydropyran-2-yloxy-phenyl)-2-[7-[4-(3-hydroxypropoxy)butylamino]-1-oxoisoindolin-2-yl]acetate (0.5 g, 0.92 mmol, 1 eq) in tetrahydrofuran (10 mL) and water (2 mL) was added lithium hydroxide (24 mg, 1.01 mmol, 1.1 eq). The mixture was stirred at 25° C. for 1 hour. LCMS showed the starting material was consumed completely and one peak with desired mass was detected. The reaction mixture was concentrated under reduced pressure. The residue was diluted with water (10 mL), the pH of the aqueous phase was adjusted to 5-6 by hydrochloric acid (1M), then extracted with ethyl acetate (20 mL×3). The combined organic layers were washed with brine (20 mL×3), dried over anhydrous sodium sulfate, filtered and concentrated under reduced pressure to give a compound 2-(5-fluoro-2-tetrahydropyran-2-yloxy-phenyl)-2-[7-[4-(3-hydroxypropoxy)butylamino]-1-oxo-isoindolin-2-yl]acetic acid (0.35 g, 0.65 mmol, 70% yield, 98% purity) as a yellow oil. LCMS: MS (ESI) m/z: 531.3 [M+1]$^+$ $^1$H NMR: (400 MHz, DMSO-d$_6$) δ: 7.28-7.31 (m, 1H), 7.07-7.24 (m, 3H), 6.59-6.63 (m, 3H), 6.07-6.09 (m, 1H), 5.38-5.67 (m, 1H), 4.50-4.57 (m, 1H), 4.38 (t, J=5.2 Hz, 1H), 3.73-3.95 (m, 2H), 3.40-3.47 (m, 6H), 3.17-3.25 (m, 2H), 1.57-1.81 (m, 12H). Chemical Formula: C$_{28}$H$_{35}$FN$_2$O$_7$, Molecular Weight: 530.59

13. Step—Synthesis of 2-(5-fluoro-2-tetrahydropyran-2-yloxy-phenyl)-2-[7-[4-(3-hydroxypropoxy)butylamino]-1-oxo-isoindolin-2-yl]-Nthiazol-2-yl-acetamide To a solution of 2-(5-fluoro-2-tetrahydropyran-2-yloxy-phenyl)-2-[7-[4-(3-hydroxypropoxy)butylamino]-1-oxo-isoindolin-2-yl]acetic acid (0.35 g, 0.65 mmol, 1 eq) in N,N-dimethylformamide (5 mL) was added diisopropylethylamine (167 mg, 1.29 mmol, 2 eq) and O-(7-azabenzotriazol-1-yl)-N,N,N',N'-tetramethyluronium hexafluorophosphate (491 mg, 1.29 mmol, 2 eq), then thiazol-2-amine (97 mg, 0.97 mmol, 1.5 eq) was added, the mixture was stirred at 25° C. for 1 hour. LCMS showed the starting material was consumed completely and one main peak with desired m/z was detected. The reaction mixture was concentrated under reduced pressure. The residue was diluted with water (20 mL), then extracted with ethyl acetate (20 mL×3). The combined organic layers were washed with brine (20 mL×3), dried over anhydrous sodium sulfate, filtered and concentrated under reduced pressure to give a residue. The residue was purified by preparative Thin layer chromatography (Petroleum ether/Ethyl acetate=1/1, Rf=0.24) to give 2-(5-fluoro-2-tetrahydropyran-2-yloxy-phenyl)-2-[7-[4-(3-hydroxypropoxy)butylamino]-1-oxo-isoindolin-2-yl]-N-thiazol-2-yl-acetamide (0.3 g, 0.49 mmol, 75% yield) as a yellow oil. LCMS: MS (ESI) m/z: 613.1 [M+1]$^+$ $^1$H NMR: (400 MHz, CDCl$_3$) δ. 7.42-7.46 (m, 1H), 7.30-7.35 (m, 1H), 7.12-7.26 (m, 2H), 6.93-7.09 (m, 2H), 6.42-6.71 (m, 4H), 5.17-5.52 (m, 1H), 4.59-4.82 (m, 1H), 4.07-4.15 (m, 1H), 3.77-3.79 (m, 2H), 3.61-3.64 (m, 2H), 3.39-3.54 (m, 4H), 3.25-3.29 (m, 2H), 1.74-1.89 (m, 12H). Chemical Formula: C$_{31}$H$_{37}$FN$_4$O$_6$S, Molecular Weight: 612.71

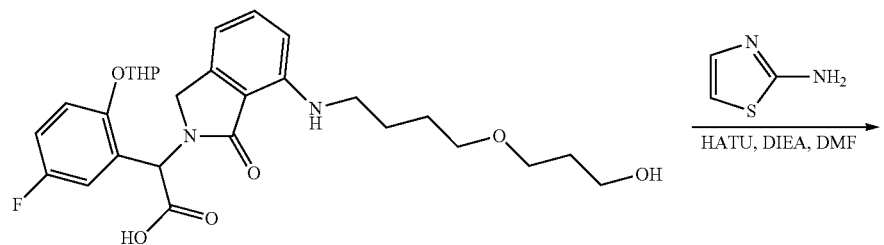

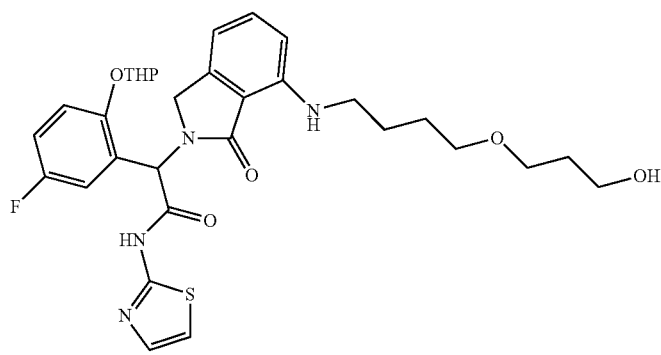

14. Step—Synthesis of 2-(5-fluoro-2-tetrahydropyran-2-yloxy-phenyl)-2-[1-oxo-7-[4-(3-oxopropoxy)butylamino]isoindolin-2-yl]-N-thiazol-2-yl-acetamide

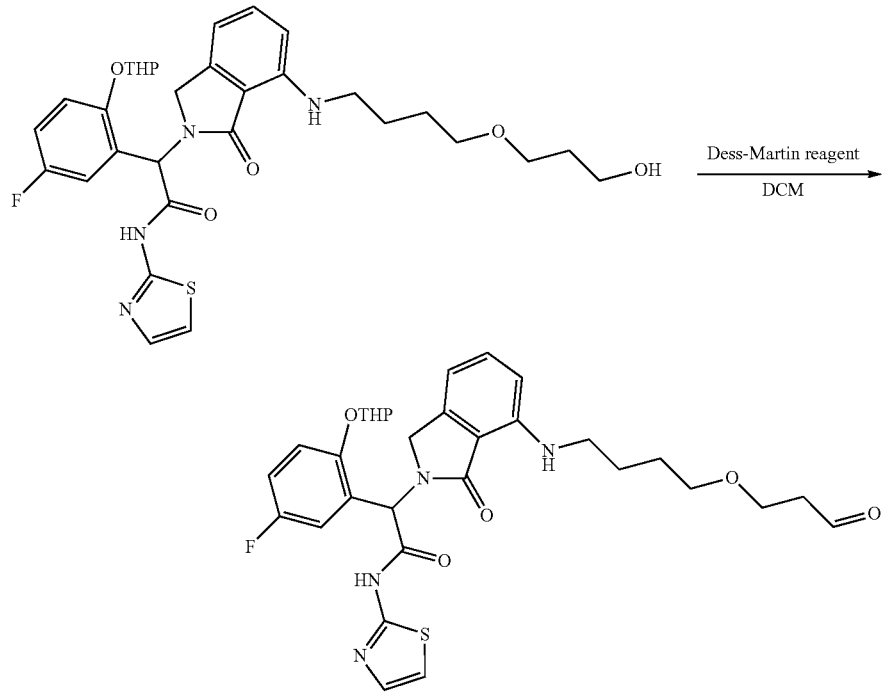

To a solution of 2-(5-fluoro-2-tetrahydropyran-2-yloxy-phenyl)-2-[7-[4-(3-hydroxypropoxy)butylamino]-1-oxo-isoindolin-2-yl]-N-thiazol-2-yl-acetamide (300 mg, 0.49 mmol, 1 eq) in dichloromethane (50 mL) was added 1,1,1-triacetoxy-1,1-dihydro-1,2-benziodoxol-3(1H)-one (311 mg, 0.73 mmol, 1.5 eq). The mixture was stirred at 25° C. for 0.5 hour. High Performance Liquid Chromatography showed the starting material was consumed completely. The reaction mixture was filtered and concentrated under reduced pressure to give a residue. The residue was purified by preparative Thin layer chromatography (Petroleum ether/Ethyl acetate=1/1, Rf=0.14) to give 2-(5-fluoro-2-tetrahydropyran-2-yloxy-phenyl)-2-[1-oxo-7-[4-(3-oxopropoxy)butylamino]isoindolin-2-yl]-N-thiazol-2-yl-acetamide (160 mg, 0.26 mmol, 53% yield) as a yellow solid. $^1$H NMR: (400 MHz, CDCl$_3$) δ: 9.81 (s, 1H), 7.43-7.47 (m, 1H), 7.30-7.35 (m, 1H), 7.13-7.25 (m, 2H), 7.02-7.10 (m, 1H), 6.97-7.00 (m, 1H), 6.53-6.63 (m, 4H), 5.15-5.52 (m, 1H), 4.58-4.84 (m, 1H), 4.04-4.16 (m, 1H), 3.78 (t, J=6.4 Hz, 2H), 3.42-3.50 (m, 4H), 3.24-3.28 (m, 2H), 2.68 (t, J=6.4 Hz, 2H), 1.66-1.85 (m, 10H). Chemical Formula: C$_{31}$H$_{35}$FN$_4$O$_6$S, Molecular Weight: 610.70

15. Step—Synthesis of tert-butyl 4-[4-[2-(2,6-dioxo-3-piperidyl)-1,3-dioxo-isoindolin-5-yl]piperazin-1-yl]piperidine-1-carboxylate

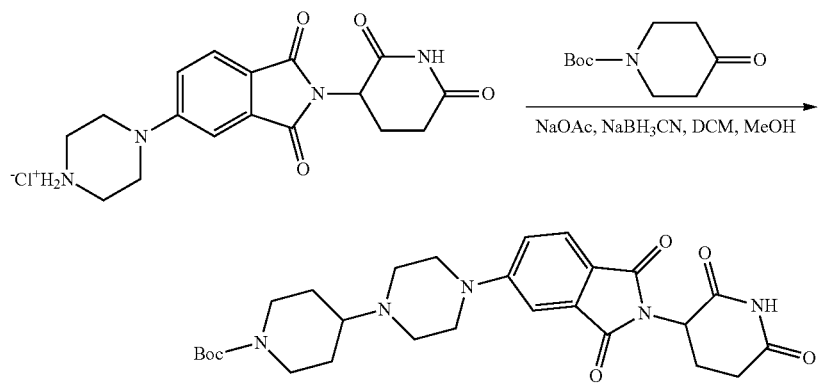

To a solution of 2-(2,6-dioxo-3-piperidyl)-5-piperazin-1-yl-isoindoline-1,3-dione (1 g, 2.64 mmol, 1 eq, hydrochloride) in dichloromethane (5 mL) and methanol (5 mL) was added sodium acetate (866 mg, 10.56 mmol, 4 eq), the mixture was stirred at 25° C. for 1 hour, then tert-butyl 4-oxopiperidine-1-carboxylate (526 mg, 2.64 mmol, 1 eq) was added, the mixture was stirred at 25° C. for 4 hours, then sodium cyanoborohydride (331 mg, 5.28 mmol, 2 eq) was added, the mixture was stirred at 25° C. for another 7 hours. The desired MS was observed by LCMS. The mixture was concentrated under reduced pressure. The residue was purified by preparative High Performance Liquid Chromatography (column: Phenomenex Synergi Max-RP 250*50 mm*10 um; mobile phase: [water(0.225% FA)-ACN]; B %: 20ACN %-50ACN %, 30 min, 87% min) to afford tert-butyl 4-[4-[2-(2,6-dioxo-3-piperidyl)-1,3-dioxo-isoindolin-5-yl]piperazin-1-yl]piperidine-1-carboxylate (0.68 g, 1.29 mmol, 49.01% yield) as a yellow solid. LCMS: MS (ESI) m/z: 526.3 [M+1]$^+$. $^1$H NMR: (400 MHz, MeOD) δ: 8.24 (s, 1H), 7.71 (d, J=8.4 Hz, 1H), 7.40 (d, J=2.4 Hz, 1H), 7.27 (dd, J=8.4, 2.4 Hz, 1H), 5.05-5.10 (m, 1H), 4.15-4.20 (m, 2H), 3.50-3.61 (m, 4H), 2.95-3.05 (m, 4H), 2.63-2.88 (m, 6H), 2.06-2.17 (m, 1H), 1.98-2.05 (m, 2H), 1.47-1.53 (m, 2H), 1.46 (s, 9H). Chemical Formula: C$_{27}$H$_{35}$N$_5$O$_6$, Molecular Weight: 525.60

16. Step—Synthesis of 2-(2,6-dioxo-3-piperidyl)-5-[4-(4-piperidyl) piperazin-1-yl]isoindoline-1,3-dione

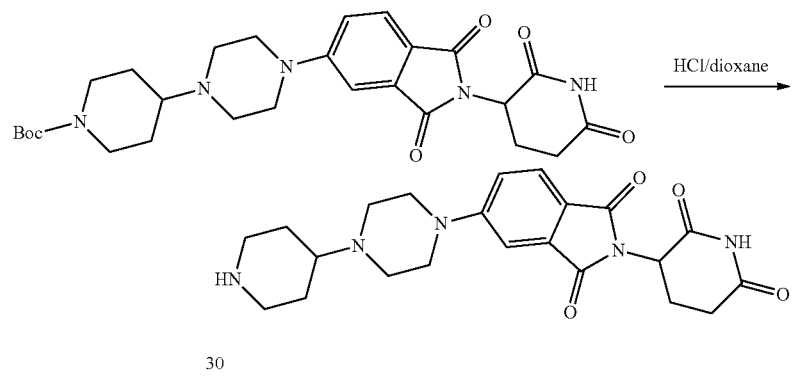

A solution of tert-butyl 4-[4-[2-(2,6-dioxo-3-piperidyl)-1,3-dioxo-isoindolin-5-yl]piperazin-1-yl]piperidine-1-carboxylate (0.54 g, 1.03 mmol, 1 eq) in hydrochloric acid/1,4-dioxane (4 M, 10 mL) was stirred at 25° C. for 1 hour. The desired MS was observed by LCMS. The mixture was concentrated under reduced pressure to afford 2-(2,6-dioxo-3-piperidyl)-5-[4-(4-piperidyl)piperazin-1-yl]isoindoline-1,3-dione (0.48 g, 0.96 mmol, 94% yield, 93% purity, hydrochloride) as a yellow solid. LCMS: MS (ESI) m/z: 426.2 [M+1]$^+$. Chemical Formula: C$_{22}$H$_{27}$N$_5$O$_4$, Molecular Weight: 425.48

17. Step—Synthesis of 2-[7-[4-[3-[4-[4-[2-(2,6-dioxo-3-piperidyl)-1,3-dioxo-isoindolin-5-yl]piperazin-1-yl]-1-piperidyl]propoxy]butylamino]-1-oxo-isoindolin-2-yl]-2-(5-fluoro-2-tetrahydropyran-2-yloxy-phenyl)-N-thiazol-2-yl-acetamide

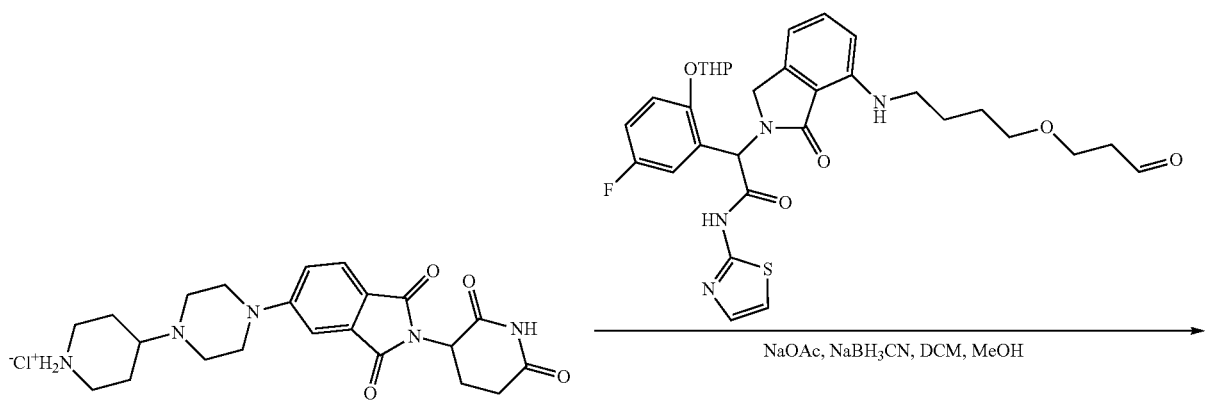

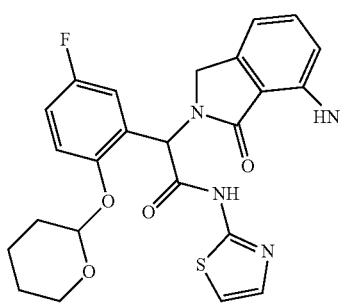
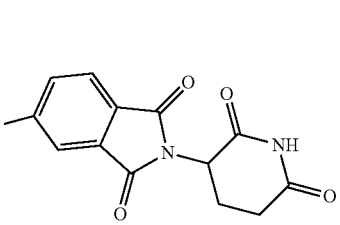

To a solution of 2-(2,6-dioxo-3-piperidyl)-5-[4-(4-piperidyl)piperazin-1-yl]isoindoline-1,3-dione (83 mg, 0.18 mmol, 1 eq, hydrochloride) in dichloromethane (0.5 mL) and methanol (0.5 mL) was added sodium acetate (59 mg, 0.72 mmol, 4 eq), the mixture was stirred at 25° C. for 0.5 hour, then 2-(5-fluoro-2-tetrahydropyran-2-yloxy-phenyl)-2-[1-oxo-7-[4-(3-oxopropoxy)butylamino]isoindolin-2-yl]-N-thiazol-2-yl-acetamide (110 mg, 0.18 mmol, 1 eq) was LCMS: MS (ESI) m/z: 1020.2 [M+1]$^+$. Chemical Formula: $C_{53}H_{62}FN_9O_9S$, Molecular Weight: 1020.18

18. Step—Synthesis of 2-[7-[4-[3-[4-[4-[2-(2,6-dioxo-3-piperidyl)-1,3-dioxo-isoindolin-5-yl]piperazin-1-yl]-1-piperidyl]propoxy]butylamino]-1-oxo-isoindolin-2-yl]-2-(5-fluoro-2-hydroxy-phenyl)-N-thiazol-2-yl-acetamide

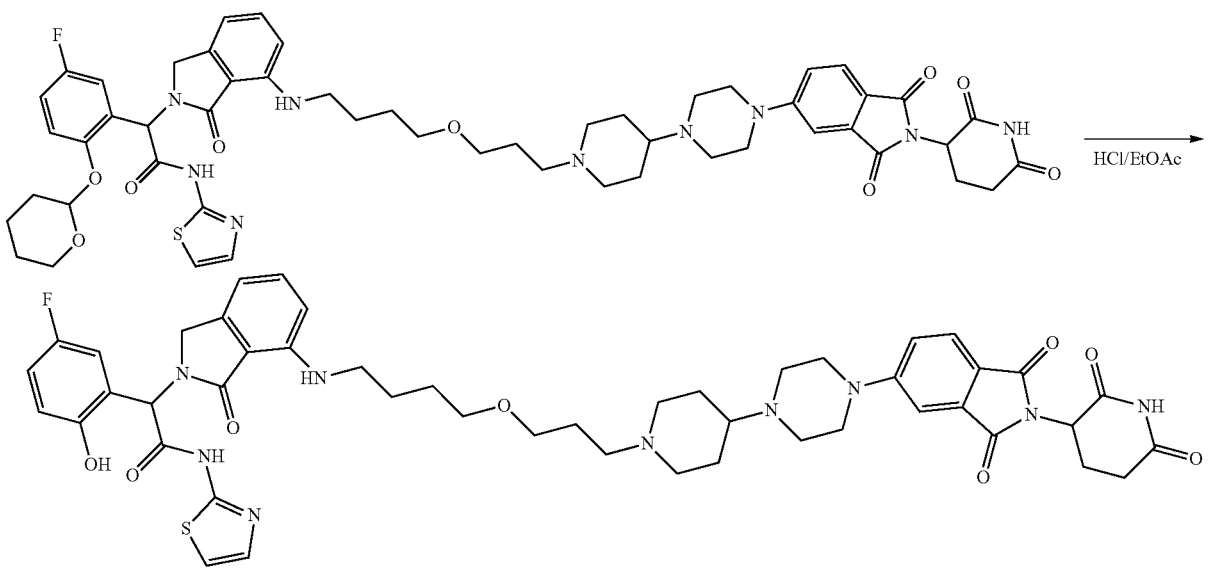

added, the mixture was stirred for 0.5 hour, then sodium cyanoborohydride (22 mg, 0.36 mmol, 2 eq) was added, the mixture was stirred at 25° C. for 0.5 hour. LCMS showed the starting material was consumed completely and one main peak with desired m/z was detected. The reaction mixture was concentrated under reduced pressure. The residue was diluted with water (20 mL), then extracted with ethyl acetate (10 mL×3). The combined organic layers were washed with brine (10 mL×3), dried over anhydrous sodium sulfate, filtered and concentrated under reduced pressure to give a residue. The residue was purified by preparative Thin Layer Chromatography (dichloromethane/methanol=10/1, Rf=0.24) to give 2-[7-[4-[3-[4-[4-[2-(2,6-dioxo-3-piperidyl)-1,3-dioxo-isoindolin-5-yl]piperazin-1-yl]-1-piperidyl]propoxy]butylamino]-1-oxo-isoindolin-2-yl]-2-(5-fluoro-2-tetrahydropyran-2-yloxy-phenyl)-N-thiazol-2-yl-acetamide (40 mg, 0.04 mmol, 21% yield) as a yellow solid.

To a solution of 2-[7-[4-[3-[4-[4-[2-(2,6-dioxo-3-piperidyl)-1,3-dioxo-isoindolin-5-yl]piperazin-1-yl]-1-piperidyl]propoxy]butylamino]-1-oxo-isoindolin-2-yl]-2-(5-fluoro-2-tetrahydropyran-2-yloxy-phenyl)-N-thiazol-2-yl-acetamide (0.04 g, 0.04 mmol, 1 eq) in ethyl acetate (0.5 mL) was added Hydrochloric acid/Ethyl acetate (4 M, 0.5 mL). The mixture was stirred at 25° C. for 0.5 hour. LCMS showed one main peak with desired m/z was detected. The reaction mixture was concentrated under reduced pressure. The residue was purified by preparative High Performance Liquid Chromatography (Formic acid as additive) to afford 2-[7-[4-[3-[4-[4-[2-(2,6-dioxo-3-piperidyl)-1,3-dioxo-isoindolin-5-yl]piperazin-1-yl]-1-piperidyl]propoxy]butylamino]-1-oxo-isoindolin-2-yl]-2-(5-fluoro-2-hydroxy-phenyl)-N-thiazol-2-yl-acetamide (19.2 mg, 0.02 mmol, 49% yield, 98% purity, formate) as a yellow solid. LCMS: MS (ESI) m/z: 936.2 [M+1]$^+$ $^1$H NMR: (400 MHz, CDCl$_3$) δ: 8.64 (s, 1H), 7.70 (d, J=8.8 Hz, 1H), 7.42 (d, J=3.6 Hz, 1H), 7.28-7.33 (m, 1H), 7.10-7.15 (m, 1H), 7.02-7.05 (m, 1H), 6.98 (d, J=3.6 Hz, 1H), 6.90-6.94 (m, 2H), 6.72 (s, 1H), 6.53-6.60 (m, 2H), 6.48 (d, J=8.4 Hz, 1H), 4.86-4.98 (m, 2H), 4.13 (d, J=17.2 Hz, 1H), 3.45-3.55 (m, 5H), 3.35-3.42 (m, 4H), 3.22-3.28 (m, 2H), 3.10-3.18 (m, 2H), 2.67-2.94 (m, 6H), 2.62-2.66 (m, 4H), 2.42-2.47 (m, 2H), 1.95-2.11 (m, 8H), 1.68-1.75 (m, 2H). Chemical Formula: $C_{48}H_{54}FN_9O_8S$, Molecular Weight: 936.06

Synthesis of Example 320

(2S,4R)-1-((S)-18-(tert-butyl)-1-(5-(4-((3-chloro-4-((3-fluorobenzyl)oxy)phenyl)amino)quinazolin-6-yl)furan-2-yl)-16-oxo-2,5,8,11,14-pentaoxa-17-azanonadecan-19-oyl)-4-hydroxy-N-(4-(4-methylthiazol-5-yl)benzyl)pyrrolidine-2-carboxamide

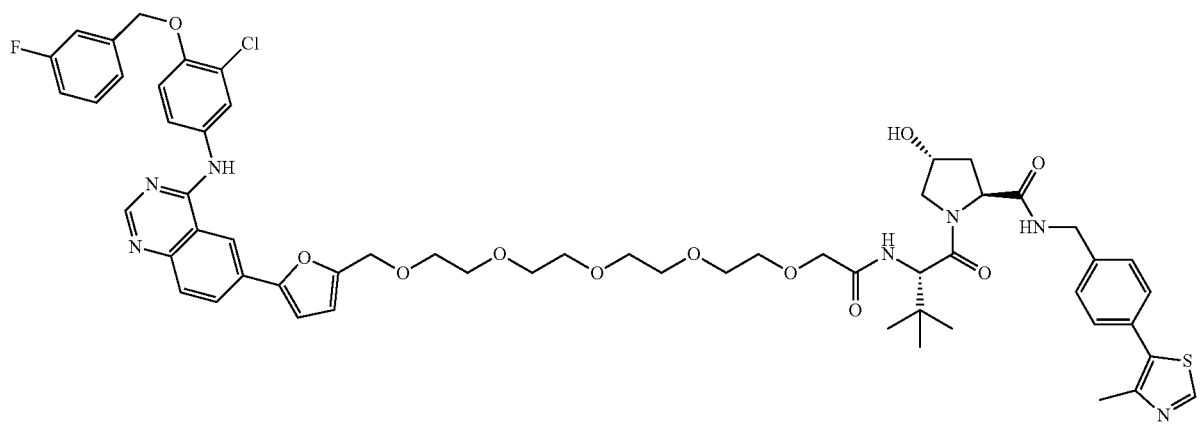 [SMILES: Cc1ncsc1-c1ccc(CNC(=O)[C@@H]2C[C@@H](O)CN2C(=O)[C@@H](NC(=O)COCCOCCOCCOCCOCc2ccc(-c3ccc4ncnc(Nc5ccc(OCc6cccc(F)c6)c(Cl)c5)c4c3)o2)C(C)(C)C)cc1]

Synthetic scheme:

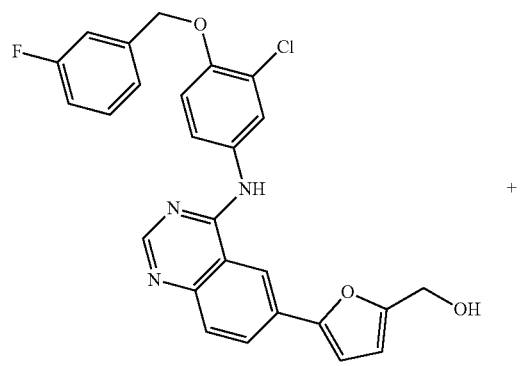

Bioorganic & Medicinal Chemistry Letters 27(7), 1584-1587; 2017

+

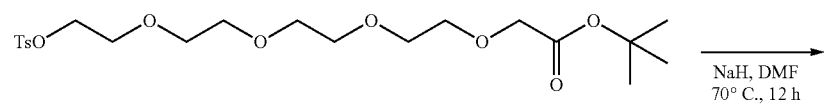

Chemistry of Materials, 28(4), 1170-1178; 2016

NaH, DMF
70° C., 12 h

-continued
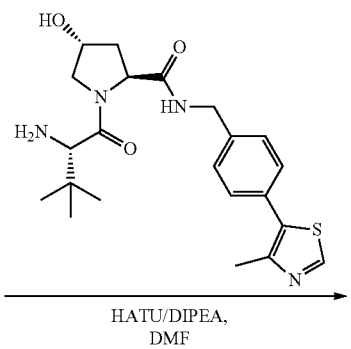
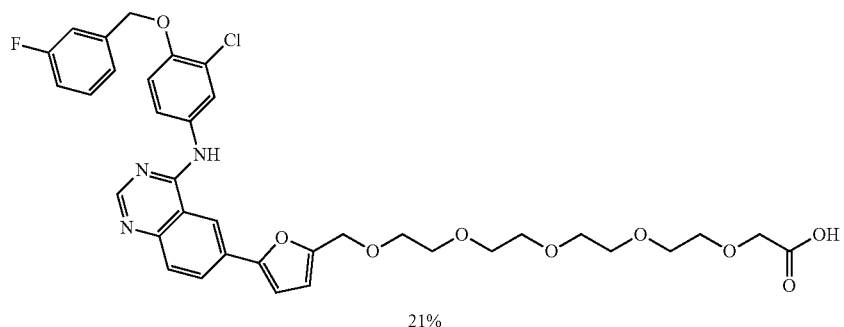
21%
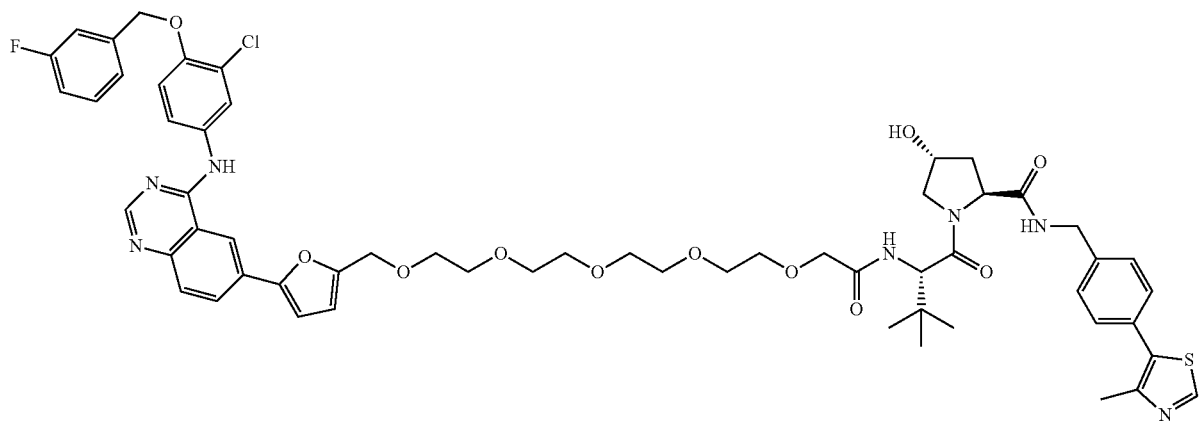
Example 320 (44%)
1. Step—Synthesis of 2-[2-[2-[2-[2-[[5-[4-[3-Chloro-4-[(3-fluorophenyl) methoxy]anilino]quinazolin-6-yl]-2-furyl]methoxy]ethoxy]ethoxy]ethoxy]ethoxy]acetic acid
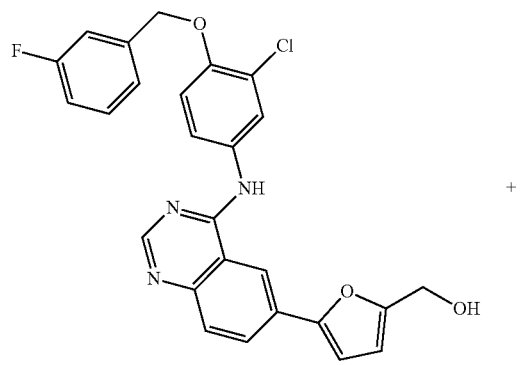
Bioorganic & Medicinal Chemistry Letters
27(7), 1584-1587; 2017

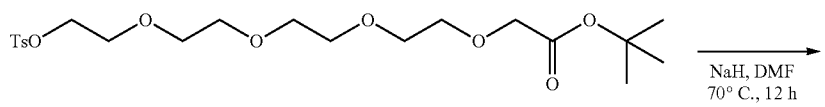

Chemistry of Materials, 28(4), 1170-1178; 2016

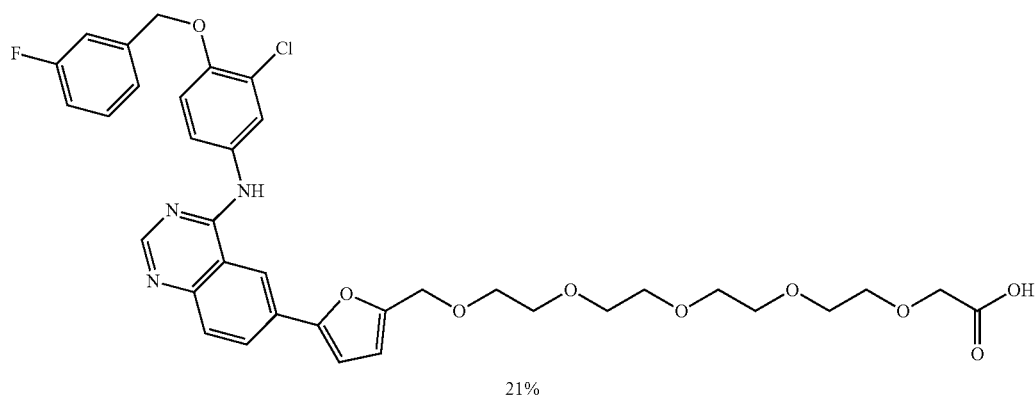

21%

To a solution of [5-[4-[3-chloro-4-[(3-fluorophenyl)methoxy]anilino]quinazolin-6-yl]-2-furyl]methanol (1) (47.59 mg, 0.1 mmol) in N,N-Dimethylformamide (1.5 ml) was added NaH (60%, 13 mg, 0.32 mmol) at room temperature. The reaction mixture was stirred for 30 min. at the same temperature. Then tert-butyl 2-[2-[2-[2-[2-(p-tolylsulfonyloxy)ethoxy]ethoxy]ethoxy]ethoxy]acetate (69.38 mg, 0.15 mmol) was added and the reaction mixture was stirred for 20 min. at room temperature and then stirred for 12 h (overnight) at 70° C. external temperature (oil bath). Solvent was removed under high vacuum and crude product was purified by PTLC (DCM:MeOH:NH$_4$OH, 90:9:1), to give 15 mg of product 2-[2-[2-[2-[2-[[5-[4-[3-Chloro-4-[(3-fluorophenyl)methoxy]anilino]quinazolin-6-yl]-2-furyl]methoxy]ethoxy]ethoxy]ethoxy]ethoxy]acetic acid. $^1$H NMR (400 MHz, DMSO-d6) δ 10.71 (s, 1H), 8.94 (s, 1H), 8.54 (s, 1H), 8.15 (dd, J=8.7, 1.6 Hz, 1H), 8.08 (d, J=2.4 Hz, 1H), 7.84-7.74 (m, 2H), 7.47 (td, J=8.0, 6.0 Hz, 1H), 7.37-7.28 (m, 3H), 7.25 (d, J=9.1 Hz, 1H), 7.18 (td, J=8.7, 2.2 Hz, 1H), 7.11 (d, J=3.3 Hz, 1H), 6.64 (d, J=3.3 Hz, 1H), 5.25 (s, 2H), 4.55 (s, 2H), 3.76 (s, 2H), 3.70-3.39 (m, 16H). LC-MS (ESI); m/z [M+H]+: Calcd. for C$_{36}$H$_{38}$ClFN$_3$O$_9$, 710.2280. Found 710.2403.

2. Step—Synthesis of (2S,4R)-1-((S)-18-(tert-butyl)-1-(5-(4-((3-chloro-4-((3-fluorobenzyl)oxy)phenyl)amino)quinazolin-6-yl)furan-2-yl)-16-oxo-2,5,8,11,14-pentaoxa-17-azanonadecan-19-oyl)-4-hydroxy-N-(4-(4-methylthiazol-5-yl)benzyl)pyrrolidine-2-carboxamide

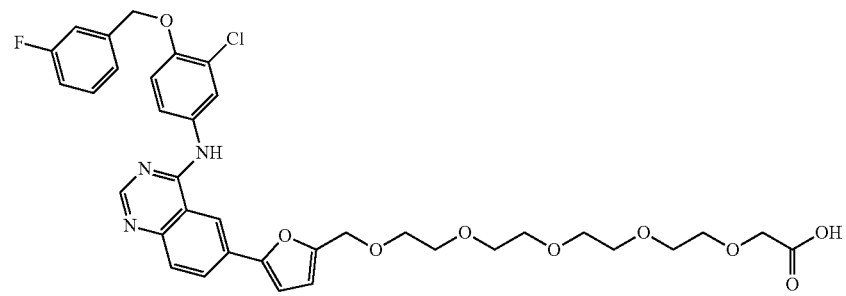

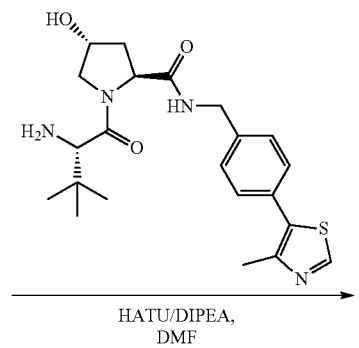

-continued

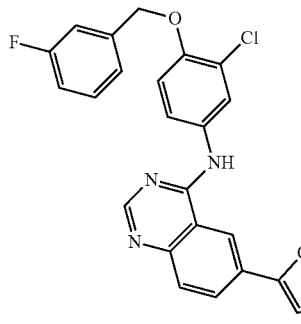

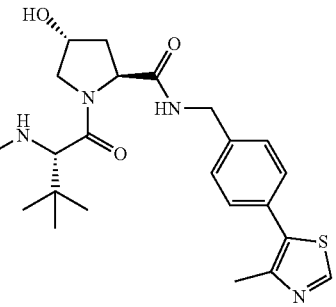

Example 320 (44%)

To a solution of 2-[2-[2-[2-[2-[[5-[4-[3-chloro-4-[(3-fluorophenyl)methoxy]anilino]quinazolin-6-yl]-2-furyl]methoxy]ethoxy]ethoxy]ethoxy]acetic acid (3) (10 mg, 0.01 mmol) and (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (5) (7 mg, 0.015 mmol) in N,N-Dimethylformamide (2 ml) was added N,N-Diisopropylethylamine (0.1 ml, 0.6 mmol) and O-(7-Azabenzotriazol-1-yl)-N,N,N',N'-tetramethyluronium hexafluorophosphate (8 mg, 0.021 mmol) at room temperature. The reaction mixture was stirred for 12 h (overnight) at the same temperature. TLC (DCM:MeOH:NH$_4$OH, 90:9:1) shows no starting materials. Reaction mixture was diluted with AcOEt (20 mL), washed with water (4×15 mL), dried (Na$_2$SO$_4$) and evaporated under vacuum. Crude product was purified by PTLC (DCM:MeOH:NH$_4$OH, 90:9:1), to give 7 mg of product (2S,4R)-1-((S)-18-(tert-butyl)-1-(5-(4-((3-chloro-4-((3-fluorobenzyl)oxy)phenyl)amino)quinazolin-6-yl)furan-2-yl)-16-oxo-2,5,8,11,14-pentaoxa-17-azanonadecan-19-oyl)-4-hydroxy-N-(4-(4-methylthiazol-5-yl)benzyl)pyrrolidine-2-carboxamide (44% yield). 1H NMR (400 MHz, DMSO-d6) δ 9.98 (s, 1H), 8.97 (s, 1H), 8.76 (s, 1H), 8.67-8.57 (m, 1H), 8.55 (s, 1H), 8.17 (d, J=8.5 Hz, 1H), 8.00 (s, 1H), 7.80 (d, J=8.7 Hz, 1H), 7.74 (d, J=10.3 Hz, 1H), 7.64-7.24 (m, 9H), 7.19 (t, J=8.2 Hz, 1H), 7.09 (d, J=2.8 Hz, 1H), 6.65 (d, J=2.7 Hz, 1H), 5.26 (s, 2H), 5.15 (d, 1H), 4.61-4.54 (m, 1H), 4.54 (s, 2H), 4.49-4.15 (m, 6H), 3.94 (s, 2H), 3.73-3.40 (m, 17H), 2.43 (s, 3H), 2.11-2.01 (m, 1H), 1.95-1.84 (m, 1H), 0.93 (s, 9H). LC-MS (ESI); m/z [M+H]$^+$: Calcd. for C$_{58}$H$_{66}$ClFN$_7$O$_{11}$S 1122.4213. Found 1122.0.

Synthesis of Example 349

1-(5-(4-((3-chloro-4-((3-fluorobenzyl)oxy)phenyl)amino)quinazolin-6-yl)furan-2-yl)-N-(2-((2-(2,6-dioxopiperidin-3-yl)-1,3-dioxoisoindolin-4-yl)oxy)ethyl)-2,5,8,11,14-pentaoxahexadecan-16-amide

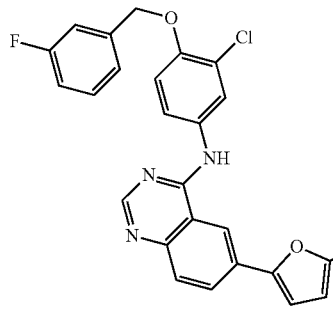

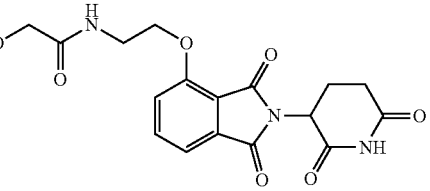

Synthetic scheme:

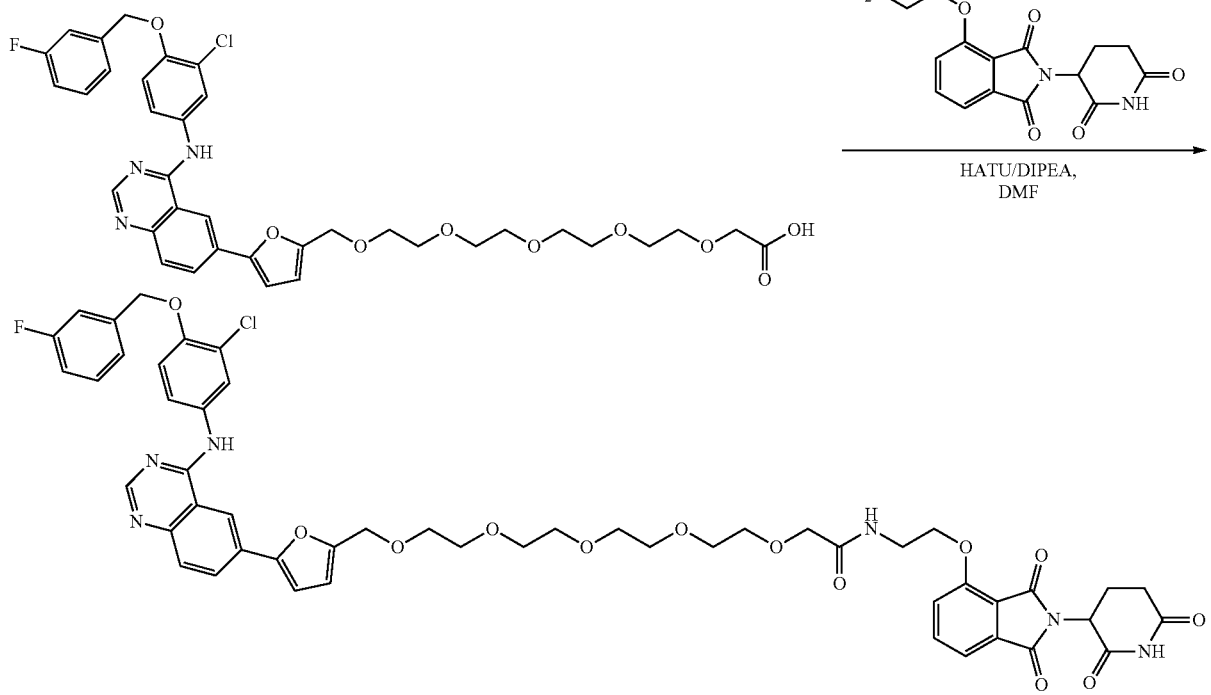

Example 349 (72%)

1. Step—Synthesis of 1-(5-(4-((3-chloro-4-((3-fluorobenzyl)oxy)phenyl)amino)quinazolin-6-yl)furan-2-yl)-N-(2-((2-(2,6-dioxopiperidin-3-yl)-1,3-dioxoisoindolin-4-yl)oxy)ethyl)-2,5,8,11,14-pentaoxahexadecan-16-amide To a solution of 2-[2-[2-[2-[2-[[5-[4-[3-chloro-4-[(3-fluorophenyl)methoxy]anilino]quinazolin-6-yl]-2-furyl]methoxy]ethoxy]ethoxy]ethoxy]ethoxy]acetic acid (7 mg, 0.01 mmol) and 4-(2-aminoethoxy)-2-(2,6-dioxo-3-piperidyl)isoindoline-1,3-dione 2,2,2-trifluoroacetate salt (6.38 mg, 0.01 mmol) in N,N-Dimethylformamide (2 ml) was added N,N-Diisopropylethylamine (0.1 ml, 0.6 mmol) and O-(7-Azabenzotriazol-1-yl)-N,N,N',N'-tetramethyluronium hexafluorophosphate (5.62 mg, 0.01 mmol) at room temperature. The reaction mixture was stirred for 12 h (overnight) at the same temperature. TLC (DCM:MeOH:NH$_4$OH, 90:9:1) shows no starting materials. Reaction mixture was diluted with AcOEt (20 mL), washed with water (4×15 mL), dried (Na$_2$SO$_4$) and evaporated under vacuum. Crude product was purified by PTLC (DCM:MeOH:NH$_4$OH, 90:9:1), to give 7.2 mg of product 1-(5-(4-((3-chloro-4-((3-fluorobenzyl)oxy)phenyl)amino)quinazolin-6-yl)furan-2-yl)-N-(2-((2-(2,6-dioxopiperidin-3-yl)-1,3-dioxoisoindolin-4-yl)oxy)ethyl)-2,5,8,11,14-pentaoxahexadecan-16-amide (72% yield). $^1$H NMR (400 MHz, DMSO-d6) δ 10.27 (s, 1H), 9.14 (s, 1H), 7.93 (s, 1H), 7.72 (s, 1H), 7.34 (dd, J=8.8, 1.7 Hz, 1H), 7.18 (d, J=2.6 Hz, 1H), 7.08-6.87 (m, 4H), 6.76-6.56 (m, 3H), 6.56-6.42 (m, 3H), 6.36 (td, J=8.8, 2.3 Hz, 1H), 6.26 (d, J=3.3 Hz, 1H), 5.82 (d, J=3.3 Hz, 1H), 4.44 (s, 2H), 4.25 (dd, J=12.7, 5.4 Hz, 1H), 3.71 (s, 2H), 3.43 (t, J=6.0 Hz, 2H), 2.87-2.58 (m, 16H), 2.12-1.99 (m, 1H), 1.80-1.60 (m, 2H), 1.23-1.13 (m, 1H). 13C NMR (151 MHz, DMSO-d6) δ 172.76, 169.89, 169.70, 166.76, 165.19, 163.00, 161.39, 157.63, 155.56, 154.37, 152.52, 152.30, 149.79, 149.03, 139.68, 139.63, 136.97, 133.23, 133.03, 130.60, 130.54, 128.82, 128.52, 128.05, 124.42, 123.35, 123.33, 122.62, 121.00, 119.98, 116.70, 116.48, 115.52, 115.32, 114.77, 114.63, 114.25, 114.11, 113.97, 112.24, 107.89, 70.21, 69.86, 69.77, 69.74, 69.72, 69.50, 69.39, 69.38, 68.89, 67.09, 64.17, 48.74, 37.35, 30.94, 22.00. LC-MS (ESI); m/z [M+H]$^+$: Calcd. for C$_{51}$H$_{51}$ClFN$_6$O$_{13}$, 1009.3186. Found 1009.3224.

Synthesis of Examples 350 and 351

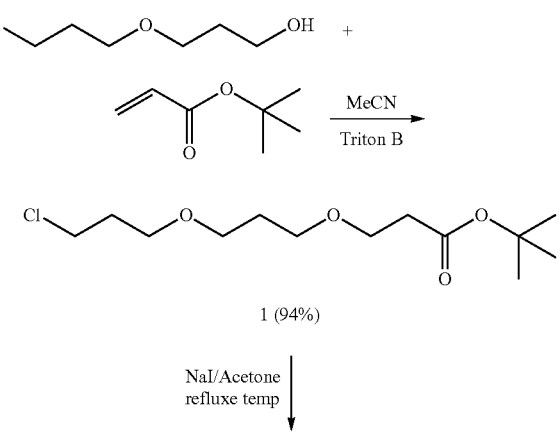

1 (94%)

NaI/Acetone
refluxe temp

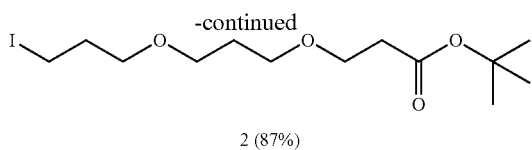

2 (87%)

tert-Butyl 3-(3-(3-chloropropoxy)propoxy)propanoate (1)

3-(3-chloropropoxy)propan-1-ol (66 mg, 0.43 mmol) in acetonitrile (3 mL) was added tert-butyl prop-2-enoate (0.31 ml, 2.16 mmol) followed by Triton B (54 mg, 0.1 mmol, 40% by weight in water). The mixture was stirred at room temperature for 72 hour. The mixture was concentrated under vacuum and crude product was purified by column chromatography (SiO$_2$, gradient Hex:EtOAc, 95:5 to 9:1) to give 115 mg of product (1) as an oil (94% yield). $^1$H NMR (500 MHz, Chloroform-d) δ 3.70-3.59 (m, 4H), 3.59-3.42 (m, 6H), 2.47 (t, J=6.5 Hz, 2H), 2.04-1.96 (m, 2H), 1.82 (p, J=6.3 Hz, 2H), 1.45 (s, 9H). $^{13}$C NMR (151 MHz, Chloroform-d) δ 171.13, 80.63, 68.02, 67.97, 67.27, 66.64, 42.17, 36.50, 32.88, 30.09, 28.25. LC-MS (ESI); m/z [M+Na]$^+$: Calcd. for C$_{13}$H$_{25}$C$_1$O$_4$Na, 303.1339. Found 303.1381.

tert-Butyl 3-(3-(3-iodopropoxy)propoxy)propanoate (2)

To a solution of tert-butyl 3-[3-(3-chloropropoxy) propoxy]propanoate (161 mg, 0.57 mmol) in Acetone (5 ml) was added NaI (429 mg, 2.87 mmol). The reaction mixture was stirred at reflux temperature for 24 h, then the solvent was removed under vacuum and crude product was dissolved in EtOAc (15 mL), washed with water (10 mL), and with an aqueous solution of Na$_2$SO$_3$ (10%, 10 mL). Organic layer was separated, washed with water (10 mL), dried (Na$_2$SO$_4$) and evaporated under vacuum. Crude product was pure by NMR (>98% purity, 186 mg, 87% yield), product (2) was used in the next step without any further purification. $^1$H NMR (400 MHz, Chloroform-d) δ 3.66 (t, J=6.5 Hz, 2H), 3.57-3.40 (m, 6H), 3.27 (t, J=6.8 Hz, 2H), 2.48 (t, J=6.5 Hz, 2H), 2.08-1.99 (m, 2H), 1.82 (p, J=6.4 Hz, 2H), 1.45 (s, 9H). $^{13}$C NMR (151 MHz, Chloroform-d) δ 171.13, 80.64, 70.18, 68.01, 67.98, 66.65, 36.50, 33.57, 30.10, 28.26, 3.72. LC-MS (ESI): m/z [M+Na]$^+$ Calcd. for C$_{13}$H$_{25}$IO$_4$Na: 395.0695, Found: 395.0719.

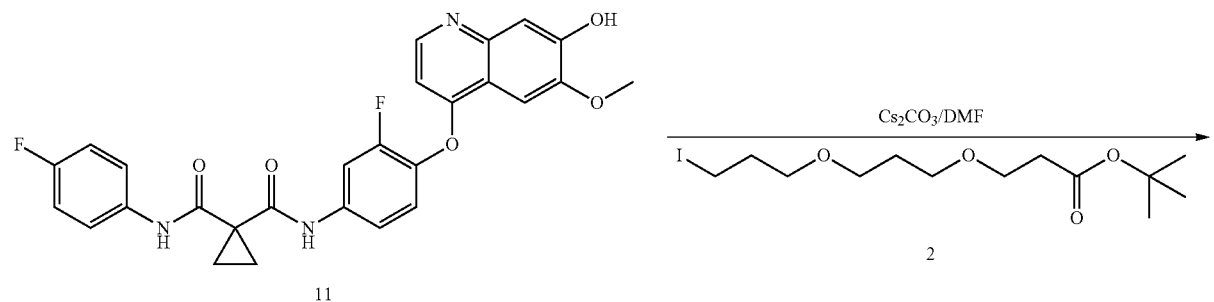

11

2

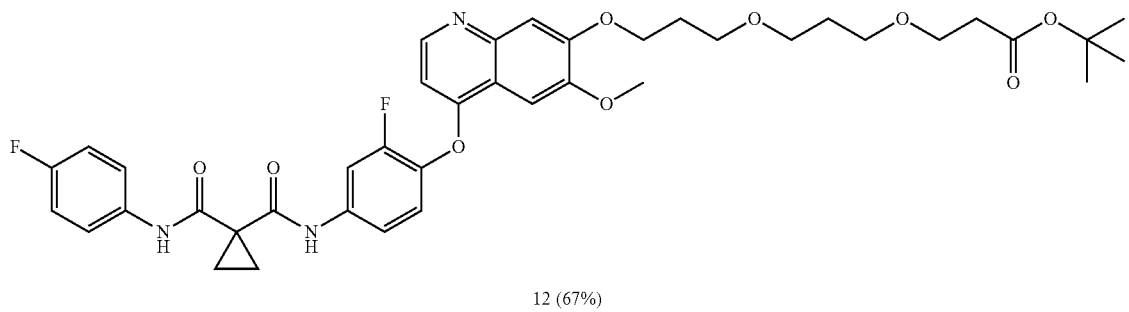

12 (67%)

tert-Butyl 3-(3-(3-((4-(2-fluoro-4-(1-((4-fluorophenyl)carbamoyl)cyclopropane-1-carboxamido)-phenoxy)-6-methoxyquinolin-7-yl)oxy)propoxy)propoxy)propanoate (12)

To a mixture of N1'-[3-fluoro-4-[(7-hydroxy-6-methoxy-4-quinolyl)oxy]phenyl]-N1-(4-fluorophenyl)cyclopropane-1,1-dicarboxamide (11) (15 mg, 0.03 mmol) and tert-butyl 3-[3-(3-iodopropoxy)propoxy]propanoate (2) (16.57 mg, 0.04 mmol) in N,N-Dimethylformamide (1 mL) was added Cs$_2$CO$_3$ (29.01 mg, 0.09 mmol). After stirring at room temperature for 12 hrs (overnight), the reaction mixture was diluted with AcOEt (20 mL) and washed with water (5×10 mL), organic phase was evaporated under vacuum. Crude product was purified by PTLC (DCM:MeOH:NH$_4$OH, 92:7:1) to give 15 mg of product (12) (67% yield). $^1$H NMR (400 MHz, DMSO-d6) δ 10.39 (s, 1H), 10.01 (s, 1H), 8.46 (d, J=5.2 Hz, 1H), 7.90 (d, J=13.2 Hz, 1H), 7.71-7.58 (m, 2H), 7.51 (d, J=7.4 Hz, 2H), 7.46-7.35 (m, 2H), 7.15 (t, J=8.9 Hz, 2H), 6.41 (d, J=5.1 Hz, 1H), 4.21 (t, J=6.2 Hz, 2H), 3.95 (s, 3H), 3.60-3.37 (m, 8H), 2.37 (d, J=12.2 Hz, 2H), 2.04 (p, J=6.4 Hz, 2H), 1.71 (p, J=6.4 Hz, 2H), 1.47 (s, 4H), 1.37 (s, 9H). $^{13}$C NMR (151 MHz, DMSO-d6) δ 170.45, 168.27, 167.87, 159.29, 159.07, 157.48, 154.07, 152.44, 151.89, 149.56, 148.82, 146.37, 138.05, 137.98, 135.70, 135.61, 135.20, 135.19, 123.82, 122.46, 122.41, 116.90, 115.11, 115.09, 114.96, 114.47, 109.04, 108.88, 108.50, 101.95, 99.01, 79.64, 67.07, 66.55, 65.92, 65.45, 55.79, 35.87, 31.93, 29.53, 28.90, 27.76, 27.73, 15.31. LC-MS (ESI): m/z [M+H]$^+$ Calcd. for $C_{40}H_{46}F_2N_3O_9$, 750.3202. Found 750.3509.

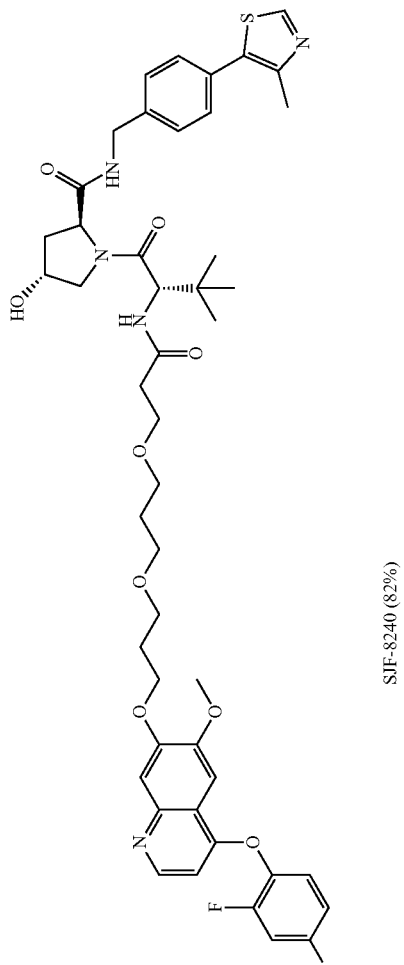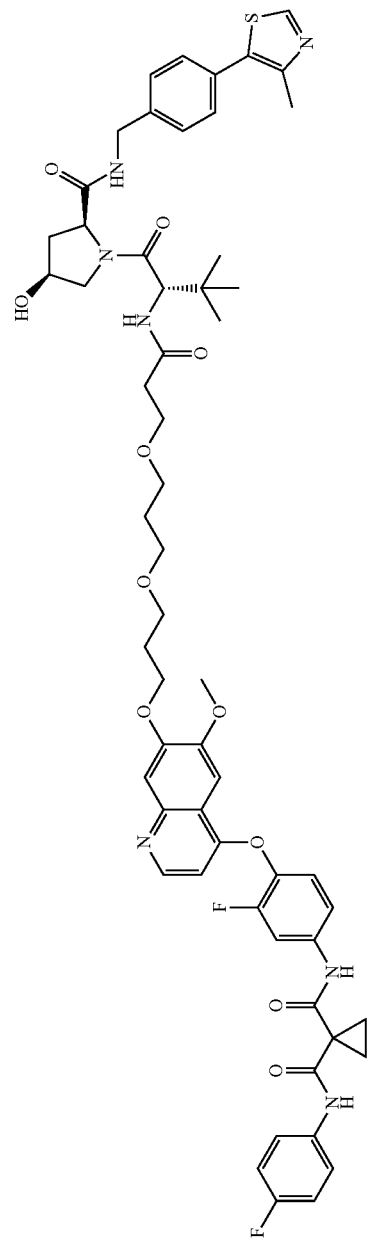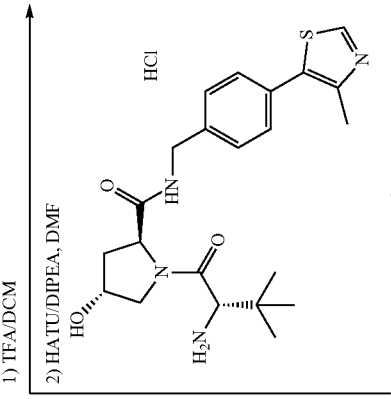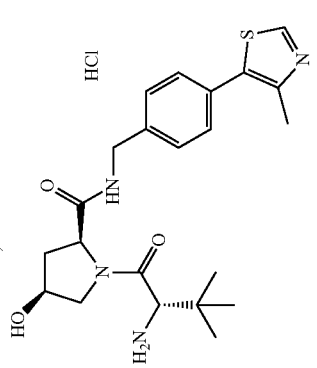

N-(3-Fluoro-4-((7-(3-(3-(3-(((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl) amino)-3-oxopropoxy)propoxy)propoxy)-6-methoxyquinolin-4-yl)oxy)phenyl)-N-(4-fluorophenyl)cyclopropane-1,1-dicarboxamide (SJF-8240, PROTAC 7)

A solution of tert-butyl 3-[3-[3-[[4-[2-fluoro-4-[[1-[(4-fluorophenyl)carbamoyl]cyclopropanecarbonyl]amino]phenoxy]-6-methoxy-7-quinolyl]oxy]propoxy]propoxy]propanoate (12) (15 mg, 0.02 mmol) in a mixture of TFA (1 ml, 13.46 mmol) and Dichloromethane (3 ml) was stirred for 2 h. Then the solvent was removed under vacuum and crude product was dried under high vacuum for 2 h. Crude product was used in the next step without any further purification (13.8 mg, quantitative yield). LC-MS (ESI): m/z [M+H]+ Calcd. for $C_{36}H_{38}F_2N_3O_9$, 694.2576. Found 694.2324. To a solution of crude product from above (13.8 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]-pyrrolidine-2-carboxamide; hydrochloride (8) (11.15 mg, 0.02 mmol) in N,N-Dimethylformamide (2 ml) was added DIPEA (0.17 ml, 0.99 mmol) and HATU (11.35 mg, 0.03 mmol) at room temperature. The reaction mixture was stirred for 12 h (overnight) at the same temperature. Reaction mixture was diluted with ACOEt (20 mL), washed with water (4×15 mL), dried ($Na_2SO_4$) and evaporated under vacuum. Crude product was purified by PTLC (DCM:MeOH:$NH_4OH$, 90:9:1), to give 18 mg of product (82% yield). $^1H$ NMR (500 MHz, DMSO-d6) δ 10.38 (s, 1H), 10.00 (s, 1H), 8.97 (s, 1H), 8.56 (t, J=6.1 Hz, 1H), 8.46 (d, J=5.2 Hz, 1H), 7.96-7.85 (m, 2H), 7.69-7.59 (m, 2H), 7.51 (d, J=8.8 Hz, 2H), 7.45-7.33 (m, 5H), 7.15 (t, J=8.9 Hz, 2H), 6.41 (d, J=5.1 Hz, 1H), 5.12 (d, J=3.3 Hz, 1H), 4.55 (d, J=9.4 Hz, 1H), 4.43 (ddd, J=10.9, 6.7, 3.3 Hz, 2H), 4.27-4.16 (m, 3H), 3.94 (s, 3H), 3.76-3.33 (m, 10H), 2.58-2.51 (m, 1H), 2.43 (s, 3H), 2.35-2.25 (m, 1H), 2.03 (p, J=5.7 Hz, 3H), 1.95-1.83 (m, 1H), 1.72 (p, J=6.4 Hz, 2H), 1.48 (d, J=3.9 Hz, 4H), 0.92 (s, 9H). $^{13}C$ NMR (126 MHz, DMSO-d6) δ 171.89, 169.97, 169.51, 168.26, 167.88, 159.31, 159.22, 157.31, 154.21, 152.26, 151.90, 151.39, 149.56, 148.75, 147.69, 146.29, 139.47, 138.01, 137.94, 135.70, 135.60, 135.17, 135.15, 131.13, 129.61, 128.81, 128.61, 127.40, 123.77, 122.46, 122.40, 116.90, 115.09, 114.92, 114.47, 109.53, 109.05, 108.87, 108.45, 101.94, 99.03, 68.85, 67.16, 67.09, 66.62, 66.54, 65.47, 58.69, 56.35, 56.24, 55.77, 41.64, 37.92, 35.69, 35.36, 31.87, 29.60, 28.89, 26.28, 15.91, 15.31. LC-MS (ESI): m/z [M+H]+ Calcd. for $C_{58}H_{66}F_2N_7O_{11}S$, 1106.4509. Found 1106.4510.

N-(3-Fluoro-4-((7-(3-(3-(3-(((S)-1-((2S,4S)-4-hydroxy-2-((4-(4-methylthiazol-5-yl)benzyl)carbamoyl)-pyrrolidin-1-yl)-3,3-dimethyl-1-oxobutan-2-yl) amino)-3-oxopropoxy)propoxy)propoxy)-6-methoxyquinolin-4-yl)oxy)phenyl)-N-(4-fluorophenyl)cyclopropane-1,1-dicarboxamide (SJF-8240-epimer, PROTAC 8)

It was prepared from (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (10) (10.42 mg, 0.022 mmol) and following the same procedure than above. Crude product was purified by PTLC (DCM:MEOH:$NH_4OH$, 90:9:1), to give 9.7 mg of the expected product (47% yield). $^1H$ NMR (500 MHz, DMSO-d6) δ 10.38 (s, 1H), 10.00 (s, 1H), 8.97 (s, 1H), 8.63 (t, J=6.0 Hz, 1H), 8.46 (d, J=5.2 Hz, 1H), 7.90 (d, J=9.7 Hz, 2H), 7.71-7.57 (m, 2H), 7.51 (d, J=8.7 Hz, 2H), 7.44-7.28 (m, 5H), 7.15 (t, J=8.9 Hz, 2H), 6.41 (d, J=5.1 Hz, 1H), 5.43 (d, J=7.2 Hz, 1H), 4.56-4.38 (m, 2H), 4.36 (dd, J=8.6, 6.1 Hz, 1H), 4.32-4.13 (m, 4H), 3.94 (s, 3H), 3.97-3.82 (m, 1H), 3.64-3.46 (m, 4H), 3.48-3.35 (m, 4H), 2.57-2.45 (m, 2H), 2.43 (s, 3H), 2.36-2.26 (m, 2H), 2.03 (p, J=6.3 Hz, 2H), 1.73 (dp, J=13.0, 6.2 Hz, 3H), 1.55-1.38 (m, 4H), 0.93 (s, 9H). $^{13}C$ NMR (126 MHz, DMSO-d6) δ 171.89, 169.97, 169.51, 168.26, 167.88, 159.31, 159.22, 157.31, 154.21, 152.26, 151.90, 151.39, 149.56, 148.75, 147.69, 146.29, 139.47, 138.01, 137.94, 135.70, 135.60, 135.17, 135.15, 131.13, 129.61, 128.81, 128.61, 127.40, 123.77, 122.46, 122.40, 116.90, 115.09, 114.92, 114.47, 109.53, 109.05, 108.87, 108.45, 101.94, 99.03, 68.85, 67.16, 67.09, 66.62, 66.54, 65.47, 58.69, 56.35, 56.24, 55.77, 41.64, 37.92, 35.69, 35.36, 31.87, 29.60, 28.89, 26.28, 15.91, 15.31. LC-MS (ESI): m/z [M+H]+ Calcd. for $C_{58}H_{66}F_2N_7O_{11}S$, 1106.4509. Found 1106.5096.

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

EXAMPLES

With reference to the appended figures and accompanying descriptions.

Figures 1A, 1B:
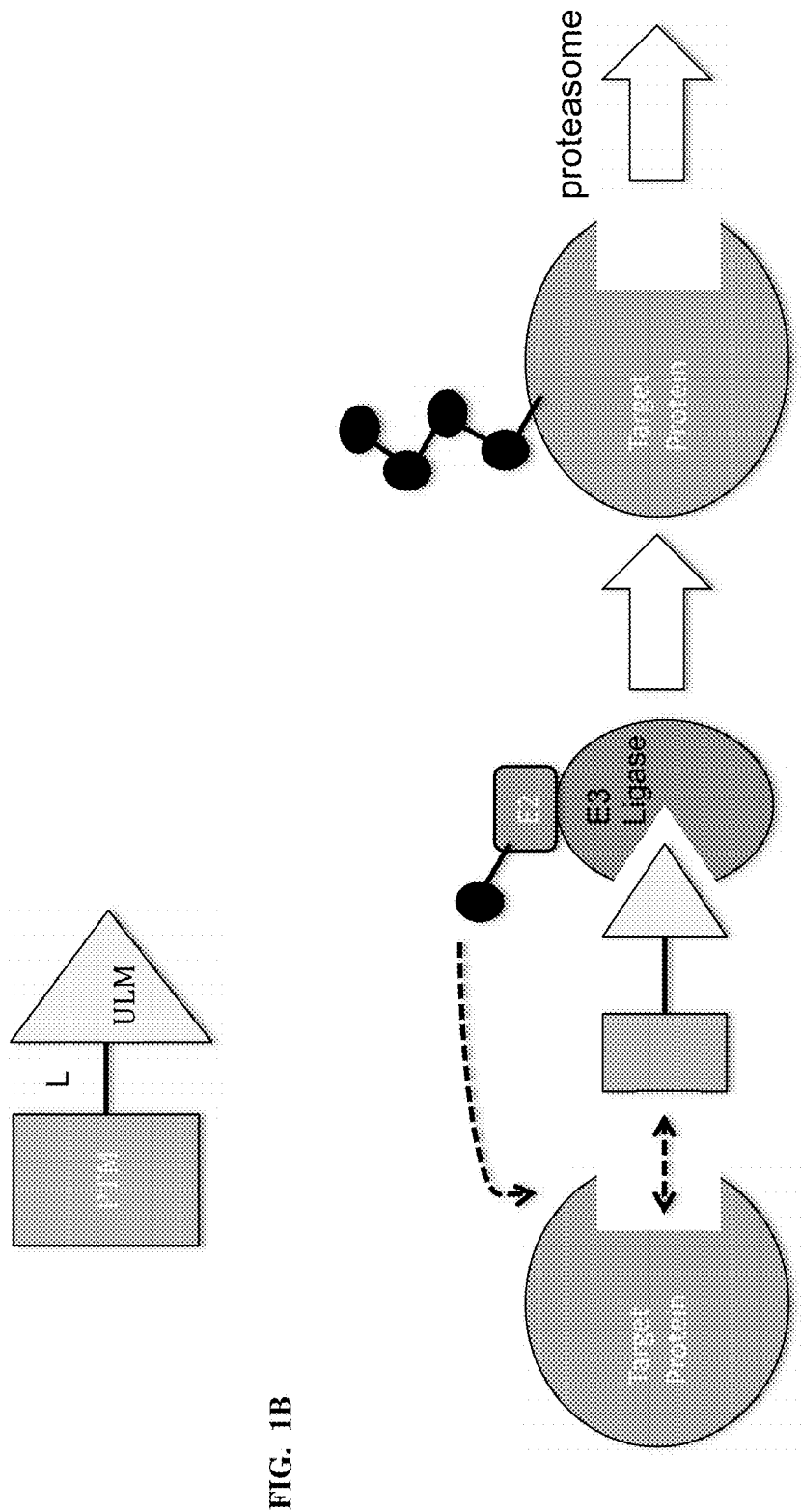
FIGS. 1A and 1B. Illustration of general principle for PROTAC function. (1A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (1B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

FIGS. 1A and 1B provides an illustration of general principle for PROTAC function. FIG. 1A provides exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. FIG. 1B illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

FIG. 2 provides a table of exemplary PROTAC compounds (compounds 1-351) as described herein. The compounds are exemplary and the description is expressly intended to encompass combinations of the exemplified compounds respective PTM, Linker, and ULM components. For example, the PTM of compound example 1, can be combined with any of the linkers exemplified in examples 2-351 and/or any of the ULMs in examples 2-351, and so on.

Small Molecule Induced Degradation of EGFR and Mutants.

Epidermal Growth Factor Receptor (EGFR), also known as ErbB1/HER1, is a proto-oncogene that has been implicated in a range of cancers including glioblastoma multiforme, head and neck, and non-small cell lung cancer. Overexpression and/or activating mutations of EGFR are associated with a poor prognosis, therefore significant effort has focused on targeting EGFR with both small molecule and antibody-based therapies. Small molecule kinase inhibitors competitively bind to the kinase domain, thereby preventing signalling, while antibodies are capable of preferentially binding the cognate ligand recognition site, thus preventing kinase activation. Furthermore, degradation of EGFR by FDA-approved antibodies has been implicated in their clinical success, suggesting that degradation may be advantageous. With this rationale in mind, small molecules capable of inducing EGFR degradation were developed (i.e., EGFR-targeting PROTACs).

By conjugating an EGFR binding element, e.g., kinase inhibitor, such as lapatinib (FIG. 3), to a ligand that binds to the E3 ligase, VHL, exemplary molecules were synthesized capable of penetrating the cell membrane and inducing EGFR degradation at low nanomolar concentrations (FIGS. 4A-6C). Interestingly, inversion of the hydroxyproline stereochemistry on the VHL-recruiting moiety of the PROTAC can affect its ability to degrade EGFR (FIG. 4B). This diastereomeric version (PROTAC Diastereomer 2) of the PROTAC provides an excellent control compound with nearly identical physicochemical properties (see FIGS. 6A-6C) but capable of only inhibiting EGFR; an ideal tool with which to directly assess the advantages of EGFR degradation over kinase inhibition without variations in probe solubility, membrane permeability, or chemical stability obscuring a head-to-head comparison (as would be the case if comparisons were drawn directly with lapatinib itself).

Having demonstrated that recruitment of VHL to EGFR via a lapatinib-based PROTAC is capable of efficiently inducing degradation of a receptor tyrosine kinase (RTK), different EGFR-binding elements were employed to degrade different clinically relevant forms of EGFR. As shown in FIG. 4C, the lapatinib-based PROTAC 1, is also capable of degrading an exon-20 insertion mutant form of EGFR (ASV duplication). Switching to a warhead based on mutant-EGFR selective gefitinib (PROTAC 3) enabled the degradation of both exon-19 deletion EGFR as well as the mutant isoform containing the L858R activating point mutation (FIG. 4D/4E), while sparing the WT EGFR (see FIGS. 5A-5D). Finally employing the second-generation inhibitor afatinib yielded PROTAC 4 capable of degrading the gefitinib-resistant double mutant (L858R/T790M) EGFR (FIG. 4F).

The choice of warhead can be crucial for successful target degradation; here it is demonstrated that careful selection of the recruiting element can also allow degradation of proteins in different mutational states. For some of the aforementioned PROTACs, a "hook effect" was observed on substrate degradation, which has been previously reported and results from the formation of unproductive dimers (rather than productive 'trimers') at higher concentrations. The lack of this 'hook effect' in other PROTACs might arise from additive target: E3 ligase protein-protein interactions that they induce.

Selective PROTAC-Mediated Degradation of HER2 and Implications for Kinome Re-Wiring.

Since lapatinib is also a potent binder to other HER family RTKs, the potential for HER2 degradation by lapatinib-based PROTACs was explored. Similar to EGFR, HER2 overexpression is an oncogenic driver of many forms of cancer including ovarian, breast, and gastric cancers. Immunoblotting analysis revealed that PROTAC 1, which utilizes a diethylene glycol linker to tether lapatinib to the VHL recruiting element, could concurrently degrade both EGFR and HER2 (FIG. 5A). However, extension of the linker by an additional ethylene glycol unit to create PROTAC 5 enabled the selective degradation of EGFR while sparing HER2. This observation suggests that affinity for both target protein and E3 ligase is not sufficient for the development of a successful PROTAC, and that a more complex dynamic process may be responsible.

The advantages of PROTAC-mediated degradation over kinase inhibition become apparent when the effect on cell proliferation is compared (FIG. 5B). SKBr3 cells, a HER2-driven breast cancer cell line, are more responsive to PROTAC 1 than the cognate diastereomeric control 2 that has equivalent cell permeability and kinase inhibitory properties but is incapable of inducing HER2 degradation (FIG. 6B/6C). PROTAC 1 treatment induces a greater response in terms of anti-proliferative efficacy than does diastereomer 2, and at a greater potency (PROTAC 1 $IC_{50}$=102 nM, diastereomer 2 $IC_{50}$=171 nM).

Comparison of PROTAC 1 with diastereomer 2 also reveals additional advantages of degradation over inhibition following an extended treatment period. Inhibition of EGFR/HER2 in SKBr3 cells has previously been shown to rapidly induce kinome "re-wiring", whereby alternative, uninhibited kinases are recruited as heterodimerization partners leading to the phosphorylation of the same downstream effectors to restore oncogenic signalling via RTK crosstalk.

To investigate this phenomenon, SKBr3 cells were treated with equal, saturating concentrations (FIG. 6B/6C) of either PROTAC 1 or diastereomer 2, which provided a direct and head-to-head comparison of degradation versus inhibition given their similar physicochemical properties. Interestingly, degradation appears to have a protective effect against kinome re-wiring, particularly in the case of ERK1/2 phosphorylation and specific HER3 and AKT phosphorylation sites. Cells treated with the inhibitor (diastereomer) 2 led to transient suppression of activation of ERK1/2, phosphorylation of Akt (Thr308), c-Met and HER3, the latter being a major node for preventing apoptosis and promoting survival (FIG. 5C). However, within 24 to 48 hours, this suppression was reversed despite continued presence of the inhibitor.

Quite strikingly, treatment with an equivalent concentration of PROTAC 1 itself yielded sustained suppression of downstream signalling, suggesting that removal of the target RTKs discourages kinome re-wiring and permits longer sustained growth suppression. Inhibition transiently prevents downstream signalling but degradation may also impact the scaffolding roles exhibited by RTKs, particularly in instances of kinome re-wiring by receptor cross-talk. For example, heterodimerization of EGFR with c-Met and signalling via the c-Met kinase domain has been implicated in resistance to some inhibitors/antibodies. Analysis of the c-Met phosphorylation status after 48 hours of PROTAC 1 or diastereomer 2 treatment revealed a substantial increase in signalling via c-Met kinase domain in diastereomer-treated cells compared to the PROTAC treated cells, presumably by trans-activation (FIG. 5D). These results demonstrate the advantages gained from RTK degradation compared to kinase inhibition with regards to prevention of downstream signalling and delayed onset of kinome re-wiring.

Since PROTACs proved successful in degrading both EGFR and HER2, PROTACs were made to a different RTK family. C-Met is the receptor for Hepatocyte Growth Factor (HGF), which is also known as the "scatter factor" for its ability to promote tumor metastasis. Upon binding of HGF, c-Met dimerizes and transphosphorylates on tyrosine residues within its kinase domain (Y1234 and Y1235) as well as on its unique c-terminal multifunctional docking domain (Y1313, Y1349, Y1356 and Y1365). The docking domain contains recognition sites for diverse cellular effectors such as Src, Gab1, Crk, Grb2, SHC and PI-3 kinase, which potently activate downstream mitogenic pathways. Inhibitors, such as foretinib, which competitively displace ATP from the c-Met kinase domain block HGF-stimulated activation of ERK and Akt, the primary downstream effectors of c-Met signalling. Despite this, however, small molecule c-Met inhibitors have performed disappointingly in clinical trials suggesting the possibility of a kinase-independent function driving oncogenesis and highlighting the potential advantage of c-Met degradation over inhibition.

FIGS. 6A-6C demonstrate that a Gefitinib-based PROTAC (PROTAC 3) spares WT EGFR (FIG. 6A). OVCAR8 Cells were treated for 24 hours with increasing doses of PROTAC 3 or with DMSO control before immunoblotting. FIG. 6B/6C—Characterization of PROTAC 1 (6B) and diastereomer 2 (6C) in SKBr3 cells. Cells were treated for 24 hours in full serum with increasing doses of PROTAC 1 or with diastereomer 2 before immunoblotting. The characterization of foretinib-based PROTACs in GTL16 cells is shown in FIGS. 7A-7F. GTL16 cells were treated with increasing concentrations of PROTAC 7 (7A) or diastereomer 8 (7B) in media containing full serum for 24 hours before immunoblotting analysis. FIG. 7C—Representative blot of cells treated with 500 nM PROTAC 7 or 500 nM diastereomer 8 for 48 hr before immunoblotting analysis. FIG. 7D shows the quantification of washout experiments. c-MET levels normalized to tubulin after treatment with the indicated compounds at the indicated time points. Average of 3 independent repeats and error bars represent S.E.M. The structure of VHL-Ligand 9 used in competition experiments is shown in FIG. 7E. FIG. 7F shows co-treatment competition of PROTAC 7 with VHL-Ligand 9 in MDA-MB-231 cells for 24 hours.

Employing the c-Met inhibitor foretinib as a recruiting element, we developed a PROTAC, compound 7, capable of recruiting VHL to, and thereby inducing degradation of c-Met in a dose- and time-dependent fashion. MDA-MB-231 cells treated with increasing concentrations of foretinib-based PROTAC 7 (see FIG. 3 and FIG. 8A) or its cognate diastereomer 8 (see FIG. 3 and FIG. 8B), in the presence or absence of an HGF pulse, demonstrated that treatment with approximately 10-fold higher concentration of diastereomer is required to completely inhibit agonist-driven AKT phosphorylation. We observed a similar level of inhibition of Akt phosphorylation in GTL16 cells, a c-Met-overexpressing cell line, when grown and treated in full serum with PROTAC 7 and diastereomer 8. The reduced potency differential between PROTAC 7 and diastereomer 8 inhibition of Akt phosphorylation likely results from the steady-state versus agonist-challenged activation of the signaling cascade between the two cell lines (GTL16 and MDA-MB-231, respectively). The foretinib-based PROTAC 7 is also greater than 2-fold more potent than its corresponding diastereomer 8 at inhibiting the proliferation of GTL16 cells (FIG. 8C), again highlighting the advantages of developing probes capable of protein degradation, especially in oncogene-addicted contexts. Additionally, clearance of WT c-Met from the cell is relatively rapid, requiring only 6 hr of treatment to significantly reduce protein levels in MDA-MB-231 cells (FIG. 8D), providing a temporal advantage over RNA-mediated knockdown techniques as well as abrogating the requirement for transfection reagents or exogenous selection pressure that may interfere with other normal cellular activities.

Subsequent to demonstrating the catalytic nature of PROTACs, the duration of their effect was studied. Cells were treated for 24 hr with DMSO control, foretinib-based PROTAC 7, or its corresponding diastereomer 8 before being dissociated from the culture dishes, rinsed with PBS to wash out extracellular treatment compound, and replated into fresh medium and on new culture dishes for additional 24- or 48-hr periods followed by lysis. PROTAC-treated cells exhibited a prolonged reduction in c-Met levels out to 48 hr post washout. Crucially, in cells treated with PROTAC 7, c-Met levels could be rescued by treatment with 50-fold excess free VHL ligand following the washout. The free VHL ligand prevents E3 ligase recruitment to the RTK by PROTAC 7, indicating that the sustained knockdown in PROTAC-treated cells is mediated post-translationally by disrupting PROTAC 7:Met:VHL complexes remaining in the cell (catalytic mode of action) rather than a response at the translational level, as has been observed with other small molecules. Moreover, when MDA-MB-231 cells are co-treated with PROTAC 7 and increasing doses of free VHL ligand, the ability of the PROTAC to degrade c-Met is hindered, further demonstrating the necessity and specificity for VHL recruitment. Additionally, foretinib-based PROTAC 7 is also capable of preventing inhibitor-induced compensatory signaling in a way similar to that of the aforementioned lapatinib-based PROTACs. GTL16 cells display profound kinome rewiring after 48 hr, as evidenced by ERK1/2 phosphorylation in diastereomer 8-treated cells, but not in PROTAC 7-treated cells.

Having proven that RTKs could be degraded via the PROTAC technology the mechanism of degradation was assessed. Initially, real-time qPCR was performed over time to demonstrate that the observed decrease in c-Met protein levels in response to PROTAC treatment occurs at the post-transcriptional level. Additionally, co-treatment with pharmacological agents that inhibit either the proteasome (epoxomicin) or the ubiquitination cascade (NEDD8-activating enzyme E1 inhibitor, MLN-4924) were able to restore protein levels to untreated levels, demonstrating not only that ubiquitination is crucial for c-Met degradation but also that it progresses via the proteasome. Furthermore, RTKs are known to rely on the heatshock protein 90 (HSP90) chaperone for proper folding as well as being cycled between the plasma membrane and early endosomes in a HSP90-dependent fashion.

As such the effect of the HSP90 inhibitor 17-AAG (17-N-allylamino-17-demethoxygeldanamycin) on PROTAC-mediated degradation was explored. Co-treatment with PROTAC 7 and 17-AAG has an additive effect on c-Met protein degradation in the MDA-MB-231 cell line, suggesting that HSP90 may be intercepting c-Met in a separate compartment from PROTAC 7, thereby enhancing the degradation of total c-Met within the cell. Previous work has shown c-Met to be a client protein of HSP90 and that geldanamycin and 17-AAG could promote its ubiquitination and proteasome-dependent degradation.

It was then determined whether PROTAC-targeted RTKs were removed directly from the cell surface or were intercepted at some point in the secretory pathway to the membrane. Employing a cell-surface biotinylation degradation assay, it was demonstrated that PROTAC 7 induces the degradation of the c-Met mature form (145 kDa) from the cell surface, suggesting that VHL recruitment is capable of, either directly or indirectly, inducing RTK internalization (FIGS. 9A and 9B). We confirmed PROTAC 7-mediated RTK internalization by confocal immunofluorescence microscopy: untreated cells exhibit cell-surface c-Met immunofluorescence but treatment with PROTAC 7 (FIG. 9C) or HGF shows internalization and localization to a perinuclear compartment as previously described. This perinuclear compartment also stains positive for the early endosome antigen 1 (EEA1) and appears to be distinct from the Golgi apparatus, which is c-Met positive in untreated cells (FIGS. 12A-12E). These large EEA1-positive vesicle-like structures have previously been reported in MDA-MB-231 cells. This provides, to the best of our knowledge, the first evidence of small-molecule-induced internalization of an endogenous RTK and further suggests sorting into endosomes prior to degradation via the proteasome. Interestingly, preliminary small interfering RNA experiments suggest that this process is clathrin independent (FIG. 12E).

Next, the advantages of degradation over inhibition was assessed in the Hs746T gastric cancer cell line, which expresses an exon 14 splice variant of c-Met. Exon 14 skipping results in the expression of c-Met lacking the juxtamembrane domain recruitment site (Y1003) for Cb1, the endogenous E3 ligase that promotes HGF-dependent internalization and subsequent degradation of c-Met. This clinically relevant mutation results in prolonged downstream signaling, since the naturally occurring "off-switch" for HGF-induced signaling is no longer present. The lack of this regulatory domain also increases the intrinsic stability of c-Met protein in the absence of any other degradation signal. Cycloheximide chase experiments (FIG. 10A) revealed that WT c-Met has a basal half-life of 4.4 hr, while the basal half-life of the exon 14 mutant c-Met is >8 hr. HGF treatment results in rapid degradation of WT c-Met (FIGS. 10A and 10C) but not exon 14-deleted c-Met (FIGS. 10A, 10B, and 10D); this lack of internalization/degradation results in sustained downstream signaling (FIGS. 10C and 10D), enhancing the cell proliferation and tumorigenesis of exon 14 mutant c-Met-expressing cells.

Interestingly, PROTAC 7 treatment can induce the degradation of exon 14-deleted c-Met (FIGS. 10A and 10E) despite that fact that it is not degraded by the major natural mechanism (i.e., HGF). The degradation half-life of PROTAC 7-treated exon 14-deleted c-Met is only marginally longer than that of PROTAC 7-treated WT c-Met (4.2 hr versus 2.5 hr, respectively), in contrast to the wide differential in their respective HGF-induced, native degradation rates (>8 hr versus 1.66 hr, respectively) (FIG. 10B). The fact that PROTAC 7 is able to degrade exon 14-deleted c-Met suggests that this process in Cb1 independent as well as clathrin independent.

This provided another instance whereby target degradation by PROTAC might prove advantageous over inhibition alone, in that inhibition can temporarily block signaling at the level of kinase activity, but only degradation can provide a lasting "off-switch" for the receptor itself as demonstrated in FIGS. 10F and 10G. Pre-treatment of Hs746T cells, which express an exon 14 mutant c-Met, with PROTAC 7 reduces HGF-induced activation of Akt. There remains a brief elevation of phospho-Akt in these cells at 0.5 hr following HGF treatment; more importantly, however, is that the sustained signaling observed in DMSO-treated cells (up to 6 hr) is not observed in the PROTAC 7-treated cells (FIG. 10G). This restoration of a WT phenotype to a mutant protein via a PROTAC is intriguing, and the approach could prove potentially advantageous in cancer patients bearing exon 14 splice variants of c-Met. As a result of this apparent restoration of a WT phenotype to a mutant protein via treatment with PROTAC, we sought to investigate the PROTAC 7-induced ubiquitination state of c-Met through immunoprecipitation experiments in the exon 14 mutant cells. After 4 hr of treatment with PROTAC 7, immunoprecipitated c-Met is ubiquitinated to a greater extent than vehicle control samples (FIG. 10H).

Furthermore, Hs746T lysate was subjected to tandem ubiquitin binding entity 1 (TUBE1) immunoprecipitation in an effort to enrich for polyubiquitinated substrates within the cell. PROTAC 7-treated Hs746T cells display marked TUBE1 enrichment of c-Met when compared with vehicle control-treated cells (FIG. 10I). These experiments provide evidence that PROTAC 7 induces polyubiquitination of c-Met, even in an exon 14 skipped context lacking the natural phosphodegron. While the general applicability of PROTAC-mediated degradation to RTKs may be inferred beyond the specific examples described in this study, we are continuing to investigate other instances of this broad superfamily of proteins as well as the larger considerations of harnessing the PROTAC approach to the entire proteome. Additionally, the advantages of inducing degradation over inhibition of target proteins gleaned from this "case study" provide a strong foundation for future PROTAC-based paradigms.

FIG. 11A-D. FIG. 11A—Quantitative real time PCR was performed at the indicated timepoints after PROTAC treatment (500 nM). Data is normalized to beta-Tubulin. FIG. 11B-11D Representative Western blots and quantitation for cotreatment experiments. FIG. 11B—Co-treatment of PROTAC 7 (500 nM) with proteasome inhibitor epoxomicin (500 nM) for 6 hours in MDA-MB-231 cells. Quantified data represent average of 2 repeats. FIG. 11C—Co-treatment of PROTAC 7 (500 nM) with neddylation inhibitor MLN-4924 (1 µM) for 6 hours in MDA-MB-231 cells. Quantified data represent average of 2 repeats. FIG. 11D—Co-treatment of PROTAC 7 (500 nM) with HSP90 inhibitor 17-AAG (1 µM) for 6 hours in MDA-MB-231 cells. Quantified data represent average of 2 repeats.

FIG. 12A-12E. Representative confocal microscopy images of HGF-mediated internalization of c-Met. FIG. 12A—MDA-MB-231 cells treated with 100 ng/ml HGF for the indicated times before fixing, permeabilizing, and immunostaining for c-Met. FIG. 12B—Representative confocal microscopy images demonstrating PROTAC-mediated colocalization with early endosome antigen 1 (EEA1). MDA-MB-231 cells treated with 500 nM PROTAC 7 for the indicated times before fixing, permeabilizing, and immunostaining for c-Met and EEA1. FIG. 12C—Representative confocal microscopy images demonstrating c-Met co-localization with p230 (a trans-Golgi marker). FIG. 12D—Quantification of images from FIG. 9C. Percentage of cellular pixels occupied by c-Met immunofluorescence and average cellular pixel intensity were used as a proxy for puncta formation and reduction in cell surface c-Met. FIG. 12E—Clathrin heavy chain (CHC) siRNA experiment. MDA-MB-231 cells were transfected with CHC siRNA before treatment with PROTAC 7 for 24 hours prior to lysis and immunoblotting.

Cycloheximide pulse-chase western blots. FIG. 13A—MDA-MB-231 cells were treated with cycloheximide followed by DMSO, PROTAC 7 or HGF and lysed at the indicated incubation times—Set 1. FIG. 13B—MDA-MB231 cells were treated with cycloheximide followed by DMSO, PROTAC 7 or HGF and lysed at the indicated incubation times—Set 2. FIG. 13C—Hs746T cells were treated with cycloheximide followed by DMSO, PROTAC 7 or HGF and lysed at the indicated incubation times. FIG. 13D—c-Met immunoprecipitation experiments.Hs746T cells were treated with 2 uM epoxomicin for 30 minutes before the addition of PROTAC 7 for 4 hours prior to c-Met immunoprecipitation. (WCL=Whole-cell lysate). FIG. 13E—Hs746T cells were treated as in D prior to TUBE1 immunoprecipitation experiments.

Structures of exemplary PROTAC compounds as described herein (Lapatinib-based (furan) PROTACs) are shown in FIG. 14. Degradation activity of exemplary PROTAC compounds of FIG. 14. FIGS. 15A and 15B demonstrate the degradation activity of exemplary PROTAC compounds of FIG. 14. FIG. 15A—the percent degraded HER1 and HER2 protein at 1 uM, linker atoms, linker length (in Angstroms), linker type and E3 ligase binding moiety (ULM) is indicated. FIG. 15B—demonstrates the degradation activity (dose-response) of HER1 in OVCAR8 cells by lapatinib-based PROTACS as indicated.

FIGS. 16A and 16B show structures of exemplary lapatinib (furan)-based PROTACs (FIG. 16A). FIG. 16B—Western blot demonstrating degradation activity of compounds of FIG. 16A. OVCAR8 treated cells for 24 hours. NRG (5 ng/mL) stimulation for the last 5 minutes. Anti-EGFR rabbit (CST), anti-HER2 (Santa Cruz Biotechnologies), and anti-tubulin (Sigma-Aldrich) were used for detection of proteins.

Degradation activity of exemplary PROTAC compounds. FIG. 17A—shows structures of exemplary lapatinib (phenyl)-based PROTACs. FIG. 17B—Western blot demonstrating degradation activity of compounds of FIG. 14A. OVCAR8 treated cells for 24 hours. NRG (5 ng/mL) stimulation for the last 5 minutes. Anti-EGFR rabbit (CST), anti-HER2 (Santa Cruz Biotechnologies), and anti-tubulin (Sigma-Aldrich) were used for detection of proteins.

Tables 1 and 2 provide IC50 and protein degradation data, respectively, for the indicated exemplary EGFR-PROTACs as described herein (see FIG. 2). The data demonstrate the ability to inhibit and degrade wild type (WT) and mutant forms of EGFR in multiple cell types, including at clinically relevant concentrations.

TABLE 1

Time Resolved (TR)-FRET results for exemplary EGFR PROTACs of FIG. 2. Lower $IC_{50}$ values (Lower $IC_{50}$ values (50% of the maximum inhibition of the corresponding kinase activity by the test compound) indicate higher affinity for the corresponding protein. Values in micromolar, geometric mean if measured more than once.

| Ex. # | EGFR WT $IC_{50}$ (μM) | EGFR Δ19/746/750 $IC_{50}$ (μM) | EGFR Δ19/746/750 T790M $IC_{50}$ (μM) | EGFR Exon20NPG $IC_{50}$ (μM) | EGFR L858R $IC_{50}$ (μM) | EGFR L858R/ T790M $IC_{50}$ (μM) | EGFR L858R/ T790M/ C797S $IC_{50}$ (μM) | HER2WT $IC_{50}$ (μM) | HER2 InsYVMA $IC_{50}$ (μM) | HER3 $IC_{50}$ (μM) |
|---|---|---|---|---|---|---|---|---|---|---|
| 1 | 0.065 | 0.0021 | 6.1 | 0.23 | 0.014 | 12 | 4.5 | 1.2 | | |
| 2 | 0.059 | 0.0040 | 7.1 | 0.51 | 0.012 | >30 | 3.6 | 2.3 | | |
| 3 | 0.21 | 0.0055 | 6.6 | 0.86 | 0.024 | 14 | 14 | 1.5 | | |
| 4 | 0.045 | 0.0042 | 24 | 0.29 | 0.0083 | 22 | 10 | 1.8 | | |
| 5 | 0.040 | 0.0041 | 7.3 | 0.53 | 0.011 | 19 | 5.4 | 1.5 | | |
| 6 | 0.064 | 0.0029 | 2.2 | 0.23 | 0.047 | 8.9 | 3 | 0.52 | | |
| 7 | 0.058 | 0.0010 | 3.4 | 0.11 | 0.040 | 8.5 | 2.7 | 0.30 | | |
| 8 | 0.089 | 0.0017 | 4.8 | 0.45 | 0.011 | 7.2 | 3.2 | 1.2 | | |
| 9 | 0.027 | 0.0019 | 3.9 | 0.26 | 0.0049 | 6.8 | 3.1 | 0.59 | | |
| 10 | 1.7 | 3.7 | 28 | 3.2 | 3.5 | 16 | 5.5 | 3.7 | | |
| 11 | 0.0084 | 0.00014 | 17 | 0.049 | 0.00040 | >30 | 3.5 | 0.19 | | |
| 12 | 0.50 | 0.083 | 8.2 | 5.7 | 0.15 | 9.1 | 10 | >30 | | |
| 13 | 0.76 | 0.037 | >30 | 5.3 | 0.13 | >30 | >30 | >30 | | |
| 14 | 0.84 | 0.20 | >30 | 4.4 | 0.17 | >30 | 7.3 | 11 | | |
| 15 | 0.69 | 0.14 | >30 | 4.7 | 0.20 | >30 | 17 | 19 | | |
| 17 | 0.22 | | | 0.19 | | 7.2 | 4.9 | | | |
| 48 | 0.0047 | | | 0.12 | | 3 | 7 | | | 20 |
| 66 | 0.011 | | | 0.066 | | 1.2 | 1.4 | | | 6.6 |
| 70 | >30 | >30 | 11 | | >30 | 15 | 16 | >30 | 19 | |
| 71 | 30 | >30 | 3.1 | >30 | 26 | 0.12 | 0.096 | >30 | 13 | |
| 72 | >30 | | | 22 | | >30 | 30 | | | >30 |
| 73 | 20 | 8.1 | 6.8 | | 9.8 | 11 | 14 | >30 | 3.4 | |
| 74 | >30 | | | >30 | | >30 | 10 | | | >30 |
| 75 | >30 | | | >30 | | >30 | >30 | | | >30 |
| 76 | 17 | | | 14 | | 0.36 | 0.036 | | | 8.6 |
| 77 | 24 | | | 12 | | 9.1 | 9.4 | | | >30 |
| 78 | 5.7 | | | 5.6 | | 0.25 | 0.025 | | | 25 |
| 79 | >30 | | | >30 | | 29 | 7.6 | | | >30 |
| 80 | 4.7 | | | 13 | | 4.7 | 2.2 | | | >30 |
| 81 | 2.4 | | | 7.1 | | 8.6 | >30 | | | >30 |
| 82 | 3.8 | | | >30 | | 0.77 | 0.45 | | | >30 |
| 83 | 3 | | | >30 | | 2.5 | 1.2 | | | >30 |
| 84 | 1.8 | | | 5.3 | | 0.68 | 0.27 | | | >30 |
| 85 | >30 | | | >30 | | 16 | 3.9 | | | |
| 86 | >30 | | | 24 | | 12 | 2.4 | | | |
| 87 | >30 | | | 14 | | 15 | 3.3 | | | |
| 88 | >30 | | | 3.1 | | 11 | 9.4 | | | |
| 89 | >30 | | | >30 | | 1.6 | 0.65 | | | >30 |
| 90 | 1.3 | | | 3.4 | | 0.74 | 0.69 | | | 29 |
| 91 | 4.3 | | | 8.3 | | 4.7 | 0.66 | | | |
| 92 | 9.8 | | | 3.1 | | 6.2 | 1.1 | | | |
| 93 | 11 | | | 3.3 | | 3.5 | 0.53 | | | |
| 94 | 2.1 | | | 1.5 | | 6 | 1.8 | | | |
| 95 | 4.2 | | | 3.3 | | 6.7 | 2.2 | | | |
| 96 | 1.9 | | | 2.5 | | 10 | 4.6 | | | |
| 97 | 1.5 | | | >30 | | >30 | >30 | | | 29 |
| 101 | 0.012 | | | 0.069 | | 3.4 | 3.6 | | | |

TABLE 1-continued

Time Resolved (TR)-FRET results for exemplary EGFR PROTACs of FIG. 2. Lower $IC_{50}$ values (Lower $IC_{50}$ values (50% of the maximum inhibition of the corresponding kinase activity by the test compound) indicate higher affinity for the corresponding protein. Values in micromolar, geometric mean if measured more than once.

| Ex. # | EGFR WT $IC_{50}$ (μM) | EGFR Δ19/746/750 $IC_{50}$ (μM) | EGFR Δ19/746/750 T790M $IC_{50}$ (μM) | EGFR Exon20NPG $IC_{50}$ (μM) | EGFR L858R $IC_{50}$ (μM) | EGFR L858R/ T790M $IC_{50}$ (μM) | EGFR L858R/ T790M/ C797S $IC_{50}$ (μM) | HER2WT $IC_{50}$ (μM) | HER2 InsYVMA $IC_{50}$ (μM) | HER3 $IC_{50}$ (μM) |
|---|---|---|---|---|---|---|---|---|---|---|
| 103 | 0.59 | | | 0.75 | | >30 | 23 | | | |
| 104 | 0.59 | | | 0.51 | | 12 | 8.2 | | | |
| 105 | 0.97 | | | 0.82 | | >30 | 24 | | | |
| 106 | 0.47 | | | 1.9 | | 4.9 | 5.2 | | | |
| 107 | 0.14 | | | 0.6 | | 6.7 | 6 | | | |
| 108 | 0.77 | | | 0.98 | | 10 | 7.8 | | | |
| 109 | 0.18 | | | 0.58 | | 6 | 8.9 | | | |
| 110 | 0.77 | | | 1.8 | | 8.6 | 12 | | | |
| 254 | 1.1 | | | 5.7 | | 1 | 0.10 | | | |
| 255 | 0.58 | | | 4.7 | | 0.83 | 0.14 | | | |
| 256 | 2.5 | | | 6.1 | | 14 | 1.4 | | | |
| 257 | 5.7 | | | >30 | | >30 | 2.7 | | | |
| 258 | 1.7 | | | 4.9 | | 5.9 | 4 | | | |
| 259 | 2.1 | | | 2.1 | | 3.1 | 0.55 | | | |
| 260 | 3.2 | | | >30 | | 20 | 0.56 | | | |
| 261 | 2.2 | | | 4.9 | | 3.5 | 0.18 | | | |
| 262 | 3.7 | | | 7.4 | | 0.43 | 0.25 | | | |
| 263 | 8.6 | | | 12 | | 11 | 0.79 | | | |
| 264 | 4.2 | | | 24 | | >30 | 1.1 | | | |
| 265 | 3.6 | | | 20 | | 27 | 0.29 | | | |
| 266 | 10 | | | >30 | | >30 | 2.6 | | | |
| 267 | 30 | | | 30 | | 30 | 1.4 | | | |
| 275 | 0.66 | | | 9.1 | | 0.88 | 0.069 | | | |
| 276 | 20 | | | >30 | | 23 | 29 | | | |
| 277 | >30 | | | >30 | | >30 | >30 | | | |
| 278 | 30 | | | >30 | | >30 | >30 | | | |
| 279 | 16 | | | >30 | | 29 | >30 | | | |
| 280 | >30 | | | >30 | | >30 | >30 | | | |
| 281 | 12 | | | >30 | | >30 | 15 | | | |
| 282 | 12 | | | >30 | | >30 | 23 | | | |
| 283 | 1.2 | | | 4.6 | | 2.8 | 0.82 | | | |
| 284 | 14 | | | 30 | | >30 | 12 | | | |
| 285 | 26 | | | | | 35 | 17 | | | |
| 286 | 7.3 | | | | | 0.48 | 0.17 | | | |
| 287 | 6.7 | | | | | 0.074 | 0.016 | | | |
| 288 | 5.9 | | | | | 6.9 | 2 | | | |
| 289 | 1.2 | | | | | 1.7 | 0.19 | | | |
| 290 | 1.1 | | | | | 2.7 | 0.14 | | | |
| 291 | 14 | | | | | >60 | >60 | | | |
| 292 | 39 | | | | | 19 | 11 | | | |
| 293 | 1.7 | | | | | 4.2 | 0.64 | | | |
| 294 | 3.5 | | | | | 0.81 | 0.17 | | | |
| 295 | 34 | | | | | 3.1 | 0.71 | | | |
| 296 | 1.6 | | | | | 1.5 | 0.61 | | | |
| 297 | 1.8 | | | | | 1.8 | 0.31 | | | |
| 298 | 1.6 | | | | | 1.4 | 0.54 | | | |
| 299 | 0.24 | | | | | 4.6 | 0.20 | | | |
| 300 | 2.7 | | | | | 20 | 3.1 | | | |
| 301 | 2.8 | 1.6 | 0.27 | | | 0.24 | 0.034 | | | |
| 302 | >30 | | | | | 0.67 | 0.32 | | | |
| 303 | >30 | | | | | 0.55 | 0.25 | | | |
| 304 | >30 | | | | | 0.092 | 0.017 | | | |
| 305 | 2.1 | | | | | 0.0098 | 0.0013 | | | |
| 306 | 13 | 0.38 | 0.021 | | | 0.053 | 0.016 | | | |
| 307 | 0.37 | 3.8 | 1.8 | | | 0.71 | 0.18 | | | |
| 308 | 0.12 | 0.053 | 0.0021 | | | 0.00091 | 0.00027 | | | |
| 309 | 0.0072 | 1.9 | 5.1 | | | 0.12 | 0.025 | | | |
| 310 | 0.14 | 6 | 8.4 | | | 0.11 | 0.022 | | | |
| 311 | 0.097 | 9 | 4.6 | | | 0.065 | 0.016 | | | |
| 312 | 0.095 | 0.17 | 0.0049 | | | 0.00067 | 0.00035 | | | |
| 313 | 0.0014 | 0.0075 | 0.0016 | | | 0.00029 | 0.00026 | | | |
| 314 | 0.089 | 10 | 5.2 | | | 0.098 | 0.020 | | | |
| 319 | 0.0042 | 0.0013 | 0.0003 | | | 0.0023 | 0.0008 | | | |

TABLE 2

Degradation of EGFR protein in various cell lines. Degradation of exemplary compounds (see FIG. 2) data are categorized as follows: A: ≤50% EGFR protein remaining after 72 hours of incubation with the test compound at a concentration between 300 nM and 10 nM; B: ≤80% and >50% EGFR protein remaining after 72 hours of incubation with the test compound at a concentration between 300 nM and 10 nM; C: >80% EGFR protein remaining after 72 hours of incubation with the test compound at a concentration of 300 nM.

| Ex. # | EGFR-wt MDA-MB-231 or MCF7 or A549 or OVCAR8 | EGFR-Δ19 HCC827 | EGFR Exon 20 ASV HeLa* | EGFR L858R/T790M Double mutant H1975 | EGFR L858R/T790M/C797S Triple mutant H520* |
|---|---|---|---|---|---|
| 1 | C | | C | C | |
| 2 | C | | C | C | |
| 3 | C | | C | C | |
| 4 | C | | C | C | |
| 5 | C | | C | C | |
| 6 | C | | C | C | |
| 7 | C | | C | | |
| 8 | C | | C | | |
| 9 | C | | C | | |
| 10 | C | | C | | |
| 11 | C | | C | | |
| 12 | C | | C | | |
| 13 | C | | C | | |
| 14 | C | | C | | |
| 15 | C | | C | | |
| 16 | C | | C | | |
| 17 | C | | C | | |
| 36 | | A | | C | |
| 41 | A | A | | B | |
| 42 | | A | | | |
| 43 | B | B | | | |
| 44 | B | A | | | |
| 45 | | A | | | |
| 46 | | A | | | |
| 47 | A | A | | A | |
| 48 | B | A | C | B | |
| 49 | | A | | | |
| 50 | | A | | | |
| 51 | A | A | | A | |
| 56 | | | | A | |
| 61 | | | | A | |
| 64 | | | | A | |
| 66 | A | | B | A | C |
| 69 | | | | A | |
| 70 | | | | C | |
| 71 | | | | C | |
| 72 | | | | C | |
| 73 | | | | C | |
| 74 | | | | C | |
| 75 | | | | C | |
| 76 | | | | C | C |
| 77 | | | | C | |
| 78 | | | | C | C |
| 79 | | | | C | |
| 80 | | | | C | C |
| 81 | | | | C | |
| 82 | | | | C | |
| 83 | | | | C | |
| 84 | | | | C | |
| 85 | | | | C | |
| 86 | | | | C | |
| 87 | | | | C | C |
| 88 | | | | C | |
| 89 | | | | C | |
| 90 | | | | C | C |
| 91 | | | | C | |
| 92 | | | | C | C |
| 93 | | | | C | C |
| 94 | | | | C | |
| 95 | | | | C | C |
| 96 | | | | C | |
| 97 | A | | A | B | |
| 98 | C | | | | |
| 99 | A | | | | |
| 100 | C | | | | |
| 101 | C | | C | | |
| 102 | C | | C | | |

TABLE 2-continued

Degradation of EGFR protein in various cell lines. Degradation of exemplary compounds (see FIG. 2) data are categorized as follows: A: ≤50% EGFR protein remaining after 72 hours of incubation with the test compound at a concentration between 300 nM and 10 nM; B: ≤80% and >50% EGFR protein remaining after 72 hours of incubation with the test compound at a concentration between 300 nM and 10 nM; C: >80% EGFR protein remaining after 72 hours of incubation with the test compound at a concentration of 300 nM.

| Ex. # | EGFR-wt MDA-MB-231 or MCF7 or A549 or OVCAR8 | EGFR-Δ19 HCC827 | EGFR Exon 20 ASV HeLa* | EGFR L858R/T790M Double mutant H1975 | EGFR L858R/T790M/C797S Triple mutant H520* |
|---|---|---|---|---|---|
| 103 | C | | C | | |
| 104 | C | | C | | |
| 105 | C | | C | | |
| 106 | C | | C | | |
| 107 | C | | C | | |
| 108 | C | | C | | |
| 109 | C | | C | | |
| 110 | C | | C | | |
| 121 | C | | C | | |
| 254 | | | | C | C |
| 255 | | | | C | B |
| 256 | | | | C | C |
| 257 | | | | C | C |
| 258 | | | | C | C |
| 259 | | | | C | C |
| 260 | | | | C | C |
| 261 | | | | C | C |
| 262 | | | | C | C |
| 263 | | | | C | |
| 264 | | | | C | |
| 265 | | | | C | C |
| 266 | | | | C | C |
| 267 | | | | C | C |
| 268 | | | | C | |
| 269 | | | | C | |
| 270 | | | | C | |
| 271 | | | | C | |
| 273 | | | | C | |
| 275 | C | | | C | B |
| 276 | | | | C | |
| 277 | | | | C | |
| 280 | | | | | C |
| 283 | | | | | C |
| 284 | | | | | C |
| 289 | | | | | C |
| 290 | | | | | B |
| 291 | | | | | C |
| 294 | | | | | C |
| 295 | | | | | C |
| 296 | | | | | C |
| 297 | | | | | B |
| 298 | | | | | C |
| 299 | | | | | C |
| 300 | | | | | C |
| 301 | | | | | C |
| 302 | | | | | A |
| 303 | | | | | A |
| 304 | C | | | | A |
| 305 | | | | | C |
| 306 | | | | | A |
| 307 | | | | | A |
| 308 | | | | | B |
| 309 | | | | | C |
| 310 | | | | | B |
| 311 | | | | | B |
| 312 | | | | | B |
| 313 | C | | | | A |
| 314 | | | | | C |
| 319 | | | | | A |
| 320 | A | | | | |
| 324 | A | | | | |
| 325 | A | | | | |
| 326 | A | | | | |
| 327 | C | | | | |
| 328 | A | | | | |
| 329 | C | | | | |
| 330 | B | | | | |

TABLE 2-continued

Degradation of EGFR protein in various cell lines. Degradation of exemplary compounds (see FIG. 2) data are categorized as follows: A: ≤50% EGFR protein remaining after 72 hours of incubation with the test compound at a concentration between 300 nM and 10 nM; B: ≤80% and >50% EGFR protein remaining after 72 hours of incubation with the test compound at a concentration between 300 nM and 10 nM; C: >80% EGFR protein remaining after 72 hours of incubation with the test compound at a concentration of 300 nM.

| Ex. # | EGFR-wt MDA-MB-231 or MCF7 or A549 or OVCAR8 | EGFR-Δ19 HCC827 | EGFR Exon 20 ASV HeLa* | EGFR L858R/ T790M Double mutant H1975 | EGFR L858R/T790M/ C797S Triple mutant H520* |
|---|---|---|---|---|---|
| 331 | A | | | | |
| 332 | A | | | | |
| 333 | B | | | | |
| 334 | B | | | | |
| 335 | B | | | | |
| 336 | C | | | | |
| 338 | B | | | | |
| 350 | C | | | | |
| 351 | C | | | | |

In certain embodiments, or in combination with any of the embodiments described herein, the compounds as described herein have an IC50 (half maximal inhibitory concentration) for RTK activity (e.g., EGFR activity) of less than about 1 pM, from about 1 pM to about 1 nM, from about 1 nM to about 1 µM, or from about 1 µM to about 1 mM. In certain additional embodiments, the compounds as described herein have an IC50 of from about 1 pM to about 100 µM, from about 10 pM to about 100 µM, or from about 100 pM to about 100 µM. In certain embodiments, the compounds as described herein have an IC50 of from about 1 pM to about 1 µM, from about 10 pM to about 1 µM, or from about 100 pM to about 1 µM. In further embodiments, the compounds as described herein have an IC50 of from about 1 nM to about 1 M, from about 10 nM to about 1 µM, or from about 100 nM to about 1 µM. In certain embodiments, the IC50 is determined by TR-FRET method as described herein.

In certain additional embodiments, or in combination with any of the embodiments described herein, the compounds as described herein exhibit degradation activity of about ≤50% RTK protein remaining after 72 hours of incubation with the test compound at a concentration between about 300 nM and about 10 nM; from about ≤80% to about >50% RTK protein remaining after 72 hours of incubation with the test compound at a concentration between about 300 nM and about 10 nM; or about >80% RTK protein remaining after 72 hours of incubation with the test compound at a concentration of 300 nM. In certain embodiments, the degradation is determined in an in vitro degradation assay as described herein. In certain embodiments, the in vitro degradation assay is determined in a cell line selected from OVCAR8, HCC827, HeLa, H1975, or H520 cells.

As described herein, for the first time it was demonstrated that PROTACs are capable of inducing the degradation of active receptor tyrosine kinases and provide examples of successful degradation of three separate RTKs—EGFR, HER2, and c-Met, including multiple mutants of EGFR and c-Met. Degradation may provide advantages over inhibition in several key ways. In most cases compounds capable of degradation inhibit downstream signalling and cell proliferation at lower concentrations than similar compounds that only inhibit. Furthermore, degradation provides a more sustained reduction in signalling as evidenced by the reduction in kinome re-wiring observed previously with EGFR, HER2 and c-Met inhibitors, as well as the sustained duration of response even after washout. Also, PROTACs are capable of disposing of proteins that are mutated to avoid their natural "off-switch". This work significantly expands upon the potential protein targets of PROTACs to include transmembrane proteins and establishes that recruitment of VHL to RTKs is capable of efficiently removing this class of protein targets from the membrane in a similar fashion to their response to growth factor. Control experiments using the inactive diastereomeric compounds with identical physicochemical properties that degradation is leveraged over inhibition alone, highlighting the potential advantages of this pharmacologic modality.

Exemplary Methods

EGFR Protein Degradation assay

HeLa cells or H520 cells stably transfected with flag-tagged EGFR (exon 20 insert), parental HeLa cells (wild-type EGFR), NCI-H1975 cells (EGFR: L858R, T790M double-mutant), and A549 cells (wild-type EGFR) were screened.

Cells expressing the appropriate form of EGFR were seeded in 6-well plates (300,000 cells per well) and allowed to adhere to the plate overnight. Compound (2× concentration) was added in a volume of media equal to that of media in each well to give final concentrations of 3 µM, 1 µM, 0.3 µM, 0.1 µM, 0.03 µM, together with a DMSO control. Cells were incubated with compound for 24 hours. To harvest cells, media was removed and cells were washed once with ice-cold phosphate-buffered saline (PBS) prior to the addition of 400 µl lysis buffer (Cell Signaling Technology) supplemented with a protease inhibitor cocktail (Thermo Scientific). Cells were scraped from the plate and the cell lysate transferred to an Eppendorf tube and then clarified by a single spin at 10 000 rpm for 10 minutes. The protein concentration of each lysate was determined (BCA kit, Thermo Scientific) prior to the addition of loading buffer (Invitrogen) and reducing agent (Invitrogen). 10 µg protein of each lysate was loaded on an SDS/PAGE gel and run at 165V for 2 hours. Following transfer to a PVDF membrane (iBlot2, Thermo Fisher Scientific), the membrane was blocked in Tris-buffered saline containing 0.1% Tween-20 (TBS-T) and supplemented with 5% powdered milk for 1 hour. Membranes were then probed with EGFR and tubulin (loaded control) primary antibodies in TBS-T containing 3% bovine serum albumin (BSA) overnight at 4° C. Membranes were washed thrice with TBS-T before incubation with secondary antibody in TBS-T containing 3% bovine serum albumin (BSA) and incubated for 1 hour at room temperature. Following 3 further washes with TBS, membrane proteins of interest were detected by enzyme-linked chemiluminescence (ECL) using a Chemidoc (Bio-Rad).

H520 cells (ATCC: #HTB-182) stably expressing EGFR triple mutant (L858R, T790M, C797S) were seeded in 1 ml media in 12-well plates at a density of 100 000 cells per well. Cells were incubated overnight at 37° C., 5% $CO_2$ prior to compound addition. A 10 mM compound stock in DMSO was serially diluted in DMSO to provide the following stock concentrations: 1, 0.3, 0.1, 0.03 and 0.01 mM. An appropriate volume of each compound dilution, together with a DMSO vehicle control, was added to media to provide a 2× compound solution. 1 ml of each compound solution was then added to the appropriate well in the 12-well plate to give the following final compound titrations on cells: DMSO, 1, 0.3, 0.1, 0.03 and 0.01 M. Following compound addition, cells were incubated for 72 hours at 37° C., 5% $CO_2$. At the end of the compound treatment, cells were washed once with ice-cold phosphate-buffered saline (PBS) and treated with lysis solution (1× lysis buffer, Cell Signaling Technologies (CST #9803) supplemented with Piarce™ protease inhibitors, #A32953, Thermo Fisher Scientific, TFS). Lysates were collected and clarified of cell debris by spinning at 10K rpm for 10 minutes. A specific volume of supernatant was retrieved for protein quantification (Pierce™ BCA kit, TFS #23225) and for Western analysis. Loading buffer supplemented with EDTA and reducing agent was added to each supernatant. A specific volume of supernatant (determined by protein assay: 1-5 g protein loaded per sample) was loaded into a NuPAGE™ 4-12% Bis-Tris gel (TFS). Samples were run at 165V in MOPS running buffer for 2 hours and then transferred to PVDF blotting membrane using a dry blotting system (iBlot2, TFS). Membranes were blocked in Tris-buffered saline supplemented with Tween, 0.1% (TBST) containing 5% non-fat dry milk, (AmericanBio). Following block, membranes were washed once with TBST. Each membrane was cut to allow separate staining for EGFR and tubulin and then appropriate primary antibodies (EGFR, L858R mutant CST, #3197; β-tubulin, CST #2128) diluted 1:1000 and 1:5000 respectively in TBST with 3% BSA were added and membranes incubated overnight on a rocker at 4° C. Membranes were washed 3× with TBST prior to addition of secondary antibody (1:10 000, anti-rabbit HRP-linked, CST #7074) in TBST with 3% BSA and then incubated at room temperature for one hour. Membranes were then washed 3× with TBS and signal developed by exposure to developer (SuperSignal West Femto, TFS) for 5 minutes. Membranes were then immediately imaged using a BioRad Chemidoc.

H520 cells stably expressing EGFR triple mutant (L858R, T790M, C797S) were seeded in 1 ml media in 12-well plates at a density of 100 000 cells per well. Cells were incubated overnight at 37° C., 5% $CO_2$ prior to compound addition. Working stock concentrations were prepared as for the degradation assay. 1 ml appropriate compound solution or DMSO vehicle control was added to 1 ml media in the appropriate of well of the 12-well plate. Cells were incubated for 2 hours at 37° C., 5% $CO_2$. Following compound treatment, cells were harvested using methods identical to those for the degradation assay. Western analysis was performed exactly as performed for the degradation assay except the primary antibodies used were phosphoEGFR Y1068 (CST #2234) and β-tubulin (CST #2128) diluted in TBST with 3% BSA at 1:1000 and 1:5000 dilution respectively.

Inhibition of Cell Proliferation Assay

Cells expressing the appropriate form of EGFR were seeded in 96-well plates (2000 cells per well) and allowed to adhere to the plate overnight. Compound (2× concentration) was added in a volume of media equal to that of media in each well to give a 9-point concentration response curve, with 10 μM top concentration and diluted 3-fold together with a DMSO control. Cells were incubated with compound for 72 hours. Cell-titre Glo® reagent (Promega) was added to each well and incubated for 30 minutes and the luminescent signal was then read using a Cytation plate reader (BioTek). Luminescent values for each compound concentration were normalized to the DMSO vehicle control and data were plotted and curve fit using GraphPad Prism.

TR-FRET Assay for ERBB Kinases

All compounds and PROTACs were serially diluted in three-fold increments using 100% DMSO, followed by an intermediate 10-fold dilution using Buffer A (50 mM HEPES, pH 7.5, 50 mM NaCl, 10 mM MgCl2, 1 mM DTT, and 0.1% Pluronic F-68). Two microliters of serially diluted compound or PROTAC were then transferred to black 384-well Proxiplates (PerkinElmer, #6008260) using an Integra Viaflo96. Next, 10 uL of protein kinase in Buffer A was added to each well of the assay plate and pre-incubated with compound for 10 minutes. Kinase reactions were then initiated by addition of 5 uL substrate mix containing 3 mM ATP and 30 uM fluorescein-labeled Poly-GluTyr (Thermo Fisher, #PV3610) in Buffer A and allowed to proceed for 10 minutes at room temperature. Reactions were quenched by addition of a 5 uL mixture containing 5 nM LanthaScreen® Tb-pY20 Antibody (Thermo Fisher, #PV3552) and 40 mM EDTA in Buffer A. Assay plates were then read using a Synergy2 (Biotek Instruments, Winooski, Vt.) via excitation thru a 340/20 nm bandpass filter and emission collected thru 490/10 nm (donor) and 520/25 nm (acceptor) bandpass filters. The final kinase concentrations used for each 15 uL reaction were as follows: 0.2 nM EGFR Exon20NPG (SignalChem, #E10-132GG), 0.1 nM wild type EGFR (BPS Bioscience, #40187), 0.3 nM EGFR L858R/T790M/C797S (BPS Bioscience, #40351), 0.1 nM EGFR L858R (BPS Bioscience, #40189), 0.4 nM L858R/T790M (BPS Bioscience, #40350), InM EGFR Dell9 (SignalChem, #E10-122JG), 10 nM EGFR Dell9 T790M (SignalChem, #E10-122KG), 0.3 nM Her2 (BPS Bioscience, #40230), 15 nM Her2 InsYVMA (SignalChem, #E27-13BG).

Experimental Model and Subject Details

MDA-MB-231, SKBr-3, HCC-827, and H1975 cells were obtained from the American Type Culture Collection (ATCC). OVCAR8 cells were a gift from Joyce Liu (Dana Farber). H3255 cells were a gift from Katerina Politi (Yale University). All of the aforementioned cell lines were cultured in RPMI-1640 (IX) medium containing 10% fetal bovine serum (FBS) and 1% penicillin-streptomycin and grown in a humidified incubator at 37° C., 5% $CO_2$. GTL-16 cells were a gift from F. Maina (Developmental Biology Institute of Marseille-Luminy) and similarly grown in RPMI-1640 medium containing 10% FBS and 1% penicillin-streptomycin. To generate an Exon 20-insertion EGFR stable cell line, HeLa cells (ATCC) were transduced with a lentiviral mammalian expression vector pD2119-EFs-3× FLAG-EGFR-Exon20ins (purchased from DNA 2.0) and selected with 2 ug/ml puromycin in Dulbecco's modified Eagle's medium (DMEM) containing 10% FBS. This vector contains a 767 ASV duplication of exon 20.

Immunoblotting.

Cells were treated with the indicated concentrations of PROTAC or corresponding inhibiting diastereomer for the specified time and then harvested in lysis buffer (25 mM Tris.HCl pH 7.5 with 1% NP-40 and 0.25% deoxycholate, supplemented with 10 mM sodium pyrophosphate, 20 mM ß-glycerophosphate, 10 mM sodium fluoride, 1 mM sodium orthovanadate, 0.1 mM phenylarsine oxide, 10 µg/ml leupeptin, 10 µg/ml pepstatin A, 30 µg/ml bestatin, 0.3 trypsin inhibitor units/ml aprotinin and 1 mM PMSF). Following centrifugation at 16,000×g for 10 min at 4° C. to pellet insoluble materials, the protein concentrations of the supernatants were quantitated by BCA assay (Thermo Fisher Scientific). Protein samples were resolved by 8% SDS-PAGE, electrophoretically transferred to nitrocellulose and probed with the antibodies listed above. Immunoblots were developed using enhanced chemiluminescence and visualized using a Bio-Rad Chemi-Doc MP Imaging System and quantitated with Image Lab v.5.2.1 software (Bio-Rad Laboratories).

Cell Proliferation Assays

Following PROTAC or diastereomer treatment of cells as indicated, culture medium was supplemented with 330 µg/ml MTS (Promega Corp., Madison, Wis.) and 25 µM phenazine methosulfate (Sigma, St. Louis, Mo.) and incubated at 37° C. Mitochondrial reduction of MTS to the formazan derivative was monitored by measuring the medium's absorbance at 490 nm using a Wallac Victor$^2$ platereader (Perkin-Elmer Life Sciences, Waltham, Mass.). Data analysis and statistics performed using Prism v7.0 software (GraphPad Software).

Cell Surface Biotinylation Degradation Assay

A protocol was adapted from Joffre et. al to measure the removal of c-Met from the cell surface of MDA-MB-231 cells (Joffre et al., 2011). Cells were plated in full serum, allowed to adhere, and switched to serum-free RPMI-1640 for 16 hr. After this time, cells were placed on ice and rinsed with ice-cold 1×PBS-CM (0.1 mM CaCl2, 1 mM MgCl2) twice and incubated with PBS-CM for 5 min at 4° C. PBS-CM was aspirated, at which point cells were labelled with a cell membrane impermeant reagent, EZ-link Sulfo-NHS-SS-biotin at 0.5 mg/ml for 30 min at 4° C. with gentle rocking. This step enabled covalent labelling of all cell surface proteins. All of the following were carried out at 4° C. to prevent trafficking of said proteins. Cells were subsequently rinsed with ice-cold PBS-CM twice and excess biotin was quenched with Tris-glycine buffer (100 mM Tris pH 8.0, 150 mM NaCl, 0.1 mM CaCl2, 1 mM MgCl2 10 mM glycine, 1% BSA) for 15 min at 4° C. with gentle rocking. Cells were then rinsed with ice-cold PBS-CM three times before being chased with warm serum-free RPMI-1640 medium containing either HGF (100 ng/ml) or PROTAC (500 nM) and placed in a humidified incubator at 37° C. for the indicated amount of time, at which point the cells were lysed with lysis buffer (50 mM Tris, pH 7.5, 100 mM NaCl, 10% glycerol, 1% NP-40, 1 mM EDTA) supplemented with 1× protease inhibitors (Roche). Lysates were spun down at 14,000×g at 4° C. for 10 min and protein content was measured by BCA assay. Protein lysate was normalized and aliquoted onto pre-equilibrated NeutrAvidin agarose beads for 2 hrs at 4° C., with gentle rotation. Beads were washed three times with wash buffer (100 mM Tris, pH 7.5, 300 mM NaCl, and 1% Triton X-100) and resuspended in 2× elution buffer (62.5 mM Tris, pH 6.8, 3% SDS, 10% glycerol, 0.02% bromophenol blue, 160 mM DTT). Protein was eluted off of the beads by heating at 95° C. for 5 min and the supernatant was run on an SDS-PAGE gel and evaluated for the presence of cell surface c-Met protein. Whole-cell lysate refers to the lysate loaded onto NeutrAvidin beads, thereby representing the total c-Met protein.

Cycloheximide Chase Assay

MDA-MB-231 cells were plated at $3 \times 10^5$ cells per well in a 6-well dish, allowed to adhere, and switched to serum-free RPMI-1640 for 16 hr. Cells were then pre-treated with cycloheximide (Sigma) at 100 ug/ml for 1 hr prior to addition of either HGF (100 ng/ml), PROTAC (500 nM), or vehicle. At the indicated time points, cells were immediately placed on ice, rinsed with PBS, lysed, and boiled.

Immunofluorescence Microscopy

MDA-MB-231 cells were plated at a density of $1 \times 10^5$ cells/ml onto 12 mm round coverslips, cultured overnight, switched to serum free media for >12 hours and then treated with 500 nM PROTAC 7 or 100 ng/ml HGF for the indicated times before washing with PBS. Cells were fixed with 4% formaldehyde for 20 minutes at room temperature, washed with ice-cold PBS, permeabilized and blocked with 0.25% Triton X-100/1% BSA in PBS for 30 minutes. Fixed cells were incubated with c-Met Antibody (1:3000 dilution, Cell Signalling #8198) for 1 hour, washed three times with PBS for 5 minutes, incubated with Alexa Fluor-488 conjugated anti-rabbit antibody (1:1000 dilution, ThermoFisher A-11008) for 1 hour washed three times with PBS for 5 minutes and mounted in vectashield containing DAPI. Imaged on Zeiss Axio Observer Z1 inverted microscope.

siRNA Experiments

The siRNA (4 µL of 10 µM stock solution, 40 pMol) was diluted with Opti-MEM media (150 µL) then added to a solution of Lipofectamine RNAiMAX (9 µL in 150 µL in Opti-MEM) and incubated for 10 minutes before being added to MDA-MB-231 cells at ~80% confluency. The following day, the transfected cells were plated out and used for experiments as described above.

Immunoprecipitation Experiments

Hs746T cells ($2.5 \times 10^6$) were seeded into 10 cm dishes, allowed to adhere, switched to serum-free DMEM media for 16 hr. After this time, cells were pre-treated with 2 uM epoxomicin for 30 minutes at 37° C. After this pre-treatment, 10 cm plates were treated with either 1 uM Compound 7 or vehicle for 4 hours at 37° C., after which they were placed on ice, rinsed twice with ice-cold 1×PBS and lysed with 500 uL modified 1×RIPA buffer (25 mM Tris-HCl pH 7.6, 150 mM NaCl, 1% NP-40, 1% sodium deoxycholate, 0.1% SDS) containing 5 mM 1,10-phenanthroline monohydrate, 10 mM N-ethylmaleimide, 20 uM PR-619, and 1× cOmplete protease inhibitor cocktail (Roche). Lysates were spun down at 14,000×g at 4° C. for 10 min and protein content was measured by BCA assay. Protein lysate was normalized and 500 ug of lysate was aliquoted onto naked Protein A-Sepharose 4B beads (Sigma), and pre-cleared for 1 hr at 4° C. with gentle rotation. After this 1 hr incubation, samples were spun down at 3,000×g at 4° C. for 2 min and the normalized, pre-cleared lysate were subsequently loaded onto Protein A-Sepharose 4B beads coupled with 5 ug of Met (CST, #8198) antibody. MET was immunoprecipitated from Hs746T lysates for 2 hr at 4° C. with gentle rotation, after which samples were spun down at 3,000×g at 4° C. for 2 min, flow-thru was collected to assess pulldown efficiency (see FIG. S6D), and the beads were washed once with ice-cold lysis buffer and thrice with ice-cold 1×TBS-T (137 mM NaCl, 2.7 mM KCl, 19 mM Tris-HCl pH 7.5, 0.02% Tween-20). The beads were resuspended in 1×LDS sample buffer containing 5% BME. Immunoprecipitated protein was eluted off of the beads by heating at 95C for 5 min and the supernatant was run on an SDS-PAGE gel and evaluated for the presence of immunoprecipitated total Met (CST,

3127), as well as ubiquitinated Met (CST, #3936). Whole-cell lysate refers to the normalized, input lysate loaded onto Protein A-Sepharose beads.

TUBE1 Immunoprecipitation Experiments

TUBE1 immunoprecipitations were carried out exactly as described in the previous section (Immunoprecipitation Experiments), except for the fact that 1 mg of Hs746T lysate was used and loaded onto 20 uL TUBE1 agarose (LifeSensors) resin per sample.

Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

In certain aspects, the description provides a bifunctional compound having the chemical structure: PTM-Linker-ULM, or a pharmaceutically acceptable salt, enantiomer, stereoisomer, solvate, polymorph or prodrug thereof, wherein: ULM is a small molecule E3 ubiquitin ligase binding moiety that binds an E3 ubiquitin ligase; PTM is a small molecule receptor tyrosine kinase (RTK) protein targeting moiety, wherein the PTM is at least one of; and Linker (L) is a bond or a chemical linking moiety covalently coupling the ULM and the PTM.

In any of the aspects or embodiments described herein, the ULM is a moiety that binds an E3 ligase protein selected from the group consisting of Von Hippel-Lindau, cereblon, mouse double-minute homolog2, and IAP as described and exemplified herein. In any of the aspects or embodiments described herein, the described compounds include a PTM that comprises the structure of any of formulas I-XVII as described herein, including all variations described. In any of the aspects or embodiments described herein, the PTM is coupled to the ULM via a linker, wherein the linker (L) is a bond or chemical linker moiety as described herein. In any of the aspects or embodiments described herein, the linker is coupled to the PTM via an R group as described for formulas I-XVII.

In any of the aspects or embodiments described herein, the compound includes a linker (L) moiety having a structure as described herein coupling the PTM to the ULM. For example, in any of the aspects or embodiments, the linker comprises a chemical structural unit represented by the formula: -(A$^L$)$_q$-, wherein: (A$^L$)$_q$ is a group which is connected to at least one of a ULM, a PTM moiety, or a combination thereof; q is an integer greater than or equal to 1; each A$^L$ is independently selected from the group consisting of, a bond, CRL1RL2, O, S, SO, SO2, NRL3, SO2NRL3, SONRL3, CONRL3, NRL3CONRL4, NRL3SO2NRL4, CO, CRL1=CRL2, C=C, SiRL1RL2, P(O)RL1, P(O)ORL1, NRL3C(=NCN)NRL4, NRL3C(=NCN), NRL3C(=CNO2)NRL4, C3-11cycloalkyl optionally substituted with 0-6 RL1 and/or RL2 groups, C3-11heterocyclyl optionally substituted with 0-6 RL1 and/or RL2 groups, aryl optionally substituted with 0-6 RL1 and/or RL2 groups, heteroaryl optionally substituted with 0-6 RL1 and/or RL2 groups, where RL1 or RL2, each independently are optionally linked to other groups to form cycloalkyl and/or heterocyclyl moiety, optionally substituted with 0-4 RL5 groups; and RL1, RL2, RL3, RL4 and RL5 are, each independently, H, halo, C1-8alkyl, OC1-8alkyl, SC1-8alkyl, NHC1-8alkyl, N(C1-8alkyl)2, C3-11cycloalkyl, aryl, heteroaryl, C3-11heterocyclyl, OC1-8cycloalkyl, SC1-8cycloalkyl, NHC1-8cycloalkyl, N(C1-8cycloalkyl)2, N(C1-8cycloalkyl)(C1-8alkyl), OH, NH2, SH, SO2C1-8alkyl, P(O)(OC1-8alkyl)(C1-8alkyl), P(O)(OC1-8alkyl)2, CC-C1-8alkyl, CCH, CH=CH(C1-8alkyl), C(C1-8alkyl)=CH(C1-8alkyl), C(C1-8alkyl)=C(C1-8alkyl)2, Si(OH)3, Si(C1-8alkyl)3, Si(OH)(C1-8alkyl)2, COC1-8alkyl, CO2H, halogen, CN, CF3, CHF2, CH2F, NO2, SF5, SO2NHC1-8alkyl, SO2N(C1-8alkyl)2, SONHC1-8alkyl, SON(C1-8alkyl)2, CONHC1-8alkyl, CON(C1-8alkyl)2, N(C1-8alkyl)CONH(C1-8alkyl), N(C1-8alkyl)CON(C1-8alkyl)2, NHCONH(C1-8alkyl), NHCON(C1-8alkyl)2, NHCONH2, N(C1-8alkyl)SO2NH(C1-8alkyl), N(C1-8alkyl) SO2N(C1-8alkyl)2, NH SO2NH(C1-8alkyl), NH SO2N(C1-8alkyl)2, NH SO2NH2.

In any of the aspects or embodiments, the linker (L) has a chemical structure selected from:

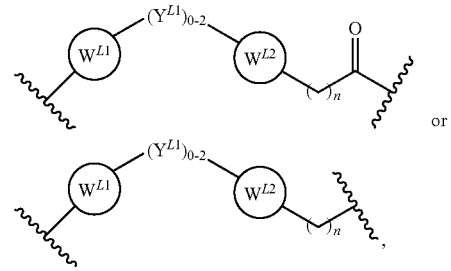

or wherein W$^{L1}$ and W$^{L2}$ are each independently a 4-8 membered ring with 0-4 heteroatoms, optionally substituted with R$^Q$, each R$^Q$ is independently a H, halo, OH, CN, CF$_3$, C$_1$-C$_6$ alkyl (linear, branched, optionally substituted), C$_1$-C$_6$ alkoxy (linear, branched, optionally substituted), or 2 R$^Q$ groups taken together with the atom they are attached to, form a 4-8 membered ring system containing 0-4 heteroatoms; Y$^{L1}$ is each independently a bond, C$_1$-C$_6$ alkyl (linear, branched, optionally substituted) and optionally one or more C atoms are replaced with O; or C$_1$-C$_6$ alkoxy (linear, branched, optionally substituted); n is 0-10; and a dashed line indicates the attachment point to the PTM or ULM moieties.

In any of the aspects or embodiments described herein, the compound comprises a linker (L) which is a polyethylenoxy group optionally substituted with aryl or phenyl comprising from 1 to 10 ethylene glycol units.

In any of the aspects or embodiments described herein, the compound has the structure selected from compounds 1-351 (FIG. 2), including analogs, derivatives, salts, prodrugs, polymorphs, analogs, derivatives, and deuterated forms thereof. In an additional aspect, the description provides a therapeutic composition comprising an effective amount of at least one of compounds 1-351 (FIG. 2), and pharmaceutically acceptable carrier. In any of the aspects or embodiments described herein, the composition further comprises at least one of an additional bioactive agent or another PROTAC compound as described and/or exemplified herein. In any of the aspects or embodiments, the additional bioactive agent is an anti-cancer (i.e., anti-oncologic) or anti-inflammatory agent. In any of the aspects or embodiments, the PROTAC compounds as described herein are co-administered (together or separately) with an anti-oncologic agent. In any of the aspects or embodiments described herein, the anti-oncologic is an anti-PD1 or anti-PD-L1 antibody. In an aspect, the description provides a therapeutic composition for co-administration comprising an effective amount of a compound as described herein, and an effective amount additional biologically active agent, for example, an anti-oncologic agent. In certain embodiments, the effective amount of the compounds as described herein, and the effective amount of the additional biologically active agent are comprised in separate containers.

In an aspect, the description provides a composition comprising a pharmaceutically acceptable carrier and an effective amount of at least one compound as described herein for treating a disease or disorder in a subject. In any of the aspects or embodiments, the disease or disorder is associated with receptor tyrosine kinase, e.g., EGFR, c-MET, HER1-3, or VEGFR, overexpression or hyperactivity. In any of the aspects or embodiments, the disease or disorder is cancer. In any of the aspects or embodiments, the disease or disorder is at least one of squamous-cell carcinoma of the lung, colon and anal cancers, glioblastoma, and epithelial tumors of the head and neck, psoriasis, eczema and atherosclerosis or a combination thereof.

In additional aspects, the description provides methods of treating a receptor tyrosine kinase (RTK)-related disease or disorder in a subject comprising administering to a subject in need thereof an effective amount of at least one compound as described herein, or a therapeutic composition comprising the same, wherein the at least one compound or composition is effective for ameliorating at least one symptom of the RTK-related disease or disorder. In any of the aspects or embodiments described herein, the RTK-related disease or disorder is cancer, inflammatory disease or reduced hair growth, that is associated with RTK overexpression or hyper-activity. In any of the aspects or embodiments described herein, the disease or disorder is related to EGFR overexpression or hyper-activity.

What is claimed is:

1. A bifunctional compound having the chemical structure:

PTM-Linker-ULM, or a pharmaceutically acceptable salt, enantiomer, stereoisomer, or solvate,
wherein:
(i) the ULM is a small molecule E3 ubiquitin ligase binding moiety that binds a cereblon E3 ubiquitin ligase and has a chemical structure selected from:

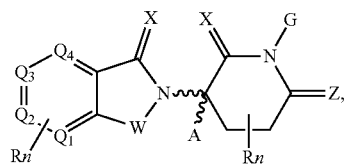 (a)

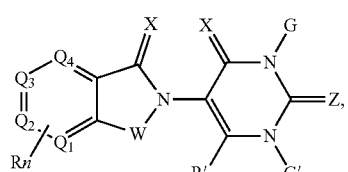 (b)

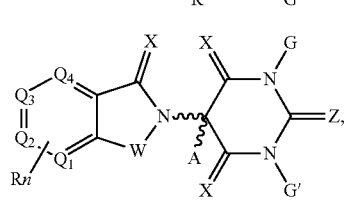 (c)

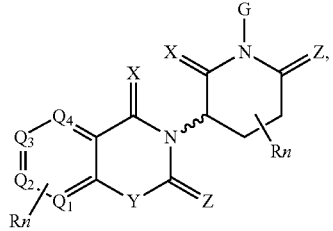 (d)

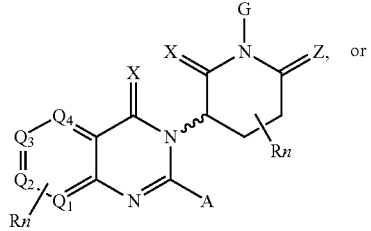 (e)

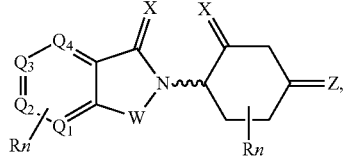 (f)

wherein:
W is selected from the group consisting of $CH_2$, CHR, C=O, $SO_2$, NH, and N-alkyl;
each X is independently selected from the group consisting of absent, O, and S;
Y is selected from the group consisting of $CH_2$, —C=CR', NH, N-alkyl, N-aryl, N-hetaryl, N-cycloalkyl, N-heterocyclyl, O, and S;
Z is selected from the group consisting of absent, O, and S;
G and G' are independently selected from the group consisting of H, optionally substituted alkyl, OH, R'OCOOR, R'OCONRR", $CH_2$-heterocyclyl optionally substituted with R', and benzyl optionally substituted with R';
$Q_1$, $Q_2$, $Q_3$, and $Q_4$ represent a carbon C substituted with a group independently selected from H, R, N or N-oxide;
A of the ULM is independently selected from the group H, alkyl, cycloalkyl, Cl and F;
n is an integer from 1 to 10;
R is selected from the group consisting of: —CONR'R", —OR', —NR'R", —SR', —$SO_2$R', —$SO_2$NR'R", —CR'R"—, —CR'NR'R"—, (—CR'O)$_n$R", -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR' COR", —$NO_2$, —$CO_2$R', —C(C=N—OR') R", —CR'=CR' R", —CCR', —S(C=O)(C=N—R') R", —$SF_5$ and —$OCF_3$, wherein one R is covalently joined via the linker (L) to the PTM;
R' and R" are independently selected from the group consisting of a H, optionally substituted alkyl, optionally substituted cycloalkyl, optionally substituted aryl, optionally substituted heteroaryl, optionally substituted heterocyclic, —C(=O)R, and optionally substituted heterocyclyl; and
~~~ represents a bond that may be stereospecific ((R) or (S)) or non-stereospecific;
(ii) the PTM is a small molecule protein targeting moiety selected from (a), (b), (c), or (d), wherein:
(a) PTM according to the structure of formula XIII:

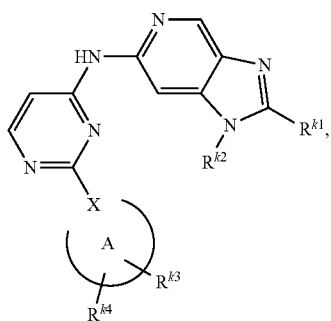

(XIII)

wherein:
A of formula XIII is a saturated or unsaturated 4-8 atom carbocyclic or heterocyclic ring comprising 1-7 heteroatoms;
$R^{k1}$ is selected from H, alkyl, cycloalkyl, alkenyl, alkynyl, aryl, or heteroaryl, wherein the said alkyl, aryl or heteroaryl is optionally substituted with 1 to 2 substituents selected from alkyl, halogen, haloalkyl, hydroxyl, alkoxy, amino, alkylamino, dialkylamino and cyano;
$R^{k2}$ is selected from H, alkyl, cycloalkyl, aryl, or heteroaryl, wherein the said alkyl, aryl or heteroaryl is optionally substituted with 1 to 2 substituents selected from alkyl, halogen, haloalkyl, hydroxyl, alkoxy, amino, alkylamino, dialkylamino and cyano;
$R^{k3}$ and $R^{k4}$ are independently selected from H, hydroxyl, alkyl, alkoxy, aryl, —SO$^2$R$^{k2}$, or halogen, wherein the said hydroxyl, alkyl, aryl or alkoxy is optionally substituted with 1 to 2 substituents selected from alkyl, halogen, haloalkyl, hydroxyl, alkoxy, amino, alkylamino, dialkylamino and cyano; and
X is N or CH or C with a double bond to the neighbor atom in the ring,
wherein the PTM is coupled via the linker (L) to the ULM;
(b) the PTM according to the structure of formula XV:

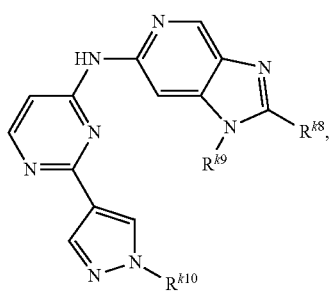

(XV)

wherein:
$R^{k8}$ is selected from H, alkyl, alkenyl, alkynyl, aryl, or heteroaryl, wherein the said alkyl, aryl or heteroaryl can be further substituted with 1 to 2 substituents selected from alkyl, halogen, haloalkyl, hydroxyl, alkoxy, amino, alkylamino, dialkylamino and cyano;
$R^{k9}$ is selected from H, alkyl, or cycloalkyl, wherein the said alkyl or cycloalkyl is optionally substituted with 1 to 3 substituents selected from alkyl, halogen, haloalkyl, hydroxyl, alkoxy, amino, alkylamino, dialkylamino and cyano; and
$R^{k10}$ is selected from H, alkyl, alkylsulfone, alkylcarboxamide or aryl, wherein the said alkyl or aryl is optionally substituted with 1 to 2 substituents selected from alkyl, halogen, alkylsulfone, alkylsulfonamide, amide, carboxamide, haloalkyl, hydroxyl, alkoxy, amino, amide, alkylamino, dialkylamino and cyano,
wherein the PTM is coupled via the linker (L) to the ULM;
(c) the PTM according to the structure of formula XVI:

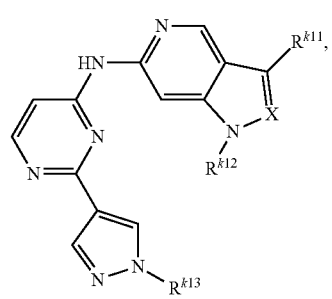

(XVI)

wherein:
$R^{k11}$ is selected from H, alkyl, alkoxy, —C(O)NHR, wherein R is selected from H, alkyl, cycloalkyl or a saturated heterocycle with 4-6 ring atoms;
$R^{k12}$ is selected from H, linear or branched alkyl, aryl, cycloalkyl or heteroaryl, wherein the alkyl, aryl or heteroaryl is optionally substituted with 1 to 2 substituents selected from alkyl, halogen, haloalkyl, hydroxyl, alkoxy, amino, alkylamino, dialkylamino and cyano;
$R^{k13}$ is selected from H, alkyl, —C(O)NHR, —C(O)R, —S(O)$_2$R, wherein R is H, alkyl or cycloalkyl, which can be further substituted with 1 to 2 substituents selected from alkyl, halogen, alkylsulfone, alkylsulfonamide, amide, carboxamide, haloalkyl, hydroxyl, alkoxy, amino, amide, alkylamino, dialkylamino and cyano; and
X is N or CH,
wherein the PTM is coupled via the linker (L) to the ULM; or (d) the PTM according to the structure of formula XVII:

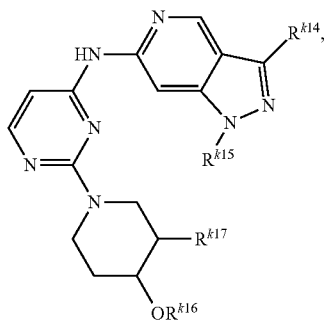

(XVII)

wherein:
R$^{k14}$ is selected from H, N, alkyl, alkoxy, —C(O)NHR, wherein R is selected from H, alkyl, cycloalkyl or a saturated heterocycle with 4-6 ring atoms;
R$^{k15}$ is selected from H, linear or branched alkyl, aryl, cycloalkyl or heteroaryl, wherein the said alkyl, aryl or heteroaryl is optionally substituted with 1 to 2 substituents selected from alkyl, halogen, haloalkyl, hydroxyl, alkoxy, amino, alkylamino, dialkylamino and cyano;
R$^{k16}$ is selected from H, alkyl or cycloalkyl, which is optionally substituted with 1 to 2 substituents selected from alkyl, halogen, alkylsulfone, alkylsulfonamide, amide, carboxamide, haloalkyl, hydroxyl, alkoxy, amino, amide, alkylamino, dialkylamino and cyano; and
R$^{k17}$ is selected from H, halogen, CN,
wherein the PTM is coupled via the linker (L) to the ULM; and
(iii) the linker (L) is a chemical linking moiety covalently coupling the ULM and the PTM and comprises a chemical structural unit represented by the formula:

-(A$^L$)$_q$-, wherein:
(A$^L$)$_q$ is a group which is connected to at least one of a ULM, a PTM moiety, or a combination thereof;
q is an integer greater than or equal to 1;
each A$^L$ is independently selected from the group consisting of CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L1}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{3-11}$heterocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$ cycloalkyl, aryl, heteroaryl, C$_{3-11}$heterocyclyl, OC$_{1-8}$cycloalkyl, SC$_{3-8}$cycloalkyl, NHC$_{3-8}$cycloalkyl, N(C$_{3-8}$ cycloalkyl)$_2$, N(C$_{3-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, and NH SO$_2$NH$_2$.

2. The compound according to claim 1, wherein the PTM comprises the structure of formula XIII:

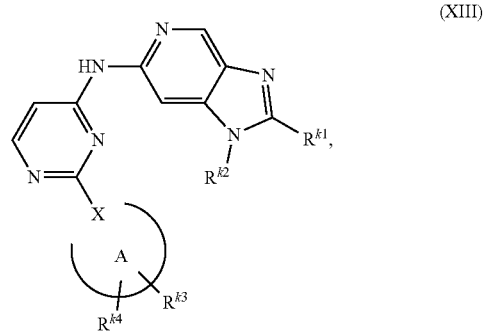

(XIII)

wherein:
A of formula XIII is a saturated or unsaturated 4-8 atom carbocyclic or heterocyclic ring comprising 1-7 heteroatoms;
R$^{k1}$ is selected from H, alkyl, cycloalkyl, alkenyl, alkynyl, aryl, or heteroaryl, wherein the said alkyl, aryl or heteroaryl is optionally substituted with 1 to 2 substituents selected from alkyl, halogen, haloalkyl, hydroxyl, alkoxy, amino, alkylamino, dialkylamino and cyano;
R$^{k2}$ is selected from H, alkyl, cycloalkyl, aryl, or heteroaryl, wherein the said alkyl, aryl or heteroaryl is optionally substituted with 1 to 2 substituents selected from alkyl, halogen, haloalkyl, hydroxyl, alkoxy, amino, alkylamino, dialkylamino and cyano;
R$^{k3}$ and R$^{k4}$ are independently selected from H, hydroxyl, alkyl, alkoxy, aryl, —SO$^2$R$^{k2}$, or halogen, wherein the said hydroxyl, alkyl, aryl or alkoxy is optionally substituted with 1 to 2 substituents selected from alkyl, halogen, haloalkyl, hydroxyl, alkoxy, amino, alkylamino, dialkylamino and cyano; and
X is N or CH or C with a double bond to the neighbor atom in the ring,
wherein the PTM is coupled via the linker (L) to the ULM.

3. The compound according to claim 1, wherein the PTM comprises the structure of formula XV

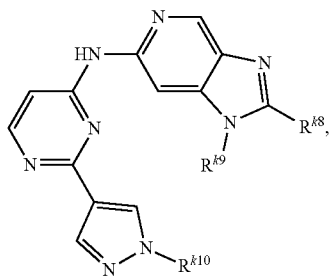

(XV)

wherein:
R$^{k8}$ is selected from H, alkyl, alkenyl, alkynyl, aryl, or heteroaryl, wherein the said alkyl, aryl or heteroaryl can be further substituted with 1 to 2 substituents selected from alkyl, halogen, haloalkyl, hydroxyl, alkoxy, amino, alkylamino, dialkylamino and cyano;

R$^{k9}$ is selected from H, alkyl, or cycloalkyl, wherein the said alkyl or cycloalkyl is optionally substituted with 1 to 3 substituents selected from alkyl, halogen, haloalkyl, hydroxyl, alkoxy, amino, alkylamino, dialkylamino and cyano; and R$^{k10}$ is selected from H, alkyl, alkylsulfone, alkylcarboxamide or aryl, wherein the said alkyl or aryl is optionally substituted with 1 to 2 substituents selected from alkyl, halogen, alkylsulfone, alkylsulfonamide, amide, carboxamide, haloalkyl, hydroxyl, alkoxy, amino, amide, alkylamino, dialkylamino and cyano, wherein the PTM is coupled via the linker (L) to the ULM.

4. The compound according to claim 1, wherein the PTM comprises the structure of formula XVI

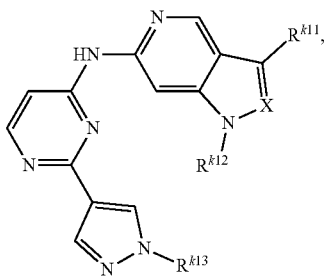

(XVI)

wherein:
R$^{k11}$ is selected from H, alkyl, alkoxy, —C(O)NHR, wherein R is selected from H, alkyl, cycloalkyl or a saturated heterocycle with 4-6 ring atoms;

R$^{k12}$ is selected from H, linear or branched alkyl, aryl, cycloalkyl or heteroaryl, wherein the alkyl, aryl or heteroaryl is optionally substituted with 1 to 2 substituents selected from alkyl, halogen, haloalkyl, hydroxyl, alkoxy, amino, alkylamino, dialkylamino and cyano;

R$^{k13}$ is selected from H, alkyl, —C(O)NHR, —C(O)R, —S(O)$_2$R, wherein R is H, alkyl or cycloalkyl, which can be further substituted with 1 to 2 substituents selected from alkyl, halogen, alkylsulfone, alkylsulfonamide, amide, carboxamide, haloalkyl, hydroxyl, alkoxy, amino, amide, alkylamino, dialkylamino and cyano; and X is N or CH,
wherein the PTM is coupled via the linker (L) to the ULM.

5. The compound according to claim 1, wherein the PTM comprises the structure of formula XVII

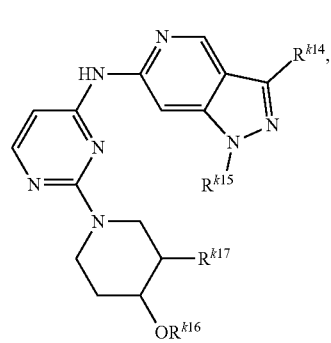

(XVII)

wherein:
R$^{k14}$ is selected from H, N, alkyl, alkoxy, —C(O)NHR, wherein R is selected from H, alkyl, cycloalkyl or a saturated heterocycle with 4-6 ring atoms;

R$^{k15}$ is selected from H, linear or branched alkyl, aryl, cycloalkyl or heteroaryl, wherein the said alkyl, aryl or heteroaryl is optionally substituted with 1 to 2 substituents selected from alkyl, halogen, haloalkyl, hydroxyl, alkoxy, amino, alkylamino, dialkylamino and cyano;

R$^{k16}$ is selected from H, alkyl or cycloalkyl, which is optionally substituted with 1 to 2 substituents selected from alkyl, halogen, alkylsulfone, alkylsulfonamide, amide, carboxamide, haloalkyl, hydroxyl, alkoxy, amino, amide, alkylamino, dialkylamino and cyano; and R$^{k17}$ is selected from H, halogen, CN,
wherein the PTM is coupled via the linker (L) to the ULM.

6. The compound according to claim 1, wherein the linker (L) is coupled to the PTM via R$^{k1}$, R$^{k2}$, R$^{k3}$, R$^{k4}$, R$^{k8}$, R$^{k9}$, R$^{k10}$, R$^{k11}$, R$^{k12}$, R$^{k13}$, R$^{k14}$, R$^{k15}$, R$^{k16}$, or R$^{k17}$.

7. The compound according to claim 2, wherein the linker (L) is coupled to the PTM via R$^{k1}$, R$^{k2}$, R$^{k3}$, or R$^{k4}$.

8. The compound according to claim 3, wherein the linker (L) is coupled to the PTM via R$^{k8}$, R$^{k9}$, or R$^{k10}$.

9. The compound according to claim 4, wherein the linker (L) is coupled to the PTM via R$^{k11}$, R$^{k12}$, or R$^{k13}$.

10. The compound according to claim 5, wherein the linker (L) is coupled to the PTM via R$^{k14}$, R$^{k15}$, R$^{k16}$, or R$^{k17}$.

11. The compound according to claim 1, wherein the compound is selected from the group consisting of:
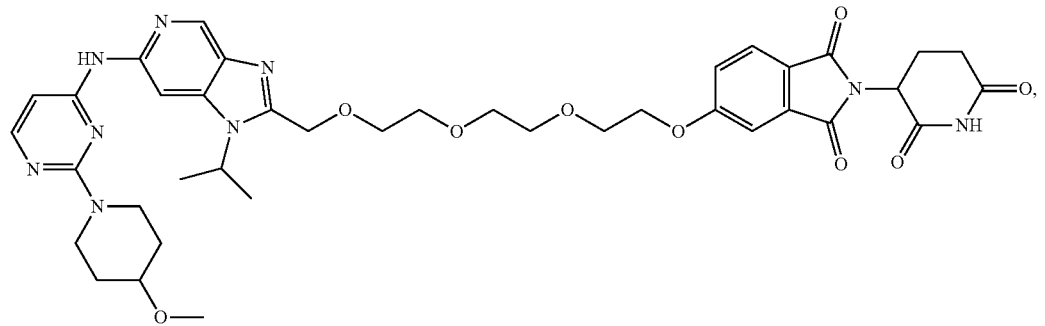
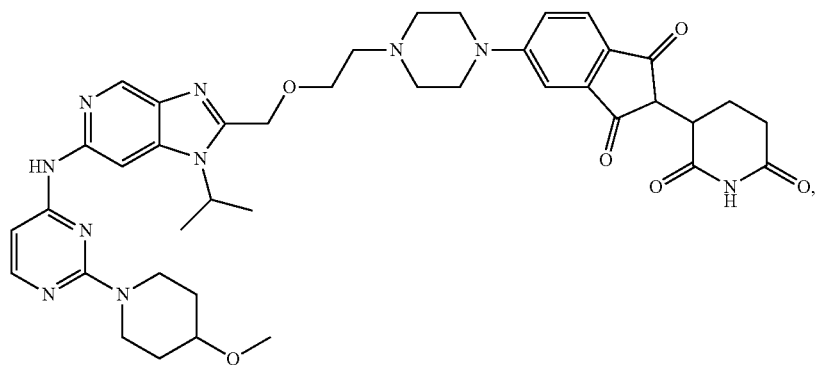
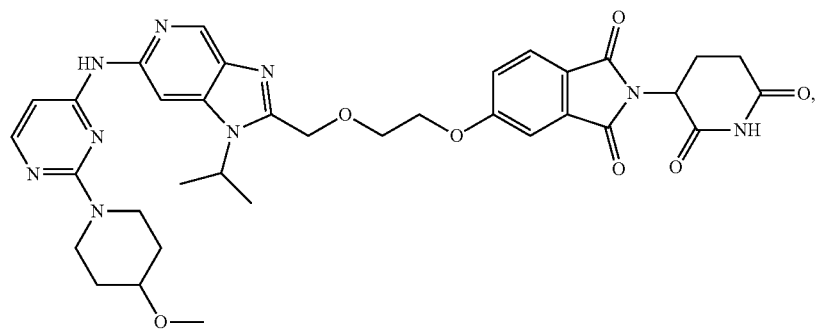
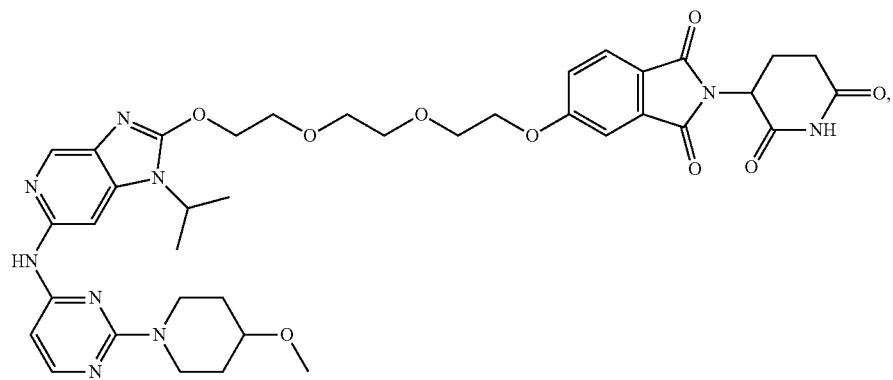

827 828
-continued
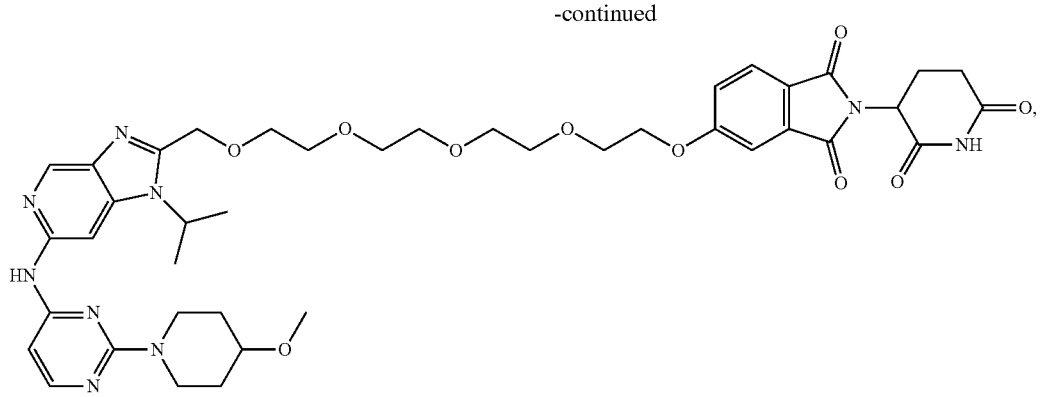
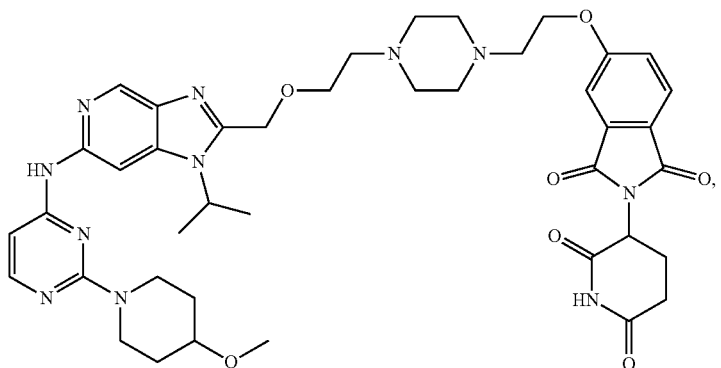
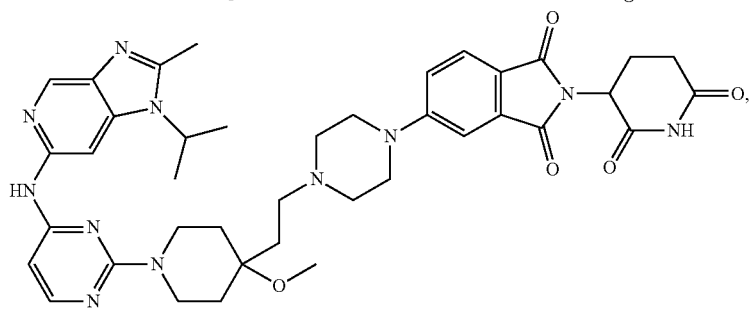
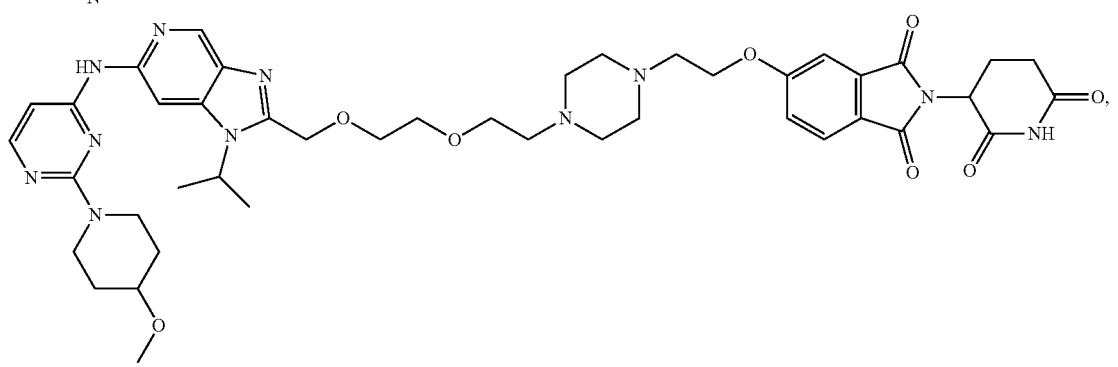
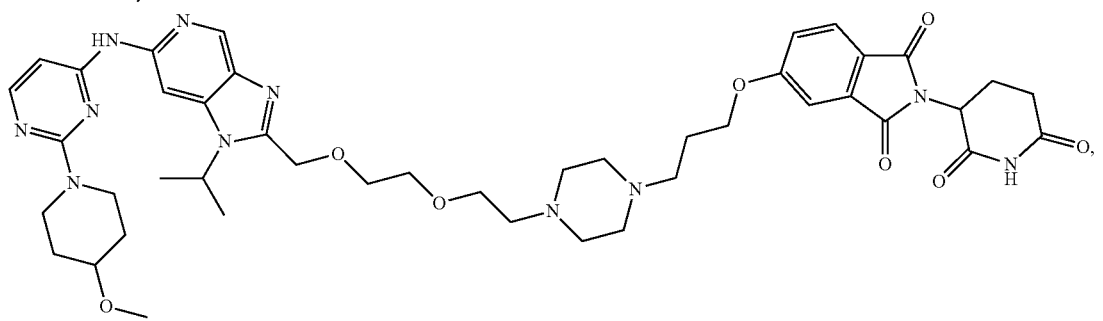

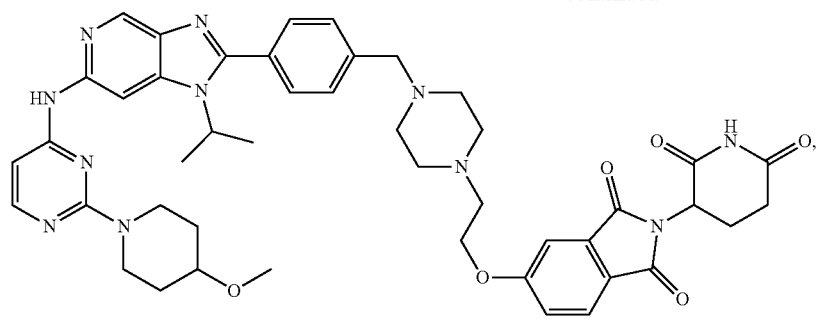
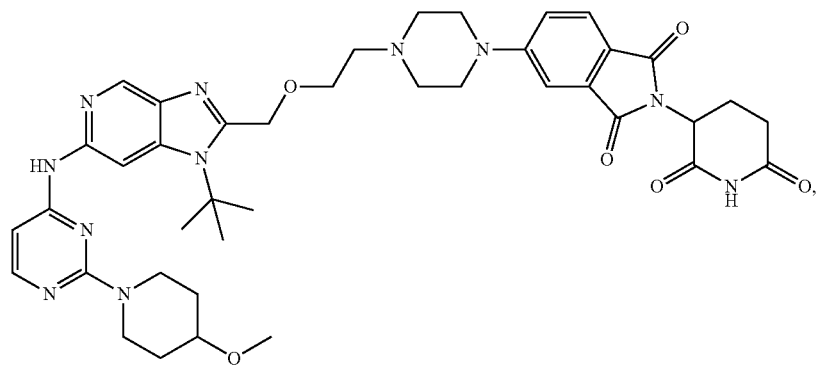
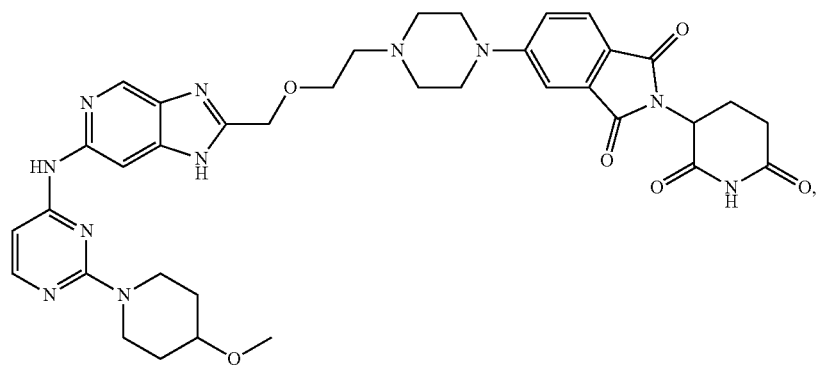
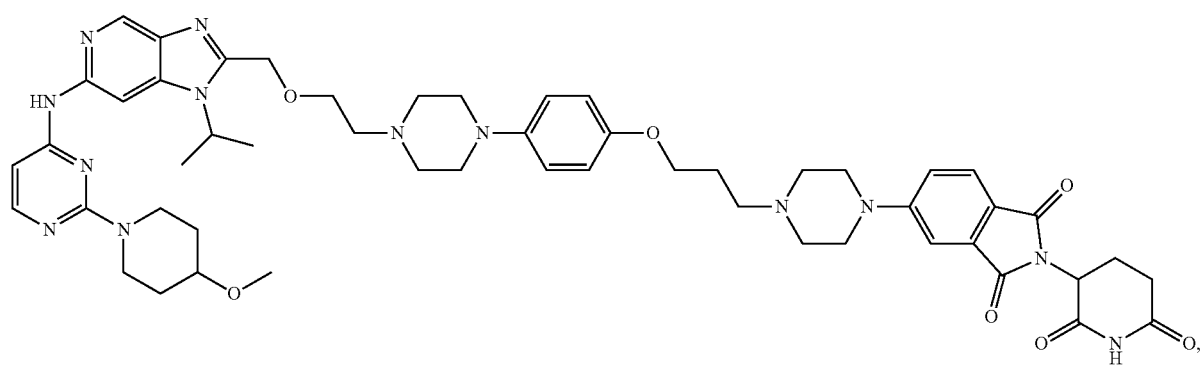

831 832
-continued
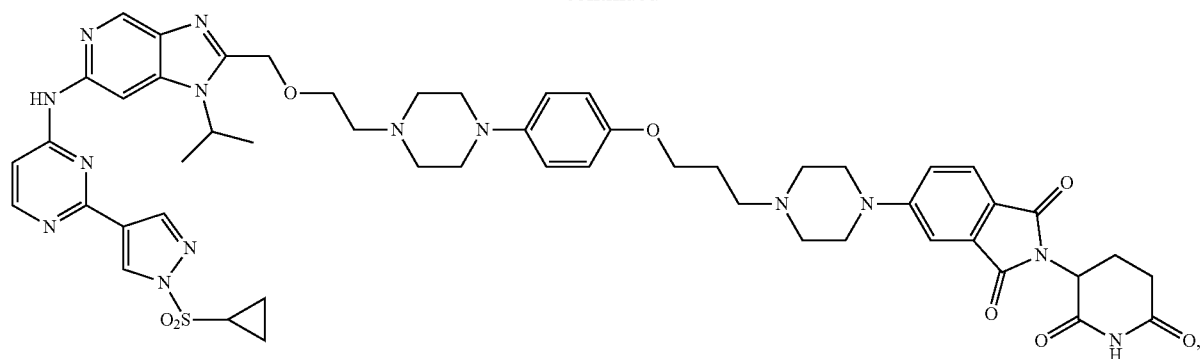
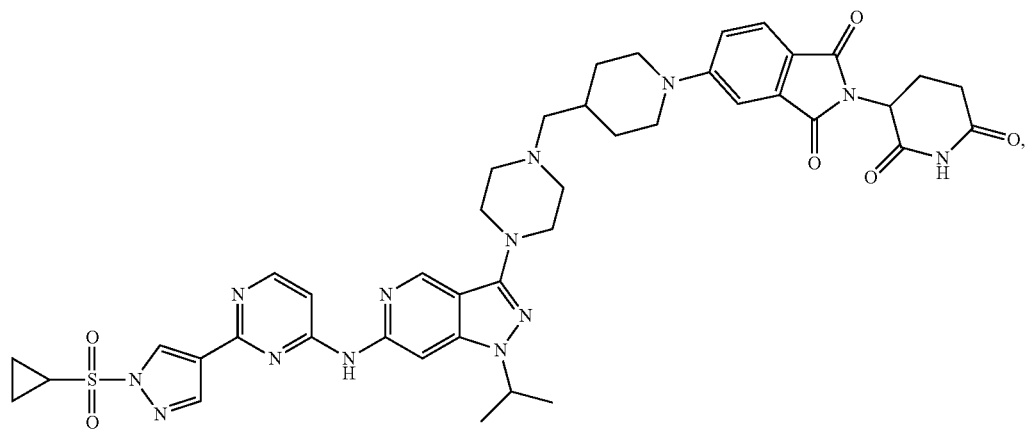
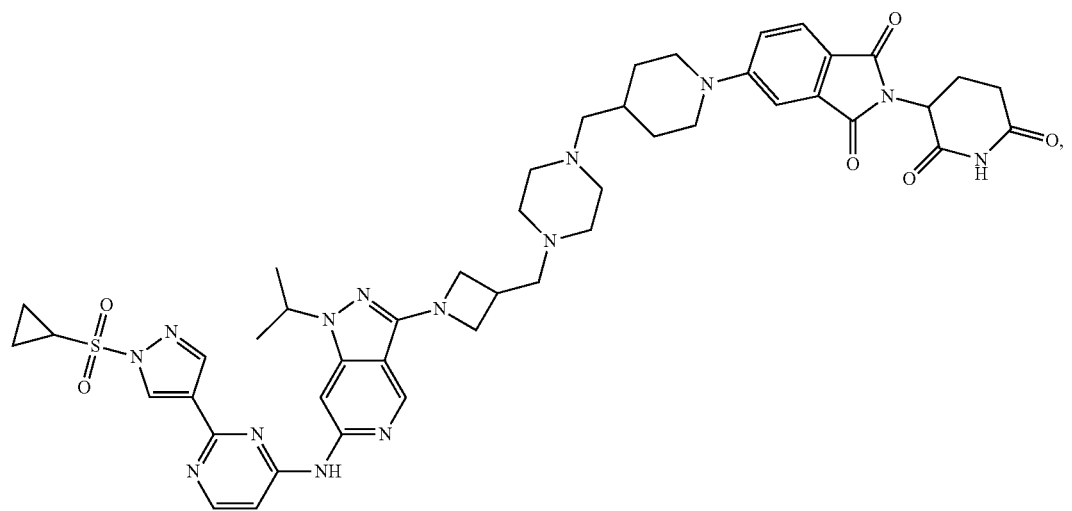

-continued
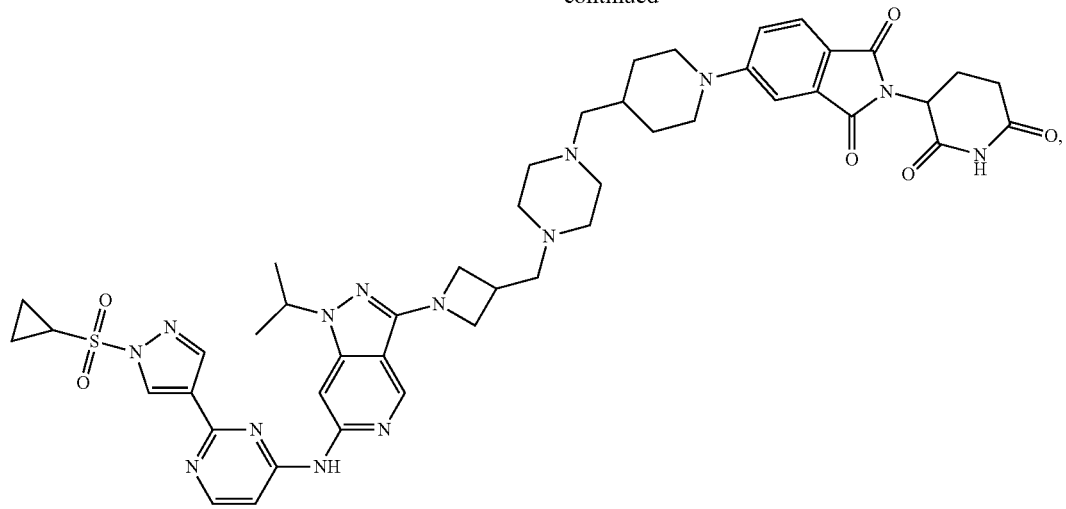
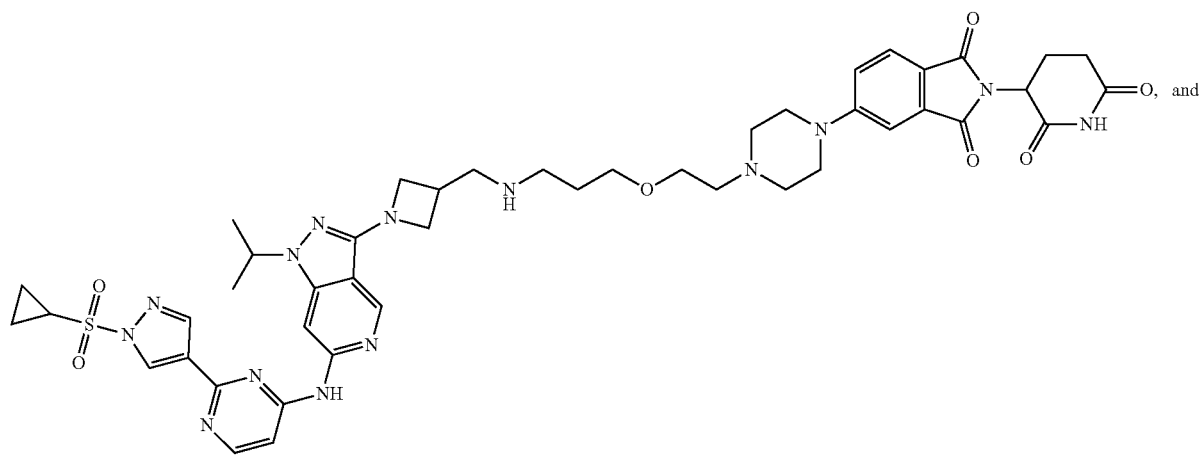
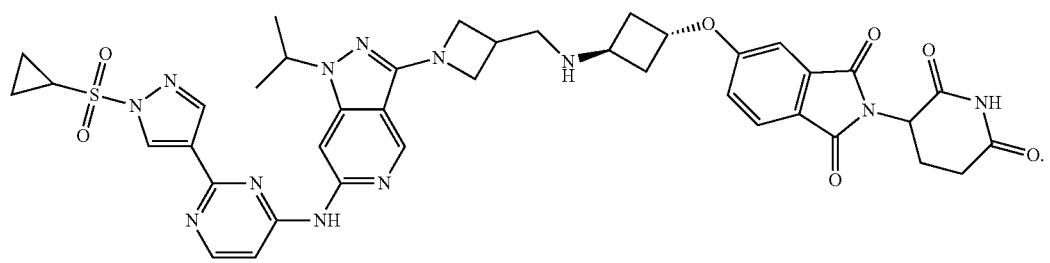
12. The compound of claim 1, wherein the ULM has a chemical structure represented by:
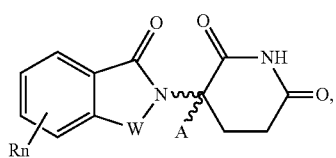
wherein:
W is independently selected from the group CH$_2$, C=O, NH, and N-alkyl;
A is independently selected from a H, methyl, optionally substituted alkyl;
n is an integer from 1 to 4; and
⌇ represents a bond that may be stereospecific ((R) or (S)) or non-stereospecific.

13. The compound of claim 1, wherein the linker (L) comprises a group represented by a structure selected from the group consisting of:
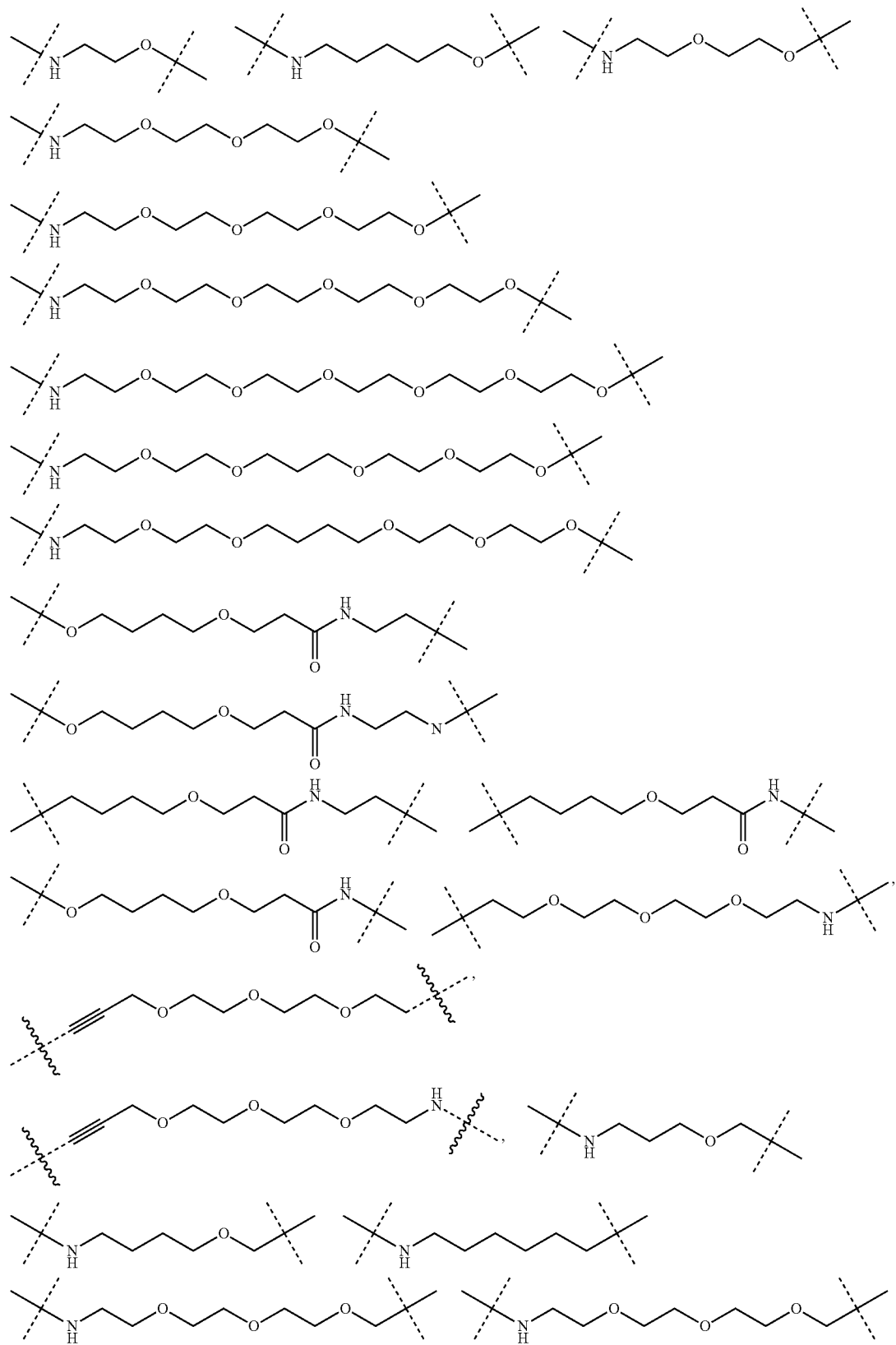

-continued
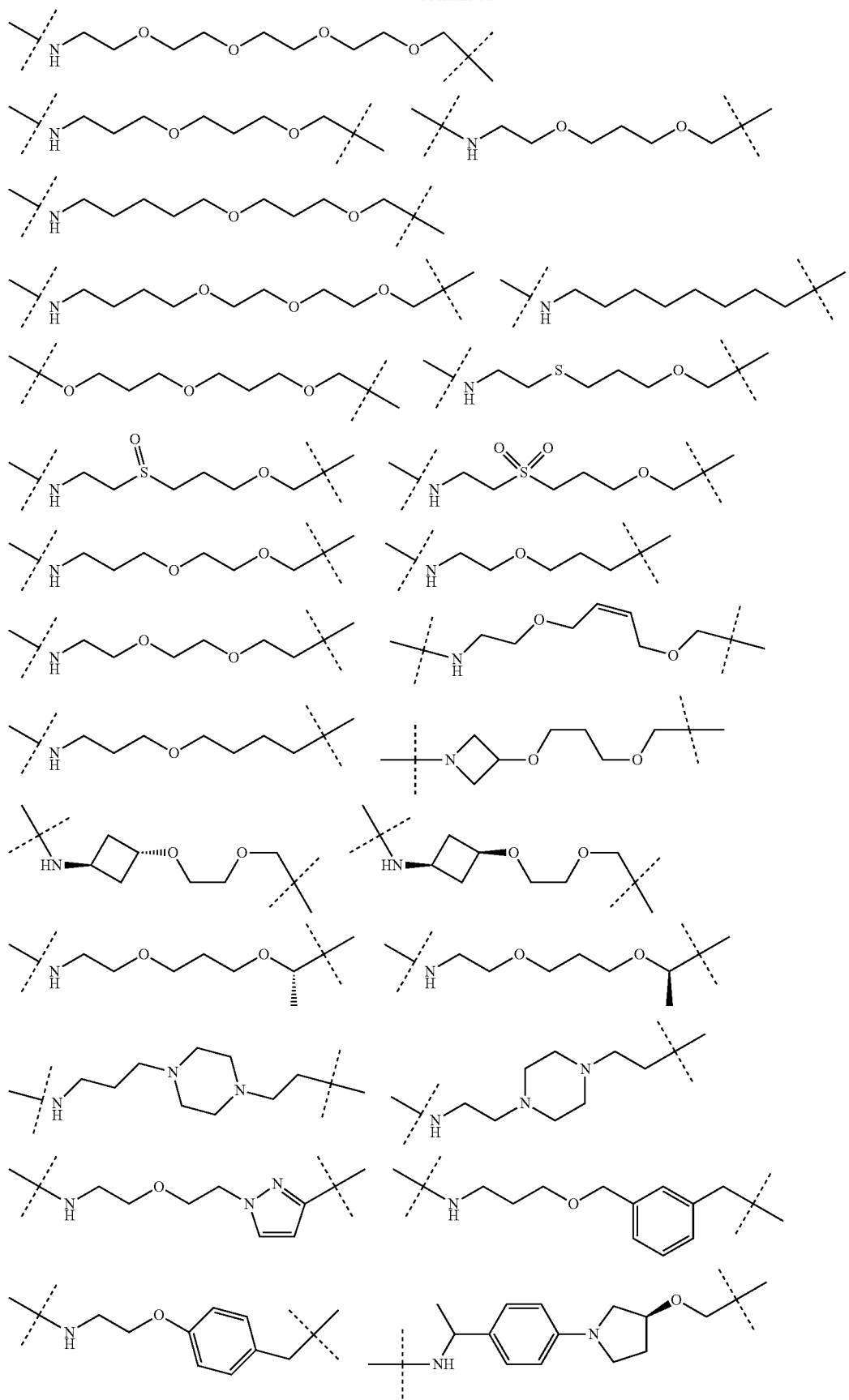

-continued
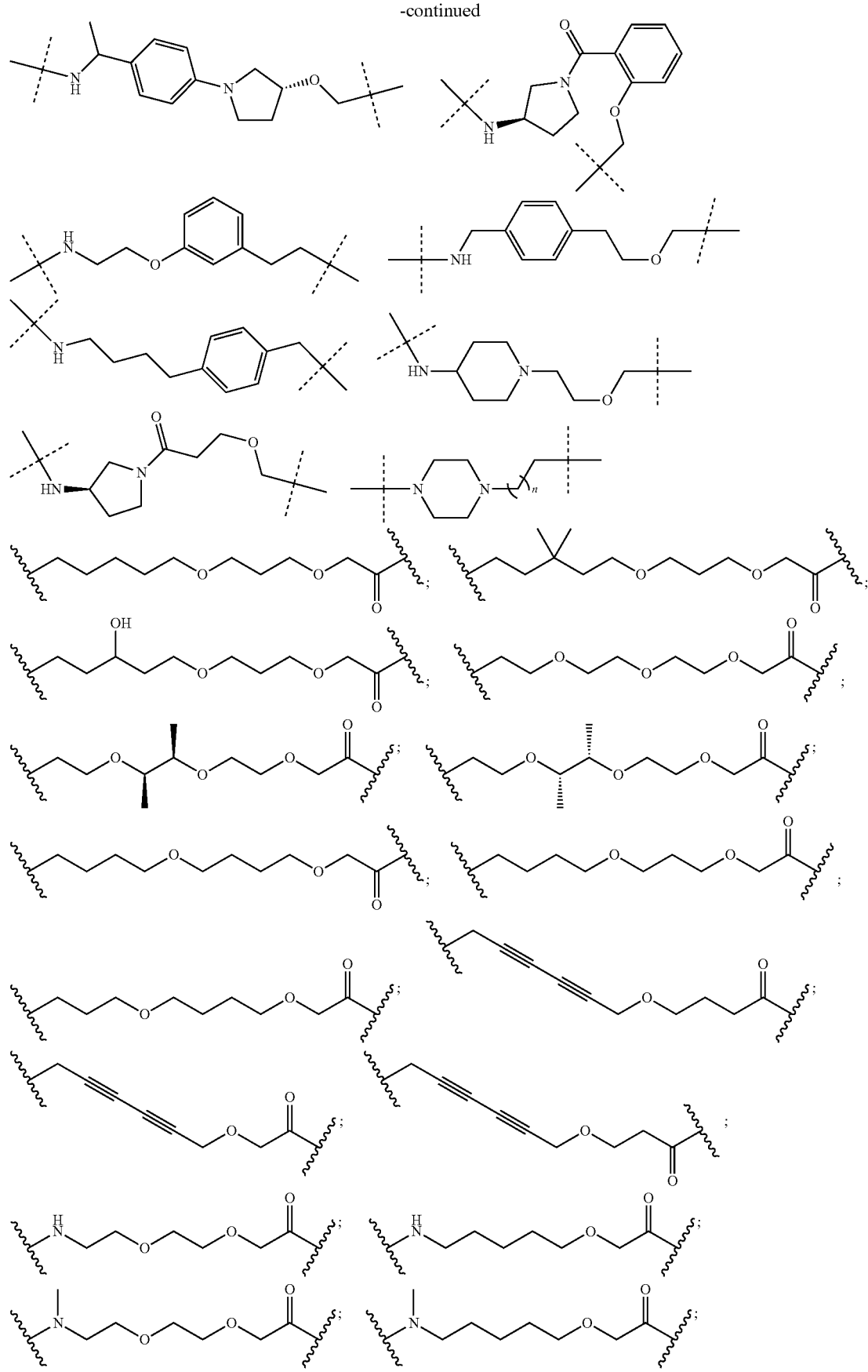

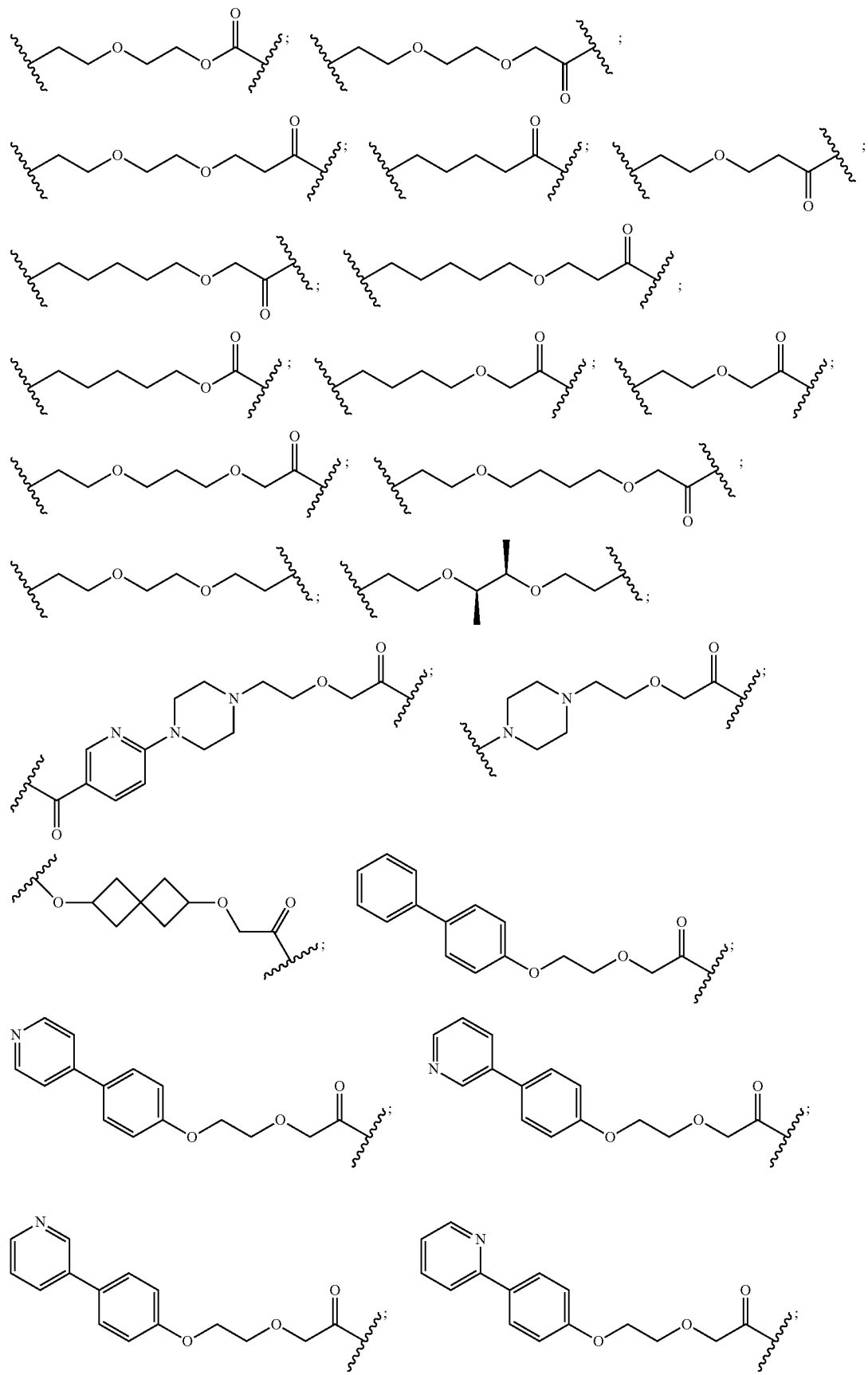

843 844
-continued
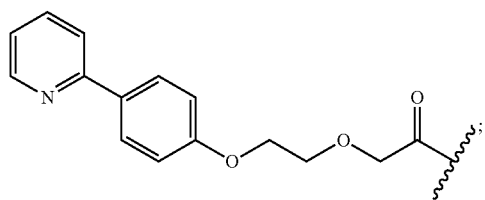 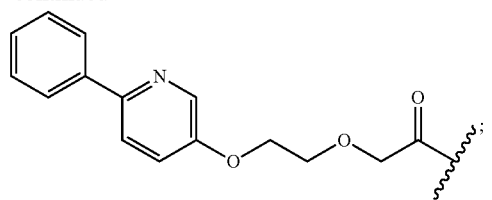
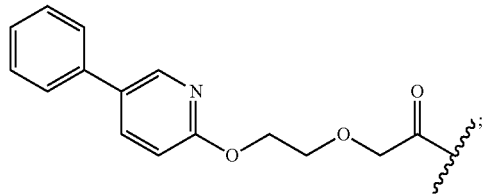 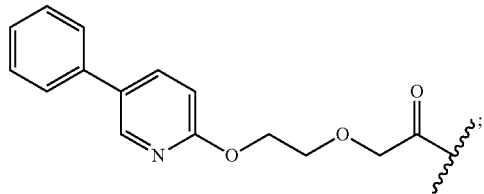
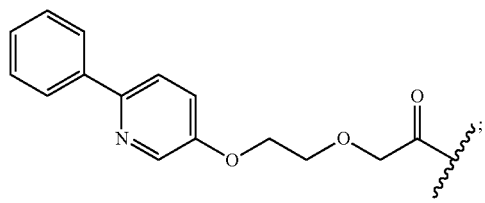 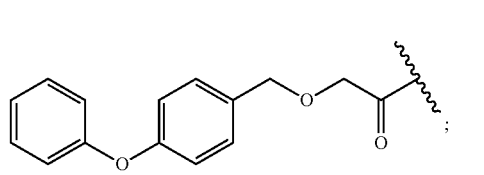
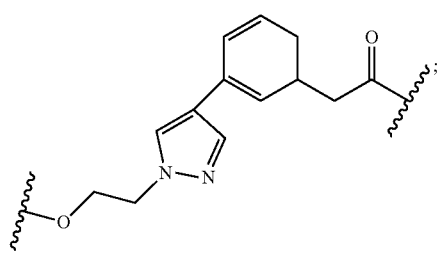 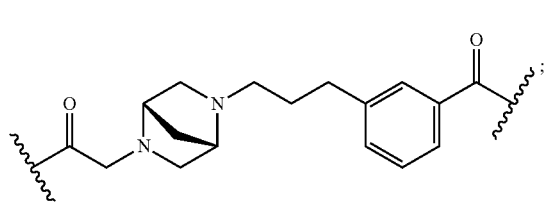
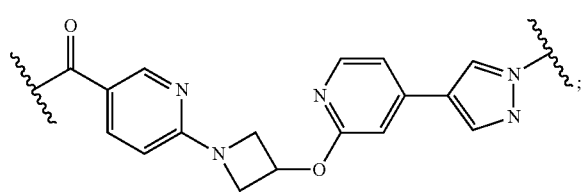
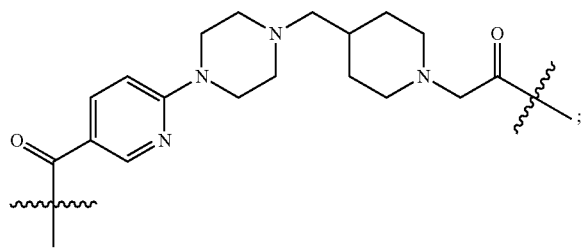
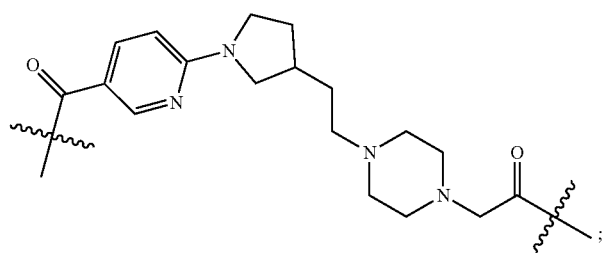

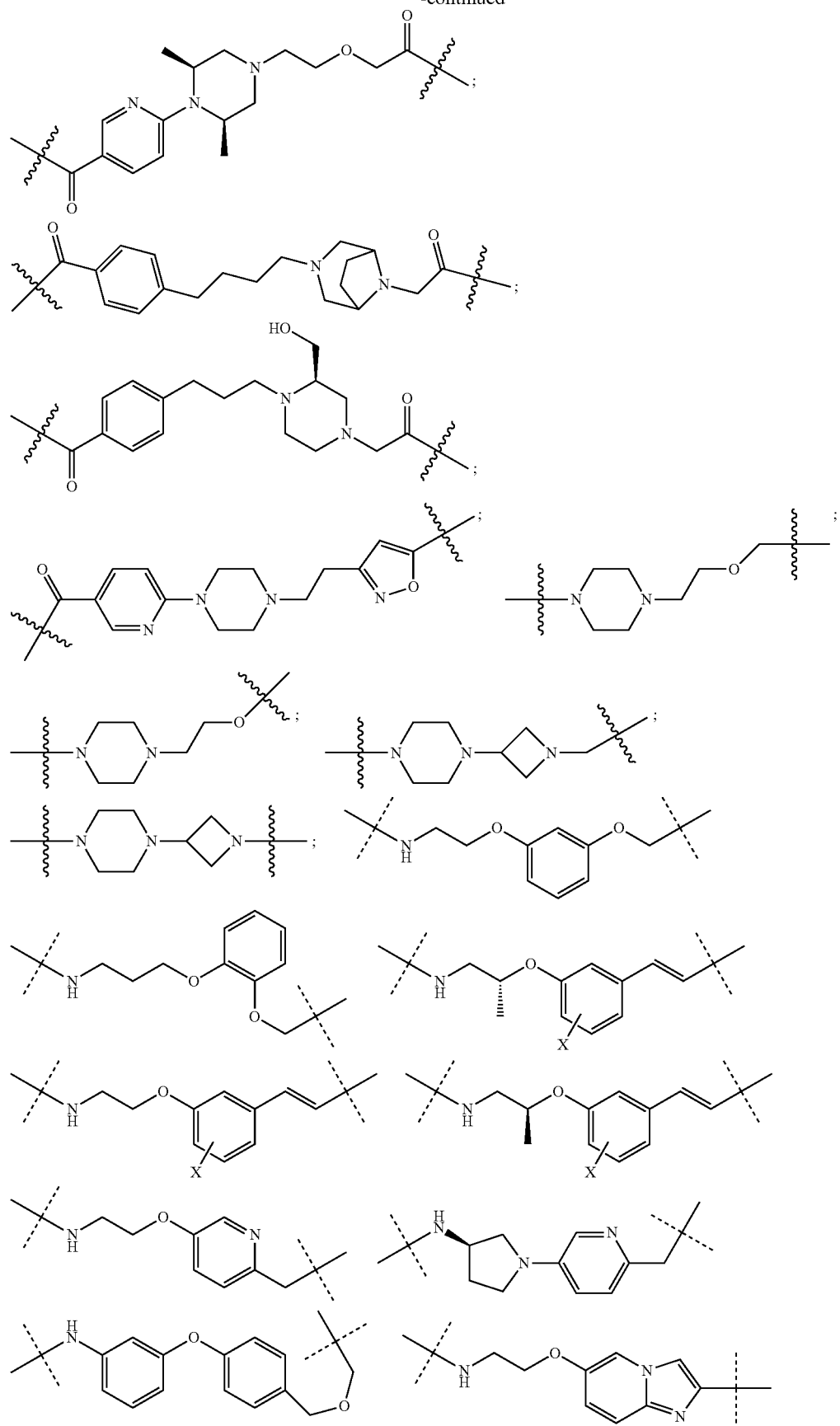

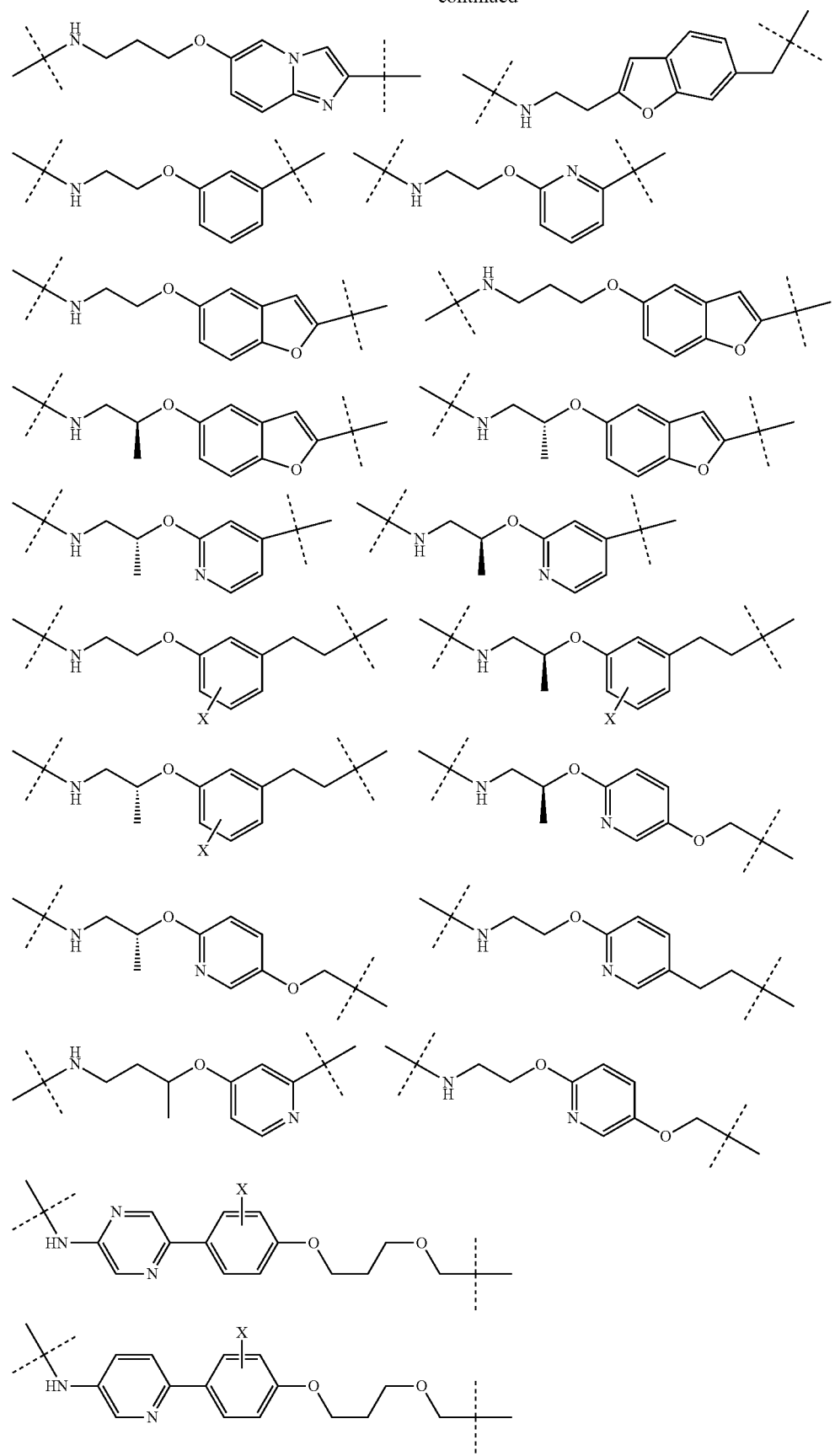

-continued
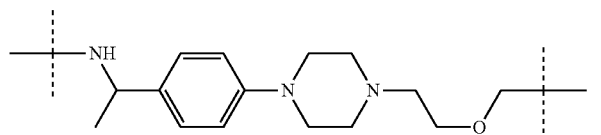
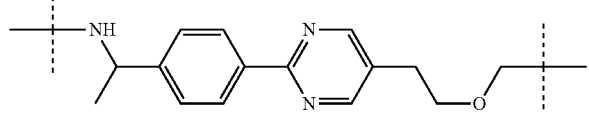
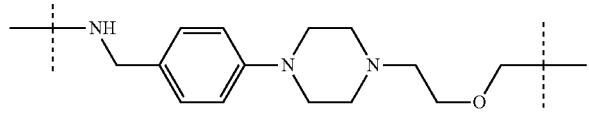
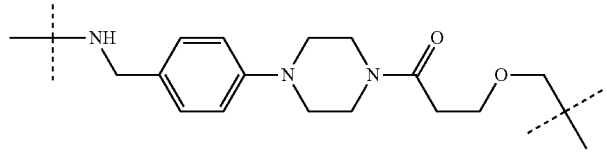
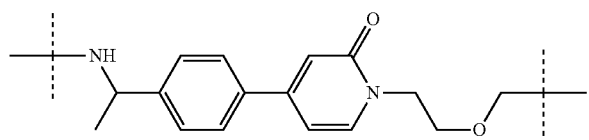
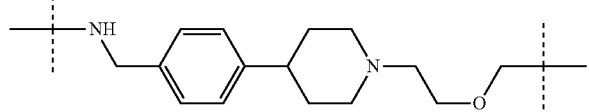
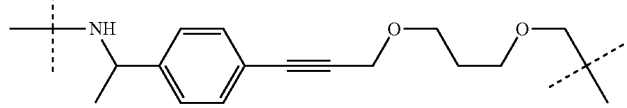
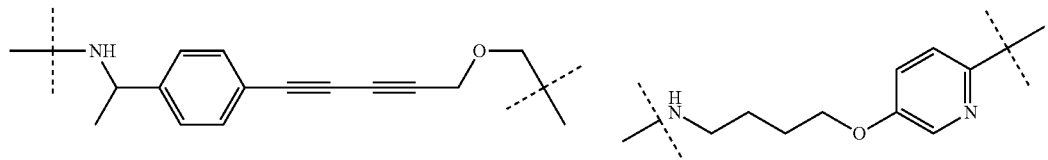
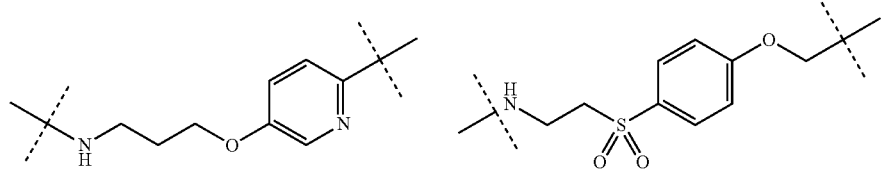
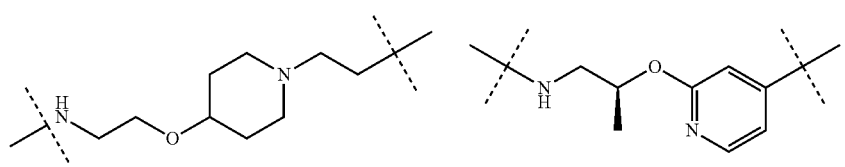

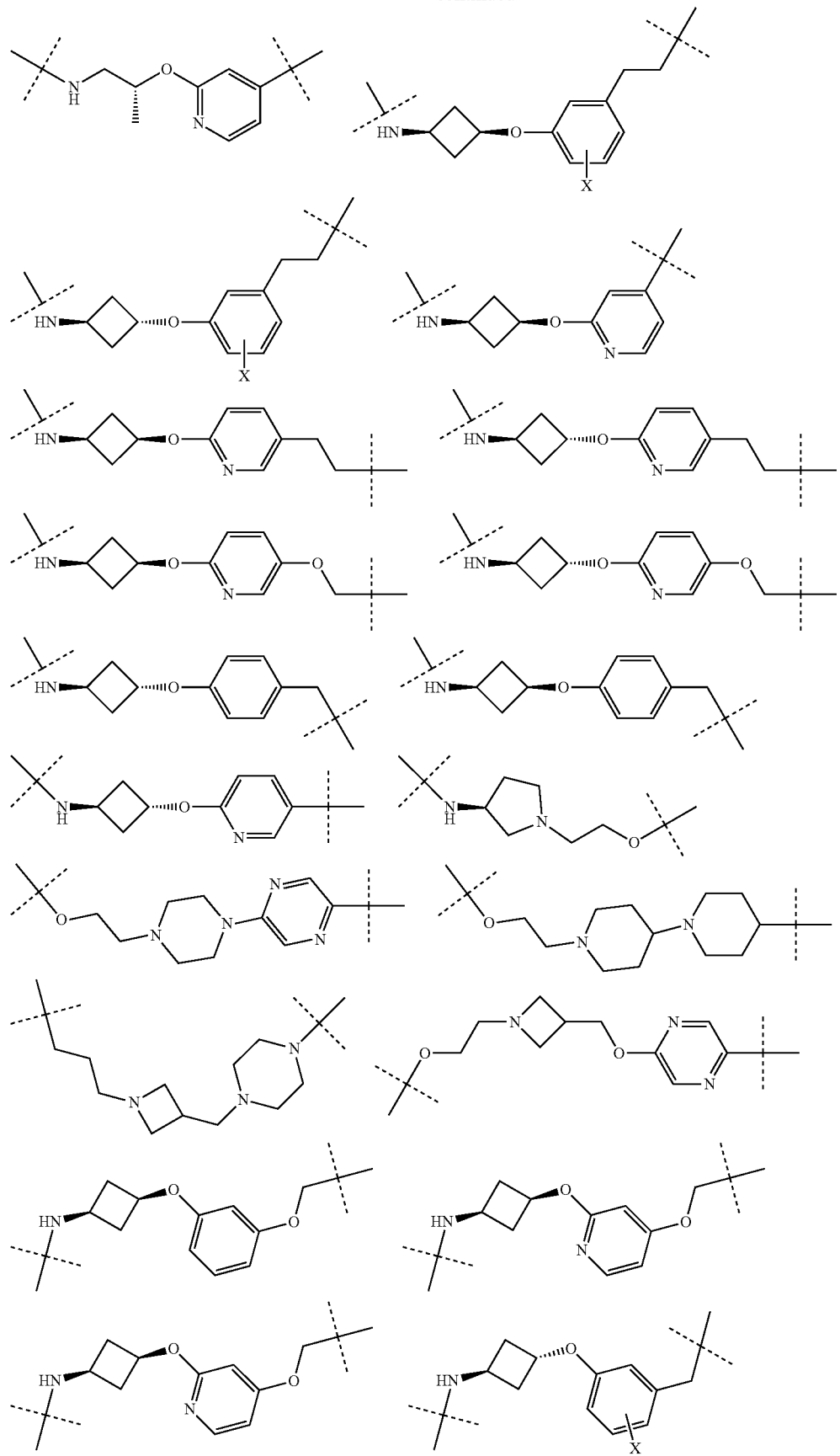

-continued
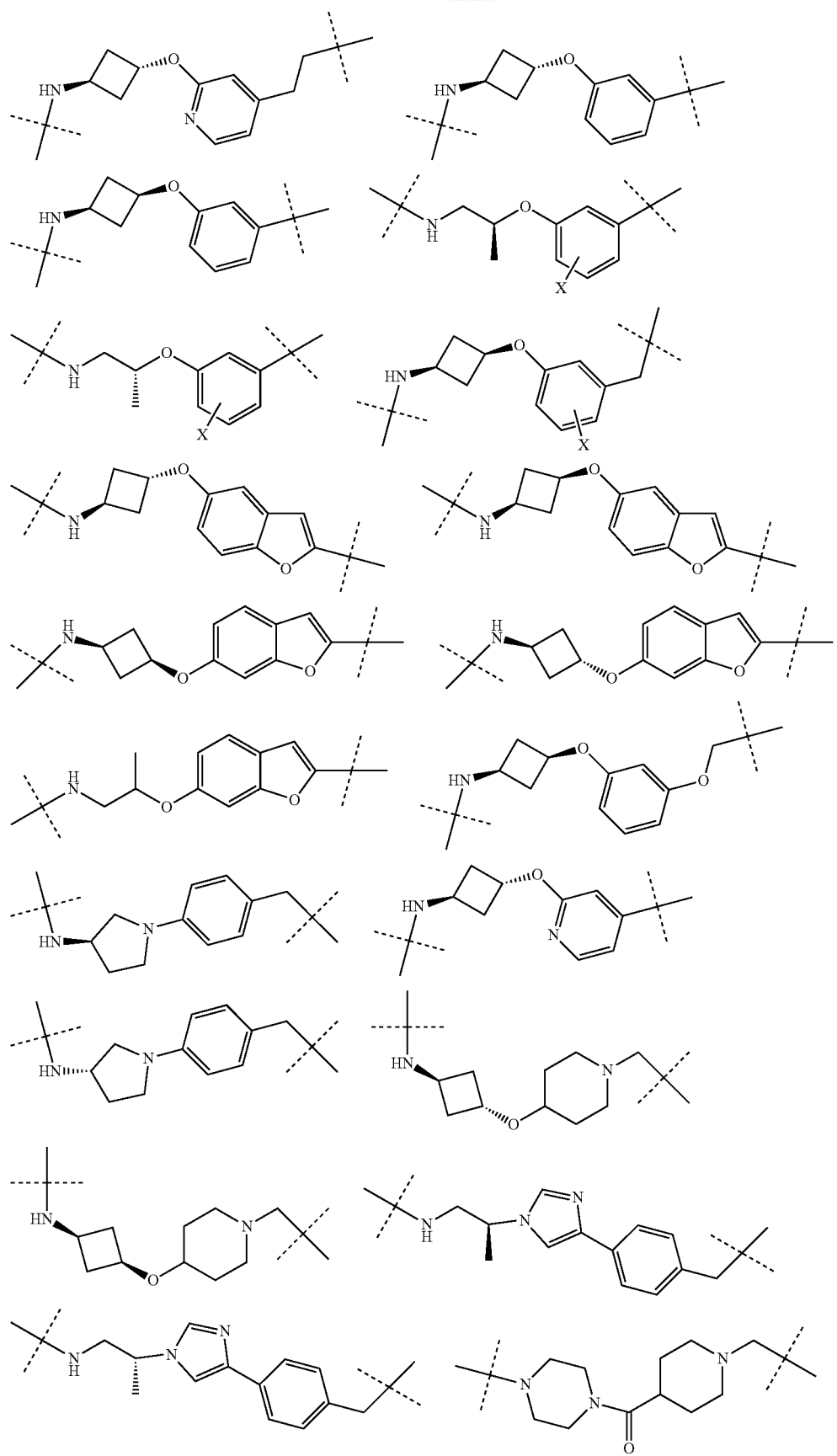

-continued
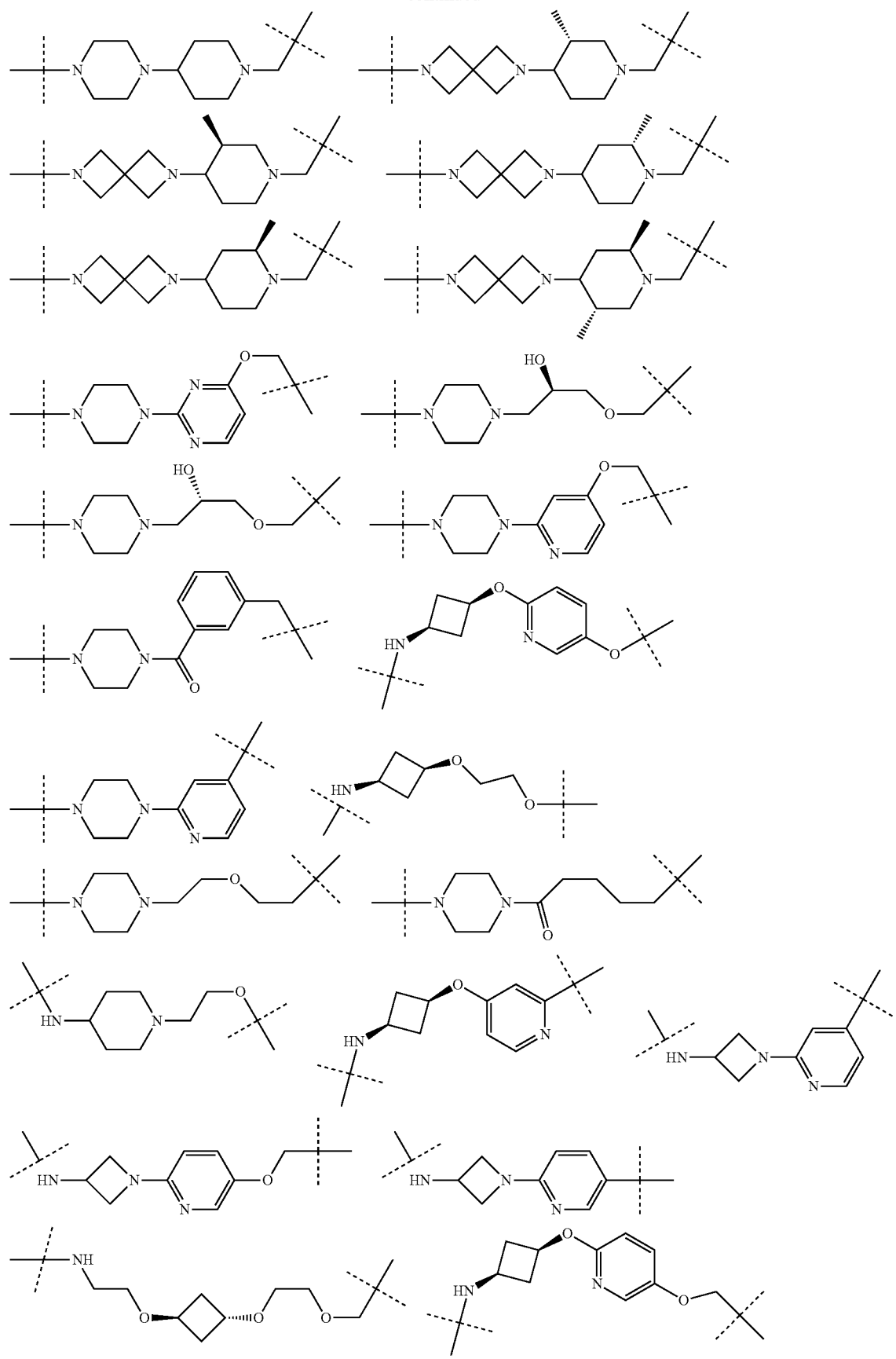

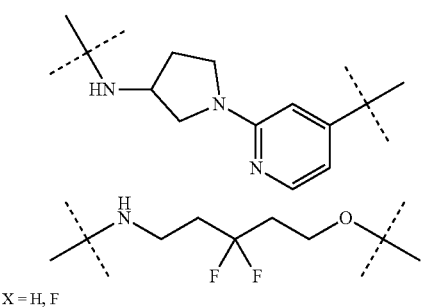
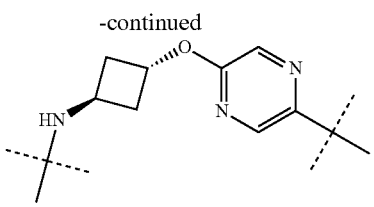
-continued
X = H, F
15
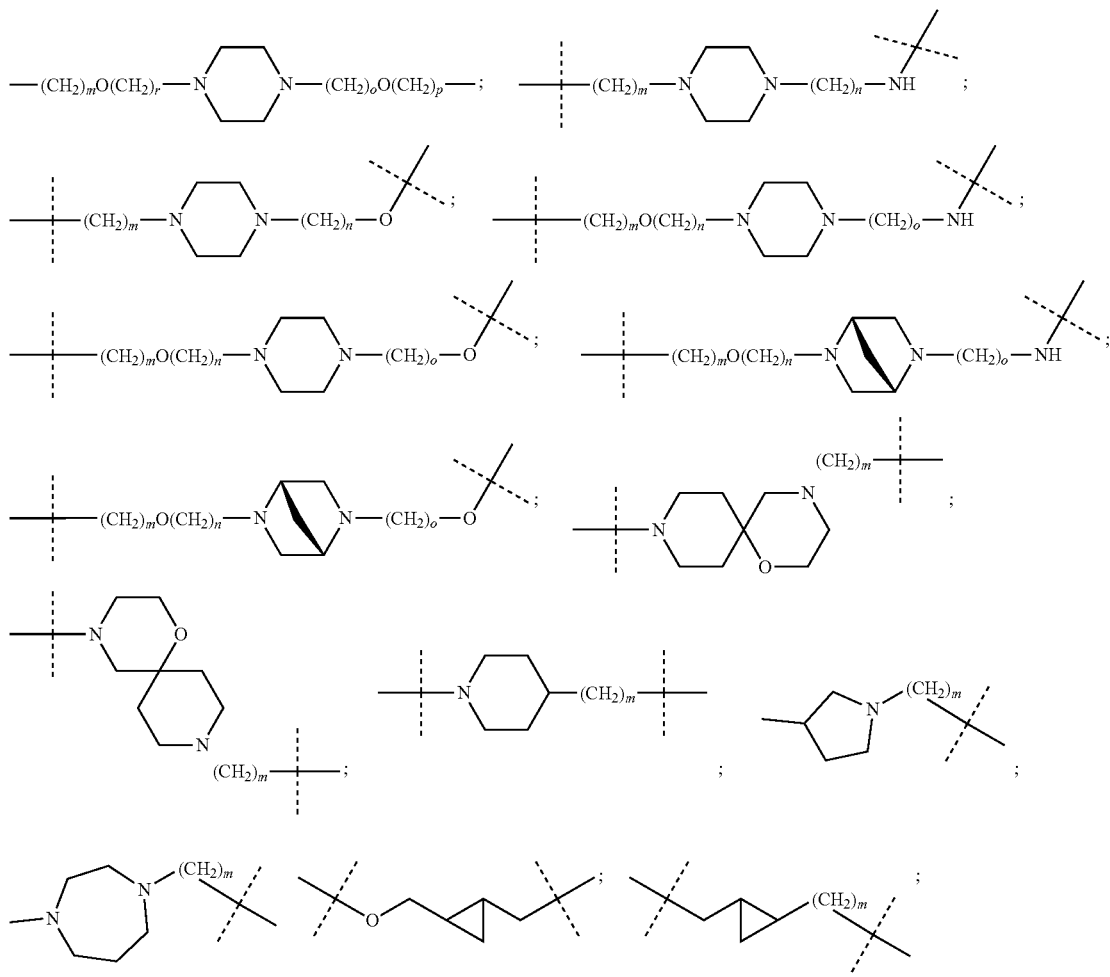

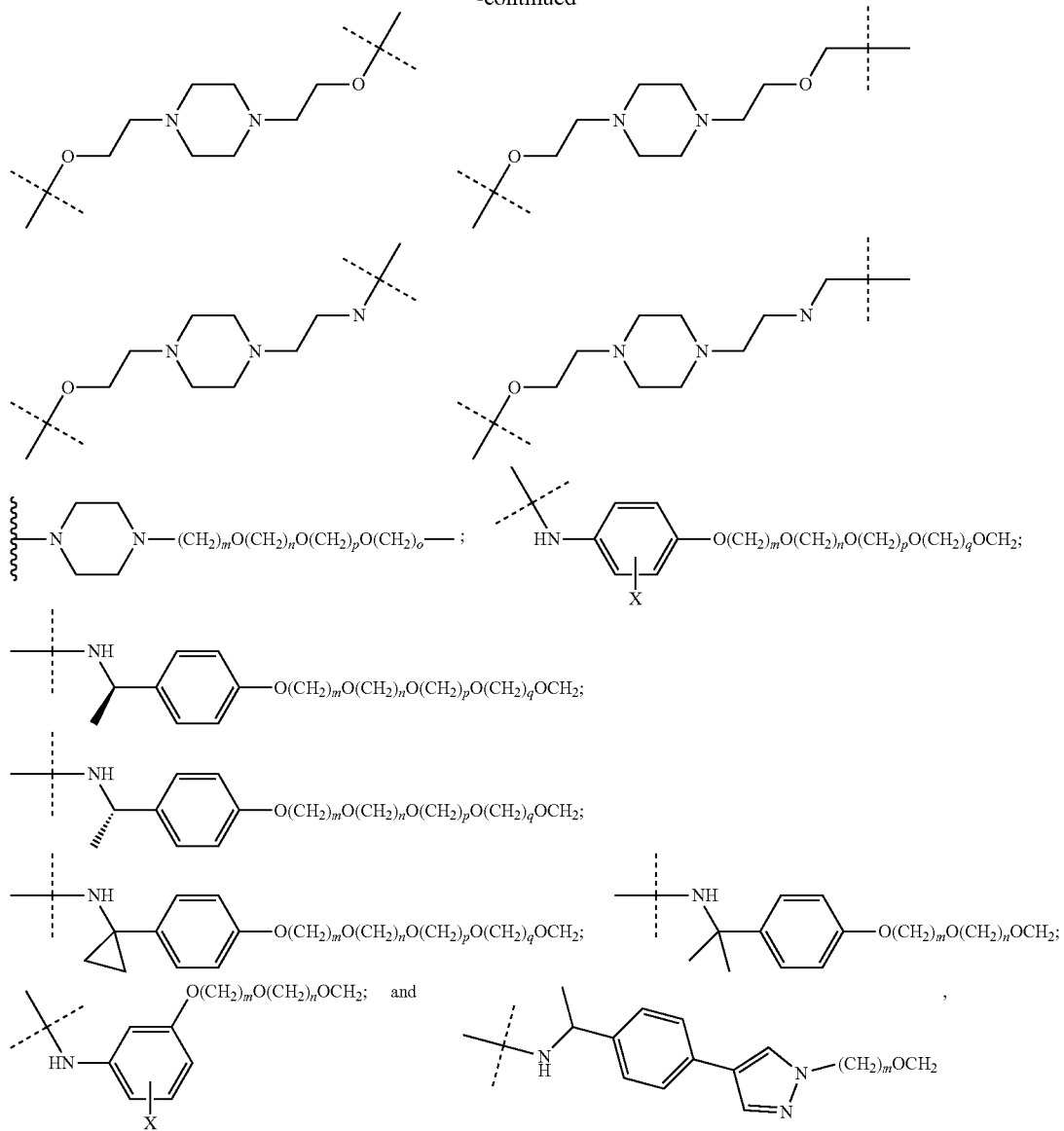
wherein m, n, o, p, q, and r, are independently 0, 1, 2, 3, 4, 5, 6, 7, 8, 9, 10, 11, 12, 13, 14, 15, 16, 17, 18, 19, 20, with the proviso that when m, n, o, p, q, or r is zero, there is no N—O or O—O bond, R is selected from the group H, methyl and ethyl, and X is selected from the group H and F.
14. The compound of claim 1, wherein the linker (L) is selected from the group consisting of:
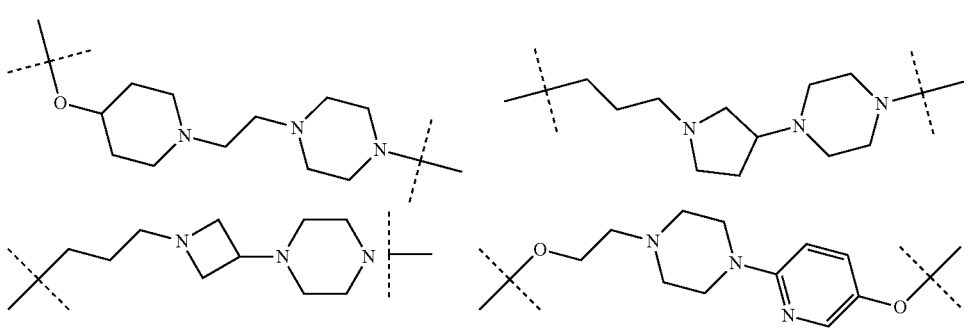

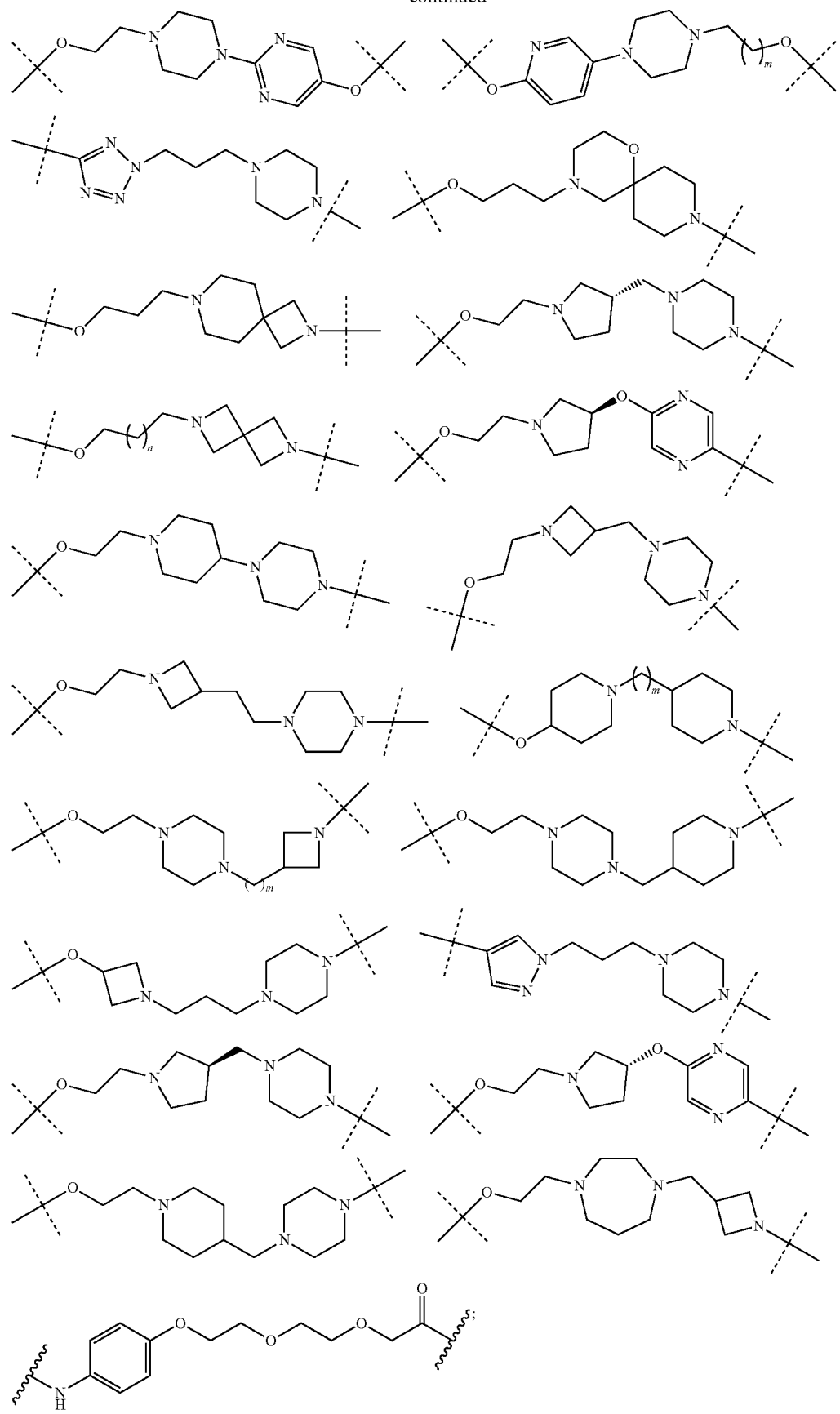

-continued
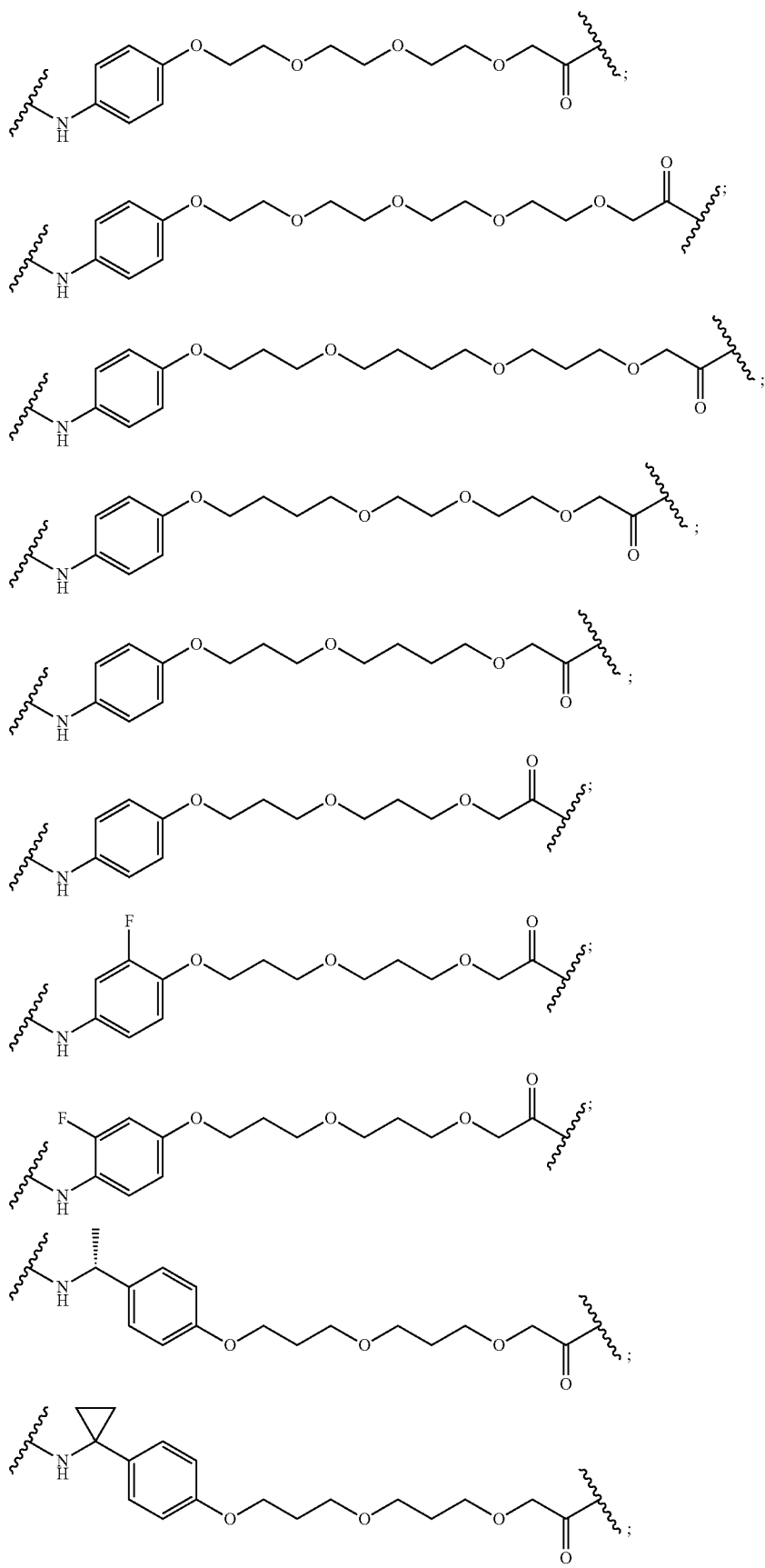

-continued
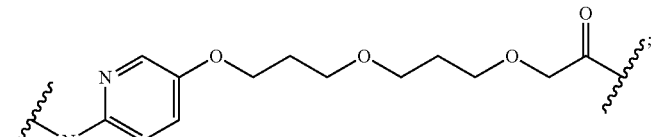
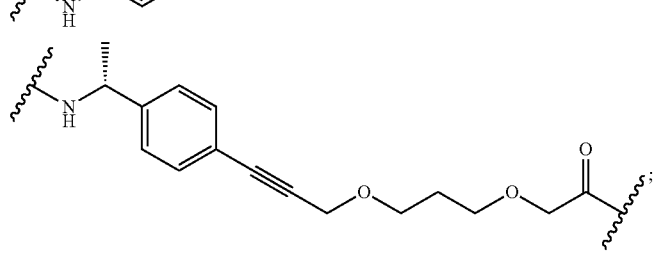
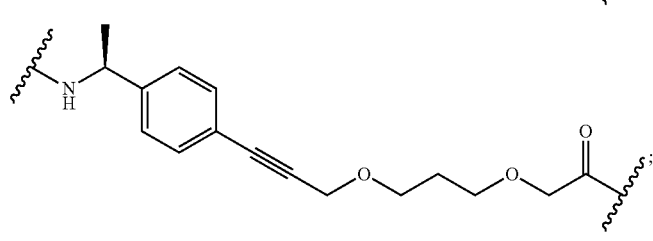
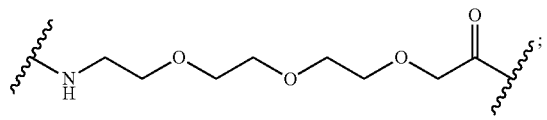
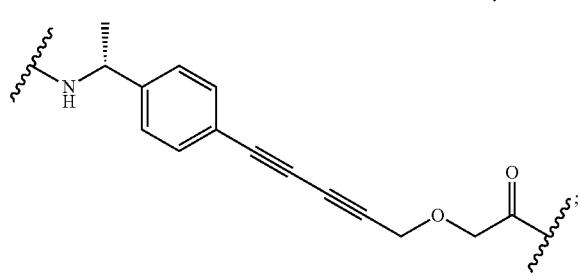
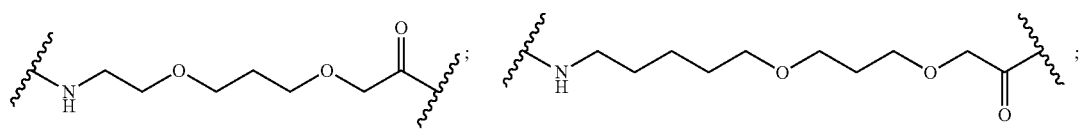
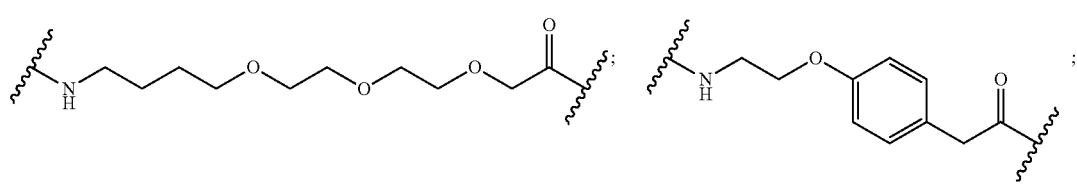
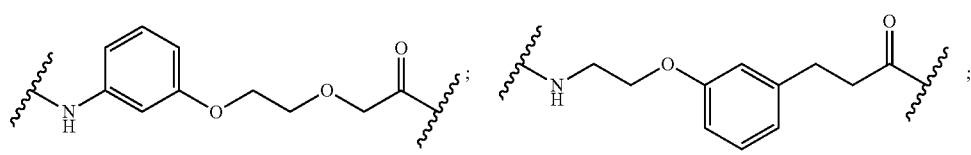
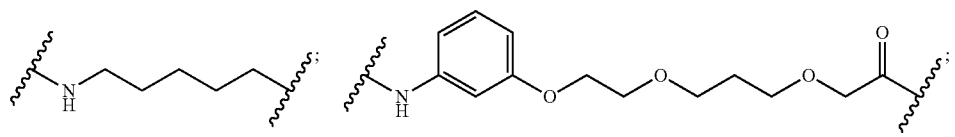

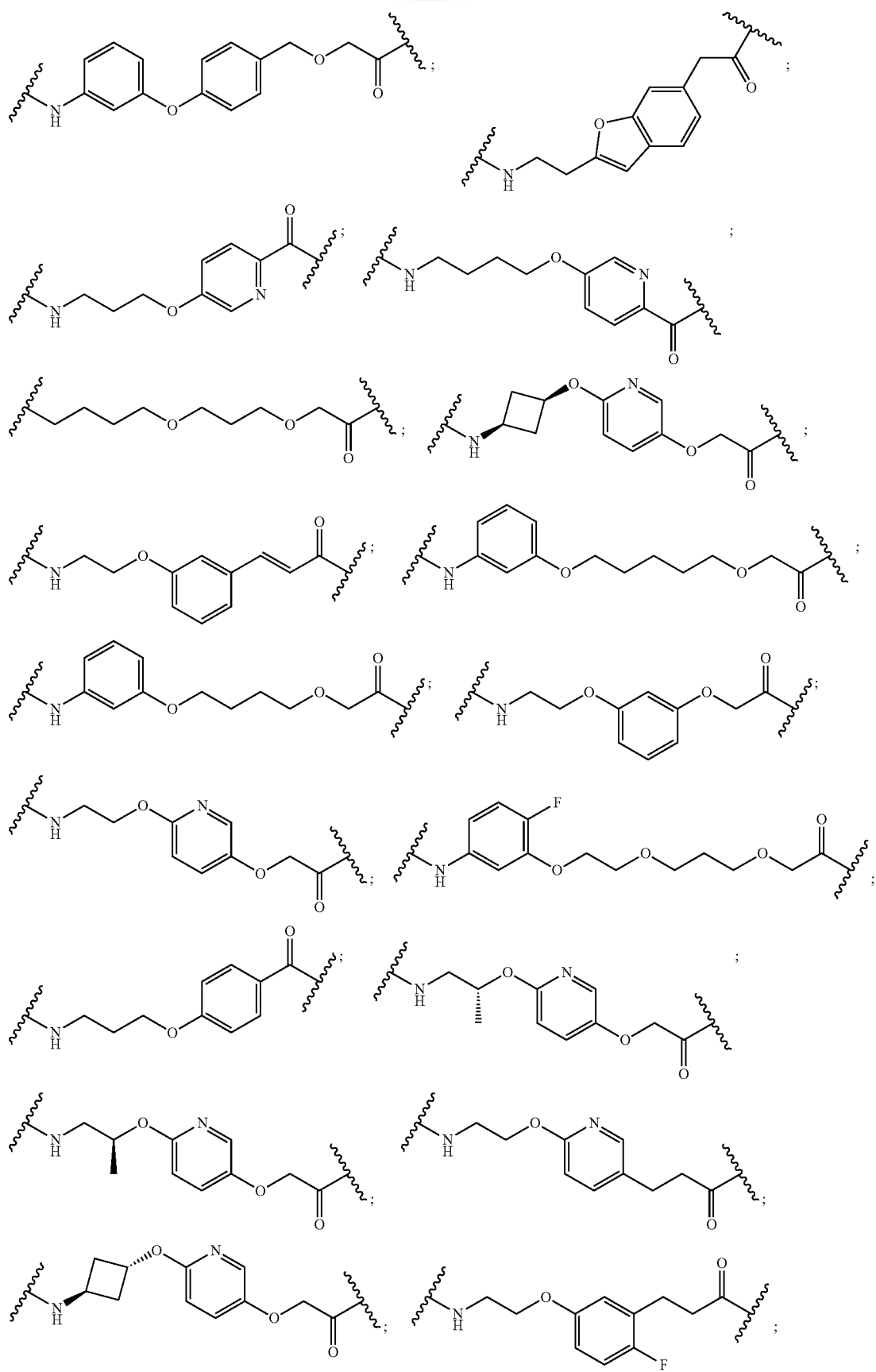

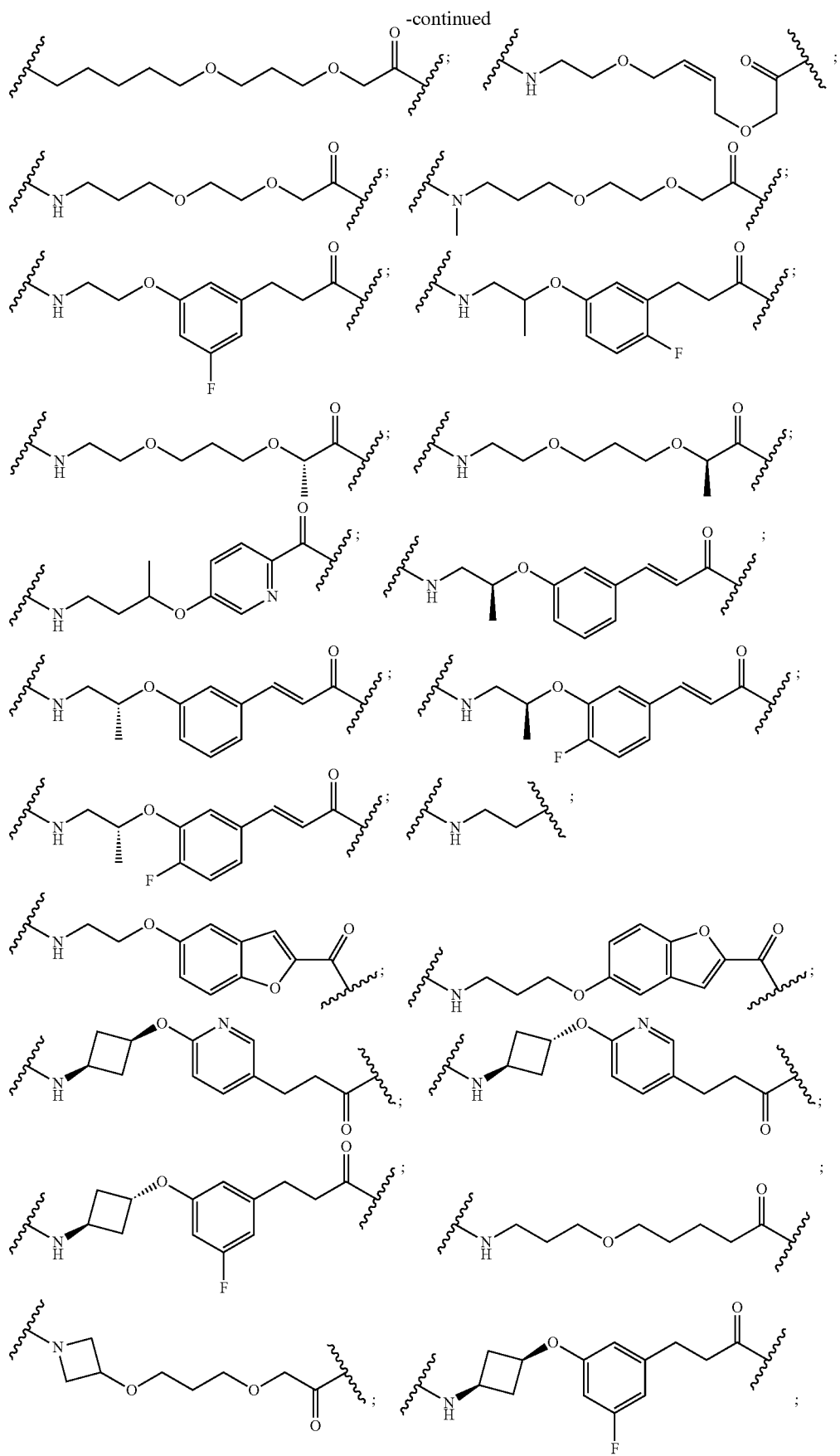

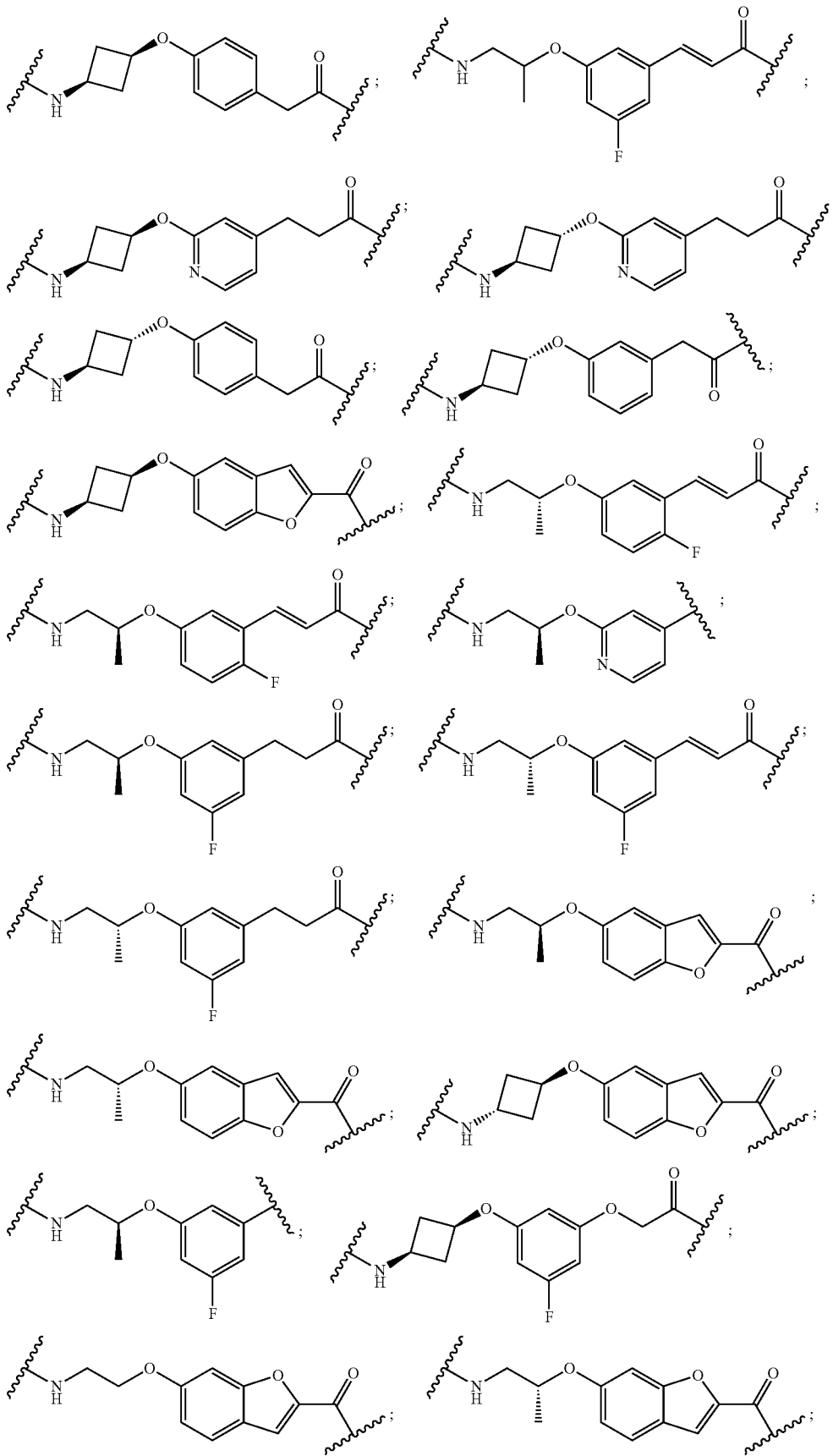

-continued
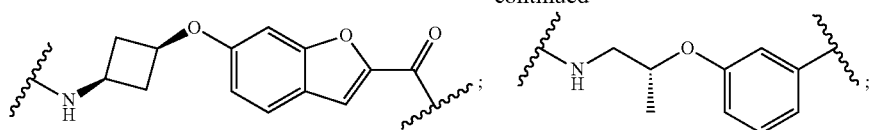
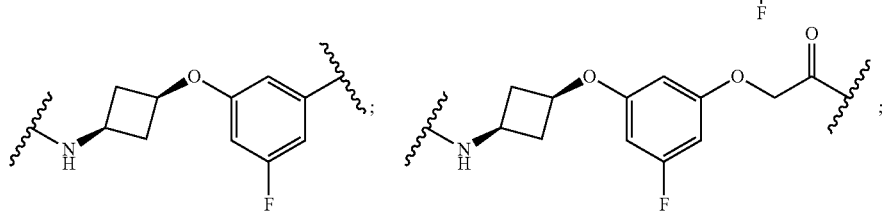
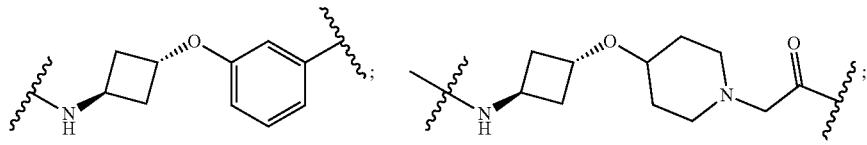
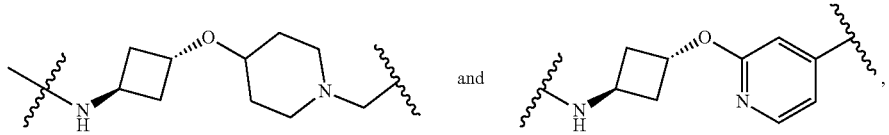
wherein each m and n is independently selected from 0, 1, 2, 3, 4, 5, or 6.
15. The compound of claim 1, wherein the linker (L) is selected from the group consisting of:
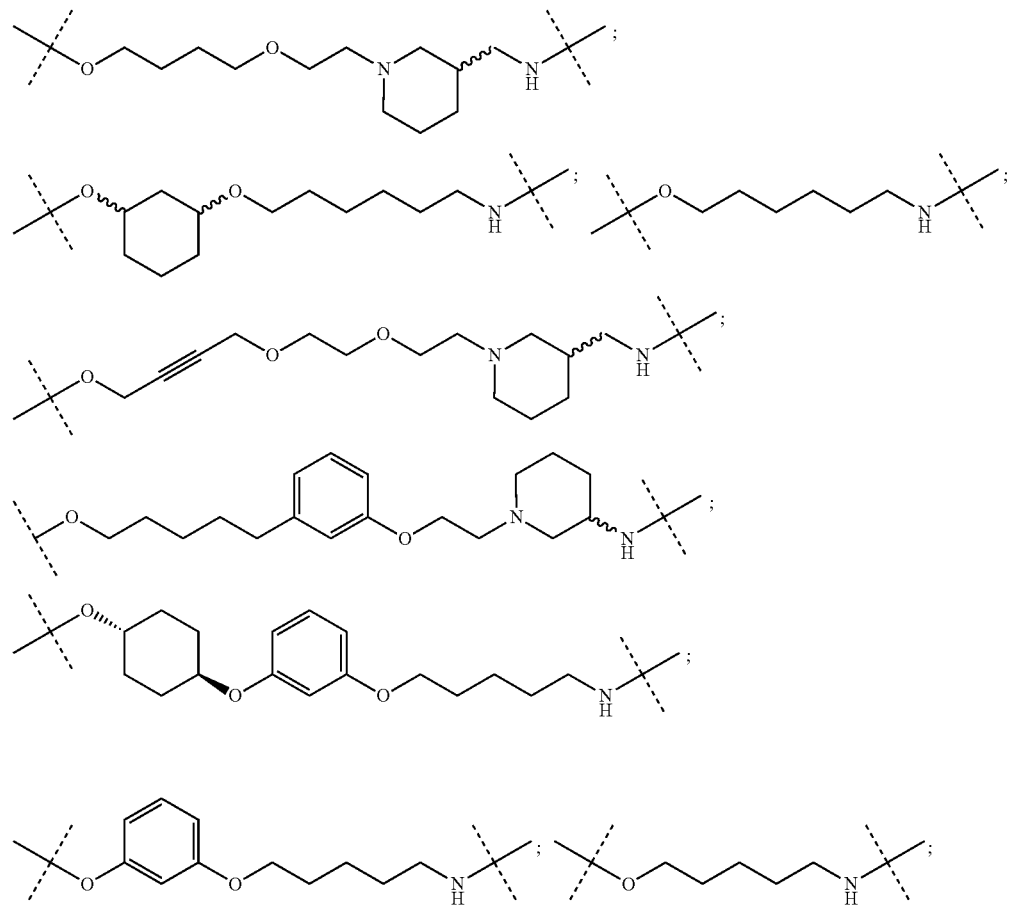

-continued
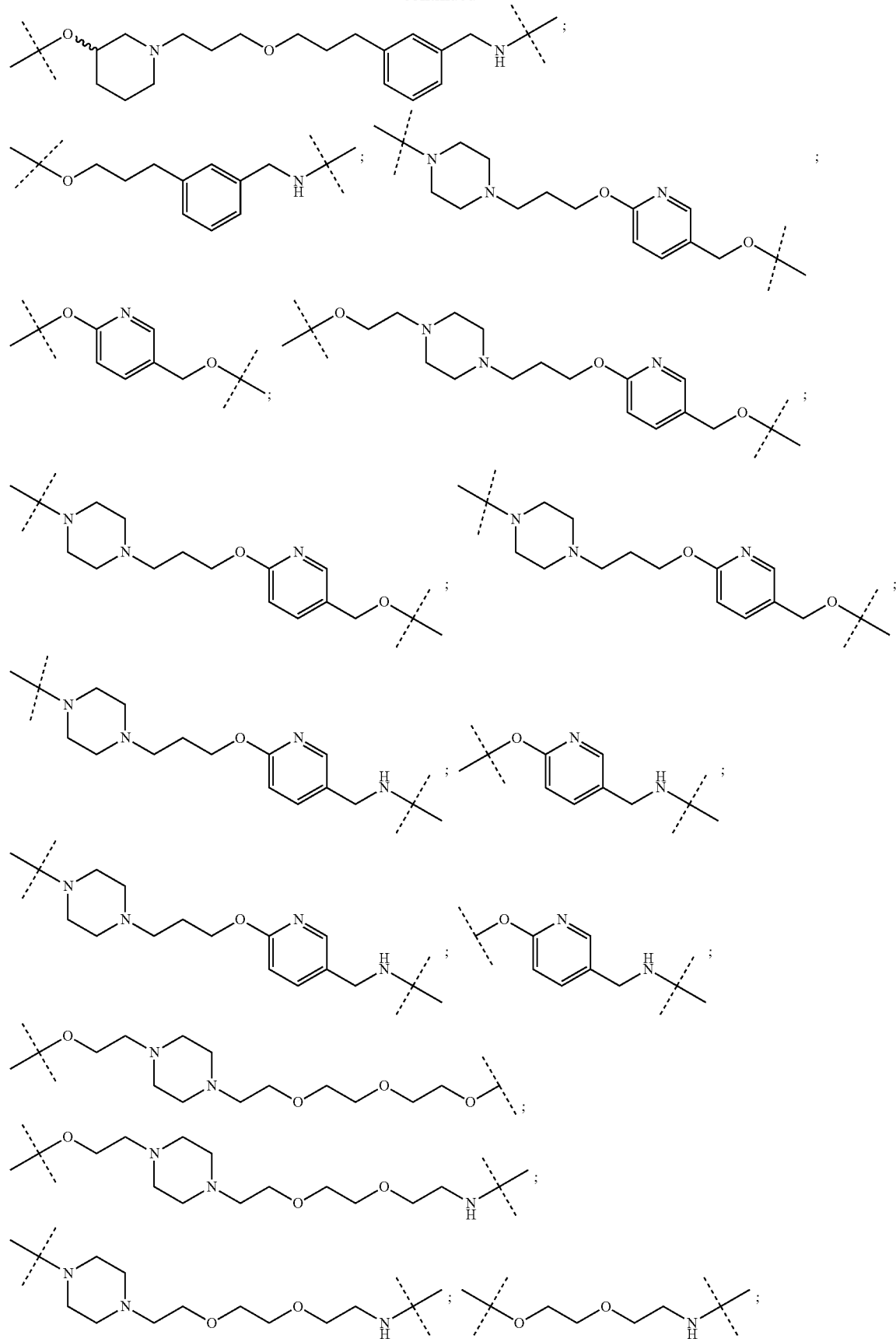

-continued
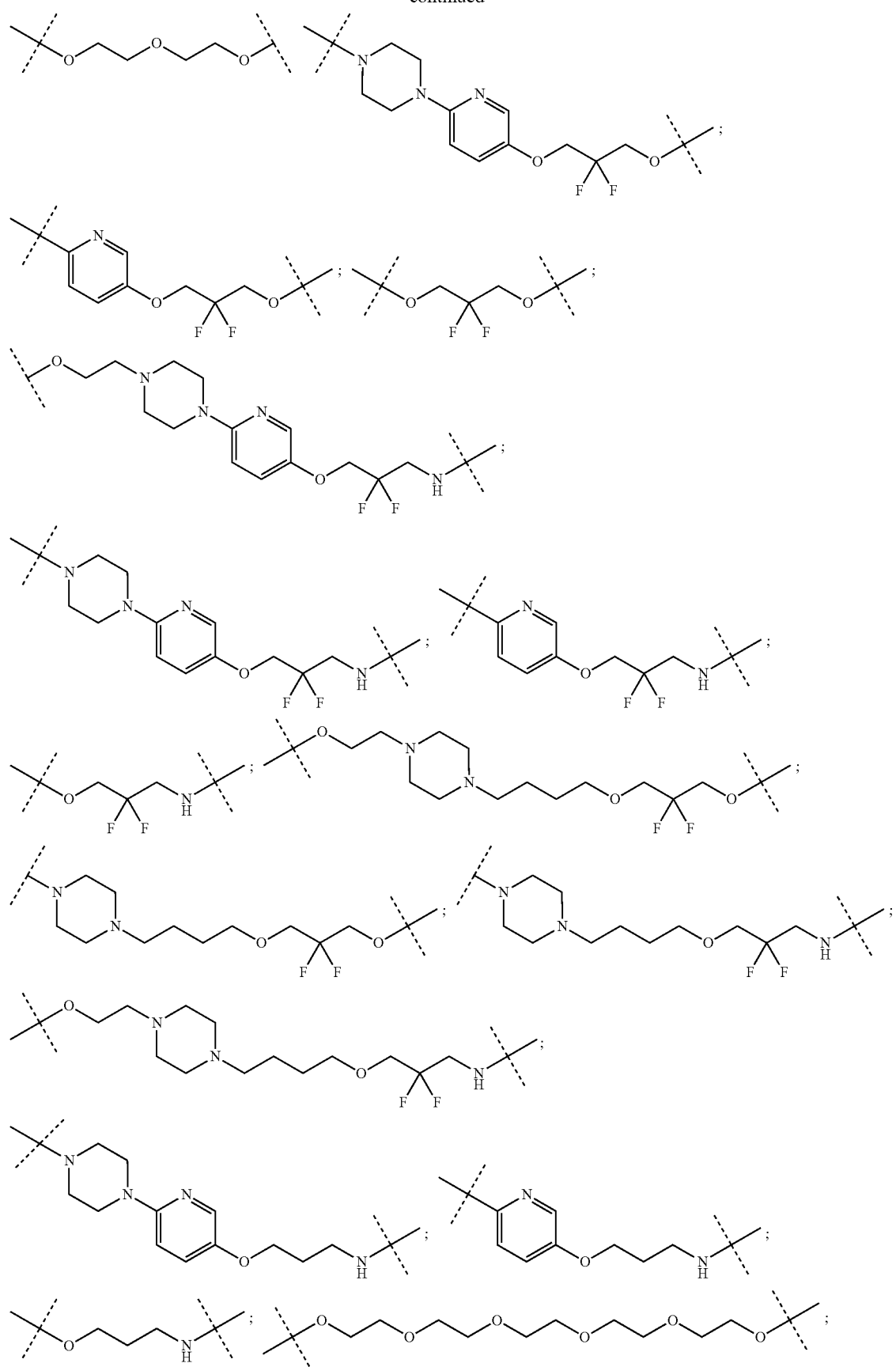

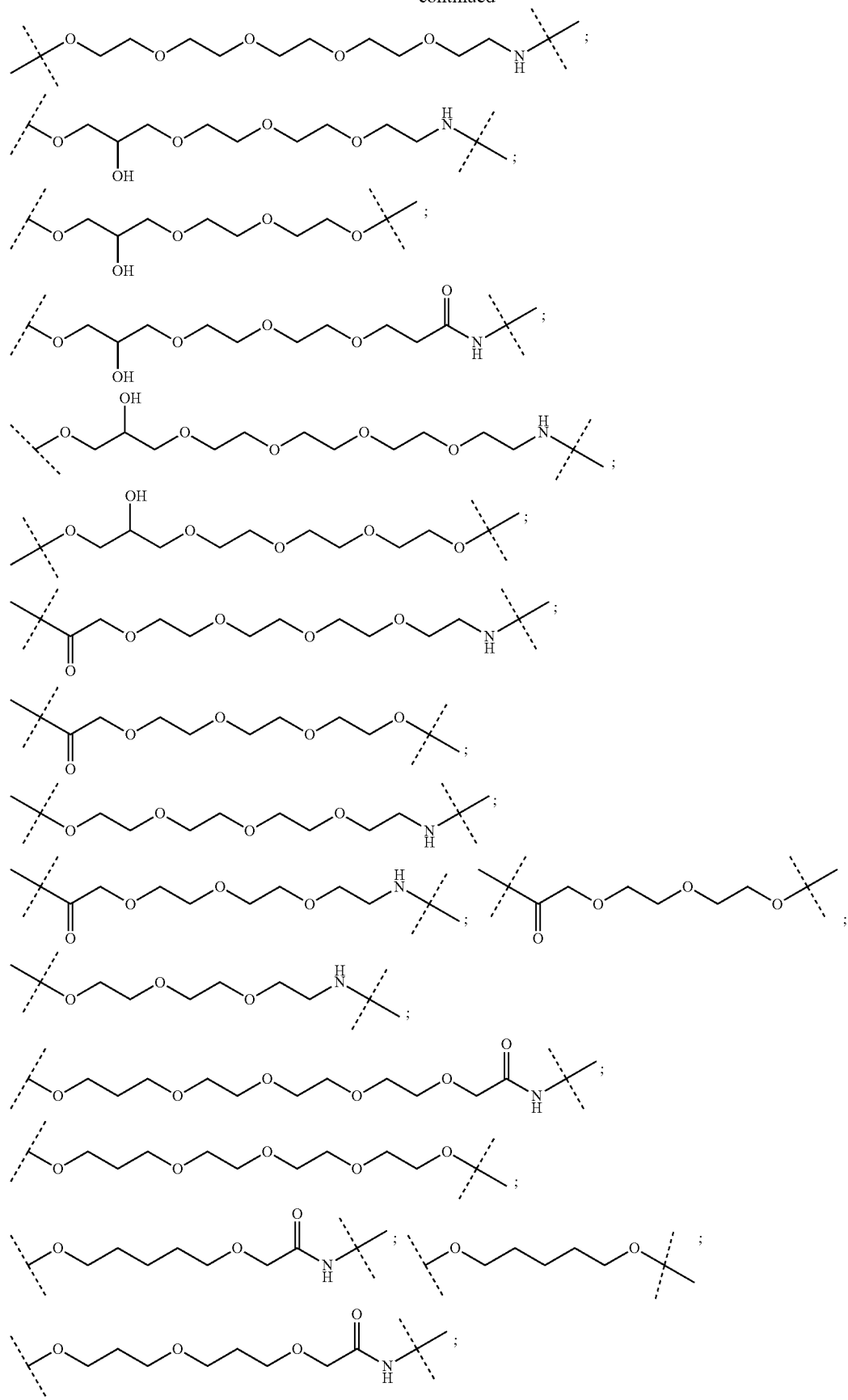

-continued
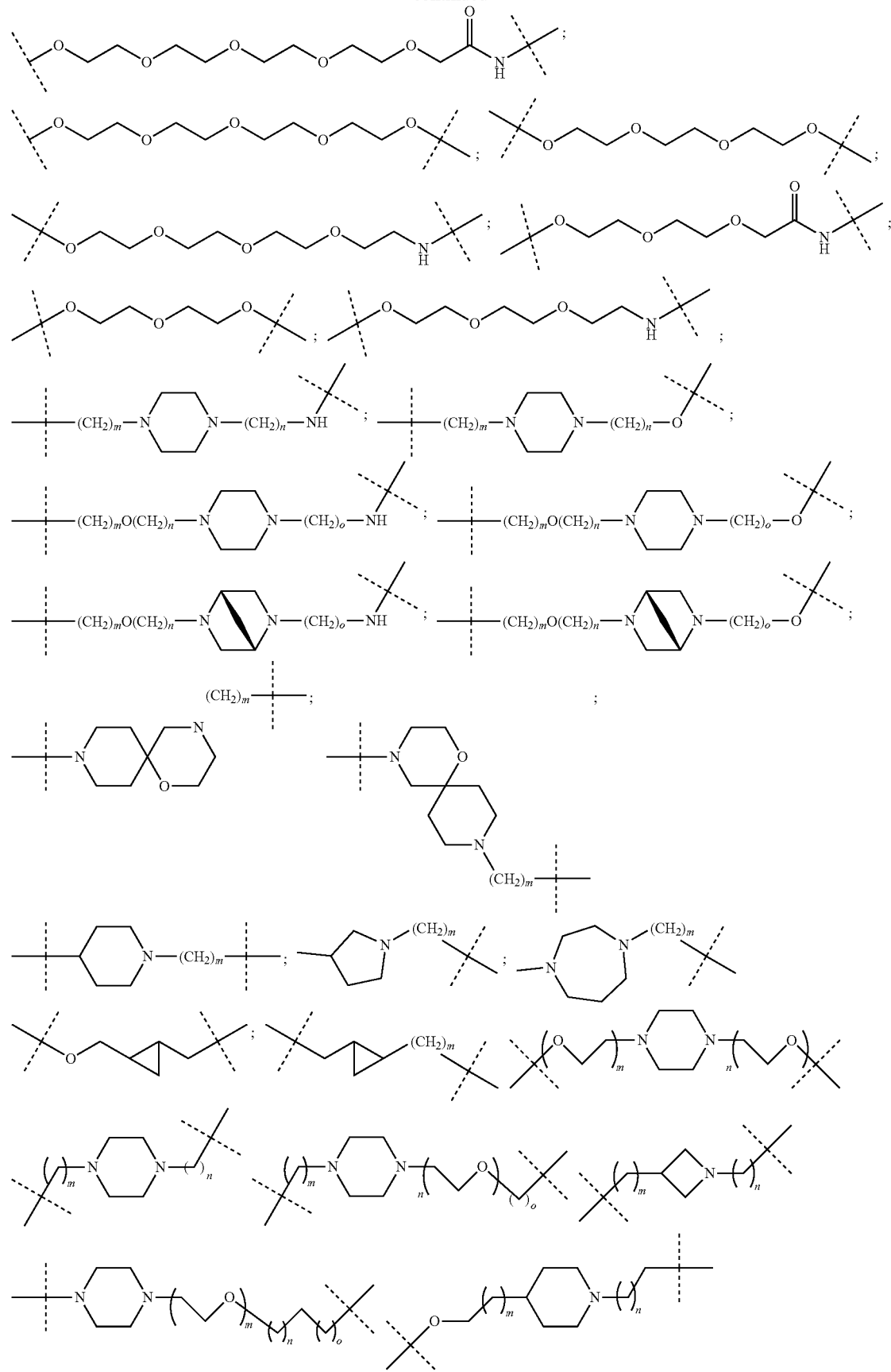

-continued
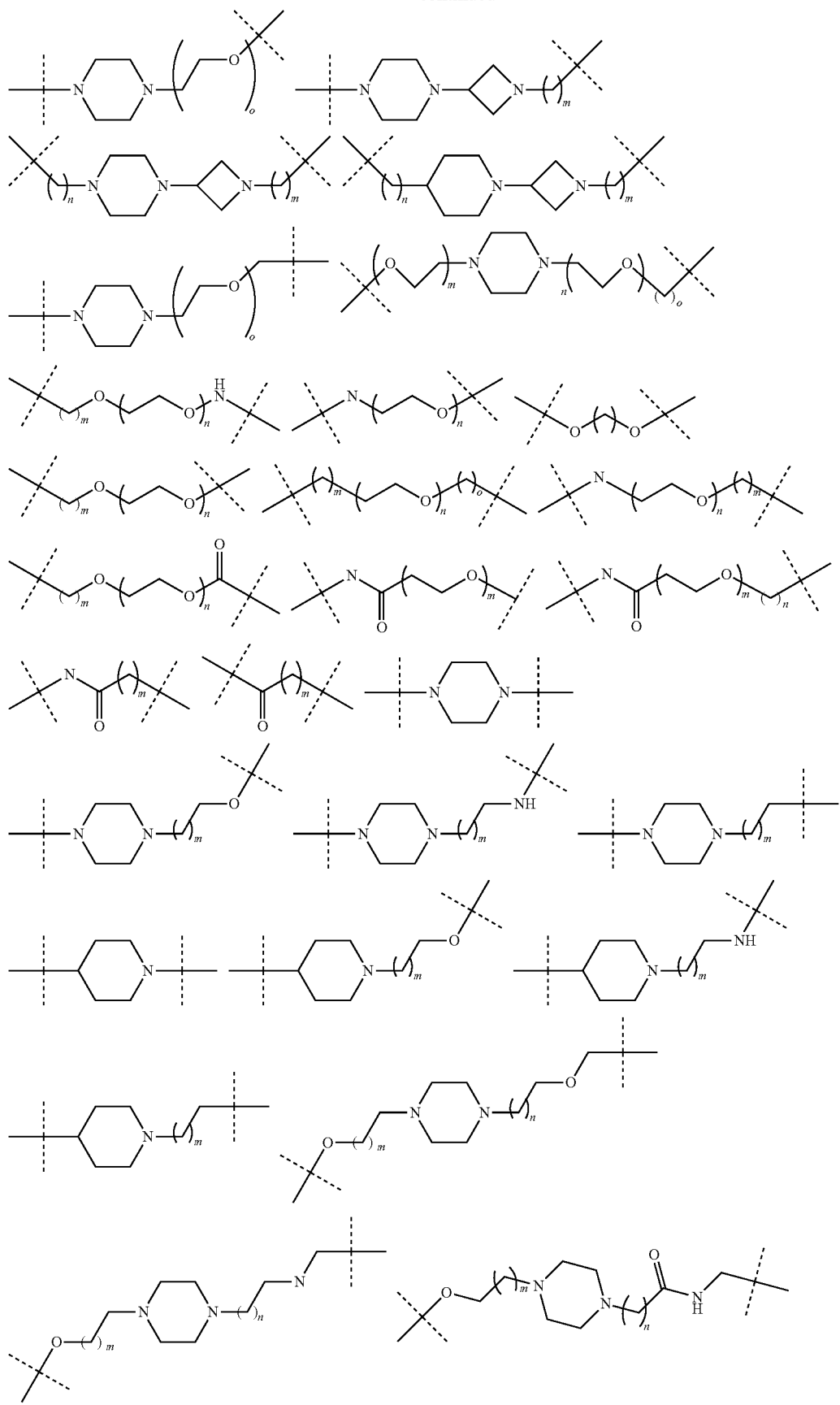

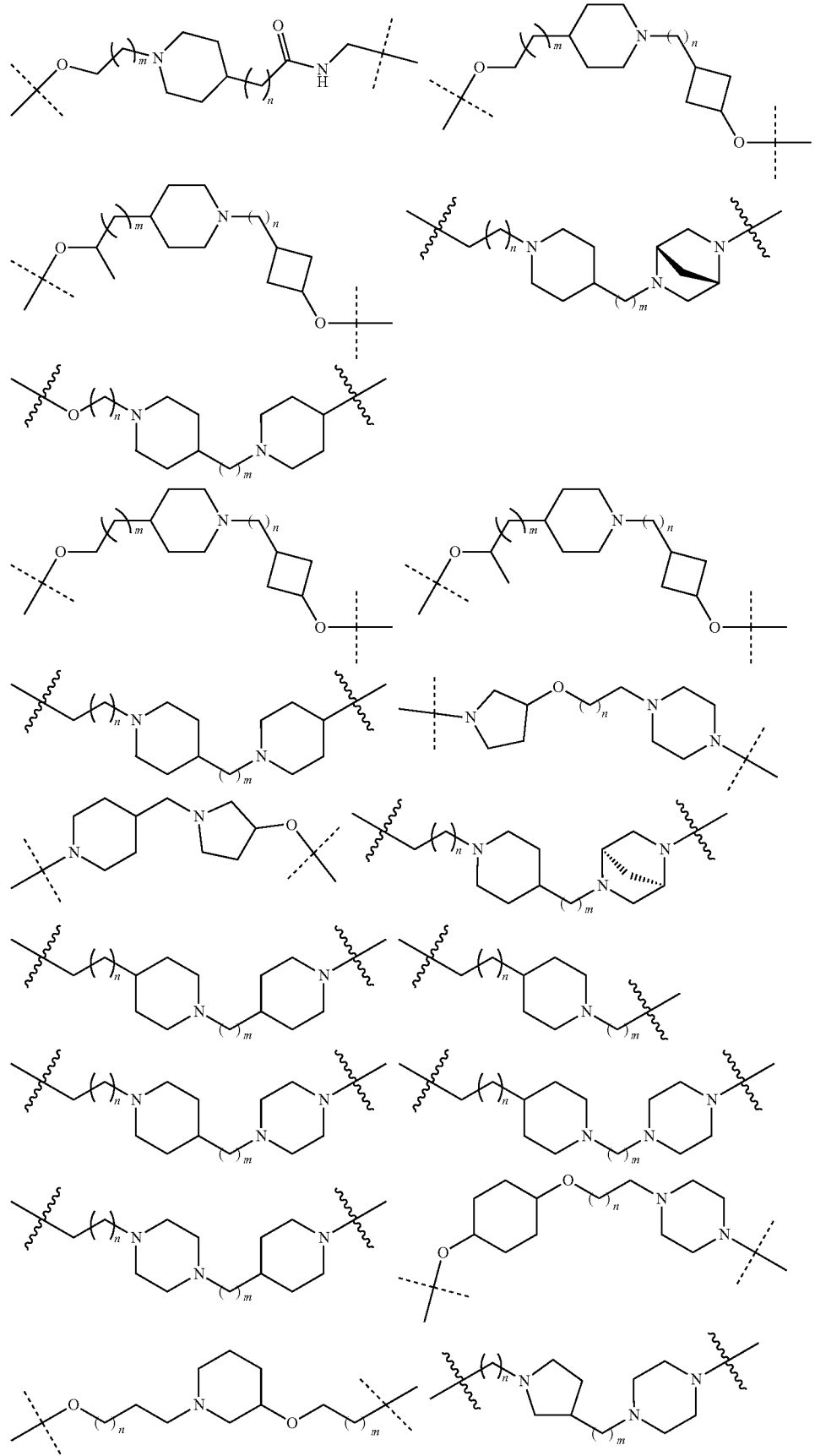

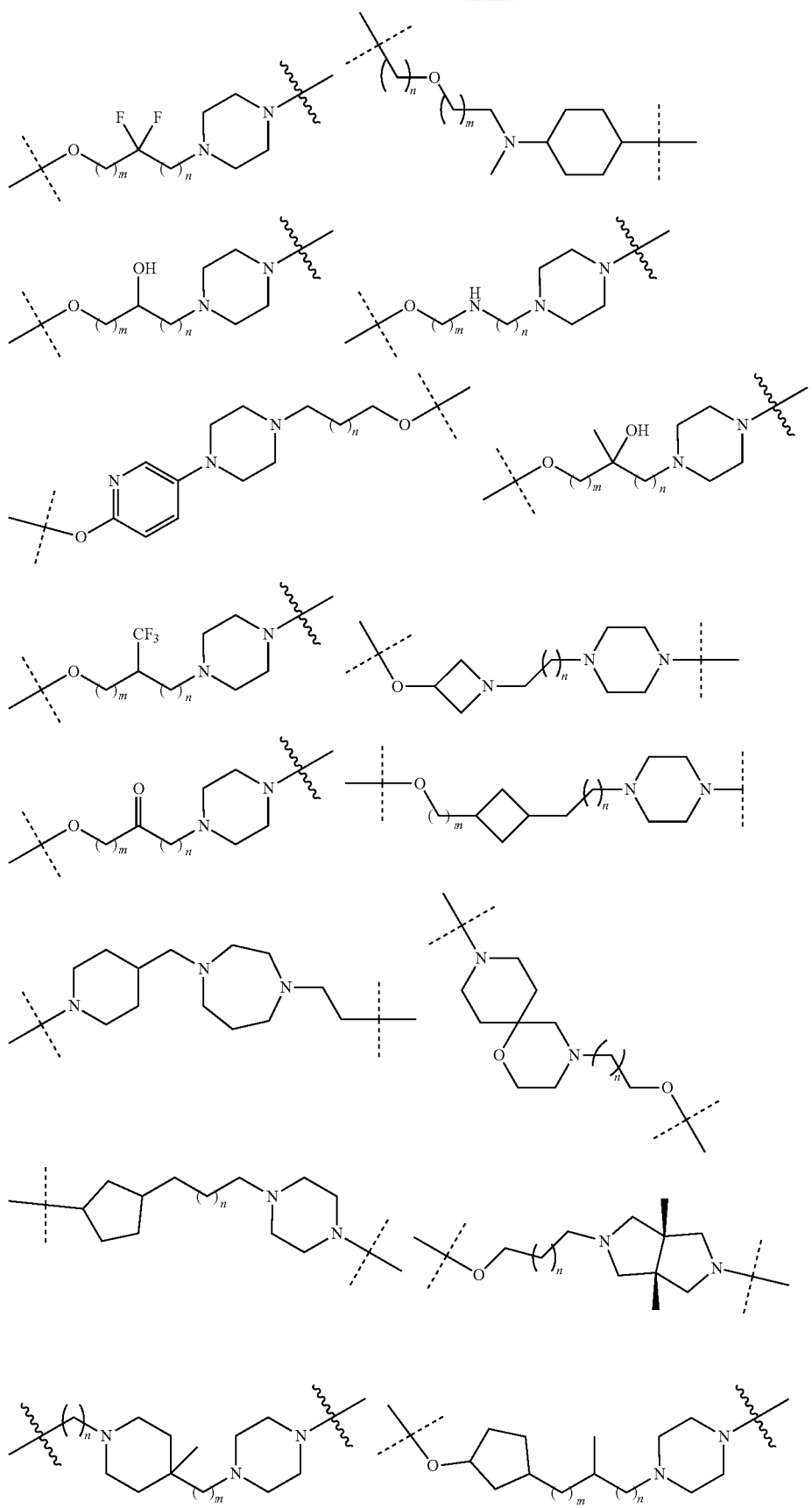

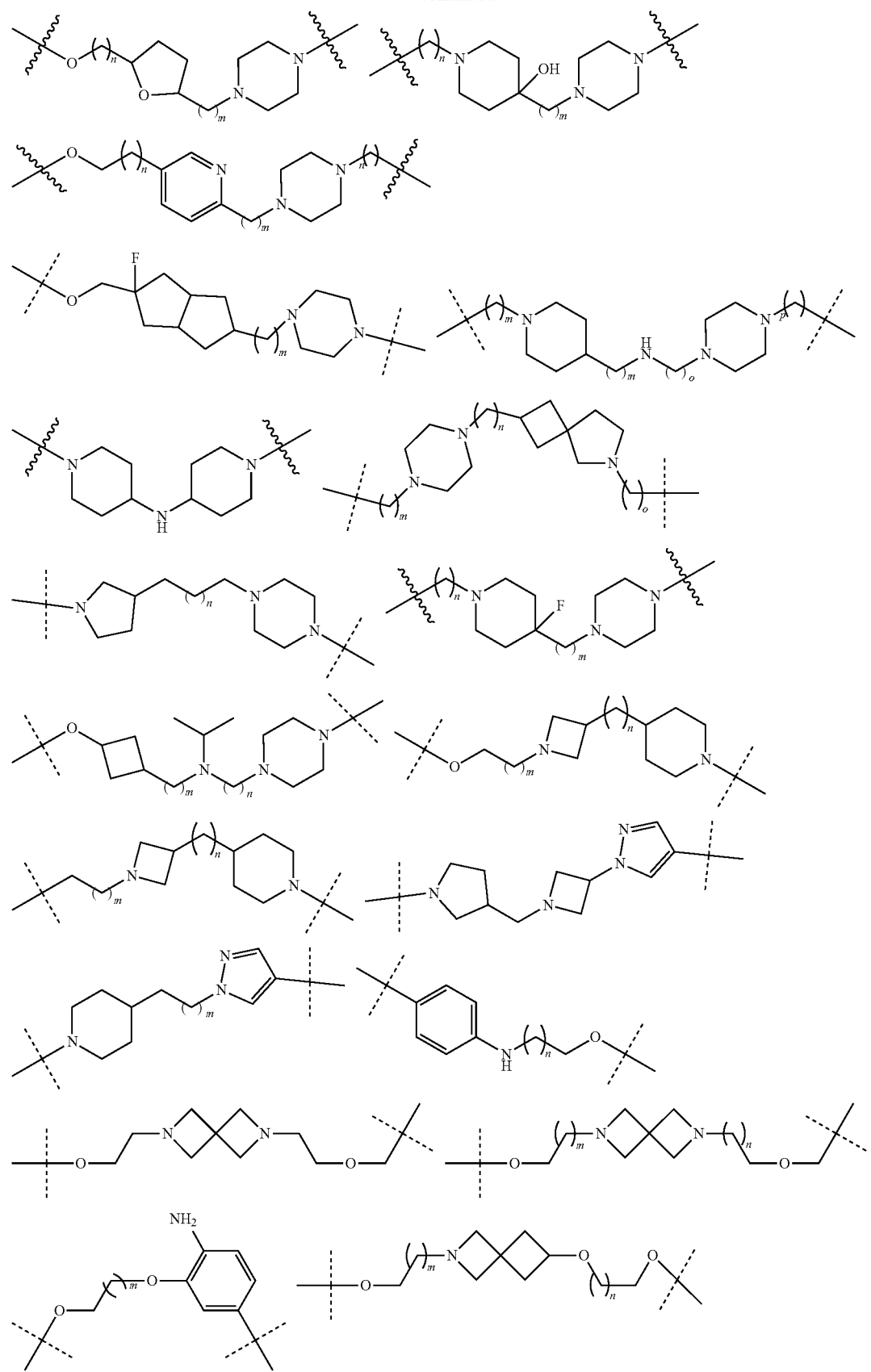

-continued
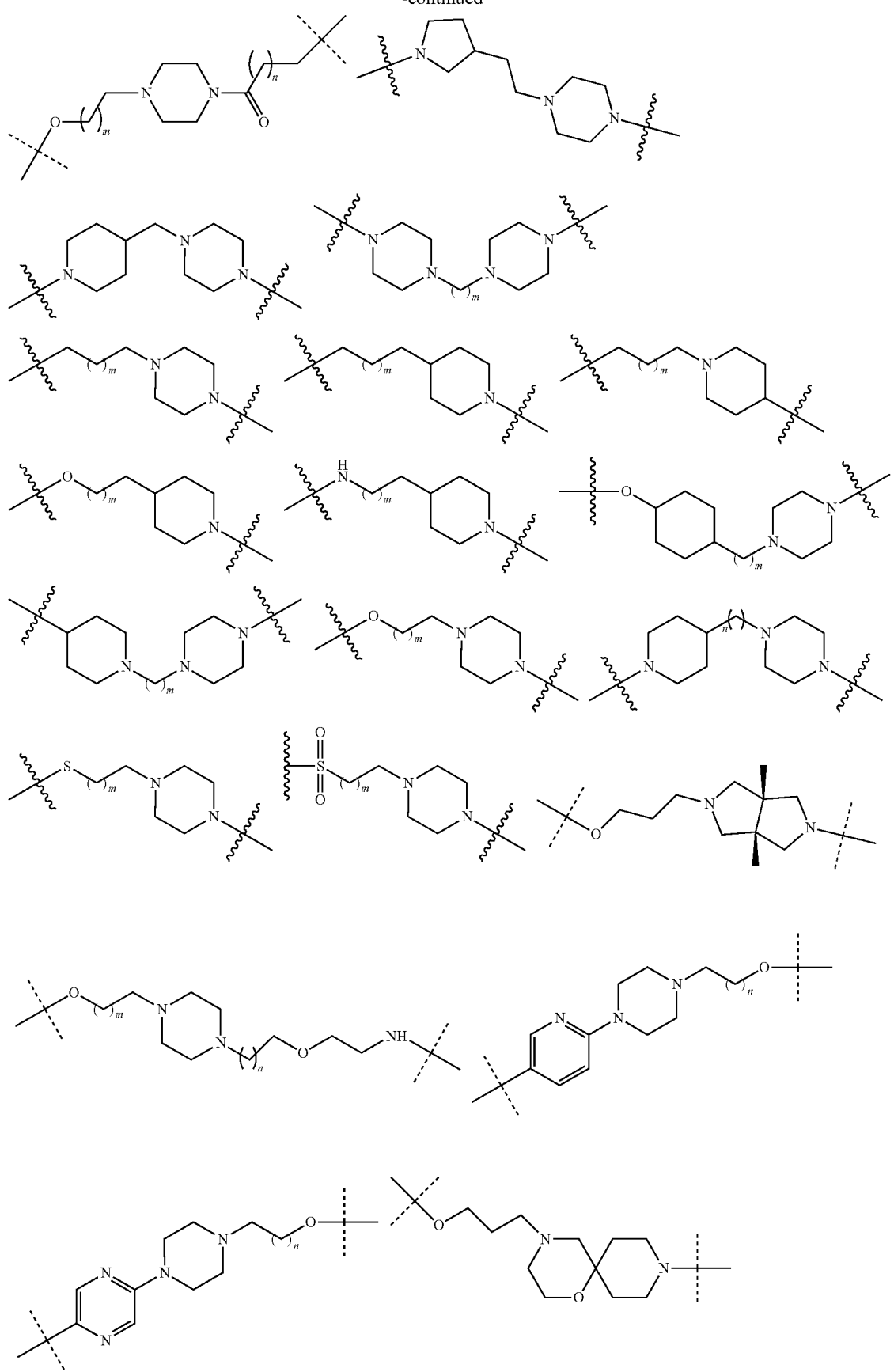

-continued
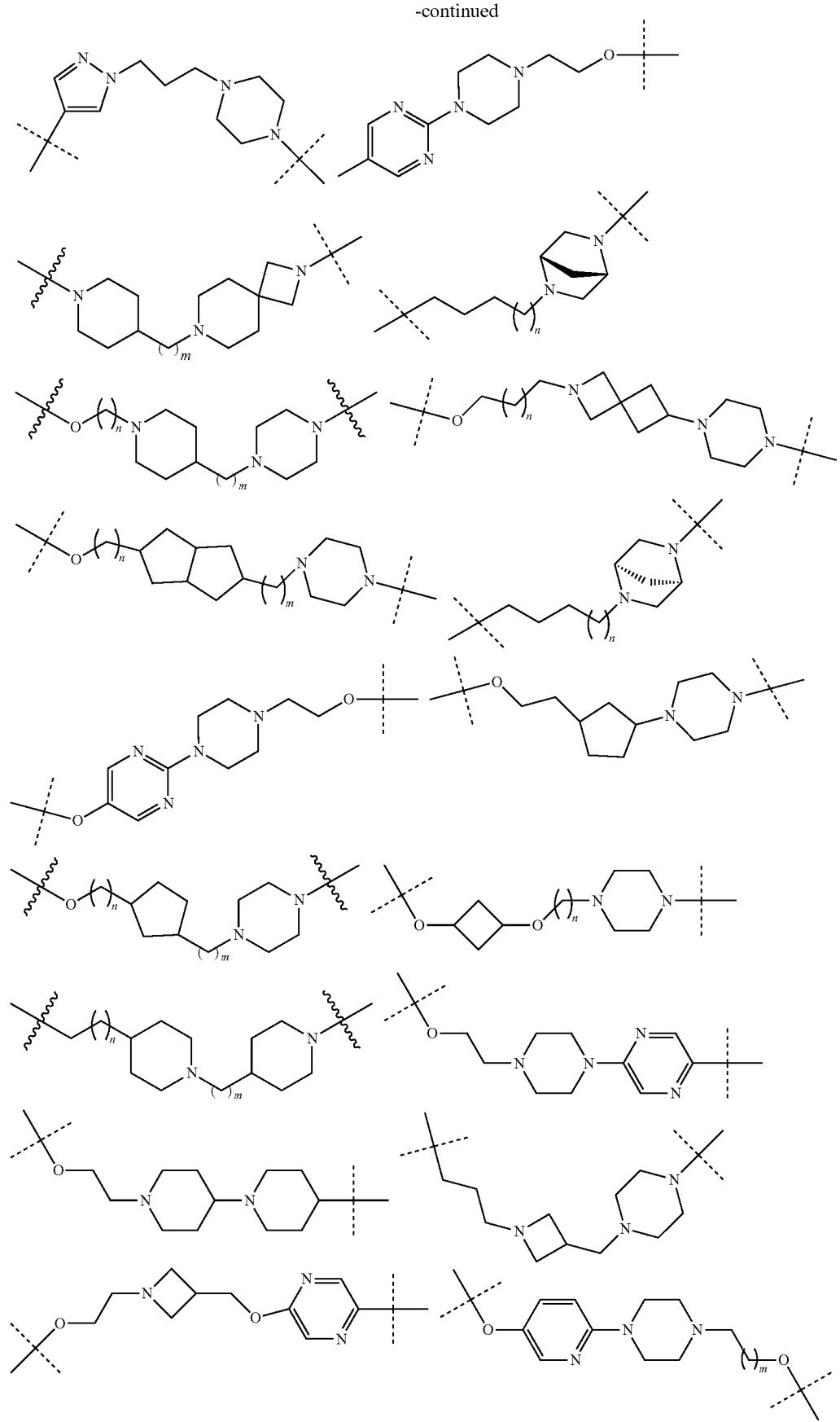

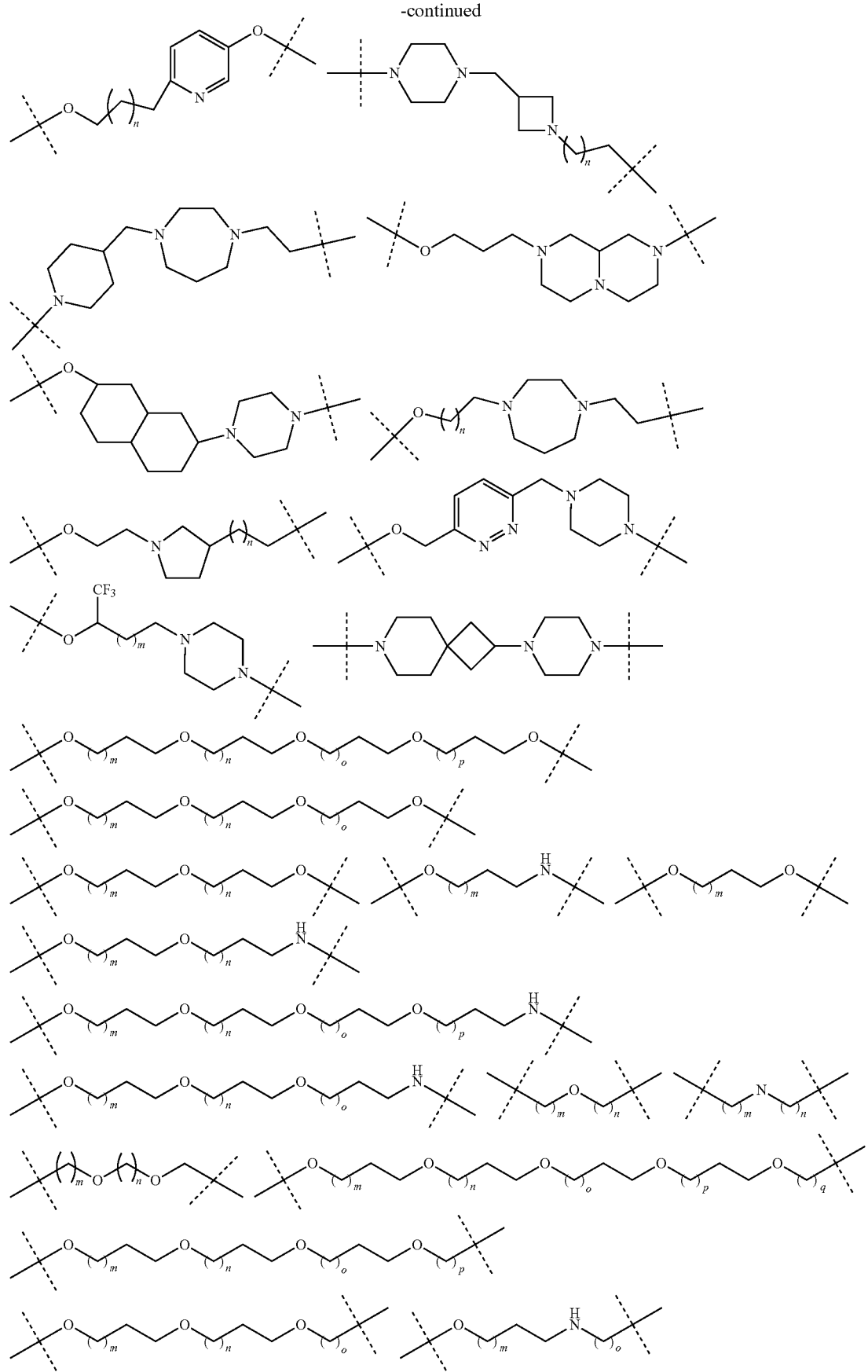

-continued
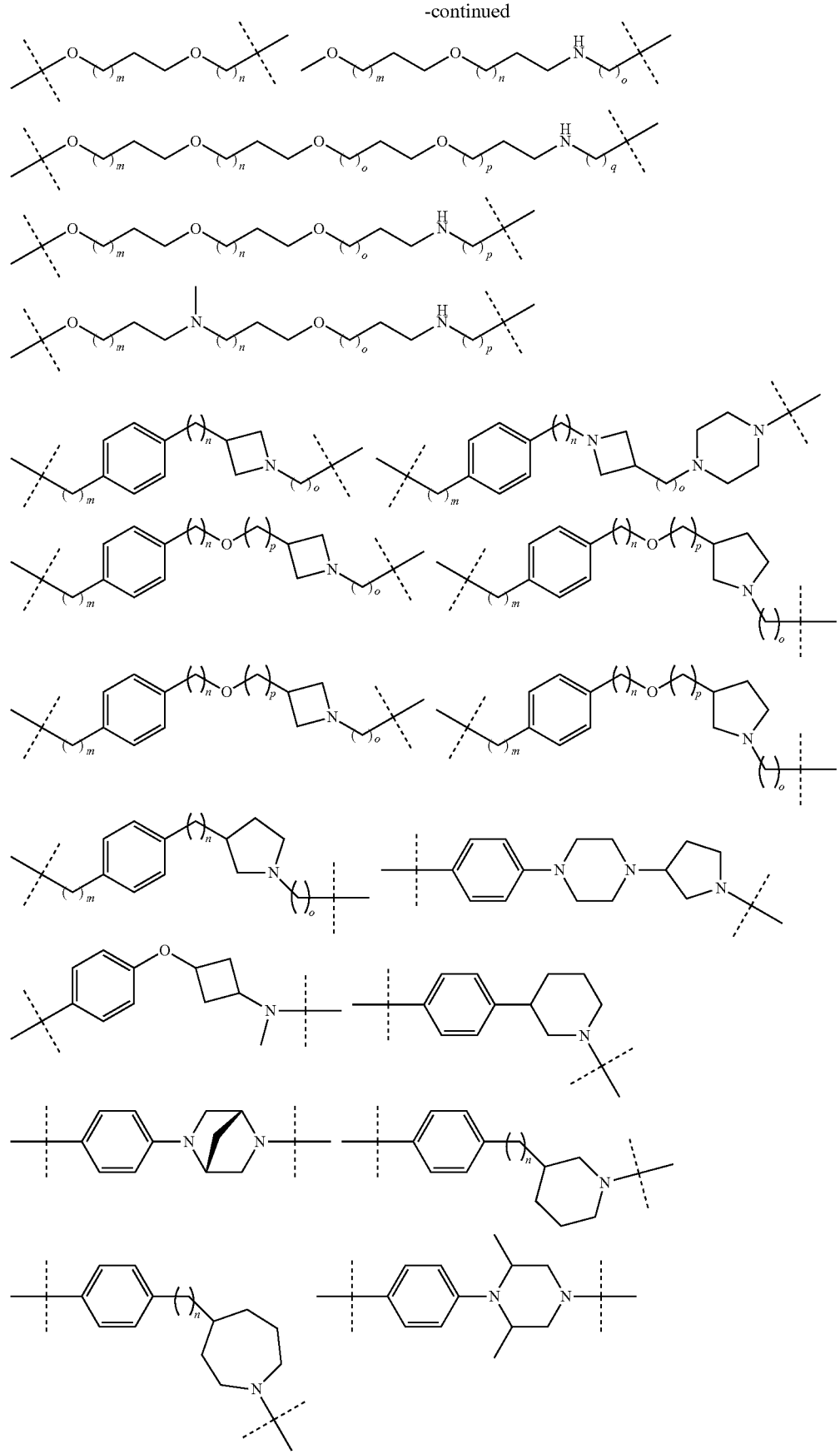

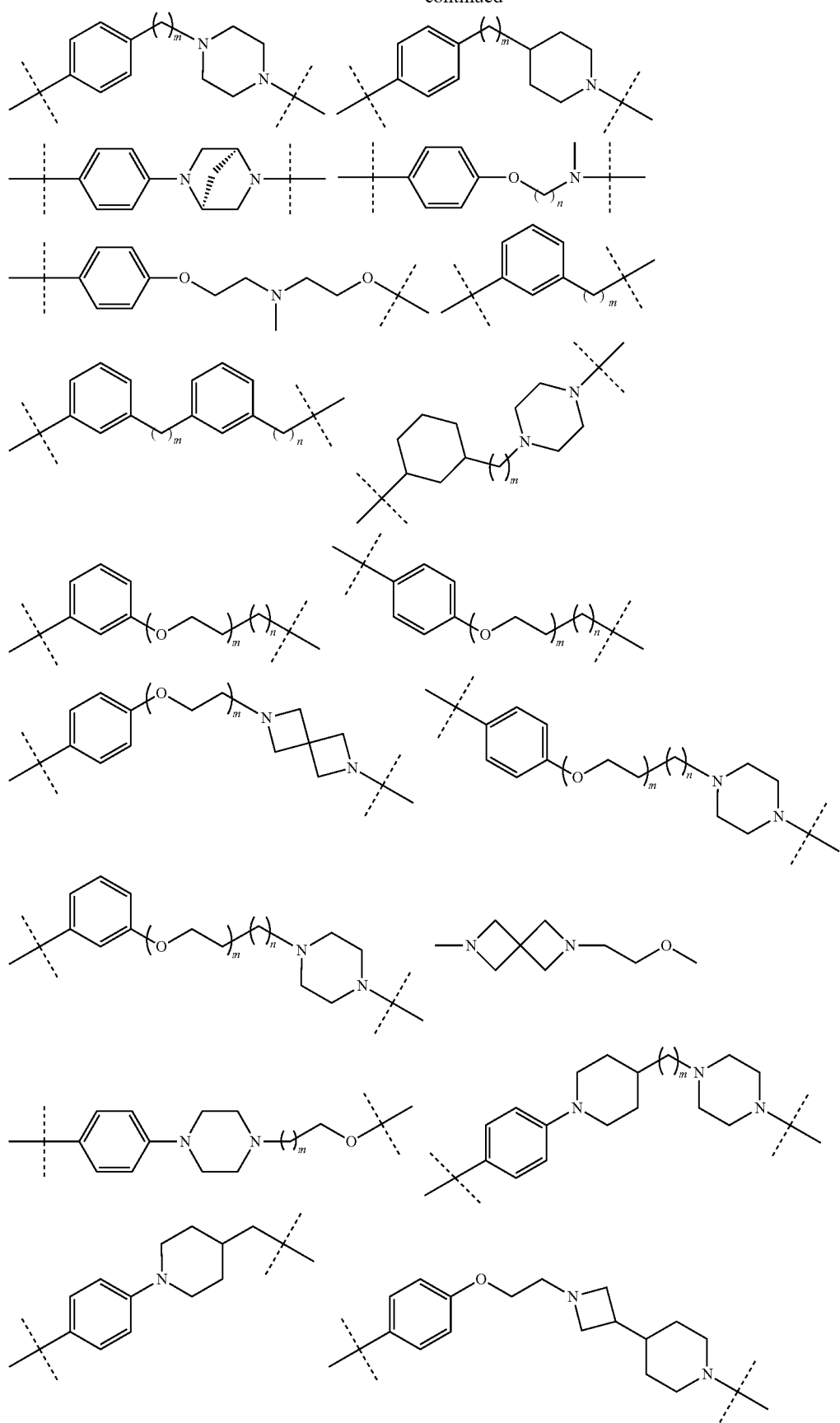

-continued
| 901 | 902 |
|---|---|
| 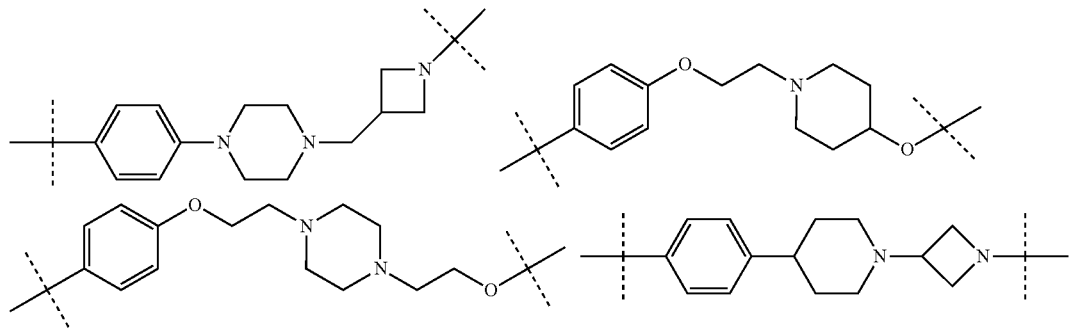 | |
| 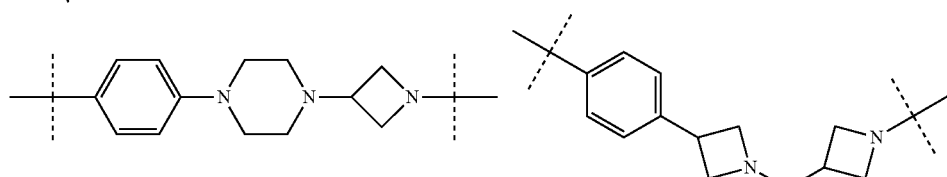 | |
| 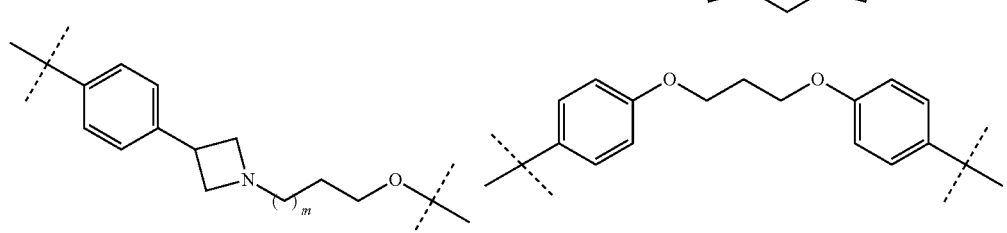 | |
| 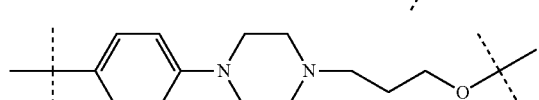 | |
| 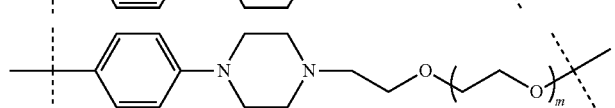 | |
| 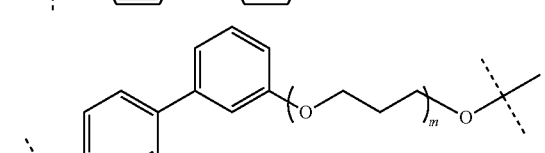 | |
| 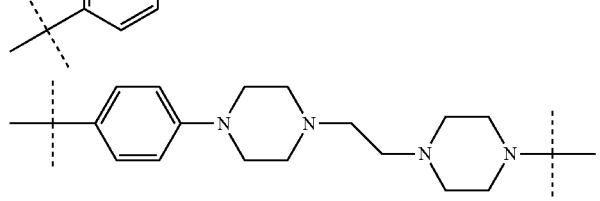 | |
| 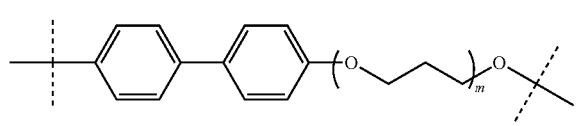 | |
| 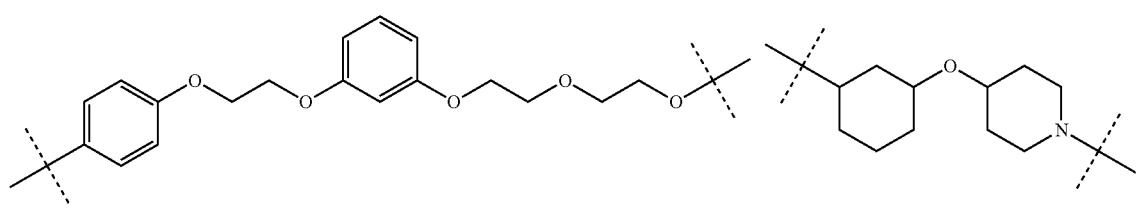 | |

903 904
-continued
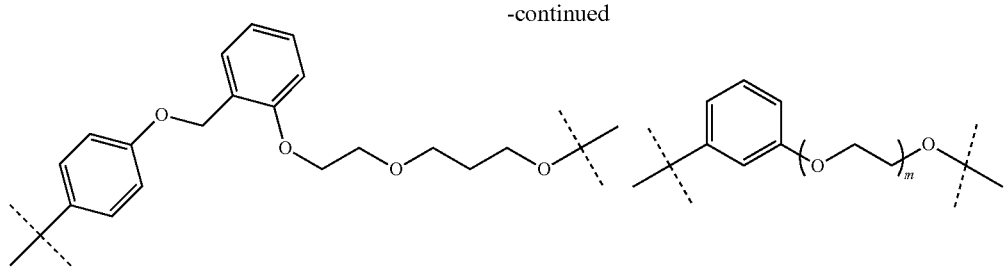
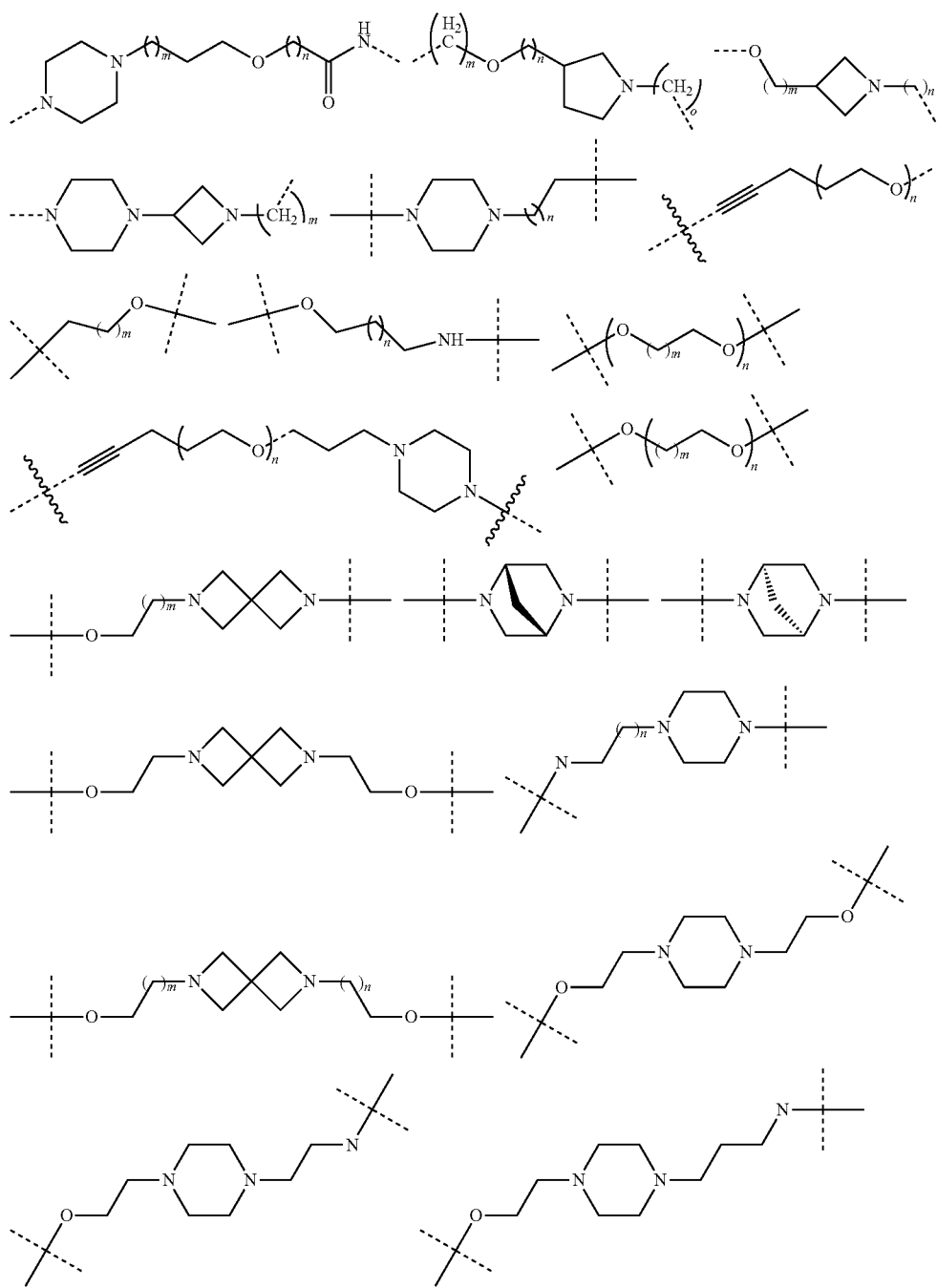

905 906
-continued
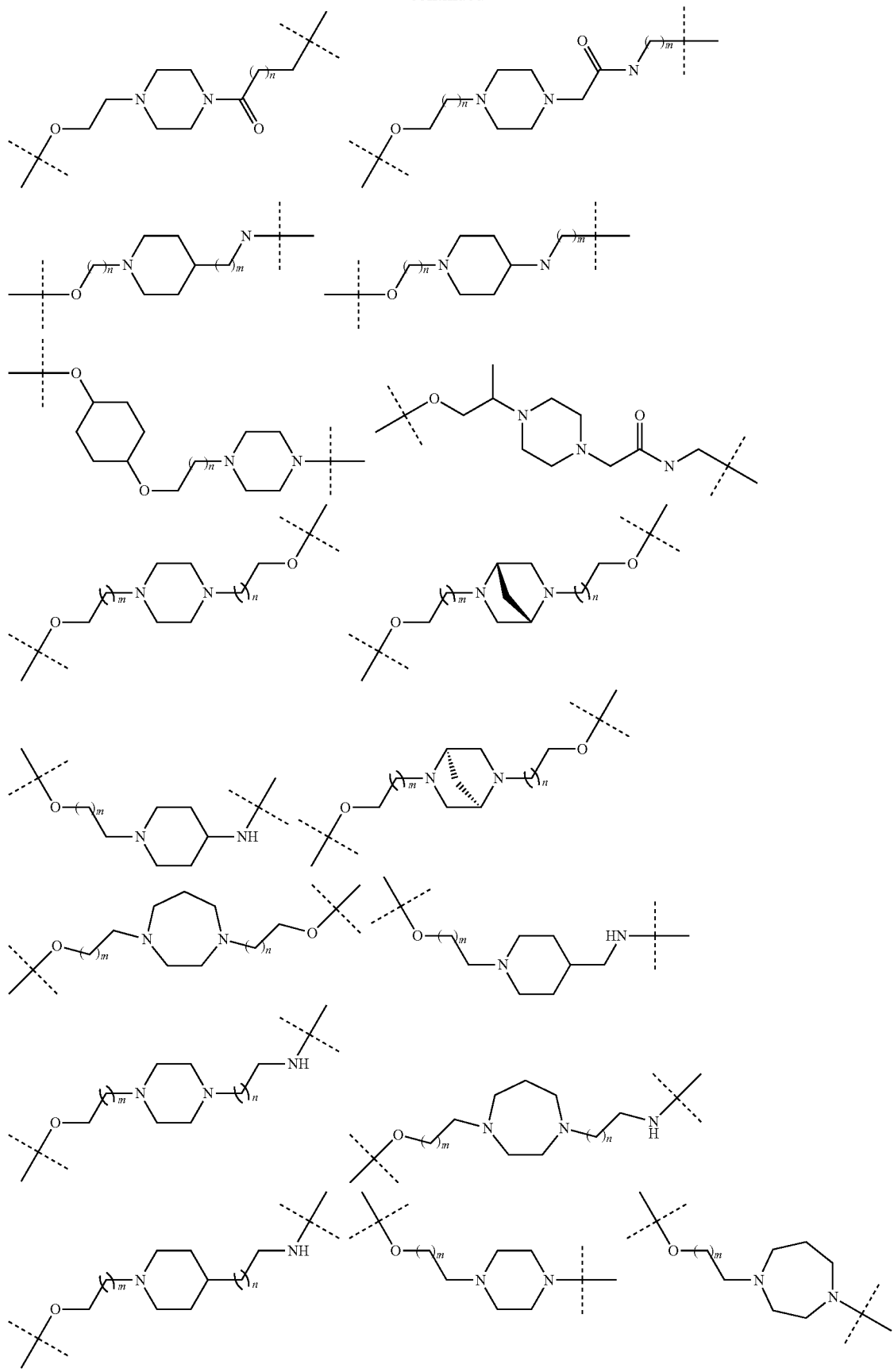

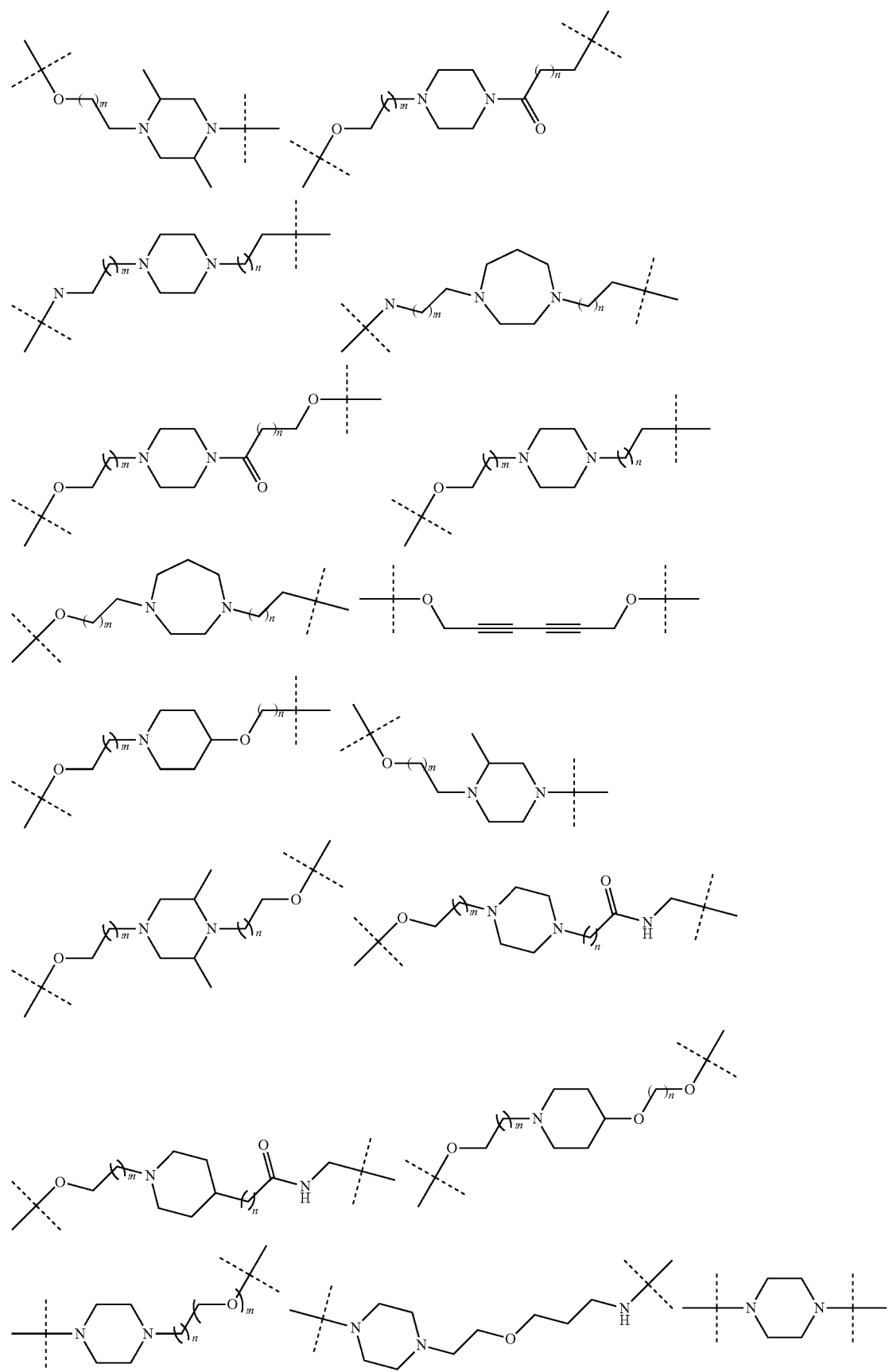

-continued
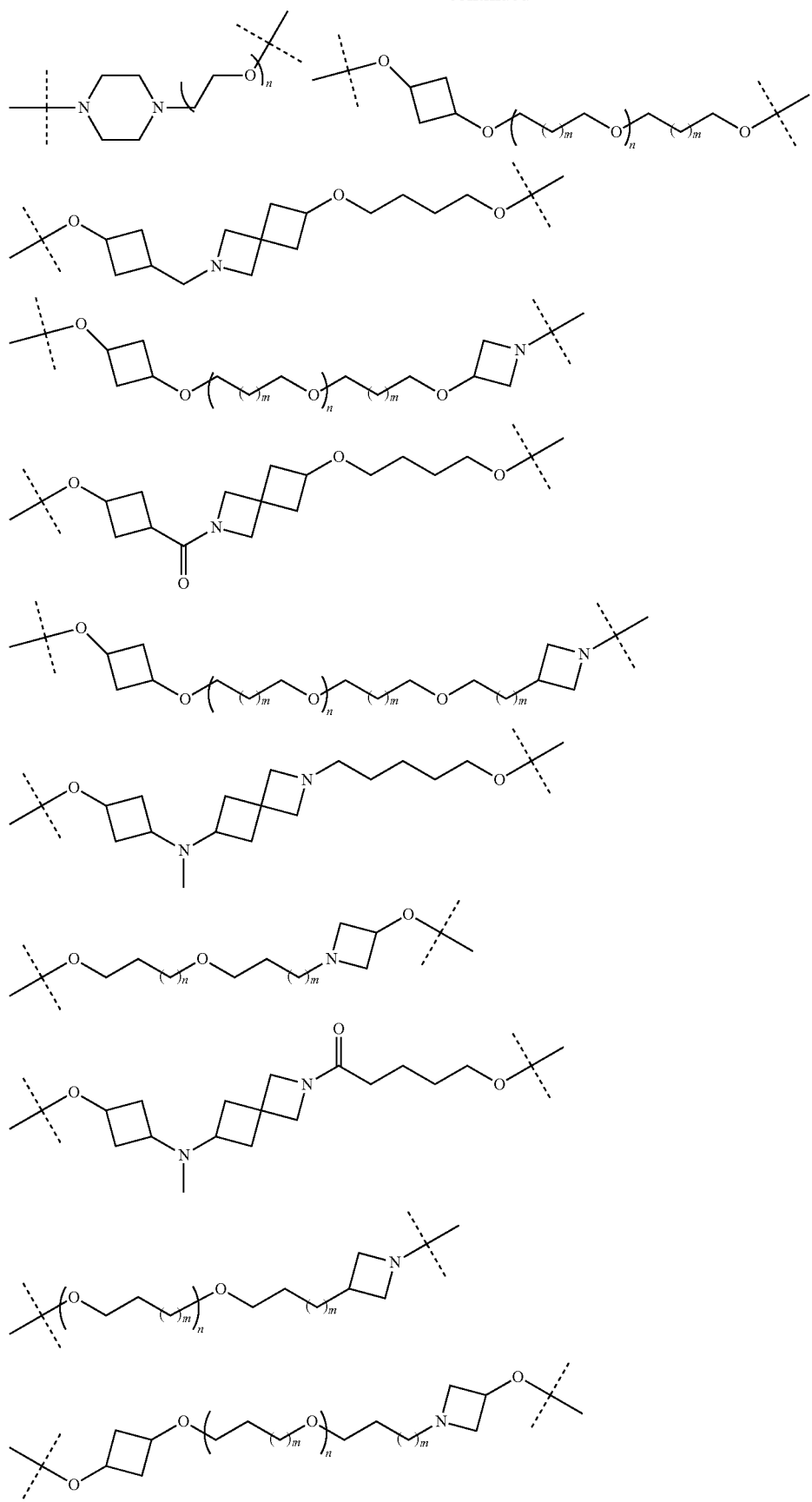

-continued
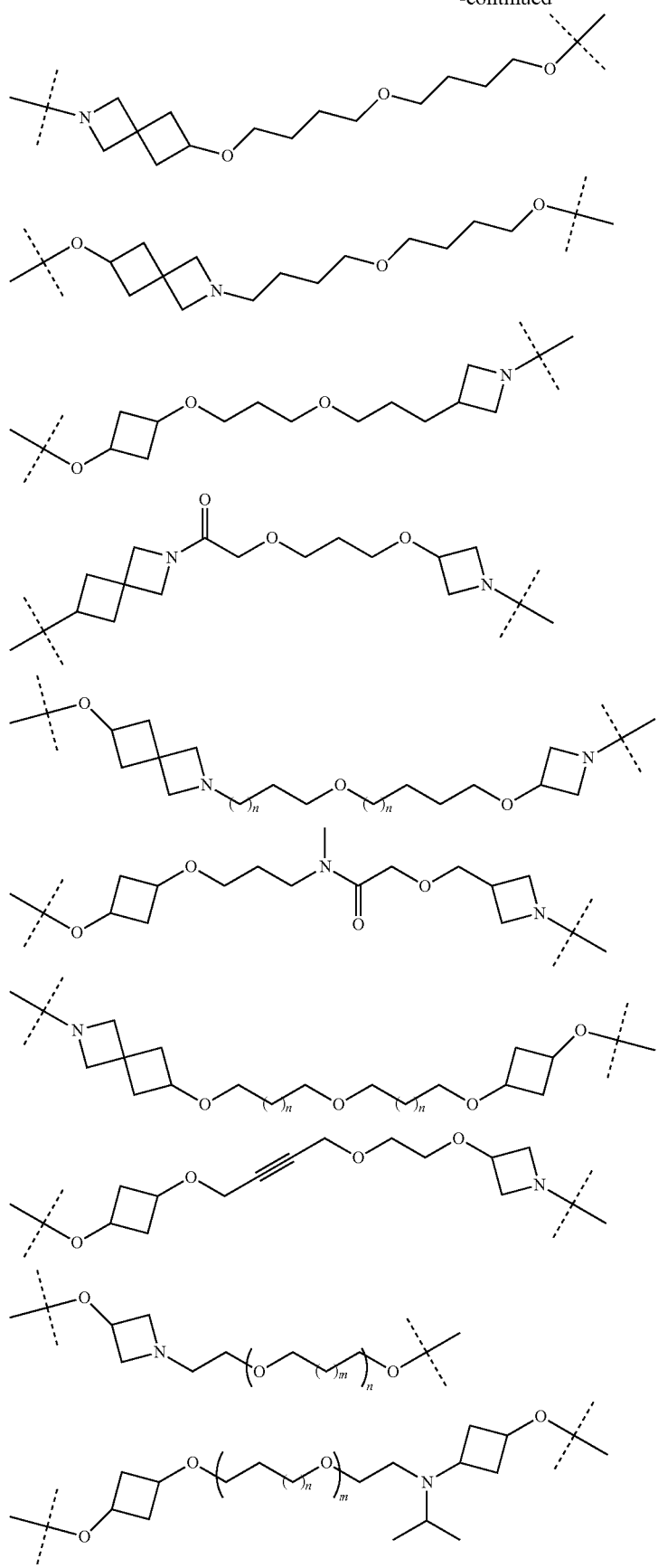

-continued
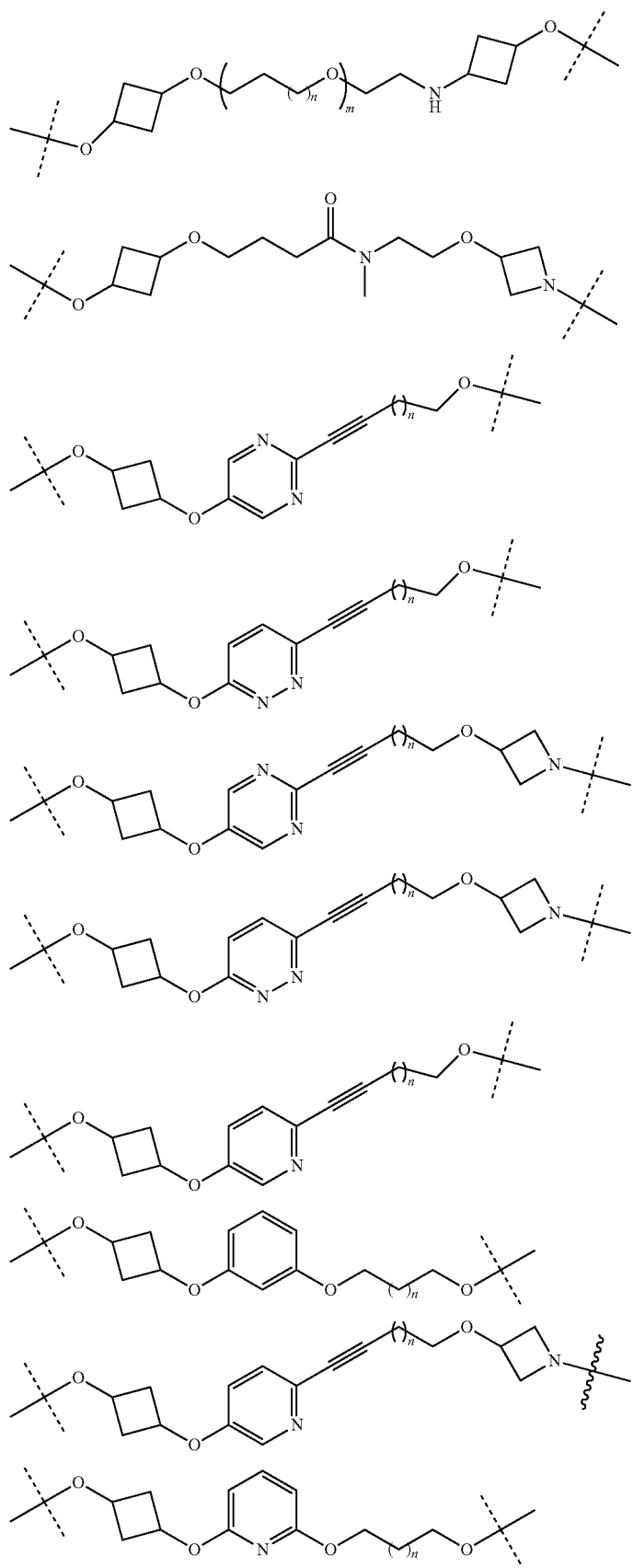

-continued
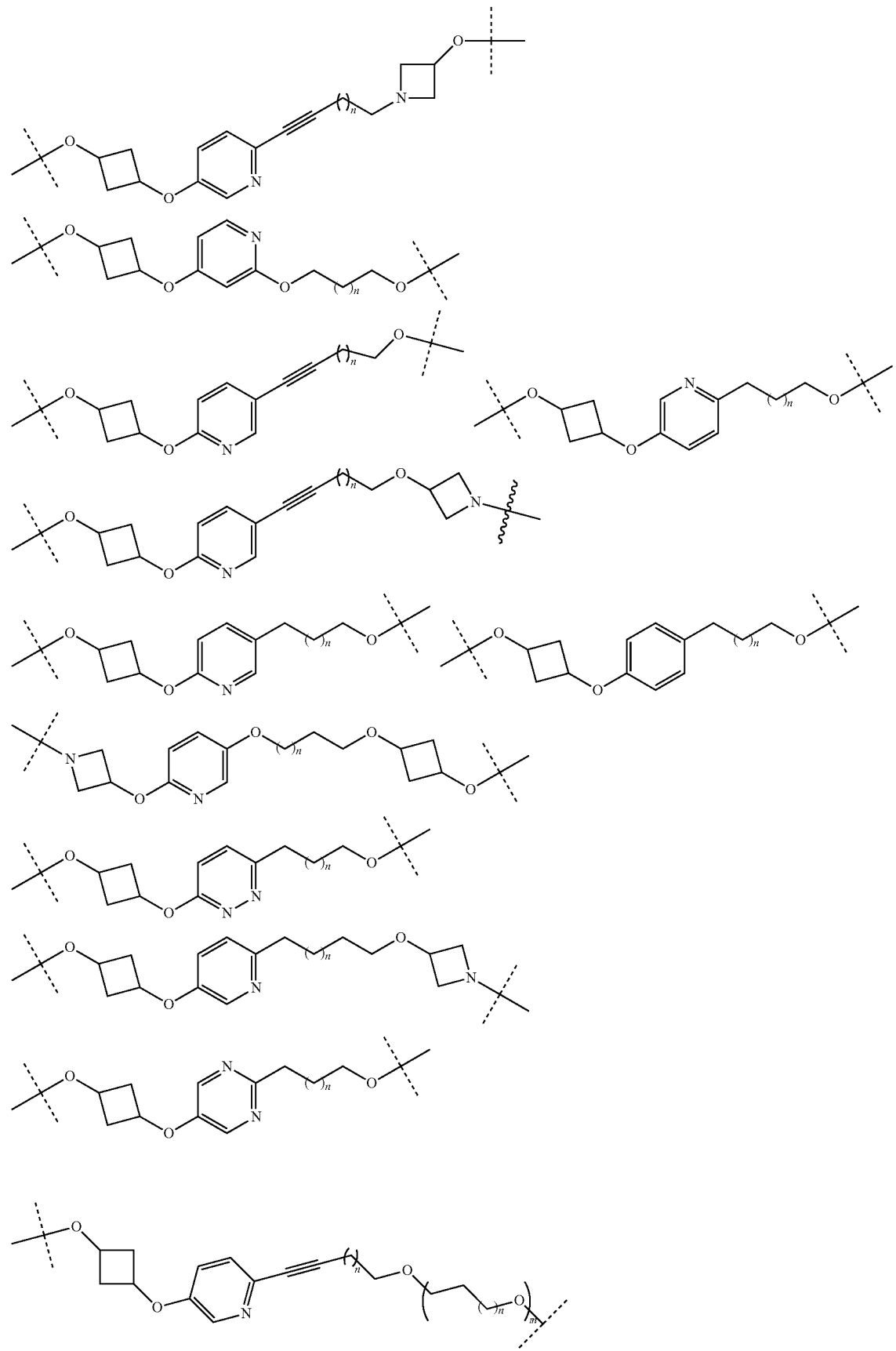

-continued
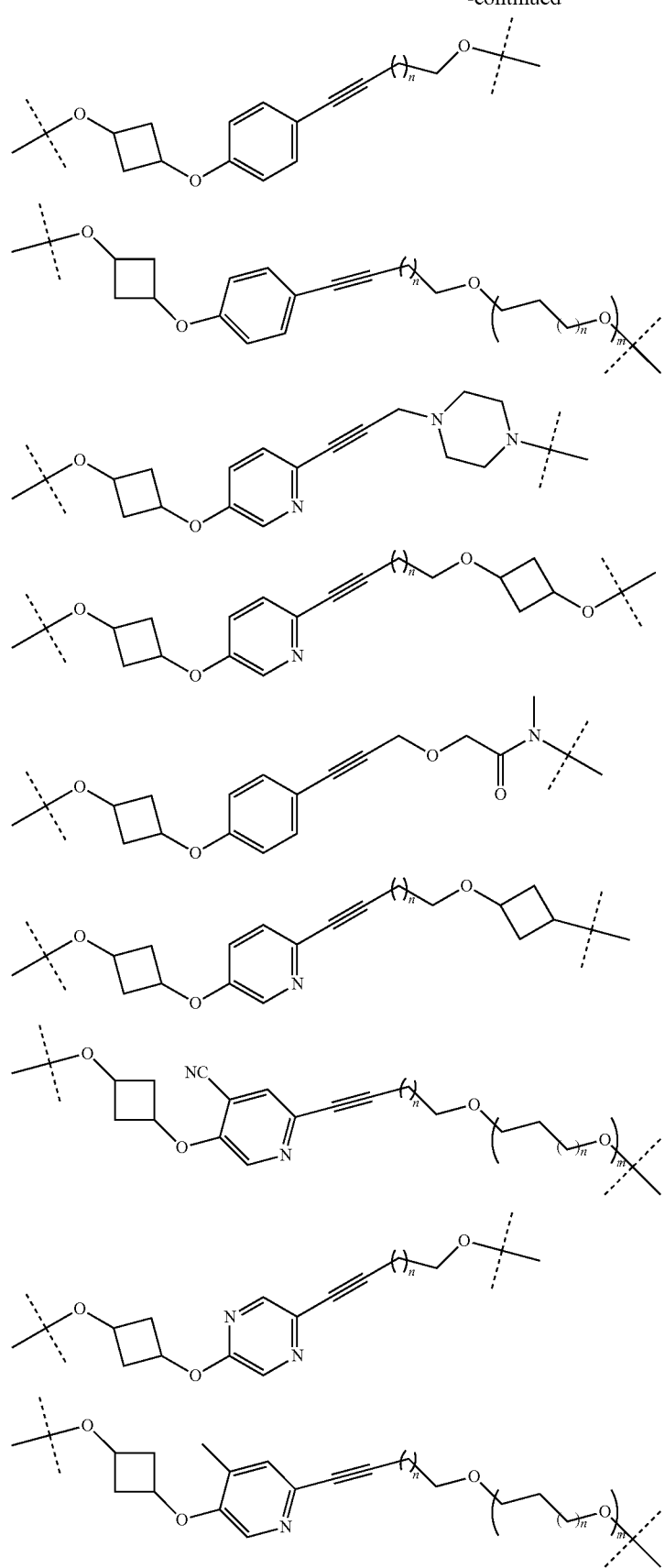

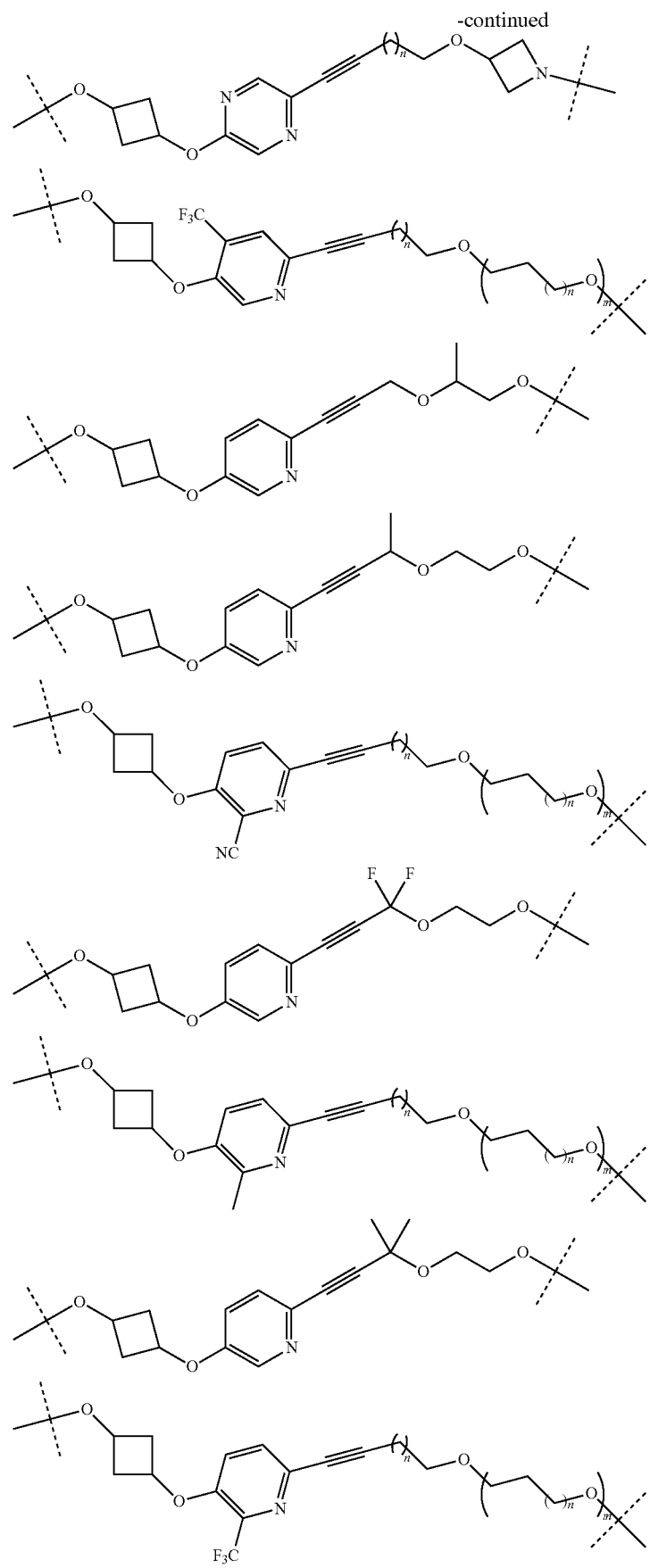

-continued
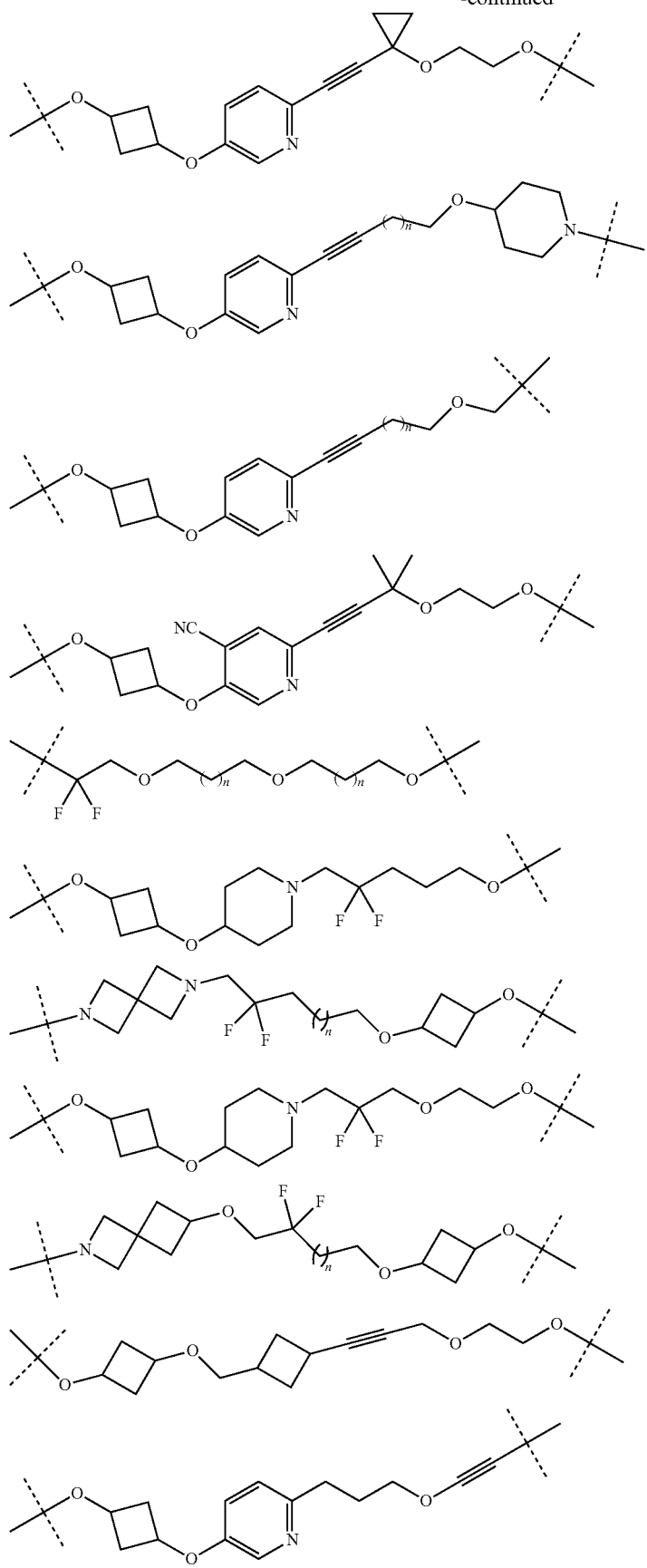

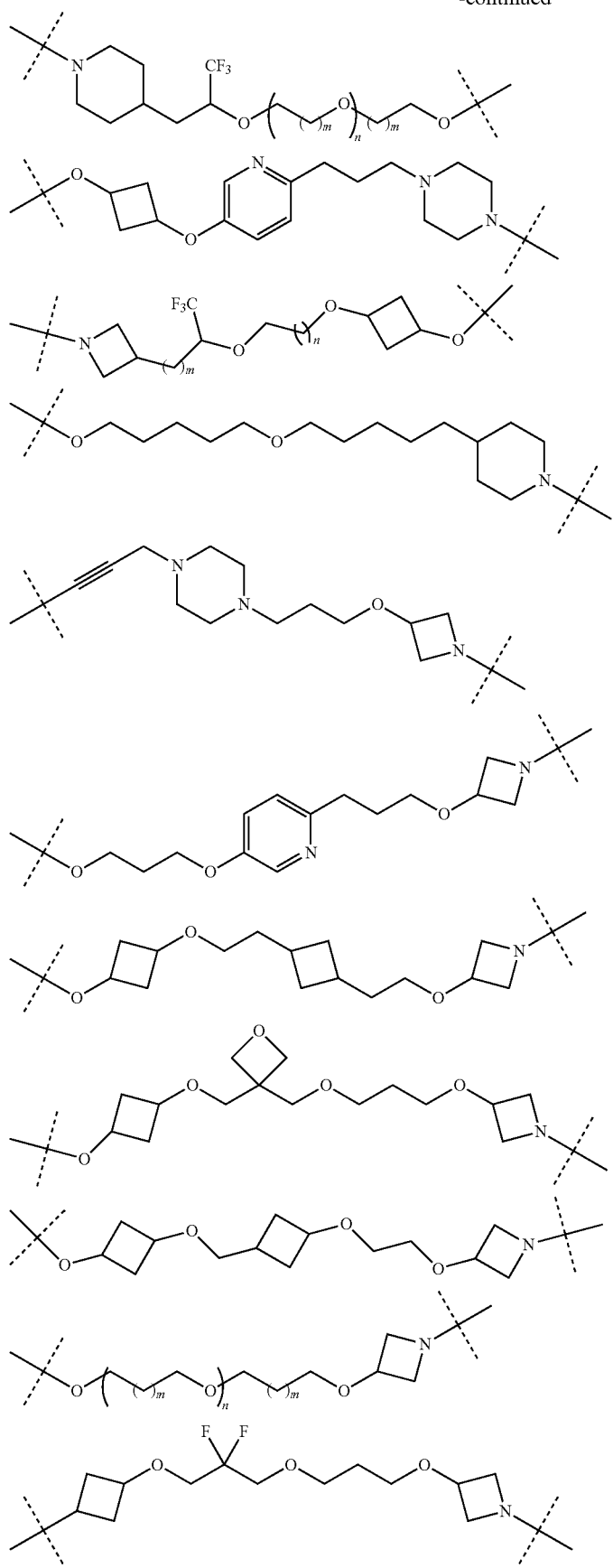

-continued
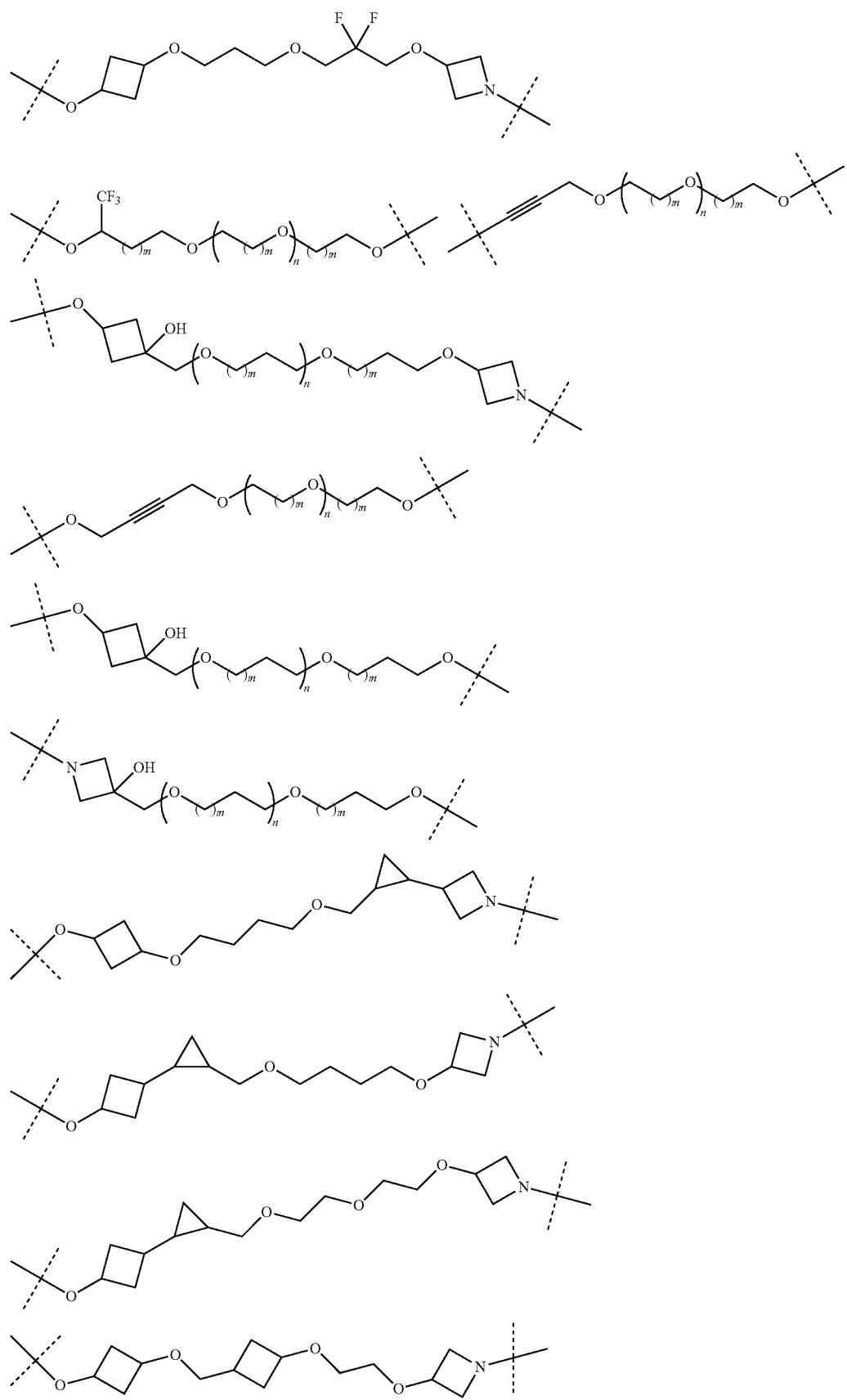

927
928
-continued
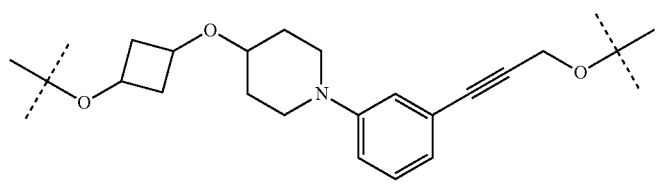
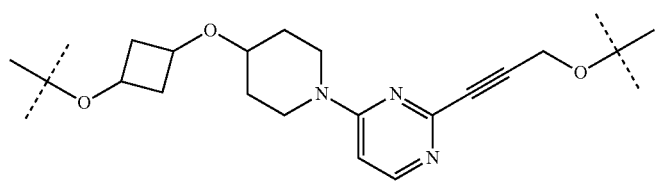
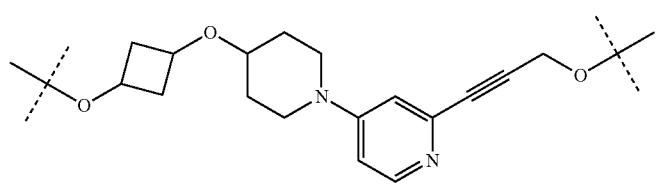
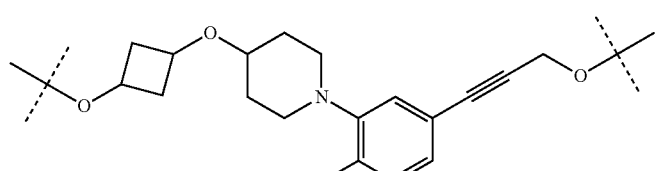
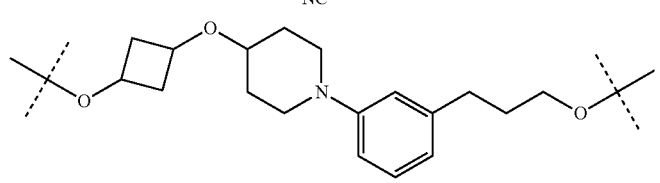
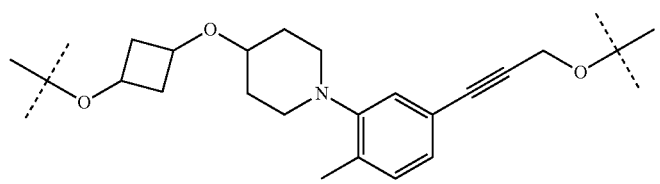
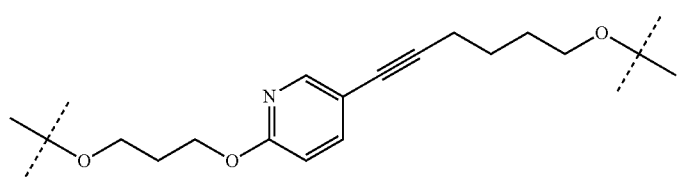
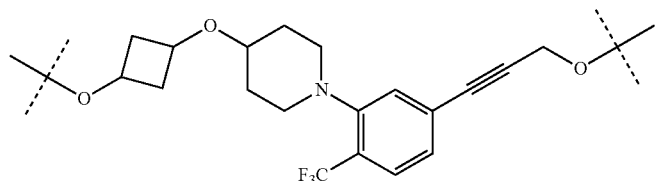
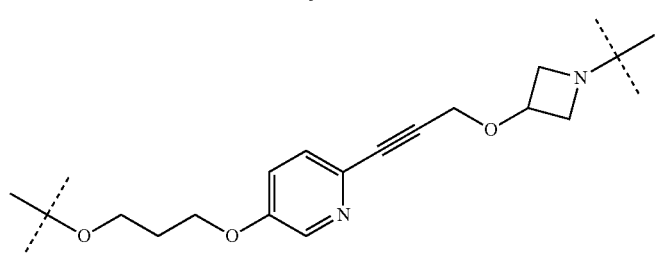

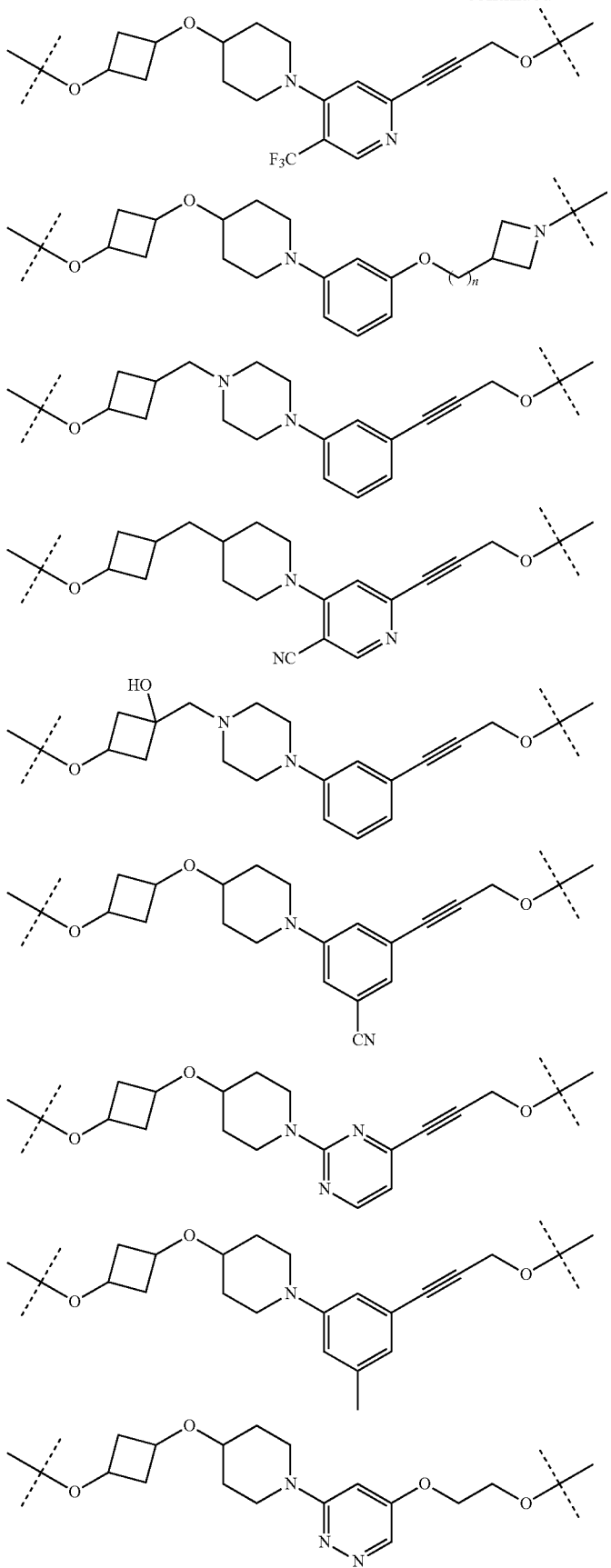

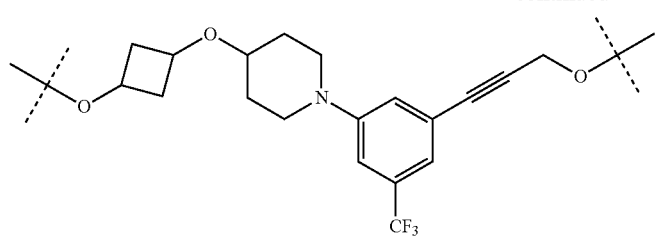
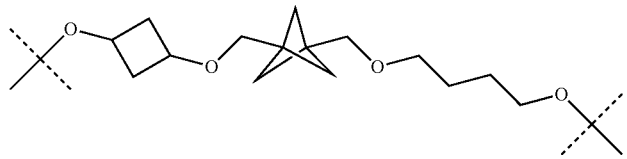
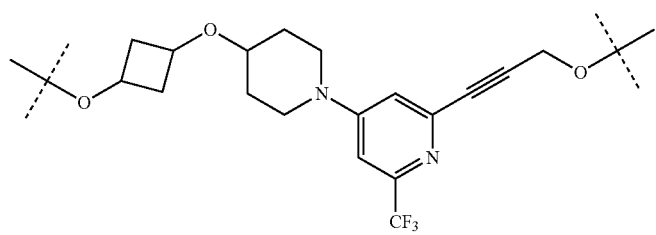
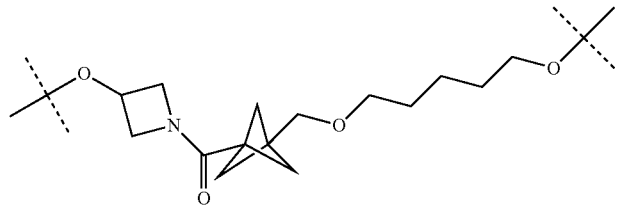
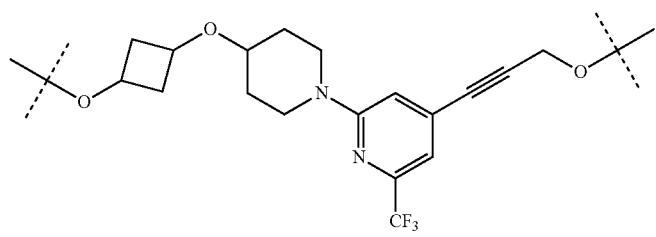
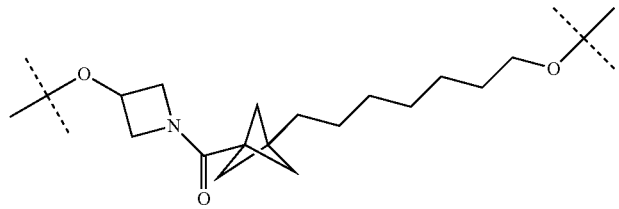
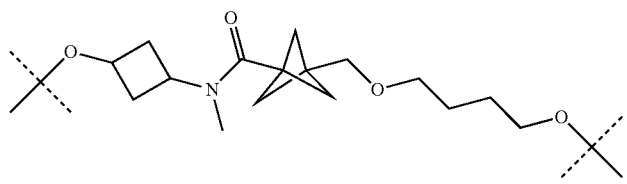
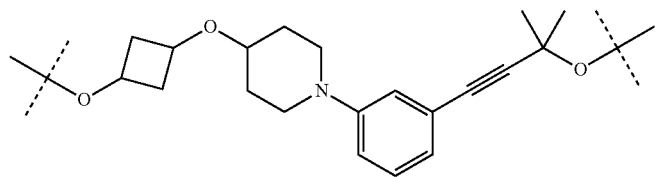

-continued
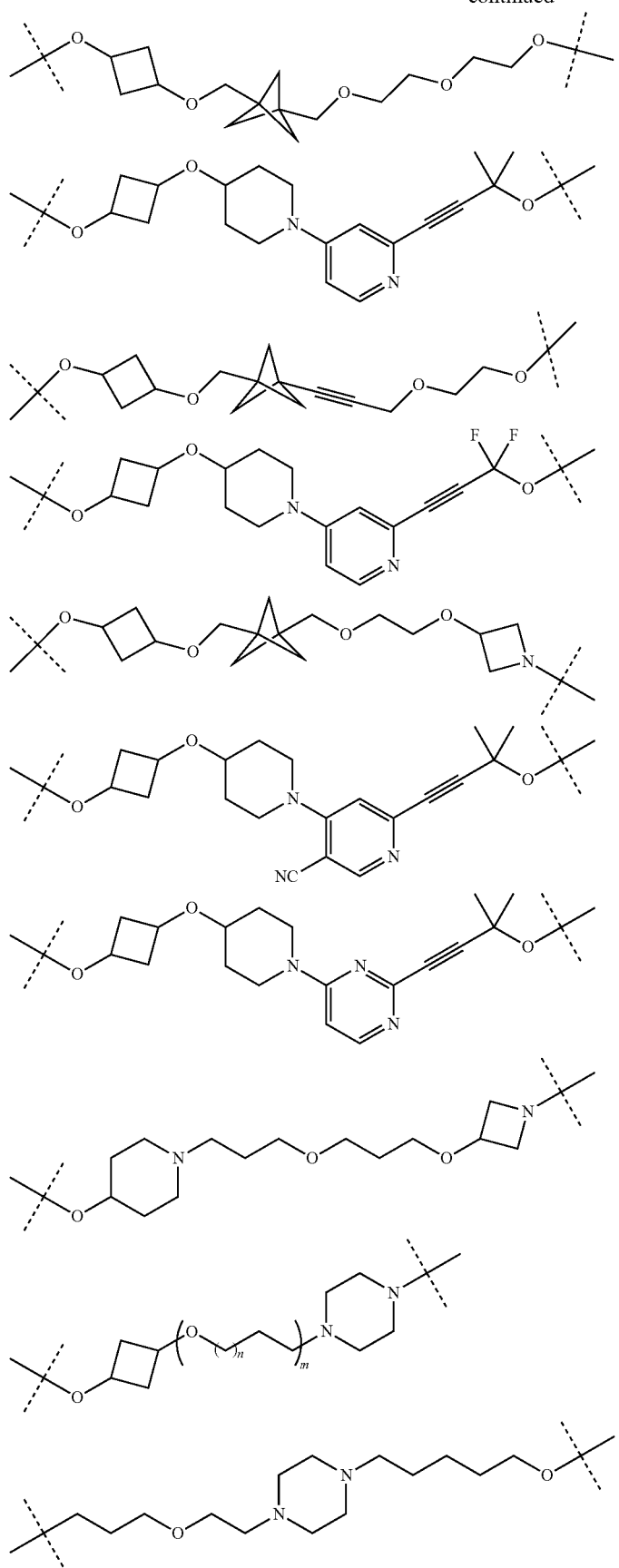

-continued
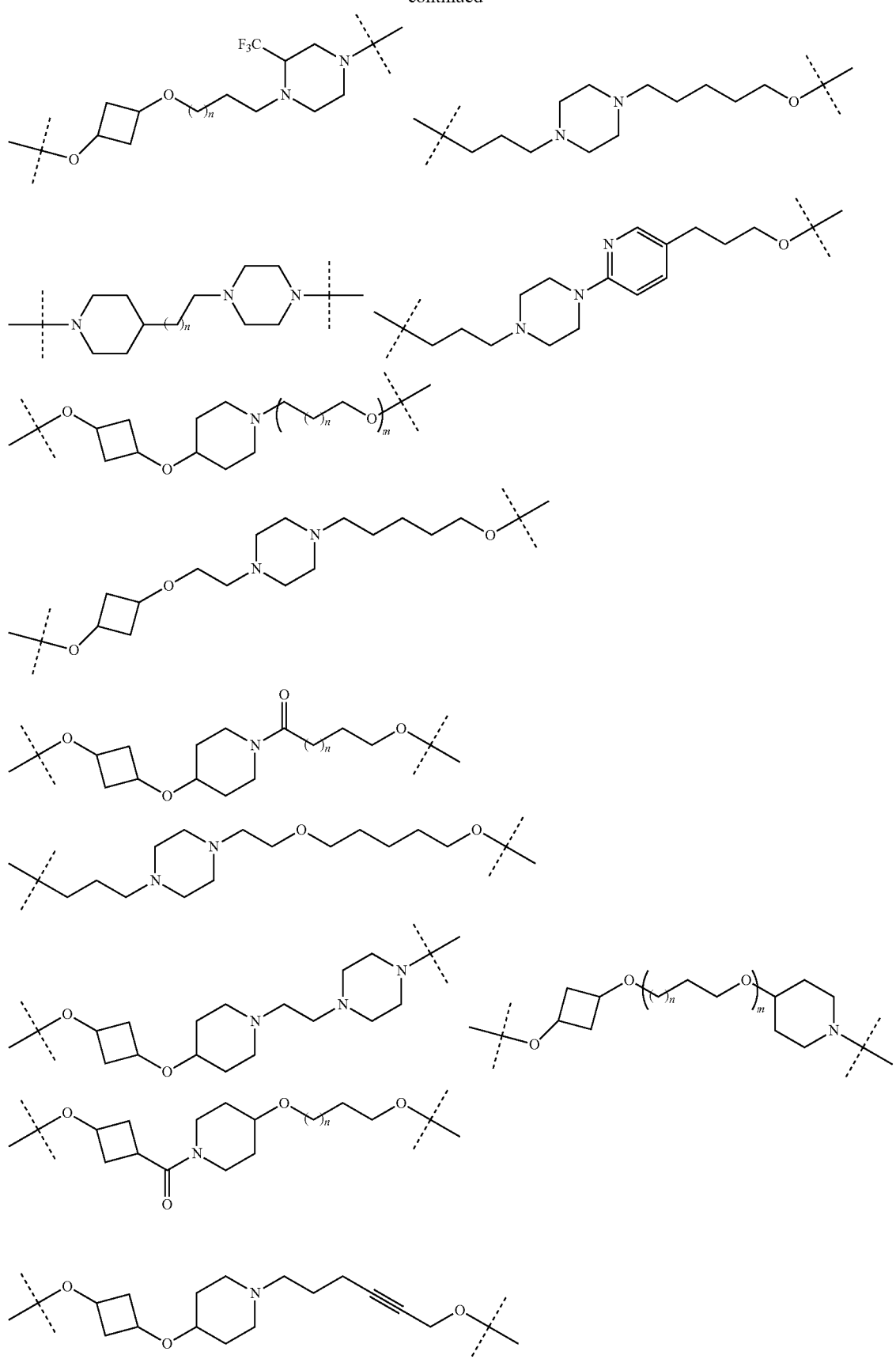

-continued
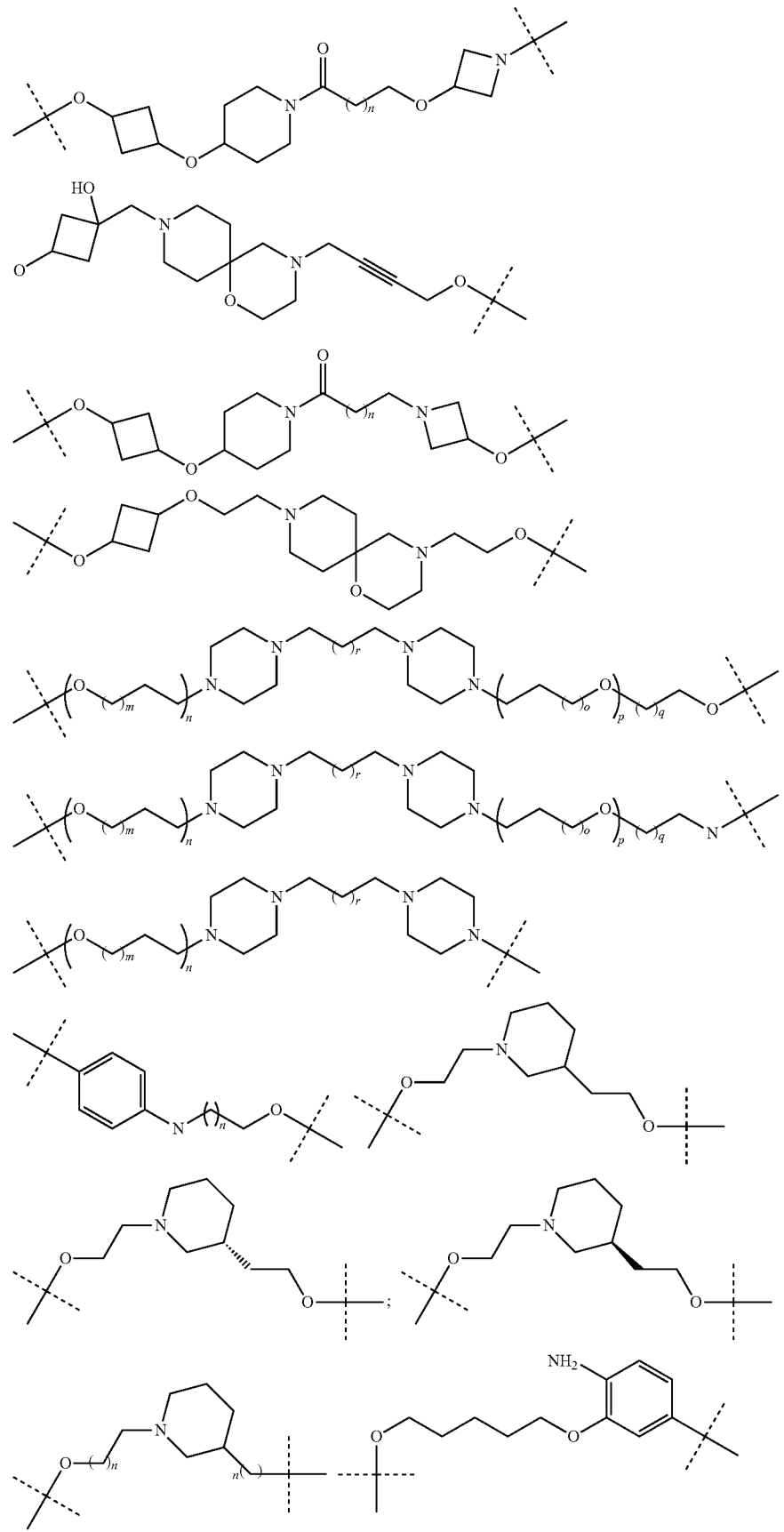

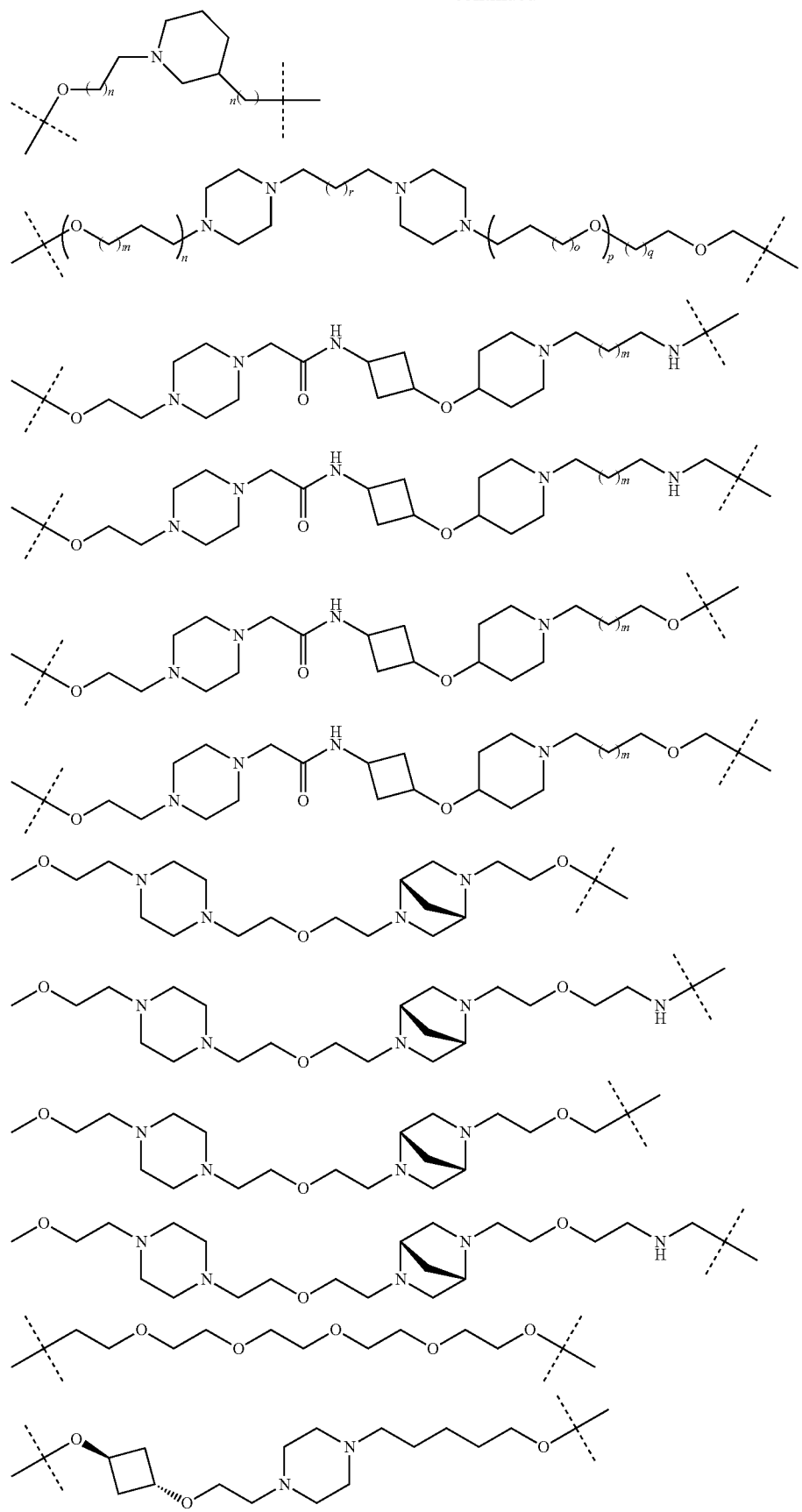

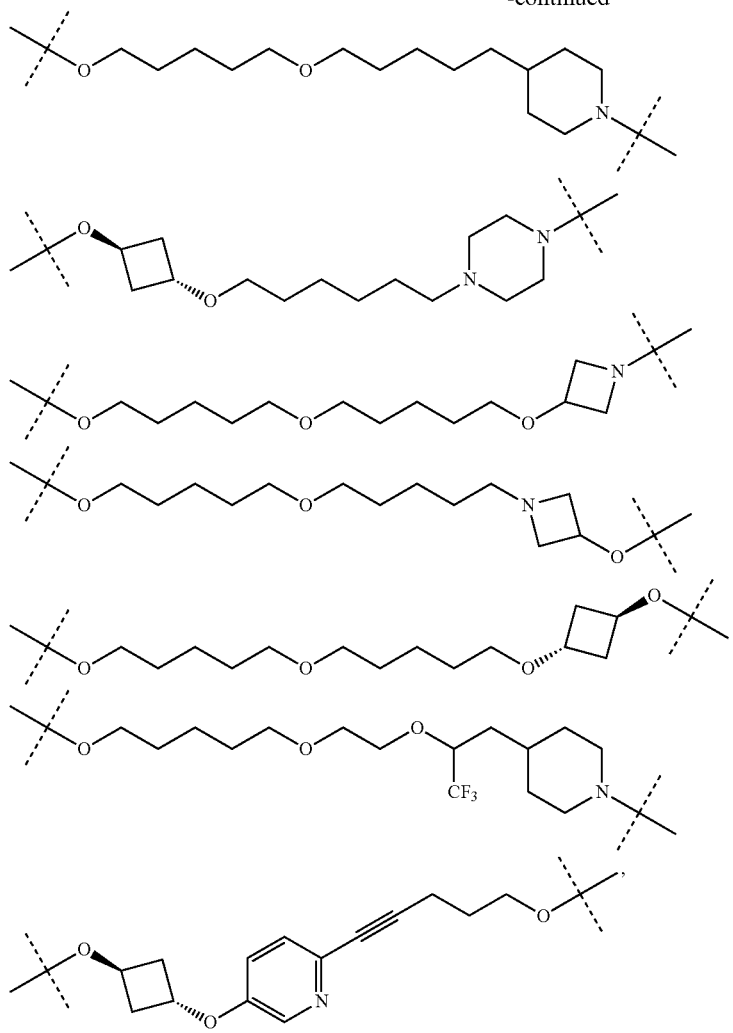
wherein each m, n, o, p, q, and r is independently 0, 1, 2, 3, 4, 5, 6, 7, 8, 9, 10, 11, 12, 13, 14, 15, 16, 17, 18, 19, or 20.
16. The compound of claim 1, wherein the linker (L) is selected from the group consisting of:
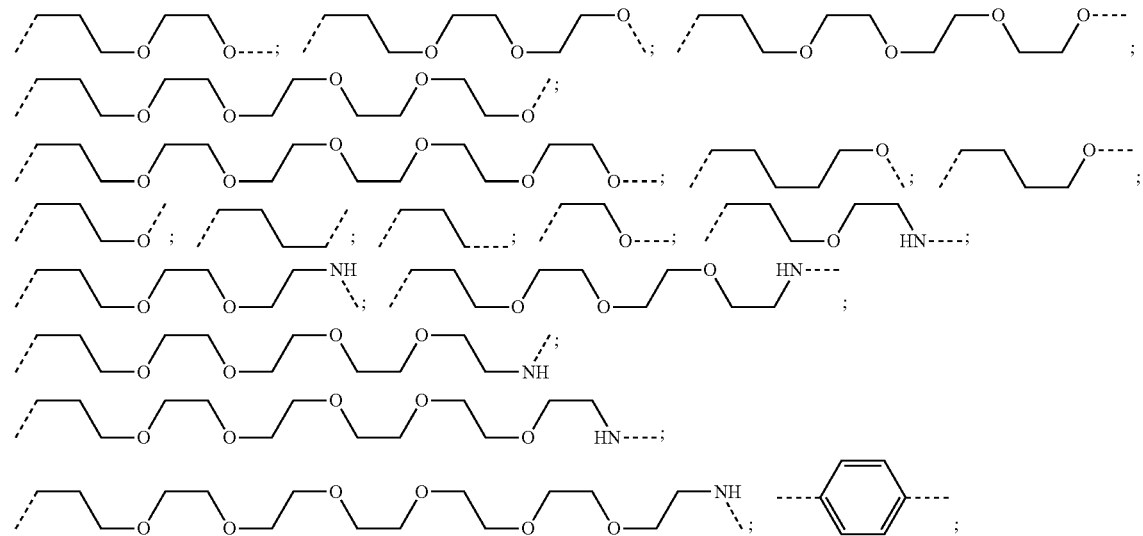

-continued
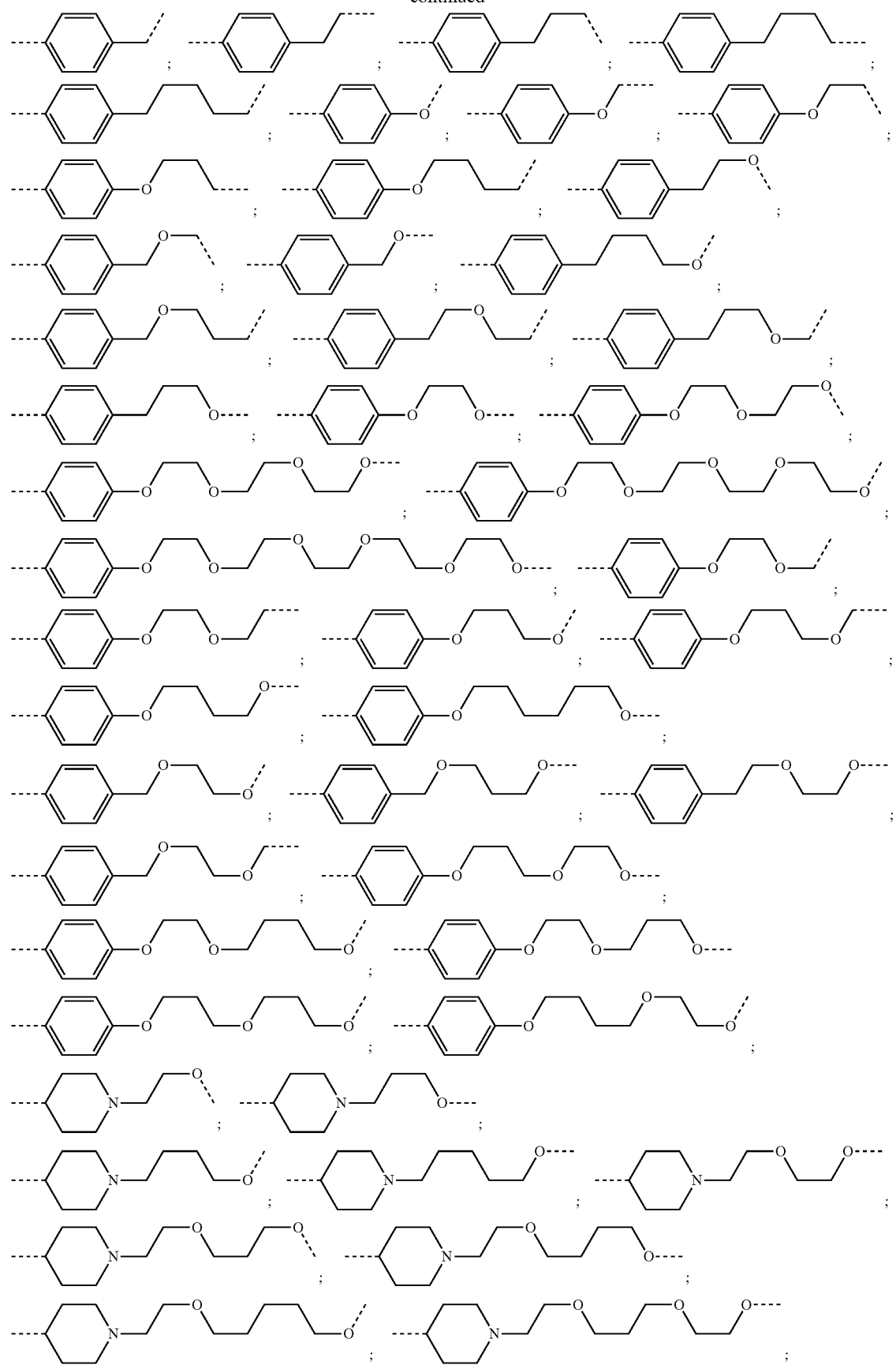

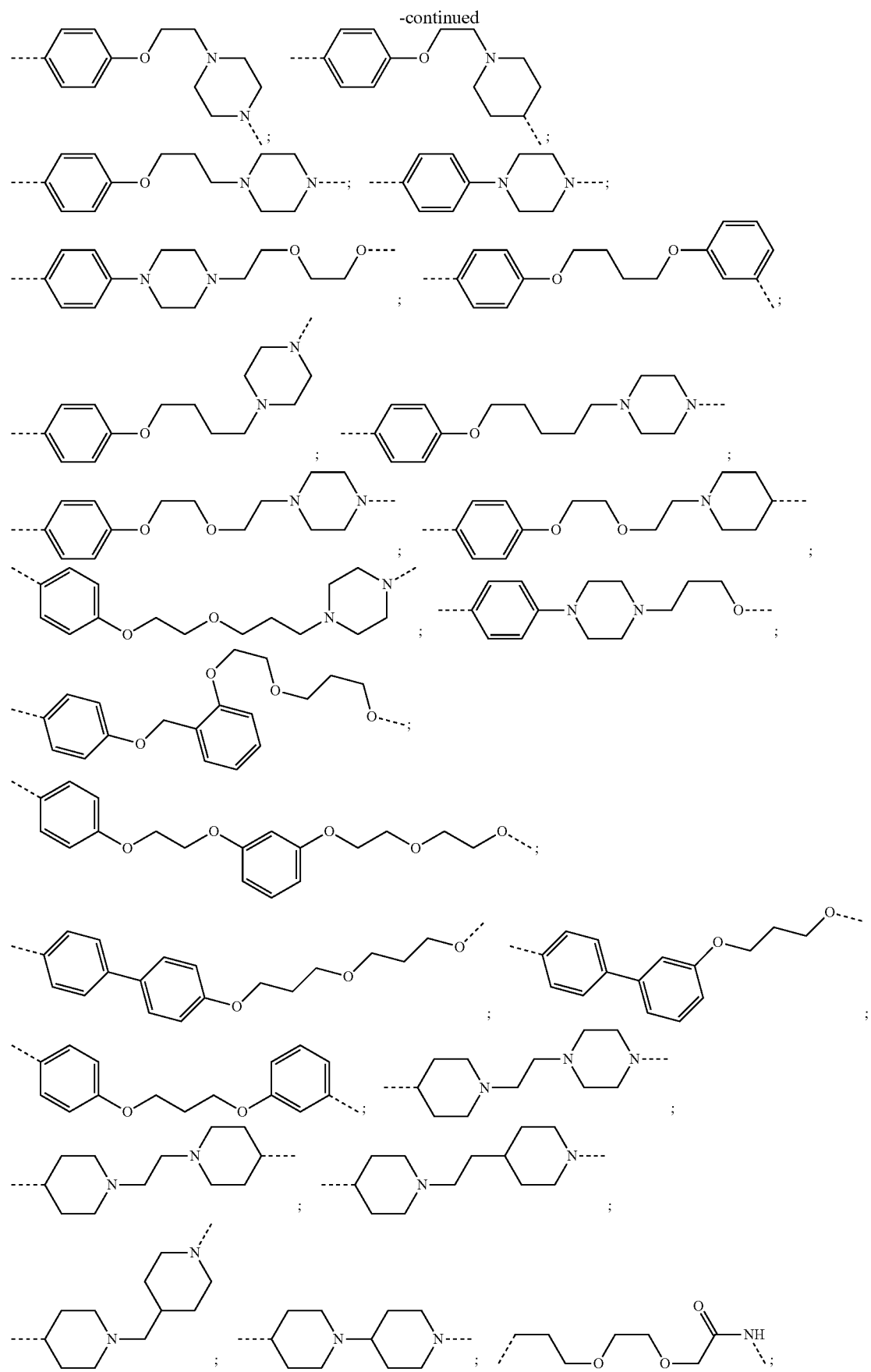

947 948
-continued
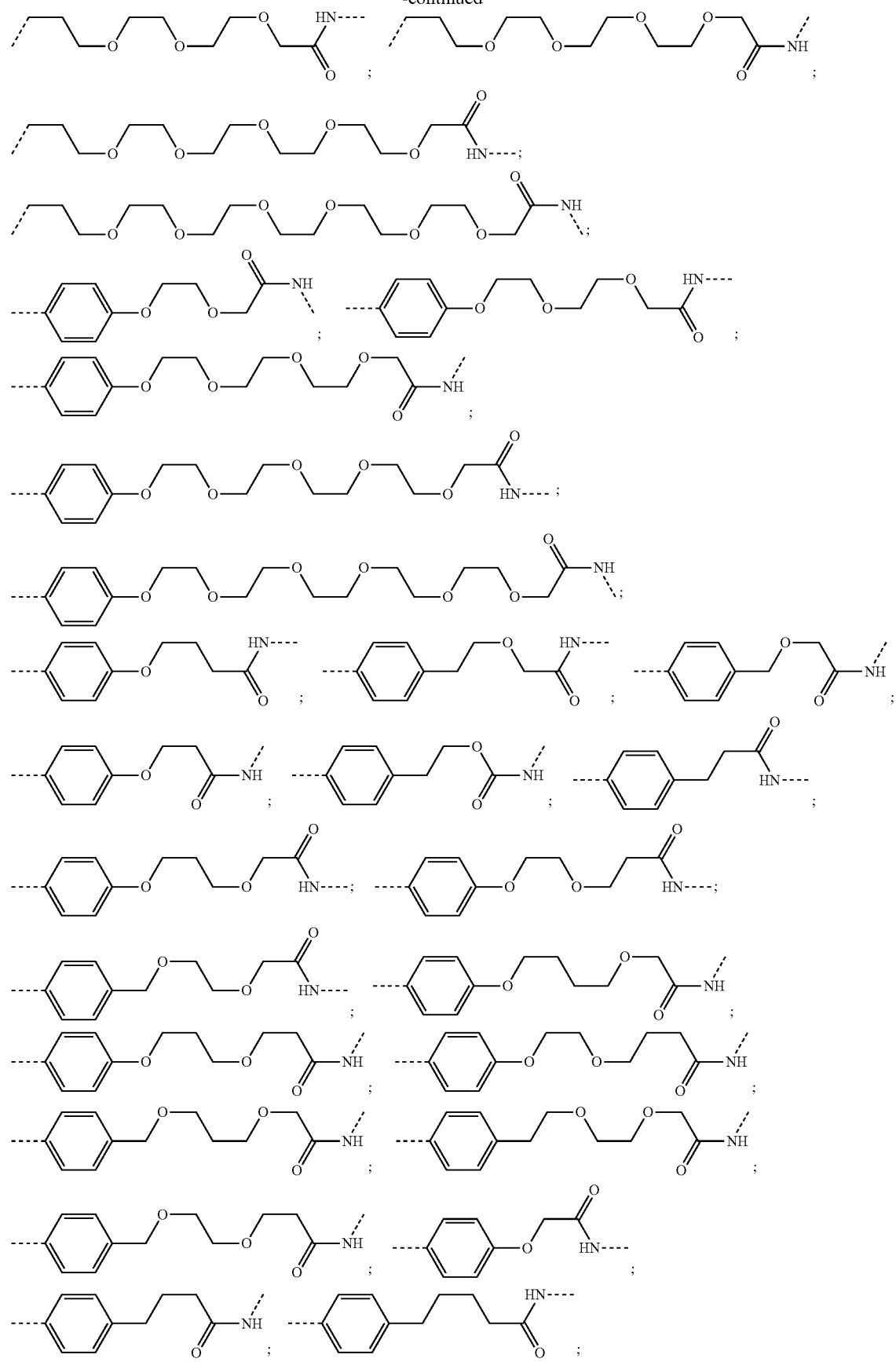

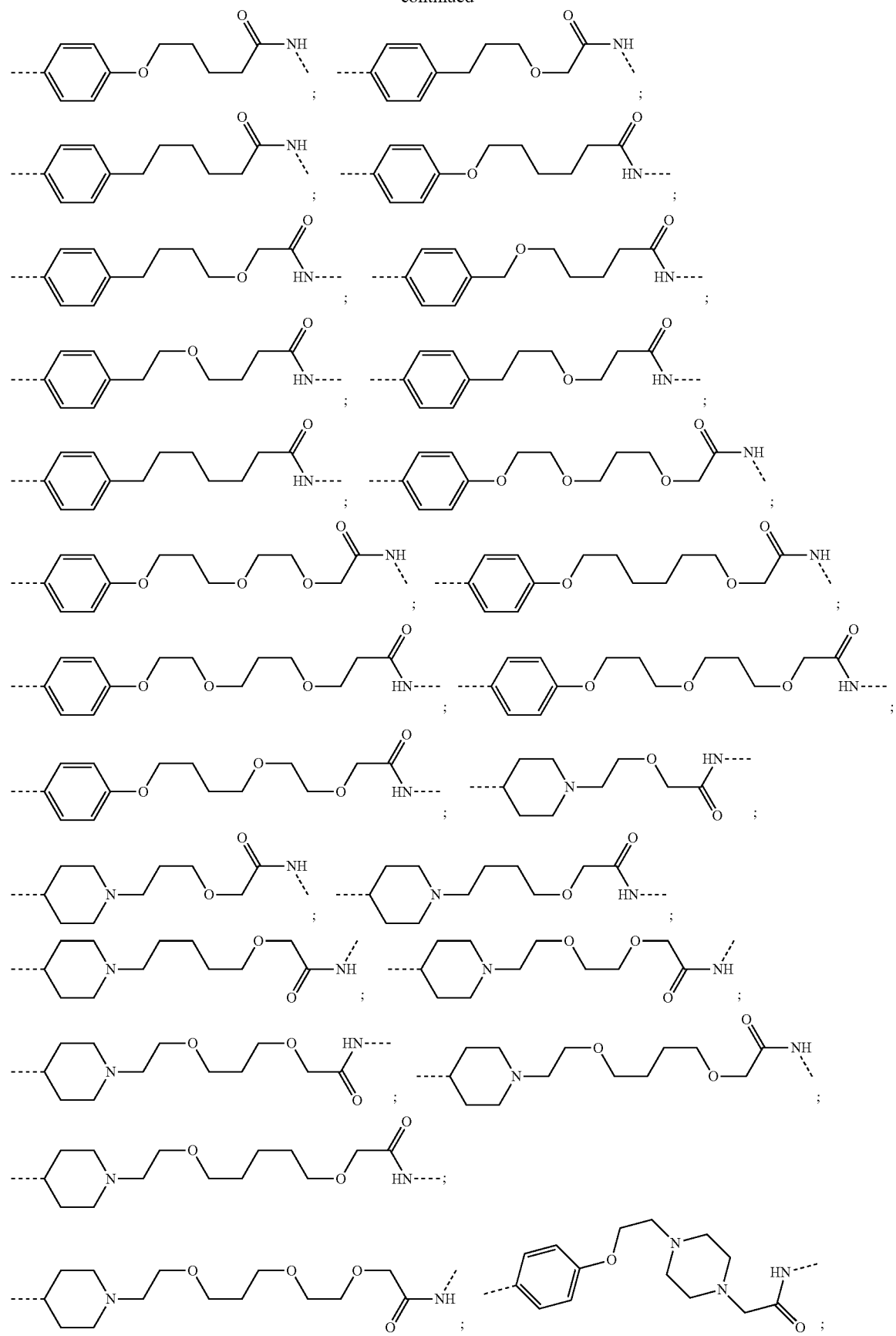

951  952
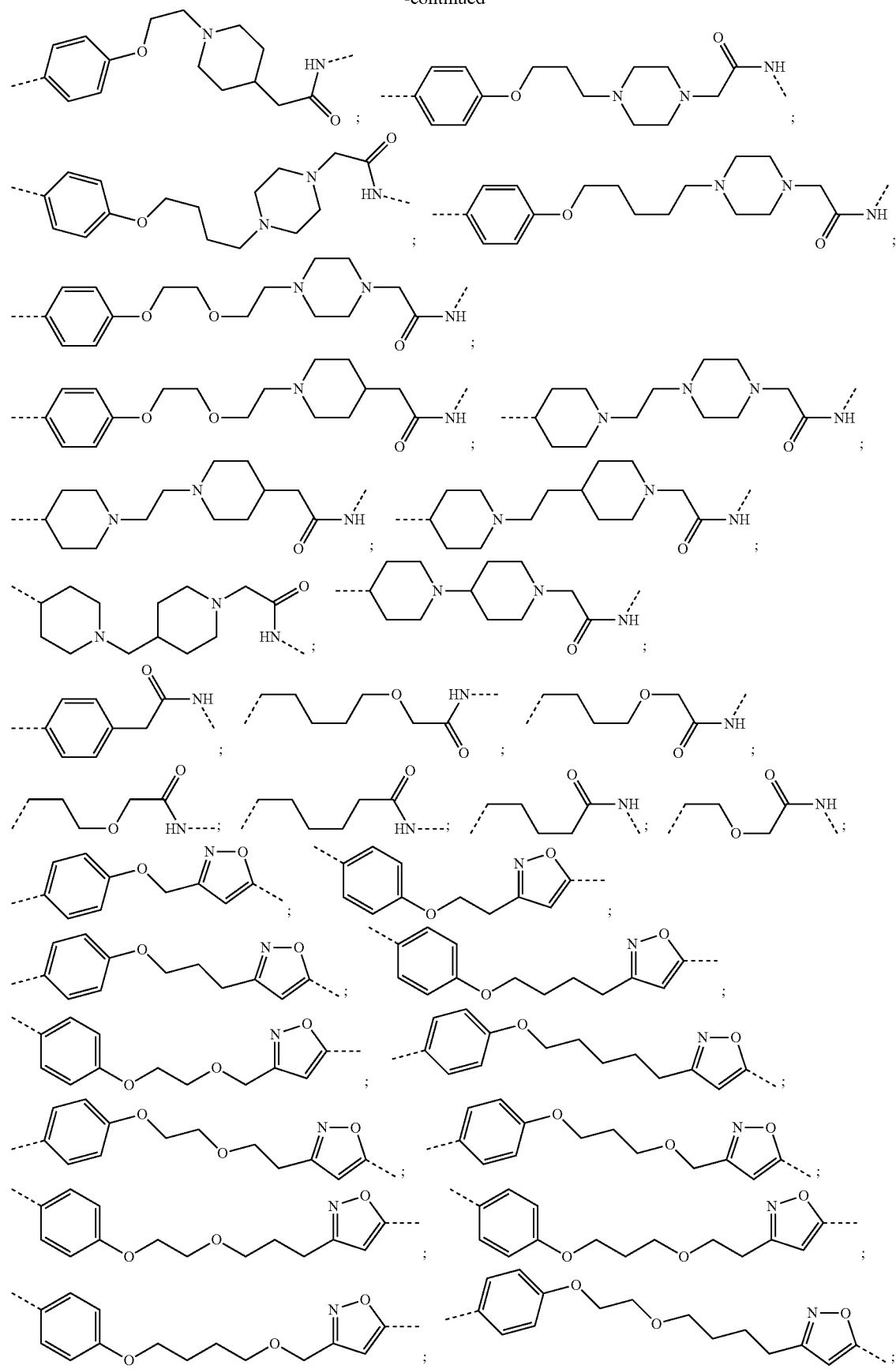

-continued
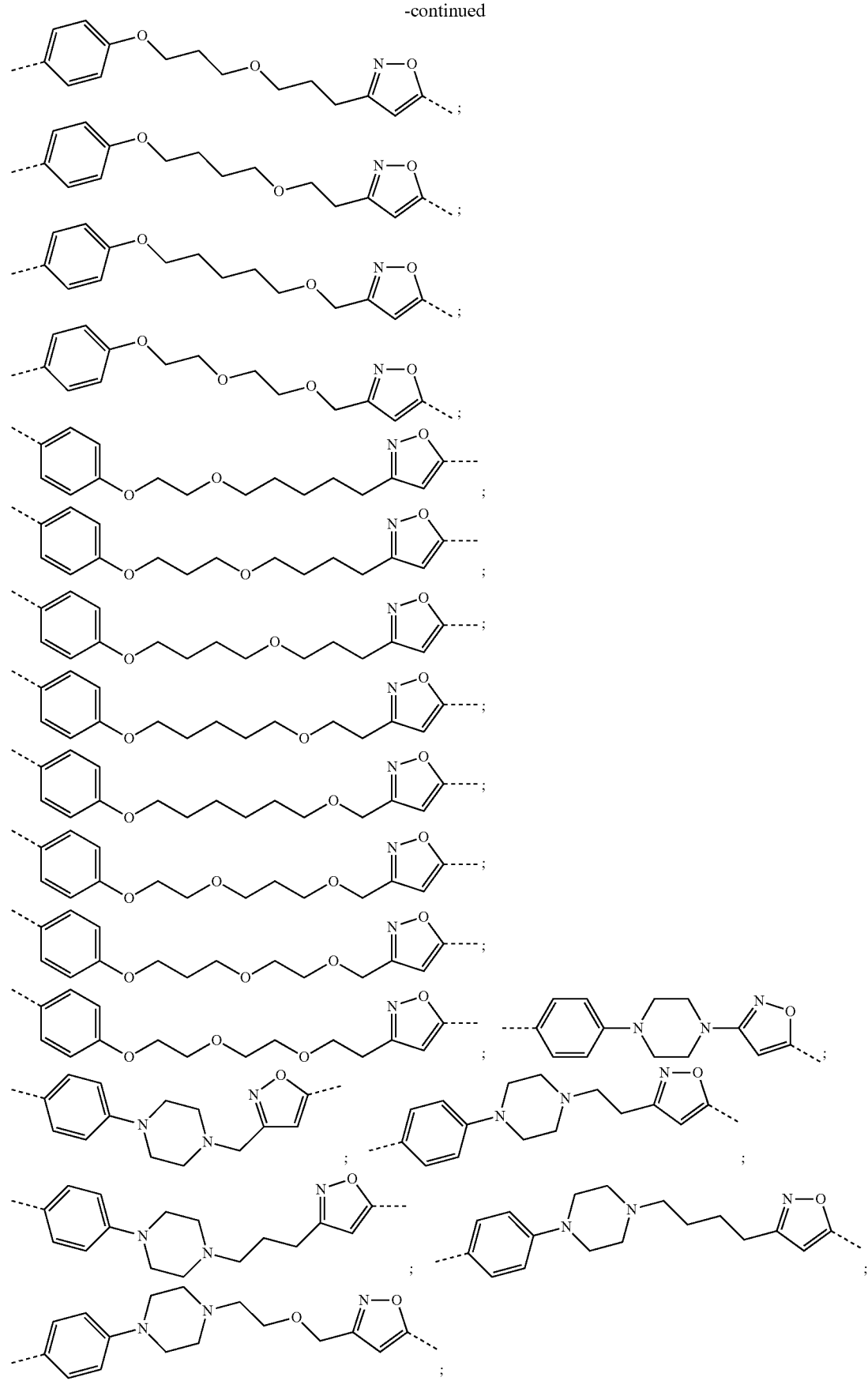

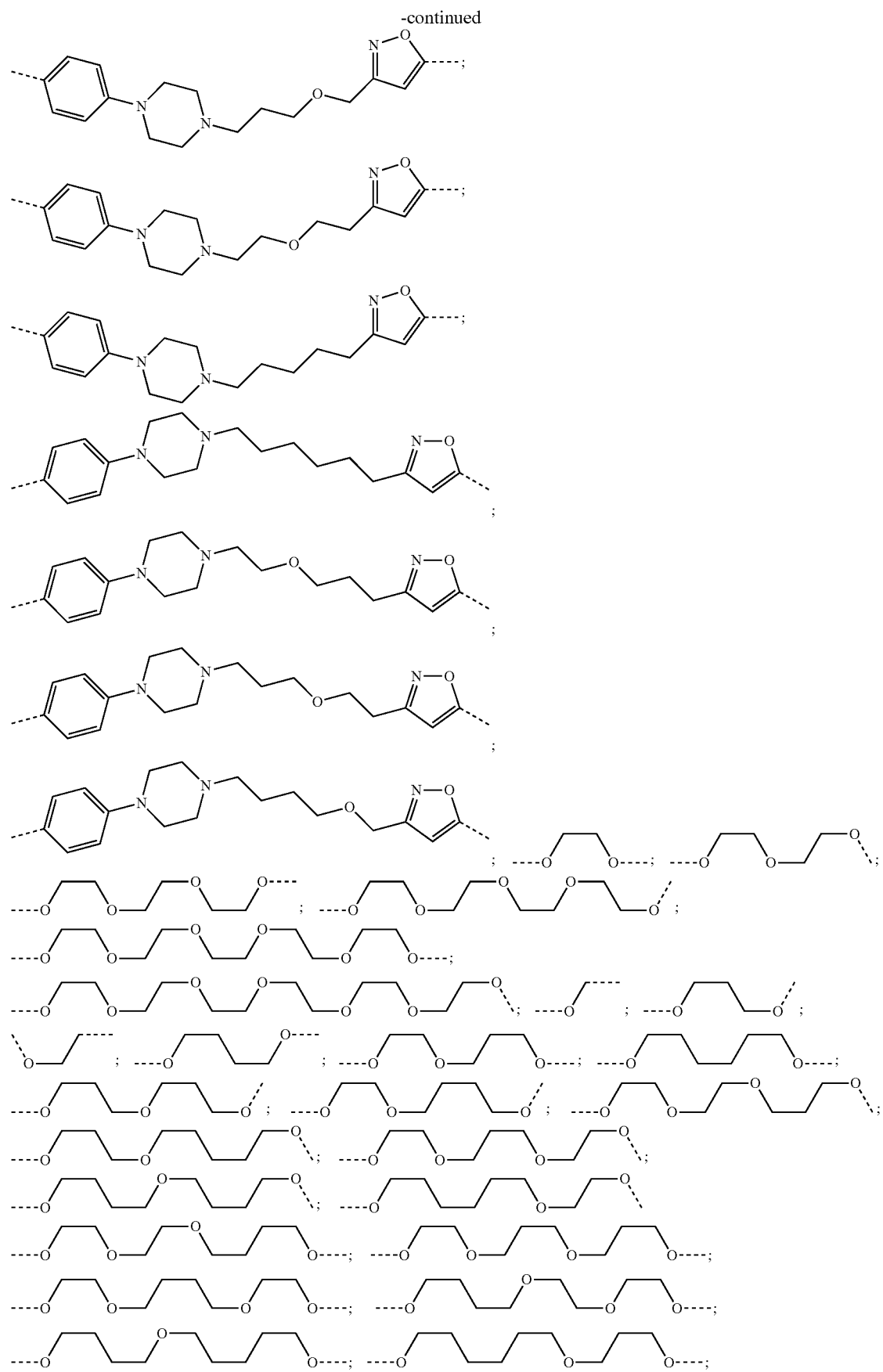

-continued
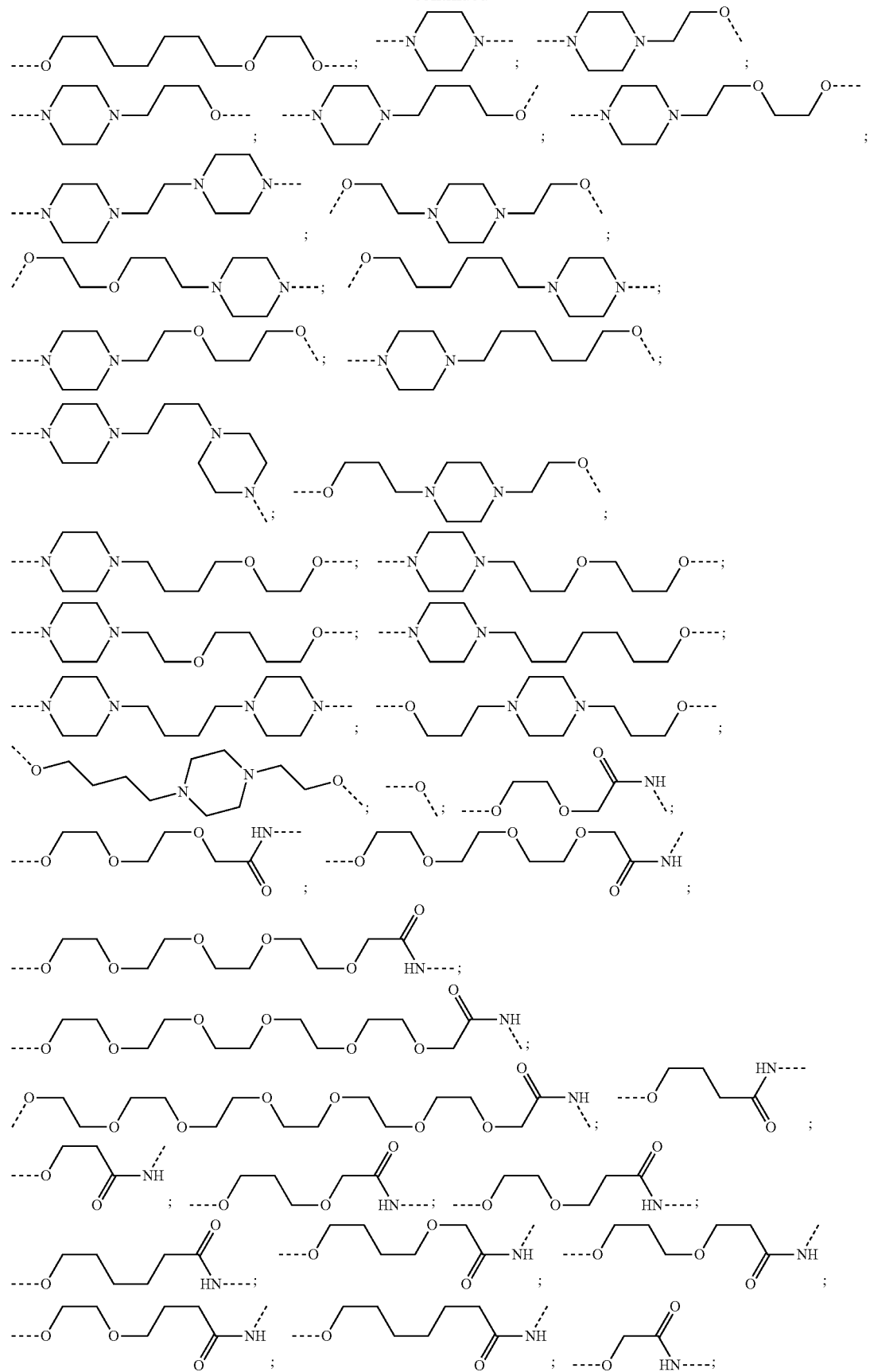

-continued
959 960
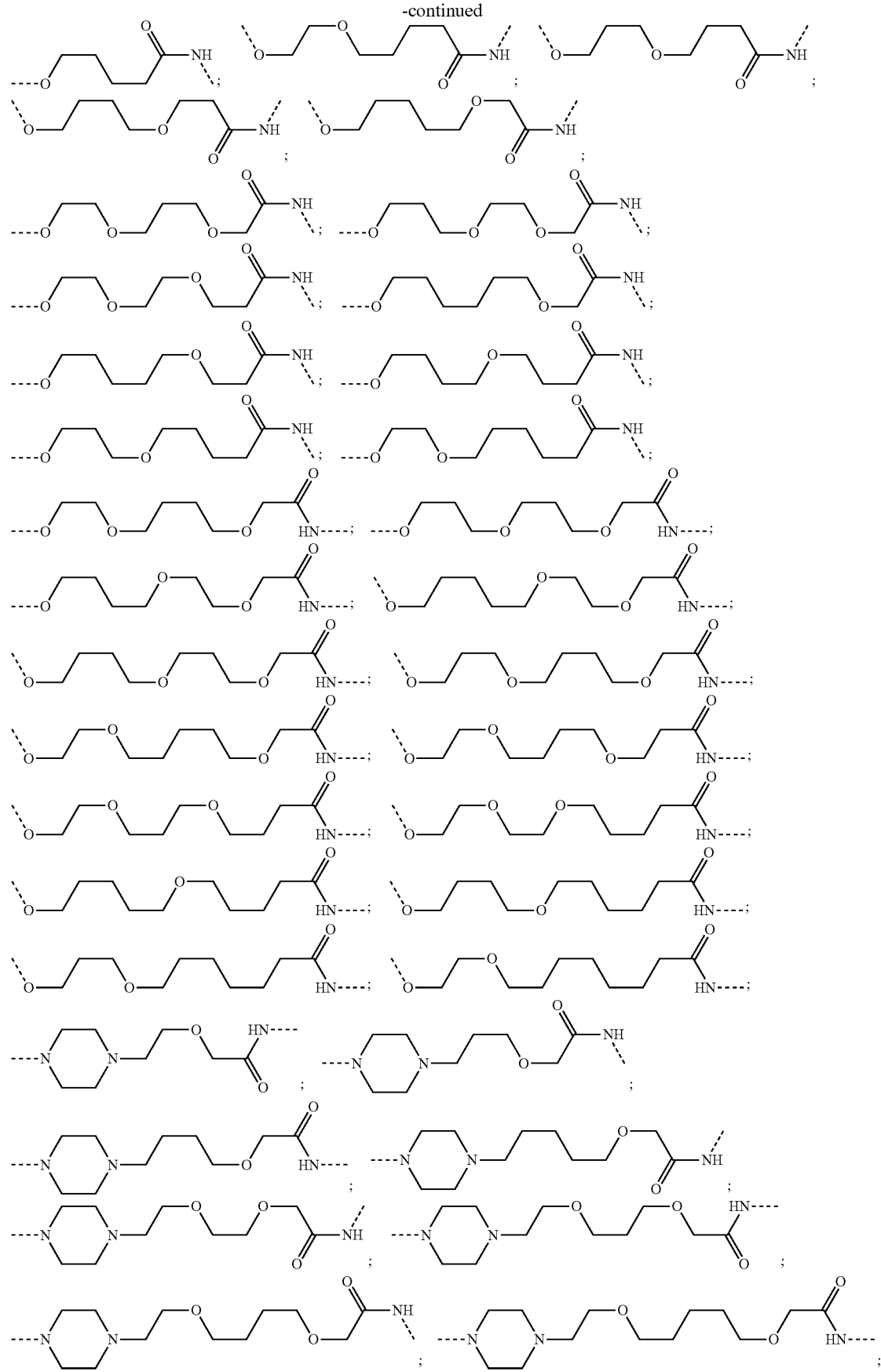

-continued
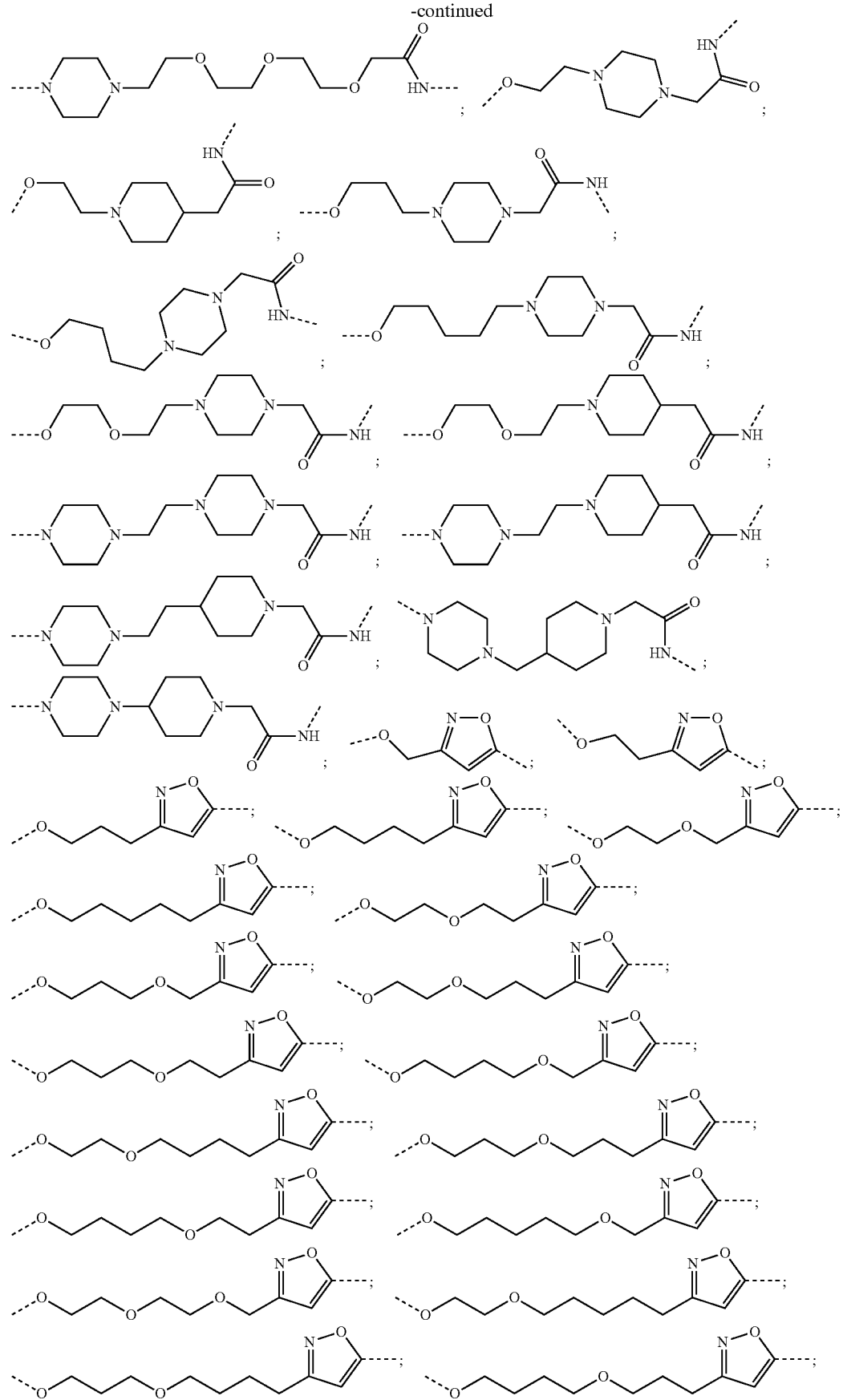

-continued

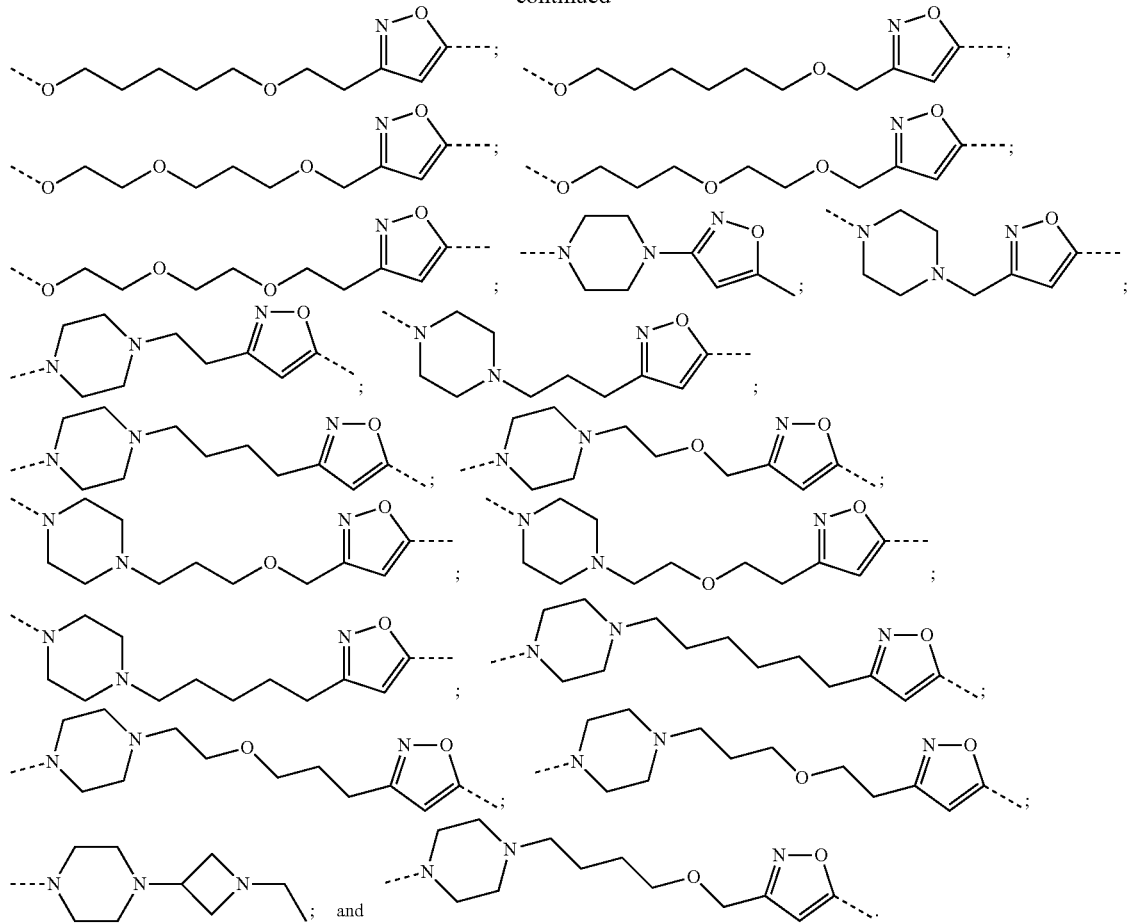

17. The compound of claim 1, wherein the linker (L) has a chemical structure selected from:

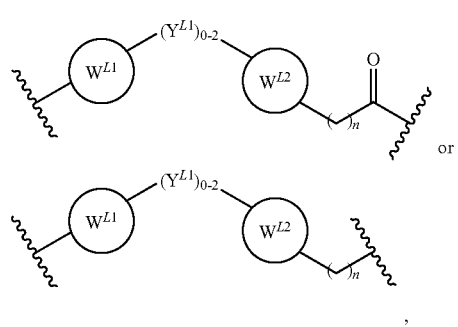

wherein:
W$^{L1}$ and W$^{L2}$ are each independently a 4-8 membered ring with 0-4 heteroatoms, independently optionally substituted with H, halo, OH, CN, CF$_3$, optionally substituted linear or branched C$_1$-C$_6$ alkyl, optionally substituted linear or branched C$_1$-C$_6$ alkoxy, or groups taken together with the atom they are attached to, form a 4-8 membered ring system containing 0-4 heteroatoms;
Y$^{L1}$ is each independently a bond, optionally substituted linear or branched C$_1$-C$_6$ alkyl and optionally one or more C atoms are replaced with O; or optionally substituted linear or branched C$_1$-C$_6$ alkoxy;

n is 0-10; and indicates the attachment point to the PTM or ULM moieties.

18. The compound of claim 1, wherein the linker (L) has a chemical structure selected from:

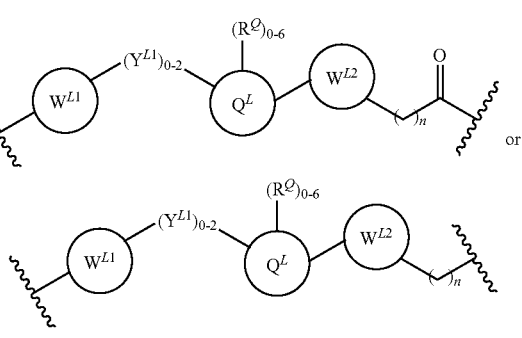

wherein:
- $W^{L1}$ and $W^{L2}$ are each independently aryl, heteroaryl, cyclic, heterocyclic, $C_{1-6}$ alkyl, bicyclic, biaryl, biheteroaryl, or biheterocyclic, each independently optionally substituted with is independently a H, halo, OH, CN, $NH_2$, $NR^{Y1}R^{Y2}$, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, $OC_{1-3}$alkyl optionally substituted by 1 or more —F, or groups taken together with the atom they are attached to, form a 4-8 membered ring system containing 0-4 heteroatoms;
- $Y^{L1}$ is each independently a bond, $NR^{YL1}$, O, S, $NR^{YL2}$, $CR^{YL1}R^{YL2}$, C=O, C=S, SO, $SO_2$, optionally substituted linear or branched $C_1$-$C_6$ alkyl and optionally one or more C atoms are replaced with O; optionally substituted linear or branched $C_1$-$C_6$ alkoxy;
- $Q^L$ is a 3-6 membered alicyclic or aromatic ring with 0-4 heteroatoms, optionally bridged, optionally substituted with 0-6 $R^Q$, each $R^Q$ is independently H, linear or branched $C_{1-6}$ alkyl optionally substituted by 1 or more halo or $C_{1-6}$ alkoxyl, or 2 $R^Q$ groups taken together with the atom they are attached to, form a 3-8 membered ring system containing 0-2 heteroatoms;
- $R^{YL1}$ $R^{YL2}$ are each independently H, OH, linear or branched $C_{1-6}$ alkyl optionally substituted by 1 or more halo or $C_{1-6}$ alkoxyl, or $R^1$, $R^2$ together with the atom they are attached to, form a 3-8 membered ring system containing 0-2 heteroatoms;
- n is 0-10; and

indicates the attachment point to the PTM or ULM moieties.

19. The compound of claim 1, wherein the linker (L) is a polyethylenoxy group optionally substituted with aryl or phenyl comprising from 1 to 10 ethylene glycol units.

20. A composition comprising an effective amount of a compound of claim 1, and a pharmaceutically acceptable carrier or excipient.

21. The composition of claim 20, wherein the composition further comprises at least one of an additional bioactive agent or an additional compound of claim 1.

22. The composition of claim 21, wherein the additional bioactive agent is an anti-cancer or anti-inflammatory agent.

23. A composition comprising a pharmaceutically acceptable carrier and an effective amount of at least one compound selected from the group consisting of:

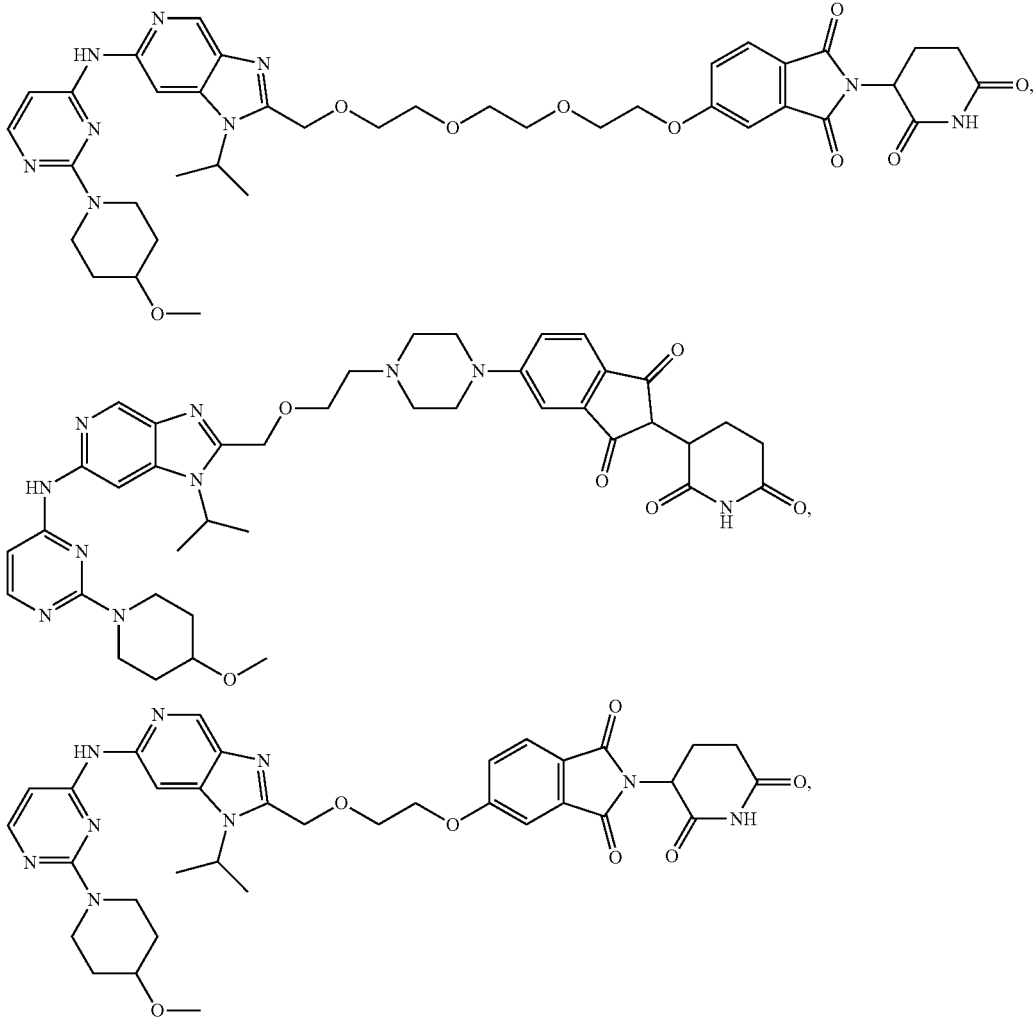

-continued
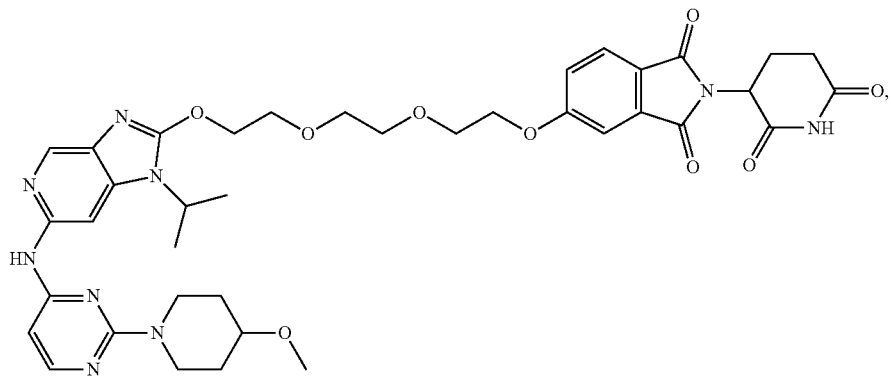
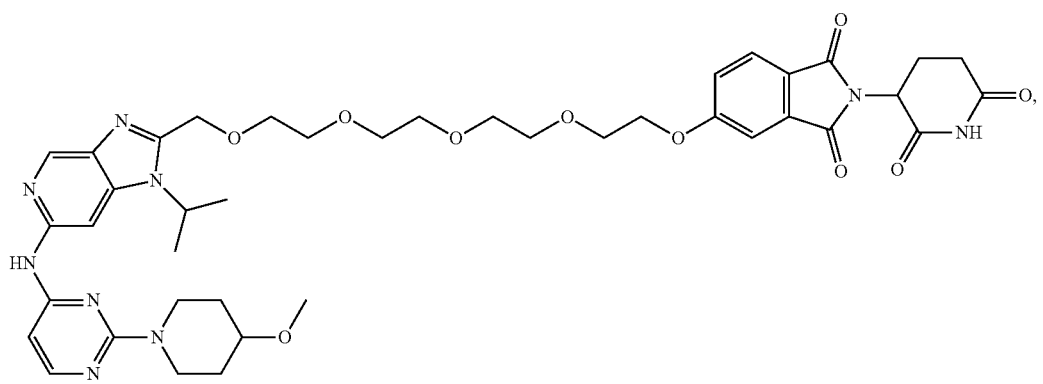
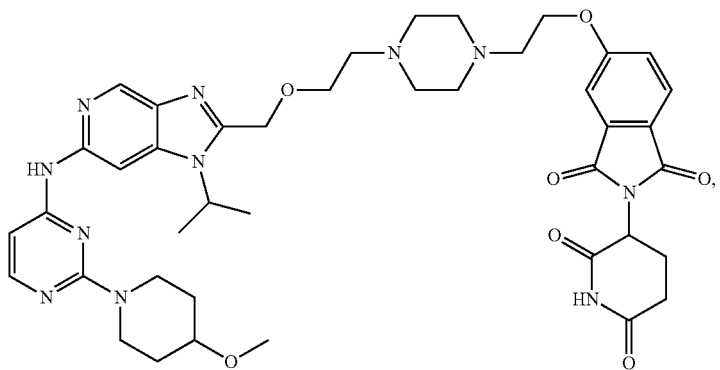
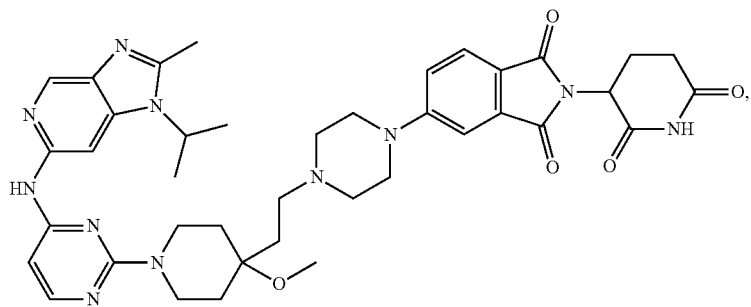

969
970
-continued
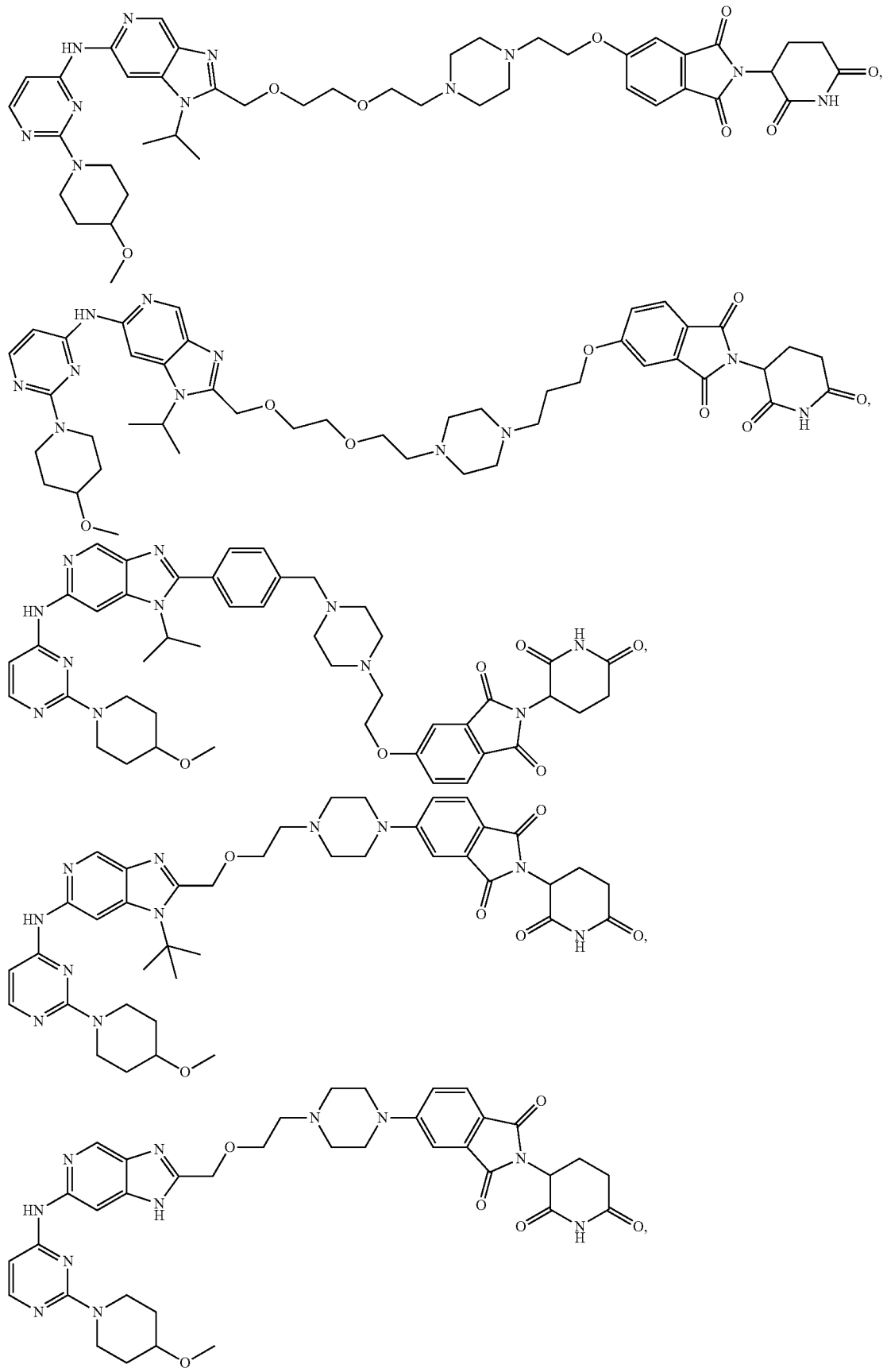

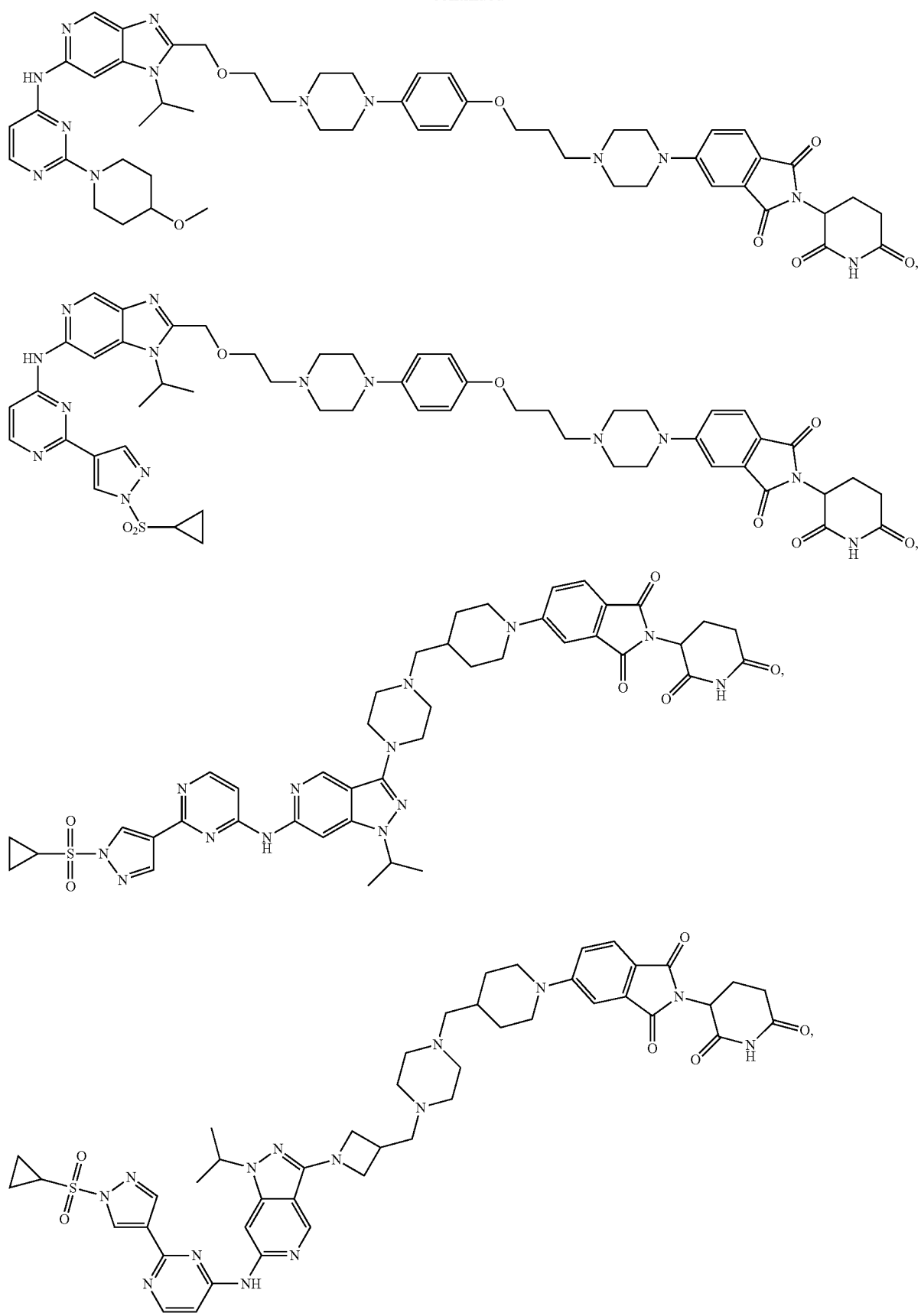

973
974
-continued
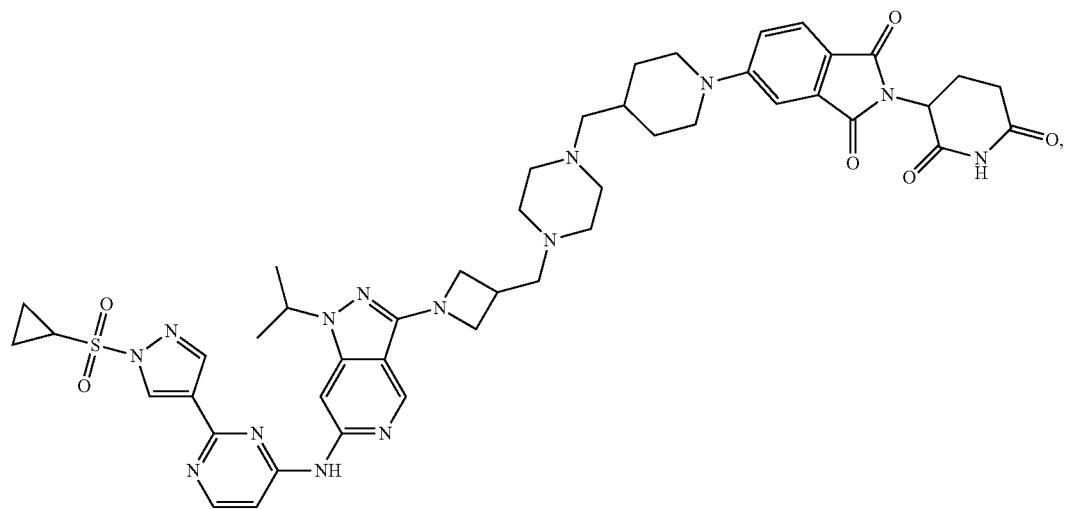
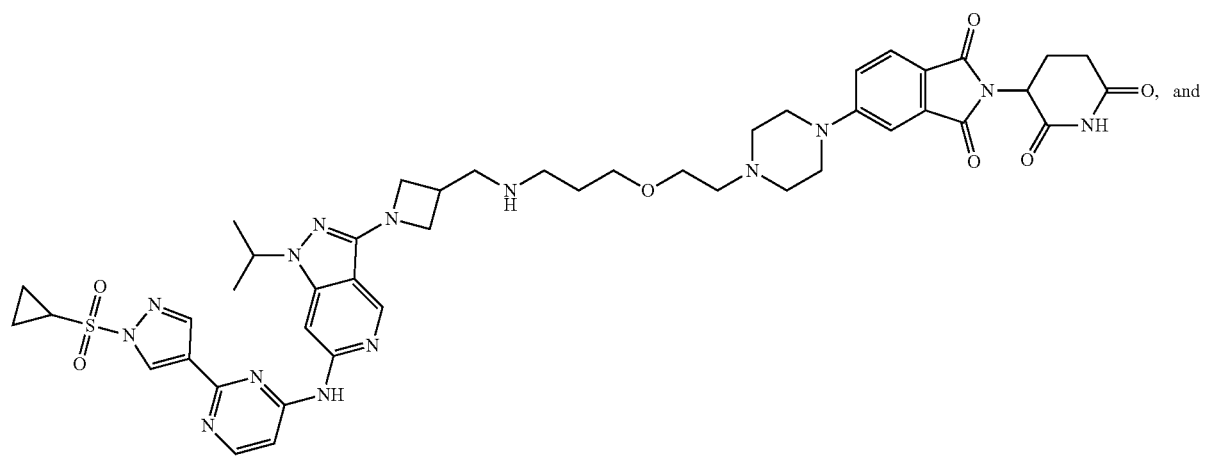
, and
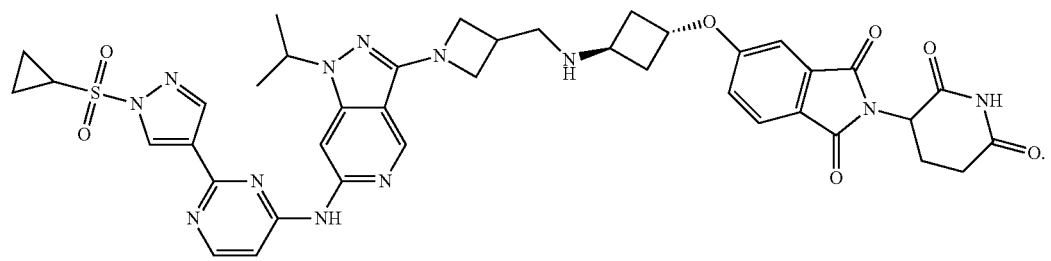
.

24. A method of treating squamous-cell carcinoma of the lung comprising administering to a subject in need thereof an effective amount of a compound of claim 1.
25. A compound selected from the group consisting of:
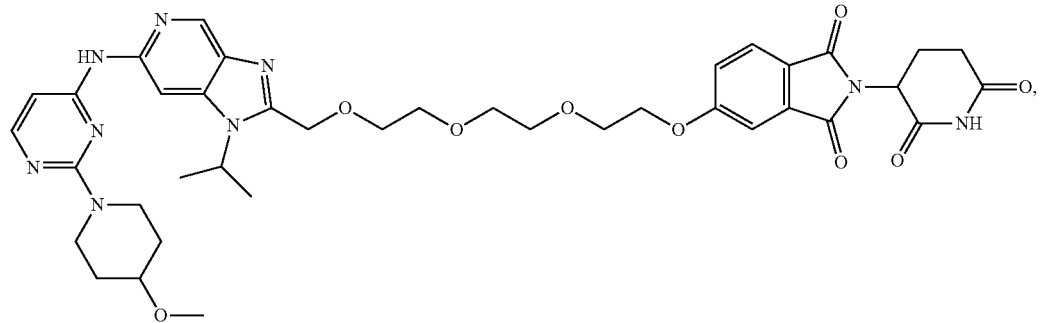
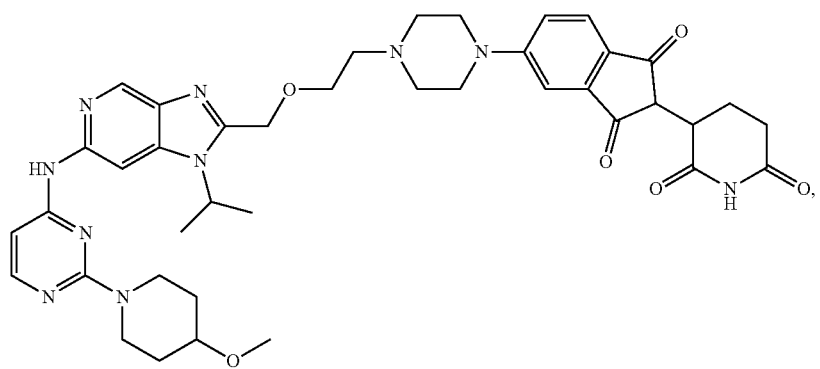
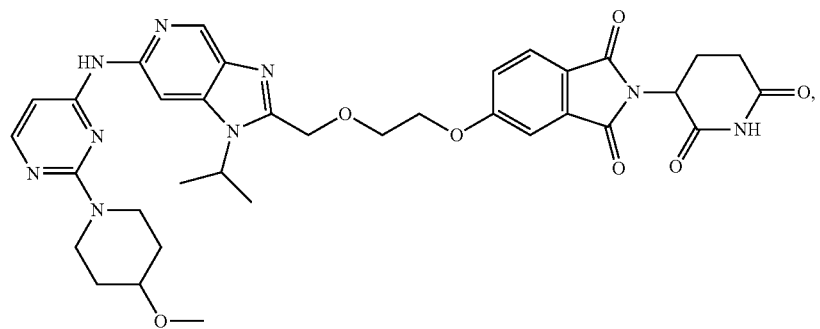
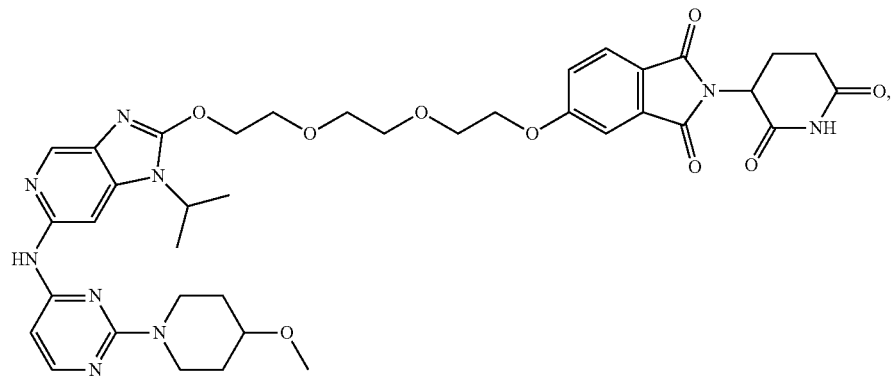

977 978
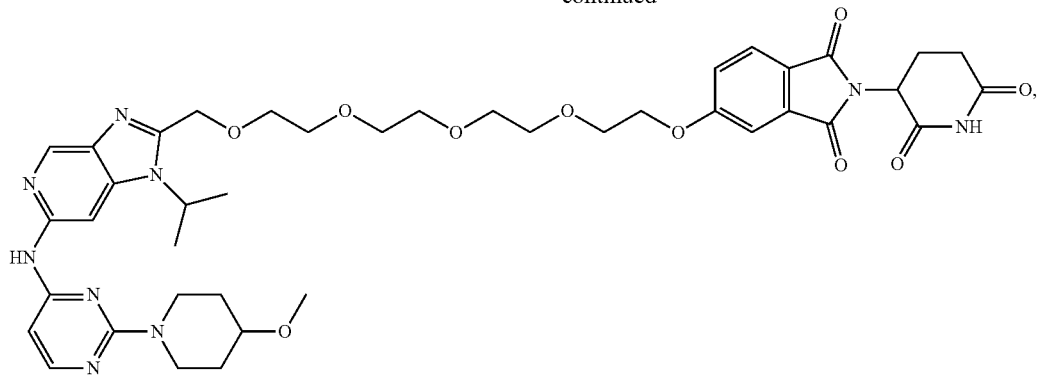
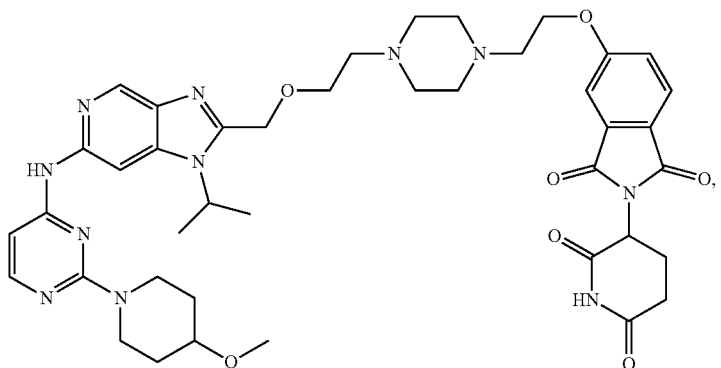
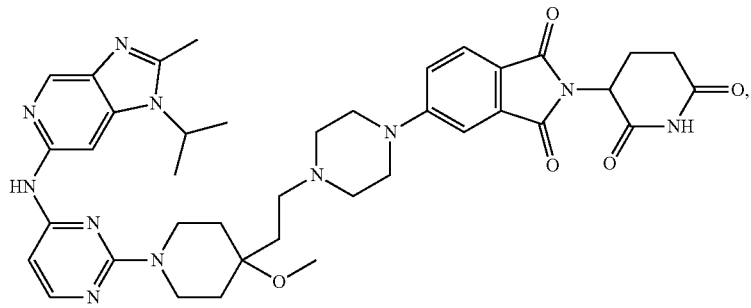
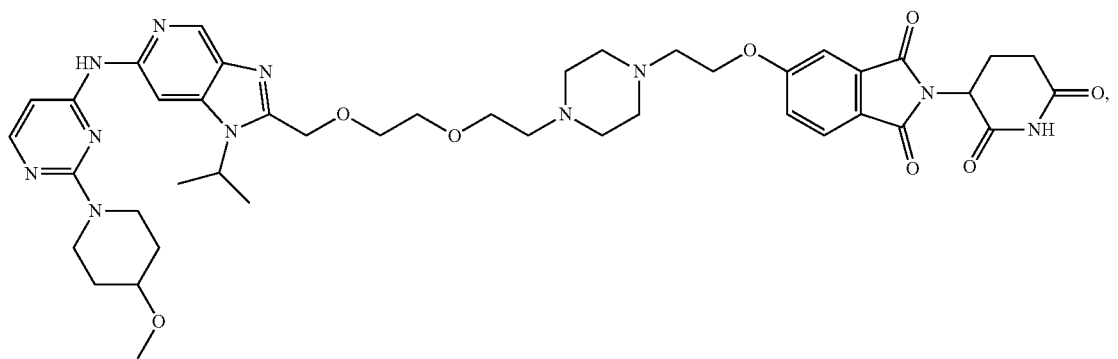
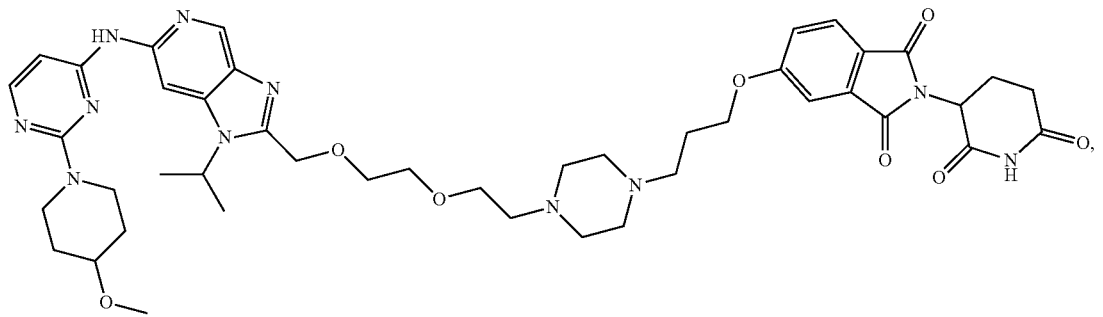

979 980
-continued
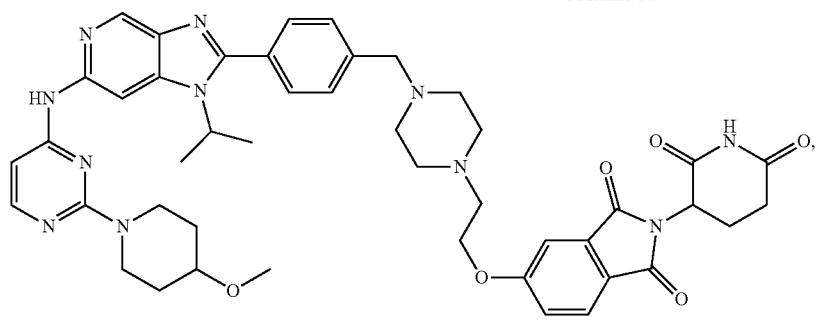
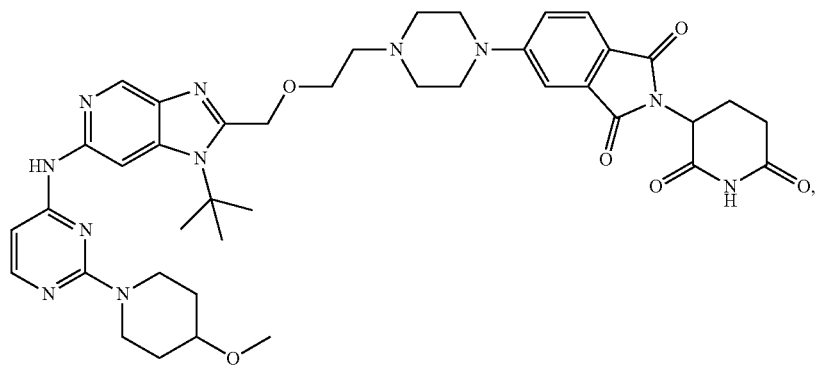
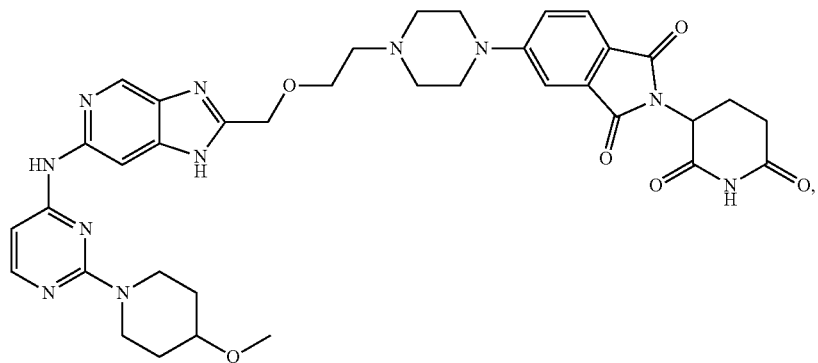
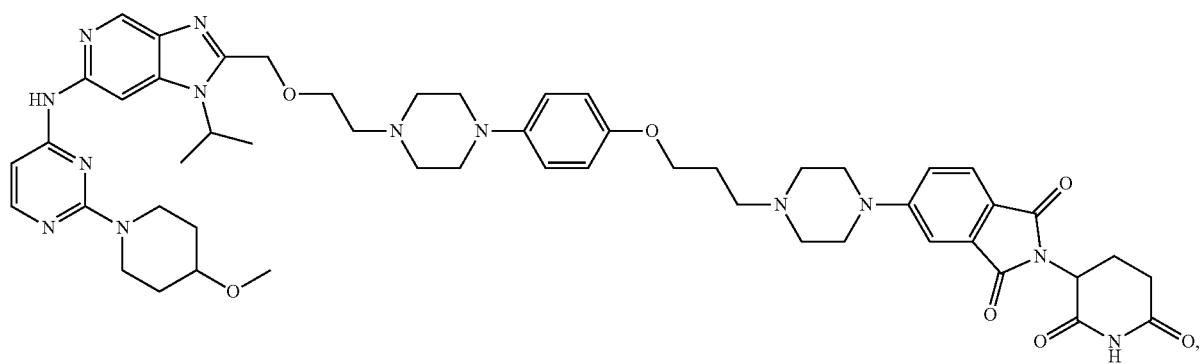

981 982
-continued
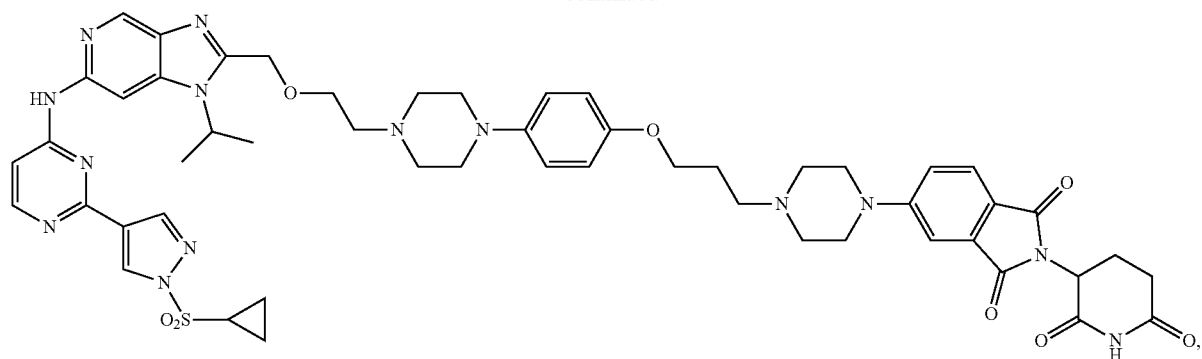
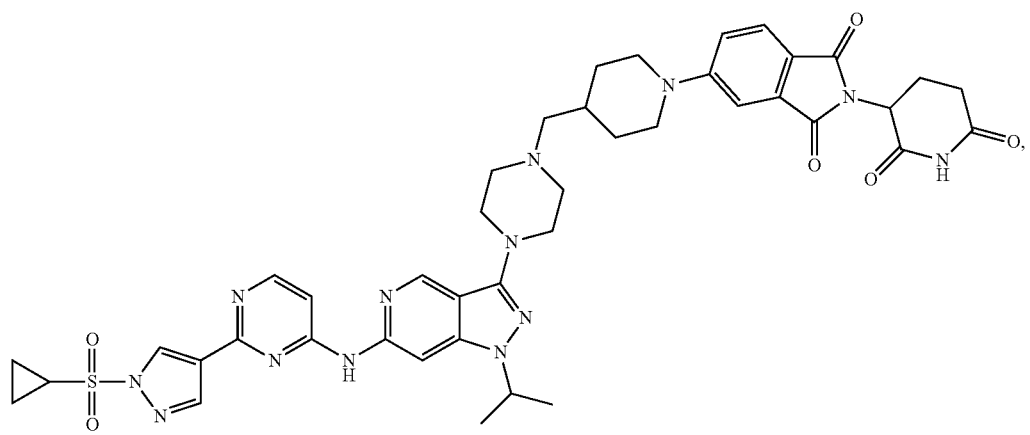
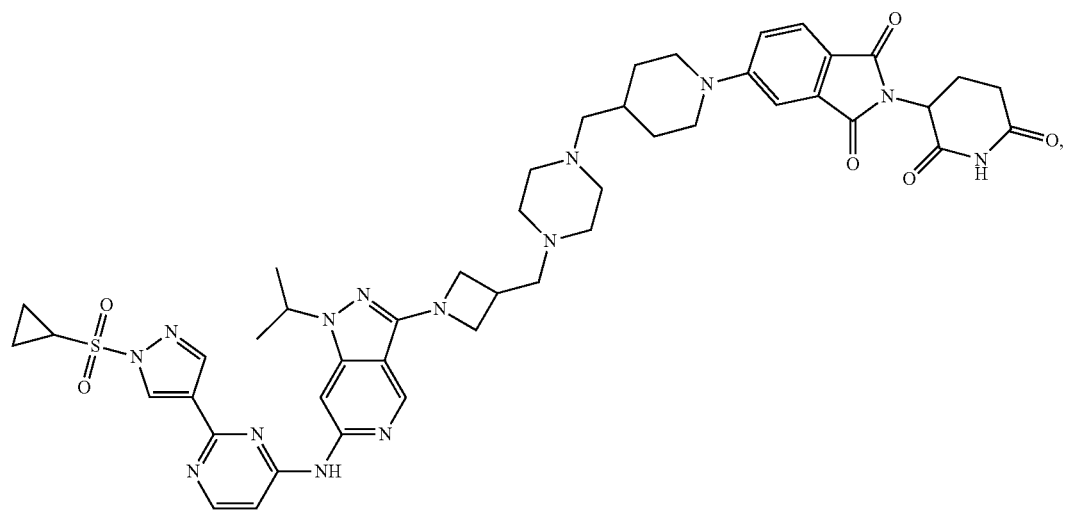

983 984
-continued
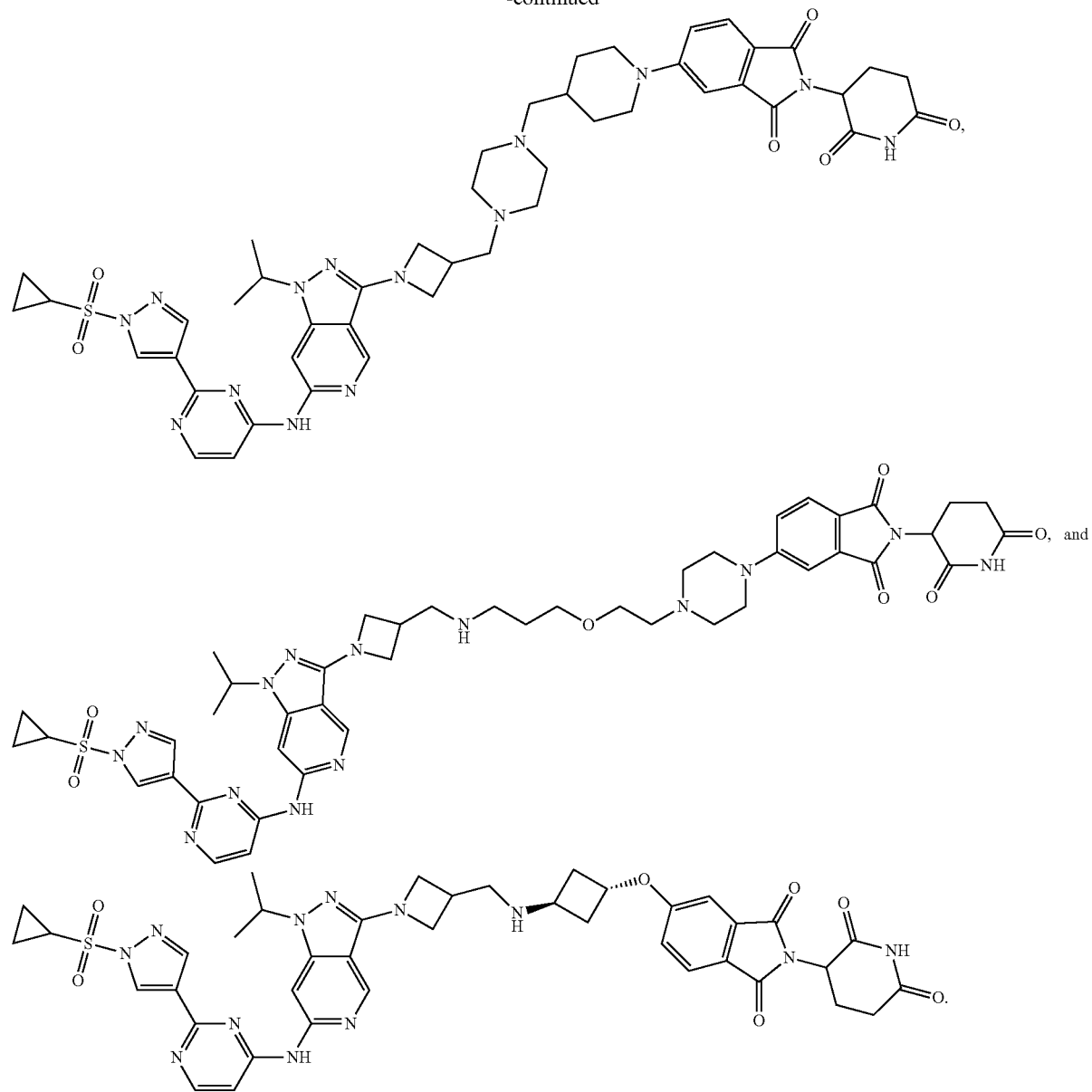
* * * * *